US012594275B2

(12) United States Patent
Shokat et al.

(10) Patent No.: US 12,594,275 B2
(45) Date of Patent: Apr. 7, 2026

(54) IMMUNOPHILIN BINDING AGENTS AND USES THEREOF

(71) Applicant: The Regents of the University of California, Oakland, CA (US)

(72) Inventors: Kevan M. Shokat, San Francisco, CA (US); Ziyang Zhang, San Francisco, CA (US); William A. Weiss, San Francisco, CA (US); QiWen Fan, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1140 days.

(21) Appl. No.: 17/427,039

(22) PCT Filed: Feb. 6, 2020

(86) PCT No.: PCT/US2020/017012

§ 371 (c)(1),
(2) Date: Jul. 29, 2021

(87) PCT Pub. No.: WO2020/163594

PCT Pub. Date: Aug. 13, 2020

(65) Prior Publication Data

US 2023/0063768 A1 Mar. 2, 2023

Related U.S. Application Data

(60) Provisional application No. 62/802,668, filed on Feb. 7, 2019.

(51) Int. Cl.

*A61K 31/506* (2006.01)
*A61K 31/444* (2006.01)
*A61K 31/496* (2006.01)
*A61K 31/517* (2006.01)

(52) U.S. Cl.

CPC .......... *A61K 31/506* (2013.01); *A61K 31/444* (2013.01); *A61K 31/496* (2013.01); *A61K 31/517* (2013.01)

(58) Field of Classification Search

CPC .. A61K 31/506; A61K 31/444; A61K 31/496; A61K 31/517; A61K 31/519; A61P 25/00
See application file for complete search history.

(56) References Cited

U.S. PATENT DOCUMENTS

| | | | |
|---|---|---|---|
| 3,929,992 | A | 12/1975 | Sehgal et al. |
| 4,316,885 | A | 2/1982 | Rakhit |
| 4,650,803 | A | 3/1987 | Stella et al. |
| 5,023,263 | A | 6/1991 | Von Burg |
| 5,023,264 | A | 6/1991 | Caufield et al. |
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,130,307 | A | 7/1992 | Failli et al. |
| 5,151,413 | A | 9/1992 | Caufield et al. |
| 5,162,333 | A | 11/1992 | Failli et al. |
| 5,177,203 | A | 1/1993 | Failli et al. |
| 5,221,670 | A | 6/1993 | Caufield |
| 5,233,036 | A | 8/1993 | Hughes |
| 5,252,579 | A | 10/1993 | Skotnicki et al. |
| 5,256,790 | A | 10/1993 | Nelson |
| 5,258,389 | A | 11/1993 | Goulet et al. |
| 5,260,300 | A | 11/1993 | Goulet et al. |
| 5,262,423 | A | 11/1993 | Kao |
| 5,302,584 | A | 4/1994 | Kao et al. |
| 5,362,718 | A | 11/1994 | Skotnicki et al. |
| 5,373,014 | A | 12/1994 | Failli et al. |
| 5,378,836 | A | 1/1995 | Kao et al. |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,411,967 | A | 5/1995 | Kao et al. |
| 5,463,048 | A | 10/1995 | Skotnicki et al. |
| 5,480,988 | A | 1/1996 | Failli et al. |
| 5,480,989 | A | 1/1996 | Kao et al. |
| 5,489,680 | A | 2/1996 | Failli et al. |
| 5,491,231 | A | 2/1996 | Nelson et al. |

(Continued)

FOREIGN PATENT DOCUMENTS

| | | | |
|---|---|---|---|
| EP | 0 184 162 | A2 | 6/1986 |
| WO | WO-91/004025 | A1 | 4/1991 |

(Continued)

OTHER PUBLICATIONS

Bierer, B. E.; et al. "Probing Inmunmosuppressant Action with a Nonnatural Immunophilin Ligand" 1990, Science, vol. 250, pp. 556-559. (Year: 1990).*
Palmer, A. M. "The role of the blood-CNS barrier in CNS disorders and their treatment" 2010, Neurobiology of Disease, vol. 37, pp. 3-12. (Year: 2010).*
Peluffo, H.; et al. "BBB-targeting, protein-based nanomedicines for drug and nucleic acid delivery to the CNS" 2015, Biotechnology Advances, vol. 33, pp. 277-287. (Year: 2015).*
Gabaluther, R. "Approaches to transport therapeutic drugs across the blood-brain barrier to treat brain diseases" 2010, Neurobiology of Disease, vol. 37, pp. 48-57. (Year: 2010).*

(Continued)

*Primary Examiner* — Eric Olson
*Assistant Examiner* — Benjamin M Brandsen
(74) *Attorney, Agent, or Firm* — Mintz, Levin, Cohn, Ferris, Glovsky and Popeo, P.C.

(57) ABSTRACT

Described herein, inter alia, are immunophilin binding compounds and methods of heating CNS diseases, including co-administering outside the CNS of a subject an anti-CNS disease drug and a compound described herein.

20 Claims, 69 Drawing Sheets

Specification includes a Sequence Listing.

(56) References Cited

U.S. PATENT DOCUMENTS

| | | | |
|---|---|---|---|
| 5,504,091 A | 4/1996 | Molnar-Kimber et al. | |
| 5,563,145 A | 10/1996 | Failli et al. | |
| 5,665,772 A | 9/1997 | Cottens et al. | |
| 5,780,462 A | 7/1998 | Lee et al. | |
| 6,277,983 B1 | 8/2001 | Shaw et al. | |
| 6,358,969 B1 | 3/2002 | Shelley et al. | |
| 6,887,842 B1 | 5/2005 | Briesewitz et al. | |
| 6,921,531 B2 | 7/2005 | Briesewitz et al. | |
| 7,390,784 B2 | 6/2008 | Briesewitz et al. | |
| 7,498,025 B1 | 3/2009 | Briesewitz et al. | |
| 7,696,165 B2 | 4/2010 | Molino | |
| 8,044,099 B2 | 10/2011 | Briesewitz et al. | |
| 9,260,484 B2 | 2/2016 | Briesewitz et al. | |
| 9,956,207 B2 | 5/2018 | Covel et al. | |
| 10,117,945 B2 | 11/2018 | Shokat et al. | |
| 10,568,872 B2 | 2/2020 | Covel et al. | |
| 10,646,577 B2 | 5/2020 | Shokat et al. | |
| 11,000,514 B2 | 5/2021 | Covel et al. | |
| 11,452,780 B2 | 9/2022 | Shokat et al. | |
| 2004/0110666 A1 | 6/2004 | Or et al. | |
| 2004/0157768 A1 | 8/2004 | Or et al. | |
| 2005/0209146 A1 | 9/2005 | Briesewitz et al. | |
| 2005/0209173 A1 | 9/2005 | Graef et al. | |
| 2005/0209265 A1 | 9/2005 | Briesewitz et al. | |
| 2006/0069015 A1 | 3/2006 | Molino et al. | |
| 2006/0074015 A1 | 4/2006 | Molino et al. | |
| 2007/0054348 A1 | 3/2007 | Gestwicki et al. | |
| 2008/0306098 A1 | 12/2008 | Mutz et al. | |
| 2009/0054334 A1 * | 2/2009 | Mutz | A61K 31/4523 514/6.9 |
| 2014/0200186 A1 | 7/2014 | Briesewitz et al. | |
| 2016/0331730 A1 * | 11/2016 | Covel | A61K 31/425 |
| 2016/0333054 A1 | 11/2016 | Briesewitz et al. | |
| 2017/0246305 A1 | 8/2017 | Shokat et al. | |
| 2022/0193242 A1 | 6/2022 | Shokat et al. | |
| 2025/0108052 A1 | 4/2025 | Shokat et al. | |

FOREIGN PATENT DOCUMENTS

| | | | | |
|---|---|---|---|---|
| WO | WO-92/05179 A1 | 4/1992 | | |
| WO | WO-93/11130 A1 | 6/1993 | | |
| WO | WO-94/02136 A1 | 2/1994 | | |
| WO | WO-94/02485 A1 | 2/1994 | | |
| WO | WO-94/09010 A1 | 4/1994 | | |
| WO | WO-95/14023 A1 | 5/1995 | | |
| WO | WO-95/16691 A1 | 6/1995 | | |
| WO | WO-96/41807 A1 | 12/1996 | | |
| WO | WO-2004/082629 A2 | 9/2004 | | |
| WO | WO-2004/082629 A3 | 9/2004 | | |
| WO | WO-2006/095185 A1 | 9/2006 | | |
| WO | WO-2007/053792 A2 | 5/2007 | | |
| WO | WO-2007/053792 A3 | 5/2007 | | |
| WO | WO-2007/112345 A2 | 10/2007 | | |
| WO | WO-2007/112345 A3 | 10/2007 | | |
| WO | WO-2007/112345 A8 | 10/2007 | | |
| WO | WO-2007/112352 A2 | 10/2007 | | |
| WO | WO-2007/112352 A3 | 10/2007 | | |
| WO | WO-2007/112357 A2 | 10/2007 | | |
| WO | WO-2007/112357 A3 | 10/2007 | | |
| WO | WO-2009/055042 A1 | 4/2009 | | |
| WO | WO-2010/065110 A2 | 6/2010 | | |
| WO | WO-2010/065110 A3 | 6/2010 | | |
| WO | WO-2010/077317 A2 | 7/2010 | | |
| WO | WO-2010/077317 A3 | 7/2010 | | |
| WO | WO-2010/132852 A2 | 11/2010 | | |
| WO | WO-2010/132852 A3 | 11/2010 | | |
| WO | WO-2011/130317 A2 | 10/2011 | | |
| WO | WO-2011/130317 A3 | 4/2012 | | |
| WO | WO-2012/047762 A2 | 4/2012 | | |
| WO | WO-2012/047762 A3 | 4/2012 | | |
| WO | WO-2012/079172 A1 | 6/2012 | | |
| WO | WO-2013/030208 A1 | 3/2013 | | |
| WO | WO-2013/181339 A2 | 12/2013 | | |
| WO | WO-2013/181339 A3 | 12/2013 | | |
| WO | WO-2014/037260 A1 | 3/2014 | | |
| WO | WO-2015/057511 A1 | 4/2015 | | |
| WO | WO-2015/106283 A1 | 7/2015 | | |
| WO | WO-2016040806 A1 * | 3/2016 | | A61K 31/436 |
| WO | WO-2016/112321 A1 | 7/2016 | | |
| WO | WO-2016/160362 A1 | 10/2016 | | |
| WO | WO-2017/136708 A1 | 8/2017 | | |
| WO | WO-2018/148508 A1 | 8/2018 | | |
| WO | WO-2020/154455 A1 | 7/2020 | | |
| WO | WO-2020/163598 A1 | 8/2020 | | |

OTHER PUBLICATIONS

Kallen, J.; et al. "X-ray Structures and Analysis of 11 Cyclosporin Derivatives Complexed with Cyclophilin A" 1998, Journal of Molecular Biology, vol. 283, pp. 435-449. (Year: 1998).*

Hainsworth, J. D.; et al. "Phase II Study of Concurrent Radiation Therapy, Temozolomide, and Bevacizumab Followed by Bevacizumab/Everolimus as First-Line Treatment for Patients With Glioblastoma" 2012, Clinical Advances in Hematology & Oncology, vol. 240, pp. 240-246. (Year: 2012).*

Grzmil, M.; et al. "Overcoming resistance to rapalogs in gliomas by combinatory therapies" 2013, Biochimica et Biophysica Acta, vol. 1834, pp. 1371-1380. (Year: 2013).*

Rodrik-Outmezguine, V. S.; et al. "Overcoming mTOR resistance mutations with a new-generation mTOR inhibitor" 2016, Nature, vol. 534, pp. 272-276. (Year: 2016).*

Luan, F. L.; et al. "Rapamycin Blocks Tumor Progression: Unlinking Immunosuppression From Antitumor Efficacy" 2002, Transplantation, vol. 73, pp. 1565-1572. (Year: 2002).*

Choi, W.H.; et al. "Extremely Delayed Brain Metastasis from Renal Cell Carcinoma" 2013, Brain Tumor Research Treatment, vol. 1, pp. 99-102. (Year: 2013).*

Cloughesy, T. F.; et al. "Antitumor Activity of Rapamycin in a Phase I Trial for Patients with Recurrent PTEN-Deficient Glioblastoma" PLoS Medicine 2008, vol. 5, e8, pp. 0139-01511. (Year: 2008).*

Begley, D. J.; et al. "Permeability of the Blood-Brain Barrier to the Immunosuppressive Cyclic Peptide Cyclosporin A" Journal of Neurochemistry 1990, vol. 55, pp. 1222-1230. (Year: 1990).*

Saganová, K.; et al. "Immunosuppressant FK506: Focusing on neuroprotective effects following brain and spinal cord injury", Life Sciences 2012, vol. 91, pp. 77-82. (Year: 2012).*

Arcella, A.; et al. "Rapamycin inhibits the growth of glioblastoma", Brain Research 2013, vol. 1495, pp. 37-51. (Year: 2013).*

Bové, J.; et al. "Fighting neurodegeneration with rapamycin: mechanistic insights", Nature Reviews Neuroscience 2011, vol. 12, pp. 437-452. (Year: 2011).*

Drachman, J.G. et al. (2013). "Antibody-drug conjugates: the chemistry behind empowering antibodies to fight cancer," *Hematology Am Soc Hematol Educ Program* 2013:306-310.

Harmsen, S. et al. (2012). "Kinase Inhibitor Conjugates," *Current Pharmaceutical Design* 18:2891-2900.

International Search Report mailed Jun. 23, 2020, for PCT Application No. PCT/US2020/017017, filed Feb. 6, 2020, 5 pages.

Written Opinion mailed Jun. 23, 2020, for PCT Application No. PCT/US2020/017017, filed Feb. 6, 2020, 4 pages.

Álvarez-García, O et al. (Sep. 2010). "Rapamycin induces growth retardation by disrupting angiogenesis in the growth plate," *Kidney Int* 78(6):561-568.

Bos, P.H. et al. (Dec. 19, 2019). "Development of MAP4 Kinase Inhibitors as Motor Neuron-Protecting Agents," *Cell Chem Biol* 26(12):1703-1715.e37.

Braun, P.D. et al. (Jun. 25, 2003). "A bifunctional molecule that displays context-dependent cellular activity," *J Am Chem Soc* 125(25):7575-7580.

Briesewitz, R. et al. (Mar. 2, 1999). "Affinity modulation of small-molecule ligands by borrowing endogenous protein surfaces," *PNAS USA* 96(5):1953-1958.

Carry, J.-C. et al. Semisynthetic Di- and Tri-Functionalized Non-Immunosuppressive Cyclosporin A Derivatives as Potential Anti-HIV 1 Drugs. *Synlett* 2:316-320.

Dunyak, B.M. et al. (Nov. 20, 2015). "Selective Targeting of Cells via Bispecific Molecules That Exploit Coexpression of Two Intracellular Proteins," *ACS Chem Biol* 10(11):2441-2447.

(56) References Cited

OTHER PUBLICATIONS

Estrada, A.A. et al. (Nov. 26, 2012). "Discovery of highly potent, selective, and brain-penetrable leucine-rich repeat kinase 2 (LRRK2) small molecule inhibitors," *J Med Chem* 55(22):9416-9433.

Fan, Q.W. et al. (Mar. 2017). "A Kinase Inhibitor Targeted to mTORC1 Drives Regression in Glioblastoma," *Cancer Cell* 31(3):424-435.

Fan, Q.W. et al. (Jan. 1, 2018). "Inhibiting 4EBP1 in Glioblastoma," *Clin Cancer Res* 24(1):14-21.

Flygare, J.A. et al. (Jan. 2013). "Antibody-drug conjugates for the treatment of cancer," *Chem Biol Drug Des* 81(1):113-121.

Galat, A. (Sep. 2013). "Functional diversity and pharmacological profiles of the FKBPs and their complexes with small natural ligands," *Cell Mol Life Sci* 70(18):3243-3275.

Gestwicki, J.E. et al. (Oct. 29, 2004). "Harnessing chaperones to generate small-molecule inhibitors of amyloid beta aggregation," *Science* 306(5697):865-869.

González, D. et al. (Jun. 2011). "Growth of kidney-transplanted pediatric patients treated with sirolimus," *Pediatr Nephrol* 26(6):961-966.

Guo, Z.-F. et al. (2014). "Facile functionalization of FK506 for biological studies by the thiol-ene 'click' reaction," *RSC Adv* 4:11400-11403.

Guo, Z. et al. (Mar. 2019). "Rapamycin-inspired macrocycles with new target specificity," *Nat Chem* 11(3):254-263.

Holt, D. A. et al. (1993). "Design, synthesis, and kinetic evaluation of high-affinity FKBP ligands and the X-ray crystal structures of their complexes with FKBP12," *J. Am Chem. Soc.* 115:9925-9938.

International Search Report mailed Jun. 12, 2020, for PCT Application No. PCT/US2020/017012, filed Feb. 6, 2020, 5 pages.

Ko, S.Y. et al. (Nov. 1992). "Conformation of cyclosporin A in polar solvents," *Int J Pept Protein Res* 40(5):380-382.

Marinec, P.S. et al. (Jun. 2008). "Bifunctional molecules evade cytochrome P450 metabolism by forming protective complexes with FK506-binding protein," *Mol. Bio Syst.* 4(6):571-578.

Marinec, P.S. et al. (Feb. 3, 2009). "FK506-binding protein (FKBP) partitions a modified HIV protease inhibitor into blood cells and prolongs its lifetime in vivo," *PNAS USA* 106(5):1336-1341.

Marinec, P.S. et al. Aug. 15, 2009). "Synthesis of orthogonally reactive FK506 derivatives via olefin cross metathesis," *Bioorg Med Chem* 17(16):5763-5768.

Nambu, M. et al. (Jun. 1, 2017). "A calcineurin antifungal strategy with analogs of FK506," *Bioorg Med Chem Lett* 27(11):2465-2471.

Paprica, P.A. et al. (Jan-Feb. 1992). "Preparation of novel cyclosporin A derivatives," *Bioconjug Chem* 3(1):32-36.

Park, S.B. et al. (1989). "A Semi-Synthetic Approach to Olefinic Analogs of Amino Acid One (MeBMT) in Cyclosporin A," *Tetrahedron Letters* 30(32):4215-4218.

Rutaganira, F.U. et al. (Mar. 10, 2016). "Design and Structural Characterization of Potent and Selective Inhibitors of Phosphatidylinositol 4 Kinase IIIB," *J Med Chem* 59(5):1830-1839.

Sellmyer, M.A. et al. (May 15, 2007). "Engineering small molecule specificity in nearly identical cellular environments," *Bioorg Med Chem Lett* 17(10):2703-2705.

Siu, M. et al. (Sep. 27, 2018). "Dual Leucine Zipper Kinase Inhibitors for the Treatment of Neurodegeneration," *J Med Chem* 61(18):8078-8087.

Winter, G.E. et al. (Jun. 19, 2015). "Drug Development. Phthalimide conjugation as a strategy for in vivo target protein degradation," *Science* 348(6241):1376-1381.

Written Opinion mailed Jun. 12, 2020, for PCT Application No. PCT/US2020/017012, filed Feb. 6, 2020, 6 pages.

Wu, X. et al. (Sep. 12, 2011). "Creating diverse target-binding surfaces on FKBP12: synthesis and evaluation of a rapamycin analogue library," *ACS Comb Sci* 13(5):486-495.

Gold, B.G. (Oct. 2000). "Neuroimmunophilin ligands: evaluation of their therapeutic potential for the treatment of neurological disorders," Expert Opinion on Investigational Drugs 9(10):2331-2342.

Juvvadi, P.R. et al. (Sep. 19, 2019). "Harnessing calcineurin-FK506-FKBP12 crystal structures from invasive fungal pathogens to develop antifungal agents," *Nature Communications* 10(1):4275.

Klettner, A. et al. (Jun. 2003). "FK506 and its analogs—therapeutic potential for neurological disorders," *Curr Drug Targets CNS Neurol Disord* 2(3):153-162.

Piggott, A.M. et al. (Oct. 1, 2009). "Rapid isolation of novel FK506 binding proteins from multiple organisms using gDNA and cDNA T7 phage display," *Bioorg Med Chem* 17(19):6841-6850.

Registry 1054668-19-7, entered STN Sep. 29, 2008, 1 page.

Wang, Y. et al. (Aug. 19, 2019). "One-step Heck Reaction Generates Nonimmunosuppressive FK506 Analogs for Pharmacological BMP Activation," *ACS Med Chem Lett* 10(9):1279-1283.

Wassarman, D.R. et al. (Sep. 20, 2022). "Tissue-restricted inhibition of mTOR using chemical genetics," *PNAS USA* 119(38):e2204083119.

Zhang, Z. et al. (Nov. 4, 2019). "Bifunctional Small-Molecule Ligands of K-Ras Induce Its Association with Immunophilin Proteins," *Angew Chem Int Ed* 58(45):16314-16319.

Zhang, Z. et al. (Sep. 22, 2022). "Brain-restricted mTOR inhibition with binary pharmacology," *Nature* 609:822-828.

Ayral-Kaloustian, S. et al. (Jan. 14, 2010). "Hybrid inhibitors of phosphatidylinositol 3-kinase (PI3K) and the mammalian target of rapamycin (mTOR): design, synthesis, and superior antitumor activity of novel wortmannin-rapamycin conjugates," *J Med Chem* 53(1):452-459.

Bonner, J.M. et al. (Oct. 2017). "Diverse structures, functions and uses of FK506 binding proteins," *Cellular Signaling* 38:97-105.

Cai, J. et al. (2024). "Effect and Mechanism of Rapamycin on Cognitive Deficits in Animal Models of Alzheimer's Disease: A Systematic Review and Meta-analysis of Preclinical Studies," *J Alzheimer's Dis* 99(1):53-84.

Cassano, T. et al. (Jan. 2019). "Early intrathecal infusion of everolimus restores cognitive function and mood in a murine model of Alzheimer's disease," *Exp Neurol* 311:88-105.

Cihan, Y.B. (Jul. 1, 2019). "Lapatinib? or Radiotherapy? In Cranial Metastasis of Breast Cancer," *Eur J Breast Health* 15(3):205-206.

French, J.A. et al. (Oct. 29, 2016). "Adjunctive everolimus therapy for treatment-resistant focal-onset seizures associated with tuberous sclerosis (EXIST-3): a phase 3, randomised, double-blind, placebo-controlled study," *Lancet* 388(10056):2153-2163.

Hou, S.-J. et al. (Oct. 2, 2023). "Rapamycin Responds to Alzheimer's Disease: A Potential Translational Therapy," *Clin Interv Aging* 18:1629-1639.

Jhanwar-Uniyal, M. (2017). "Mighty RapaLink-1 Vanquishes Undruggable Mutant mTOR in Glioblastoma," *Translational Cancer Research* 6(Suppl 7):S1143-S1148.

Kaeberlein, M. et al. (Jan. 23, 2019). "Rapamycin and Alzheimer's disease: Time for a clinical trial?" *Sci Transl Med* 111(476):doi:10.1126/scitranslmed.aar4289.

Kavanagh, M.E. et al. (Jul. 1, 2013). "The development of CNS-active LRRK2 inhibitors using property-directed optimization," *Bioorg Med Chem Lett* 23(13):3690-3696.

Lin, A.-L. et al. (Jun. 2020). "APOE genotype-dependent pharmacogenetic responses to rapamycin for preventing Alzheimer's disease," *Neurobiol Dis* 139:104834.

Manzoni, C. et al. (Oct. 12, 2016). "mTOR independent regulation of macroautophagy by Leucine Rich Repeat Kinase 2 via Beclin-1," *Sci Rep* 6:35106.

Mukherjee, S. et al. (2009). "A Comprehensive Review of Immunosuppression Used for Liver Transplantation," *J Transplant* 2009:701464.

Nambu, M. et al. (Jun. 1, 2017). "A calcineurin antifungal strategy with analogs of FK506," *Bioorg Med Chem Lett* 27(11):2465-2471; with Supporting Information.

Porkka, K. et al. (Aug. 15, 2008). "Dasatinib crosses the blood-brain barrier and is an efficient therapy for central nervous system Philadelphia chromosome-positive leukemia," *Blood* 112(4):1005-1012.

Tanaka, H. et al. (1987). "Structure of FK506, a novel immunosuppressant isolated from *Streptomyces*," *Journal of the American Chemical Society* 109(16):5031-5033.

Taymans, J.-M. et al. (Jul. 1, 2023). "Perspective on the current state of the LRRK2 field," *NPJ Parkinsons Dis* 9(1):104.

(56) References Cited

OTHER PUBLICATIONS

Terceiro, L.E.L. et al. (Jul. 27, 2023). "Navigating the Blood-Brain Barrier: Challenges and Therapeutic Strategies in Breast Cancer Brain Metastases," *Int J Mol Sci* 24(15):12034.
Xie, P.-L. et al. (May 30, 2024). "Pharmacological mTOR inhibitors in ameliorating Alzheimer's disease: current review and perspectives," *Front Pharmacol* 15:1366061.
Zhu, Z. et al. (Feb. 8, 2019). "Balancing mTOR Signaling and Autophagy in the Treatment of Parkinson's Disease," *Int J Mol Sci* 20(3):728.

* cited by examiner

RapaLink-1

FIG. 14A
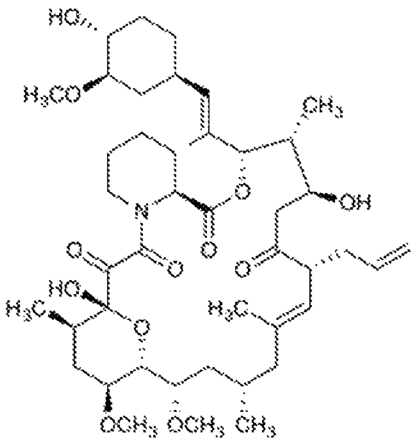
FK506
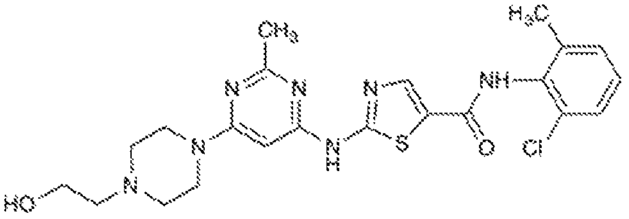
Dasatinib
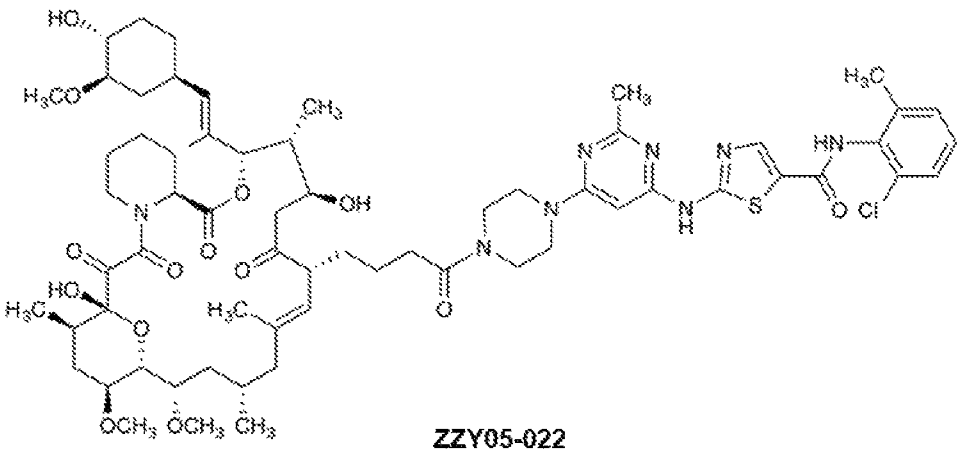
ZZY05-022
(FK506-Dasatinib)

| Kinase | Average Inhibition [Dasatinib] | Average Inhibition [05-022] |
|---|---|---|
| ABL1 | 100 | 100 |
| YES1 | 100 | 97 |
| GAK | 100 | 98 |
| BLK | 100 | 100 |
| SIK2 | 100 | 100 |
| ABL2 | 100 | 100 |
| SRC | 100 | 100 |
| CSK | 94 | 90 |
| LCK | 92 | 86 |

FIG. 17A
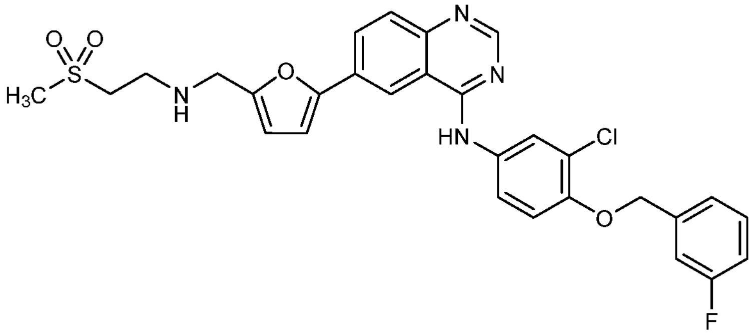
Lapatinib
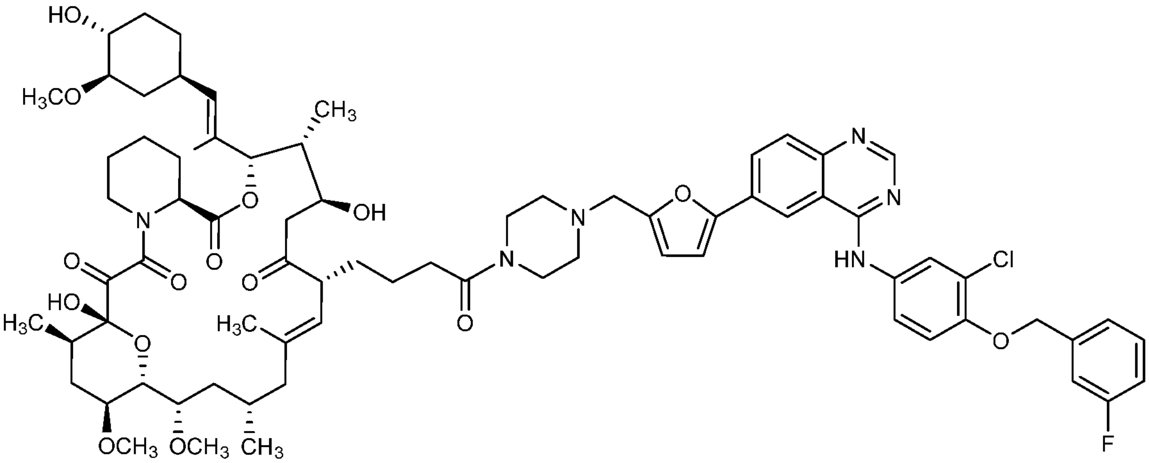
08-047
(FK506-Lapatinib)

FIG. 17D
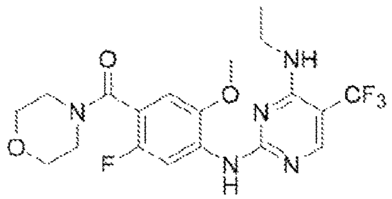
GNE7915
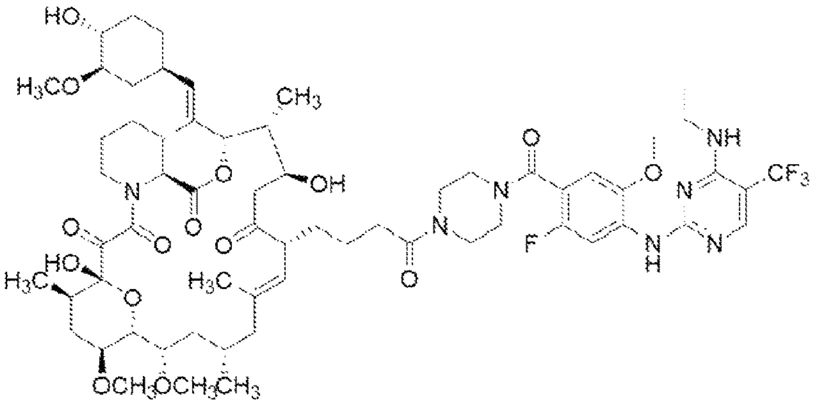
08-074
(FK506-GNE7915)
FIG. 17E
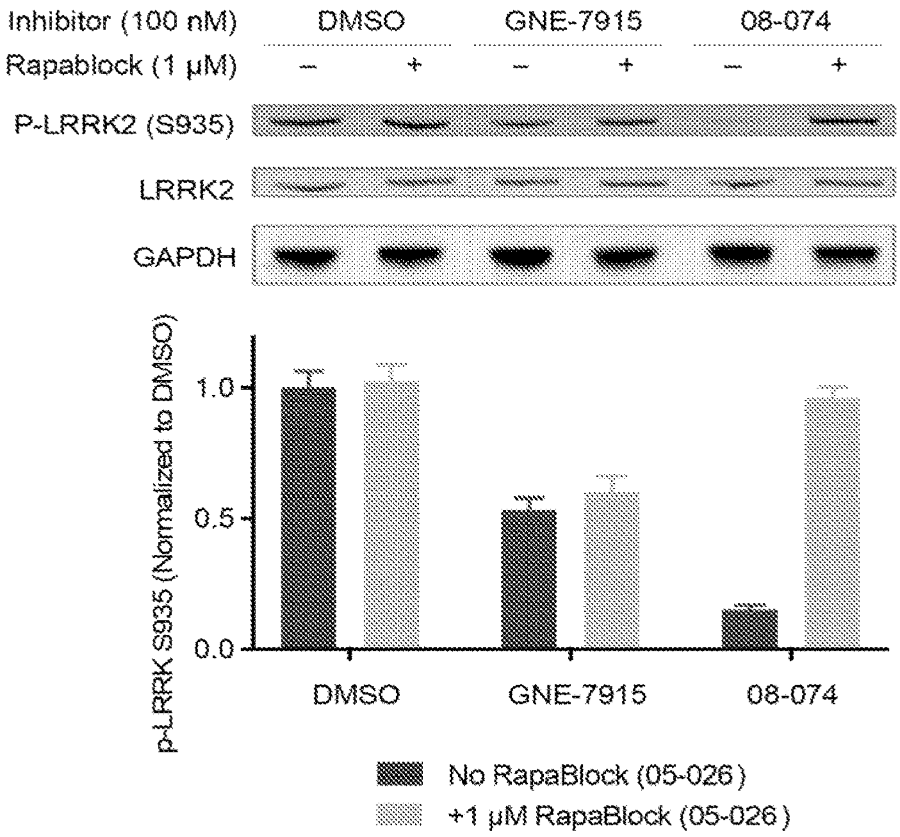

FIG. 19A
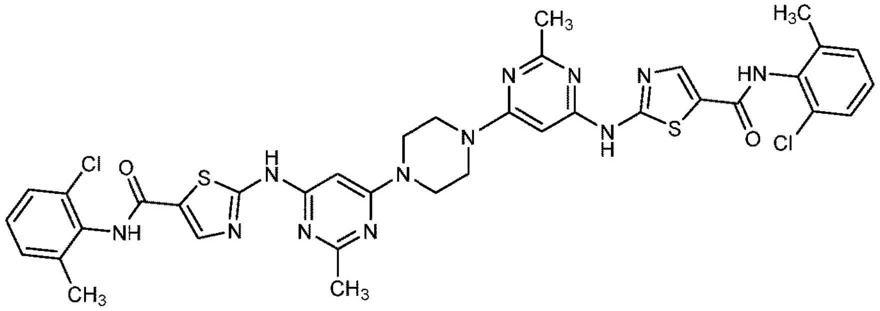
Dasa Dimer 0
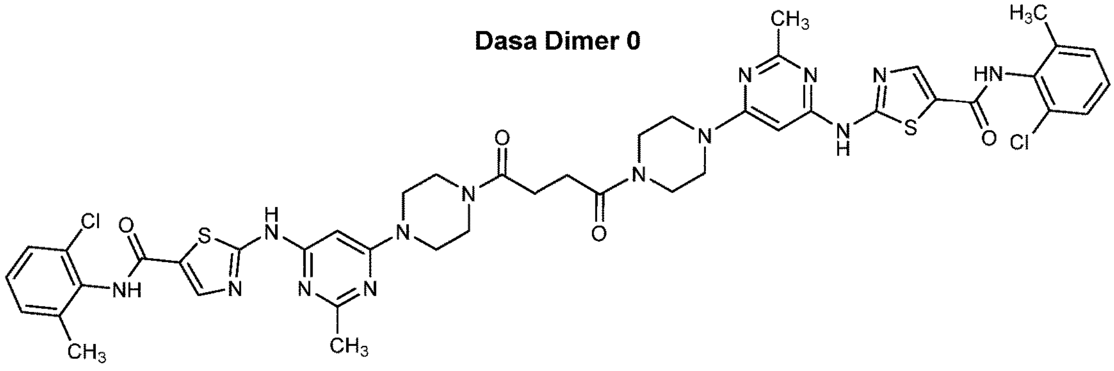
Dasa Dimer 4
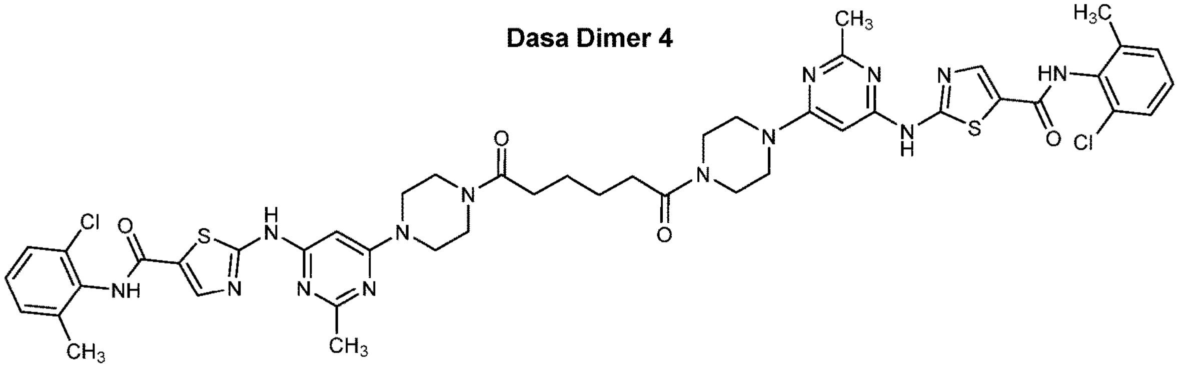
Dasa Dimer 6

| Gene Name | Average Inhibition [Dasatinib] | Average Inhibition [05-022] |
|---|---|---|
| ABL1 | 100 | 100 |
| YES1 | 100 | 97 |
| GAK | 100 | 98 |
| BLK | 100 | 100 |
| SIK2 | 100 | 100 |
| ABL2 | 100 | 100 |
| SRC | 100 | 100 |
| CSK | 94 | 90 |
| LCK | 92 | 86 |

FIG. 21C

Immunophilin-dependent Kinase Inhibitors
+Immunophilin "Blocker"

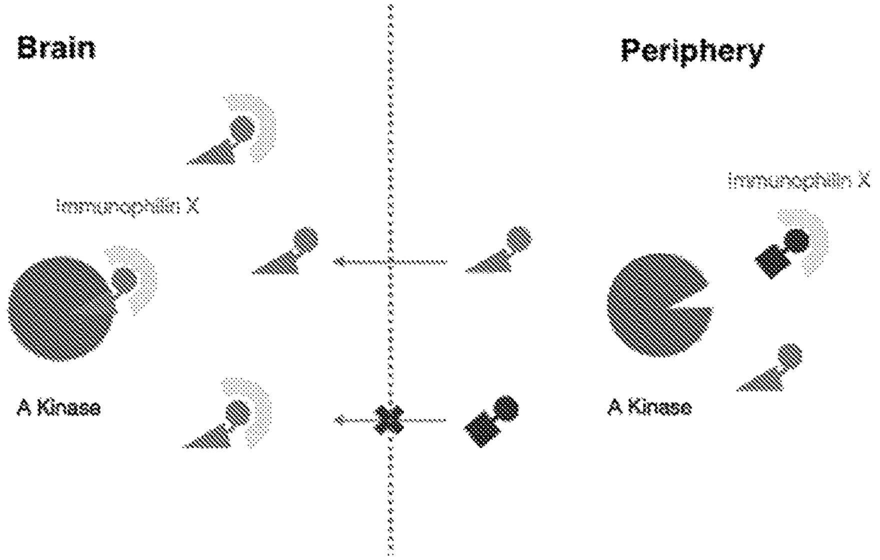

*FKBP12 is highly expressed in the brain.

FIG. 22

TABLE 1 Distribution of [$^3$H]FK506 binding sites in brain and peripheral tissues

| Tissue | Membrane | Soluble |
|---|---|---|
| Cortex | 24.5 ± 2.2 | 17.5 ± 1.0 |
| Cerebellum | 4.0 ± 0.3 | 9.6 ± 0.7 |
| Striatum | 45.8 ± 3.9 | 33.8 ± 2.5 |
| Hippocampus | 34.7 ± 1.5 | 42.6 ± 3.2 |
| Brainstem | 5.9 ± 0.6 | 9.7 ± 0.4 |
| Hypothalamus | 10.3 ± 0.9 | 7.5 ± 0.5 |
| Midbrain | 12.8 ± 1.0 | 29.9 ± 1.0 |
| Pituitary | * | 11.3 ± 1.2 |
| Thymus | 1.8 ± 0.2 | 3.1 ± 0.4 |
| Spleen | 1.4 ± 0.2 | 2.0 ± 0.1 |
| Heart | * | 3.6 ± 0.4 |
| Kidney | 0.5 ± 0.02 | 3.4 ± 0.4 |
| Liver | * | 3.7 ± 0.5 |
| Lung | 0.7 ± 0.04 | 2.6 ± 0.3 |

[$^3$H]FK506 bound is expressed as pmol per mg protein. Regions of rat brain were dissected, homogenized at 100 mg $ml^{-1}$ wet weight in 50 mM Tris-HCl, pH 7.4, 1 mM sodium EDTA, 100 μg $ml^{-1}$ phenylmethylsul- Steiner, J. P. *et al.* High brain densities of the immunophilin FKBP colocalized with calcineurin. *Nature* 358, 584–587 (1992).

FIG. 24
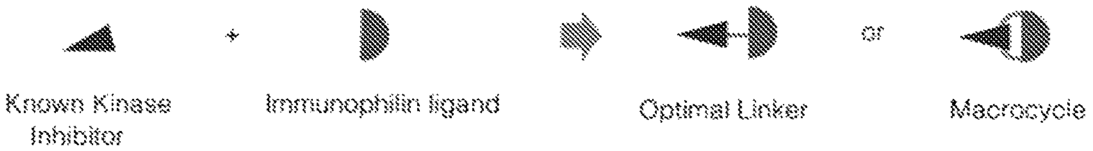
FIG. 25
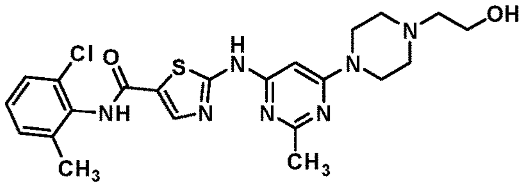
Dasatinib
Src family kinase, Abl
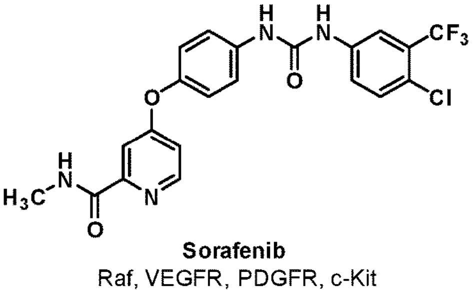
Sorafenib
Raf, VEGFR, PDGFR, c-Kit
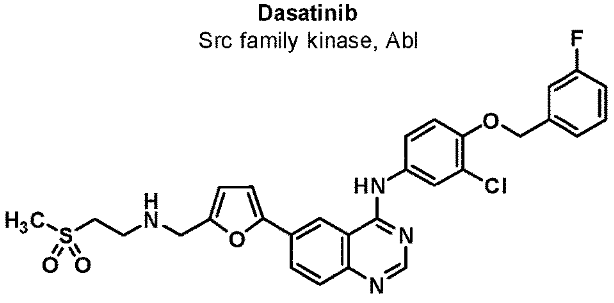
Lapatinib
EGFR, HER2
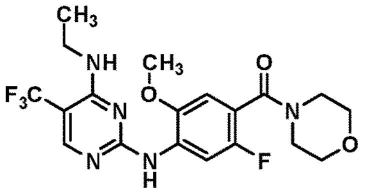
GNE-7915
LRRK2

SLF
Kd(FKBP12) = 13 nM

FK506
Kd(FKBP12) = 0.6 nM

Cyclosporin A
Kd(CypA) = 17 nM

Sanglifehrin A
Kd(CypA) = 0.2 nM

Cyclosporin

Dasatinib 05-082 (CsA-Dasatinib)

FK506

Dasatinib 05-022 (FK506-Dasatinib)

FIG. 28
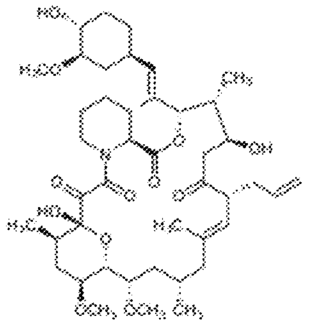
$K_d$ (FKBP12)
0.6 nM
FK506
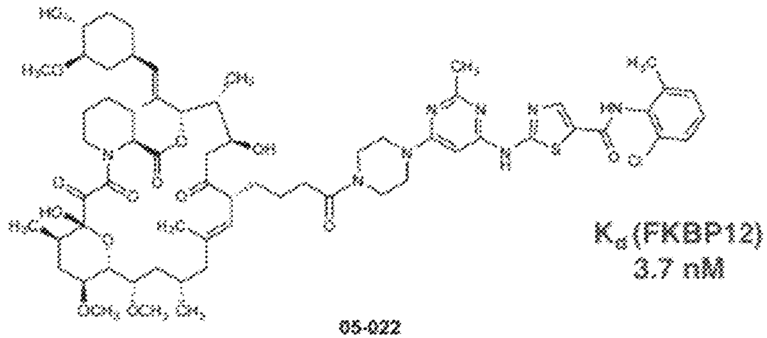
$K_d$ (FKBP12)
3.7 nM
05-022
(FK506-Dasatinib)
FKBP12 Fluorescence Polarization Assay:
1 nM FKBP12, 0.5 nM Rapa-FITC, x nM ligand, 20 mM HEPES 8.0, 0.01% Triton X-100, 5% DMSO. Average of triplicate.
Src Kinase Assay
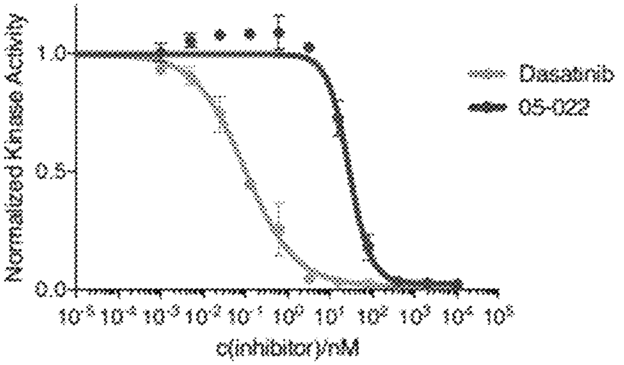
Src Kinase Assay:
0.4 ng/μL kinase, 125 μM ATP, 0.4 μg/μL Poly $E_4Y_1$, 60 min, 23 °C. Average of triplicate.

0.4 ng/μL kinase, 125 μM ATP, 0.4 μg/μL Poly $E_4Y_1$, 60 min, 23 °C.

Au-Yeung BB, Deindl S, Hsu LY, Palacios EH, Levin SE, Kuriyan J, Weiss A 2009. The structure, regulation, and function of ZAP-70. Immunol Rev 228:41–57

Au-Yeung BB, Deindl S, Hsu LY, Palacios EH, Levin SE, Kuriyan J, Weiss A 2009. The structure, regulation, and function of ZAP-70. Immunol Rev 228:41–57

FIG. 38
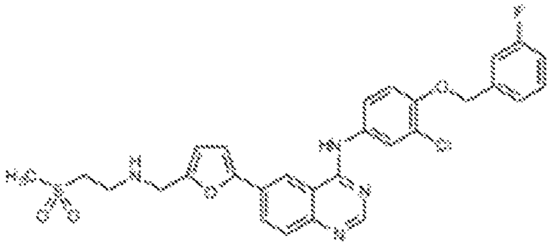
Lapatinib
Lapatinib
Erlotinib
Gefitinib
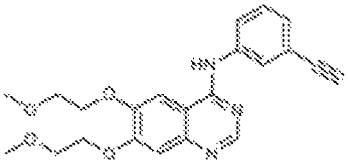
Erlotinib
Focused optimization of
- Attachment point
- Linker chemistry
~20 compounds
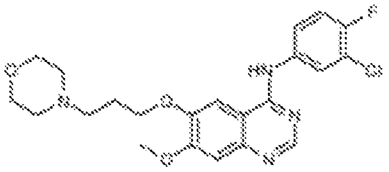
Gefitinib
FK-Lap (ZZY-08-047)
FK-Erlo (ZZY-08-068)
FK-Gefi (ZZY-08-069)

FIG. 41
It is active at concentrations where GNE-7915 was sub-efficacious.
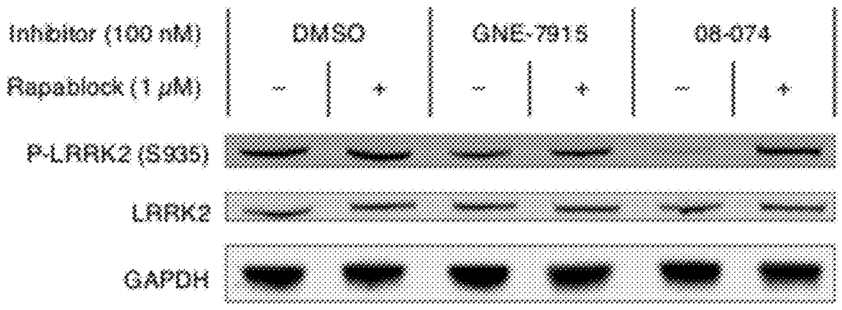
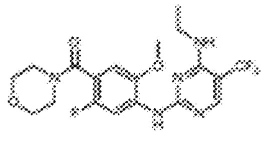
GNE-7915
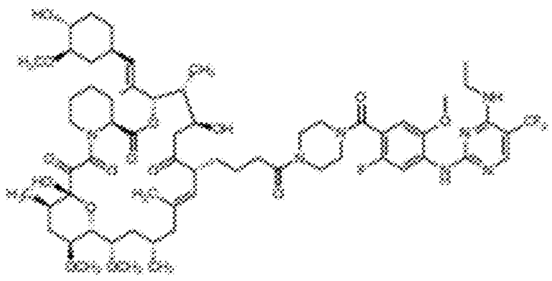
08-074
(FK506-GNE7915)
The degree of inhibition can be quantified with a sandwich TR-FRET assay
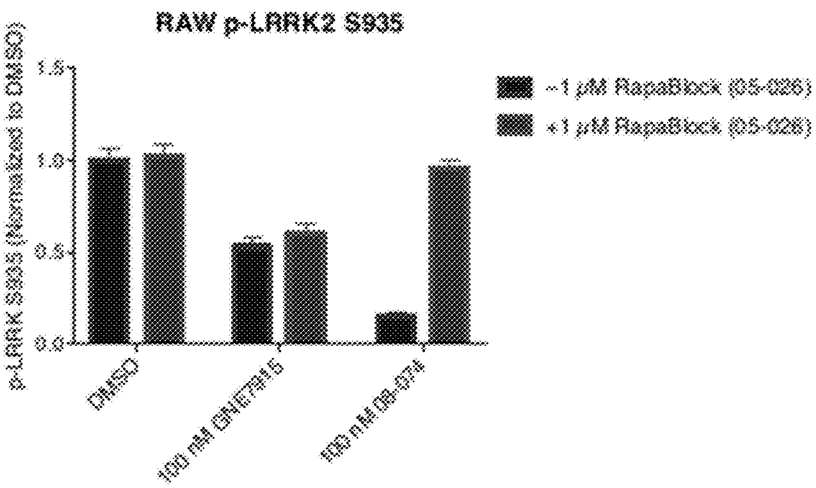

Dose-Response confirms potent inhibition of p-LRRK2

| IC50 (nM) | 3T3 | RAW264.7 |
|---|---|---|
| GNE-7915 | 75.6±10.2 | 81.3±12.2 |
| ZZY08-074 | 8.51±0.71 | 6.47±0.64 |

FIG. 46
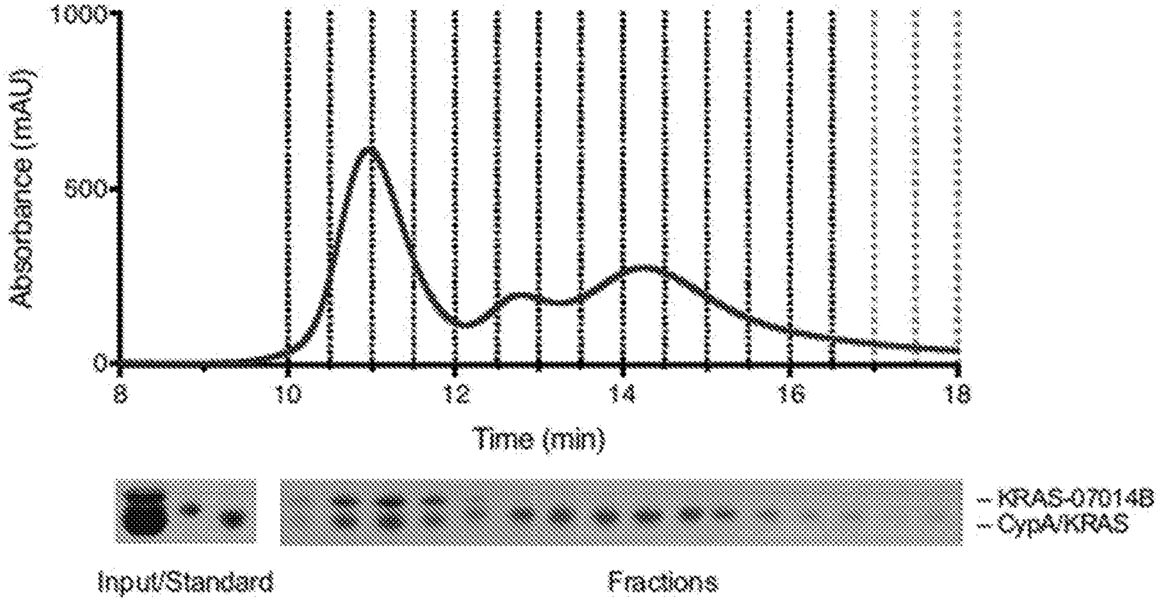
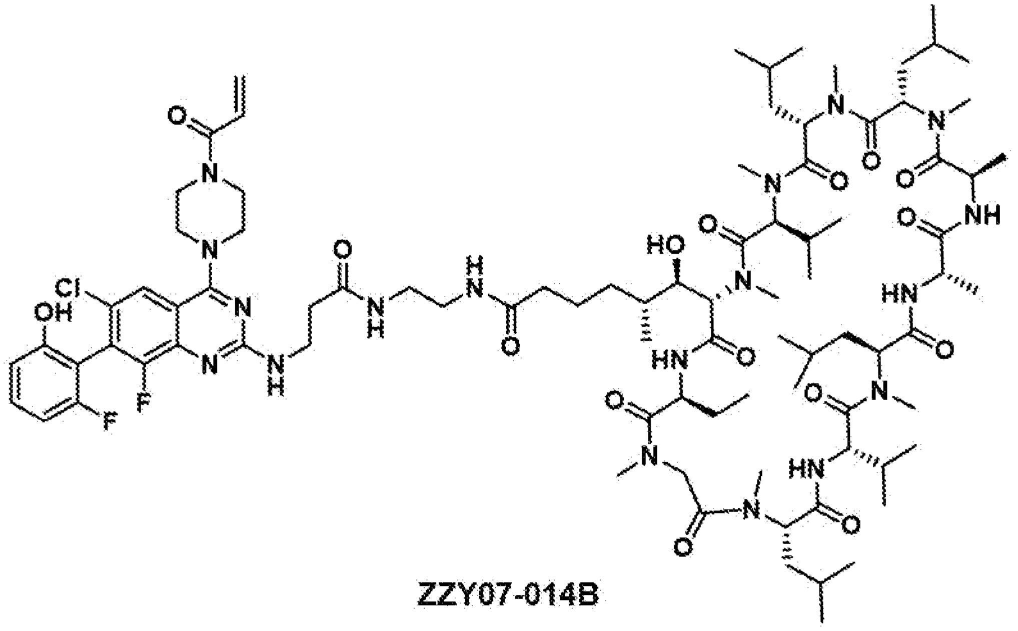
ZZY07-014B

This likely indicates a first melting event of CypA, then a second melting event of labeled KRAS at a higher temperature.
Not shown: CypA and KRAS alone both melt at 50 °C.

FIG. 53
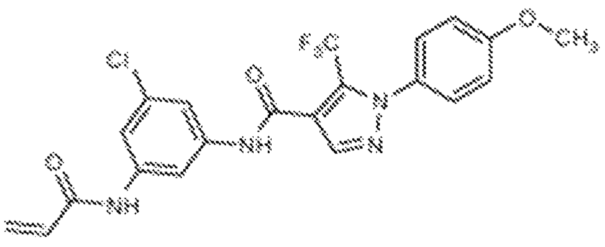
KRAS (M72C) inhibitor
Binds both GDP- and GTP-state
$K_i$ ~ 300 μM
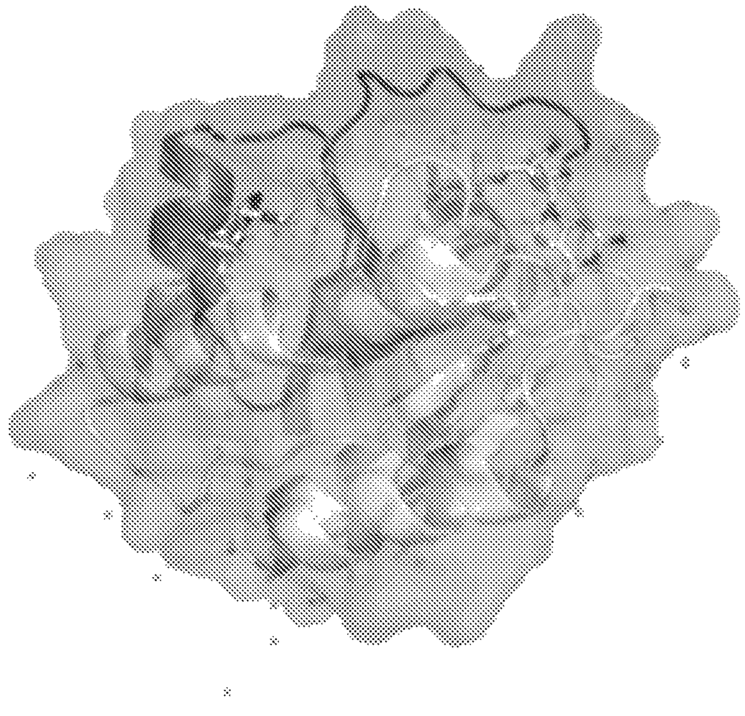

FIG. 55
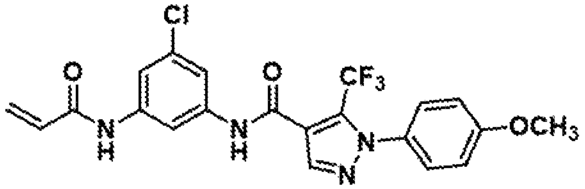
06-031
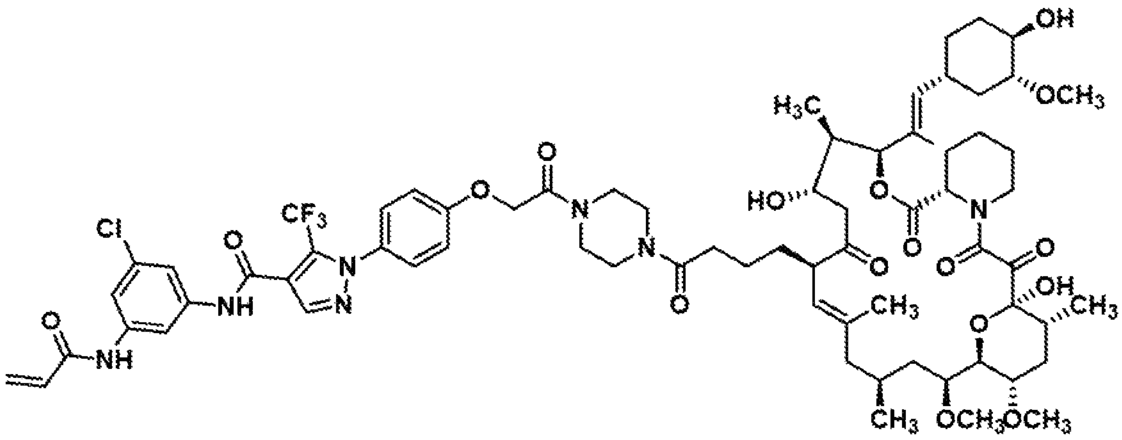
06-057

FIG. 58
To avoid complications of a bead-based assay that involves extensive washing, a homogeneous TR-FRET assay was used here.
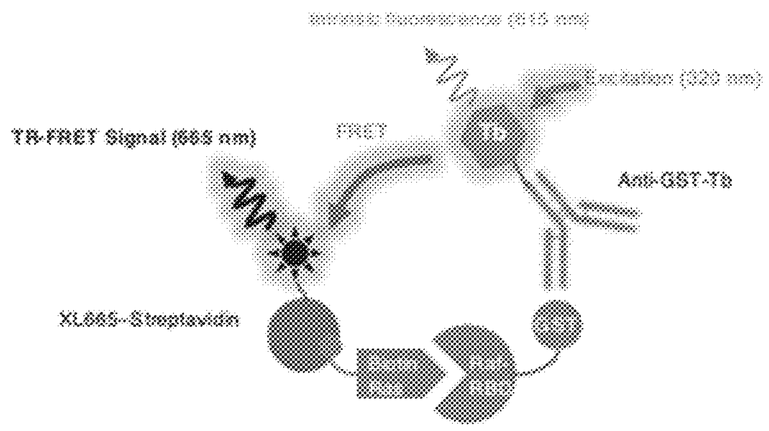
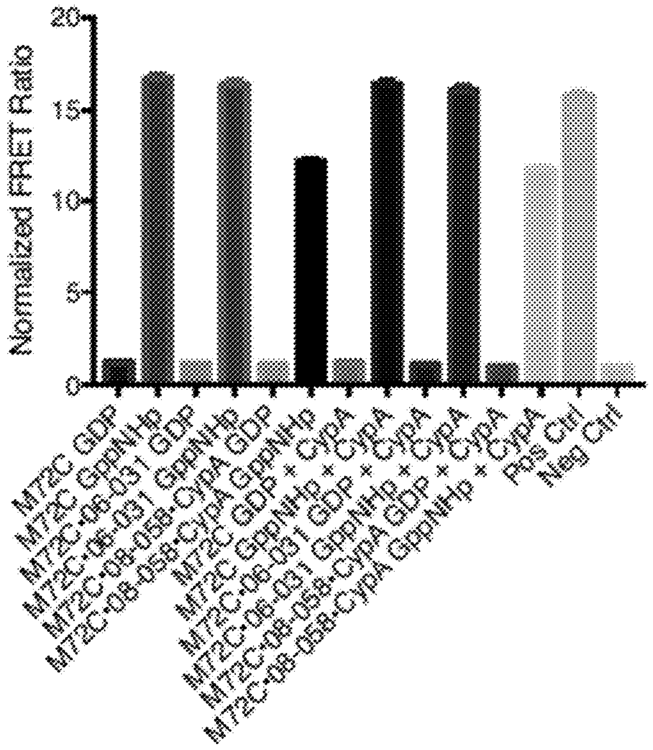

FIG. 60
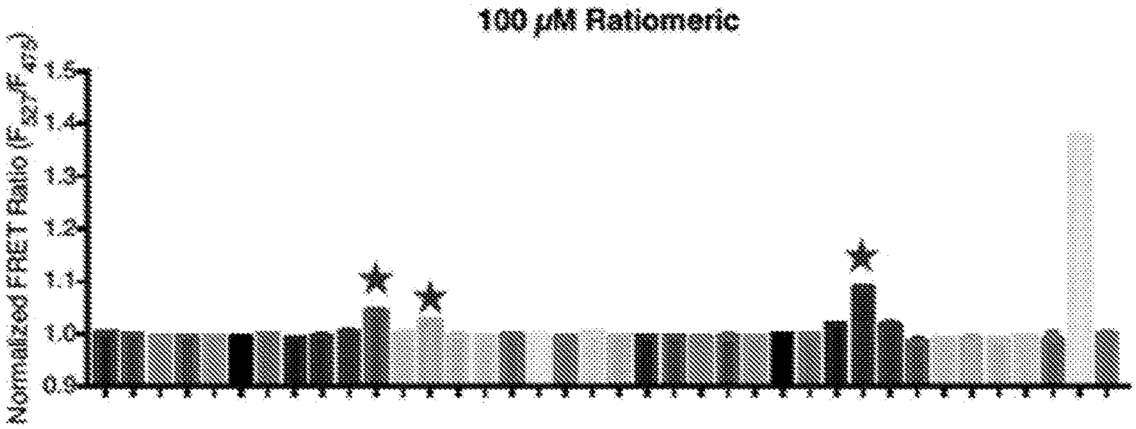
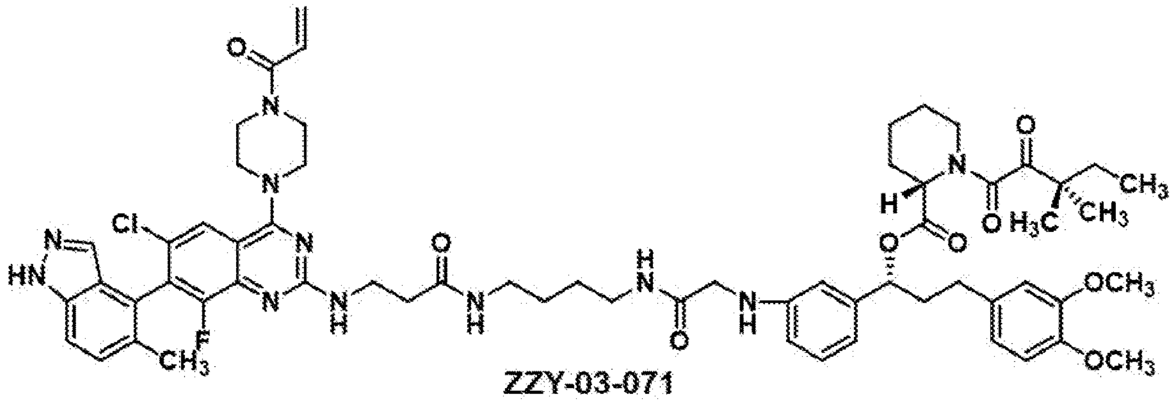
ZZY-03-071

FIG. 63
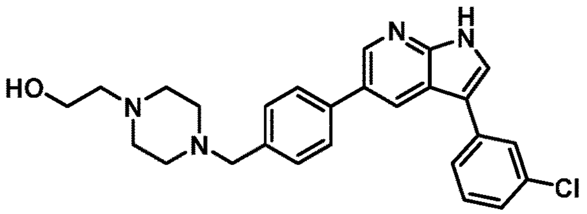
HGK inhibitor 12k
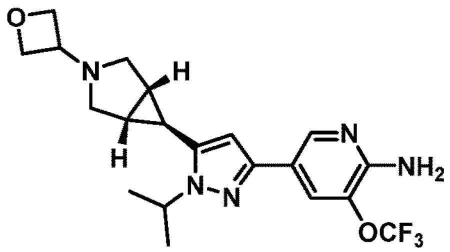
DLK inhibitor 8
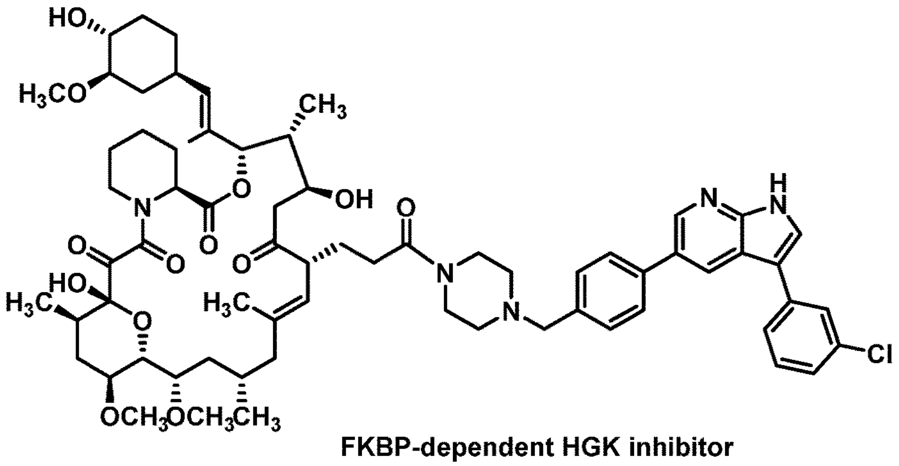
FKBP-dependent HGK inhibitor
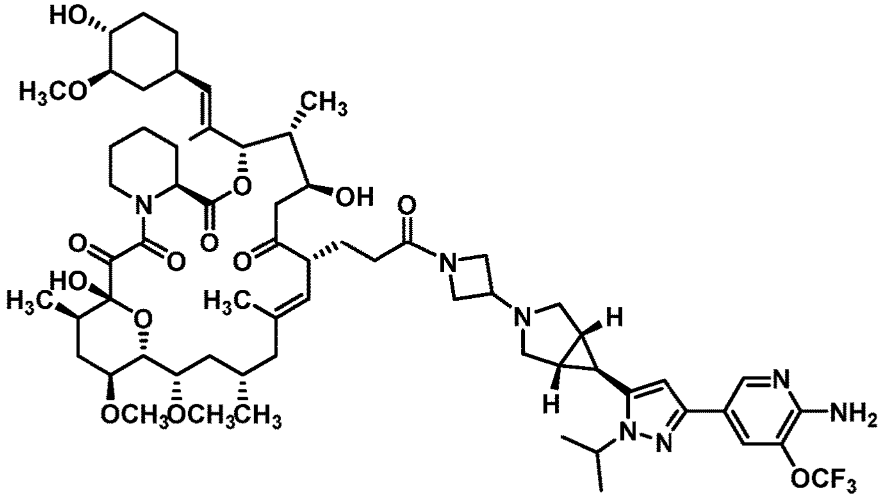
FKBP-dependent DLK inhibitor FIG. 64
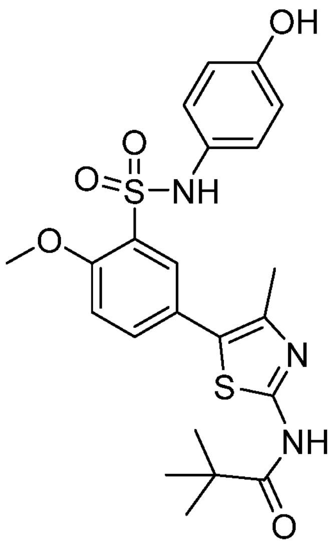
PI4K inhibitor of interest
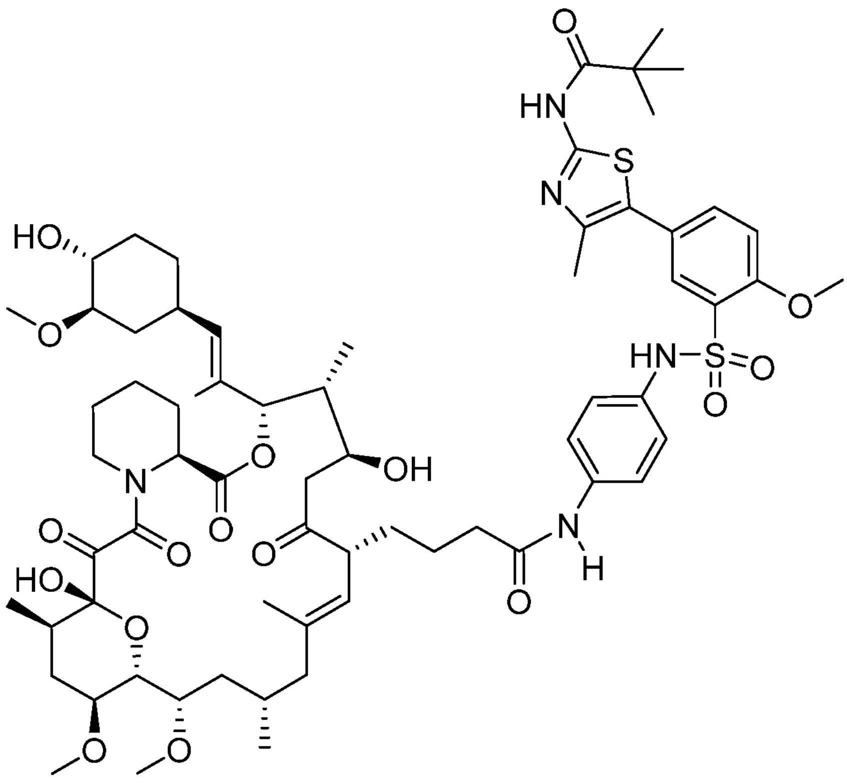
example of an FKBP-dependent PI4K inhibitor

IMMUNOPHILIN BINDING AGENTS AND USES THEREOF

CROSS-REFERENCES TO RELATED APPLICATIONS

This application is the national stage filing under 35 U.S.C. § 371 of International Application No. PCT/US2020/017012 filed Feb. 6, 2020, which claims the benefit of U.S. Provisional Application No. 62/802,668, filed Feb. 7, 2019, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. UI9 AH09622 and R01 CA221969 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-636N01US_Sequence-Listing_ST25.TXT, created Jul. 9, 2021, 150,844 bytes, machine format IBM-PC, MS-Windows operating system, is hereby incorporated herein by reference in its entirety.

BACKGROUND mTOR is a protein kinase that plays a central role in regulating cell growth and proliferation, and is estimated to be overactivated in 30% of cancers. Therapeutic agents targeting mTOR have been widely pursued as potential therapies for cancer, as well as neurological disorders such as epilepsy. However, the success of these therapies is often hampered by insufficient amount of drug that can cross the blood-brain barrier. Even when this condition is met, the application of these drugs is sometimes confounded by the toxicity caused by system-wide inhibition of mTOR (e.g., immunosuppression, hyperglycemia, mucocytis in particular is a class specific effect of all mTOR inhibitors). Disclosed herein, inter alia, are solutions to these and other problems in the art.

BRIEF SUMMARY

In an aspect is provided a compound having the formula: $A^B$-$L^{B1}$-$R^{B1}$, or a pharmaceutically acceptable salt thereof.

$A^B$ is an immunophilin-binding moiety.

$L^{B1}$-$R^{B1}$ is a polar moiety.

$L^{B1}$ is a bond, covalent linker, or bioconjugate linker.

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —NHC(O)$NR^{B1A}R^{B1B}$, —$N(O)_{mB1}$, —$NR^{B1A}R^{B1B}$, —$C(O)R^{B1C}$, —$C(O)OR^{B1C}$, —$C(O)NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B1C}$, —$NR^{B1A}OR^{B1C}$, —$NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{B1A}$, $R^{B1B}$, $R^{B1C}$, and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl.

nB1 is independently an integer from 0 to 4.

mB1 and vB1 are independently 1 or 2.

$X^{B1}$ is independently —F, —Cl, —Br, or —I.

When $L^{B1}$ is a bond, $R^{B1}$ is not H.

Subsequent to administration to a subject, the concentration of the compound in circulating blood of the subject is greater than the concentration of the compound in the CNS of the subject.

In an aspect is provided a pharmaceutical composition including a compound described herein and a pharmaceutically acceptable excipient.

In an aspect is provided a method of treating a CNS disease in a subject in need of such treatment, including co-administering outside the CNS of the subject an anti-CNS disease drug and a compound described herein.

BRIEF DESCRIPTION OF THE DRAWINGS

FIG. 1A: RapaLink-1 suppresses growth of glioblastoma PDX in mice (Fan, Q. et al., 2017, Cancer Cell 31(3): 424-435). FIG. 1B: Structure of RapaLink-1.

FIG. 13A: RapaBlock (ZZY05-026) reverses the inhibition of phosphotyrosine signaling by FK506-dasatinib but not that by dasatinib. FIG. 13B: Dasatinib and FK506-dasatinib both inhibit the growth of K562 cells at sub-nanomolar concentration, and the activity of the latter is diminished by RapaBlock.

FIGS. 14A-14D. Design and biochemical characterization of a bi specific kinase inhibitor. FIG. 14A: Structures of FK506, dasatinib, and FK506-dasatinib. FIG. 14B: Dose-dependent inhibition of Src, Csk and DDR2 by dasatinib and FK506-dasatinib in the absence or presence of supplemented 10 μM recombinant FKBP12 protein. Data is the average of two replicates. FIG. 14C: Profiling of dasatinib and FK506-dasatinib against a panel of 485 purified kinases (SelectScreen™) in the presence of FKBP12. Each dot on the scatter plot represent one kinase colored by the extent of their inhibition by dasatinib. FIG. 14D: Schematic illustration of FK506, dasatinib, FK506-dasatinib and FKBP-presented FK506-dasatinib.

FIG. 15A: A mixture of recombinant Src kinase domain and FKBP12 (1:1.5 molar ratio) was incubated with buffer, dasatinib or FK506-dasatinib for 1 h and analyzed by size exclusion chromatography (Superdex 75 10/300). Fractions of 0.5 mL were collected and analyzed by SDS-PAGE. Coomassie-stained gel image of fractions from the FK506-dasatinib-treated sample is shown. FIG. 15B: Thermal denaturation curves of a 1:1 mixture of Src kinase domain and FKBP12 treated with buffer, dasatinib, or FK506-dasatinib. FIG. 15C: Immunoprecipitation of HA-FKBP12 from Jurkat cell lysate (1 mg/mL) treated with DMSO, 1 μM FK506 or 1 μM FK506-dasatinib.

FIGS. 16A and 16C: FK506-Dasatinib potently inhibits TCR signaling, whereas dasatinib dimers failed to show cellular activity. FIG. 16B: Profiling of intracellular kinase inhibition by dasatinib and FK506-dasatinib using the chemoproteomic probe XO44. Each dot in the scatter plot represents one kinase captured by XO44, and kinases that show statistically significant inhibition ($p<0.05$, comparing to DMSO-treated samples, Student's t-test) in both dasatinib and FK506-dasatinib-treated samples are colored blue. FIG. 16D: Jurkat cells were treated with dasatinib or FK506-dasatinib for 1 h and the drug-containing media were removed and replaced with fresh media. The phosphotyrosine levels were monitored by Western blot at various time points over 24 h.

FIGS. 17A-17F. A general approach to construct FKBP-dependent, programmable kinase inhibitors. FIGS. 17A-17C: Structures of lapatinib and FK506-lapatinib, their effects on HER2 signaling and the growth inhibition of SK-BR-3 cells by these compounds. FIGS. 17D-17F: Structures of GNE7915 and FK506-GNE7915 and their inhibition of LRRK2 autophosphorylation.

FIGS. 19A-19B. The structure of three dasatinib homodimers (FIG. 19A). Dasatinib homodimers are ineffective at inhibiting Src family kinases (FIG. 19B).

FIGS. 21A-21C. Immunophilin-dependent kinase inhibitors.

FIG. 22. Immunophilin-dependent kinase inhibitors: Distribution of [$^3$H]FK506 binding sites in brain and peripheral tissues.

FIG. 23A: Improvement in potency and blocking protein-protein interactions. FIG. 23B: Possible increase in selectivity and greater intracellular retention. FIG. 23C: Tissue-specific effects.

FIG. 24. Proof of concept approach.

FIG. 25. Selected kinase inhibitors.

FIG. 28. FK506-dasatinib hybrid maintains potent FKBP12 binding but attenuated kinase inhibition.

FIG. 30A: A scatter plot comparing inhibitory activity of dasatinib and ZZY05-022. FIG. 30B: Percent inhibition of dasatinib and ZZY05-022 against various kinases.

FIG. 38. Generation of FKBP-dependent EGFR inhibitors through multiple rounds of chemical evolution.

FIG. 41. FK506-GNE7915 hydrid potently inhibits LRRK2 phosphorylation.

FIG. 46. $KRAS^{G12C}$, once labeled with ZZY07-014B, forms a stable 1:1 complex with CypA.

FIG. 53. The M72C inhibitor scaffold offers a handle to tackle the GTP state.

FIG. 55. Molecules built on the M72C inhibitor scaffold (e.g., 06-031, 06-027, 07-026, 06-057, 07-015, 07-025, and 08-058) display similar dependence on immunophilins.

FIG. 58. Independent Ras•Raf binding TR-FRET assay confirm no significant inhibition of Raf binding.

FIG. 60. Data from a screen of a limited SLF analog library. SLF analogs listed from left to right: SLF, Rapa, FK506, 01-025, 01-038, 01-040, 01-041, 01-043, 01-044, 01-059, 01-065, 01-060A, 01-060B, 01-070, 01-072, 01-083, 02-014, 02-032, 02-033, 02-055, 02-096, 03-022, 03-084, 03-077, 03-083, 03-087, 03-091, 03-048, 03-071, 03-088, 03-025, 03-026, 02-075, 04-059, DMSO, DMSO, Pos Ctrl, Neg Ctrl. Assay conditions: 0.6 μM KRAS(G12C)-ECFP, 1.0 μM EYFP-FKBP, 100 μM Compound, 10 mM HEPES 8.0, 0.05% Tween-20, 1% DMSO, 23° C., 4 h incubation.

FIG. 63. Additional brain targets and inhibitors. HGK inhibitor 12k (Bos et al. Cell Chem. Bio 2019), DLK inhibitor 8 (Siu et al. J. Med. Chem. 2018), FKBP-dependent HGK inhibitor, and FKBP-dependent DLK inhibitor.

FIG. 64. PI4K inhibitor of interest (Rutanganira, et al. *J. Med Chem.,* 2016, 59 (5), 1830-1839) and an example of an FKBP-dependent PI4K inhibitor.

DETAILED DESCRIPTION

I. Definitions

Figure 1A:
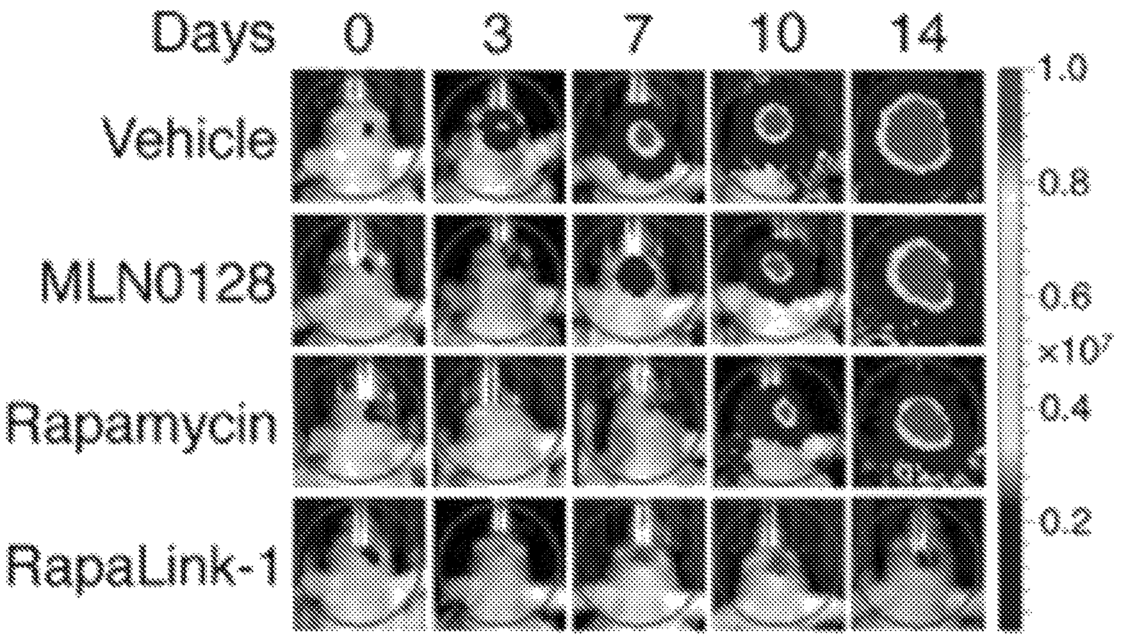
FIGS. 1A-1B. mTOR inhibition is an attractive therapeutic strategy for glioblastoma.
Figure 1B:
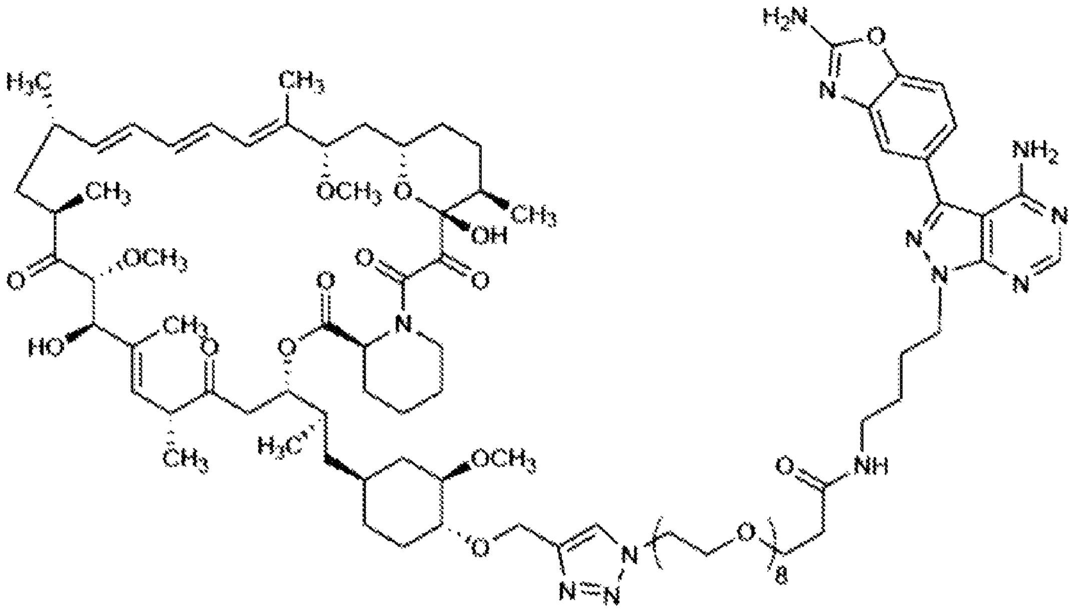
Figure 2:
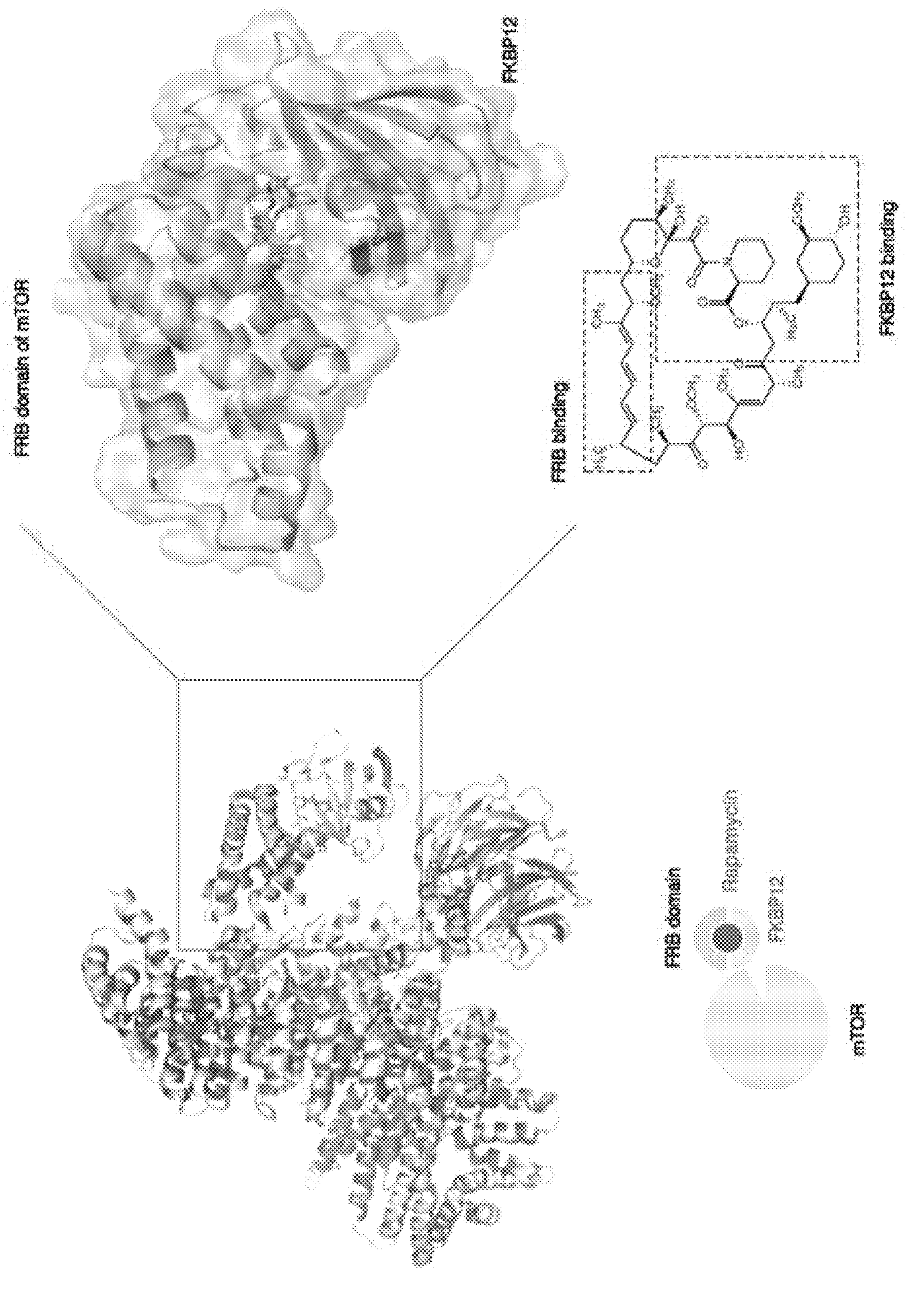
FIG. 2. Rapamycin binds FKBP to inhibit mTORC1.
Figure 3:
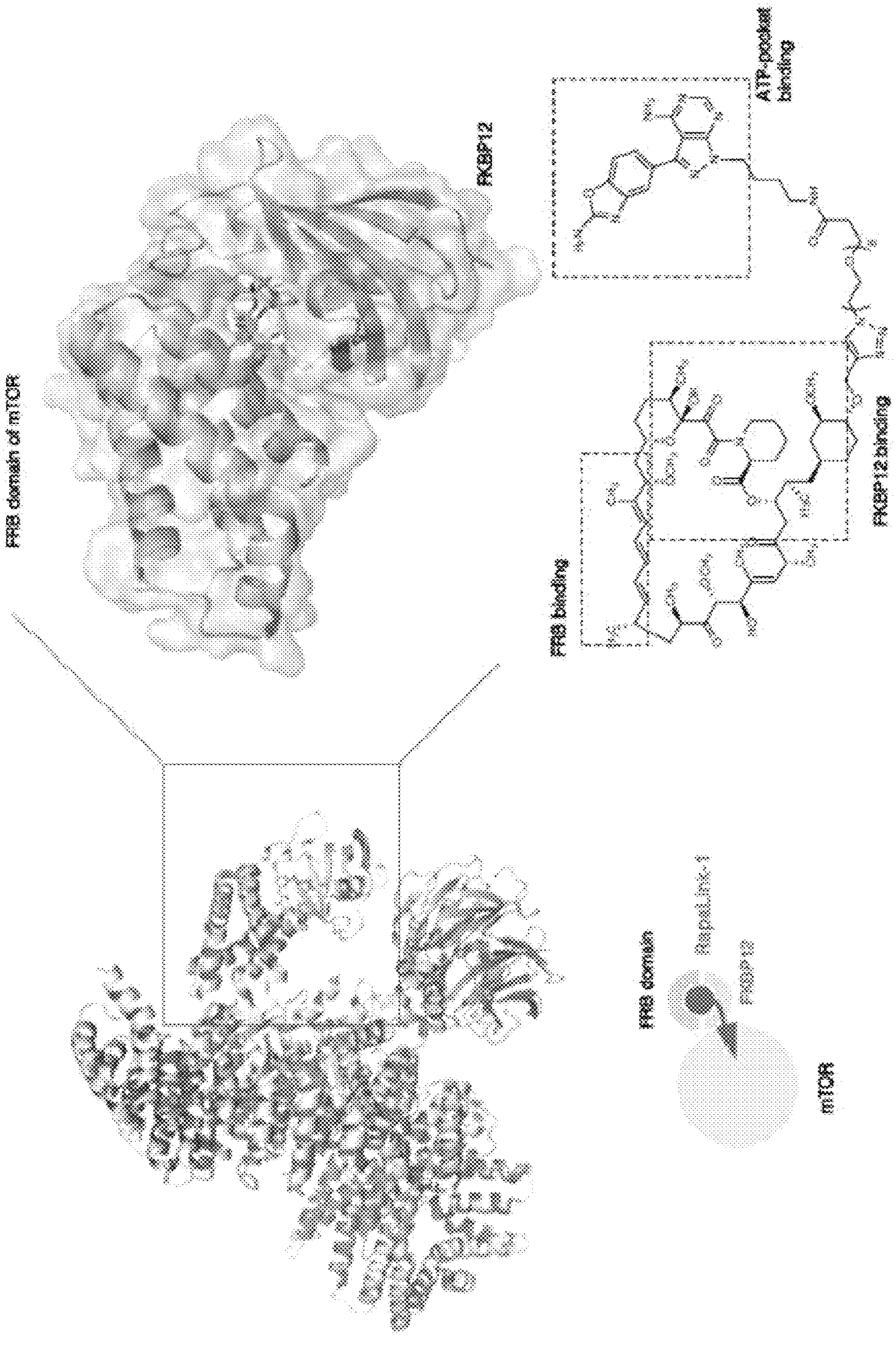
FIG. 3. RapaLink-1 binds FKBP to inhibit mTORC1.
Figure 4:
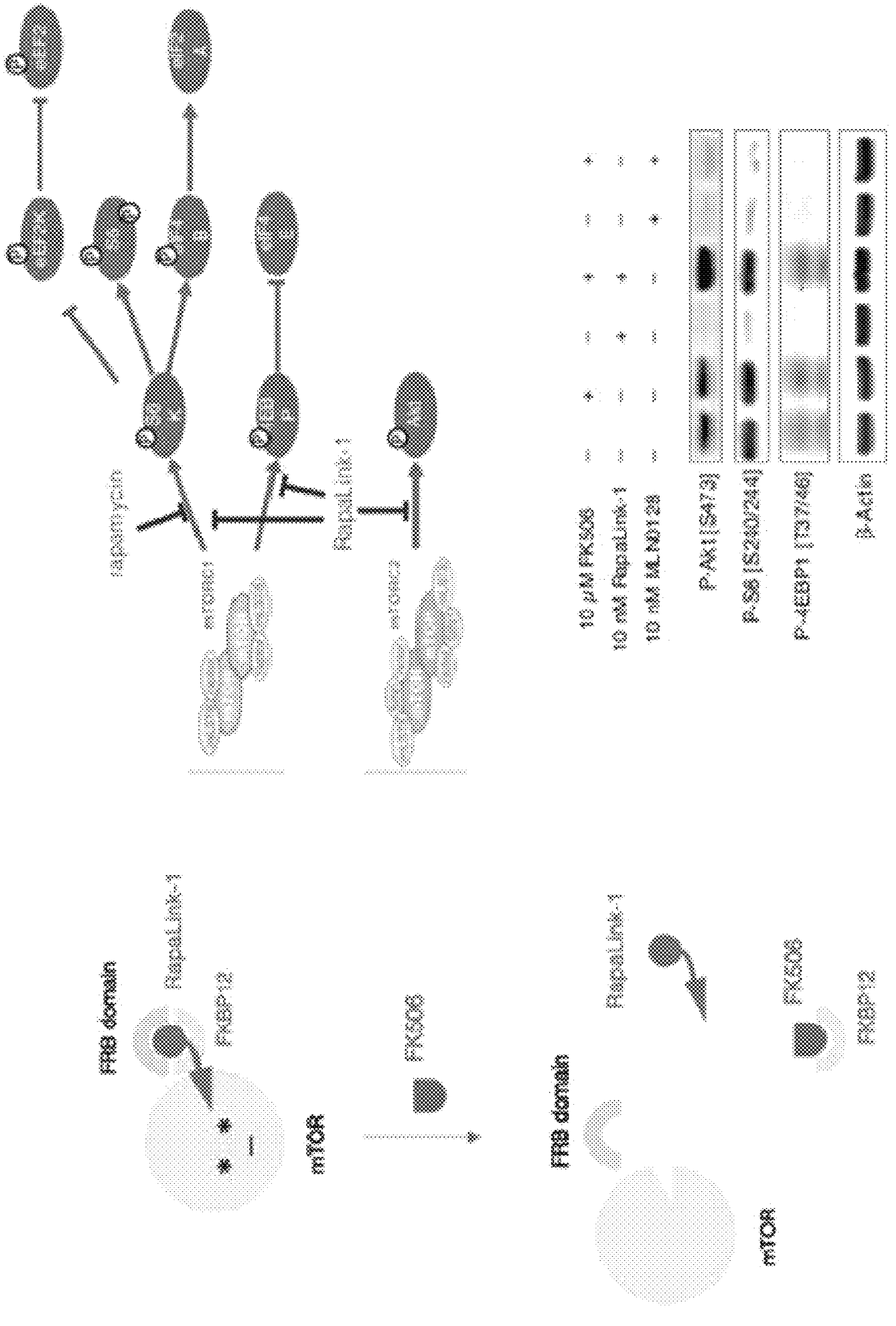
FIG. 4. FKBP is essential for the function of Rapamycin/RapaLink-1. MCF7 cells dosed at 50% confluency, 37° C., 24 h.
Figure 5A:
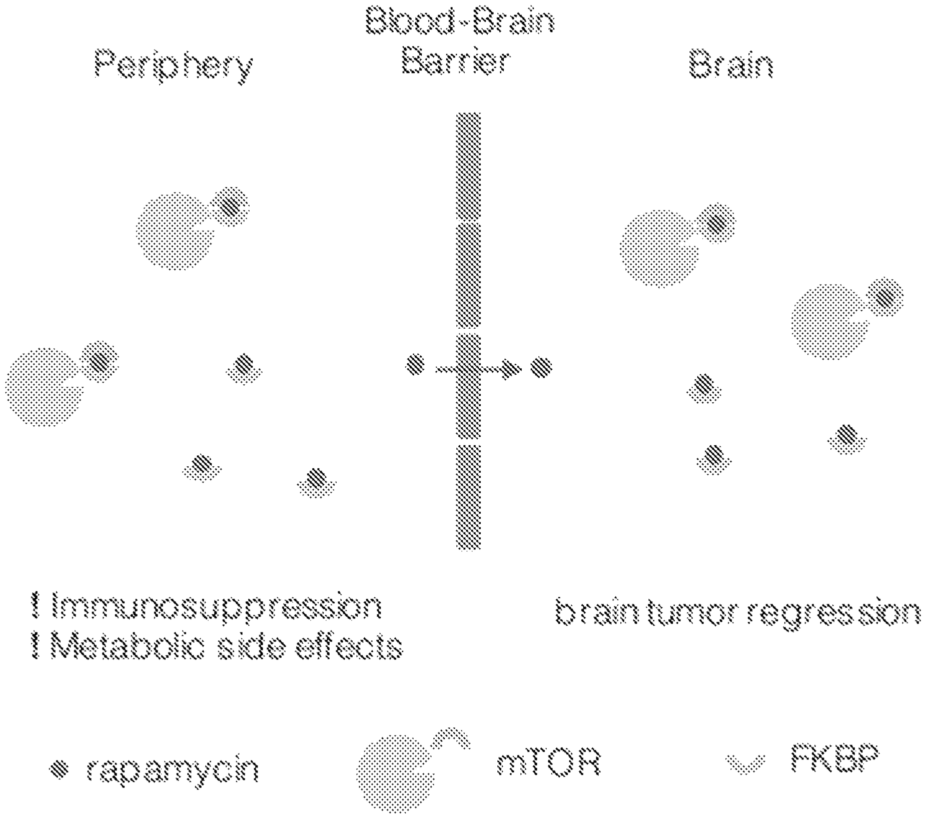
FIGS. 5A-5B. Concentrating rapaymycin/Rapalink-1 in the brain.
Figure 5B:
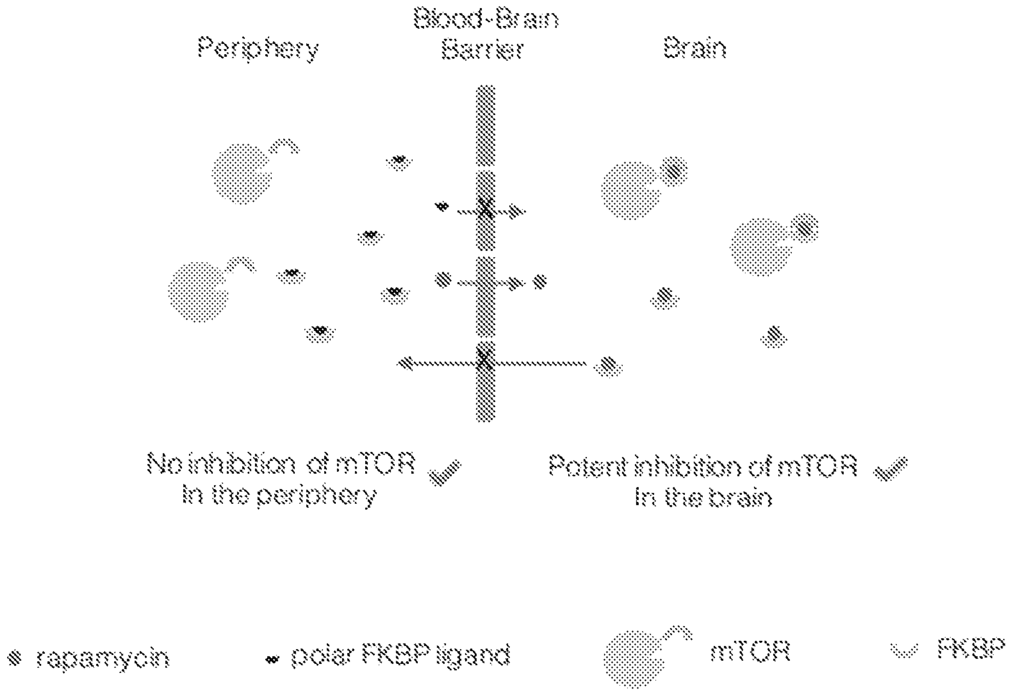
Figure 6:
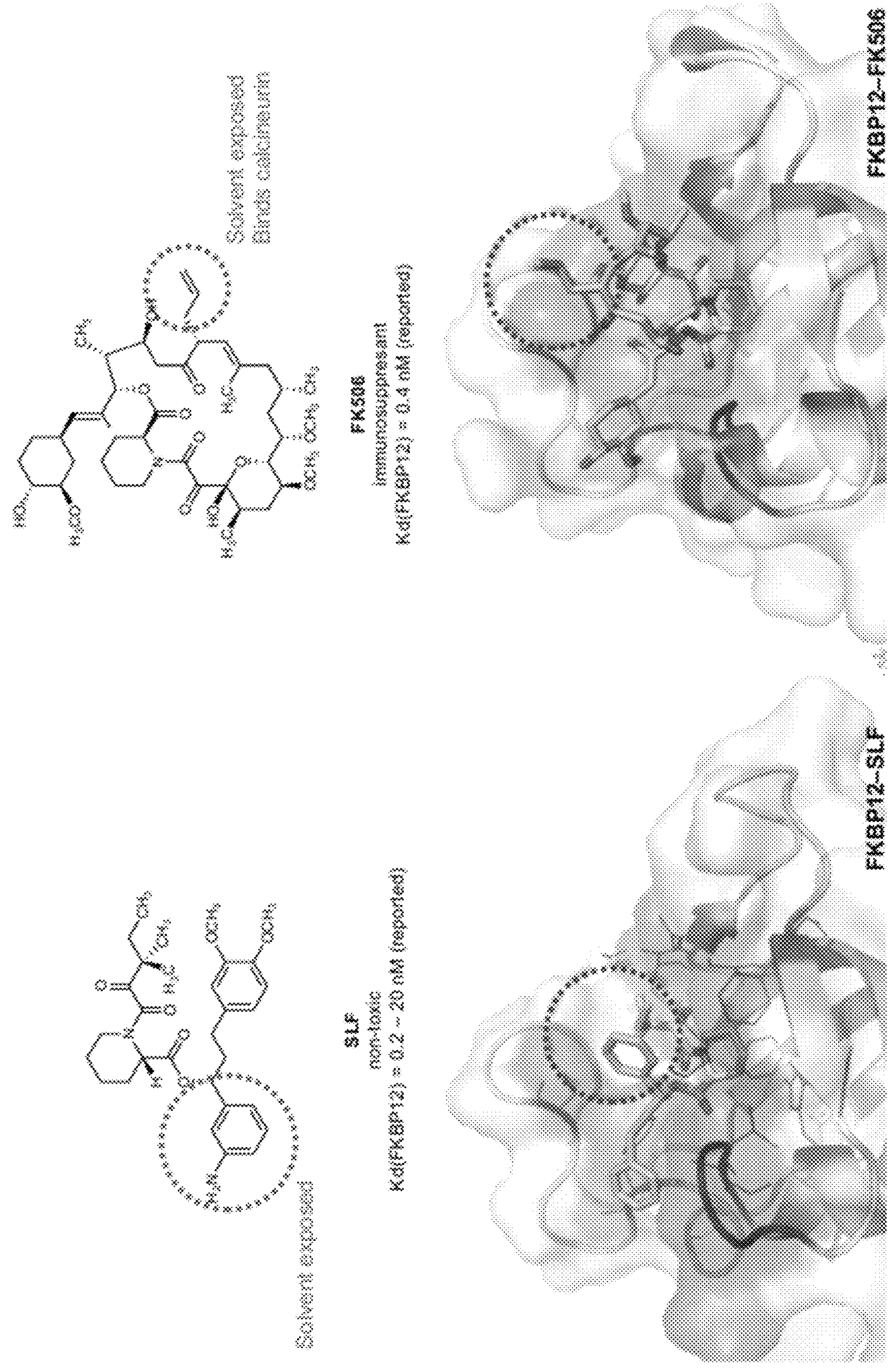
FIG. 6. Building polar components onto existing high-affinity FKBP ligand scaffolds.
Figure 7:
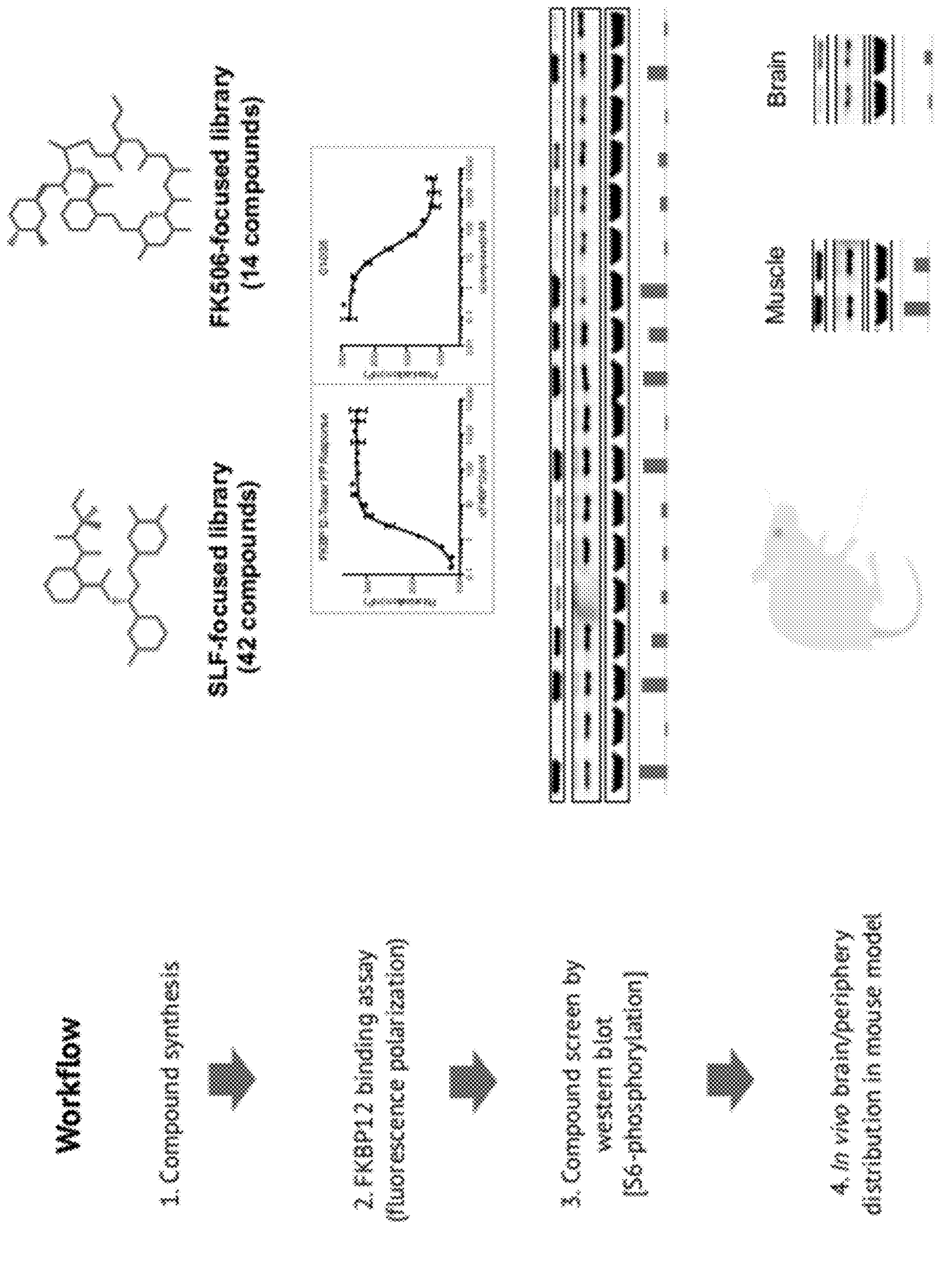
FIG. 7. Building a focused, non-BBB permeable FKBP ligand library.
Figure 8:
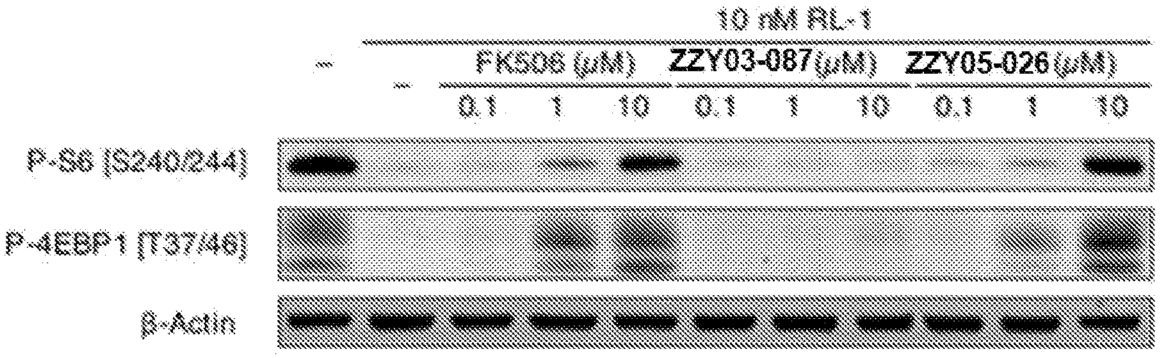
FIG. 8. FK506-derived compounds block RapaLink-1 function in cell culture. MCF7 cells, 24 h treatment. P-AKT and total protein blots are omitted for clarity.
Figure 9:
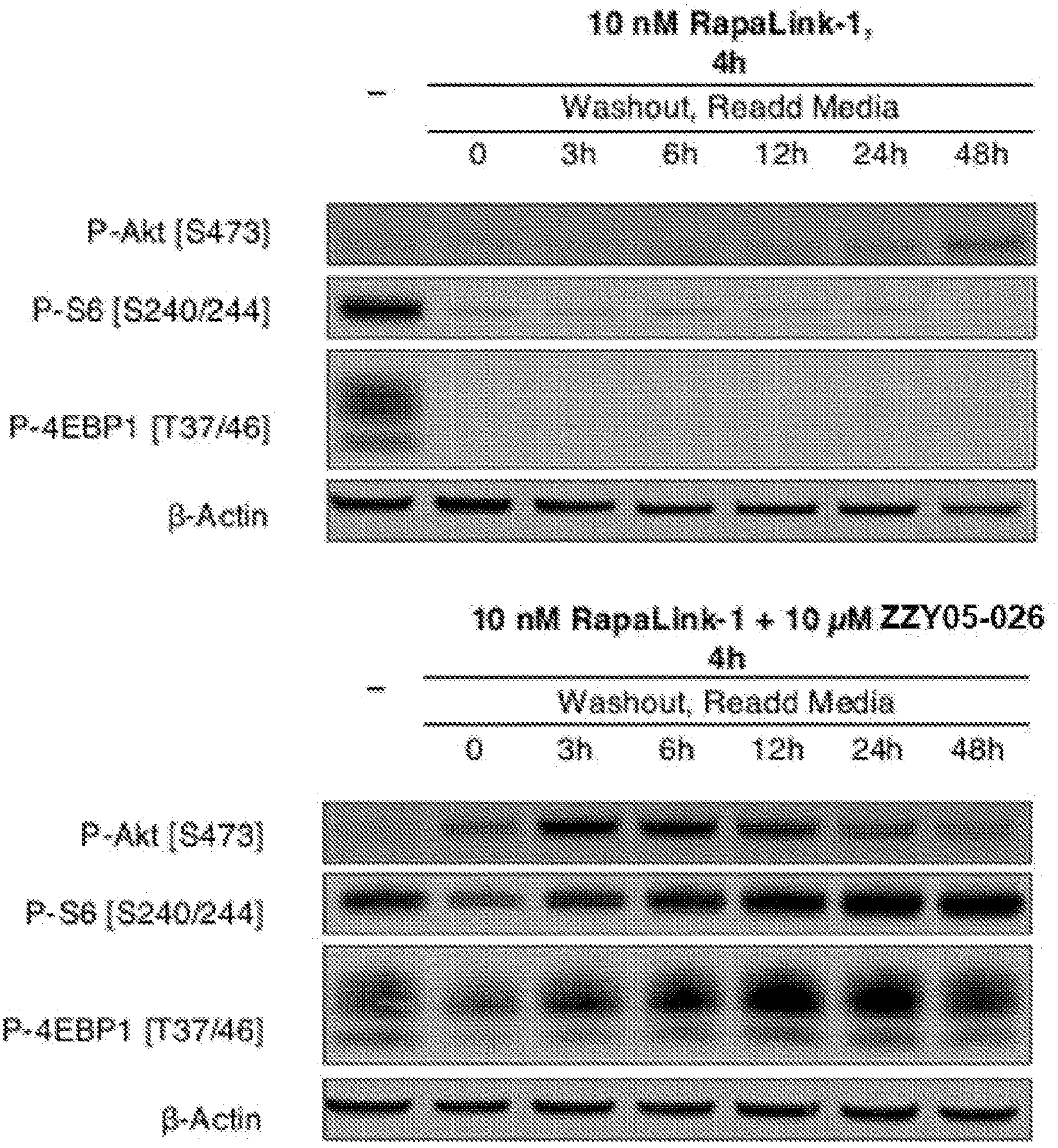
FIG. 9. The protective effects of 05-026 are durable even after washout. MCF7 cells, 24 h treatment. Total protein blots are omitted for clarity.
Figure 10:
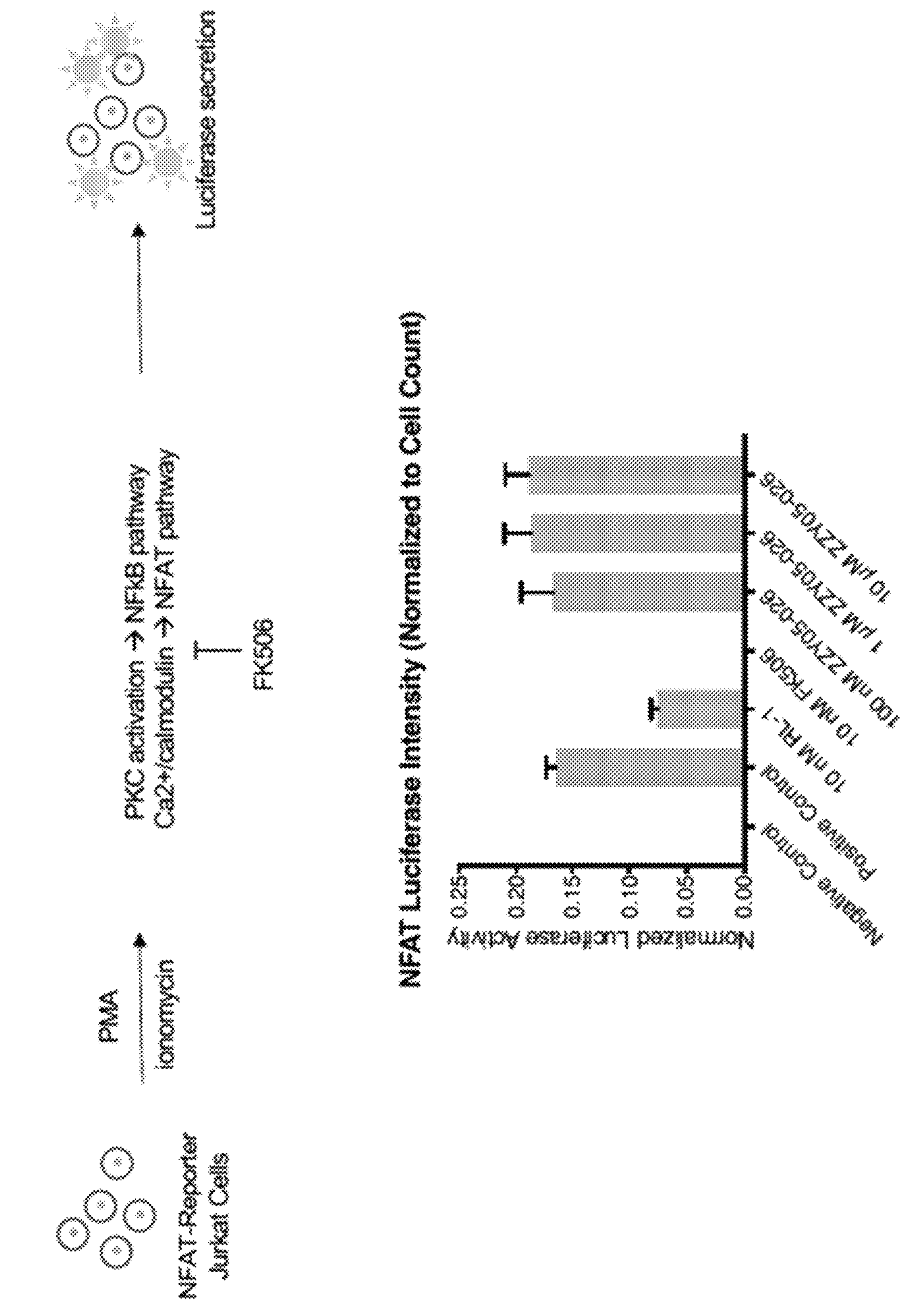
FIG. 10. ZZY05-026 is not immunosuppressive at up to 10 μM. Jurkat cells stably expressing a secreted luciferase (Invivogen) under NF AT promoter was stimulated with PMA (10 ng/mL) and ionomycin (1 μg/mL) in the presence of drugs for 16 h. Positive control: PMA/ionomycin+DMSO. Negative control: DMSO only.
Figure 11:
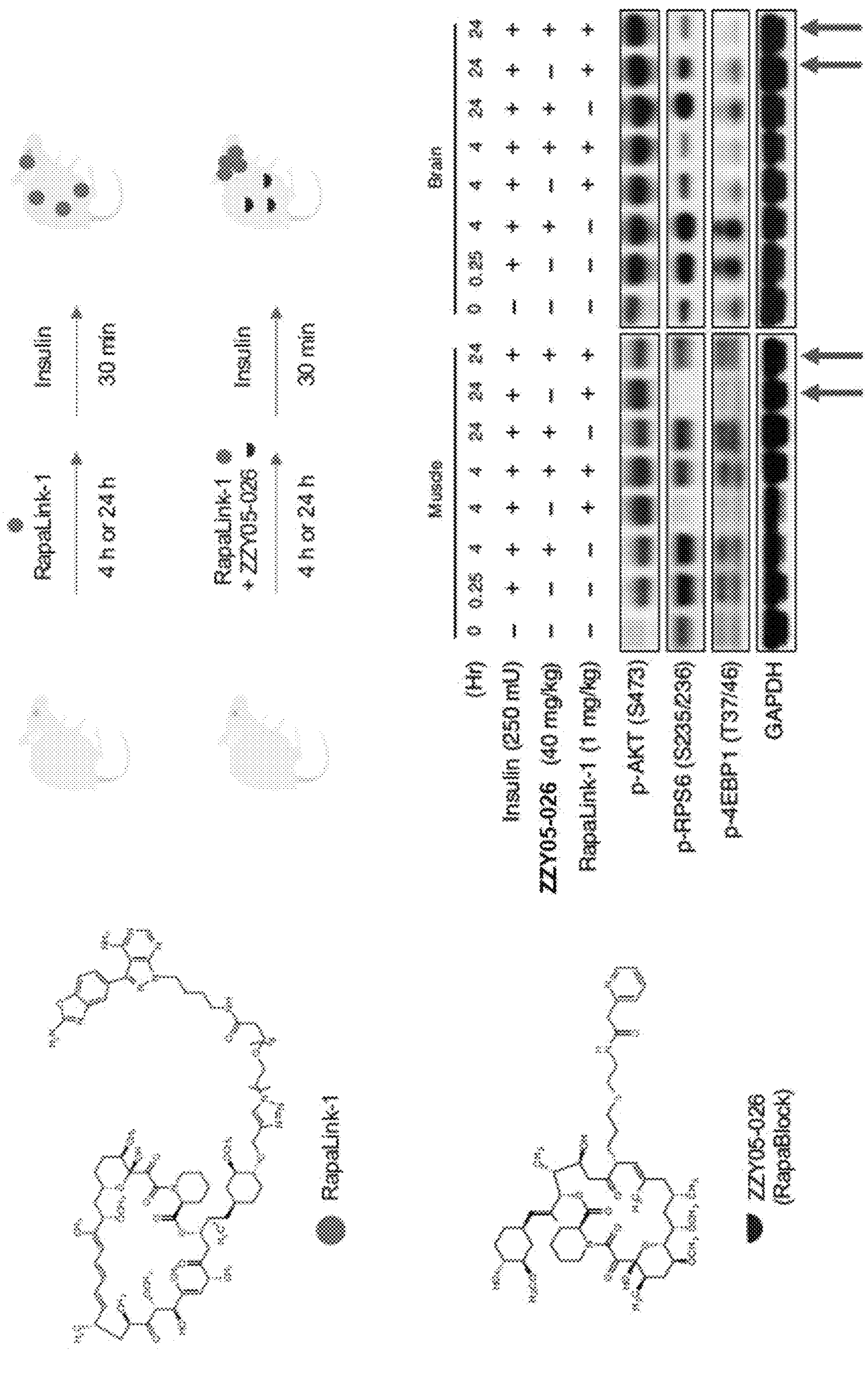
FIG. 11. ZZY05-026 protects mouse peripheral tissue from RapaLink-1.
Figure 12:
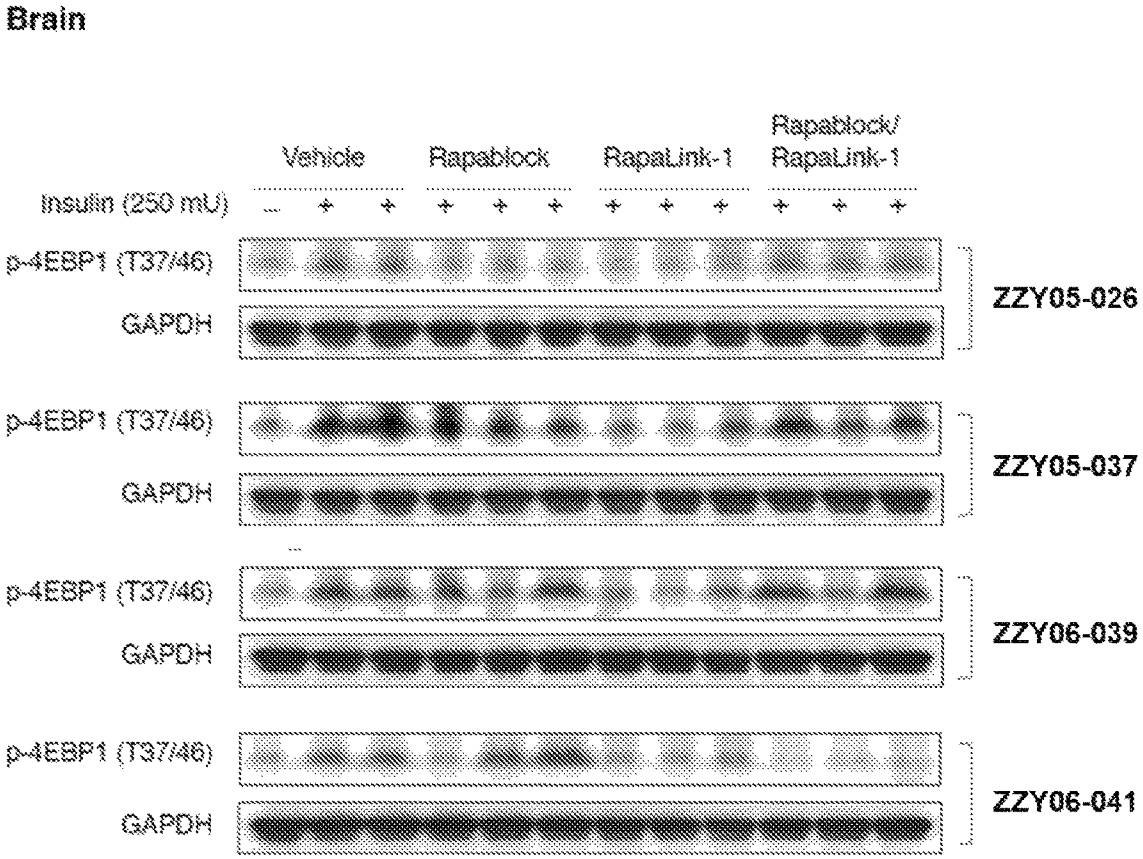
FIG. 12. Evaluation of RapaBlock molecules in augmenting the mTOR inhibitory activity of RapaLink-1 in brain tissues. All animal experiments were conducted using protocols approved by University of California, San Francisco's Institutional Animal Care and Use Committee (IACUC). BALB/Cnu/nu mice were treated with i.p. injection of vehicle (20% DMSO, 40% PEG-300, and 40% PBS [v/v], daily), RapaLink-1 (1 mg/kg), RapaBlock (40 mg/kg), or RapaLink-1+ RapaBlock combination (1 mg/kg+40 mg/kg). After 4 or 24 h, mice were treated by i.p. injection of 250 mU insulin or saline, then euthanized 15 min later. Skeletal muscle and brain of each mouse were lysed, and analyzed by western blotting.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—S—CH_2—CH_2$, $—S(O)—CH_3$, $—CH_2—CH_2—S(O)_2—CH_3$, $—CH=CH—O—CH_3$, $—Si(CH_3)_3$, $—CH_2—CH=N—OCH_3$, $—CH=CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R'', —OR', —SR', and/or $—SO_2R'$. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term “cycloalkenyl” is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term “heterocyclyl” as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5- yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

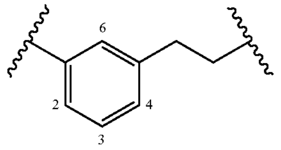

or

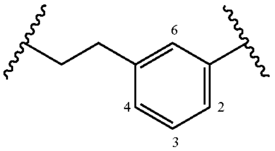

.

An alkylarylene moiety may be substituted (e.g., with a substituent group) on the alkylene moiety or the arylene linker (e.g., at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl")

includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —$CO_2$R', —CONR'R", —OC(O)NR'R", —NR"C(O)R', —NR'—C(O)NR"R'", —NR"$C(O)_2$R', —NR—C(NR'R"R'")=NR"", —NR—C(NR'R")=NR'", —S(O)R', —$S(O)_2$R', —$S(O)_2$NR'R", —NR$SO_2$R', —NR'NR"R'", —ONR'R", —NR'C(O)NR"NR'"R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —$CO_2$R', —CONR'R", —OC(O)NR'R", —NR"C(O)R', —NR'—C(O)NR"R'", —NR"$C(O)_2$R', —NR—C(NR'R"R'")=NR"", —NR—C(NR'R")=NR'", —S(O)R', —$S(O)_2$R', —$S(O)_2$NR'R", —NR$SO_2$R', —NR'NR"R'", —ONR'R", —NR'C(O)NR"NR'"R"", —CN, —$NO_2$, —R, —$N_3$, —CH$(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T—C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'— $(C"R"R'")_d$—, where s and d are independently integers of from 0 to 3, and X' is —O—, —NR'—, —S—, —S(O)—, —$S(O)_2$—, or —$S(O)_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen(O), nitrogen (N), sulfur (S), phosphorus (P), and silicon (Si).

A "substituent group," as used herein, means a group selected from the following moieties:

(A) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refer to the resulting association between atoms or molecules of bioconjugate reactive groups or bioconjugate reactive moieties. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.;
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido or maleimide groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold, or react with maleimides;
(h) amine or sulfhydryl groups (e.g., present in cysteine), which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g., phosphines) to form, for example, phosphate diester bonds;
(n) azides coupled to alkynes using copper catalyzed cycloaddition click chemistry; and
(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and/or appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$ $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154\text{-}1581}Gd$, $^{161}Tb$, $^{166}Dy$, $^{166}HO$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154,1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolyl sulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Compounds or functional moieties are "polar" when there are opposing charges (i.e., having partial positive and partial negative charges) from polar bonds arranged asymmetrically. The polarity of a molecule can be measured, for example, by its partition coefficient, P, defined as the ratio of the concentrations of a solute between two immiscible solvents. When one of the solvents is water, the clogP value is a measure of lipophilicity or hydrophobicity. In embodiments, the compound has a clogP of about 5. In embodiments, the compound has a clogP of less than 5. Polarity can also be measured, for example, by ts topological polar surface area (PSA), which is the surface sum over all polar atoms, primarily oxygen and nitrogen, also including their attached hydrogen atoms. Molecules with a PSA of greater than 140 Å tend to be poor at permeating cell membranes. In embodiments, for molecules to penetrate the blood-brain barrier, a PSA less than 90 Å is usually necessary. In embodiments, the compound described herein has a PSA between 90 Å and 140 Å. In embodiments, the compound described herein has a PSA between 100 Å and 140 Å.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Co-administer" is meant that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease. In embodiments, treating is preventing. In embodiments, treating does not include preventing. In embodiments, the treating or treatment is no prophylactic treatment.

An "effective amount" is an amount sufficient for a compound to accomplish a stated purpose relative to the absence of the compound (e.g., achieve the effect for which it is administered, treat a disease, reduce enzyme activity, increase enzyme activity, reduce signaling pathway, reduce one or more symptoms of a disease or condition. An example of an "effective amount" is an amount sufficient to contribute to the treatment, prevention, or reduction of a symptom or symptoms of a disease, which could also be referred to as a "therapeutically effective amount" when referred to in this context. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington; The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g., signaling pathway) of a protein in the absence of a compound as described herein (including embodiments, examples, figures, or Tables).

"Contacting" is used in accordance with its plain ordinary meaning and refers to the process of allowing at least two distinct species (e.g., chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a cellular component (e.g., protein, ion, lipid, nucleic acid, nucleotide, amino acid, protein, particle, organelle, cellular compartment, microorganism, virus, lipid droplet, vesicle, small molecule, protein complex, protein aggregate, or macromolecule). In some embodiments contacting includes allowing a compound described herein to interact with a cellular component (e.g., protein, ion, lipid, nucleic acid, nucleotide, amino acid, protein, particle, virus, lipid droplet, organelle, cellular compartment, microorganism, vesicle, small molecule, protein complex, protein aggregate, or macromolecule) that is involved in a signaling pathway.

As defined herein, the term "inhibition," "inhibit," "inhibiting" and the like in reference to a cellular component-inhibitor interaction means negatively affecting (e.g., decreasing) the activity or function of the cellular component (e.g., decreasing the signaling pathway stimulated by a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)), relative to the activity or function of the cellular component in the absence of the inhibitor. In some embodiments inhibition refers to reduction of a disease or symptoms of disease. In some embodiments, inhibition refers to a reduction in the activity of a signal transduction pathway or signaling pathway (e.g., reduction of a pathway involving the cellular component). Thus, inhibition includes, at least in part, partially or totally blocking stimulation, decreasing, preventing, or delaying activation, or inactivating, desensitizing, or down-regulating the signaling pathway or enzymatic activity or the amount of a cellular component.

The term "modulator" refers to a composition that increases or decreases the level of a target molecule or the function of a target molecule or the physical state of the target of the molecule (e.g., a target may be a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)) relative to the absence of the composition.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g., caused by) a cellular component (e.g., protein, ion, lipid, nucleic acid, nucleotide, amino acid, protein, particle, organelle, cellular compartment, microorganism, vesicle, small molecule, protein complex, protein aggregate, or macromolecule).

As used herein, the term "cancer" refers to all types of cancer, neoplasm or malignant tumors found in mammals (e.g., humans), including leukemia, lymphoma, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, Schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressier's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Tumer syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "neurodegenerative disease" or "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis (ALS), Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis.

"Anti-neurodegenerative disease agent" is used in accordance with its plain ordinary meaning and refers to a composition (e.g., compound, drug, antagonist, inhibitor, modulator) capable of inhibiting neurodegeneration. In some embodiments, an anti-neurodegenerative disease agent is an agent identified herein having utility in methods of treating a neurodegenerative disease. In some embodiments, an anti-neurodegenerative disease agent is an agent approved by the FDA or similar regulatory agency of a country other than the USA, for treating a neurodegenerative disease. Examples of anti-neurodegenerative disease agents include, but are not limited to, galantamine, rivastigmine, donepezil, memantine, imatinib, tamibarotene, bexarotene, carmustine, thalidomide, sildenafil, trazodone, clioquinol, nilvadipine, levodopa, pramipexole, repinirole, rotigotine, apomorphine, selegiline, rasagiline, safinamide, amantadine, milotinib, zonisamide, selegiline, methylphenidate, salbutamol, exenatide, tetrabenazine, tiapride, clozapine, olanzapine, risperidone, quetiapine, memantine, mitoxantrone, cyclophosphamide, cladribine, amiloride, ibudilast, mastinib, dolutegravir, abacavir, lamivudine, retigabine, and tamoxifen.

The term "central nervous system" or "CNS" is used with its plain ordinary meaning and refers to the part of the nervous system consisting of the brain and spinal cord. The "blood-brain barrier (BBB)" is a highly selective semipermeable border that separates the circulating blood from the brain and extracellular fluid in the CNS. The BBB allows passage of water, some gases, and lipid-soluble molecules by passive diffusion, as well as selective transport of molecules that are crucial to neural function. In embodiments, the brain/periphery distribution is measured in an in vivo mouse model.

"Anti-CNS disease drug" is used in accordance with its plain ordinary meaning and refers to a drug capable of inhibiting a CNS disease. In embodiments, a CNS disease is a neurodegenerative disease. In some embodiments, an anti-CNS disease drug is a drug identified herein having utility in methods of treating a CNS disease. In some embodiments, an anti-CNS disease drug is a drug approved by the FDA or similar regulatory agency of a country other than the USA, for treating a CNS disease. Examples of anti-CNS disease drugs include, but are not limited to, sirolimus, temsirolimus, everolimus, dactolisib, GSK2126458, XL765, AZD8055, INK128/MLN0128, OSI027, and RapaLinks. In embodiments, an anti-CNS disease drug is an anti-neurodegenerative disease drug. In embodiments, an anti-CNS disease drug is an anti-cancer agent.

As used herein, the term "metabolic disease" or "metabolic disorder" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

The term "cellular component associated disease" (e.g., the cellular component may be a protein, ion, lipid, nucleic acid, nucleotide, amino acid, protein, particle, organelle, cellular compartment, microorganism, virus, vesicle, small molecule, protein complex, protein aggregate, or macromolecule; the disease may be a neurodegenerative disease, cancer, a metabolic disease, autoimmune disease, inflammatory disease, or infectious disease) (also referred to herein as "cellular component related disease") refers to a disease caused by the cellular component. Other diseases that are associated with aberrant activity or level of the cellular component are well known in the art and determining such diseases are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compounds described herein can be used in combination with one another, with other active agents known to be useful in treating a disease associated with cells expressing a disease associated cellular component, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}In$, $^{90}Y$, or $^{131}I$, etc.).

In a further embodiment, the compounds described herein can be co-administered with conventional radiotherapeutic agents including, but not limited to, radionuclides such as $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, and $^{212}Bi$, optionally conjugated to antibodies directed against tumor antigens.

In therapeutic use for the treatment of a disease, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer, a neurodegenerative disease, a metabolic disease, an autoimmune disease, an inflammatory disease, or an infectious disease, or with adjunctive agents that may not be effective alone, but may contribute to the efficacy of the active agent.

The term "associated" or "associated with" in the context of a substance or substance activity or function associated with a disease (e.g., a protein associated disease, disease associated with a cellular component) means that the disease (e.g., neurodegenerative disease, cancer) is caused by (in whole or in part), or a symptom of the disease is caused by (in whole or in part) the substance or substance activity or function or the disease or a symptom of the disease may be treated by modulating (e.g., inhibiting or activating) the substance (e.g., cellular component). For example, a neurodegenerative disease associated with a protein aggregate may be a neurodegenerative disease that results (entirely or partially) from aberrant protein aggregation or a neurodegenerative disease wherein a particular symptom of the disease is caused (entirely or partially) by aberrant protein aggregation. As used herein, what is described as being associated with a disease, if a causative agent, could be a target for treatment of the disease. For example, a neurodegenerative disease associated with aberrant protein aggregation or a protein aggregate associated neurodegenerative disease, may be treated with a protein aggregate modulator or protein aggregate targeted autophagy degrader, in the instance where increased protein aggregation causes the neurodegenerative disease.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

"Anti-cancer agent" is used in accordance with its plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. In embodiments, an anti-cancer agent is an agent with antineoplastic properties that has not (e.g., yet) been approved by the FDA or similar regulatory agency of a country other than the USA, for treating cancer. Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17—N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaR-estM3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride;

tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rlL.sub.2), interferon alfa-2a; interferon alfa-2b; interferon alfa-n1; interferon alfa-n3; interferon beta-la; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds comprising the taxane skeleton, Erbulozole (i.e., R-55104), Dolastatin 10 (i.e., DLS-10 and NSC-376128), Mivobulin isethionate (i.e., as CI-980), Vincristine, NSC-639829, Discodermolide (i.e., as NVP-XX-A-296), ABT-751 (Abbott, i.e., E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e., LU-103793 and NSC-D-669356), Epothilones (e.g., Epothilone A, Epothilone B, Epothilone C (i.e., desoxyepothilone A or dEpoA), Epothilone D (i.e., KOS-862, dEpoB, and desoxyepothilone B), Epothilone E, Epothilone F, Epothilone B N-oxide, Epothilone A N-oxide, 16-aza-epothilone B, 21-aminoepothilone B (i.e., BMS-310705), 21-hydroxyepothilone D (i.e., Desoxyepothilone F and dEpoF), 26-fluoroepothilone, Auristatin PE (i.e., NSC-654663), Soblidotin (i.e., TZT-1027), LS-4559-P (Pharmacia, i.e., LS-4577), LS-4578 (Pharmacia, i.e., LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e., ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e., LY-355703), AC-7739 (Ajinomoto, i.e., AVE-8063A and CS-39.HCl), AC-7700 (Ajinomoto, i.e., AVE-8062, AVE-8062A, CS-39-L-Ser-.HCl, and RPR-258062A), Vitilevuamide, Tubulysin A, Canadensol, Centaureidin (i.e., NSC-106969), T-138067 (Tularik, i.e., T-67, TL-138067 and TI-138067), COBRA-1 (Parker Hughes Institute, i.e., DDE-261 and WHI-261), H10 (Kansas State University), H16 (Kansas State University), Oncocidin A1 (i.e., BTO-956 and DIME), DDE-313 (Parker Hughes Institute), Fijianolide B, Laulimalide, SPA-2 (Parker Hughes Institute), SPA-1 (Parker Hughes Institute, i.e., SPIKET-P), 3—IAABU (Cytoskeleton/Mt. Sinai School of Medicine, i.e., MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e., MF-191), TMPN (Arizona State University), Vanadocene acetylacetonate, T-138026 (Tularik), Monsatrol, Inanocine (i.e., NSC-698666), 3—IAABE (Cytoskeleton/Mt. Sinai School of Medicine), A-204197 (Abbott), T-607 (Tuiarik, i.e., T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e., NSCL-96F037), D-68838 (Asta Medica), D-68836 (Asta Medica), Myoseverin B, D-43411 (Zentaris, i.e., D-81862), A-289099 (Abbott), A-318315 (Abbott), HTI-286 (i.e., SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}In$, $^{90}Y$, or $^{131}I$, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. A moiety of an anti-cancer agent is a monovalent anti-cancer agent (e.g., a monovalent form of an agent listed above).

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent," "electrophilic chemical moiety," or "electrophilic moiety" refers to an electron-poor chemical group, substituent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue and may be referred to as a "covalent cysteine modifier moiety" or "covalent cysteine modifier substituent." The covalent bond formed between the electrophilic substituent and the sulfhydryl group of the cysteine may be a reversible or irreversible bond. In some embodiments, the electrophilic substituent of the compound is capable of reacting with a lysine residue. In some embodiments, the electrophilic substituent of the compound is capable of reacting with a serine residue. In some embodiments, the electrophilic substituent of the compound is capable of reacting with a methionine residue.

"Nucleophilic" as used herein refers to a chemical group that is capable of donating electron density.

An amino acid residue in a protein "corresponds" to a given residue when it occupies the same essential structural position within the protein as the given residue. Instead of a primary sequence alignment, a three dimensional structural alignment can also be used, e.g., where the structure of the selected protein is aligned for maximum correspondence with the human protein and the overall structures compared. In this case, an amino acid that occupies the same essential position as a specified amino acid in the structural model is said to correspond to the specified residue.

The term "isolated," when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide," and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "protein complex" is used in accordance with its plain ordinary meaning and refers to a protein which is associated with an additional substance (e.g., another protein, protein subunit, or a compound). Protein complexes typically have defined quaternary structure. The association between the protein and the additional substance may be a covalent bond. In embodiments, the association between the protein and the additional substance (e.g., compound) is via non-covalent interactions. In embodiments, a protein complex refers to a group of two or more polypeptide chains. Proteins in a protein complex are linked by non-covalent protein-protein interactions. A non-limiting example of a protein complex is the proteasome.

The term "protein aggregate" is used in accordance with its plain ordinary meaning and refers to an aberrant collection or accumulation of proteins (e.g., misfolded proteins). Protein aggregates are often associated with diseases (e.g., amyloidosis). Typically, when a protein misfolds as a result of a change in the amino acid sequence or a change in the native environment which disrupts normal non-covalent interactions, and the misfolded protein is not corrected or degraded, the unfolded/misfolded protein may aggregate. There are three main types of protein aggregates that may form: amorphous aggregates, oligomers, and amyloid fibrils. In embodiments, protein aggregates are termed aggresomes. In embodiments, the protein aggregate is TDP43, HTT, APP, SNCA, or MAPT. In embodiments, the protein aggregate includes the protein Beta amyloid, Amyloid precursor protein, IAPP, Alpha-synuclein, PrPSc, PrPSc, Huntingtin, Calcitonin, Atrial natriuretic factor, Apolipoprotein AI, Serum amyloid A, Medin, Prolactin, Transthyretin, Lysozyme, Beta-2 microglobulin, Gelsolin, Keratoepithelin, Beta amyloid, Cystatin, Immunoglobulin light chain AL, TDP43, or S-IBM.

The term "vesicle" is used in accordance with its plain ordinary meaning and refers to a small membrane enclosed compartment within a cell. Vesicles are typically involved in transport, buoyancy control, or enzyme storage within a cell. Some vesicles, for example a lysosome, may include enzymes, proteins, polysaccharides, lipids, nucleic acids, or organelles within the compartment. Vesicles are typically formed within cells as a result of exocytosis or phagocytosis, however some vesicles are formed at the Golgi complex and transported to the cell membrane. Vesicles may be unilamellar or multilamellar.

The term "small molecule" is used in accordance with its well understood meaning and refers to a low molecular weight organic compound that may regulate a biological process. In embodiments, the small molecule is a compound that weighs less than 900 daltons. In embodiments, the small molecule weighs less than 800 daltons. In embodiments, the small molecule weighs less than 700 daltons. In embodiments, the small molecule weighs less than 600 daltons. In embodiments, the small molecule weighs less than 500 daltons. In embodiments, the small molecule weighs less than 450 daltons. In embodiments, the small molecule weighs less than 400 daltons.

The term "pseudokinase" is used in accordance with its well understood meaning in Biology and Chemistry and refers to proteins that are variants of kinases (e.g., having similar or identical protein structures or folds) that are catalytically deficient in kinase enzymatic activity.

The term "GTPase" is used in accordance with its well understood meaning in Biology and Chemistry and refers to hydrolase enzymes capable of binding and hydrolyzing GTP.

The term "histone modifying enzyme" is used in accordance with its well understood meaning in Biology and Chemistry and refers to proteins that are capable of modifying histones at one or more of various sites. In embodiments a histone modifying enzyme is an enzyme capable of acetylation, methylation, demethylation, phosphorylation, uqibuitination, sumoylation, ADP-ribosylation, deamination, and/or proline isomerization; all of one or more histone proteins. In embodiments, the histone modifying enzyme is a histone deacetylase, histone methyltransferase, or histone acetyltransferase. In embodiments, the histone modifying enzyme is SETD3.

The terms "virus" or "virus particle" are used according to its plain ordinary meaning within Virology and refers to a virion including the viral genome (e.g., DNA, RNA, single strand, double strand), viral capsid and associated proteins, and in the case of enveloped viruses (e.g., herpesvirus), an envelope including lipids and optionally components of host cell membranes, and/or viral proteins.

The term "viral disease" is an infection that occurs when an organisms's body is invaded by pathogenic viruses and infectious virus particles attach to and enter susceptible cells.

The term "kinase inhibitor" refers to an agent (e.g., small molecule, nucleic acid, protein, or antibody) that can reduce the activity or level of a kinase.

The term "pseudokinase inhibitor" refers to an agent (e.g., small molecule, nucleic acid, protein, or antibody) that can reduce the activity or level of a pseudokinase.

The term "GTPase inhibitor" refers to an agent (e.g., small molecule, nucleic acid, protein, or antibody) that can reduce the activity or level of a GTPase.

The term "histone modifying enzyme inhibitor" refers to an agent (e.g., small molecule, nucleic acid, protein, or antibody) that can reduce the activity or level of a histone modifying enzyme.

The term "monovalent anti-viral agent" refers to a monovalent form of an agent (e.g., small molecule, nucleic acid, protein, or antibody) that can reduce the activity or level of a virus (e.g., in a subject or patient).

The term "mTOR" refers to the protein "mechanistic target of rapamycin (serine/threonine kinase)" or "mammalian target of rapamycin." The term "mTOR" may refer to the nucleotide sequence or protein sequence of human mTOR (e.g., Entrez 2475, Uniprot P42345, RefSeq NM_004958, or RefSeq NP_004949). The term "mTOR" includes both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ refers to a nucleotide sequence or protein of a mutant mTOR wherein the Y numbered amino acid of mTOR that normally has an X amino acid in the wildtype, instead has a Z amino acid in the mutant. In embodiments, an mTOR is the human mTOR. In embodiments, the mTOR has the following amino acid sequence:

(SEQ ID NO: 1)
MLGTGPAAATTAATTSSNVSVLQQFASGLKSRNEETRAKAAKELQHYVTM

ELREMSQEESTRFYDQLNHHIFELVSSSDANERKGGILAIASLIGVEGGN

-continued

```
ATRIGRFANYLRNLLPSNDPVVMEMASKAIGRLAMAGDTFTAEYVEFEVK

RALEWLGADRNEGRRHAAVLVLRELAISVPTFFFQQVQPFFDNIFVAVWD

PKQAIREGAVAALRACLILTTQREPKEMQKPQWYRHTFEEAEKGFDETLA

KEKGMNRDDRIHGALLILNELVRISSMEGERLREEMEEITQQQLVHDKYC

KDLMGFGTKPRHITPFTSFQAVQPQQSNALVGLLGYSSHQGLMGFGTSPS

PAKSTLVESRCCRDLMEEKFDQVCQWVLKCRNSKNSLIQMTILNLLPRLA

AFRPSAFTDTQYLQDTMNHVLSCVKKEKERTAAFQALGLLSVAVRSEFKV

YLPRVLDIIRAALPPKDFAHKRQKAMQVDATVFTCISMLARAMGPGIQQD

IKELLEPMLAVGLSPALTAVLYDLSRQIPQLKKDIQDGLLKMLSLVLMHK

PLRHPGMPKGLAHQLASPGLTTLPEASDVGSITLALRTLGSFEFEGHSLT

QFVRHCADHFLNSEHKEIRMEAARTCSRLLTPSIHLISGHAHVVSQTAVQ

VVADVLSKLLVVGITDPDPDIRYCVLASLDERFDAHLAQAENLQALFVAL

NDQVFEIRELAICTVGRLSSMNPAFVMPFLRKMLIQILTELEHSGIGRIK

EQSARMLGHLVSNAPRLIRPYMEPILKALILKLKDPDPDPNPGVINNVLA

TIGELAQVSGLEMRKWVDELFIIIMDMLQDSSLLAKRQVALWTLGQLVAS

TGYVVEPYRKYPTLLEVLLNFLKTEQNQGTRREAIRVLGLLGALDPYKHK

VNIGMIDQSRDASAVSLSESKSSQDSSDYSTSEMLVNMGNLPLDEFYPAV

SMVALMRIFRDQSLSHHHTMVVQAITFIFKSLGLKCVQFLPQVMPTFLNV

IRVCDGAIREFLFQQLGMLVSFVKSHIRPYMDEIVTLMREFWVMNTSIQS

TIILLIEQIVVALGGEFKLYLPQLIPHMLRVFMHDNSPGRIVSIKLLAAI

QLFGANLDDYLHLLLPPIVKLFDAPEAPLPSRKAALETVDRLTESLDFTD

YASRIIHPIVRTLDQSPELRSTAMDTLSSLVFQLGKKYQIFIPMVNKVLV

RHRINHQRYDVLICRIVKGYTLADEEEDPLIYQHRMLRSGQGDALASGPV

ETGPMKKLHVSTINLQKAWGAARRVSKDDWLEWLRRLSLELLKDSSSPSL

RSCWALAQAYNPMARDLFNAAFVSCWSELNEDQQDELIRSIELALTSQDI

AEVTQTLLNLAEFMEHSDKGPLPLRDDNGIVLLGERAAKCRAYAKALHYK

ELEFQKGPTPAILESLISINNKLQQPEAAAGVLEYAMKHFGELEIQATWY

EKLHEWEDALVAYDKKMDTNKDDPELMLGRMRCLEALGEWGQLHQQCCEK

WTLVNDETQAKMARMAAAAAWGLGQWDSMEEYTCMIPRDTHDGAFYRAVL

ALHQDLFSLAQQCIDKARDLLDAELTAMAGESYSRAYGAMVSCHMLSELE

EVIQYKLVPERREIIRQIWWERLQGCQRIVEDWQKILMVRSLVVSPHEDM

RTWLKYASLCGKSGRLALAHKTLVLLLGVDPSRQLDHPLPTVHPQVTYAY

MKNMWKSARKIDAFQHMQHFVQTMQQQAQHAIATEDQQHKQELHKLMARC

FLKLGEWQLNLQGINESTIPKVLQYYSAATEHDRSWYKAWHAWAVMNFEA

VLHYKHQNQARDEKKKLRHASGANITNATTAATTAATATTTASTEGSNSE

SEAESTENSPTPSPLQKKVTEDLSKTLLMYTVPAVQGFFRSISLSRGNNL

QDTLRVLTLWFDYGHWPDVNEALVEGVKAIQIDTWLQVIPQLIARIDTPR

PLVGRLIHQLLTDIGRYHPQALIYPLTVASKSTTTARHNAANKILKNMCE

HSNTLVQQAMMVSEELIRVAILWHEMWHEGLEEASRLYFGERNVKGMFEV

LEPLHAMMERGPQTLKETSFNQAYGRDLMEAQEWCRKYMKSGNVKDLTQA

WDLYYHVFRRISKQLPQLTSLELQYVSPKLLMCRDLELAVPGTYDPNQPI
```

-continued

```
IRIQSIAPSLQVITSKQRPRKLTLMGSNGHEFVFLLKGHEDLRQDERVMQ

LFGLVNTLLANDPTSLRKNLSIQRYAVIPLSTNSGLIGWVPHCDTLHALI

RDYREKKKILLNIEHRIMLRMAPDYDHLTLMQKVEVFEHAVNNTAGDDLA

KLLWLKSPSSEVWFDRRTNYTRSLAVMSMVGYILGLGDRHPSNLMLDRLS

GKILHIDFGDCFEVAMTREKFPEKIPFRLTRMLTNAMEVTGLDGNYRITC

HTVMEVLREHKDSVMAVLEAFVYDPLLNWRLMDTNTKGNKRSRTRTDSYS

AGQSVEILDGVELGEPAHKKTGTTVPESIHSFIGDGLVKPEALNKKAIQI

INRVRDKLTGRDFSHDDTLDVPTQVELLIKQATSHENLCQCYIGWCPFW.
```

The term “mTORC1” refers to the protein complex including mTOR and Raptor (regulatory-associated protein of mTOR). mTORC1 may also include MLST8 (mammalian lethal with SEC 13 protein 8), PRAS40, and/or DEPTOR. mTORC1 may function as a nutrient/energy/redox sensor and regulator of protein synthesis. The term “mTORC1 pathway” or “mTORC1 signal transduction pathway” refers to a cellular pathway including mTORC1. An mTORC1 pathway includes the pathway components upstream and downstream from mTORC1. An mTORC1 pathway is a signaling pathway that is modulated by modulation of mTORC1 activity. In embodiments, an mTORC1 pathway is a signaling pathway that is modulated by modulation of mTORC1 activity but not by modulation of mTORC2 activity. In embodiments, an mTORC1 pathway is a signaling pathway that is modulated to a greater extent by modulation of mTORC1 activity than by modulation of mTORC2 activity.

The term “mTORC2” refers to the protein complex including mTOR and RICTOR (rapamycin-insensitive companion of mTOR). mTORC2 may also include GPL, mSINl (mammalian stress-activated protein kinase interacting protein 1), Protor 1/2, DEPTOR, TTI1, and/or TEL2. mTORC2 may regulate cellular metabolism and the cytoskeleton. The term “mTORC2 pathway” or “mTORC2 signal transduction pathway” refers to a cellular pathway including mTORC2. An mTORC2 pathway includes the pathway components upstream and downstream from mTORC2. An mTORC2 pathway is a signaling pathway that is modulated by modulation of mTORC2 activity. In embodiments, an mTORC2 pathway is a signaling pathway that is modulated by modulation of mTORC2 activity but not by modulation of mTORC1 activity. In embodiments, an mTORC2 pathway is a signaling pathway that is modulated to a greater extent by modulation of mTORC2 activity than by modulation of mTORC1 activity.

The term “active site mTOR inhibitor” refers to a compound that inhibits the activity of mTOR (e.g., kinase activity) and binds to the the active site of mTOR (e.g., the ATP binding site, overlapping with the ATP binding site, blocking access by ATP to the ATP binding site of mTOR). Examples of active site mTOR inhibitors include, but are not limited to, INK128, PP242, PP121, MLN0128, AZD8055, AZD2014, NVP-BEZ235, BGT226, SF1126, Torin 1, Torin 2, WYE 687, WYE 687 salt (e.g., hydrochloride), PF04691502, PI-103, CC-223, OSI-027, XL388, KU-0063794, GDC-0349, andPKI-587. In embodiments, an active site mTOR inhibitor is an asTORi.

The term “rapamycin analog” or “rapalog” refer to analogs or derivatives (e.g., prodrugs) of rapamycin. Examples of rapamycin analogs include, but are not limited to, deforolimus (AP23573, MK-8669, ridaforolimus), temsirolimus (CCI-779), ABT478, and everolimus (RAD001). In embodiments, rapamycin analogs include esters, ethers, amides, carbonates, carbamates, sulfonates, oximes, hydrazones, or hydroxyamines of rapamycin. In embodiments, rapamycin analogs include rapamycins in which functional groups on rapamycin have been modified, (e.g., through reduction or oxidation, replacement with a nucleophile). In embodiments, rapamycin analogs include a metabolite of rapamycin (e.g., a desmethylrapamycin derivative or a linear rapamycin (e.g., secorapamycin, as described in U.S. Pat. No. 5,252, 579). In embodiments, rapamycin analogs include O-desmethylrapamycin, desmethylrapamycin, or desmethoxyrapamycin (for example, as described in WO 2006/095185, U.S. Pat. No. 6,358,969). In embodiments, rapamycin analogs include ester derivatives or ether derivatives of rapamycin, including alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. Nos. 5,118,678; 5,411,967; 5,480,989; 5,480,988; 5,489,680); amino carbamate esters (U.S. Pat. No. 5,463,048); silyl ethers (U.S. Pat. No. 5,120,842); aminoesters (U.S. Pat. No. 5,130,307); acetals; aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385, 910); amino alkanoic esters (U.S. Pat. No. 5,389,639); phosphorylcarbamate esters (U.S. Pat. No. 5,391,730); hindered N-oxide esters (U.S. Pat. No. 5,491,231); biotin esters (U.S. Pat. No. 5,504,091); O-alkyl ethers (U.S. Pat. No. 5,665,772); and PEG esters (U.S. Pat. No. 5,780,462); all of rapamycin. In embodiments, rapamycin analogs include ester, oxime, hydrazone, ether, or hydroxylamine derivatives of rapamycin, including those described in U.S. Pat. Nos. 5,256,790, 5,373,014, 5,378,836, 5,023,264, 5,563,145, and 5,023,263. In embodiments, rapamycin analogs include rapamycin 42-ester with 3-hydroxy-2-(hydroxymethyl)-2-methylpropionic acid (U.S. Pat. No. 5,362,718), 42-Q-(2-hydroxy)ethyl rapamycin (U.S. Pat. No. 5,665,772), and 42-epi-tetrazolyl rapamycin, or those described in U.S. Pat. Nos. 3,929,992, 5,362,718, and 6,277,983 (e.g., position 42 corresponding to position 40 shown in Example tables). In embodiments, rapamycin analogs include a substituted rapamycin e.g., a 40—O-substituted rapamycin e.g., as described in U.S. Pat. No. 5,258,389, WO 94/09010, WO 92/05179, U.S. Pat. Nos. 5,118,677, 5,118,678, 5,100,883, 5,151,413, 5,120,842, WO 93/11130, WO 94/02136, WO 94/02485 or WO 95/14023. In embodiments, rapamycin analogs include a 16—O-substituted rapamycin e.g., as disclosed in WO 94/02136, WO 95/16691 or WO 96/41807. In embodiments, rapamycin analogs include a 32-hydrogenated rapamycin e.g., as described in WO 96/41807 or U.S. Pat. No. 5,256,790. In embodiments, rapamycin analogs include 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40—O-(2-hydroxyethyl)-rapamycin or 40—O-(2-hydroxyethyl)-rapamycin. In embodiments, rapamycin analogs include 40—O-(2-hydroxyethyl)-rapamycin, 40-[3-hydroxy-2-(hydroxymethyl)-2-methylpropanoate]-rapamycin (also called CCI779), 40-epi-(tetrazolyl)-rapamycin (also called ABT578), 32-deoxorapamycin, 16-pent-2-ynyloxy-32(S)-dihydro rapamycin, or TAFA-93. The publications, patents, and applications described above are incorporated by reference in their entireties for all purposes.

The term "FKBP" refers to a protein peptidyl-prolyl cis-trans isomerase. For non-limiting examples of FKBP, see Cell Mol Life Sci. 2013 September; 70(18):3243-75. In embodiments, "FKBP" refers to "FKBP-12" or "FKBP 12" or "FKBP1A". In embodiments, "FKBP" refers to the human protein. Included in the term "FKBP" is the wildtype and mutant forms of the protein. In embodiments, "FKBP" refers to the wildtype human protein. In embodiments, "FKBP" refers to the wildtype human nucleic acid. In embodiments, the FKBP is a mutant FKBP. In embodiments, the mutant FKBP is associated with a disease that is not associated with wildtype FKBP. In embodiments, the FKBP includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype FKBP. In embodiments, FKBP refers to human AIP, AIPL1, FKBP1A, FKBP1B, FKBP2, FKBP3, FKBP5, FKBP6, FKBP7, FKBP8, FKBP9, FKBP9L, FKBP10, FKBP11, FKBP14, FKBP15, FKBP52, FKBP51, or LOC541473.

The term "FKBP-12" or "FKBP 12" or "FKBP1A" refers to the protein "peptidyl-prolyl cis-trans isomerase FKBP1A." In embodiments, "FKBP-12" or "FKBP 12" or "FKBP1A" refers to the human protein. Included in the term "FKBP-12" or "FKBP 12" or "FKBP1A" are the wildtype and mutant forms of the protein. In embodiments, "FKBP-12" or "FKBP 12" or "FKBP1A" refers to the protein associated with Entrez Gene 2280, OMIM 186945, UniProt P62942, and/or RefSeq (protein)NP_000792. In embodiments, the reference numbers immediately above refer to the protein, and associated nucleic acids, known as of the date of filing of this application. In embodiments, "FKBP-12" or "FKBP 12" or "FKBP1A" refers to the wildtype human protein. In embodiments, "FKBP-12" or "FKBP 12" or "FKBP1A" refers to the wildtype human nucleic acid. In embodiments, the FKBP-12 is a mutant FKBP-12. In embodiments, the mutant FKBP-12 is associated with a disease that is not associated with wildtype FKBP-12. In embodiments, the FKBP-12 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype FKBP-12. In embodiments, the FKBP-12 has the protein sequence corresponding to RefSeq NP_000792.1. In embodiments, the FKBP-12 has the protein sequence corresponding to RefSeq NM_000801.5.

The term "calcineurin" refers to a protein, which is a calcium and calmodulin dependent serine/threonine protein phosphatase, also known as a protein phosphatase 3, and calcium-dependent serine-threonine phosphatase. Calcineurin is a heterodimer of a 61-kD calmodulin-binding catalytic subunit, calcineurin A and a 19-kD Ca2+-binding regulatory subunit, calcineurin B. There are three isozymes of the catalytic subunit, each encoded by a separate gene (PPP3CA, PPP3CB, and PPP3CC) and two isoforms of the regulatory, also encoded by separate genes (PPP3R1, PPP3R2).

The term "immunophilins" refers to cytosolic peptidyl-prolyl isomerases that catalyze the interconversion between the cis and trans isomers of peptide bonds containing the amino acid proline. Immunophilins can be classified into two main families: "cyclosporin-binding cyclophilins" and "FK506-binding proteins." Immunophilins act as receptors for immunosuppressive drugs, such as cyclosporin and tacrolimus (or FK506), which inhibit the prolyl isomerase activity of immunophilins. In embodiments, the compound described herein is an immunophilin-binding compound. In embodiments, the compound includes an immunophilin-binding moiety.

The term "cyclophilin" refers to a family of proteins that bind to cyclosporin, which is an immunosuppressant usually used to suppress rejection after internal organ transplants. Cyclophilins have peptidyl prolyl isomerase activity. In embodiments, the compound described herein is a cyclophilin-binding compound. In embodiments, the compound includes a cyclophilin-binding moiety.

The term "FK506-binding protein" or "FKBP" refers to a family of proteins that have peptidyl prolyl isomerase activity. FKBP12 is notable in humans for binding tacrolimus (or FK506), which is an immunosuppressant used in treating subjects after organ transplant as well as subjects suffering from autoimmune disorders. Both the FKBP-FK506 complex and the cyclosporin-cyclophilin complex inhibit calcineurin, thus blocking signal transduction in the T-lymphocyte transduction pathway.

The term "EGFR" or "ErbB-1" or "HER1" refers to the protein "Epidermal growth factor receptor". In embodiments, "EGFR" or "ErbB-1" or "HER1" refers to the human protein. Included in the term ""EGFR" or "ErbB-1" or "HER1" are the wildtype and mutant forms of the protein. In embodiments, "EGFR" or "ErbB-1" or "HER1" refers to the protein associated with Entrez Gene 1956, OMIM 131550, UniProt P00533, and/or RefSeq (protein) NP_005219, RefSeq (protein)NP_958439, RefSeq (protein) NP_958440, or RefSeq (protein) NP_958441. In embodiments, the reference numbers immediately above refer to the protein, and associated nucleic acids, known as of the date of filing of this application. In embodiments, "EGFR" or "ErbB-1" or "HER1" refers to the wildtype human protein. In embodiments, "EGFR" or "ErbB-1" or "HER1" refers to the wildtype human nucleic acid. In embodiments, the EGFR is a mutant EGFR. In embodiments, the mutant EGFR is associated with a disease that is not associated with wildtype EGFR. In embodiments, the mutant EGFR is associated with cancer. In embodiments, the EGFR includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype EGFR. In embodiments, the EGFR has the protein sequence corresponding to RefSeq NP_005219.2. In embodiments, the EGFR has the protein sequence corresponding to RefSeq NM_005219.2. In embodiments, the EGFR has the following amino acid sequence:

(SEQ ID NO: 2)

MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

-continued

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFMRRRHIVRKRTLRRLLQERELVEPLTPSGEAPN

QALLRILKETEFKKIKVLGSGAFGTVYKGLWIPEGEKVKIPVAIKELREA

TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDGIPASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNST

FDSPAHWAQKGSHQISLDNPDYQQDFFPKEAKPNGIFKGSTAENAEYLRV

APQSSEFIGA.

The term "HER2" or "ErbB-2" or "ERBB2" refers to the protein "human epidermal growth factor receptor 2". In embodiments, "HER2" or "ErbB-2" or "ERBB2" refers to the protein "receptor tyrosine-protein kinase erbB-2". In embodiments, "HER2" or "ErbB-2" or "ERBB2" refers to the human protein. Included in the term "HER2" or "ErbB-2" or "ERBB2" are the wildtype and mutant forms of the protein. In embodiments, "HER2" or "ErbB-2" or "ERBB2" refers to the protein associated with Entrez Gene 2064, OMIM 164870, UniProt P04626, and/or RefSeq (protein) NP_004439. In embodiments, the reference numbers immediately above refer to the protein, and associated nucleic acids, known as of the date of filing of this application. In embodiments, "HER2" or "ErbB-2" or "ERBB2" refers to the wildtype human protein. In embodiments, "HER2" or "ErbB-2" or "ERBB2" refers to the wildtype human nucleic acid. In embodiments, the HER2 protein is a mutant HER2 protein. In embodiments, the mutant HER2 protein is associated with a disease that is not associated with wildtype HER-2. In embodiments, the mutant HER-2 is associated with cancer. In embodiments, the mutant HER-2 is associated with breast cancer. In embodiments, the HER-2 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype HER-2. In embodiments, the HER-2 protein has the protein sequence corresponding to RefSeq NP_004439.2. In embodiments, the HER-2 protein has the protein sequence corresponding to RefSeq NM_004448.3. In embodiments, the HER2 has the following amino acid sequence:

(SEQ ID NO: 3)

MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

-continued

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV.

The term “LRRK” or “LRKK2” or “dardarin” refers to the protein “Leucine-rich repeat kinase 2”. In embodiments, “LRRK” or “LRKK2” or “dardarin” refers to the human protein. Included in the term “LRRK” or “LRKK2” or “dardarin” are the wildtype and mutant forms of the protein. In embodiments, “LRRK” or “LRKK2” or “dardarin” refers to the protein associated with Entrez Gene 120892, OMIM 609007, UniProt Q5S007, and/or RefSeq (protein) NP_940980. In embodiments, the reference numbers immediately above refer to the protein, and associated nucleic acids, known as of the date of filing of this application. In embodiments, “LRRK” or “LRKK2” or “dardarin” refers to the wildtype human protein. In embodiments, “LRRK” or “LRKK2” or “dardarin” refers to the wildtype human nucleic acid. In embodiments, the LRKK2 is a mutant LRKK2 protein. In embodiments, the mutant LRKK2 is associated with a disease that is not associated with wildtype LRKK2. In embodiments, the LRKK2 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype LRKK2. In embodiments, the LRKK2 protein has the protein sequence corresponding to RefSeq NP_940980.3. In embodiments, the LRKK2 protein has the protein sequence corresponding to RefSeq NM_198578.3. In embodiments, the LRRK2 has the following amino acid sequence:

(SEQ ID NO: 4)

MASGSCQGCEEDEETLKKLIVRLNNVQEGKQIETLVQILEDLLVFTYSER

ASKLFQGKNIHVPLLIVLDSYMRVASVQQVGWSLLCKLIEVCPGTMQSLM

GPQDVGNDWEVLGVHQLILKMLTVHNASVNLSVIGLKTLDLLLTSGKITL

LILDEESDIFMLIFDAMHSFPANDEVQKLGCKALHVLFERVSEEQLTEFV

ENKDYMILLSALTNFKDEEEIVLHVLHCLHSLAIPCNNVEVLMSGNVRCY

NIVVEAMKAFPMSERIQEVSCCLLHRLTLGNFFNILVLNEVHEFVVKAVQ

QYPENAALQISALSCLALLTETIFLNQDLEEKNENQENDDEGEEDKLFWL

EACYKALTWHRKNKHVQEAACWALNNLLMYQNSLHEKIGDEDGHFPAHRE

VMLSMLMHSSSKEVFQASANALSTLLEQNVNFRKILLSKGIHLNVLELMQ

KHIHSPEVAESGCKMLNHLFEGSNTSLDIMAAVVPKILTVMKRHETSLPV

QLEALRAILHFIVPGMPEESREDTEFHHKLNMVKKQCFKNDIHKLVLAAL

NRFIGNPGIQKCGLKVISSIVHFPDALEMLSLEGAMDSVLHTLQMYPDDQ

EIQCLGLSLIGYLITKKNVFIGTGHLLAKILVSSLYRFKDVAEIQTKGFQ

TILAILKLSASFSKLLVHHSFDLVIFHQMSSNIMEQKDQQFLNLCCKCFA

KVAMDDYLKNVMLERACDQNNSIMVECLLLLGADANQAKEGSSLICQVCE

KESSPKLVELLLNSGSREQDVRKALTISIGKGDSQIISLLLRRLALDVAN

NSICLGGFCIGKVEPSWLGPLFPDKTSNLRKQTNIASTLARMVIRYQMKS

AVEEGTASGSDGNFSEDVLSKFDEWTFIPDSSMDSVFAQSDDLDSEGSEG

SFLVKKKSNSISVGEFYRDAVLQRCSPNLQRHSNSLGPIFDHEDLLKRKR

KILSSDDSLRSSKLQSHMRHSDSISSLASEREYITSLDLSANELRDIDAL

SQKCCISVHLEHLEKLELHQNALTSFPQQLCETLKSLTHLDLHSNKFTSF

PSYLLKMSCIANLDVSRNDIGPSVVLDPTVKCPTLKQFNLSYNQLSFVPE

NLTDVVEKLEQLILEGNKISGICSPLRLKELKILNLSKNHISSLSENFLE

ACPKVESFSARMNFLAAMPFLPPSMTILKLSQNKFSCIPEAILNLPHLRS

LDMSSNDIQYLPGPAHWKSLNLRELLFSHNQISILDLSEKAYLWSRVEKL

HLSHNKLKEIPPEIGCLENLTSLDVSYNLELRSFPNEMGKLSKIWDLPLD

ELHLNFDFKHIGCKAKDIIRFLQQRLKKAVPYNRMKLMIVGNTGSGKTTL

LQQLMKTKKSDLGMQSATVGIDVKDWPIQIRDKRKRDLVLNVWDFAGREE

FYSTHPHFMTQRALYLAVYDLSKGQAEVDAMKPWLFNIKARASSSPVILV

GTHLDVSDEKQRKACMSKITKELLNKRGFPAIRDYHFVNATEESDALAKL

RKTIINESLNFKIRDQLVVGQLIPDCYVELEKIILSERKNVPIEFPVIDR

KRLLQLVRENQLQLDENELPHAVHFLNESGVLLHFQDPALQLSDLYFVEP

KWLCKIMAQILTVKVEGCPKHPKGIISRRDVEKFLSKKRKFPKNYMSQYF

KLLEKFQIALPIGEEYLLVPSSLSDHRPVIELPHCENSEIIIRLYEMPYF

PMGFWSRLINRLLEISPYMLSGRERALRPNRMYWRQGIYLNWSPEAYCLV

GSEVLDNHPESFLKITVPSCRKGCILLGQVVDHIDSLMEEWFPGLLEIDI

CGEGETLLKKWALYSFNDGEEHQKILLDDLMKKAEEGDLLVNPDQPRLTI

PISQIAPDLILADLPRNIMLNNDELEFEQAPEFLLGDGSFGSVYRAAYEG

EEVAVKIFNKHTSLRLLRQELVVLCHLHHPSLISLLAAGIRPRMLVMELA

SKGSLDRLLQQDKASLTRTLQHRIALHVADGLRYLHSAMITYRDLKPHNV

-continued

LLFTLYPNAAIIAKIADYGIAQYCCRMGIKTSEGTPGFRAPEVARGNVIY

NQQADVYSFGLLLYDILTTGGRIVEGLKFPNEFDELEIQGKLPDPVKEYG

CAPWPMVEKLIKQCLKENPQERPTSAQVFDILNSAELVCLTRRILLPKNV

IVECMVATHHNSRNASIWLGCGHTDRGQLSFLDLNTEGYTSEEVADSRIL

CLALVHLPVEKESWIVSGTQSGTLLVINTEDGKKRHTLEKMTDSVTCLYC

NSFSKQSKQKNFLLVGTADGKLAIFEDKTVKLKGAAPLKILNIGNVSTPL

MCLSESTNSTERNVMWGGCGTKIFSFSNDFTIQKLIETRTSQLFSYAAFS

DSNIITVVVDTALYIAKQNSPVVEVWDKKTEKLCGLIDCVHFLREVMVKE

NKESKHKMSYSGRVKTLCLQKNTALWIGTGGGHILLLDLSTRRLIRVIYN

FCNSVRVMMTAQLGSLKNVMLVLGYNRKNTEGTQKQKEIQSCLTVWDINL

PHEVQNLEKHIEVRKELAEKMRRTSVE.

The term "KRAS" or "K-Ras" or "Ki-ras" refers to the protein "Kirsten Rat Sarcoma". In embodiments, "KRAS" or "K-Ras" or "Ki-ras" refers to the human protein. Included in the term "KRAS" or "K-Ras" or "Ki-ras" are the wildtype and mutant forms of the protein. In embodiments, "KRAS" or "K-Ras" or "Ki-ras" refers to the protein associated with Entrez Gene 3845, OMIM 190070, UniProt P01116, and/or RefSeq (protein) NP_004976, RefSeq (protein) NP_004976.2, or RefSeq (protein)NP_203524. In embodiments, the reference numbers immediately above refer to the protein, and associated nucleic acids, known as of the date of filing of this application. In embodiments, "KRAS" or "K-Ras" or "Ki-ras" refers to the wildtype human protein. In embodiments, "KRAS" or "K-Ras" or "Ki-ras" refers to the wildtype human nucleic acid. In embodiments, the KRAS is a mutant KRAS protein. In embodiments, the mutant KRAS is associated with a disease that is not associated with wildtype KRAS. In embodiments, the KRAS includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype KRAS. In embodiments, the KRAS protein has the protein sequence corresponding to RefSeq NP_004976.2. In embodiments, the KRAS protein has the protein sequence corresponding to RefSeq NM_004985.4. In embodiments, the KRAS has the following amino acid sequence:

(SEQ ID NO: 5)

MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

RVEDAFYTLVREIRQYRLKKISKEEKTPGCVKIKKCIIM.

In embodiments, the KRAS has the following amino acid sequence:

(SEQ ID NO: 6)

MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEKMSKDGKKKKKKSKTKCVIM.

The term "PI4KA" or "PI4K-ALPHA" refers to the protein "Phosphatidylinositol 4-kinase alpha". In embodiments, "PI4KA" or "PI4K-ALPHA" refers to the human protein. Included in the term "PI4KA" or "PI4K-ALPHA" are the wildtype and mutant forms of the protein. In embodiments, "PI4KA" refers to PI4KIIIβ. In embodiments, "PI4KA" or "PI4K-ALPHA" refers to the protein associated with Entrez Gene 5297, UniProt P42356, and/or RefSeq (protein)NP_477352. In embodiments, the reference numbers immediately above refer to the protein, and associated nucleic acids, known as of the date of filing of this application. In embodiments, "PI4KA" or "PI4K-ALPHA" refers to the wildtype human protein. In embodiments, "PI4KA" or "PI4K-ALPHA" refers to the wildtype human nucleic acid. In embodiments, the PI4KA is a mutant PI4KA protein. In embodiments, the mutant PI4KA is associated with a disease that is not associated with wildtype PI4KA. In embodiments, the PI4KA includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype PI4KA. In embodiments, the PI4KA protein has the protein sequence corresponding to RefSeq NP_477352.3. In embodiments, the PI4KA protein has the protein sequence corresponding to RefSeq NM_058004.3. In embodiments, the PI4KA has the following amino acid sequence:

(SEO ID NO: 7)

MAAAPARGGGGGGGGGGGGCSGSGSSASRGFYFNTVLSLARSLAVQRPASL

EKVQKLLCMCPVDFHGIFQLDERRRDAVIALGIFLIESDLQHKDCVVPYL

LRLLKGLPKVYWVEESTARKGRGALPVAESFSFCLVTLLSDVAYRDPSLR

DEILEVLLQVLHVLLGMCQALEIQDKEYLCKYAIPCLIGISRAFGRYSNM

EESLLSKLFPKIPPHSLRVLEELEGVRRRSFNDFRSILPSNLLTVCQEGT

LKRKTSSVSSISQVSPERGMPPPSSPGGSAFHYFEASCLPDGTALEPEYY

FSTISSSFSVSPLFNGVTYKEFNIPLEMLRELLNLVKKIVEEAVLKSLDA

IVASVMEANPSADLYYTSFSDPLYLTMFKMLRDTLYYMKDLPTSFVKEIH

DFVLEQFNTSQGELQKILHDADRIHNELSPLKLRCQANAACVDLMVWAVK

DEQGAENLCIKLSEKLQSKTSSKVIIAHLPLLICCLQGLGRLCERFPVVV

HSVTPSLRDFLVIPSPVLVKLYKYHSQYHTVAGNDIKISVTNEHSESTLN

VMSGKKSQPSMYEQLRDIAIDNICRCLKAGLTVDPVIVEAFLASLSNRLY

ISQESDKDAHLIPDHTIRALGHIAVALRDTPKVMEPILQILQQKFCQPPS

PLDVLIIDQLGCLVITGNQYIYQEVWNLFQQISVKASSVVYSATKDYKDH

GYRHCSLAVINALANIAANIQDEHLVDELLMNLLELFVQLGLEGKRASER

ASEKGPALKASSSAGNLGVLIPVIAVLTRRLPPIKEAKPRLQKLFRDFWL

YSVLMGFAVEGSGLWPEEWYEGVCEIATKSPLLTFPSKEPLRSVLQYNSA

MKNDTVTPAELSELRSTIINLLDPPPEVSALINKLDFAMSTYLLSVYRLE

YMRVLRSTDPDRFQVMFCYFEDKAIQKDKSGMMQCVIAVADKVFDAFLNM

MADKAKTKENEEELERHAQFLLVNFNHIHKRIRRVADKYLSGLVDKFPHL

LWSGTVLKTMLDILQTLSLSLSADIHKDQPYYDIPDAPYRITVPDTYEAR

ESIVKDFAARCGMILQEAMKWAPTVTKSHLQEYLNKHQNWVSGLSQHTGL

AMATESILHFAGYNKQNTTLGATQLSERPACVKKDYSNFMASLNLRNRYA

GEVYGMIRFSGTTGQMSDLNKMMVQDLHSALDRSHPQHYTQAMFKLTAML

ISSKDCDPQLLHHLCWGPLRMFNEHGMETALACWEWLLAGKDGVEVPFMR

-continued

EMAGAWHMTVEQKFGLFSAEIKEADPLAASEASQPKPCPPEVTPHYIWID

FLVQRFEIAKYCSSDQVEIFSSLLQRSMSLNIGGAKGSMNRHVAAIGPRF

KLLTLGLSLLHADVVPNATIRNVLREKIYSTAFDYFSCPPKFPTQGEKRL

REDISIMIKFWTAMFSDKKYLTASQLVPPDNQDTRSNLDITVGSRQQATQ

GWINTYPLSSGMSTISKKSGMSKKTNRGSQLHKYYMKRRTLLLSLLATEI

ERLITWYNPLSAPELELDQAGENSVANWRSKYISLSEKQWKDNVNLAWSI

SPYLAVQLPARFKNTEAIGNEVTRLVRLDPGAVSDVPEAIKFLVTWHTID

ADAPELSHVLCWAPTDPPTGLSYFSSMYPPHPLTAQYGVKVLRSFPPDAI

LFYIPQIVQALRYDKMGYVREYILWAASKSQLLAHQFIWNMKTNIYLDEE

GHQKDPDIGDLLDQLVEEITGSLSGPAKDFYQREFDFFNKITNVSAIIKP

YPKGDERKKACLSALSEVKVQPGCYLPSNPEAIVLDIDYKSGTPMQSAAK

APYLAKFKVKRCGVSELEKEGLRCRSDSEDECSTQEADGQKISWQAAIFK

VGDDCRQDMLALQIIDLFKNIFQLVGLDLFVFPYRVVATAPGCGVIECIP

DCTSRDQLGRQTDFGMYDYFTRQYGDESTLAFQQARYNFIRSMAAYSLLL

FLLQIKDRHNGNIMLDKKGHIIHIDFGFMFESSPGGNLGWEPDIKLTDEM

VMIMGGKMEATPFKWFMEMCVRGYLAVRPYMDAVVSLVTLMLDTGLPCFR

GQTIKLLKHRFSPNMTEREAANFIMKVIQSCFLSNRSRTYDMIQYYQNDI

PY.

The term "PIP5K" or "PI4P5K" or "PI5K" refers to the protein "Phosphatidylinositol 4-phosphate 5-kinase". In embodiments, "PIP5K" or "PI4P5K" or "PI5K" refers to the human protein. Included in the term "PIP5K" or "PI4P5K" or "PI5K" are the wildtype and mutant forms of the protein. In embodiments, "PIP5K" or "PI4P5K" or "PI5K" refers to the protein associated with UniProt Q99755, and/or RefSeq (protein) NP_001129110. In embodiments, the reference numbers immediately above refer to the protein, and associated nucleic acids, known as of the date of filing of this application. In embodiments, "PIP5K" refers to "PIP5K1A." In embodiments, "PIP5K" or "PI4P5K" or "PI5K" refers to the wildtype human protein. In embodiments, "PIP5K" or "PI4P5K" or "PI5K" refers to the wildtype human nucleic acid. In embodiments, the PIP5K is a mutant PIP5K protein. In embodiments, the mutant PIP5K is associated with a disease that is not associated with wildtype PIP5K. In embodiments, the PIP5K includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype PIP5K. In embodiments, the PIP5K protein has the protein sequence corresponding to RefSeq NP_001129110.1. In embodiments, the PIP5K protein has the protein sequence corresponding to RefSeq NM_001135638.2. In embodiments, the PIP5K has the following amino acid sequence:

(SEQ ID NO: 8)

MASASSGPSSSVGFSSFDPAVPSCTLSSAASGIKRPMASEVLEARQDSYI

SLVPYASGMPIKKIGHRSVDSSGETTYKKTTSSALKGAIQLGITHTVGSL

STKPERDVLMQDFYVVESIFFPSEGSNLTPAHHYNDFRFKTYAPVAFRYF

RELFGIRPDDYLYSLCSEPLIELCSSGASGSLFYVSSDDEFIIKTVQHKE

-continued

AEFLQKLLPGYYMNLNQNPRTLLPKFYGLYCVQAGGKNIRIVVMNNLLPR

SVKMHIKYDLKGSTYKRRASQKEREKPLPTFKDLDFLQDIPDGLFLDADM

YNALCKTLQRDCLVLQSFKIMDYSLLMSIHNIDHAQREPLSSETQYSVDT

RRPAPQKALYSTAMESIQGEARRGGTMETDDHMGGIPARNSKGERLLLYI

GIIDILQSYRFVKKLEHSWKALVHDGDTVSVHRPGFYAERFQRFMCNTVF

KKIPLKPSPSKKFRSGSSFSRRAGSSGNSCITYQPSVSGEHKAQVTTKAE

VEPGVHLGRPDVLPQTPPLEEISEGSPIPDPSFSPLVGETLQMLTTSTTL

EKLEVAESEFTH.

The term "SETD3" refers to the protein "SET domain containing 3 protein". In embodiments, the term "SETD3" refers to the protein "Su(var)3-9, Enhancer of Zeste, Trithorax domain containing Hi stone-ly sine N-methyl transferase". In embodiments, "SETD3" refers to the human protein. Included in the term "SETD3" are the wildtype and mutant forms of the protein. In embodiments, "SETD3" refers to the protein associated with Entrez Gene 84193, UniProt Q86TU7, and/or RefSeq (protein)NP_115609. In embodiments, the reference numbers immediately above refer to the protein, and associated nucleic acids, known as of the date of filing of this application. In embodiments, "SETD3" refers to the wildtype human protein. In embodiments, "SETD3" refers to the wildtype human nucleic acid. In embodiments, the SETD3 is a mutant SETD3 protein. In embodiments, the mutant SETD3 is associated with a disease that is not associated with wildtype SETD3. In embodiments, the SETD3 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype SETD3. In embodiments, the SETD3 protein has the protein sequence corresponding to RefSeq NP_115609.2. In embodiments, the SETD3 protein has the protein sequence corresponding to RefSeq NM_032233.3. In embodiments, the SETD3 has the following amino acid sequence:

(SEQ ID NO: 9)

MGKKSRVKTQKSGTGATATVSPKEILNLTSELLQKCSSPAPGPGKEWEEY

VQIRTLVEKIRKKQKGLSVTFDGKREDYFPDLMKWASENGASVEGFEMVN

FKEEGFGLRATRDIKAEELFLWVPRKLLMTVESAKNSVLGPLYSQDRILQ

AMGNIALAFHLLCERASPNSFWQPYIQTLPSEYDTPLYFEEDEVRYLQST

QAIHDVFSQYKNTARQYAYFYKVIQTHPHANKLPLKDSFTYEDYRWAVSS

VMTRQNQIPTEDGSRVTLALIPLWDMCNHTNGLITTGYNLEDDRCECVAL

QDFRAGEQIYIFYGTRSNAEFVIHSGFFFDNNSHDRVKIKLGVSKSDRLY

AMKAEVLARAGIPTSSVFALHFTEPPISAQLLAFLRVFCMTEEELKEHLL

GDSAIDRIFTLGNSEFPVSWDNEVKLWTFLEDRASLLLKTYKTTIEEDKS

VLKNHDLSVRAKMAIKLRLGEKEILEKAVKSAAVNREYYRQQMEEKAPLP

KYEESNLGLLESSVGDSRLPLVLRNLEEEAGVQDALNIREAISKAKATEN

GLVNGENSIPNGTRSENESLNQESKRAVEDAKGSSSDSTAGVKE.

The term "TRRAP" refers to the protein "Transformation/transcription domain-associated protein". In embodiments, "TRRAP" refers to the human protein. Included in the term "TRRAP" are the wildtype and mutant forms of the protein. In embodiments, "TRRAP" refers to the protein associated with Entrez Gene 8295, UniProt Q9Y4A5, and/or RefSeq (protein)NP_001231509. In embodiments, the reference numbers immediately above refer to the protein, and associated nucleic acids, known as of the date of filing of this application. In embodiments, "TRRAP" refers to the wild-type human protein. In embodiments, "TRRAP" refers to the wildtype human nucleic acid. In embodiments, the TRRAP is a mutant TRRAP protein. In embodiments, the mutant TRRAP is associated with a disease that is not associated with wildtype TRRAP. In embodiments, the TRRAP includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to wildtype TRRAP. In embodiments, the TRRAP protein has the protein sequence corresponding to RefSeq NP_001231509.1. In embodiments, the TRRAP protein has the protein sequence corresponding to RefSeq NM_001244580.1. In embodiments, the TRRAP has the following amino acid sequence:

(SEQ ID NO: 10)

```
MAFVATQGATVVDQTTLMKKYLQFVAALTDVNTPDETKLKMMQEVSENFE
NVTSSPQYSTFLEHIIPRFLTFLQDGEVQFLQEKPAQQLRKLVLEIIHRI
PTNEHLRPHTKNVLSVMFRFLETENEENVLICLRIIIELHKQFRPPITQE
IHHFLDFVKQIYKELPKVVNRYFENPQVIPENTVPPPEMVGMITTIAVKV
NPEREDSETRTHSIIPRGSLSLKVLAELPIIVVLMYQLYKLNIHNVVAEF
VPLIMNTIAIQVSAQARQHKLYNKELYADFIAAQIKTLSFLAYIIRIYQE
LVTKYSQQMVKGMLQLLSNCPAETAHLRKELLIAAKHILTTELRNQFIPC
MDKLFDESILIGSGYTARETLRPLAYSTLADLVHHVRQHLPLSDLSLAVQ
LFAKNIDDESLPSSIQTMSCKLLLNLVDCIRSKSEQESGNGRDVLMRMLE
VFVLKFHTIARYQLSAIFKKCKPQSELGAVEAALPGVPTAPAAPGPAPSP
APVPAPPPPPPPPPPATPVTPAPVPPFEKQGEKDKEDKQTFQVTDCRSLV
KTLVCGVKTITWGITSCKAPGEAQFIPNKQLQPKETQIYIKLVKYAMQAL
DIYQVQIAGNGQTYIRVANCQTVRMKEEKEVLEHFAGVFTMMNPLTFKEI
FQTTVPYMVERISKNYALQIVANSFLANPTTSALFATILVEYLLDRLPEM
GSNVELSNLYLKLFKLVFGSVSLFAAENEQMLKPHLHKIVNSSMELAQTA
KEPYNYFLLLRALFRSIGGGSHDLLYQEFLPLLPNLLQGLNMLQSGLHKQ
HMKDLFVELCLTVPVRLSSLLPYLPMLMDPLVSALNGSQTLVSQGLRTLE
LCVDNLQPDFLYDHIQPVRAELMQALWRTLRNPADSISHVAYRVLGKFGG
SNRKMLKESQKLHYVVTEVQGPSITVEFSDCKASLQLPMEKAIETALDCL
KSANTEPYYRRQAWEVIKCFLVAMMSLEDNKHALYQLLAHPNFTEKTIPN
VIISHRYKAQDTPARKTFEQALTGAFMSAVIKDLRPSALPFVASLIRHYT
MVAVAQQCGPFLLPCYQVGSQPSTAMFHSEENGSKGMDPLVLIDAIAICM
AYEEKELCKIGEVALAVIFDVASIILGSKERACQLPLFSYIVERLCACCY
EQAWYAKLGGVVSIKFLMERLPLTWVLQNQQTFLKALLFVMMDLTGEVSN
GAVAMAKTTLEQLLMRCATPLKDEERAEEIVAAQEKSFHHVTHDLVREVT
SPNSTVRKQAMHSLQVLAQVTGKSVTVIMEPHKEVLQDMVPPKKHLLRHQ
PANAQIGLMEGNTFCTTLQPRLFTMDLNVVEHKVFYTELLNLCEAEDSAL
TKLPCYKSLPSLVPLRIAALNALAACNYLPQSREKIIAALFKALNSTNSE
```

-continued

```
LQEAGEACMRKFLEGATIEVDQIHTHMRPLLMMLGDYRSLTLNVVNRLTS
VTRLFPNSFNDKFCDQMMQHLRKWMEVVVITHKGGQRSDGNESISECGRC
PLSPFCQFEEMKICSAIINLFHLIPAAPQTLVKPLLEVVMKTERAMLIEA
GSPFREPLIKFLTRHPSQTVELFMMEATLNDPQWSRMFMSFLKHKDARPL
RDVLAANPNRFITLLLPGGAQTAVRPGSPSTSTMRLDLQFQAIKIISIIV
KNDDSWLASQHSLVSQLRRVWVSENFQERHRKENMAATNWKEPKLLAYCL
LNYCKRNYGDIELLFQLLRAFTGRFLCNMTFLKEYMEEEIPKNYSIAQKR
ALFFRFVDFNDPNFGDELKAKVLQHILNPAFLYSFEKGEGEQLLGPPNPE
GDNPESITSVFITKVLDPEKQADMLDSLRIYLLQYATLLVEHAPHHIHDN
NKNRNSKLRRLMTFAWPCLLSKACVDPACKYSGHLLLAHIIAKFAIHKKI
VLQVFHSLLKAHAMEARAIVRQAMAILTPAVPARMEDGHQMLTHWTRKII
VEEGHTVPQLVHILHLIVQHFKVYYPVRHHLVQHMVSAMQRLGFTPSVTI
EQRRLAVDLSEVVIKWELQRIKDQQPDSDMDPNSSGEGVNSVSSSIKRGL
SVDSAQEVKRFRTATGAISAVFGRSQSLPGADSLLAKPIDKQHTDTVVNF
LIRVACQVNDNTNTAGSPGEVLSRRCVNLLKTALRPDMWPKSELKLQWFD
KLLMTVEQPNQVNYGNICTGLEVLSFLLTVLQSPAILSSFKPLQRGIAAC
MTCGNTKVLRAVHSLLSRLMSIFPTEPSTSSVASKYEELECLYAAVGKVI
YEGLTNYEKATNANPSQLFGTLMILKSACSNNPSYIDRLISVFMRSLQKM
VREHLNPQAASGSTEATSGTSELVMLSLELVKTRLAVMSMEMRKNFIQAI
LTSLIEKSPDAKILRAVVKIVEEWVKNNSPMAANQTPTLREKSILLVKMM
TYIEKRFPEDLELNAQFLDLVNYVYRDETLSGSELTAKLEPAFLSGLRCA
QPLIRAKFFEVFDNSMKRRVYERLLYVTCSQNWEAMGNHFWIKQCIELLL
AVCEKSTPIGTSCQGAMLPSITNVINLADSHDRAAFAMVTHVKQEPRERE
NSESKEEDVEIDIELAPGDQTSTPKTKELSEKDIGNQLHMLTNRHDKFLD
TLREVKTGALLSAFVQLCHISTTLAEKTWVQLFPRLWKILSDRQQHALAG
EISPFLCSGSHQVQRDCQPSALNCFVEAMSQCVPPIPIRPCVLKYLGKTH
NLWFRSTLMLEHQAFEKGLSLQIKPKQTTEFYEQESITPPQQEILDSLAE
LYSLLQEEDMWAGLWQKRCKYSETATAIAYEQHGFFEQAQESYEKAMDKA
KKEHERSNASPAIFPEYQLWEDHWIRCSKELNQWEALTEYGQSKGHINPY
LVLECAWRVSNWTAMKEALVQVEVSCPKEMAWKVNMYRGYLAICHPEEQQ
LSFIERLVEMASSLAIREWRRLPHVVSHVHTPLLQAAQQIIELQEAAQIN
AGLQPTNLGRNNSLHDMKTVVKTWRNRLPIVSDDLSHWSSIFMWRQHHYQ
GKPTWSGMHSSSIVTAYENSSQHDPSSNNAMLGVHASASAIIQYGKIARK
QGLVNVALDILSRIHTIPTVPIVDCFQKIRQQVKCYLQLAGVMGKNECMQ
GLEVIESTNLKYFTKEMTAEFYALKGMFLAQINKSEEANKAFSAAVQMHD
VLVKAWAMWGDYLENIFVKERQLHLGVSAITCYLHACRHQNESKSRKYLA
KVLWLLSFDDDKNTLADAVDKYCIGVPPIQWLAWIPQLLTCLVGSEGKLL
LNLISQVGRVYPQAVYFPIRTLYLTLKIEQRERYKSDPGPIRATAPMWRC
SRIMHMQRELHPTLLSSLEGIVDQMVWFRENWHEEVLRQLQQGLAKCYSV
AFEKSGAVSDAKITPHTLNFVKKLVSTFGVGLENVSNVSTMFSSAASESL
```

-continued

ARRAQATAQDPVFQKLKGQFTTDFDFSVPGSMKLHNLISKLKKWIKILEA

KTKQLPKFFLIEEKCRFLSNFSAQTAEVEIPGEFLMPKPTHYYIKIARFM

PRVEIVQKHNTAARRLYIRGHNGKIYPYLVMNDACLTESRREERVLQLLR

LLNPCLEKRKETTKRHLFFTVPRVVAVSPQMRLVEDNPSSLSLVEIYKQR

CAKKGIEHDNPISRYYDRLATVQARGTQASHQVLRDILKEVQSNMVPRSM

LKEWALHTFPNATDYWTFRKMFTIQLALIGFAEFVLHLNRLNPEMLQIAQ

DTGKLNVAYFRFDINDATGDLDANRPVPFRLTPNISEFLTTIGVSGPLTA

SMIAVARCFAQPNFKVDGILKTVLRDEIIAWHKKTQEDTSSPLSAAGQPE

NMDSQQLVSLVQKAVTAIMTRLHNLAQFEGGESKVNTLVAAANSLDNLCR

MDPAWHPWL.

The term “MAP4K” or “mitogen-activated protein kinase kinase kinase kinase” refers to the family of serine/threonine kinases involved in cellular signal transduction. In embodiments, MAP4K is MAP4K1 or hematopoietic progenitor kinase 1 (HPK1). In embodiments, MAP4K is MAP4K2 or germinal center kinase (GCK). In embodiments, MAP4K is MAP4K3 or germinal center kinase-like kinase (GLK). In embodiments, MAP4K is MAP4K4 or hepatocyte progenitor kinase-like/germinal center kinase-like kinase (HGK). In embodiments, MAP4K is MAP4K5 or kinase homologous to SPS1/STE20 (KHS). In embodiments, MAP4K is MAP4K6 or misshapen-like kinase 1 (MINK).

The term “hepatocyte progenitor kinase-like/germinal center kinase-like kinase” or “HGK” or “MAP4K4” is encoded by the MAP4K4 gene. The term “HGK” may refer to the nucleotide sequence or protein sequence of human HGK (e.g., Entrez 9448, Uniprot 095819, RefSeq NM_00124559.1, RefSeq NM_001242560, RefSeq NM_004834.4, RefSeq NM_145686.3, RefSeq NM_145687.3, RefSeq NP_001229488.1, RefSeq NP_001229489, RefSeq NP_004825.3, RefSeq NP_663719.2, or RefSeq NP_663720.1). The term “HGK” includes both the wild-type form of the nucleotide sequences or proteins as well as any mutants thereof. In some embodiments, “HGK” is wild-type HGK. In some embodiments, “HGK” is one or more mutant forms. The term “HGK” XYZ refers to a nucleotide sequence 30 or protein of a mutant HGK wherein the Y numbered amino acid of HGK that normally has an X amino acid in the wildtype, instead has a Z amino acid in the mutant. In embodiments, an HGK is the human HGK. In embodiments, the HGK has the following amino acid sequence:

(SEQ ID NO: 11)

MANDSPAKSLVDIDLSSLRDPAGIFELVEVVGNGTYGQVYKGRHVKTGQL

AAIKVMDVTEDEEEEIKLEINMLKKYSHHRNIATYYGAFIKKSPPGHDDQ

LWLVMEFCGAGSITDLVKNTKGNTLKEDWIAYISREILRGLAHLHIHHVI

HRDIKGQNVLLTENAEVKLVDFGVSAQLDRTVGRRNTFIGTPYWMAPEVI

ACDENPDATYDYRSDLWSCGITAIEMAEGAPPLCDMHPMRALFLIPRNPP

PRLKSKKWSKKFFSFIEGCLVKNYMQRPSTEQLLKHPFIRDQPNERQVRI

QLKDHIDRTRKKRGEKDETEYEYSGSEEEEEEVPEQEGEPSSIVNVPGES

TLRRDFLRLQQENKERSEALRRQQLLQEQQLREQEEYKRQLLAERQKRIE

QQKEQRRRLEEQQRREREARRQQEREQRRREQEEKRRLEELERRRKEEEE

-continued

RRRAEEEKRRVEREQEYIRRQLEEEQRHLEVLQQQLLQEQAMLLECRWRE

MEEHRQAERLQRQLQQEQAYLLSLQHDHRRPHPQHSQQPPPPQQERSKPS

FHAPEPKAHYEPADRAREVEDRFRKTNHSSPEAQSKQTGRVLEPPVPSRS

ESFSNGNSESVHPALQRPAEPQVPVRTTSRSPVLSRRDSPLQGSGQQNSQ

AGQRNSTSIEPRLLWERVEKLVPRPGSGSSSGSSNSGSQPGSHPGSQSGS

GERFRVRSSSKSEGSPSQRLENAVKKPEDKKEVFRPLKPADLTALAKELR

AVEDVRPPHKVTDYSSSSEESGTTDEEDDDVEQEGADESTSGPEDTRAAS

SLNLSNGETESVKTMIVHDDVESEPAMTPSKEGTLIVRQTQSASSTLQKH

KSSSSFTPFIDPRLLQISPSSGTTVTSVVGFSCDGMRPEAIRQDPTRKGS

VVNVNPTNTRPQSDTPEIRKYKKRFNSEILCAALWGVNLLVGTESGLMLL

DRSGQGKVYPLINRRRFQQMDVLEGLNVLVTISGKKDKLRVYYLSWLRNK

ILHNDPEVEKKQGWTTVGDLEGCVHYKVVKYERIKFLVIALKSSVEVYAW

APKPYHKFMAFKSFGELVHKPLLVDLTVEEGQRLKVIYGSCAGFHAVDVD

SGSVYDIYLPTHIQCSIKPHAIIILPNTDGMELLVCYEDEGVYVNTYGRI

TKDVVLQWGEMPTSVAYIRSNQTMGWGEKAIEIRSVETGHLDGVFMHKRA

QRLKFLCERNDKVFFASVRSGGSSQVYFMTLGRTSLLSW.

The term “MAP3K” or “mitogen-activated protein kinase kinase kinase” refers to the family of serine/threonine-specific protein kinases. In embodiments, MAP3K is MAP3K12 or dual leucine zipper bearing kinase (DLK).

The term “dual leucine zipper bearing kinase” or “DLK” or “MAP3K12” is encoded by the MAP3K12 gene. The term “DLK” may refer to the nucleotide sequence or protein sequence of human DLK (e.g., Entrez 7786, Uniprot Q12852, RefSeq NM_001193511.1, RefSeq NM_006301.3, RefSeq NP_001180440.1, or RefSeq NP_006292.3). The term “DLK” includes both the wild-type form of the nucleotide sequences or proteins as well as any mutants thereof. In some embodiments, “DLK” is wild-type DLK. In some embodiments, “DLK” is one or more mutant forms. The term “DLK” XYZ refers to a nucleotide sequence or protein of a mutant DLK wherein the Y numbered amino acid of DLK that normally has an X amino acid in the wildtype, instead has a Z amino acid in the mutant. In embodiments, an DLK is the human DLK. In embodiments, the DLK has the following amino acid sequence:

(SEQ ID NO: 12)

MACLHETRTPSPSFGGFVSTLSEASMRKLDPDTSDCTPEKDLTPTHVLQL

HEQDAGGPGGAAGSPESRASRVRADEVRLQCQSGSGFLEGLFGCLRPVWT

MIGKAYSTEHKQQQEDLWEVPFEEILDLQWVGSGAQGAVFLGRFHGEEVA

VKKVRDLKETDIKHLRKLKHPNIITFKGVCTQAPCYCILMEFCAQGQLYE

VLRAGRPVTPSLLVDWSMGIAGGMNYLHLHKIIHRDLKSPNMLITYDDVV

KISDFGTSKELSDKSTKMSFAGTVAWMAPEVIRNEPVSEKVDIWSFGVVL

WELLTGEIPYKDVDSSAIIWGVGSNSLHLPVPSSCPDGFKILLRQCWNSK

PRNRPSFRQILLHLDIASADVLSTPQETYFKSQAEWREEVKLHFEKIKSE

GTCLHRLEEELVMRRREELRHALDIREHYERKLERANNLYMELNALMLQL

ELKERELLRREQALERRCPGLLKPHPSRGLLHGNTMEKLIKKRNVPQKLS

-continued

```
PHSKRPDILKTESLLPKLDAALSGVGLPGCPKGPPSPGRSRRGKTRHRKA

SAKGSCGDLPGLRTAVPPHEPGGPGSPGGLGGGPSAWEACPPALRGLHHD

LLLRKMSSSSPDLLSAALGSRGRGATGGAGDPGSPPPARGDTPPSEGSAP

GSTSPDSPGGAKGEPPPPVGPGEGVGLLGTGREGTSGRGGSRAGSQHLTP

AALLYRAAVTRSQKRGISSEEEEGEVDSEVELTSSQRWPQSLNMRQSLST

FSSENPSDGEEGTASEPSPSGTPEVGSTNTDERPDERSDDMCSQGSEIPL

DPPPSEVIPGPEPSSLPIPHQELLRERGPPNSEDSDCDSTELDNSNSVDA

LRPPASLPP.
```

An "immunophilin blocking agent" is an agent (e.g., compound, small molecule, nucleic acid, or protein) capable of inhibiting or reducing contact between an immunophilin binding compound described herein and an immunophilin wherein the immunophilin blocking agent is deficient in biological activity (e.g., not capable of inhibiting an immune response or T cell activity, reduced or lacking binding to calcineurin) not associated with blocking binding to immunophilin of a separate immunophilin binding compound (e.g., compound described herein).

II. Compounds

In an aspect is provided a compound having the formula: $A^{B}$-$L^{B1}$-$R^{B1}$, or a pharmaceutically acceptable salt thereof.

$A^{B}$ is an immunophilin-binding moiety.

$L^{B1}$-$R^{B1}$ is a polar moiety.

$L^{B1}$ is a bond, covalent linker, or bioconjugate linker.

$R^{B1}$ is hydrogen, halogen, $—CX^{B1}_3$, $—CHX^{B1}_2$, $—CH_2X^{B1}$, $—OCX^{B1}_3$, $—OCH_2X^{B1}$, $—OCHX^{B1}_2$, —CN, $—SO_{nB1}R^{B1D}$, $—SO_{vB1}NR^{B1A}R^{B1B}$, $—NHC(O)NR^{B1A}R^{B1B}$, $—N(O)_{mB1}$, $—NR^{B1A}R^{B1B}$, $—C(O)R^{B1C}$, $—C(O)OR^{B1C}$, $—C(O)NR^{B1A}R^{B1B}$, $—OR^{B1D}$, $—NR^{B1A}SO_2R^{B1D}$, $—NR^{B1A}C(O)R^{B1C}$, $—NR^{B1A}C(O)OR^{B1C}$, $—NR^{B1A}OR^{B1C}$, $—NR^{B1A}C(NR^{B1C})R^{B1D}$, $—NR^{B1D}C(NR^{B1C})NR^{B1A}R^{B1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{B1A}$, $R^{B1B}$, $R^{B1C}$, and $R^{B1D}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl.

nB1 is independently an integer from 0 to 4.

mB1 and vB1 are independently 1 or 2.

$X^{B1}$ is independently —F, —Cl, —Br, or —I.

When $L^{B1}$ is a bond, $R^{B1}$ is not H.

Subsequent to administration to a subject, the concentration of the compound in circulating blood of the subject is greater than the concentration of the compound in the CNS of the subject.

In embodiments, the compound has the formula:

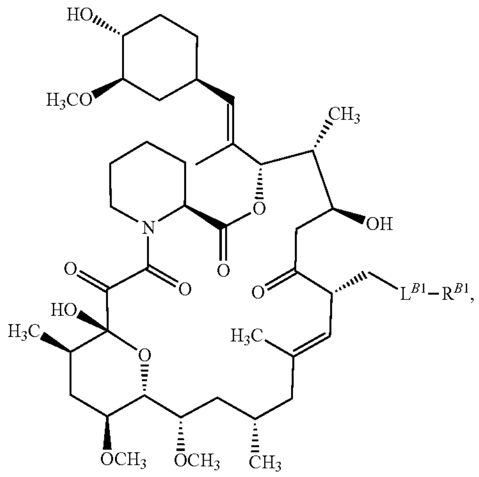

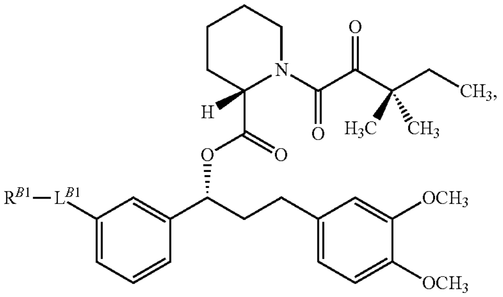

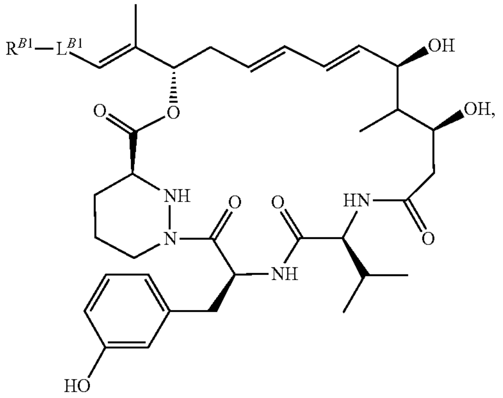

-continued
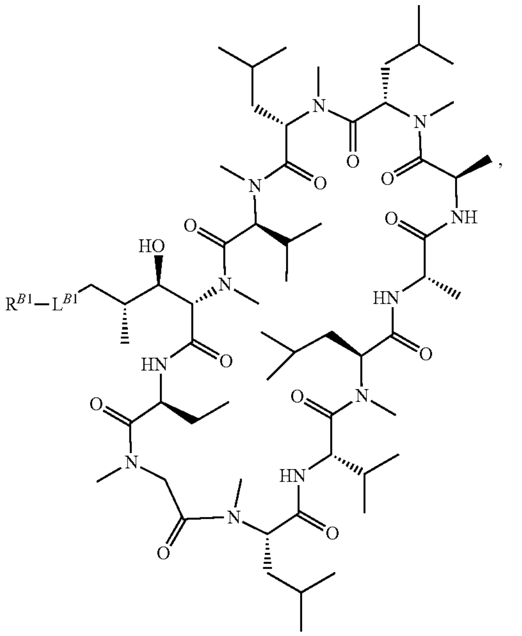
or
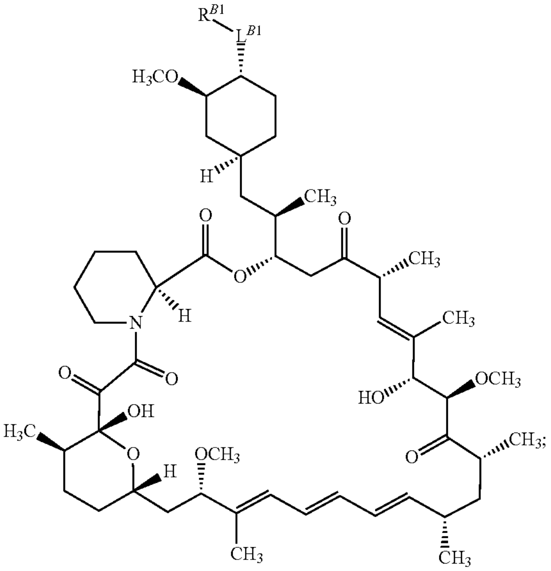
or an analog thereof. In embodiments, the compound has the formula
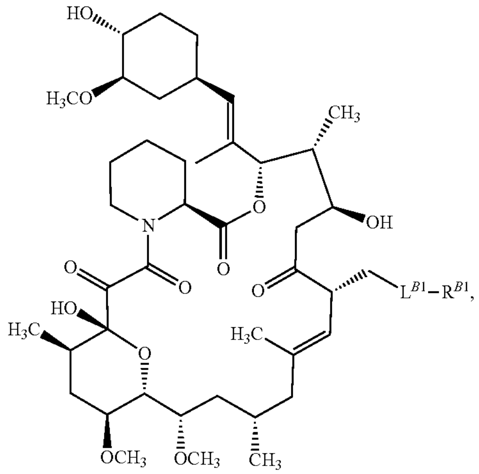
or an analog thereof. In embodiments, the compound has the formula
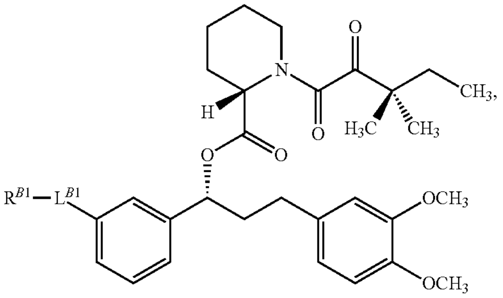
or an analog thereof. In embodiments, the compound has the formula
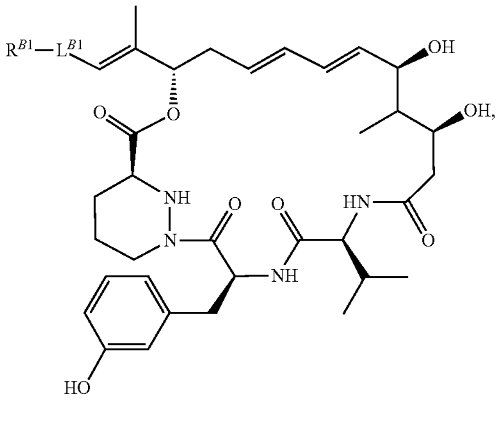
or an analog thereof. In embodiments, the compound has the formula

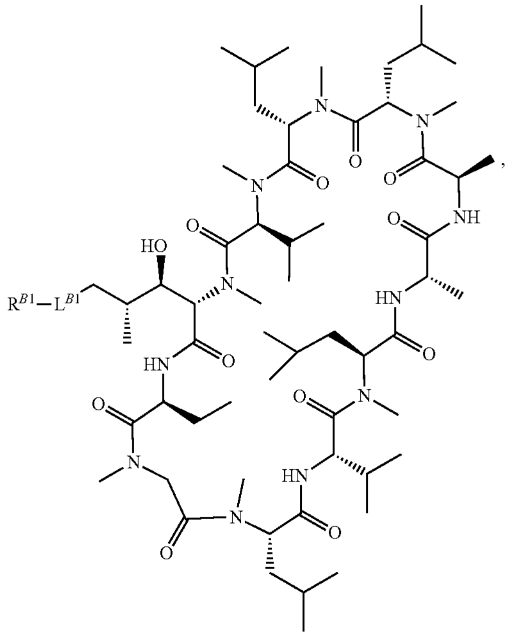
or an analog thereof. In embodiments, the compound has the formula
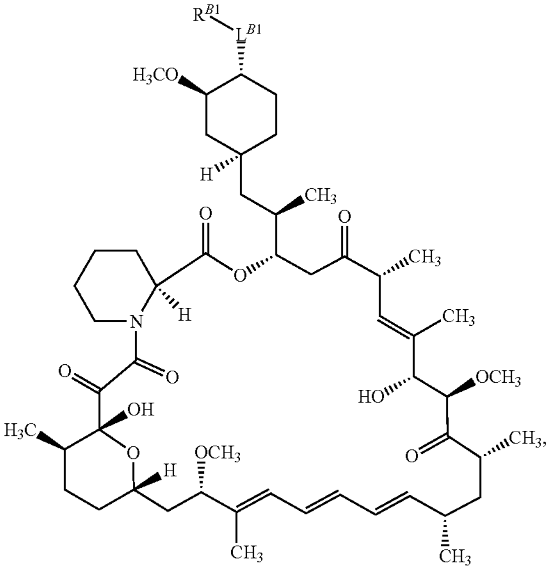
or an analog thereof. In embodiments, the compound has the formula
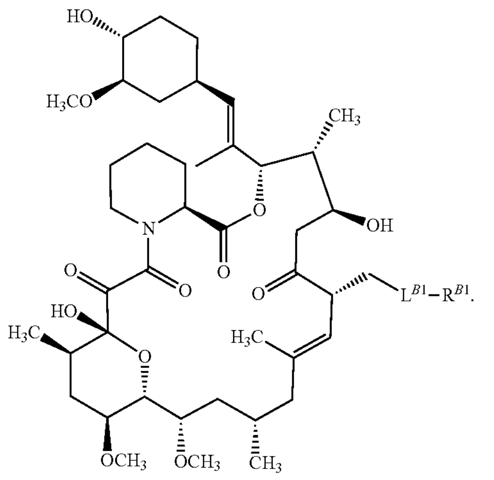
In embodiments, the compound has the formula
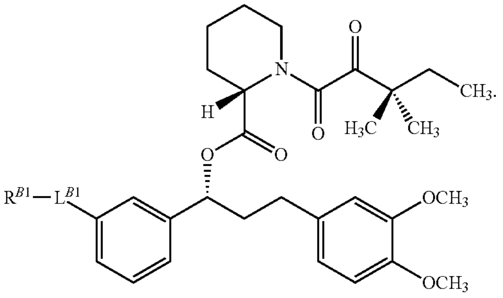
In embodiments, the compound has the formula
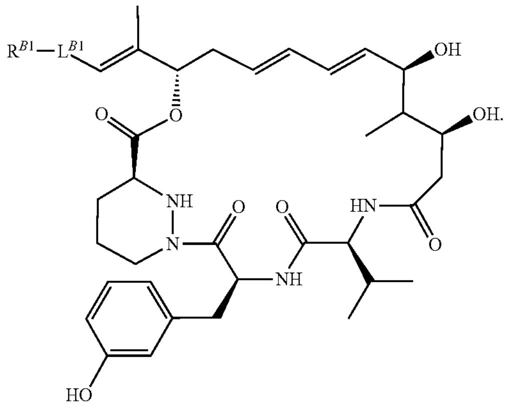

In embodiments, the compound has the formula
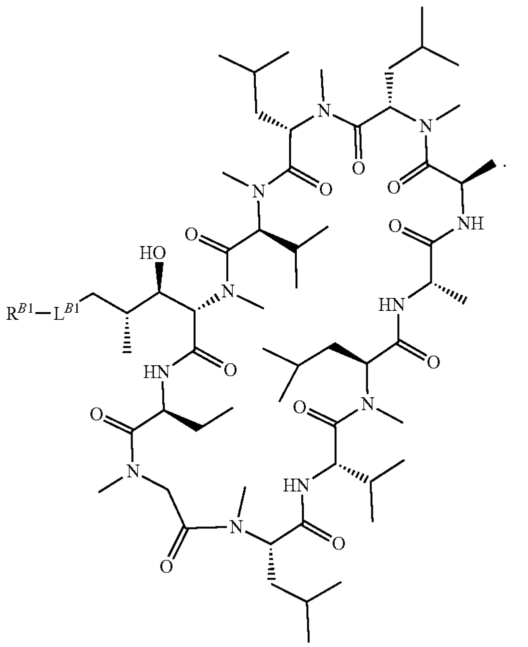
In embodiments, the compound has the formula
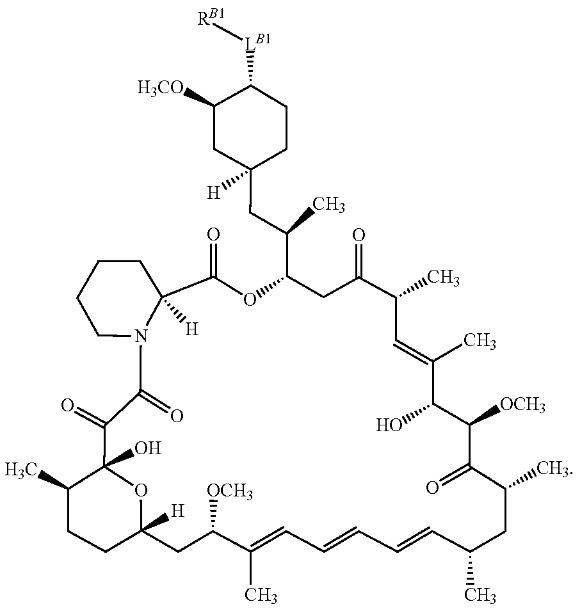
In embodiments, the compound has the formula
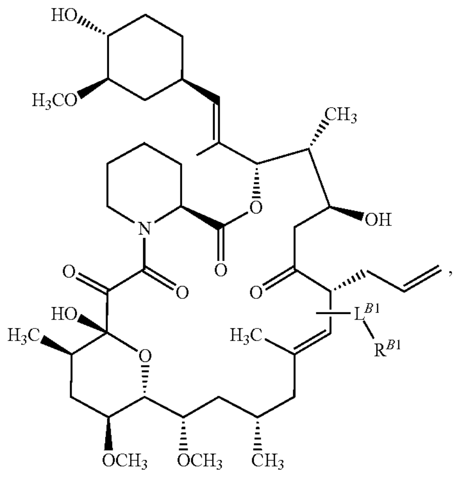
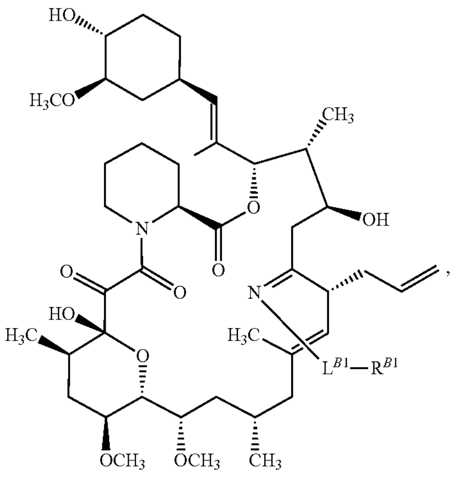

-continued
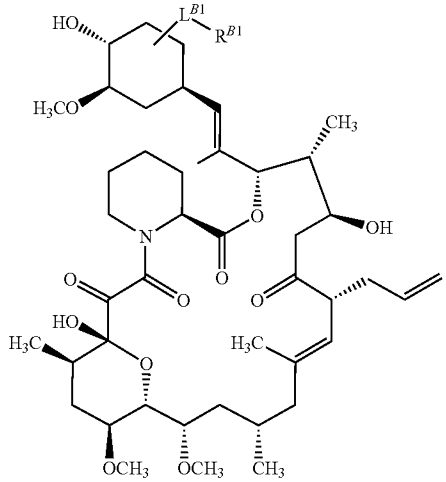
,
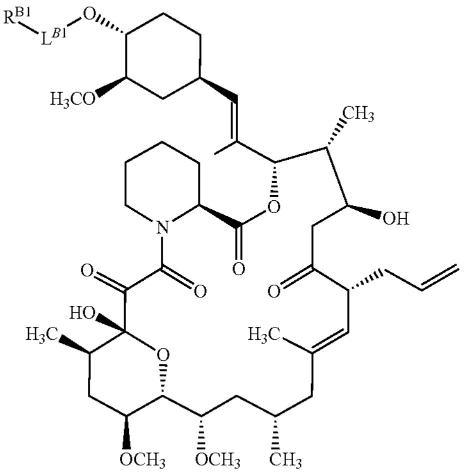
,
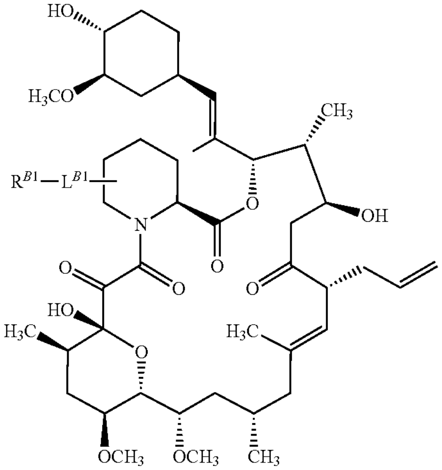
,
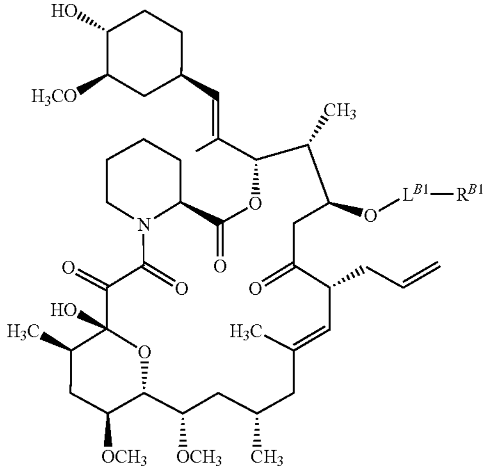
,
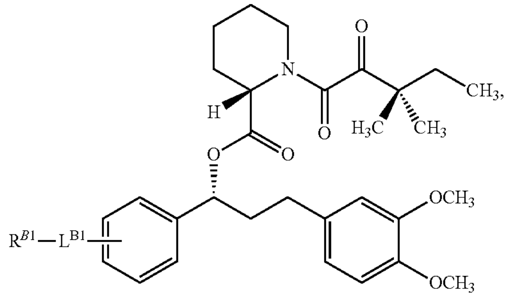
,
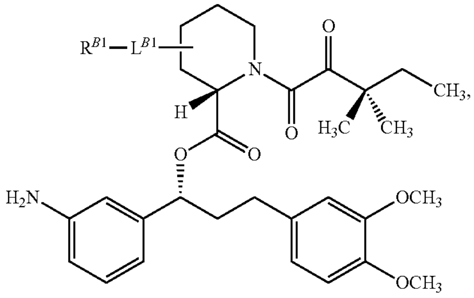
,
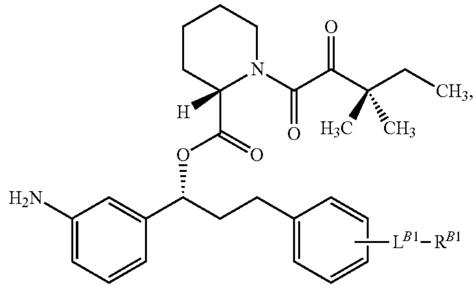
, -continued
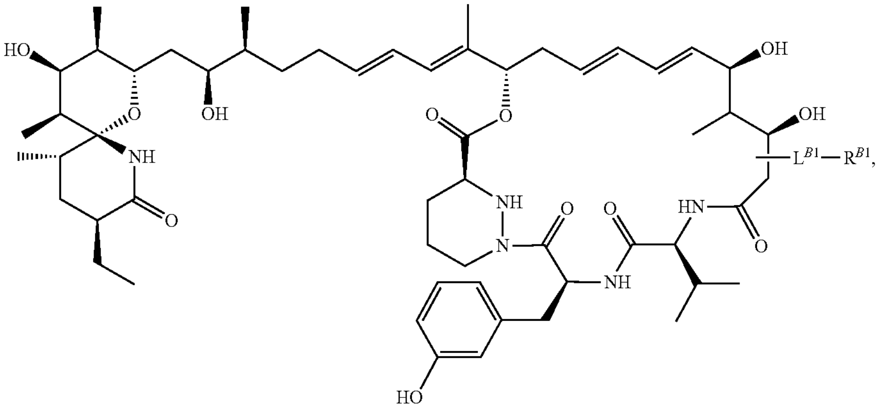
,
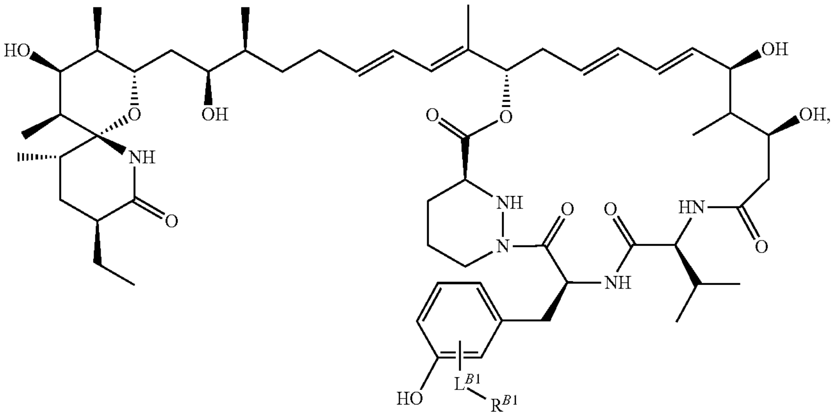
, -continued
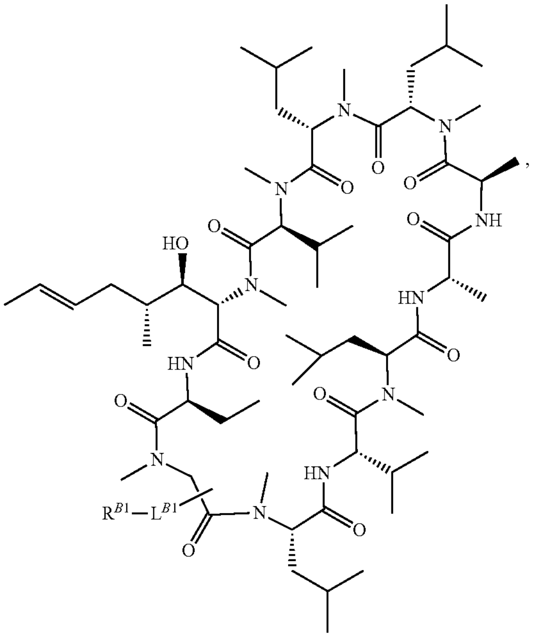
,
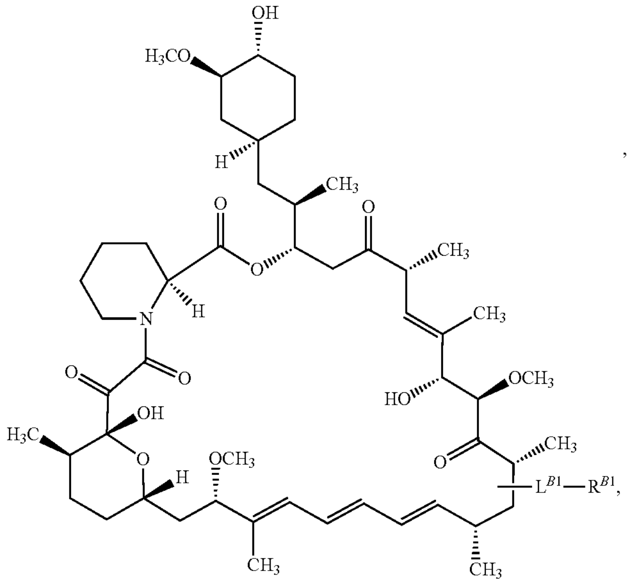
,
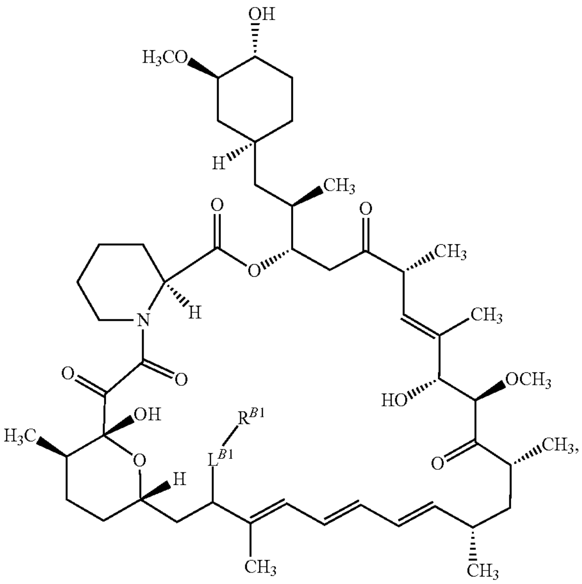
, -continued
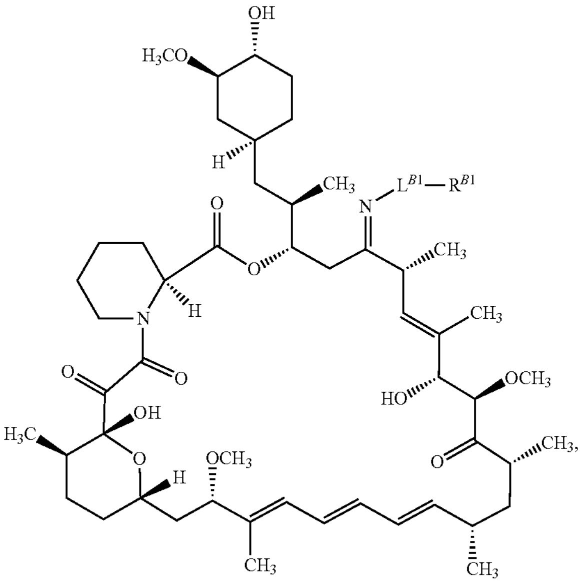
or
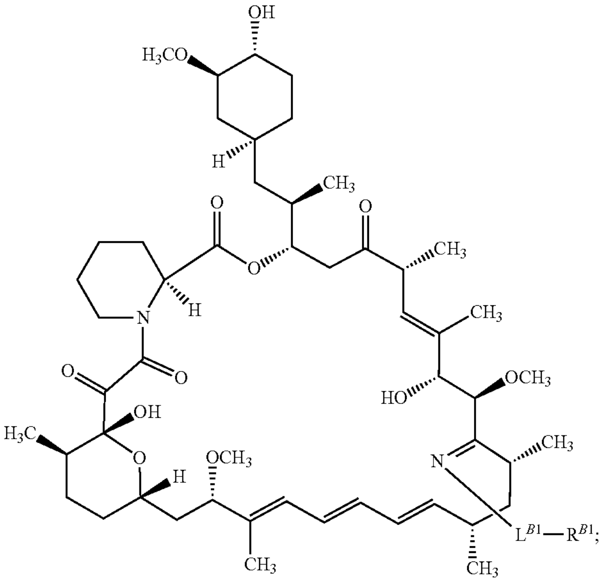
;

or an analog thereof. In embodiments, the compound has the formula

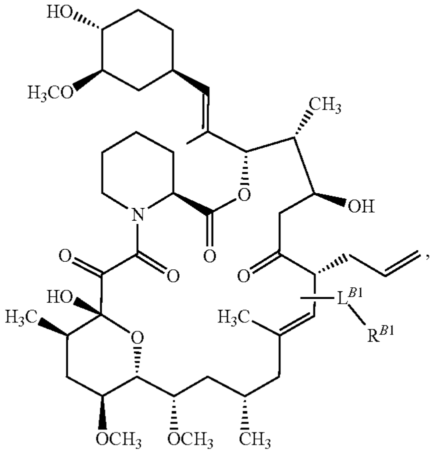

or an analog thereof. In embodiments, the compound has the formula

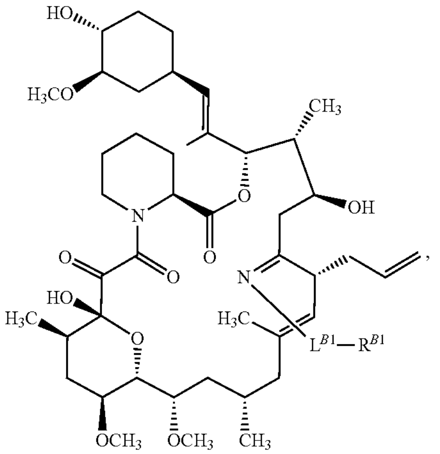

or an analog thereof. In embodiments, the compound has the formula

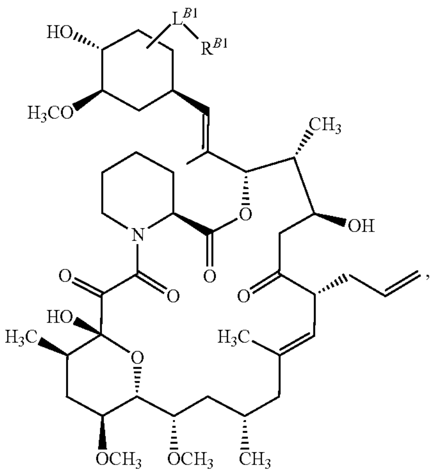

or an analog thereof. In embodiments, the compound has the formula

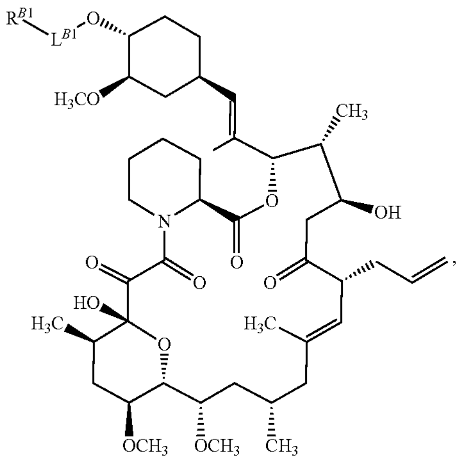

or an analog thereof. In embodiments, the compound has the formula

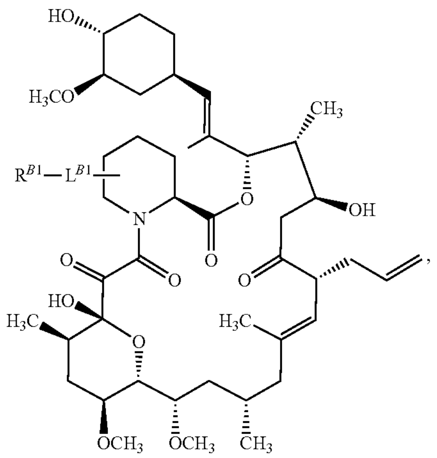

or an analog thereof. In embodiments, the compound has the formula

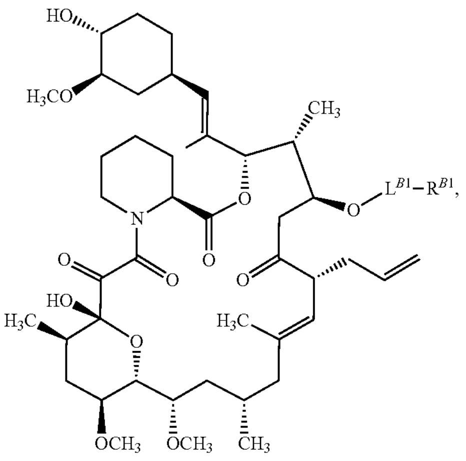
or an analog thereof. In embodiments, the compound has the formula
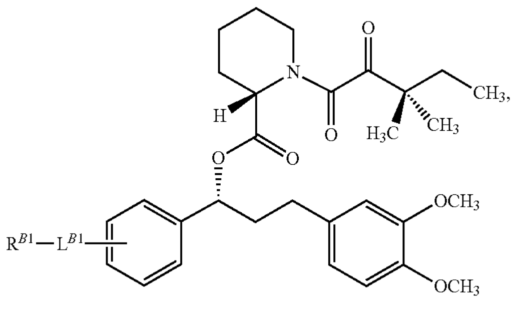
or an analog thereof. In embodiments, the compound has the formula
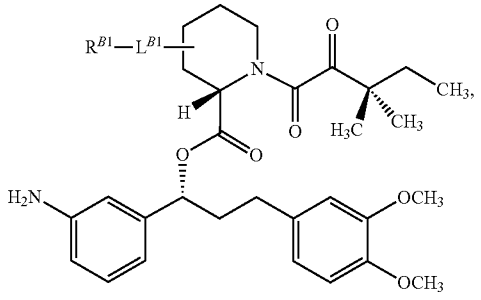
or an analog thereof. In embodiments, the compound has the formula
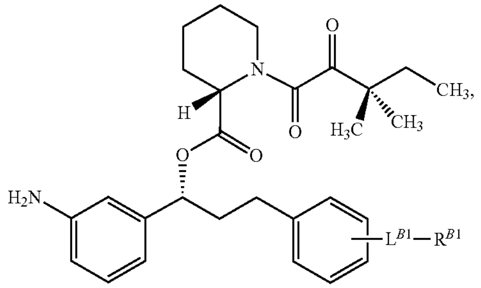
or an analog thereof. In embodiments, the compound has the formula
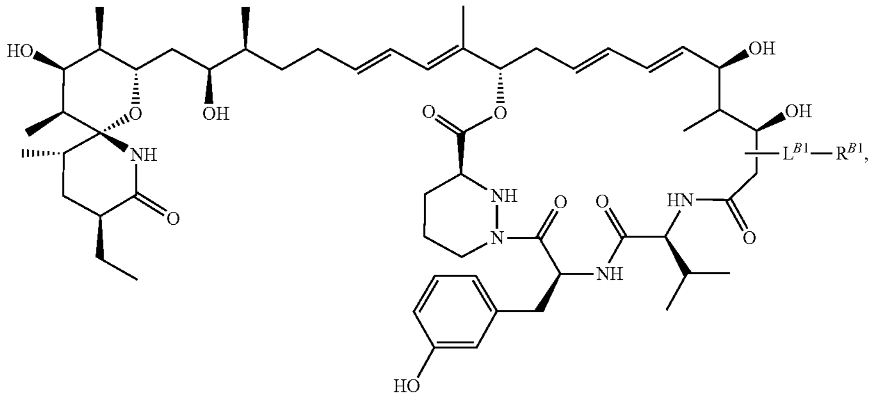

or an analog thereof. In embodiments, the compound has the formula
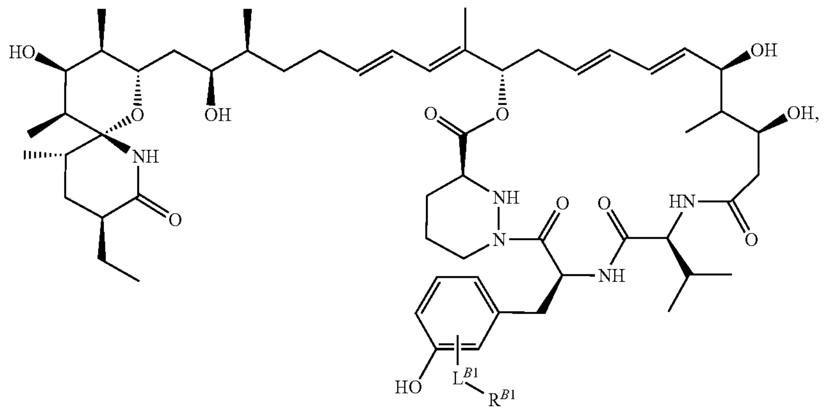
or an analog thereof. In embodiments, the compound has the formula
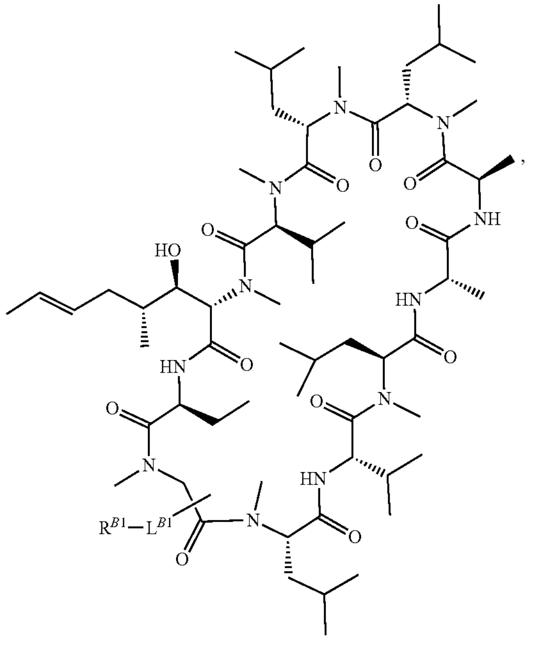
or an analog thereof. In embodiments, the compound has the formula
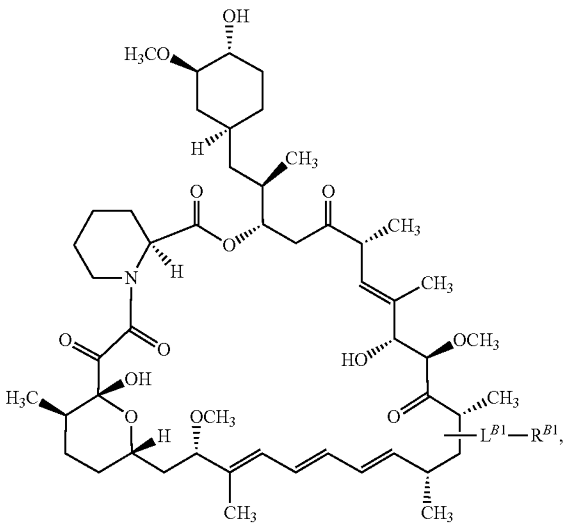

or an analog thereof. In embodiments, the compound has the formula
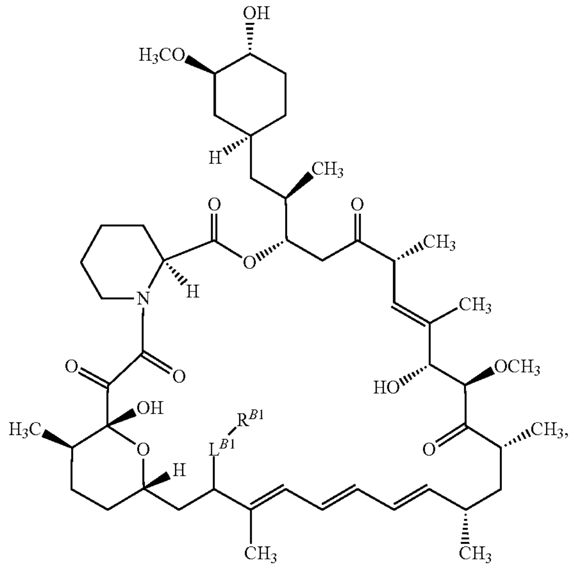
or an analog thereof. In embodiments, the compound has the formula
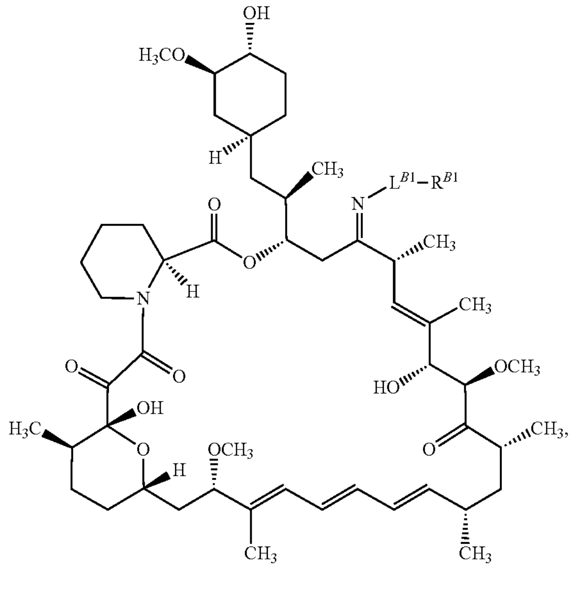
or an analog thereof. In embodiments, the compound has the formula
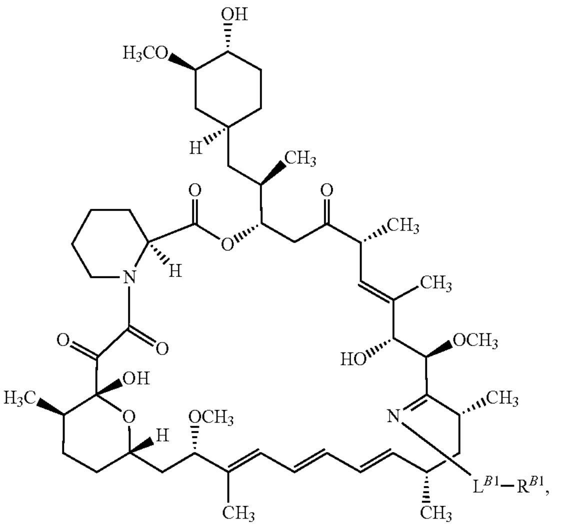
or an analog thereof. In embodiments, the compound has the formula
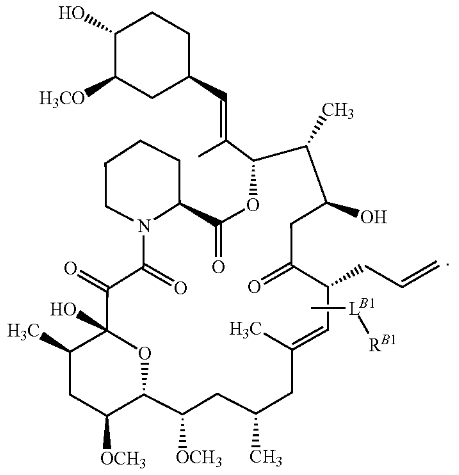
In embodiments, the compound has the formula
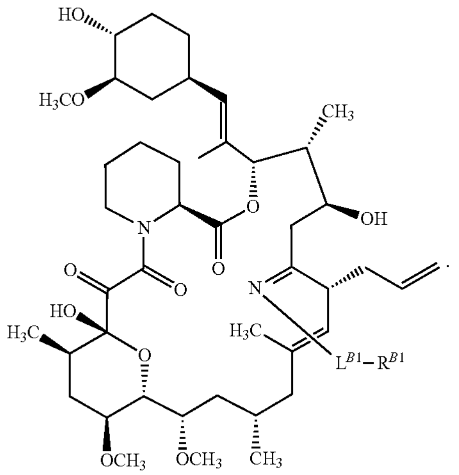

In embodiments, the compound has the formula
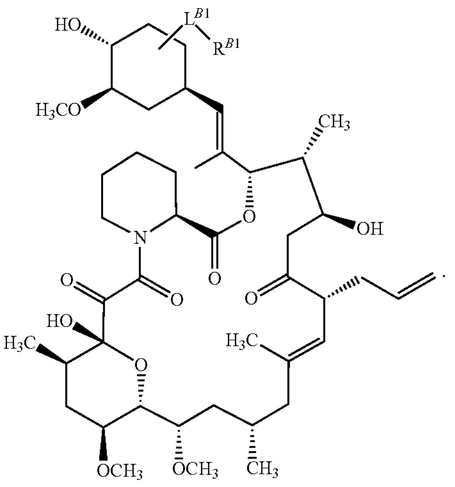
In embodiments, the compound has the formula
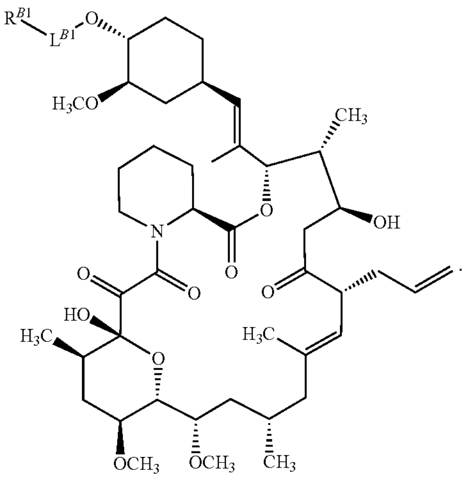
In embodiments, the compound has the formula
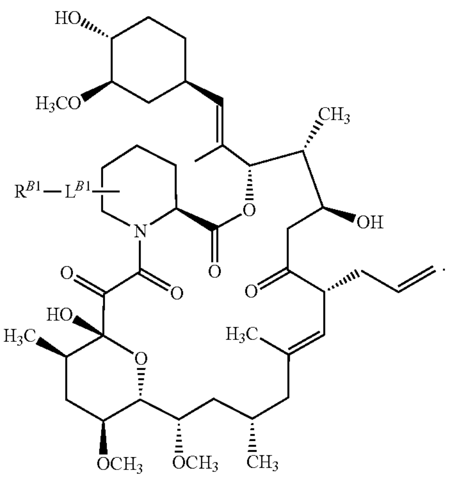
In embodiments, the compound has the formula
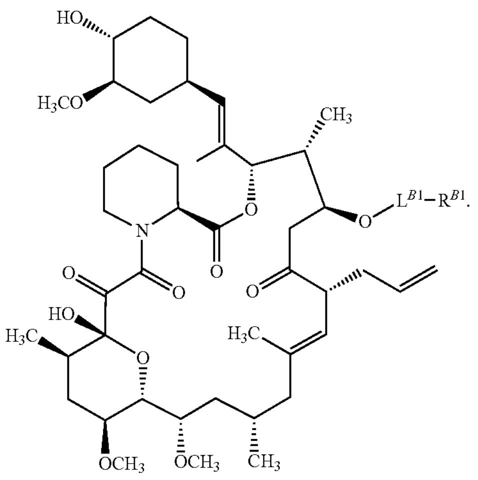
In embodiments, the compound has the formula
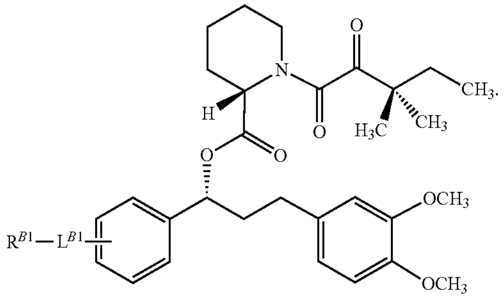
In embodiments, the compound has the formula
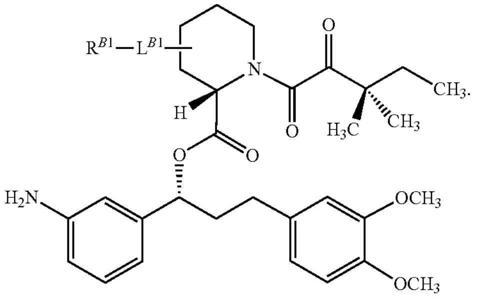

In embodiments, the compound has the formula
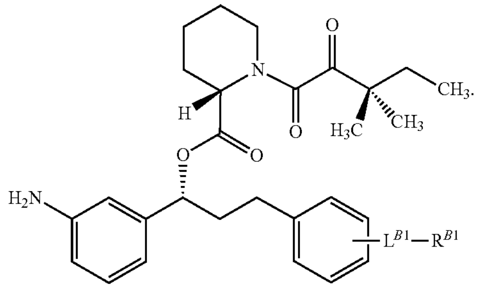
In embodiments, the compound has the formula
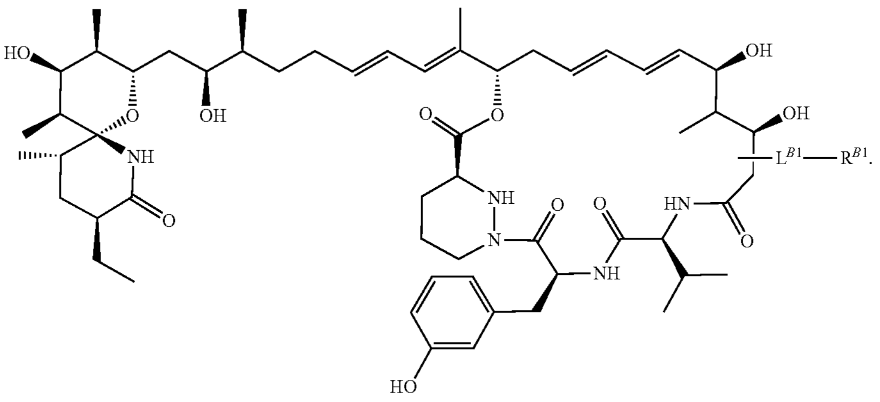
In embodiments, the compound has the formula
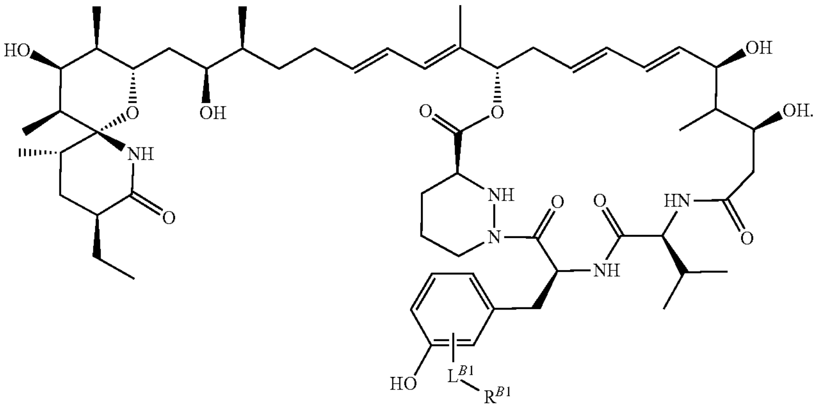

In embodiments, the compound has the formula
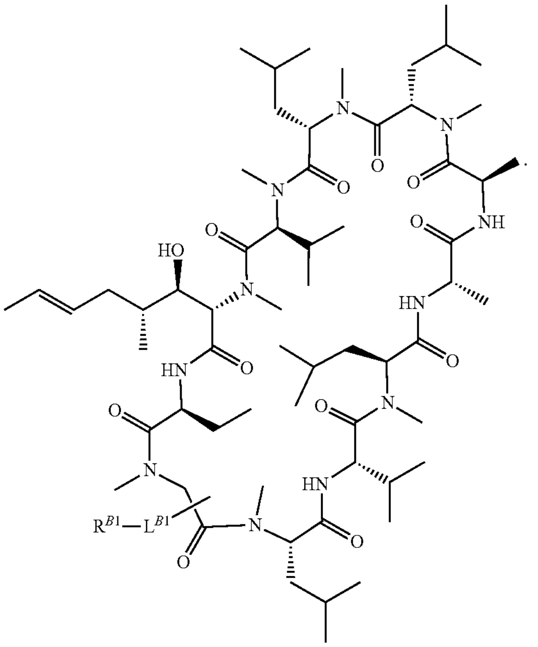
In embodiments, the compound has the formula
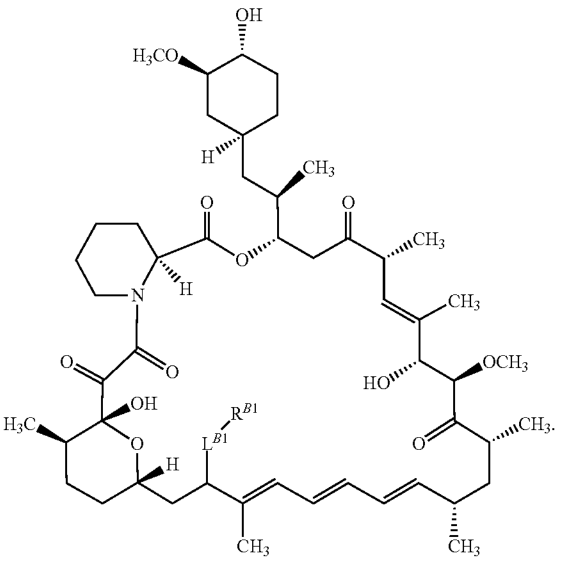
In embodiments, the compound has the formula
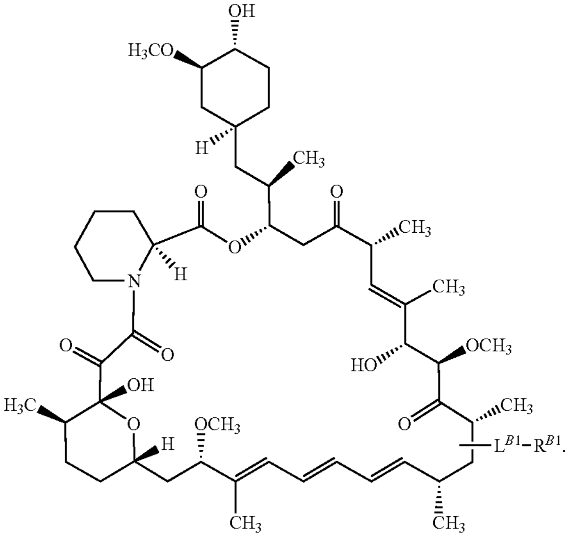
In embodiments, the compound has the formula
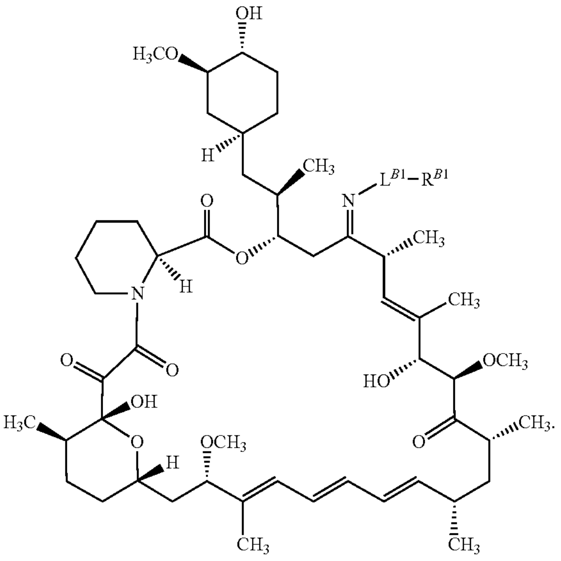

In embodiments, the compound has the formula

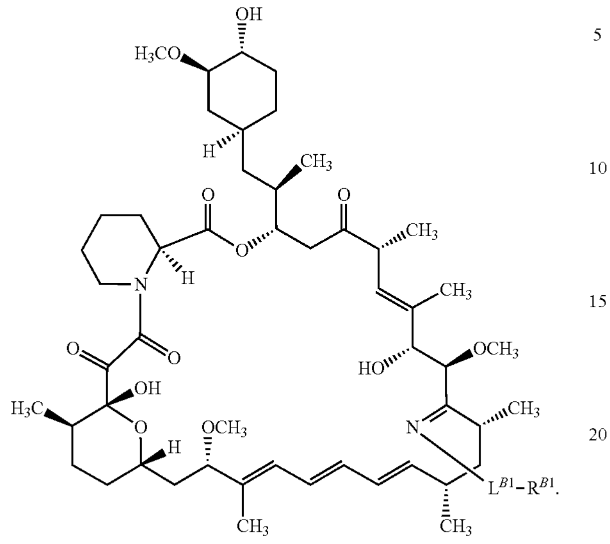

In embodiments, $A^B$ is a cyclophilin-binding moiety or an FKBP-binding moiety. In embodiments, $A^B$ is a cyclophilin-binding moiety. In embodiments, $A^B$ is a cyclophilin-binding moiety or an FKBP-binding moiety. In embodiments, $A^B$ is a cyclophilin-binding moiety. In embodiments, $A^B$ is an FKBP-binding moiety. In embodiments, the FKBP is FKBP12. In embodiments, the FKBP-binding moiety is an FK506 moiety, or an analog thereof.

In embodiments, the immunophilin-binding moiety is

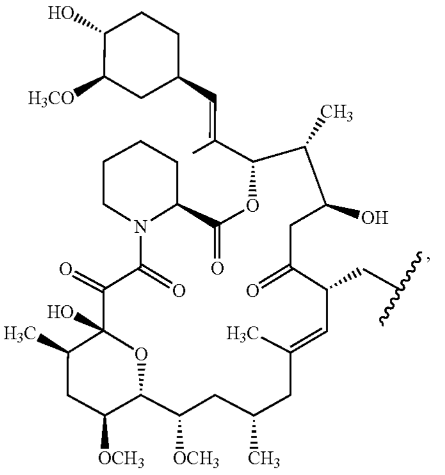

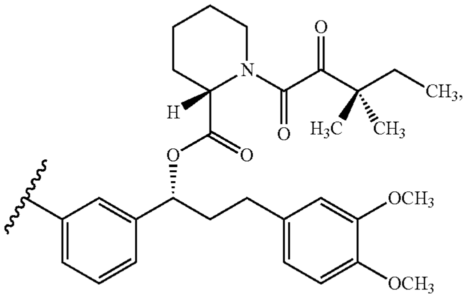

-continued

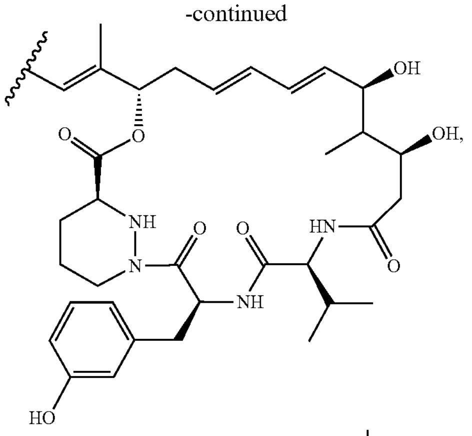

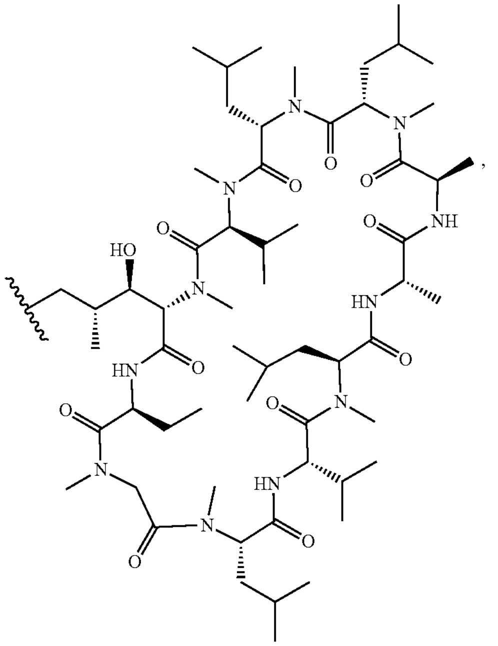

or

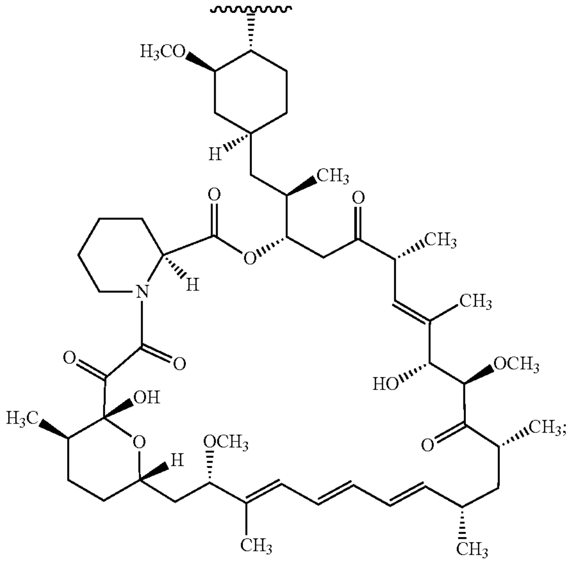 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or an analog thereof. In embodiments, the immunophilin-binding moiety is

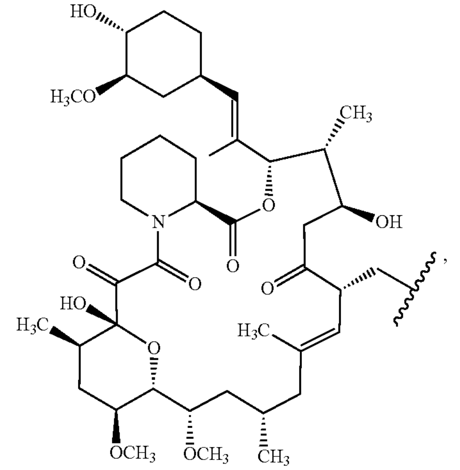 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof. In embodiments, the immunophilin-binding moiety is

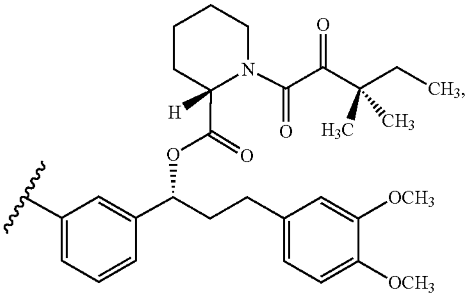

or an analog thereof. In embodiments, the immunophilin-binding moiety is

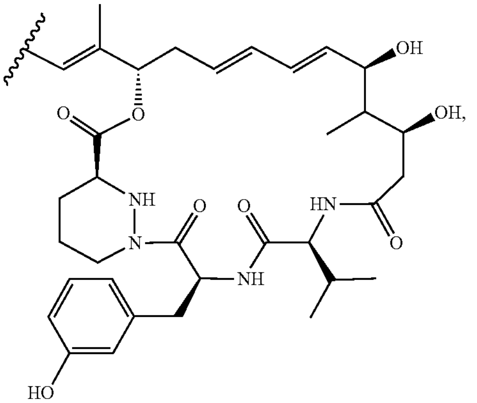 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]

or an analog thereof. In embodiments, the immunophilin-binding moiety is

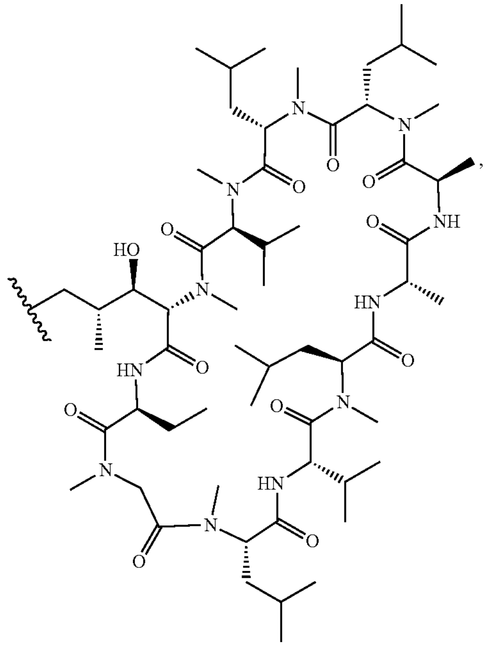 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

or an analog thereof. In embodiments, the immunophilin-binding moiety is

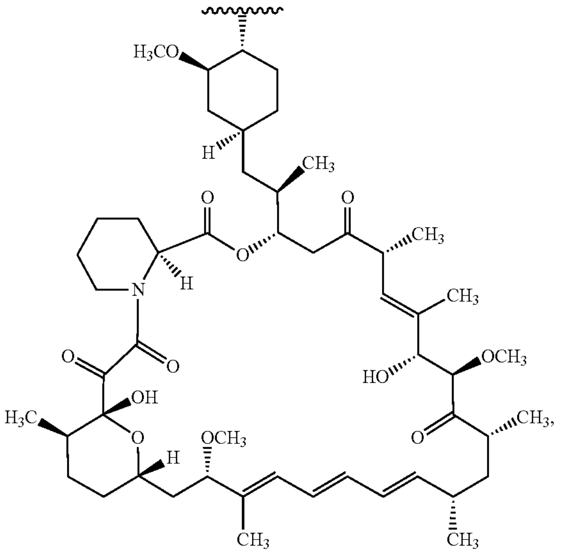 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or an analog thereof. In embodiments, the immunophilin-binding moiety is

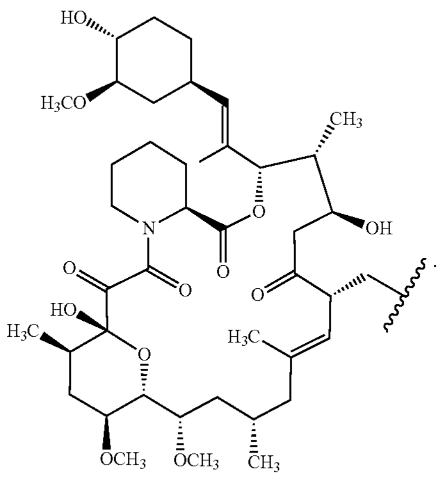 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
In embodiments, the immunophilin-binding moiety is
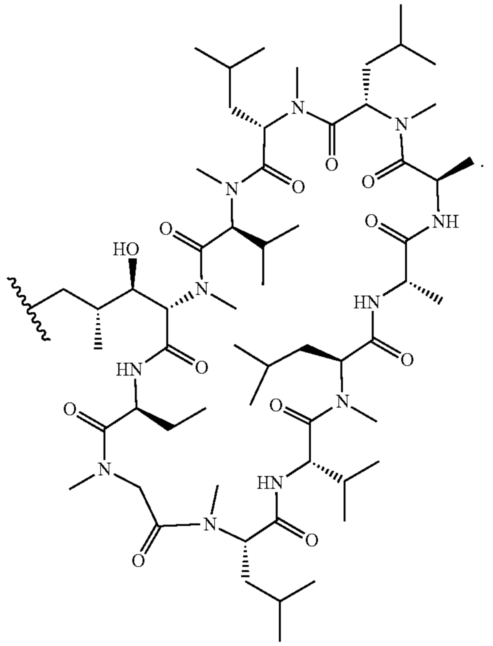
In embodiments, the immunophilin-binding moiety is
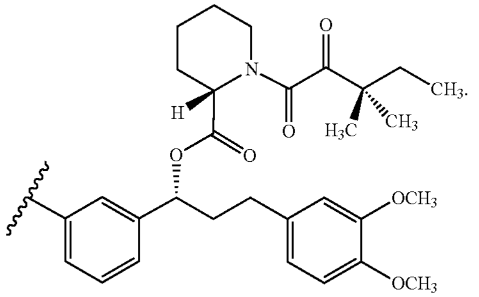
In embodiments, the immunophilin-binding moiety is
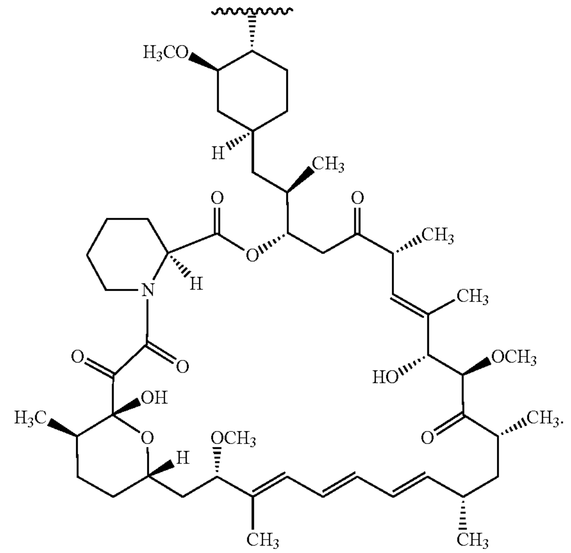
In embodiments, the immunophilin-binding moiety is
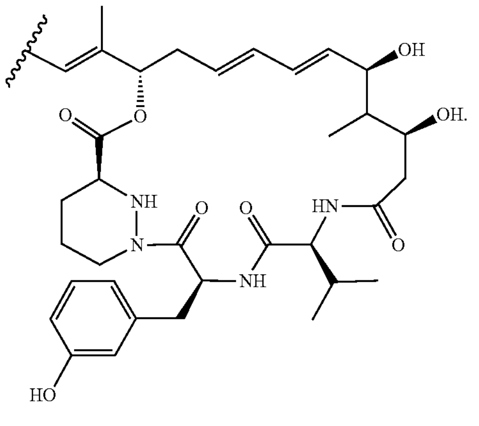 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
In embodiments, the immunophilin-binding moiety is
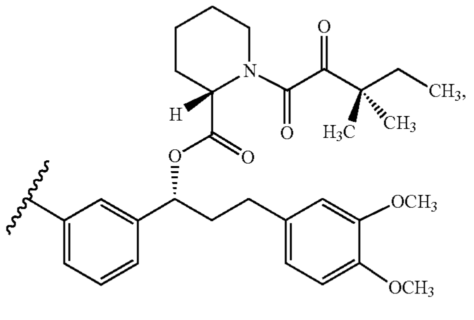

-continued
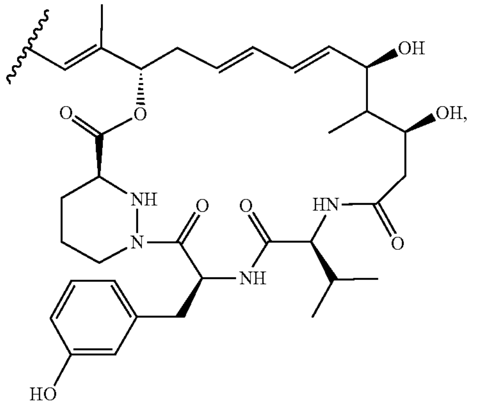
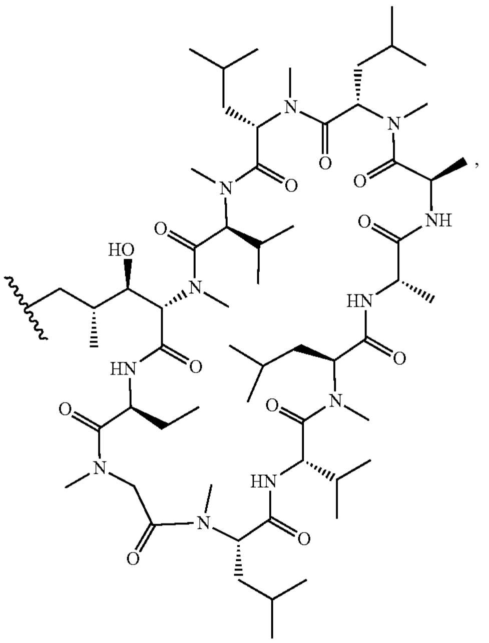
or
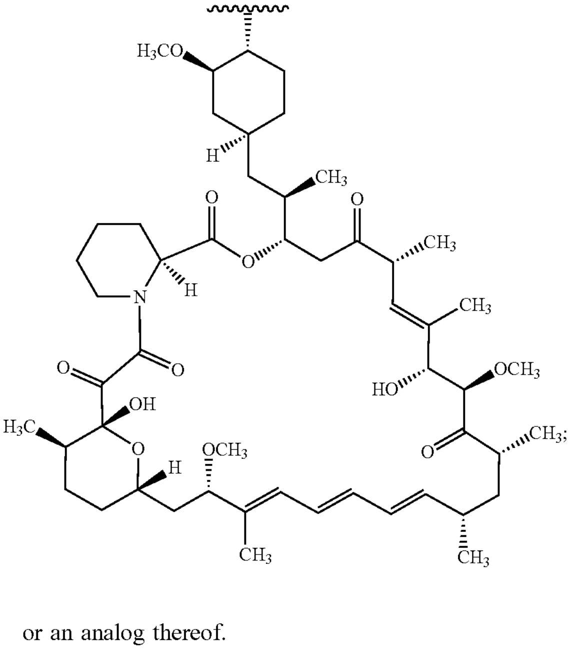
or an analog thereof.
In embodiments, the FKBP-binding moiety is
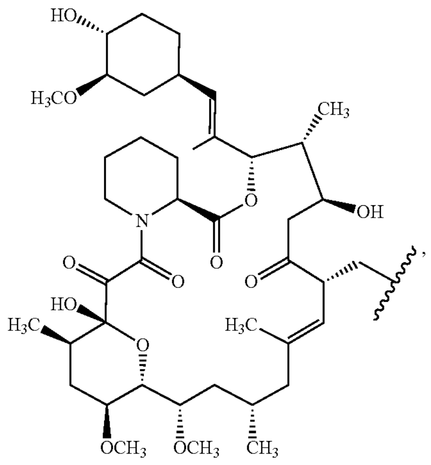 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
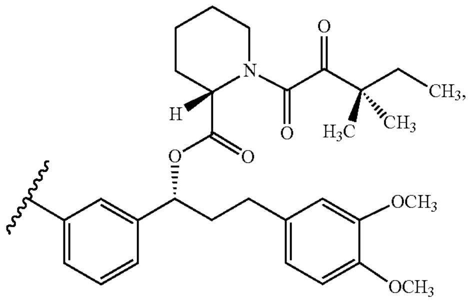
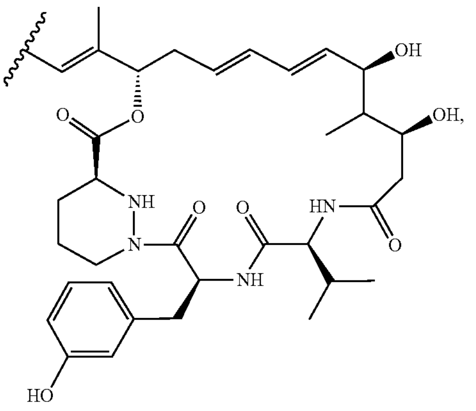 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
or -continued
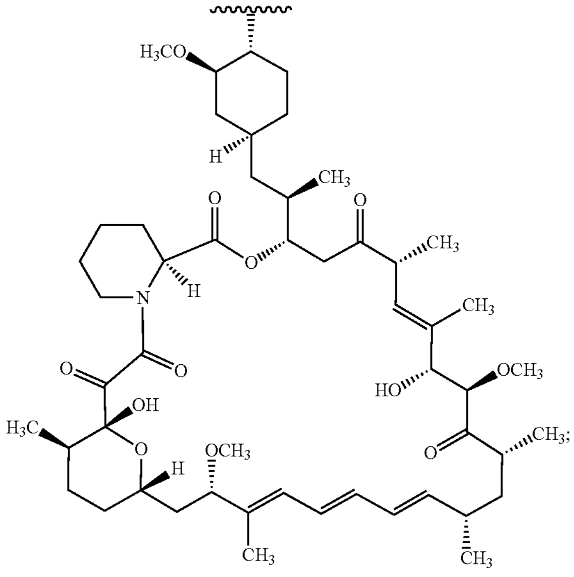
or an analog thereof. In embodiments, the FKBP-binding moiety is
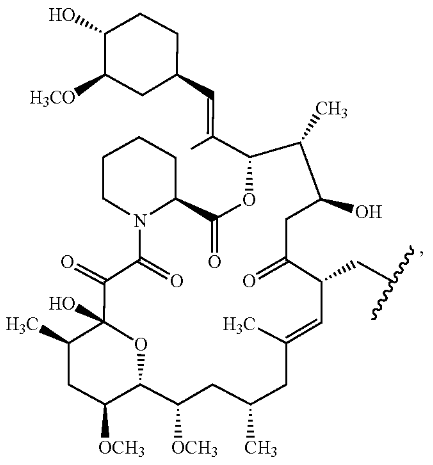
or an analog thereof. In embodiments, the FKBP-binding moiety is
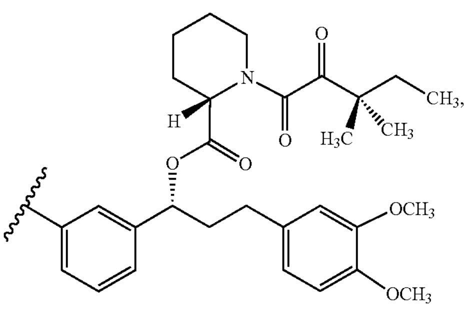
or an analog thereof. In embodiments, the FKBP-binding moiety is
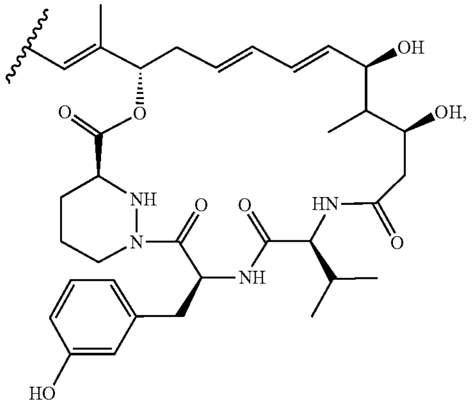
or an analog thereof. In embodiments, the FKBP-binding moiety is
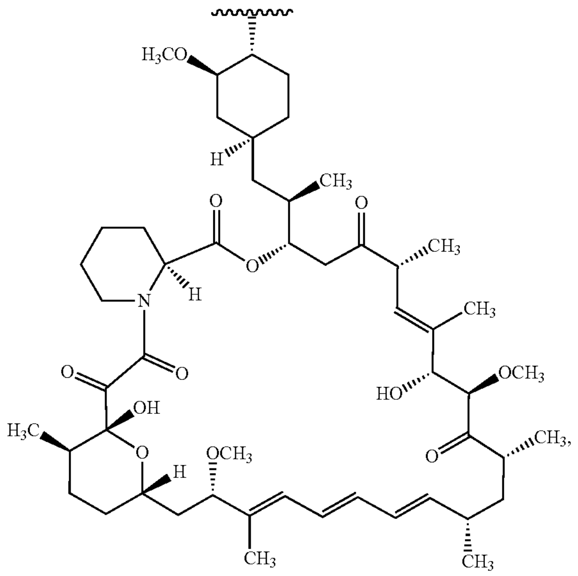 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
or an analog thereof.

In embodiments, the cyclophilin-binding moiety is
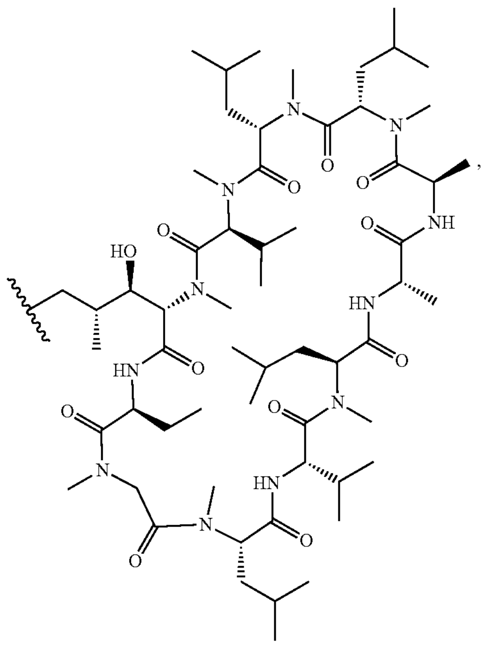 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
or an analog thereof.
In embodiments, the immunophilin-binding moiety is
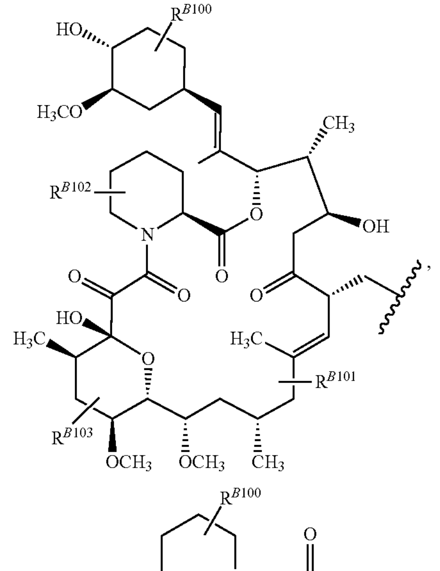
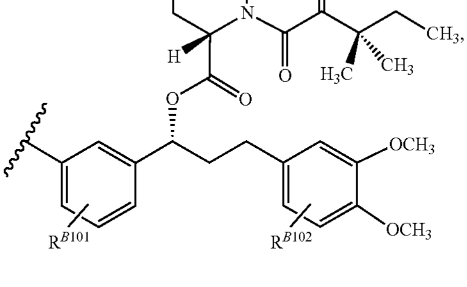
-continued
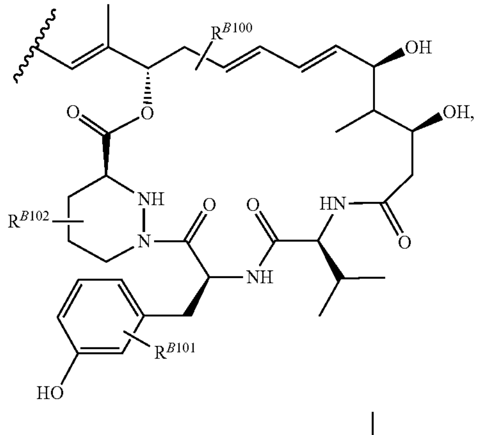
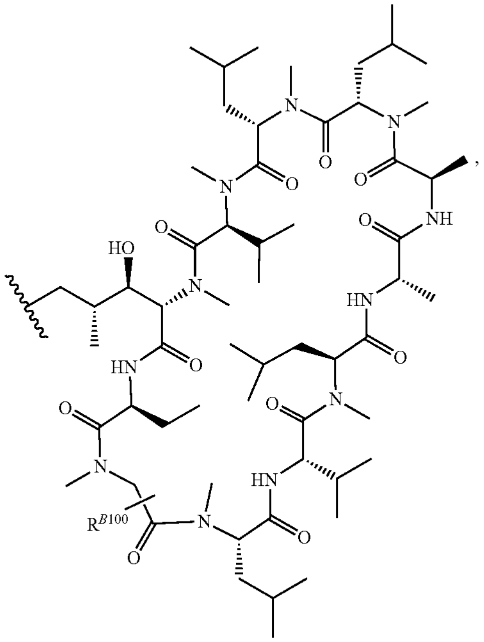
, or
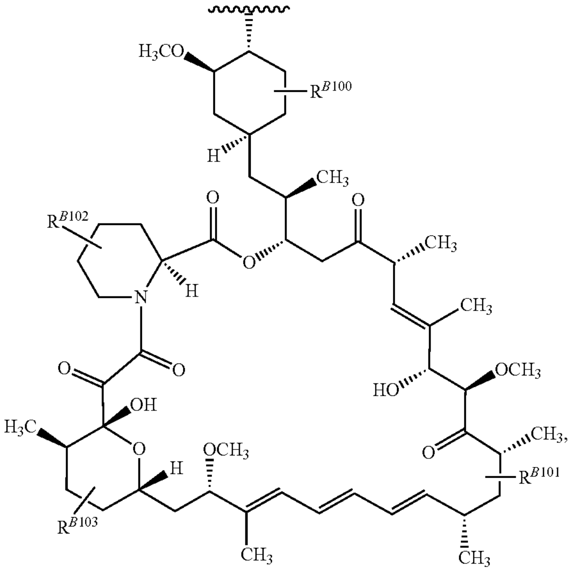
wherein $R^{B100}$, $R^{B101}$, $R^{B102}$, and $R^{B103}$ are as described herein and may be bonded to any atom in the ring ($R^{B100}$, $R^{B101}$, $R^{B102}$, and $R^{B103}$ are floating substituents). In embodiments, the immunophilin-binding moiety is

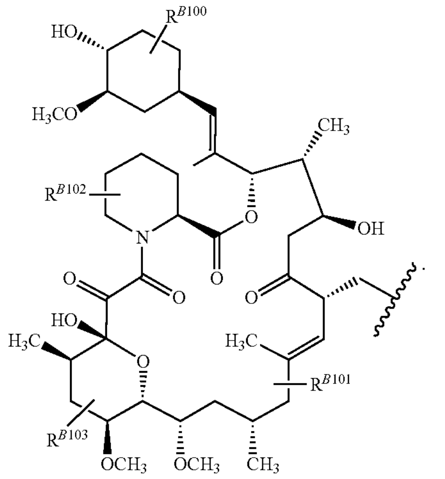

$R^{B100}$, $R^{B101}$, $R^{B102}$, and $R^{B103}$ are as described herein. In embodiments, the immunophilin-binding moiety is

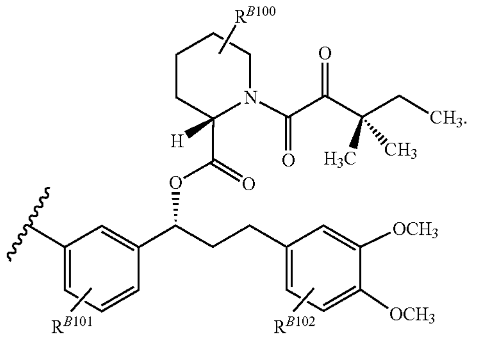

$R^{B100}$, $R^{B101}$, and $R^{B102}$ are as described herein. In embodiments, the immunophilin-binding moiety is

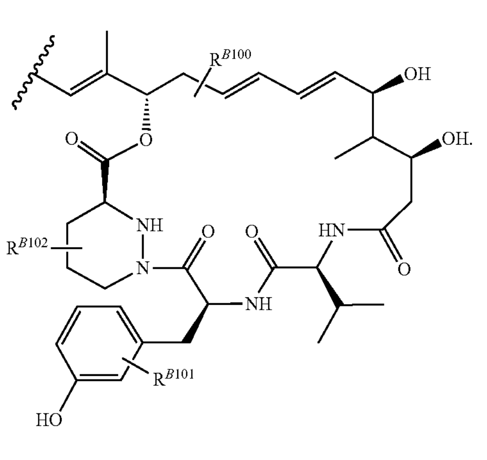

$R^{B100}$, $R^{B101}$, and $R^{B102}$ are as described herein. In embodiments, the immunophilin-binding moiety is

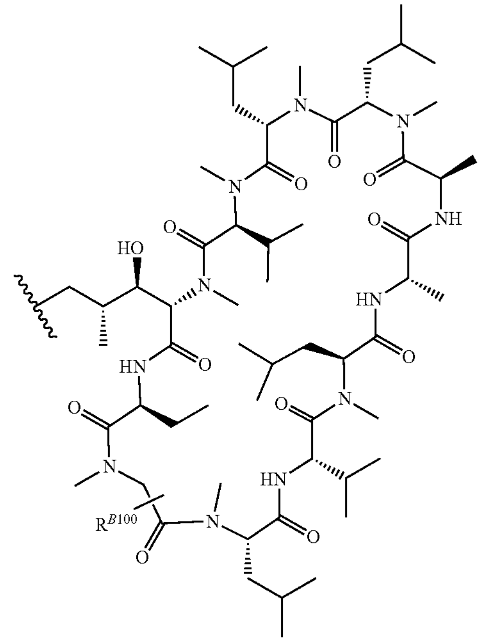

$R^{B10o}$ is as described herein. In embodiments, the immunophilin-binding moiety is

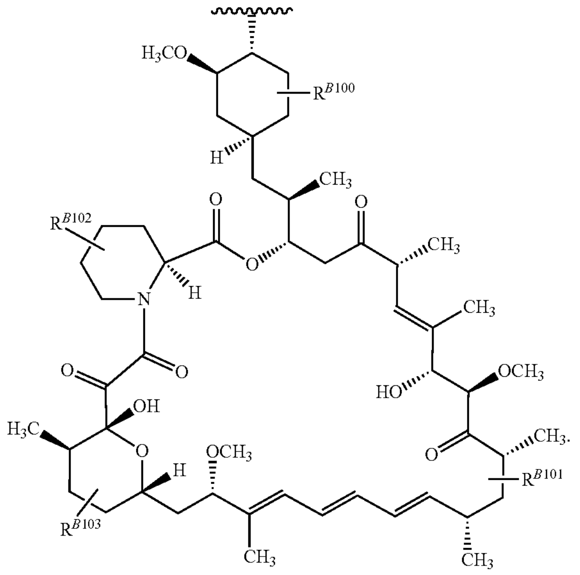

$R^{B100}$, $R^{B101}$, $R^{B102}$, and $R^{B103}$ are as described herein.

In embodiments, the immunophilin-binding moiety is not

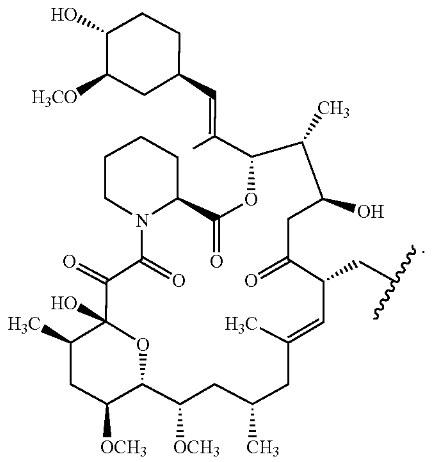 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

$R^{B100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B100}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B100}$ is substituted with a plurality of groups selected from substituent groups, size-limited substituent groups, and lower substituent groups; each substituent group, size-limited substituent group, and/or lower substituent group may optionally be different. In embodiments, when $R^{B100}$ is substituted, it is substituted with at least one substituent group. In embodiments, when $R^{B100}$ is substituted, it is substituted with at least one size-limited substituent group. In embodiments, when $R^{B10o}$ is substituted, it is substituted with at least one lower substituent group.

In embodiments, $R^{B100}$ is independently hydrogen. In embodiments, $R^{B100}$ is independently halogen. In embodiments, $R^{B100}$ is independently —$CCl_3$. In embodiments, $R^{B100}$ independently —$CBr_3$. In embodiments, $R^{B100}$ is independently —$CF_3$. In embodiments, $R^{B100}$ is independently —$CI_3$. In embodiments, $R^{B100}$ is independently —$CH_2Cl$. In embodiments, $R^{B100}$ is independently —$CH_2Br$. In embodiments, $R^{B100}$ is independently —$CH_2F$. In embodiments, $R^{B100}$ is independently —$CH_2I$. In embodiments, $R^{B100}$ is independently —$CHCl_2$. In embodiments, $R^{B100}$ is independently —$CHBr_2$. In embodiments, $R^{B100}$ independently —$CHF_2$. In embodiments, $R^{B100}$ is independently —$CHI_2$. In embodiments, $R^{B100}$ is independently —CN. In embodiments, $R^{B100}$ is independently —OH. In embodiments, $R^{B100}$ is independently —$NH_2$. In embodiments, $R^{B100}$ is independently —COOH. In embodiments, $R^{B100}$ is independently —$CONH_2$. In embodiments, $R^{B100}$ is independently —$NO_2$. In embodiments, $R^{B100}$ is independently —SH. In embodiments, $R^{B100}$ is independently —$SO_3H$. In embodiments, $R^{B100}$ is independently —$SO_4H$. In embodiments, $R^{B100}$ independently —$SO_2NH_2$. In embodiments, $R^{B100}$ is independently —$NHNH_2$. In embodiments, $R^{B100}$ is independently —$ONH_2$. In embodiments, $R^{B100}$ is independently —NHC(O)$NHNH_2$. In embodiments, $R^{B100}$ is independently —NHC(O)$NH_2$. In embodiments, $R^{B100}$ independently —$NHSO_2H$. In embodiments, $R^{B100}$ is independently —NHC(O)H. In embodiments, $R^{B100}$ is independently —NHC(O)OH. In embodiments, $R^{B100}$ is independently —NHC(NH)H. In embodiments, $R^{B100}$ is independently —NHC(NH)$NH_2$. In embodiments, $R^{B100}$ is independently —NHOH. In embodiments, $R^{B100}$ is independently —$OCCl_3$. In embodiments, $R^{B100}$ is independently —$OCBr_3$. In embodiments, $R^{B100}$ is independently —$OCF_3$. In embodiments, $R^{B100}$ is independently —$OCI_3$. In embodiments, $R^{B100}$ independently —$OCH_2Cl$. In embodiments, $R^{B100}$ is independently —$OCH_2Br$. In embodiments, $R^{B100}$ is independently —$OCH_2F$. In embodiments, $R^{B100}$ is independently —$OCH_2I$. In embodiments, $R^{B100}$ is independently —$OCHCl_2$. In embodiments, $R^{B100}$ is independently —$OCHBr_2$. In embodiments, $R^{B100}$ is independently —$OCHF_2$. In embodiments, $R^{B100}$ independently —$OCHI_2$. In embodiments, $R^{B100}$ is independently —$N_3$. In embodiments, $R^{B100}$ is independently substituted or unsubstituted alkyl (e.g., $C_1$-$C_8$, $C_1$-$C_6$, $C_1$-$C_4$, or $C_1$-$C_2$). In embodiments, $R^{B100}$ is independently substituted alkyl (e.g., $C_1$-$C_8$, $C_1$-$C_6$, $C_1$-$C_4$, or $C_1$-$C_2$). In embodiments, $R^{B100}$ is independently unsubstituted alkyl (e.g., $C_1$-$C_8$, $C_1$-$C_6$, $C_1$-$C_4$, or $C_1$-$C_2$). In embodiments, $R^{B100}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B100}$ is independently substituted heteroalkyl (e.g., 2 to 8 membered, 2 to 6 membered, 4 to 6 membered, 2 to 3 membered, or 4 to 5 membered). In embodiments, $R^{B100}$ is independently unsubstituted heteroalkyl (e.g., 2 to 8 membered, 2 to 6 membered, 4 to 6 membered, 2 to 3 membered, or 4 to 5 membered). In embodiments, $R^{B100}$ is independently substituted or unsubstituted cycloalkyl (e.g., $C_3$-$C_8$, $C_3$-$C_6$, $C_4$-$C_6$, or $C_5$-$C_6$). In embodiments, $R^{B100}$ is independently substituted cycloalkyl (e.g., $C_3$-$C_8$, $C_3$-$C_6$, $C_4$-$C_6$, or $C_5$-$C_6$). In embodiments, $R^{B100}$ is independently unsubstituted cycloalkyl (e.g., $C_3$-$C_8$, $C_3$-$C_6$, $C_4$-$C_6$, or $C_5$-$C_6$). In embodiments, $R^{B100}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B100}$ is independently substituted heterocycloalkyl (e.g., 3 to 8 membered, 3 to 6 membered, 4 to 6 membered, 4 to 5 membered, or 5 to 6 membered). In embodiments, $R^{B100}$ is independently unsubstituted heterocycloalkyl (e.g., 3 to 8 membered, 3 to 6 membered, 4 to 6 membered, 4 to 5 membered, or 5 to 6 membered). In embodiments, $R^{B100}$ is independently substituted or unsubstituted aryl (e.g., $C_6$-$C_{10}$ or phenyl). In embodiments, $R^{B100}$ is independently substituted aryl (e.g., $C_6$-$C_{10}$ or phenyl). In embodiments, $R^{B100}$ is independently unsubstituted aryl (e.g., $C_6$-$C_{10}$ or phenyl). In embodiments, $R^{B100}$ is independently substituted or unsubstituted heteroaryl (e.g., 5 to 10 membered, 5 to 9 membered, or 5 to 6 membered). In embodiments, $R^{B100}$ is independently substituted heteroaryl (e.g., 5 to 10 membered, 5 to 9 membered, or 5 to 6 membered). In embodiments, $R^{B100}$ is independently unsubstituted heteroaryl (e.g., 5 to 10 membered, 5 to 9 membered, or 5 to 6 membered).

$R^{B101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B101}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B101}$ is substituted with a plurality of groups selected from substituent groups, size-limited substituent groups, and lower substituent groups; each substituent group, size-limited substituent group, and/or lower substituent group may optionally be different. In embodiments, when $R^{B101}$ is substituted, it is substituted with at least one substituent group. In embodiments, when $R^{B101}$ is substituted, it is substituted with at least one size-limited substituent group. In embodiments, when $R^{B101}$ is substituted, it is substituted with at least one lower substituent group.

In embodiments, $R^{B101}$ is independently hydrogen. In embodiments, $R^{B101}$ is independently halogen. In embodiments, $R^{B101}$ is independently —$CCl_3$. In embodiments, $R^{B101}$ is independently —$CBr_3$. In embodiments, $R^{B101}$ is independently —$CF_3$. In embodiments, $R^{B101}$ is independently —$CI_3$. In embodiments, $R^{B101}$ is independently —$CH_2Cl$. In embodiments, $R^{B101}$ is independently —$CH_2Br$. In embodiments, $R^{B101}$ is independently —$CH_2F$. In embodiments, $R^{B101}$ is independently —$CH_2I$. In embodiments, $R^{B101}$ is independently —$CHCl_2$. In embodiments, $R^{B101}$ is independently —$CHBr_2$. In embodiments, $R^{B101}$ is independently —$CHF_2$. In embodiments, $R^{B101}$ is independently —$CHI_2$. In embodiments, $R^{B101}$ is independently —CN. In embodiments, $R^{B101}$ is independently —OH. In embodiments, $R^{B101}$ is independently —$NH_2$. In embodiments, $R^{B101}$ is independently —COOH. In embodiments, $R^{B101}$ is independently —$CONH_2$. In embodiments, $R^{B101}$ is independently —$NO_2$. In embodiments, $R^{B101}$ is independently —SH. In embodiments, $R^{B101}$ is independently —$SO_3H$. In embodiments, $R^{B101}$ is independently —$SO_4H$. In embodiments, $R^{B101}$ is independently —$SO_2NH_2$. In embodiments, $R^{B101}$ is independently —$NHNH_2$. In embodiments, $R^{B101}$ is independently —$ONH_2$. In embodiments, $R^{B101}$ is independently —NHC(O)$NHNH_2$. In embodiments, $R^{B101}$ is independently —NHC(O)$NH_2$. In embodiments, $R^{B101}$ is independently —$NHSO_2H$. In embodiments, $R^{B101}$ is independently —NHC(O)H. In embodiments, $R^{B101}$ is independently —NHC(O)OH. In embodiments, $R^{B101}$ is independently —NHC(NH)H. In embodiments, $R^{B101}$ is independently —NHC(NH)$NH_2$. In embodiments, $R^{B101}$ is independently —NHOH. In embodiments, $R^{B101}$ is independently —$OCCl_3$. In embodiments, $R^{B101}$ is independently —$OCBr_3$. In embodiments, $R^{B101}$ is independently —$OCF_3$. In embodiments, $R^{B101}$ is independently —$OCI_3$. In embodiments, $R^{B101}$ is independently —$OCH_2Cl$. In embodiments, $R^{B101}$ is independently —$OCH_2Br$. In embodiments, $R^{B101}$ is independently —$OCH_2F$. In embodiments, $R^{B101}$ is independently —$OCH_2I$. In embodiments, $R^{B101}$ is independently —$OCHCl_2$. In embodiments, $R^{B101}$ is independently —$OCHBr_2$. In embodiments, $R^{B101}$ is independently —$OCHF_2$. In embodiments, $R^{B101}$ is independently —$OCHI_2$. In embodiments, $R^{B101}$ is independently —$N_3$. In embodiments, $R^{B101}$ is independently substituted or unsubstituted alkyl (e.g., $C_1$-$C_8$, $C_1$-$C_6$, $C_1$-$C_4$, or $C_1$-$C_2$). In embodiments, $R^{B101}$ is independently substituted alkyl (e.g., $C_1$-$C_8$, $C_1$-$C_6$, $C_1$-$C_4$, or $C_1$-$C_2$). In embodiments, $R^{B101}$ is independently unsubstituted alkyl (e.g., $C_1$-$C_8$, $C_1$-$C_6$, $C_1$-$C_4$, or $C_1$-$C_2$). In embodiments, $R^{B101}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B101}$ is independently substituted heteroalkyl (e.g., 2 to 8 membered, 2 to 6 membered, 4 to 6 membered, 2 to 3 membered, or 4 to 5 membered). In embodiments, $R^{B101}$ is independently unsubstituted heteroalkyl (e.g., 2 to 8 membered, 2 to 6 membered, 4 to 6 membered, 2 to 3 membered, or 4 to 5 membered). In embodiments, $R^{B101}$ is independently substituted or unsubstituted cycloalkyl (e.g., $C_3$-$C_8$, $C_3$-$C_6$, $C_4$-$C_6$, or $C_5$-$C_6$). In embodiments, $R^{B101}$ is independently substituted cycloalkyl (e.g., $C_3$-$C_8$, $C_3$-$C_6$, $C_4$-$C_6$, or $C_5$-$C_6$). In embodiments, $R^{B101}$ is independently unsubstituted cycloalkyl (e.g., $C_3$-$C_8$, $C_3$-$C_6$, $C_4$-$C_6$, or $C_5$-$C_6$). In embodiments, $R^{B101}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B101}$ is independently substituted heterocycloalkyl (e.g., 3 to 8 membered, 3 to 6 membered, 4 to 6 membered, 4 to 5 membered, or 5 to 6 membered). In embodiments, $R^{B101}$ is independently unsubstituted heterocycloalkyl (e.g., 3 to 8 membered, 3 to 6 membered, 4 to 6 membered, 4 to 5 membered, or 5 to 6 membered). In embodiments, $R^{B101}$ is independently substituted or unsubstituted aryl (e.g., $C_6$-$C_{10}$ or phenyl). In embodiments, $R^{B101}$ is independently substituted aryl (e.g., $C_6$-$C_{10}$ or phenyl). In embodiments, $R^{B101}$ is independently unsubstituted aryl (e.g., $C_6$-$C_{10}$ or phenyl). In embodiments, $R^{B101}$ is independently substituted or unsubstituted heteroaryl (e.g., 5 to 10 membered, 5 to 9 membered, or 5 to 6 membered). In embodiments, $R^{B101}$ is independently substituted heteroaryl (e.g., 5 to 10 membered, 5 to 9 membered, or 5 to 6 membered). In embodiments, $R^{B101}$ is independently unsubstituted heteroaryl (e.g., 5 to 10 membered, 5 to 9 membered, or 5 to 6 membered).

$R^{B102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B102}$ is substituted with a plurality of groups selected from substituent groups, size-limited substituent groups, and lower substituent groups; each substituent group, size-limited substituent group, and/or lower substituent group may optionally be different. In embodiments, when $R^{B102}$ is substituted, it is substituted with at least one substituent group. In embodiments, when $R^{B102}$ is substituted, it is substituted with at least one size-limited substituent group. In embodiments, when $R^{B102}$ is substituted, it is substituted with at least one lower substituent group.

In embodiments, $R^{B102}$ is independently hydrogen. In embodiments, $R^{B102}$ is independently halogen. In embodiments, $R^{B102}$ is independently —$CCl_3$. In embodiments, $R^{B102}$ independently —$CBr_3$. In embodiments, $R^{B102}$ is independently —$CF_3$. In embodiments, $R^{B102}$ is independently —$CI_3$. In embodiments, $R^{B102}$ is independently —$CH_2Cl$. In embodiments, $R^{B102}$ is independently —$CH_2Br$. In embodiments, $R^{B102}$ is independently —$CH_2F$. In embodiments, $R^{B102}$ is independently —$CH_2I$. In embodiments, $R^{B102}$ is independently —$CHCl_2$. In embodiments, $R^{B102}$ is independently —$CHBr_2$. In embodiments, $R^{B102}$ independently —$CHF_2$. In embodiments, $R^{B102}$ is independently —$CHI_2$. In embodiments, $R^{B102}$ is independently —CN. In embodiments, $R^{B102}$ is independently —OH. In embodiments, $R^{B102}$ is independently —$NH_2$. In embodiments, $R^{B102}$ is independently —COOH. In embodiments, $R^{B102}$ is independently —$CONH_2$. In embodiments, $R^{B102}$ is independently —$NO_2$. In embodiments, $R^{B102}$ is independently —SH. In embodiments, $R^{B102}$ is independently —$SO_3H$. In embodiments, $R^{B102}$ is independently —$SO_4H$. In embodiments, $R^{B102}$ independently —$SO_2NH_2$. In embodiments, $R^{B102}$ is independently —$NHNH_2$. In embodiments, $R^{B102}$ is independently —$ONH_2$. In embodiments, $R^{B102}$ is independently —NHC(O)$NHNH_2$. In embodiments, $R^{B102}$ is independently —NHC(O)$NH_2$. In embodiments, $R^{B102}$ independently —$NHSO_2H$. In embodiments, $R^{B102}$ is independently —NHC(O)H. In embodiments, $R^{B102}$ is independently —NHC(O)OH. In embodiments, $R^{B102}$ is independently —NHC(NH)H. In embodiments, $R^{B102}$ is independently —NHC(NH)$NH_2$. In embodiments, $R^{B102}$ is independently —NHOH. In embodiments, $R^{B102}$ is independently —$OCCl_3$. In embodiments, $R^{B102}$ is independently —$OCBr_3$. In embodiments, $R^{B102}$ is independently —$OCF_3$. In embodiments, $R^{B102}$ is independently —$OCI_3$. In embodiments, $R^{B102}$ independently —$OCH_2Cl$. In embodiments, $R^{B102}$ is independently —$OCH_2Br$. In embodiments, $R^{B102}$ is independently —$OCH_2F$. In embodiments, $R^{B102}$ is independently —$OCH_2I$. In embodiments, $R^{B102}$ is independently —$OCHCl_2$. In embodiments, $R^{B102}$ is independently —$OCHBr_2$. In embodiments, $R^{B1020}$ is independently —$OCHF_2$. In embodiments, $R^{B102}$ is independently —$OCHI_2$. In embodiments, $R^{B102}$ is independently —$N_3$. In embodiments, $R^{B102}$ is independently substituted or unsubstituted alkyl (e.g., $C_1$-$C_8$, $C_1$-$C_6$, $C_1$-$C_4$, or $C_1$-$C_2$). In embodiments, $R^{B102}$ is independently substituted alkyl (e.g., $C_1$-$C_8$, $C_1$-$C_6$, $C_1$-$C_4$, or $C_1$-$C_2$). In embodiments, $R^{B102}$ is independently unsubstituted alkyl (e.g., $C_1$-$C_8$, $C_1$-$C_6$, $C_1$-$C_4$, or $C_1$-$C_2$). In embodiments, $R^{B102}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B102}$ is independently substituted heteroalkyl (e.g., 2 to 8 membered, 2 to 6 membered, 4 to 6 membered, 2 to 3 membered, or 4 to 5 membered). In embodiments, $R^{B102}$ is independently unsubstituted heteroalkyl (e.g., 2 to 8 membered, 2 to 6 membered, 4 to 6 membered, 2 to 3 membered, or 4 to 5 membered). In embodiments, $R^{B102}$ is independently substituted or unsubstituted cycloalkyl (e.g., $C_3$-$C_8$, $C_3$-$C_6$, $C_4$-$C_6$, or $C_5$-$C_6$). In embodiments, $R^{B102}$ is independently substituted cycloalkyl (e.g., $C_3$-$C_8$, $C_3$-$C_6$, $C_4$-$C_6$, or $C_5$-$C_6$). In embodiments, $R^{B102}$ is independently unsubstituted cycloalkyl (e.g., $C_3$-$C_8$, $C_3$-$C_6$, $C_4$-$C_6$, or $C_5$-$C_6$). In embodiments, $R^{B102}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B102}$ is independently substituted heterocycloalkyl (e.g., 3 to 8 membered, 3 to 6 membered, 4 to 6 membered, 4 to 5 membered, or 5 to 6 membered). In embodiments, $R^{B102}$ is independently unsubstituted heterocycloalkyl (e.g., 3 to 8 membered, 3 to 6 membered, 4 to 6 membered, 4 to 5 membered, or 5 to 6 membered). In embodiments, $R^{B102}$ is independently substituted or unsubstituted aryl (e.g., $C_6$-$C_{10}$ or phenyl). In embodiments, $R^{B102}$ is independently substituted aryl (e.g., $C_6$-$C_{10}$ or phenyl). In embodiments, $R^{B102}$ is independently unsubstituted aryl (e.g., $C_6$-$C_{10}$ or phenyl). In embodiments, $R^{B102}$ is independently substituted or unsubstituted heteroaryl (e.g., 5 to 10 membered, 5 to 9 membered, or 5 to 6 membered). In embodiments, $R^{B102}$ is independently substituted heteroaryl (e.g., 5 to 10 membered, 5 to 9 membered, or 5 to 6 membered). In embodiments, $R^{B102}$ is independently unsubstituted heteroaryl (e.g., 5 to 10 membered, 5 to 9 membered, or 5 to 6 membered).

$R^{B103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B103}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B103}$ is substituted with a plurality of groups selected from substituent groups, size-limited substituent groups, and lower substituent groups; each substituent group, size-limited substituent group, and/or lower substituent group may optionally be different. In embodiments, when $R^{B103}$ is substituted, it is substituted with at least one substituent group. In embodiments, when $R^{B103}$ is substituted, it is substituted with at least one size-limited substituent group. In embodiments, when $R^{B103}$ is substituted, it is substituted with at least one lower substituent group.

In embodiments, $R^{B103}$ is independently hydrogen. In embodiments, $R^{B103}$ is independently halogen. In embodiments, $R^{B103}$ is independently $-CCl_3$. In embodiments, $R^{B103}$ is independently $-CBr_3$. In embodiments, $R^{B103}$ is independently $-CF_3$. In embodiments, $R^{B103}$ is independently $-CI_3$. In embodiments, $R^{B103}$ is independently $-CH_2Cl$. In embodiments, $R^{B103}$ is independently $-CH_2Br$. In embodiments, $R^{B103}$ is independently $-CH_2F$. In embodiments, $R^{B103}$ is independently $-CH_2I$. In embodiments, $R^{B103}$ is independently $-CHCl_2$. In embodiments, $R^{B103}$ is independently $-CHBr_2$. In embodiments, $R^{B103}$ is independently $-CHF_2$. In embodiments, $R^{B103}$ is independently $-CHI_2$. In embodiments, $R^{B103}$ is independently —CN. In embodiments, $R^{B103}$ is independently —OH. In embodiments, $R^{B103}$ is independently $-NH_2$. In embodiments, $R^{B103}$ is independently —COOH. In embodiments, $R^{B103}$ is independently $-CONH_2$. In embodiments, $R^{B103}$ is independently $-NO_2$. In embodiments, $R^{B103}$ is independently —SH. In embodiments, $R^{B103}$ is independently $-SO_3H$. In embodiments, $R^{B103}$ is independently $-SO_4H$. In embodiments, $R^{B103}$ is independently $-SO_2NH_2$. In embodiments, $R^{B103}$ is independently $-NHNH_2$. In embodiments, $R^{B103}$ is independently $-ONH_2$. In embodiments, $R^{B103}$ is independently $-NHC(O)NHNH_2$. In embodiments, $R^{B103}$ is independently $-NHC(O)NH_2$. In embodiments, $R^{B103}$ is independently $-NHSO_2H$. In embodiments, $R^{B103}$ is independently —NHC(O)H. In embodiments, $R^{B103}$ is independently —NHC(O)OH. In embodiments, $R^{B103}$ is independently —NHC(NH)H. In embodiments, $R^{B103}$ is independently $-NHC(NH)NH_2$. In embodiments, $R^{B103}$ is independently —NHOH. In embodiments, $R^{B103}$ is independently $-OCCl_3$. In embodiments, $R^{B103}$ is independently $-OCBr_3$. In embodiments, $R^{B103}$ is independently $-OCF_3$. In embodiments, $R^{B103}$ is independently $-OCI_3$. In embodiments, $R^{B103}$ is independently $-OCH_2Cl$. In embodiments, $R^{B103}$ is independently $-OCH_2Br$. In embodiments, $R^{B103}$ is independently $-OCH_2F$. In embodiments, $R^{B103}$ is independently $-OCH_2I$. In embodiments, $R^{B103}$ is independently $-OCHCl_2$. In embodiments, $R^{B103o}$ is independently $-OCHBr_2$. In embodiments, $R^{B103}$ is independently $-OCHF_2$. In embodiments, $R^{B103}$ is independently $-OCHI_2$. In embodiments, $R^{B103}$ is independently $-N_3$. In embodiments, $R^{B103}$ is independently substituted or unsubstituted alkyl (e.g., $C_1$-$C_8$, $C_1$-$C_6$, $C_1$-$C_4$, or $C_1$-$C_2$). In embodiments, $R^{B103}$ is independently substituted alkyl (e.g., $C_1$-$C_8$, $C_1$-$C_6$, $C_1$-$C_4$, or $C_1$-$C_2$). In embodiments, $R^{B103}$ is independently unsubstituted alkyl (e.g., $C_1$-$C_8$, $C_1$-$C_6$, $C_1$-$C_4$, or $C_1$-$C_2$). In embodiments, $R^{B103}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B103}$ is independently substituted heteroalkyl (e.g., 2 to 8 membered, 2 to 6 membered, 4 to 6 membered, 2 to 3 membered, or 4 to 5 membered). In embodiments, $R^{B103}$ is independently unsubstituted heteroalkyl (e.g., 2 to 8 membered, 2 to 6 membered, 4 to 6 membered, 2 to 3 membered, or 4 to 5 membered). In embodiments, $R^{B103}$ is independently substituted or unsubstituted cycloalkyl (e.g., $C_3$-$C_8$, $C_3$-$C_6$, $C_4$-$C_6$, or $C_5$-$C_6$). In embodiments, $R^{B103}$ is independently substituted cycloalkyl (e.g., $C_3$-$C_8$, $C_3$-$C_6$, $C_4$-$C_6$, or $C_5$-$C_6$). In embodiments, $R^{B103}$ is independently unsubstituted cycloalkyl (e.g., $C_3$-$C_8$, $C_3$-$C_6$, $C_4$-$C_6$, or $C_5$-$C_6$). In embodiments, $R^{B103}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B103}$ is independently substituted heterocycloalkyl (e.g., 3 to 8 membered, 3 to 6 membered, 4 to 6 membered, 4 to 5 membered, or 5 to 6 membered). In embodiments, $R^{B103}$ is independently unsubstituted heterocycloalkyl (e.g., 3 to 8 membered, 3 to 6 membered, 4 to 6 membered, 4 to 5 membered, or 5 to 6 membered). In embodiments, $R^{B103}$ is independently substituted or unsubstituted aryl (e.g., $C_6$-$C_{10}$ or phenyl). In embodiments, $R^{B103}$ is independently substituted aryl (e.g., $C_6$-$C_{10}$ or phenyl). In embodiments, $R^{B103}$ is independently unsubstituted aryl (e.g., $C_6$-$C_{10}$ or phenyl). In embodiments, $R^{B103}$ is independently substituted or unsubstituted heteroaryl (e.g., 5 to 10 membered, 5 to 9 membered, or 5 to 6 membered). In embodiments, $R^{B103}$ is independently substituted heteroaryl (e.g., 5 to 10 membered, 5 to 9 membered, or 5 to 6 membered). In embodiments, $R^{B103}$ is independently unsubstituted heteroaryl (e.g., 5 to 10 membered, 5 to 9 membered, or 5 to 6 membered).

In embodiments, $L^{B1}$ is a bond or covalent linker.

In embodiments, $L^{B1}$ is $L^{B2}$-$L^{B3}$-$L^{B4}$-$L^{B5}$-$L^{B6}$.

In embodiments, $L^{B1}$ is $L^{B2}$-$L^{B3}$-$L^{B4}$.

$L^{B2}$ is a bond, $-S(O)_2-$, $-N(R^{B2})-$, —O—, —S—, —C(O)—, $-C(O)N(R^{B2})-$, $-N(R^{B2})C(O)-$, $-N(R^{B2})C(O)NH-$, $-NHC(O)N(R^{B2})-$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B3}$ is a bond, $-S(O)_2-$, $-N(R^{B3})-$, —O—, —S—, —C(O)—, $-C(O)N(R^{B3})-$, $-N(R^{B3})C(O)-$, $-N(R^{B3})C(O)NH-$, $-NHC(O)N(R^{B3})-$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B4}$ is a bond, $-S(O)_2-$, $-N(R^{B4})-$, —O—, —S—, —C(O)—, $-C(O)N(R^{B4})-$, $-N(R^{B4})C(O)-$, $-N(R^{B4})C(O)NH-$, $-NHC(O)N(R^{B4})-$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B5}$ is a bond, $-S(O)_2-$, $-N(R^{B5})-$, —O—, —S—, —C(O)—, $-C(O)N(R^{B5})-$, $-N(R^{B5})C(O)-$, $-N(R^{B5})C(O)NH-$, $-NHC(O)N(R^{B5})-$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

$L^{B6}$ is a bond, $-S(O)_2-$, $-N(R^{B6})-$, —O—, —S—, —C(O)—, $-C(O)N(R^{B6})-$, $-N(R^{B6})C(O)-$, $-N(R^{B6})C(O)NH-$, $-NHC(O)N(R^{B6})-$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker.

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B3}$ is a bond, —S(O)$_2$—, —N($R^{B3}$)—, —O—, —S—, —C(O)—, —C(O)N($R^{B3}$)—, —N($R^{B3}$)C(O)—, —N($R^{B3}$)C(O)NH—, —NHC(O)N($R^{B3}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B4}$ is a bond, —S(O)$_2$—, —N($R^{B4}$)—, —O—, —S—, —C(O)—, —C(O)N($R^{B4}$)—, —N($R^{B4}$)C(O)—, —N($R^{B4}$)C(O)NH—, —NHC(O)N($R^{B4}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B5}$ is a bond, —S(O)$_2$—, —N($R^{B5}$)—, —O—, —S—, —C(O)—, —C(O)N($R^{B5}$)—, —N($R^{B5}$)C(O)—, —N($R^{B5}$)C(O)NH—, —NHC(O)N($R^{B5}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{B6}$ is a bond, —S(O)$_2$—, —N($R^{B6}$)—, —O—, —S—, —C(O)—, —C(O)N($R^{B6}$)—, —N($R^{B6}$)C(O)—, —N($R^{B6}$)C(O)NH—, —NHC(O)N($R^{B6}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^{B2}$, $R^{B3}$, $R^{B4}$, $R^{B5}$, and $R^{B6}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B2}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B2}$ is substituted with a plurality of groups selected from substituent groups, size-limited substituent groups, and lower substituent groups; each substituent group, size-limited substituent group, and/or lower substituent group may optionally be different. In embodiments, when $L^{B2}$ is substituted, it is substituted with at least one substituent group. In embodiments, when $L^{B2}$ is substituted, it is substituted with at least one size-limited substituent group. In embodiments, when $L^{B2}$ is substituted, it is substituted with at least one lower substituent group.

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted or unsubstituted $C_1$-$C_6$ alkylene, or substituted or unsubstituted 2 to 6 membered heteroalkylene.

In embodiments, $L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, $R^{B2}$-substituted or unsubstituted alkylene, $R^{B2}$-substituted or unsubstituted heteroalkylene, $R^{B2}$-substituted or unsubstituted cycloalkylene, $R^{B2}$-substituted or unsubstituted heterocycloalkylene, $R^{B2}$-substituted or unsubstituted arylene, or $R^{B2}$-substituted or unsubstituted heteroarylene.

In embodiments, $R^{B2}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B2}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B2}$ is substituted with a plurality of groups selected from substituent groups, size-limited substituent groups, and lower substituent groups; each substituent group, size-limited substituent group, and/or lower substituent group may optionally be different. In embodiments, when $R^{B2}$ is substituted, it is substituted with at least one substituent group. In embodiments, when $R^{B2}$ is substituted, it is substituted with at least one size-limited substituent group. In embodiments, when $R^{B2}$ is substituted, it is substituted with at least one lower substituent group.

In embodiments, $R^{B2}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $R^{B20}$-substituted or unsubstituted alkyl, $R^{B20}$-substituted or unsubstituted heteroalkyl, $R^{B20}$-substituted or unsubstituted cycloalkyl, $R^{B20}$-substituted or unsubstituted heterocycloalkyl, $R^{B20}$-substituted or unsubstituted aryl, or $R^{B20}$-substituted or unsubstituted heteroaryl.

$R^{B20}$ is independently halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B20}$ is independently halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B3}$ is a bond, $-S(O)_2-$, $-N(R^{B3})-$, $-O-$, $-S-$, $-C(O)-$, $-C(O)N(R^{B3})-$, $-N(R^{B3})C(O)-$, $-N(R^{B3})C(O)NH-$, $-NHC(O)N(R^{B3})-$, $-C(O)O-$, $-OC(O)-$, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{B3}$ is a bond, $-S(O)_2-$, $-N(R^{B3})-$, $-O-$, $-S-$, $-C(O)-$, $-C(O)N(R^{B3})-$, $-N(R^{B3})C(O)-$, $-N(R^{B3})C(O)NH-$, $-NHC(O)N(R^{B3})-$, $-C(O)O-$, $-OC(O)-$, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B3}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B3}$ is substituted with a plurality of groups selected from substituent groups, size-limited substituent groups, and lower substituent groups; each substituent group, size-limited substituent group, and/or lower substituent group may optionally be different. In embodiments, when $L^{B3}$ is substituted, it is substituted with at least one substituent group. In embodiments, when $L^{B3}$ is substituted, it is substituted with at least one size-limited substituent group. In embodiments, when $L^{B3}$ is substituted, it is substituted with at least one lower substituent group.

In embodiments, $L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted $C_1$-$C_6$ alkylene, or substituted or unsubstituted 2 to 6 membered heteroalkylene.

In embodiments, $L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, $R^{B3}$-substituted or unsubstituted alkylene, $R^{B3}$-substituted or unsubstituted heteroalkylene, $R^{B3}$-substituted or unsubstituted cycloalkylene, $R^{B3}$-substituted or unsubstituted heterocycloalkylene, $R^{B3}$-substituted or unsubstituted arylene, or $R^{B3}$-substituted or unsubstituted heteroarylene.

In embodiments, $R^{B3}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B3}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B3}$ is substituted with a plurality of groups selected from substituent groups, size-limited substituent groups, and lower substituent groups; each substituent group, size-limited substituent group, and/or lower substituent group may optionally be different. In embodiments, when $R^{B3}$ is substituted, it is substituted with at least one substituent group. In embodiments, when $R^{B3}$ is substituted, it is substituted with at least one size-limited substituent group. In embodiments, when $R^{B3}$ is substituted, it is substituted with at least one lower substituent group.

In embodiments, $R^{B3}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, $R^{B30}$-substituted or unsubstituted alkyl, $R^{B30}$-substituted or unsubstituted heteroalkyl, $R^{B30}$-substituted or unsubstituted cycloalkyl, $R^{B30}$-substituted or unsubstituted heterocycloalkyl, $R^{B30}$-substituted or unsubstituted aryl, or $R^{B30}$-substituted or unsubstituted heteroaryl.

$R^{B3o}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B3o}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{B4}$ is a bond, —S(O)$_2$—, —N($R^{B4}$)—, —O—, —S—, —C(O)—, —C(O)N($R^{B4}$)—, —N($R^{B4}$)C(O)—, —N($R^{B4}$)C(O)NH—, —NHC(O)N($R^{B4}$)—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B4}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B4}$ is substituted with a plurality of groups selected from substituent groups, size-limited substituent groups, and lower substituent groups; each substituent group, size-limited substituent group, and/or lower substituent group may optionally be different. In embodiments, when $L^{B4}$ is substituted, it is substituted with at least one substituent group. In embodiments, when $L^{B4}$ is substituted, it is substituted with at least one size-limited substituent group. In embodiments, when $L^{B4}$ is substituted, it is substituted with at least one lower substituent group.

In embodiments, $L^{B4}$ is a bond, —S(O)$_2$—, —N($R^{B4}$)—, —O—, —S—, —C(O)—, —C(O)N($R^{B4}$)—, —N($R^{B4}$)C(O)—, —N($R^{B4}$)C(O)NH—, —NHC(O)N($R^{B4}$)—, —C(O)O—, —OC(O)—, substituted or unsubstituted $C_1$-$C_6$ alkylene, or substituted or unsubstituted 2 to 6 membered heteroalkylene.

In embodiments, $L^{B4}$ is a bond, —S(O)$_2$—, —N($R^{B4}$)—, —O—, —S—, —C(O)—, —C(O)N($R^{B4}$)—, —N($R^{B4}$)C(O)—, —N($R^{B4}$)C(O)NH—, —NHC(O)N($R^{B4}$)—, —C(O)O—, —OC(O)—, $R^{B4}$-substituted or unsubstituted alkylene, $R^{B4}$-substituted or unsubstituted heteroalkylene, $R^{B4}$-substituted or unsubstituted cycloalkylene, $R^{B4}$-substituted or unsubstituted heterocycloalkylene, $R^{B4}$-substituted or unsubstituted arylene, or $R^{B4}$-substituted or unsubstituted heteroarylene.

In embodiments, $R^{B4}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B4}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B4}$ is substituted with a plurality of groups selected from substituent groups, size-limited substituent groups, and lower substituent groups; each substituent group, size-limited substituent group, and/or lower substituent group may optionally be different. In embodiments, when $R^{B4}$ is substituted, it is substituted with at least one substituent group. In embodiments, when $R^{B4}$ is substituted, it is substituted with at least one size-limited substituent group. In embodiments, when $R^{B4}$ is substituted, it is substituted with at least one lower substituent group.

In embodiments, $R^{B4}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, $R^{B40}$-substituted or unsubstituted alkyl, $R^{B40}$-substituted or unsubstituted heteroalkyl, $R^{B40}$-substituted or unsubstituted cycloalkyl, $R^{B40}$-substituted or unsubstituted heterocycloalkyl, $R^{B40}$-substituted or unsubstituted aryl, or $R^{B40}$-substituted or unsubstituted heteroaryl.

$R^{B40}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B40}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B5}$ is a bond, —$S(O)_2$—, —N($R^{B5}$)—, —O—, —S—, —C(O)—, —C(O)N($R^{B5}$)—, —N($R^{B5}$)C(O)—, —N($R^{B5}$)C(O)NH—, —NHC(O)N($R^{B5}$)—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B5}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B5}$ is substituted with a plurality of groups selected from substituent groups, size-limited substituent groups, and lower substituent groups; each substituent group, size-limited substituent group, and/or lower substituent group may optionally be different. In embodiments, when $L^{B5}$ is substituted, it is substituted with at least one substituent group. In embodiments, when $L^{B5}$ is substituted, it is substituted with at least one size-limited substituent group. In embodiments, when $L^{B5}$ is substituted, it is substituted with at least one lower substituent group.

In embodiments, $L^{B5}$ is a bond, —$S(O)_2$—, —N($R^{B5}$)—, —O—, —S—, —C(O)—, —C(O)N($R^{B5}$)—, —N($R^{B5}$)C(O)—, —N($R^{B5}$)C(O)NH—, —NHC(O)N($R^{B5}$)—, —C(O)O—, —OC(O)—, substituted or unsubstituted $C_1$-$C_6$ alkylene, or substituted or unsubstituted 2 to 6 membered heteroalkylene.

In embodiments, $L^{B5}$ is a bond, —$S(O)_2$—, —N($R^{B5}$)—, —O—, —S—, —C(O)—, —C(O)N($R^{B5}$)—, —N($R^{B5}$)C(O)—, —N($R^{B5}$)C(O)NH—, —NHC(O)N($R^{B5}$)—, —C(O)O—, —OC(O)—, $R^{B5}$-substituted or unsubstituted alkylene, $R^{B5}$-substituted or unsubstituted heteroalkylene, $R^{B5}$-substituted or unsubstituted cycloalkylene, $R^{B5}$-substituted or unsubstituted heterocycloalkylene, $R^{B5}$-substituted or unsubstituted arylene, or $R^{B5}$-substituted or unsubstituted heteroarylene.

In embodiments, $R^{B5}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B5}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B5}$ is substituted with a plurality of groups selected from substituent groups, size-limited substituent groups, and lower substituent groups; each substituent group, size-limited substituent group, and/or lower substituent group may optionally be different. In embodiments, when $R^{B5}$ is substituted, it is substituted with at least one substituent group. In embodiments, when $R^{B5}$ is substituted, it is substituted with at least one size-limited substituent group. In embodiments, when $R^{B5}$ is substituted, it is substituted with at least one lower substituent group.

In embodiments, $R^{B5}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, $R^{B50}$-substituted or unsubstituted alkyl, $R^{B50}$-substituted or unsubstituted heteroalkyl, $R^{B50}$-substituted or unsubstituted cycloalkyl, $R^{B50}$-substituted or unsubstituted heterocycloalkyl, $R^{B50}$-substituted or unsubstituted aryl, or $R^{B50}$-substituted or unsubstituted heteroaryl.

$R^{B50}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B50}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B6}$ is a bond, —$S(O)_2$—, —N($R^{B6}$)—, —O—, —S—, —C(O)—, —C(O)N($R^{B6}$)—, —N($R^{B6}$)C(O)—, —N($R^{B6}$)C(O)NH—, —NHC(O)N($R^{B6}$)—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, or $C_1$-$C_4$), substituted (e.g., substituted with at least one substituent group, size-limited substituent group, or lower substituent group) or unsubstituted heteroalkylene (e.g., 2 to 8 membered, 2 to 6 membered, or 2 to 4 membered), substituted (e.g., substituted with at least one substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, or 5 to 6 membered), substituted (e.g., substituted with at least one substituent group, size-limited substituent group, or lower substituent group) or unsubstituted arylene (e.g., $C_6$-$C_{10}$, $C_{10}$, or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{B6}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{B6}$ is substituted with a plurality of groups selected from substituent groups, size-limited substituent groups, and lower substituent groups; each substituent group, size-limited substituent group, and/or lower substituent group may optionally be different. In embodiments, when $L^{B6}$ is substituted, it is substituted with at least one substituent group. In embodiments, when $L^{B6}$ is substituted, it is substituted with at least one size-limited substituent group. In embodiments, when $L^{B6}$ is substituted, it is substituted with at least one lower substituent group.

In embodiments, $L^{B6}$ is a bond, —$S(O)_2$—, —N($R^{B6}$)—, —O—, —S—, —C(O)—, —C(O)N($R^{B6}$)—, —N($R^{B6}$)C(O)—, —N($R^{B6}$)C(O)NH—, —NHC(O)N($R^{B6}$)—, —C(O)O—, —OC(O)—, substituted or unsubstituted $C_1$-$C_6$ alkylene, or substituted or unsubstituted 2 to 6 membered heteroalkylene.

In embodiments, $L^{B6}$ is a bond, —$S(O)_2$—, —N($R^{B6}$)—, —O—, —S—, —C(O)—, —C(O)N($R^{B6}$)—, —N($R^{B6}$)C(O)—, —N($R^{B6}$)C(O)NH—, —NHC(O)N($R^{B6}$)—, —C(O)O—, —OC(O)—, $R^{B6}$-substituted or unsubstituted alkylene, $R^{B6}$-substituted or unsubstituted heteroalkylene, $R^{B6}$-substituted or unsubstituted cycloalkylene, $R^{B6}$-substituted or unsubstituted heterocycloalkylene, $R^{B6}$-substituted or unsubstituted arylene, or $R^{B6}$-substituted or unsubstituted heteroarylene.

In embodiments, $R^{B6}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B6}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B6}$ is substituted with a plurality of groups selected from substituent groups, size-limited substituent groups, and lower substituent groups; each substituent group, size-limited substituent group, and/or lower substituent group may optionally be different. In embodiments, when $R^{B6}$ is substituted, it is substituted with at least one substituent group. In embodiments, when $R^{B6}$ is substituted, it is substituted with at least one size-limited substituent group. In embodiments, when $R^{B6}$ is substituted, it is substituted with at least one lower substituent group.

In embodiments, $R^{B6}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, $R^{B60}$-substituted or unsubstituted alkyl, $R^{B60}$-substituted or unsubstituted heteroalkyl, $R^{B60}$-substituted or unsubstituted cycloalkyl, $R^{B60}$-substituted or unsubstituted heterocycloalkyl, $R^{B60}$-substituted or unsubstituted aryl, or $R^{B60}$-substituted or unsubstituted heteroaryl.

$R^{B60}$ is independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{B60}$ is independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{B1}$ is

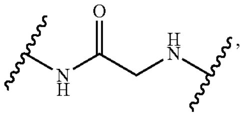,
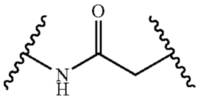,
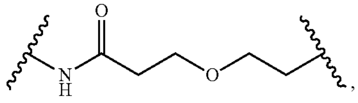,

-continued

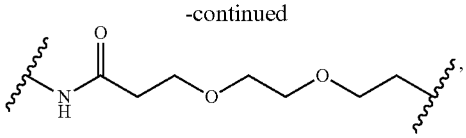,
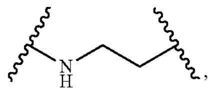,
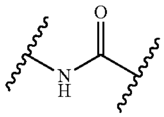,
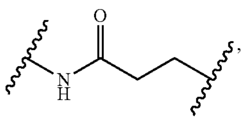,
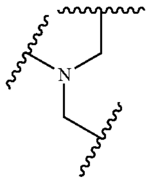,
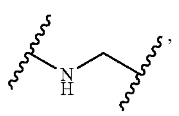,
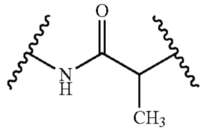,
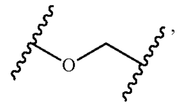,
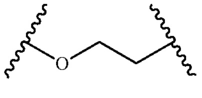,
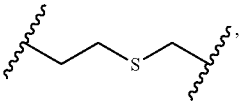,
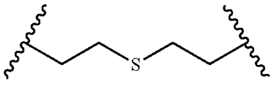,
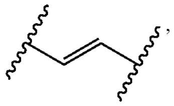,
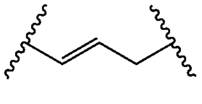,
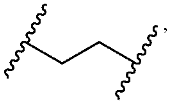,
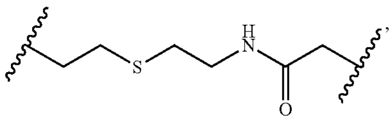,
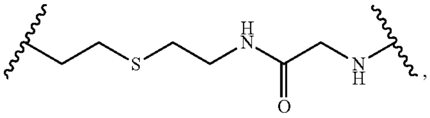,
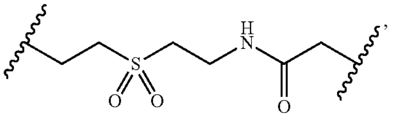, or
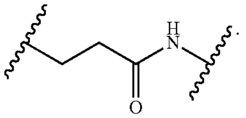.

In embodiments, $R^{B1}$ is hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, $—N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{B1}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1}$ is substituted with a plurality of groups selected from substituent groups, size-limited substituent groups, and lower substituent groups; each substituent group, size-limited substituent group, and/or lower substituent group may optionally be different. In embodiments, when $R^{B1}$ is substituted, it is substituted with at least one substituent group. In embodiments, when $R^{B1}$ is substituted, it is substituted with at least one size-limited substituent group. In embodiments, when $R^{B1}$ is substituted, it is substituted with at least one lower substituent group.

In embodiments, $R^{B1}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted $C_1$-$C_4$ alkyl, substituted or unsubstituted 2 to 4 membered heteroalkyl, or substituted or unsubstituted 5 to 6 membered heteroaryl.

In embodiments, $R^{B1}$ is substituted or unsubstituted pyridyl. In embodiments, $R^{B1}$ is unsubstituted pyridyl or pyridyl N-oxide. In embodiments, $R^{B1}$ is unsubstituted pyridyl. In embodiments, $R^{B1}$ is pyridyl N-oxide.

In embodiments, $R^{B1}$ is independently hydrogen, halogen, —$CX^{B1}_3$, —$CHX^{B1}2$, —$CH_2X^{B1}$, —$OCX^{B1}_3$, —$OCH_2X^{B1}$, —$OCHX^{B1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$N_3$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^{B1}$ is independently hydrogen, halogen, —$CX^{B1}_3$, —$CHX^{B1}_2$, —$CH_2X^{B1}$, —OH, —$NH_2$, —SH, —$OCX^{B1}_3$, —$OCHX^{B1}_2$, —$OCH_2X^{B1}$, —$CH_3$, —$CH_2CH_3$, —$OCH_3$, —$OCH_2CH_3$, —$SCH_3$, or —$SCH_2CH_3$, or —$N_3$. In embodiments, $R^{B1}$ is independently hydrogen, halogen, —$CF_3$, —$CHF_2$, —$CH_2F$, —OH, —$NH_2$, —SH, —$OCF_3$, —$OCHF_2$, —$OCH_2F$, —$CH_3$, —$CH_2CH_3$, —$OCH_3$, —$OCH_2CH_3$, —$SCH_3$, or —$SCH_2CH_3$, or —$N_3$. In embodiments, $R^{B1}$ is substituted or unsubstituted $C_1$-$C_6$ alkyl. In embodiments, $R^{B1}$ is substituted or unsubstituted 2 to 6 membered heteroalkyl. In embodiments, $R^{B1}$ is substituted or unsubstituted $C_3$-$C_8$ cycloalkyl. In embodiments, $R^{B1}$ is substituted or unsubstituted 3 to 8 membered heterocycloalkyl. In embodiments, $R^{B1}$ is substituted or unsubstituted phenyl. In embodiments, $R^{B1}$ is substituted or unsubstituted 5 to 6 membered heteroaryl. In embodiments, $R^{B1}$ is substituted or unsubstituted pyridyl. In embodiments, $R^{B1}$ is independently hydrogen. In embodiments, $R^{B1}$ is independently halogen. In embodiments, $R^{B1}$ is independently-$CX^{B1}_3$. In embodiments, $R^{B1}$ is independently—$CHX^{B1}_2$. In embodiments, $R^{B1}$ is independently —$CH_2X^{B1}$. In embodiments, $R^{B1}$ is independently —$OCX^{B1}_3$. In embodiments, $R^{B1}$ is independently —$OCH_2X^{B1}$. In embodiments, $R^{B1}$ is independently —$OCHX^{B1}_2$. In embodiments, $R^{B1}$ is independently —$OCH_2X^{B1}$. In embodiments, $R^{B1}$ is independently —CN. In embodiments, $R^{B1}$ is independently —$SO_{nB1}R^{B10}$. In embodiments, $R^{B1}$ is independently —$SR^{B1D}$. In embodiments, $R^{B1}$ is independently —$SO_{vB1}NR^{B1A}R^{B1B}$. In embodiments, $R^{B1}$ is independently —NHC(O)$NR^{B1A}R^{B1B}$. In embodiments, $R^{B1}$ is independently —$NR^{B1A}C(NR^{B1C})R^{B1D}$. In embodiments, $R^{B1}$ is independently —$NR^{B1A}C(NR^{B1C})NR^{B1A}R^{B1B}$. In embodiments, $R^{B1}$ is independently —$N(O)_{mB1}$. In embodiments, $R^{B1}$ is independently —$NR^{B1A}R^{B1B}$. In embodiments, $R^{B1}$ is independently —$C(O)R^{B1C}$. In embodiments, $R^{B1}$ is independently —$C(O)OR^{B1C}$. In embodiments, $R^{B1}$ is independently —$C(O)NR^{B1A}R^{B1B}$. In embodiments, $R^{B1}$ is independently —$OR^{B1D}$. In embodiments, $R^{B1}$ is independently —$NR^{B1A}SO_2R^{B1D}$. In embodiments, $R^{B1}$ is independently —$NR^{B1A}C(O)R^{B1C}$. In embodiments, $R^{B1}$ is independently —$NR^{B1A}C(O)OR^{B1C}$. In embodiments, $R^{B1}$ is independently —$NR^{B1A}OR^{B1C}$. In embodiments, $R^{B1}$ is independently —OH. In embodiments, $R^{B1}$ is independently —$NH_2$. In embodiments, $R^{B1}$ is independently —COOH. In embodiments, $R^{B1}$ is independently —$CONH_2$. In embodiments, $R^{B1}$ is independently —$NO_2$. In embodiments, $R^{B1}$ is independently —SH. In embodiments, $R^{B1}$ is independently-$CF_3$. In embodiments, $R^{B1}$ is independently—$CHF_2$. In embodiments, $R^{B1}$ is independently —$CH_2F$. In embodiments, $R^{B1}$ is independently —$OCF_3$. In embodiments, $R^{B1}$ is independently —$OCH_2F$. In embodiments, $R^{B1}$ is independently —$OCHF_2$. In embodiments, $R^{B1}$ is independently —$OCH_3$. In embodiments, $R^{B1}$ is independently —$OCH_2CH_3$. In embodiments, $R^{B1}$ is independently —$OCH_2CH_2CH_3$. In embodiments, $R^{B1}$ is independently —$OCH(CH_3)_2$. In embodiments, $R^{B1}$ is independently —$OC(CH_3)_3$. In embodiments, $R^{B1}$ is independently —$N(CH_3)_3^+$. In embodiments, $R^{B1}$ is independently —$SCH_3$. In embodiments, $R^{B1}$ is independently —$SCH_2CH_3$. In embodiments, $R^{B1}$ is independently —$SCH_2CH_2CH_3$. In embodiments, $R^{B1}$ is independently —$SCH(CH_3)_2$. In embodiments, $R^{B1}$ is independently —$SC(CH_3)_3$. In embodiments, $R^{B1}$ is independently —$N_3$. In embodiments, $R^{B1}$ is independently —$CH_3$. In embodiments, $R^{B1}$ is independently —$CH_2CH_3$. In embodiments, $R^{B1}$ is independently —$CH_2CH_2CH_3$. In embodiments, $R^{B1}$ is independently —$CH(CH_3)_2$. In embodiments, $R^{B1}$ is independently —$C(CH_3)_3$. In embodiments, $R^{B1}$ is independently —F. In embodiments, $R^{B1}$ is independently —Cl. In embodiments, $R^{B1}$ is independently —Br. In embodiments, $R^{B1}$ is independently —I. $X^{B1}$ is independently —F, —Cl, —Br, or —I.

In embodiments, $R^{B1A}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1A}$ is substituted with a plurality of groups selected from substituent groups, size-limited substituent groups, and lower substituent groups; each substituent group, size-limited substituent group, and/or lower substituent group may optionally be different. In embodiments, when $R^{B1A}$ is substituted, it is substituted with at least one substituent group. In embodiments, when $R^{B1A}$ is substituted, it is substituted with at least one size-limited substituent group. In embodiments, when $R^{B1A}$ is substituted, it is substituted with at least one lower substituent group.

In embodiments, $R^{B1A}$ is independently hydrogen. In embodiments, $R^{B1A}$ is independently —$CX^{B1A}_3$. In embodiments, $R^{B1A}$ is independently —$CHX^{B1A}$2. In embodiments, $R^{B1A}$ is independently —$CH_2X^{B1A}$. In embodiments, $R^{B1A}$ is independently —$OCX^{B1A}_3$. In embodiments, $R^{B1A}$ is independently —$OCHX^{B1A}$2. In embodiments, $R^{B1A}$ is independently —$OCH_2X^{B1A}$. In embodiments, $R^{B1A}$ is independently —OH. In embodiments, $R^{B1A}$ is independently —CN. In embodiments, $R^{B1A}$ is independently —COOH. In embodiments, $R^{B1A}$ is independently —$CONH_2$. $X^{B1A}$ is independently —F, —Cl, —Br, or —I.

In embodiments, $R^{B1A}$ is independently substituted or unsubstituted alkyl (e.g., $C_1$-$C_8$, $C_1$-$C_6$, $C_1$-$C_4$, or $C_1$-$C_2$). In embodiments, $R^{B1A}$ is independently substituted alkyl (e.g., $C_1$-$C_8$, $C_1$-$C_6$, $C_1$-$C_4$, or $C_1$-$C_2$). In embodiments, $R^{B1A}$ is independently unsubstituted alkyl (e.g., $C_1$-$C_8$, $C_1$-$C_6$, $C_1$-$C_4$, or $C_1$-$C_2$). In embodiments, $R^{B1A}$ is independently unsubstituted methyl. In embodiments, $R^{B1A}$ is independently unsubstituted ethyl. In embodiments, $R^{B1A}$ is independently unsubstituted propyl. In embodiments, $R^{B1A}$ is independently unsubstituted isopropyl. In embodiments, $R^{B1A}$ is independently unsubstituted tert-butyl. In embodiments, $R^{B1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1A}$ is independently substituted heteroalkyl (e.g., 2 to 8 membered, 2 to 6 membered, 4 to 6 membered, 2 to 3 membered, or 4 to 5 membered). In embodiments, $R^{B1A}$ is independently unsubstituted heteroalkyl (e.g., 2 to 8 membered, 2 to 6 membered, 4 to 6 membered, 2 to 3 membered, or 4 to 5 membered). In embodiments, $R^{B1A}$ is independently substituted or unsubstituted cycloalkyl (e.g., $C_3$-$C_8$, $C_3$-$C_6$, $C_4$-$C_6$, or $C_5$-$C_6$). In embodiments, $R^{B1A}$ is independently substituted cycloalkyl (e.g., $C_3$-$C_8$, $C_3$-$C_6$, $C_4$-$C_6$, or $C_5$-$C_6$). In embodiments, $R^{B1A}$ is independently unsubstituted cycloalkyl (e.g., $C_3$-$C_8$, $C_3$-$C_6$, $C_4$-$C_6$, or $C_5$-$C_6$). In embodiments, $R^{B1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1A}$ is independently substituted heterocycloalkyl (e.g., 3 to 8 membered, 3 to 6 membered, 4 to 6 membered, 4 to 5 membered, or 5 to 6 membered). In embodiments, $R^{B1A}$ is independently unsubstituted heterocycloalkyl (e.g., 3 to 8 membered, 3 to 6 membered, 4 to 6 membered, 4 to 5 membered, or 5 to 6 membered). In embodiments, $R^{B1A}$ is independently substituted or unsubstituted aryl (e.g., $C_6$-$C_{10}$ or phenyl). In embodiments, $R^{B1A}$ is independently substituted aryl (e.g., $C_6$-$C_{10}$ or phenyl). In embodiments, $R^{B1A}$ is independently unsubstituted aryl (e.g., $C_6$-$C_{10}$ or phenyl). In embodiments, $R^{B1A}$ is independently substituted or unsubstituted heteroaryl (e.g., 5 to 10 membered, 5 to 9 membered, or 5 to 6 membered). In embodiments, $R^{B1A}$ is independently substituted heteroaryl (e.g., 5 to 10 membered, 5 to 9 membered, or 5 to 6 membered). In embodiments, $R^{B1A}$ is independently pyridyl N-oxide. In embodiments, $R^{B1A}$ is independently unsubstituted heteroaryl (e.g., 5 to 10 membered, 5 to 9 membered, or 5 to 6 membered). In embodiments, $R^{B1A}$ is independently unsubstituted pyridyl.

In embodiments, $R^{B1B}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHC(NH)H, —NHC(NH)NH$_2$, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1B}$ is substituted with a plurality of groups selected from substituent groups, size-limited substituent groups, and lower substituent groups; each substituent group, size-limited substituent group, and/or lower substituent group may optionally be different. In embodiments, when $R^{B1B}$ is substituted, it is substituted with at least one substituent group. In embodiments, when $R^{B1B}$ is substituted, it is substituted with at least one size-limited substituent group. In embodiments, when $R^{B1B}$ is substituted, it is substituted with at least one lower substituent group.

In embodiments, $R^{B1B}$ is independently hydrogen. In embodiments, $R^{B1B}$ is independently —$CX^{B1B}_3$. In embodiments, $R^{B1B}$ is independently —$CHX^{B1B}$2. In embodiments, $R^{B1B}$ is independently —$CH_2X^{B1B}$. In embodiments, $R^{B1B}$ is independently —$OCX^{B1B}_3$. In embodiments, $R^{B1B}$ is independently —$OCHX^{B1B}$2. In embodiments, $R^{B1B}$ is independently —$OCH_2X^{B1B}$. In embodiments, $R^{B1B}$ is independently —OH. In embodiments, $R^{B1B}$ is independently —CN. In embodiments, $R^{B1B}$ is independently —COOH. In embodiments, $R^{B1B}$ is independently —CONH$_2$. $X^{B1B}$ is independently —F, —Cl, —Br, or —I.

In embodiments, $R^{B1B}$ is independently substituted or unsubstituted alkyl (e.g., $C_1$-$C_8$, $C_1$-$C_6$, $C_1$-$C_4$, or $C_1$-$C_2$). In embodiments, $R^{B1B}$ is independently substituted alkyl (e.g., $C_1$-$C_8$, $C_1$-$C_6$, $C_1$-$C_4$, or $C_1$-$C_2$). In embodiments, $R^{B1B}$ is independently unsubstituted alkyl (e.g., $C_1$-$C_8$, $C_1$-$C_6$, $C_1$-$C_4$, or $C_1$-$C_2$). In embodiments, $R^{B1B}$ is independently unsubstituted methyl. In embodiments, $R^{B1B}$ is independently unsubstituted ethyl. In embodiments, $R^{B1B}$ is independently unsubstituted propyl. In embodiments, $R^{B1B}$ is independently unsubstituted isopropyl. In embodiments, $R^{B1B}$ is independently unsubstituted tert-butyl. In embodiments, $R^{B1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1B}$ is independently substituted heteroalkyl (e.g., 2 to 8 membered, 2 to 6 membered, 4 to 6 membered, 2 to 3 membered, or 4 to 5 membered). In embodiments, $R^{B1B}$ is independently unsubstituted heteroalkyl (e.g., 2 to 8 membered, 2 to 6 membered, 4 to 6 membered, 2 to 3 membered, or 4 to 5 membered). In embodiments, $R^{B1B}$ is independently substituted or unsubstituted cycloalkyl (e.g., $C_3$-$C_8$, $C_3$-$C_6$, $C_4$-$C_6$, or $C_5$-$C_6$). In embodiments, $R^{B1B}$ is independently substituted cycloalkyl (e.g., $C_3$-$C_8$, $C_3$-$C_6$, $C_4$-$C_6$, or $C_5$-$C_6$). In embodiments, $R^{B1B}$ is independently unsubstituted cycloalkyl (e.g., $C_3$-$C_8$, $C_3$-$C_6$, $C_4$-$C_6$, or $C_5$-$C_6$). In embodiments, $R^{B1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1B}$ is independently substituted heterocycloalkyl (e.g., 3 to 8 membered, 3 to 6 membered, 4 to 6 membered, 4 to 5 membered, or 5 to 6 membered). In embodiments, $R^{B1B}$ is independently unsubstituted heterocycloalkyl (e.g., 3 to 8 membered, 3 to 6 membered, 4 to 6 membered, 4 to 5 membered, or 5 to 6 membered). In embodiments, $R^{B1B}$ is independently substituted or unsubstituted aryl (e.g., $C_6$-$C_{10}$ or phenyl). In embodiments, $R^{B1B}$ is independently substituted aryl (e.g., $C_6$-$C_{10}$ or phenyl). In embodiments, $R^{B1B}$ is independently unsubstituted aryl (e.g., $C_6$-$C_{10}$ or phenyl). In embodiments, $R^{B1B}$ is independently substituted or unsubstituted heteroaryl (e.g., 5 to 10 membered, 5 to 9 membered, or 5 to 6 membered). In embodiments, $R^{B1B}$ is independently substituted heteroaryl (e.g., 5 to 10 membered, 5 to 9 membered, or 5 to 6 membered). In embodiments, $R^{B1B}$ is independently pyridyl N-oxide. In embodiments, $R^{B1B}$ is independently unsubstituted heteroaryl (e.g., 5 to 10 membered, 5 to 9 membered, or 5 to 6 membered). In embodiments, $R^{B1B}$ is independently unsubstituted pyridyl.

In embodiments, $R^{B1A}$ and $R^{B1B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{B1A}$ and $R^{B1B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{B1A}$ and $R^{B1B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{B1A}$ and $R^{B1B}$ substituents bonded to the same nitrogen atom is substituted, it is substituted with at least one substituent group. In embodiments, when the moiety formed by joining $R^{B1A}$ and $R^{B1B}$ substituents bonded to the same nitrogen atom is substituted, it is substituted with at least one size-limited substituent group. In embodiments, when the moiety formed by joining $R^{B1A}$ and $R^{B1B}$ substituents bonded to the same nitrogen atom is substituted, it is substituted with at least one lower substituent group.

In embodiments, $R^{B1A}$ and $R^{B1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{B1A}$ and $R^{B1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form a substituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form an unsubstituted heteroaryl (e.g., 5 to 10 membered, 5 to 9 membered, or 5 to 6 membered).

In embodiments, $R^{B1C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1C}$ is substituted with a plurality of groups selected from substituent groups, size-limited substituent groups, and lower substituent groups; each substituent group, size-limited substituent group, and/or lower substituent group may optionally be different. In embodiments, when $R^{B1C}$ is substituted, it is substituted with at least one substituent group. In embodiments, when $R^{B1C}$ is substituted, it is substituted with at least one size-limited substituent group. In embodiments, when $R^{B1C}$ is substituted, it is substituted with at least one lower substituent group.

In embodiments, $R^{B1C}$ is independently hydrogen. In embodiments, $R^{B1C}$ is independently $-CX^{B1C}_3$. In embodiments, $R^{B1C}$ is independently $-CHX^{B1C}2$. In embodiments, $R^{B1C}$ is independently $-CH_2X^{B1C}$. In embodiments, $R^{B1C}$ is independently $-OCX^{B1C}_3$. In embodiments, $R^{B1C}$ is independently $-OCHX^{B1C}2$. In embodiments, $R^{B1C}$ is independently $-OCH_2X^{B1C}$. In embodiments, $R^{B1C}$ is independently $-OH$. In embodiments, $R^{B1C}$ is independently $-CN$. In embodiments, $R^{B1C}$ is independently $-COOH$. In embodiments, $R^{B1C}$ is independently $-CONH_2$. In embodiments, $X^{B1C}$ is independently $-F$, $-Cl$, $-Br$, or $-I$.

In embodiments, $R^{B1C}$ is independently substituted or unsubstituted alkyl (e.g., $C_1$-$C_8$, $C_1$-$C_6$, $C_1$-$C_4$, or $C_1$-$C_2$). In embodiments, $R^{B1C}$ is independently substituted alkyl (e.g., $C_1$-$C_8$, $C_1$-$C_6$, $C_1$-$C_4$, or $C_1$-$C_2$). In embodiments, $R^{B1C}$ is independently unsubstituted alkyl (e.g., $C_1$-$C_8$, $C_1$-$C_6$, $C_1$-$C_4$, or $C_1$-$C_2$). In embodiments, $R^{B1C}$ is independently unsubstituted methyl. In embodiments, $R^{B1C}$ is independently unsubstituted ethyl. In embodiments, $R^{B1C}$ is independently unsubstituted propyl. In embodiments, $R^{B1C}$ is independently unsubstituted isopropyl. In embodiments, $R^{B1C}$ is independently unsubstituted tert-butyl. In embodiments, $R^{B1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted heteroalkyl (e.g., 2 to 8 membered, 2 to 6 membered, 4 to 6 membered, 2 to 3 membered, or 4 to 5 membered). In embodiments, $R^{B1C}$ is independently unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted or unsubstituted cycloalkyl (e.g., $C_3$-$C_8$, $C_3$-$C_6$, $C_4$-$C_6$, or $C_5$-$C_6$). In embodiments, $R^{B1C}$ is independently substituted cycloalkyl (e.g., $C_3$-$C_8$, $C_3$-$C_6$, $C_4$-$C_6$, or $C_5$-$C_6$). In embodiments, $R^{B1C}$ is independently unsubstituted cycloalkyl (e.g., $C_3$-$C_8$, $C_3$-$C_6$, $C_4$-$C_6$, or $C_5$-$C_6$). In embodiments, $R^{B1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted heterocycloalkyl (e.g., 3 to 8 membered, 3 to 6 membered, 4 to 6 membered, 4 to 5 membered, or 5 to 6 membered). In embodiments, $R^{B1C}$ is independently unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted or unsubstituted aryl (e.g., $C_6$-$C_{10}$ or phenyl). In embodiments, $R^{B1C}$ is independently substituted aryl (e.g., $C_6$-$C_{10}$ or phenyl). In embodiments, $R^{B1C}$ is independently unsubstituted aryl (e.g., $C_6$-$C_{10}$ or phenyl). In embodiments, $R^{B1C}$ is independently substituted or unsubstituted heteroaryl (e.g., 5 to 10 membered, 5 to 9 membered, or 5 to 6 membered). In embodiments, $R^{B1C}$ is independently substituted heteroaryl (e.g., 5 to 10 membered, 5 to 9 membered, or 5 to 6 membered). In embodiments, $R^{B1C}$ is independently pyridyl N-oxide. In embodiments, $R^{B1C}$ is independently unsubstituted heteroaryl (e.g., 5 to 10 membered, 5 to 9 membered, or 5 to 6 membered). In embodiments, $R^{B1C}$ is independently unsubstituted pyridyl.

In embodiments, $R^{B1D}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B1D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B1D}$ is substituted with a plurality of groups selected from substituent groups, size-limited substituent groups, and lower substituent groups; each substituent group, size-limited substituent group, and/or lower substituent group may optionally be different. In embodiments, when $R^{B1D}$ is substituted, it is substituted with at least one substituent group. In embodiments, when $R^{B1D}$ is substituted, it is substituted with at least one size-limited substituent group. In embodiments, when $R^{B1D}$ is substituted, it is substituted with at least one lower substituent group.

In embodiments, $R^{B1D}$ is independently hydrogen. In embodiments, $R^{B1D}$ is independently —$CX^{B1D}_3$. In embodiments, $R^{B1D}$ is independently —$CHX^{B1D}2$. In embodiments, $R^{B1D}$ is independently —$CH_2X^{B1D}$. In embodiments, $R^{B1D}$ is independently —$OCX^{B1D}_3$. In embodiments, $R^{B1D}$ is independently —$OCHX^{B1D}2$. In embodiments, $R^{B1D}$ is independently —$OCH_2X^{B1D}$. In embodiments, $R^{B1D}$ is independently —OH. In embodiments, $R^{B1D}$ is independently —CN. In embodiments, $R^{B1D}$ is independently —COOH. In embodiments, $R^{B1D}$ is independently —$CONH_2$. In embodiments, $X^{B1D}$ is independently —F, —Cl, —Br, or —I.

In embodiments, $R^{B1D}$ is independently substituted or unsubstituted alkyl (e.g., $C_1$-$C_8$, $C_1$-$C_6$, $C_1$-$C_4$, or $C_1$-$C_2$). In embodiments, $R^{B1D}$ is independently substituted alkyl (e.g., $C_1$-$C_8$, $C_1$-$C_6$, $C_1$-$C_4$, or $C_1$-$C_2$). In embodiments, $R^{B1D}$ is independently unsubstituted alkyl (e.g., $C_1$-$C_8$, $C_1$-$C_6$, $C_1$-$C_4$, or $C_1$-$C_2$). In embodiments, $R^{B1D}$ is independently unsubstituted methyl. In embodiments, $R^{1D}$ is independently unsubstituted ethyl. In embodiments, $R^{B1D}$ is independently unsubstituted propyl. In embodiments, $R^{B1D}$ is independently unsubstituted isopropyl. In embodiments, $R^{B1D}$ is independently unsubstituted tert-butyl. In embodiments, $R^{B1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1D}$ is independently substituted heteroalkyl (e.g., 2 to 8 membered, 2 to 6 membered, 4 to 6 membered, 2 to 3 membered, or 4 to 5 membered). In embodiments, $R^{B1D}$ is independently unsubstituted heteroalkyl (e.g., 2 to 8 membered, 2 to 6 membered, 4 to 6 membered, 2 to 3 membered, or 4 to 5 membered). In embodiments, $R^{B1D}$ is independently substituted or unsubstituted cycloalkyl (e.g., $C_3$-$C_8$, $C_3$-$C_6$, $C_4$-$C_6$, or $C_5$-$C_6$). In embodiments, $R^{B1D}$ is independently substituted cycloalkyl (e.g., $C_3$-$C_8$, $C_3$-$C_6$, $C_4$-$C_6$, or $C_5$-$C_6$). In embodiments, $R^{B1D}$ is independently unsubstituted cycloalkyl (e.g., $C_3$-$C_8$, $C_3$-$C_6$, $C_4$-$C_6$, or $C_5$-$C_6$). In embodiments, $R^{B1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1D}$ is independently substituted heterocycloalkyl (e.g., 3 to 8 membered, 3 to 6 membered, 4 to 6 membered, 4 to 5 membered, or 5 to 6 membered). In embodiments, $R^{B1D}$ is independently unsubstituted heterocycloalkyl (e.g., 3 to 8 membered, 3 to 6 membered, 4 to 6 membered, 4 to 5 membered, or 5 to 6 membered). In embodiments, $R^{B1D}$ is independently substituted or unsubstituted aryl (e.g., $C_6$-$C_{10}$ or phenyl). In embodiments, $R^{B1D}$ is independently substituted aryl (e.g., $C_6$-$C_{10}$ or phenyl). In embodiments, $R^{B1D}$ is independently unsubstituted aryl (e.g., $C_6$-$C_{10}$ or phenyl). In embodiments, $R^{B1D}$ is independently substituted or unsubstituted heteroaryl (e.g., 5 to 10 membered, 5 to 9 membered, or 5 to 6 membered). In embodiments, $R^{B1D}$ is independently substituted heteroaryl (e.g., 5 to 10 membered, 5 to 9 membered, or 5 to 6 membered). In embodiments, $R^{B1D}$ is independently pyridyl N-oxide. In embodiments, $R^{B1D}$ is independently unsubstituted heteroaryl (e.g., 5 to 10 membered, 5 to 9 membered, or 5 to 6 membered). In embodiments, $R^{B1D}$ is independently unsubstituted pyridyl.

In embodiments, $R^{B1}$ is independently hydrogen, halogen, —$CX^{B1}_3$, —$CHX^{B1}2$, —$CH_2X^{B1}$, —$OCX^{B1}_3$, —$OCH_2X^{B1}$, —$OCHX^{B1}2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —NHC(NH)H, —NHC(NH)$NH_2$, —$NHSO_2H$, —NHC(O)H, —NHC(O)OH, —NHOH, —$N_3$, $R^{B10}$-substituted or unsubstituted alkyl (e.g., $C_1$-$C_8$, $C_1$-$C_6$, $C_1$-$C_4$, or $C_1$-$C_2$), $R^{B10}$-substituted or unsubstituted heteroalkyl (e.g., 2 to 8 membered, 2 to 6 membered, 4 to 6 membered, 2 to 3 membered, or 4 to 5 membered), $R^{B10}$-substituted or unsubstituted cycloalkyl (e.g., $C_3$-$C_8$, $C_3$-$C_6$, $C_4$-$C_6$, or $C_5$-$C_6$), $R^{B10}$-substituted or unsubstituted heterocycloalkyl (e.g., 3 to 8 membered, 3 to 6 membered, 4 to 6 membered, 4 to 5 membered, or 5 to 6 membered), $R^{B10}$-substituted or unsubstituted aryl (e.g., $C_6$-$C_{10}$ or phenyl), or $R^{B10}$-substituted or unsubstituted heteroaryl (e.g., 5 to 10 membered, 5 to 9 membered, or 5 to 6 membered). In embodiments, $R^{B1}$ is independently hydrogen, halogen, —$CX^{B1}_3$, —$CHX^{B1}2$, —$CH_2X^{B1}$, —$OCX^{B1}_3$, —$OCH_2X^{B1}$, —$OCHX^{B1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —NHC(NH)H, —NHC(NH)$NH_2$, —$NHSO_2H$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{B1}$ is independently —F, —Cl, —Br, or —I. In embodiments, $R^{B1}$ is independently —COOH. In embodiments, $R^{B1}$ is independently unsubstituted pyridyl. In embodiments, $R^{B1}$ is independently pyridyl N-oxide. In embodiments, $R^{B1}$ is independently $R^{B10}$-substituted pyridyl N-oxide. In embodiments, $R^{B1}$ is independently unsubstituted pyridyl N-oxide. In embodiments, $R^{B1}$ is independently $R^{B10}$-substituted pyridin-2-yl N-oxide. In embodiments, $R^{B1}$ is independently unsubstituted pyridin-2-yl N-oxide. In embodiments, $R^{B1}$ is independently $R^{B10}$-substituted pyridin-3-yl N-oxide. In embodiments, $R^{B1}$ is independently unsubstituted pyridin-3-yl N-oxide. In embodiments, $R^{B1}$ is independently $R^{B10}$-substituted pyridin-4-yl N-oxide. In embodiments, $R^{B1}$ is independently unsubstituted pyridin-4-yl N-oxide.

$R^{B10}$ is oxo, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—NR^{B10A}C(NR^{B10C})R^{B10D}$, $—NR^{B10D}C(NR^{B10C})NR^{B10A}R^{B10B}$, $—N(O)_{mB10}—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B10A}$, $R^{B10B}$, $R^{B10C}$, and $R^{B10D}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B10A}$ and $R^{B10B}$ substituents bonded to the same nitrogen atom may be joined to form a substituted or unsubstituted heterocycloalkyl or substituted or unsubstituted heteroaryl; nB10 is independently an integer from 0 to 4; mB10 and v10 are independently 1 or 2; and $X^{B10}$ is independently —F, —Cl, —Br, or —I.

In embodiments, $R^{B10}$ is halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—NR^{B10A}C(NR^{B10C})R^{B10D}$, $—NR^{B10A}C(NR^{B10C})NR^{B10A}R^{B10B}$, $—N(O)_{mB10}—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10}$ is substituted with a plurality of groups selected from substituent groups, size-limited substituent groups, and lower substituent groups; each substituent group, size-limited substituent group, and/or lower substituent group may optionally be different. In embodiments, when $R^{B10}$ is substituted, it is substituted with at least one substituent group. In embodiments, when $R^{B10}$ is substituted, it is substituted with at least one size-limited substituent group. In embodiments, when $R^{B10}$ is substituted, it is substituted with at least one lower substituent group.

In embodiments, $R^{B10}$ is halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—NR^{B10A}C(NR^{B10C})R^{B10D}$, $—NR^{B10A}C(NR^{B10C})NR^{B10A}R^{B10B}$, $—N(O)_{mB10}$, $—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B10A}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10A}$ is substituted with a plurality of groups selected from substituent groups, size-limited substituent groups, and lower substituent groups; each substituent group, size-limited substituent group, and/or lower substituent group may optionally be different. In embodiments, when $R^{B10A}$ is substituted, it is substituted with at least one substituent group. In embodiments, when $R^{B10A}$ is substituted, it is substituted with at least one size-limited substituent group. In embodiments, when $R^{B10A}$ is substituted, it is substituted with at least one lower substituent group.

In embodiments, $R^{B10B}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10B}$ is substituted with a plurality of groups selected from substituent groups, size-limited substituent groups, and lower substituent groups; each substituent group, size-limited substituent group, and/or lower substituent group may optionally be different. In embodiments, when $R^{B10B}$ is substituted, it is substituted with at least one substituent group. In embodiments, when $R^{B10B}$ is substituted, it is substituted with at least one size-limited substituent group. In embodiments, when $R^{B10B}$ is substituted, it is substituted with at least one lower substituent group.

In embodiments, $R^{B10A}$ and $R^{B10B}$ substituents bonded to the same nitrogen atom may be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{B10A}$ and $R^{B10B}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{B10A}$ and $R^{B10B}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{B10A}$ and $R^{B10B}$ substituents bonded to the same nitrogen atom is substituted, it is substituted with at least one substituent group. In embodiments, when the moiety formed by joining $R^{B10A}$ and $R^{B10B}$ substituents bonded to the same nitrogen atom is substituted, it is substituted with at least one size-limited substituent group. In embodiments, when the moiety formed by joining $R^{B10A}$ and $R^{B10B}$ substituents bonded to the same nitrogen atom is substituted, it is substituted with at least one lower substituent group.

In embodiments, $R^{B10C}$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10C}$ is substituted with a plurality of groups selected from substituent groups, size-limited substituent groups, and lower substituent groups; each substituent group, size-limited substituent group, and/or lower substituent group may optionally be different. In embodiments, when $R^{B10C}$ is substituted, it is substituted with at least one substituent group. In embodiments, when $R^{B10C}$ is substituted, it is substituted with at least one size-limited substituent group. In embodiments, when $R^{B10C}$ is substituted, it is substituted with at least one lower substituent group.

In embodiments, $R^{B10D}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{B10D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{B10D}$ is substituted with a plurality of groups selected from substituent groups, size-limited substituent groups, and lower substituent groups; each substituent group, size-limited substituent group, and/or lower substituent group may optionally be different. In embodiments, when $R^{B10D}$ is substituted, it is substituted with at least one substituent group. In embodiments, when $R^{B10D}$ is substituted, it is substituted with at least one size-limited substituent group. In embodiments, when $R^{B10D}$ is substituted, it is substituted with at least one lower substituent group.

In embodiments, $R^{B10}$ is independently oxo, halogen, $—CX^{B10}_3$, $—CHX^{B10}2$, $—CH_2X^{B10}$, $—OCX^{B10}_3$, $—OCH_2X^{B10}$, $—OCHX^{B10}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, —NHC(NH)H, $—NHC(NH)NH_2$, $—NHSO_2H$, —NHC(O)H, —NHC(O)OH, —NHOH, $—N_3$, $R^{B11}$-substituted or unsubstituted alkyl (e.g., $C_1$-$C_8$, $C_1$-$C_6$, $C_1$-$C_4$, or $C_1$-$C_2$), $R^{B11}$-substituted or unsubstituted heteroalkyl (e.g., 2 to 8 membered, 2 to 6 membered, 4 to 6 membered, 2 to 3 membered, or 4 to 5 membered), $R^{B11}$-substituted or unsubstituted cycloalkyl (e.g., $C_3$-$C_8$, $C_3$-$C_6$, $C_4$-$C_6$, or $C_5$-$C_6$), $R^{B11}$-substituted or unsubstituted heterocycloalkyl (e.g., 3 to 8 membered, 3 to 6 membered, 4 to 6 membered, 4 to 5 membered, or 5 to 6 membered), $R^{B11}$-substituted or unsubstituted aryl (e.g., $C_6$-$C_{10}$ or phenyl), or $R^{B11}$-substituted or unsubstituted heteroaryl (e.g., 5 to 10 membered, 5 to 9 membered, or 5 to 6 membered). $X^{B10}$ is independently —F, —Cl, —Br, or —I. In embodiments, $R^{B10}$ is independently substituted or unsubstituted $C_1$-$C_4$ alkyl. In embodiments, $R^{B10}$ is independently unsubstituted methyl. In embodiments, $R^{B10}$ is independently —COOH. In embodiments, $R^{B10}$ is independently unsubstituted pyridyl. In embodiments, $R^{B10}$ is independently pyridyl N-oxide. In embodiments, $R^{B10}$ is independently $R^{B11}$-substituted pyridin-2-yl N-oxide. In embodiments, $R^{B10}$ is independently unsubstituted pyridin-2-yl N-oxide. In embodiments, $R^{B10}$ is independently $R^{B11}$-substituted pyridin-3-yl N-oxide. In embodiments, $R^{B10}$ is independently unsubstituted pyridin-3-yl N-oxide. In embodiments, $R^{B10}$ is independently $R^{B11}$-substituted pyridin-4-yl N-oxide. In embodiments, $R^{B10}$ is independently unsubstituted pyridin-4-yl N-oxide.

$R^{B11}$ is independently oxo, halogen, $—CX^{B11}_3$, $—CHX^{B11}_2$, $—CH_2X^{B11}$, $—OCX^{B11}_3$, $—OCH_2X^{B11}$, $—OCHX^{B11}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, —NHC(NH)H, $—NHC(NH)NH_2$, $—NHSO_2H$, —NHC(O)H, —NHC(O)OH, —NHOH, $—N_3$, $R^{B12}$-substituted or unsubstituted alkyl (e.g., $C_1$-$C_8$, $C_1$-$C_6$, $C_1$-$C_4$, or $C_1$-$C_2$), $R^{B12}$-substituted or unsubstituted heteroalkyl (e.g., 2 to 8 membered, 2 to 6 membered, 4 to 6 membered, 2 to 3 membered, or 4 to 5 membered), $R^{B12}$-substituted or unsubstituted cycloalkyl (e.g., $C_3$-$C_8$, $C_3$-$C_6$, $C_4$-$C_6$, or $C_5$-$C_6$), $R^{B12}$-substituted or unsubstituted heterocycloalkyl (e.g., 3 to 8 membered, 3 to 6 membered, 4 to 6 membered, 4 to 5 membered, or 5 to 6 membered), $R^{B12}$-substituted or unsubstituted aryl (e.g., $C_6$-$C_{10}$ or phenyl), or $R^{B12}$-substituted or unsubstituted heteroaryl (e.g., 5 to 10 membered, 5 to 9 membered, or 5 to 6 membered). $X^{B11}$ is independently —F, —Cl, —Br, or —I. In embodiments, $R^{B11}$ is independently substituted or unsubstituted $C_1$-$C_4$ alkyl. In embodiments, $R^{B11}$ is independently unsubstituted methyl. In embodiments, $R^{B11}$ is independently —COOH. In embodiments, $R^{B11}$ is independently unsubstituted pyridyl. In embodiments, $R^{B11}$ is independently pyridyl N-oxide. In embodiments, $R^{B11}$ is independently $R^{B12}$-substituted pyridin-2-yl N-oxide. In embodiments, $R^{B11}$ is independently unsubstituted pyridin-2-yl N-oxide. In embodiments, $R^{B11}$ is independently $R^{B12}$-substituted pyridin-3-yl N-oxide. In embodiments, $R^{B11}$ is independently unsubstituted pyridin-3-yl N-oxide. In embodiments, $R^{B11}$ is independently $R^{B12}$-substituted pyridin-4-yl N-oxide. In embodiments, $R^{B11}$ is independently unsubstituted pyridin-4-yl N-oxide.

$R^{B12}$ is independently oxo, halogen, $—CX^{B12}_3$, $—CHX^{B12}_2$, $—CH_2X^{B12}$, $—OCX^{B12}_3$, $—OCH_2X^{B12}$, $—OCHX^{B12}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, —NHC (NH)H, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), or unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{B12}$ is independently —F, —Cl, —Br, or —I. In embodiments, $R^{B12}$ is independently unsubstituted methyl. In embodiments, $R^{B12}$ is independently —COOH. In embodiments, $R^{B12}$ is independently unsubstituted pyridyl. In embodiments, $R^{B12}$ is independently —$O^-$.

In embodiments, nB1 is 0. In embodiments, nB1 is 1. In embodiments, nB1 is 2. In embodiments, nB1 is 3. In embodiments, nB1 is 4. In embodiments, mB1 is 1. In embodiments, mB1 is 2. In embodiments, vB1 is 1. In embodiments, vB1 is 2. In embodiments, $X^{B1}$ is independently —F. In embodiments, $X^{B1}$ is independently —Cl. In embodiments, $X^{B1}$ is independently —Br. In embodiments, $X^{B1}$ is independently —I.

In embodiments, nB10 is 0. In embodiments, nB10 is 1. In embodiments, nB10 is 2. In embodiments, nB10 is 3. In embodiments, nB10 is 4. In embodiments, mB10 is 1. In embodiments, mB10 is 2. In embodiments, vB10 is 1. In embodiments, vB10 is 2. In embodiments, $X^{B10}$ is independently —F. In embodiments, $X^{B10}$ is independently —Cl. In embodiments, $X^{B10}$ is independently —Br. In embodiments, $X^{B10}$ is independently —I.

In embodiments, $X^{B11}$ is independently —F. In embodiments, $X^{B11}$ is independently —Cl. In embodiments, $X^{B11}$ is independently-Br. In embodiments, $X^{B11}$ is independently —I.

In embodiments, $X^{B12}$ is independently —F. In embodiments, $X^{B12}$ is independently —Cl. In embodiments, $X^{B12}$ is independently —Br. In embodiments, $X^{B12}$ is independently —I.

In embodiments, $R^{B1}$ is halogen, —$NR^{B1A}R^{B1B}$, —$N_3$, —$SR^{B1D}$,

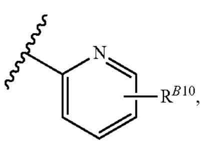 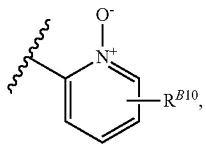

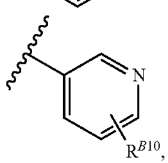 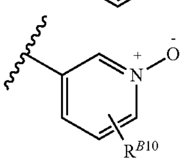 ,

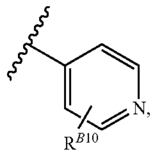 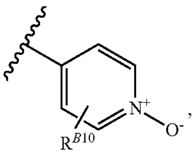

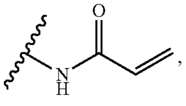 , 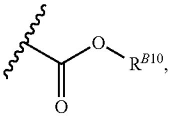 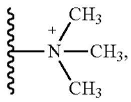

-continued

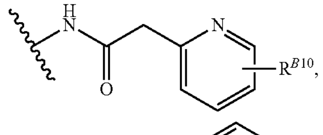

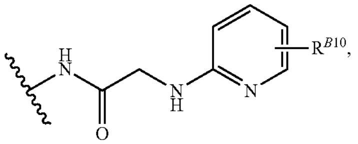

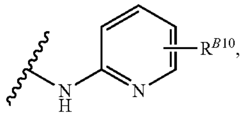 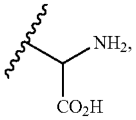

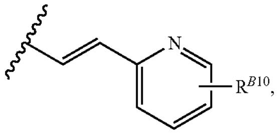 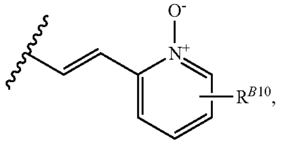

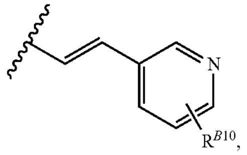 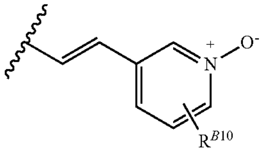 ,

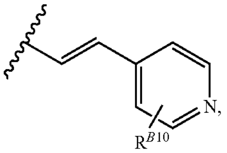 or 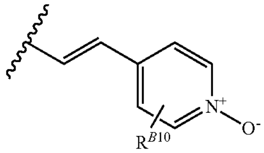 .

$R^{B1A}$, $R^{B1B}$, $R^{B1D}$, and $R^{B10}$ areas described herein, including in embodiments.

In embodiments, $R^{B1}$ is —Cl, —$NH_2$, —$N_3$, —SH, —$N(CH_3)_3^+$,

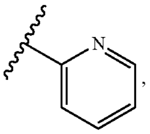 , 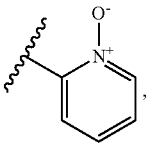 ,

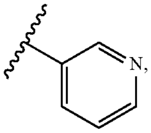 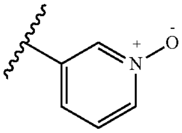 ,

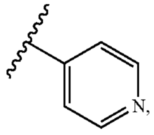 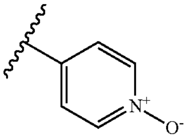

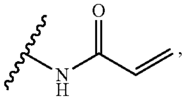 , 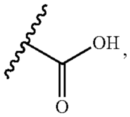 , 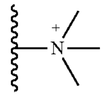 ,

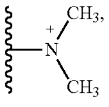 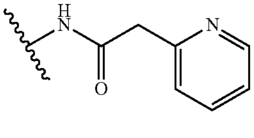 ,

-continued
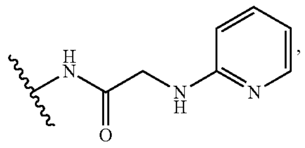
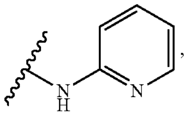
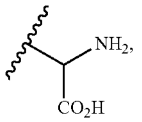
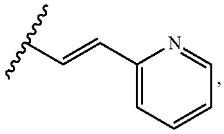
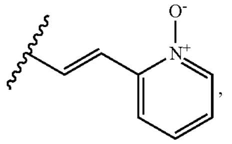
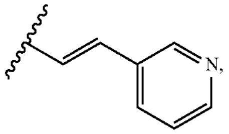
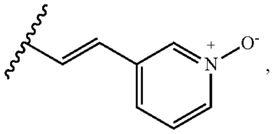
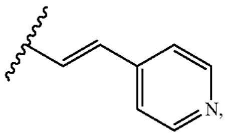
or
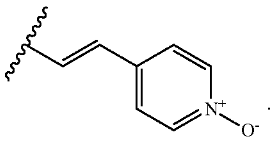
In embodiments, $L^{B1}$-$R^{B1}$ is
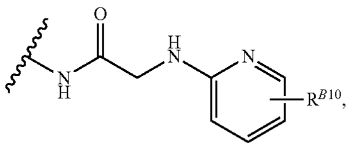
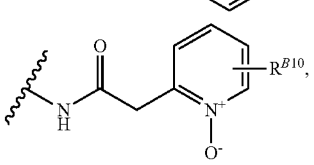
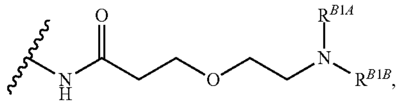
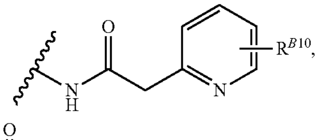
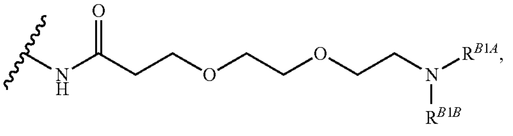
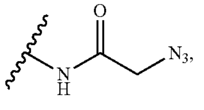
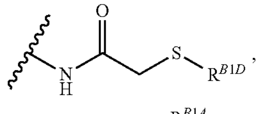
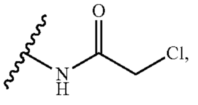
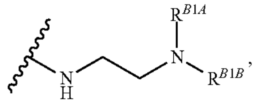
-continued
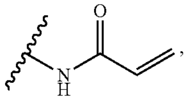
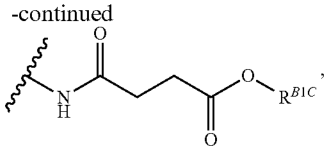
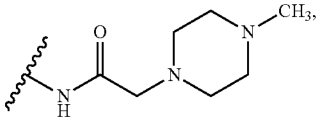
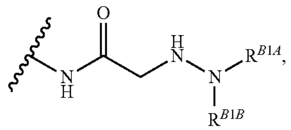
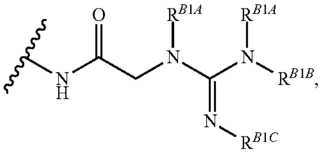
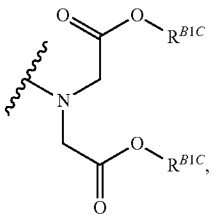
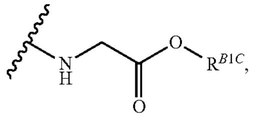
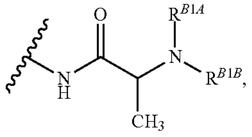
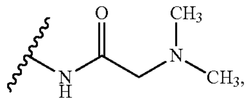
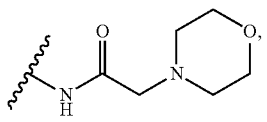
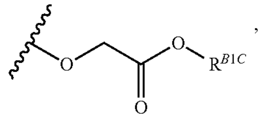
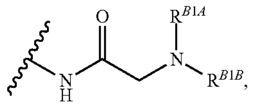
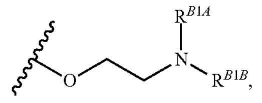
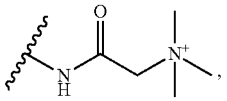
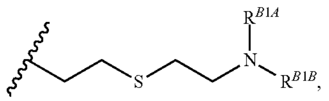
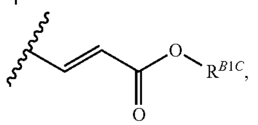
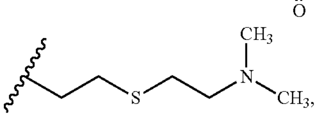
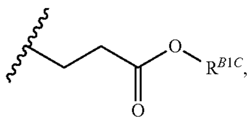
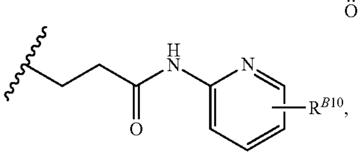
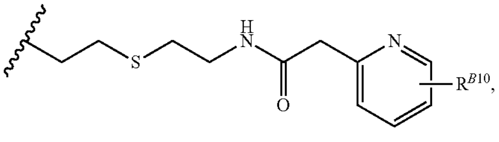

-continued
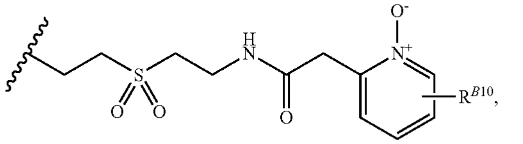
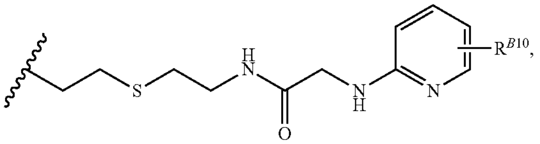
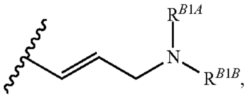
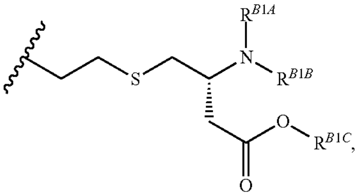
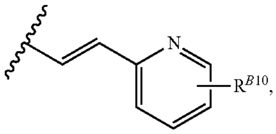 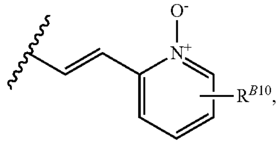
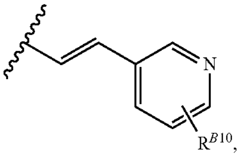 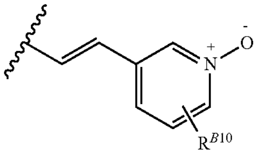
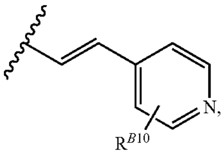 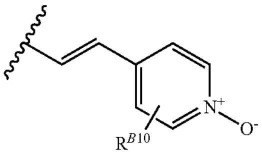
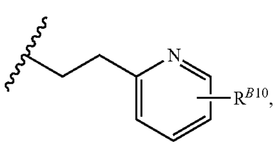 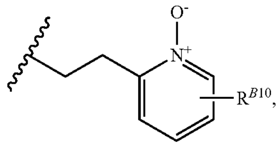
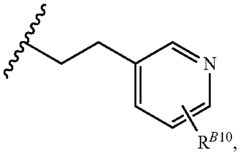 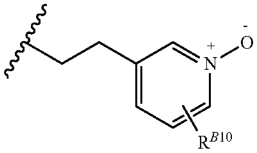
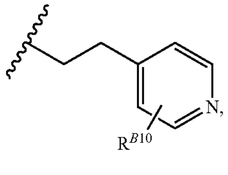 or 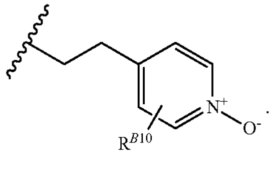
$R^{B1A}$, $R^{B1B}$, $R^{B1D}$, and $R^{B10}$ are as described herein, including in embodiments.
In embodiments, $L^{B1}$-$R^{B1}$ is
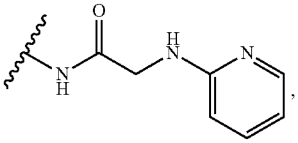
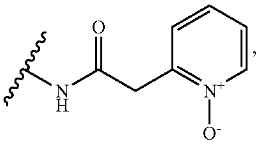
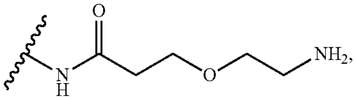
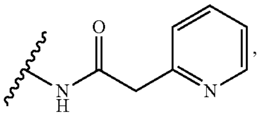
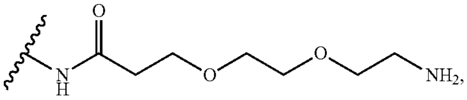
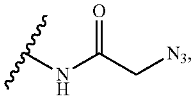 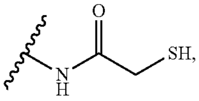
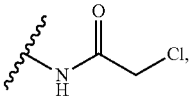 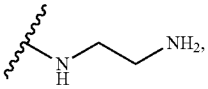
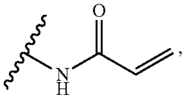 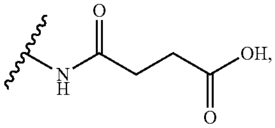
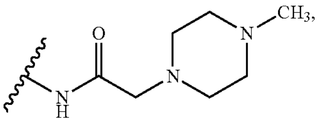
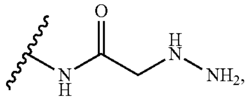
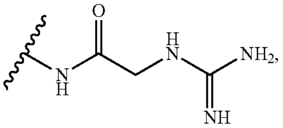
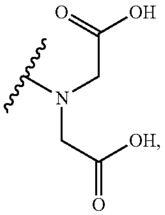 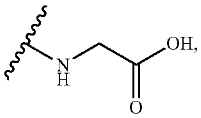
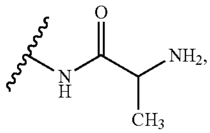 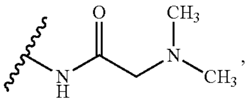

-continued
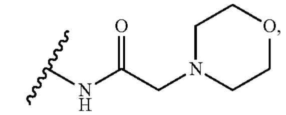,
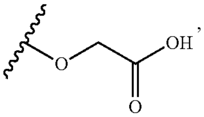,
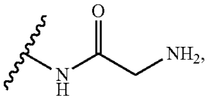,
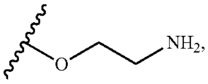,
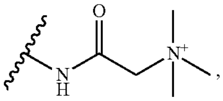,
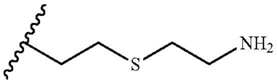,
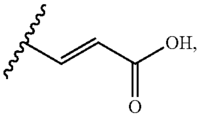,
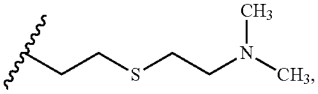,
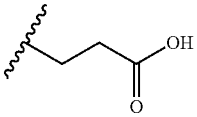,
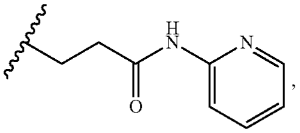,
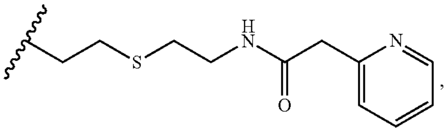,
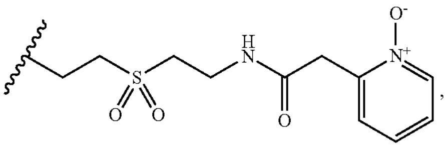,
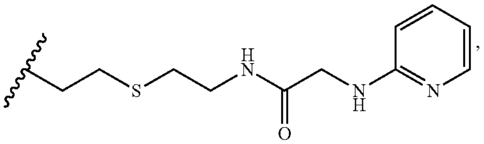,
-continued
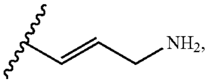,
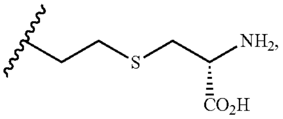,
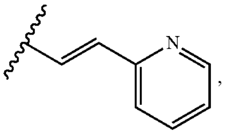,
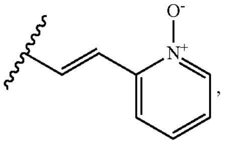,
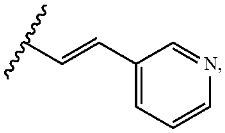,
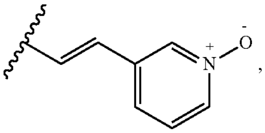,
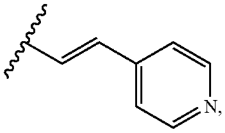,
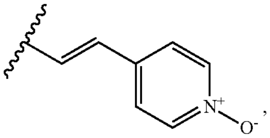,
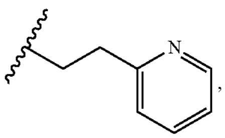,
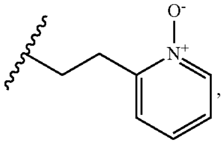,
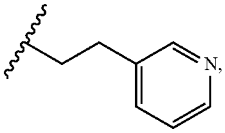,
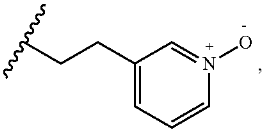,
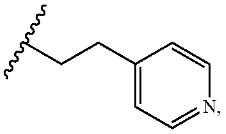, or
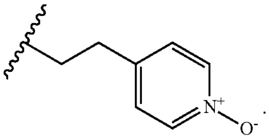.
In embodiments, the compound is not
(FK506, (I))
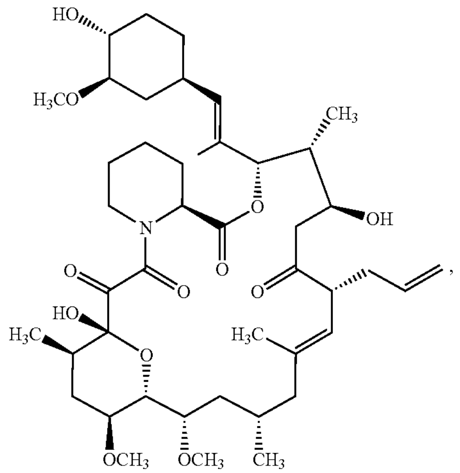,
(SLF, (II))
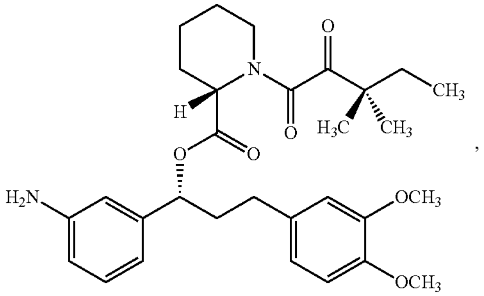, -continued
(Sanglefehrin A (III))
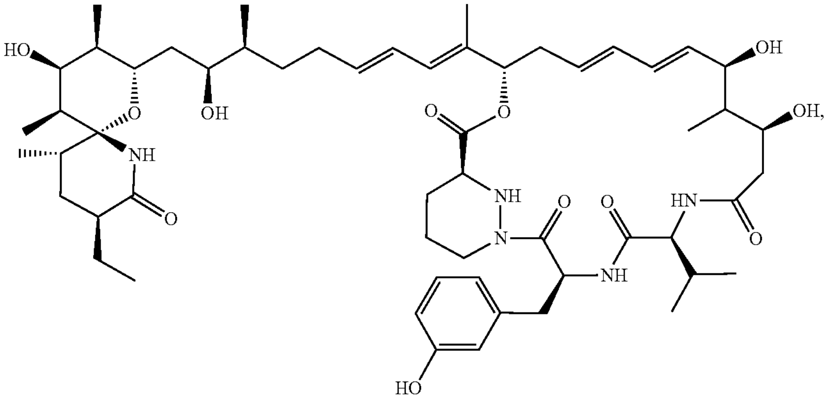
(Cyclosporin A (IV))
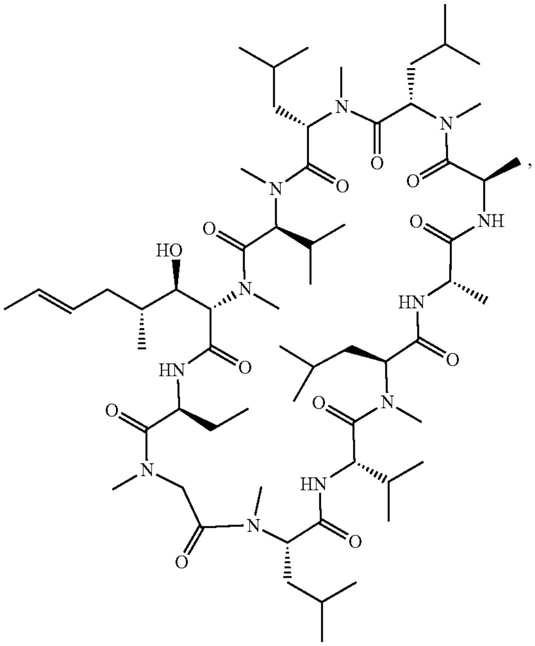
, or
(Rapamycin (V))
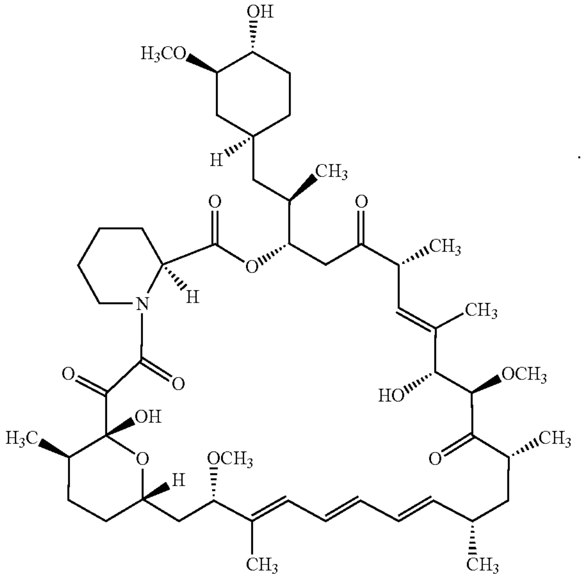
.

In embodiments, the compound is not
(FK506, (I))
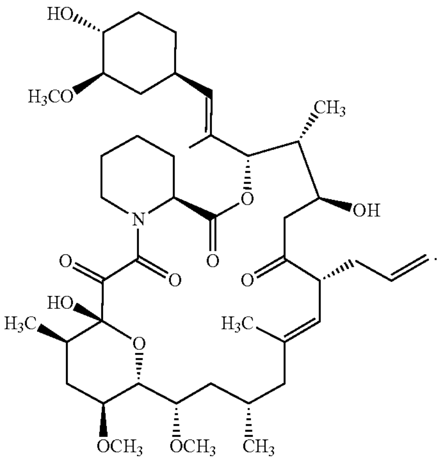
In embodiments, the compound is not
(SLF, (II))
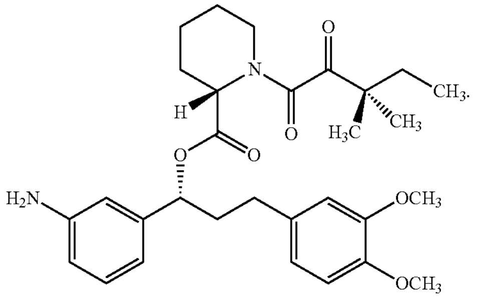
In embodiments, the compound is not
(Sanglefehrin A (III))
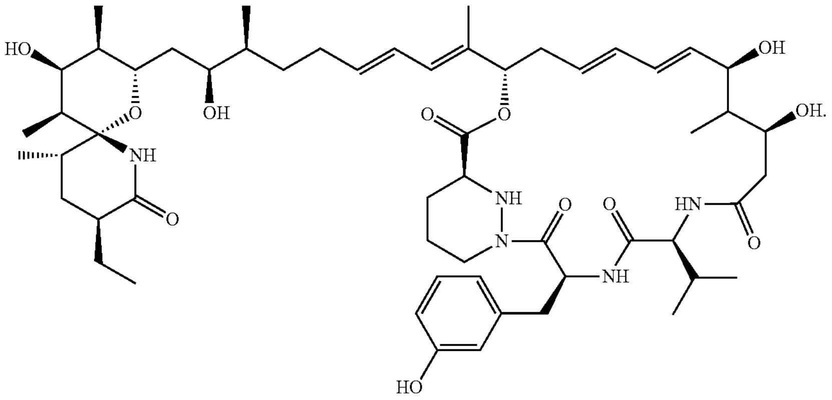
In embodiments, the compound is not
(Cyclosporin A (IV));
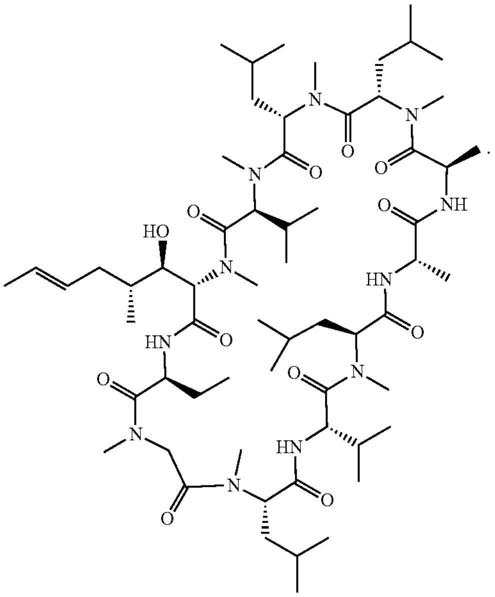

In embodiments, the compound is not
(Rapamycin (V))
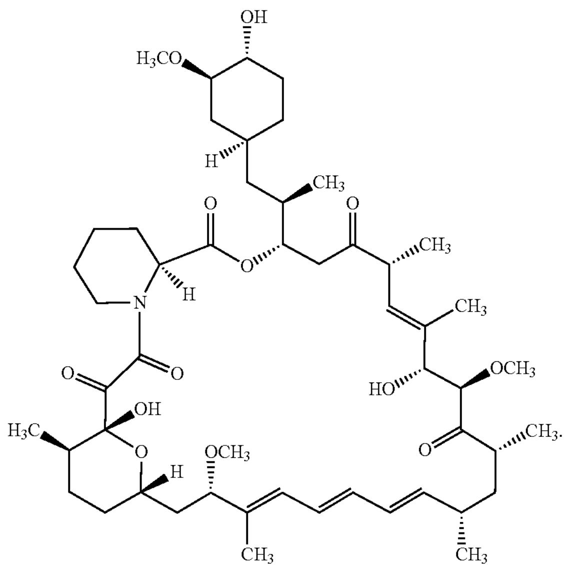
In embodiments, the compound is not
(SLF, (II))
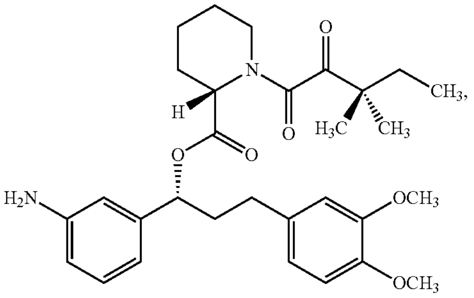
(Sanglefehrin A (III))
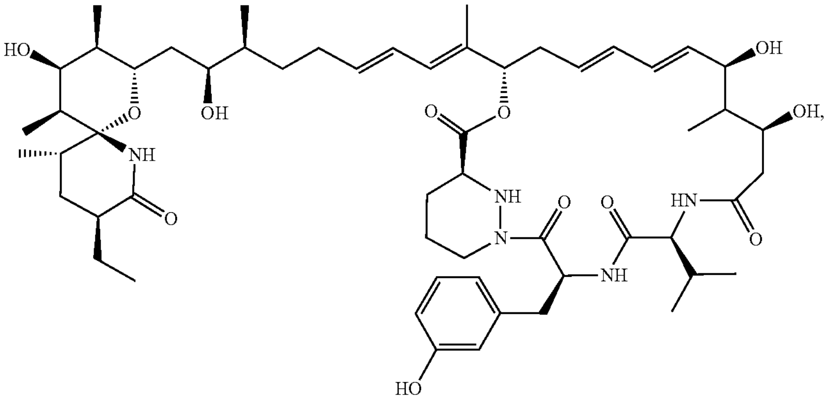

-continued (Cyclosporin A (IV))

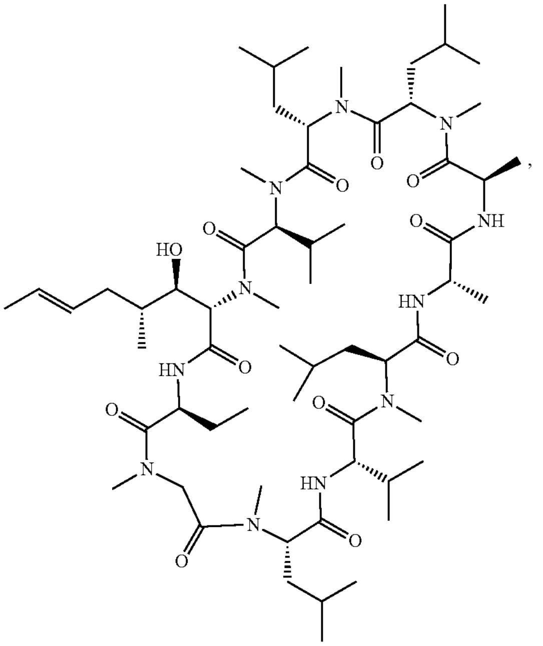

, or (Rapamycin (V))

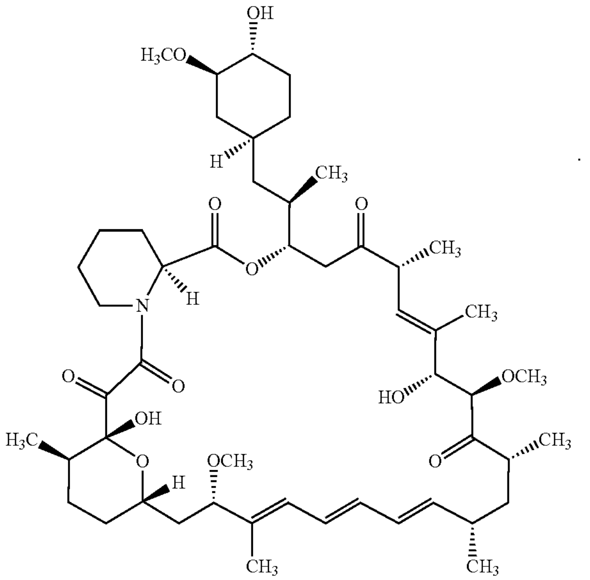

In embodiments, $A^B$ is an immunophilin-binding moiety having the formula

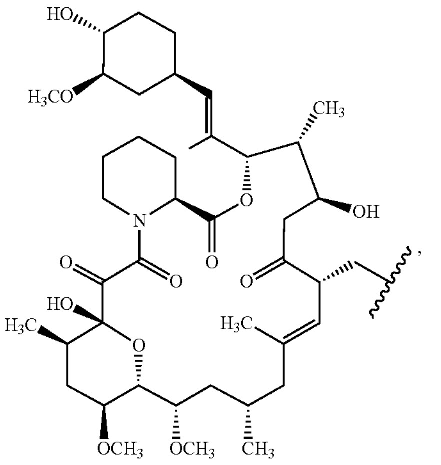 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof; $L^{B1}$ is $L^{B2}$-$L^{B3}$-$L^{B4}$; $L^{B2}$ is $—S(O)_2—$, $—N(R^{B2})—$, —O—, —S—, $—C(O)N(R^{B2})—$, $—N(R^{B2})C(O)—$, $—N(R^{B2})C(O)NH—$, $—NHC(O)N(R^{B2})—$, —C(O)O—, —OC(O)—; $L^{B3}$ is a bond, $—S(O)_2—$, $—N(R^{B3})—$, —O—, —S—, —C(O)—, $—C(O)N(R^{B3})—$, $—N(R^{B3})C(O)—$, $—N(R^{B3})C(O)NH—$, $—NHC(O)N(R^{B3})—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{B4}$ is a bond, $—S(O)_2—$, $—N(R^{B4})—$, —O—, —S—, —C(O)—, $—C(O)N(R^{B4})—$, $—N(R^{B4})C(O)—$, $—N(R^{B4})C(O)NH—$, $—NHC(O)N(R^{B4})—$, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{B2}$ $R^{B3}$, and $R^{B4}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1}$ is hydrogen, halogen, $—CX^{B1}_3$, $—CHX^{B1}_2$, $—CH_2X^{B1}$, $—OCX^{B1}_3$, $—OCH_2X^{B1}$, $—OCHX^{B1}_2$, —CN, $—SO_{nB1}R^{B1D}$, $—SO_{vB1}NR^{B1A}R^{B1B}$, $—NHC(O)NR^{B1A}R^{B1B}$, $—N(O)_{mB1}$, $—NR^{B1A}R^{B1B}$, $—C(O)R^{B1C}$, $—C(O)OR^{B1C}$, $—C(O)NR^{B1A}R^{B1B}$, $—OR^{B1D}$, $—NR^{B1A}SO_2R^{B1D}$, $—NR^{B1A}C(O)R^{B1C}$, $—NR^{B1A}C(O)OR^{B1C}$, $—NR^{B1A}OR^{B1C}$, $—NR^{B1A}C(NR^{B1C})R^{B1D}$, $—NR^{B1A}C(NR^{B1C})NR^{B1A}R^{B1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl; nB1 is independently an integer from 0 to 4; mB1 and vB1 are independently 1 or 2; and $X^{B1}$ is independently —F, —Cl, —Br, or —I.

In embodiments, $L^{B1}$ is

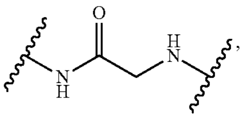
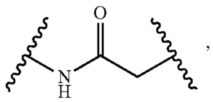
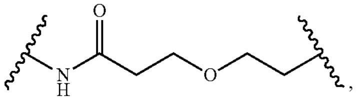
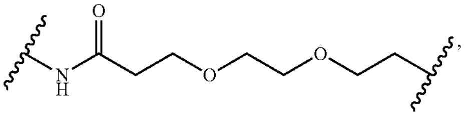
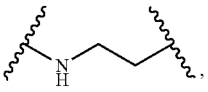
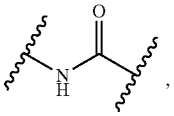
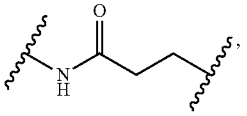
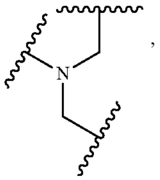
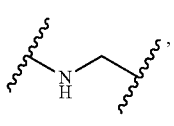
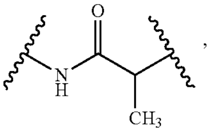
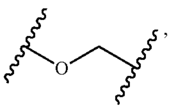
or
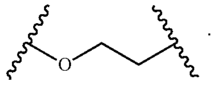

In embodiments, $L^{B1}$-$R^{B1}$ is

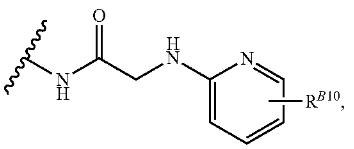

-continued

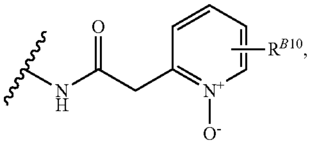
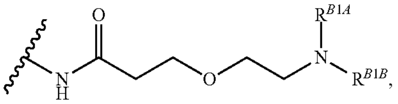
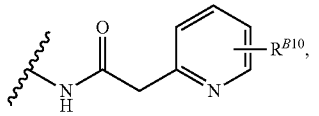
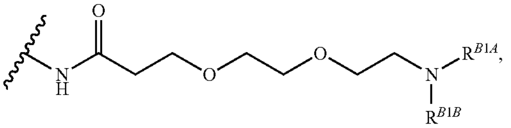
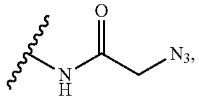
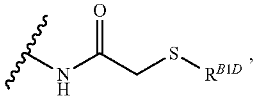
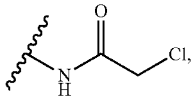
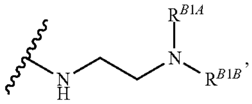
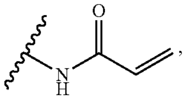
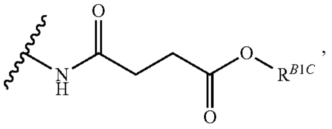
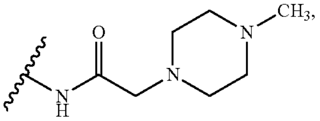
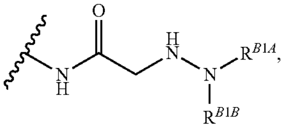
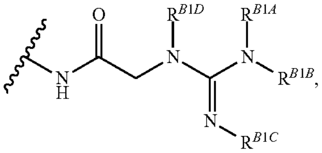
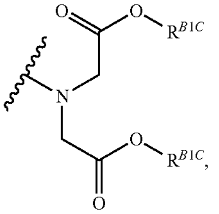
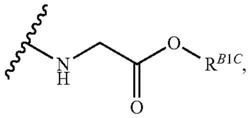
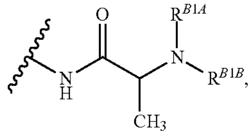
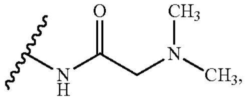
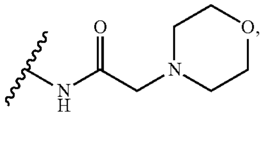
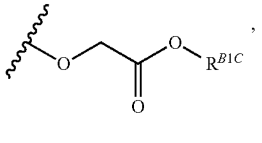

-continued

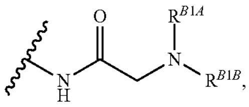
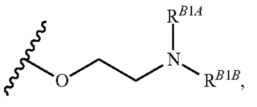
or
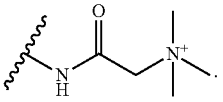

$R^{B1A}$, $R^{B1B}$, $R^{B1D}$, and $R^{B10}$ are as described herein, including in embodiments.

In embodiments, $L^{B1}$-$R^{B1}$ is

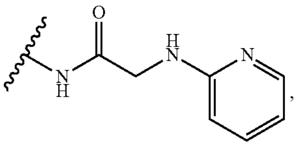
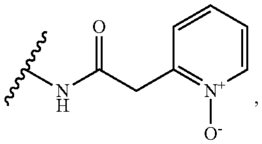
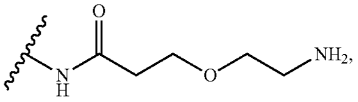
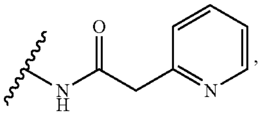
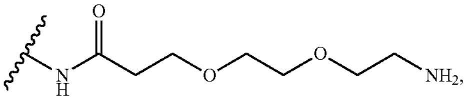
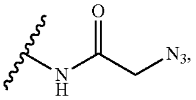
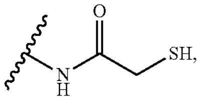
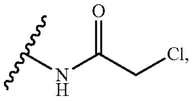
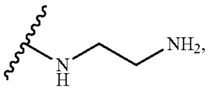
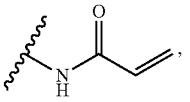
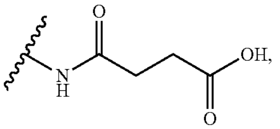
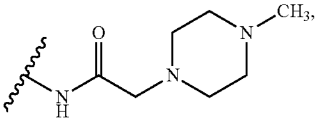
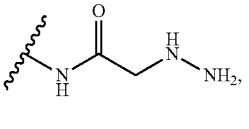
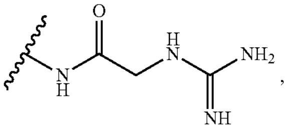
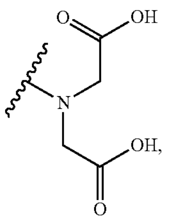
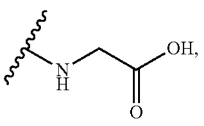

-continued

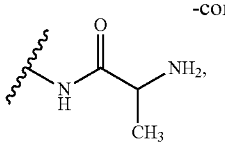
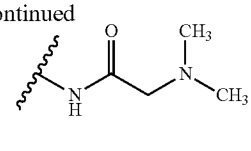
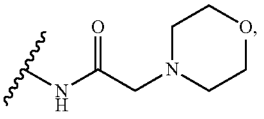
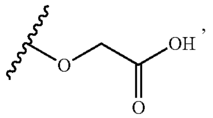
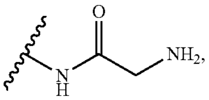
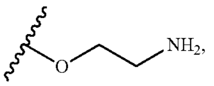
or
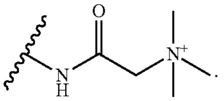

In embodiments, $A^{B}$ is an immunophilin-binding moiety having the formula

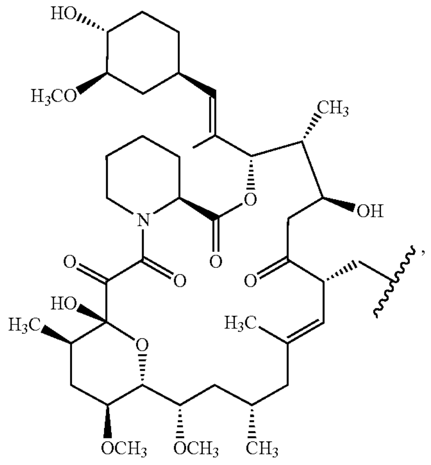 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or an analog thereof; $L^{B1}$ is

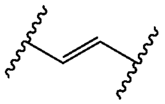
or
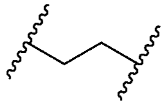
;

$R^{B1}$ is substituted or unsubstituted heteroaryl. In embodiments, $R^{B1}$ is independently substituted or unsubstituted heteroaryl (e.g., 5 to 10 membered, 5 to 9 membered, or 5 to 6 membered). In embodiments, $R^{B1}$ is independently substituted heteroaryl (e.g., 5 to 10 membered, 5 to 9 membered, or 5 to 6 membered). In embodiments, $R^{B1}$ is substituted or unsubstituted pyridyl. In embodiments, $R^{B1}$ is independently pyridyl N-oxide. In embodiments, $R^{B1}$ is independently unsubstituted heteroaryl (e.g., 5 to 10 membered, 5 to 9 membered, or 5 to 6 membered). In embodiments, $R^{B1}$ is independently unsubstituted pyridyl. In embodiments, $R^{B1}$ is independently $R^{B10}$-substituted pyridyl N-oxide. In embodiments, $R^{B1}$ is independently unsubstituted pyridyl N-oxide. In embodiments, $R^{B1}$ is independently $R^{B10}$-substituted pyridin-2-yl N-oxide. In embodiments, $R^{B1}$ is independently unsubstituted pyridin-2-yl N-oxide. In embodiments, $R^{B1}$ is independently $R^{B10}$-substituted pyridin-3-yl N-oxide. In embodiments, $R^{B1}$ is independently unsubstituted pyridin-3-yl N-oxide. In embodiments, $R^{B1}$ is independently $R^{B10}$-substituted pyridin-4-yl N-oxide. In embodiments, $R^{B1}$ is independently unsubstituted pyridin-4-yl N-oxide.

In embodiments, $A^{B}$ is an immunophilin-binding moiety having the formula

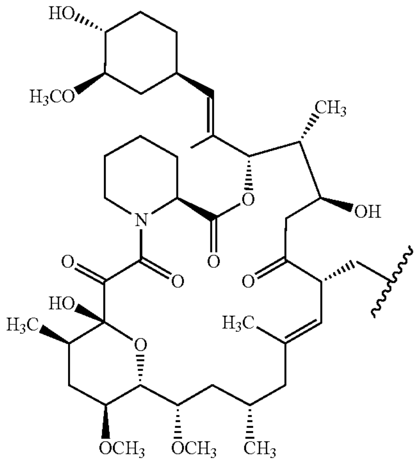

or an analog thereof; $L^{B1}$ is

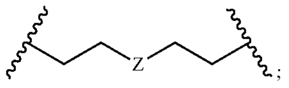

Z is —S— or —$SO_2$—; $R^{B1}$ is —$NR^{B1A}R^{B1B}$ or —NHC(O)$CH_2R^{B1C}$.

In embodiments, $R^{B1A}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B1A}$ is independently —$CX^{B1A}_3$. In embodiments, $R^{B1A}$ is independently —$CHX^{B1A}2$. In embodiments, $R^{B1A}$ is independently —$CH_2X^{B1A}$. In embodiments, $R^{B1A}$ is independently —$OCX^{B1A}_3$. In embodiments, $R^{B1A}$ is independently —$OCHX^{B1A}2$. In embodiments, $R^{B1A}$ is independently —$OCH_2X^{B1A}$. In embodiments, $R^{B1A}$ is independently —OH. In embodiments, $R^{B1A}$ is independently —CN. In embodiments, $R^{B1A}$ is independently —COOH. In embodiments, $R^{B1A}$ is independently —$CONH_2$. In embodiments, $X^{B1A}$ is independently —F, —Cl, —Br, or —I.

In embodiments, $R^{B1B}$ is independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B1B}$ is independently —$CX^{B1B}_3$. In embodiments, $R^{B1B}$ is independently —$CHX^{B1B}_2$. In embodiments, $R^{B1B}$ is independently —$CH_2X^{B1B}$. In embodiments, $R^{B1B}$ is independently —$OCX^{B1B}_3$. In embodiments, $R^{B1B}$ is independently —$OCHX^{B1B}_2$. In embodiments, $R^{B1B}$ is independently —$OCH_2X^{B1B}$. In embodiments, $R^{B1B}$ is independently —OH. In embodiments, $R^{B1B}$ is independently —CN. In embodiments, $R^{B1B}$ is independently —COOH. In embodiments, $R^{B1B}$ is independently —$CONH_2$. In embodiments, $X^{B1B}$ is independently —F, —Cl, —Br, or —I.

In embodiments, $R^{B1A}$ and $R^{B1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{B1A}$ and $R^{B1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{B1A}$ and $R^{B1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form a substituted heteroaryl (e.g., 5 to 10 membered, 5 to 9 membered, or 5 to 6 membered). In embodiments, $R^{B1A}$ and $R^{B1B}$ substituents bonded to the same nitrogen atom may be joined to form an unsubstituted heteroaryl (e.g., 5 to 10 membered, 5 to 9 membered, or 5 to 6 membered).

In embodiments, $R^{B1C}$ is substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{B1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted heteroalkyl (e.g., 2 to 8 membered, 2 to 6 membered, 4 to 6 membered, 2 to 3 membered, or 4 to 5 membered). In embodiments, $R^{B1C}$ is independently unsubstituted heteroalkyl (e.g., 2 to 8 membered, 2 to 6 membered, 4 to 6 membered, 2 to 3 membered, or 4 to 5 membered). In embodiments, $R^{B1C}$ is independently substituted or unsubstituted cycloalkyl (e.g., $C_3$-$C_8$, $C_3$-$C_6$, $C_4$-$C_6$, or $C_5$-$C_6$). In embodiments, $R^{B1C}$ is independently substituted cycloalkyl (e.g., $C_3$-$C_8$, $C_3$-$C_6$, $C_4$-$C_6$, or $C_5$-$C_6$). In embodiments, $R^{B1C}$ is independently unsubstituted cycloalkyl (e.g., $C_3$-$C_8$, $C_3$-$C_6$, $C_4$-$C_6$, or $C_5$-$C_6$). In embodiments, $R^{B1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted heterocycloalkyl (e.g., 3 to 8 membered, 3 to 6 membered, 4 to 6 membered, 4 to 5 membered, or 5 to 6 membered). In embodiments, $R^{B1C}$ is independently unsubstituted heterocycloalkyl (e.g., 3 to 8 membered, 3 to 6 membered, 4 to 6 membered, 4 to 5 membered, or 5 to 6 membered). In embodiments, $R^{B1C}$ is independently substituted or unsubstituted aryl (e.g., $C_6$-$C_{10}$ or phenyl). In embodiments, $R^{B1C}$ is independently substituted aryl (e.g., $C_6$-$C_{10}$ or phenyl). In embodiments, $R^{B1C}$ is independently unsubstituted aryl (e.g., $C_6$-$C_{10}$ or phenyl). In embodiments, $R^{B1C}$ is independently substituted or unsubstituted heteroaryl (e.g., 5 to 10 membered, 5 to 9 membered, or 5 to 6 membered). In embodiments, $R^{B1C}$ is independently substituted heteroaryl (e.g., 5 to 10 membered, 5 to 9 membered, or 5 to 6 membered). In embodiments, $R^{B1C}$ is independently pyridyl N-oxide. In embodiments, $R^{B1C}$ is independently unsubstituted heteroaryl (e.g., 5 to 10 membered, 5 to 9 membered, or 5 to 6 membered). In embodiments, $R^{B1C}$ is independently unsubstituted pyridyl.

In embodiments, the compound is

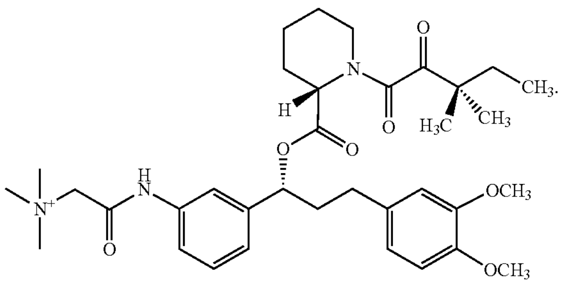

In embodiments, the compound is

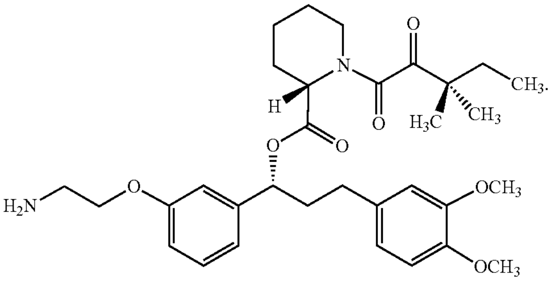

In embodiments, the compound is

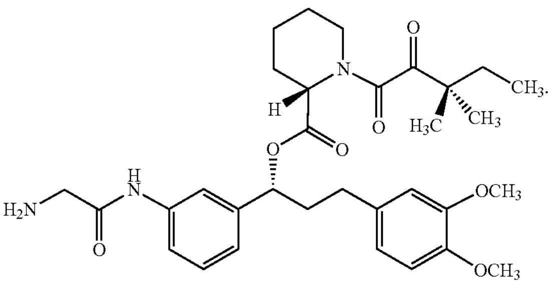

In embodiments, the compound is

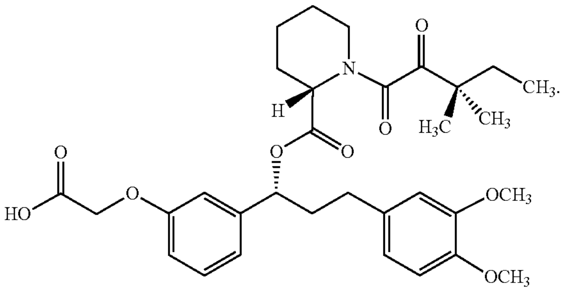

In embodiments, the compound is

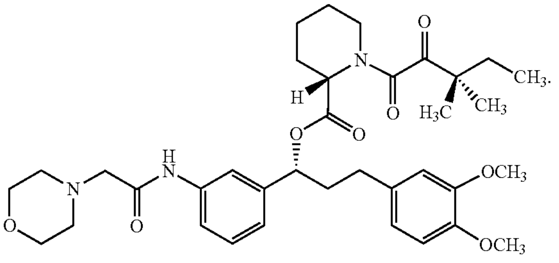

In embodiments, the compound is

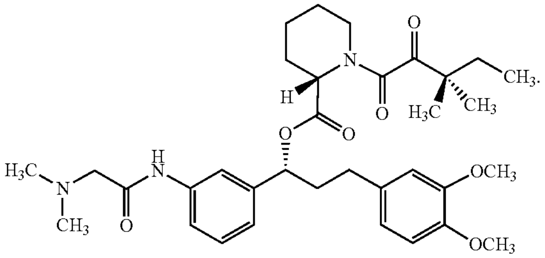

In embodiments, the compound is

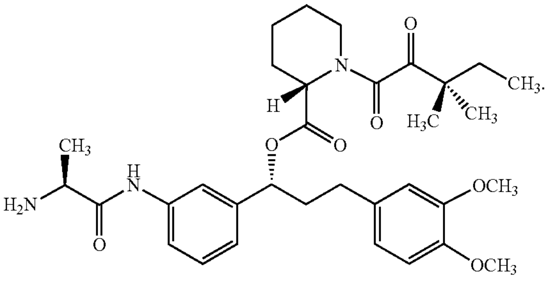

In embodiments, the compound is
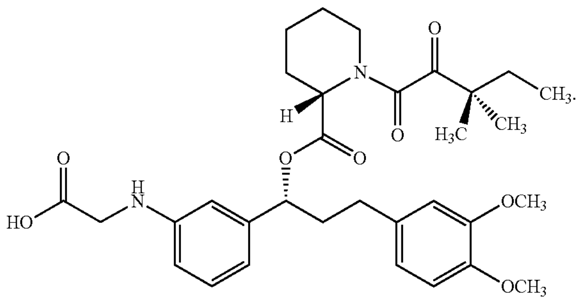
In embodiments, the compound is
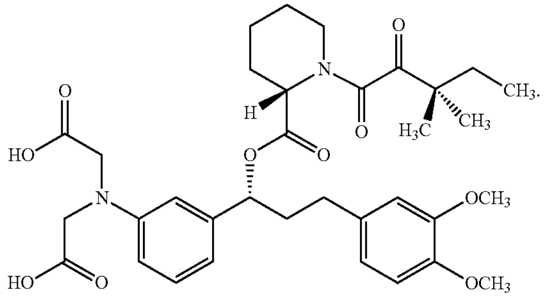
In embodiments, the compound is
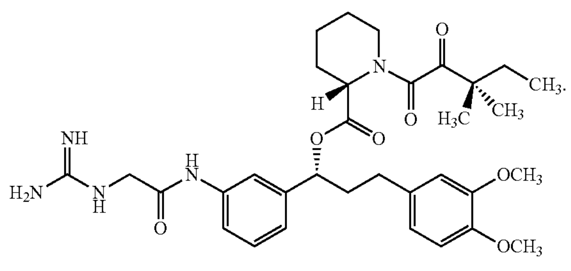
In embodiments, the compound is
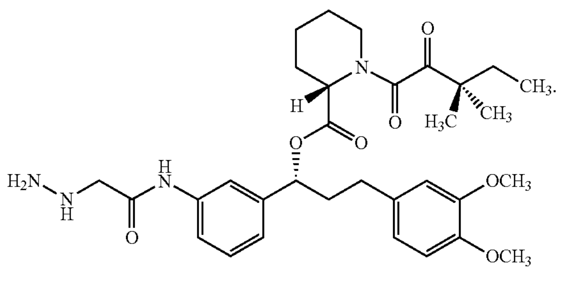
In embodiments, the compound is
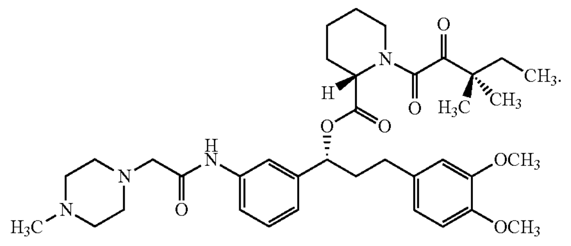
In embodiments, the compound is
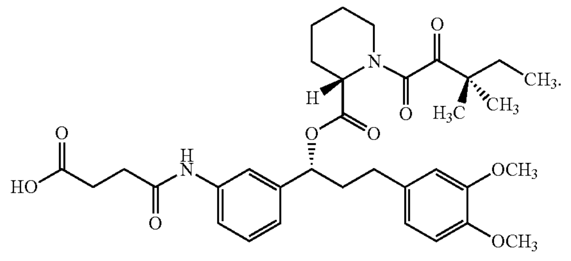
In embodiments, the compound is
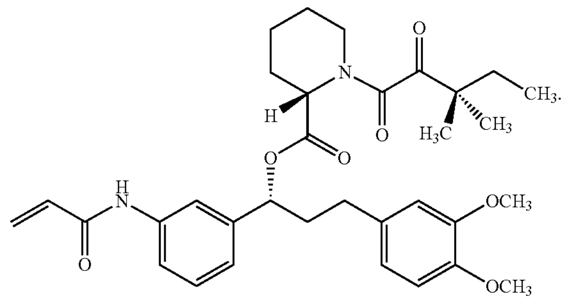
In embodiments, the compound is
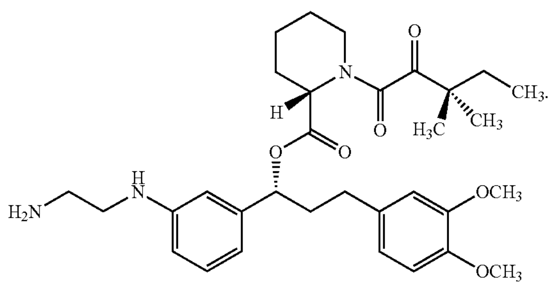

In embodiments, the compound is
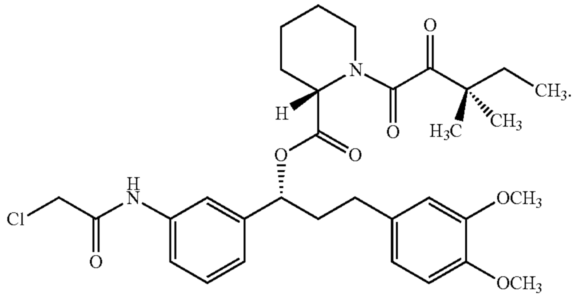
In embodiments, the compound is
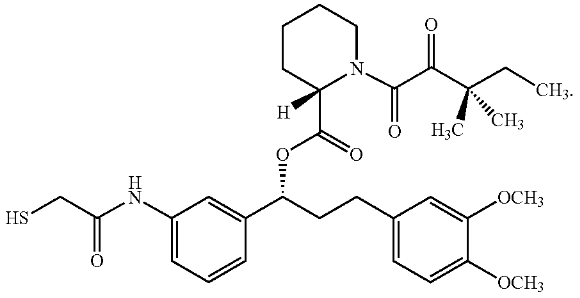
In embodiments, the compound is
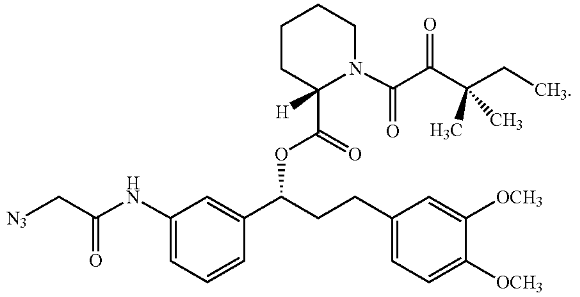
In embodiments, the compound is
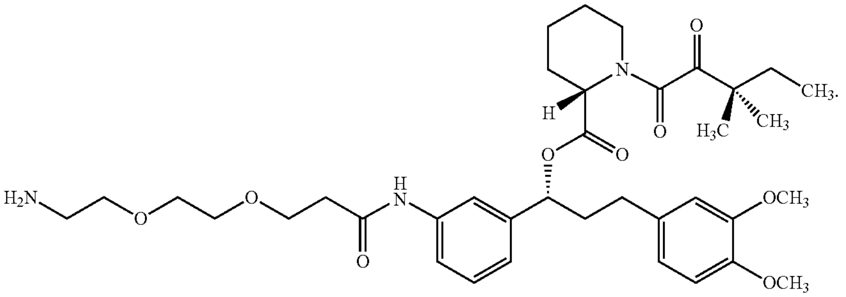
In embodiments, the compound is
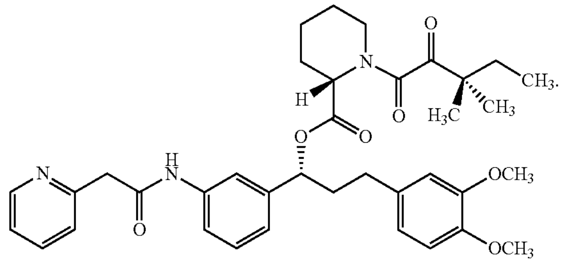
In embodiments, the compound is
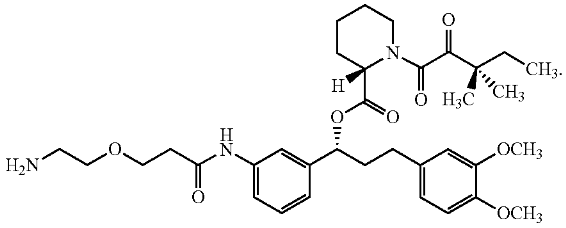
In embodiments, the compound is
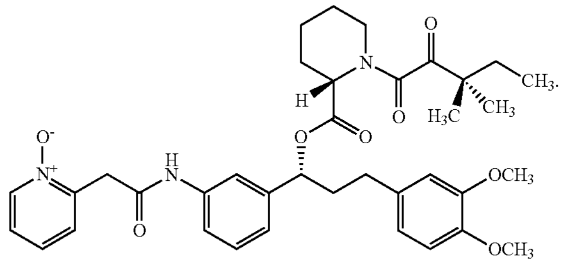

In embodiments, the compound is
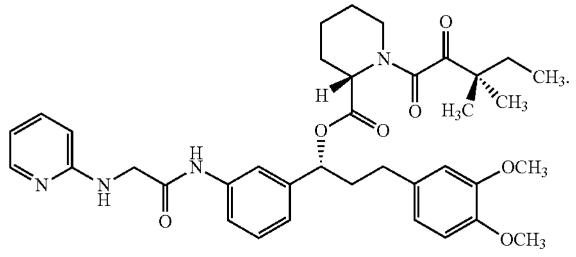
In embodiments, the compound is
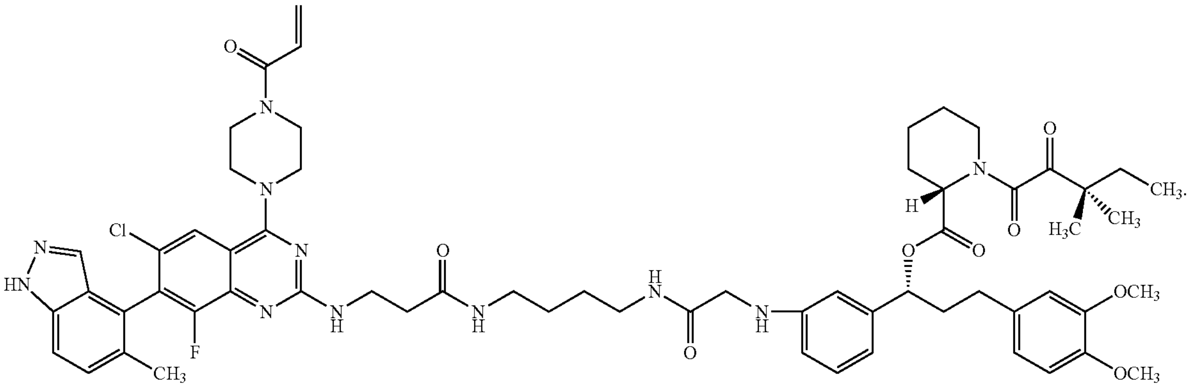
In embodiments, the compound is
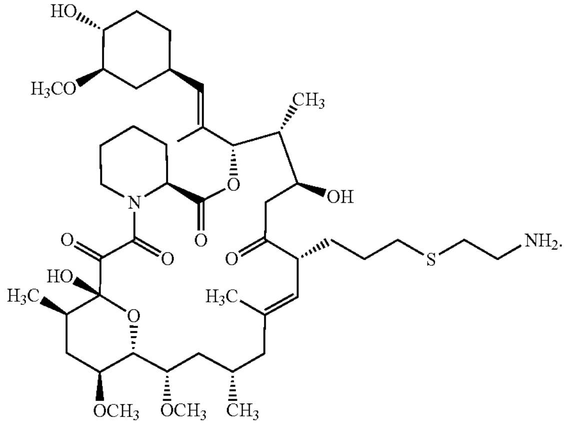 [SMILES: CO[C@H]1C[C@@H](C)C/C(C)=C/[C@@H](CCCSCCN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
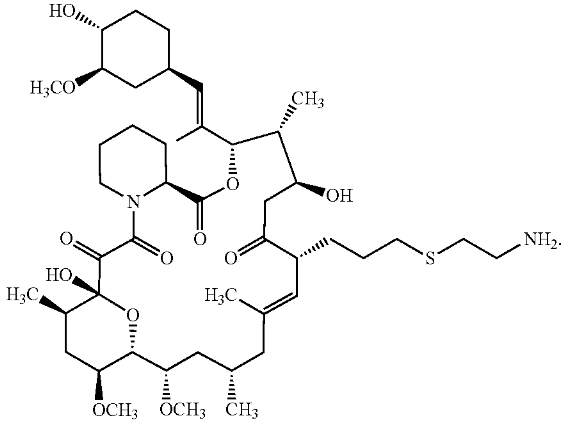 [SMILES: CO[C@H]1C[C@@H](C)C/C(C)=C/[C@@H](CCCSCCN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is
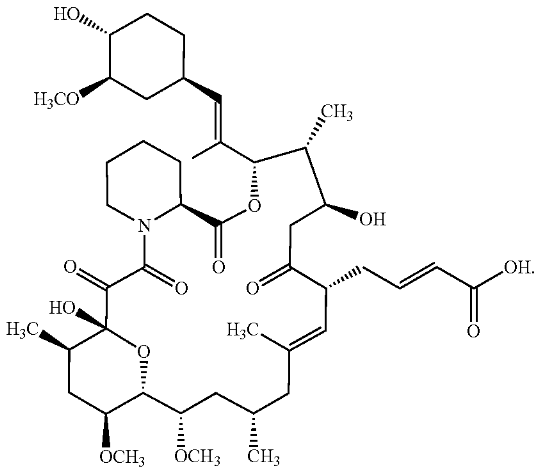 [SMILES: CO[C@H]1C[C@@H](C)C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
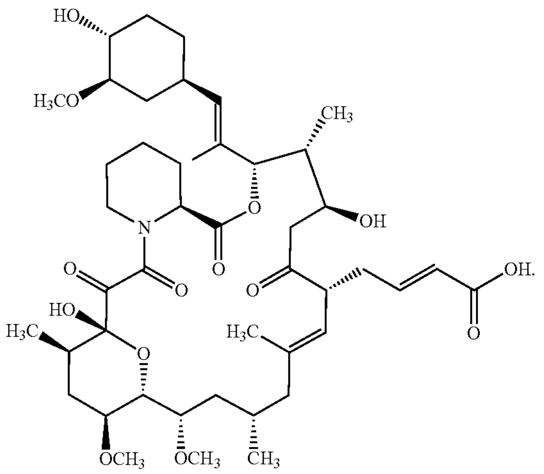 [SMILES: CO[C@H]1C[C@@H](C)C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
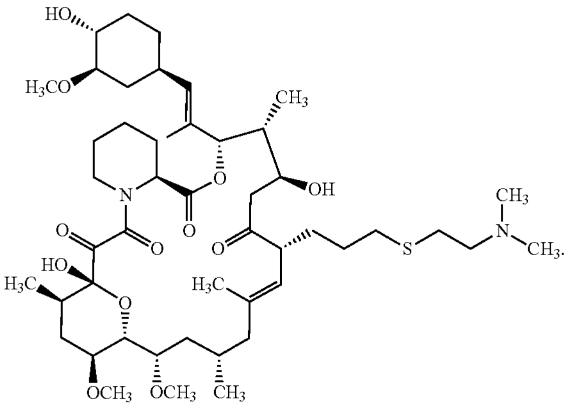 [SMILES: CO[C@H]1C[C@@H](C)C/C(C)=C/[C@@H](CCCSCCN(C)C)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
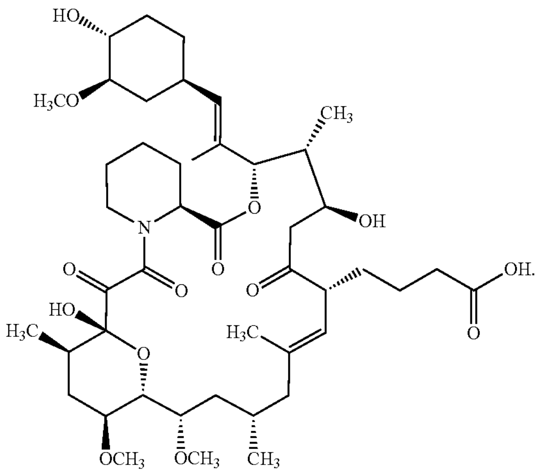 [SMILES: CO[C@H]1C[C@@H](C)C/C(C)=C/[C@@H](CCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
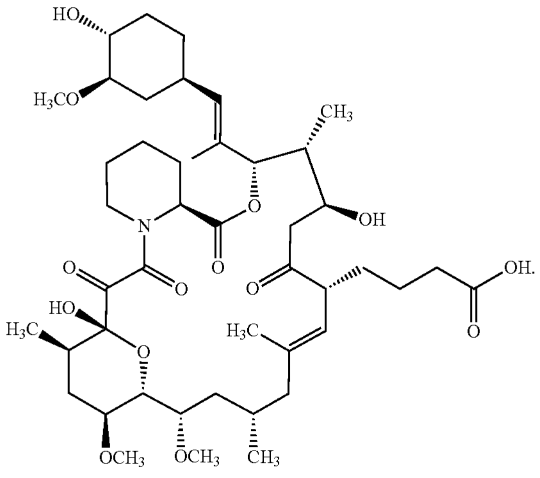 [SMILES: CO[C@H]1C[C@@H](C)C/C(C)=C/[C@@H](CCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is
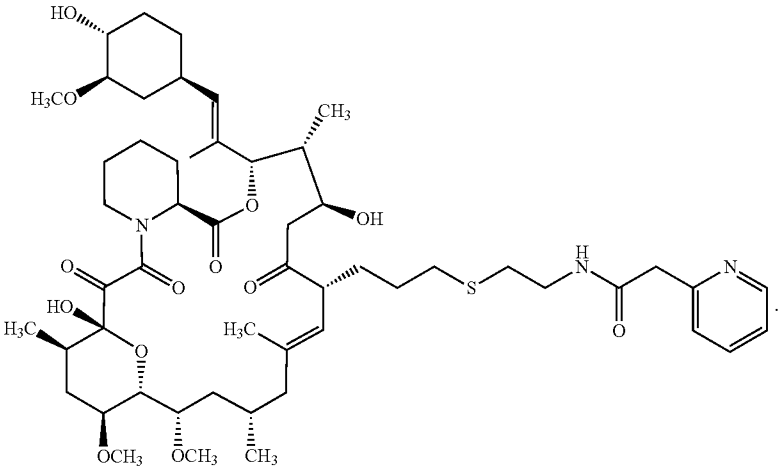 [SMILES: CO[C@H]1C[C@@H](C)C/C(C)=C/[C@@H](CCCSCCNC(=O)Cc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
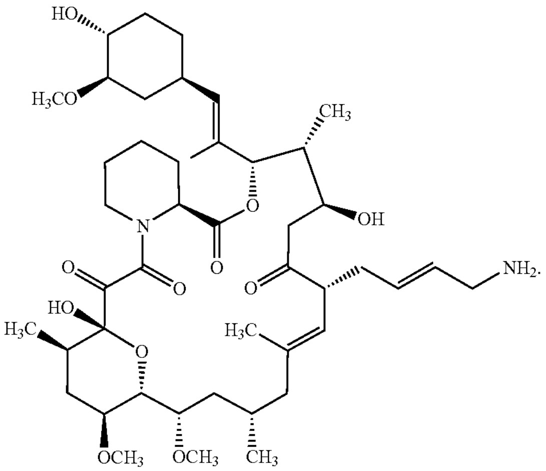 [SMILES: CO[C@H]1C[C@@H](C)C/C(C)=C/[C@@H](C/C=C/CN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
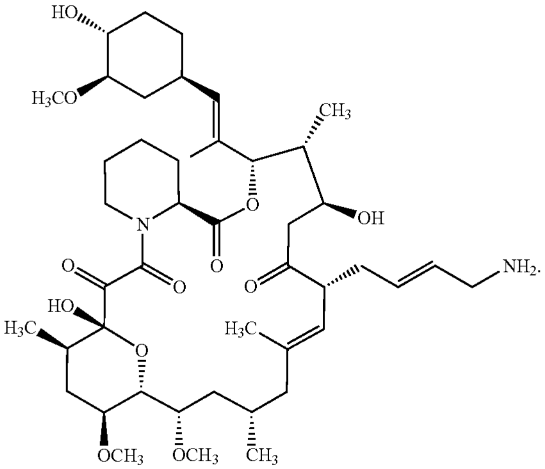 [SMILES: CO[C@H]1C[C@@H](C)C/C(C)=C/[C@@H](C/C=C/CN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
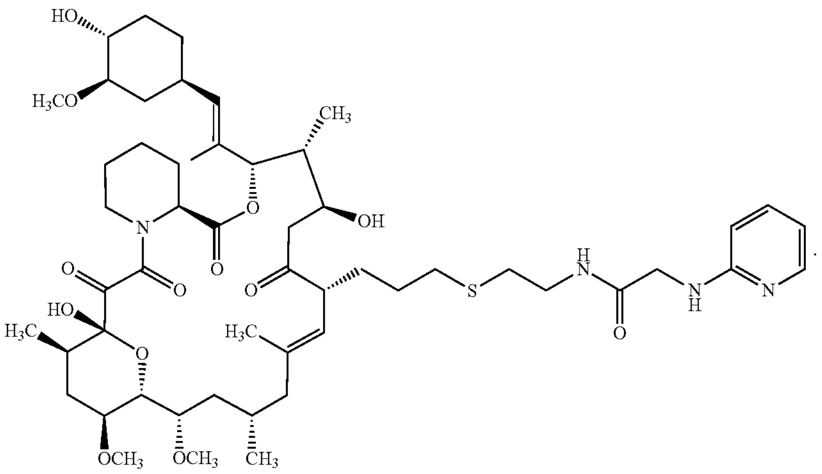 [SMILES: CO[C@H]1C[C@@H](C)C/C(C)=C/[C@@H](CCCSCCNC(=O)CNc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is
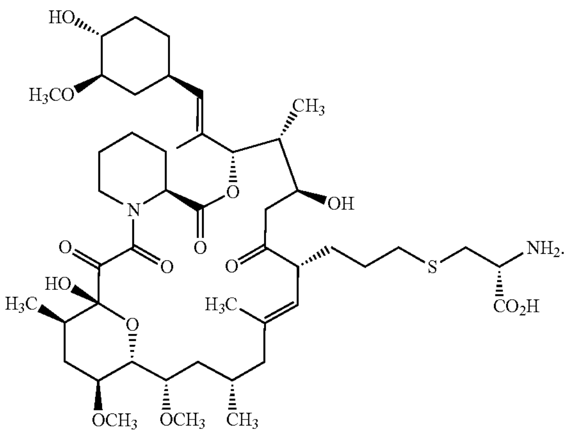 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
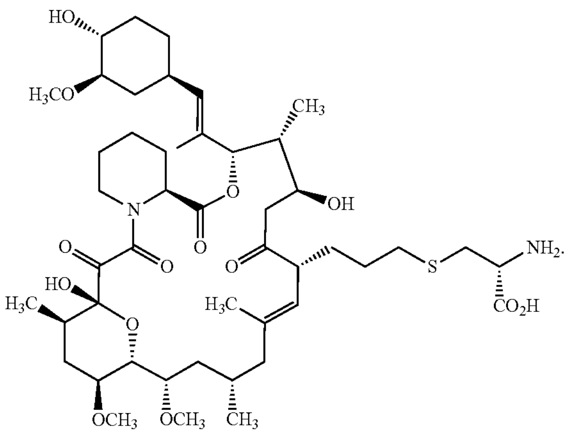 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
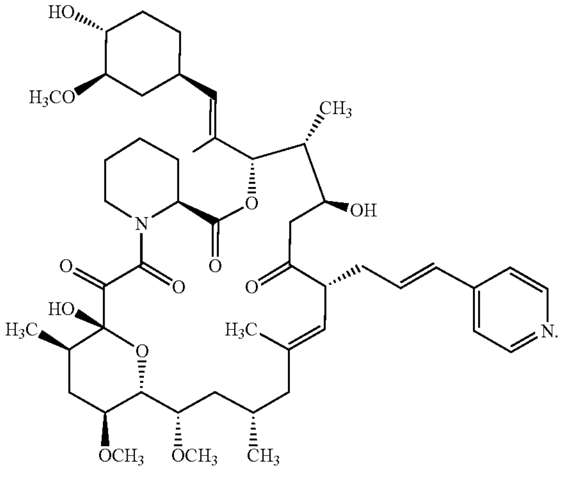 [SMILES: CO[C@H]1C[C@@H](C)C/C(C)=C/[C@@H](C/C=C/c2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
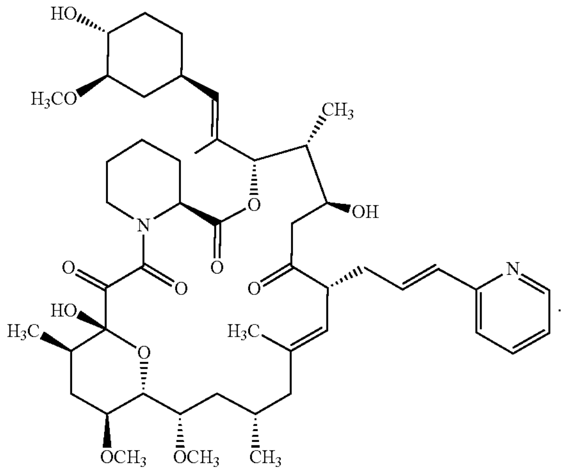
In embodiments, the compound is
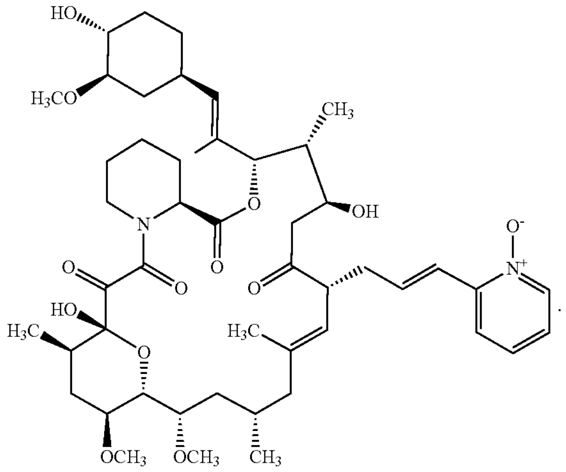 [SMILES: CO[C@H]1C[C@@H](C)C/C(C)=C/[C@@H](C/C=C/c2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
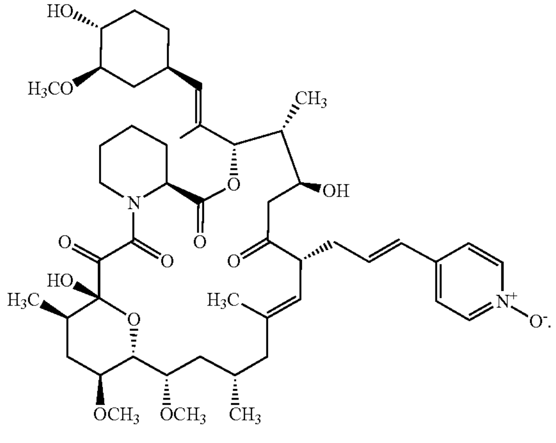

In embodiments, the compound is
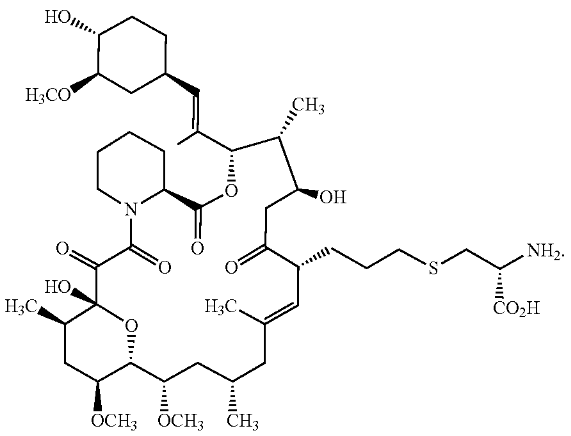 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is not
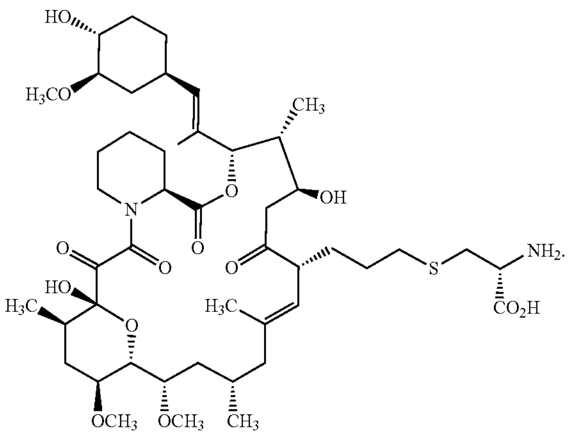 [SMILES: CO[C@H]1C[C@@H](C)C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
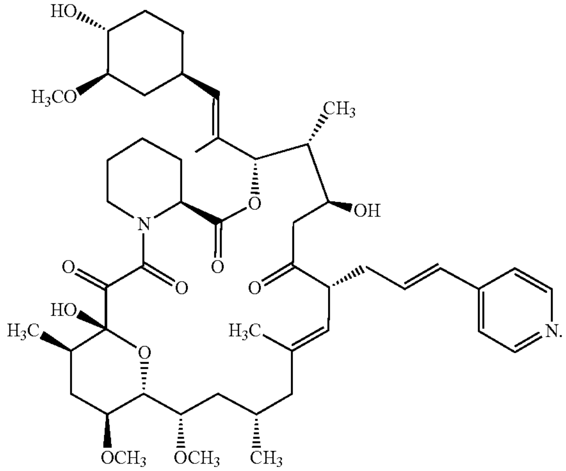
In embodiments, the compound is
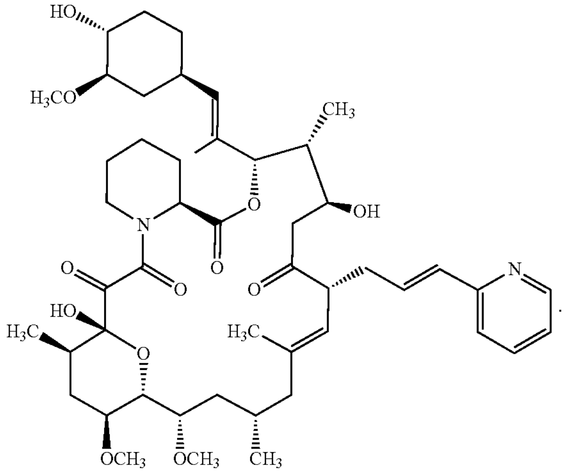
In embodiments, the compound is
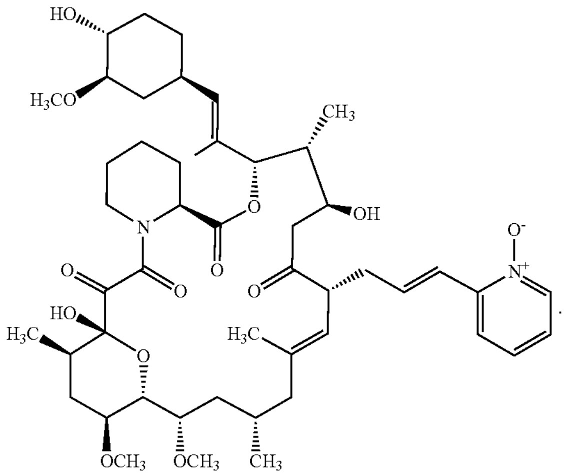
In embodiments, the compound is
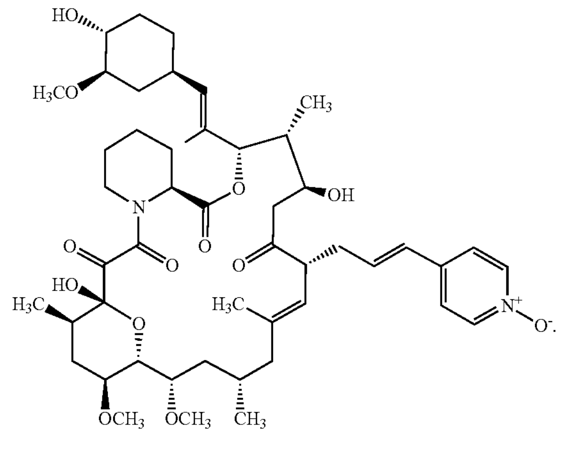

In embodiments, the compound is
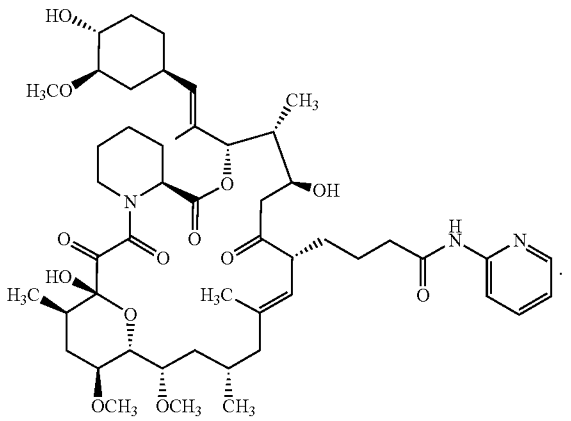 [SMILES: CO[C@H]1C[C@@H](C)C/C(C)=C/[C@@H](CCCC(=O)Nc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the compound is
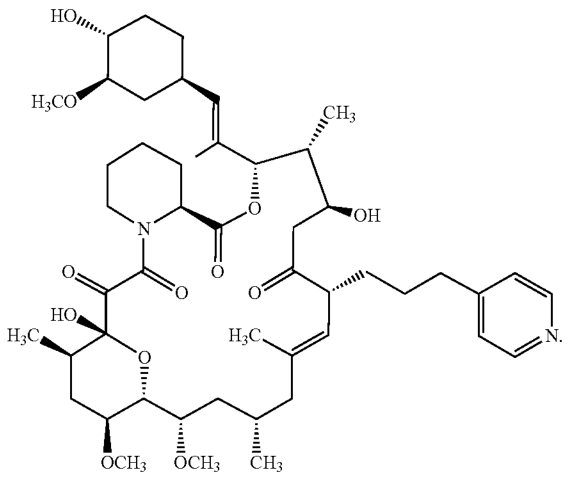
In embodiments, the compound is
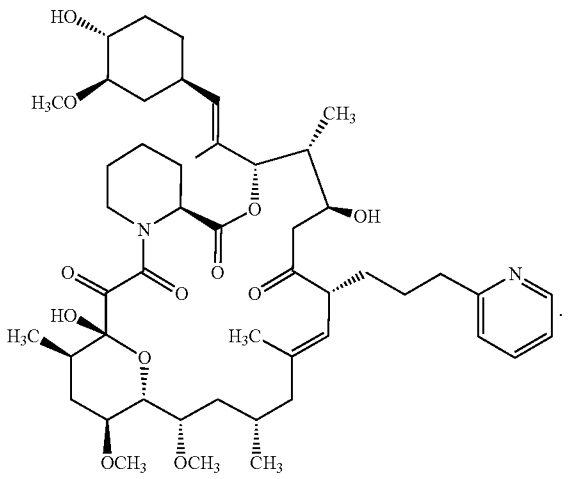
In embodiments, the compound is
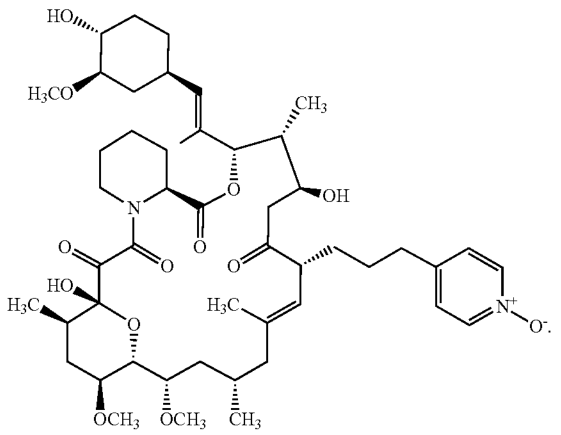
In embodiments, the compound is
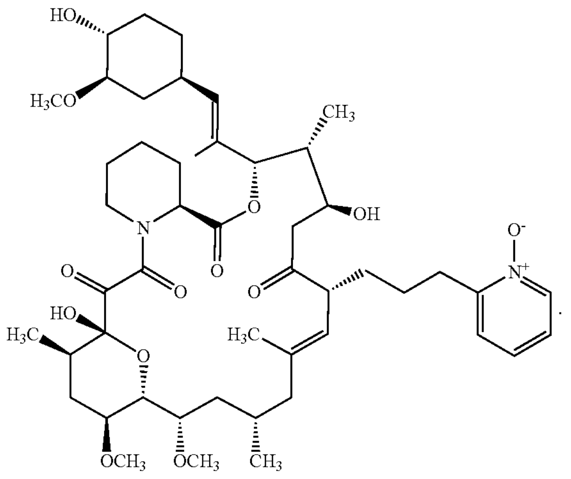

In embodiments, the compound is

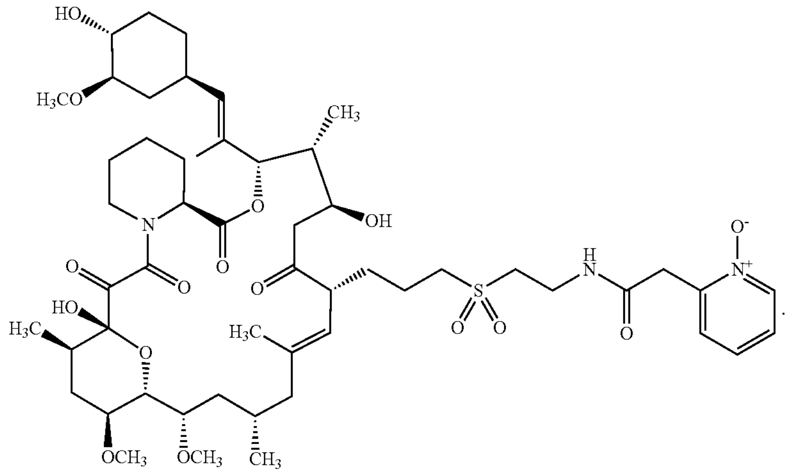 [SMILES: CO[C@H]1C[C@@H](C)C/C(C)=C/[C@@H](CCCS(=O)(=O)CCNC(=O)Cc2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the compound is a compound described herein.

III. Pharmaceutical Compositions

In an aspect is provided a pharmaceutical composition including a compound described herein and a pharmaceutically acceptable excipient.

In embodiments, the pharmaceutical composition includes both a compound (e.g., as described herein) and a second agent (e.g., an anti-CNS disease drug as described herein). In embodiments, a first pharmaceutical composition includes the compound (e.g., as described herein), and a second pharmaceutical composition includes a second agent (e.g., an anti-CNS disease drug as described herein), and both the first and second pharmaceutical compositions are intended to be co-administered.

In embodiments, the pharmaceutical composition includes an effective amount of the compound. In embodiments, the pharmaceutical composition includes a therapeutically effective amount of the compound. In embodiments, the pharmaceutical composition includes an anti-CNS disease drug. In embodiments of the pharmaceutical compositions, the pharmaceutical composition includes an anti-CNS disease drug in a therapeutically effective amount.

In embodiments, the anti-CNS disease drug includes a monovalent active site mTOR inhibitor covalently bound to a monovalent rapamycin or a monovalent rapamycin analog.

In embodiments, the anti-CNS disease drug includes a divalent linker that binds the monovalent active site mTOR inhibitor (active site mTOR inhibitor moiety) to the monovalent rapamycin (rapamycin moiety) or the monovalent rapamycin analog (rapamycin analog moiety). In embodiments, the divalent linker may be bonded to rapamycin or a rapamycin analog at a position capable of being modified to include a linker. For example, a linker may be bonded to rapamycin or a rapamycin analog at position 10, 16, 27, 28, 39, or 40, among others (as indicated in figure immediately below). In embodiments, a linker is bonded to position 10 of rapamycin or a rapamycin analog. In embodiments, a linker is bonded to position 16 of rapamycin or a rapamycin analog. In embodiments, a linker is bonded to position 27 of rapamycin or a rapamycin analog. In embodiments, a linker is bonded to position 28 of rapamycin or a rapamycin analog. In embodiments, a linker is bonded to position 39 of rapamycin or a rapamycin analog. In embodiments, a linker is bonded to position 40 of rapamycin or a rapamycin analog.

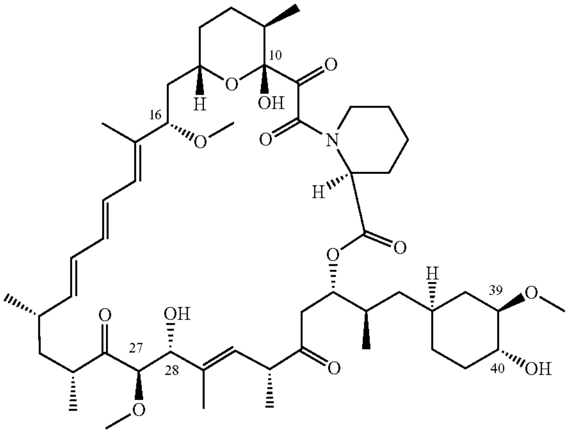

In embodiments, the divalent linker is at least about or about 5 Å in length (e.g., at least about or about 5.0, 5.1, 5.2, 5.3, 5.4, 5.5, 5.6, 5.7, 5.8, 5.9, 6.0, 6.1, 6.2, 6.3, 6.4, 6.5, 6.6, 1, 7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 2, 8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 3, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Å in length). In embodiments, the divalent linker is at least about or about the length of 5 methylene groups (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the divalent linker is at least about or about the length of 11 methylene groups (e.g., at least about or about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the divalent linker is at least about or about the length of 27 methylene groups (e.g., 27, 28, 29, 30, 31, 32, 33, 34, 35, 36, 37, 38, 39, 40, 41, 42, 43, 44, 45, 46, 47, 48, 49, or 50 methylene groups).

The specified length of a linker is the through space distance between the ends of the linker (i.e., the ends or termini that are connected to the two parts of the molecule connected by the linker) wherein the length of the linker is measured when the linker is fully extended and wherein the linker termini are the furthest apart they may naturally exist in solution (i.e., the longest distance between the ends of the linker wherein the linker adopts allowable conformations, bond lengths, and bond angles following the principles of Chemistry), (e.g., without adopting non-natural bond lengths, non-allowed or non-preferred bond angles, or high energy non-preferred or non-natural interactions of different components of the linker). In embodiments, the linker length is measured when included in a compound as described herein (e.g., aspect, embodiment, example, figures, table, or claim). It will be understood that a linker may adopt a through space distance (e.g., in solution, when bound to mTORC1, when bound to mTOR) that is less than the fully extended conformation used to define the linker length.

In embodiments, the linker is a hydrolysable linker (e.g., in solution). In embodiments, the linker is a non-hydrolysable linker (e.g., in solution). In embodiments, the linker may be cleaved by an enzyme (e.g., hydrolase, protease, cytochrome). In embodiments, the linker is not cleavable by an enzyme (e.g., under normal cellular conditions). In embodiments, the linker is a polyethylene glycol linker. In embodiments, the linker is hydrophilic. In embodiments, the linker is hydrophobic. In embodiments, the linker includes a disulfide bond. In embodiments, the linker includes a hydrazone bond. In embodiments, the linker includes an ester. In embodiments, the linker includes a sulfonyl. In embodiments, the linker includes a thioether. In embodiments, the linker includes a phosphinate. In embodiments, the linker includes an alkyloxime bond. In embodiments, the linker includes one or more amino acids. In embodiments, the linker consists of amino acids. In embodiments, the linker includes an amino acid analog. In embodiments, the linker includes an amino acid mimetic. In embodiments, the linker is a linker known in the art for use in linking antibodies to agents (e.g., antibody drug conjugates). In embodiments, the linker is a linker as described in Bioconjugate Techniques (Second Edition) by Greg T. Hermanson (2008), which is herein incorporated by referenced in its entirety for all purposes. In embodiments, the linker is a linker as described in Flygare J. A., Pillow T. H., Aristoff P., Antibody-drug conjugates for the treatment of cancer, Chemical Biology and Drug Design, 2013 January; 81(1): 113-21, which is herein incorporated by referenced in its entirety for all purposes. In embodiments, the linker is a linker as described in Drachman J. G., Senter P. D., Antibody-drug conjugates: the chemistry behind empowering antibodies to fight cancer, Hematology Am Soc Hematol Educ Program, 2013; 2013: 306-10, which is herein incorporated by referenced in its entirety for all purposes.

In embodiments, the anti-CNS disease drug includes a divalent linker covalently bound to the monovalent active site mTOR inhibitor and the monovalent rapamycin or monovalent rapamycin analog. In embodiments, the anti-CNS disease drug includes a divalent linker covalently bound directly to the monovalent active site mTOR inhibitor and directly to the monovalent rapamycin or monovalent rapamycin analog.

In embodiments, the anti-CNS disease drug has the formula:

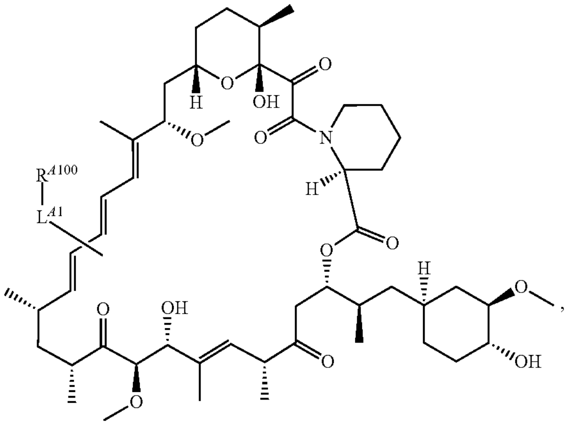

wherein $L^{A1}$ is as described herein and may be bonded to any atom in the ring ($L^{A1}$ is a floating substituent) and $R^{A100}$ is a monovalent active site mTOR inhibitor.

In embodiments, the anti-CNS disease drug has the formula:

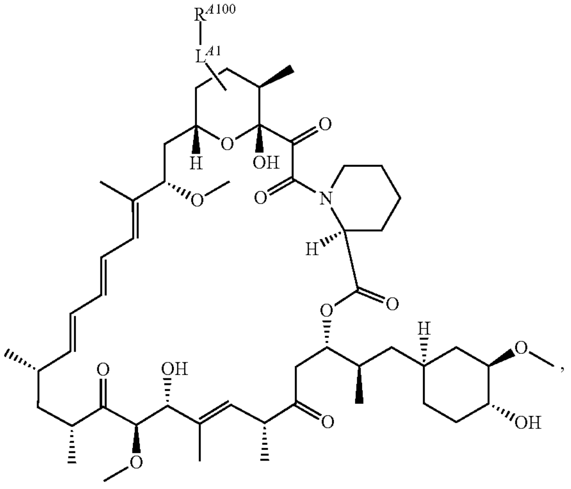

wherein $L^{A1}$ is as described herein and may be bonded to any atom in the ring ($L^{A1}$ is a floating substituent) and $R^{A100}$ is a monovalent active site mTOR inhibitor.

In embodiments, the anti-CNS disease drug has the formula:

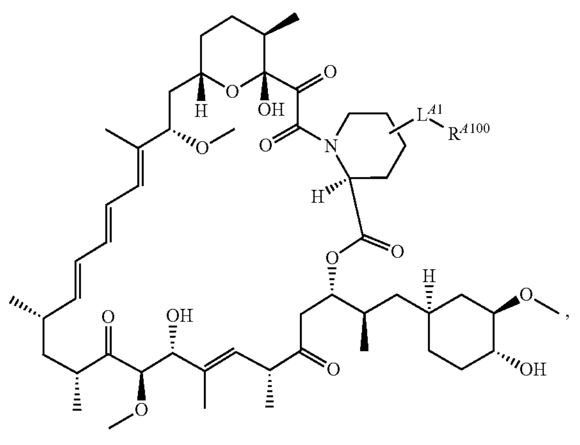

wherein $L^{A1}$ is as described herein and may be bonded to any atom in the ring ($L^{A1}$ is a floating substituent) and $R^{A100}$ is a monovalent active site mTOR inhibitor.

In embodiments, the anti-CNS disease drug has the formula:

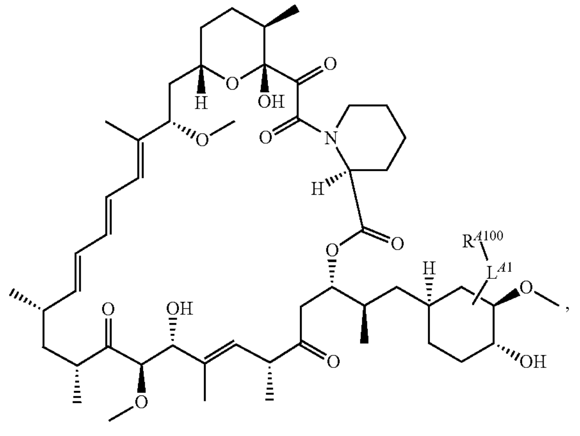

wherein $L^{A1}$ is as described herein and may be bonded to any atom in the ring ($L^{A1}$ is a floating substituent) and $R^{A100}$ is a monovalent active site mTOR inhibitor.

$R^{A100}$ is a monovalent active site mTOR inhibitor. In embodiments, $R^{A100}$ is

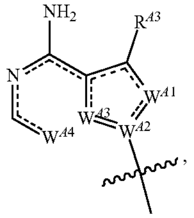

wherein $W^{A1}$, $W^{A2}$, $W^{A3}$, $W^{A4}$, and $R^{A3}$ are as described herein. In embodiments, $R^{A100}$ is

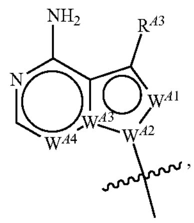

wherein $W^{A1}$, $W^{A2}$, $W^{A3}$, $W^{A4}$, and $R^{A3}$ are as described herein. In embodiments, $R^{A100}$ is

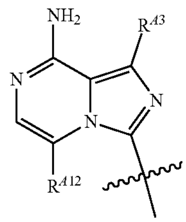

wherein $R^{A3}$ and $R^{A12}$ are as described herein. In embodiments, $R^{A100}$ is

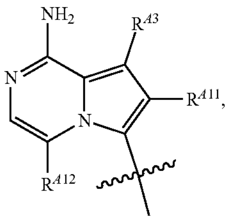

wherein $R^{A3}$, $R^{A11}$, and $R^{A12}$ are as described herein. In embodiments, $R^{A100}$ is

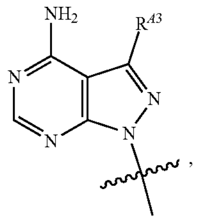

wherein $R^{A3}$ is as described herein. In embodiments, $R^{A100}$ is

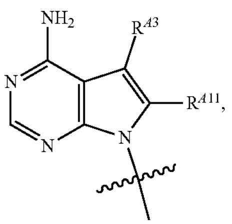

wherein $R^{A3}$ and $R^{A11}$ are as described herein. In embodiments, $R^{A100}$ is

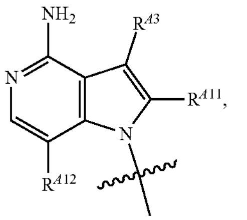

wherein $R^{A3}$, $R^{A11}$, and $R^{A12}$ are as described herein. In embodiments, $R^{A100}$ is

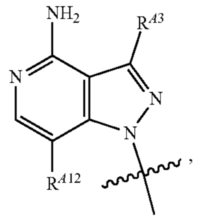

wherein $R^{A3}$ and $R^{A12}$ are as described herein.

In embodiments, the anti-CNS disease drug has the formula:

(VI)

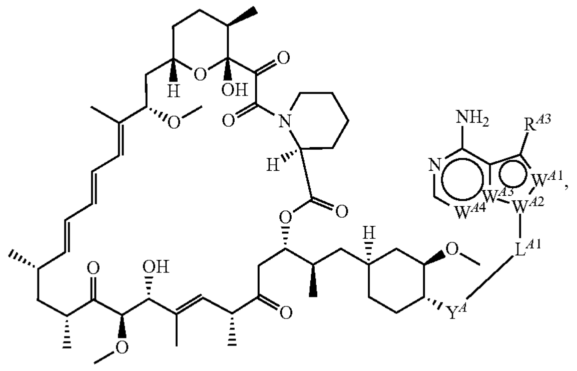

wherein $W^{A1}$, $W^{A2}$, $W^{A3}$, $W^{A4}$, $L^{A1}$, $Y^{A}$, and $R^{A3}$ are as described herein.

In embodiments, the anti-CNS disease drug has the formula:

(VIa)

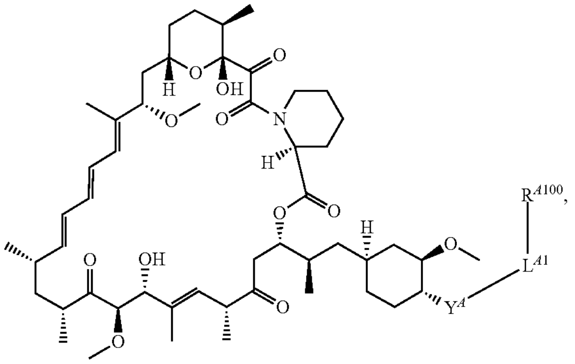

wherein $L^{A1}$, $Y^{A}$, and $R^{A100}$ are as described herein.

In embodiments, the anti-CNS disease drug has the formula:

(VIb)

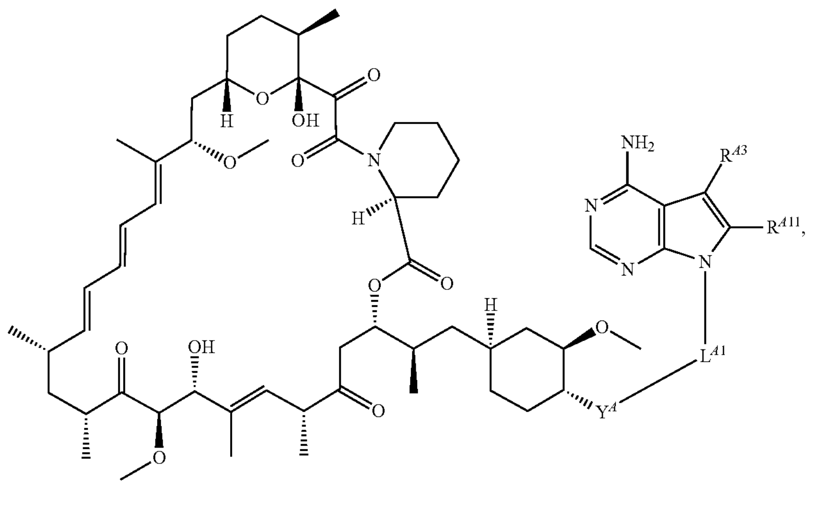

wherein $L^{A1}$, $Y^{A}$, $R^{A3}$, and $R^{A11}$ are as described herein.

In embodiments, the anti-CNS disease drug has the formula:

(VIc)

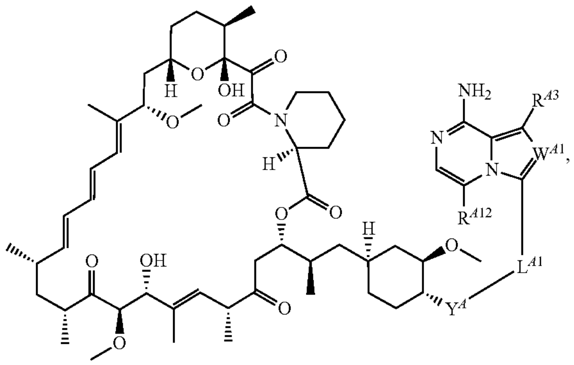

wherein $L^{A1}$, $Y^{A}$, $R^{A3}$, $W^{A1}$, and $R^{A12}$ are as described herein.

In embodiments, the anti-CNS disease drug has the formula:

(VId)

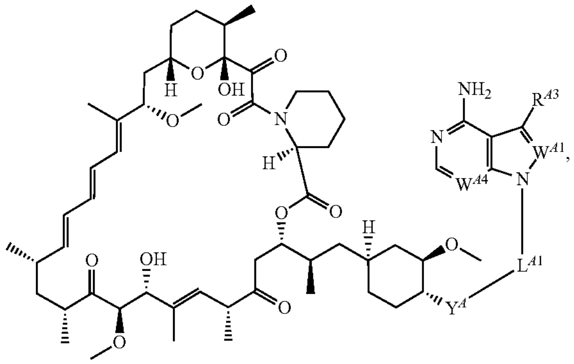

wherein $L^{A1}$, $Y^{A}$, $R^{A3}$, $W^{A1}$, and $W^{A4}$ are as described herein.

$L^{A1}$ is a divalent linker as described herein. $W^{A1}$ is N or $CR^{A11}$. $W^{A2}$ is N and $W^{A3}$ is C or, alternatively, $W^{A2}$ is C and $W^{A3}$ is N. $W^{A4}$ is N or $CR^{A12}$. $Y^{A}$ is O or $NR^{A13}$. $R^{A3}$ is hydrogen, oxo, halogen, $—CX^{A}_3$, —CN, $—SO_2Cl$, $—SO_{nA}R^{A10}$, $—SO_{vA}NR^{A7}R^{A8}$, $—NHNH_2$, $—ONR^{A7}R^{A8}$, $—NHC(O)NHNH_2$, $—NHC(O)NR^{A7}R^{A8}$, $—N(O)_{mA}$, $—NR^{A7}R^{A8}$, $—C(O)R^{A9}$, $—C(O)OR^{A9}$, $—C(O)NR^{A7}R^{A8}$, $—OR^{A10}$, $—NR^{A7}SO_2R^{A10}$, $—NR^{A7}C(O)R^{A9}$, $—NR^{A7}C(O)OR^{A9}$, $—NR^{A7}OR^{A9}$, $—OCX^{A}_3$, $—OCHX^{A}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{A7}$, $R^{A8}$, $R^{A9}$, $R^{A10}$, $R^{A11}$, $R^{A12}$, and $R^{A13}$ are independently hydrogen, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{A7}$ and $R^{A8}$ substituents bonded to the same nitrogen atom may optionally be joined to form a substituted or unsubstituted heterocycloalkyl or substituted or unsubstituted heteroaryl. The variables mA and vA are independently 1 or 2. The variable nA is independently an integer from 0 to 4. The variable $X^{A}$ is independently —Cl, —Br, —I, or —F. In embodiments, $L^{A1}$ is a divalent linker including one or more amino acids. In embodiments, $L^{A1}$ is a divalent linker consisting of amino acids (i.e., a peptidyl linker). In embodiments, $L^{A1}$ is a divalent linker (e.g., a peptidyl linker) including an amino acid analog. In embodiments, $L^{A1}$ is a divalent linker (e.g., a peptidyl linker) including an amino acid mimetic. In embodiments, $L^{A1}$ is a divalent linker consisting of amino acid analogs (also referred to herein as a peptidyl analog linker). In embodiments, $L^{A1}$ is a divalent linker consisting of amino acid mimetics (also referred to herein as a peptidyl mimetic linker).

In embodiments, the anti-CNS disease drug has the formula:

(VII)

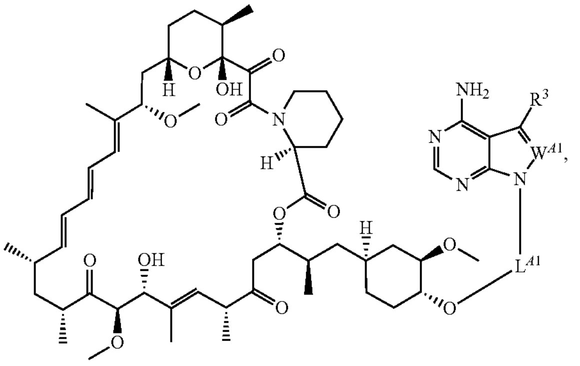

wherein $W^{A1}$ is N or CH. In embodiments, $W^{A1}$ is N. In embodiments, $W^{A1}$ is CH.

In embodiments, the anti-CNS disease drug has the formula:

(VIII)

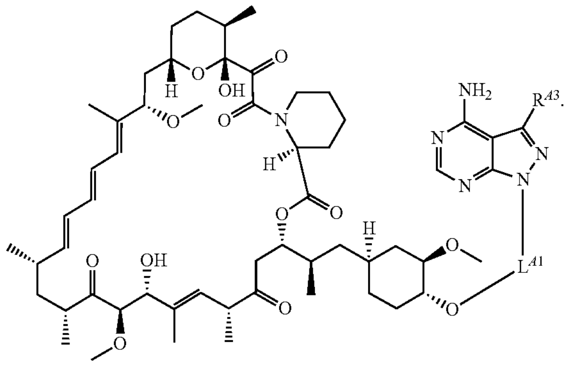

In embodiments, $R^{A3}$ is hydrogen, oxo, halogen, $—CX^{A}_3$, —CN, $—SO_2Cl$, $—SO_{nA}R^{A10}$, $—SO_{vA}NR^{A7}R^{A8}$, $—NHNH_2$, $—ONR^{A7}R^{A8}$, $—NHC(O)NHNH_2$, $—NHC(O)NR^{A7}R^{A8}$, $—N(O)_{mA}$, $—NR^{A7}R^{A8}$, $—C(O)R^{A9}$, —C(O)

$OR^{A9}$, $—C(O)NR^{A7}R^{A8}$, $—OR^{A10}$, $—NR^{A7}SO_2R^{A10}$, $—NR^{A7}C(O)R^{A9}$, $—NR^{A7}C(O)OR^{A9}$, $—NR^{A7}OR^{A9}$, $—OCX^{A}_3$, $—OCHX^{A}2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A3}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A3}$ is substituted with a plurality of groups selected from substituent groups, size-limited substituent groups, and lower substituent groups; each substituent group, size-limited substituent group, and/or lower substituent group may optionally be different. In embodiments, when $R^{A3}$ is substituted, it is substituted with at least one substituent group. In embodiments, when $R^{A3}$ is substituted, it is substituted with at least one size-limited substituent group. In embodiments, when $R^{A3}$ is substituted, it is substituted with at least one lower substituent group.

In embodiments, $R^{A3}$ is

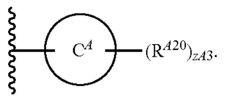

$R^{A20}$ is as described herein. Ring $C^A$ is an aryl (e.g., phenyl, diphenyl, or fused ring aryl) or a heteroaryl (e.g., monocyclic heteroaryl or fused ring heteroaryl). Ring $C^A$ may be any of the aryl or heteroaryl rings in the embodiments of $R^{A3}$ described herein (e.g., benzoxazolyl, indolyl, phenyl, or naphthyl). The symbol zA3 is an integer from 0 to 7. In embodiments, zA3 is 0. In embodiments, zA3 is 1. In embodiments, zA3 is 2. In embodiments, zA3 is 3. In embodiments, zA3 is 4. In embodiments, zA3 is 5. In embodiments, zA3 is 6. In embodiments, zA3 is 7.

In embodiments, Ring $C^A$ is an aryl (e.g., $C_6$-$C_{10}$ or phenyl) or a heteroaryl (e.g., 5 to 10 membered, 5 to 9 membered, or 5 to 6 membered).

In embodiments, $R^{A3}$ is independently substituted benzoxazolyl, substituted pyrimidinyl, substituted thiophenyl, substituted furanyl, substituted indolyl, substituted benzoxadiazolyl, substituted benzodioxolyl, substituted benzodioxanyl, substituted thianaphthanyl, substituted pyrrolopyridinyl, substituted indazolyl, substituted quinolinyl, substituted quinoxalinyl, substituted pyridopyrazinyl, substituted quinazolinonyl, substituted benzoisoxazolyl, substituted imidazopyridinyl, substituted benzofuranyl, substituted benzothiophenyl, substituted phenyl, substituted naphthyl, substituted biphenyl, substituted pyrrolyl, substituted pyrazolyl, substituted imidazolyl, substituted pyrazinyl, substituted oxazolyl, substituted isoxazolyl, substituted thiazolyl, substituted furylthienyl, substituted pyridyl, substituted pyrimidyl, substituted benzothiazolyl, substituted purinyl, substituted benzimidazolyl, substituted isoquinolyl, substituted thiadiazolyl, substituted oxadiazolyl, substituted pyrrolyl, substituted diazolyl, substituted triazolyl, substituted tetrazolyl, substituted benzothiadiazolyl, substituted isothiazolyl, substituted pyrazolopyrimidinyl, substituted pyrrolopyrimidinyl, substituted benzotriazolyl, or substituted quinolyl. In embodiments, $R^3$ is independently substituted benzoxazolyl.

In some embodiments of the anti-CNS disease drugs provided herein, $R^{A3}$ is independently hydrogen, oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A20}$-substituted or unsubstituted alkyl, $R^{A20}$-substituted or unsubstituted heteroalkyl, $R^{A20}$-substituted or unsubstituted cycloalkyl, $R^{A20}$-substituted or unsubstituted heterocycloalkyl, $R^{A20}$-substituted or unsubstituted aryl, or $R^{A20}$-substituted or unsubstituted heteroaryl.

In some embodiments, $R^{A3}$ is substituted with one or more substituents independently selected from halogen, $—CF_3$, —OH, and $—NH_2$. In some embodiments, $R^{A3}$ is substituted heteroaryl, such as benzoxazolyl or benzothiazolyl. In some embodiments, $R^{A3}$ is heteroaryl, such as benzoxazolyl or benzothiazolyl, substituted with one or more substituents independently selected from halogen, $—CF_3$, —OH, and $—NH_2$.

In embodiments, $R^{A3}$ is independently $R^{A20}$-substituted benzoxazolyl, $R^{A20}$-substituted pyrimidinyl, $R^{A20}$-substituted thiophenyl, $R^{A20}$-substituted furanyl, $R^{A20}$-substituted indolyl, $R^{A20}$-substituted benzoxadiazolyl, $R^{A20}$-substituted benzodioxolyl, $R^{A20}$-substituted benzodioxanyl, $R^{A20}$-substituted thianaphthanyl, $R^{A20}$-substituted pyrrolopyridinyl, $R^{A20}$-substituted indazolyl, $R^{A20}$-substituted quinolinyl, $R^{A20}$-substituted quinoxalinyl, $R^{A20}$-substituted pyridopyrazinyl, $R^{A20}$-substituted quinazolinonyl, $R^{A20}$-substituted benzoisoxazolyl, $R^{A20}$-substituted imidazopyridinyl, $R^{A20}$-substituted benzofuranyl, $R^{A20}$-substituted benzothiophenyl, $R^{A20}$-substituted phenyl, $R^{A20}$-substituted naphthyl, $R^{A20}$-substituted biphenyl, $R^{A20}$-substituted pyrrolyl, $R^{A20}$-substituted pyrazolyl, $R^{A20}$-substituted imidazolyl, $R^{A20}$-substituted pyrazinyl, $R^{A20}$-substituted oxazolyl, $R^{A20}$-substituted isoxazolyl, $R^{A20}$-substituted thiazolyl, $R^{A20}$-substituted furylthienyl, $R^{A20}$-substituted pyridyl, $R^{A20}$-substituted pyrimidyl, $R^{A20}$-substituted benzothiazolyl, $R^{A20}$-substituted purinyl, $R^{A20}$-substituted benzimidazolyl, $R^{A20}$-substituted isoquinolyl, $R^{A20}$-substituted thiadiazolyl, $R^{A20}$-substituted oxadiazolyl, $R^{A20}$-substituted pyrrolyl, $R^{A20}$-substituted diazolyl, $R^{A20}$-substituted triazolyl, $R^{A20}$-substituted tetrazolyl, $R^{A20}$-substituted benzothiadiazolyl, $R^{A20}$-substituted isothiazolyl, $R^{A20}$-substituted pyrazolopyrimidinyl, $R^{A20}$-substituted pyrrolopyrimidinyl, $R^{A20}$-substituted benzotriazolyl, or $R^{A20}$-substituted quinolyl. In embodiments, $R^{A3}$ is independently $R^{A20}$-substituted benzoxazolyl.

$R^{A20}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)

NHNH$_2$, —NHC(O)NH$_2$, —NHSO$_2$H, —NHC(O)H, —NHC(O)OH, —NHOH, —OCF$_3$, —OCHF$_2$, $R^{A21}$-substituted or unsubstituted alkyl, $R^{A21}$-substituted or unsubstituted heteroalkyl, $R^{A21}$-substituted or unsubstituted cycloalkyl, $R^{A21}$-substituted or unsubstituted heterocycloalkyl, $R^{A21}$-substituted or unsubstituted aryl, or $R^{A21}$-substituted or unsubstituted heteroaryl.

In embodiments, $R^{A20}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, $R^{A21}$-substituted or unsubstituted alkyl (e.g., $C_1$-$C_8$, $C_1$-$C_6$, $C_1$-$C_4$, or $C_1$-$C_2$), $R^{A21}$-substituted or unsubstituted heteroalkyl (e.g., 2 to 8 membered, 2 to 6 membered, 4 to 6 membered, 2 to 3 membered, or 4 to 5 membered), $R^{A21}$-substituted or unsubstituted cycloalkyl (e.g., $C_3$-$C_8$, $C_3$-$C_6$, $C_4$-$C_6$, or $C_5$-$C_6$), $R^{A21}$-substituted or unsubstituted heterocycloalkyl (e.g., 3 to 8 membered, 3 to 6 membered, 4 to 6 membered, 4 to 5 membered, or 5 to 6 membered), $R^{A21}$-substituted or unsubstituted aryl (e.g., $C_6$-$C_{10}$ or phenyl), or $R^{A21}$-substituted or unsubstituted heteroaryl (e.g., 5 to 10 membered, 5 to 9 membered, or 5 to 6 membered).

$R^{A21}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, $R^{A22}$-substituted or unsubstituted alkyl, $R^{A22}$-substituted or unsubstituted heteroalkyl, $R^{A22}$-substituted or unsubstituted cycloalkyl, $R^{A22}$-substituted or unsubstituted heterocycloalkyl, $R^{A22}$-substituted or unsubstituted aryl, or $R^{A22}$-substituted or unsubstituted heteroaryl.

In embodiments, $R^{A21}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, $R^{A22}$-substituted or unsubstituted alkyl (e.g., $C_1$-$C_8$, $C_1$-$C_6$, $C_1$-$C_4$, or $C_1$-$C_2$), $R^{A22}$-substituted or unsubstituted heteroalkyl (e.g., 2 to 8 membered, 2 to 6 membered, 4 to 6 membered, 2 to 3 membered, or 4 to 5 membered), $R^{A22}$-substituted or unsubstituted cycloalkyl (e.g., $C_3$-$C_8$, $C_3$-$C_6$, $C_4$-$C_6$, or $C_5$-$C_6$), $R^{A22}$-substituted or unsubstituted heterocycloalkyl (e.g., 3 to 8 membered, 3 to 6 membered, 4 to 6 membered, 4 to 5 membered, or 5 to 6 membered), $R^{A22}$-substituted or unsubstituted aryl (e.g., $C_6$-$C_{10}$ or phenyl), or $R^{A22}$-substituted or unsubstituted heteroaryl (e.g., 5 to 10 membered, 5 to 9 membered, or 5 to 6 membered).

$R^{A22}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A22}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A7}$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A7}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A7}$ is substituted with a plurality of groups selected from substituent groups, size-limited substituent groups, and lower substituent groups; each substituent group, size-limited substituent group, and/or lower substituent group may optionally be different. In embodiments, when $R^{A7}$ is substituted, it is substituted with at least one substituent group. In embodiments, when $R^{A7}$ is substituted, it is substituted with at least one size-limited substituent group. In embodiments, when $R^{A7}$ is substituted, it is substituted with at least one lower substituent group.

In embodiments, $R^{A7}$ is independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, $R^{A38}$-substituted or unsubstituted alkyl, $R^{A38}$-substituted or unsubstituted heteroalkyl, $R^{A38}$-substituted or unsubstituted cycloalkyl, $R^{A38}$-substituted or unsubstituted heterocycloalkyl, $R^{A38}$-substituted or unsubstituted aryl, or $R^{A38}$-substituted or unsubstituted heteroaryl.

In embodiments, $R^{A7}$ is independently hydrogen, —CF$_3$, —CN, —COOH, —CONH$_2$, $R^{A38}$-substituted or unsubstituted alkyl, $R^{A38}$-substituted or unsubstituted heteroalkyl, $R^{A38}$-substituted or unsubstituted cycloalkyl, $R^{A38}$-substituted or unsubstituted heterocycloalkyl, $R^{A38}$-substituted or unsubstituted aryl, or $R^{A38}$-substituted or unsubstituted heteroaryl. In embodiments, $R^{A7}$ is independently $R^{A38}$-substituted or unsubstituted $C_1$-$C_4$ alkyl, $R^{A38}$-substituted or unsubstituted 2 to 4 membered heteroalkyl, $R^{A38}$-substituted or unsubstituted $C_3$-$C_6$ cycloalkyl, $R^{A38}$-substituted or unsubstituted 3 to 6 membered heterocycloalkyl, $R^{A38}$-substituted or unsubstituted phenyl, or $R^{A38}$-substituted or unsubstituted 5 to 6 membered heteroaryl. In embodiments, $R^{A7}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A7}$ is independently an unsubstituted $C_1$-$C_4$ alkyl. In embodiments, $R^{A7}$ is independently an unsubstituted methyl. In embodiments, $R^{A7}$ is independently an unsubstituted ethyl. In embodiments, $R^{A7}$ is independently an unsubstituted isopropyl. In embodiments, $R^{A7}$ is independently an unsubstituted tert-butyl. In embodiments, $R^{A7}$ is independently hydrogen.

$R^{A38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —S(O)$_2CHCH_2$, —NHS(O)$_2CHCH_2$, $R^{A39}$-substituted or unsubstituted alkyl, $R^{A39}$-substituted or unsubstituted heteroalkyl, $R^{A39}$-substituted or unsubstituted cycloalkyl, $R^{A39}$-substituted or unsubstituted heterocycloalkyl, $R^{A39}$-substituted or unsubstituted aryl, or $R^{A39}$-substituted or unsubstituted heteroaryl.

In embodiments, $R^{A38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —S(O)$_2CHCH_2$, —NHS(O)$_2CHCH_2$, $R^{A39}$-substituted or unsubstituted alkyl (e.g., $C_1$-$C_8$, $C_1$-$C_6$, $C_1$-$C_4$, or $C_1$-$C_2$), $R^{A39}$-substituted or unsubstituted heteroalkyl (e.g., 2 to 8 membered, 2 to 6 membered, 4 to 6 membered, 2 to 3 membered, or 4 to 5 membered), $R^{A39}$-substituted or unsubstituted cycloalkyl (e.g., $C_3$-$C_8$, $C_3$-$C_6$, $C_4$-$C_6$, or $C_5$-$C_6$), $R^{A39}$-substituted or unsubstituted heterocycloalkyl (e.g., 3 to 8 membered, 3 to 6 membered, 4 to 6 membered, 4 to 5 membered, or 5 to 6 membered), $R^{A39}$-substituted or unsubstituted aryl (e.g., $C_6$-$C_{10}$ or phenyl), or $R^{A39}$-substituted or unsubstituted heteroaryl (e.g., 5 to 10 membered, 5 to 9 membered, or 5 to 6 membered).

$R^{A39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —S(O)$_2CHCH_2$, —NHS(O)$_2CHCH_2$, $R^{A40}$-substituted or unsubstituted alkyl, $R^{A40}$-substituted or unsubstituted heteroalkyl, $R^{A40}$-substituted or unsubstituted cycloalkyl, $R^{A40}$-substituted or unsubstituted heterocycloalkyl, $R^{A40}$-substituted or unsubstituted aryl, or $R^{A40}$-substituted or unsubstituted heteroaryl.

In embodiments, $R^{A39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —S(O)$_2CHCH_2$, —NHS(O)$_2CHCH_2$, $R^{A40}$-substituted or unsubstituted alkyl (e.g., $C_1$-$C_8$, $C_1$-$C_6$, $C_1$-$C_4$, or $C_1$-$C_2$), $R^{A40}$-substituted or unsubstituted heteroalkyl (e.g., 2 to 8 membered, 2 to 6 membered, 4 to 6 membered, 2 to 3 membered, or 4 to 5 membered), $R^{A40}$-substituted or unsubstituted cycloalkyl (e.g., $C_3$-$C_8$, $C_3$-$C_6$, $C_4$-$C_6$, or $C_5$-$C_6$), $R^{A40}$-substituted or unsubstituted heterocycloalkyl (e.g., 3 to 8 membered, 3 to 6 membered, 4 to 6 membered, 4 to 5 membered, or 5 to 6 membered), $R^{A40}$-substituted or unsubstituted aryl (e.g., $C_6$-$C_{10}$ or phenyl), or $R^{A40}$-substituted or unsubstituted heteroaryl (e.g., 5 to 10 membered, 5 to 9 membered, or 5 to 6 membered).

$R^{A40}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —S(O)$_2$$CHCH_2$, —NHS(O)$_2CHCH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A40}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —S(O)$_2CHCH_2$, —NHS(O)$_2CHCH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A8}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A8}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A8}$ is substituted with a plurality of groups selected from substituent groups, size-limited substituent groups, and lower substituent groups; each substituent group, size-limited substituent group, and/or lower substituent group may optionally be different. In embodiments, when $R^{A8}$ is substituted, it is substituted with at least one substituent group. In embodiments, when $R^{A8}$ is substituted, it is substituted with at least one size-limited substituent group. In embodiments, when $R^{A8}$ is substituted, it is substituted with at least one lower substituent group.

In embodiments, $R^{A7}$ and $R^{A8}$ substituents bonded to the same nitrogen atom may optionally be joined to form a substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered) or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted moiety formed by joining $R^{A7}$ and $R^{A8}$ substituents bonded to the same nitrogen atom (e.g., substituted heterocycloalkyl and/or substituted heteroaryl) is substituted with at least one substituent group, size-limited substituent group, or lower substituent group; wherein if the substituted moiety formed by joining $R^{A7}$ and $R^{A8}$ substituents bonded to the same nitrogen atom is substituted with a plurality of groups selected from substituent groups, size-limited substituent groups, and lower substituent groups; each substituent group, size-limited substituent group, and/or lower substituent group may optionally be different. In embodiments, when the moiety formed by joining $R^{A7}$ and $R^{A8}$ substituents bonded to the same nitrogen atom is substituted, it is substituted with at least one substituent group. In embodiments, when the moiety formed by joining $R^{A7}$ and $R^{A8}$ substituents bonded to the same nitrogen atom is substituted, it is substituted with at least one size-limited substituent group. In embodiments, when the moiety formed by joining $R^{A7}$ and $R^{A8}$ substituents bonded to the same nitrogen atom is substituted, it is substituted with at least one lower substituent group.

In embodiments, $R^{A8}$ is independently hydrogen, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A41}$-substituted or unsubstituted alkyl, $R^{A41}$-substituted or unsubstituted heteroalkyl, $R^{A41}$-substituted or unsubstituted cycloalkyl, $R^{A41}$-substituted or unsubstituted heterocycloalkyl, $R^{A41}$-substituted or unsubstituted aryl, or $R^{A41}$-substituted or unsubstituted heteroaryl.

In embodiments, $R^{A8}$ is independently hydrogen, $—CF_3$, —CN, —COOH, $—CONH_2$, $R^{A41}$-substituted or unsubstituted alkyl, $R^{A41}$-substituted or unsubstituted heteroalkyl, $R^{A41}$-substituted or unsubstituted cycloalkyl, $R^{A41}$-substituted or unsubstituted heterocycloalkyl, $R^{A41}$-substituted or unsubstituted aryl, or $R^{A41}$-substituted or unsubstituted heteroaryl. In embodiments, $R^{A8}$ is independently an $R^{A41}$-substituted or unsubstituted $C_1$-$C_4$ alkyl, $R^{A41}$-substituted or unsubstituted 2 to 4 membered heteroalkyl, $R^{A41}$-substituted or unsubstituted $C_3$-$C_6$ cycloalkyl, $R^{A41}$-substituted or unsubstituted 3 to 6 membered heterocycloalkyl, $R^{A41}$-substituted or unsubstituted phenyl, or $R^{A41}$-substituted or unsubstituted 5 to 6 membered heteroaryl. In embodiments, $R^{A8}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A8}$ is independently an unsubstituted $C_1$-$C_4$ alkyl. In embodiments, $R^{A8}$ is independently an unsubstituted methyl. In embodiments, $R^{A8}$ is independently an unsubstituted ethyl. In embodiments, $R^{A8}$ is independently an unsubstituted isopropyl. In embodiments, $R^{A8}$ is independently an unsubstituted tert-butyl. In embodiments, $R^{A8}$ is independently hydrogen.

$R^{A41}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $—S(O)_2CHCH_2$, $—NHS(O)_2CHCH_2$, $R^{A42}$-substituted or unsubstituted alkyl, $R^{A42}$-substituted or unsubstituted heteroalkyl, $R^{A42}$-substituted or unsubstituted cycloalkyl, $R^{A42}$-substituted or unsubstituted heterocycloalkyl, $R^{A42}$-substituted or unsubstituted aryl, or $R^{A42}$-substituted or unsubstituted heteroaryl.

In embodiments, $R^{A41}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $—S(O)_2CHCH_2$, $—NHS(O)_2CHCH_2$, $R^{A42}$-substituted or unsubstituted alkyl (e.g., $C_1$-$C_8$, $C_1$-$C_6$, $C_1$-$C_4$, or $C_1$-$C_2$), $R^{A42}$-substituted or unsubstituted heteroalkyl (e.g., 2 to 8 membered, 2 to 6 membered, 4 to 6 membered, 2 to 3 membered, or 4 to 5 membered), $R^{A42}$-substituted or unsubstituted cycloalkyl (e.g., $C_3$-$C_8$, $C_3$-$C_6$, $C_4$-$C_6$, or $C_5$-$C_6$), $R^{A42}$-substituted or unsubstituted heterocycloalkyl (e.g., 3 to 8 membered, 3 to 6 membered, 4 to 6 membered, 4 to 5 membered, or 5 to 6 membered), $R^{A42}$-substituted or unsubstituted aryl (e.g., $C_6$-$C_{10}$ or phenyl), or $R^{A42}$-substituted or unsubstituted heteroaryl (e.g., 5 to 10 membered, 5 to 9 membered, or 5 to 6 membered).

$R^{A42}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $—S(O)_2CHCH_2$, $—NHS(O)_2CHCH_2$, $R^{A43}$-substituted or unsubstituted alkyl, $R^{A43}$-substituted or unsubstituted heteroalkyl, $R^{A43}$-substituted or unsubstituted cycloalkyl, $R^{A43}$-substituted or unsubstituted heterocycloalkyl, $R^{A43}$-substituted or unsubstituted aryl, or $R^{A43}$-substituted or unsubstituted heteroaryl.

In embodiments, $R^{A42}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $—S(O)_2CHCH_2$, $—NHS(O)_2CHCH_2$, $R^{A43}$-substituted or unsubstituted alkyl (e.g., $C_1$-$C_8$, $C_1$-$C_6$, $C_1$-$C_4$, or $C_1$-$C_2$), $R^{A43}$-substituted or unsubstituted heteroalkyl (e.g., 2 to 8 membered, 2 to 6 membered, 4 to 6 membered, 2 to 3 membered, or 4 to 5 membered), $R^{A43}$-substituted or unsubstituted cycloalkyl (e.g., $C_3$-$C_8$, $C_3$-$C_6$, $C_4$-$C_6$, or $C_5$-$C_6$), $R^{A43}$-substituted or unsubstituted heterocycloalkyl (e.g., 3 to 8 membered, 3 to 6 membered, 4 to 6 membered, 4 to 5 membered, or 5 to 6 membered), $R^{A43}$-substituted or unsubstituted aryl (e.g., $C_6$-$C_{10}$ or phenyl), or $R^{A43}$-substituted or unsubstituted heteroaryl (e.g., 5 to 10 membered, 5 to 9 membered, or 5 to 6 membered).

$R^{A43}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $—S(O)_2CHCH_2$, $—NHS(O)_2CHCH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A43}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A9}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A9}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A9}$ is substituted with a plurality of groups selected from substituent groups, size-limited substituent groups, and lower substituent groups; each substituent group, size-limited substituent group, and/or lower substituent group may optionally be different. In embodiments, when $R^{A9}$ is substituted, it is substituted with at least one substituent group. In embodiments, when $R^{A9}$ is substituted, it is substituted with at least one size-limited substituent group. In embodiments, when $R^{A9}$ is substituted, it is substituted with at least one lower substituent group.

In embodiments, $R^{A9}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A44}$-substituted or unsubstituted alkyl, $R^{A44}$-substituted or unsubstituted heteroalkyl, $R^{A44}$-substituted or unsubstituted cycloalkyl, $R^{A44}$-substituted or unsubstituted heterocycloalkyl, $R^{A44}$-substituted or unsubstituted aryl, or $R^{A44}$-substituted or unsubstituted heteroaryl.

In embodiments, $R^{A9}$ is independently hydrogen, —$CF_3$, —CN, —COOH, —$CONH_2$, $R^{A44}$-substituted or unsubstituted alkyl, $R^{A44}$-substituted or unsubstituted heteroalkyl, $R^{A44}$-substituted or unsubstituted cycloalkyl, $R^{A44}$-substituted or unsubstituted heterocycloalkyl, $R^{A44}$-substituted or unsubstituted aryl, or $R^{A44}$-substituted or unsubstituted heteroaryl. In embodiments, $R^{A9}$ is independently an $R^{A44}$-substituted or unsubstituted $C_1$-$C_4$ alkyl, $R^{A44}$-substituted or unsubstituted 2 to 4 membered heteroalkyl, $R^{A44}$-substituted or unsubstituted $C_3$-$C_6$ cycloalkyl, $R^{A44}$-substituted or unsubstituted 3 to 6 membered heterocycloalkyl, $R^{A44}$-substituted or unsubstituted phenyl, or $R^{A44}$-substituted or unsubstituted 5 to 6 membered heteroaryl. In embodiments, $R^{A9}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A9}$ is independently an unsubstituted $C_1$-$C_4$ alkyl. In embodiments, $R^{A9}$ is independently an unsubstituted methyl. In embodiments, $R^{A9}$ is independently an unsubstituted ethyl. In embodiments, $R^{A9}$ is independently an unsubstituted isopropyl. In embodiments, $R^{A9}$ is independently an unsubstituted tert-butyl. In embodiments, $R^{A9}$ is independently hydrogen.

$R^{A44}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A45}$-substituted or unsubstituted alkyl, $R^{A45}$-substituted or unsubstituted heteroalkyl, $R^{A45}$-substituted or unsubstituted cycloalkyl, $R^{A45}$-substituted or unsubstituted heterocycloalkyl, $R^{A45}$-substituted or unsubstituted aryl, or $R^{A45}$-substituted or unsubstituted heteroaryl.

In embodiments, $R^{A44}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A45}$-substituted or unsubstituted alkyl (e.g., $C_1$-$C_8$, $C_1$-$C_6$, $C_1$-$C_4$, or $C_1$-$C_2$), $R^{A45}$-substituted or unsubstituted heteroalkyl (e.g., 2 to 8 membered, 2 to 6 membered, 4 to 6 membered, 2 to 3 membered, or 4 to 5 membered), $R^{A45}$-substituted or unsubstituted cycloalkyl (e.g., $C_3$-$C_8$, $C_3$-$C_6$, $C_4$-$C_6$, or $C_5$-$C_6$), $R^{A45}$-substituted or unsubstituted heterocycloalkyl (e.g., 3 to 8 membered, 3 to 6 membered, 4 to 6 membered, 4 to 5 membered, or 5 to 6 membered), $R^{A45}$-substituted or unsubstituted aryl (e.g., $C_6$-$C_{10}$ or phenyl), or $R^{A45}$-substituted or unsubstituted heteroaryl (e.g., 5 to 10 membered, 5 to 9 membered, or 5 to 6 membered).

$R^{A45}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A46}$-substituted or unsubstituted alkyl, $R^{A46}$-substituted or unsubstituted heteroalkyl, $R^{A46}$-substituted or unsubstituted cycloalkyl, $R^{A46}$-substituted or unsubstituted heterocycloalkyl, $R^{A46}$-substituted or unsubstituted aryl, or $R^{A46}$-substituted or unsubstituted heteroaryl.

In embodiments, $R^{A45}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A46}$-substituted or unsubstituted alkyl (e.g., $C_1$-$C_8$, $C_1$-$C_6$, $C_1$-$C_4$, or $C_1$-$C_2$), $R^{A46}$-substituted or unsubstituted heteroalkyl (e.g., 2 to 8 membered, 2 to 6 membered, 4 to 6 membered, 2 to 3 membered, or 4 to 5 membered), $R^{A46}$-substituted or unsubstituted cycloalkyl (e.g., $C_3$-$C_8$, $C_3$-$C_6$, $C_4$-$C_6$, or $C_5$-$C_6$), $R^{A46}$-substituted or unsubstituted heterocycloalkyl (e.g., 3 to 8 membered, 3 to 6 membered, 4 to 6 membered, 4 to 5 membered, or 5 to 6 membered), $R^{A46}$-substituted or unsubstituted aryl (e.g., $C_6$-$C_{10}$ or phenyl), or $R^{A46}$-substituted or unsubstituted heteroaryl (e.g., 5 to 10 membered, 5 to 9 membered, or 5 to 6 membered).

$R^{A46}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A46}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A1o}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A1o}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A1o}$ is substituted with a plurality of groups selected from substituent groups, size-limited substituent groups, and lower substituent groups; each substituent group, size-limited substituent group, and/or lower substituent group may optionally be different. In embodiments, when $R^{A1o}$ is substituted, it is substituted with at least one substituent group. In embodiments, when $R^{A1o}$ is substituted, it is substituted with at least one size-limited substituent group. In embodiments, when $R^{A1o}$ is substituted, it is substituted with at least one lower substituent group.

In embodiments, $R^{A1o}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A47}$-substituted or unsubstituted alkyl, $R^{A47}$-substituted or unsubstituted heteroalkyl, $R^{A47}$-substituted or unsubstituted cycloalkyl, $R^{A47}$-substituted or unsubstituted heterocycloalkyl, $R^{A47}$-substituted or unsubstituted aryl, or $R^{A47}$-substituted or unsubstituted heteroaryl.

In embodiments, $R^{A1o}$ is independently hydrogen, —$CF_3$, —CN, —COOH, —$CONH_2$, $R^{A47}$-substituted or unsubstituted alkyl, $R^{A47}$-substituted or unsubstituted heteroalkyl, $R^{A47}$-substituted or unsubstituted cycloalkyl, $R^{A47}$-substituted or unsubstituted heterocycloalkyl, $R^{A47}$-substituted or unsubstituted aryl, or $R^{A47}$-substituted or unsubstituted heteroaryl. In embodiments, $R^{A1o}$ is independently an $R^{A47}$-substituted or unsubstituted $C_1$-$C_4$ alkyl, $R^{A47}$-substituted or unsubstituted 2 to 4 membered heteroalkyl, $R^{A47}$-substituted or unsubstituted $C_3$-$C_6$ cycloalkyl, $R^{A47}$-substituted or unsubstituted 3 to 6 membered heterocycloalkyl, $R^{A47}$-substituted or unsubstituted phenyl, or $R^{A47}$-substituted or unsubstituted 5 to 6 membered heteroaryl. In embodiments, $R^{A1o}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A1o}$ is independently an unsubstituted $C_1$-$C_4$ alkyl. In embodiments, $R^{A1o}$ is independently an unsubstituted methyl. In embodiments, $R^{A1o}$ is independently an unsubstituted ethyl. In embodiments, $R^{A1o}$ is independently an unsubstituted isopropyl. In embodiments, $R^{A1o}$ is independently an unsubstituted tert-butyl. In embodiments, $R^{A1o}$ is independently hydrogen.

$R^{A47}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A48}$-substituted or unsubstituted alkyl, $R^{A48}$-substituted or unsubstituted heteroalkyl, $R^{A48}$-substituted or unsubstituted cycloalkyl, $R^{A48}$-substituted or unsubstituted heterocycloalkyl, $R^{A48}$-substituted or unsubstituted aryl, or $R^{A48}$-substituted or unsubstituted heteroaryl.

In embodiments, $R^{A47}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A48}$-substituted or unsubstituted alkyl (e.g., $C_1$-$C_8$, $C_1$-$C_6$, $C_1$-$C_4$, or $C_1$-$C_2$), $R^{A48}$-substituted or unsubstituted heteroalkyl (e.g., 2 to 8 membered, 2 to 6 membered, 4 to 6 membered, 2 to 3 membered, or 4 to 5 membered), $R^{A48}$-substituted or unsubstituted cycloalkyl (e.g., $C_3$-$C_8$, $C_3$-$C_6$, $C_4$-$C_6$, or $C_5$-$C_6$), $R^{A48}$-substituted or unsubstituted heterocycloalkyl (e.g., 3 to 8 membered, 3 to 6 membered, 4 to 6 membered, 4 to 5 membered, or 5 to 6 membered), $R^{A48}$-substituted or unsubstituted aryl (e.g., $C_6$-$C_{10}$ or phenyl), or $R^{A48}$-substituted or unsubstituted heteroaryl (e.g., 5 to 10 membered, 5 to 9 membered, or 5 to 6 membered).

$R^{A48}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A49}$-substituted or unsubstituted alkyl, $R^{A49}$-substituted or unsubstituted heteroalkyl, $R^{A49}$-substituted or unsubstituted cycloalkyl, $R^{A49}$-substituted or unsubstituted heterocycloalkyl, $R^{A49}$-substituted or unsubstituted aryl, or $R^{A49}$-substituted or unsubstituted heteroaryl.

In embodiments, $R^{A48}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A49}$-substituted or unsubstituted alkyl (e.g., $C_1$-$C_8$, $C_1$-$C_6$, $C_1$-$C_4$, or $C_1$-$C_2$), $R^{A49}$-substituted or unsubstituted heteroalkyl (e.g., 2 to 8 membered, 2 to 6 membered, 4 to 6 membered, 2 to 3 membered, or 4 to 5 membered), $R^{A49}$-substituted or unsubstituted cycloalkyl (e.g., $C_3$-$C_8$, $C_3$-$C_6$, $C_4$-$C_6$, or $C_5$-$C_6$), $R^{A49}$-substituted or unsubstituted heterocycloalkyl (e.g., 3 to 8 membered, 3 to 6 membered, 4 to 6 membered, 4 to 5 membered, or 5 to 6 membered), $R^{A49}$-substituted or unsubstituted aryl (e.g., $C_6$-$C_{10}$ or phenyl), or $R^{A49}$-substituted or unsubstituted heteroaryl (e.g., 5 to 10 membered, 5 to 9 membered, or 5 to 6 membered).

$R^{A49}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A49}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A11}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A11}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A11}$ is substituted with a plurality of groups selected from substituent groups, size-limited substituent groups, and lower substituent groups; each substituent group, size-limited substituent group, and/or lower substituent group may optionally be different. In embodiments, when $R^{A11}$ is substituted, it is substituted with at least one substituent group. In embodiments, when $R^{A11}$ is substituted, it is substituted with at least one size-limited substituent group. In embodiments, when $R^{A11}$ is substituted, it is substituted with at least one lower substituent group.

In embodiments, $R^{A11}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A50}$-substituted or unsubstituted alkyl, $R^{A50}$-substituted or unsubstituted heteroalkyl, $R^{A50}$-substituted or unsubstituted cycloalkyl, $R^{A50}$-substituted or unsubstituted heterocycloalkyl, $R^{A50}$-substituted or unsubstituted aryl, or $R^{A50}$-substituted or unsubstituted heteroaryl.

In embodiments, $R^{A11}$ is independently hydrogen, —$CF_3$, —CN, —COOH, —$CONH_2$, $R^{A50}$-substituted or unsubstituted alkyl, $R^{A50}$-substituted or unsubstituted heteroalkyl, $R^{A50}$-substituted or unsubstituted cycloalkyl, $R^{A50}$-substituted or unsubstituted heterocycloalkyl, $R^{A50}$-substituted or unsubstituted aryl, or $R^{A50}$-substituted or unsubstituted heteroaryl. In embodiments, $R^{A11}$ is independently an $R^{A50}$-substituted or unsubstituted $C_1$-$C_4$ alkyl, $R^{A50}$-substituted or unsubstituted 2 to 4 membered heteroalkyl, $R^{A50}$-substituted or unsubstituted $C_3$-$C_6$ cycloalkyl, $R^{A50}$-substituted or unsubstituted 3 to 6 membered heterocycloalkyl, $R^{A50}$-substituted or unsubstituted phenyl, or $R^{A50}$-substituted or unsubstituted 5 to 6 membered heteroaryl. In embodiments, $R^{A11}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A11}$ is independently an unsubstituted $C_1$-$C_4$ alkyl. In embodiments, $R^{A11}$ is independently an unsubstituted methyl. In embodiments, $R^{A11}$ is independently an unsubstituted ethyl. In embodiments, $R^{A11}$ is independently an unsubstituted isopropyl. In embodiments, $R^{A11}$ is independently an unsubstituted tert-butyl. In embodiments, $R^{A11}$ is independently hydrogen. In embodiments, $R^{A11}$ is independently an $R^{A50}$-substituted or unsubstituted $C_1$-$C_4$ alkyl. In embodiments, $R^{A11}$ is independently an $R^{A50}$-substituted or unsubstituted 2 to 4 membered heteroalkyl. In embodiments, $R^{A11}$ is independently an $R^{A50}$-substituted or unsubstituted $C_3$-$C_6$ cycloalkyl. In embodiments, $R^{A11}$ is independently an $R^{A50}$-substituted or unsubstituted 3 to 6 membered heterocycloalkyl. In embodiments, $R^{A11}$ is independently an $R^{A50}$-substituted or unsubstituted phenyl. In embodiments, $R^{A11}$ is independently an $R^{A50}$-substituted or unsubstituted 5 to 6 membered heteroaryl. In embodiments, $R^{A11}$ is independently an unsubstituted $C_1$-$C_4$ alkyl. In embodiments, $R^{A11}$ is independently an unsubstituted 2 to 4 membered heteroalkyl. In embodiments, $R^{A11}$ is independently an unsubstituted $C_3$-$C_6$ cycloalkyl. In embodiments, $R^{A11}$ is independently an unsubstituted 3 to 6 membered heterocycloalkyl. In embodiments, $R^{A11}$ is independently an unsubstituted phenyl. In embodiments, $R^{A11}$ is independently an unsubstituted 5 to 6 membered heteroaryl.

$R^{A5o}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, $R^{A51}$-substituted or unsubstituted alkyl, $R^{A51}$-substituted or unsubstituted heteroalkyl, $R^{A51}$-substituted or unsubstituted cycloalkyl, $R^{A51}$-substituted or unsubstituted heterocycloalkyl, $R^{A51}$-substituted 6 or unsubstituted aryl, or $R^{A51}$-substituted or unsubstituted heteroaryl.

In embodiments, $R^{A5o}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, $R^{A51}$-substituted or unsubstituted alkyl (e.g., $C_1$-$C_8$, $C_1$-$C_6$, $C_1$-$C_4$, or $C_1$-$C_2$), $R^{A51}$-substituted or unsubstituted heteroalkyl (e.g., 2 to 8 membered, 2 to 6 membered, 4 to 6 membered, 2 to 3 membered, or 4 to 5 membered), $R^{A51}$-substituted or unsubstituted cycloalkyl (e.g., $C_3$-$C_8$, $C_3$-$C_6$, $C_4$-$C_6$, or $C_5$-$C_6$), $R^{A51}$-substituted or unsubstituted heterocycloalkyl (e.g., 3 to 8 membered, 3 to 6 membered, 4 to 6 membered, 4 to 5 membered, or 5 to 6 membered), $R^{A51}$-substituted or unsubstituted aryl (e.g., $C_6$-$C_{10}$ or phenyl), or $R^{A51}$-substituted or unsubstituted heteroaryl (e.g., 5 to 10 membered, 5 to 9 membered, or 5 to 6 membered).

$R^{A51}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, $R^{A52}$-substituted or unsubstituted alkyl, $R^{A52}$-substituted or unsubstituted heteroalkyl, $R^{A52}$-substituted or unsubstituted cycloalkyl, $R^{A52}$-substituted or unsubstituted heterocycloalkyl, $R^{A52}$-substituted or unsubstituted aryl, or $R^{A52}$-substituted or unsubstituted heteroaryl.

In embodiments, $R^{A51}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, $R^{A52}$-substituted or unsubstituted alkyl (e.g., $C_1$-$C_8$, $C_1$-$C_6$, $C_1$-$C_4$, or $C_1$-$C_2$), $R^{A52}$-substituted or unsubstituted heteroalkyl (e.g., 2 to 8 membered, 2 to 6 membered, 4 to 6 membered, 2 to 3 membered, or 4 to 5 membered), $R^{A52}$-substituted or unsubstituted cycloalkyl (e.g., $C_3$-$C_8$, $C_3$-$C_6$, $C_4$-$C_6$, or $C_5$-$C_6$), $R^{A52}$-substituted or unsubstituted heterocycloalkyl (e.g., 3 to 8 membered, 3 to 6 membered, 4 to 6 membered, 4 to 5 membered, or 5 to 6 membered), $R^{A52}$-substituted or unsubstituted aryl (e.g., $C_6$-$C_{10}$ or phenyl), or $R^{A52}$-substituted or unsubstituted heteroaryl (e.g., 5 to 10 membered, 5 to 9 membered, or 5 to 6 membered).

$R^{A52}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A52}$ is independently oxo, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A12}$ is independently hydrogen, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A12}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A12}$ is substituted with a plurality of groups selected from substituent groups, size-limited substituent groups, and lower substituent groups; each substituent group, size-limited substituent group, and/or lower substituent group may optionally be different. In embodiments, when $R^{A12}$ is substituted, it is substituted with at least one substituent group. In embodiments, when $R^{A12}$ is substituted, it is substituted with at least one size-limited substituent group. In embodiments, when $R^{A12}$ is substituted, it is substituted with at least one lower substituent group.

In embodiments, $R^{A12}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A53}$-substituted or unsubstituted alkyl, $R^{A53}$-substituted or unsubstituted heteroalkyl, $R^{A53}$-substituted or unsubstituted cycloalkyl, $R^{A53}$-substituted or unsubstituted heterocycloalkyl, $R^{A53}$-substituted or unsubstituted aryl, or $R^{A53}$-substituted or unsubstituted heteroaryl.

In embodiments, $R^{A12}$ is independently hydrogen, —$CF_3$, —CN, —COOH, —$CONH_2$, $R^{A53}$-substituted or unsubstituted alkyl, $R^{A53}$-substituted or unsubstituted heteroalkyl, $R^{A53}$-substituted or unsubstituted cycloalkyl, $R^{A53}$-substituted or unsubstituted heterocycloalkyl, $R^{A53}$-substituted or unsubstituted aryl, or $R^{A53}$-substituted or unsubstituted heteroaryl. In embodiments, $R^{A12}$ is independently an $R^{A53}$-substituted or unsubstituted $C_1$-$C_4$ alkyl, $R^{A53}$-substituted or unsubstituted 2 to 4 membered heteroalkyl, $R^{A53}$-substituted or unsubstituted $C_3$-$C_6$ cycloalkyl, $R^{A53}$-substituted or unsubstituted 3 to 6 membered heterocycloalkyl, $R^{A53}$-substituted or unsubstituted phenyl, or $R^{A53}$-substituted or unsubstituted 5 to 6 membered heteroaryl. In embodiments, $R^{A12}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A12}$ is independently an unsubstituted $C_1$-$C_4$ alkyl. In embodiments, $R^{A12}$ is independently an unsubstituted methyl. In embodiments, $R^{A12}$ is independently an unsubstituted ethyl. In embodiments, $R^{A12}$ is independently an unsubstituted isopropyl. In embodiments, $R^{A12}$ is independently an unsubstituted tert-butyl. In embodiments, $R^{A12}$ is independently hydrogen. In embodiments, $R^{A12}$ is independently an $R^{A53}$-substituted or unsubstituted $C_1$-$C_4$ alkyl. In embodiments, $R^{A12}$ is independently an $R^{A53}$-substituted or unsubstituted 2 to 4 membered heteroalkyl. In embodiments, $R^{A12}$ is independently an $R^{A53}$-substituted or unsubstituted $C_3$-$C_6$ cycloalkyl. In embodiments, $R^{A12}$ is independently an $R^{A53}$-substituted or unsubstituted 3 to 6 membered heterocycloalkyl. In embodiments, $R^{A12}$ is independently an $R^{A53}$-substituted or unsubstituted phenyl. In embodiments, $R^{A12}$ is independently an $R^{A53}$-substituted or unsubstituted 5 to 6 membered heteroaryl. In embodiments, $R^{A12}$ is independently an unsubstituted $C_1$-$C_4$ alkyl. In embodiments, $R^{A12}$ is independently an unsubstituted 2 to 4 membered heteroalkyl. In embodiments, $R^{A12}$ is independently an unsubstituted $C_3$-$C_6$ cycloalkyl. In embodiments, $R^{A12}$ is independently an unsubstituted 3 to 6 membered heterocycloalkyl. In embodiments, $R^{A12}$ is independently an unsubstituted phenyl. In embodiments, $R^{A12}$ is independently an unsubstituted 5 to 6 membered heteroaryl.

$R^{A53}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, $R^{A54}$-substituted or unsubstituted alkyl, $R^{A54}$-substituted or unsubstituted heteroalkyl, $R^{A54}$-substituted or unsubstituted cycloalkyl, $R^{A54}$-substituted or unsubstituted heterocycloalkyl, $R^{A54}$-substituted or unsubstituted aryl, or $R^{A54}$-substituted or unsubstituted heteroaryl.

In embodiments, $R^{A53}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, $R^{A54}$-substituted or unsubstituted alkyl (e.g., $C_1$-$C_8$, $C_1$-$C_6$, $C_1$-$C_4$, or $C_1$-$C_2$), $R^{A54}$-substituted or unsubstituted heteroalkyl (e.g., 2 to 8 membered, 2 to 6 membered, 4 to 6 membered, 2 to 3 membered, or 4 to 5 membered), $R^{A54}$-substituted or unsubstituted cycloalkyl (e.g., $C_3$-$C_8$, $C_3$-$C_6$, $C_4$-$C_6$, or $C_5$-$C_6$), $R^{A54}$-substituted or unsubstituted heterocycloalkyl (e.g., 3 to 8 membered, 3 to 6 membered, 4 to 6 membered, 4 to 5 membered, or 5 to 6 membered), $R^{A54}$-substituted or unsubstituted aryl (e.g., $C_6$-$C_{10}$ or phenyl), or $R^{A54}$-substituted or unsubstituted heteroaryl (e.g., 5 to 10 membered, 5 to 9 membered, or 5 to 6 membered).

$R^{A54}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A55}$-substituted or unsubstituted alkyl, $R^{A55}$-substituted or unsubstituted heteroalkyl, $R^{A55}$-substituted or unsubstituted cycloalkyl, $R^{A55}$-substituted or unsubstituted heterocycloalkyl, $R^{A55}$-substituted or unsubstituted aryl, or $R^{A55}$-substituted or unsubstituted heteroaryl.

In embodiments, $R^{A54}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A55}$-substituted or unsubstituted alkyl (e.g., $C_1$-$C_8$, $C_1$-$C_6$, $C_1$-$C_4$, or $C_1$-$C_2$), $R^{A55}$-substituted or unsubstituted heteroalkyl (e.g., 2 to 8 membered, 2 to 6 membered, 4 to 6 membered, 2 to 3 membered, or 4 to 5 membered), $R^{A55}$-substituted or unsubstituted cycloalkyl (e.g., $C_3$-$C_8$, $C_3$-$C_6$, $C_4$-$C_6$, or $C_5$-$C_6$), $R^{A55}$-substituted or unsubstituted heterocycloalkyl (e.g., 3 to 8 membered, 3 to 6 membered, 4 to 6 membered, 4 to 5 membered, or 5 to 6 membered), $R^{A55}$-substituted or unsubstituted aryl (e.g., $C_6$-$C_{10}$ or phenyl), or $R^{A55}$-substituted or unsubstituted heteroaryl (e.g., 5 to 10 membered, 5 to 9 membered, or 5 to 6 membered).

$R^{A55}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A55}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{A13}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{A13}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{A13}$ is substituted with a plurality of groups selected from substituent groups, size-limited substituent groups, and lower substituent groups; each substituent group, size-limited substituent group, and/or lower substituent group may optionally be different. In embodiments, when $R^{A13}$ is substituted, it is substituted with at least one substituent group. In embodiments, when $R^{A13}$ is substituted, it is substituted with at least one size-limited substituent group. In embodiments, when $R^{A13}$ is substituted, it is substituted with at least one lower substituent group.

In embodiments, $R^{A13}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A56}$-substituted or unsubstituted alkyl, $R^{A56}$-substituted or unsubstituted heteroalkyl, $R^{A56}$-substituted or unsubstituted cycloalkyl, $R^{A56}$-substituted or unsubstituted heterocycloalkyl, $R^{A56}$-substituted or unsubstituted aryl, or $R^{A56}$-substituted or unsubstituted heteroaryl.

In embodiments, $R^{A13}$ is independently hydrogen, —$CF_3$, —CN, —COOH, —$CONH_2$, $R^{A56}$-substituted or unsubstituted alkyl, $R^{A56}$-substituted or unsubstituted heteroalkyl, $R^{A56}$-substituted or unsubstituted cycloalkyl, $R^{A56}$-substituted or unsubstituted heterocycloalkyl, $R^{A56}$-substituted or unsubstituted aryl, or $R^{A56}$-substituted or unsubstituted heteroaryl. In embodiments, $R^{A13}$ is independently an $R^{A56}$-substituted or unsubstituted $C_1$-$C_4$ alkyl, $R^{A56}$-substituted or unsubstituted 2 to 4 membered heteroalkyl, $R^{A56}$-substituted or unsubstituted $C_3$-$C_6$ cycloalkyl, $R^{A56}$-substituted or unsubstituted 3 to 6 membered heterocycloalkyl, $R^{A56}$-substituted or unsubstituted phenyl, or $R^{A56}$-substituted or unsubstituted 5 to 6 membered heteroaryl. In embodiments, $R^{A13}$ is independently an unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{A13}$ is independently an unsubstituted $C_1$-$C_4$ alkyl. In embodiments, $R^{A13}$ is independently an unsubstituted methyl. In embodiments, $R^{A13}$ is independently an unsubstituted ethyl. In embodiments, $R^{A13}$ is independently an unsubstituted isopropyl. In embodiments, $R^{A13}$ is independently an unsubstituted tert-butyl. In embodiments, $R^{A13}$ is independently hydrogen. In embodiments, $R^{A13}$ is independently an $R^{A56}$-substituted or unsubstituted $C_1$-$C_4$ alkyl. In embodiments, $R^{A13}$ is independently an $R^{A56}$-substituted or unsubstituted 2 to 4 membered heteroalkyl. In embodiments, $R^{A13}$ is independently an $R^{A56}$-substituted or unsubstituted $C_3$-$C_6$ cycloalkyl. In embodiments, $R^{A13}$ is independently an $R^{A56}$-substituted or unsubstituted 3 to 6 membered heterocycloalkyl. In embodiments, $R^{A13}$ is independently an $R^{A56}$-substituted or unsubstituted phenyl. In embodiments, $R^{A13}$ is independently an $R^{A56}$-substituted or unsubstituted 5 to 6 membered heteroaryl. In embodiments, $R^{A13}$ is independently an unsubstituted $C_1$-$C_4$ alkyl. In embodiments, $R^{A13}$ is independently an unsubstituted 2 to 4 membered heteroalkyl. In embodiments, $R^{A13}$ is independently an unsubstituted $C_3$-$C_6$ cycloalkyl. In embodiments, $R^{A13}$ is independently an unsubstituted 3 to 6 membered heterocycloalkyl. In embodiments, $R^{A13}$ is independently an unsubstituted phenyl. In embodiments, $R^{A13}$ is independently an unsubstituted 5 to 6 membered heteroaryl.

$R^{A56}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A57}$-substituted or unsubstituted alkyl, $R^{A57}$-substituted or unsubstituted heteroalkyl, $R^{A57}$-substituted or unsubstituted cycloalkyl, $R^{A57}$-substituted or unsubstituted heterocycloalkyl, $R^{A57}$-substituted or unsubstituted aryl, or $R^{A57}$-substituted or unsubstituted heteroaryl.

In embodiments, $R^{A56}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A57}$-substituted or unsubstituted alkyl (e.g., $C_1$-$C_8$, $C_1$-$C_6$, $C_1$-$C_4$, or $C_1$-$C_2$), $R^{A57}$-substituted or unsubstituted heteroalkyl (e.g., 2 to 8 membered, 2 to 6 membered, 4 to 6 membered, 2 to 3 membered, or 4 to 5 membered), $R^{A57}$-substituted or unsubstituted cycloalkyl (e.g., $C_3$-$C_8$, $C_3$-$C_6$, $C_4$-$C_6$, or $C_5$-$C_6$), $R^{A57}$-substituted or unsubstituted heterocycloalkyl (e.g., 3 to 8 membered, 3 to 6 membered, 4 to 6 membered, 4 to 5 membered, or 5 to 6 membered), $R^{A57}$-substituted or unsubstituted aryl (e.g., $C_6$-$C_{10}$ or phenyl), or $R^{A57}$-substituted or unsubstituted heteroaryl (e.g., 5 to 10 membered, 5 to 9 membered, or 5 to 6 membered).

$R^{A57}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A458}$-substituted or unsubstituted alkyl, $R^{A458}$-substituted or unsubstituted heteroalkyl, $R^{A458}$-substituted or unsubstituted cycloalkyl, $R^{A458}$-substituted or unsubstituted heterocycloalkyl, $R^{A458}$-substituted or unsubstituted aryl, or $R^{A458}$-substituted or unsubstituted heteroaryl.

In embodiments, $R^{A457}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{A458}$-substituted or unsubstituted alkyl (e.g., $C_1$-$C_8$, $C_1$-$C_6$, $C_1$-$C_4$, or $C_1$-$C_2$), $R^{A458}$-substituted or unsubstituted heteroalkyl (e.g., 2 to 8 membered, 2 to 6 membered, 4 to 6 membered, 2 to 3 membered, or 4 to 5 membered), $R^{A458}$-substituted or unsubstituted cycloalkyl (e.g., $C_3$-$C_8$, $C_3$-$C_6$, $C_4$-$C_6$, or $C_5$-$C_6$), $R^{A458}$-substituted or unsubstituted heterocycloalkyl (e.g., 3 to 8 membered, 3 to 6 membered, 4 to 6 membered, 4 to 5 membered, or 5 to 6 membered), $R^{A458}$-substituted or unsubstituted aryl (e.g., $C_6$-$C_{10}$ or phenyl), or $R^{A458}$-substituted or unsubstituted heteroaryl (e.g., 5 to 10 membered, 5 to 9 membered, or 5 to 6 membered).

$R^{A458}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl, or unsubstituted heteroalkyl, unsubstituted cycloalkyl, unsubstituted heterocycloalkyl, unsubstituted aryl, or unsubstituted heteroaryl.

In embodiments, $R^{A458}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^{A1}$ is a bond, —NH—, —$NR^{A423}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A1}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A1}$ is substituted with a plurality of groups selected from substituent groups, size-limited substituent groups, and lower substituent groups; each substituent group, size-limited substituent group, and/or lower substituent group may optionally be different. In embodiments, when $L^{A1}$ is substituted, it is substituted with at least one substituent group. In embodiments, when $L^{A1}$ is substituted, it is substituted with at least one size-limited substituent group. In embodiments, when $L^{A1}$ is substituted, it is substituted with at least one lower substituent group.

In embodiments, $L^{A1}$ is a bond, —NH—, —$NR^{A423}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A1}$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A1}$ is $L^{A2}$-$L^{A3}$-$L^{A4}$-$L^{A5}$. $L^{A2}$ is connected directly to a monovalent rapamycin or a monovalent rapamycin analog. $L^{A2}$ is a bond, —NH—, —$NR^{A426}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^{A3}$ is a bond, —NH—, —$NR^{A429}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^{A4}$ is a bond, —NH—, —$NR^{A432}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^{A5}$ is a bond, —NH—, —$NR^{A435}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A2}$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A3}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A4}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A5}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{A1}$ is a divalent linker including one or more amino acids. In embodiments, $L^{A1}$ is a divalent linker consisting of amino acids. In embodiments, $L^{A1}$ is a divalent linker including an amino acid analog. In embodiments, $L^{A1}$ is a divalent linker including an amino acid mimetic. In embodiments, $L^{A1}$ is a divalent linker consisting of amino acid analogs. In embodiments, $L^{A1}$ is a divalent linker consisting of amino acid mimetics.

In embodiments, $L^{A2}$ is a bond, —NH—, —$NR^{A26}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A2}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A2}$ is substituted with a plurality of groups selected from substituent groups, size-limited substituent groups, and lower substituent groups; each substituent group, size-limited substituent group, and/or lower substituent group may optionally be different. In embodiments, when $L^{A2}$ is substituted, it is substituted with at least one substituent group. In embodiments, when $L^{A2}$ is substituted, it is substituted with at least one size-limited substituent group. In embodiments, when $L^{A2}$ is substituted, it is substituted with at least one lower substituent group.

In embodiments, $L^{A2}$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A2}$ is substituted or unsubstituted 3 to 8 membered heteroalkylene. In embodiments, $L^{A2}$ is —$CH_2CH_2OCH_2$—. In embodiments, $L^{A2}$ is unsubstituted 3 to 8 membered heteroalkylene. In embodiments, $L^{A2}$ is unsubstituted 3 to 6 membered heteroalkylene. In embodiments, $L^{A2}$ is unsubstituted 3 to 5 membered heteroalkylene. In embodiments, $L^{A2}$ is a divalent linker including one or more amino acids. In embodiments, $L^{A2}$ is a divalent linker consisting of amino acids. In embodiments, $L^{A2}$ is a divalent linker including an amino acid analog. In embodiments, $L^{A2}$ is a divalent linker including an amino acid mimetic. In embodiments, $L^{A2}$ is a divalent linker consisting of amino acid analogs. In embodiments, $L^{A2}$ is a divalent linker consisting of amino acid mimetics.

In embodiments, $L^{A3}$ is a bond, —NH—, —$NR^{A29}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A3}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A3}$ is substituted with a plurality of groups selected from substituent groups, size-limited substituent groups, and lower substituent groups; each substituent group, size-limited substituent group, and/or lower substituent group may optionally be different. In embodiments, when $L^{A3}$ is substituted, it is substituted with at least one substituent group. In embodiments, when $L^{A3}$ is substituted, it is substituted with at least one size-limited substituent group. In embodiments, when $L^{A3}$ is substituted, it is substituted with at least one lower substituent group.

In embodiments, $L^{A3}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A3}$ is a substituted or unsubstituted 5 to 10 membered heteroarylene. In embodiments, $L^{A3}$ is a bond. In embodiments, $L^{A3}$ is a substituted or unsubstituted 5 to 6 membered heteroarylene. In embodiments, $L^{A3}$ is unsubstituted 5 to 6 membered heteroarylene. In embodiments, $L^{A3}$ is unsubstituted divalent triazole. In embodiments, $L^{A3}$ is unsubstituted divalent 1H-1,2,3-triazole. In embodiments, $L^{A3}$ is unsubstituted divalent 2H-1,2,3-triazole. In embodiments, $L^{A3}$ is a divalent linker including one or more amino acids. In embodiments, $L^{A3}$ is a divalent linker consisting of amino acids. In embodiments, $L^{A3}$ is a divalent linker including an amino acid analog. In embodiments, $L^{A3}$ is a divalent linker including an amino acid mimetic. In embodiments, $L^{A3}$ is a divalent linker consisting of amino acid analogs. In embodiments, $L^{A3}$ is a divalent linker consisting of amino acid mimetics.

In embodiments, $L^{A4}$ is a bond, —NH—, —$NR^{A32}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A4}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A4}$ is substituted with a plurality of groups selected from substituent groups, size-limited substituent groups, and lower substituent groups; each substituent group, size-limited substituent group, and/or lower substituent group may optionally be different. In embodiments, when $L^{A4}$ is substituted, it is substituted with at least one substituent group. In embodiments, when $L^{A4}$ is substituted, it is substituted with at least one size-limited substituent group. In embodiments, when $L^{A4}$ is substituted, it is substituted with at least one lower substituent group.

In embodiments, $L^{A4}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A4}$ is a substituted or unsubstituted 2 to 12 membered heteroalkylene. In embodiments, $L^{A4}$ is a substituted or unsubstituted 2 to 32 membered heteroalkylene. In embodiments, $L^{A4}$ is a bond. In embodiments, $L^{A4}$ is a divalent linker including one or more amino acids. In embodiments, $L^{A4}$ is a divalent linker consisting of amino acids. In embodiments, $L^{A4}$ is a divalent linker including an amino acid analog. In embodiments, $L^{A4}$ is a divalent linker including an amino acid mimetic. In embodiments, $L^{A4}$ is a divalent linker consisting of amino acid analogs. In embodiments, $L^{A4}$ is a divalent linker consisting of amino acid mimetics.

In embodiments, $L^{A5}$ is a bond, —NH—, —$NR^{A35}$—, —S—, —O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^{A5}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{A5}$ is substituted with a plurality of groups selected from substituent groups, size-limited substituent groups, and lower substituent groups; each substituent group, size-limited substituent group, and/or lower substituent group may optionally be different. In embodiments, when $L^{A5}$ is substituted, it is substituted with at least one substituent group. In embodiments, when $L^{A5}$ is substituted, it is substituted with at least one size-limited substituent group. In embodiments, when $L^{A5}$ is substituted, it is substituted with at least one lower substituent group.

In embodiments, $L^{A5}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{A5}$ is a substituted or unsubstituted 2 to 12 membered heteroalkylene. In embodiments, $L^{A5}$ is a substituted or unsubstituted 2 to 32 membered heteroalkylene. In embodiments, $L^{A5}$ is a bond. In embodiments, $L^{A5}$ is a divalent linker including one or more amino acids. In embodiments, $L^{A5}$ is a divalent linker consisting of amino acids. In embodiments, $L^{A5}$ is a divalent linker including an amino acid analog. In embodiments, $L^{A5}$ is a divalent linker including an amino acid mimetic. In embodiments, $L^{A5}$ is a divalent linker consisting of amino acid analogs. In embodiments, $L^{A5}$ is a divalent linker consisting of amino acid mimetics.

In embodiments, $L^{A5}$ is a divalent oligomer of ethylene oxide. In embodiments, $L^{A5}$ is a divalent polyethylene glycol. In embodiments, $L^{A5}$ is a divalent oligomer of ethylene oxide having 2 to 30 linear atoms (carbon and oxygen) between the two termini connecting to the remainder of the compound. In embodiments, $L^{A5}$ is a —$(CH_2)_4C(O)NH$—. In embodiments, $L^{A5}$ is a 2 to 8 membered substituted heteroalkylene. In embodiments, $L^{A5}$ is a 3 to 6 membered substituted heteroalkylene. In embodiments, $L^{A5}$ is a 5 to 6 membered substituted heteroalkylene. In embodiments, $L^{A5}$ is a 5 to 7 membered oxo substituted heteroalkylene. In embodiments, $L^{A5}$ is an unsubstituted $C_1$-$C_6$ alkylene.

In embodiments, $L^{A4}$ is a divalent oligomer of ethylene oxide. In embodiments, $L^{A4}$ is a divalent polyethylene glycol. In embodiments, $L^{A4}$ is a divalent oligomer of ethylene oxide having 2 to 30 linear atoms (carbon and oxygen)

between the two termini connecting to the remainder of the compound. In embodiments, $L^{A4}$ is $—(CH_2CH_2O)_{eA}CH_2CH_2—$ and eA is an integer from 1 to 16. In embodiments, $L^{A4}$ is $—(CH_2CH_2O)_{eA}CH_2—$ and eA is an integer from 1 to 16. In embodiments, $L^{A4}$ is $—(CH_2CH_2O)_{eA}—$ and eA is an integer from 1 to 16. In embodiments, eA is an integer from 2 to 15. In embodiments, eA is an integer from 3 to 14. In embodiments, eA is an integer from 4 to 12. In embodiments, eA is an integer from 5 to 10. In embodiments, eA is an integer from 5 to 8. In embodiments, eA is an integer from 6 to 7.

In embodiments, the linker is formed by a conjugation or bioconjugation reaction combining a first reactant moiety covalently bonded to the rapamycin or rapamycin analog and a second reactant moiety covalently bonded to the active site mTOR inhibitor. In such embodiments, the anti-CNS disease drug formed by such conjugation or bioconjugation reaction (including compounds as described herein) may be referred to as a conjugate.

In some embodiments, $L^{A1}$ is $L^{A2}$-$L^{A3}$-$L^{A4}$-$L^{A5}$; $L^{A3}$ is $—CH_2CH_2OCH_2—$; $L^{A3}$ is 5 to 10 membered heteroarylene; $L^{A4}$ is $—(CH_2CH_2O)_{eA}—$; eA is an integer from 2 to 8; $L^{A5}$ is $—CH_2CH_2C(O)NH(CH_2)_{eA10}—$; and eA10 is an integer from 1 to 6. In some embodiments, $L^{A1}$ is $L^{A2}$-$L^{A3}$-$L^{A4}$-$L^{A5}$; $L^{A2}$ is 2 to 8 membered heteroalkylene comprising at least one NH or O; $L^{A3}$ is 5 to 10 membered heteroarylene; $L^{A4}$ is $—[(CH_2)_{eA11}O]_{eA12}—$; eA11 is an integer from 1 to 3; eA12 is an integer from 1 to 8; $L^{A5}$ is $—CH_2CH_2C(O)NH(CH_2)_{eA10}$; and eA10 is an 2 integer from 1 to 6. In some embodiments, $L^{A1}$ is $L^{A2}$-$L^{A3}$-$L^{A4}$-$L^{A5}$; $L^{A2}$ is $—CH_2CH_2OCH_2—$; 3 $L^{A3}$ is 5 membered heteroarylene; $L^{A4}$ is $—(CH_2CH_2O)_{eA}—$; eA is an integer from 4 to 8; and 4 $L^{A5}$ is $—CH_2CH_2C(O)NH(CH_2)_4$. In some embodiments, $L^{A1}$ is $L^{A2}$-$L^{A3}$-$L^{A4}$-$L^{A5}$; $L^{A2}$ is $—CH_2CH_2OCH_2—$; $L^{A3}$ is triazolylene; $L^{A4}$ is $—(CH_2CH_2O)_{eA}—$; eA is an integer from 4 to 8; and $L^{A5}$ is $—CH_2CH_2C(O)NH(CH_2)_4$. In some embodiments, $L^{A1}$ is $L^{A2}$-$L^{A3}$-$L^{A4}$-$L^{A5}$; $L^{A2}$ is $—CH_2CH_2OCH_2—$; $L^{A3}$ is 5 to 10 membered heteroarylene; $L^{A4}$ is $—(CH_2)_{eA}—$; eA is an integer from 2 to 8; and $L^{A5}$ is a bond.

$R^{A23}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A24}$-substituted or unsubstituted alkyl, $R^{A24}$-substituted or unsubstituted heteroalkyl, $R^{A24}$-substituted or unsubstituted cycloalkyl, $R^{A24}$-substituted or unsubstituted heterocycloalkyl, $R^{A24}$-substituted or unsubstituted aryl, or $R^{A24}$-substituted or unsubstituted heteroaryl.

In embodiments, $R^{A23}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A24}$-substituted or unsubstituted alkyl (e.g., $C_1$-$C_8$, $C_1$-$C_6$, $C_1$-$C_4$, or $C_1$-$C_2$), $R^{A24}$-substituted or unsubstituted heteroalkyl (e.g., 2 to 8 membered, 2 to 6 membered, 4 to 6 membered, 2 to 3 membered, or 4 to 5 membered), $R^{A24}$-substituted or unsubstituted cycloalkyl (e.g., $C_3$-$C_8$, $C_3$-$C_6$, $C_4$-$C_6$, or $C_5$-$C_6$), $R^{A24}$-substituted or unsubstituted heterocycloalkyl (e.g., 3 to 8 membered, 3 to 6 membered, 4 to 6 membered, 4 to 5 membered, or 5 to 6 membered), $R^{A24}$-substituted or unsubstituted aryl (e.g., $C_6$-$C_{10}$ or phenyl), or $R^{A24}$-substituted or unsubstituted heteroaryl (e.g., 5 to 10 membered, 5 to 9 membered, or 5 to 6 membered).

$R^{A24}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A25}$-substituted or unsubstituted alkyl, $R^{A25}$-substituted or unsubstituted heteroalkyl, $R^{A25}$-substituted or unsubstituted cycloalkyl, $R^{A25}$-substituted or unsubstituted heterocycloalkyl, $R^{A25}$-substituted or unsubstituted aryl, or $R^{A25}$-substituted or unsubstituted heteroaryl.

In embodiments, $R^{A24}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A25}$-substituted or unsubstituted alkyl (e.g., $C_1$-$C_8$, $C_1$-$C_6$, $C_1$-$C_4$, or $C_1$-$C_2$), $R^{A25}$-substituted or unsubstituted heteroalkyl (e.g., 2 to 8 membered, 2 to 6 membered, 4 to 6 membered, 2 to 3 membered, or 4 to 5 membered), $R^{A25}$-substituted or unsubstituted cycloalkyl (e.g., $C_3$-$C_8$, $C_3$-$C_6$, $C_4$-$C_6$, or $C_5$-$C_6$), $R^{A25}$-substituted or unsubstituted heterocycloalkyl (e.g., 3 to 8 membered, 3 to 6 membered, 4 to 6 membered, 4 to 5 membered, or 5 to 6 membered), $R^{A25}$-substituted or unsubstituted aryl (e.g., $C_6$-$C_{10}$ or phenyl), or $R^{A25}$-substituted or unsubstituted heteroaryl (e.g., 5 to 10 membered, 5 to 9 membered, or 5 to 6 membered).

$R^{A25}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A25}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the anti-CNS disease drugs provided herein, $L^{A2}$ is independently a bond, $R^{A26}$-substituted or unsubstituted alkylene, $R^{A26}$-substituted or unsubstituted heteroalkylene, $R^{A26}$-substituted or unsubstituted cycloalkylene, $R^{A26}$-substituted or unsubstituted heterocycloalkylene, $R^{A26}$-substituted or unsubstituted arylene, or $R^{A26}$-substituted or unsubstituted heteroarylene.

$R^{A26}$ is independently oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCF_3$, $—OCHF_2$, $R^{A27}$-substituted or unsubstituted alkyl, $R^{A27}$-substituted or unsubstituted heteroalkyl, $R^{A27}$-substituted or unsubstituted cycloalkyl, $R^{A27}$-substituted or unsubstituted heterocycloalkyl, $R^{A27}$-substituted or unsubstituted aryl, or $R^{A27}$-substituted or unsubstituted heteroaryl.

In embodiments, $R^{A26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A27}$-substituted or unsubstituted alkyl (e.g., $C_1$-$C_8$, $C_1$-$C_6$, $C_1$-$C_4$, or $C_1$-$C_2$), $R^{A2}$-substituted or unsubstituted heteroalkyl (e.g., 2 to 8 membered, 2 to 6 membered, 4 to 6 membered, 2 to 3 membered, or 4 to 5 membered), $R^{A27}$-substituted or unsubstituted cycloalkyl (e.g., $C_3$-$C_8$, $C_3$-$C_6$, $C_4$-$C_6$, or $C_5$-$C_6$), $R^{A27}$-substituted or unsubstituted heterocycloalkyl (e.g., 3 to 8 membered, 3 to 6 membered, 4 to 6 membered, 4 to 5 membered, or 5 to 6 membered), $R^{A27}$-substituted or unsubstituted aryl (e.g., $C_6$-$C_{10}$ or phenyl), or $R^{A27}$-substituted or unsubstituted heteroaryl (e.g., 5 to 10 membered, 5 to 9 membered, or 5 to 6 membered)

$R^{A27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A28}$-substituted or unsubstituted alkyl, $R^{A28}$-substituted or unsubstituted heteroalkyl, $R^{A28}$-substituted or unsubstituted cycloalkyl, $R^{A28}$-substituted or unsubstituted heterocycloalkyl, $R^{A28}$-substituted or unsubstituted aryl, or $R^{A28}$-substituted or unsubstituted heteroaryl.

In embodiments, $R^{A27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A28}$-substituted or unsubstituted alkyl (e.g., $C_1$-$C_8$, $C_1$-$C_6$, $C_1$-$C_4$, or $C_1$-$C_2$), $R^{A28}$-substituted or unsubstituted heteroalkyl (e.g., 2 to 8 membered, 2 to 6 membered, 4 to 6 membered, 2 to 3 membered, or 4 to 5 membered), $R^{A28}$-substituted or unsubstituted cycloalkyl (e.g., $C_3$-$C_8$, $C_3$-$C_6$, $C_4$-$C_6$, or $C_5$-$C_6$), $R^{A28}$-substituted or unsubstituted heterocycloalkyl (e.g., 3 to 8 membered, 3 to 6 membered, 4 to 6 membered, 4 to 5 membered, or 5 to 6 membered), $R^{A28}$-substituted or unsubstituted aryl (e.g., $C_6$-$C_{10}$ or phenyl), or $R^{A28}$-substituted or unsubstituted heteroaryl (e.g., 5 to 10 membered, 5 to 9 membered, or 5 to 6 membered)

$R^{A28}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A28}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the compounds provided herein, $L^{A3}$ is independently a bond, $R^{A29}$-substituted or unsubstituted alkylene, $R^{A29}$-substituted or unsubstituted heteroalkylene, $R^{A29}$-substituted or unsubstituted cycloalkylene, $R^{A29}$-substituted or unsubstituted heterocycloalkylene, $R^{A29}$-substituted or unsubstituted arylene, or $R^{A29}$-substituted or unsubstituted heteroarylene.

$R^{A29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A30}$-substituted or unsubstituted alkyl, $R^{A30}$-substituted or unsubstituted heteroalkyl, $R^{A30}$-substituted or unsubstituted cycloalkyl, $R^{A30}$-substituted or unsubstituted heterocycloalkyl, $R^{A30}$-substituted or unsubstituted aryl, or $R^{A30}$-substituted or unsubstituted heteroaryl.

In embodiments, $R^{A29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A30}$-substituted or unsubstituted alkyl (e.g., $C_1$-$C_8$, $C_1$-$C_6$, $C_1$-$C_4$, or $C_1$-$C_2$), $R^{A30}$-substituted or unsubstituted heteroalkyl (e.g., 2 to 8 membered, 2 to 6 membered, 4 to 6 membered, 2 to 3 membered, or 4 to 5 membered), $R^{A30}$-substituted or unsubstituted cycloalkyl (e.g., $C_3$-$C_8$, $C_3$-$C_6$, $C_4$-$C_6$, or $C_5$-$C_6$), $R^{A30}$-substituted or unsubstituted heterocycloalkyl (e.g., 3 to 8 membered, 3 to 6 membered, 4 to 6 membered, 4 to 5 membered, or 5 to 6 membered), $R^{A30}$-substituted or unsubstituted aryl (e.g., $C_6$-$C_{10}$ or phenyl), or $R^{A30}$-substituted or unsubstituted heteroaryl (e.g., 5 to 10 membered, 5 to 9 membered, or 5 to 6 membered).

$R^{A3o}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$OCF_3$, —$OCHF_2$, $R^{A31}$-substituted or unsubstituted alkyl, $R^{A31}$-substituted or unsubstituted heteroalkyl, $R^{A31}$-substituted or unsubstituted cycloalkyl, $R^{A31}$-substituted or unsubstituted heterocycloalkyl, $R^{A31}$-substituted or unsubstituted aryl, or $R^{A31}$-substituted or unsubstituted heteroaryl.

In embodiments, $R^{A3o}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A31}$-substituted or unsubstituted alkyl (e.g., $C_1$-$C_8$, $C_1$-$C_6$, $C_1$-$C_4$, or $C_1$-$C_2$), $R^{A31}$-substituted or unsubstituted heteroalkyl (e.g., 2 to 8 membered, 2 to 6 membered, 4 to 6 membered, 2 to 3 membered, or 4 to 5 membered), $R^{A31}$-substituted or unsubstituted cycloalkyl (e.g., $C_3$-$C_8$, $C_3$-$C_6$, $C_4$-$C_6$, or $C_5$-$C_6$), $R^{A31}$-substituted or unsubstituted heterocycloalkyl (e.g., 3 to 8 membered, 3 to 6 membered, 4 to 6 membered, 4 to 5 membered, or 5 to 6 membered), $R^{A31}$-substituted or unsubstituted aryl (e.g., $C_6$-$C_{10}$ or phenyl), or $R^{A31}$-substituted or unsubstituted heteroaryl (e.g., 5 to 10 membered, 5 to 9 membered, or 5 to 6 membered).

$R^{A31}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A31}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the compounds provided herein, $L^{A4}$ is independently a bond, $R^{A32}$-substituted or unsubstituted alkylene, $R^{A32}$-substituted or unsubstituted heteroalkylene, $R^{A32}$-substituted or unsubstituted cycloalkylene, $R^{A32}$-substituted or unsubstituted heterocycloalkylene, $R^{A32}$-substituted or unsubstituted arylene, or $R^{A32}$-substituted or unsubstituted heteroarylene.

$R^{A32}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A33}$-substituted or unsubstituted alkyl, $R^{A33}$-substituted or unsubstituted heteroalkyl, $R^{A33}$-substituted or unsubstituted cycloalkyl, $R^{A33}$-substituted or unsubstituted heterocycloalkyl, $R^{A33}$-substituted or unsubstituted aryl, or $R^{A33}$-substituted or unsubstituted heteroaryl.

In embodiments, $R^{A32}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A33}$-substituted or unsubstituted alkyl (e.g., $C_1$-$C_8$, $C_1$-$C_6$, $C_1$-$C_4$, or $C_1$-$C_2$), $R^{A58}$-substituted or unsubstituted heteroalkyl (e.g., 2 to 8 membered, 2 to 6 membered, 4 to 6 membered, 2 to 3 membered, or 4 to 5 membered), $R^{A33}$-substituted or unsubstituted cycloalkyl (e.g., $C_3$-$C_8$, $C_3$-$C_6$, $C_4$-$C_6$, or $C_5$-$C_6$), $R^{A33}$-substituted or unsubstituted heterocycloalkyl (e.g., 3 to 8 membered, 3 to 6 membered, 4 to 6 membered, 4 to 5 membered, or 5 to 6 membered), $R^{A33}$-substituted or unsubstituted aryl (e.g., $C_6$-$C_{10}$ or phenyl), or $R^{A33}$-substituted or unsubstituted heteroaryl (e.g., 5 to 10 membered, 5 to 9 membered, or 5 to 6 membered).

$R^{A33}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A34}$-substituted or unsubstituted alkyl, $R^{A34}$-substituted or unsubstituted heteroalkyl, $R^{A34}$-substituted or unsubstituted cycloalkyl, $R^{A34}$-substituted or unsubstituted heterocycloalkyl, $R^{A34}$-substituted or unsubstituted aryl, or $R^{A34}$-substituted or unsubstituted heteroaryl.

In embodiments, $R^{A33}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A34}$-substituted or unsubstituted alkyl (e.g., $C_1$-$C_8$, $C_1$-$C_6$, $C_1$-$C_4$, or $C_1$-$C_2$), $R^{A34}$-substituted or unsubstituted heteroalkyl (e.g., 2 to 8 membered, 2 to 6 membered, 4 to 6 membered, 2 to 3 membered, or 4 to 5 membered), $R^{A34}$-substituted or unsubstituted cycloalkyl (e.g., $C_3$-$C_8$, $C_3$-$C_6$, $C_4$-$C_6$, or $C_5$-$C_6$), $R^{A34}$-substituted or unsubstituted heterocycloalkyl (e.g., 3 to 8 membered, 3 to 6 membered, 4 to 6 membered, 4 to 5 membered, or 5 to 6 membered), $R^{A34}$-substituted or unsubstituted aryl (e.g., $C_6$-$C_{10}$ or phenyl), or $R^{A34}$-substituted or unsubstituted heteroaryl (e.g., 5 to 10 membered, 5 to 9 membered, or 5 to 6 membered).

$R^{A34}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A34}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In some embodiments of the compounds provided herein, $L^{A5}$ is independently a bond, $R^{A35}$-substituted or unsubstituted alkylene, $R^{A35}$-substituted or unsubstituted heteroalkylene, $R^{A35}$-substituted or unsubstituted cycloalkylene, $R^{A35}$-substituted or unsubstituted heterocycloalkylene, $R^{A35}$-substituted or unsubstituted arylene, or $R^{A35}$-substituted or unsubstituted heteroarylene.

$R^{A35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A36}$-substituted or unsubstituted alkyl, $R^{A36}$-substituted or unsubstituted heteroalkyl, $R^{A36}$-substituted or unsubstituted cycloalkyl, $R^{A36}$-substituted or unsubstituted heterocycloalkyl, $R^{A36}$-substituted or unsubstituted aryl, or $R^{A36}$-substituted or unsubstituted heteroaryl.

In embodiments, $R^{A35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A36}$-substituted or unsubstituted alkyl (e.g., $C_1$-$C_8$, $C_1$-$C_6$, $C_1$-$C_4$, or $C_1$-$C_2$), $R^{A36}$-substituted or unsubstituted heteroalkyl (e.g., 2 to 8 membered, 2 to 6 membered, 4 to 6 membered, 2 to 3 membered, or 4 to 5 membered), $R^{A36}$-substituted or unsubstituted cycloalkyl (e.g., $C_3$-$C_8$, $C_3$-$C_6$, $C_4$-$C_6$, or $C_5$-$C_6$), $R^{A36}$-substituted or unsubstituted heterocycloalkyl (e.g., 3 to 8 membered, 3 to 6 membered, 4 to 6 membered, 4 to 5 membered, or 5 to 6 membered), $R^{A36}$-substituted or unsubstituted aryl (e.g., $C_6$-$C_{10}$ or phenyl), or $R^{A36}$-substituted or unsubstituted heteroaryl (e.g., 5 to 10 membered, 5 to 9 membered, or 5 to 6 membered).

$R^{A36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A37}$-substituted or unsubstituted alkyl, $R^{A37}$-substituted or unsubstituted heteroalkyl, $R^{A37}$-substituted or unsubstituted cycloalkyl, $R^{A37}$-substituted or unsubstituted heterocycloalkyl, $R^{A37}$-substituted or unsubstituted aryl, or $R^{A37}$-substituted or unsubstituted heteroaryl.

In embodiments, $R^{A36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{A37}$-substituted or unsubstituted alkyl (e.g., $C_1$-$C_8$, $C_1$-$C_6$, $C_1$-$C_4$, or $C_1$-$C_2$), $R^{A37}$-substituted or unsubstituted heteroalkyl (e.g., 2 to 8 membered, 2 to 6 membered, 4 to 6 membered, 2 to 3 membered, or 4 to 5 membered), $R^{A37}$-substituted or unsubstituted cycloalkyl (e.g., $C_3$-$C_8$, $C_3$-$C_6$, $C_4$-$C_6$, or $C_5$-$C_6$), $R^{A37}$-substituted or unsubstituted heterocycloalkyl (e.g., 3 to 8 membered, 3 to 6 membered, 4 to 6 membered, 4 to 5 membered, or 5 to 6 membered), $R^{A37}$-substituted or unsubstituted aryl (e.g., $C_6$-$C_{10}$ or phenyl), or $R^{A37}$-substituted or unsubstituted heteroaryl (e.g., 5 to 10 membered, 5 to 9 membered, or 5 to 6 membered).

$R^{A37}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A37}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, the anti-CNS disease drug competes with rapamycin for binding to mTORC1. In embodiments, the anti-CNS disease drug binds an overlapping region of mTORC1 with the binding region of rapamycin. In embodiments, the anti-CNS disease drug competes with ATP for binding to mTOR. In embodiments, the anti-CNS disease drug competes with ATP for binding to mTORC1. In embodiments, the anti-CNS disease drug competes with rapamycin and ATP for binding to mTORC1.

In embodiments, the anti-CNS disease drug is an mTORC1 specific inhibitor. In embodiments, the anti-CNS disease drug has a slow off-rate from mTORC1. In embodiments, the anti-CNS disease drug has an off-rate of slower than 0.1 per minute. In embodiments, the anti-CNS disease drug has an off-rate of slower than 0.01 per minute. In embodiments, the anti-CNS disease drug has an off-rate of slower than 0.001 per minute. In embodiments, the anti-CNS disease drug has an off-rate of slower than 0.0001 per minute. In embodiments, the anti-CNS disease drug-mTORC1 complex has a half-life of at least 10 minutes. In embodiments, the anti-CNS disease drug-mTORC1 complex has a half-life of at least 100 minutes. In embodiments, the anti-CNS disease drug-mTORC1 complex has a half-life of at least 300 minutes. In embodiments, the anti-CNS disease drug-mTORC1 complex has a half-life of at least 1000 minutes. In embodiments, the anti-CNS disease drug-mTORC1 complex has a half-life of at least 3000 minutes. In embodiments, the anti-CNS disease drug-mTORC1 complex has a half-life of at least 10000 minutes.

In embodiments, the anti-CNS disease drug is

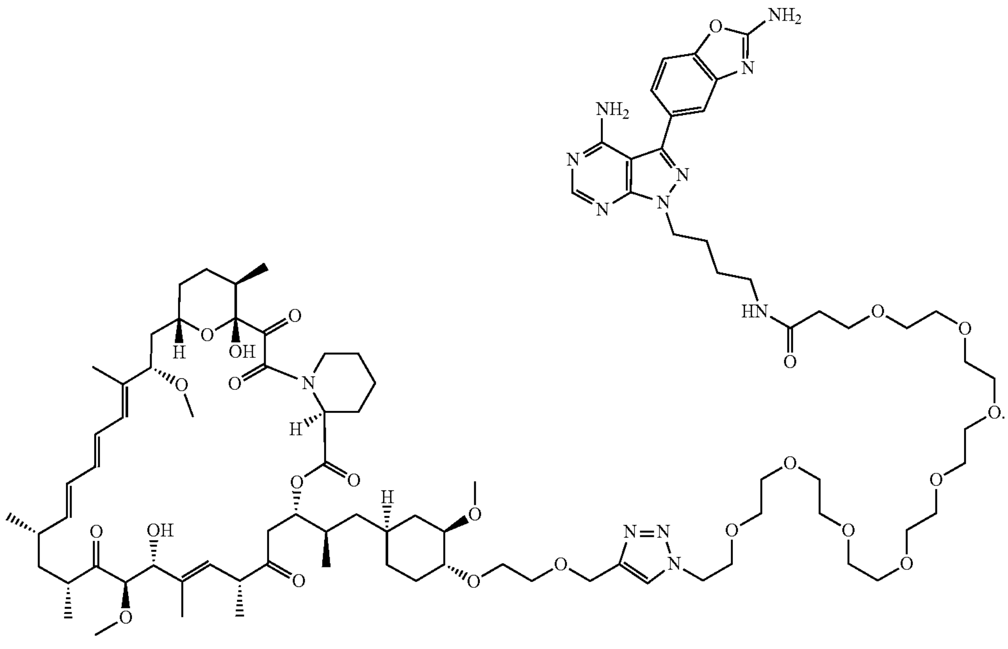 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

In embodiments, the anti-CNS disease drug is
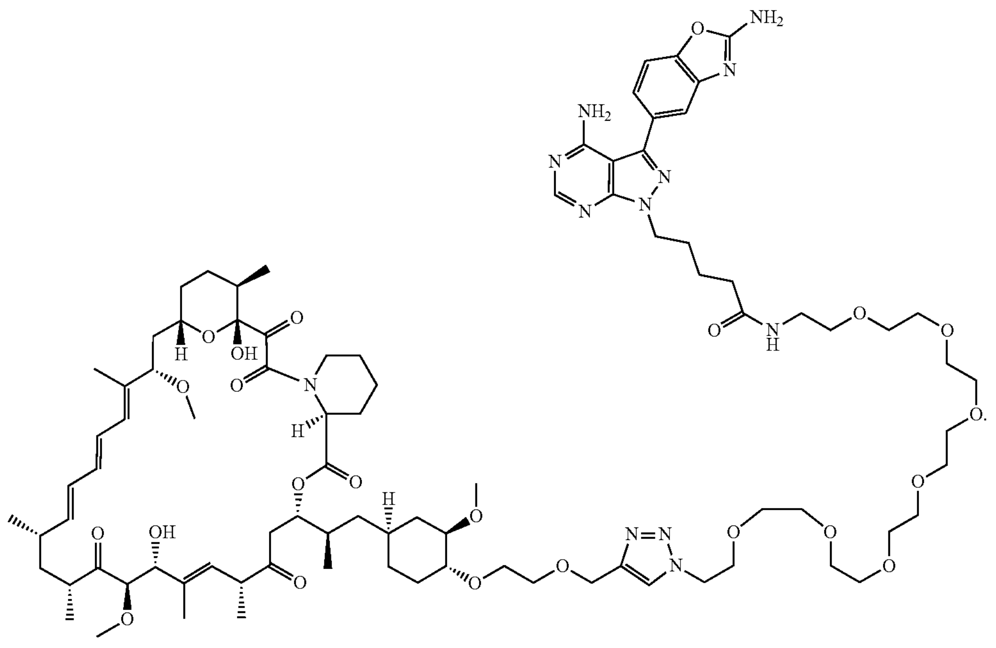 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCOCCOCCOCCNC(=O)CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]
In embodiments, the anti-CNS disease drug is
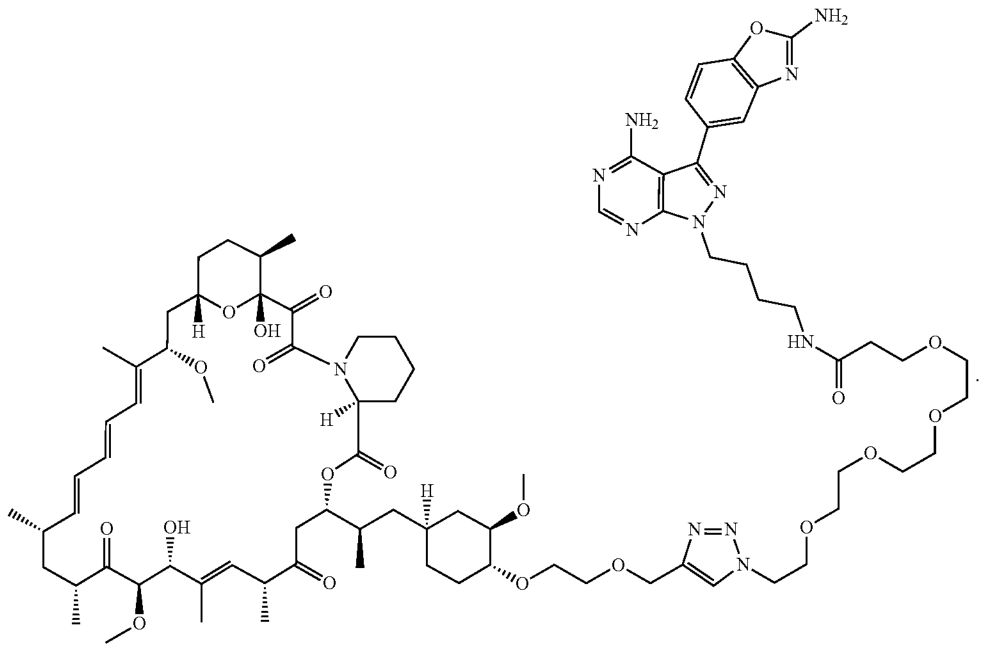 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCOCCOCCOCCOCCC(=O)NCCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

In embodiments, the anti-CNS disease drug is

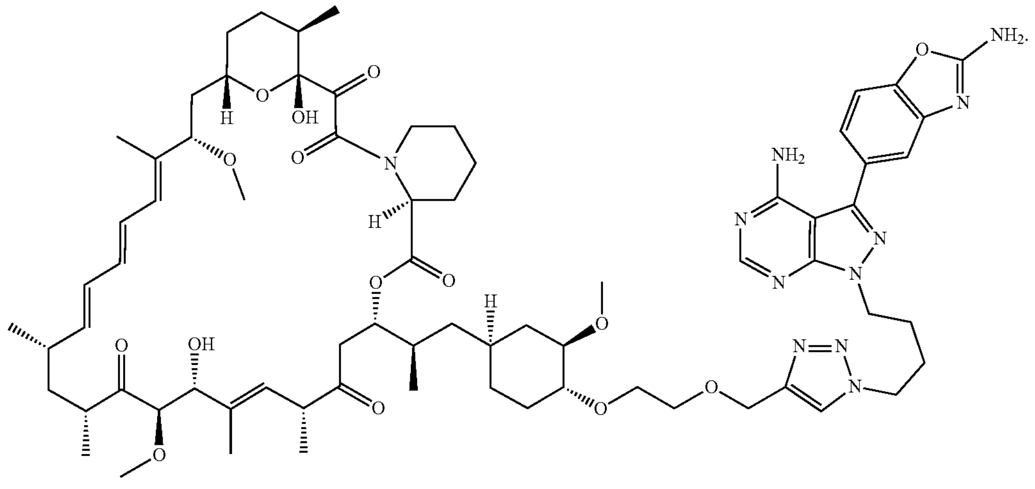 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOCc3cn(CCCCn4nc(-c5ccc6oc(N)nc6c5)c5c(N)ncnc54)nn3)[C@H](OC)C2)CC(=O)[C@H](C)/C=C(\C)[C@@H](O)[C@@H](OC)C(=O)[C@H](C)C[C@H](C)/C=C/C=C/C=C/1C]

In embodiments, the anti-CNS disease drug is M-1071. In embodiments, the anti-CNS disease drug is M-1111. In embodiments, the anti-CNS disease drug is M-3059. In embodiments, the anti-CNS disease drug is M-1115. In embodiments, the anti-CNS disease drug is not M-1115. In embodiments, the anti-CNS disease drug is E1010. In embodiments, the anti-CNS disease drug is E1035.

In embodiments, the active site mTOR inhibitor is a monovalent MLN0128.

In embodiments, the active site mTOR inhibitor is

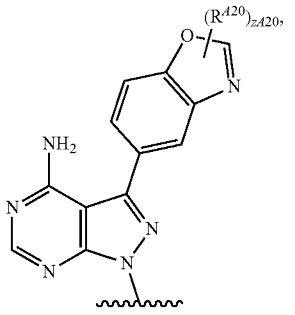

wherein $R^{A20}$ is as described herein, including in embodiments. In embodiments, zA20 is an integer from 0 to 4. In embodiments, zA20 is 0. In embodiments, zA20 is 1. In embodiments, zA20 is 2. In embodiments, zA20 is 3. In embodiments, zA20 is 4. In embodiments, the active site mTOR inhibitor is

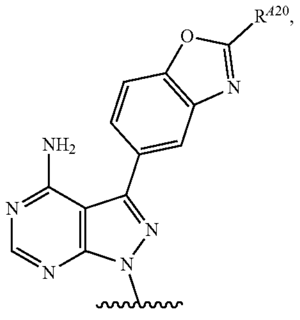

is.

wherein $R^{A20}$ is as described herein, including in embodiments. In embodiments, the active site mTOR inhibitor

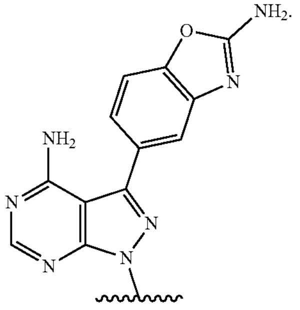 [SMILES: *n1nc(-c2ccc3oc(N)nc3c2)c2c(N)ncnc21]

In embodiments, the active site mTOR inhibitor is

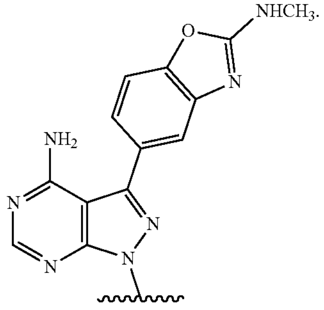 [SMILES: *n1nc(-c2ccc3oc(NC)nc3c2)c2c(N)ncnc21]

In embodiments, the active site mTOR inhibitor is

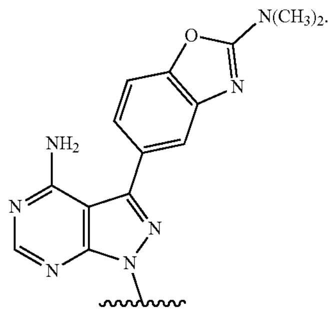 [SMILES: *n1nc(-c2ccc3oc(N(C)C)nc3c2)c2c(N)ncnc21]

In embodiments, the active site mTOR inhibitor is

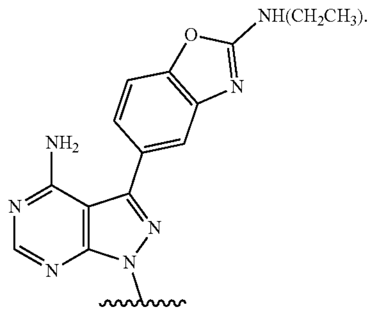

In embodiments, the active site mTOR inhibitor is

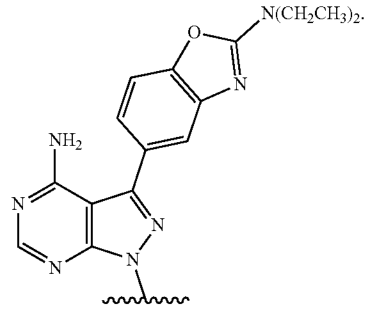

In embodiments, the active site mTOR inhibitor is

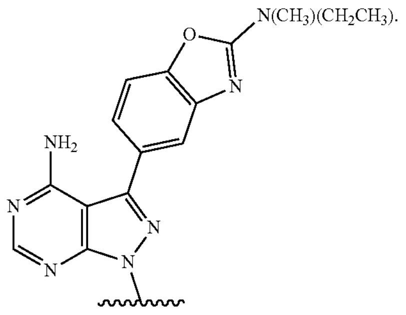

In embodiments, the active site mTOR inhibitor is

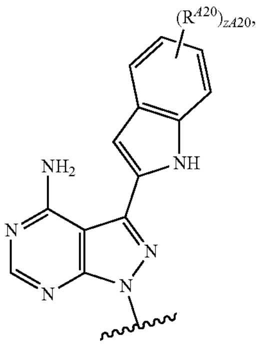

wherein $R^{A20}$ is as described herein, including in embodiments. zA20 is an integer from 0 to 5. In embodiments, zA20 is 0. In embodiments, zA20 is 1. In embodiments, zA20 is 2. In embodiments, zA20 is 3. In embodiments, zA20 is 4. In embodiments, zA20 is 5. In embodiments, the active site mTOR inhibitor is

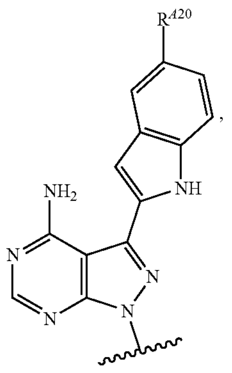

wherein $R^{A20}$ is as described herein. In embodiments, the active site mTOR inhibitor is

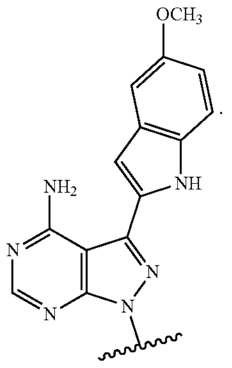 [SMILES: *n1nc(-c2cc3cc(OC)ccc3[nH]2)c2c(N)ncnc21]

In embodiments, the active site mTOR inhibitor is

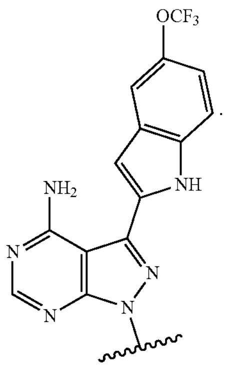 [SMILES: *n1nc(-c2cc3cc(OC(F)(F)F)ccc3[nH]2)c2c(N)ncnc21]

In embodiments, the active site mTOR inhibitor is

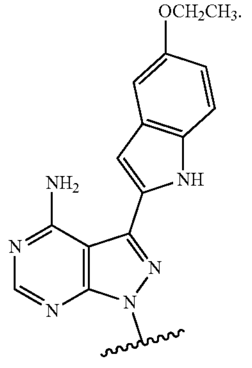 [SMILES: *n1nc(-c2cc3cc(OCC)ccc3[nH]2)c2c(N)ncnc21]

In embodiments, the active site mTOR inhibitor is

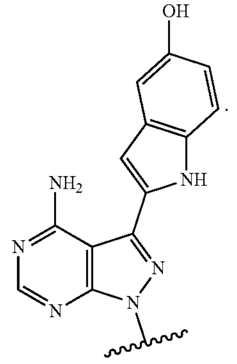 [SMILES: *n1nc(-c2cc3cc(O)ccc3[nH]2)c2c(N)ncnc21]

In embodiments, the active site mTOR inhibitor (e.g., asTORi) has a weaker binding affinity for mTOR than MLN0128. In embodiments, the active site mTOR inhibitor has a binding affinity that results in preferential binding to mTORC1 over mTORC2 that is greater than the same compound wherein the active site mTOR inhibitor is MLN0128. In embodiments, the active site mTOR inhibitor has a binding affinity that results in preferential binding to mTORC1 over mTORC2 that is greater than the same compound wherein the active site mTOR inhibitor is PP242. In embodiments, the active site mTOR inhibitor has a binding affinity that results in preferential binding to mTORC1 over mTORC2 that is greater than the same compound wherein the active site mTOR inhibitor is PP242 wherein the —OH substituent on the indoyly moiety is replaced with an unsubstituted methoxy moiety. Without being limited by mechanism, the compound may include an active site mTOR inhibitor that results in a preferential binding of the compound to mTORC1 over mTORC2 of at least 1.1-fold (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold). Without being limited by mechanism, the compound may include an active site mTOR inhibitor that results in a preferential inhibition of mTORC1 over mTORC2 by the compound of at least 1.1-fold (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 701, 30000, 40000, 50000, 60000, 70000, 80000, 90000, 100000, 100000, 200000, 300000, 702, 400000, 500000, 600000, 700000, 800000, 900000, or 1000000 fold).

In embodiments, the anti-CNS disease drug is included in a drug-eluting stent.

In embodiments, the anti-CNS disease drug has the formula: A-$L^1$-$R^1$; A is an immunophilin-binding moiety; $L^1$ is a bond or a covalent linker; and $R^1$ is a monovalent kinase inhibitor, a monovalent pseudokinase inhibitor, a monovalent GTPase inhibitor, a monovalent histone-modifying enzyme inhibitor, or monovalent anti-viral agent.

In embodiments, the anti-CNS disease drug is

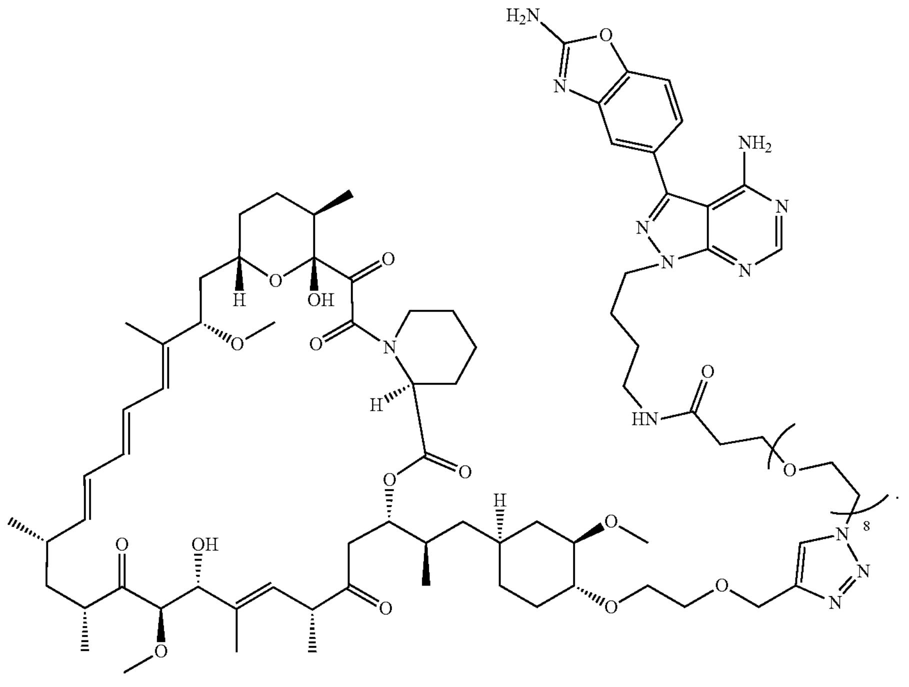

In embodiments, the anti-CNS disease drug is not
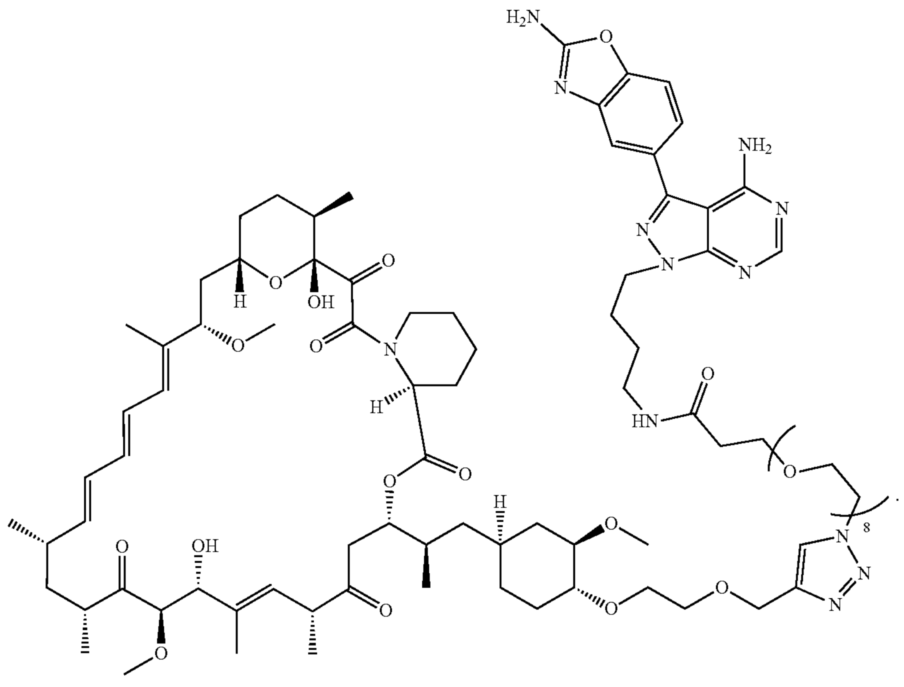
In embodiments, the immunophilin-binding moiety is a cyclophilin-binding moiety or an FKBP-binding moiety. In embodiments, the immunophilin-binding moiety is
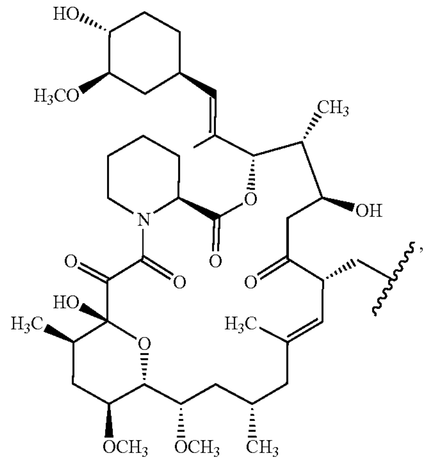 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
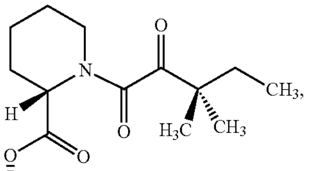
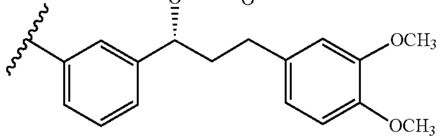
-continued
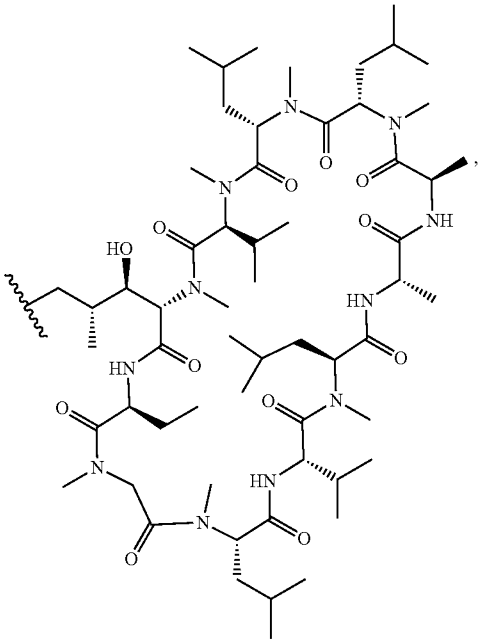

-continued
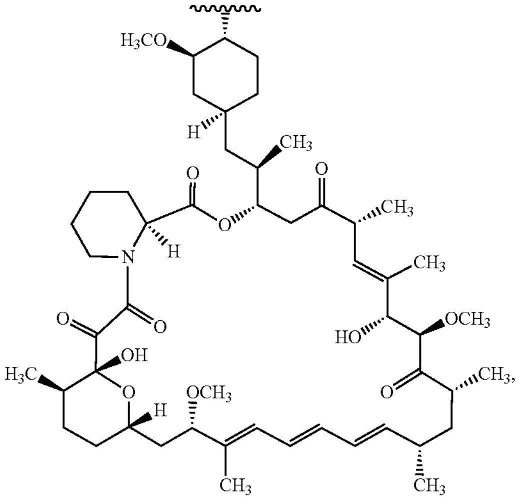
or
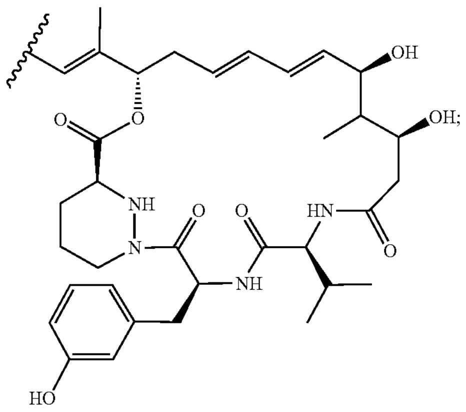
or an analog thereof.
In embodiments, the immunophilin-binding moiety is
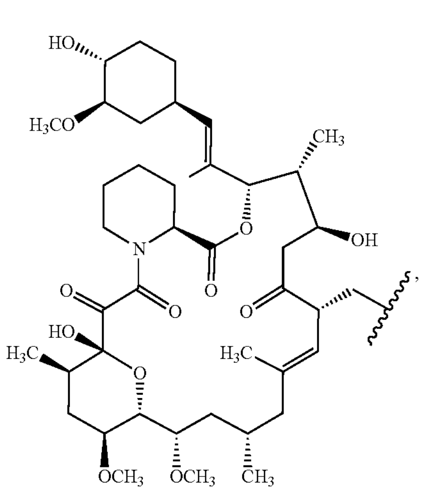
or an analog thereof.
In embodiments, the immunophilin-binding moiety is
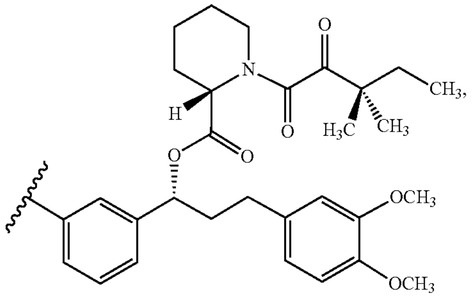
or an analog thereof.
In embodiments, the immunophilin-binding moiety is
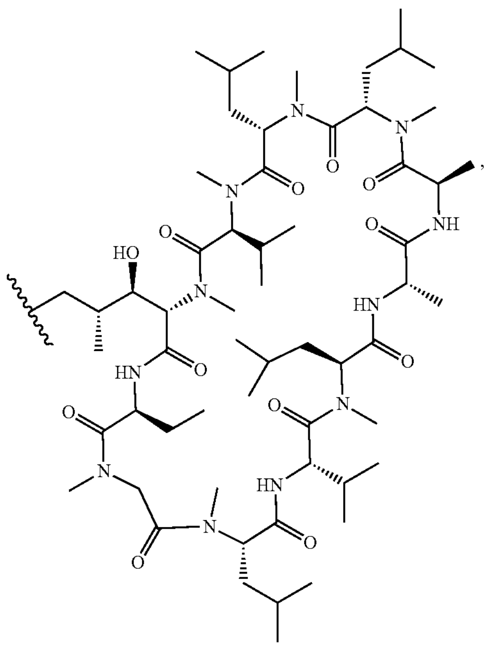 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
or an analog thereof.

In embodiments, the immunophilin-binding moiety is
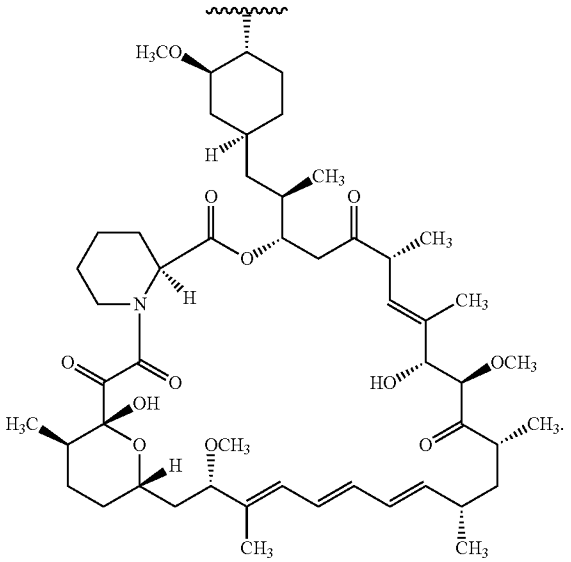 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]
or an analog thereof.
In embodiments, the immunophilin-binding moiety is
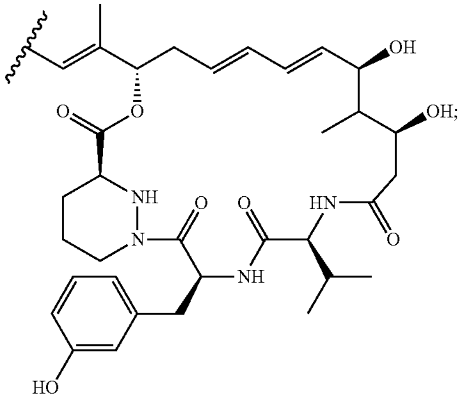 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
or an analog thereof.
In embodiments, the immunophilin-binding moiety is
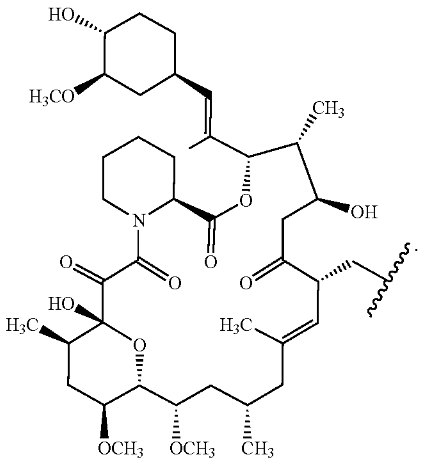 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
In embodiments, the immunophilin-binding moiety is
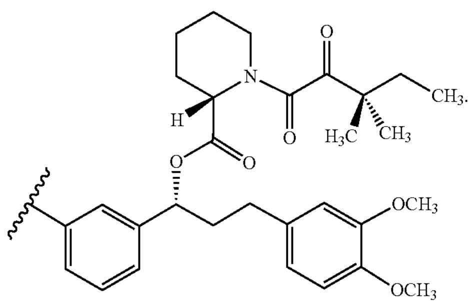
In embodiments, the immunophilin-binding moiety is
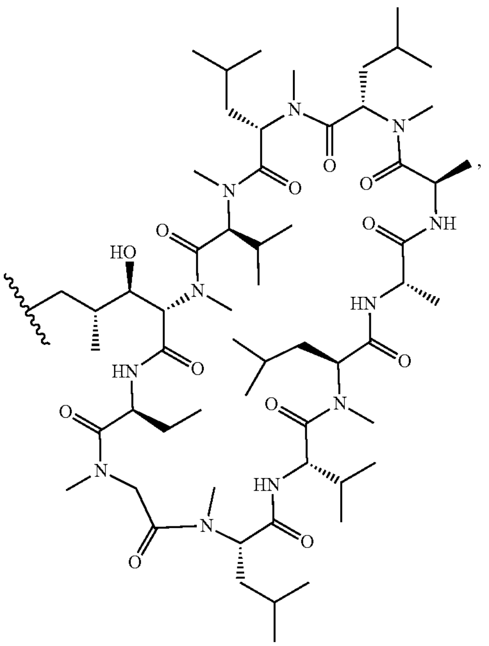 [SMILES: *C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
In embodiments, the immunophilin-binding moiety is
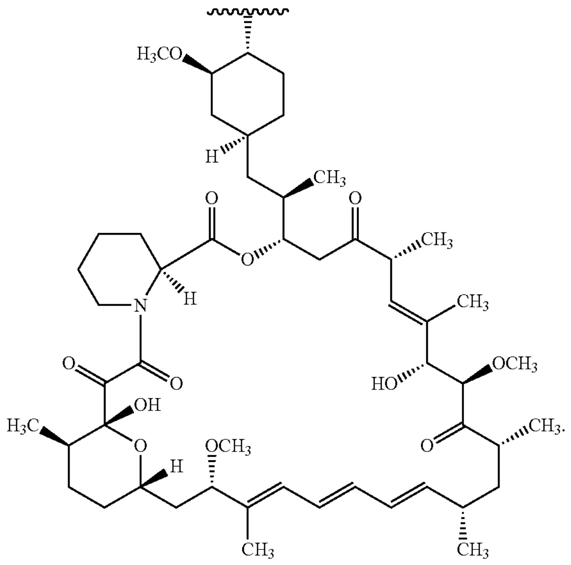 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

In embodiments, the immunophilin-binding moiety is
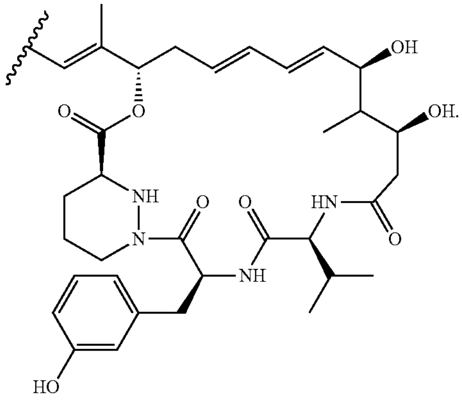 [SMILES: */C=C(\C)[C@@H]1C/C=C/C=C/[C@@H](O)C(C)[C@@H](O)CC(=O)N[C@@H](C(C)C)C(=O)N[C@@H](Cc2cccc(O)c2)C(=O)N2CCC[C@H](N2)C(=O)O1]
In embodiments, the immunophilin-binding moiety is
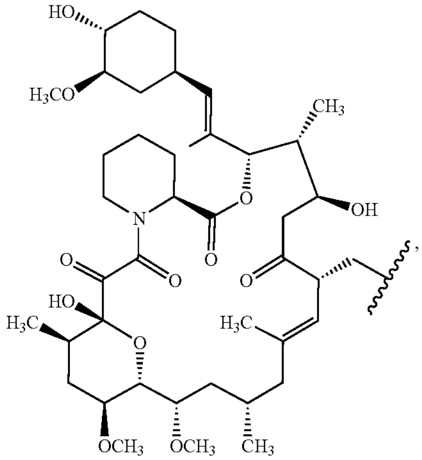
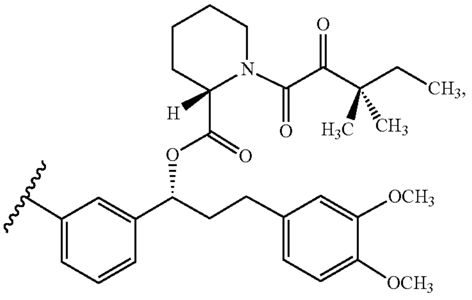
-continued
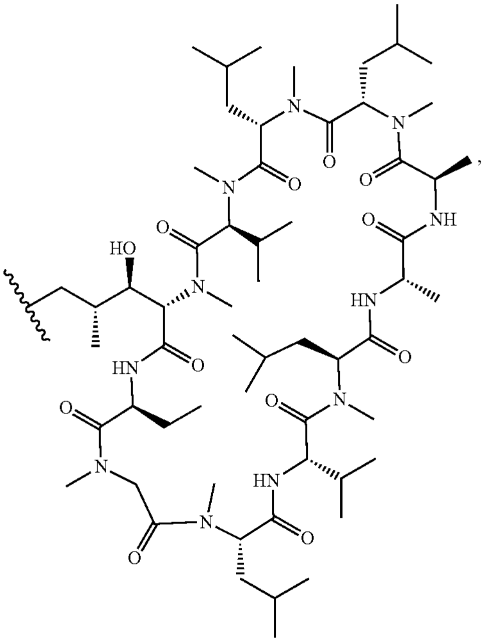
or
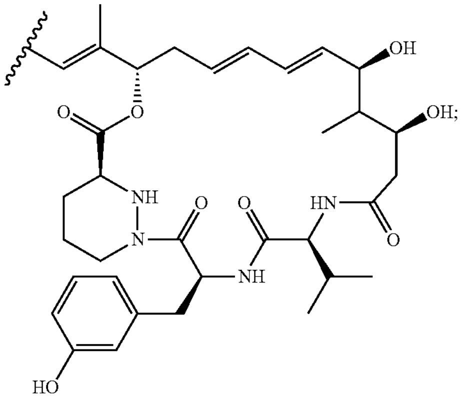
or an analog thereof.
In embodiments, the immunophilin-binding moiety is
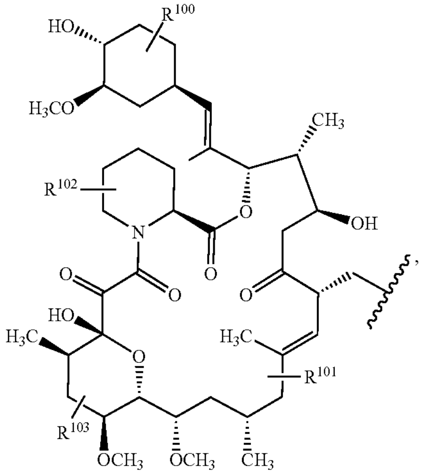

-continued
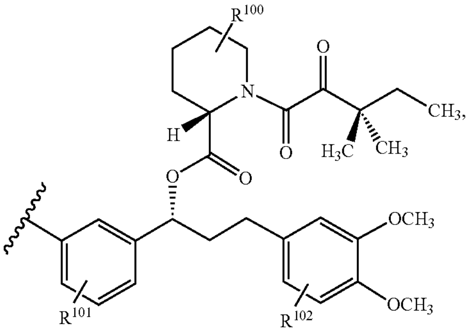
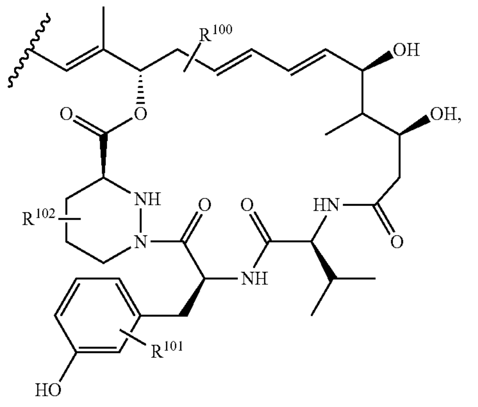
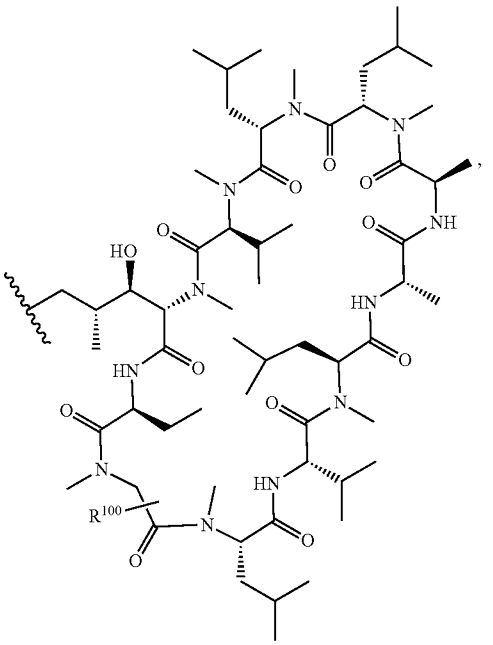
or
-continued
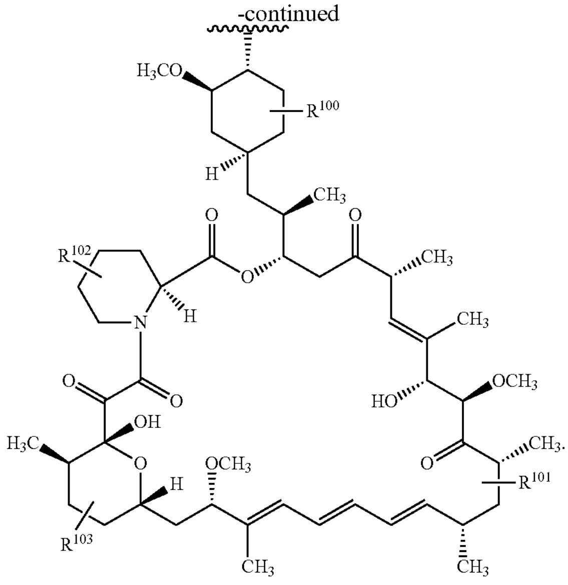
wherein $R^{100}$, $R^{101}$, $R^{102}$, and $R^{103}$ are as described herein and may be bonded to any atom in the ring ($R^{100}$, $R^{101}$, $R^{102}$, and $R^{103}$ are floating substituents). In embodiments, the immunophilin-binding moiety is
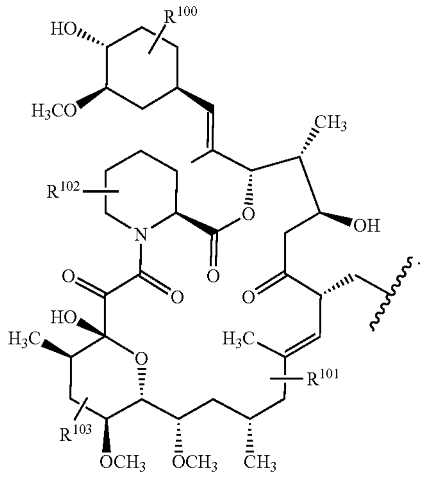
$R^{100}$, $R^{101}$, $R^{102}$, and $R^{103}$ are as described herein. In embodiments, the immunophilin-binding moiety is
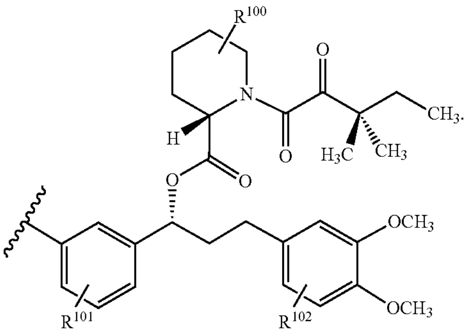

$R^{100}$, $R^{101}$, and $R^{102}$ are as described herein. In embodiments, the immunophilin-binding moiety is

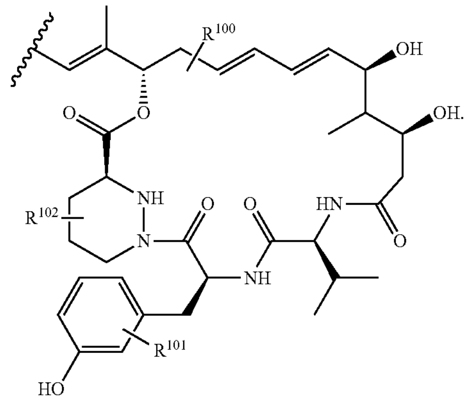

$R^{100}$, $R^{101}$, and $R^{102}$ are as described herein. In embodiments, the immunophilin-binding moiety is

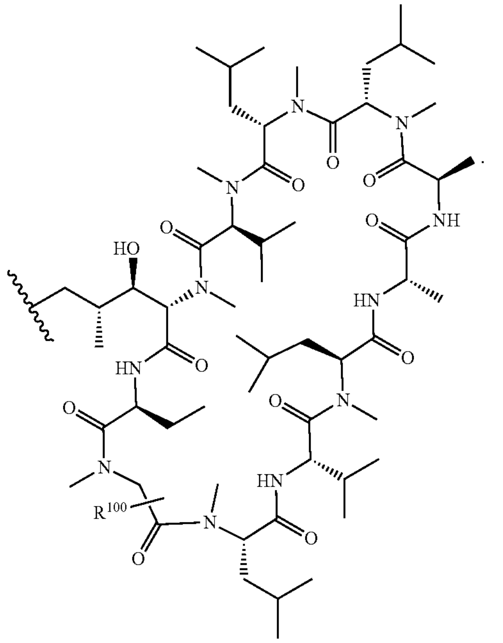

$R^{100}$ is as described herein. In embodiments, the immunophilin-binding moiety is

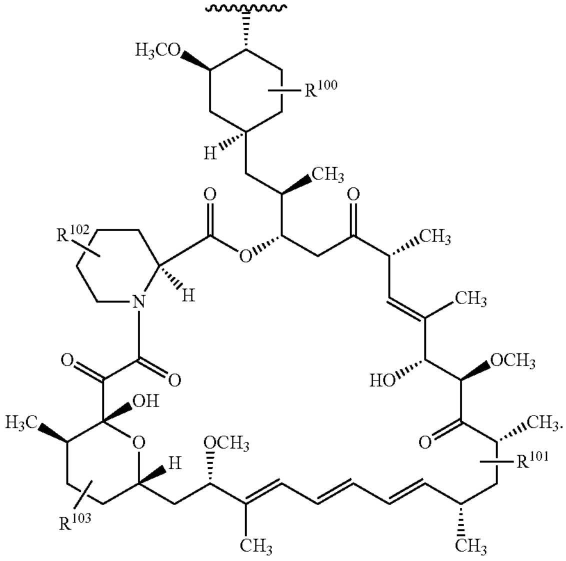

$R^{100}$, $R^{101}$, $R^{102}$, and $R^{103}$ are as described herein.

$R^{100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{100}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{100}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{100}$ is substituted with a plurality of groups selected from substituent groups, size-limited substituent groups, and lower substituent groups; each substituent group, size-limited substituent group, and/or lower substituent group may optionally be different. In embodiments, when $R^{100}$ is substituted, it is substituted with at least one substituent group. In embodiments, when $R^{100}$ is substituted, it is substituted with at least one size-limited substituent group. In embodiments, when $R^{100}$ is substituted, it is substituted with at least one lower substituent group.

In embodiments, $R^{100}$ is independently hydrogen. In embodiments, $R^{100}$ is independently halogen. In embodiments, $R^{100}$ is independently —$CCl_3$. In embodiments, $R^{100}$ is independently —$CBr_3$. In embodiments, $R^{100}$ is independently —$CF_3$. In embodiments, $R^{100}$ is independently —$CI_3$. In embodiments, $R^{100}$ is independently —$CH_2Cl$. In embodiments, $R^{100}$ is independently —$CH_2Br$. In embodiments, $R^{100}$ is independently —$CH_2F$. In embodiments, $R^{100}$ is independently —$CH_2I$. In embodiments, $R^{100}$ is independently —$CHCl_2$. In embodiments, $R^{100}$ is independently —$CHBr_2$. In embodiments, $R^{100}$ is independently —$CHF_2$. In embodiments, $R^{100}$ is independently —$CHI_2$. In embodiments, $R^{100}$ is independently —CN. In embodiments, $R^{100}$ is independently —OH. In embodiments, $R^{100}$ is independently —$NH_2$. In embodiments, $R^{100}$ is independently —COOH. In embodiments, $R^{100}$ is independently —$CONH_2$. In embodiments, $R^{100}$ is independently —$NO_2$. In embodiments, $R^{100}$ is independently —SH. In embodiments, $R^{100}$ is independently —$SO_3H$. In embodiments, $R^{100}$ is independently —$SO_4H$. In embodiments, $R^{100}$ is independently —$SO_2NH_2$. In embodiments, $R^{100}$ is independently —$NHNH_2$. In embodiments, $R^{100}$ is independently —$ONH_2$. In embodiments, $R^{100}$ is independently —$NHC(O)NHNH_2$. In embodiments, $R^{100}$ is independently —$NHC(O)NH_2$. In embodiments, $R^{100}$ is independently —$NHSO_2H$ In embodiments, $R^{100}$ is independently —NHC(O)H. In embodiments, $R^{100}$ is independently —NHC(O)OH. In embodiments, $R^{100}$ is independently —NHC(NH)H. In embodiments, $R^{100}$ is independently —$NHC(NH)NH_2$. In embodiments, $R^{100}$ is independently —NHOH. In embodiments, $R^{100}$ is independently —$OCCl_3$. In embodiments, $R^{100}$ is independently —$OCBr_3$. In embodiments, $R^{100}$ is independently —$OCF_3$. In embodiments, $R^{100}$ is independently —$OCI_3$. In embodiments, $R^{100}$ is independently —$OCH_2Cl$. In embodiments, $R^{100}$ is independently —$OCH_2Br$. In embodiments, $R^{100}$ is independently —$OCH_2F$. In embodiments, $R^{100}$ is independently —$OCH_2I$. In embodiments, $R^{100}$ is independently —$OCHCl_2$. In embodiments, $R^{100}$ is independently —$OCHBr_2$. In embodiments, $R^{100}$ is independently —$OCHF_2$. In embodiments, $R^{100}$ is independently —$OCHI_2$. In embodiments, $R^{100}$ is independently —$N_3$. In embodiments, $R^{100}$ is independently substituted or unsubstituted alkyl (e.g., $C_1$-$C_8$, $C_1$-$C_6$, $C_1$-$C_4$, or $C_1$-$C_2$). In embodiments, $R^{100}$ is independently substituted alkyl (e.g., $C_1$-$C_8$, $C_1$-$C_6$, $C_1$-$C_4$, or $C_1$-$C_2$). In embodiments, $R^{100}$ is independently unsubstituted alkyl (e.g., $C_1$-$C_8$, $C_1$-$C_6$, $C_1$-$C_4$, or $C_1$-$C_2$). In embodiments, $R^{100}$ is independently substituted or unsubstituted heteroalkyl (e.g., 2 to 8 membered, 2 to 6 membered, 4 to 6 membered, 2 to 3 membered, or 4 to 5 membered). In embodiments, $R^{100}$ is independently substituted heteroalkyl (e.g., 2 to 8 membered, 2 to 6 membered, 4 to 6 membered, 2 to 3 membered, or 4 to 5 membered). In embodiments, $R^{100}$ is independently unsubstituted heteroalkyl (e.g., 2 to 8 membered, 2 to 6 membered, 4 to 6 membered, 2 to 3 membered, or 4 to 5 membered). In embodiments, $R^{100}$ is independently substituted or unsubstituted cycloalkyl (e.g., $C_3$-$C_8$, $C_3$-$C_6$, $C_4$-$C_6$, or $C_5$-$C_6$). In embodiments, $R^{100}$ is independently substituted cycloalkyl (e.g., $C_3$-$C_8$, $C_3$-$C_6$, $C_4$-$C_6$, or $C_5$-$C_6$). In embodiments, $R^{100}$ is independently unsubstituted cycloalkyl (e.g., $C_3$-$C_8$, $C_3$-$C_6$, $C_4$-$C_6$, or $C_5$-$C_6$). In embodiments, $R^{100}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{100}$ is independently substituted heterocycloalkyl (e.g., 3 to 8 membered, 3 to 6 membered, 4 to 6 membered, 4 to 5 membered, or 5 to 6 membered). In embodiments, $R^{100}$ is independently unsubstituted heterocycloalkyl (e.g., 3 to 8 membered, 3 to 6 membered, 4 to 6 membered, 4 to 5 membered, or 5 to 6 membered). In embodiments, $R^{100}$ is independently substituted or unsubstituted aryl (e.g., $C_6$-$C_{10}$ or phenyl). In embodiments, $R^{100}$ is independently substituted aryl (e.g., $C_6$-$C_{10}$ or phenyl). In embodiments, $R^{100}$ is independently unsubstituted aryl (e.g., $C_6$-$C_{10}$ or phenyl). In embodiments, $R^{100}$ is independently substituted or unsubstituted heteroaryl (e.g., 5 to 10 membered, 5 to 9 membered, or 5 to 6 membered). In embodiments, $R^{100}$ is independently substituted heteroaryl (e.g., 5 to 10 membered, 5 to 9 membered, or 5 to 6 membered). In embodiments, $R^{100}$ is independently unsubstituted heteroaryl (e.g., 5 to 10 membered, 5 to 9 membered, or 5 to 6 membered).

$R^{101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{101}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{101}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{101}$ is substituted with a plurality of groups selected from substituent groups, size-limited substituent groups, and lower substituent groups; each substituent group, size-limited substituent group, and/or lower substituent group may optionally be different. In embodiments, when $R^{101}$ is substituted, it is substituted with at least one substituent group. In embodiments, when $R^{101}$ is substituted, it is substituted with at least one size-limited substituent group. In embodiments, when $R^{101}$ is substituted, it is substituted with at least one lower substituent group.

In embodiments, $R^{101}$ is independently hydrogen. In embodiments, $R^{101}$ is independently halogen. In embodiments, $R^{101}$ is independently —$CCl_3$. In embodiments, $R^{101}$ is independently —$CBr_3$. In embodiments, $R^{101}$ is independently —$CF_3$. In embodiments, $R^{101}$ is independently —$CI_3$. In embodiments, $R^{101}$ is independently —$CH_2Cl$. In embodiments, $R^{101}$ is independently —$CH_2Br$. In embodiments, $R^{101}$ is independently —$CH_2F$. In embodiments, $R^{101}$ is independently —$CH_2I$. In embodiments, $R^{101}$ is independently —$CHCl_2$. In embodiments, $R^{101}$ is independently —$CHBr_2$. In embodiments, $R^{101}$ is independently —$CHF_2$. In embodiments, $R^{101}$ is independently —$CHI_2$. In embodiments, $R^{101}$ is independently —CN. In embodiments, $R^{101}$ is independently —OH. In embodiments, $R^{101}$ is independently —$NH_2$. In embodiments, $R^{101}$ is independently —COOH. In embodiments, $R^{101}$ is independently —$CONH_2$. In embodiments, $R^{101}$ is independently —$NO_2$. In embodiments, $R^{101}$ is independently —SH. In embodiments, $R^{101}$ is independently —$SO_3H$. In embodiments, $R^{101}$ is independently —$SO_4H$. In embodiments, $R^{101}$ is independently —$SO_2NH_2$. In embodiments, $R^{101}$ is independently —$NHNH_2$. In embodiments, $R^{101}$ is independently —$ONH_2$. In embodiments, $R^{101}$ is independently —NHC(O)$NHNH_2$. In embodiments, $R^{101}$ is independently —NHC(O)$NH_2$. In embodiments, $R^{101}$ is independently —$NHSO_2H$ In embodiments, $R^{101}$ is independently —NHC(O)H. In embodiments, $R^{101}$ is independently —NHC(O)OH. In embodiments, $R^{101}$ is independently —NHC(NH)H. In embodiments, $R^{101}$ is independently —NHC(NH)$NH_2$. In embodiments, $R^{101}$ is independently —NHOH. In embodiments, $R^{101}$ is independently —$OCCl_3$. In embodiments, $R^{101}$ is independently —$OCBr_3$. In embodiments, $R^{101}$ is independently —$OCF_3$. In embodiments, $R^{101}$ is independently —$OCI_3$. In embodiments, $R^{101}$ is independently —$OCH_2Cl$. In embodiments, $R^{101}$ is independently —$OCH_2Br$. In embodiments, $R^{101}$ is independently —$OCH_2F$. In embodiments, $R^{101}$ is independently —$OCH_2I$. In embodiments, $R^{101}$ is independently —$OCHCl_2$. In embodiments, $R^{101}$ is independently —$OCHBr_2$. In embodiments, $R^{101}$ is independently —$OCHF_2$. In embodiments, $R^{101}$ is independently —$OCHI_2$. In embodiments, $R^{101}$ is independently —$N_3$. In embodiments, $R^{101}$ is independently substituted or unsubstituted alkyl (e.g., $C_1$-$C_8$, $C_1$-$C_6$, $C_1$-$C_4$, or $C_1$-$C_2$). In embodiments, $R^{101}$ is independently substituted alkyl (e.g., $C_1$-$C_8$, $C_1$-$C_6$, $C_1$-$C_4$, or $C_1$-$C_2$). In embodiments, $R^{101}$ is independently unsubstituted alkyl (e.g., $C_1$-$C_8$, $C_1$-$C_6$, $C_1$-$C_4$, or $C_1$-$C_2$). In embodiments, $R^{101}$ is independently substituted or unsubstituted heteroalkyl (e.g., 2 to 8 membered, 2 to 6 membered, 4 to 6 membered, 2 to 3 membered, or 4 to 5 membered). In embodiments, $R^{101}$ is independently substituted heteroalkyl (e.g., 2 to 8 membered, 2 to 6 membered, 4 to 6 membered, 2 to 3 membered, or 4 to 5 membered). In embodiments, $R^{101}$ is independently unsubstituted heteroalkyl (e.g., 2 to 8 membered, 2 to 6 membered, 4 to 6 membered, 2 to 3 membered, or 4 to 5 membered). In embodiments, $R^{101}$ is independently substituted or unsubstituted cycloalkyl (e.g., $C_3$-$C_8$, $C_3$-$C_6$, $C_4$-$C_6$, or $C_5$-$C_6$). In embodiments, $R^{101}$ is independently substituted cycloalkyl (e.g., $C_3$-$C_8$, $C_3$-$C_6$, $C_4$-$C_6$, or $C_5$-$C_6$). In embodiments, $R^{101}$ is independently unsubstituted cycloalkyl (e.g., $C_3$-$C_8$, $C_3$-$C_6$, $C_4$-$C_6$, or $C_5$-$C_6$). In embodiments, $R^{101}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{101}$ is independently substituted heterocycloalkyl (e.g., 3 to 8 membered, 3 to 6 membered, 4 to 6 membered, 4 to 5 membered, or 5 to 6 membered). In embodiments, $R^{101}$ is independently unsubstituted heterocycloalkyl (e.g., 3 to 8 membered, 3 to 6 membered, 4 to 6 membered, 4 to 5 membered, or 5 to 6 membered). In embodiments, $R^{101}$ is independently substituted or unsubstituted aryl (e.g., $C_6$-$C_{10}$ or phenyl). In embodiments, $R^{101}$ is independently substituted aryl (e.g., $C_6$-$C_{10}$ or phenyl). In embodiments, $R^{101}$ is independently unsubstituted aryl (e.g., $C_6$-$C_{10}$ or phenyl). In embodiments, $R^{101}$ is independently substituted or unsubstituted heteroaryl (e.g., 5 to 10 membered, 5 to 9 membered, or 5 to 6 membered). In embodiments, $R^{101}$ is independently substituted heteroaryl (e.g., 5 to 10 membered, 5 to 9 membered, or 5 to 6 membered). In embodiments, $R^{101}$ is independently unsubstituted heteroaryl (e.g., 5 to 10 membered, 5 to 9 membered, or 5 to 6 membered).

$R^{102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{102}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102}$ is substituted with a plurality of groups selected from substituent groups, size-limited substituent groups, and lower substituent groups; each substituent group, size-limited substituent group, and/or lower substituent group may optionally be different. In embodiments, when $R^{102}$ is substituted, it is substituted with at least one substituent group. In embodiments, when $R^{102}$ is substituted, it is substituted with at least one size-limited substituent group. In embodiments, when $R^{102}$ is substituted, it is substituted with at least one lower substituent group.

In embodiments, $R^{102}$ is independently hydrogen. In embodiments, $R^{102}$ is independently halogen. In embodiments, $R^{102}$ is independently-$CCl_3$. In embodiments, $R^{102}$ is independently —$CBr_3$. In embodiments, $R^{102}$ is independently —$CF_3$. In embodiments, $R^{102}$ is independently —$CI_3$. In embodiments, $R^{102}$ is independently —$CH_2Cl$. In embodiments, $R^{102}$ is independently —$CH_2Br$. In embodiments, $R^{102}$ is independently —$CH_2F$. In embodiments, $R^{102}$ is independently —$CH_2I$. In embodiments, $R^{102}$ is independently —$CHCl_2$. In embodiments, $R^{102}$ is independently —$CHBr_2$. In embodiments, $R^{102}$ is independently —$CHF_2$. In embodiments, $R^{102}$ is independently —$CHI_2$. In embodiments, $R^{102}$ is independently —CN. In embodiments, $R^{102}$ is independently —OH. In embodiments, $R^{102}$ is independently —$NH_2$. In embodiments, $R^{102}$ is independently —COOH. In embodiments, $R^{102}$ is independently —$CONH_2$. In embodiments, $R^{102}$ is independently —$NO_2$. In embodiments, $R^{102}$ is independently —SH. In embodiments, $R^{102}$ is independently —$SO_3H$. In embodiments, $R^{102}$ is independently —$SO_4H$. In embodiments, $R^{102}$ is independently —$SO_2NH_2$. In embodiments, $R^{102}$ is independently —$NHNH_2$. In embodiments, $R^{102}$ is independently —$ONH_2$. In embodiments, $R^{102}$ is independently —NHC(O)$NHNH_2$. In embodiments, $R^{102}$ is independently —NHC(O)$NH_2$. In embodiments, $R^{102}$ is independently —$NHSO_2H$ In embodiments, $R^{102}$ is independently —NHC(O)H. In embodiments, $R^{102}$ is independently —NHC(O)OH. In embodiments, $R^{102}$ is independently —NHC(NH)H. In embodiments, $R^{102}$ is independently —NHC(NH)$NH_2$. In embodiments, $R^{102}$ is independently —NHOH. In embodiments, $R^{102}$ is independently —$OCCl_3$. In embodiments, $R^{102}$ is independently —$OCBr_3$. In embodiments, $R^{102}$ is independently —$OCF_3$. In embodiments, $R^{102}$ is independently —$OCI_3$. In embodiments, $R^{102}$ is independently —$OCH_2Cl$. In embodiments, $R^{102}$ is independently —$OCH_2Br$. In embodiments, $R^{102}$ is independently —$OCH_2F$. In embodiments, $R^{102}$ is independently —$OCH_2I$. In embodiments, $R^{102}$ is independently —$OCHCl_2$. In embodiments, $R^{102}$ is independently—$OCHBr_2$. In embodiments, $R^{102}$ is independently—$OCHF_2$. In embodiments, $R^{102}$ is independently —$OCHI_2$. In embodiments, $R^{102}$ is independently —$N_3$. In embodiments, $R^{102}$ is independently substituted or unsubstituted alkyl (e.g., $C_1$-$C_8$, $C_1$-$C_6$, $C_1$-$C_4$, or $C_1$-$C_2$). In embodiments, $R^{102}$ is independently substituted alkyl (e.g., $C_1$-$C_8$, $C_1$-$C_6$, $C_1$-$C_4$, or $C_1$-$C_2$). In embodiments, $R^{102}$ is independently unsubstituted alkyl (e.g., $C_1$-$C_8$, $C_1$-$C_6$, $C_1$-$C_4$, or $C_1$-$C_2$). In embodiments, $R^{102}$ is independently substituted or unsubstituted heteroalkyl (e.g., 2 to 8 membered, 2 to 6 membered, 4 to 6 membered, 2 to 3 membered, or 4 to 5 membered). In embodiments, $R^{102}$ is independently substituted heteroalkyl (e.g., 2 to 8 membered, 2 to 6 membered, 4 to 6 membered, 2 to 3 membered, or 4 to 5 membered). In embodiments, $R^{102}$ is independently unsubstituted heteroalkyl (e.g., 2 to 8 membered, 2 to 6 membered, 4 to 6 membered, 2 to 3 membered, or 4 to 5 membered). In embodiments, $R^{102}$ is independently substituted or unsubstituted cycloalkyl (e.g., $C_3$-$C_8$, $C_3$-$C_6$, $C_4$-$C_6$, or $C_5$-$C_6$). In embodiments, $R^{102}$ is independently substituted cycloalkyl (e.g., $C_3$-$C_8$, $C_3$-$C_6$, $C_4$-$C_6$, or $C_5$-$C_6$). In embodiments, $R^{102}$ is independently unsubstituted cycloalkyl (e.g., $C_3$-$C_8$, $C_3$-$C_6$, $C_4$-$C_6$, or $C_5$-$C_6$). In embodiments, $R^{102}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{102}$ is independently substituted heterocycloalkyl (e.g., 3 to 8 membered, 3 to 6 membered, 4 to 6 membered, 4 to 5 membered, or 5 to 6 membered). In embodiments, $R^{102}$ is independently unsubstituted heterocycloalkyl (e.g., 3 to 8 membered, 3 to 6 membered, 4 to 6 membered, 4 to 5 membered, or 5 to 6 membered). In embodiments, $R^{102}$ is independently substituted or unsubstituted aryl (e.g., $C_6$-$C_{10}$ or phenyl). In embodiments, $R^{102}$ is independently substituted aryl (e.g., $C_6$-$C_{10}$ or phenyl). In embodiments, $R^{102}$ is independently unsubstituted aryl (e.g., $C_6$-$C_{10}$ or phenyl). In embodiments, $R^{102}$ is independently substituted or unsubstituted heteroaryl (e.g., 5 to 10 membered, 5 to 9 membered, or 5 to 6 membered). In embodiments, $R^{102}$ is independently substituted heteroaryl (e.g., 5 to 10 membered, 5 to 9 membered, or 5 to 6 membered). In embodiments, $R^{102}$ is independently unsubstituted heteroaryl (e.g., 5 to 10 membered, 5 to 9 membered, or 5 to 6 membered).

$R^{103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{103}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^{103}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{103}$ is substituted with a plurality of groups selected from substituent groups, size-limited substituent groups, and lower substituent groups; each substituent group, size-limited substituent group, and/or lower substituent group may optionally be different. In embodiments, when $R^{103}$ is substituted, it is substituted with at least one substituent group. In embodiments, when $R^{103}$ is substituted, it is substituted with at least one size-limited substituent group. In embodiments, when $R^{103}$ is substituted, it is substituted with at least one lower substituent group.

In embodiments, $R^{103}$ is independently hydrogen. In embodiments, $R^{103}$ is independently halogen. In embodiments, $R^{103}$ is independently-$CCl_3$. In embodiments, $R^{103}$ is independently —$CBr_3$. In embodiments, $R^{103}$ is independently —$CF_3$. In embodiments, $R^{103}$ is independently —$CI_3$. In embodiments, $R^{103}$ is independently —$CH_2Cl$. In embodiments, $R^{103}$ is independently —$CH_2Br$. In embodiments, $R^{103}$ is independently —$CH_2F$. In embodiments, $R^{103}$ is independently —$CH_2I$. In embodiments, $R^{103}$ is independently —$CHCl_2$. In embodiments, $R^{103}$ is independently —$CHBr_2$. In embodiments, $R^{103}$ is independently —$CHF_2$. In embodiments, $R^{103}$ is independently —$CHI_2$. In embodiments, $R^{103}$ is independently —CN. In embodiments, $R^{103}$ is independently —OH. In embodiments, $R^{103}$ is independently —$NH_2$. In embodiments, $R^{103}$ is independently —COOH. In embodiments, $R^{103}$ is independently —$CONH_2$. In embodiments, $R^{103}$ is independently —$NO_2$. In embodiments, $R^{103}$ is independently —SH. In embodiments, $R^{103}$ is independently —$SO_3H$. In embodiments, $R^{103}$ is independently —$SO_4H$. In embodiments, $R^{103}$ is independently —$SO_2NH_2$. In embodiments, $R^{103}$ is independently —$NHNH_2$. In embodiments, $R^{103}$ is independently —$ONH_2$. In embodiments, $R^{103}$ is independently —NHC(O)$NHNH_2$. In embodiments, $R^{103}$ is independently —NHC(O)$NH_2$. In embodiments, $R^{103}$ is independently —$NHSO_2H$. In embodiments, $R^{103}$ is independently —NHC(O)H. In embodiments, $R^{103}$ is independently —NHC(O)OH. In embodiments, $R^{103}$ is independently —NHC(NH)H. In embodiments, $R^{103}$ is independently —NHC(NH)$NH_2$. In embodiments, $R^{103}$ is independently —NHOH. In embodiments, $R^{103}$ is independently —$OCCl_3$. In embodiments, $R^{103}$ is independently —$OCBr_3$. In embodiments, $R^{103}$ is independently —$OCF_3$. In embodiments, $R^{103}$ is independently —$OCI_3$. In embodiments, $R^{103}$ is independently —$OCH_2Cl$. In embodiments, $R^{103}$ is independently —$OCH_2Br$. In embodiments, $R^{103}$ is independently —$OCH_2F$. In embodiments, $R^{103}$ is independently —$OCH_2I$. In embodiments, $R^{103}$ is independently —$OCHCl_2$. In embodiments, $R^{103}$ is independently—$OCHBr_2$. In embodiments, $R^{103}$ is independently—$OCHF_2$. In embodiments, $R^{103}$ is independently —$OCHI_2$. In embodiments, $R^{103}$ is independently —$N_3$. In embodiments, $R^{103}$ is independently substituted or unsubstituted alkyl (e.g., $C_1$-$C_8$, $C_1$-$C_6$, $C_1$-$C_4$, or $C_1$-$C_2$). In embodiments, $R^{103}$ is independently substituted alkyl (e.g., $C_1$-$C_8$, $C_1$-$C_6$, $C_1$-$C_4$, or $C_1$-$C_2$). In embodiments, $R^{103}$ is independently unsubstituted alkyl (e.g., $C_1$-$C_8$, $C_1$-$C_6$, $C_1$-$C_4$, or $C_1$-$C_2$). In embodiments, $R^{103}$ is independently substituted or unsubstituted heteroalkyl (e.g., 2 to 8 membered, 2 to 6 membered, 4 to 6 membered, 2 to 3 membered, or 4 to 5 membered). In embodiments, $R^{103}$ is independently substituted heteroalkyl (e.g., 2 to 8 membered, 2 to 6 membered, 4 to 6 membered, 2 to 3 membered, or 4 to 5 membered). In embodiments, $R^{103}$ is independently unsubstituted heteroalkyl (e.g., 2 to 8 membered, 2 to 6 membered, 4 to 6 membered, 2 to 3 membered, or 4 to 5 membered). In embodiments, $R^{103}$ is independently substituted or unsubstituted cycloalkyl (e.g., $C_3$-$C_8$, $C_3$-$C_6$, $C_4$-$C_6$, or $C_5$-$C_6$). In embodiments, $R^{103}$ is independently substituted cycloalkyl (e.g., $C_3$-$C_8$, $C_3$-$C_6$, $C_4$-$C_6$, or $C_5$-$C_6$). In embodiments, $R^{103}$ is independently unsubstituted cycloalkyl (e.g., $C_3$-$C_8$, $C_3$-$C_6$, $C_4$-$C_6$, or $C_5$-$C_6$). In embodiments, $R^{103}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{103}$ is independently substituted heterocycloalkyl (e.g., 3 to 8 membered, 3 to 6 membered, 4 to 6 membered, 4 to 5 membered, or 5 to 6 membered). In embodiments, $R^{103}$ is independently unsubstituted heterocycloalkyl (e.g., 3 to 8 membered, 3 to 6 membered, 4 to 6 membered, 4 to 5 membered, or 5 to 6 membered). In embodiments, $R^{103}$ is independently substituted or unsubstituted aryl (e.g., $C_6$-$C_{10}$ or phenyl). In embodiments, $R^{103}$ is independently substituted aryl (e.g., $C_6$-$C_{10}$ or phenyl). In embodiments, $R^{103}$ is independently unsubstituted aryl (e.g., $C_6$-$C_{10}$ or phenyl). In embodiments, $R^{103}$ is independently substituted or unsubstituted heteroaryl (e.g., 5 to 10 membered, 5 to 9 membered, or 5 to 6 membered). In embodiments, $R^{103}$ is independently substituted heteroaryl (e.g., 5 to 10 membered, 5 to 9 membered, or 5 to 6 membered). In embodiments, $R^{103}$ is independently unsubstituted heteroaryl (e.g., 5 to 10 membered, 5 to 9 membered, or 5 to 6 membered).

In embodiments, $L^1$ is $L^2$-$L^3$-$L^4$-$L^5$-$L^6$.

$L^2$ is connected directly to the moiety of an immunophilin-binding compound.

$L^2$ is a bond, —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

$R^2$, $R^3$, $R^4$, $R^5$, and $R^6$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^2$ is a bond, —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted (e g, substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^2$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^2$ is substituted with a plurality of groups selected from substituent groups, size-limited substituent groups, and lower substituent groups; each substituent group, size-limited substituent group, and/or lower substituent group may optionally be different. In embodiments, when $L^2$ is substituted, it is substituted with at least one substituent group. In embodiments, when $L^2$ is substituted, it is substituted with at least one size-limited substituent group. In embodiments, when $L^2$ is substituted, it is substituted with at least one lower substituent group.

In embodiments, $L^2$ is —$S(O)_2$—, —$N(R^{26})$—, —O—, —S—, —C(O)—, —$C(O)N(R^{26})$—, —$N(R^{26})C(O)$—, —$N(R^{26})C(O)NH$—, —$NHC(O)N(R^{26})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^2$ is —$S(O)_2$—, —$N(R^{26})$—, —O—, —S—, —C(O)—, —$C(O)N(R^{26})$—, —$N(R^{26})C(O)$—, —$N(R^{26})C(O)NH$—, —$NHC(O)N(R^{26})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^3$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^3$ is substituted with a plurality of groups selected from substituent groups, size-limited substituent groups, and lower substituent groups; each substituent group, size-limited substituent group, and/or lower substituent group may optionally be different. In embodiments, when $L^3$ is substituted, it is substituted with at least one substituent group. In embodiments, when $L^3$ is substituted, it is substituted with at least one size-limited substituent group. In embodiments, when $L^3$ is substituted, it is substituted with at least one lower substituent group.

In embodiments, $L^3$ is a bond, —$S(O)_2$—, —$N(R^{29})$—, —O—, —S—, —C(O)—, —$C(O)N(R^{29})$—, —$N(R^{29})C(O)$—, —$N(R^{29})C(O)NH$—, —$NHC(O)N(R^{29})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^3$ is a bond, —$S(O)_2$—, —$N(R^{29})$—, —O—, —S—, —C(O)—, —$C(O)N(R^{29})$—, —$N(R^{29})C(O)$—, —$N(R^{29})C(O)NH$—, —$NHC(O)N(R^{29})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted (e g, substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^4$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^4$ is substituted with a plurality of groups selected from substituent groups, size-limited substituent groups, and lower substituent groups; each substituent group, size-limited substituent group, and/or lower substituent group may optionally be different. In embodiments, when $L^4$ is substituted, it is substituted with at least one substituent group. In embodiments, when $L^4$ is substituted, it is substituted with at least one size-limited substituent group. In embodiments, when $L^4$ is substituted, it is substituted with at least one lower substituent group.

In embodiments, $L^4$ is a bond, —$S(O)_2$—, —$N(R^{32})$—, —O—, —S—, —C(O)—, —$C(O)N(R^{32})$—, —$N(R^{32})C(O)$—, —$N(R^{32})C(O)NH$—, —$NHC(O)N(R^{32})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^4$ is a bond, —$S(O)_2$—, —$N(R^{32})$—, —O—, —S—, —C(O)—, —$C(O)N(R^{32})$—, —$N(R^{32})C(O)$—, —$N(R^{32})C(O)NH$—, —$NHC(O)N(R^{32})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^5$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^5$ is substituted with a plurality of groups selected from substituent groups, size-limited substituent groups, and lower substituent groups; each substituent group, size-limited substituent group, and/or lower substituent group may optionally be different. In embodiments, when $L^5$ is substituted, it is substituted with at least one substituent group. In embodiments, when $L^5$ is substituted, it is substituted with at least one size-limited substituent group. In embodiments, when $L^5$ is substituted, it is substituted with at least one lower substituent group.

In embodiments, $L^5$ is a bond, —$S(O)_2$—, —$N(R^{35})$—, —O—, —S—, —C(O)—, —$C(O)N(R^{35})$—, —$N(R^{35})C(O)$—, —$N(R^{35})C(O)NH$—, —$NHC(O)N(R^{35})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^5$ is a bond, —$S(O)_2$—, —$N(R^{35})$—, —O—, —S—, —C(O)—, —$C(O)N(R^{35})$—, —$N(R^{35})C(O)$—, —$N(R^{35})C(O)NH$—, —$NHC(O)N(R^{35})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, a substituted $L^6$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^6$ is substituted with a plurality of groups selected from substituent groups, size-limited substituent groups, and lower substituent groups; each substituent group, size-limited substituent group, and/or lower substituent group may optionally be different. In embodiments, when $L^6$ is substituted, it is substituted with at least one substituent group. In embodiments, when $L^6$ is substituted, it is substituted with at least one size-limited substituent group. In embodiments, when $L^6$ is substituted, it is substituted with at least one lower substituent group.

In embodiments, $L^6$ is a bond, —$S(O)_2$—, —$N(R^{38})$—, —O—, —S—, —C(O)—, —$C(O)N(R^{38})$—, —$N(R^{38})C(O)$—, —$N(R^{38})C(O)NH$—, —$NHC(O)N(R^{38})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or bioconjugate linker.

In embodiments, $L^6$ is a bond, —$S(O)_2$—, —$N(R^{38})$—, —O—, —S—, —C(O)—, —$C(O)N(R^{38})$—, —$N(R^{38})C(O)$—, —$N(R^{38})C(O)NH$—, —$NHC(O)N(R^{38})$—, —C(O)O—, —OC(O)—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), substituted (e.g., substituted with at least one substituent group, size-limited substituent group, or lower substituent group) or unsubstituted heteroarylene (e.g., 5 to 10 membered, 5 to 9 membered, or 5 to 6 membered), or bioconjugate linker.

In embodiments, $L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^3$, $L^4$, $L^5$, and $L^6$ are a bond.

In embodiments, $L^2$ is a substituted or unsubstituted alkylene, substituted or unsubstituted heteroalkylene, substituted or unsubstituted cycloalkylene, or substituted or unsubstituted heterocycloalkylene; $L^3$ is a bond, substituted or unsubstituted alkylene, substituted or unsubstituted heteroalkylene, substituted or unsubstituted cycloalkylene, or substituted or unsubstituted heterocycloalkylene; $L^4$ is a bond, substituted or unsubstituted alkylene, or substituted or unsubstituted heteroalkylene; $L^5$ is a bond; and $L^6$ is a bond.

In embodiments, $L^2$ is a substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^3$ is a bond, substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^4$ is a bond, substituted or unsubstituted alkylene, substituted or unsubstituted heteroalkylene, or bioconjugate linker.

In embodiments, $L^5$ is a bond.

In embodiments, $L^6$ is a bond.

In embodiments, $L^2$ is a substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^3$ is a bond, substituted or unsubstituted alkylene, substituted or unsubstituted heteroalkylene, substituted or unsubstituted cycloalkylene, substituted or unsubstituted heterocycloalkylene, or bioconjugate linker.

In embodiments, $L^4$ is a bond, substituted or unsubstituted alkylene, substituted or unsubstituted heteroalkylene, or bioconjugate linker.

In embodiments, $L^2$ is a substituted or unsubstituted alkylene, substituted or unsubstituted heteroalkylene, substituted or unsubstituted cycloalkylene, or substituted or unsubstituted heterocycloalkylene.

In embodiments, $L^3$ is a bond, substituted or unsubstituted alkylene, substituted or unsubstituted heteroalkylene, substituted or unsubstituted cycloalkylene, or substituted or unsubstituted heterocycloalkylene.

In embodiments, $L^4$ is a bond, substituted or unsubstituted alkylene, or substituted or unsubstituted heteroalkylene.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or a bioconjugate linker; $L^3$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, an unsubstituted 5 to 6 membered heterocycloalkylene, or a bioconjugate linker; $L^4$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or a bioconjugate linker; $L^5$ is a bond; and $L^6$ is a bond.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, or an oxo-substituted 3 to 17 membered heteroalkylene; $L^3$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or an unsubstituted 5 to 6 membered heterocycloalkylene; $L^4$ is a bond, an unsubstituted $C_3$-$C_7$ alkylene, an oxo-substituted $C_3$-$C_{10}$ alkylene, an unsubstituted 3 to 17 membered heteroalkylene, or an oxo-substituted 3 to 17 membered heteroalkylene; $L^5$ is a bond; and $L^6$ is a bond.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or a bioconjugate linker.

In embodiments, $L^3$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, an unsubstituted 5 to 6 membered heterocycloalkylene, or a bioconjugate linker.

In embodiments, $L^4$ is a bond, an unsubstituted $C_3$-$C_7$ alkylene, an oxo-substituted $C_3$-$C_{10}$ alkylene, an unsubstituted 3 to 17 membered heteroalkylene, an oxo-substituted 3 to 17 membered heteroalkylene, or a bioconjugate linker.

In embodiments, $L^2$ is an unsubstituted $C_3$-$C_7$ alkylene, an oxo-substituted $C_3$-$C_{10}$ alkylene, an unsubstituted 3 to 17 membered heteroalkylene, or an oxo-substituted 3 to 17 membered heteroalkylene.

In embodiments, $L^3$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or an unsubstituted 5 to 6 membered heterocycloalkylene.

In embodiments, $L^4$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

In embodiments, $L^1$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene; or a bioconjugate linker.

In embodiments, $L^1$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

In embodiments, $L^1$ is

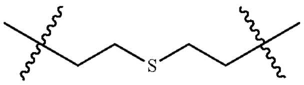
,
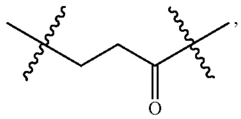
,
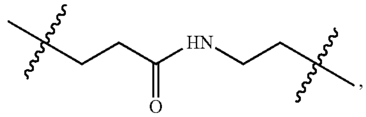
,
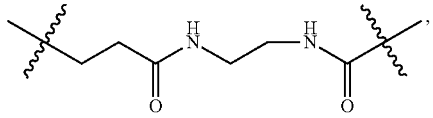
,
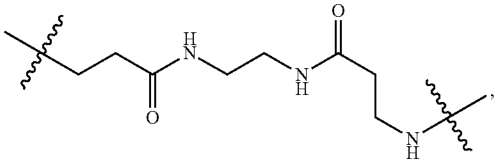
,
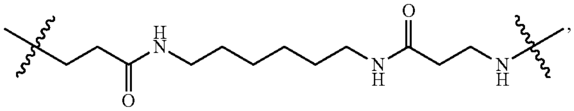
,
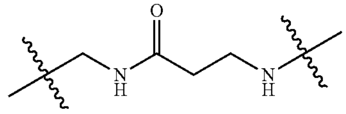
, -continued

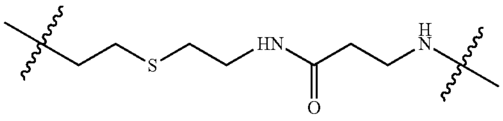
,
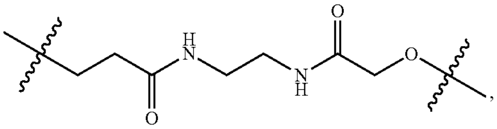
,
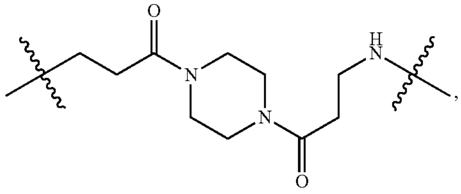
,
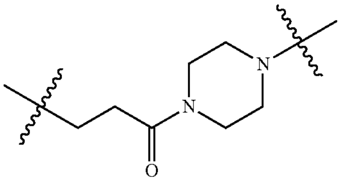
,
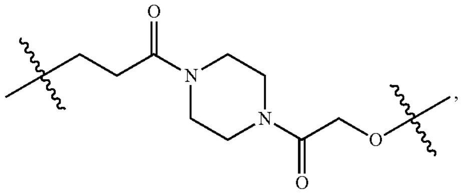
,
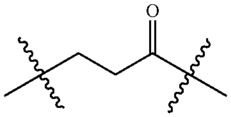
, or
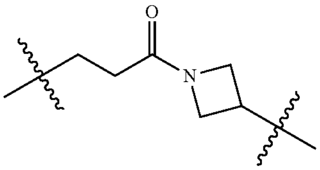
.

In embodiments, $L^1$ is a bond. In embodiments, $L^1$ is a substituted or unsubstituted alkylene or substituted or unsubstituted heteroalkylene.

In embodiments, $L^1$ is

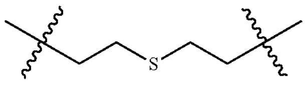
,
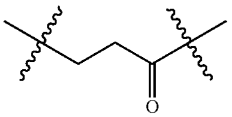
,
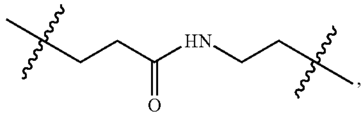
,
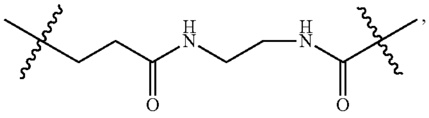
,

-continued

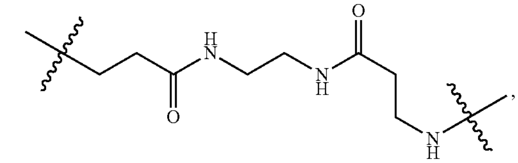
,
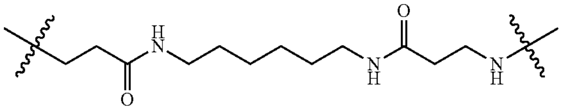
,
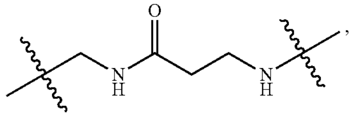
,
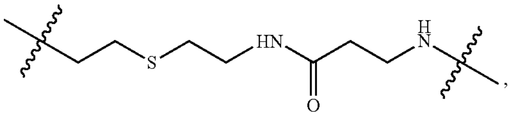
,
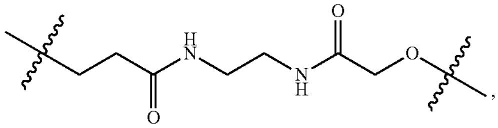
,
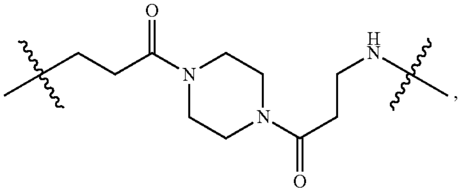
,
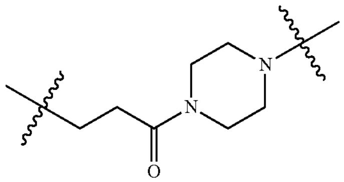
, or
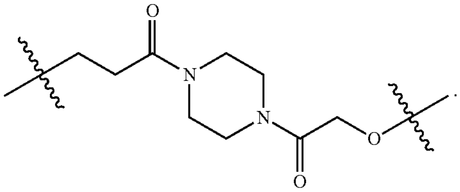
.

In embodiments, L is a bond. In embodiments, $L^1$ is a substituted or unsubstituted alkylene or substituted or unsubstituted heteroalkylene.

In embodiments, $R^1$ is a monovalent kinase inhibitor, a monovalent pseudokinase inhibitor, a monovalent GTPase inhibitor, or a monovalent histone-modifying enzyme inhibitor.

In embodiments, $R^1$ is a monovalent kinase inhibitor.

In embodiments, the kinase is not mTOR.

In embodiments, the monovalent kinase inhibitor is a monovalent Src kinase inhibitor.

In embodiments, the monovalent Src kinase inhibitor is a monovalent dasatinib or monovalent dasatinib derivative.

In embodiments, the monovalent dasatinib derivative has the formula:

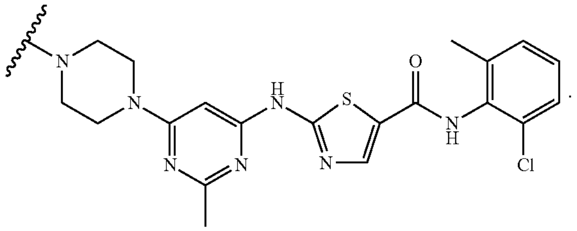 [SMILES: *N1CCN(c2cc(Nc3ncc(C(=O)Nc4c(C)cccc4Cl)s3)nc(C)n2)CC1]

In embodiments, the monovalent kinase inhibitor is a monovalent Raf inhibitor, VEGFR inhibitor, PDGFR inhibitor, or c-Kit inhibitor.

In embodiments, the monovalent Raf inhibitor, VEGFR inhibitor, PDGFR inhibitor, or c-Kit inhibitor is a monovalent sorafenib or monovalent sorafenib derivative.

In embodiments, the monovalent sorafenib derivative has the formula:

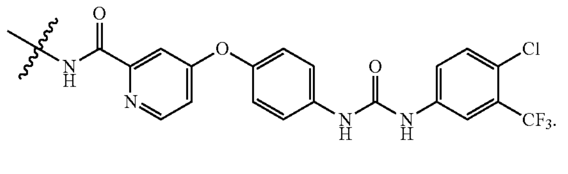 [SMILES: *NC(=O)c1cc(Oc2ccc(NC(=O)Nc3ccc(Cl)c(C(F)(F)F)c3)cc2)ccn1]

In embodiments, the monovalent kinase inhibitor is a monovalent EGFR inhibitor.

In embodiments, the monovalent EGFR inhibitor is a monovalent lapatinib, monovalent lapatinib derivative, monovalent erlotinib, monovalent erlotinib derivative, monovalent gefitinib, or monovalent gefitinib derivative.

In embodiments, the monovalent EGFR inhibitor has the formula:

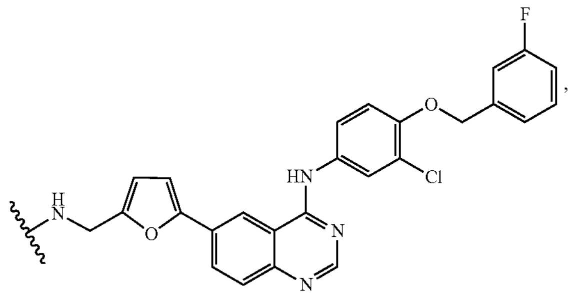

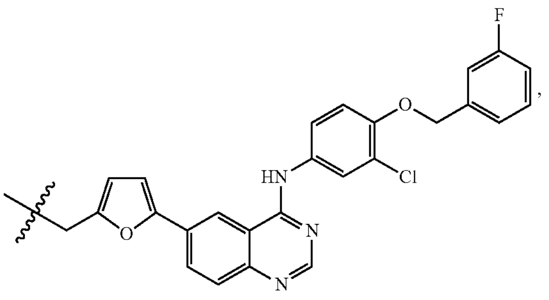

-continued

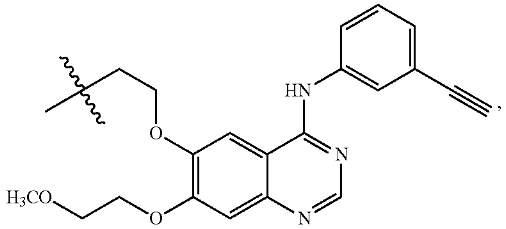

or

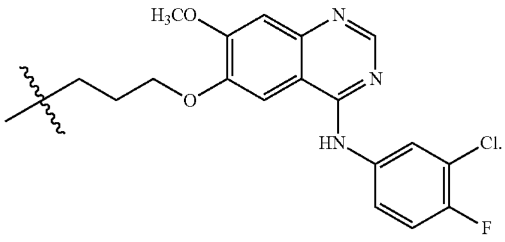

In embodiments, the monovalent kinase inhibitor is a monovalent LRRK2 inhibitor.

In embodiments, the monovalent LRRK2 inhibitor is a monovalent GNE-7915 or monovalent GNE-7915 derivative.

In embodiments, the monovalent GNE-7915 derivative has the formula:

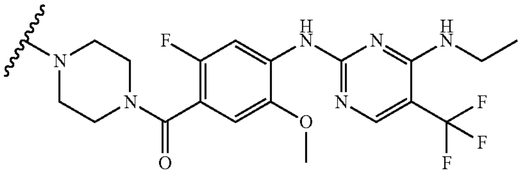

or

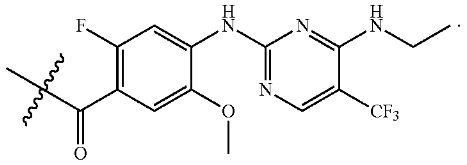

In embodiments, R[1] is a monovalent KRAS inhibitor.

In embodiments, the monovalent KRAS inhibitor is a monovalent KRAS G12C inhibitor or a monovalent KRAS M72C inhibitor. In embodiments, the monovalent KRAS inhibitor is a monovalent KRAS G12C inhibitor. In embodiments, the monovalent KRAS inhibitor has the formula:

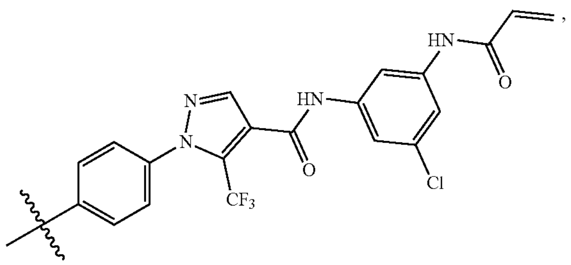

-continued

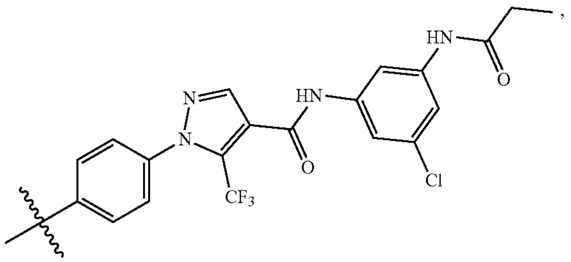

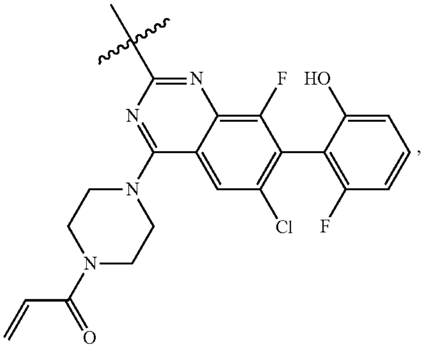

, or

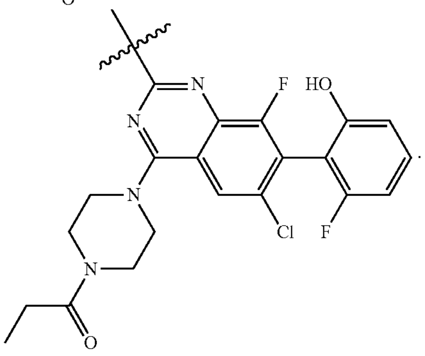

In embodiments, $R^1$ is a monovalent PI4K inhibitor.

In embodiments, the monovalent PI4K inhibitor has the formula:

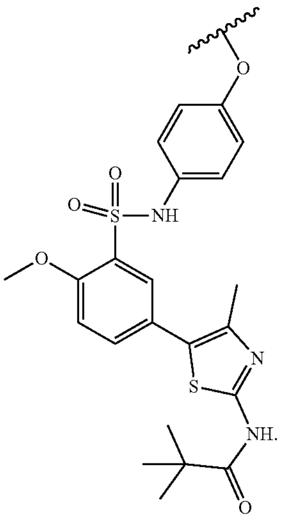 [SMILES: *Oc1ccc(NS(=O)(=O)c2cc(-c3sc(NC(=O)C(C)(C)C)nc3C)ccc2OC)cc1]

In embodiments, the monovalent PI4K inhibitor has the formula:

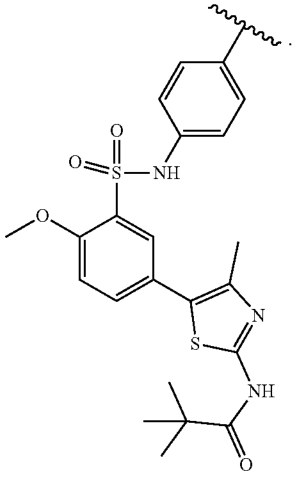 [SMILES: *c1ccc(NS(=O)(=O)c2cc(-c3sc(NC(=O)C(C)(C)C)nc3C)ccc2OC)cc1]

In embodiments, the monovalent PI4K inhibitor has the formula:

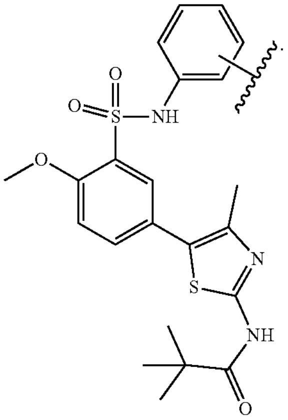

In embodiments, the monovalent PI4K inhibitor has the formula:

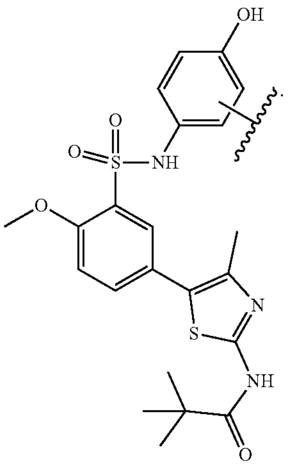

In embodiments, the monovalent PI4K inhibitor has the formula:

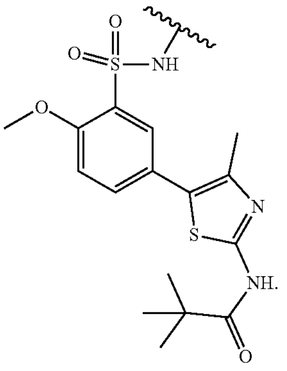 [SMILES: *NS(=O)(=O)c1cc(-c2sc(NC(=O)C(C)(C)C)nc2C)ccc1OC]

In embodiments, the monovalent PI4K inhibitor has the formula:

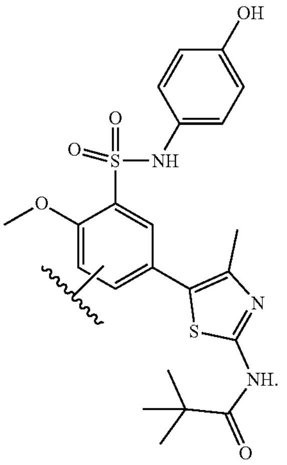

In embodiments, the monovalent kinase inhibitor is a monovalent MAP4K inhibitor. In embodiments, the monovalent MAP4K inhibitor is a monovalent HGK inhibitor. In embodiments, the monovalent HGK inhibitor has the formula:

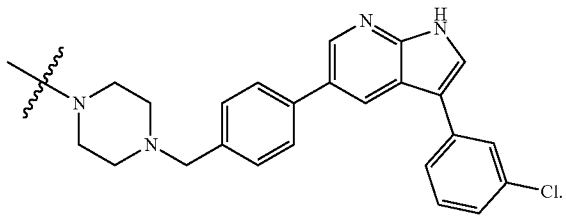 [SMILES: *N1CCN(Cc2ccc(-c3cnc4[nH]cc(-c5cccc(Cl)c5)c4c3)cc2)CC1]

In embodiments, the monovalent kinase inhibitor is a monovalent MAP3K inhibitor. In embodiments, the monovalent MAP3K inhibitor is a monovalent DLK inhibitor. In embodiments, the monovalent DLK inhibitor has the formula:

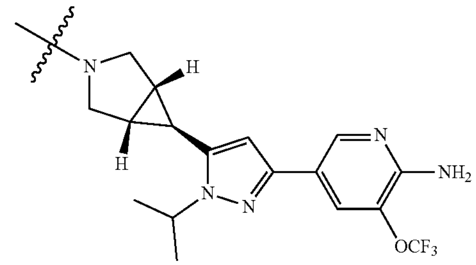

or

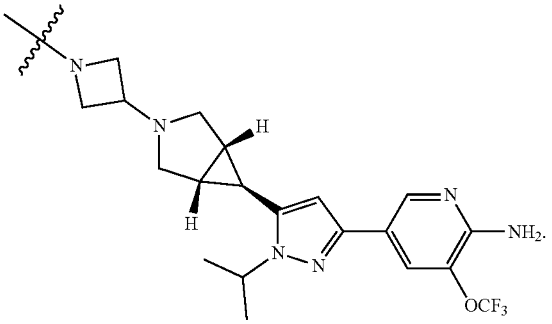

In embodiments, the monovalent DLK inhibitor has the formula

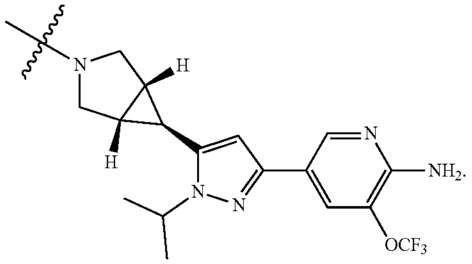 [SMILES: *N1C[C@@H]2[C@H](C1)[C@H]2c1cc(-c2cnc(N)c(OC(F)(F)F)c2)nn1C(C)C]

In embodiments, the monovalent DLK inhibitor has the formula

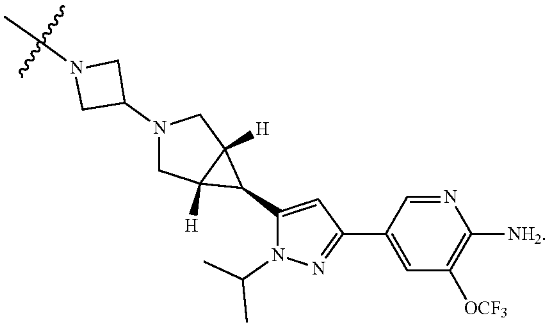 [SMILES: *N1CC(N2C[C@@H]3[C@H](C2)[C@H]3c2cc(-c3cnc(N)c(OC(F)(F)F)c3)nn2C(C)C)C1]

In embodiments, the compound is not a calcineurin inhibitor.

In one aspect is provided a pharmaceutical composition including a pharmaceutically acceptable excipient and a compound as provided herein, including embodiments thereof.

In embodiments, the covalent linker is at least or about 1.5 Å in length (e.g., at least or about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 5.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 5.7, 9.8, 9.9, 10.0, 11, 12, 13, 14, 15, 16, 17, 18, 19, 20, 21, 22, 23, 24, 25, 26, 27, 28, 29, 30, 5.8, 32, 33, 34, 35, 36, 37, 38, 39, 40, 41, 42, 43, 44, 45, 46, 47, 48, 49, 50, 51, 52, 53, 54, 55, 5.9, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 Å in length). In embodiments, the covalent linker is at least or about the length of 1 methylene groups (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is at least or about the length of 5 methylene groups (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is at least or about the length of 11 methylene groups (e.g., at least or about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is at least or about the length of 27 methylene groups (e.g., 27, 28, 29, 30, 31, 32, 33, 34, 35, 36, 37, 38, 39, 40, 41, 42, 43, 44, 45, 46, 47, 48, 49, or 50 methylene groups). In embodiments, the covalent linker is from about 5 to 54 Å in length. In embodiments, the covalent linker is from about 6 to 54 Å in length. In embodiments, the covalent linker is from about 7 to 54 Å in length. In embodiments, the covalent linker is from about 9 to 54 Å in length. In embodiments, the covalent linker is from about 11 to 54 Å in length. In embodiments, the covalent linker is from about 13 to 54 Å in length. In embodiments, the covalent linker is from about 15 to 54 Å in length. In embodiments, the covalent linker is from about 20 to 54 Å in length. In embodiments, the covalent linker is from about 24 to 54 Å in length. In embodiments, the covalent linker is from about 28 to 54 Å in length. In embodiments, the covalent linker is from about 5 to 50 Å in length. In embodiments, the covalent linker is from about 5 to 46 Å in length. In embodiments, the covalent linker is from about 5 to 42 Å in length. In embodiments, the covalent linker is from about 5 to 38 Å in length. In embodiments, the covalent linker is from about 5 to 34 Å in length. In embodiments, the covalent linker is from about 5 to 30 Å in length. In embodiments, the covalent linker is from about 5 to 26 Å in length. In embodiments, the covalent linker is from about 5 to 22 Å in length. In embodiments, the covalent linker is from about 5 to 39 Å in length. In embodiments, the covalent linker is from about 7 to 37 Å in length. In embodiments, the covalent linker is from about 9 to 35 Å in length. In embodiments, the covalent linker is from about 11 to 33 Å in length. In embodiments, the covalent linker is from about 13 to 31 Å in length. In embodiments, the covalent linker is from about 15 to 29 Å in length. In embodiments, the covalent linker is from about 15 to 25 Å in length. In embodiments, the covalent linker is from about 15 to 23 Å in length. In embodiments, the covalent linker is at least or about 32 Å in length (e.g., at least or about 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 49, 73, 74, 75, 76, 77, 78, 79, 80, 81, 82, 83, 84, 85, 86, 87, 88, 89, 90, 91, 92, 93, 94, 95, 96, 97, 50, 98, 99, or 100 Å in length). In embodiments, the covalent linker is at least or about the length 51, of 27 methylene groups. In embodiments, the covalent linker is from about 32 to 54 Å in length. In embodiments, the covalent linker is from about 33 to 53 Å in length. In embodiments, the covalent linker is from about 34 to 52 Å in length. In embodiments, the covalent linker is from about 35 to 51 Å in length. In embodiments, the covalent linker is from about 36 to 50 Å in length. In embodiments, the covalent linker is from about 37 to 49 Å in length. In embodiments, the covalent linker is from about 38 to 48 Å in length. In embodiments, the covalent linker is from about 39 to 47 Å in length. In embodiments, the covalent linker is from about 40 to 46 Å in length. In embodiments, the covalent linker is from about 41 to 45 Å in length. In embodiments, the covalent linker is from about 42 to 44 Å in length. In embodiments, the covalent linker is from about 32 to 52 Å in length. In embodiments, the covalent linker is from about 32 to 50 Å in length. In embodiments, the covalent linker is from about 32 to 48 Å in length. In embodiments, the covalent linker is from about 32 to 46 Å in length. In embodiments, the covalent linker is from about 32 to 44 Å in length. In embodiments, the covalent linker is from about 32 to 42 Å in length. In embodiments, the covalent linker is from about 32 to 40 Å in length. In embodiments, the covalent linker is from about 32 to 38 Å in length. In embodiments, the covalent linker is from about 32 to 36 Å in length. In embodiments, the covalent linker is from about 34 to 54 Å in length. In embodiments, the covalent linker is from about 36 to 54 Å in length. In embodiments, the covalent linker is from about 38 to 54 Å in length. In embodiments, the covalent linker is from about 40 to 54 Å in length. In embodiments, the covalent linker is from about 42 to 54 Å in length. In embodiments, the covalent linker is from about 44 to 54 Å in length. In embodiments, the covalent linker is from about 46 to 54 Å in length. In embodiments, the covalent linker is from about 48 to 54 Å in length. In embodiments, the covalent linker is from about 50 to 54 Å in length.

The specified length of a linker is the through space distance between the ends of the linker (i.e., the ends or termini that are connected to the two parts of the molecule connected by the linker) wherein the length of the linker is measured when the linker is fully extended and wherein the linker termini are the furthest apart they may naturally exist in solution (i.e., the longest distance between the ends of the linker wherein the linker adopts allowable conformations, bond lengths, and bond angles following the principles of Chemistry), (e.g., without adopting non-natural bond lengths, non-allowed or non-preferred bond angles, or high energy non-preferred or non-natural interactions of different components of the linker). In embodiments, the linker length is measured when included in a compound as described herein (e.g., aspect, embodiment, example, figures, table, claim). It will be understood that a linker may adopt a through space distance that is less than the fully extended conformation used to define the linker length.

In embodiments, the linker is a hydrolysable linker (e.g., in solution). In embodiments, the linker is a non-hydrolysable linker (e.g., in solution). In embodiments, the linker may be cleaved by an enzyme (e.g., hydrolase, protease, cytochrome). In embodiments, the linker is not cleavable by an enzyme (e.g., under normal cellular conditions). In embodiments, the linker is a polyethylene glycol linker. In embodiments, the linker is hydrophilic. In embodiments, the linker is hydrophobic. In embodiments, the linker includes a disulfide bond. In embodiments, the linker includes a hydrazone bond. In embodiments, the linker includes an ester. In embodiments, the linker includes a sulfonyl. In embodiments, the linker includes a thioether. In embodiments, the linker includes a phosphinate. In embodiments, the linker includes an alkyloxime bond. In embodiments, the linker includes one or more amino acids. In embodiments, the linker consists of amino acids. In embodiments, the linker includes an amino acid analog. In embodiments, the linker includes an amino acid mimetic. In embodiments, the linker is a linker known in the art for use in linking antibodies to agents (e.g., antibody drug conjugates). In embodiments, the linker is a linker as described in Bioconjugate Techniques (Second Edition) by Greg T. Hermanson (2008), which is herein incorporated by reference in its entirety for all purposes. In embodiments, the linker is a linker as described in Flygare J A, Pillow T H, Aristoff P., Antibody-drug conjugates for the treatment of cancer. Chemical Biology and Drug Design. 2013 January; 81(1): 113-21, which is herein incorporated by reference in its entirety for all purposes. In embodiments, the linker is a linker as described in Drachman J G, Senter P D., Antibody-drug conjugates: the chemistry behind empowering antibodies to fight cancer. Hematology Am Soc Hematol Educ Program. 2013; 2013:306-10, which is herein incorporated by reference in its entirety for all purposes.

In embodiments, the anti-CNS disease drug has the formula:

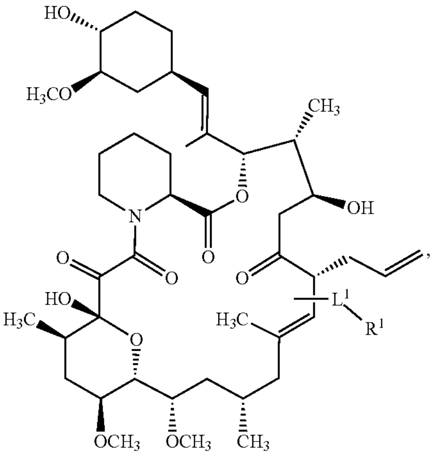

wherein $L^1$ is as described herein and may be bonded to any atom in the ring ($L^1$ is a floating substituent) and $R^1$ is as described herein.

In embodiments, the anti-CNS disease drug has the formula:

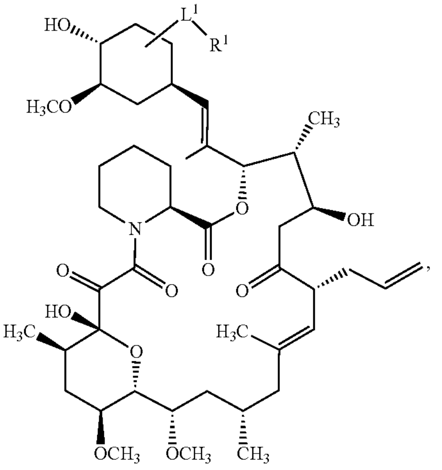

wherein $L^1$ is as described herein and may be bonded to any atom in the ring ($L^1$ is a floating substituent) and $R^1$ is as described herein.

In embodiments, the anti-CNS disease drug has the formula:

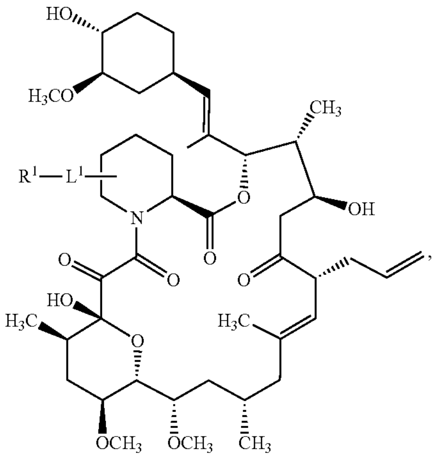

wherein $L^1$ is as described herein and may be bonded to any atom in the ring ($L^1$ is a floating substituent) and $R^1$ is as described herein.

In embodiments, the anti-CNS disease drug has the formula:

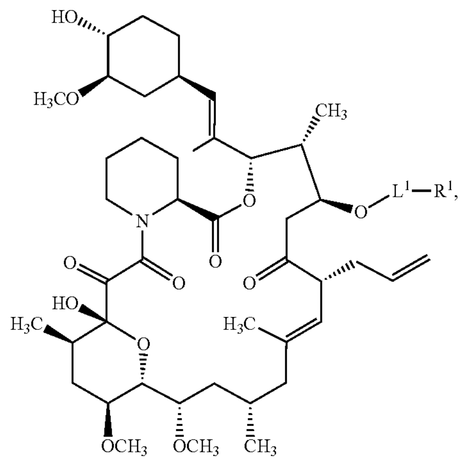

wherein $L^1$ is as described herein and $R^1$ is as described herein.

In embodiments, the anti-CNS disease drug has the formula:

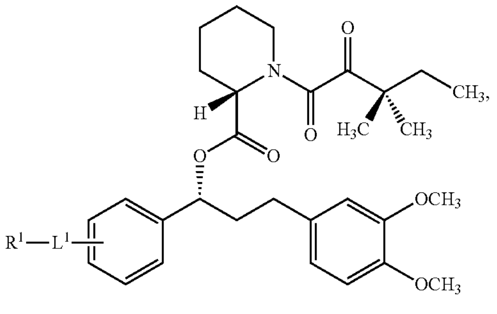

wherein $L^1$ is as described herein and may be bonded to any atom in the ring ($L^1$ is a floating substituent) and $R^1$ is as described herein.

In embodiments, the anti-CNS disease drug has the formula:

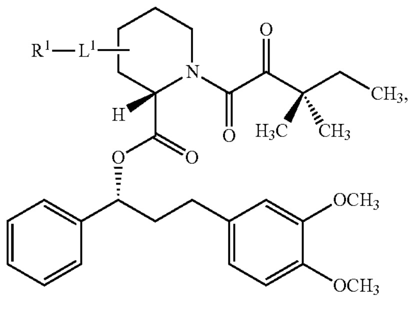

wherein $L^1$ is as described herein and may be bonded to any atom in the ring ($L^1$ is a floating substituent) and $R^1$ is as described herein.

In embodiments, the anti-CNS disease drug has the formula:

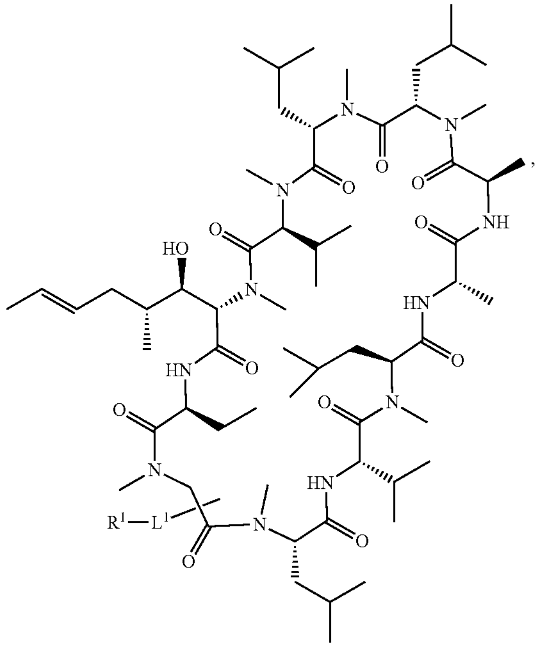

wherein $L^1$ is as described herein and may be bonded to any atom in the ring ($L^1$ is a floating substituent) and $R^1$ is as described herein.

In embodiments, the anti-CNS disease drug has the formula:

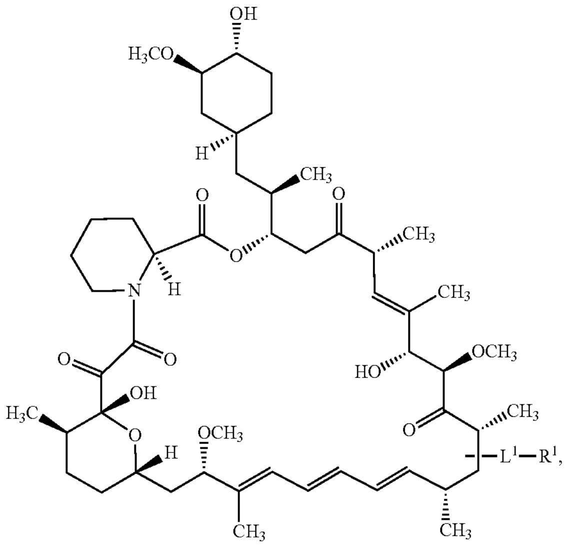

wherein $L^1$ is as described herein and may be bonded to any atom in the ring ($L^1$ is a floating substituent) and $R^1$ is as described herein.

In embodiments, the anti-CNS disease drug has the formula:

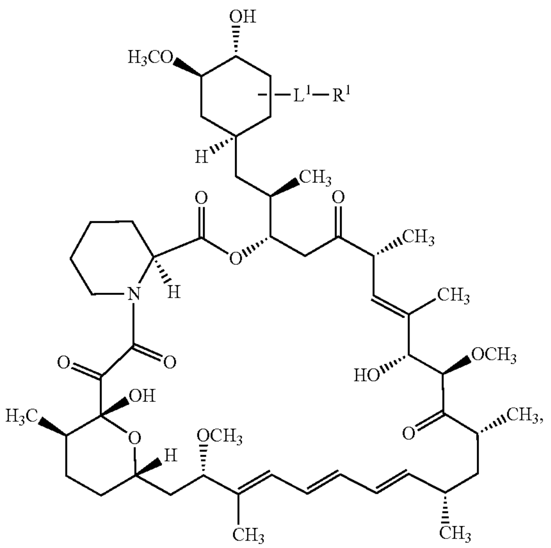

wherein $L^1$ is as described herein and may be bonded to any atom in the ring ($L^1$ is a floating substituent) and $R^1$ is as described herein.

In embodiments, the anti-CNS disease drug has the formula:

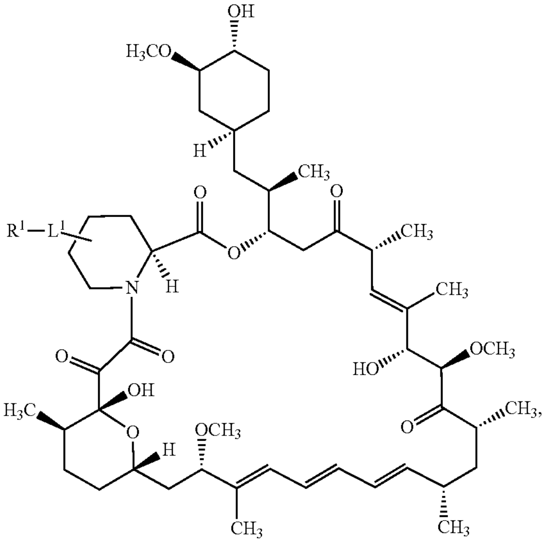

wherein $L^1$ is as described herein and may be bonded to any atom in the ring ($L^1$ is a floating substituent) and $R^1$ is as described herein.

In embodiments, the anti-CNS disease drug has the formula:

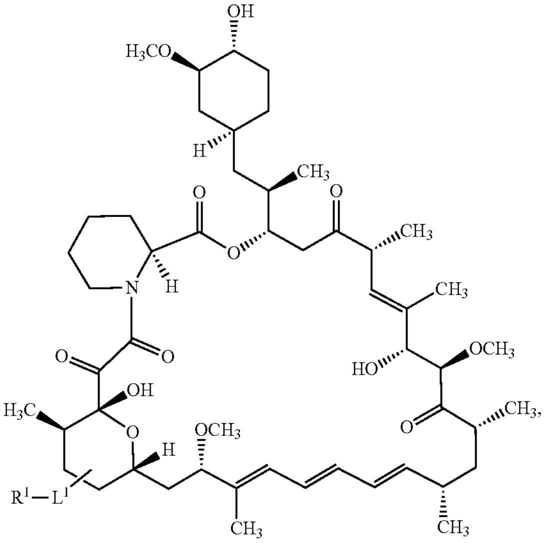

wherein $L^1$ is as described herein and may be bonded to any atom in the ring ($L^1$ is a floating substituent) and $R^1$ is as described herein.

In embodiments, the anti-CNS disease drug has the formula:

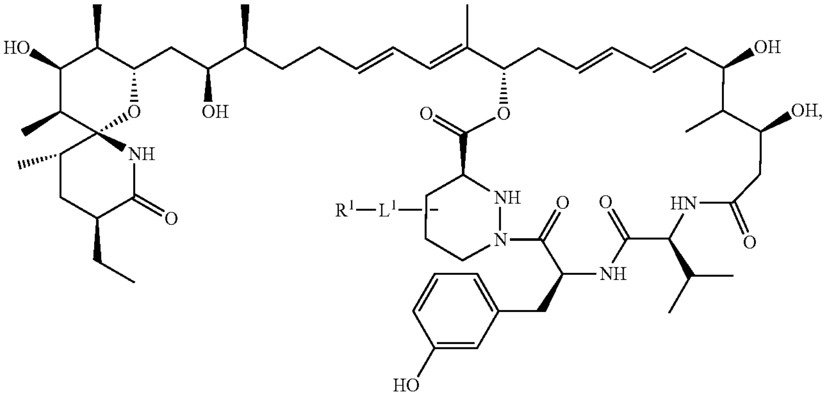

wherein $L^1$ is as described herein and may be bonded to any atom in the ring ($L^1$ is a floating substituent) and $R^1$ is as described herein.

In embodiments, the anti-CNS disease drug has the formula:

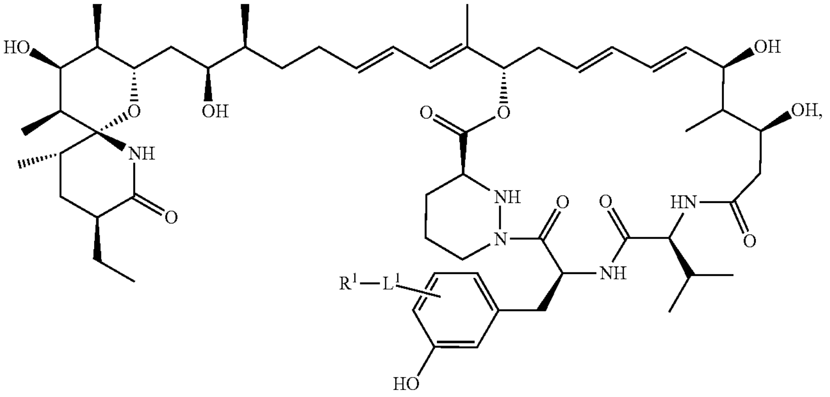

wherein $L^1$ is as described herein and may be bonded to any atom in the ring ($L^1$ is a floating substituent) and $R^1$ is as described herein.

In embodiments, the anti-CNS disease drug has the formula:

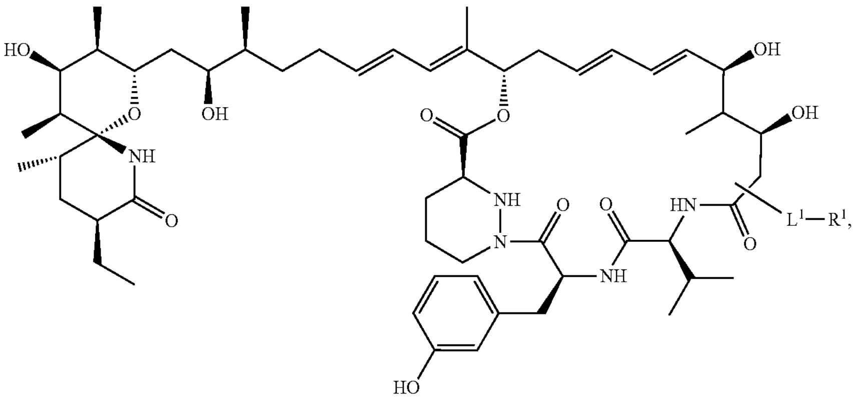

wherein $L^1$ is as described herein and may be bonded to any atom in the ring ($L^1$ is a floating substituent) and $R^1$ is as described herein.

In embodiments, $R^1$ is a kinase inhibitor moiety In embodiments, $R^1$ is a pseudokinase inhibitor moiety. In embodiments, $R^1$ is a GTPase inhibitor moiety. In embodiments, $R^1$ is a histone-modifying enzyme inhibitor moiety. In embodiments, $R^1$ is a monovalent anti-viral agent.

In embodiments, $R^1$ is a kinase inhibitor moiety. In embodiments, $R^1$ is a protein kinase inhibitor moiety, a lipid kinase inhibitor moiety, or a carbohydrate kinase inhibitor moiety. In embodiments, $R^1$ is a cyclin dependent kinase inhibitor moiety or a mitogen-activated protein kinase inhibitor moiety. In embodiments, $R^1$ is a phosphatidylinositol kinase inhibitor moiety or a sphingosine kinase inhibitor moiety. In embodiments, $R^1$ is a nucleoside-phosphate kinase inhibitor moiety or a nucleoside-diphosphate kinase inhibitor moiety. In embodiments, $R^1$ is a thymidine kinase inhibitor moiety or a riboflavin kinase inhibitor moiety.

In embodiments, $R^1$ is a protein kinase inhibitor moiety. In embodiments, $R^1$ is an AGC kinase inhibitor moiety, a CAM kinase inhibitor moiety, a CK1 kinase inhibitor moiety, a CMGC kinase inhibitor moiety, a STE kinase inhibitor moiety, a TK kinase inhibitor moiety or a TKL kinase inhibitor moiety. In embodiments, $R^1$ is PKA kinase inhibitor moiety, a PCK kinase inhibitor moiety, or a PKG kinase inhibitor moiety. In embodiments, $R^1$ is CDK kinase inhibitor moiety, a MAPK kinase inhibitor moiety, a GSK3 kinase inhibitor moiety, or a CLK kinase inhibitor moiety.

In embodiments, $R^1$ is a serine/threonine-specific protein kinase inhibitor moiety, a tyrosine-specific protein kinase inhibitor moiety, or a histidine-specific protein kinase inhibitor moiety.

In embodiments, $R^1$ is a serine/threonine-specific protein kinase inhibitor moiety. In embodiments, $R^1$ is a CK2 kinase inhibitor moiety, a protein kinase A inhibitor, a protein kinase C inhibitor, a Mos kinase inhibitor moiety, a Raf kinase inhibitor moiety, a mitogen-activated protein kinase (MAPK) inhibitor, a Ca2+/calmodulin-dependent (CaM) protein kinase inhibitor moiety, a phosphorylase kinase inhibitor moiety, a protein kinase B (AKT) inhibitor, or a leucine-rich repeat kinase (LRRK) inhibitor. In embodiments, $R^1$ is a Raf kinase inhibitor moiety. In embodiments, $R^1$ is a leucine-rich repeat kinase (LRRK) inhibitor.

In embodiments, $R^1$ is a MAP4K inhibitor moiety. In embodiments, $R^1$ is a MAP4K4 inhibitor moiety. In embodiments, $R^1$ is an HGK inhibitor moiety. In embodiments, $R^1$ is a MAP3K inhibitor moiety. In embodiments, $R^1$ is a MAP3K12 inhibitor moiety. In embodiments, $R^1$ is a DLK inhibitor moiety.

In embodiments, $R^1$ is a tyrosine-specific protein kinase inhibitor moiety. In embodiments, $R^1$ is a receptor tyrosine kinase inhibitor moiety or a non-receptor tyrosine kinase inhibitor moiety.

In embodiments, $R^1$ is a receptor tyrosine kinase inhibitor moiety. In embodiments, $R^1$ is a platelet-derived growth factor (PDGFR) kinase inhibitor moiety, an epidermal growth factor (EGFR) kinase inhibitor moiety, a HER2 kinase inhibitor moiety, an insulin receptor kinase inhibitor moiety, an insulin-like growth factor 1 (IGF1R) kinase inhibitor moiety, a vascular endothelial growth factor (VEGFR) inhibitor, a stem cell factor (SCF) kinase inhibitor moiety, a fibroblast growth factor (FGF) kinase inhibitor moiety, a colon carcinoma kinase 4 (CCK4) kinase inhibitor moiety, a NGF kinase inhibitor moiety, a c-KIT kinase inhibitor moiety, or a hepatocyte growth factor receptor (HGFR) kinase inhibitor moiety. In embodiments, $R^1$ is a platelet-derived growth factor (PDGFR) kinase inhibitor moiety. In embodiments, $R^1$ is an epidermal growth factor (EGFR) kinase inhibitor moiety. In embodiments, $R^1$ is a vascular endothelial growth factor (VEGFR) kinase inhibitor moiety. In embodiments, $R^1$ is a c-KIT kinase inhibitor moiety.

In embodiments, $R^1$ is a non-receptor tyrosine kinase inhibitor moiety. In embodiments, $R^1$ is an Abi kinase inhibitor moiety, an Ack kinase inhibitor moiety, a Csk kinase inhibitor moiety, a Fak kinase inhibitor moiety, a Fes kinase inhibitor moiety, a Frk kinase inhibitor moiety, a Jak kinase inhibitor moiety, a Src kinase inhibitor moiety, a Syk kinase inhibitor moiety, or a Tec kinase inhibitor moiety. In embodiments, $R^1$ is a Src kinase inhibitor moiety. In embodiments, $R^1$ is a PERK kinase inhibitor moiety. In embodiments, $R^1$ is a GSK3 kinase inhibitor moiety. In embodiments, $R^1$ is a p38a MAPK kinase inhibitor moiety.

In embodiments, $R^1$ is a pseudokinase inhibitor moiety (e.g., a HER3 inhibitor moiety).

In embodiments, $R^1$ is a GTPase inhibitor moiety (e.g., K-Ras inhibitor, K-RAs4A inhibitor, K-Ras4B inhibitor).

In embodiments, $R^1$ is a histone modifying enzyme inhibitor moiety (e.g., SET3D).

In embodiments, $R^1$ is a monovalent an anti-cancer agent (e.g., as described herein). In embodiments, $R^1$ is a monovalent a chemotherapeutic agent (e.g., as described herein). In embodiments, $R^1$ is a monovalent anti-neurodegenerative disease agent (e.g., as described herein). In embodiments, $R^1$ is a monovalent anti-viral agent (e.g., as described herein).

In embodiments, $R^1$ is a monovalent anti-viral agent. In embodiments, $R^1$ is not a monovalent anti-viral agent. In embodiments, $R^1$ is not an anti-HIV agent. In embodiments, $R^1$ is not an HIV inhibitor. In embodiments, $R^1$ is not an HIV protease inhibitor. In embodiments, $R^1$ is not a viral protease inhibitor.

In embodiments, $R^1$ is not a monovalent HIV inhibitor. In embodiments, $R^1$ is not a monovalent HIV protease inhibitor. In embodiments, $R^1$ is not a monovalent viral protease inhibitor. In embodiments, $R^1$ is not a monovalent amprenavir, or analog thereof. In embodiments, $R^1$ is not a monovalent amprenavir. In embodiments, $R^1$ is not a monovalent 4-methoxy amprenavir, or analog thereof. In embodiments, $R^1$ is not a monovalent 4-methoxy amprenavir.

In embodiments, $R^1$ is not an amyloid P aggregation inhibitor. In embodiments, $R^1$ is not a monovalent Congo red, or analog thereof. In embodiments, $R^1$ is not a monovalent thioflavin T, or analog thereof. In embodiments, $R^1$ is not a monovalent curcumin, or analog thereof.

In embodiments, the monovalent Src kinase inhibitor is a monovalent dasatinib, monovalent saracatinib, monovalent bosutinib, or monovalent KX01, or an analog thereof.

In embodiments, the monovalent Raf, VEGFR, PDGFR, or c-Kit inhibitor is a monovalent sorafenib, monovalent imatinib, monovalent nilotinib, monovalent sunitinib, monovalent dasatinib, monovalent pazopanib, monovalent vandetanib, monovalent axitinib, monovalent levatinib, monovalent regorafenib, or an analog thereof.

In embodiments, the monovalent EGFR inhibitor is a monovalent lapatinib, monovalent erlotinib, monovalent gefitinib, monovalent vandetanib, monovalent osimertinib, monovalent regorafenib, monovalent AZD 9291, monovalent AG 1478, monovalent dacomitinib, monovalent afatinib, monovalent WZ 4002, monovalent CO-1686, monovalent neratinib, monovalent canertinib, monovalent AC-480, monovalent AZD 8931, monovalent AST 1306, or monovalent EKB 569, or an analog thereof.

In embodiments, the monovalent LRRK2 inhibitor is a monovalent staurosporine, monovalent K-252a, monovalent K-252b, monovalent G66976, monovalent GF109203X, monovalent Ro31-8220, monovalent 5-iodotubericidin, monovalent sorafenib, monovalent GW5074 (Raf-1 kinase inhibitor), monovalent indirubin-3'-monooxime, monovalent sunitinib, monovalent H-1152, monovalent Compound 4, monovalent Y-27632, monovalent SP600125, monovalent damnacanthal, monovalent LDN-73794, monovalent LDN-22684, monovalent CZC-25146, monovalent CZC-54252, monovalent LRRK2—IN-1, monovalent HG-10-102-1, monovalent GSK2578215A, monovalent JH-II-127, monovalent GNE-0877, monovalent GNE-9605, monovalent PF-06447475, monovalent MLi-2, or monovalent DNL201, or analog thereof.

In embodiments, the monovalent KRAS inhibitor is a monovalent KRAS G12C inhibitor, monovalent KRAS M72C inhibitor, monovalent AMG510, monovalent MRTX849, monovalent ARS-1620, or analog thereof.

In embodiments, the monovalent KRAS inhibitor is a monovalent KRAS G12C inhibitor, monovalent KRAS M72C inhibitor, monovalent MRTX849, monovalent ARS-1620, or analog thereof.

In embodiments, the monovalent PI4KIIIβ inhibitor is as described in *J. Med. Chem.,* 2016, 59 (5), 1830-1839.

In embodiments, the monovalent PI4KIIIβ inhibitor is a monovalent form of a PI4K inhibitor as shown in FIG. 64 (and as described in *J. Med. Chem.,* 2016, 59 (5), 1830-1839, which is herein incorporated by reference in its entirety for all purposes). In embodiments, the monovalent PI4KIIIβ inhibitor is

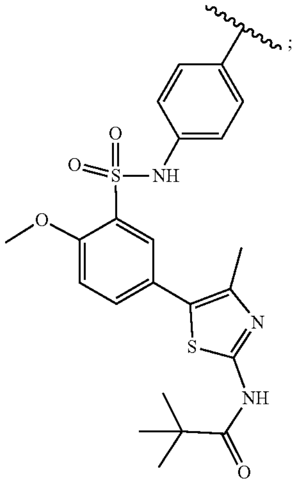 [SMILES: *c1ccc(NS(=O)(=O)c2cc(-c3sc(NC(=O)C(C)(C)C)nc3C)ccc2OC)cc1]

or an analog thereof.

In embodiments, $R^1$ is a monovalent MAP4K inhibitor. In embodiments, $R^1$ is a monovalent MAP4K4 inhibitor. In embodiments, $R^1$ is a monovalent HGK inhibitor. In embodiments, $R^1$ is a monovalent MAP3K inhibitor. In embodiments, $R^1$ is a monovalent MAP3K12 inhibitor. In embodiments, $R^1$ is a monovalent DLK inhibitor.

In embodiments, the monovalent HGK inhibitor is a monovalent compound 12k (as shown in FIG. 63 and as described in *Cell Chemical Biology,* 2019, 26, 1703-1715, which is herein incorporated by reference in its entirety and for all purposes). In embodiments, the monovalent HGK inhibitor is a monovalent URMC-099, a monovalent PF06260933, or a monovalent GNE-495.

In embodiments, the monovalent DLK inhibitor is a monovalent DLK inhibitor 8 (as shown in FIG. 63 and as described in *J. Med. Chem.,* 2018, 61, 8078-8087, which is herein incorporated by reference in its entirety and for all purposes). In embodiments, the monovalent DLK inhibitor is a monovalent sunitinib, monovalent tozasertib, monovalent GNE-8505, or monovalent GNE-3511.

In embodiments, $R^1$ is a monovalent form of an anti-cancer agent (e.g., as described herein).

In embodiments, $R^1$ is a monovalent form of

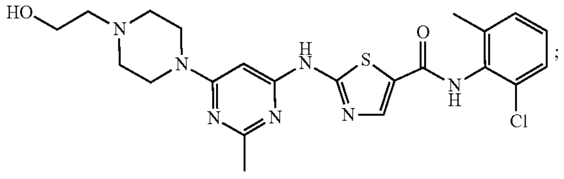 [SMILES: Cc1nc(Nc2ncc(C(=O)Nc3c(C)cccc3Cl)s2)cc(N2CCN(CCO)CC2)n1]

or an analog thereof.

In embodiments, $R^1$ is

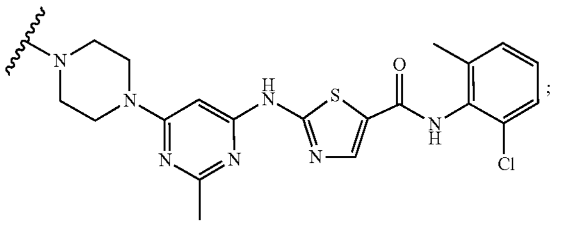 [SMILES: *N1CCN(c2cc(Nc3ncc(C(=O)Nc4c(C)cccc4Cl)s3)nc(C)n2)CC1]

or an analog thereof.

In embodiments, $R^1$ is

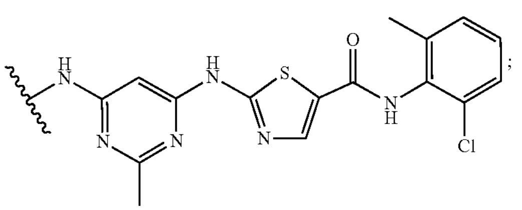 [SMILES: *Nc1cc(Nc2ncc(C(=O)Nc3c(C)cccc3Cl)s2)nc(C)n1]

or an analog thereof.

In embodiments, $R^1$ is

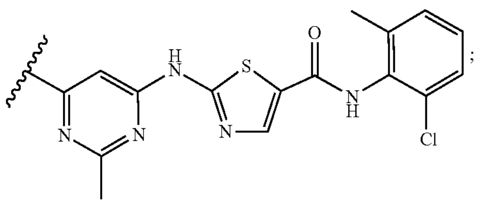 [SMILES: *c1cc(Nc2ncc(C(=O)Nc3c(C)cccc3Cl)s2)nc(C)n1]

or an analog thereof.

In embodiments, $R^1$ is

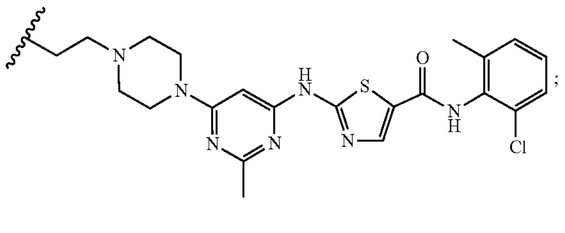 [SMILES: *CCN1CCN(c2cc(Nc3ncc(C(=O)Nc4c(C)cccc4Cl)s3)nc(C)n2)CC1]

or an analog thereof.

In embodiments, $R^1$ is

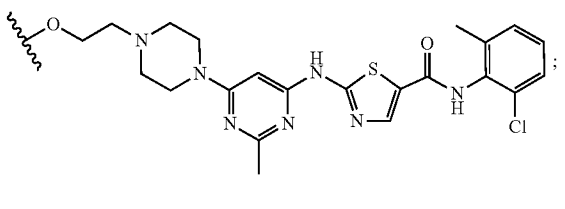 [SMILES: *OCCN1CCN(c2cc(Nc3ncc(C(=O)Nc4c(C)cccc4Cl)s3)nc(C)n2)CC1]

or an analog thereof.

In embodiments, $R^1$ is a monovalent form of

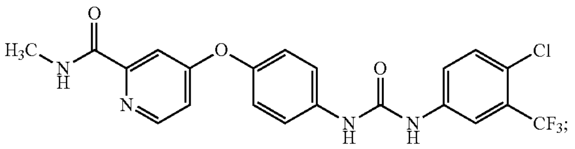 [SMILES: CNC(=O)c1cc(Oc2ccc(NC(=O)Nc3ccc(Cl)c(C(F)(F)F)c3)cc2)ccn1]

or an analog thereof.

In embodiments, $R^1$ is

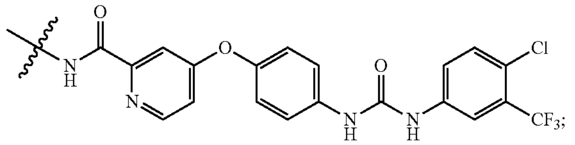 [SMILES: *NC(=O)c1cc(Oc2ccc(NC(=O)Nc3ccc(Cl)c(C(F)(F)F)c3)cc2)ccn1]

or an analog thereof.

In embodiments, $R^1$ is

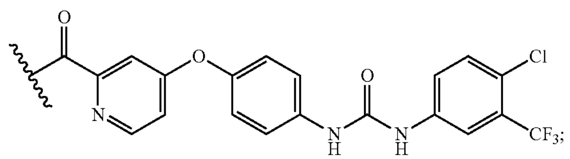 [SMILES: *C(=O)c1cc(Oc2ccc(NC(=O)Nc3ccc(Cl)c(C(F)(F)F)c3)cc2)ccn1]

or an analog thereof.

In embodiments, $R^1$ is

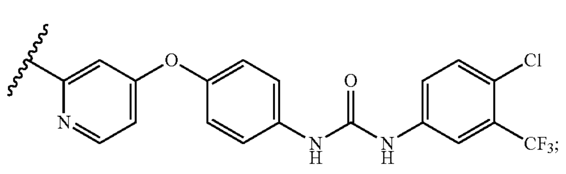 [SMILES: *c1cc(Oc2ccc(NC(=O)Nc3ccc(Cl)c(C(F)(F)F)c3)cc2)ccn1]

or an analog thereof.

In embodiments, $R^1$ is

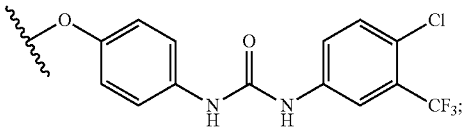 [SMILES: *Oc1ccc(NC(=O)Nc2ccc(Cl)c(C(F)(F)F)c2)cc1]

or an analog thereof.

In embodiments, $R^1$ is a monovalent form of
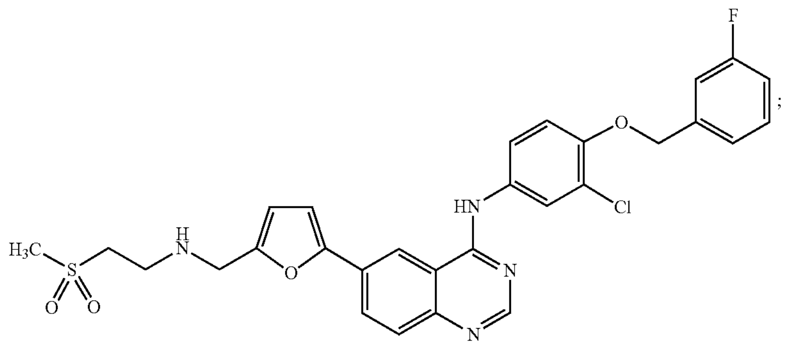 [SMILES: CS(=O)(=O)CCNCc1ccc(-c2ccc3ncnc(Nc4ccc(OCc5cccc(F)c5)c(Cl)c4)c3c2)o1]
or an analog thereof.
In embodiments, $R^1$ is
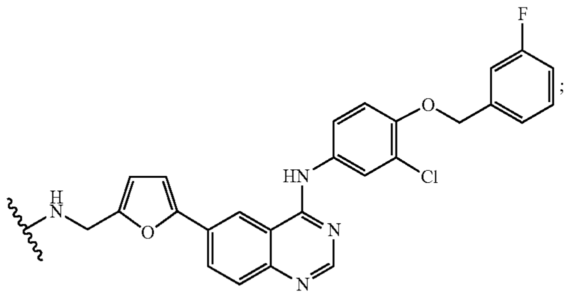 [SMILES: *NCc1ccc(-c2ccc3ncnc(Nc4ccc(OCc5cccc(F)c5)c(Cl)c4)c3c2)o1]
or an analog thereof.
In embodiments, $R^1$ is
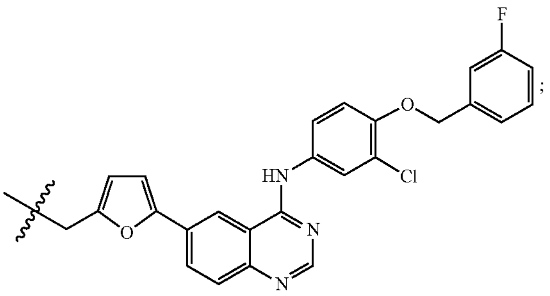 [SMILES: *Cc1ccc(-c2ccc3ncnc(Nc4ccc(OCc5cccc(F)c5)c(Cl)c4)c3c2)o1]
or an analog thereof.
In embodiments, $R^1$ is
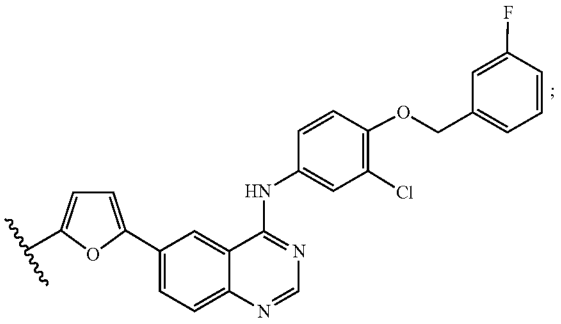 [SMILES: *c1ccc(-c2ccc3ncnc(Nc4ccc(OCc5cccc(F)c5)c(Cl)c4)c3c2)o1]
or an analog thereof.
In embodiments, $R^1$ is
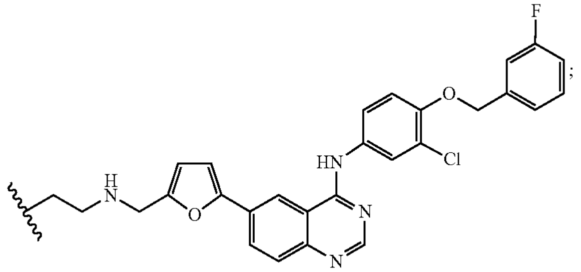 [SMILES: *CCNCc1ccc(-c2ccc3ncnc(Nc4ccc(OCc5cccc(F)c5)c(Cl)c4)c3c2)o1]
or an analog thereof.
In embodiments, $R^1$ is
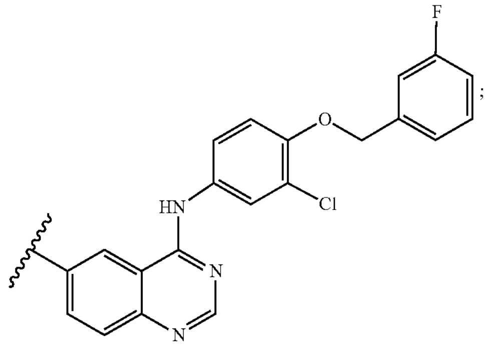 [SMILES: *c1ccc2ncnc(Nc3ccc(OCc4cccc(F)c4)c(Cl)c3)c2c1]
or an analog thereof.

In embodiments, $R^1$ is a monovalent form of

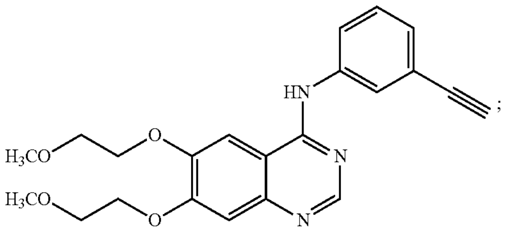 [SMILES: C#Cc1cccc(Nc2ncnc3cc(OCCOC)c(OCCOC)cc23)c1]

or an analog thereof.

In embodiments, $R^1$ is

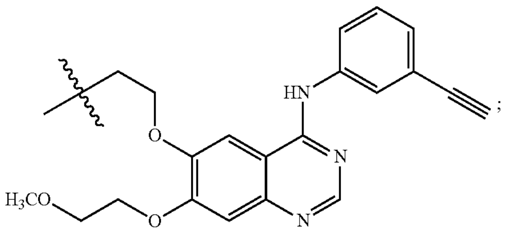 [SMILES: *CCOc1cc2c(Nc3cccc(C#C)c3)ncnc2cc1OCCOC]

or an analog thereof.

In embodiments, $R^1$ is

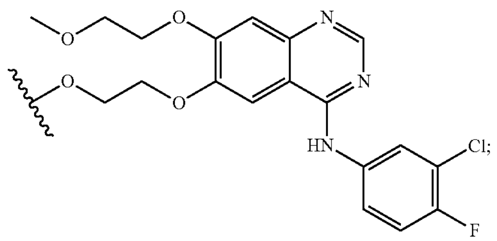 [SMILES: *OCCOc1cc2c(Nc3ccc(F)c(Cl)c3)ncnc2cc1OCCOC]

or an analog thereof.

In embodiments, $R^1$ is

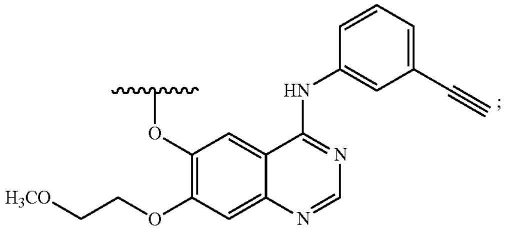 [SMILES: *Oc1cc2c(Nc3cccc(C#C)c3)ncnc2cc1OCCOC]

or an analog thereof.

In embodiments, $R^1$ is

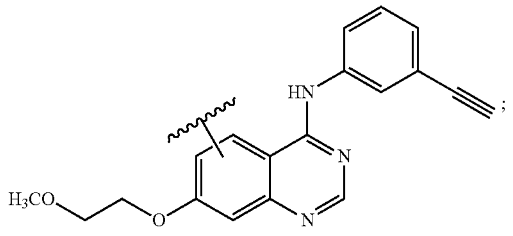

or an analog thereof.

In embodiments, $R^1$ is a monovalent form of F

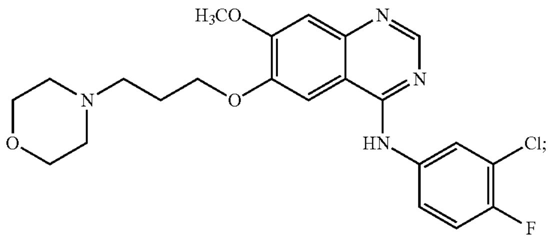 [SMILES: COc1cc2ncnc(Nc3ccc(F)c(Cl)c3)c2cc1OCCCN1CCOCC1]

or an analog thereof.

In embodiments, $R^1$ is

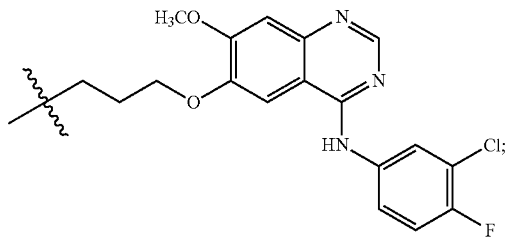 [SMILES: *CCCOc1cc2c(Nc3ccc(F)c(Cl)c3)ncnc2cc1OC]

or an analog thereof.

In embodiments, $R^1$ is

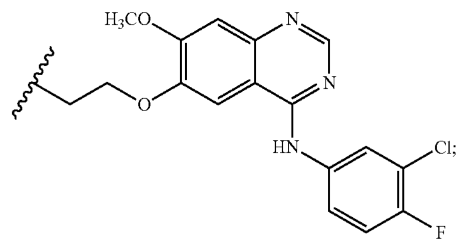 [SMILES: *CCOc1cc2c(Nc3ccc(F)c(Cl)c3)ncnc2cc1OC]

or an analog thereof.

In embodiments, $R^1$ is

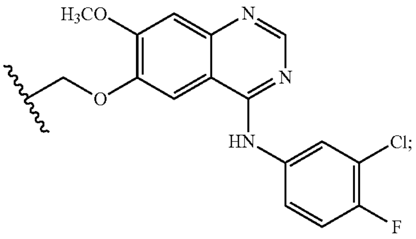 [SMILES: *COc1cc2c(Nc3ccc(F)c(Cl)c3)ncnc2cc1OC]

or an analog thereof.

In embodiments, $R^1$ is

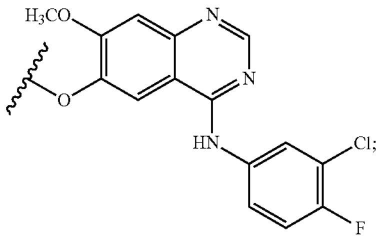 [SMILES: *Oc1cc2c(Nc3ccc(F)c(Cl)c3)ncnc2cc1OC]

or an analog thereof.

In embodiments, $R^1$ is

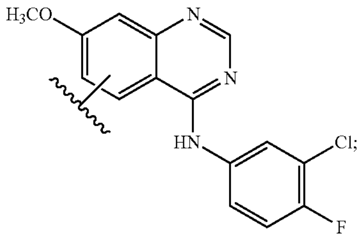

or an analog thereof.

In embodiments, $R^1$ is

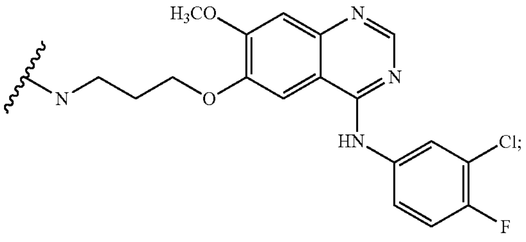 [SMILES: *NCCCOc1cc2c(Nc3ccc(F)c(Cl)c3)ncnc2cc1OC]

or an analog thereof.

In embodiments, $R^1$ is a monovalent form of

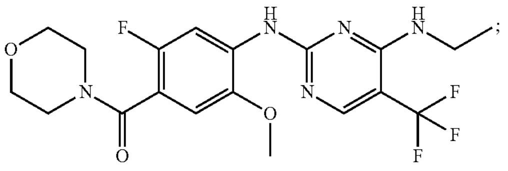 [SMILES: CCNc1nc(Nc2cc(F)c(C(=O)N3CCOCC3)cc2OC)ncc1C(F)(F)F]

or an analog thereof.

In embodiments, $R^1$ is

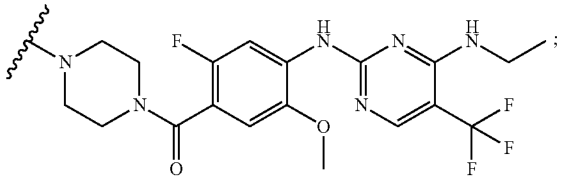 [SMILES: *N1CCN(C(=O)c2cc(OC)c(Nc3ncc(C(F)(F)F)c(NCC)n3)cc2F)CC1]

or an analog thereof.

In embodiments, $R^1$ is

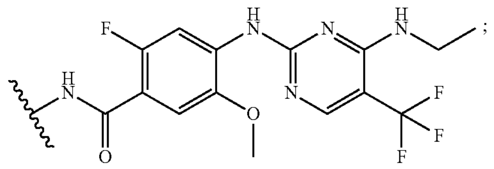 [SMILES: *NC(=O)c1cc(OC)c(Nc2ncc(C(F)(F)F)c(NCC)n2)cc1F]

or an analog thereof.

In embodiments, $R^1$ is

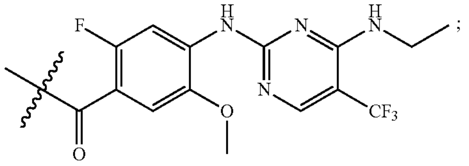 [SMILES: *C(=O)c1cc(OC)c(Nc2ncc(C(F)(F)F)c(NCC)n2)cc1F]

or an analog thereof.

In embodiments, $R^1$ is a monovalent form of

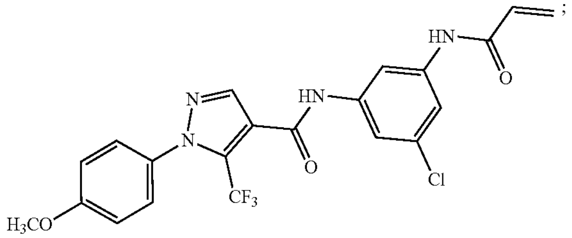 [SMILES: C=CC(=O)Nc1cc(Cl)cc(NC(=O)c2cnn(-c3ccc(OC)cc3)c2C(F)(F)F)c1]

or an analog thereof.

In embodiments, $R^1$ is
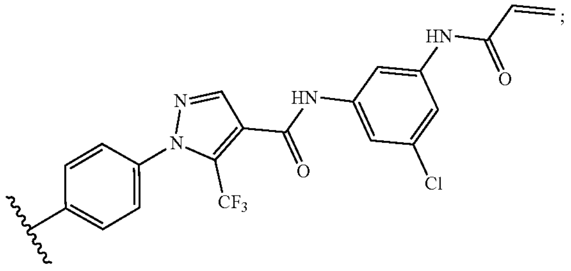 [SMILES: *c1ccc(-n2ncc(C(=O)Nc3cc(Cl)cc(NC(=O)C=C)c3)c2C(F)(F)F)cc1]
or an analog thereof.
In embodiments, $R^1$ is
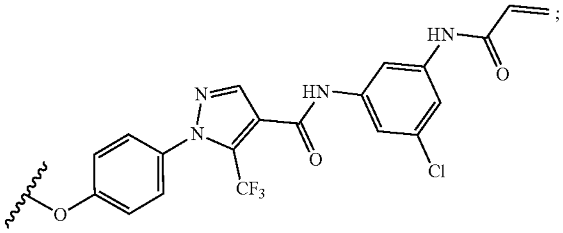 [SMILES: *Oc1ccc(-n2ncc(C(=O)Nc3cc(Cl)cc(NC(=O)C=C)c3)c2C(F)(F)F)cc1]
or an analog thereof.
In embodiments, $R^1$ is
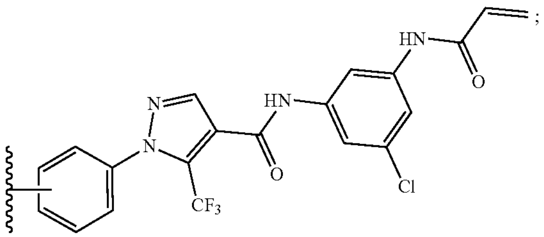
or an analog thereof.
In embodiments, $R^1$ is
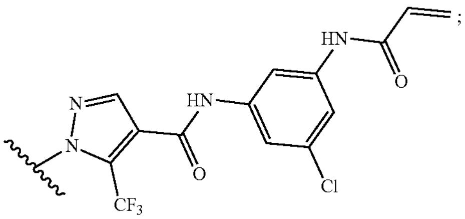 [SMILES: *n1ncc(C(=O)Nc2cc(Cl)cc(NC(=O)C=C)c2)c1C(F)(F)F]
or an analog thereof.
In embodiments, $R^1$ is
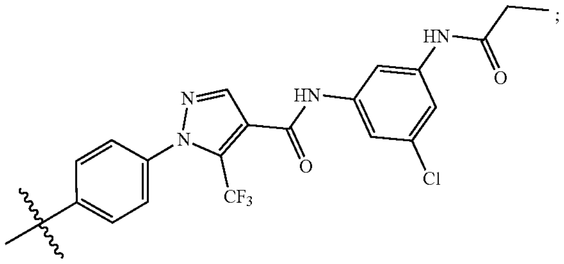 [SMILES: *c1ccc(-n2ncc(C(=O)Nc3cc(Cl)cc(NC(=O)CC)c3)c2C(F)(F)F)cc1]
or an analog thereof.
In embodiments, $R^1$ is
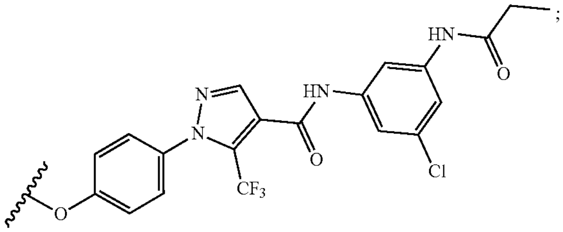 [SMILES: *Oc1ccc(-n2ncc(C(=O)Nc3cc(Cl)cc(NC(=O)CC)c3)c2C(F)(F)F)cc1]
or an analog thereof.
In embodiments, R is
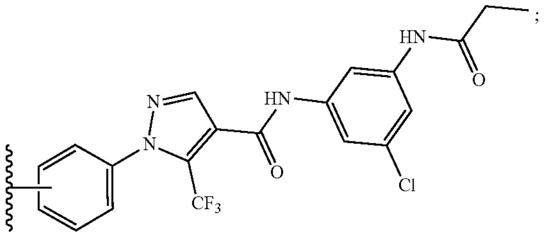
or an analog thereof.
In embodiments, $R^1$ is
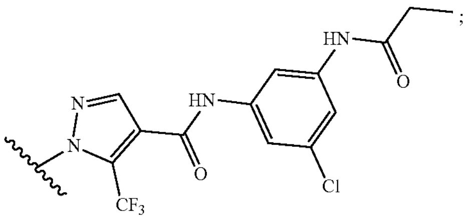 [SMILES: *n1ncc(C(=O)Nc2cc(Cl)cc(NC(=O)CC)c2)c1C(F)(F)F]
or an analog thereof.

In embodiments, $R^1$ is a monovalent form of

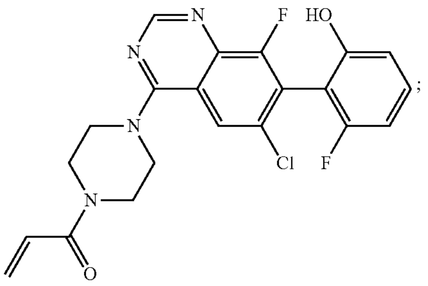 [SMILES: C=CC(=O)N1CCN(c2ncnc3c(F)c(-c4c(O)cccc4F)c(Cl)cc23)CC1]

or an analog thereof.

In embodiments, $R^1$ is

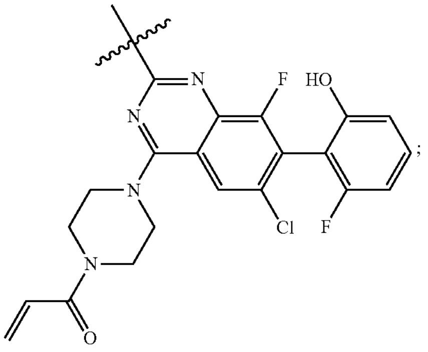 [SMILES: *c1nc(N2CCN(C(=O)C=C)CC2)c2cc(Cl)c(-c3c(O)cccc3F)c(F)c2n1]

or an analog thereof.

In embodiments, $R^1$ is

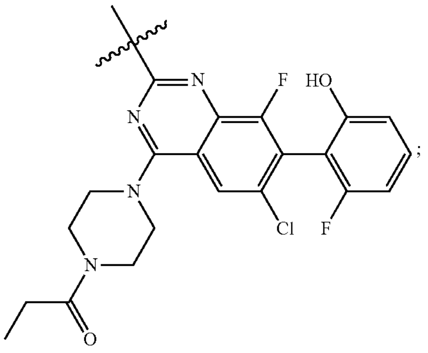 [SMILES: *c1nc(N2CCN(C(=O)CC)CC2)c2cc(Cl)c(-c3c(O)cccc3F)c(F)c2n1]

or an analog thereof.

In embodiments, $R^1$ is

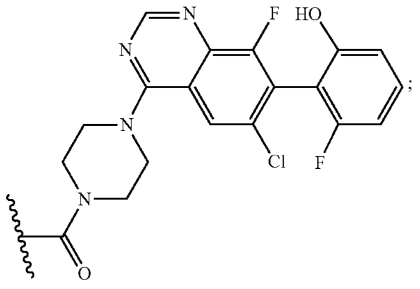 [SMILES: *C(=O)N1CCN(c2ncnc3c(F)c(-c4c(O)cccc4F)c(Cl)cc23)CC1]

or an analog thereof.

In embodiments, $R^1$ is

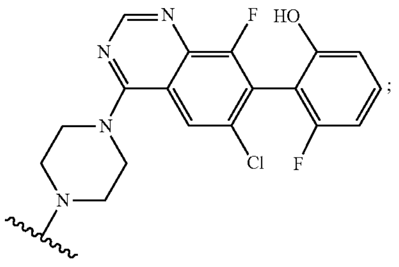 [SMILES: *N1CCN(c2ncnc3c(F)c(-c4c(O)cccc4F)c(Cl)cc23)CC1]

or an analog thereof.

In embodiments, $R^1$ is

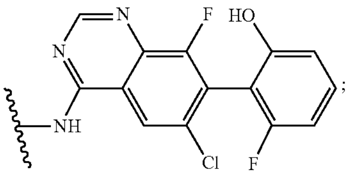 [SMILES: *Nc1ncnc2c(F)c(-c3c(O)cccc3F)c(Cl)cc12]

or an analog thereof.

In embodiments, $R^1$ is

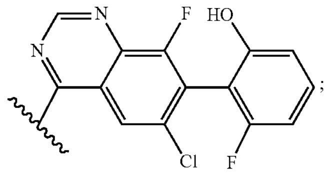 [SMILES: *c1ncnc2c(F)c(-c3c(O)cccc3F)c(Cl)cc12]

or an analog thereof.

In embodiments, $R^1$ is

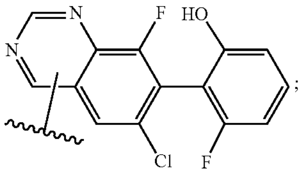

or an analog thereof.

In embodiments, $R^1$ is a monovalent form of

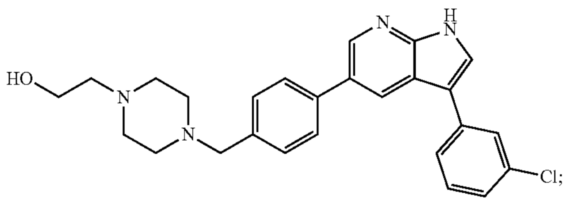 [SMILES: OCCN1CCN(Cc2ccc(-c3cnc4[nH]cc(-c5cccc(Cl)c5)c4c3)cc2)CC1]

or an analog thereof.

In embodiments, $R^1$ is

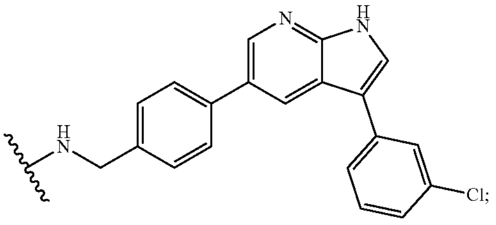 [SMILES: *NCc1ccc(-c2cnc3[nH]cc(-c4cccc(Cl)c4)c3c2)cc1]

or an analog thereof.

In embodiments, $R^1$ is

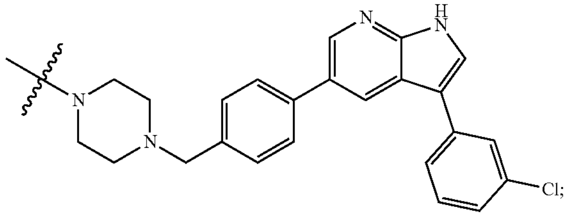 [SMILES: *N1CCN(Cc2ccc(-c3cnc4[nH]cc(-c5cccc(Cl)c5)c4c3)cc2)CC1]

or an analog thereof.

In embodiments, $R^1$ is

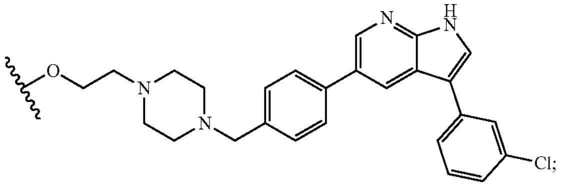 [SMILES: *OCCN1CCN(Cc2ccc(-c3cnc4[nH]cc(-c5cccc(Cl)c5)c4c3)cc2)CC1]

or an analog thereof.

In embodiments, $R^1$ is

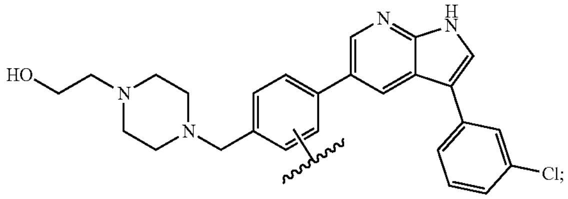

or an analog thereof.

In embodiments, $R^1$ is a monovalent form of

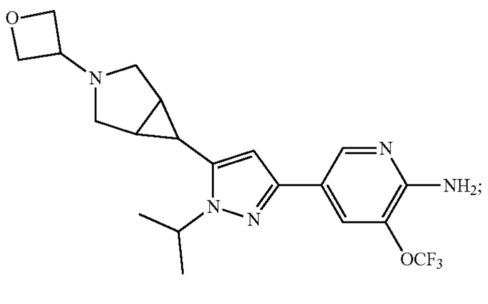 [SMILES: CC(C)n1nc(-c2cnc(N)c(OC(F)(F)F)c2)cc1C1C2CN(C3COC3)CC21]

or an analog thereof.

In embodiments, $R^1$ is

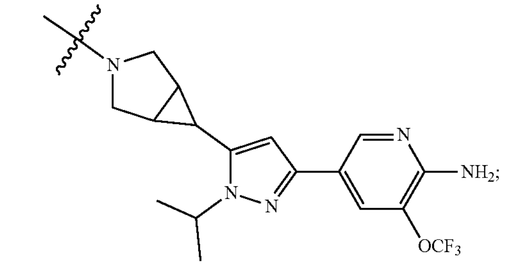 [SMILES: *N1CC2C(C1)C2c1cc(-c2cnc(N)c(OC(F)(F)F)c2)nn1C(C)C]

or an analog thereof.

In embodiments, $R^1$ is

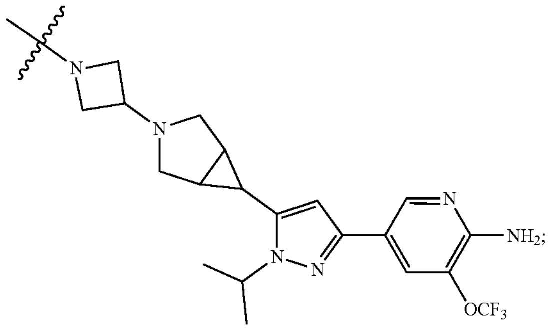 [SMILES: *N1CC(N2CC3C(C2)C3c2cc(-c3cnc(N)c(OC(F)(F)F)c3)nn2C(C)C)C1]

or an analog thereof.

In embodiments, $R^1$ is

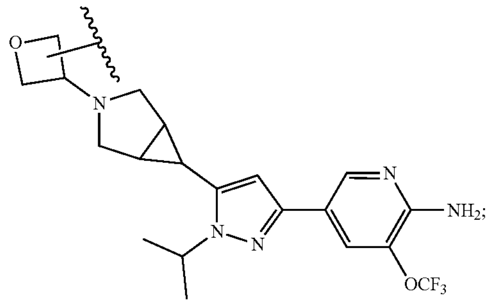

or an analog thereof.

In embodiments, $R^1$ is

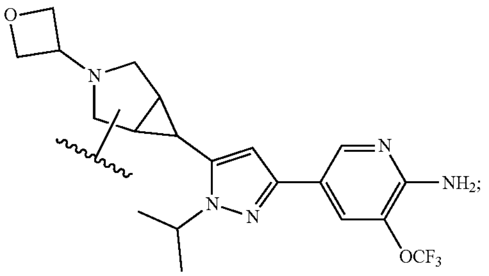

or an analog thereof.

In embodiments, $R^1$ is a monovalent form of
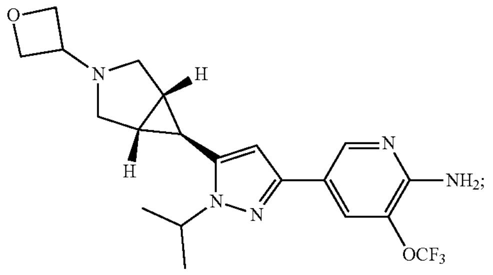 [SMILES: CC(C)n1nc(-c2cnc(N)c(OC(F)(F)F)c2)cc1[C@H]1[C@@H]2CN(C3COC3)C[C@@H]21]
or an analog thereof.
In embodiments, $R^1$ is
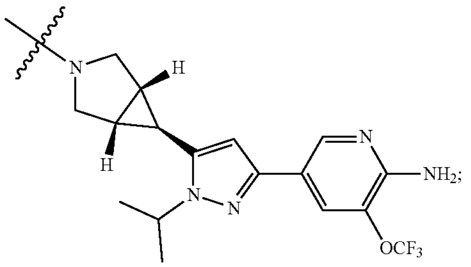 [SMILES: *N1C[C@@H]2[C@H](C1)[C@H]2c1cc(-c2cnc(N)c(OC(F)(F)F)c2)nn1C(C)C]
or an analog thereof.
In embodiments, $R^1$ is
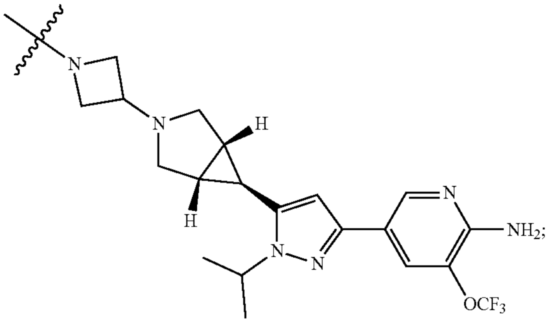 [SMILES: *N1CC(N2C[C@@H]3[C@H](C2)[C@H]3c2cc(-c3cnc(N)c(OC(F)(F)F)c3)nn2C(C)C)C1]
or an analog thereof.
In embodiments, $R^1$ is
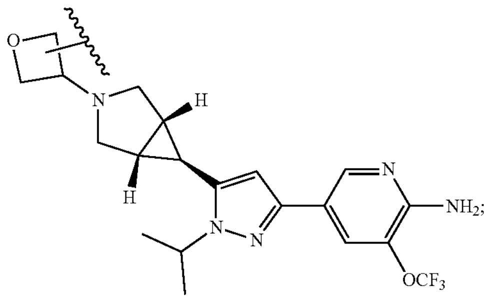
or an analog thereof.
In embodiments, $R^1$ is
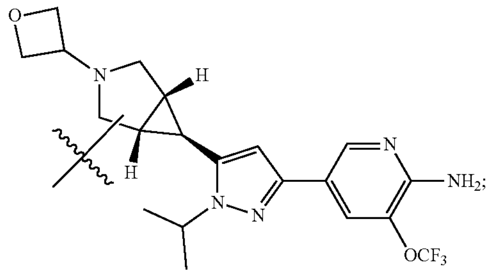
or an analog thereof.
In embodiments, $R^1$ is a monovalent form of
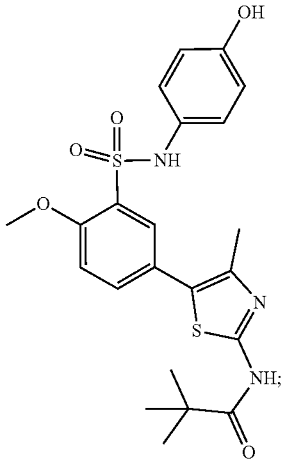 [SMILES: COc1ccc(-c2sc(NC(=O)C(C)(C)C)nc2C)cc1S(=O)(=O)Nc1ccc(O)cc1]
or an analog thereof.
In embodiments, $R^1$ is
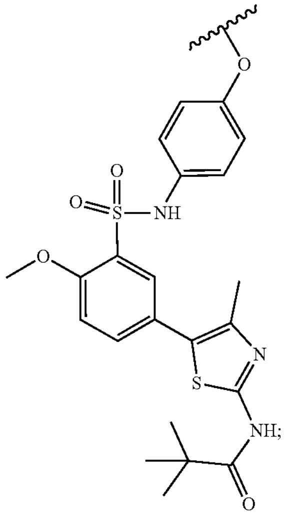 [SMILES: *Oc1ccc(NS(=O)(=O)c2cc(-c3sc(NC(=O)C(C)(C)C)nc3C)ccc2OC)cc1]
or an analog thereof.

In embodiments, $R^1$ is

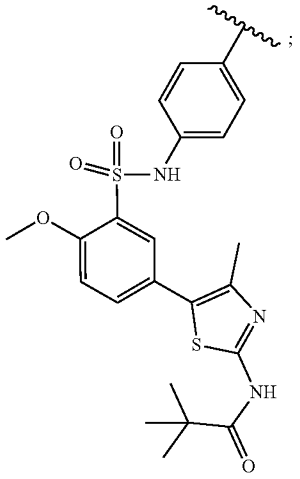 [SMILES: *c1ccc(NS(=O)(=O)c2cc(-c3sc(NC(=O)C(C)(C)C)nc3C)ccc2OC)cc1]

or an analog thereof.

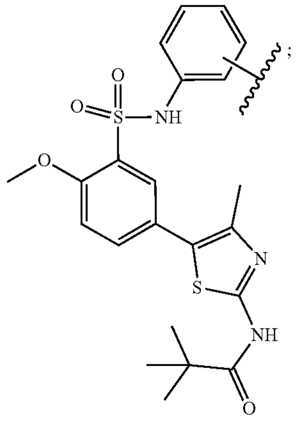

In embodiments, $R^1$ is

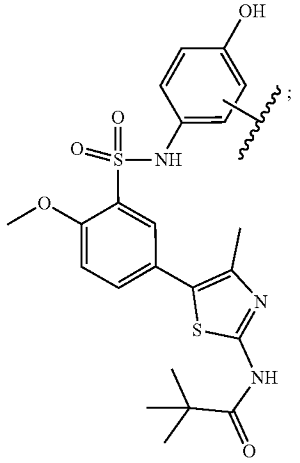

or an analog thereof.

In embodiments, $R^1$ is

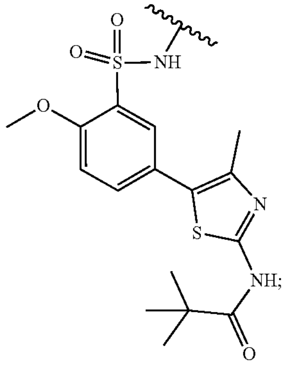 [SMILES: *NS(=O)(=O)c1cc(-c2sc(NC(=O)C(C)(C)C)nc2C)ccc1OC]

or an analog thereof.

In embodiments, $R^1$ is

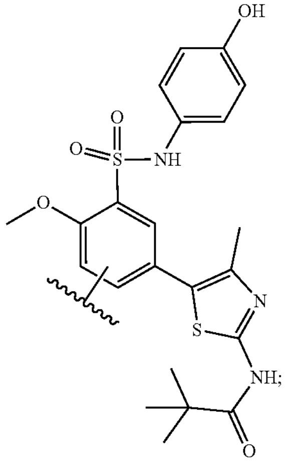

or an analog thereof.

In embodiments, $L^1$ is substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted arylene (e.g., $C_6$-$C_{10}$ or phenylene), or substituted (e.g., substituted with at least one substituent group, size-limited substituent group, or lower substituent group) or unsubstituted heteroarylene (e.g., 5 to 10 membered, 5 to 9 membered, or 5 to 6 membered).

In embodiments, a substituted $L^1$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^1$ is substituted with a plurality of groups selected from substituent groups, size-limited substituent groups, and lower substituent groups; each substituent group, size-limited substituent group, and/or lower substituent group may optionally be different. In embodiments, when $L^1$ is substituted, it is substituted with at least one substituent group. In embodiments, when $L^1$ is substituted, it is substituted with at least one size-limited substituent group. In embodiments, when $L^1$ is substituted, it is substituted with at least one lower substituent group.

In embodiments, $L^1$ is substituted or unsubstituted alkylene, substituted or unsubstituted heteroalkylene, substituted or unsubstituted heterocycloalkylene.

In embodiments, $L^1$ is substituted or unsubstituted $C_1$-$C_{10}$ alkylene, substituted or unsubstituted 2 to 15 membered heteroalkylene, or substituted or unsubstituted 5 to 6 membered heterocycloalkylene.

In embodiments, $L^1$ is substituted or unsubstituted $C_1$-$C_{10}$ alkylene. In embodiments, $L^1$ is substituted or unsubstituted $C_1$-$C_5$ alkylene. In embodiments, $L^1$ is substituted or unsubstituted $C_1$-$C_3$ alkylene. In embodiments, $L^1$ is substituted or unsubstituted $C_1$-$C_2$ alkylene. In embodiments, $L^1$ is substituted or unsubstituted 2 to 15 membered heteroalkylene. In embodiments, $L^1$ is substituted or unsubstituted 2 to 10 membered heteroalkylene. In embodiments, $L^1$ is oxo substituted 2 to 5 membered heteroalkylene. In embodiments, $L^1$ is substituted or unsubstituted 2 to 5 membered heteroalkylene. In embodiments, $L^1$ is substituted or unsubstituted 2 to 3 membered heteroalkylene. In embodiments, $L^1$ is oxo substituted 2 to 3 membered heteroalkylene. In embodiments, $L^1$ is substituted or unsubstituted 5 to 6 membered heterocycloalkylene. In embodiments, $L^1$ is substituted or unsubstituted piperazinylene. In embodiments, $L^1$ is unsubstituted piperazinylene.

In embodiments, $L^2$ is —O—, substituted or unsubstituted alkylene, substituted or unsubstituted heteroalkylene, substituted or unsubstituted heterocycloalkylene.

In embodiments, $L^2$ is —O—. In embodiments, $L^2$ is —NH—. In embodiments, $L^2$ is substituted or unsubstituted $C_1$-$C_{10}$ alkylene. In embodiments, $L^2$ is substituted or unsubstituted $C_1$-$C_5$ alkylene. In embodiments, $L^2$ is substituted or unsubstituted $C_1$-$C_3$ alkylene. In embodiments, $L^2$ is substituted or unsubstituted $C_1$-$C_2$ alkylene. In embodiments, $L^2$ is substituted or unsubstituted $C_1$-$C_2$ alkylene. In embodiments, $L^2$ is oxo substituted $C_1$-$C_{10}$ alkylene. In embodiments, $L^2$ is oxo substituted $C_2$-$C_3$ alkylene. In embodiments, $L^2$ is substituted or unsubstituted 2 to 15 membered heteroalkylene. In embodiments, $L^2$ is substituted or unsubstituted 2 to 10 membered heteroalkylene. In embodiments, $L^2$ is substituted or unsubstituted 2 to 5 membered heteroalkylene. In embodiments, $L^2$ is substituted or unsubstituted 2 to 3 membered heteroalkylene. In embodiments, $L^2$ is oxo substituted 2 to 15 membered heteroalkylene. In embodiments, $L^2$ is oxo substituted 2 to 10 membered heteroalkylene. In embodiments, $L^2$ is oxo substituted 2 to 5 membered heteroalkylene. In embodiments, $L^2$ is oxo substituted 2 to 3 membered heteroalkylene. In embodiments, $L^2$ is substituted or unsubstituted 5 to 6 membered heterocycloalkylene. In embodiments, $L^2$ is substituted or unsubstituted piperazinylene. In embodiments, $L^2$ is unsubstituted piperazinylene.

In embodiments, $L^3$ is substituted or unsubstituted alkylene, substituted or unsubstituted heteroalkylene, substituted or unsubstituted heterocycloalkylene, substituted or unsubstituted arylene, or substituted or unsubstituted heteroarylene.

In embodiments, $L^3$ is substituted or unsubstituted $C_1$-$C_{10}$ alkylene. In embodiments, $L^3$ is substituted or unsubstituted $C_1$-$C_5$ alkylene. In embodiments, $L^3$ is substituted or unsubstituted $C_1$-$C_3$ alkylene. In embodiments, $L^3$ is substituted or unsubstituted $C_1$-$C_2$ alkylene. In embodiments, $L^3$ is substituted or unsubstituted $C_1$-$C_2$ alkylene. In embodiments, $L^3$ is substituted or unsubstituted $C_1$-$C_2$ alkylene. In embodiments, $L^3$ is oxo substituted $C_1$-$C_{10}$ alkylene. In embodiments, $L^3$ is oxo substituted $C_2$-$C_3$ alkylene. In embodiments, $L^3$ is substituted or unsubstituted 2 to 15 membered heteroalkylene. In embodiments, $L^3$ is substituted or unsubstituted 2 to 10 membered heteroalkylene In embodiments, $L^3$ is substituted or unsubstituted 2 to 5 membered heteroalkylene. In embodiments, $L^3$ is substituted or unsubstituted 2 to 3 membered heteroalkylene. In embodiments, $L^3$ is oxo substituted 2 to 15 membered heteroalkylene. In embodiments, $L^3$ is oxo substituted 2 to 10 membered heteroalkylene. In embodiments, $L^3$ is oxo substituted 2 to 5 membered heteroalkylene. In embodiments, $L^3$ is oxo substituted 2 to 3 membered heteroalkylene. In embodiments, $L^3$ is substituted or unsubstituted 5 to 6 membered heterocycloalkylene. In embodiments, $L^3$ is substituted or unsubstituted piperazinylene. In embodiments, $L^3$ is 5 to 6-membered substituted or unsubstituted arylene. In embodiments, $L^3$ is substituted or unsubstituted phenylene. In embodiments, $L^3$ is 5 to 6-membered substituted or unsubstituted heteroarylene. In embodiments, $L^3$ is substituted or unsubstituted pyridinylene. In embodiments, $L^3$ is substituted or unsubstituted furanylene. In embodiments, $L^3$ is unsubstituted pyridinylene. In embodiments, $L^3$ is unsubstituted furanylene.

In embodiments, $L^4$ is —O—. In embodiments, $L^4$ is —NH—. In embodiments, $L^4$ is substituted or unsubstituted $C_1$-$C_{10}$ alkylene. In embodiments, $L^4$ is substituted or unsubstituted $C_1$-$C_5$ alkylene. In embodiments, $L^4$ is substituted or unsubstituted $C_1$-$C_3$ alkylene. In embodiments, $L^4$ is substituted or unsubstituted $C_1$-$C_2$ alkylene. In embodiments, $L^4$ is substituted or unsubstituted $C_1$-$C_2$ alkylene. In embodiments, $L^4$ is oxo substituted $C_1$-$C_{10}$ alkylene. In embodiments, $L^4$ is oxo substituted $C_2$-$C_3$ alkylene. In embodiments, $L^4$ is substituted or unsubstituted 2 to 15 membered heteroalkylene. In embodiments, $L^4$ is substituted or unsubstituted 2 to 10 membered heteroalkylene. In embodiments, $L^4$ is substituted or unsubstituted 2 to 5 membered heteroalkylene. In embodiments, $L^4$ is substituted or unsubstituted 2 to 3 membered heteroalkylene. In embodiments, $L^4$ is oxo substituted 2 to 15 membered heteroalkylene. In embodiments, $L^4$ is oxo substituted 2 to 10 membered heteroalkylene. In embodiments, $L^4$ is oxo substituted 2 to 5 membered heteroalkylene. In embodiments, $L^4$ is oxo substituted 2 to 3 membered heteroalkylene. In embodiments, $L^4$ is substituted or unsubstituted 5 to 6 membered heterocycloalkylene. In embodiments, $L^4$ is substituted or unsubstituted piperazinylene.

In embodiments, $L^1$ is —NH—, —$NR^{23}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is $L^2$-$L^3$-$L^4$-$L^5$-$L^6$. In embodiments, $L^2$ is connected directly to a monovalent FK506 or a monovalent FK506 analog. In embodiments, $L^2$ is connected directly to a monovalent SLF or a monovalent SLF analog. In embodiments, $L^2$ is connected directly to a monovalent cyclosporin A or a monovalent cyclosporin A analog. In embodiments, $L^2$ is connected directly to a monovalent rapamycin or a monovalent rapamycin analog. In embodiments, $L^2$ is connected directly to a monovalent sangliferin A or a monovalent sangliferin A analog. In embodiments, $L^2$ is a bond, —NH—, —$NR^{26}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is a bond, —NH—, —$NR^{29}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bond, —NH—, —$NR^{32}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is a bond, —NH—, —$NR^{35}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^6$ is a bond, —NH—, —$NR^{38}$—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^6$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^1$ is a divalent linker including one or more amino acids. In embodiments, $L^1$ is a divalent linker consisting of amino acids. In embodiments, $L^1$ is a divalent linker including an amino acid analog. In embodiments, $L^1$ is a divalent linker including an amino acid mimetic. In embodiments, $L^1$ is a divalent linker consisting of amino acid analogs. In embodiments, $L^1$ is a divalent linker consisting of amino acid mimetics.

In embodiments, $L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, or —OC(O)—.

In embodiments, $L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, or —OC(O)—.

In embodiments, $L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, or —OC(O)—.

In embodiments, $L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, or —OC(O)—.

In embodiments, $L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, or —OC(O)—.

In embodiments, $L^2$ is a bond. In embodiments, $L^3$ is a bond. In embodiments, $L^4$ is a bond. In embodiments, $L^5$ is a bond. In embodiments, $L^6$ is a bond.

In embodiments, $L^2$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^2$ is substituted or unsubstituted 3 to 8 membered heteroalkylene. In embodiments, $L^2$ is—$CH_2CH_2OCH_2$—. In embodiments, $L^2$ is unsubstituted 3 to 8 membered heteroalkylene. In embodiments, $L^2$ is unsubstituted 3 to 6 membered heteroalkylene. In embodiments, $L^2$ is unsubstituted 3 to 5 membered heteroalkylene. In embodiments, $L^2$ is a divalent linker including one or more amino acids. In embodiments, $L^2$ is a divalent linker consisting of amino acids. In embodiments, $L^2$ is a divalent linker including an amino acid analog. In embodiments, $L^2$ is a divalent linker including an amino acid mimetic. In embodiments, $L^2$ is a divalent linker consisting of amino acid analogs. In embodiments, $L^2$ is a divalent linker consisting of amino acid mimetics. In embodiments, $L^2$ is a bioconjugate linker.

In embodiments, $L^3$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^3$ is a substituted or unsubstituted 5 to 10 membered heteroarylene. In embodiments, $L^3$ is a bond. In embodiments, $L^3$ is a substituted or unsubstituted 5 to 6 membered heteroarylene. In embodiments, $L^3$ is a unsubstituted 5 to 6 membered heteroarylene. In embodiments, $L^3$ is unsubstituted divalent triazole. In embodiments, $L^3$ is unsubstituted divalent 1H-1,2,3-triazole. In embodiments, $L^3$ is unsubstituted divalent 2H-1,2,3-triazole. In embodiments, $L^3$ is a divalent linker including one or more amino acids. In embodiments, $L^3$ is a divalent linker consisting of amino acids. In embodiments, $L^3$ is a divalent linker including an amino acid analog. In embodiments, $L^3$ is a divalent linker including an amino acid mimetic. In embodiments, $L^3$ is a divalent linker consisting of amino acid analogs. In embodiments, $L^3$ is a divalent linker consisting of amino acid mimetics. In embodiments, $L^3$ is a bioconjugate linker.

In embodiments, $L^4$ is a bond, substituted or unsubstituted G-C20 alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^4$ is a substituted or unsubstituted 2 to 12 membered heteroalkylene. In embodiments, $L^4$ is a substituted or unsubstituted 2 to 32 membered heteroalkylene. In embodiments, $L^4$ is a bond. In embodiments, $L^4$ is a divalent linker including one or more amino acids. In embodiments, $L^4$ is a divalent linker consisting of amino acids. In embodiments, $L^4$ is a divalent linker including an amino acid analog. In embodiments, $L^4$ is a divalent linker including an amino acid mimetic. In embodiments, $L^4$ is a divalent linker consisting of amino acid analogs. In embodiments, $L^4$ is a divalent linker consisting of amino acid mimetics. In embodiments, $L^4$ is a bioconjugate linker.

In embodiments, $L^5$ is a bond, substituted or unsubstituted G-C20 alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^5$ is a substituted or unsubstituted 2 to 12 membered heteroalkylene. In embodiments, $L^5$ is a substituted or unsubstituted 2 to 32 membered heteroalkylene. In embodiments, $L^5$ is a bond. In embodiments, $L^5$ is a divalent linker including one or more amino acids. In embodiments, $L^5$ is a divalent linker consisting of amino acids. In embodiments, $L^5$ is a divalent linker including an amino acid analog. In embodiments, $L^5$ is a divalent linker including an amino acid mimetic. In embodiments, $L^5$ is a divalent linker consisting of amino acid analogs. In embodiments, $L^5$ is a divalent linker consisting of amino acid mimetics. In embodiments, $L^5$ is a bioconjugate linker.

In embodiments, $L^6$ is a bond, substituted or unsubstituted G-C20 alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^6$ is a substituted or unsubstituted 2 to 12 membered heteroalkylene. In embodiments, $L^6$ is a substituted or unsubstituted 2 to 32 membered heteroalkylene. In embodiments, $L^6$ is a bond. In embodiments, $L^6$ is a divalent linker including one or more amino acids. In embodiments, $L^6$ is a divalent linker consisting of amino acids. In embodiments, $L^6$ is a divalent linker including an amino acid analog. In embodiments, $L^6$ is a divalent linker including an amino acid mimetic. In embodiments, $L^6$ is a divalent linker consisting of amino acid analogs. In embodiments, $L^6$ is a divalent linker consisting of amino acid mimetics. In embodiments, $L^6$ is a bioconjugate linker.

In embodiments, $L^5$ is a divalent oligomer of ethylene oxide. In embodiments, $L^5$ is a divalent polyethylene glycol. In embodiments, $L^5$ is a divalent oligomer of ethylene oxide having 2 to 30 linear atoms (carbon and oxygen) between the two termini connecting to the remainder of the compound. In embodiments, $L^5$ is a $-(CH_2)_4C(O)NH-$. In embodiments, $L^5$ is a 2 to 8 membered substituted heteroalkylene. In embodiments, $L^5$ is a 3 to 6 membered substituted heteroalkylene. In embodiments, $L^5$ is a 5 to 6 membered substituted heteroalkylene. In embodiments, $L^5$ is a 5 to 7 membered oxo substituted heteroalkylene. In embodiments, $L^5$ is an unsubstituted $C_1$-$C_6$ alkylene.

In embodiments, $L^4$ is a divalent oligomer of ethylene oxide. In embodiments, $L^4$ is a divalent polyethylene glycol. In embodiments, $L^4$ is a divalent oligomer of ethylene oxide having 2 to 30 linear atoms (carbon and oxygen) between the two termini connecting to the remainder of the compound. In embodiments, $L^4$ is $-(CH_2CH_2O)_bCH_2CH_2-$ and b is an integer from 1 to 16. In embodiments, $L^4$ is $-(CH_2CH_2O)_bCH_2-$ and b is an integer from 1 to 16. In embodiments, $L^4$ is $-(CH_2CH_2O)_b-$ and b is an integer from 1 to 16. In embodiments, b is an integer from 2 to 15. In embodiments, b is an integer from 3 to 14. In embodiments, b is an integer from 4 to 12. In embodiments, b is an integer from 5 to 10. In embodiments, b is an integer from 5 to 8. In embodiments, b is an integer from 6 to 7.

In embodiments, $L^4$-$L^5$ is a 2 to 36 membered substituted heteroalkylene. In embodiments, $L^4$-$L^5$ is a 2 to 34 membered substituted heteroalkylene. In embodiments, $L^4$-$L^5$ is a 2 to 32 membered substituted heteroalkylene. In embodiments, $L^4$-$L^5$ is a 2 to 30 membered substituted heteroalkylene. In embodiments, $L^4$-$L^5$ is a 2 to 28 membered substituted heteroalkylene. In embodiments, $L^4$-$L^5$ is a 2 to 24 membered substituted heteroalkylene. In embodiments, $L^4$-$L^5$ is a 2 to 30 membered substituted heteroalkylene. In embodiments, $L^4$-$L^5$ is a 2 to 22 membered substituted heteroalkylene. In embodiments, $L^4$-$L^5$ is a 2 to 20 membered substituted heteroalkylene. In embodiments, $L^4$-$L^5$ is a 2 to 18 membered substituted heteroalkylene. In embodiments, $L^4$-$L^5$ is a 2 to 16 membered substituted heteroalkylene. In embodiments, $L^4$-$L^5$ is a 2 to 14 membered substituted heteroalkylene. In embodiments, $L^4$-$L^5$ is a 2 to 12 membered substituted heteroalkylene. In embodiments, $L^4$-$L^5$ is a 4 to 36 membered substituted heteroalkylene. In embodiments, $L^4$-$L^5$ is a 6 to 36 membered substituted heteroalkylene. In embodiments, $L^4$-$L^5$ is a 8 to 36 membered substituted heteroalkylene. In embodiments, $L^4$-$L^5$ is a 10 to 36 membered substituted heteroalkylene. In embodiments, $L^4$-$L^5$ is a 12 to 36 membered substituted heteroalkylene. In embodiments, $L^4$-$L^5$ is a 14 to 36 membered substituted heteroalkylene. In embodiments, $L^4$-$L^5$ is a 16 to 36 membered substituted heteroalkylene. In embodiments, $L^4$-$L^5$ is a 18 to 36 membered substituted heteroalkylene. In embodiments, $L^4$-$L^5$ is a 20 to 36 membered substituted heteroalkylene. In embodiments, $L^4$-$L^5$ is a 22 to 36 membered substituted heteroalkylene. In embodiments, $L^4$-$L^5$ is a 24 to 36 membered substituted heteroalkylene. In embodiments, $L^4$-$L^5$ is a 4 to 32 membered substituted heteroalkylene. In embodiments, $L^4$-$L^5$ is a 4 to 28 membered substituted heteroalkylene. In embodiments, $L^4$-$L^5$ is a 8 to 26 membered substituted heteroalkylene. In embodiments, $L^4$-$L^5$ is a 12 to 26 membered substituted heteroalkylene. In embodiments, $L^4$-$L^5$ is a 16 to 26 membered substituted heteroalkylene. In embodiments, $L^4$-$L^5$ is a 20 to 26 membered substituted heteroalkylene. In embodiments, $L^4$-$L^5$ is a 22 to 26 membered substituted heteroalkylene.

In embodiments, $R^2$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group 11 may optionally be different. In embodiments, when $R^2$ is substituted, it is substituted with at 12 least one substituent group. In embodiments, when $R^2$ is substituted, it is substituted with at 13 least one size-limited substituent group. In embodiments, when $R^2$ is substituted, it is 14 substituted with at least one lower substituent group.

In embodiments, $R^3$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^4$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^5$ is independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^6$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with at least one substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, the linker is formed by a conjugation or bioconjugation reaction combining a first reactant moiety covalently bonded to the immunophilin binding moiety and a second reactant moiety covalently bonded to the $R^1$ moiety. In such embodiments, the anti-CNS disease drug formed by such conjugation or bioconjugation reaction (including anti-CNS disease drugs as described herein) may be referred to as a conjugate or bioconjugate or bioconjugate linker.

In some embodiments of the anti-CNS disease drugs provided herein, $L^1$ is independently $R^{23}$-substituted or unsubstituted alkylene, $R^{23}$-substituted or unsubstituted heteroalkylene, $R^{23}$-substituted or unsubstituted cycloalkylene, $R^{23}$-substituted or unsubstituted heterocycloalkylene, $R^{23}$-substituted or unsubstituted arylene, or $R^{23}$-substituted or unsubstituted heteroarylene.

In embodiments, $L^1$ is a bond, —NH—, —$NR^{23}$—, —S—, —O—, —C(O)—, —NHC(O)—, —C(O)NH—, —NHC(O)NH—, —NHC(NH)NH—, —C(S)—, $R^{23}$-substituted or unsubstituted $C_1$-$C_{20}$ alkylene, $R^{23}$-substituted or unsubstituted 2 to 20 membered heteroalkylene, $R^{23}$-substituted or unsubstituted $C_3$-$C_8$ cycloalkylene, $R^{23}$-substituted or unsubstituted 3 to 8 membered heterocycloalkylene, $R^{23}$-substituted or unsubstituted $C_6$-$C_{10}$ arylene, or $R^{23}$-substituted or unsubstituted 5 to 10 membered heteroarylene. In embodiments, $L^1$ is a bond. In embodiments, $L^1$ is —NH—. In embodiments, $L^1$ is —$NR^{23}$—. In embodiments, $L^1$ is —S—. In embodiments, $L^1$ is —O—. In embodiments, $L^1$ is —C(O)—. In embodiments, $L^1$ is —NHC(O)—. In embodiments, $L^1$ is —C(O)NH—. In embodiments, $L^1$ is —NHC(O)NH—. In embodiments, $L^1$ is —NHC(NH)NH—. In embodiments, $L^1$ is —C(S)—. In embodiments, $L^1$ is $R^{23}$-substituted or unsubstituted $C_1$-$C_{20}$ alkylene. In embodiments, $L^1$ is $R^{23}$-substituted or unsubstituted 2 to 20 membered heteroalkylene. In embodiments, $L^1$ is $R^{23}$-substituted or unsubstituted $C_3$-$C_8$ cycloalkylene. In embodiments, $L^1$ is $R^{23}$-substituted or unsubstituted 3 to 8 membered heterocycloalkylene. In embodiments, $L^1$ is $R^{23}$-substituted or unsubstituted $C_6$-$C_{10}$ arylene. In embodiments, $L^1$ is $R^{23}$-substituted or unsubstituted 5 to 10 membered heteroarylene. In embodiments, $L^1$ is $R^{23}$-substituted $C_1$-$C_{20}$ alkylene. In embodiments, $L^1$ is $R^{23}$-substituted 2 to 20 membered heteroalkylene. In embodiments, $L^1$ is $R^{23}$-substituted $C_3$-$C_8$ cycloalkylene. In embodiments, $L^1$ is $R^{23}$-substituted 3 to 8 membered heterocycloalkylene. In embodiments, $L^1$ is $R^{23}$-substituted $C_6$-$C_{10}$ arylene. In embodiments, $L^1$ is $R^{23}$-substituted 5 to 10 membered heteroarylene. In embodiments, $L^1$ is unsubstituted $C_1$-$C_{20}$ alkylene. In embodiments, $L^1$ is unsubstituted 2 to 20 membered heteroalkylene. In embodiments, $L^1$ is unsubstituted $C_3$-$C_8$ cycloalkylene. In embodiments, $L^1$ is unsubstituted 3 to 8 membered heterocycloalkylene. In embodiments, $L^1$ is unsubstituted $C_6$-$C_{10}$ arylene. In embodiments, $L^1$ is unsubstituted 5 to 10 membered heteroarylene. In embodiments, $L^1$ is $R^{23}$-substituted $C_1$-$C_{15}$ alkylene. In embodiments, $L^1$ is $R^{23}$-substituted 2 to 15 membered heteroalkylene. In embodiments, $L^1$ is $R^{23}$-substituted $C_3$-$C_6$ cycloalkylene. In embodiments, $L^1$ is $R^{23}$-substituted 3 to 6 membered heterocycloalkylene. In embodiments, $L^1$ is $R^{23}$-substituted phenylene. In embodiments, $L^1$ is $R^{23}$-substituted 5 to 6 membered heteroarylene. In embodiments, $L^1$ is unsubstituted $C_1$-$C_{15}$ alkylene. In embodiments, $L^1$ is unsubstituted 2 to 15 membered heteroalkylene. In embodiments, $L^1$ is unsubstituted $C_3$-$C_6$ cycloalkylene. In embodiments, $L^1$ is unsubstituted 3 to 6 membered heterocycloalkylene. In embodiments, $L^1$ is unsubstituted phenylene. In embodiments, $L^1$ is unsubstituted 5 to 6 membered heteroarylene. In embodiments, $L^1$ is $R^{23}$-substituted $C_1$-$C_{10}$ alkylene. In embodiments, $L^1$ is $R^{23}$-substituted 2 to 10 membered heteroalkylene. In embodiments, $L^1$ is $R^{23}$-substituted $C_4$-$C_6$ cycloalkylene. In embodiments, $L^1$ is $R^{23}$-substituted 4 to 6 membered heterocycloalkylene. In embodiments, $L^1$ is $R^{23}$-substituted phenylene. In embodiments, $L^1$ is $R^{23}$-substituted 5 membered heteroarylene. In embodiments, $L^1$ is $R^{23}$-substituted $C_1$-$C_8$ alkylene. In embodiments, $L^1$ is $R^{23}$-substituted 2 to 8 membered heteroalkylene. In embodiments, $L^1$ is $R^{23}$-substituted $C_5$-$C_6$ cycloalkylene. In embodiments, $L^1$ is $R^{23}$-substituted 5 to 6 membered heterocycloalkylene. In embodiments, $L^1$ is $R^{23}$-substituted 6 membered heteroarylene. In embodiments, $L^1$ is $R^{23}$-substituted $C_1$-$C_6$ alkylene. In embodiments, $L^1$ is $R^{23}$-substituted 2 to 6 membered heteroalkylene. In embodiments, $L^1$ is $R^{23}$-substituted $C_6$-$C_{20}$ alkylene. In embodiments, $L^1$ is $R^{23}$-substituted 6 to 20 membered heteroalkylene. In embodiments, $L^1$ is unsubstituted $C_1$-$C_{10}$ alkylene. In embodiments, $L^1$ is unsubstituted 2 to 10 membered heteroalkylene. In embodiments, $L^1$ is unsubstituted $C_4$-$C_6$ cycloalkylene. In embodiments, $L^1$ is unsubstituted 4 to 6 membered heterocycloalkylene. In embodiments, $L^1$ is unsubstituted phenylene. In embodiments, $L^1$ is unsubstituted 5 membered heteroarylene. In embodiments, $L^1$ is unsubstituted $C_1$-$C_8$ alkylene. In embodiments, $L^1$ is unsubstituted 2 to 8 membered heteroalkylene. In embodiments, $L^1$ is unsubstituted $C_5$-$C_6$ cycloalkylene. In embodiments, $L^1$ is unsubstituted 5 to 6 membered heterocycloalkylene. In embodiments, $L^1$ is unsubstituted 6 membered heteroarylene. In embodiments, $L^1$ is unsubstituted $C_1$-$C_6$ alkylene. In embodiments, $L^1$ is unsubstituted 2 to 6 membered heteroalkylene. In embodiments, $L^1$ is unsubstituted $C_6$-$C_{20}$ alkylene. In embodiments, $L^1$ is unsubstituted 6 to 20 membered heteroalkylene.

$R^{23}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In embodiments, $R^{23}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered).

In embodiments, $R^{23}$ is independently —$NH_2$. In embodiments, $R^{23}$ is independently —OH. In embodiments, $R^{23}$ is independently halogen. In embodiments, $R^{23}$ is independently —CN. In embodiments, $R^{23}$ is independently oxo. In embodiments, $R^{23}$ is independently —$CF_3$. In embodiments, $R^{23}$ is independently —COOH. In embodiments, $R^{23}$ is independently —$CONH_2$. In embodiments, $R^{23}$ is independently —$NO_2$. In embodiments, $R^{23}$ is independently —SH. In embodiments, $R^{23}$ is independently —$SO_3H$. In embodiments, $R^{23}$ is independently —$SO_4H$. In embodiments, $R^{23}$ is independently —$SO_2NH_2$. In embodiments, $R^{23}$ is independently —$NHNH_2$. In embodiments, $R^{23}$ is independently —$ONH_2$. In embodiments, $R^{23}$ is independently —NHC(O)$NHNH_2$. In embodiments, $R^{23}$ is independently —NHC(O)$NH_2$. In embodiments, $R^{23}$ is independently —$NHSO_2H$. In embodiments, $R^{23}$ is independently —NHC(O)H. In embodiments, $R^{23}$ is independently —NHC(O)OH. In embodiments, $R^{23}$ is independently —NHOH. In embodiments, $R^{23}$ is independently —$OCF_3$. In embodiments, $R^{23}$ is independently —$OCHF_2$. In embodiments, $R^{23}$ is independently —$CCl_3$. In embodiments, $R^{23}$ is independently —$CBr_3$. In embodiments, $R^{23}$ is independently —$CI_3$. In embodiments, $R^{23}$ is independently —F. In embodiments, $R^{23}$ is independently —Cl. In embodiments, $R^{23}$ is independently —Br. In embodiments, $R^{23}$ is independently —I. In embodiments, $R^{23}$ is independently $R^{24}$-substituted $C_1$-$C_4$ alkyl. In embodiments, $R^{23}$ is independently $R^{24}$-substituted 2 to 4 membered heteroalkyl. In embodiments, $R^{23}$ is independently $R^{24}$-substituted $C_3$-$C_6$ cycloalkyl. In embodiments, $R^{23}$ is independently $R^{24}$-substituted 3 to 6 membered heterocycloalkyl. In embodiments, $R^{23}$ is independently $R^{24}$-substituted phenyl. In embodiments, $R^{23}$ is independently $R^{24}$-substituted 5 to 6 membered heteroaryl. In embodiments, $R^{23}$ is independently unsubstituted $C_1$-$C_4$ alkyl. In 11 embodiments, $R^{23}$ is independently unsubstituted 2 to 4 membered heteroalkyl. In 12 embodiments, $R^{23}$ is independently unsubstituted $C_3$-$C_6$ cycloalkyl. In embodiments, $R^{23}$ is 13 independently unsubstituted 3 to 6 membered heterocycloalkyl. In embodiments, $R^{23}$ is 14 independently unsubstituted phenyl. In embodiments, $R^{23}$ is independently unsubstituted 5 to 6 membered heteroaryl.

$R^{24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In embodiments, $R^{24}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 8 membered, 3 to 6 membered, 4 to 6 membered, 4 to 5 membered, or 5 to 6 membered), $R^{25}$-substituted or unsubstituted aryl (e.g., $C_6$-$C_{10}$ or phenyl), or $R^{25}$-substituted or unsubstituted heteroaryl (e.g., 5 to 10 membered, 5 to 9 membered, or 5 to 6 membered).

In embodiments, $R^{24}$ is independently —$NH_2$. In embodiments, $R^{24}$ is independently —OH. In embodiments, $R^{24}$ is independently halogen. In embodiments, $R^{24}$ is independently —CN. In embodiments, $R^{24}$ is independently oxo. In embodiments, $R^{24}$ is independently —$CF_3$. In embodiments, $R^{24}$ is independently —COOH. In embodiments, $R^{24}$ is independently —$CONH_2$. In embodiments, $R^{24}$ is independently —$NO_2$. In embodiments, $R^{24}$ is independently —SH. In embodiments, $R^{24}$ is independently —$SO_3H$. In embodiments, $R^{24}$ is independently —$SO_4H$. In embodiments, $R^{24}$ is independently —$SO_2NH_2$. In embodiments, $R^{24}$ is independently —$NHNH_2$. In embodiments, $R^{24}$ is independently —$ONH_2$. In embodiments, $R^{24}$ is independently —NHC(O)$NHNH_2$. In embodiments, $R^{24}$ is independently —NHC(O)$NH_2$. In embodiments, $R^{24}$ is independently—$NHSO_2H$. In embodiments, $R^{24}$ is independently —NHC(O)H. In embodiments, $R^{24}$ is independently —NHC(O)OH. In embodiments, $R^{24}$ is independently —NHOH. In embodiments, $R^{24}$ is independently —$OCF_3$. In embodiments, $R^{24}$ is independently —$OCHF_2$. In embodiments, $R^{24}$ is independently —$CCl_3$. In embodiments, $R^{24}$ is independently —$CBr_3$. In embodiments, $R^{24}$ is independently —$CI_3$. In embodiments, $R^{24}$ is independently-F. In embodiments, $R^{24}$ is independently —Cl. In embodiments, $R^{24}$ is independently —Br. In embodiments, $R^{24}$ is independently —I. In embodiments, $R^{24}$ is independently $R^{25}$-substituted $C_1$-$C_4$ alkyl. In embodiments, $R^{24}$ is independently $R^{25}$-substituted 2 to 4 membered heteroalkyl. In embodiments, $R^{24}$ is independently $R^{25}$-substituted $C_3$-$C_6$ cycloalkyl. In embodiments, $R^{24}$ is independently $R^{25}$-substituted 3 to 6 membered heterocycloalkyl. In embodiments, $R^{24}$ is independently $R^{25}$-substituted phenyl. In embodiments, $R^{24}$ is independently $R^{25}$-substituted 5 to 6 membered heteroaryl. In embodiments, $R^{24}$ is independently unsubstituted $C_1$-$C_4$ alkyl. In embodiments, $R^{24}$ is independently unsubstituted 2 to 4 membered heteroalkyl. In embodiments, $R^{24}$ is independently unsubstituted $C_3$-$C_6$ cycloalkyl. In embodiments, $R^{24}$ is independently unsubstituted 3 to 6 membered heterocycloalkyl. In embodiments, $R^{24}$ is independently unsubstituted phenyl. In embodiments, $R^{24}$ is independently unsubstituted 5 to 6 membered heteroaryl.

In embodiments, $L^2$ is independently a bond, $R^{26}$-substituted or unsubstituted alkylene, $R^{26}$-substituted or unsubstituted heteroalkylene, $R^{26}$-substituted or unsubstituted cycloalkylene, $R^{26}$-substituted or unsubstituted heterocycloalkylene, $R^{26}$-substituted or unsubstituted arylene, or $R^{26}$-substituted or unsubstituted heteroarylene.

In embodiments, $L^2$ is independently bond, $R^{26}$-substituted or unsubstituted alkylene, $R^{26}$-substituted or unsubstituted heteroalkylene, $R^{26}$-substituted or unsubstituted cycloalkylene, $R^{26}$-substituted or unsubstituted heterocycloalkylene, $R^{26}$-substituted or unsubstituted arylene, or $R^{26}$-substituted or unsubstituted heteroarylene.

In embodiments, $L^2$ is a bond, —NH—, —$NR^{26}$—, —S—, —O—, —C(O)—, —NHC(O)—, —C(O)NH—, —NHC(O)NH—, —NHC(NH)NH—, —C(S)—, $R^{26}$-substituted or unsubstituted $C_1$-$C_{20}$ alkylene, $R^{26}$-substituted or unsubstituted 2 to 20 membered heteroalkylene, $R^{26}$-substituted or unsubstituted $C_3$-$C_8$ cycloalkylene, $R^{26}$-substituted or unsubstituted 3 to 8 membered heterocycloalkylene, $R^{26}$-substituted or unsubstituted $C_6$-$C_{10}$ arylene, or $R^{26}$-substituted or unsubstituted 5 to 10 membered heteroarylene. In embodiments, $L^2$ is a bond. In embodiments, $L^2$ is —NH—. In embodiments, $L^2$ is —$NR^{26}$—. In embodiments, $L^2$ is —S—. In embodiments, $L^2$ is —O—. In embodiments, $L^2$ is —C(O)—. In embodiments, $L^2$ is —NHC(O)—. In embodiments, $L^2$ is —C(O)NH—. In embodiments, $L^2$ is —NHC(O)NH—. In embodiments, $L^2$ is —NHC(NH)NH—. In embodiments, $L^2$ is —C(S)—. In embodiments, $L^2$ is $R^{26}$-substituted or unsubstituted $C_1$-$C_{20}$ alkylene. In embodiments, $L^2$ is $R^{26}$-substituted or unsubstituted 2 to 20 membered heteroalkylene. In embodiments, $L^2$ is $R^{26}$-substituted or unsubstituted $C_3$-$C_8$ cycloalkylene. In embodiments, $L^2$ is $R^{26}$-substituted or unsubstituted 3 to 8 membered heterocycloalkylene. In embodiments, $L^2$ is $R^{26}$-substituted or unsubstituted $C_6$-$C_{10}$ arylene. In embodiments, $L^2$ is $R^{26}$-substituted or unsubstituted 5 to 10 membered heteroarylene. In embodiments, $L^2$ is $R^{26}$-substituted $C_1$-$C_{20}$ alkylene. In embodiments, $L^2$ is $R^{26}$-substituted 2 to 20 membered heteroalkylene. In embodiments, $L^2$ is $R^{26}$-substituted $C_3$-$C_8$ cycloalkylene. In embodiments, $L^2$ is $R^{26}$-substituted 3 to 8 membered heterocycloalkylene. In embodiments, $L^2$ is $R^{26}$-substituted $C_6$-$C_{10}$ arylene. In embodiments, $L^2$ is $R^{26}$-substituted 5 to 10 membered heteroarylene. In embodiments, $L^2$ is unsubstituted $C_1$-$C_{20}$ alkylene. In embodiments, $L^2$ is unsubstituted 2 to 20 membered heteroalkylene. In embodiments, $L^2$ is unsubstituted $C_3$-$C_8$ cycloalkylene. In embodiments, $L^2$ is unsubstituted 3 to 8 membered heterocycloalkylene. In embodiments, $L^2$ is unsubstituted $C_6$-$C_{10}$ arylene. In embodiments, $L^2$ is unsubstituted 5 to 10 membered heteroarylene. In embodiments, $L^2$ is $R^{26}$-substituted $C_1$-$C_{15}$ alkylene. In embodiments, $L^2$ is $R^{26}$-substituted 2 to 15 membered heteroalkylene. In embodiments, $L^2$ is $R^{26}$-substituted $C_3$-$C_6$ cycloalkylene. In embodiments, $L^2$ is $R^{26}$-substituted 3 to 6 membered heterocycloalkylene. In embodiments, $L^2$ is $R^{26}$-substituted phenylene. In embodiments, $L^2$ is $R^{26}$-substituted 5 to 6 membered heteroarylene. In embodiments, $L^2$ is unsubstituted $C_1$-$C_{15}$ alkylene. In embodiments, $L^2$ is unsubstituted 2 to 15 membered heteroalkylene. In embodiments, $L^2$ is unsubstituted $C_3$-$C_6$ cycloalkylene. In embodiments, $L^2$ is unsubstituted 3 to 6 membered heterocycloalkylene. In embodiments, $L^2$ is unsubstituted phenylene. In embodiments, $L^2$ is unsubstituted 5 to 6 membered heteroarylene. In embodiments, $L^2$ is $R^{26}$-substituted $C_1$-$C_{10}$ alkylene. In embodiments, $L^2$ is $R^{26}$-substituted 2 to 10 membered heteroalkylene. In embodiments, $L^2$ is $R^{26}$-substituted $C_4$-$C_6$ cycloalkylene. In embodiments, $L^2$ is $R^{26}$-substituted 4 to 6 membered heterocycloalkylene. In embodiments, $L^2$ is $R^{26}$-substituted phenylene. In embodiments, $L^2$ is $R^{26}$-substituted 5 membered heteroarylene. In embodiments, $L^2$ is $R^{26}$-substituted $C_1$-$C_8$ alkylene. In embodiments, $L^2$ is $R^{26}$-substituted 2 to 8 membered heteroalkylene. In embodiments, $L^2$ is $R^{26}$-substituted $C_5$-$C_6$ cycloalkylene. In embodiments, $L^2$ is $R^{26}$-substituted 5 to 6 membered heterocycloalkylene. In embodiments, $L^2$ is $R^{26}$-substituted 6 membered heteroarylene. In embodiments, $L^2$ is $R^{26}$-substituted $C_1$-$C_6$ alkylene. In embodiments, $L^2$ is $R^{26}$-substituted 2 to 6 membered heteroalkylene. In embodiments, $L^2$ is $R^{26}$-substituted $C_6$-$C_{20}$ alkylene. In embodiments, $L^2$ is $R^{26}$-substituted 6 to 20 membered heteroalkylene. In embodiments, $L^2$ is unsubstituted $C_1$-$C_{10}$ alkylene. In embodiments, $L^2$ is unsubstituted 2 to 10 membered heteroalkylene. In embodiments, $L^2$ is unsubstituted $C_4$-$C_6$ cycloalkylene. In embodiments, $L^2$ is unsubstituted 4 to 6 membered heterocycloalkylene. In embodiments, $L^2$ is unsubstituted phenylene. In embodiments, $L^2$ is unsubstituted 5 membered heteroarylene. In embodiments, $L^2$ is unsubstituted $C_1$-$C_8$ alkylene. In embodiments, $L^2$ is unsubstituted 2 to 8 membered heteroalkylene. In embodiments, $L^2$ is unsubstituted $C_5$-$C_6$ cycloalkylene. In embodiments, $L^2$ is unsubstituted 5 to 6 membered heterocycloalkylene. In embodiments, $L^2$ is unsubstituted 6 membered heteroarylene. In embodiments, $L^2$ is unsubstituted $C_1$-$C_6$ alkylene. In embodiments, $L^2$ is unsubstituted 2 to 6 membered heteroalkylene. In embodiments, $L^2$ is unsubstituted $C_6$-$C_{20}$ alkylene. In embodiments, $L^2$ is unsubstituted 6 to 20 membered heteroalkylene.

$R^{26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$ substituted or unsubstituted heterocycloalkyl, $R^{27}$-substituted or unsubstituted aryl, or $R^{27}$-substituted or unsubstituted heteroaryl.

In embodiments, $R^{26}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, 2 to 3 membered, or 4 to 5 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 8 membered, 3 to 6 membered, 4 to 6 membered, 4 to 5 membered, or 5 to 6 membered), $R^{27}$-substituted or unsubstituted aryl (e.g., $C_6$-$C_{10}$ or phenyl), or $R^{27}$-substituted or unsubstituted heteroaryl (e.g., 5 to 10 membered, 5 to 9 membered, or 5 to 6 membered).

In embodiments, $R^{26}$ is independently —$NH_2$. In embodiments, $R^{26}$ is independently —OH. In embodiments, $R^{26}$ is independently halogen. In embodiments, $R^{26}$ is independently —CN. In embodiments, $R^{26}$ is independently oxo. In embodiments, $R^{26}$ is independently —$CF_3$. In embodiments, $R^{26}$ is independently —COOH. In embodiments, $R^{26}$ is independently —$CONH_2$. In embodiments, $R^{26}$ is independently —$NO_2$. In embodiments, $R^{26}$ is independently —SH. In embodiments, $R^{26}$ is independently —$SO_3H$. In embodiments, $R^{26}$ is independently —$SO_4H$. In embodiments, $R^{26}$ is independently —$SO_2NH_2$. In embodiments, $R^{26}$ is independently—$NHNH_2$. In embodiments, $R^{26}$ is independently-$ONH_2$. In embodiments, $R^{26}$ is independently —NHC(O)$NHNH_2$. In embodiments, $R^{26}$ is independently —NHC(O)$NH_2$. In embodiments, $R^{26}$ is independently —$NHSO_2H$. In embodiments, $R^{26}$ is independently —NHC (O)H. In embodiments, $R^{26}$ is independently —NHC(O)OH. In embodiments, $R^{26}$ is independently —NHOH. In embodiments, $R^{26}$ is independently —$OCF_3$. In embodiments, $R^{26}$ is independently —$OCHF_2$. In embodiments, $R^{26}$ is independently —$CCl_3$. In embodiments, $R^{26}$ is independently —$CBr_3$. In embodiments, $R^{26}$ is independently —$CI_3$. In embodiments, $R^{26}$ is independently —F. In embodiments, $R^{26}$ is independently —Cl. In embodiments, $R^{26}$ is independently —Br. In embodiments, $R^{26}$ is independently —I. In embodiments, $R^{26}$ is independently $R^{27}$-substituted $C_1$-$C_4$ alkyl. In embodiments, $R^{26}$ is independently $R^{27}$-substituted 2 to 4 membered heteroalkyl. In embodiments, $R^{26}$ is independently $R^{27}$-substituted $C_3$-$C_6$ cycloalkyl. In embodiments, $R^{26}$ is independently $R^{27}$-substituted 3 to 6 membered heterocycloalkyl. In embodiments, $R^{26}$ is independently $R^{27}$-substituted phenyl. In embodiments, $R^{26}$ is independently $R^{27}$-substituted 5 to 6 membered heteroaryl. In embodiments, $R^{26}$ is independently unsubstituted $C_1$-$C_4$ alkyl. In embodiments, $R^{26}$ is independently unsubstituted 2 to 4 membered heteroalkyl. In embodiments, $R^{26}$ is independently unsubstituted $C_3$-$C_6$ cycloalkyl. In embodiments, $R^{26}$ is independently unsubstituted 3 to 6 membered heterocycloalkyl. In embodiments, $R^{26}$ is independently unsubstituted phenyl. In embodiments, $R^{26}$ is independently unsubstituted 5 to 6 membered heteroaryl.

$R^{27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In embodiments, $R^{27}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, 2 to 3 membered, or 4 to 5 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 8 membered, 3 to 6 membered, 4 to 6 membered, 4 to 5 membered, or 5 to 6 membered), $R^{28}$-substituted or unsubstituted aryl (e.g., $C_6$-$C_{10}$ or phenyl), or $R^{28}$-substituted or unsubstituted heteroaryl (e.g., 5 to 10 membered, 5 to 9 membered, or 5 to 6 membered).

In embodiments, $R^{27}$ is independently —$NH_2$. In embodiments, $R^{27}$ is independently —OH. In embodiments, $R^{27}$ is independently halogen. In embodiments, $R^{27}$ is independently —CN. In embodiments, $R^{27}$ is independently oxo. In embodiments, $R^{27}$ is independently —$CF_3$. In embodiments, $R^{27}$ is independently —COOH. In embodiments, $R^{27}$ is independently —$CONH_2$. In embodiments, $R^{27}$ is independently —$NO_2$. In embodiments, $R^{27}$ is independently —SH. In embodiments, $R^{27}$ is independently —$SO_3H$. In embodiments, $R^{27}$ is independently —$SO_4H$. In embodiments, $R^{27}$ is independently —$SO_2NH_2$. In embodiments, $R^{27}$ is independently —$NHNH_2$. In embodiments, $R^{27}$ is independently —$ONH_2$. In embodiments, $R^{27}$ is independently —NHC(O)$NHNH_2$. In embodiments, $R^{27}$ is independently —NHC(O)$NH_2$. In embodiments, $R^{27}$ is independently —$NHSO_2H$. In embodiments, $R^{27}$ is independently —NHC(O)H. In embodiments, $R^{27}$ is independently —NHC(O)—OH. In embodiments, $R^{27}$ is independently —NHOH. In embodiments, $R^{27}$ is independently —$OCF_3$. In embodiments, $R^{27}$ is independently —$OCHF_2$. In embodiments, $R^{27}$ is independently —$CCl_3$. In embodiments, $R^{27}$ is independently —$CBr_3$. In embodiments, $R^{27}$ is independently —$CI_3$. In embodiments, $R^{27}$ is independently —F. In embodiments, $R^{27}$ is independently —Cl. In embodiments, $R^{27}$ is independently —Br. In embodiments, $R^{27}$ is independently —I. In embodiments, $R^{27}$ is independently $R^{28}$-substituted $C_1$-$C_4$ alkyl. In embodiments, $R^{27}$ is independently $R^{28}$-substituted 2 to 4 membered heteroalkyl. In embodiments, $R^{27}$ is independently $R^{28}$-substituted $C_3$-$C_6$ cycloalkyl. In embodiments, $R^{27}$ is independently $R^{28}$-substituted 3 to 6 membered heterocycloalkyl. In embodiments, $R^{27}$ is independently $R^{28}$-substituted phenyl. In embodiments, $R^{27}$ is independently $R^{28}$-substituted 5 to 6 membered heteroaryl. In embodiments, $R^{27}$ is independently unsubstituted $C_1$-$C_4$ alkyl. In embodiments, $R^{27}$ is independently unsubstituted 2 to 4 membered heteroalkyl. In embodiments, $R^{27}$ is independently unsubstituted $C_3$-$C_6$ cycloalkyl. In embodiments, $R^{27}$ is independently unsubstituted 3 to 6 membered heterocycloalkyl. In embodiments, $R^{27}$ is independently unsubstituted phenyl. In embodiments, $R^{27}$ is independently unsubstituted 5 to 6 membered heteroaryl.

In embodiments, $L^3$ is independently a bond, $R^{29}$-substituted or unsubstituted alkylene, $R^{29}$-substituted or unsubstituted heteroalkylene, $R^{29}$-substituted or unsubstituted cycloalkylene, $R^{29}$-substituted or unsubstituted heterocycloalkylene, $R^{29}$-substituted or unsubstituted arylene, or $R^{29}$-substituted or unsubstituted heteroarylene.

In embodiments, $L^3$ is a bond, —NH—, —$NR^{29}$—, —S—, —O—, —C(O)—, —NHC(O)—, —C(O)NH—, —NHC(O)NH—, —NHC(NH)NH—, —C(S)—, $R^{29}$-substituted or unsubstituted $C_1$-$C_{20}$ alkylene, $R^{29}$-substituted or unsubstituted 2 to 20 membered heteroalkylene, $R^{29}$-substituted or unsubstituted $C_3$-$C_8$ cycloalkylene, $R^{29}$-substituted or unsubstituted 3 to 8 membered heterocycloalkylene, $R^{29}$-substituted or unsubstituted $C_6$-$C_{10}$ arylene, or $R^{29}$-substituted or unsubstituted 5 to 10 membered heteroarylene. In embodiments, $L^3$ is a bond. In embodiments, $L^3$ is —NH—. In embodiments, $L^3$ is —$NR^{29}$—. In embodiments, $L^3$ is —S—. In embodiments, $L^3$ is —O—. In embodiments, $L^3$ is —C(O)—. In embodiments, $L^3$ is —NHC(O)—. In embodiments, $L^3$ is —C(O)NH—. In embodiments, $L^3$ is —NHC(O)NH—. In embodiments, $L^3$ is —NHC(NH)NH—. In embodiments, $L^3$ is —C(S)—. In embodiments, $L^3$ is $R^{29}$-substituted or unsubstituted $C_1$-$C_{20}$ alkylene. In embodiments, $L^3$ is $R^{29}$-substituted or unsubstituted 2 to 20 membered heteroalkylene. In embodiments, $L^3$ is $R^{29}$-substituted or unsubstituted $C_3$-$C_8$ cycloalkylene. In embodiments, $L^3$ is $R^{29}$-substituted or unsubstituted 3 to 8 membered heterocycloalkylene. In embodiments, $L^3$ is $R^{29}$-substituted or unsubstituted $C_6$-$C_{10}$ arylene. In embodiments, $L^3$ is $R^{29}$-substituted or unsubstituted 5 to 10 membered heteroarylene. In embodiments, $L^3$ is $R^{29}$-substituted $C_1$-$C_{20}$ alkylene. In embodiments, $L^3$ is $R^{29}$-substituted 2 to 20 membered heteroalkylene. In embodiments, $L^3$ is $R^{29}$-substituted $C_3$-$C_8$ cycloalkylene. In embodiments, $L^3$ is $R^{29}$-substituted 3 to 8 membered heterocycloalkylene. In embodiments, $L^3$ is $R^{29}$-substituted $C_6$-$C_{10}$ arylene. In embodiments, $L^3$ is $R^{29}$-substituted 5 to 10 membered heteroarylene. In embodiments, $L^3$ is unsubstituted $C_1$-$C_{20}$ alkylene. In embodiments, $L^3$ is unsubstituted 2 to 20 membered heteroalkylene. In embodiments, $L^3$ is unsubstituted $C_3$-$C_8$ cycloalkylene. In embodiments, $L^3$ is unsubstituted 3 to 8 membered heterocycloalkylene. In embodiments, $L^3$ is unsubstituted $C_6$-$C_{10}$ arylene. In embodiments, $L^3$ is unsubstituted 5 to 10 membered heteroarylene. In embodiments, $L^3$ is $R^{29}$-substituted $C_1$-$C_{15}$ alkylene. In embodiments, $L^3$ is $R^{29}$-substituted 2 to 15 membered heteroalkylene. In embodiments, $L^3$ is $R^{29}$-substituted $C_3$-$C_6$ cycloalkylene. In embodiments, $L^3$ is $R^{29}$-substituted 3 to 6 membered heterocycloalkylene. In embodiments, $L^3$ is $R^{29}$-substituted phenylene. In embodiments, $L^3$ is $R^{29}$-substituted 5 to 6 membered heteroarylene. In embodiments, $L^3$ is unsubstituted $C_1$-$C_{15}$ alkylene. In embodiments, $L^3$ is unsubstituted 2 to 15 membered heteroalkylene. In embodiments, $L^3$ is unsubstituted $C_3$-$C_6$ cycloalkylene. In embodiments, $L^3$ is unsubstituted 3 to 6 membered heterocycloalkylene. In embodiments, $L^3$ is unsubstituted phenylene. In embodiments, $L^3$ is unsubstituted 5 to 6 membered heteroarylene. In embodiments, $L^3$ is $R^{29}$-substituted $C_1$-$C_{10}$ alkylene. In embodiments, $L^3$ is $R^{29}$-substituted 2 to 10 membered heteroalkylene. In embodiments, $L^3$ is $R^{29}$-substituted $C_4$-$C_6$ cycloalkylene. In embodiments, $L^3$ is $R^{29}$-substituted 4 to 6 membered heterocycloalkylene. In embodiments, $L^3$ is $R^{29}$-substituted phenylene. In embodiments, $L^3$ is $R^{29}$-substituted 5 membered heteroarylene. In embodiments, $L^3$ is $R^{29}$-substituted $C_1$-$C_8$ alkylene. In embodiments, $L^3$ is $R^{29}$-substituted 2 to 8 membered heteroalkylene. In embodiments, $L^3$ is $R^{29}$-substituted $C_5$-$C_6$ cycloalkylene. In embodiments, $L^3$ is $R^{29}$-substituted 5 to 6 membered heterocycloalkylene. In embodiments, $L^3$ is $R^{29}$-substituted 6 membered heteroarylene. In embodiments, $L^3$ is $R^{29}$-substituted $C_1$-$C_6$ alkylene. In embodiments, $L^3$ is $R^{29}$-substituted 2 to 6 membered heteroalkylene. In embodiments, $L^3$ is $R^{29}$-substituted $C_6$-$C_{20}$ alkylene. In embodiments, $L^3$ is $R^{29}$-substituted 6 to 20 membered heteroalkylene. In embodiments, $L^3$ is unsubstituted $C_1$-$C_{10}$ alkylene. In embodiments, $L^3$ is unsubstituted 2 to 10 membered heteroalkylene. In embodiments, $L^3$ is unsubstituted $C_4$-$C_6$ cycloalkylene. In embodiments, $L^3$ is unsubstituted 4 to 6 membered heterocycloalkylene. In embodiments, $L^3$ is unsubstituted phenylene. In embodiments, $L^3$ is unsubstituted 5 membered heteroarylene. In embodiments, $L^3$ is unsubstituted $C_1$-$C_8$ alkylene. In embodiments, $L^3$ is unsubstituted 2 to 8 membered heteroalkylene. In embodiments, $L^3$ is unsubstituted $C_5$-$C_6$ cycloalkylene. In embodiments, $L^3$ is unsubstituted 5 to 6 membered heterocycloalkylene. In embodiments, $L^3$ is unsubstituted 6 membered heteroarylene. In embodiments, $L^3$ is unsubstituted $C_1$-$C_6$ alkylene. In embodiments, $L^3$ is unsubstituted 2 to 6 membered heteroalkylene. In embodiments, $L^3$ is unsubstituted $C_6$-$C_{20}$ alkylene. In embodiments, $L^3$ is unsubstituted 6 to 20 membered heteroalkylene.

$R^{29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

In embodiments, $R^{29}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 8 membered, 3 to 6 membered, 4 to 6 membered, 4 to 5 membered, or 5 to 6 membered), $R^{30}$-substituted or unsubstituted aryl (e.g., $C_6$-$C_{10}$ or phenyl), or $R^{30}$-substituted or unsubstituted heteroaryl (e.g., 5 to 10 membered, 5 to 9 membered, or 5 to 6 membered).

In embodiments, $R^{29}$ is independently —$NH_2$. In embodiments, $R^{29}$ is independently —OH. In embodiments, $R^{29}$ is independently halogen. In embodiments, $R^{29}$ is independently —CN. In embodiments, $R^{29}$ is independently oxo. In embodiments, $R^{29}$ is independently —$CF_3$. In embodiments, $R^{29}$ is independently —COOH. In embodiments, $R^{29}$ is independently —$CONH_2$. In embodiments, $R^{29}$ is independently —$NO_2$. In embodiments, $R^{29}$ is independently —SH. In embodiments, $R^{29}$ is independently —$SO_3H$. In embodiments, $R^{29}$ is independently —$SO_4H$. In embodiments, $R^{29}$ is independently —$SO_2NH_2$. In embodiments, $R^{29}$ is independently —$NHNH_2$. In embodiments, $R^{29}$ is independently —$ONH_2$. In embodiments, $R^{29}$ is independently —NHC(O)$NHNH_2$. In embodiments, $R^{29}$ is independently —NHC(O)$NH_2$. In embodiments, $R^{29}$ is independently —$NHSO_2H$. In embodiments, $R^{29}$ is independently —NHC(O)H. In embodiments, $R^{29}$ is independently —NHC(O)OH. In embodiments, $R^{29}$ is independently —NHOH. In embodiments, $R^{29}$ is independently —$OCF_3$. In embodiments, $R^{29}$ is independently —$OCHF_2$. In embodiments, $R^{29}$ is independently —$CCl_3$. In embodiments, $R^{29}$ is independently —$CBr_3$. In embodiments, $R^{29}$ is independently —$CI_3$. In embodiments, $R^{29}$ is independently —F. In embodiments, $R^{29}$ is independently —Cl. In embodiments, $R^{29}$ is independently —Br. In embodiments, $R^{29}$ is independently —I. In embodiments, $R^{29}$ is independently $R^{30}$-substituted $C_1$-$C_4$ alkyl. In embodiments, $R^{29}$ is independently $R^{30}$-substituted 2 to 4 membered heteroalkyl. In embodiments, $R^{29}$ is independently $R^{30}$-substituted $C_3$-$C_6$ cycloalkyl. In embodiments, $R^{29}$ is independently $R^{30}$-substituted 3 to 6 membered heterocycloalkyl. In embodiments, $R^{29}$ is independently $R^{30}$-substituted phenyl. In embodiments, $R^{29}$ is independently $R^{30}$-substituted 5 to 6 membered heteroaryl. In embodiments, $R^{29}$ is independently unsubstituted $C_1$-$C_4$ alkyl. In embodiments, $R^{29}$ is independently unsubstituted 2 to 4 membered heteroalkyl. In embodiments, $R^{29}$ is independently unsubstituted $C_3$-$C_6$ cycloalkyl. In embodiments, $R^{29}$ is independently unsubstituted 3 to 6 membered heterocycloalkyl. In embodiments, $R^{29}$ is independently unsubstituted phenyl. In embodiments, $R^{29}$ is independently unsubstituted 5 to 6 membered heteroaryl.

$R^{30}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In embodiments, $R^{30}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{31}$-substituted or unsubstituted alkyl (e.g., $C_1$-$C_8$, $C_1$-$C_6$, $C_1$-$C_4$, or $C_1$-$C_2$), $R^{31}$-substituted or unsubstituted heteroalkyl (e.g., 2 to 8 membered, 2 to 6 membered, 4 to 6 membered, 2 to 3 membered, or 4 to 5 membered), $R^{31}$-substituted or unsubstituted cycloalkyl (e.g., $C_3$-$C_8$, $C_3$-$C_6$, $C_4$-$C_6$, or $C_5$-$C_6$), $R^{31}$-substituted or unsubstituted heterocycloalkyl (e.g., 3 to 8 membered, 3 to 6 membered, 4 to 6 membered, 4 to 5 membered, or 5 to 6 membered), $R^{31}$-substituted or unsubstituted aryl (e.g., $C_6$-$C_{10}$ or phenyl), or $R^{31}$-substituted or unsubstituted heteroaryl (e.g., 5 to 10 membered, 5 to 9 membered, or 5 to 6 membered).

In embodiments, $R^{30}$ is independently —$NH_2$. In embodiments, $R^{30}$ is independently —OH. In embodiments, $R^{30}$ is independently halogen. In embodiments, $R^{30}$ is independently —CN. In embodiments, $R^{30}$ is independently oxo. In embodiments, $R^{30}$ is independently —$CF_3$. In embodiments, $R^{30}$ is independently —COOH. In embodiments, $R^{30}$ is independently —$CONH_2$. In embodiments, $R^{30}$ is independently —$NO_2$. In embodiments, $R^{30}$ is independently —SH. In embodiments, $R^{30}$ is independently —$SO_3H$. In embodiments, $R^{30}$ is independently —$SO_4H$. In embodiments, $R^{30}$ is independently —$SO_2NH_2$. In embodiments, $R^{30}$ is independently—$NHNH_2$. In embodiments, $R^{30}$ is independently-$ONH_2$. In embodiments, $R^{30}$ is independently —NHC(O)$NHNH_2$. In embodiments, $R^{30}$ is independently —NHC(O)$NH_2$. In embodiments, $R^{30}$ is independently —$NHSO_2H$. In embodiments, $R^{30}$ is independently —NHC(O)H. In embodiments, $R^{30}$ is independently —NHC(O)OH. In embodiments, $R^{30}$ is independently —NHOH. In embodiments, $R^{30}$ is independently —$OCF_3$. In embodiments, $R^{30}$ is independently —$OCHF_2$. In embodiments, $R^{30}$ is independently —$CCl_3$. In embodiments, $R^{30}$ is independently —$CBr_3$. In embodiments, $R^{30}$ is independently —$CI_3$. In embodiments, $R^{30}$ is independently —F. In embodiments, $R^{30}$ is independently —Cl. In embodiments, $R^{30}$ is independently —Br. In embodiments, $R^{30}$ is independently —I. In embodiments, $R^{30}$ is independently $R^{31}$-substituted $C_1$-$C_4$ alkyl. In embodiments, $R^{30}$ is independently $R^{31}$-substituted 2 to 4 membered heteroalkyl. In embodiments, $R^{30}$ is independently $R^{31}$-substituted $C_3$-$C_6$ cycloalkyl. In embodiments, $R^{30}$ is independently $R^{31}$-substituted 3 to 6 membered heterocycloalkyl. In embodiments, $R^{30}$ is independently $R^{31}$-substituted phenyl. In embodiments, $R^{30}$ is independently $R^{31}$-substituted 5 to 6 membered heteroaryl. In embodiments, $R^{30}$ is independently unsubstituted $C_1$-$C_4$ alkyl. In embodiments, $R^{30}$ is independently unsubstituted 2 to 4 membered heteroalkyl. In embodiments, $R^{30}$ is independently unsubstituted $C_3$-$C_6$ cycloalkyl. In embodiments, $R^{30}$ is independently unsubstituted 3 to 6 membered heterocycloalkyl. In embodiments, $R^{30}$ is independently unsubstituted phenyl. In embodiments, $R^{30}$ is independently unsubstituted 5 to 6 membered heteroaryl.

In some embodiments of the compounds provided herein, $L^4$ is independently a bond, $R^{32}$-substituted or unsubstituted alkylene, $R^{32}$-substituted or unsubstituted heteroalkylene, $R^{32}$-substituted or unsubstituted cycloalkylene, $R^{32}$-substituted or unsubstituted heterocycloalkylene, $R^{32}$-substituted or unsubstituted arylene, or $R^{32}$-substituted or unsubstituted heteroarylene.

In embodiments, $L^4$ is a bond, —NH—, —$NR^{32}$—, —S—, —O—, —C(O)—, —NHC(O)—, —C(O)NH—, —NHC(O)NH—, —NHC(NH)NH—, —C(S)—, $R^{32}$-substituted or unsubstituted $C_1$-$C_{20}$ alkylene, $R^{32}$-substituted or unsubstituted 2 to 20 membered heteroalkylene, $R^{32}$-substituted or unsubstituted $C_3$-$C_8$ cycloalkylene, $R^{32}$-substituted or unsubstituted 3 to 8 membered heterocycloalkylene, $R^{32}$-substituted or unsubstituted $C_6$-$C_{10}$ arylene, or $R^{32}$-substituted or unsubstituted 5 to 10 membered heteroarylene. In embodiments, $L^4$ is a bond. In embodiments, $L^4$ is —NH—. In embodiments, $L^4$ is —$NR^{32}$—. In embodiments, $L^4$ is —S—. In embodiments, $L^4$ is —O—. In embodiments, $L^4$ is —C(O)—. In embodiments, $L^4$ is —NHC(O)—. In embodiments, $L^4$ is —C(O)NH—. In embodiments, $L^4$ is —NHC(O)NH—. In embodiments, $L^4$ is —NHC(NH)NH—. In embodiments, $L^4$ is —C(S)—. In embodiments, $L^4$ is $R^{32}$-substituted or unsubstituted $C_1$-$C_{20}$ alkylene. In embodiments, $L^4$ is $R^{32}$-substituted or unsubstituted 2 to 20 membered heteroalkylene. In embodiments, $L^4$ is $R^{32}$-substituted or unsubstituted $C_3$-$C_8$ cycloalkylene. In embodiments, $L^4$ is $R^{32}$-substituted or unsubstituted 3 to 8 membered heterocycloalkylene. In embodiments, $L^4$ is $R^{32}$-substituted or unsubstituted $C_6$-$C_{10}$ arylene. In embodiments, $L^4$ is $R^{32}$-substituted or unsubstituted 5 to 10 membered heteroarylene. In embodiments, $L^4$ is $R^{32}$-substituted $C_1$-$C_{20}$ alkylene. In embodiments, $L^4$ is $R^{32}$-substituted 2 to 20 membered heteroalkylene. In embodiments, $L^4$ is $R^{32}$-substituted $C_3$-$C_8$ cycloalkylene. In embodiments, $L^4$ is $R^{32}$-substituted 3 to 8 membered heterocycloalkylene. In embodiments, $L^4$ is $R^{32}$-substituted $C_6$-$C_{10}$ arylene. In embodiments, $L^4$ is $R^{32}$-substituted 5 to 10 membered heteroarylene. In embodiments, $L^4$ is unsubstituted $C_1$-$C_{20}$ alkylene. In embodiments, $L^4$ is unsubstituted 2 to 20 membered heteroalkylene. In embodiments, $L^4$ is unsubstituted $C_3$-$C_8$ cycloalkylene. In embodiments, $L^4$ is unsubstituted 3 to 8 membered heterocycloalkylene. In embodiments, $L^4$ is unsubstituted $C_6$-$C_{10}$ arylene. In embodiments, $L^4$ is unsubstituted 5 to 10 membered heteroarylene. In embodiments, $L^4$ is $R^{32}$-substituted $C_1$-$C_{15}$ alkylene. In embodiments, $L^4$ is $R^{32}$-substituted 2 to 15 membered heteroalkylene. In embodiments, $L^4$ is $R^{32}$-substituted $C_3$-$C_6$ cycloalkylene. In embodiments, $L^4$ is $R^{32}$-substituted 3 to 6 membered heterocycloalkylene. In embodiments, $L^4$ is $R^{32}$-substituted phenylene. In embodiments, $L^4$ is $R^{32}$-substituted 5 to 6 membered heteroarylene. In embodiments, $L^4$ is unsubstituted $C_1$-$C_{15}$ alkylene. In embodiments, $L^4$ is unsubstituted 2 to 15 membered heteroalkylene. In embodiments, $L^4$ is unsubstituted $C_3$-$C_6$ cycloalkylene. In embodiments, $L^4$ is unsubstituted 3 to 6 membered heterocycloalkylene. In embodiments, $L^4$ is unsubstituted phenylene. In embodiments, $L^4$ is unsubstituted 5 to 6 membered heteroarylene. In embodiments, $L^4$ is $R^{32}$-substituted $C_1$-$C_{10}$ alkylene. In embodiments, $L^4$ is $R^{32}$-substituted 2 to 10 membered heteroalkylene. In embodiments, $L^4$ is $R^{32}$-substituted $C_4$-$C_6$ cycloalkylene. In embodiments, $L^4$ is $R^{32}$-substituted 4 to 6 membered heterocycloalkylene. In embodiments, $L^4$ is $R^{32}$-substituted phenylene. In embodiments, $L^4$ is $R^{32}$-substituted 5 membered heteroarylene. In embodiments, $L^4$ is $R^{32}$-substituted $C_1$-$C_8$ alkylene. In embodiments, $L^4$ is $R^{32}$-substituted 2 to 8 membered heteroalkylene. In embodiments, $L^4$ is $R^{32}$-substituted $C_5$-$C_6$ cycloalkylene. In embodiments, $L^4$ is $R^{32}$-substituted 5 to 6 membered heterocycloalkylene. In embodiments, $L^4$ is $R^{32}$-substituted 6 membered heteroarylene. In embodiments, $L^4$ is $R^{32}$-substituted $C_1$-$C_6$ alkylene. In embodiments, $L^4$ is $R^{32}$-substituted 2 to 6 membered heteroalkylene. In embodiments, $L^4$ is $R^{32}$-substituted $C_6$-$C_{20}$ alkylene. In embodiments, $L^4$ is $R^{32}$-substituted 6 to 20 membered heteroalkylene. In embodiments, $L^4$ is unsubstituted $C_1$-$C_{10}$ alkylene. In embodiments, $L^4$ is unsubstituted 2 to 10 membered heteroalkylene. In embodiments, $L^4$ is unsubstituted $C_4$-$C_6$ cycloalkylene. In embodiments, $L^4$ is unsubstituted 4 to 6 membered heterocycloalkylene. In embodiments, $L^4$ is unsubstituted phenylene. In embodiments, $L^4$ is unsubstituted 5 membered heteroarylene. In embodiments, $L^4$ is unsubstituted $C_1$-$C_8$ alkylene. In embodiments, $L^4$ is unsubstituted 2 to 8 membered heteroalkylene. In embodiments, $L^4$ is unsubstituted $C_5$-$C_6$ cycloalkylene. In embodiments, $L^4$ is unsubstituted 5 to 6 membered heterocycloalkylene. In embodiments, $L^4$ is unsubstituted 6 membered heteroarylene. In embodiments, $L^4$ is unsubstituted $C_1$-$C_6$ alkylene. In embodiments, $L^4$ is unsubstituted 2 to 6 membered heteroalkylene. In embodiments, $L^4$ is unsubstituted $C_6$-$C_{20}$ alkylene. In embodiments, $L^4$ is unsubstituted 6 to 20 membered heteroalkylene.

$R^{32}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In embodiments, $R^{32}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, 2 to 3 membered, or 4 to 5 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 8 membered, 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered).

In embodiments, $R^{32}$ is independently —$NH_2$. In embodiments, $R^{32}$ is independently —OH. In embodiments, $R^{32}$ is independently halogen. In embodiments, $R^{32}$ is independently —CN. In embodiments, $R^{32}$ is independently oxo. In embodiments, $R^{32}$ is independently —$CF_3$. In embodiments, $R^{32}$ is independently —COOH. In embodiments, $R^{32}$ is independently —$CONH_2$. In embodiments, $R^{32}$ is independently —$NO_2$. In embodiments, $R^{32}$ is independently —SH. In embodiments, $R^{32}$ is independently —$SO_3H$. In embodiments, $R^{32}$ is independently —$SO_4H$. In embodiments, $R^{32}$ is independently —$SO_2NH_2$. In embodiments, $R^{32}$ is independently—$NHNH_2$. In embodiments, $R^{32}$ is independently-$ONH_2$. In embodiments, $R^{32}$ is independently —NHC(O)$NHNH_2$. In embodiments, $R^{32}$ is independently —NHC(O)$NH_2$. In embodiments, $R^{32}$ is independently —$NHSO_2H$. In embodiments, $R^{32}$ is independently —NHC(O)H. In embodiments, $R^{32}$ is independently —NHC(O)OH. In embodiments, $R^{32}$ is independently —NHOH. In embodiments, $R^{32}$ is independently —$OCF_3$. In embodiments, $R^{32}$ is independently —$OCHF_2$. In embodiments, $R^{32}$ is independently —$CCl_3$. In embodiments, $R^{32}$ is independently —$CBr_3$. In embodiments, $R^{32}$ is independently —$CI_3$. In embodiments, $R^{32}$ is independently —F. In embodiments, $R^{32}$ is independently —Cl. In embodiments, $R^{32}$ is independently —Br. In embodiments, $R^{32}$ is independently —I. In embodiments, $R^{32}$ is independently $R^{33}$-substituted $C_1$-$C_4$ alkyl. In embodiments, $R^{32}$ is independently $R^{33}$-substituted 2 to 4 membered heteroalkyl. In embodiments, $R^{32}$ is independently $R^{33}$-substituted $C_3$-$C_6$ cycloalkyl. In embodiments, $R^{32}$ is independently $R^{33}$-substituted 3 to 6 membered heterocycloalkyl. In embodiments, $R^{32}$ is independently $R^{33}$-substituted phenyl. In embodiments, $R^{32}$ is independently $R^{33}$-substituted 5 to 6 membered heteroaryl. In embodiments, $R^{32}$ is independently unsubstituted $C_1$-$C_4$ alkyl. In embodiments, $R^{32}$ is independently unsubstituted 2 to 4 membered heteroalkyl. In embodiments, $R^{32}$ is independently unsubstituted $C_3$-$C_6$ cycloalkyl. In embodiments, $R^{32}$ is independently unsubstituted 3 to 6 membered heterocycloalkyl. In embodiments, $R^{32}$ is independently unsubstituted phenyl. In embodiments, $R^{32}$ is independently unsubstituted 5 to 6 membered heteroaryl.

$R^{33}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In embodiments, $R^{33}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{34}$-substituted or unsubstituted alkyl (e.g., $C_1$-$C_8$, $C_1$-$C_6$, $C_1$-$C_4$, or $C_1$-$C_2$), $R^{34}$-substituted or unsubstituted heteroalkyl (e.g., 2 to 8 membered, 2 to 6 membered, 4 to 6 membered, 2 to 3 membered, or 4 to 5 membered), $R^{34}$-substituted or unsubstituted cycloalkyl (e.g., $C_3$-$C_8$, $C_3$-$C_6$, $C_4$-$C_6$, or $C_5$-$C_6$), $R^{34}$-substituted or unsubstituted heterocycloalkyl (e.g., 3 to 8 membered, 3 to 6 membered, 4 to 6 membered, 4 to 5 membered, or 5 to 6 membered), $R^{34}$-substituted or unsubstituted aryl (e.g., $C_6$-$C_{10}$ or phenyl), or $R^{34}$-substituted or unsubstituted heteroaryl (e.g., 5 to 10 membered, 5 to 9 membered, or 5 to 6 membered).

In embodiments, $R^{33}$ is independently —$NH_2$. In embodiments, $R^{33}$ is independently —OH. In embodiments, $R^{33}$ is independently halogen. In embodiments, $R^{33}$ is independently —CN. In embodiments, $R^{33}$ is independently oxo. In embodiments, $R^{33}$ is independently —$CF_3$. In embodiments, $R^{33}$ is independently —COOH. In embodiments, $R^{33}$ is independently —$CONH_2$. In embodiments, $R^{33}$ is independently —$NO_2$. In embodiments, $R^{33}$ is independently —SH. In embodiments, $R^{33}$ is independently —$SO_3H$. In embodiments, $R^{33}$ is independently —$SO_4H$. In embodiments, $R^{33}$ is independently —$SO_2NH_2$. In embodiments, $R^{33}$ is independently —$NHNH_2$. In embodiments, $R^{33}$ is independently —$ONH_2$. In embodiments, $R^{33}$ is independently —NHC(O)$NHNH_2$. In embodiments, $R^{33}$ is independently —NHC(O)$NH_2$. In embodiments, $R^{33}$ is independently —$NHSO_2H$. In embodiments, $R^{33}$ is independently —NHC(O)H. In embodiments, $R^{33}$ is independently —NHC(O)OH. In embodiments, $R^{33}$ is independently —NHOH. In embodiments, $R^{33}$ is independently —$OCF_3$. In embodiments, $R^{33}$ is independently —$OCHF_2$. In embodiments, $R^{33}$ is independently —$CCl_3$. In embodiments, $R^{33}$ is independently —$CBr_3$. In embodiments, $R^{33}$ is independently —$CI_3$. In embodiments, $R^{33}$ is independently —F. In embodiments, $R^{33}$ is independently —Cl. In embodiments, $R^{33}$ is independently —Br. In embodiments, $R^{33}$ is independently —I. In embodiments, $R^{33}$ is independently $R^{34}$-substituted $C_1$-$C_4$ alkyl. In embodiments, $R^{33}$ is independently $R^{34}$-substituted 2 to 4 membered heteroalkyl. In embodiments, $R^{33}$ is independently $R^{34}$-substituted $C_3$-$C_6$ cycloalkyl. In embodiments, $R^{33}$ is independently $R^{34}$-substituted 3 to 6 membered heterocycloalkyl. In embodiments, $R^{33}$ is independently $R^{34}$-substituted phenyl. In embodiments, $R^{33}$ is independently $R^{34}$-substituted 5 to 6 membered heteroaryl. In embodiments, $R^{33}$ is independently unsubstituted $C_1$-$C_4$ alkyl. In embodiments, $R^{33}$ is independently unsubstituted 2 to 4 membered heteroalkyl. In embodiments, $R^{33}$ is independently unsubstituted $C_3$-$C_6$ cycloalkyl. In embodiments, $R^{33}$ is independently unsubstituted 3 to 6 membered heterocycloalkyl. In embodiments, $R^{33}$ is independently unsubstituted phenyl. In embodiments, $R^{33}$ is independently unsubstituted 5 to 6 membered heteroaryl.

In embodiments, $L^5$ is independently a bond, $R^{35}$-substituted or unsubstituted alkylene, $R^{35}$-substituted or unsubstituted heteroalkylene, $R^{35}$-substituted or unsubstituted cycloalkylene, $R^{35}$-substituted or unsubstituted heterocycloalkylene, $R^{35}$-substituted or unsubstituted arylene, or $R^{35}$-substituted or unsubstituted heteroarylene.

In embodiments, $L^5$ is a bond, —NH—, —$NR^{35}$—, —S—, —O—, —C(O)—, —NHC(O)—, —C(O)NH—, —NHC(O)NH—, —NHC(NH)NH—, —C(S)—, $R^{35}$-substituted or unsubstituted $C_1$-$C_{20}$ alkylene, $R^{35}$-substituted or unsubstituted 2 to 20 membered heteroalkylene, $R^{35}$-substituted or unsubstituted $C_3$-$C_8$ cycloalkylene, $R^{35}$-substituted or unsubstituted 3 to 8 membered heterocycloalkylene, $R^{35}$-substituted or unsubstituted $C_6$-$C_{10}$ arylene, or $R^{35}$-substituted or unsubstituted 5 to 10 membered heteroarylene. In embodiments, $L^5$ is a bond. In embodiments, $L^5$ is —NH—. In embodiments, $L^5$ is —$NR^{35}$—. In embodiments, $L^5$ is —S—. In embodiments, $L^5$ is —O—. In embodiments, $L^5$ is —C(O)—. In embodiments, $L^5$ is —NHC(O)—. In embodiments, $L^5$ is —C(O)NH—. In embodiments, $L^5$ is —NHC(O)NH—. In embodiments, $L^5$ is —NHC(NH)NH—. In embodiments, $L^5$ is —C(S)—. In embodiments, $L^5$ is $R^{35}$-substituted or unsubstituted $C_1$-$C_{20}$ alkylene. In embodiments, $L^5$ is $R^{35}$-substituted or unsubstituted 2 to 20 membered heteroalkylene. In embodiments, $L^5$ is $R^{35}$-substituted or unsubstituted $C_3$-$C_8$ cycloalkylene. In embodiments, $L^5$ is $R^{35}$-substituted or unsubstituted 3 to 8 membered heterocycloalkylene. In embodiments, $L^5$ is $R^{35}$-substituted or unsubstituted $C_6$-$C_{10}$ arylene. In embodiments, $L^5$ is $R^{35}$-substituted or unsubstituted 5 to 10 membered heteroarylene. In embodiments, $L^5$ is $R^{35}$-substituted $C_1$-$C_{20}$ alkylene. In embodiments, $L^5$ is $R^{35}$-substituted 2 to 20 membered heteroalkylene. In embodiments, $L^5$ is $R^{35}$-substituted $C_3$-$C_8$ cycloalkylene. In embodiments, $L^5$ is $R^{35}$-substituted 3 to 8 membered heterocycloalkylene. In embodiments, $L^5$ is $R^{35}$-substituted $C_6$-$C_{10}$ arylene. In embodiments, $L^5$ is $R^{35}$-substituted 5 to 10 membered heteroarylene. In embodiments, $L^5$ is unsubstituted $C_1$-$C_{20}$ alkylene. In embodiments, $L^5$ is unsubstituted 2 to 20 membered heteroalkylene. In embodiments, $L^5$ is unsubstituted $C_3$-$C_8$ cycloalkylene. In embodiments, $L^5$ is unsubstituted 3 to 8 membered heterocycloalkylene. In embodiments, $L^5$ is unsubstituted $C_6$-$C_{10}$ arylene. In embodiments, $L^5$ is unsubstituted 5 to 10 membered heteroarylene. In embodiments, $L^5$ is $R^{35}$-substituted $C_1$-$C_{15}$ alkylene. In embodiments, $L^5$ is $R^{35}$-substituted 2 to 15 membered heteroalkylene. In embodiments, $L^5$ is $R^{35}$-substituted $C_3$-$C_6$ cycloalkylene. In embodiments, $L^5$ is $R^{35}$-substituted 3 to 6 membered heterocycloalkylene. In embodiments, $L^5$ is $R^{35}$-substituted phenylene. In embodiments, $L^5$ is $R^{35}$-substituted 5 to 6 membered heteroarylene. In embodiments, $L^5$ is unsubstituted $C_1$-$C_{15}$ alkylene. In embodiments, $L^5$ is unsubstituted 2 to 15 membered heteroalkylene. In embodiments, $L^5$ is unsubstituted $C_3$-$C_6$ cycloalkylene. In embodiments, $L^5$ is unsubstituted 3 to 6 membered heterocycloalkylene. In embodiments, $L^5$ is unsubstituted phenylene. In embodiments, $L^5$ is unsubstituted 5 to 6 membered heteroarylene. In embodiments, $L^5$ is $R^{35}$-substituted $C_1$-$C_{10}$ alkylene. In embodiments, $L^5$ is $R^{35}$-substituted 2 to 10 membered heteroalkylene. In embodiments, $L^5$ is $R^{35}$-substituted $C_4$-$C_6$ cycloalkylene. In embodiments, $L^5$ is $R^{35}$-substituted 4 to 6 membered heterocycloalkylene. In embodiments, $L^5$ is $R^{35}$-substituted phenylene. In embodiments, $L^5$ is $R^{35}$-substituted 5 membered heteroarylene. In embodiments, $L^5$ is $R^{35}$-substituted $C_1$-$C_8$ alkylene. In embodiments, $L^5$ is $R^{35}$-substituted 2 to 8 membered heteroalkylene. In embodiments, $L^5$ is $R^{35}$-substituted $C_5$-$C_6$ cycloalkylene. In embodiments, $L^5$ is $R^{35}$-substituted 5 to 6 membered heterocycloalkylene. In embodiments, $L^5$ is $R^{35}$-substituted 6 membered heteroarylene. In embodiments, $L^5$ is $R^{35}$-substituted $C_1$-$C_6$ alkylene. In embodiments, $L^5$ is $R^{35}$-substituted 2 to 6 membered heteroalkylene. In embodiments, $L^5$ is $R^{35}$-substituted $C_6$-$C_{20}$ alkylene. In embodiments, $L^5$ is $R^{35}$-substituted 6 to 20 membered heteroalkylene. In embodiments, $L^5$ is unsubstituted $C_1$-$C_{10}$ alkylene. In embodiments, $L^5$ is unsubstituted 2 to 10 membered heteroalkylene. In embodiments, $L^5$ is unsubstituted $C_4$-$C_6$ cycloalkylene. In embodiments, $L^5$ is unsubstituted 4 to 6 membered heterocycloalkylene. In embodiments, $L^5$ is unsubstituted phenylene. In embodiments, $L^5$ is unsubstituted 5 membered heteroarylene. In embodiments, $L^5$ is unsubstituted $C_1$-$C_8$ alkylene. In embodiments, $L^5$ is unsubstituted 2 to 8 membered heteroalkylene. In embodiments, $L^5$ is unsubstituted $C_5$-$C_6$ cycloalkylene. In embodiments, $L^5$ is unsubstituted 5 to 6 membered heterocycloalkylene. In embodiments, $L^5$ is unsubstituted 6 membered heteroarylene. In embodiments, $L^5$ is unsubstituted $C_1$-$C_6$ alkylene. In embodiments, $L^5$ is unsubstituted 2 to 6 membered heteroalkylene. In embodiments, $L^5$ is unsubstituted $C_6$-$C_{20}$ alkylene. In embodiments, $L^5$ is unsubstituted 6 to 20 membered heteroalkylene.

$R^{35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

In embodiments, $R^{35}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, 2 to 3 membered, or 4 to 5 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 8 membered, 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered).

In embodiments, $R^{35}$ is independently —$NH_2$. In embodiments, $R^{35}$ is independently —OH. In embodiments, $R^{35}$ is independently halogen. In embodiments, $R^{35}$ is independently —CN. In embodiments, $R^{35}$ is independently oxo. In embodiments, $R^{35}$ is independently —$CF_3$. In embodiments, $R^{35}$ is independently —COOH. In embodiments, $R^{35}$ is independently —$CONH_2$. In embodiments, $R^{35}$ is independently —$NO_2$. In embodiments, $R^{35}$ is independently —SH. In embodiments, $R^{35}$ is independently —$SO_3H$. In embodiments, $R^{35}$ is independently —$SO_4H$. In embodiments, $R^{35}$ is independently —$SO_2NH_2$. In embodiments, $R^{35}$ is independently —$NHNH_2$. In embodiments, $R^{35}$ is independently —$ONH_2$. In embodiments, $R^{35}$ is independently —NHC═(O)$NHNH_2$. In embodiments, $R^{35}$ is independently —NHC═(O)$NH_2$. In embodiments, $R^{35}$ is independently —$NHSO_2H$. In embodiments, $R^{35}$ is independently —NHC═(O)H. In embodiments, $R^{35}$ is independently —NHC(O)—OH. In embodiments, $R^{35}$ is independently —NHOH. In embodiments, $R^{35}$ is independently —$OCF_3$. In embodiments, $R^{35}$ is independently —$OCHF_2$. In embodiments, $R^{35}$ is independently —$CCl_3$. In embodiments, $R^{35}$ is independently —$CBr_3$. In embodiments, $R^{35}$ is independently —$CI_3$. In embodiments, $R^{35}$ is independently —F. In embodiments, $R^{35}$ is independently —Cl. In embodiments, $R^{35}$ is independently —Br. In embodiments, $R^{35}$ is independently —I. In embodiments, $R^{35}$ is independently $R^{36}$-substituted $C_1$-$C_4$ alkyl. In embodiments, $R^{35}$ is independently $R^{36}$-substituted 2 to 4 membered heteroalkyl. In embodiments, $R^{35}$ is independently $R^{36}$-substituted $C_3$-$C_6$ cycloalkyl. In embodiments, $R^{35}$ is independently $R^{36}$-substituted 3 to 6 membered heterocycloalkyl. In embodiments, $R^{35}$ is independently $R^{36}$-substituted phenyl. In embodiments, $R^{35}$ is independently $R^{36}$-substituted 5 to 6 membered heteroaryl. In embodiments, $R^{35}$ is independently unsubstituted $C_1$-$C_4$ alkyl. In embodiments, $R^{35}$ is independently unsubstituted 2 to 4 membered heteroalkyl. In embodiments, $R^{35}$ is independently unsubstituted $C_3$-$C_6$ cycloalkyl. In embodiments, $R^{35}$ is independently unsubstituted 3 to 6 membered heterocycloalkyl. In embodiments, $R^{35}$ is independently unsubstituted phenyl. In embodiments, $R^{35}$ is independently unsubstituted 5 to 6 membered heteroaryl.

$R^{36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In embodiments, $R^{36}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{37}$-substituted or unsubstituted alkyl (e.g., $C_1$-$C_8$, $C_1$-$C_6$, $C_1$-$C_4$, or $C_1$-$C_2$), $R^{37}$-substituted or unsubstituted heteroalkyl (e.g., 2 to 8 membered, 2 to 6 membered, 4 to 6 membered, 2 to 3 membered, or 4 to 5 membered), $R^{37}$-substituted or unsubstituted cycloalkyl (e.g., $C_3$-$C_8$, $C_3$-$C_6$, $C_4$-$C_6$, or $C_5$-$C_6$), $R^{37}$-substituted or unsubstituted heterocycloalkyl (e.g., 3 to 8 membered, 3 to 6 membered, 4 to 6 membered, 4 to 5 membered, or 5 to 6 membered), $R^{37}$-substituted or unsubstituted aryl (e.g., $C_6$-$C_{10}$ or phenyl), or $R^{37}$-substituted or unsubstituted heteroaryl (e.g., 5 to 10 membered, 5 to 9 membered, or 5 to 6 membered).

In embodiments, $R^{36}$ is independently —$NH_2$. In embodiments, $R^{36}$ is independently —OH. In embodiments, $R^{36}$ is independently halogen. In embodiments, $R^{36}$ is independently —CN. In embodiments, $R^{36}$ is independently oxo. In embodiments, $R^{36}$ is independently —$CF_3$. In embodiments, $R^{36}$ is independently —COOH. In embodiments, $R^{36}$ is independently —$CONH_2$. In embodiments, $R^{36}$ is independently —$NO_2$. In embodiments, $R^{36}$ is independently —SH. In embodiments, $R^{36}$ is independently —$SO_3H$. In embodiments, $R^{36}$ is independently —$SO_4H$. In embodiments, $R^{36}$ is independently —$SO_2NH_2$. In embodiments, $R^{36}$ is independently—$NHNH_2$. In embodiments, $R^{36}$ is independently-$ONH_2$. In embodiments, $R^{36}$ is independently —NHC(O)$NHNH_2$. In embodiments, $R^{36}$ is independently —NHC(O)$NH_2$. In embodiments, $R^{36}$ is independently —$NHSO_2H$. In embodiments, $R^{36}$ is independently —NHC(O)H. In embodiments, $R^{36}$ is independently —NHC(O)—OH. In embodiments, $R^{36}$ is independently —NHOH. In embodiments, $R^{36}$ is independently —$OCF_3$. In embodiments, $R^{36}$ is independently —$OCHF_2$. In embodiments, $R^{36}$ is independently —$CCl_3$. In embodiments, $R^{36}$ is independently —$CBr_3$. In embodiments, $R^{36}$ is independently —$CI_3$. In embodiments, $R^{36}$ is independently —F. In embodiments, $R^{36}$ is independently —Cl. In embodiments, $R^{36}$ is independently —Br. In embodiments, $R^{36}$ is independently —I. In embodiments, $R^{36}$ is independently $R^{37}$-substituted $C_1$-$C_4$ alkyl. In embodiments, $R^{36}$ is independently $R^{37}$-substituted 2 to 4 membered heteroalkyl. In embodiments, $R^{36}$ is independently $R^{37}$-substituted $C_3$-$C_6$ cycloalkyl. In embodiments, $R^{36}$ is independently $R^{37}$-substituted 3 to 6 membered heterocycloalkyl. In embodiments, $R^{36}$ is independently $R^{37}$-substituted phenyl. In embodiments, $R^{36}$ is independently $R^{37}$-substituted 5 to 6 membered heteroaryl. In embodiments, $R^{36}$ is independently unsubstituted $C_1$-$C_4$ alkyl. In embodiments, $R^{36}$ is independently unsubstituted 2 to 4 membered heteroalkyl. In embodiments, $R^{36}$ is independently unsubstituted $C_3$-$C_6$ cycloalkyl. In embodiments, $R^{36}$ is independently unsubstituted 3 to 6 membered heterocycloalkyl. In embodiments, $R^{36}$ is independently unsubstituted phenyl. In embodiments, $R^{36}$ is independently unsubstituted 5 to 6 membered heteroaryl.

In embodiments, $L^6$ is independently a bond, $R^{38}$-substituted or unsubstituted alkylene, $R^{38}$-substituted or unsubstituted heteroalkylene, $R^{38}$-substituted or unsubstituted cycloalkylene, $R^{38}$-substituted or unsubstituted heterocycloalkylene, $R^{38}$-substituted or unsubstituted arylene, or $R^{38}$-substituted or unsubstituted heteroarylene.

In embodiments, $L^6$ is a bond, —NH—, —$NR^{38}$—, —S—, —O—, —C(O)—, —NHC(O)—, —C(O)NH—, —NHC(O)NH—, —NHC(NH)NH—, —C(S)—, $R^{38}$-substituted or unsubstituted $C_1$-$C_{20}$ alkylene, $R^{38}$-substituted or unsubstituted 2 to 20 membered heteroalkylene, $R^{38}$-substituted or unsubstituted $C_3$-$C_8$ cycloalkylene, $R^{38}$-substituted or unsubstituted 3 to 8 membered heterocycloalkylene, $R^{38}$-substituted or unsubstituted $C_6$-$C_{10}$ arylene, or $R^{38}$-substituted or unsubstituted 5 to 10 membered heteroarylene. In embodiments, $L^6$ is a bond. In embodiments, $L^6$ is —NH—. In embodiments, $L^6$ is —$NR^{38}$—. In embodiments, $L^6$ is —S—. In embodiments, $L^6$ is —O—. In embodiments, $L^6$ is —C(O)—. In embodiments, $L^6$ is —NHC(O)—. In embodiments, $L^6$ is —C(O)NH—. In embodiments, $L^6$ is —NHC(O)NH—. In embodiments, $L^6$ is—NHC(NH)NH—. In embodiments, $L^6$ is-C(S)—. In embodiments, $L^6$ is $R^{38}$-substituted or unsubstituted $C_1$-$C_{20}$ alkylene. In embodiments, $L^6$ is $R^{38}$-substituted or unsubstituted 2 to 20 membered heteroalkylene. In embodiments, $L^6$ is $R^{38}$-substituted or unsubstituted $C_3$-$C_8$ cycloalkylene. In embodiments, $L^6$ is $R^{38}$-substituted or unsubstituted 3 to 8 membered heterocycloalkylene. In embodiments, $L^6$ is $R^{38}$-substituted or unsubstituted $C_6$-$C_{10}$ arylene. In embodiments, $L^6$ is $R^{38}$-substituted or unsubstituted 5 to 10 membered heteroarylene. In embodiments, $L^6$ is $R^{38}$-substituted $C_1$-$C_{20}$ alkylene. In embodiments, $L^6$ is $R^{38}$-substituted 2 to 20 membered heteroalkylene. In embodiments, $L^6$ is $R^{38}$-substituted $C_3$-$C_8$ cycloalkylene. In embodiments, $L^6$ is $R^{38}$-substituted 3 to 8 membered heterocycloalkylene. In embodiments, $L^6$ is $R^{38}$-substituted $C_6$-$C_{10}$ arylene. In embodiments, $L^6$ is $R^{38}$-substituted 5 to 10 membered heteroarylene. In embodiments, $L^6$ is unsubstituted $C_1$-$C_{20}$ alkylene. In embodiments, $L^6$ is unsubstituted 2 to 20 membered heteroalkylene. In embodiments, $L^6$ is unsubstituted $C_3$-$C_8$ cycloalkylene. In embodiments, $L^6$ is unsubstituted 3 to 8 membered heterocycloalkylene. In embodiments, $L^6$ is unsubstituted $C_6$-$C_{10}$ arylene. In embodiments, $L^6$ is unsubstituted 5 to 10 membered heteroarylene. In embodiments, $L^6$ is $R^{38}$-substituted $C_1$-$C_{15}$ alkylene. In embodiments, $L^6$ is $R^{38}$-substituted 2 to 15 membered heteroalkylene. In embodiments, $L^6$ is $R^{38}$-substituted $C_3$-$C_6$ cycloalkylene. In embodiments, $L^6$ is $R^{38}$-substituted 3 to 6 membered heterocycloalkylene. In embodiments, $L^6$ is $R^{38}$-substituted phenylene. In embodiments, $L^6$ is $R^{38}$-substituted 5 to 6 membered heteroarylene. In embodiments, $L^6$ is unsubstituted $C_1$-$C_{15}$ alkylene. In embodiments, $L^6$ is unsubstituted 2 to 15 membered heteroalkylene. In embodiments, $L^6$ is unsubstituted $C_3$-$C_6$ cycloalkylene. In embodiments, $L^6$ is unsubstituted 3 to 6 membered heterocycloalkylene. In embodiments, $L^6$ is unsubstituted phenylene. In embodiments, $L^6$ is unsubstituted 5 to 6 membered heteroarylene. In embodiments, $L^6$ is $R^{38}$-substituted $C_1$-$C_{10}$ alkylene. In embodiments, $L^6$ is $R^{38}$-substituted 2 to 10 membered heteroalkylene. In embodiments, $L^6$ is $R^{38}$-substituted $C_4$-$C_6$ cycloalkylene. In embodiments, $L^6$ is $R^{38}$-substituted 4 to 6 membered heterocycloalkylene. In embodiments, $L^6$ is $R^{38}$-substituted phenylene. In embodiments, $L^6$ is $R^{38}$-substituted 5 membered heteroarylene. In embodiments, $L^6$ is $R^{38}$-substituted $C_1$-$C_8$ alkylene. In embodiments, $L^6$ is $R^{38}$-substituted 2 to 8 membered heteroalkylene. In embodiments, $L^6$ is $R^{38}$-substituted $C_5$-$C_6$ cycloalkylene. In embodiments, $L^6$ is $R^{38}$-substituted 5 to 6 membered heterocycloalkylene. In embodiments, $L^6$ is $R^{38}$-substituted 6 membered heteroarylene. In embodiments, $L^6$ is $R^{38}$-substituted $C_1$-$C_6$ alkylene. In embodiments, $L^6$ is $R^{38}$-substituted 2 to 6 membered heteroalkylene. In embodiments, $L^6$ is $R^{38}$-substituted $C_6$-$C_{20}$ alkylene. In embodiments, $L^6$ is $R^{38}$-substituted 6 to 20 membered heteroalkylene. In embodiments, $L^6$ is unsubstituted $C_1$-$C_{10}$ alkylene. In embodiments, $L^6$ is unsubstituted 2 to 10 membered heteroalkylene. In embodiments, $L^6$ is unsubstituted $C_4$-$C_6$ cycloalkylene. In embodiments, $L^6$ is unsubstituted 4 to 6 membered heterocycloalkylene. In embodiments, $L^6$ is unsubstituted phenylene. In embodiments, $L^6$ is unsubstituted 5 membered heteroarylene. In embodiments, $L^6$ is unsubstituted $C_1$-$C_8$ alkylene. In embodiments, $L^6$ is unsubstituted 2 to 8 membered heteroalkylene. In embodiments, $L^6$ is unsubstituted $C_5$-$C_6$ cycloalkylene. In embodiments, $L^6$ is unsubstituted 5 to 6 membered heterocycloalkylene. In embodiments, $L^6$ is unsubstituted 6 membered heteroarylene. In embodiments, $L^6$ is unsubstituted $C_1$-$C_6$ alkylene. In embodiments, $L^6$ is unsubstituted 2 to 6 membered heteroalkylene. In embodiments, $L^6$ is unsubstituted $C_6$-$C_{20}$ alkylene. In embodiments, $L^6$ is unsubstituted 6 to 20 membered heteroalkylene.

$R^{38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl.

In embodiments, $R^{38}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 8 membered, 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered).

In embodiments, $R^{38}$ is independently —$NH_2$. In embodiments, $R^{38}$ is independently —OH. In embodiments, $R^{38}$ is independently halogen. In embodiments, $R^{38}$ is independently —CN. In embodiments, $R^{38}$ is independently oxo. In embodiments, $R^{38}$ is independently —$CF_3$. In embodiments, $R^{38}$ is independently —COOH. In embodiments, $R^{38}$ is independently —$CONH_2$. In embodiments, $R^{38}$ is independently —$NO_2$. In embodiments, $R^{38}$ is independently —SH. In embodiments, $R^{38}$ is independently-$SO_3H$. In embodiments, $R^{38}$ is independently —$SO_4H$. In embodiments, $R^{38}$ is independently —$SO_2NH_2$. In embodiments, $R^{38}$ is independently —$NHNH_2$. In embodiments, $R^{38}$ is independently —$ONH_2$. In embodiments, $R^{38}$ is independently —NHC═(O)$NHNH_2$. In embodiments, $R^{38}$ is independently —NHC═(O) $NH_2$. In embodiments, $R^{38}$ is independently —$NHSO_2H$. In embodiments, $R^{38}$ is independently—NHC═(O)H. In embodiments, $R^{38}$ is independently—NHC(O)—OH. In embodiments, $R^{38}$ is independently —NHOH. In embodiments, $R^{38}$ is independently —$OCF_3$. In embodiments, $R^{38}$ is independently —$OCHF_2$. In embodiments, $R^{38}$ is independently —$CCl_3$. In embodiments, $R^{38}$ is independently —$CBr_3$. In embodiments, $R^{38}$ is independently —$CI_3$. In embodiments, $R^{38}$ is independently —F. In embodiments, $R^{38}$ is independently —Cl. In embodiments, $R^{38}$ is independently —Br. In embodiments, $R^{38}$ is independently —I. In embodiments, $R^{38}$ is independently $R^{39}$-substituted $C_1$-$C_4$ alkyl. In embodiments, $R^{38}$ is independently $R^{39}$-substituted 2 to 4 membered heteroalkyl. In embodiments, $R^{38}$ is independently $R^{39}$-substituted $C_3$-$C_6$ cycloalkyl. In embodiments, $R^{38}$ is independently $R^{39}$-substituted 3 to 6 membered heterocycloalkyl. In embodiments, $R^{38}$ is independently $R^{39}$-substituted phenyl. In embodiments, $R^{38}$ is independently $R^{39}$-substituted 5 to 6 membered heteroaryl. In embodiments, $R^{38}$ is independently unsubstituted $C_1$-$C_4$ alkyl. In embodiments, $R^{38}$ is independently unsubstituted 2 to 4 membered heteroalkyl. In embodiments, $R^{38}$ is independently unsubstituted $C_3$-$C_6$ cycloalkyl. In embodiments, $R^{38}$ is independently unsubstituted 3 to 6 membered heterocycloalkyl. In embodiments, $R^{38}$ is independently unsubstituted phenyl. In embodiments, $R^{38}$ is independently unsubstituted 5 to 6 membered heteroaryl.

$R^{39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^{39}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 8 membered, 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered).

In embodiments, $R^{39}$ is independently —$NH_2$. In embodiments, $R^{39}$ is independently —OH. In embodiments, $R^{39}$ is independently halogen. In embodiments, $R^{39}$ is independently —CN. In embodiments, $R^{39}$ is independently oxo. In embodiments, $R^{39}$ is independently —$CF_3$. In embodiments, $R^{39}$ is independently —COOH. In embodiments, $R^{39}$ is independently —$CONH_2$. In embodiments, $R^{39}$ is independently —$NO_2$. In embodiments, $R^{39}$ is independently —SH. In embodiments, $R^{39}$ is independently —$SO_3H$. In embodiments, $R^{39}$ is independently —$SO_4H$. In embodiments, $R^{39}$ is independently —$SO_2NH_2$. In embodiments, $R^{39}$ is independently —$NHNH_2$. In embodiments, $R^{39}$ is independently —$ONH_2$. In embodiments, $R^{39}$ is independently —NHC═(O)$NHNH_2$. In embodiments, $R^{39}$ is independently —NHC═(O) $NH_2$. In embodiments, $R^{39}$ is independently —$NHSO_2H$. In embodiments, $R^{39}$ is independently —NHC═(O)H. In embodiments, $R^{39}$ is independently —NHC(O)—OH. In embodiments, $R^{39}$ is independently —NHOH. In embodiments, $R^{39}$ is independently —$OCF_3$. In embodiments, $R^{39}$ is independently —$OCHF_2$. In embodiments, $R^{39}$ is independently —$CCl_3$. In embodiments, $R^{39}$ is independently —$CBr_3$. In embodiments, $R^{39}$ is independently —$CI_3$. In embodiments, $R^{39}$ is independently —F. In embodiments, $R^{39}$ is independently —Cl. In embodiments, $R^{39}$ is independently —Br. In embodiments, $R^{39}$ is independently —I. In embodiments, $R^{39}$ is independently $R^{40}$-substituted $C_1$-$C_4$ alkyl. In embodiments, $R^{39}$ is independently $R^{40}$-substituted 2 to 4 membered heteroalkyl. In embodiments, $R^{39}$ is independently $R^{40}$-substituted $C_3$-$C_6$ cycloalkyl. In embodiments, $R^{39}$ is independently $R^{40}$-substituted 3 to 6 membered heterocycloalkyl. In embodiments, $R^{39}$ is independently $R^{40}$-substituted phenyl. In embodiments, $R^{39}$ is independently $R^{40}$-substituted 5 to 6 membered heteroaryl. In embodiments, $R^{39}$ is independently unsubstituted $C_1$-$C_4$ alkyl. In embodiments, $R^{39}$ is independently unsubstituted 2 to 4 membered heteroalkyl. In embodiments, $R^{39}$ is independently unsubstituted $C_3$-$C_6$ cycloalkyl. In embodiments, $R^{39}$ is independently unsubstituted 3 to 6 membered heterocycloalkyl. In embodiments, $R^{39}$ is independently unsubstituted phenyl. In embodiments, $R^{39}$ is independently unsubstituted 5 to 6 membered heteroaryl.

$R^{25}$, $R^{28}$, $R^{31}$, $R^{34}$, $R^{37}$, and $R^{40}$ are independently oxo, halogen, —$CF_3$, —CN, —OH, —$NH_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, the anti-CNS disease drug is

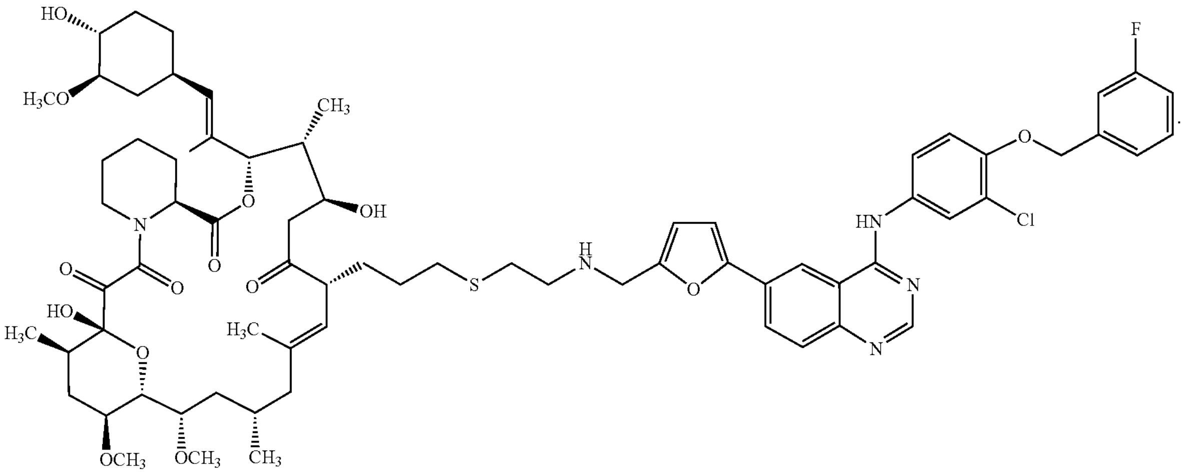 [SMILES: CO[C@H]1C[C@@H](C)C/C(C)=C/[C@@H](CCCSCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not

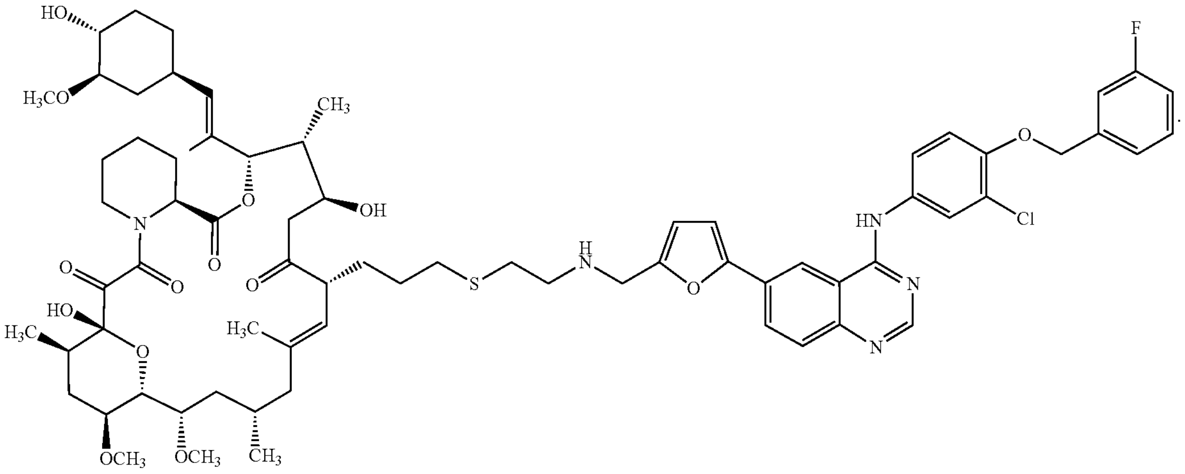 [SMILES: CO[C@H]1C[C@@H](C)C/C(C)=C/[C@@H](CCCSCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is
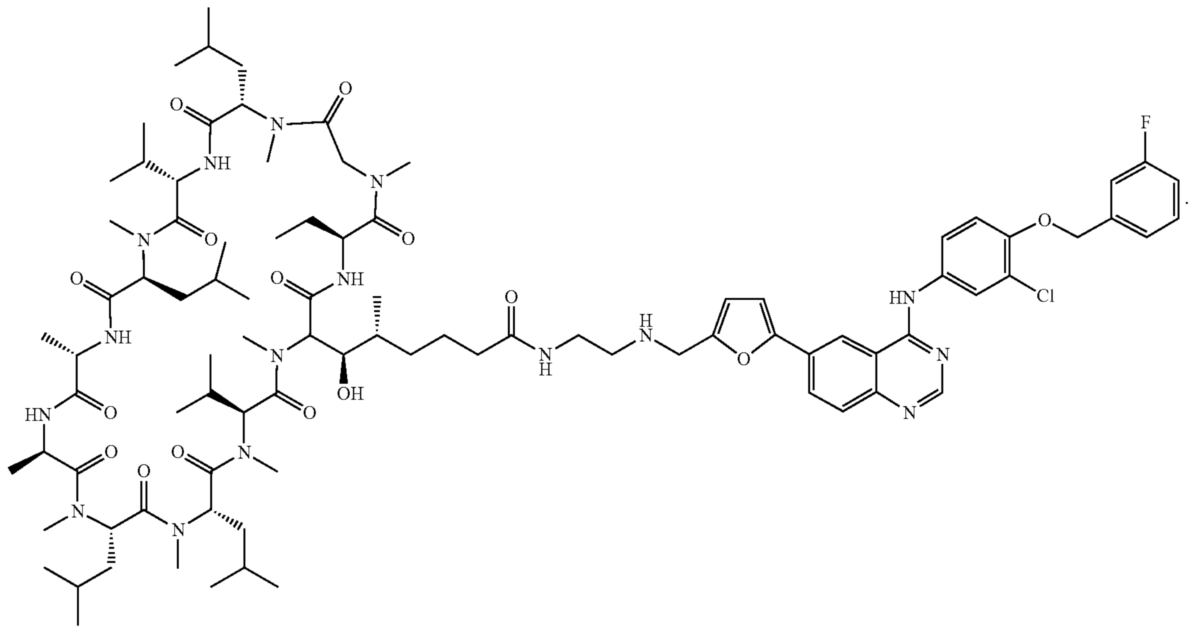 [SMILES: CC[C@@H]1NC(=O)C([C@H](O)[C@H](C)CCCC(=O)NCCNCc2ccc(-c3ccc4ncnc(Nc5ccc(OCc6cccc(F)c6)c(Cl)c5)c4c3)o2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]
In embodiments, the anti-CNS disease drug is not
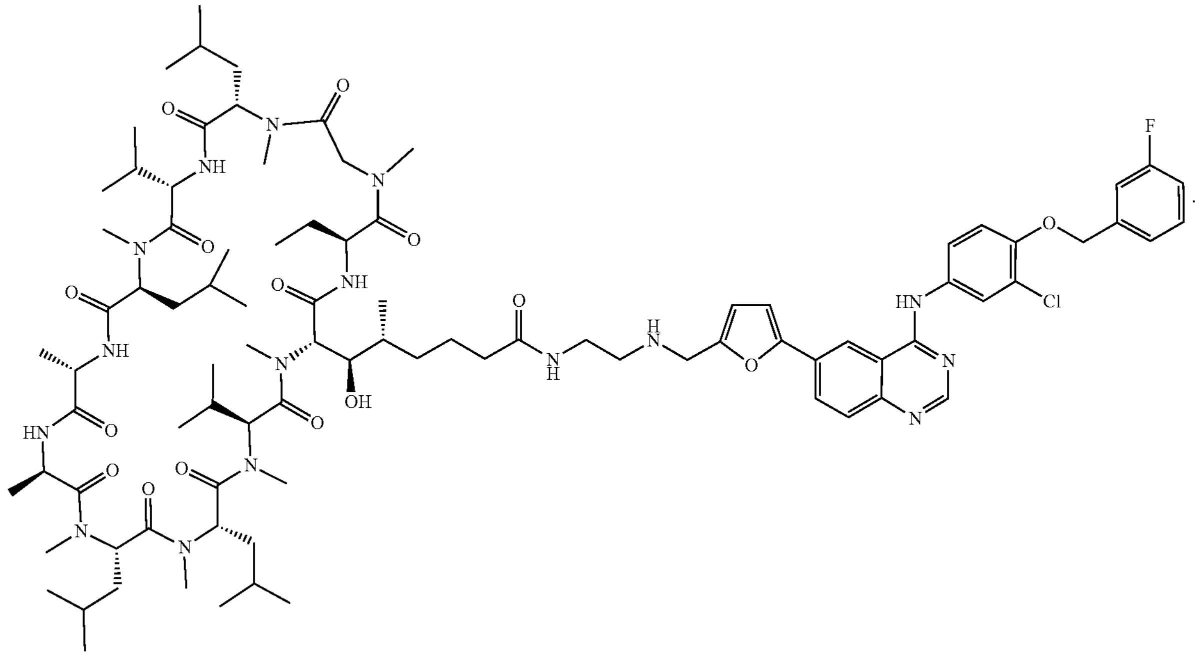 [SMILES: CC[C@@H]1NC(=O)[C@H]([C@H](O)[C@H](C)CCCC(=O)NCCNCc2ccc(-c3ccc4ncnc(Nc5ccc(OCc6cccc(F)c6)c(Cl)c5)c4c3)o2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]

In embodiments, the anti-CNS disease drug is
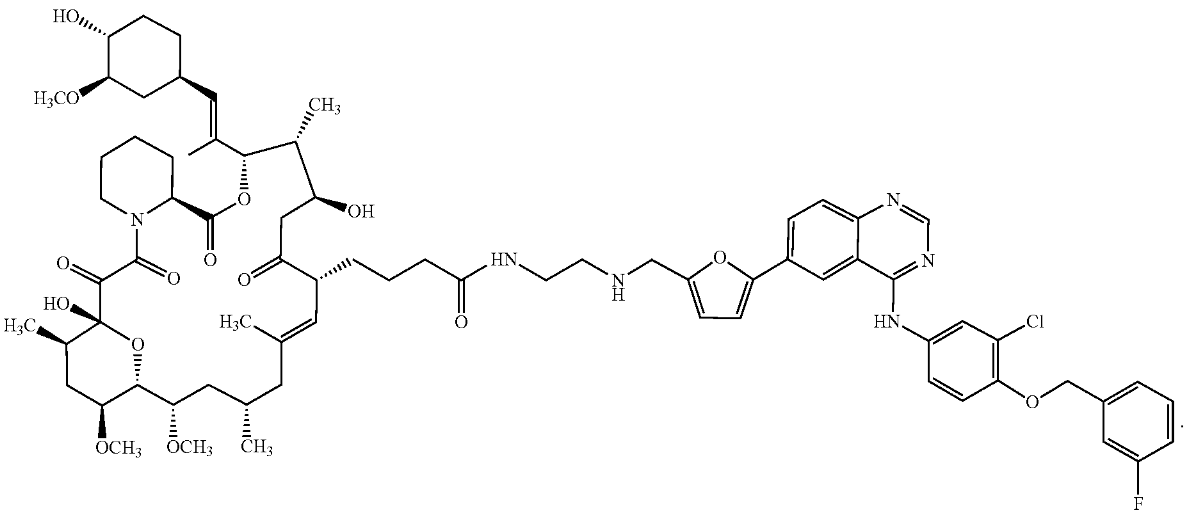 [SMILES: CO[C@H]1C[C@@H](C)C/C(C)=C/[C@@H](CCCC(=O)NCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
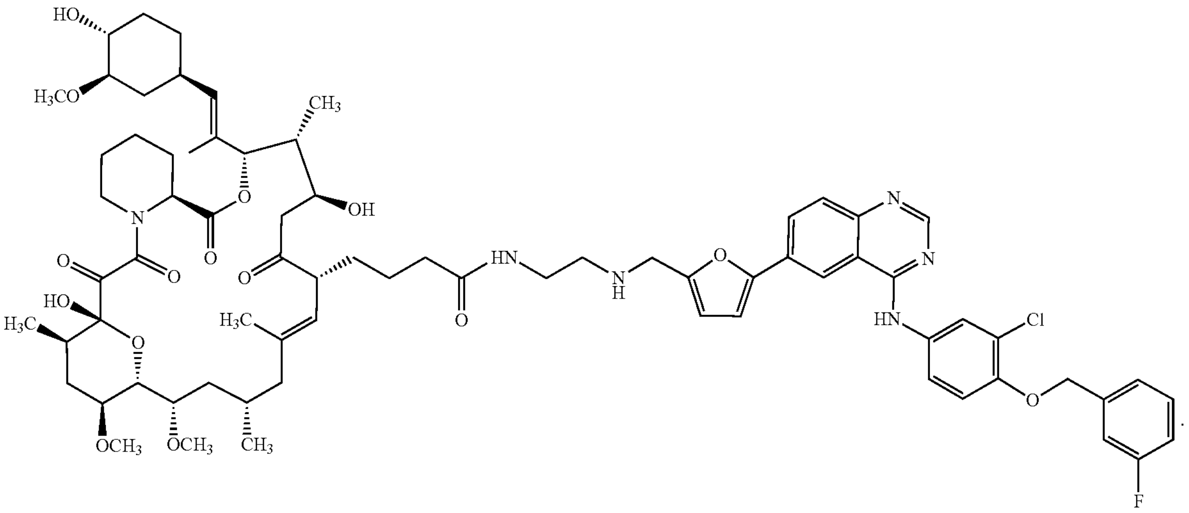 [SMILES: CO[C@H]1C[C@@H](C)C/C(C)=C/[C@@H](CCCC(=O)NCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is
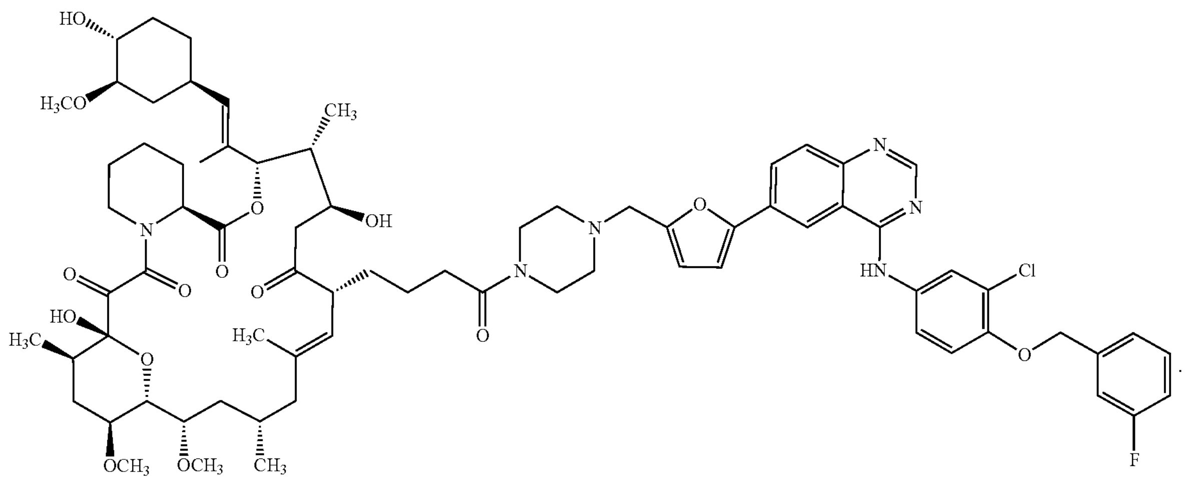 [SMILES: CO[C@H]1C[C@@H](C)C/C(C)=C/[C@@H](CCCC(=O)N2CCN(Cc3ccc(-c4ccc5ncnc(Nc6ccc(OCc7cccc(F)c7)c(Cl)c6)c5c4)o3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
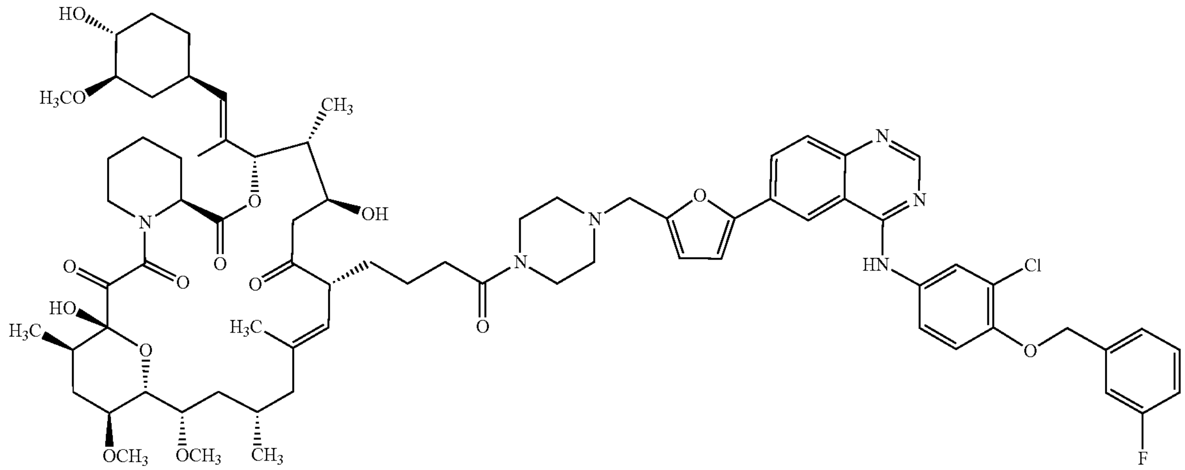 [SMILES: CO[C@H]1C[C@@H](C)C/C(C)=C/[C@@H](CCCC(=O)N2CCN(Cc3ccc(-c4ccc5ncnc(Nc6ccc(OCc7cccc(F)c7)c(Cl)c6)c5c4)o3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
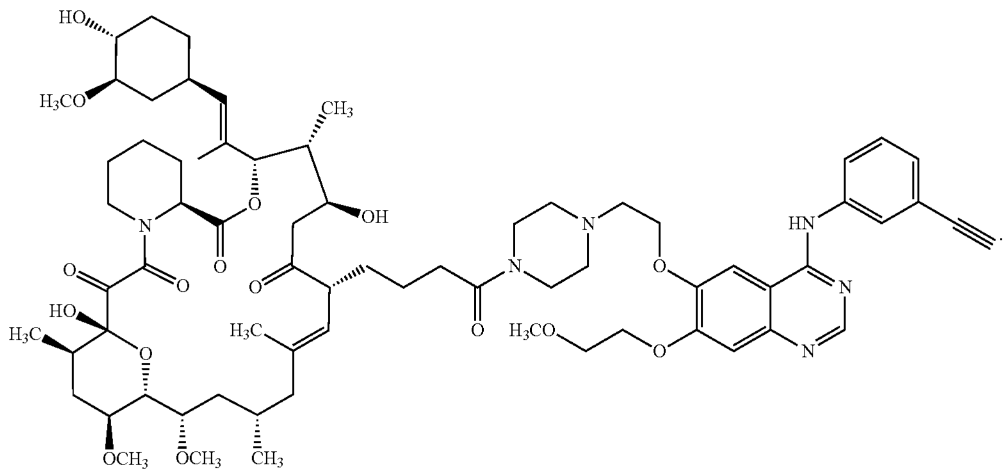 [SMILES: C#Cc1cccc(Nc2ncnc3cc(OCCOC)c(OCCN4CCN(C(=O)CCC[C@@H]5/C=C(\C)C[C@H](C)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc23)c1]

In embodiments, the anti-CNS disease drug is not
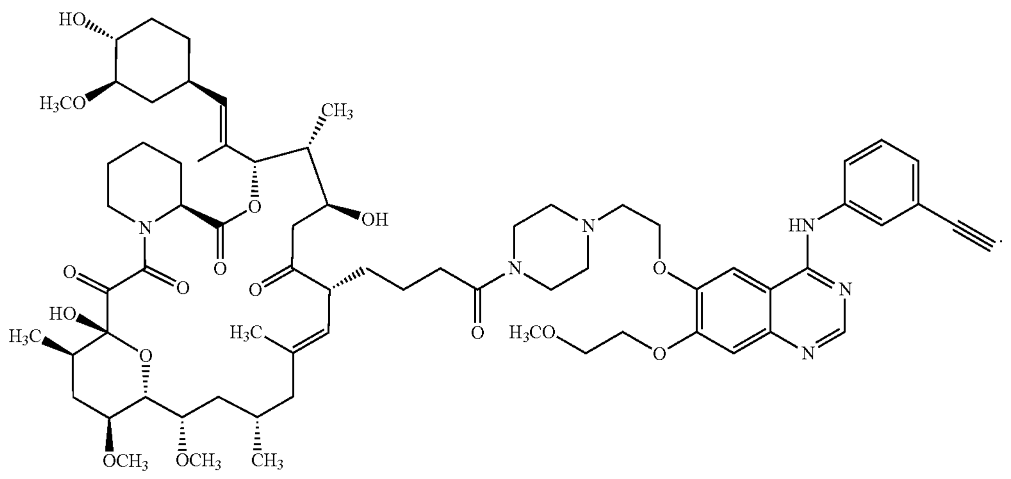 [SMILES: C#Cc1cccc(Nc2ncnc3cc(OCCOC)c(OCCN4CCN(C(=O)CCC[C@@H]5/C=C(\C)C[C@H](C)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc23)c1]
In embodiments, the anti-CNS disease drug is
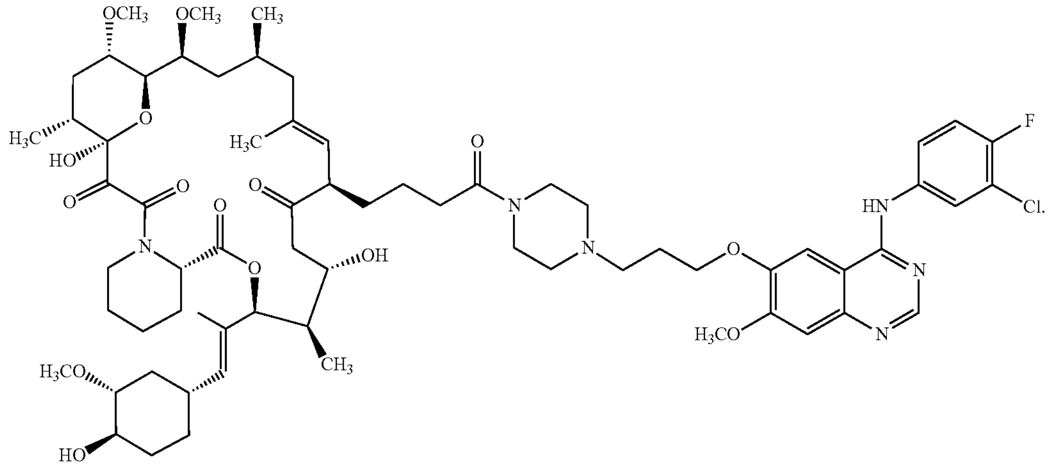 [SMILES: COc1cc2ncnc(Nc3ccc(F)c(Cl)c3)c2cc1OCCCN1CCN(C(=O)CCC[C@@H]2/C=C(\C)C[C@H](C)C[C@H](OC)[C@H]3O[C@@](O)(C(=O)C(=O)N4CCCC[C@H]4C(=O)O[C@H](/C(C)=C/[C@@H]4CC[C@@H](O)[C@H](OC)C4)[C@H](C)[C@@H](O)CC2=O)[C@H](C)C[C@@H]3OC)CC1]
In embodiments, the anti-CNS disease drug is not
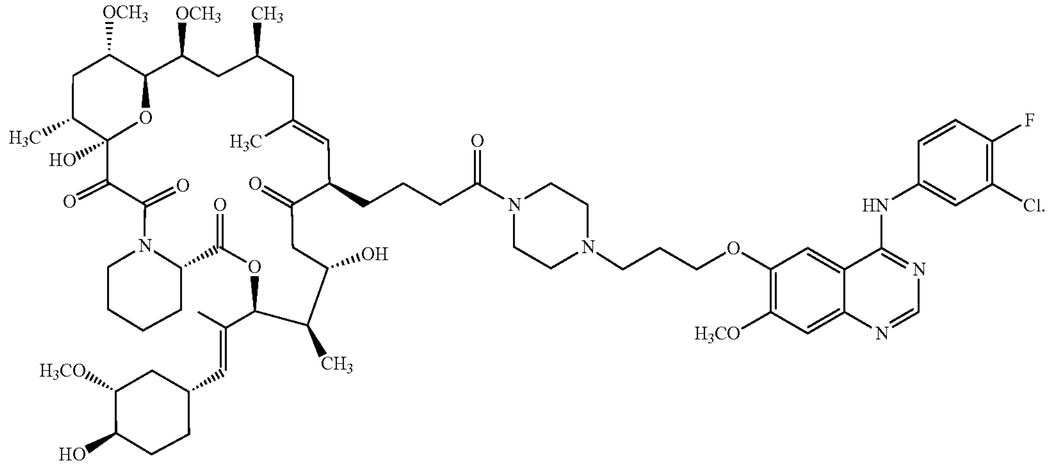 [SMILES: COc1cc2ncnc(Nc3ccc(F)c(Cl)c3)c2cc1OCCCN1CCN(C(=O)CCC[C@@H]2/C=C(\C)C[C@H](C)C[C@H](OC)[C@H]3O[C@@](O)(C(=O)C(=O)N4CCCC[C@H]4C(=O)O[C@H](/C(C)=C/[C@@H]4CC[C@@H](O)[C@H](OC)C4)[C@H](C)[C@@H](O)CC2=O)[C@H](C)C[C@@H]3OC)CC1]

In embodiments, the anti-CNS disease drug is
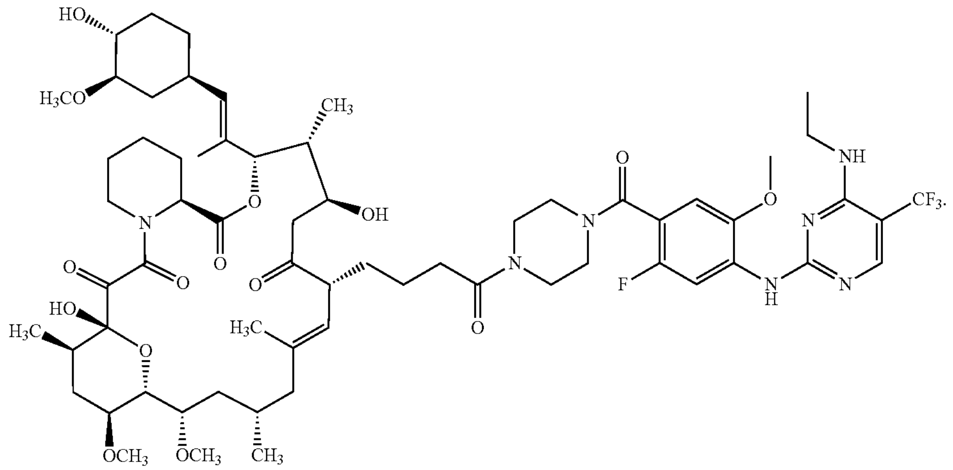 [SMILES: CCNc1nc(Nc2cc(F)c(C(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)cc2OC)ncc1C(F)(F)F]
In embodiments, the anti-CNS disease drug is not
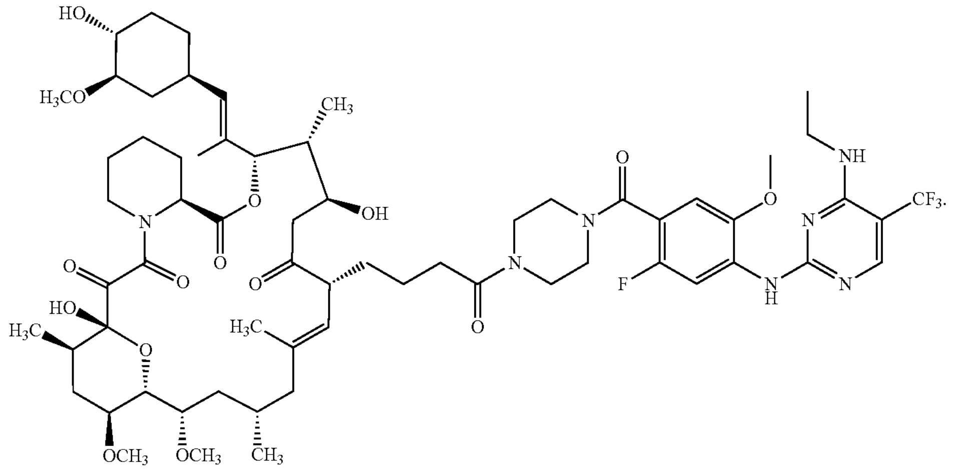 [SMILES: CCNc1nc(Nc2cc(F)c(C(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)cc2OC)ncc1C(F)(F)F]
In embodiments, the anti-CNS disease drug is
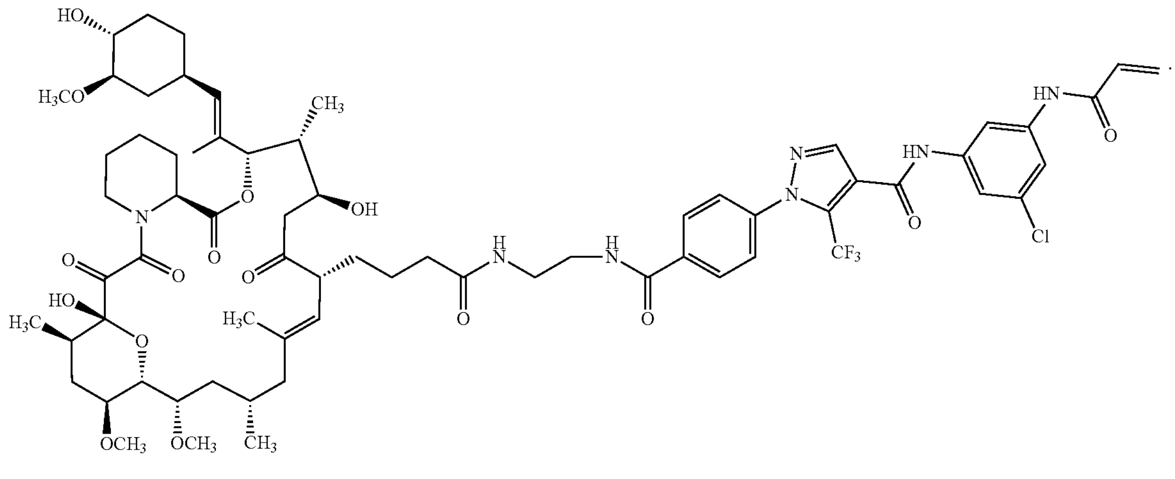 [SMILES: C=CC(=O)Nc1cc(Cl)cc(NC(=O)c2cnn(-c3ccc(C(=O)NCCNC(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]

In embodiments, the anti-CNS disease drug is not
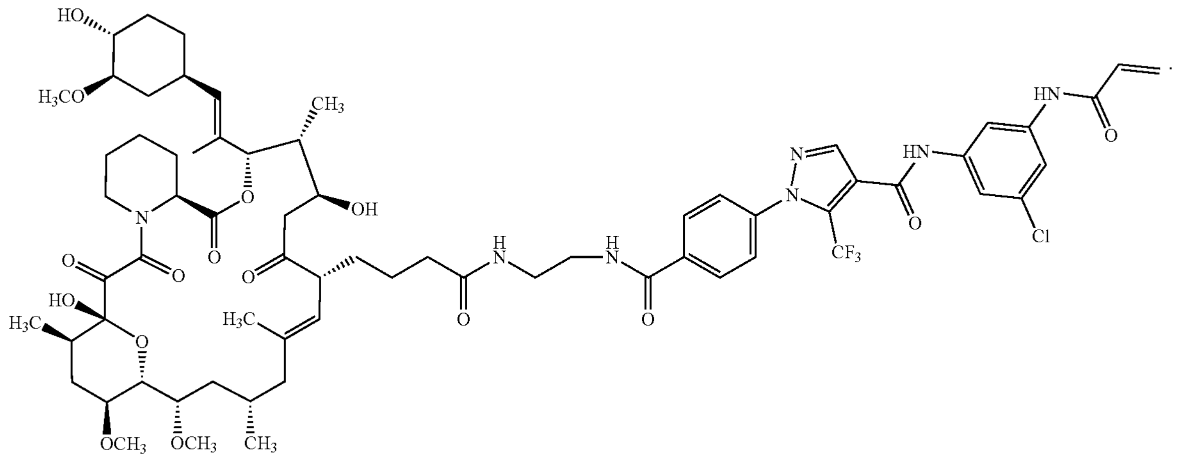 [SMILES: C=CC(=O)Nc1cc(Cl)cc(NC(=O)c2cnn(-c3ccc(C(=O)NCCNC(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]
In embodiments, the anti-CNS disease drug is
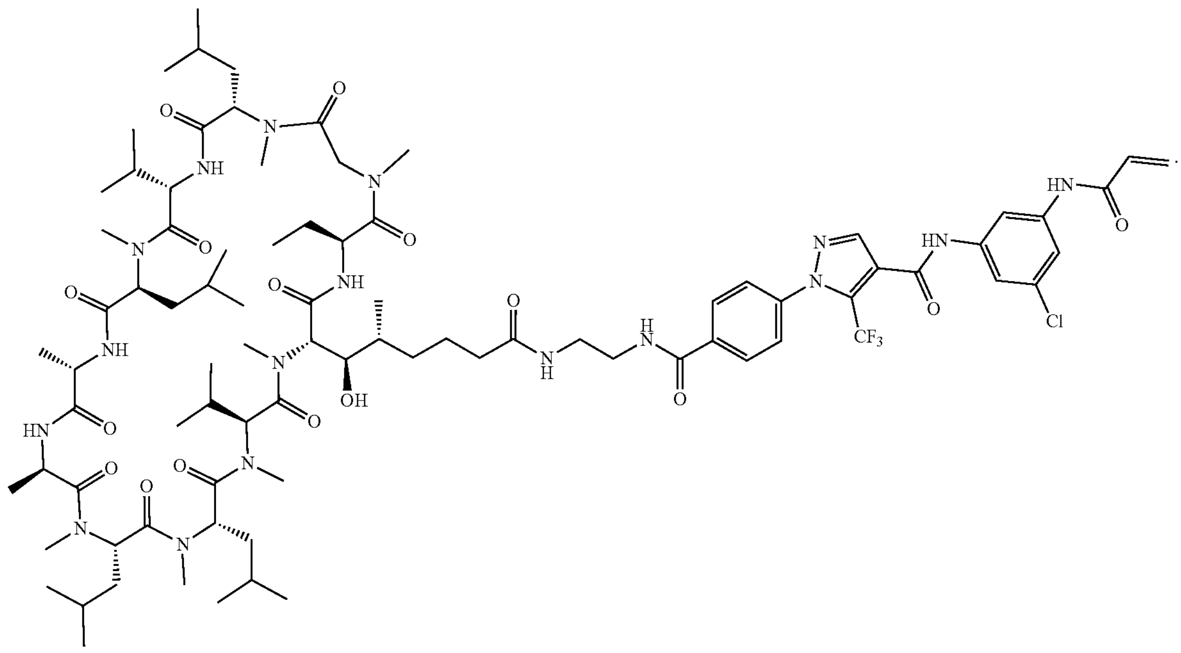 [SMILES: C=CC(=O)Nc1cc(Cl)cc(NC(=O)c2cnn(-c3ccc(C(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]

In embodiments, the anti-CNS disease drug is not
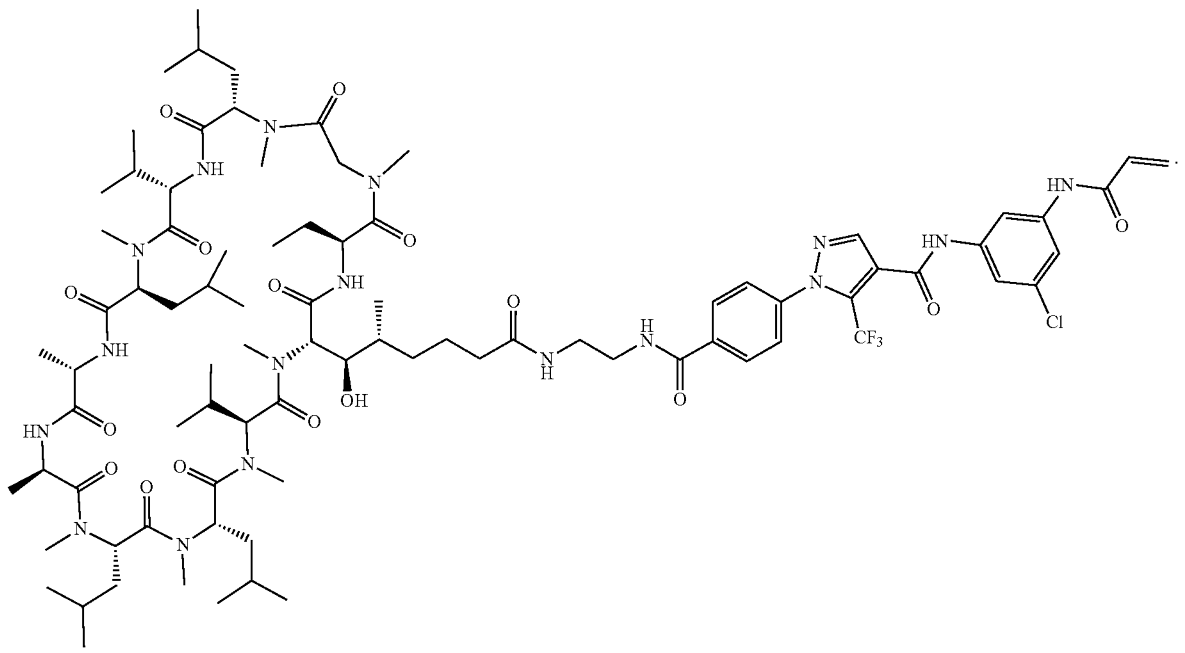 [SMILES: C=CC(=O)Nc1cc(Cl)cc(NC(=O)c2cnn(-c3ccc(C(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]
In embodiments, the anti-CNS disease drug is
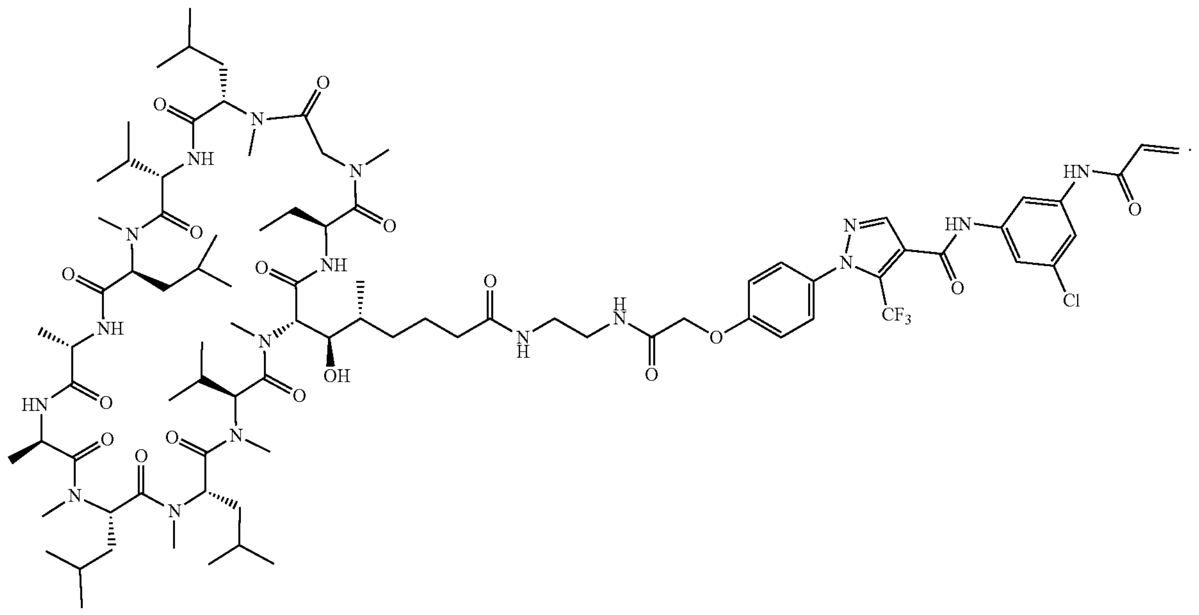 [SMILES: C=CC(=O)Nc1cc(Cl)cc(NC(=O)c2cnn(-c3ccc(OCC(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]

In embodiments, the anti-CNS disease drug is not
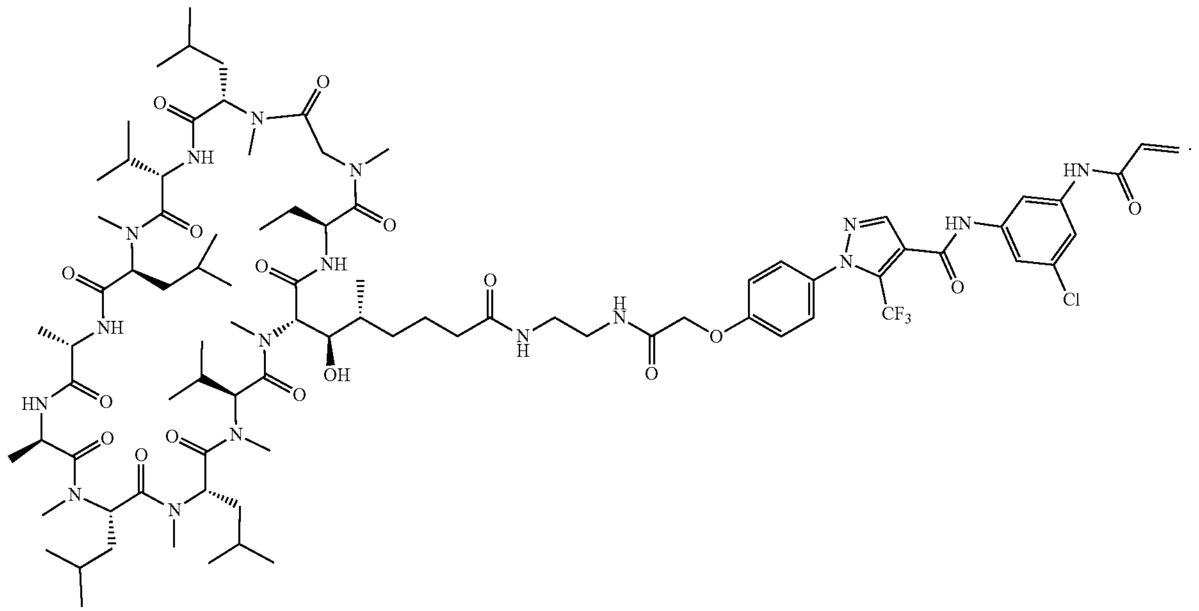 [SMILES: C=CC(=O)Nc1cc(Cl)cc(NC(=O)c2cnn(-c3ccc(OCC(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1]
In embodiments, the anti-CNS disease drug is
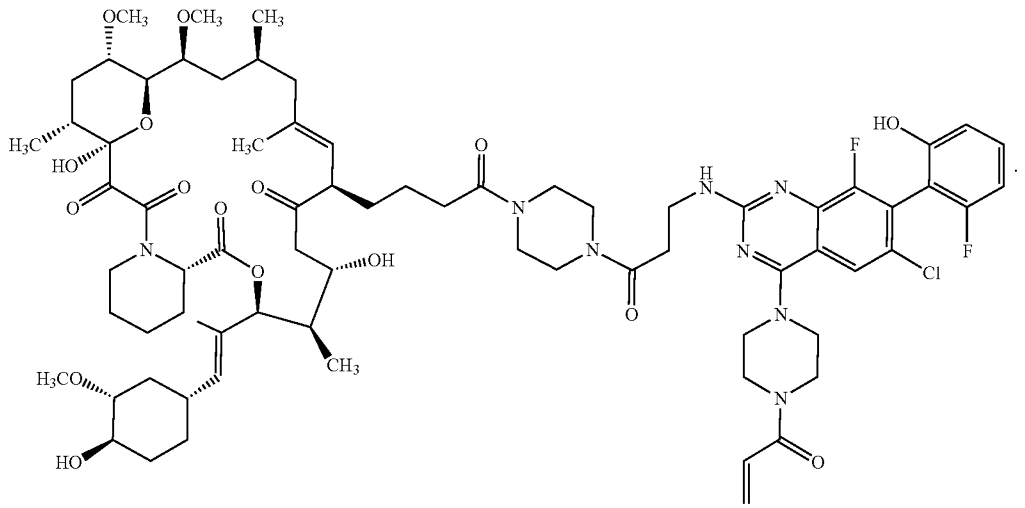 [SMILES: C=CC(=O)N1CCN(c2nc(NCCC(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)nc3c(F)c(-c4c(O)cccc4F)c(Cl)cc23)CC1]

In embodiments, the anti-CNS disease drug is not
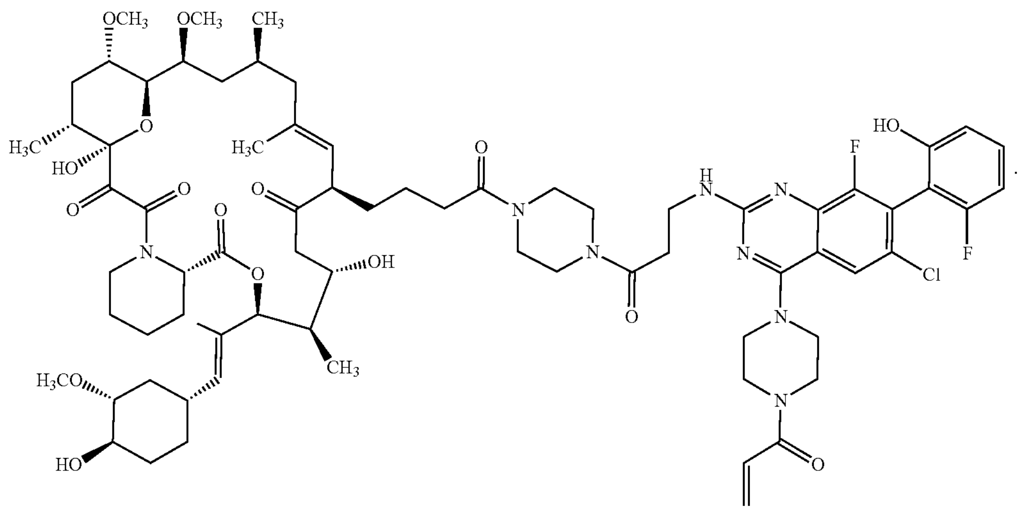 [SMILES: C=CC(=O)N1CCN(c2nc(NCCC(=O)N3CCN(C(=O)CCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)nc3c(F)c(-c4c(O)cccc4F)c(Cl)cc23)CC1]
In embodiments, the anti-CNS disease drug is
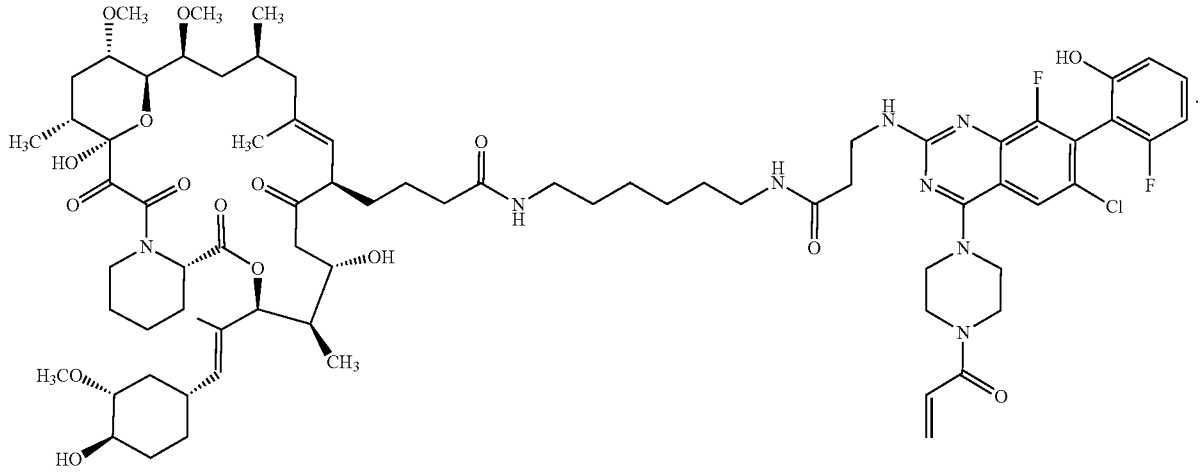 [SMILES: C=CC(=O)N1CCN(c2nc(NCCC(=O)NCCCCCCNC(=O)CCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]
In embodiments, the anti-CNS disease drug is not
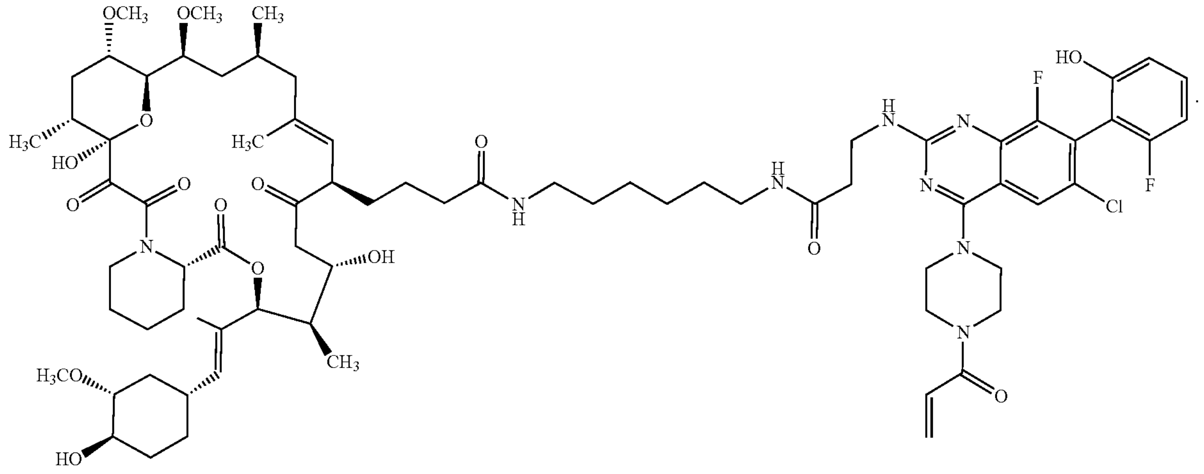 [SMILES: C=CC(=O)N1CCN(c2nc(NCCC(=O)NCCCCCCNC(=O)CCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]

In embodiments, the anti-CNS disease drug is
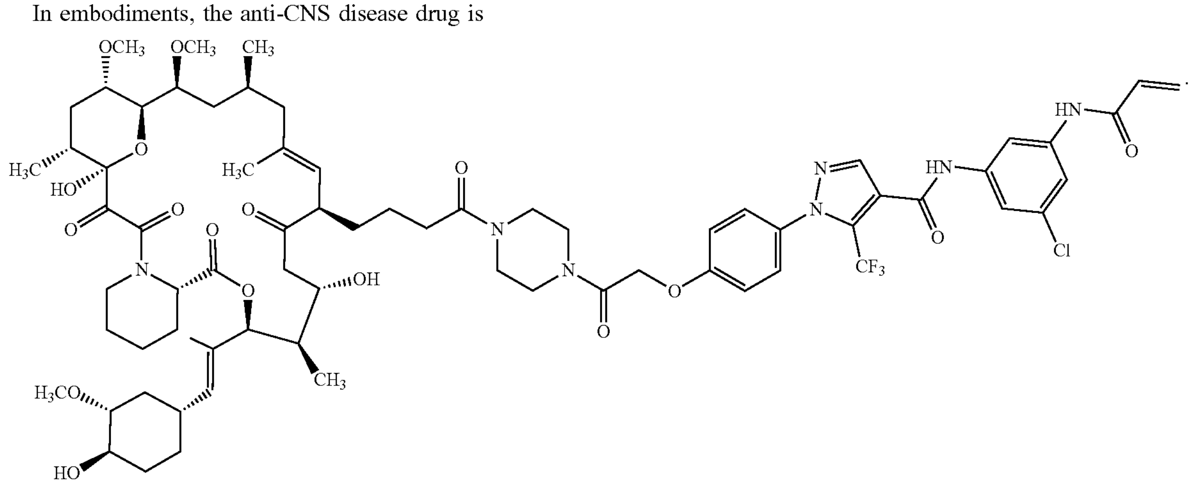
In embodiments, the anti-CNS disease drug is not
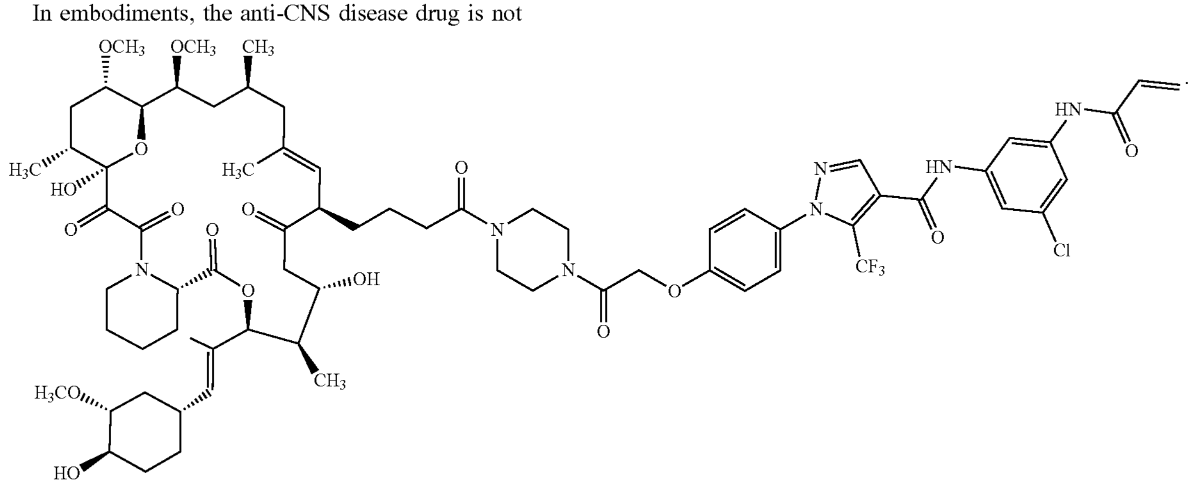
In embodiments, the anti-CNS disease drug is
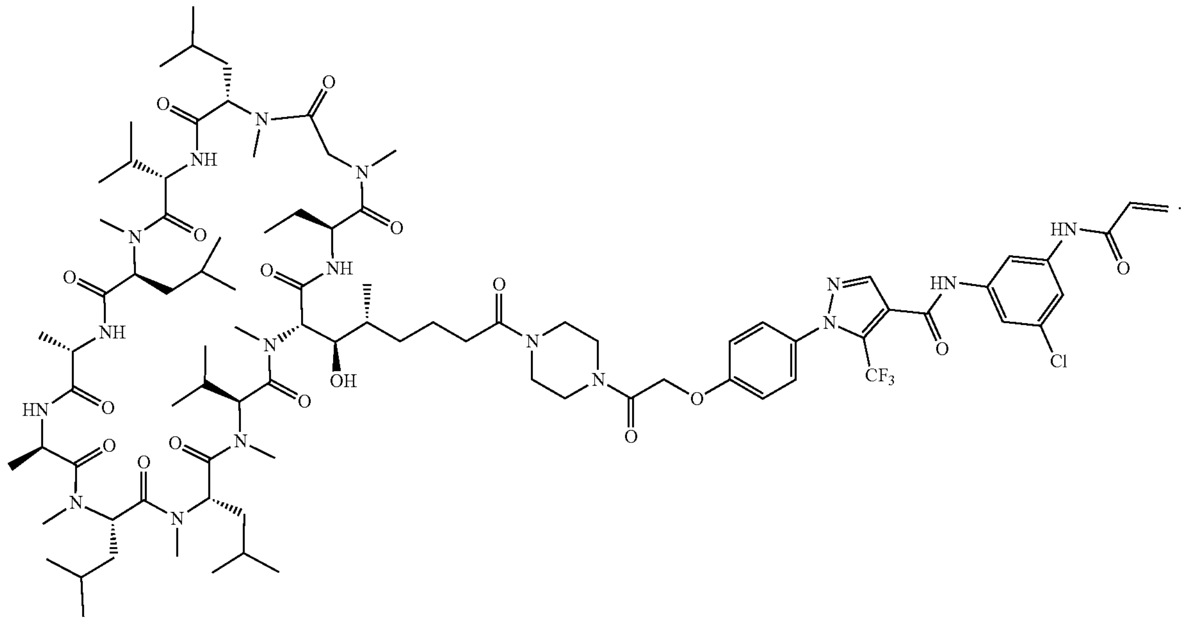 [SMILES: C=CC(=O)Nc1cc(Cl)cc(NC(=O)c2cnn(-c3ccc(OCC(=O)N4CCN(C(=O)CCC[C@@H](C)[C@@H](O)[C@H]5C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N5C)CC4)cc3)c2C(F)(F)F)c1]

In embodiments, the anti-CNS disease drug is not
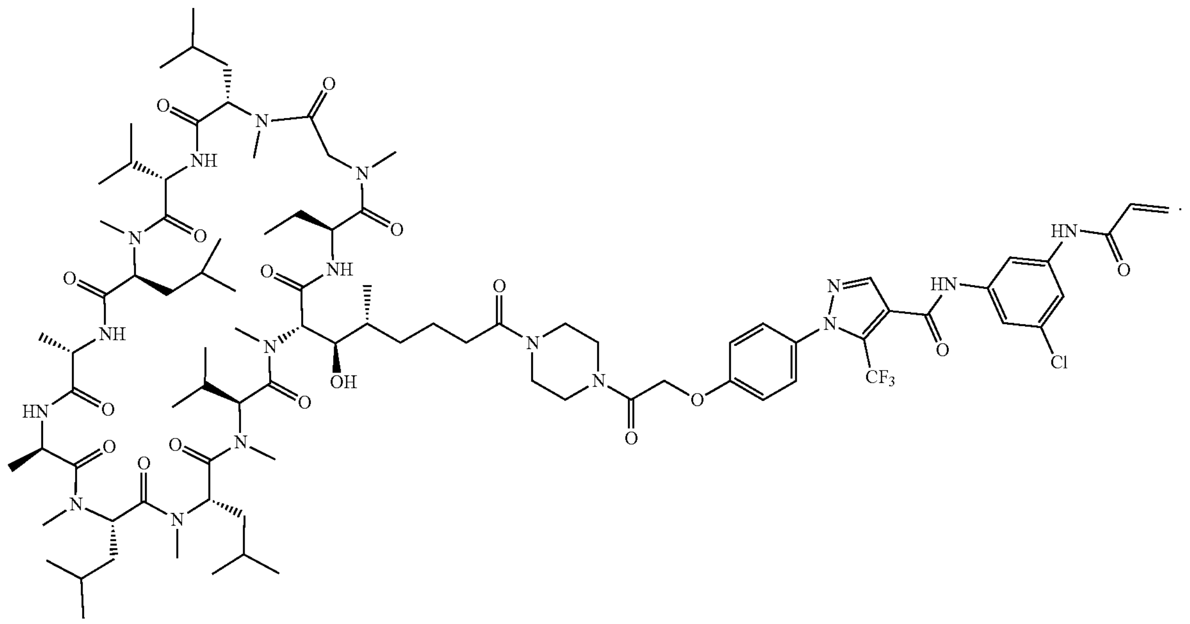 [SMILES: C=CC(=O)Nc1cc(Cl)cc(NC(=O)c2cnn(-c3ccc(OCC(=O)N4CCN(C(=O)CCC[C@@H](C)[C@@H](O)[C@H]5C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N5C)CC4)cc3)c2C(F)(F)F)c1]
In embodiments, the anti-CNS disease drug is
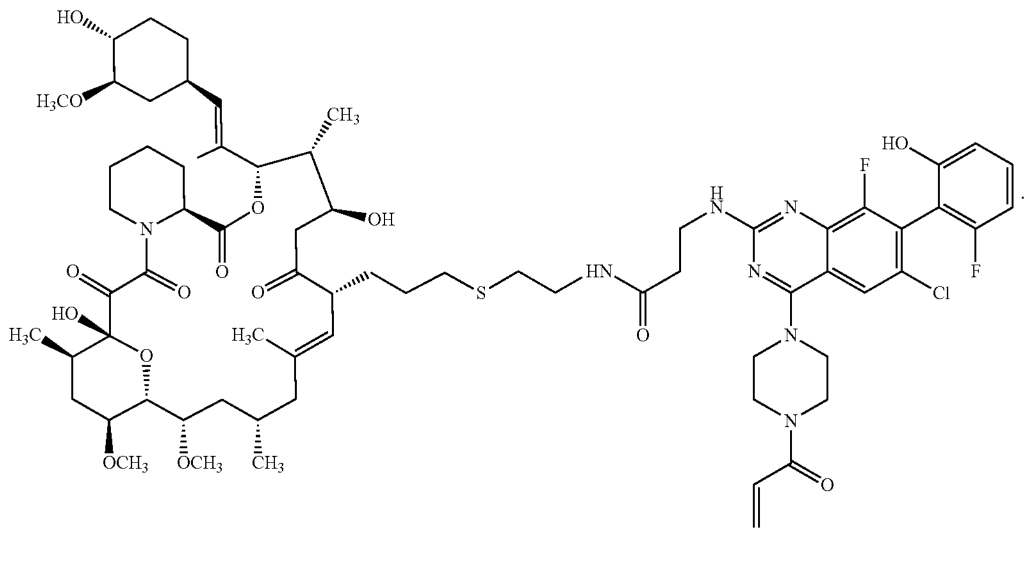 [SMILES: C=CC(=O)N1CCN(c2nc(NCCC(=O)NCCSCCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]

In embodiments, the anti-CNS disease drug is not
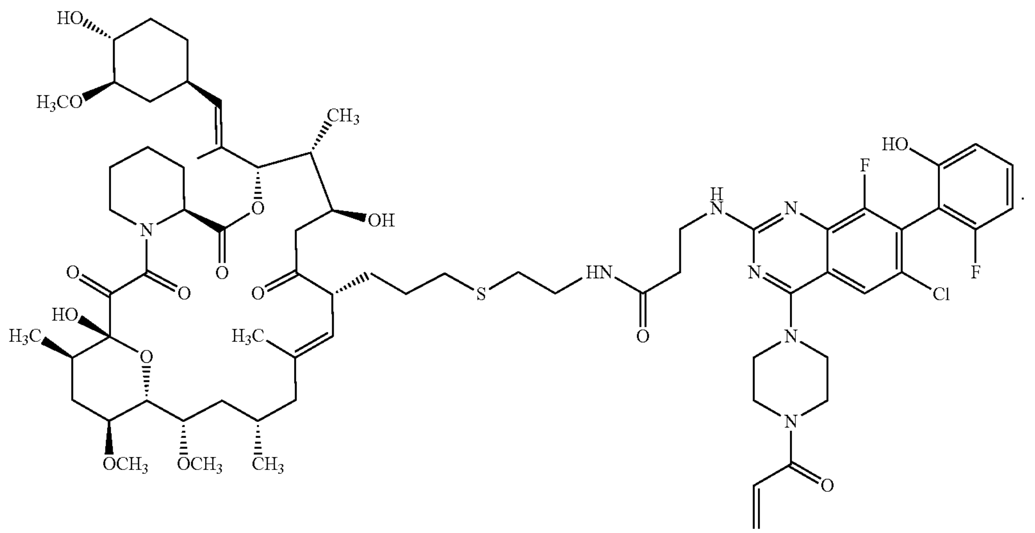 [SMILES: C=CC(=O)N1CCN(c2nc(NCCC(=O)NCCSCCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1]
In embodiments, the anti-CNS disease drug is
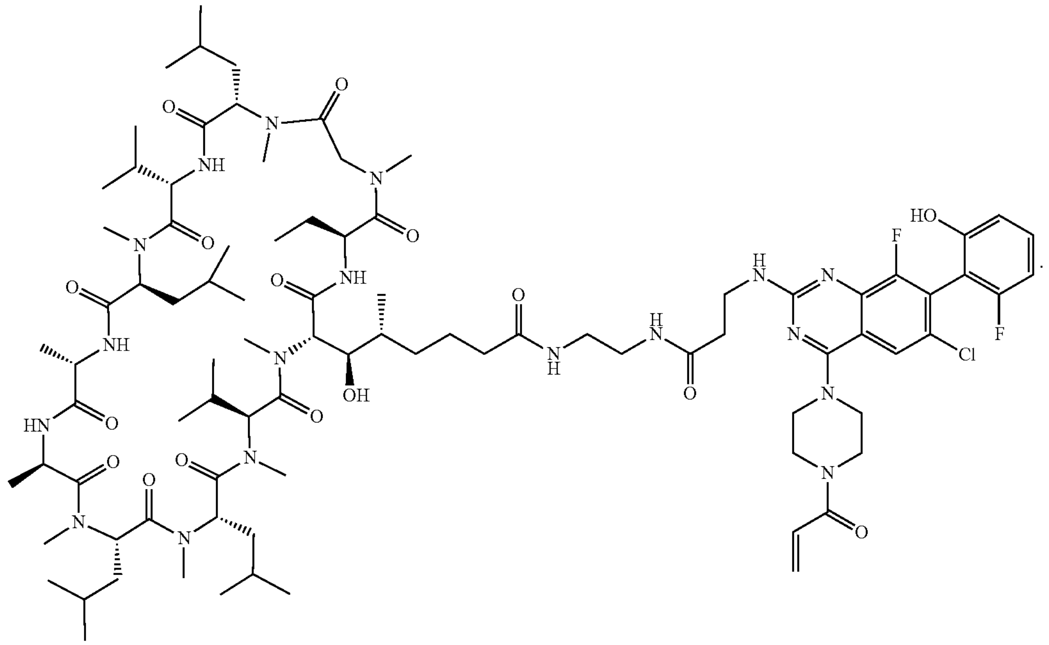 [SMILES: C=CC(=O)N1CCN(c2nc(NCCC(=O)NCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]

In embodiments, the anti-CNS disease drug is not
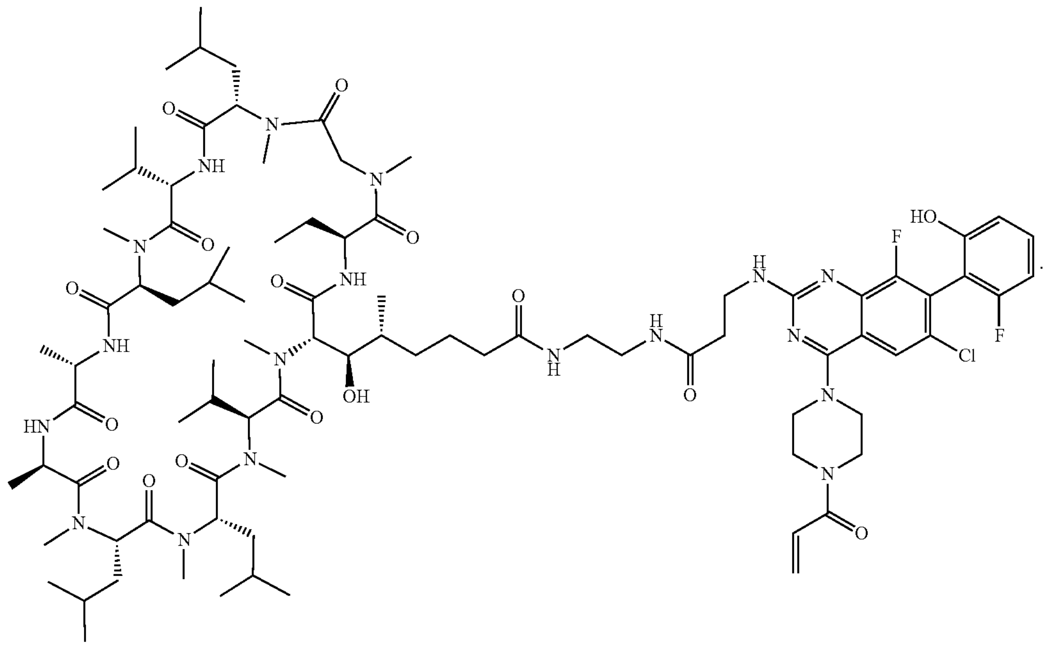 [SMILES: C=CC(=O)N1CCN(c2nc(NCCC(=O)NCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]
In embodiments, the anti-CNS disease drug is
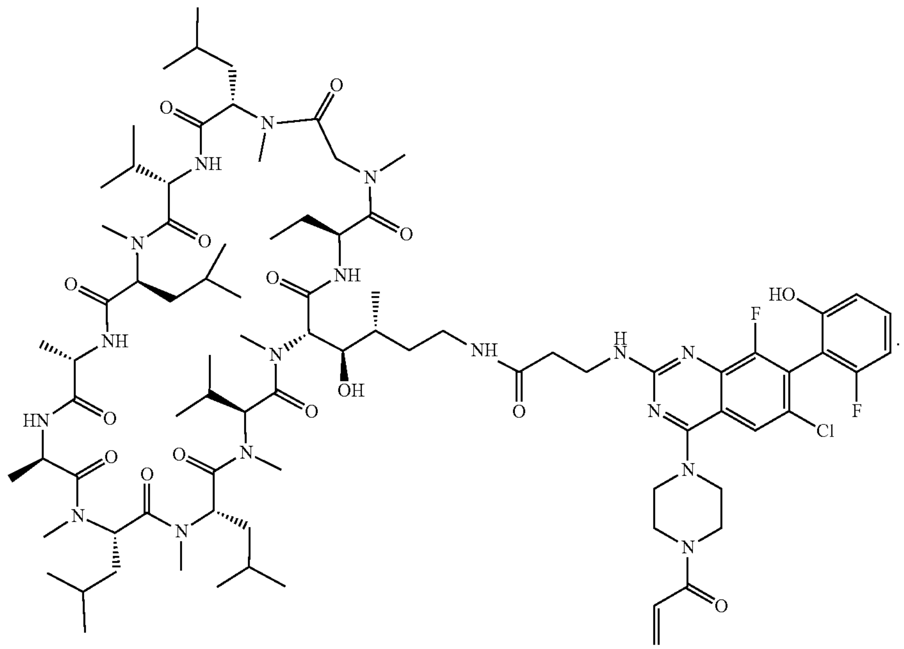 [SMILES: C=CC(=O)N1CCN(c2nc(NCCC(=O)NCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]

In embodiments, the anti-CNS disease drug is not
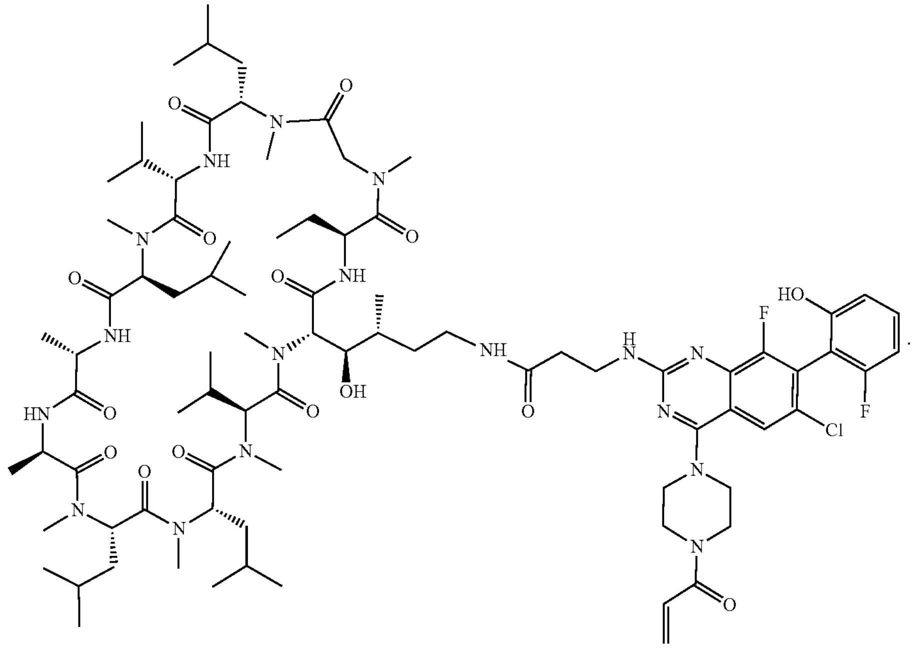 [SMILES: C=CC(=O)N1CCN(c2nc(NCCC(=O)NCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]
In embodiments, the anti-CNS disease drug is
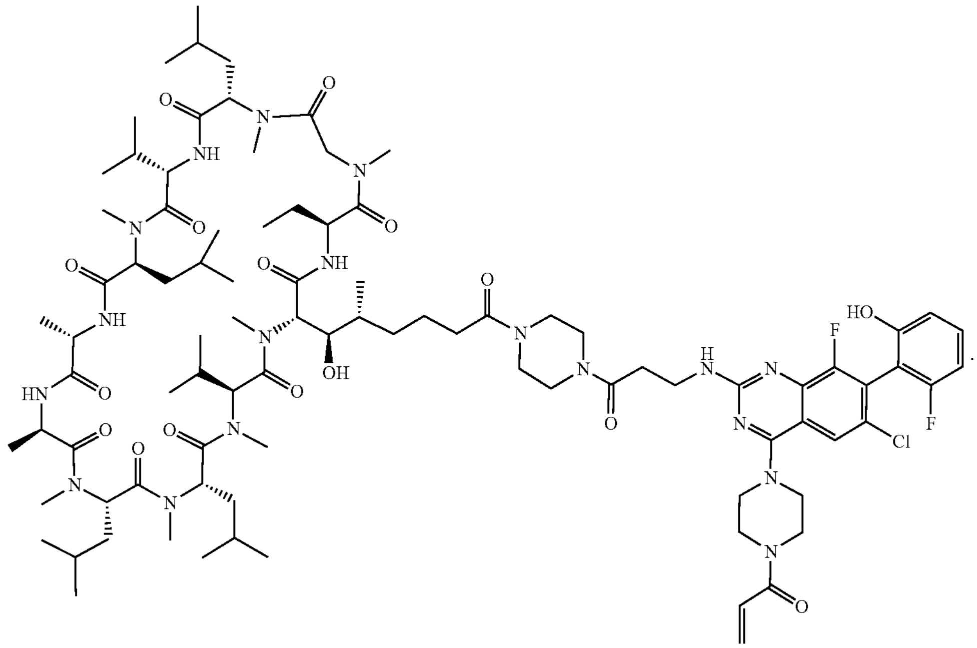 [SMILES: C=CC(=O)N1CCN(c2nc(NCCC(=O)N3CCN(C(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)CC3)nc3c(F)c(-c4c(O)cccc4F)c(Cl)cc23)CC1]

In embodiments, the anti-CNS disease drug is not
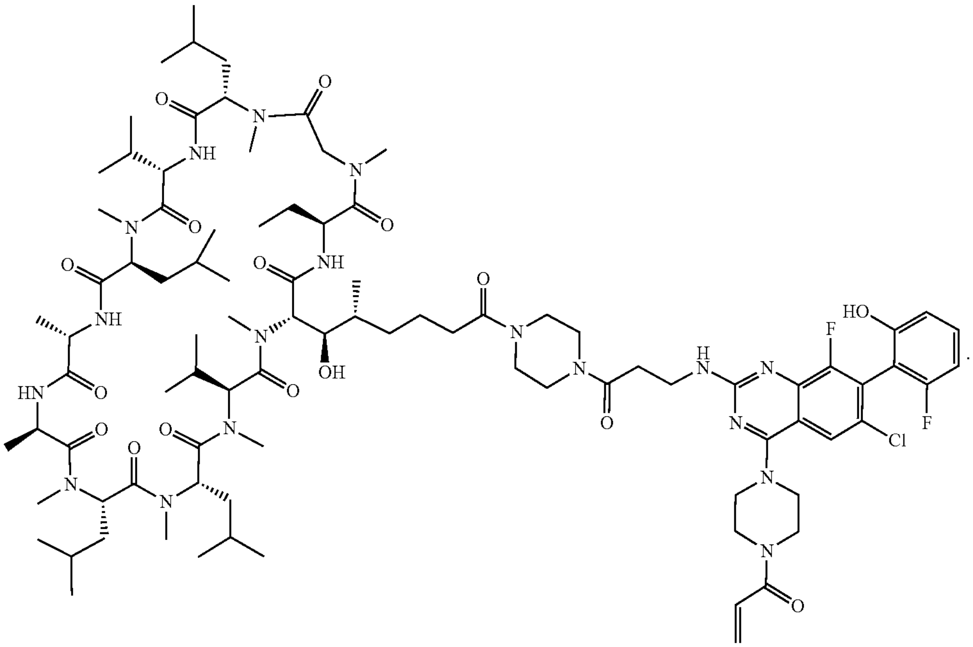 [SMILES: C=CC(=O)N1CCN(c2nc(NCCC(=O)N3CCN(C(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)CC3)nc3c(F)c(-c4c(O)cccc4F)c(Cl)cc23)CC1]
In embodiments, the anti-CNS disease drug is
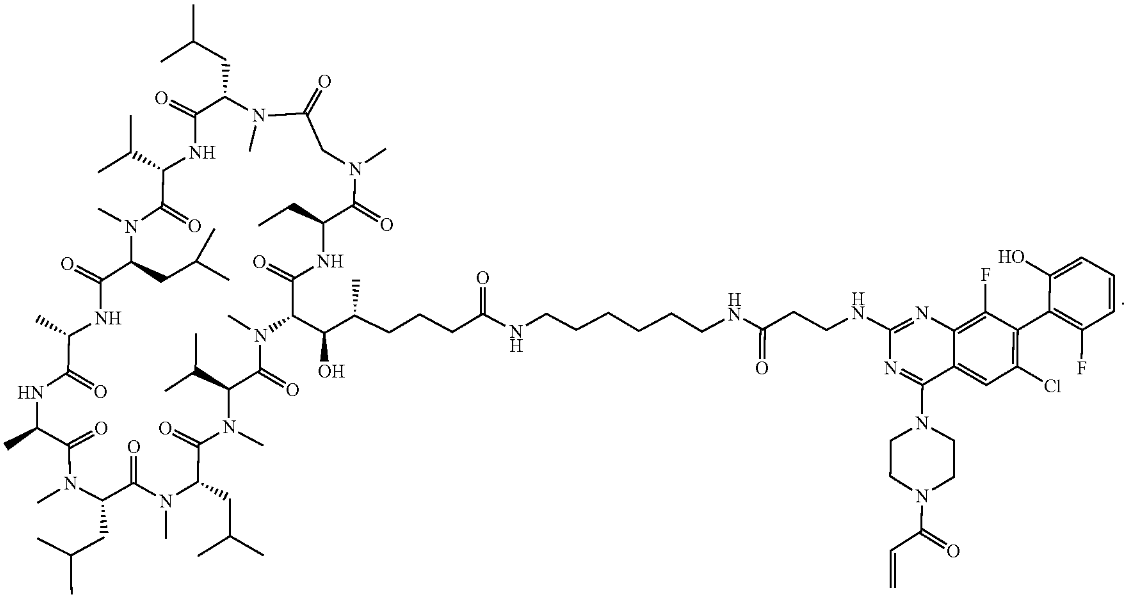 [SMILES: C=CC(=O)N1CCN(c2nc(NCCC(=O)NCCCCCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]

In embodiments, the anti-CNS disease drug is not
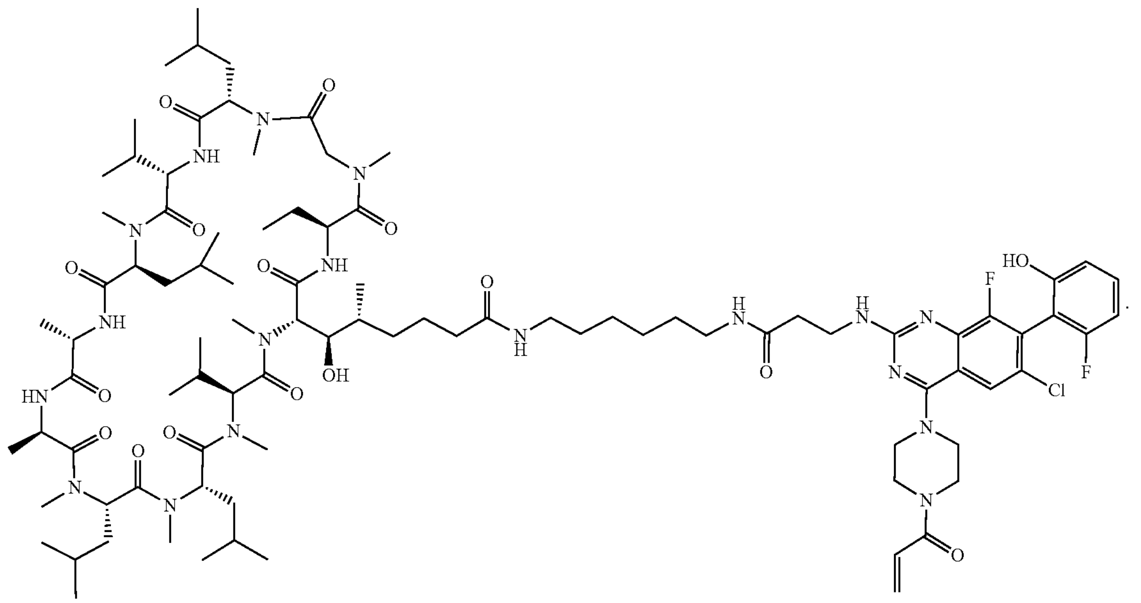 [SMILES: C=CC(=O)N1CCN(c2nc(NCCC(=O)NCCCCCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1]
In embodiments, the anti-CNS disease drug is
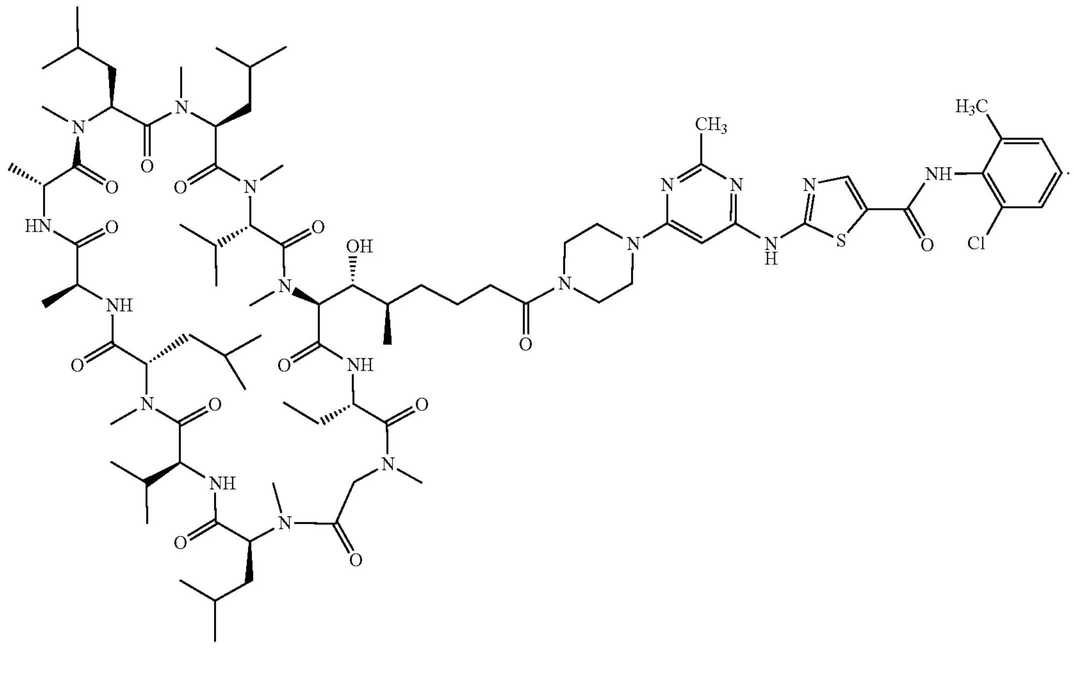

In embodiments, the anti-CNS disease drug is not
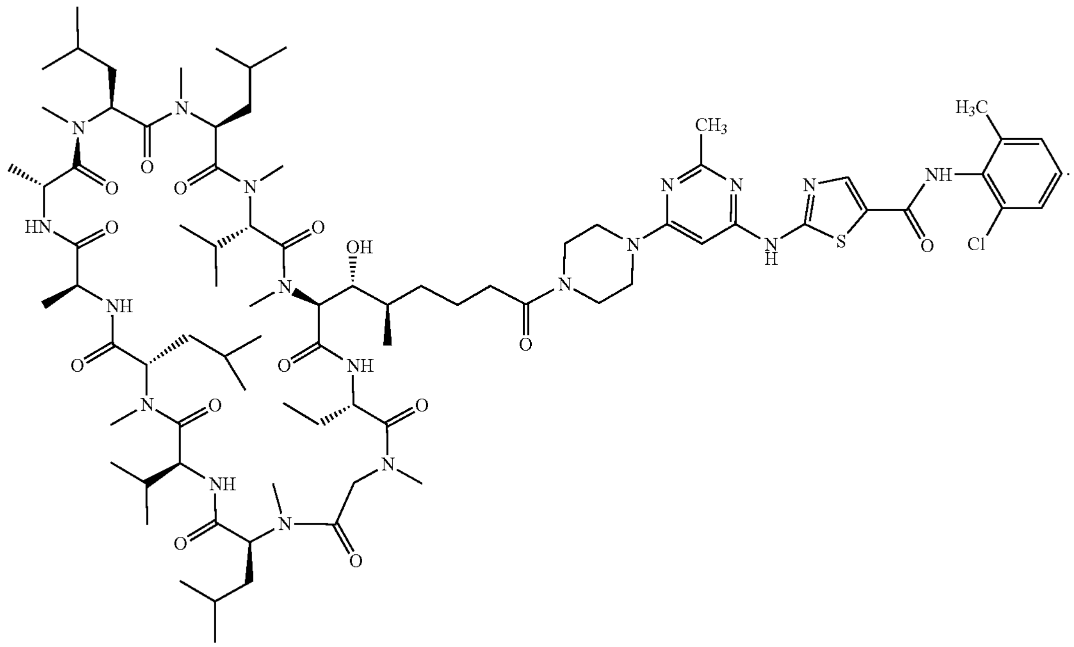
In embodiments, the anti-CNS disease drug is
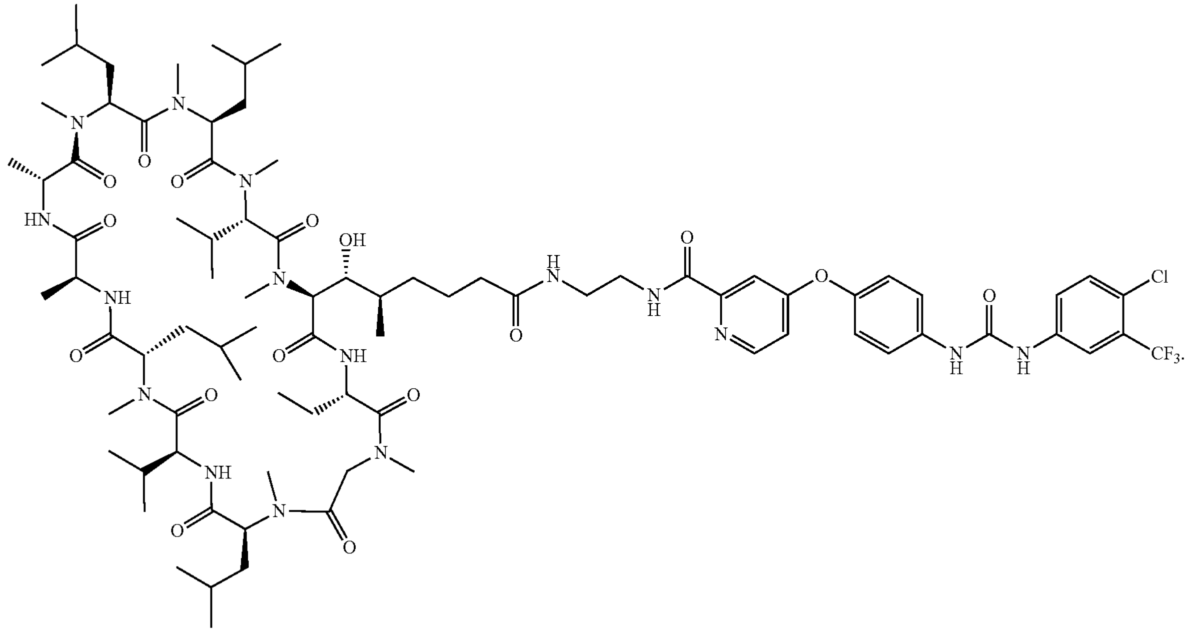

In embodiments, the anti-CNS disease drug is not
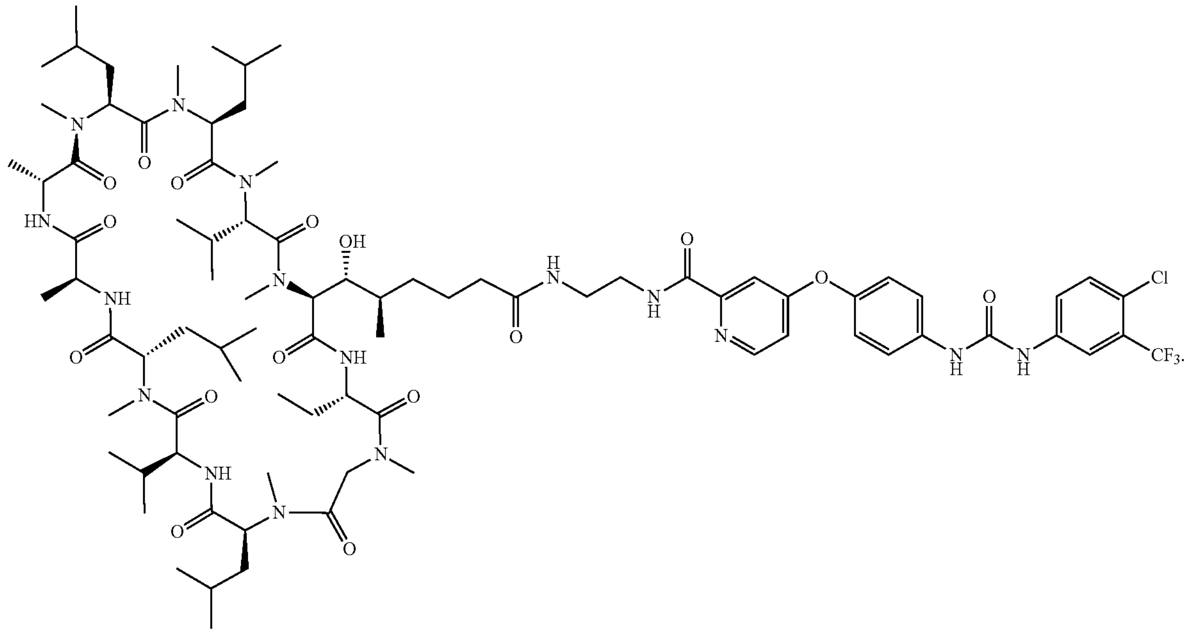
In embodiments, the anti-CNS disease drug is
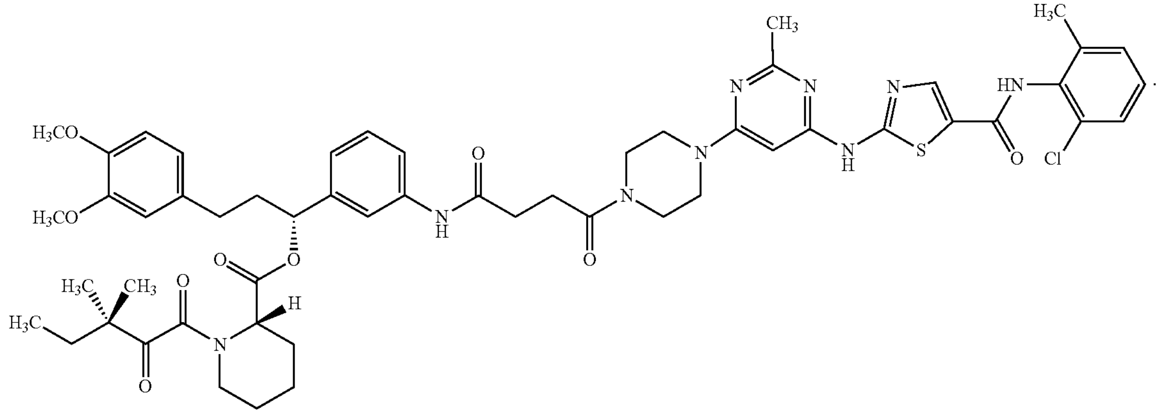
In embodiments, the anti-CNS disease drug is not
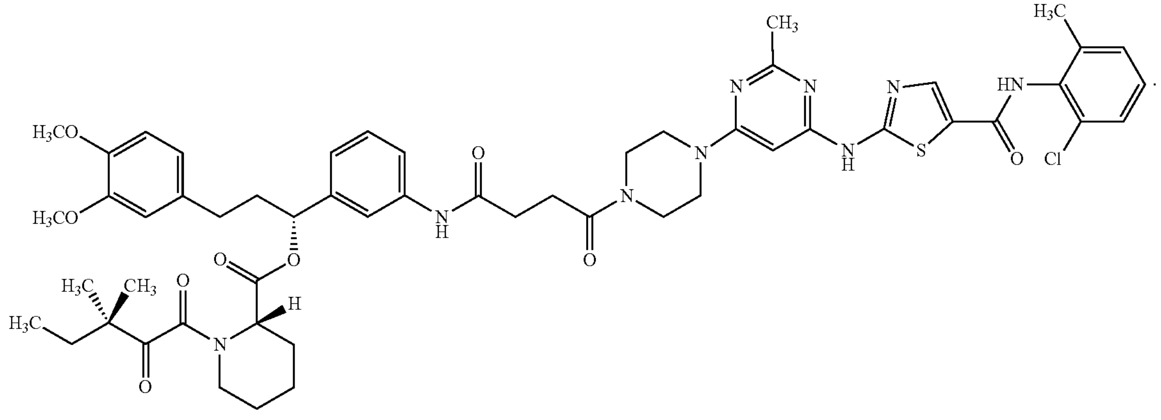

In embodiments, the anti-CNS disease drug is
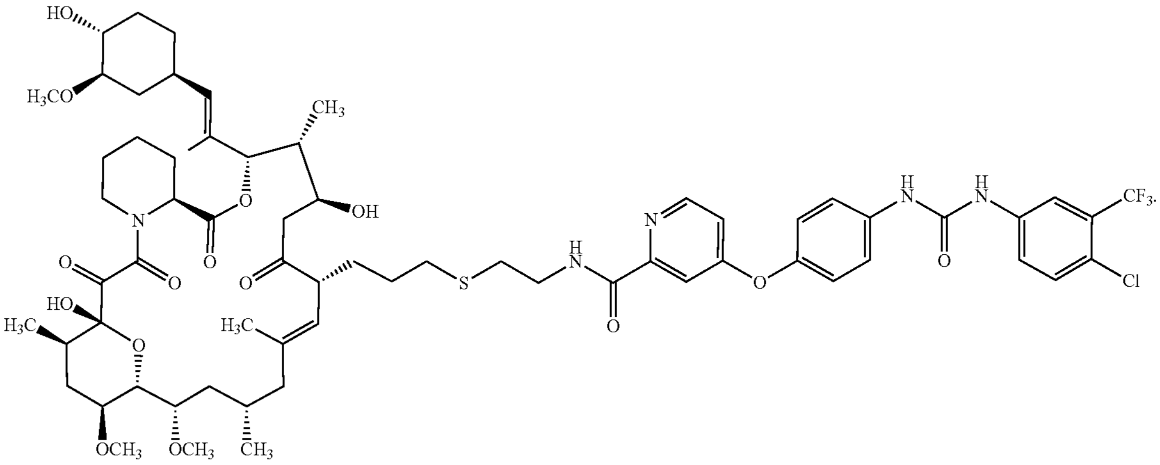 [SMILES: CO[C@H]1C[C@@H](C)C/C(C)=C/[C@@H](CCCSCCNC(=O)c2cc(Oc3ccc(NC(=O)Nc4ccc(Cl)c(C(F)(F)F)c4)cc3)ccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
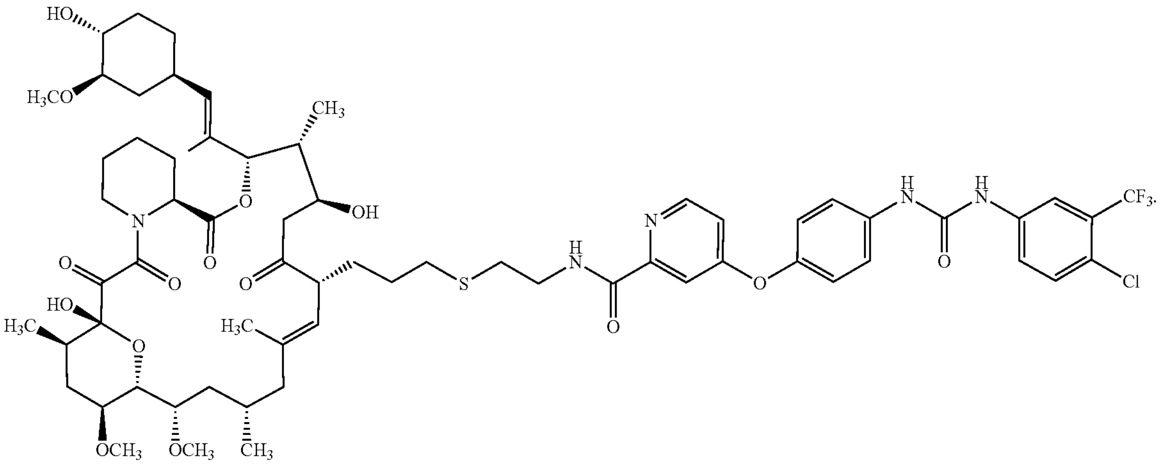 [SMILES: CO[C@H]1C[C@@H](C)C/C(C)=C/[C@@H](CCCSCCNC(=O)c2cc(Oc3ccc(NC(=O)Nc4ccc(Cl)c(C(F)(F)F)c4)cc3)ccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
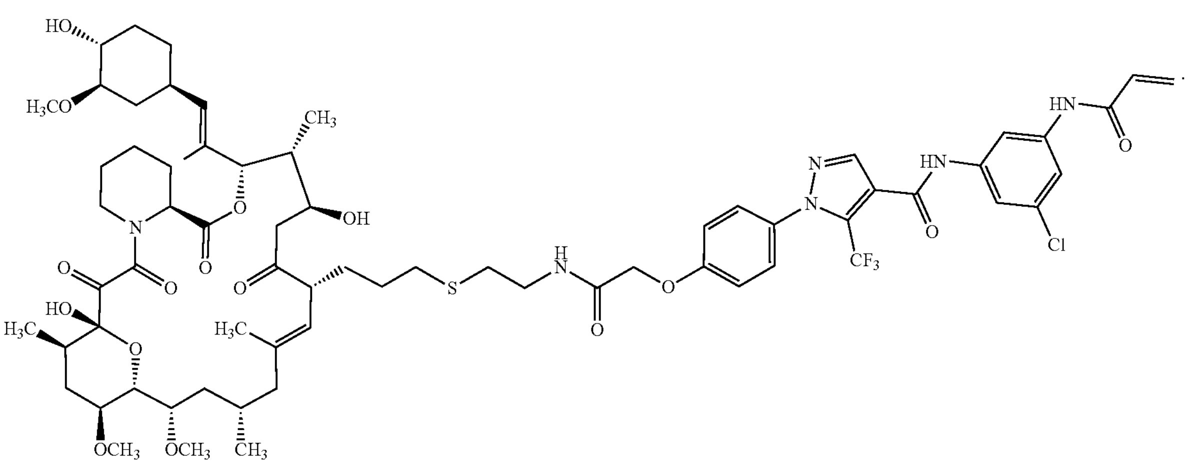 [SMILES: C=CC(=O)Nc1cc(Cl)cc(NC(=O)c2cnn(-c3ccc(OCC(=O)NCCSCCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]

In embodiments, the anti-CNS disease drug is not
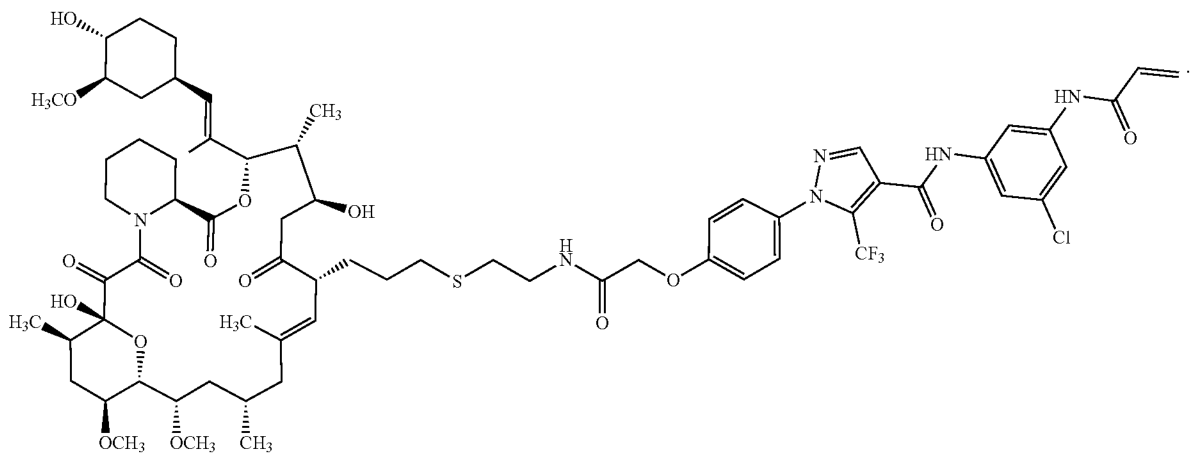 [SMILES: C=CC(=O)Nc1cc(Cl)cc(NC(=O)c2cnn(-c3ccc(OCC(=O)NCCSCCC[C@@H]4/C=C(\C)C[C@H](C)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1]
In embodiments, the anti-CNS disease drug is
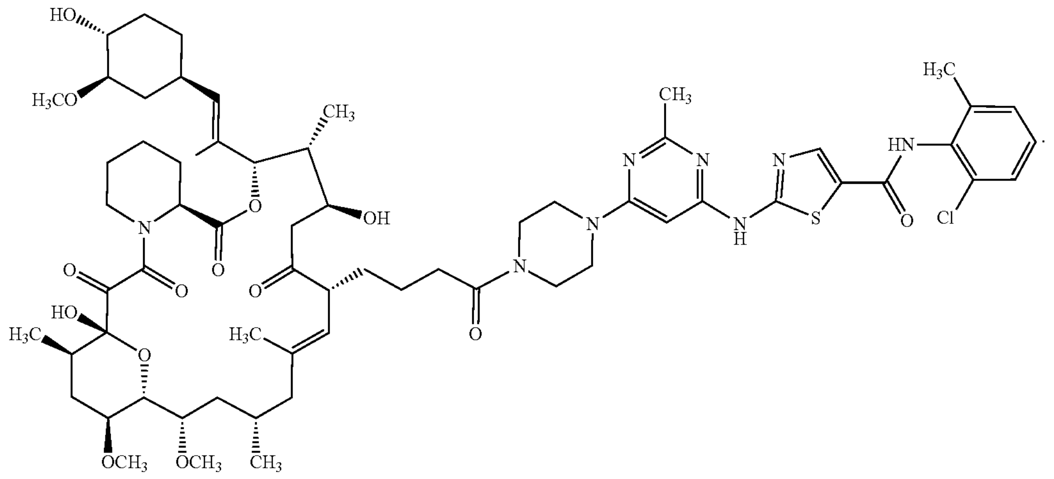 [SMILES: CO[C@H]1C[C@@H](C)C/C(C)=C/[C@@H](CCCC(=O)N2CCN(c3cc(Nc4ncc(C(=O)Nc5c(C)cccc5Cl)s4)nc(C)n3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
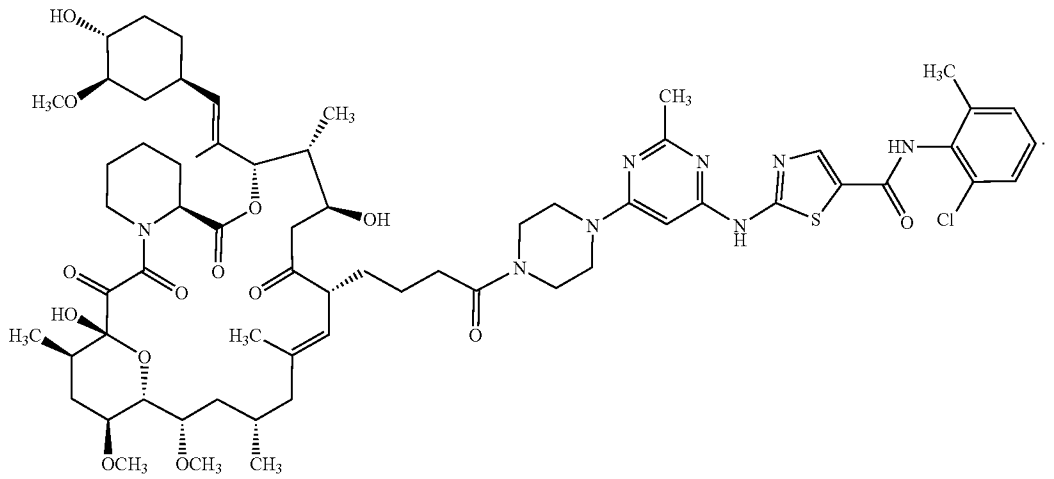 [SMILES: CO[C@H]1C[C@@H](C)C/C(C)=C/[C@@H](CCCC(=O)N2CCN(c3cc(Nc4ncc(C(=O)Nc5c(C)cccc5Cl)s4)nc(C)n3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is
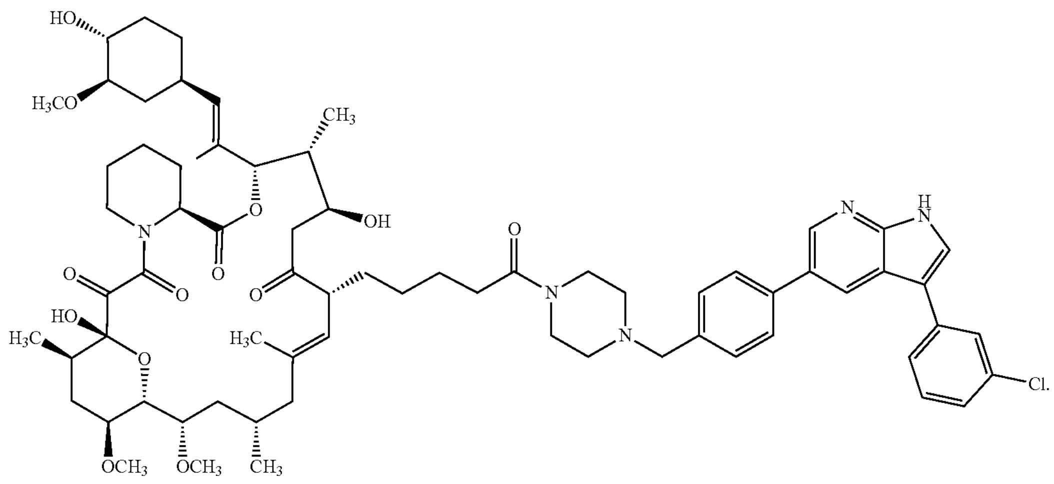 [SMILES: CO[C@H]1C[C@@H](C)C/C(C)=C/[C@@H](CCCCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
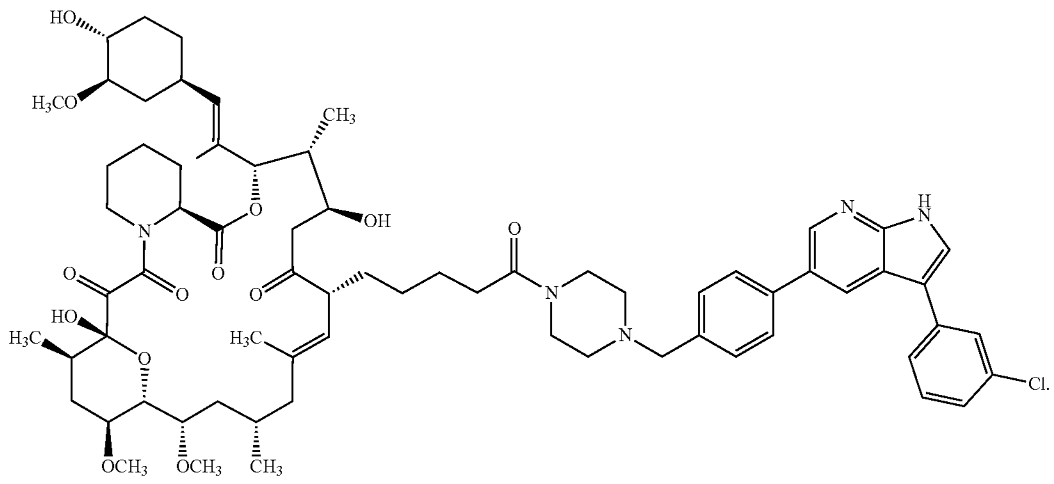 [SMILES: CO[C@H]1C[C@@H](C)C/C(C)=C/[C@@H](CCCCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
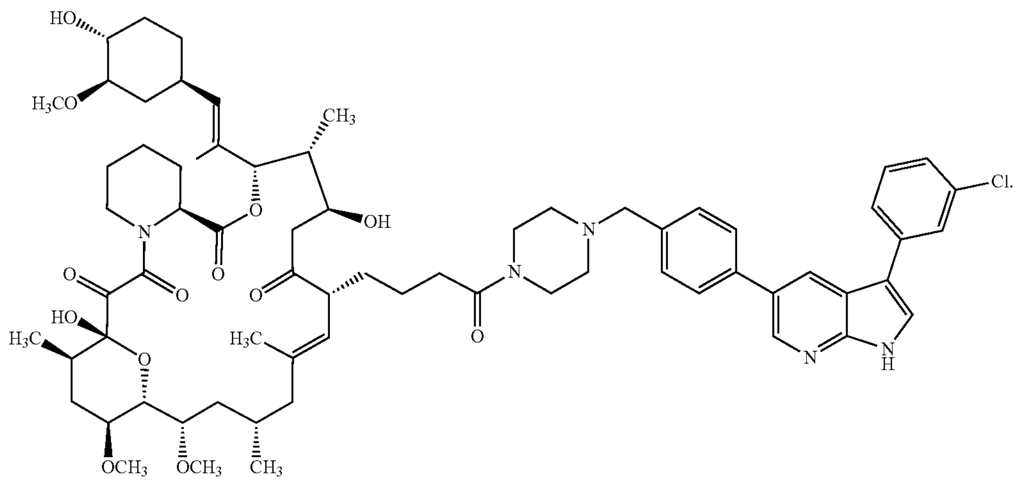 [SMILES: CO[C@H]1C[C@@H](C)C/C(C)=C/[C@@H](CCCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
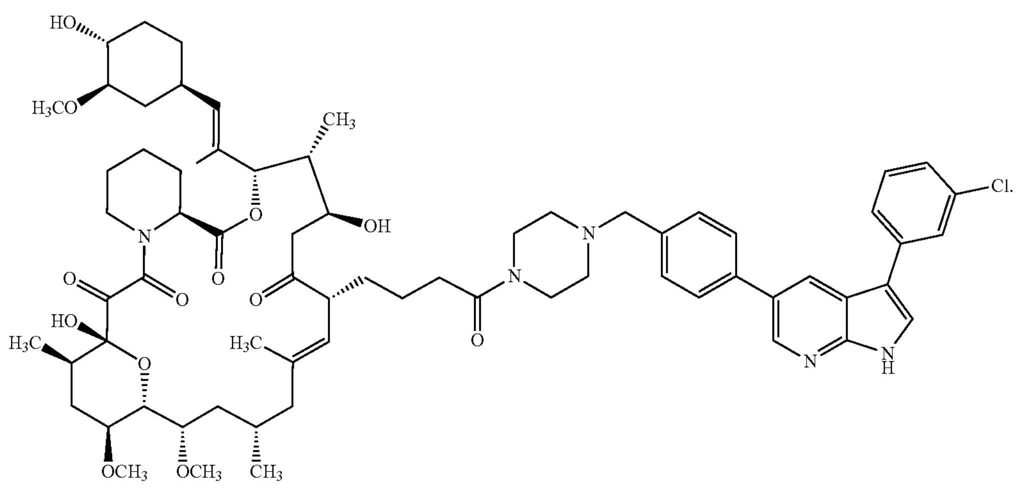 [SMILES: CO[C@H]1C[C@@H](C)C/C(C)=C/[C@@H](CCCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
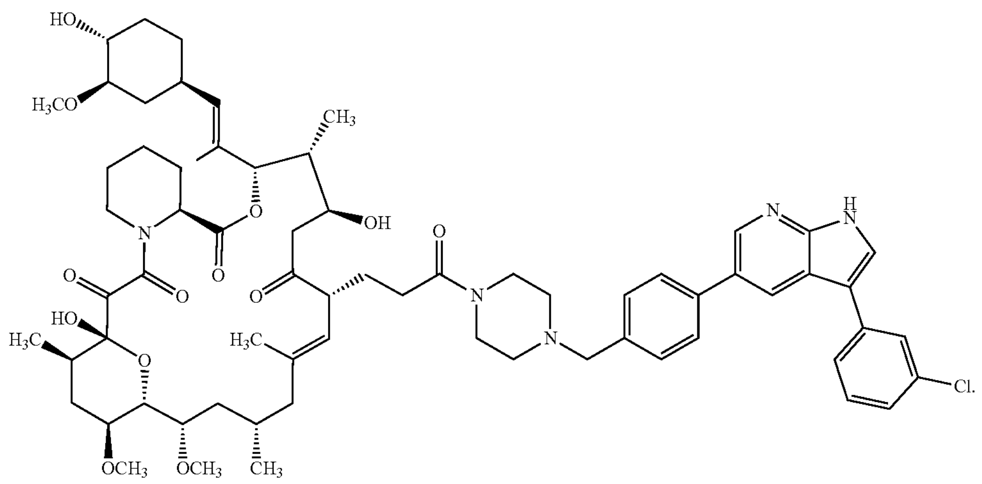 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
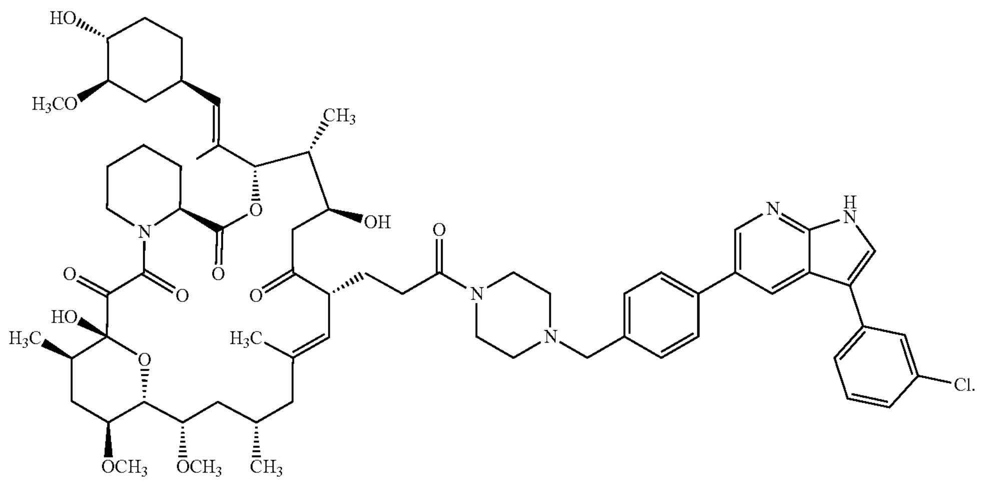 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is
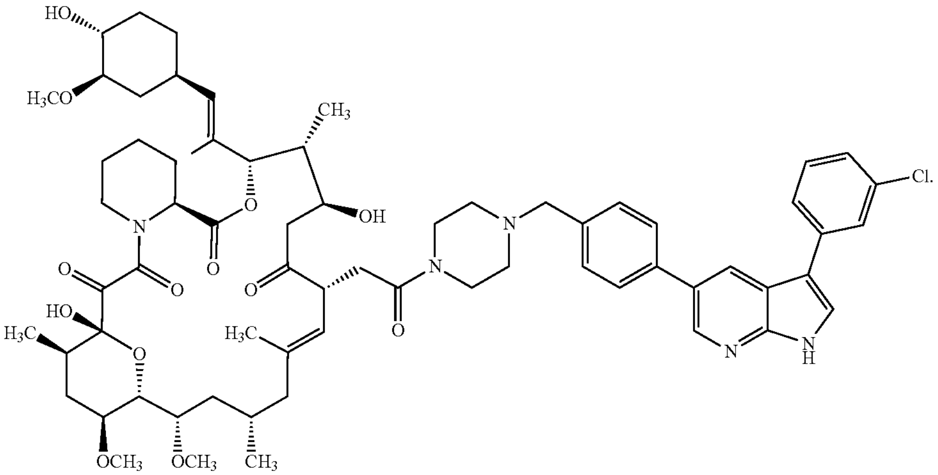 [SMILES: CO[C@H]1C[C@@H](C)C/C(C)=C/[C@@H](CC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is not
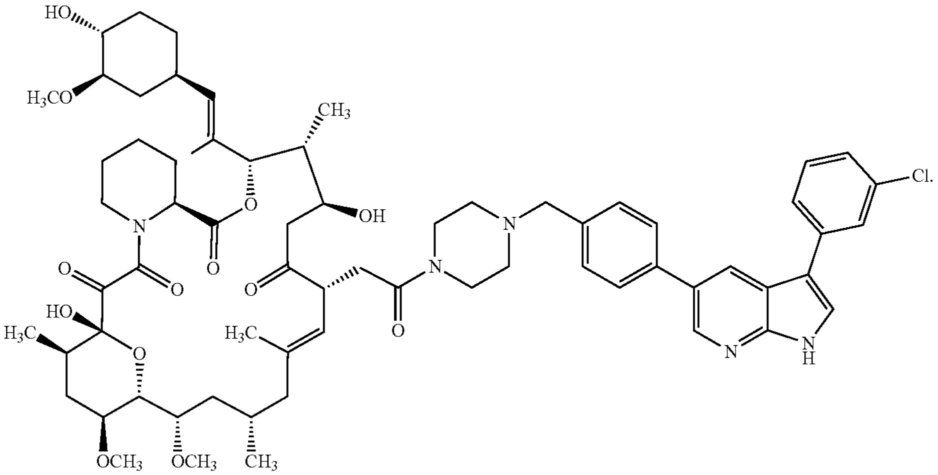 [SMILES: CO[C@H]1C[C@@H](C)C/C(C)=C/[C@@H](CC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
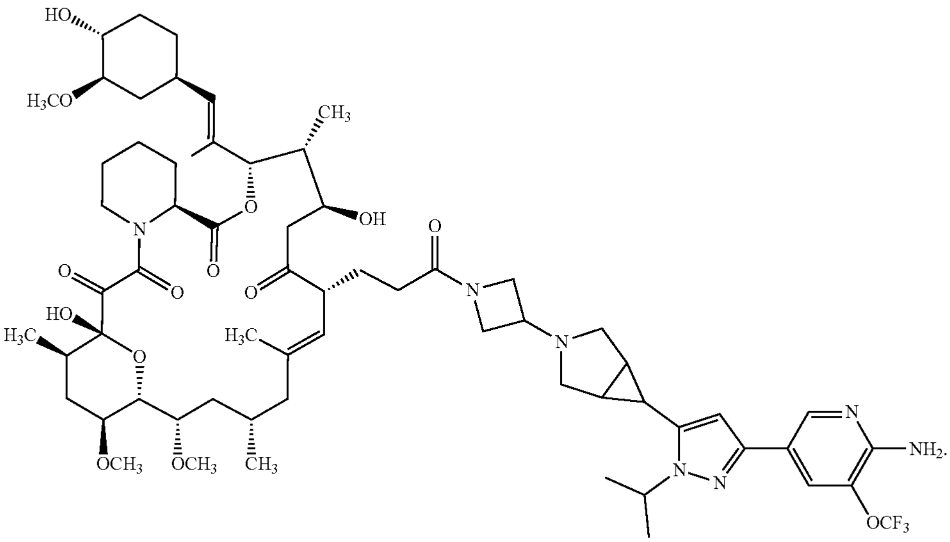 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
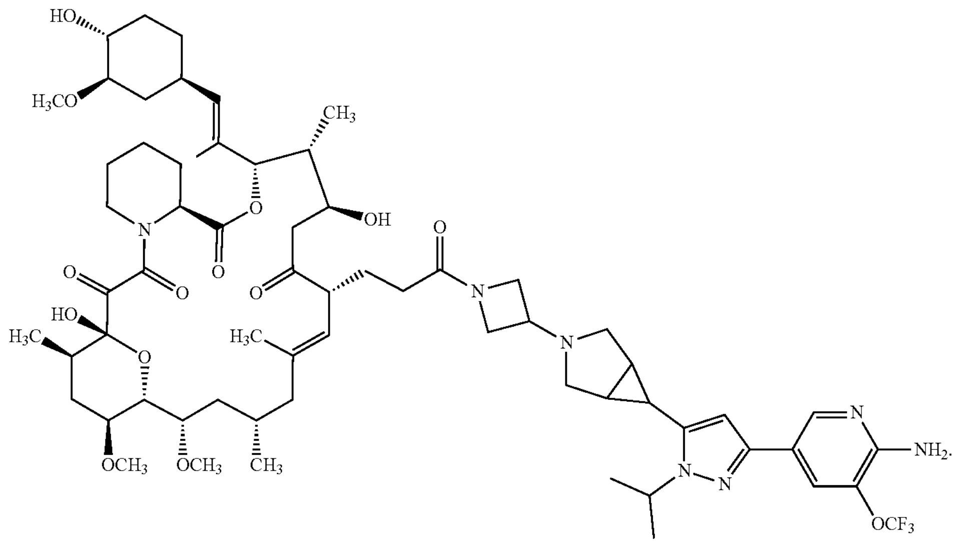 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
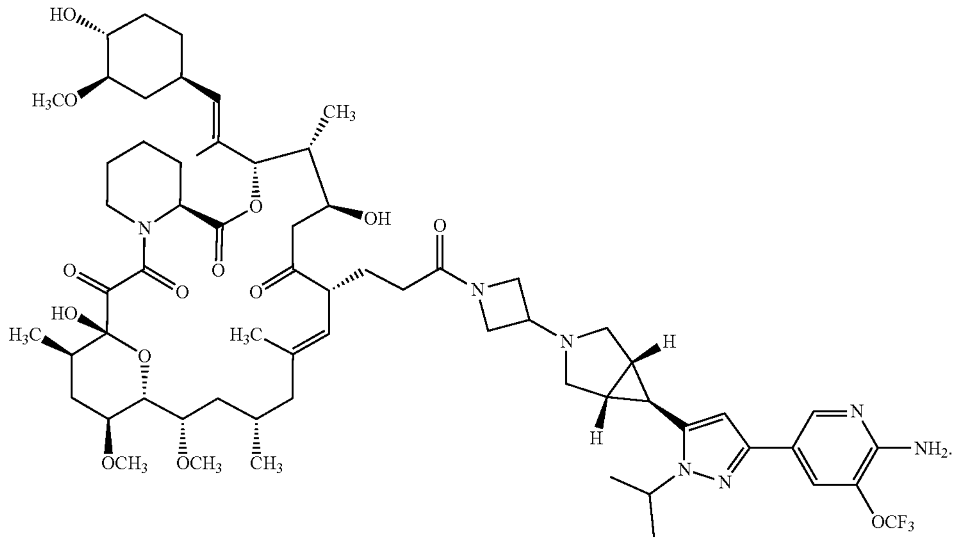 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

In embodiments, the anti-CNS disease drug is not
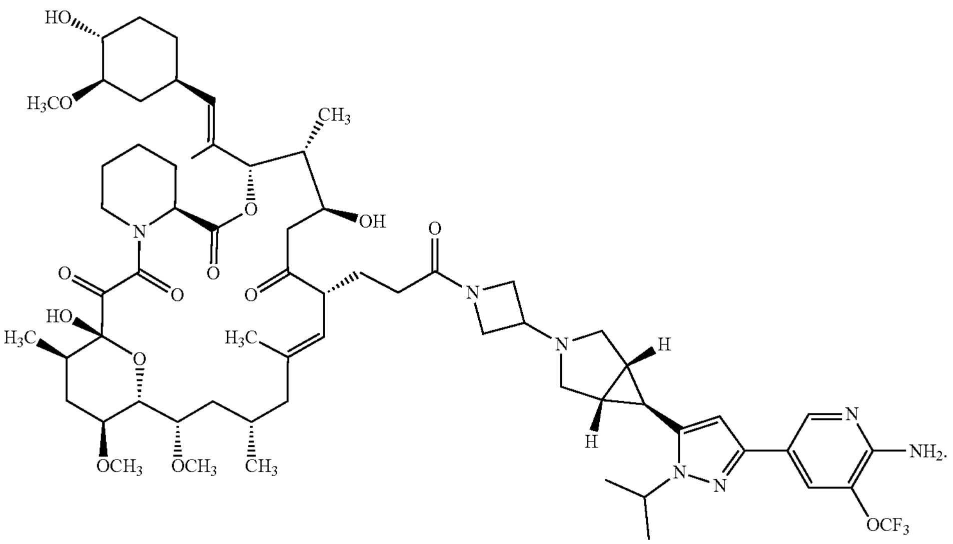 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
In embodiments, the anti-CNS disease drug is
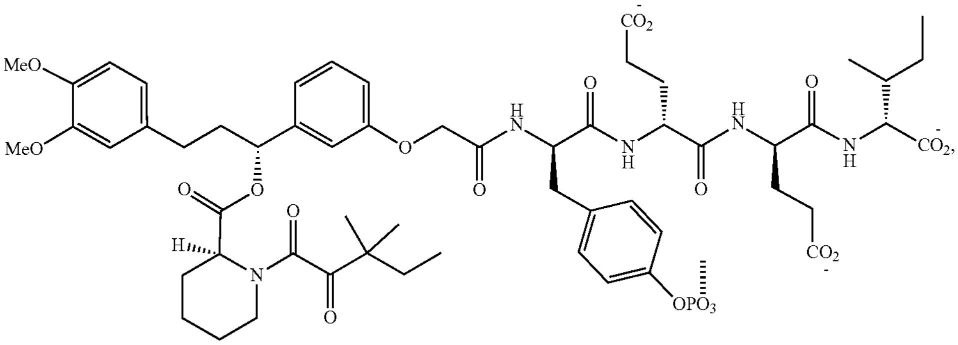
or an analog thereof.
In embodiments, the anti-CNS disease drug is not
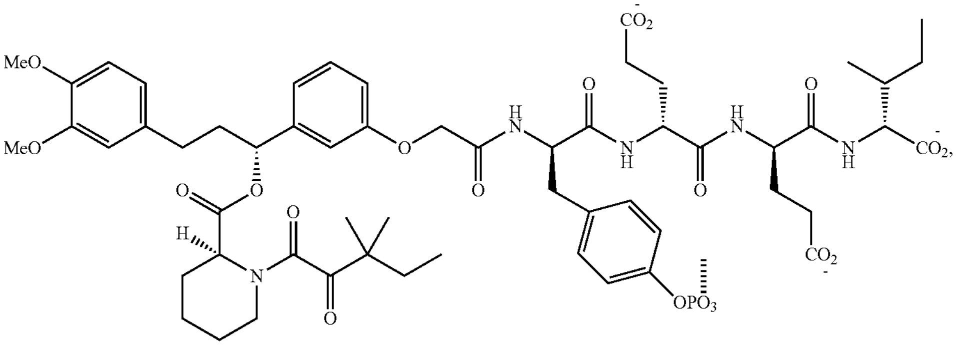
or an analog thereof.

In embodiments, the anti-CNS disease drug is
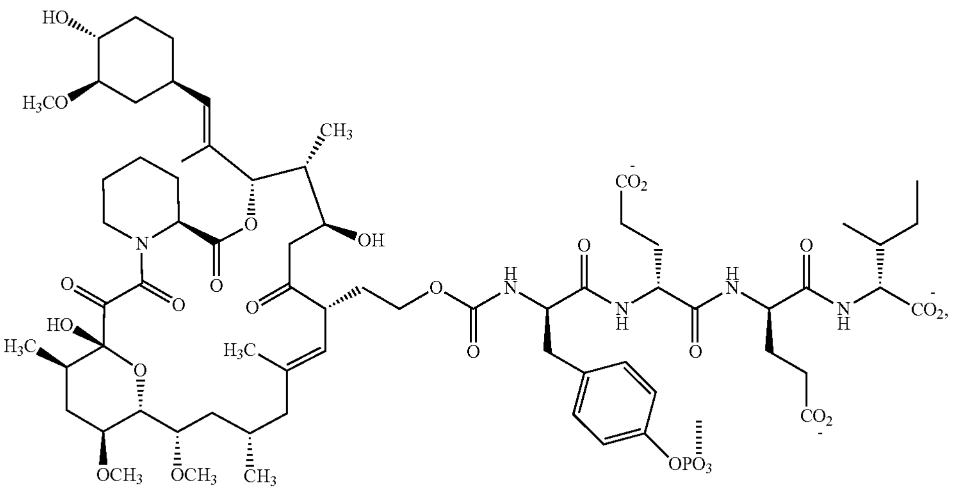
or an analog thereof.
In embodiments, the anti-CNS disease drug is not
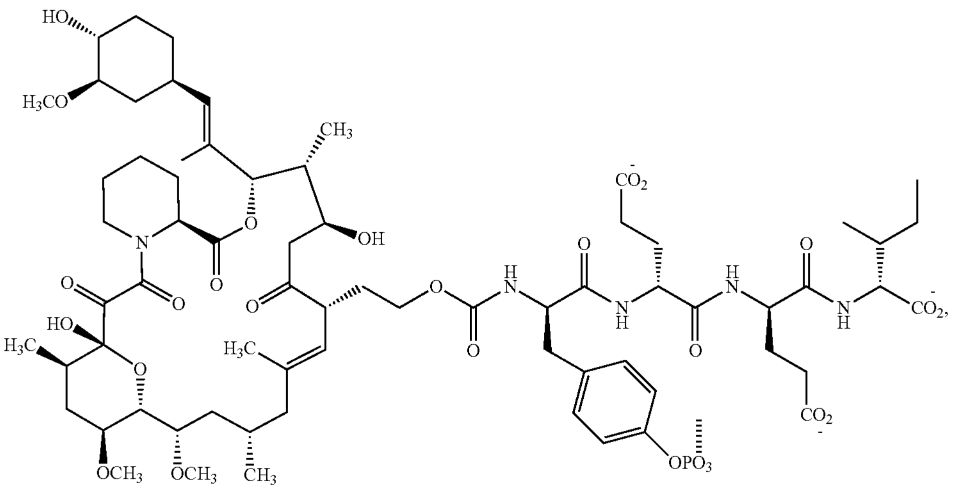
or an analog thereof.

In embodiments, the anti-CNS disease drug is
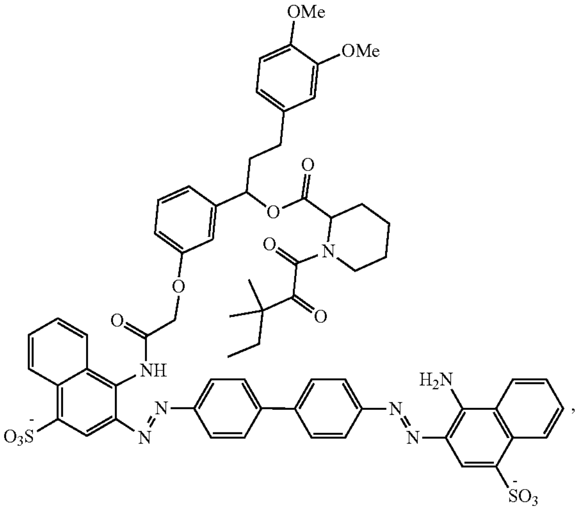
or an analog thereof.
In embodiments, the anti-CNS disease drug is not
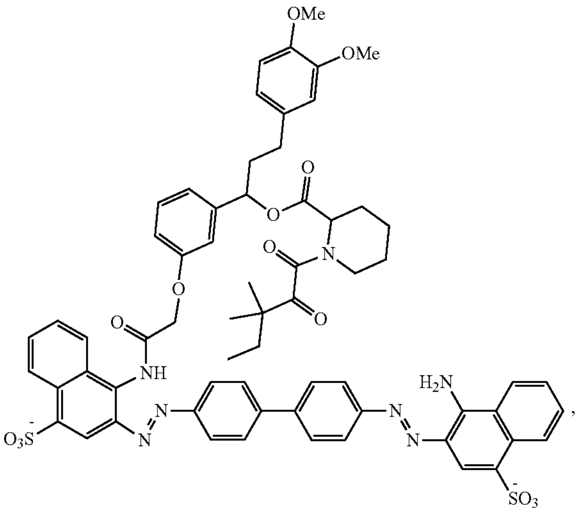
or an analog thereof.
In embodiments, the anti-CNS disease drug is
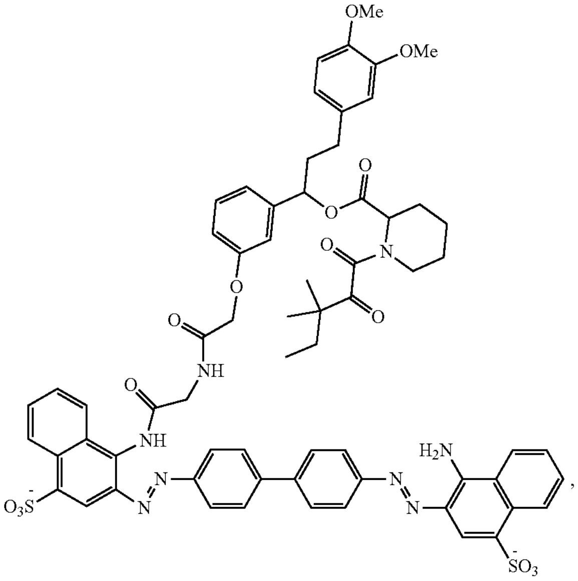
or an analog thereof.
In embodiments, the anti-CNS disease drug is not
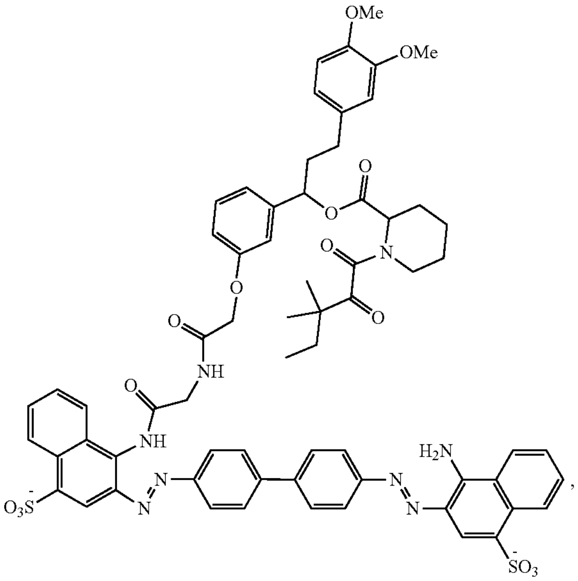
or an analog thereof.

In embodiments, the anti-CNS disease drug is
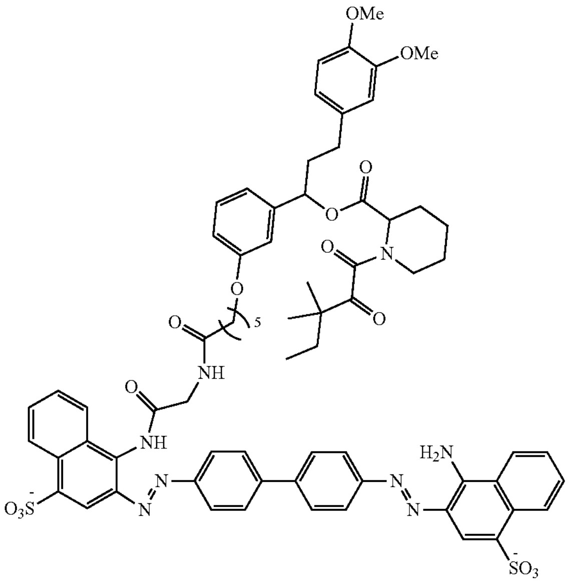
,
or an analog thereof.
In embodiments, the anti-CNS disease drug is not
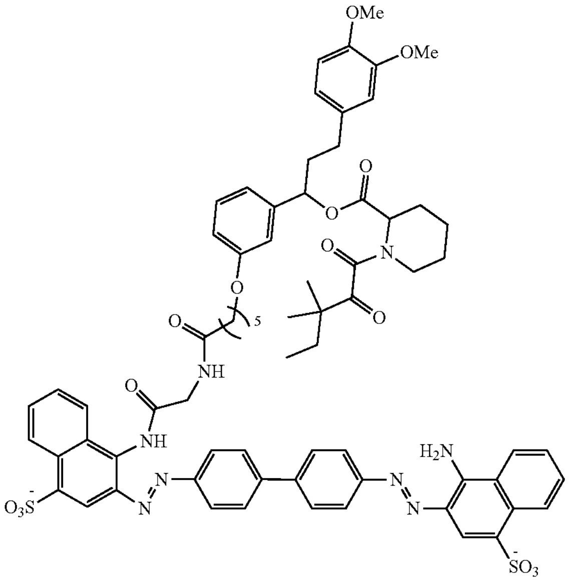
,
or an analog thereof.
In embodiments, the anti-CNS disease drug is
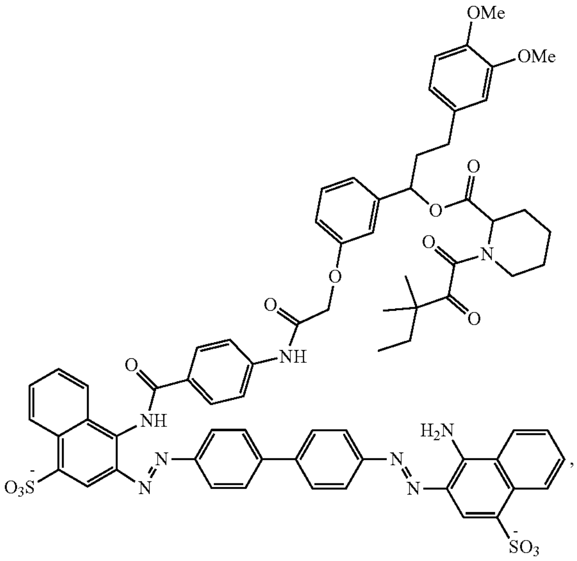
,
or an analog thereof.
In embodiments, the anti-CNS disease drug is not
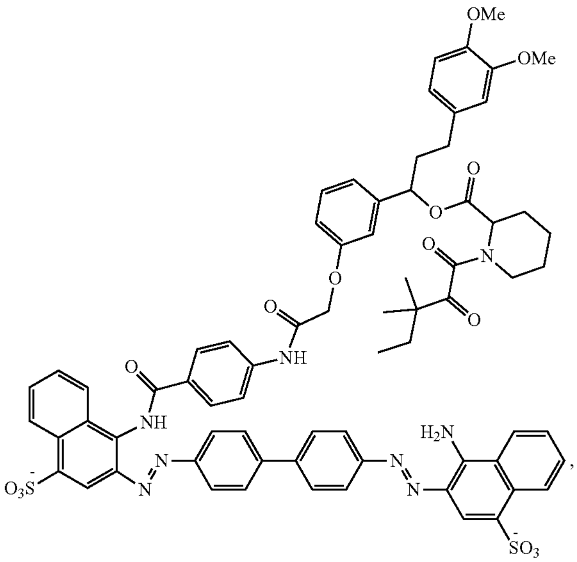
,
or an analog thereof.

In embodiments, the anti-CNS disease drug is
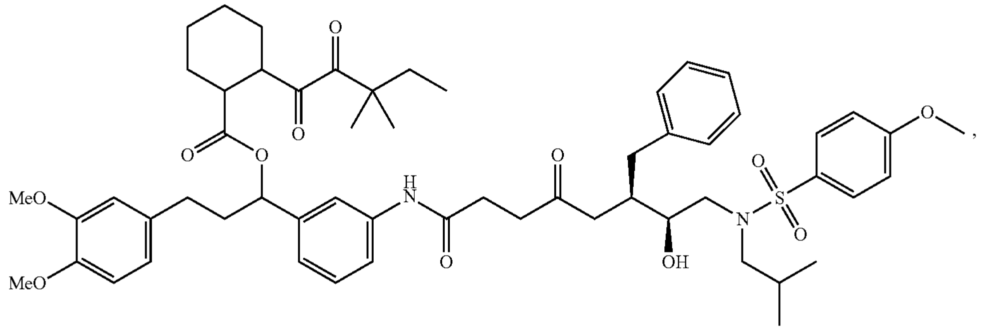 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc(OC)cc2)c1]
or an analog thereof.
In embodiments, the anti-CNS disease drug is not
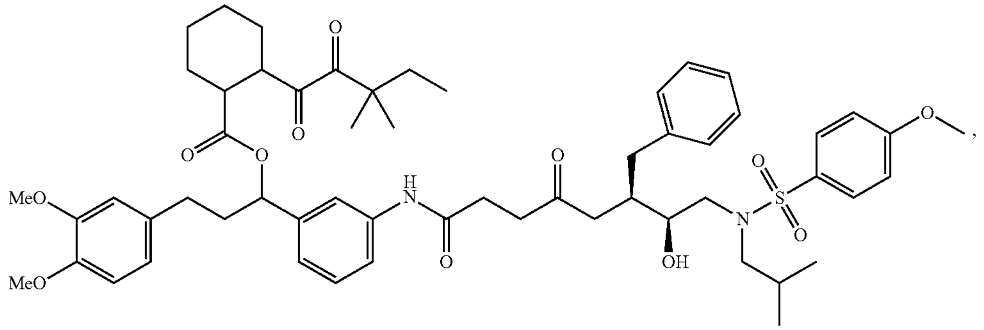 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc(OC)cc2)c1]
or an analog thereof.
In embodiments, the anti-CNS disease drug is
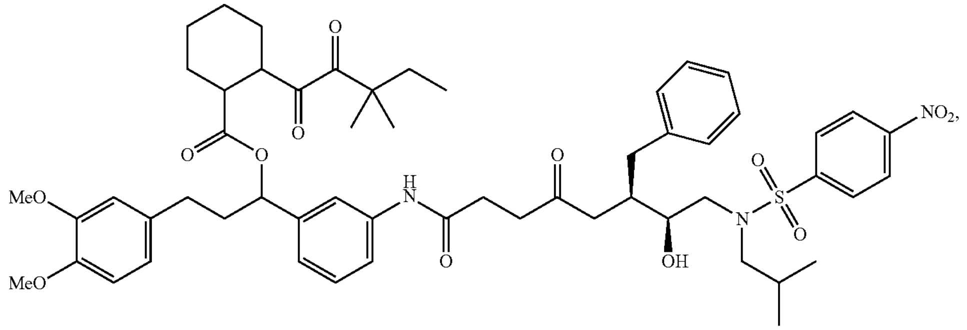 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc([N+](=O)[O-])cc2)c1]
or an analog thereof.
In embodiments, the anti-CNS disease drug is not
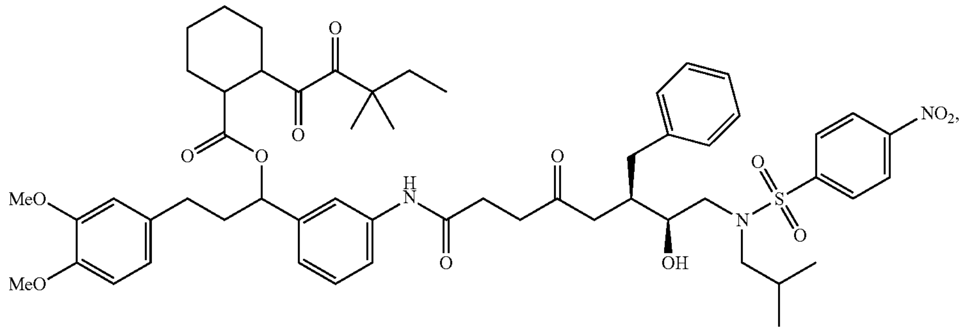 [SMILES: CCC(C)(C)C(=O)C(=O)C1CCCCC1C(=O)OC(CCc1ccc(OC)c(OC)c1)c1cccc(NC(=O)CCC(=O)C[C@@H](Cc2ccccc2)[C@H](O)CN(CC(C)C)S(=O)(=O)c2ccc([N+](=O)[O-])cc2)c1]
or an analog thereof.

In embodiments, the anti-CNS disease drug is
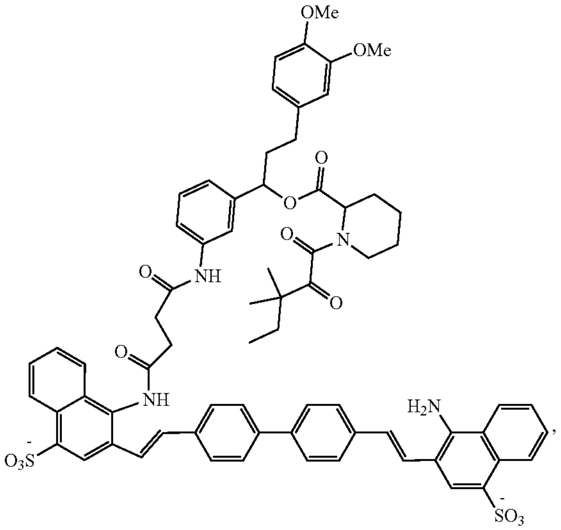
or an analog thereof.
In embodiments, the anti-CNS disease drug is not
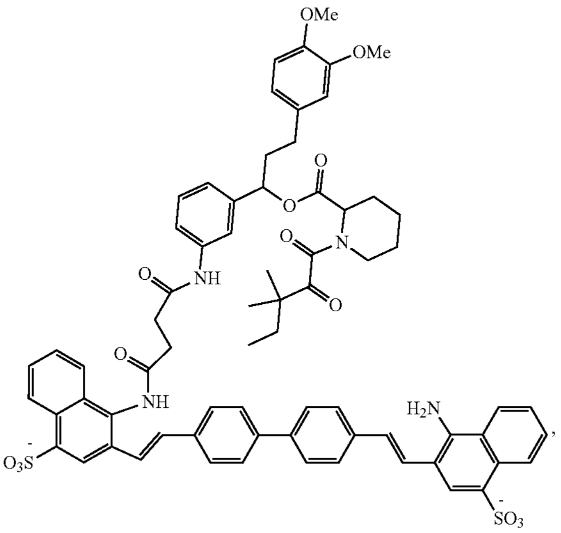
or an analog thereof.
In embodiments, the anti-CNS disease drug is
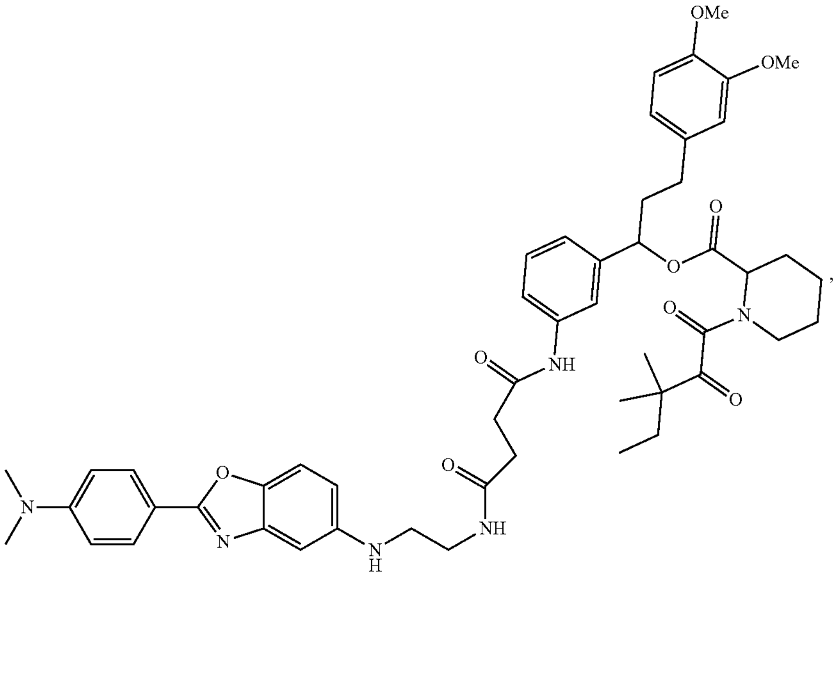 [SMILES: CCC(C)(C)C(=O)C(=O)N1CCCCC1C(=O)OC(CCc1ccc(OC)c(OC)c1)c1cccc(NC(=O)CCC(=O)NCCNc2ccc3oc(-c4ccc(N(C)C)cc4)nc3c2)c1]
or an analog thereof.

In embodiments, the anti-CNS disease drug is not
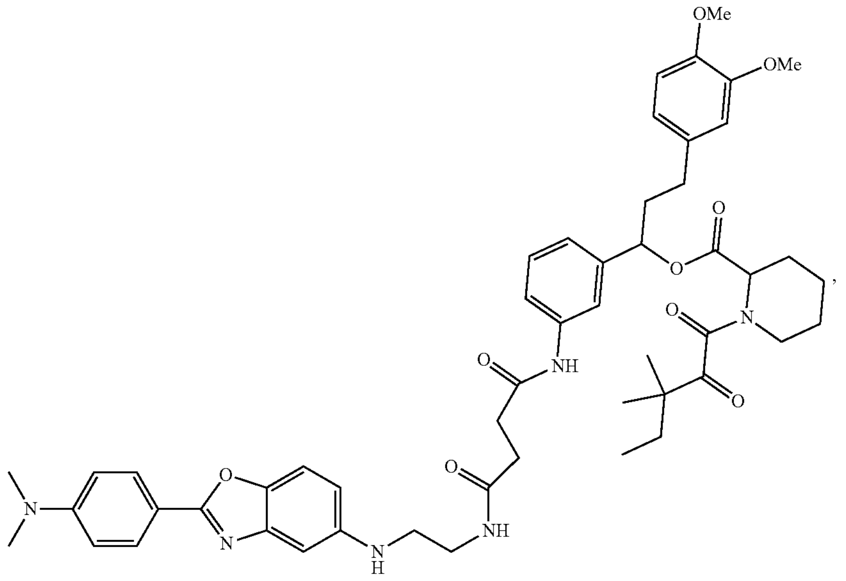 [SMILES: CCC(C)(C)C(=O)C(=O)N1CCCCC1C(=O)OC(CCc1ccc(OC)c(OC)c1)c1cccc(NC(=O)CCC(=O)NCCNc2ccc3oc(-c4ccc(N(C)C)cc4)nc3c2)c1]
or an analog thereof.
In embodiments, the anti-CNS disease drug is
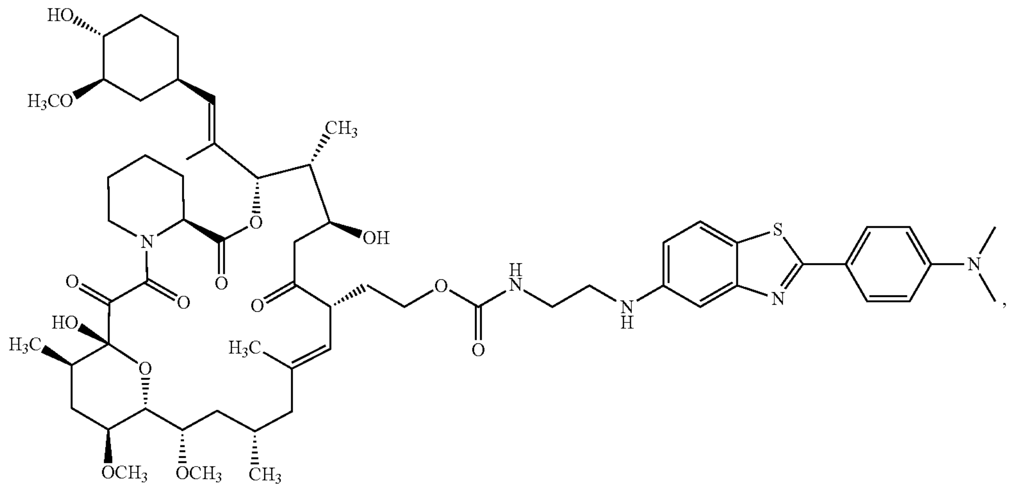
or an analog thereof.

In embodiments, the anti-CNS disease drug is not
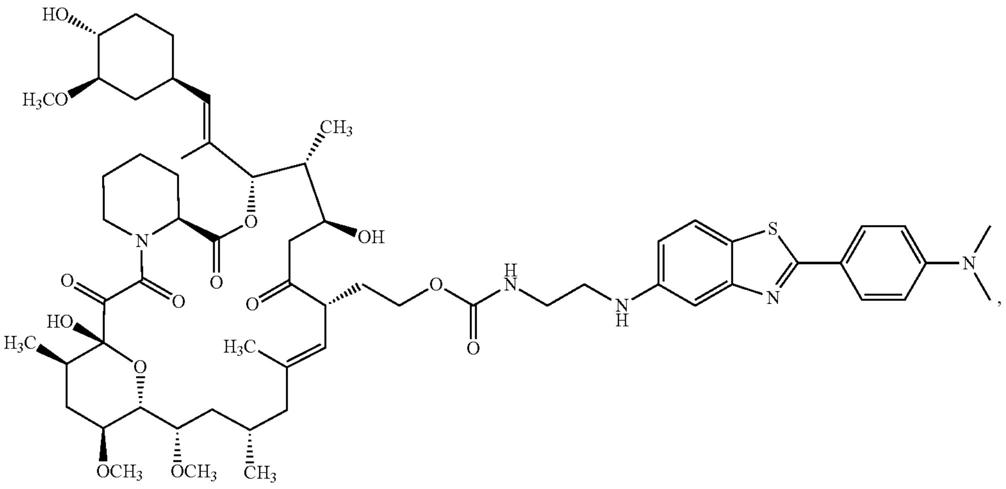
or an analog thereof.
In embodiments, the anti-CNS disease drug is
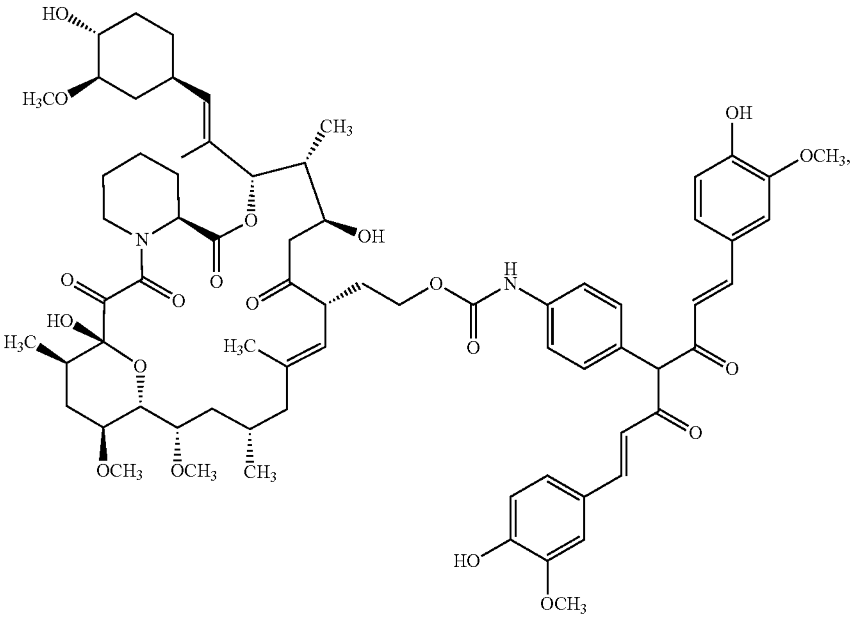 [SMILES: COc1cc(/C=C/C(=O)C(C(=O)/C=C/c2ccc(O)c(OC)c2)c2ccc(NC(=O)OCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)cc2)ccc1O]
or an analog thereof.

In embodiments, the anti-CNS disease drug is not
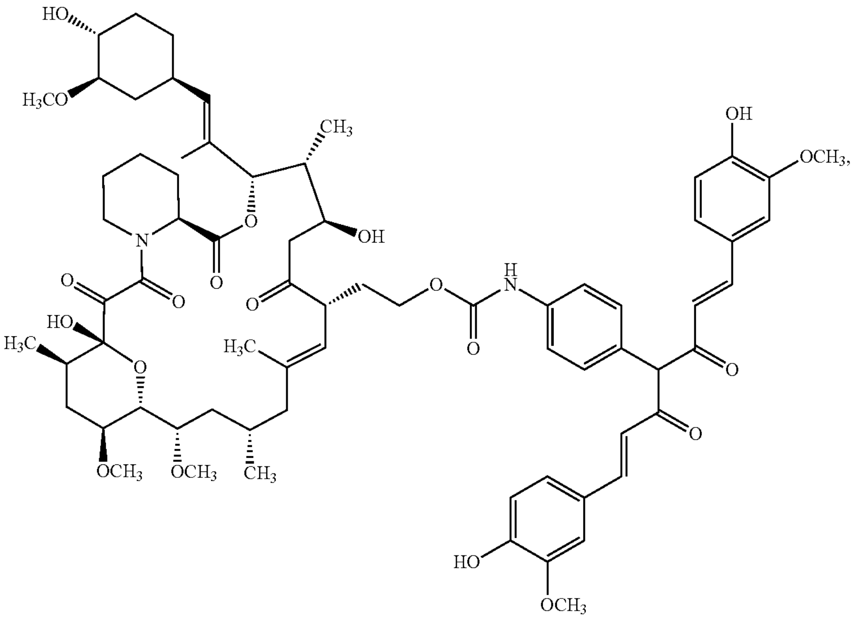 [SMILES: COc1cc(/C=C/C(=O)C(C(=O)/C=C/c2ccc(O)c(OC)c2)c2ccc(NC(=O)OCC[C@@H]3/C=C(\C)C[C@H](C)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)cc2)ccc1O]
or an analog thereof.
In embodiments, the anti-CNS disease drug is
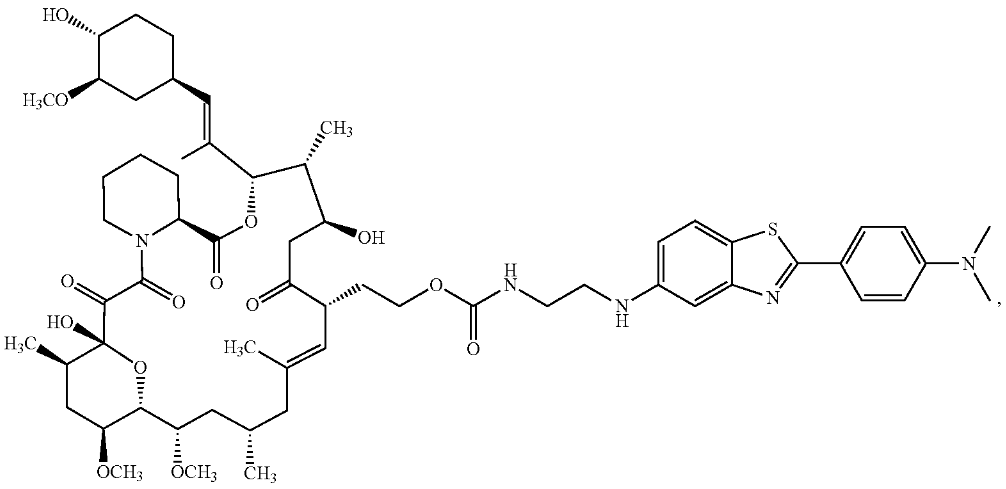
or an analog thereof.

In embodiments, the anti-CNS disease drug is not
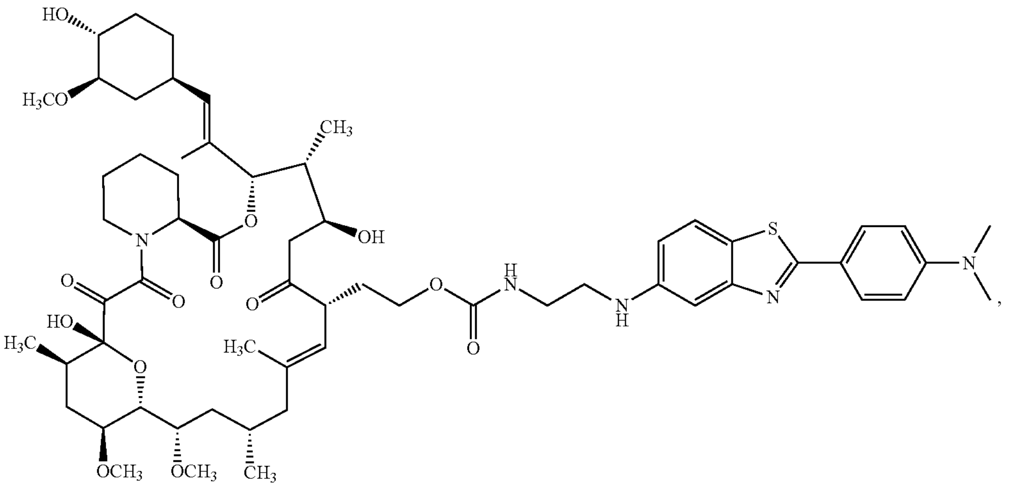
or an analog thereof.
In embodiments, the anti-CNS disease drug is
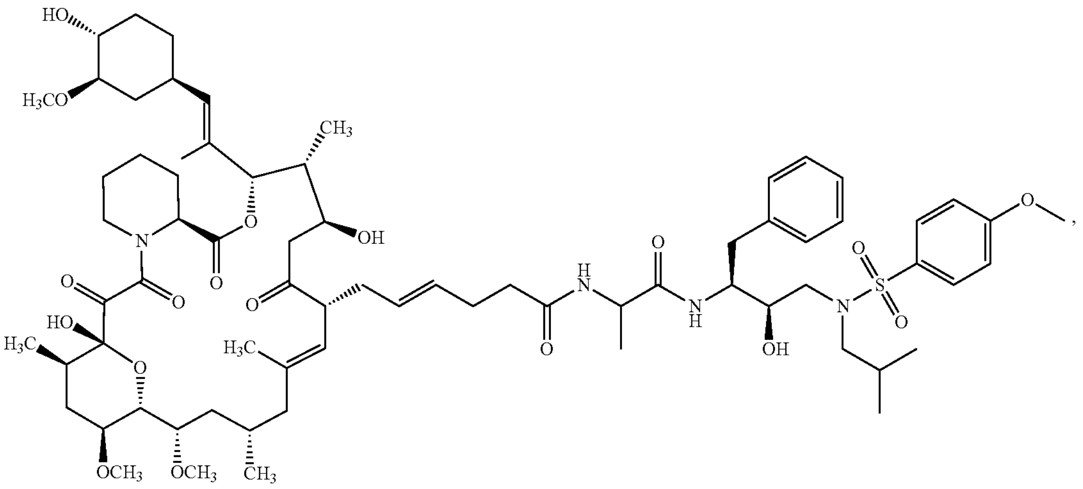
or an analog thereof.

In embodiments, the anti-CNS disease drug is not
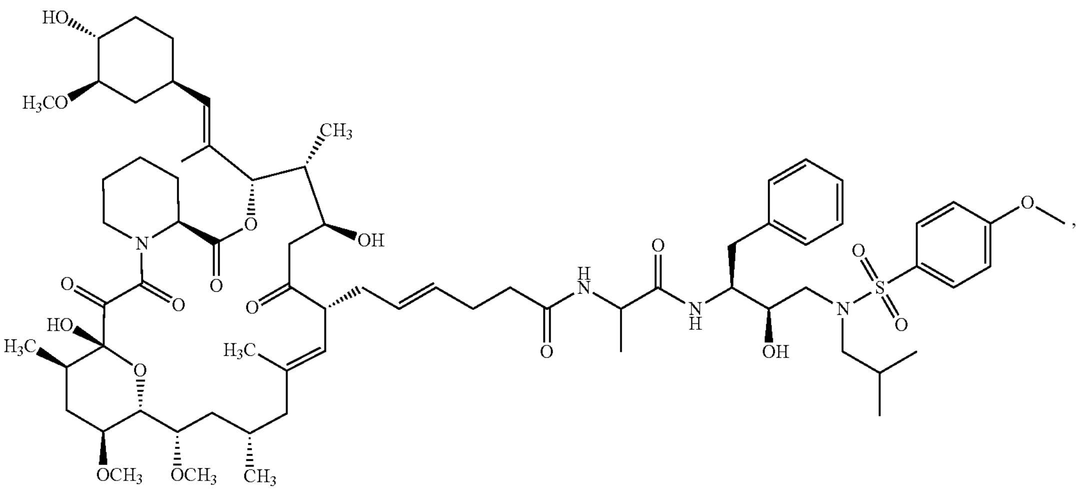
or an analog thereof.
In embodiments, the anti-CNS disease drug is
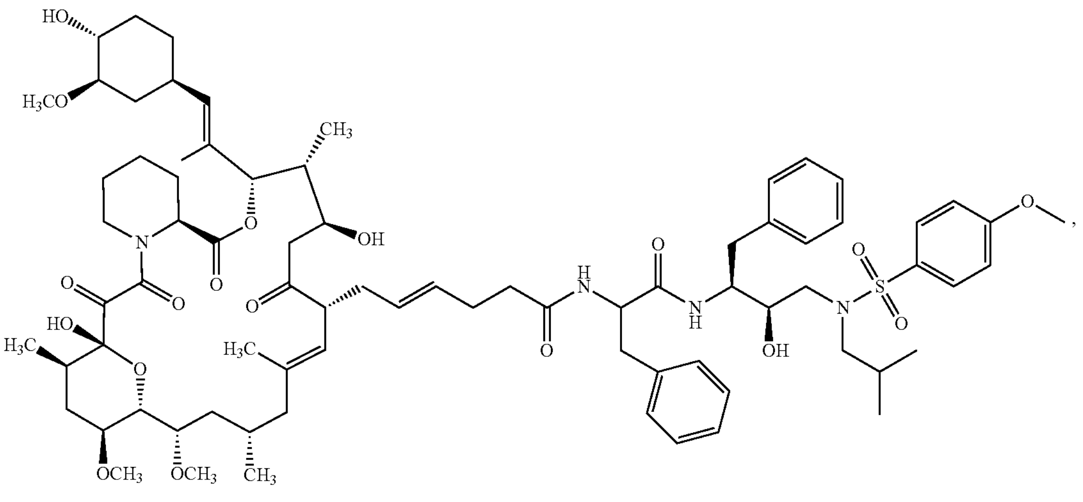
or an analog thereof.

In embodiments, the anti-CNS disease drug is not
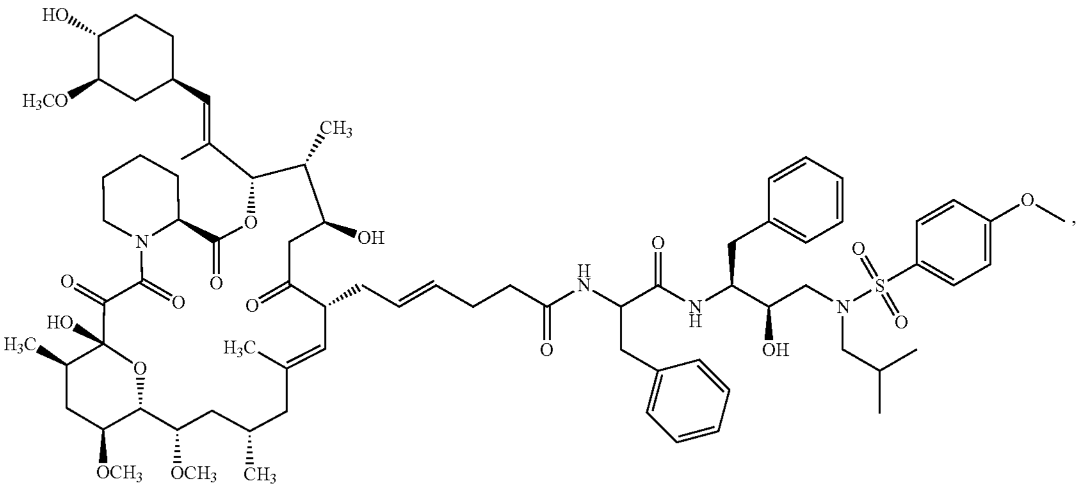
or an analog thereof.
In embodiments, the anti-CNS disease drug is
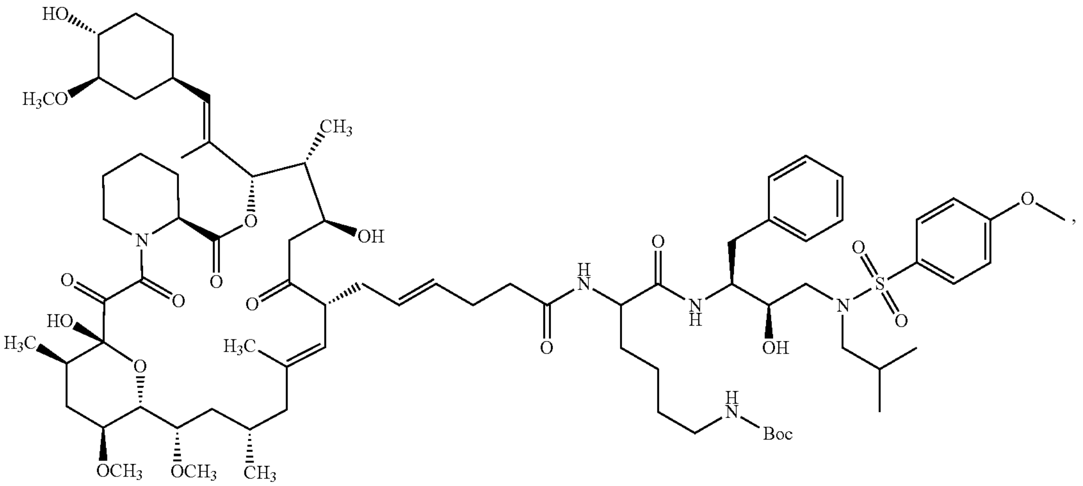
or an analog thereof.
In embodiments, the anti-CNS disease drug is not
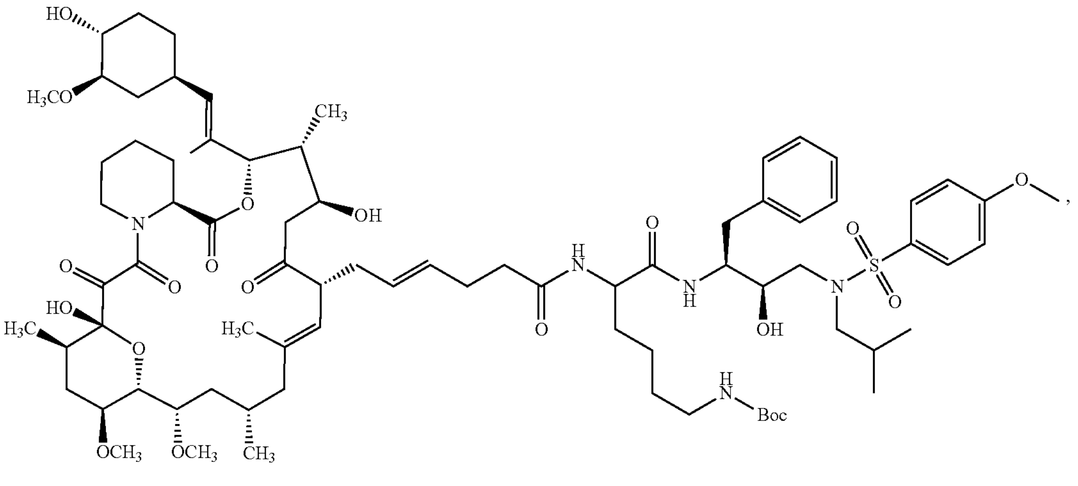
or an analog thereof.

In embodiments, the anti-CNS disease drug is
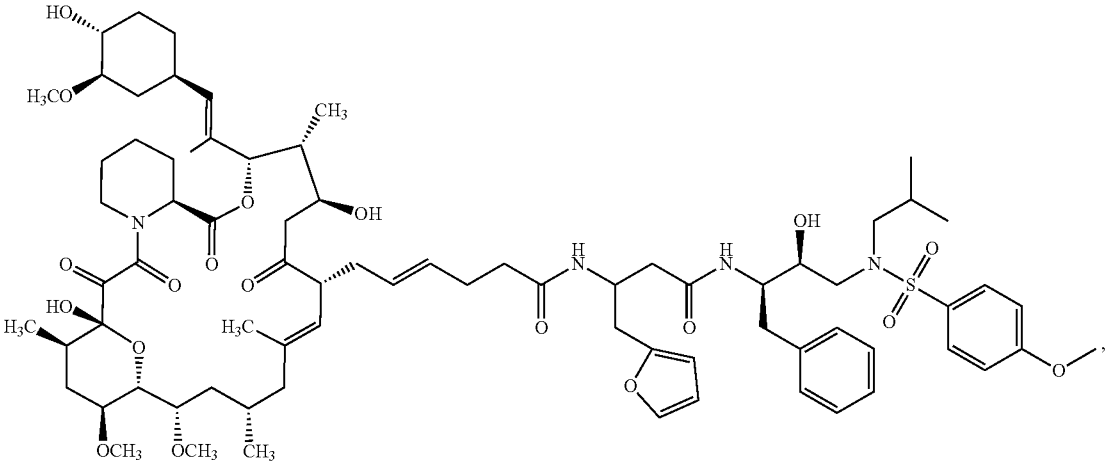
or an analog thereof.
In embodiments, the anti-CNS disease drug is not
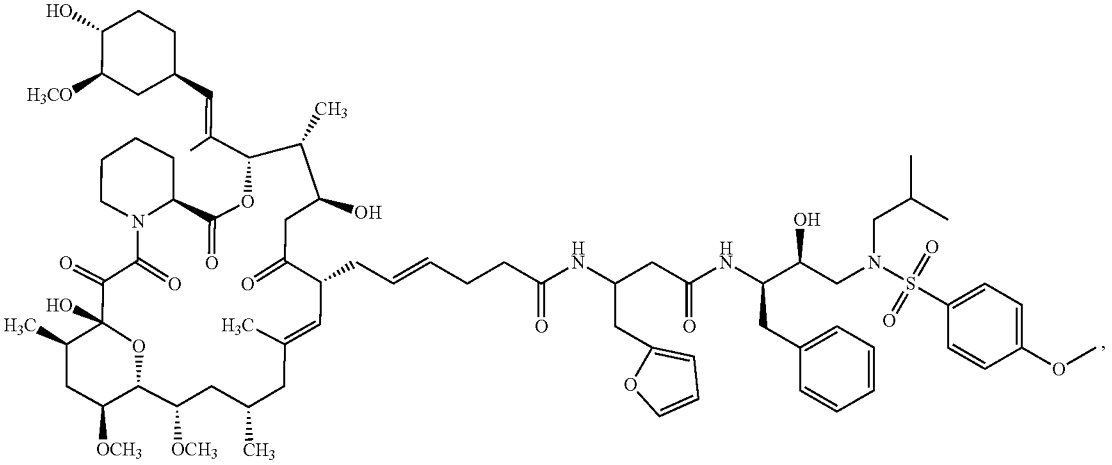
or an analog thereof.
In embodiments, the anti-CNS disease drug is
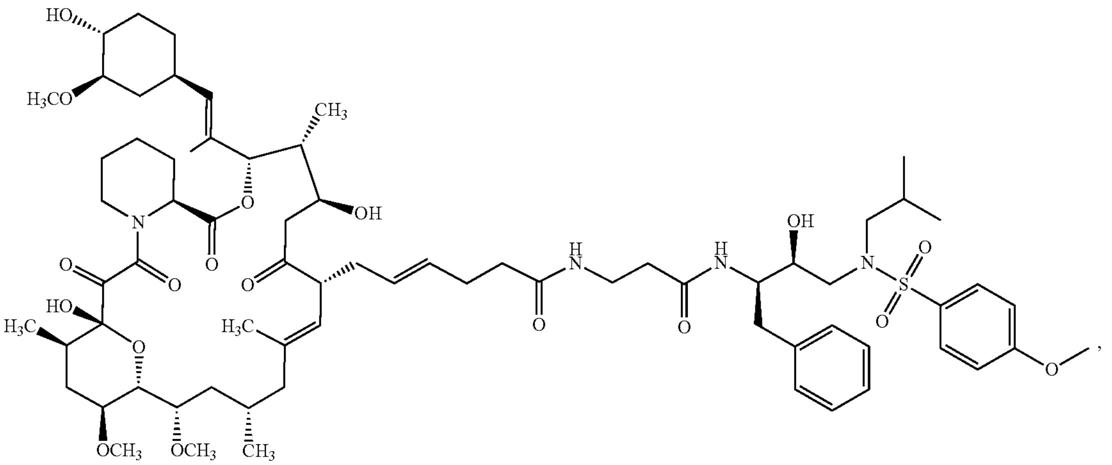
or an analog thereof.

In embodiments, the anti-CNS disease drug is not
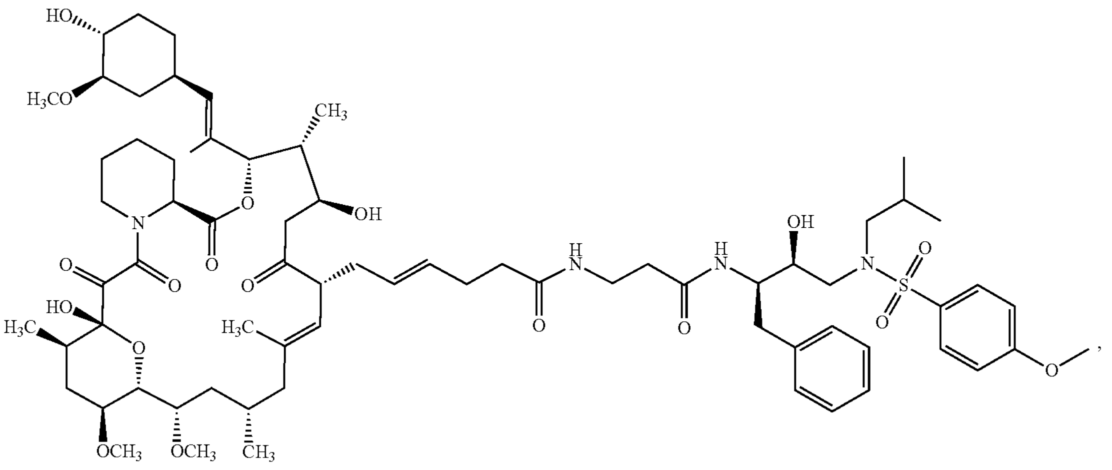
or an analog thereof.
In embodiments, the anti-CNS disease drug is
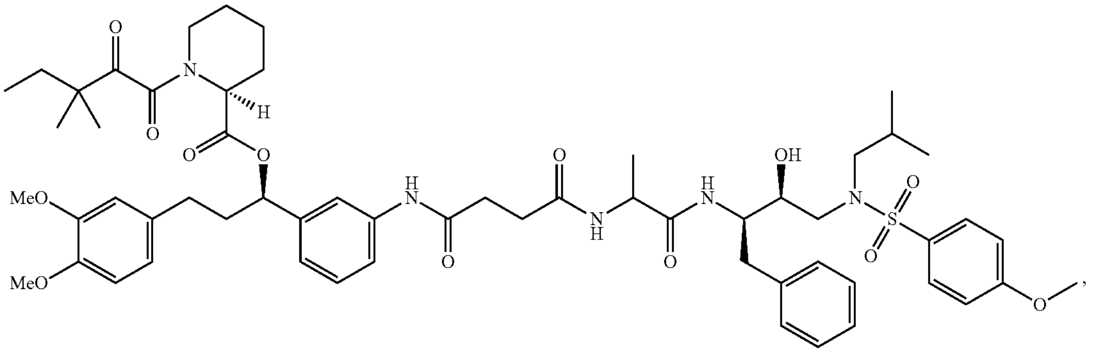 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(C)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is not
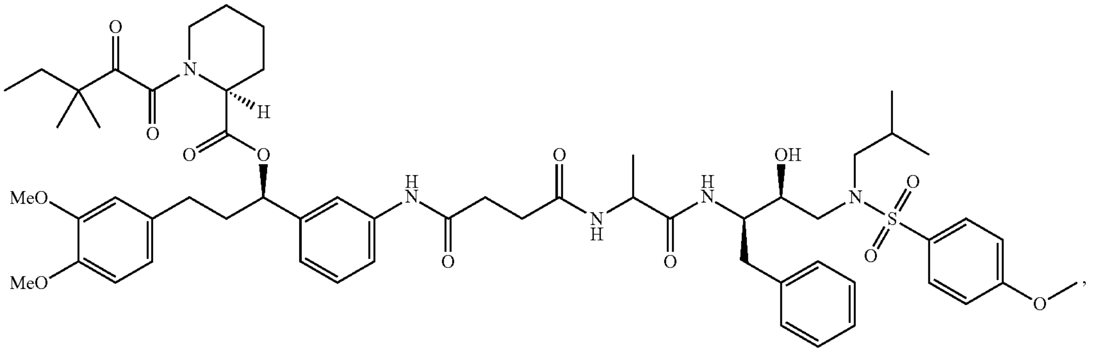 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(C)C(=O)N[C@H](Cc2ccccc2)[C@@H](O)CN(CC(C)C)S(=O)(=O)c2ccc(OC)cc2)c1]
an analog thereof.

In embodiments, the anti-CNS disease drug is
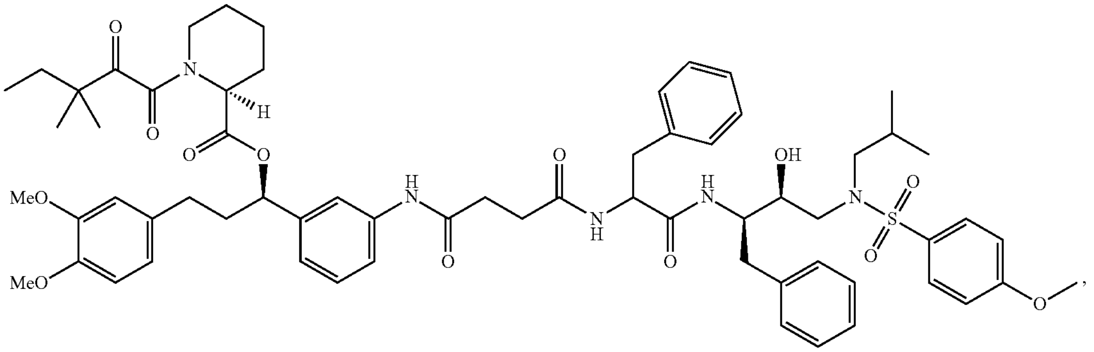 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(Cc2ccccc2)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is not
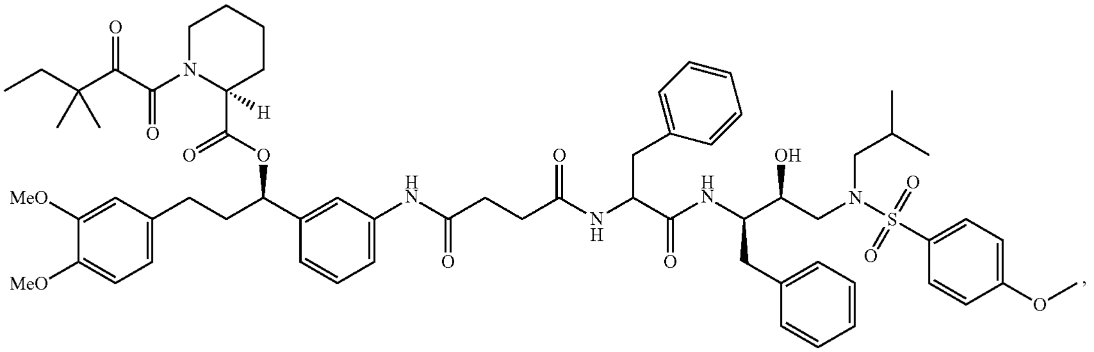 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(Cc2ccccc2)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is
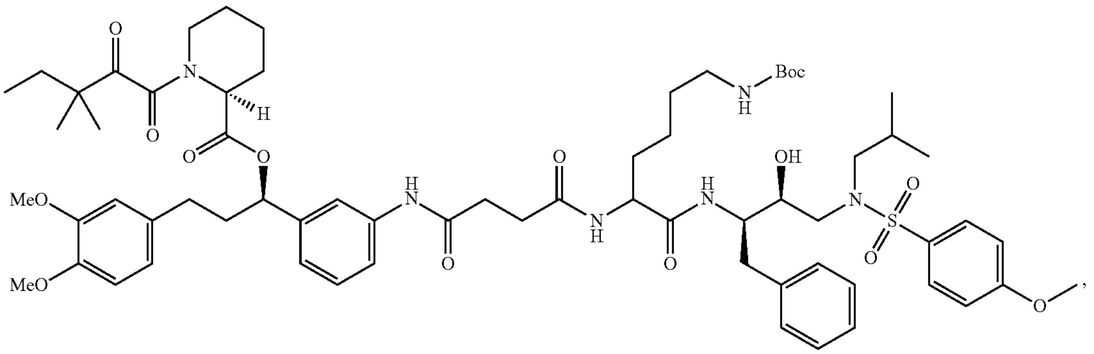 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CCCCNC(=O)OC(C)(C)C)C(=O)N[C@H](Cc2ccccc2)[C@@H](O)CN(CC(C)C)S(=O)(=O)c2ccc(OC)cc2)c1]
or an analog thereof.

In embodiments, the anti-CNS disease drug is not
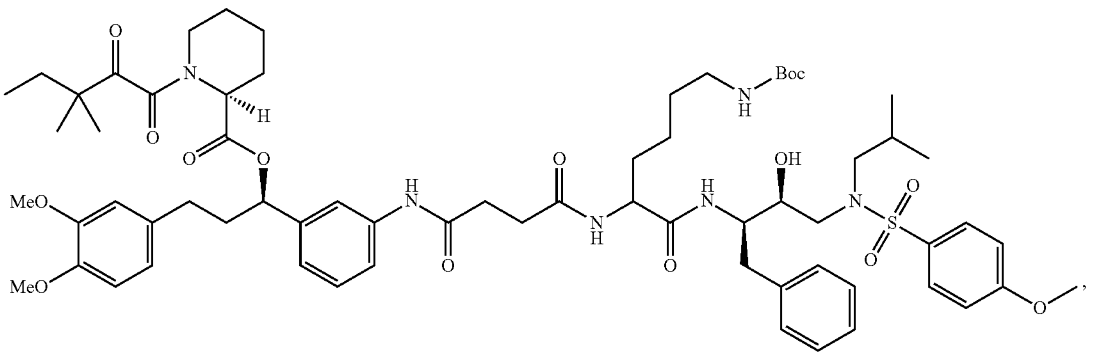 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CCCCNC(=O)OC(C)(C)C)C(=O)N[C@H](Cc2ccccc2)[C@@H](O)CN(CC(C)C)S(=O)(=O)c2ccc(OC)cc2)c1]
or an analog thereof.
In embodiments, the anti-CNS disease drug is
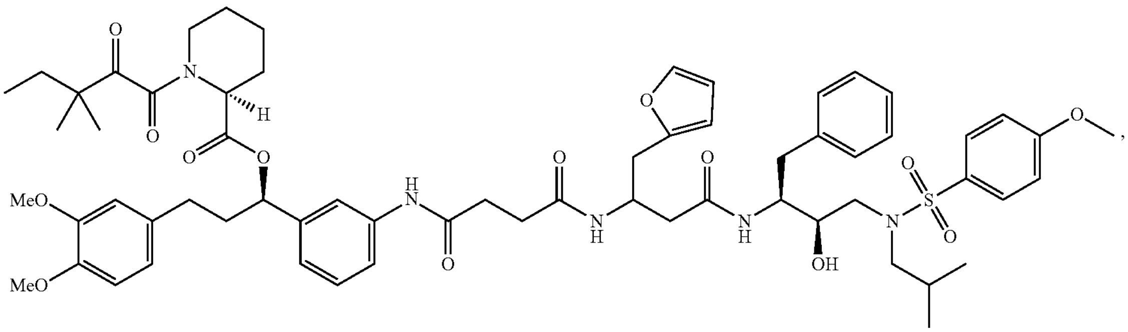 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CC(=O)N[C@@H](Cc2ccccc2)[C@H](O)CN(CC(C)C)S(=O)(=O)c2ccc(OC)cc2)Cc2ccco2)c1]
or an analog thereof.
In embodiments, the anti-CNS disease drug is not
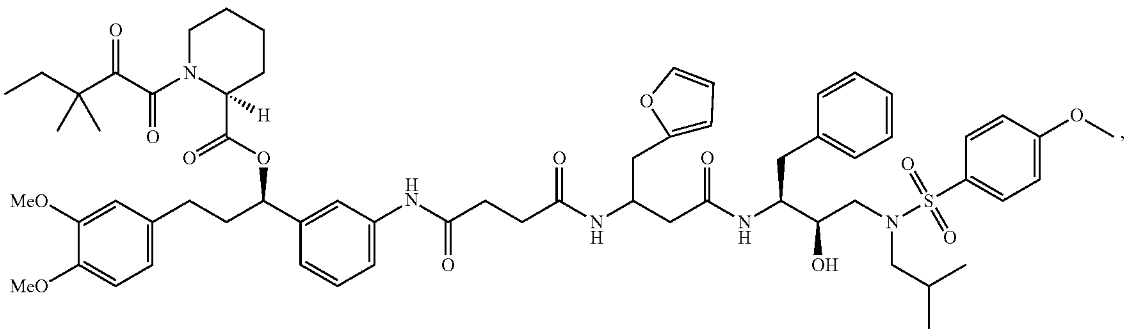 [SMILES: CCC(C)(C)C(=O)C(=O)N1CCCC[C@H]1C(=O)O[C@H](CCc1ccc(OC)c(OC)c1)c1cccc(NC(=O)CCC(=O)NC(CC(=O)N[C@@H](Cc2ccccc2)[C@H](O)CN(CC(C)C)S(=O)(=O)c2ccc(OC)cc2)Cc2ccco2)c1]
or an analog thereof.

In embodiments, the anti-CNS disease drug is
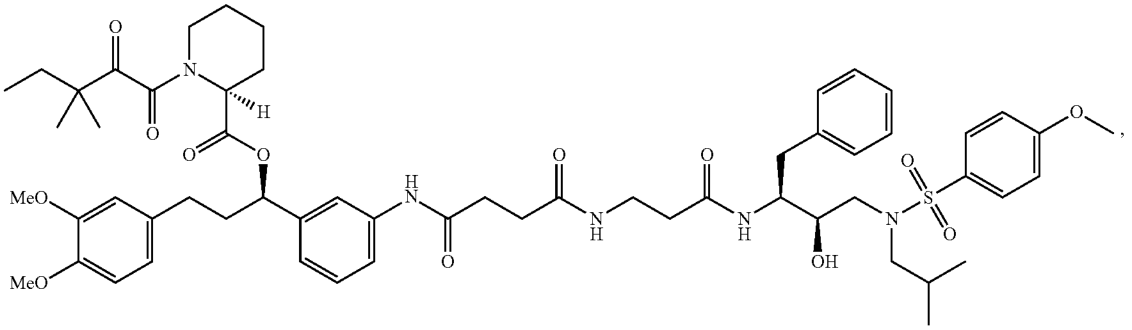 [SMILES: CCC(C)(C)C(=O)C(=O)N1CCCC[C@H]1C(=O)O[C@H](CCc1ccc(OC)c(OC)c1)c1cccc(NC(=O)CCC(=O)NCCC(=O)N[C@@H](Cc2ccccc2)[C@H](O)CN(CC(C)C)S(=O)(=O)c2ccc(OC)cc2)c1]
or an analog thereof.
In embodiments, the anti-CNS disease drug is not
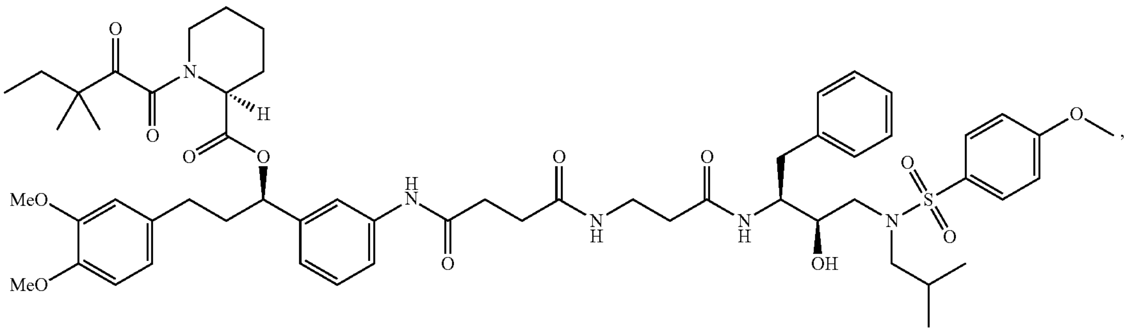 [SMILES: CCC(C)(C)C(=O)C(=O)N1CCCC[C@H]1C(=O)O[C@H](CCc1ccc(OC)c(OC)c1)c1cccc(NC(=O)CCC(=O)NCCC(=O)N[C@@H](Cc2ccccc2)[C@H](O)CN(CC(C)C)S(=O)(=O)c2ccc(OC)cc2)c1]
or an analog thereof.
In embodiments, the anti-CNS disease drug is
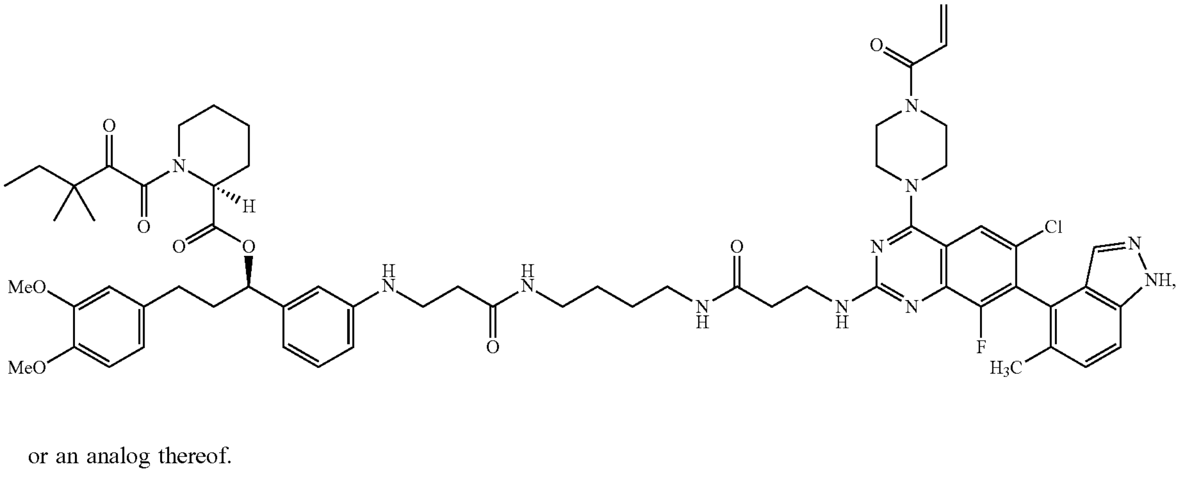
or an analog thereof.

In embodiments, the anti-CNS disease drug is not
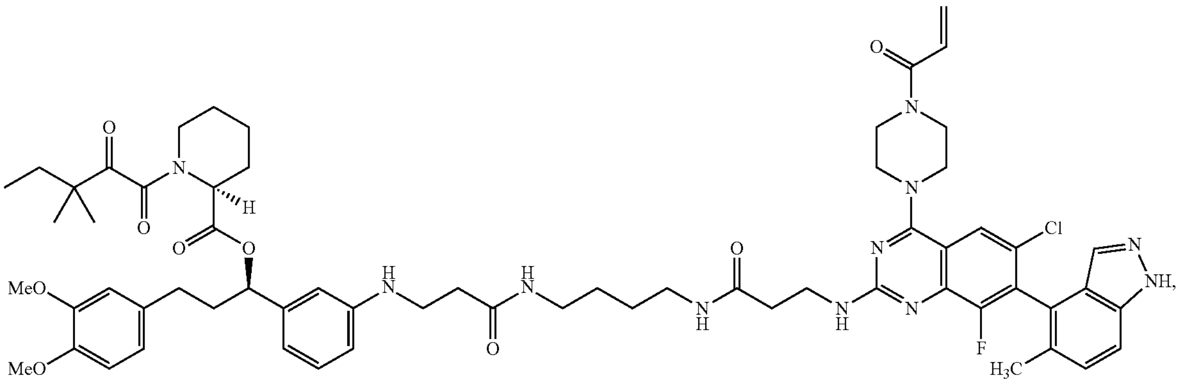 [SMILES: C=CC(=O)N1CCN(c2nc(NCCC(=O)NCCCCNC(=O)CCNc3cccc([C@@H](CCc4ccc(OC)c(OC)c4)OC(=O)[C@@H]4CCCCN4C(=O)C(=O)C(C)(C)CC)c3)nc3c(F)c(-c4c(C)ccc5[nH]ncc45)c(Cl)cc23)CC1]
or an analog thereof.
In embodiments, the anti-CNS disease drug is
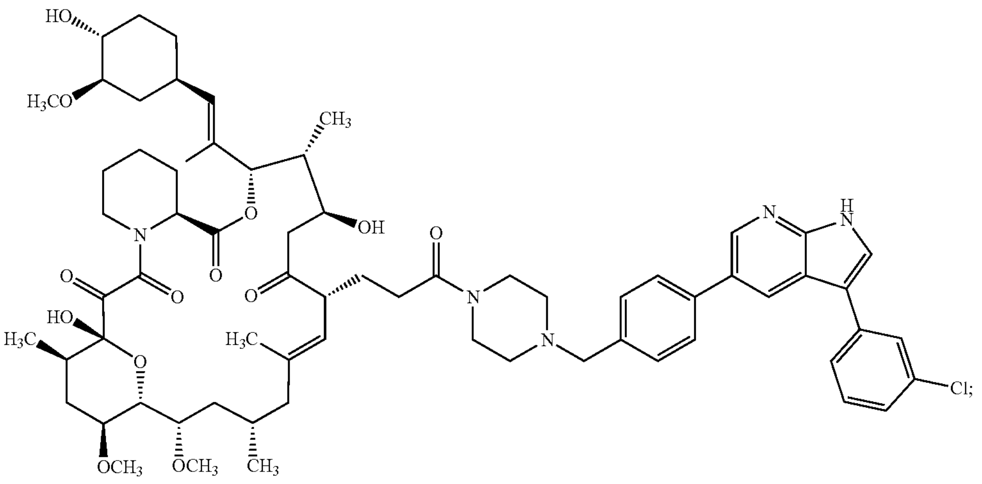 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.
In embodiments, the anti-CNS disease drug is not
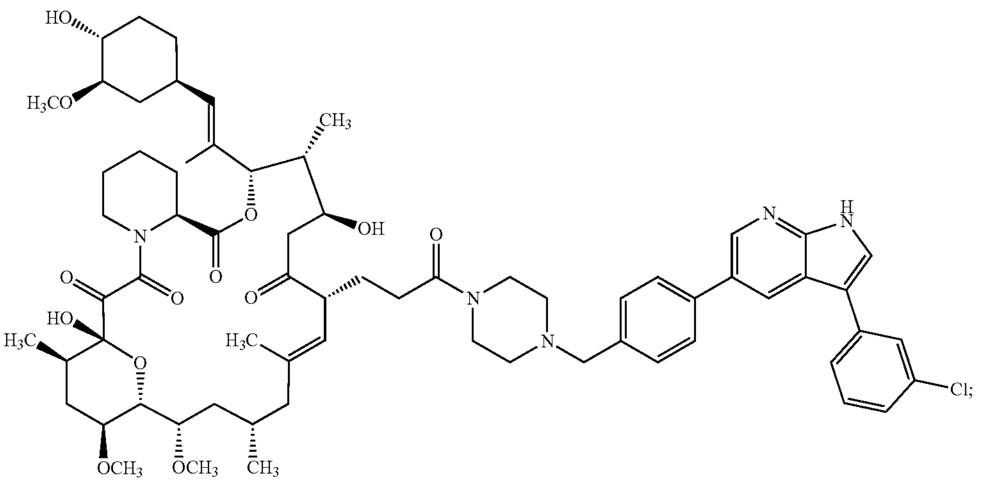 [SMILES: CO[C@H]1C[C@@H](C)C/C(C)=C/[C@@H](CCC(=O)N2CCN(Cc3ccc(-c4cnc5[nH]cc(-c6cccc(Cl)c6)c5c4)cc3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.

In embodiments, the anti-CNS disease drug is
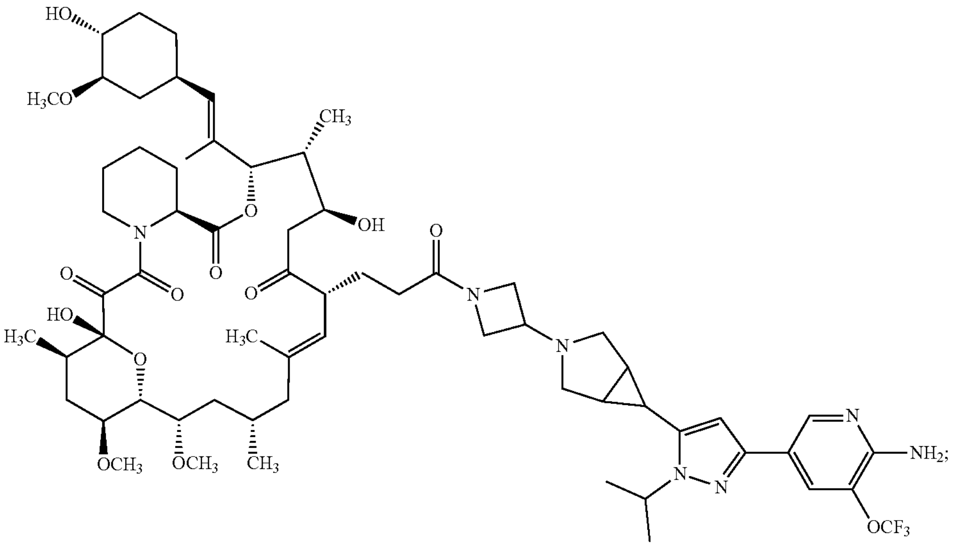 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.
In embodiments, the anti-CNS disease drug is not
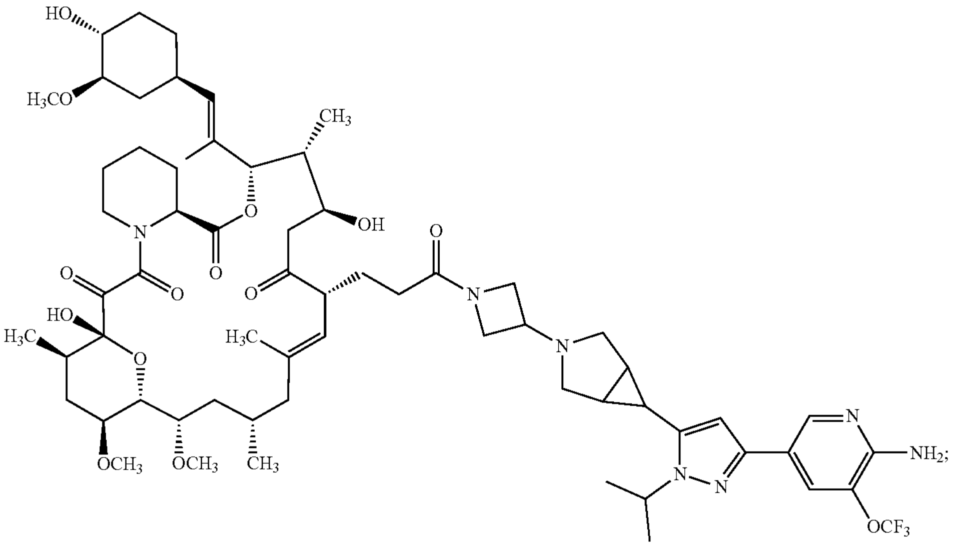 [SMILES: CO[C@H]1C[C@@H](C)C/C(C)=C/[C@@H](CCC(=O)N2CC(N3CC4C(C3)C4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.

In embodiments, the anti-CNS disease drug is
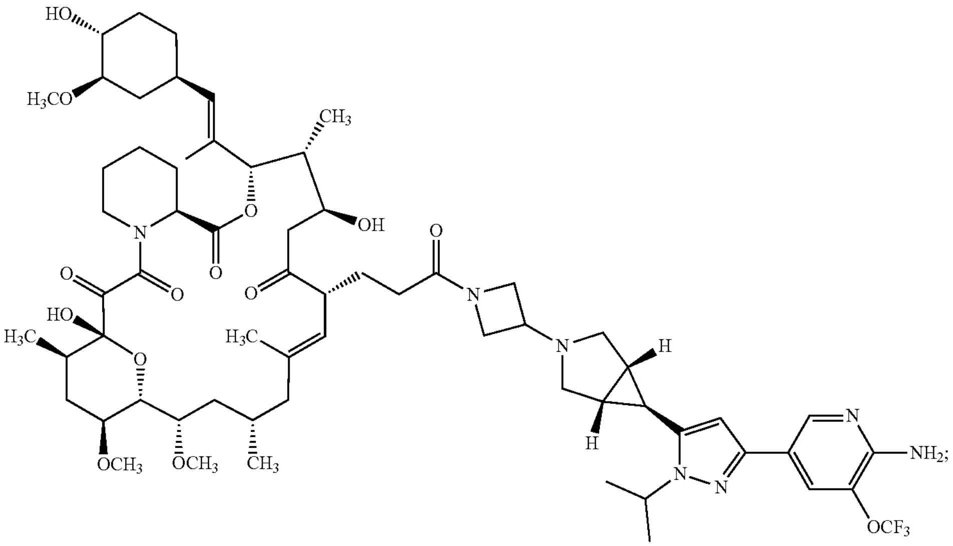 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.
In embodiments, the anti-CNS disease drug is not
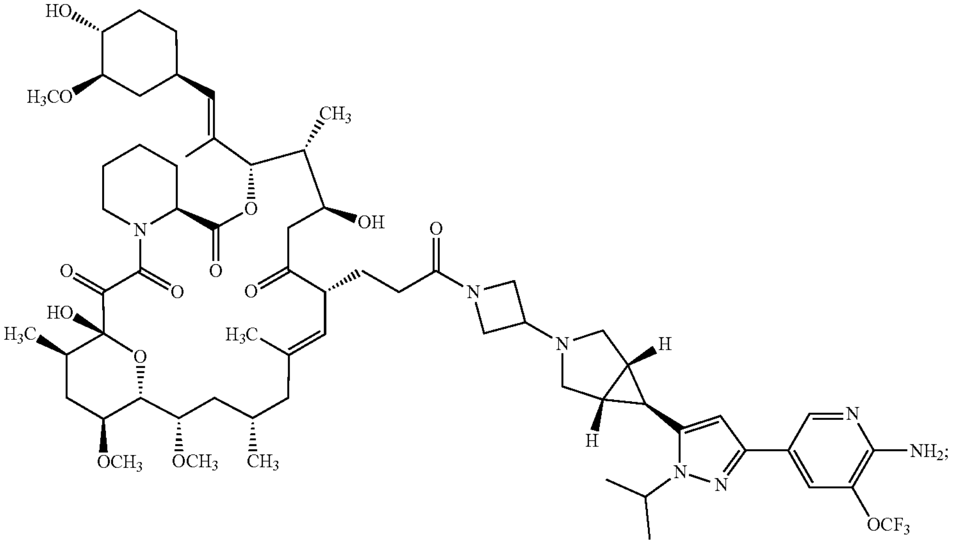 [SMILES: CO[C@H]1C[C@@H](C)C/C(C)=C/[C@@H](CCC(=O)N2CC(N3C[C@@H]4[C@H](C3)[C@H]4c3cc(-c4cnc(N)c(OC(F)(F)F)c4)nn3C(C)C)C2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]
or an analog thereof.

In embodiments, the anti-CNS disease drug is

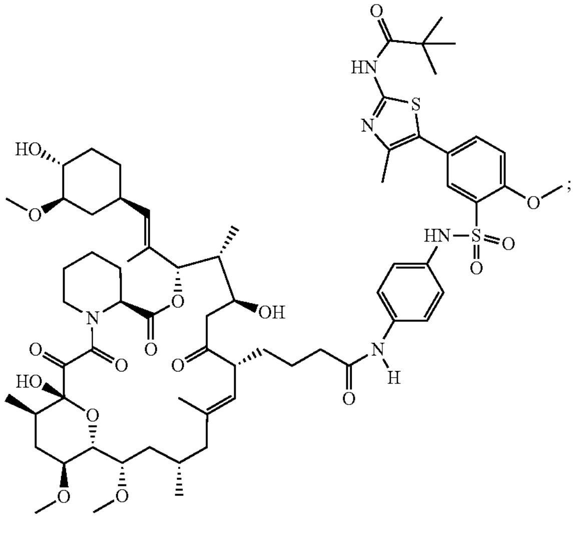

or an analog thereof.

In embodiments, the anti-CNS disease drug is not

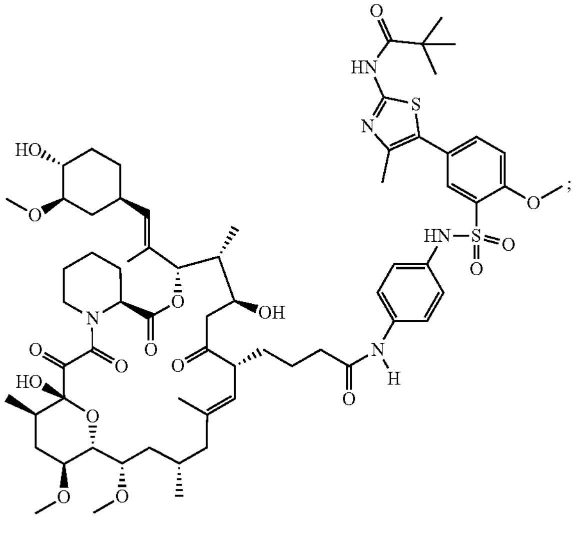

or an analog thereof.

In embodiments, the anti-CNS disease drug does not bind mTORC1. In embodiments, the anti-CNS disease drug does not bind mTOR. In embodiments, the immunophilin binding moiety is not rapamycin or an analog thereof. In embodiments, the immunophilin binding moiety is not rapamycin.

In embodiments, the anti-CNS disease drug residence time in cells is from 1 to 24 hours. In embodiments, the anti-CNS disease drug residence time in cells is from 1 to 12 hours. In embodiments, the anti-CNS disease drug residence time in cells is from 12 to 24 hours. In embodiments, the anti-CNS disease drug residence time in cells is 1, 2, 3, 4, 5, 6, 7, 8, 9, 10, 11, 12, 13, 14, 15, 16, 17, 18, 19, 20, 21, 22, 23, or 24 hours. In embodiments, the anti-CNS disease drug residence time in cells is about 1, 2, 3, 4, 5, 6, 7, 8, 9, 10, 11, 12, 13, 14, 15, 16, 17, 18, 19, 20, 21, 22, 23, or 24 hours. In embodiments, the anti-CNS disease drug residence time in cells is at least 1, 2, 3, 4, 5, 6, 7, 8, 9, 10, 11, 12, 13, 14, 15, 16, 17, 18, 19, 20, 21, 22, 23, or 24 hours. In embodiments, the anti-CNS disease drug including a monovalent kinase inhibitor, a monovalent pseudokinase inhibitor, a monovalent GTPase inhibitor, a monovalent histone-modifying enzyme inhibitor, or monovalent anti-viral agent has a residence time in cells that is at least 1.1 fold (e.g., at least 1.2, 1.3, 1.4, 1.5, 1.6, 1.7, 2, 8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 201, 9000, 10000, 20000, 30000, 40000, 50000, 60000, 70000, 80000, 90000, or 100000 fold) greater than the residence time of the corresponding kinase inhibitor, a pseudokinase inhibitor, a GTPase inhibitor, a histone-modifying enzyme inhibitor, or anti-viral agent.

IV. Methods of Use

In an aspect is provided a method of treating a CNS disease in a subject in need of such treatment, including co-administering outside the CNS of the subject an anti-CNS disease drug (e.g., as described herein) and a compound described herein. Subsequent to administration (e.g., about 1, 2, 3, 4, 5, 6, 7, 8, 9, 10, 15, 20, 25, 30, 35, 40, 45, 50, 55, 60 minutes, 2, 3, 4, 5, 6, 7, 8, 9, 10, 11, 12, 13, 14, 15, 16, 17, 18, 19, 20, 21, 22, 23 or 24 hours following administration), the concentration of the compound in circulating blood of the subject is greater than the concentration of the compound in the CNS of the subject. Subsequent to administration (e.g., at least 1, 2, 3, 4, 5, 6, 7, 8, 9, 10, 15, 20, 25, 30, 35, 40, 45, 50, 55, 60 minutes, 2, 3, 4, 5, 6, 7, 8, 9, 10, 11, 12, 13, 14, 15, 16, 17, 18, 19, 20, 21, 22, 23 or 24 hours following administration), the concentration of the compound in circulating blood of the subject is greater than the concentration of the compound in the CNS of the subject.

In embodiments, the compound (e.g., as described herein) is co-administered with a second agent (e.g., an anti-CNS disease drug as described herein). In embodiments, the compound (e.g., as described herein) is co-administered simultaneously with the second agent (e.g., the anti-CNS disease drug as described herein). In embodiments, the compound (e.g., as described herein) and the second agent (e.g., the anti-CNS disease drug as described herein) are co-administered sequentially. In embodiments, the compound is co-administered after (e.g., after about 1, 5, 10, 15, 20, or about 30 minutes) the second agent (e.g., the anti-CNS disease drug as described herein). In embodiments, the compound is co-administered after (e.g., after 1, 5, 10, 15, 20, or 30 minutes) the second agent (e.g., the anti-CNS disease drug as described herein). In embodiments, the compound is co-administered after (e.g., after about 0.5, 1, 2, 4, 6, 8, 10, 12, 16, 20, or about 24 hours) the second agent (e.g., the anti-CNS disease drug as described herein). In embodiments, the compound is co-administered after (e.g., after 0.5, 1, 2, 4, 6, 8, 10, 12, 16, 20, or 24 hours) the second agent (e.g., the anti-CNS disease drug as described herein).

In embodiments, the concentration of the compound in circulating blood is greater than 3-fold (e.g., 4-, 5-, 6-, 7-, 8-, 9-, 10-, 15-, 20-fold) the concentration of the compound in the CNS. In embodiments, the concentration of the compound in circulating blood is greater than 20-fold the concentration of the compound in the CNS. In embodiments, the compound is unable to cross the blood-brain barrier.

In embodiments, the CNS disease is glioblastoma, epilepsy, tuberous sclerosis (TSC), or alcohol use disorders. In embodiments, the CNS disease is glioblastoma. In embodiments, the CNS disease is epilepsy. In embodiments, the CNS disease is tuberous sclerosis (TSC). In embodiments, the CNS disease is alcohol use disorders.

In embodiments, the CNS disease is amyotrophic lateral sclerosis (ALS), Parkinson's disease, or Alzheimer's disease. In embodiments, the CNS disease is amyotrophic lateral sclerosis (ALS). In embodiments, the CNS disease is Parkinson's disease. In embodiments, the CNS disease is Alzheimer's disease.

In embodiments, the compound is unable to enter the central nervous system of a subject following administration to the subject outside of the central nervous system. In embodiments, the anti-CNS disease drug is capable of entering the central nervous system and the compound is incapable of entering the central nervous system following co-administration outside of the central nervous system of the subject.

In embodiments, affinity of the compound for calcineurin is lower (e.g., about 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-, 1500-, 2000-, 2500-, 3000-, 3500-, 4000-, 4500-, or 5000-fold) compared to compounds of formulae (I), (II), (III), (IV), or (V). In embodiments, affinity of the compound for calcineurin is lower (e.g., at least 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-, 1500-, 2000-, 2500-, 3000-, 3500-, 4000-, 4500-, or 5000-fold) compared to compounds of formulae (I), (II), (III), (IV), or (V). In embodiments, the compound does not bind calcineurin.

In embodiments, compound inhibition of transcription of T cell activation genes (e.g., IL-2 mRNA, IL-3 mRNA, IL-4 mRNA, GM-CSF, TNF alpha, IFN-gamma, or c-myc) is lower (e.g., about 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-fold) compared to compounds of formulae (I), (II), (III), (IV), or (V). In embodiments, compound inhibition of transcription of T cell activation genes (e.g., IL-2 mRNA, IL-3 mRNA, IL-4 mRNA, GM-CSF, TNF alpha, IFN-gamma, or c-myc) is lower (e.g., at least 2-, 3-, 4-, 5-, 6-, 7-, 8-, 9-, 10-, 15-, 20-, 25-, 30-, 35-, 40-, 45-, 50-, 60-, 70-, 80-, 90-, 100-, 200-, 300-, 400-, 500-, 600-, 700-, 800-, 900-, 1000-fold) compared to compounds of formulae (I), (II), (III), (IV), or (V). In embodiments, the compound does not inhibit development and/or proliferation of T cells.

In embodiments, the compound does not reduce the body's immune response. In embodiments, the immune response is the adaptive immune response. In embodiments, the method includes reduced side effects associated with the anti-CNS disease drug compared to absence of the compound. In embodiments, the anti-CNS disease drug binds an immunophilin. In embodiments, the anti-CNS disease drug includes an immunophilin-binding moiety (e.g., as described herein). In embodiments, the anti-CNS disease drug is as described herein, including in embodiments.

In embodiments of the method, the CNS disease is a disease associated with aberrant enzyme activity. In embodiments, the enzyme activity is a kinase activity (e.g., a kinase described herein). In embodiments, the kinase activity is in the CNS of the subject (e.g., brain).

In embodiments, the CNS disease is a cancer, a neurodegenerative disease, or a viral disease.

In embodiments, the CNS disease is cancer or a neurodegenerative disease. In embodiments, the CNS disease is cancer. In embodiments, the cancer is glioblastoma or glioma. In embodiments, the CNS disease is a neurodegenerative disease. In embodiments the neurodegenerative disease is Parkinson's disease.

In embodiments, the CNS disease is a neurodegenerative disease. In embodiments, the neurodegenerative disease is amyotrophic lateral sclerosis (ALS), Parkinson's disease, or Alzheimer's disease. In embodiments, the neurodegenerative disease is amyotrophic lateral sclerosis (ALS). In embodiments, the neurodegenerative disease is Parkinson's disease. In embodiments, the neurodegenerative disease is Alzheimer's disease.

In embodiments, the neurodegenerative disease is not Alzheimer's Disease. In embodiments, the anti-CNS disease drug is not an amyloid P aggregation inhibitor. In embodiments, the anti-CNS disease drug does not include a monovalent amyloid P aggregation inhibitor.

In embodiments, the disease is a viral disease. In embodiments, the viral disease is human immunodeficiency virus (HIV). In embodiments, the anti-CNS disease drug is an HIV inhibitor. In embodiments, the anti-CNS disease drug is an HIV protease inhibitor. In embodiments, the anti-CNS disease drug is a viral protease inhibitor. In embodiments, the anti-CNS disease drug includes an HIV inhibitor. In embodiments, the anti-CNS disease drug includes an HIV protease inhibitor. In embodiments, the anti-CNS disease drug includes a viral protease inhibitor. In embodiments, the viral disease is not human immunodeficiency virus (HIV). In embodiments, the anti-CNS disease drug is not an HIV inhibitor. In embodiments, the anti-CNS disease drug is not an HIV protease inhibitor. In embodiments, the anti-CNS disease drug is not a viral protease inhibitor. In embodiments, the anti-CNS disease drug does not include an HIV inhibitor. In embodiments, the anti-CNS disease drug does not include an HIV protease inhibitor. In embodiments, the anti-CNS disease drug does not include a viral protease inhibitor.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A method of treating a CNS disease in a subject in need of such treatment, comprising co-administering outside the CNS of said subject an anti-CNS disease drug and a compound having the formula:

$A^{B}$-$L^{B1}$-$R^{B1}$, or a pharmaceutically acceptable salt thereof;

wherein $A^{B}$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, $—CX^{B1}_3$, $—CHX^{B1}_2$, $—CH_2X^{B1}$, $—OCX^{B1}_3$, $—OCH_2X^{B1}$, $—OCHX^{B1}_2$, —CN, $—SO_{nB1}R^{B1D}$, $—SO_{vB1}NR^{B1A}R^{B1B}$, $—NHC(O)NR^{B1A}R^{B1B}$, $—N(O)_{mB1}$, $—NR^{B1A}R^{B1B}$, $—C(O)R^{B1C}$, $—C(O)OR^{B1C}$, $—C(O)NR^{B1A}R^{B1B}$, $—OR^{B1D}$, $—NR^{B1A}SO_2R^{B1D}$, $—NR^{B1A}C(O)R^{B1C}$, $—NR^{B1A}C(O)$ $OR^{B1C}$, $—NR^{B1A}OR^{B1C}$, $—NR^{B1A}C(NR^{B1C})R^{B1D}$, $—NR^{B1A}C(NR^{B1C})NR^{B1A}R^{B1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently —F, —Cl, —Br, or —I;

when $L^{B1}$ is a bond, $R^{B1}$ is not H; and wherein, subsequent to administration, the concentration of the compound in circulating blood of said subject is greater than the concentration of the compound in the CNS of said subject.

Embodiment P2. The method of embodiment P1, wherein the immunophilin-binding moiety is a cyclophilin-binding moiety or an FKBP-binding moiety.

Embodiment P3. The method of one of embodiments P1 to P2, wherein the immunophilin-binding moiety is

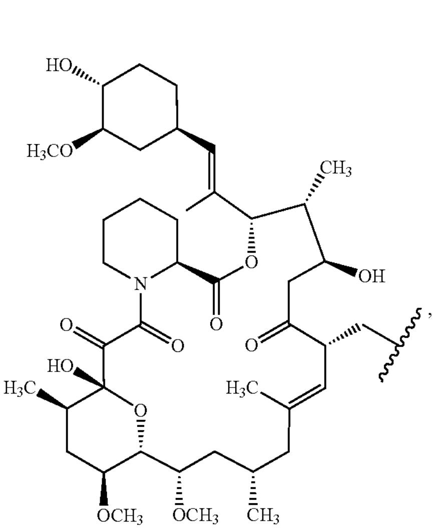 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

-continued

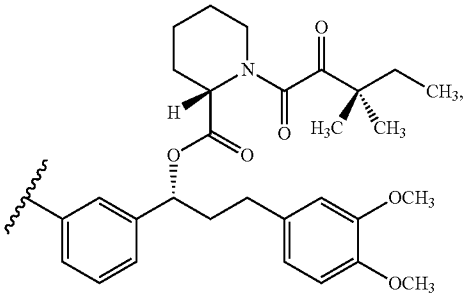

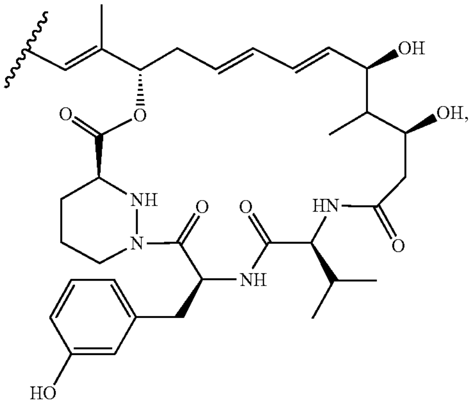

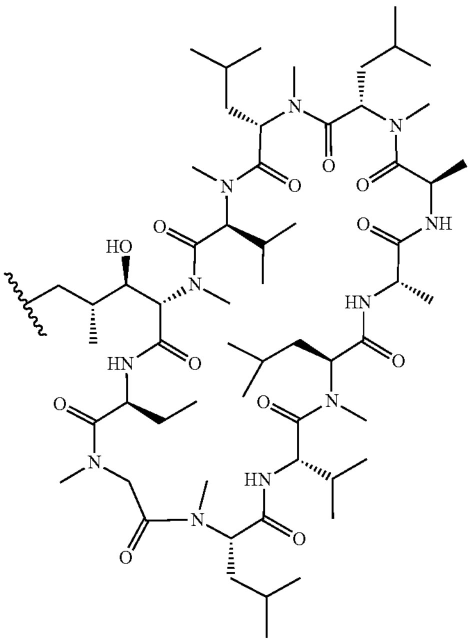

or

-continued

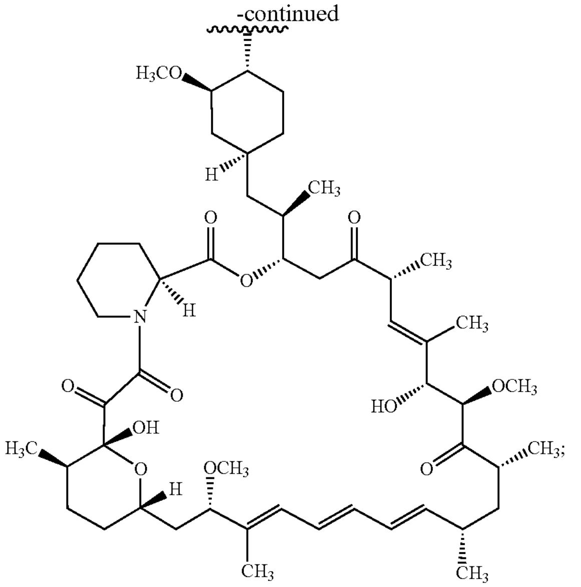

or an analog thereof.

Embodiment P4. The method of one of embodiments P1 to P3, wherein $L^{B1}$ is $L^{B2}$-$L^{B3}$-$L^{B4}$;

$L^{B2}$ is a bond, —$S(O)_2$—, —$N(R^{B2})$—, —O—, —S—, —C(O)—, —$C(O)N(R^{B2})$—, —$N(R^{B2})C(O)$—, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P5. The method of one of embodiments P1 to P4, wherein $L^{B1}$ is

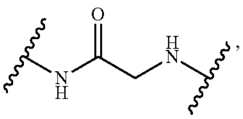, 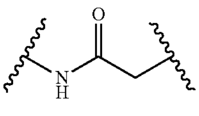,

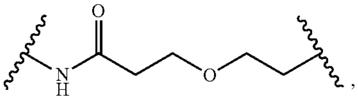,

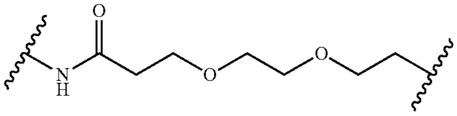,

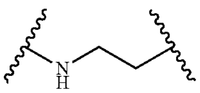, 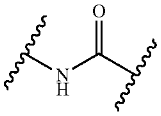,

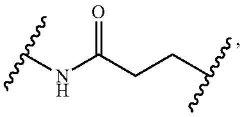, 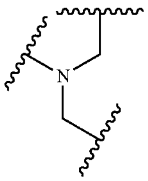,

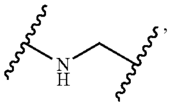, 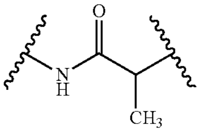,

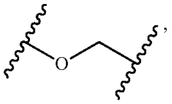, 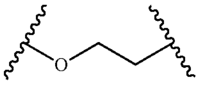,

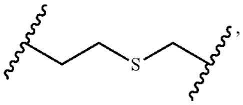, 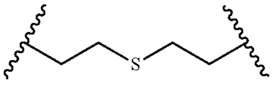,

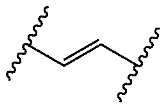, 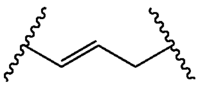,

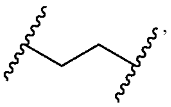,

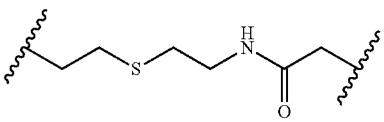,

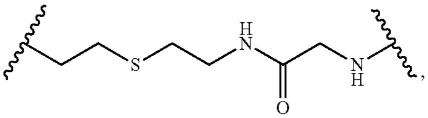,

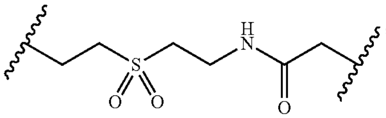 or

-continued

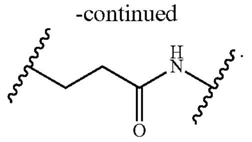.

Embodiment P6. The method of one of embodiments P1 to P5, wherein $R^{B1}$ is halogen, $—NR^{B1A}R^{B1B}$, $—N_3$, $—SR^{B1D}$,

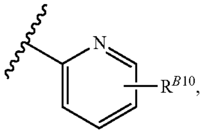, 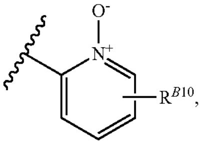, 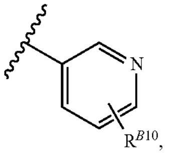, 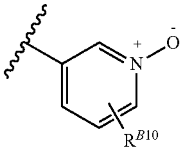, 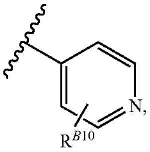, 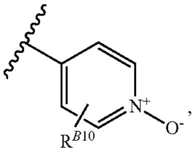, 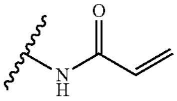, 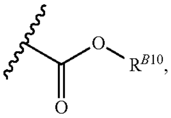, 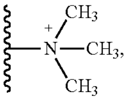, 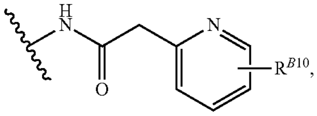, 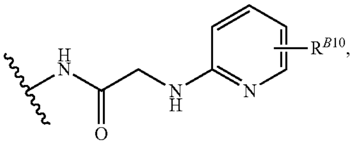, 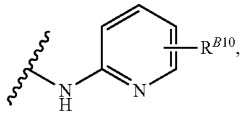, 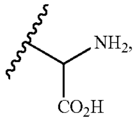, 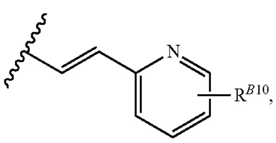, 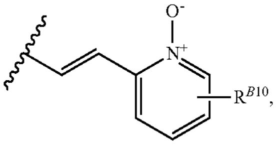, 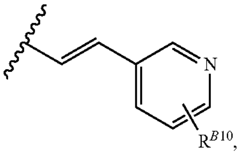, 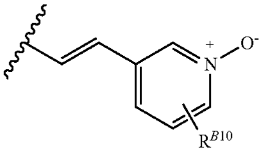, 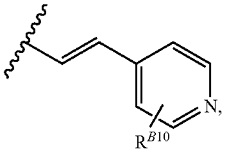 or 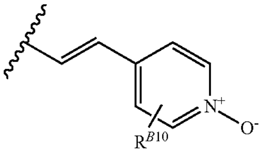;

$R^{B10}$ is hydrogen, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—N(O)_{mB10}$, $—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—NR^{B10A}C(NR^{B10C})R^{B10D}$, $—NR^{B10A}C(NR^{B10C})NR^{B10A}R^{B10B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment P7. The method of one of embodiments P1 to P6, wherein $R^{B1}$ is —Cl, $—NH_2$, $—N_3$, —SH,

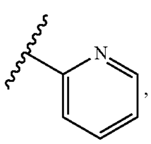, 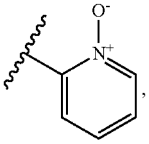, 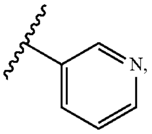, 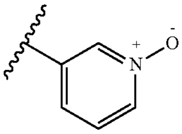, 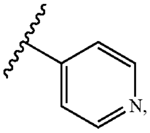, 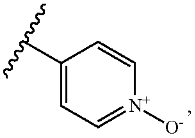, 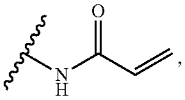, 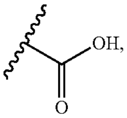, 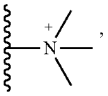, 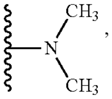, 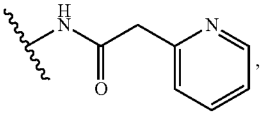, 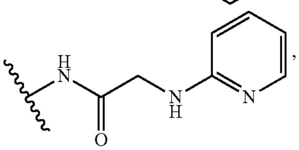, 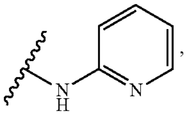, 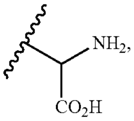, 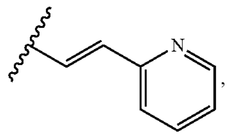, 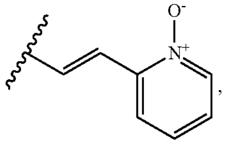, 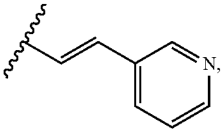, 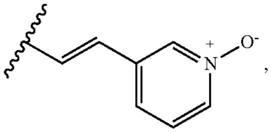, -continued
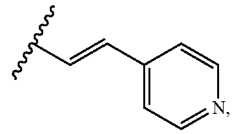
or
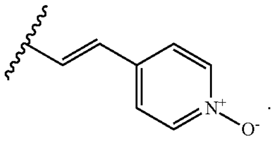
Embodiment P8. The method of one of embodiments P1 to P7, wherein $L^{B1}$-$R^{B1}$ is
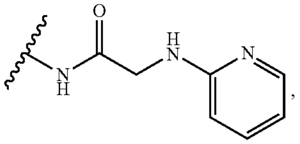
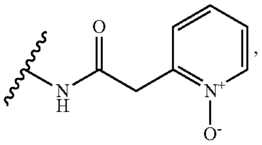
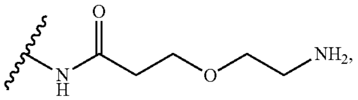
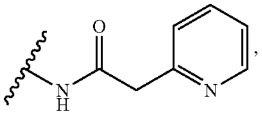
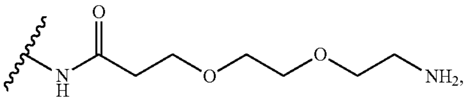
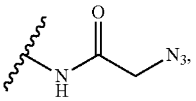
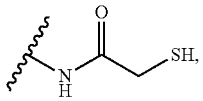
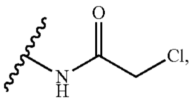
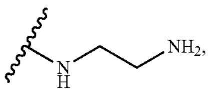
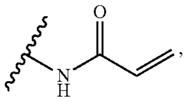
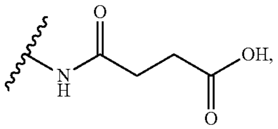
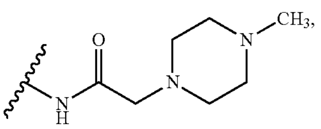
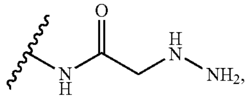
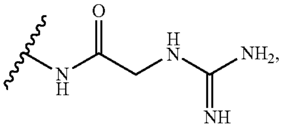
-continued
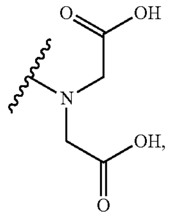
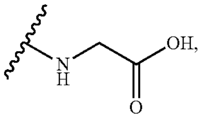
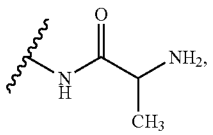
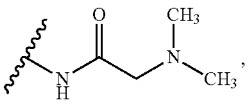
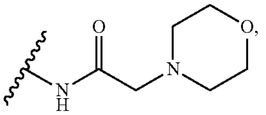
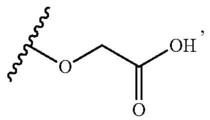
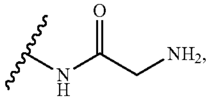
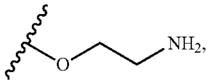
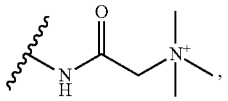
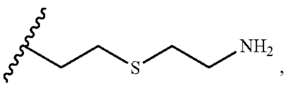
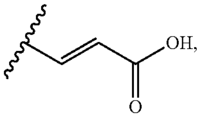
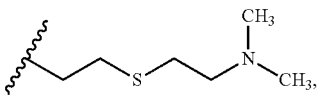
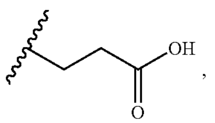
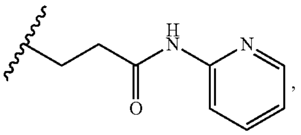
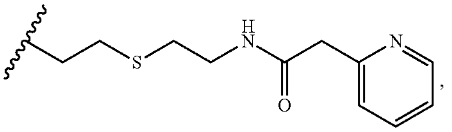
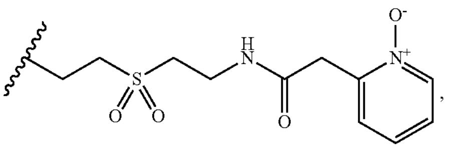
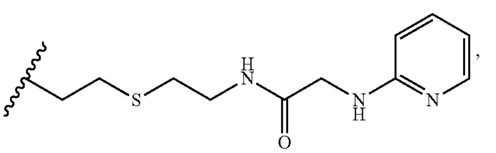
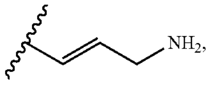
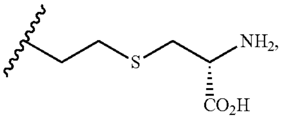

-continued

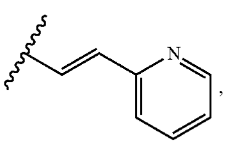
,
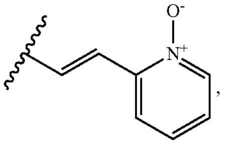
,

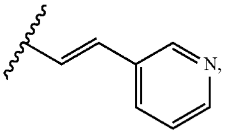
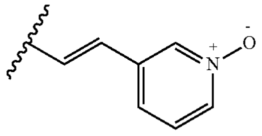
,

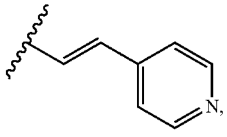
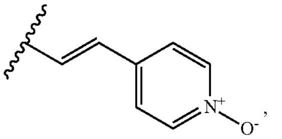
,

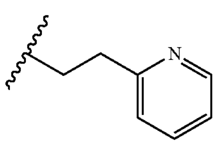
,
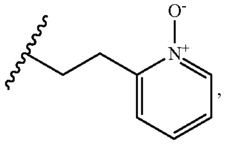
,

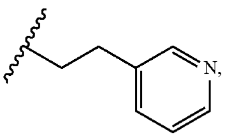
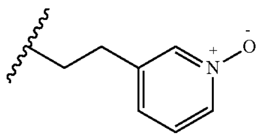
,

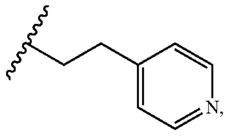
or
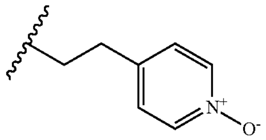
.

Embodiment P9. The method of one of embodiments P1 to P8, wherein the concentration of the compound in circulating blood is greater than 3-fold the concentration of the compound in the CNS.

Embodiment P10. The method of one of embodiments P1 to P9, wherein the concentration of the compound in circulating blood is greater than 20-fold the concentration of the compound in the CNS.

Embodiment P11. The method of one of embodiments P1 to P10, wherein the compound is unable to cross the blood-brain barrier.

Embodiment P12. The method of one of embodiments P1 to P11, wherein the compound is unable to enter the central nervous system of a subject following administration to the subject outside of the central nervous system.

Embodiment P13. The method of one of embodiments P1 to P12, wherein the anti-CNS disease drug is capable of entering the central nervous system and the compound is incapable of entering the central nervous system following co-administration outside of the central nervous system of the subject.

Embodiment P14. The method of one of embodiments P1 to P13, wherein the compound does not bind calcineurin.

Embodiment P15. The method of one of embodiments P1 to P14, wherein the compound does not inhibit development and/or proliferation of T cells.

Embodiment P16. The method of one of embodiments P1 to P15, wherein the compound does not reduce the body's immune response.

Embodiment P17. The method of one of embodiments P1 to P16, comprising reduced side effects associated with the anti-CNS disease drug compared to absence of the compound.

Embodiment P18. A compound having the formula:

$A^B$-$L^{B1}$-$R^{B1}$, or a pharmaceutically acceptable salt thereof ;

wherein $A^B$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —NHC(O)$NR^{B1A}R^{B1B}$, —$N(O)_{mB1}$, —$NR^{B1A}R^{B1B}$, —C(O)$R^{B1C}$, —C(O)$OR^{B1C}$, —C(O)$NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B1C}$, —$NR^{B1A}OR^{B1C}$, —$NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently —F, —Cl, —Br, or —I;

when $L^{B1}$ is a bond, $R^{B1}$ is not H; and $A^B$ is not

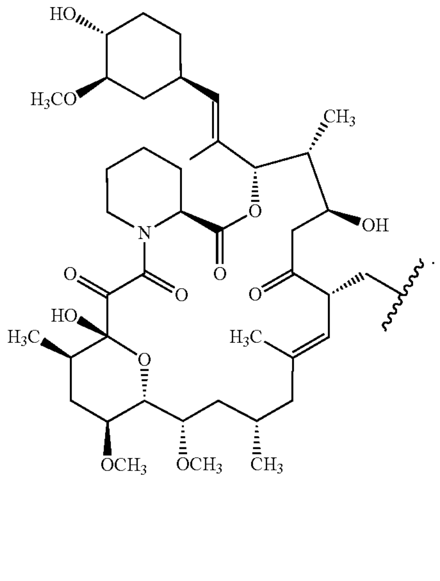 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
.

Embodiment P19. The compound of embodiment P18, wherein the immunophilin-binding moiety is

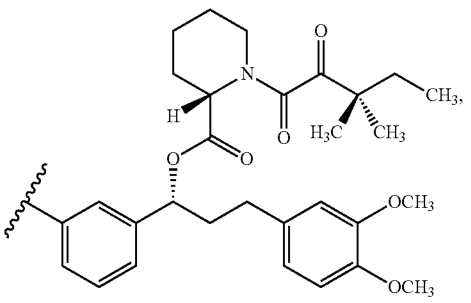

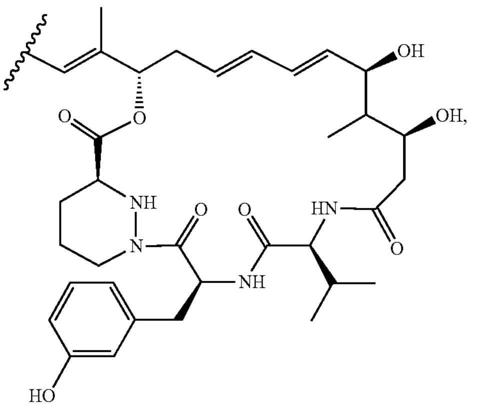

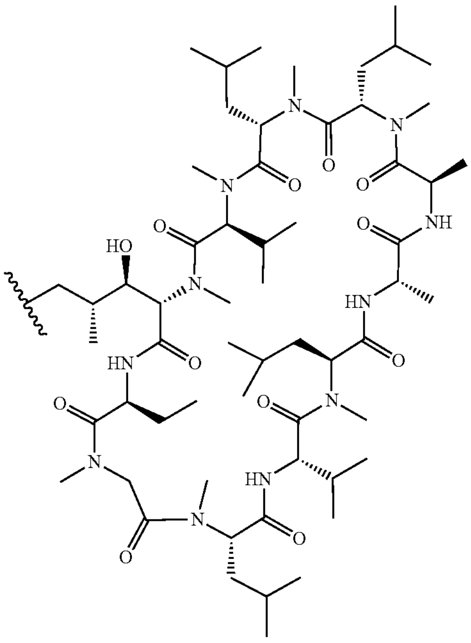

, or

-continued

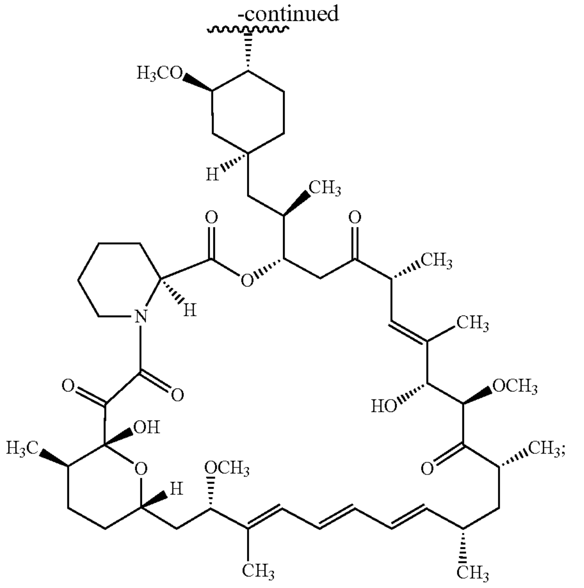

or an analog thereof.

Embodiment P20. The compound of one of embodiments P18 to P19, wherein $L^{B1}$ is $L^{B2}$-$L^{B3}$-$L^{B4}$;

$L^{B2}$ is a bond, —$S(O)_2$—, —$N(R^{B2})$—, —O—, —S—, —C(O)—, —$C(O)N(R^{B2})$—, —$N(R^{B2})C(O)$—, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P21. The compound of one of embodiments P18 to P20, wherein $L^{B1}$ is

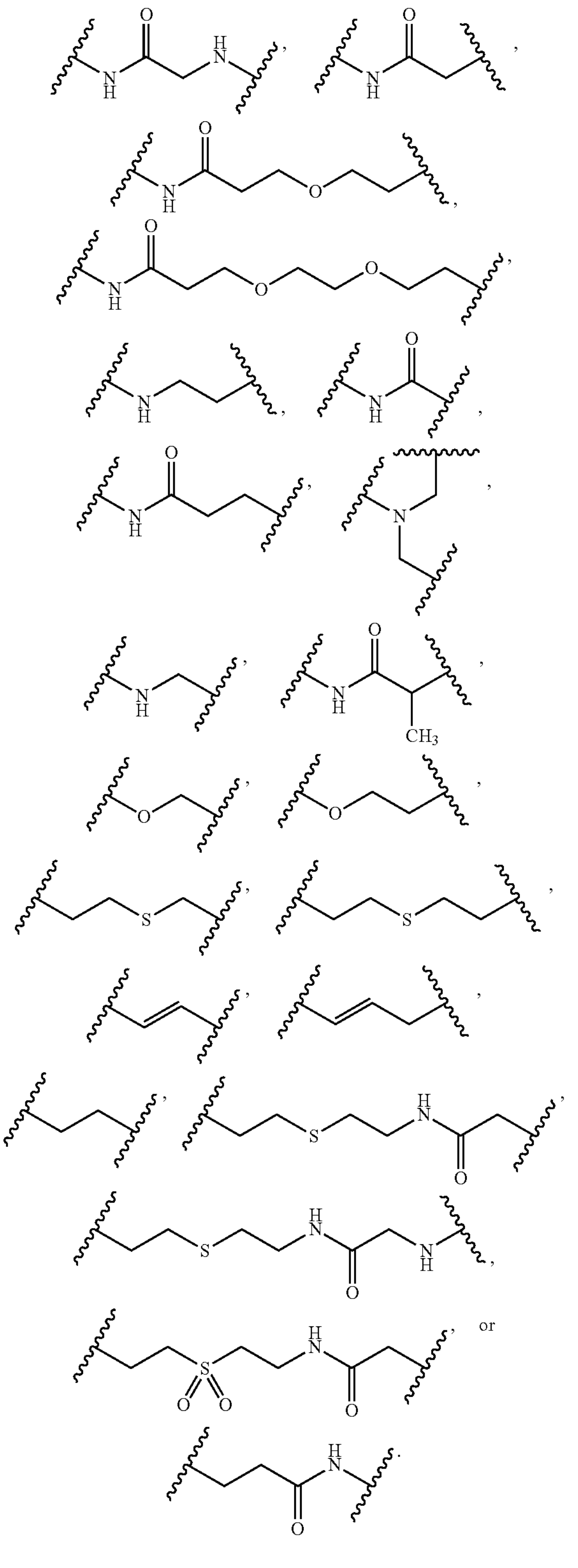

Embodiment P22. The compound of one of embodiments P18 to P21, wherein $R^{B1}$ is halogen, $—NR^{B1A}R^{B1B}$, $—N_3$, $—SR^{B1D}$,

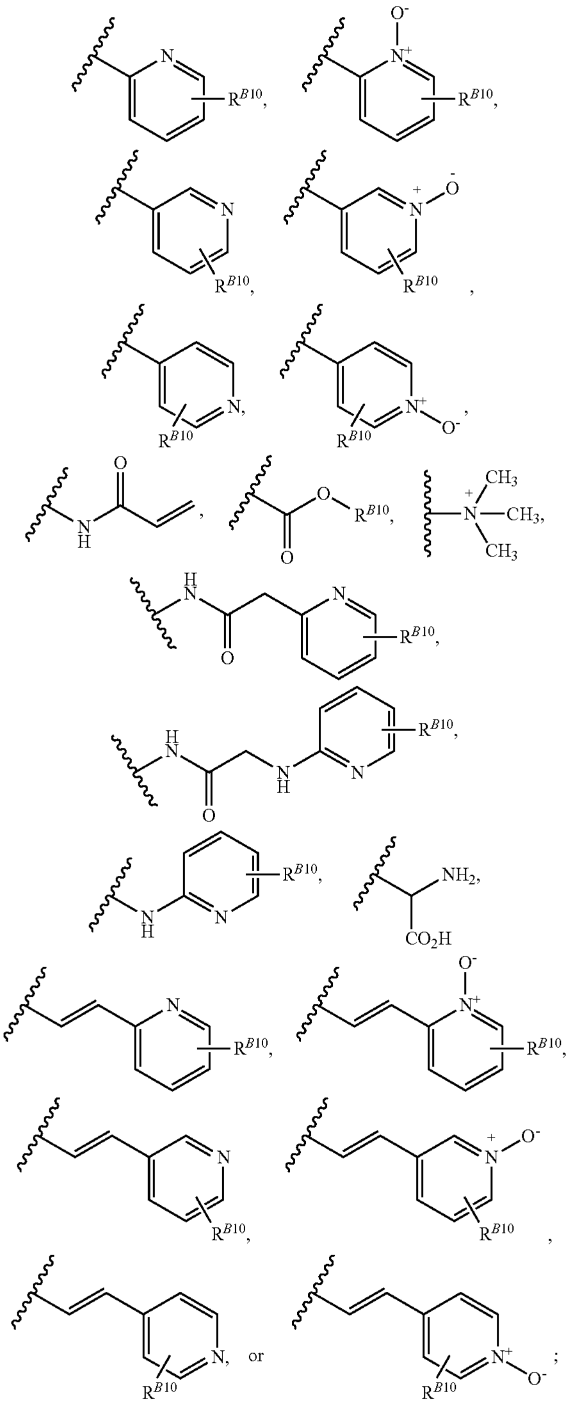

$R^{B10}$ is hydrogen, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—N(O)_{mB10}$, $—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—NR^{B10A}C(NR^{B10C})R^{B10D}$, $—NR^{B10A}C(NR^{B10C})NR^{B10A}R^{B10B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;
mB10 and v10 are independently 1 or 2; and
$X^{B10}$ is independently —F, —Cl, —Br, or —I.
Embodiment P23. The compound of one of embodiments P18 to P22, wherein $R^{B1}$ is —Cl, —$NH_2$, —$N_3$, —SH,
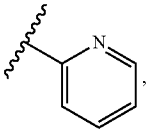
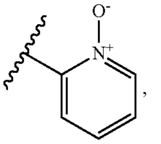
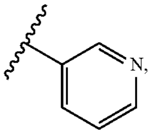
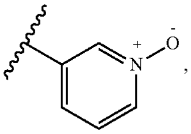
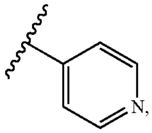
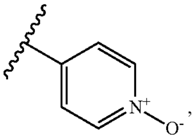
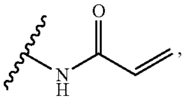
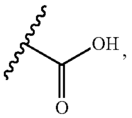
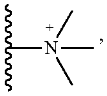
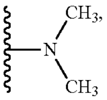
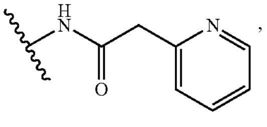
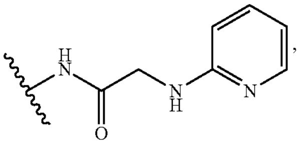
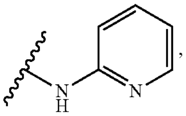
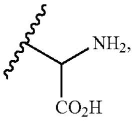
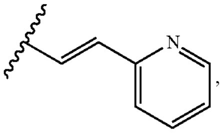
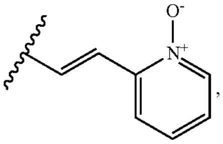
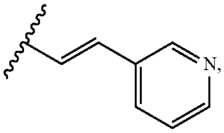
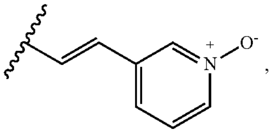
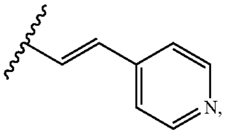
or
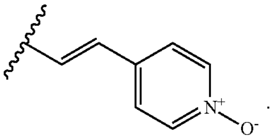
.
Embodiment P24. The compound of one of embodiments P18 to P23, wherein $L^{B1}$-$R^{B1}$ is
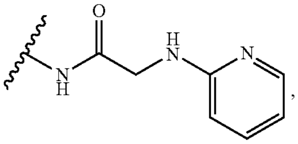
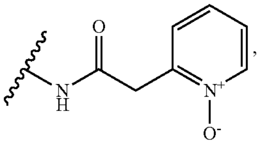
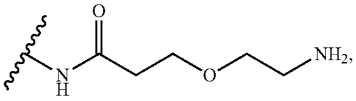
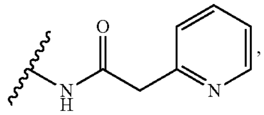
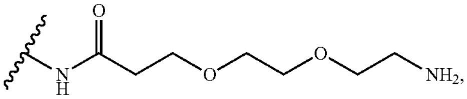
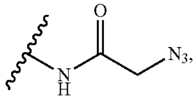
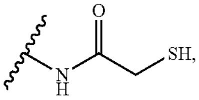
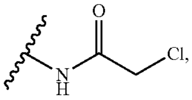
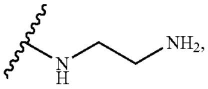
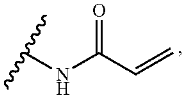
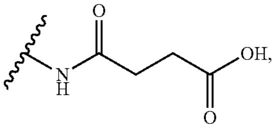
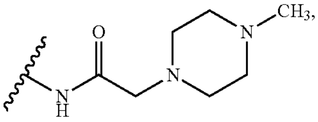
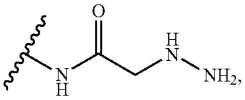
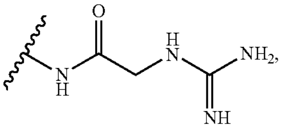
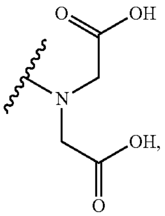
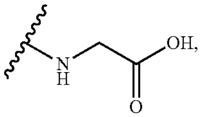
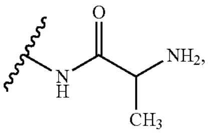
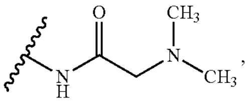

-continued
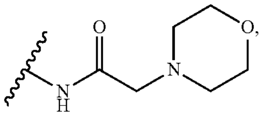
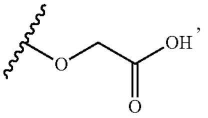
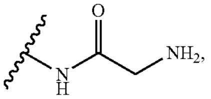
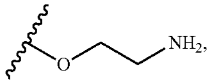
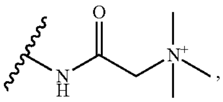
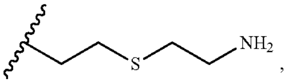
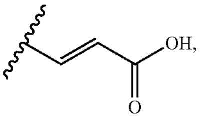
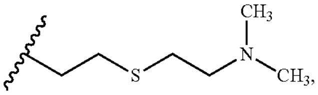
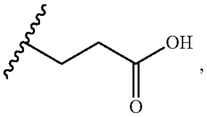
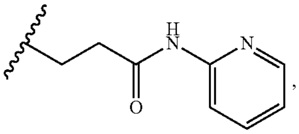
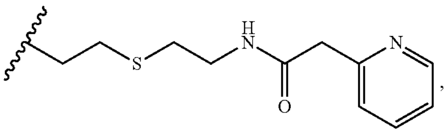
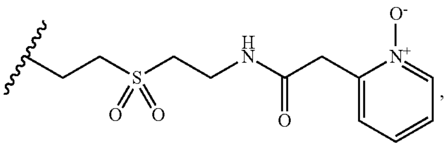
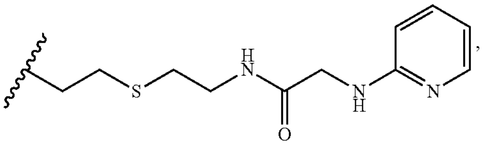
-continued
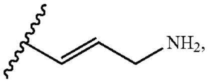
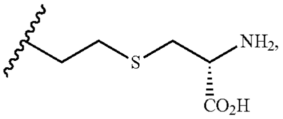
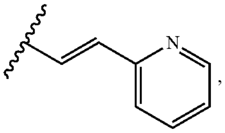
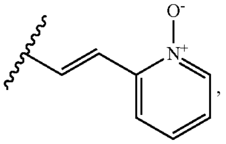
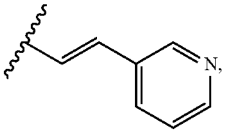
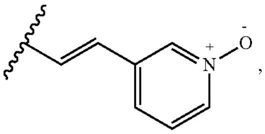
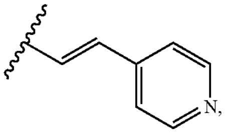
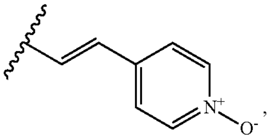
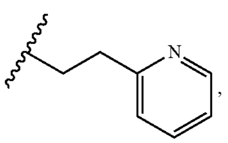
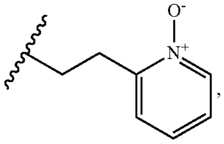
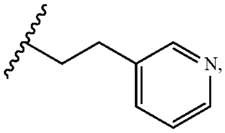
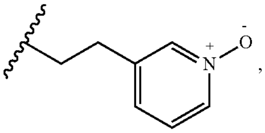
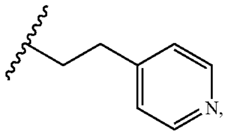
or
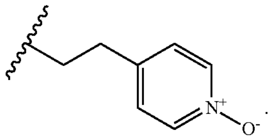
Embodiment P25. The compound of one of embodiments P18 to P24, wherein the compound is not

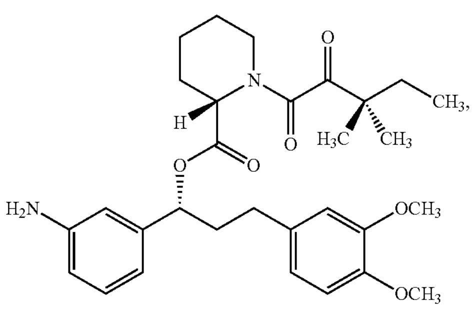
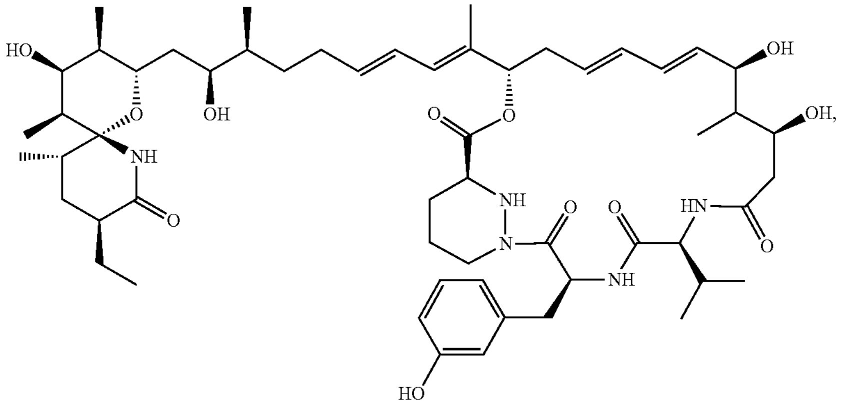
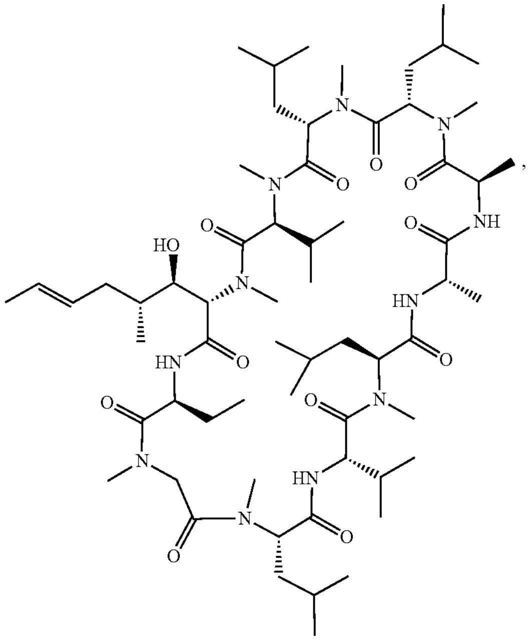
, or
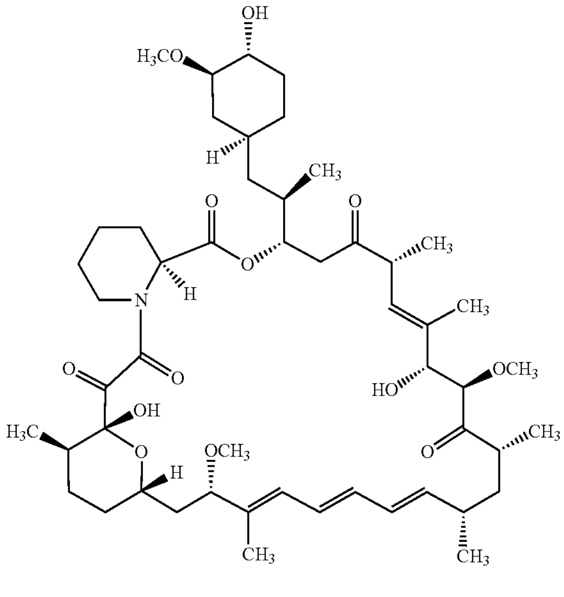
.

Embodiment P26. A compound having the formula:

$A^B$-$L^{B1}$-$R^{B1}$, or a pharmaceutically acceptable salt thereof;

wherein $A^B$ is an immunophilin-binding moiety having the formula

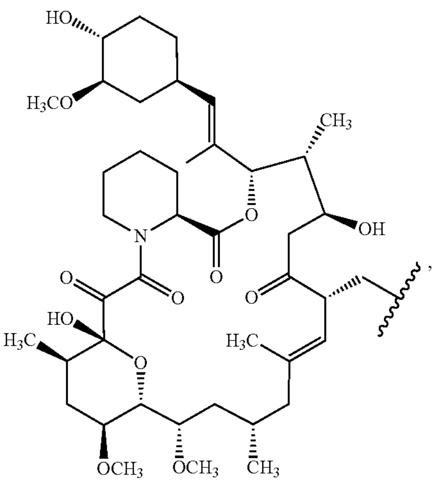

or an analog thereof;

$L^{B1}$-$R^{B1}$ is a polar moiety;

$L^{B1}$ is $L^{B2}$-$L^{B3}$-$L^{B4}$;

$L^{B2}$ is $S(O)_2$—, —$N(R^{B2})$—, —O—, —S—, —C(O)N($R^{B2}$)—, —$N(R^{B2})C(O)$—, —$N(R^{B2})C(O)NH$—, —$NHC(O)N(R^{B2})$—, —C(O)O—, —OC(O)—;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —$NHC(O)NR^{B1A}R^{B1B}$, —$N(O)_{mB1}$, —$NR^{B1A}R^{B1B}$, —$C(O)R^{B1C}$, —$C(O)OR^{B1C}$, —$C(O)NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B15C}$, —$NR^{B1A}OR^{B1C}$, —$NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2; and $X^{B1}$ is independently —F, —Cl, —Br, or —I.

Embodiment P27. The compound of embodiment P26, wherein $L^{B1}$ is

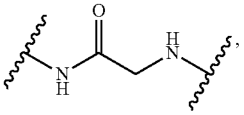,
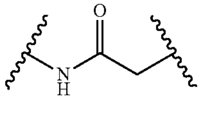,

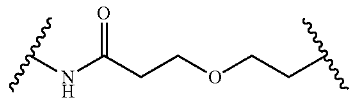,

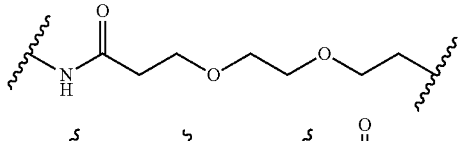,

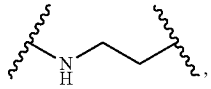,
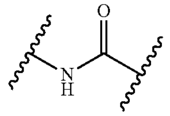,

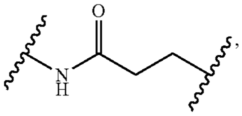,
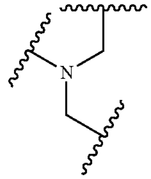,

-continued

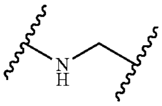,
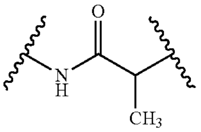,
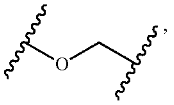, or
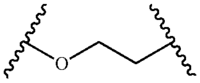.

Embodiment P28. The compound of one of embodiments P26 to P27, wherein $R^{B1}$ is halogen, $—NR^{B1A}R^{B1B}$, $—N_3$, $—SR^{B1D}$,

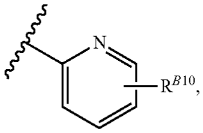
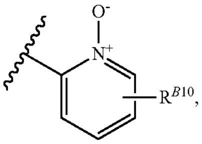
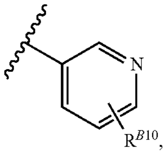
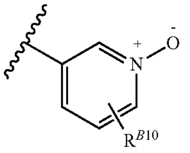,
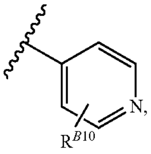
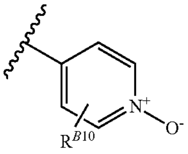,
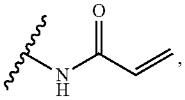,
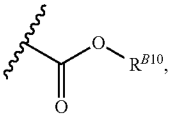
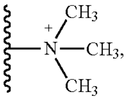
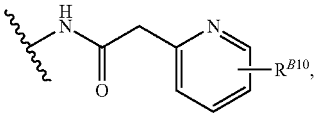
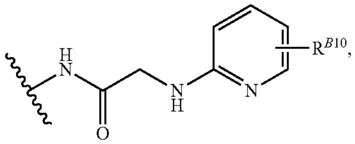
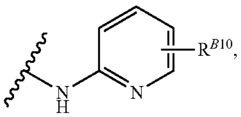
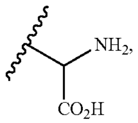
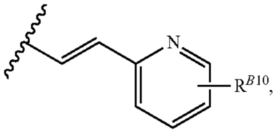
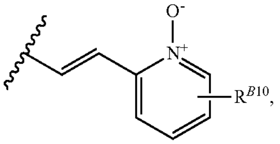
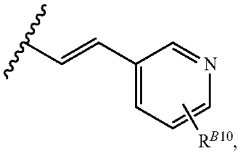
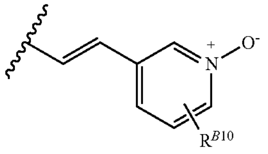, -continued

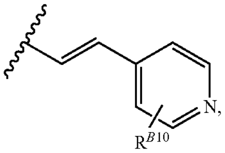 or
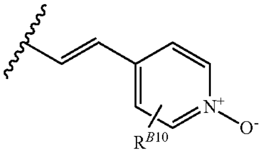;

$R^{B10}$ is hydrogen, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—N(O)_{mB10}$, $—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—NR^{B10A}C(NR^{B10C})R^{B10D}$, $—NR^{B10A}C(NR^{B10C})NR^{B10A}R^{B10B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment P29. The compound of one of embodiments P26 to P28, wherein $R^{B1}$ is —Cl, $—NH_2$, $—N_3$, —SH,

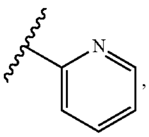,
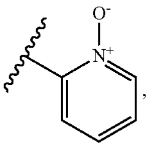,
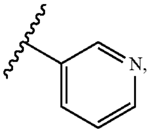
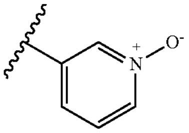,
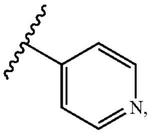
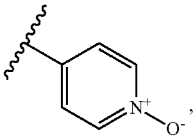,
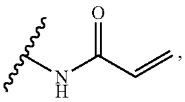,
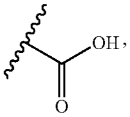
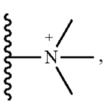,
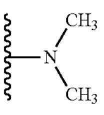,
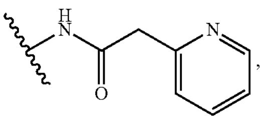,
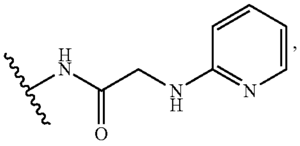,
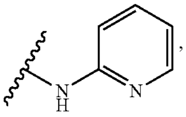,
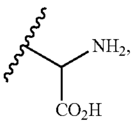

-continued

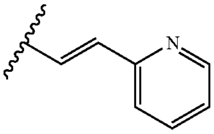, 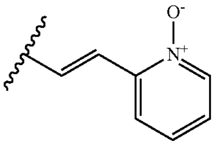,

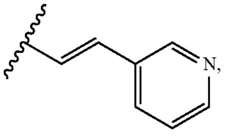 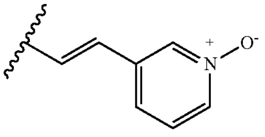,

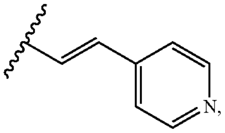 or 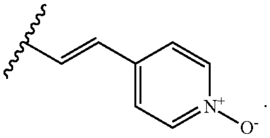.

Embodiment P30. The compound of one of embodiments P26 to P29, wherein $L^{B1}$-$R^{B1}$ is

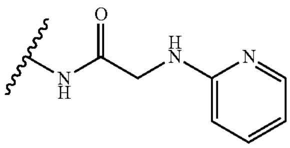, 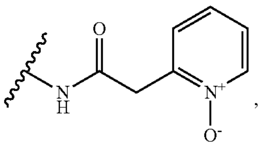,

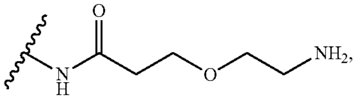

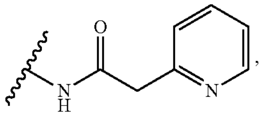

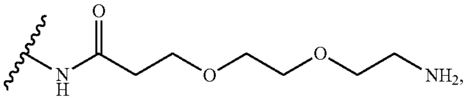

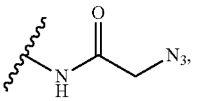 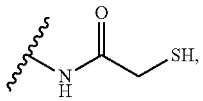

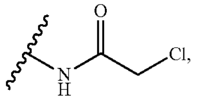 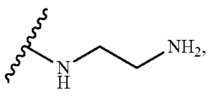

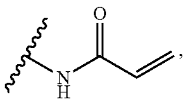, 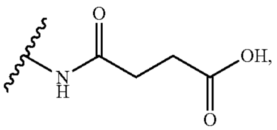

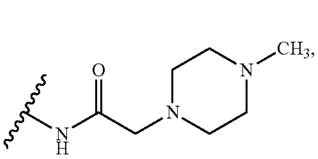

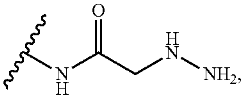 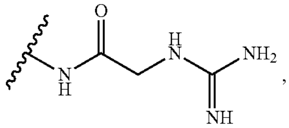,

-continued

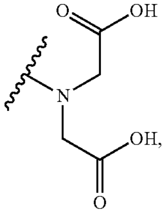 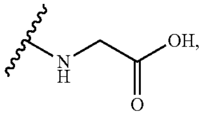

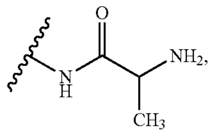 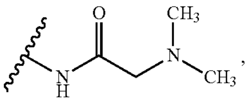,

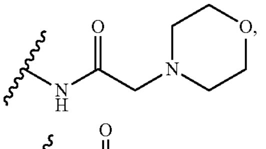 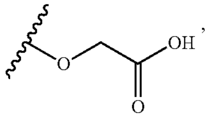,

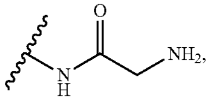 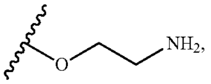 or

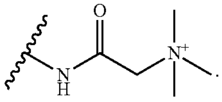.

Embodiment P31. A compound having the formula:

$A^B$-$L^{B1}$-$R^{B1}$, or a pharmaceutically acceptable salt thereof;

wherein $A^B$ is an immunophilin-binding moiety having the formula

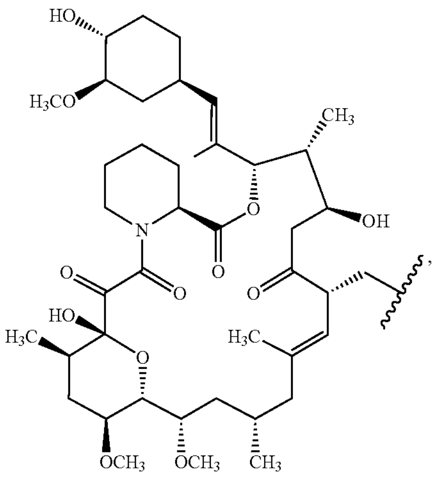, or an analog thereof;

$L^{B1}$-$R^{B1}$ is a polar moiety;

$L^{B1}$ is

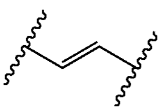 or 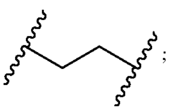;

and $R^{B1}$ is substituted or unsubstituted heteroaryl.

Embodiment P32. The compound of embodiment P31, wherein $R^{B1}$ is substituted or unsubstituted pyridyl.

Embodiment P33. A compound having the formula:

$A^B$-$L^{B1}$-$R^{B1}$, or a pharmaceutically acceptable salt thereof;

wherein $A^B$ is an immunophilin-binding moiety having the formula

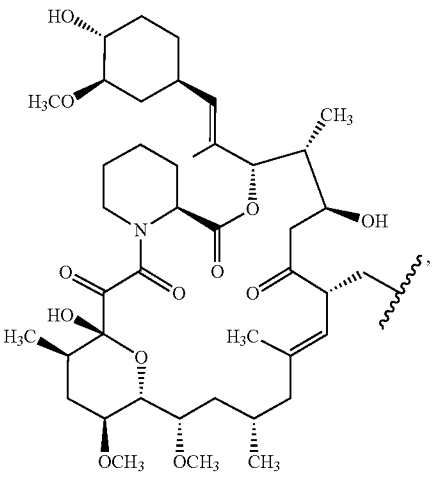

or an analog thereof;

$L^{B1}$-$R^{B1}$ is a polar moiety;

$L^{B1}$ is

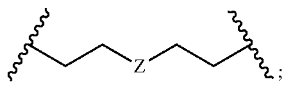;

Z is —S— or —$SO_2$—;

$R^{B1}$ is —$NR^{B1A}R^{B1B}$ or —$NHC(O)CH_2R^{B1C}$;

$R^{B1A}$ and $R^{B1B}$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{B1C}$ is substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P34. The compound of embodiment P33, wherein $R^{B1A}$, $R^{B1B}$, or $R^{B1C}$ are independently substituted or unsubstituted pyridyl.

Embodiment P35. The compound of one of embodiments P18 to P34, wherein the immunophilin-binding moiety is a cyclophilin-binding moiety or an FKBP-binding moiety.

Embodiment P36. A pharmaceutical composition comprising a pharmaceutically acceptable excipient and a compound of one of embodiments P18 to P35.

Embodiment P37. The method of one of embodiments P1 to P17, wherein the anti-CNS disease drug has the formula:

A-$L^1$-$R^1$;

wherein

A is an immunophilin-binding moiety;

$L^1$ is a bond or a covalent linker; and $R^1$ is a kinase inhibitor, a pseudokinase inhibitor, a GTPase inhibitor, a histone-modifying enzyme inhibitor, or a monovalent anti-viral agent.

Embodiment P38. The method of embodiment P37, wherein the immunophilin-binding moiety of the anti-CNS disease drug is a cyclophilin-binding moiety or an FKBP-binding moiety.

Embodiment P39. The method of one of embodiments P37 to P38, wherein the immunophilin-binding moiety of the anti-CNS disease drug is

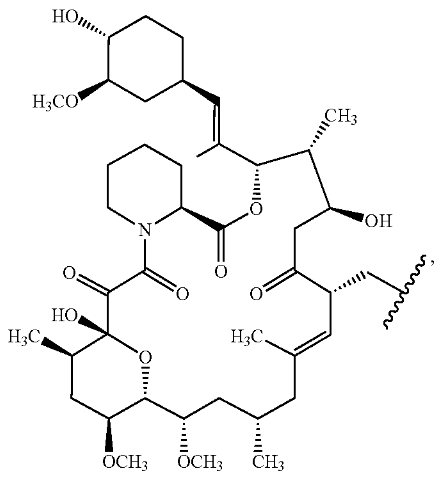 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC],

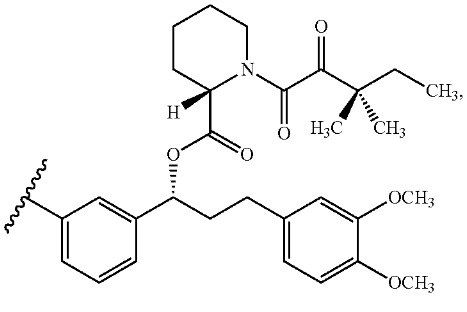,

-continued
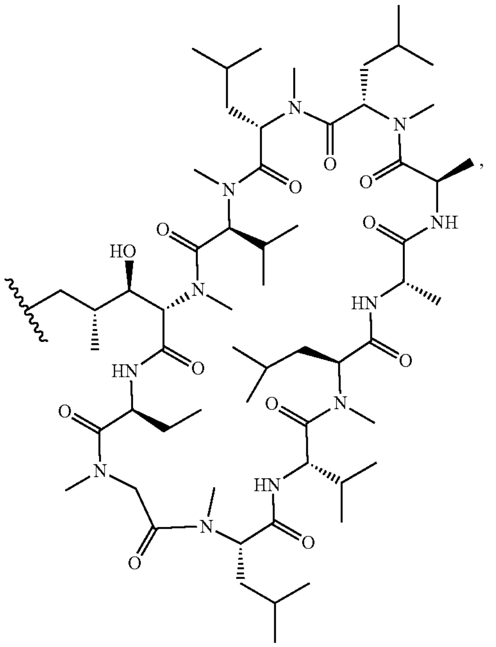
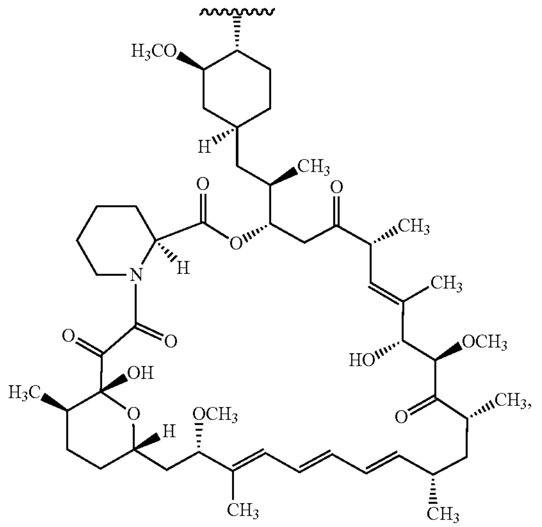
or
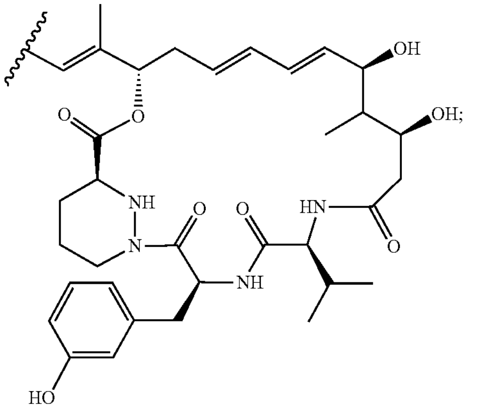
or an analog thereof.
Embodiment P40. The method of one of embodiments P37 to P38, wherein the immunophilin-binding moiety of the anti-CNS disease drug is
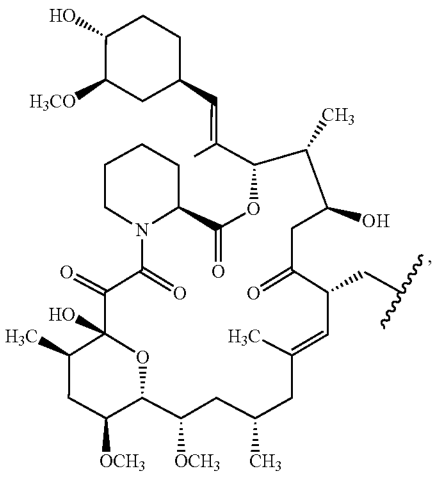 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]
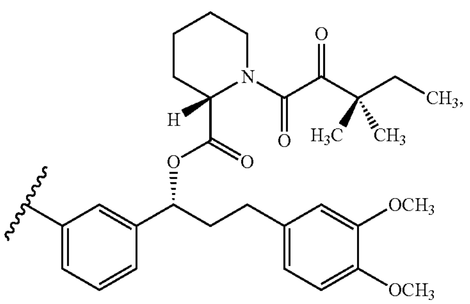
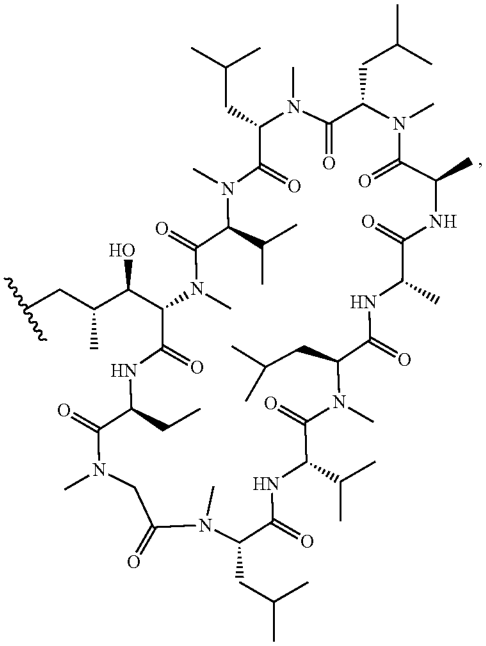
, or -continued

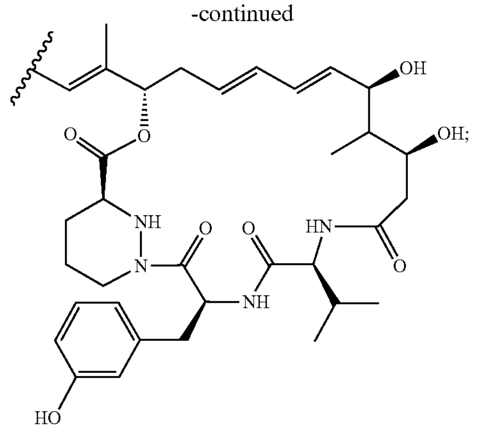

or an analog thereof.

Embodiment P41. The method of one of embodiments P37 to P39, wherein $L^1$ is $L^2$-$L^3$-$L^4$-$L^5$-$L^6$;

$L^2$ is connected directly to the moiety of an immunophilin-binding compound;

$L^2$ is —$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^2$, $R^3$, $R^4$, $R^5$, and $R^6$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P42. The method of embodiment P41, wherein $L^3$, $L^4$, $L^5$, and $L^6$ are a bond.

Embodiment P43. The method of embodiment P41, wherein $L^2$ is a substituted or unsubstituted alkylene, substituted or unsubstituted heteroalkylene, substituted or unsubstituted cycloalkylene, or substituted or unsubstituted heterocycloalkylene;

$L^3$ is a bond, substituted or unsubstituted alkylene, substituted or unsubstituted heteroalkylene, substituted or unsubstituted cycloalkylene, or substituted or unsubstituted heterocycloalkylene;

$L^4$ is a bond, substituted or unsubstituted alkylene, or substituted or unsubstituted heteroalkylene;

$L^5$ is a bond; and $L^6$ is a bond.

Embodiment P44. The method of embodiment P41, wherein $L^2$ is an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^3$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or an unsubstituted 5 to 6 membered heterocycloalkylene, and $L^4$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^5$ is a bond; and $L^6$ is a bond.

Embodiment P45. The method of one of embodiments P37 to P39, wherein $L^1$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

Embodiment P46. The method of one of embodiments P37 to P39, wherein $L^1$ is

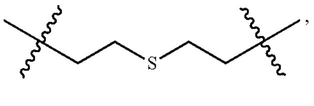
,
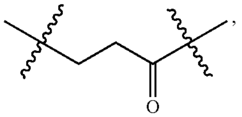
,
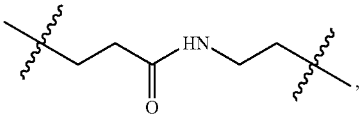
,
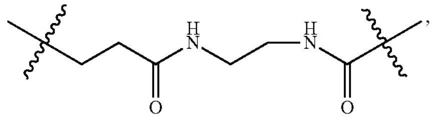
,

-continued

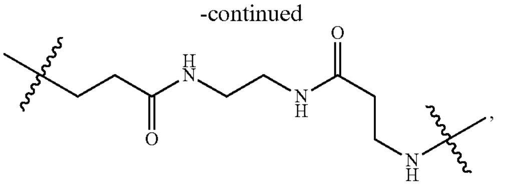

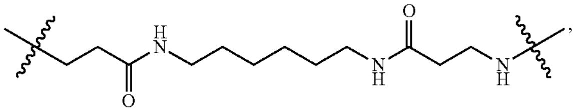

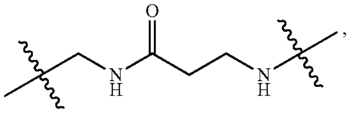

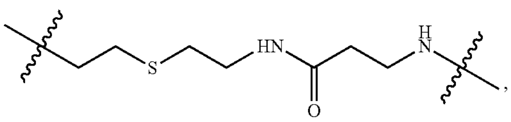

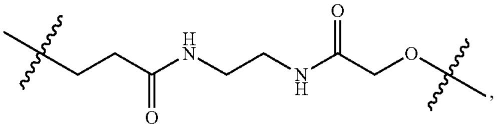

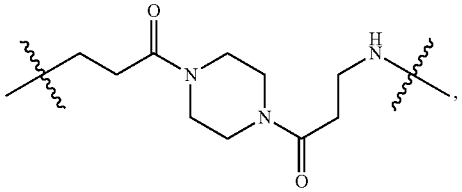

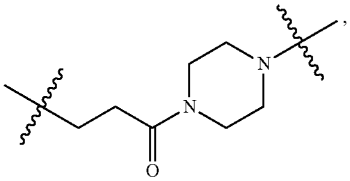

or

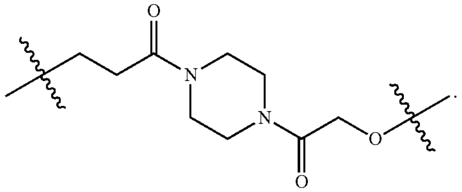

Embodiment P47. The method of one of embodiments P37 to P39, wherein $L^1$ is a bond.

Embodiment P48. The method of one of embodiments P37 to P39, wherein $L^1$ is a substituted or unsubstituted alkylene or substituted or unsubstituted heteroalkylene.

Embodiment P49. The method of one of embodiments P37 to P48, wherein $R^1$ is a monovalent kinase inhibitor.

Embodiment P50. The method of embodiment P49, wherein the kinase is not mTOR.

Embodiment P51. The method of one of embodiments P49 to P50, wherein the monovalent kinase inhibitor is a monovalent Src kinase inhibitor.

Embodiment P52. The method of embodiments P49 to P50, wherein the monovalent Src kinase inhibitor is a monovalent dasatinib or monovalent dasatinib derivative.

Embodiment P53. The method of embodiment P52, wherein the monovalent dasatinib derivative has the formula:

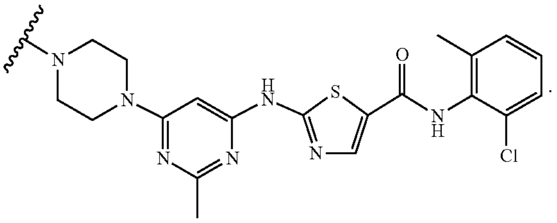 [SMILES: *N1CCN(c2cc(Nc3ncc(C(=O)Nc4c(C)cccc4Cl)s3)nc(C)n2)CC1]

Embodiment P54. The method of one of embodiments P49 to P50, wherein the monovalent kinase inhibitor is a monovalent Raf inhibitor, VEGFR inhibitor, PDGFR inhibitor, or c-Kit inhibitor.

Embodiment P55. The method of embodiment P54, wherein the monovalent Raf inhibitor, VEGFR inhibitor, PDGFR inhibitor, or c-Kit inhibitor is a monovalent sorafenib or monovalent sorafenib derivative.

Embodiment P56. The method of embodiment P55, wherein the monovalent sorafenib derivative has the formula:

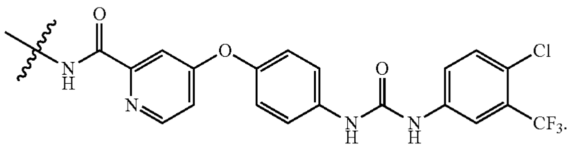 [SMILES: *NC(=O)c1cc(Oc2ccc(NC(=O)Nc3ccc(Cl)c(C(F)(F)F)c3)cc2)ccn1]

Embodiment P57. The method of one of embodiments P49 to P50, wherein the monovalent kinase inhibitor is a monovalent EGFR inhibitor.

Embodiment P58. The method of embodiment P57, wherein the monovalent EGFR inhibitor is a monovalent lapatinib, monovalent lapatinib derivative, monovalent erlotinib, monovalent erlotinib derivative, monovalent gefitinib, or monovalent gefitinib derivative.

Embodiment P59. The method of embodiment P58, wherein the monovalent EGFR inhibitor has the formula:

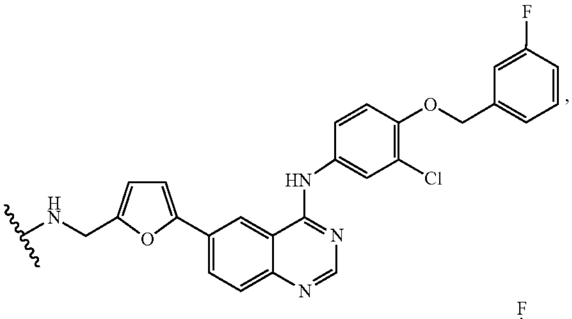

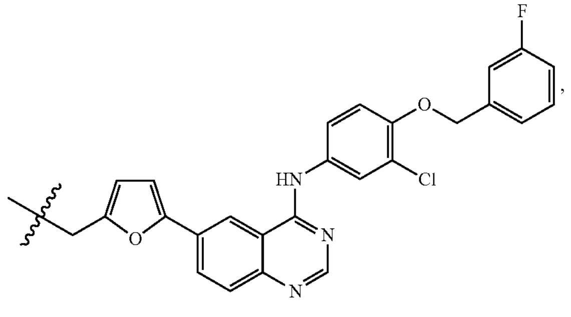

-continued

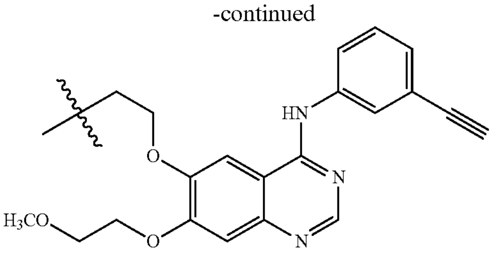

, or

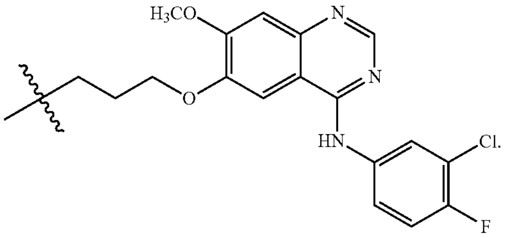

Embodiment P60. The method of one of embodiments P49 to P50, wherein the monovalent kinase inhibitor is a monovalent LRRK2 inhibitor.

Embodiment P61. The method of embodiment P60, wherein the monovalent LRRK2 inhibitor is a monovalent GNE-7915 or monovalent GNE-7915 derivative.

Embodiment P62. The method of embodiment P61, wherein the monovalent GNE-7915 derivative has the formula:

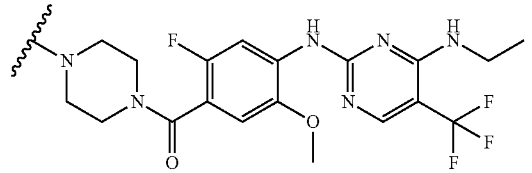

or

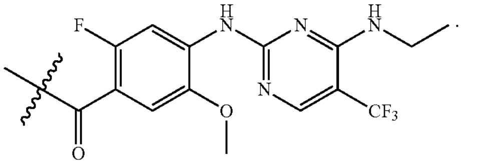

Embodiment P63. The method of one of embodiments P37 to P48, wherein $R^1$ is a monovalent KRAS inhibitor.

Embodiment P64. The method of embodiment P63, wherein the monovalent KRAS inhibitor is a monovalent KRAS G12C inhibitor or a monovalent KRAS M72C inhibitor.

Embodiment P65. The method of embodiment P44, wherein the monovalent KRAS inhibitor has the formula:

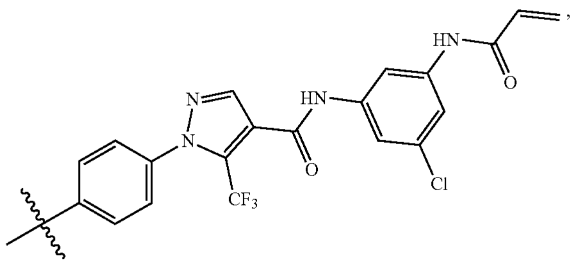

-continued

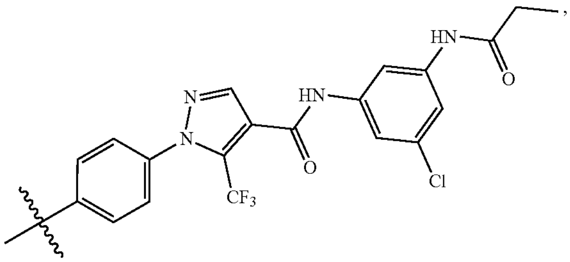

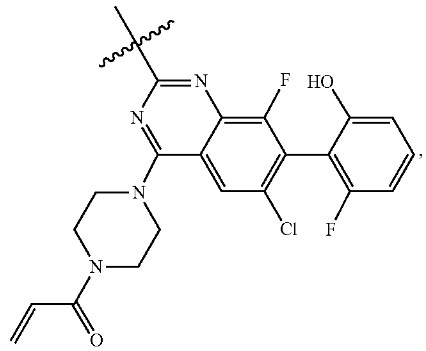

, or

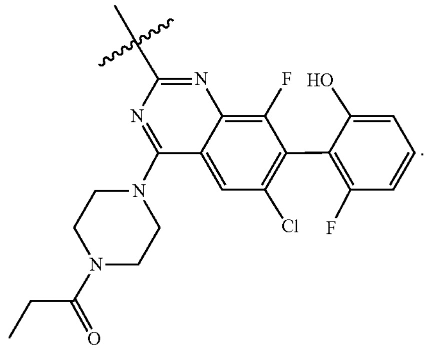

VI. Additional Embodiments

Embodiment 1. A method of treating a CNS disease in a subject in need of such treatment, comprising co-administering outside the CNS of said subject an anti-CNS disease drug and a compound having the formula:

$A^B$-$L^{B1}$-$R^{B1}$, or a pharmaceutically acceptable salt thereof;

wherein $A^B$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, $-CX^{B1}_3$, $-CHX^{B1}_2$, $-CH_2X^{B1}$, $-OCX^{B1}_3$, $-OCH_2X^{B1}$, $-OCHX^{B1}_2$, $-CN$, $-SO_{nB1}R^{B1D}$, $-SO_{vB1}NR^{B1A}R^{B1B}$, $-NHC(O)NR^{B1A}R^{B1B}$, $-N(O)_{mB1}$, $-NR^{B1A}R^{B1B}$, $-C(O)R^{B1C}$, $-C(O)OR^{B1C}$, $-C(O)NR^{B1A}R^{B1B}$, $-OR^{B1D}$, $-NR^{B1A}SO_2R^{B1D}$, $-NR^{B1A}C(O)R^{B1C}$, $-NR^{B1A}C(O)OR^{B1C}$, $-NR^{B1A}OR^{B1C}$, $-NR^{B1A}C(NR^{B1C})R^{B1D}$, $-NR^{B1A}C(NR^{B1C})NR^{B1A}R^{B1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHC(NH)H$, $-NHC(NH)NH_2$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently $-F$, $-Cl$, $-Br$, or $-I$;

when $L^{B1}$ is a bond, $R^{B1}$ is not H; and wherein, subsequent to administration, the concentration of the compound in circulating blood of said subject is greater than the concentration of the compound in the CNS of said subject.

Embodiment 2. The method of embodiment 1, wherein the immunophilin-binding moiety is a cyclophilin-binding moiety or an FKBP-binding moiety.

Embodiment 3. The method of one of embodiments 1 to 2, wherein the immunophilin-binding moiety is

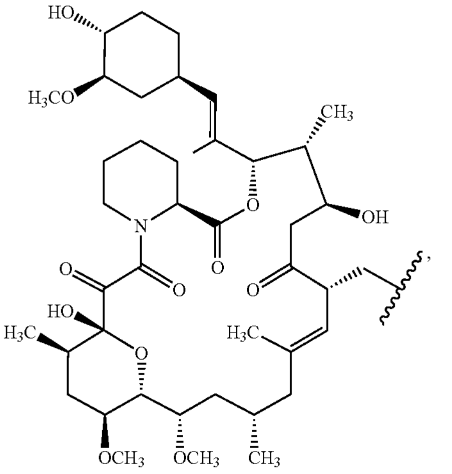

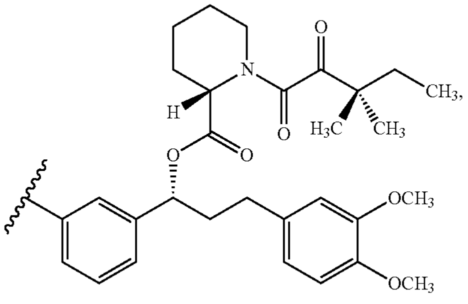

-continued

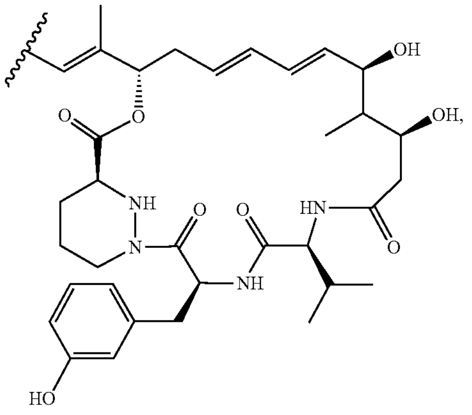

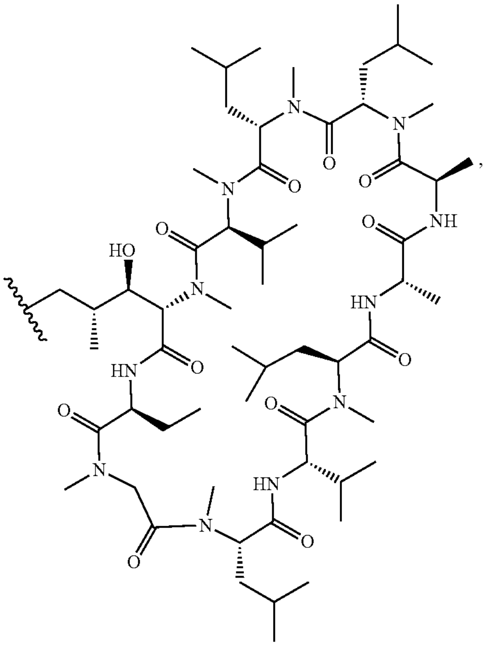

, or

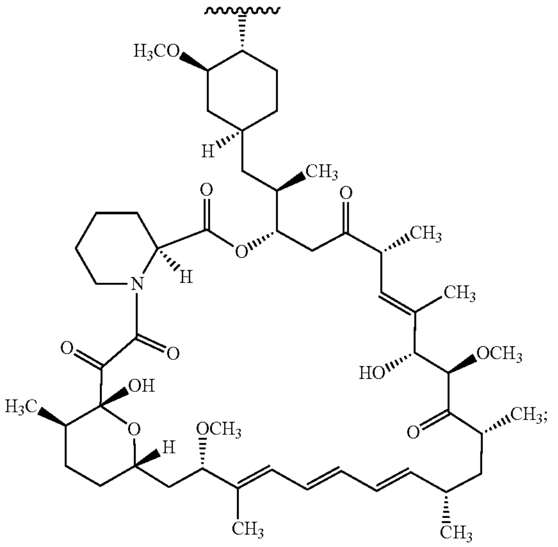 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or an analog thereof.

Embodiment 4. The method of one of embodiments 1 to 3, wherein $L^{B1}$ is $L^{B2}$-$L^{B3}$-$L^{B4}$;

$L^{B2}$ is a bond, —$S(O)_2$—, —$N(R^{B2})$—, —O—, —S—, —C(O)—, —$C(O)N(R^{B2})$—, —$N(R^{B2})C(O)$—, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 5. The method of one of embodiments 1 to 4, wherein $L^{B1}$ is

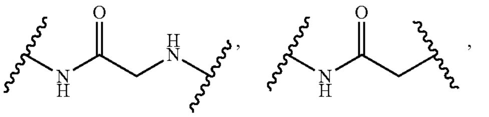

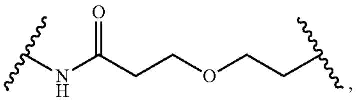

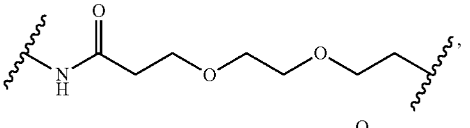

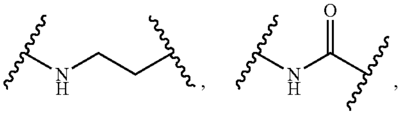

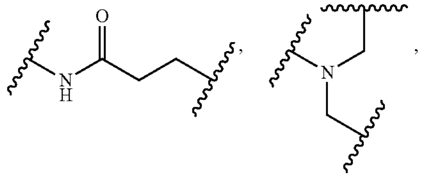

-continued

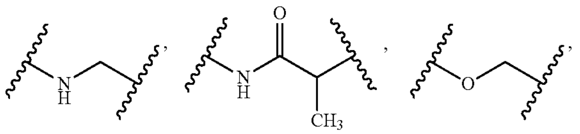

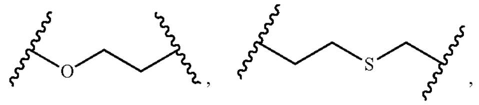

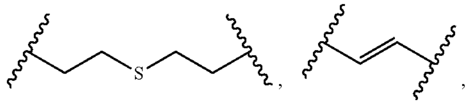

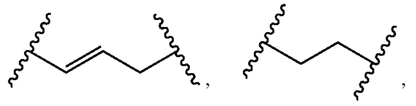

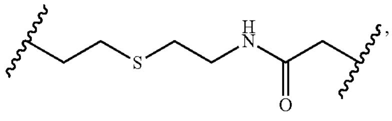

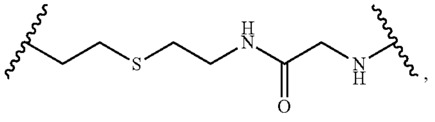

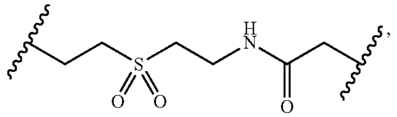

or

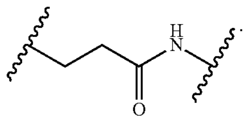

Embodiment 6. The method of one of embodiments 1 to 5, wherein $R^{B1}$ is halogen, —$NR^{B1A}R^{B1B}$, —$N_3$, —$SR^{B1D}$,

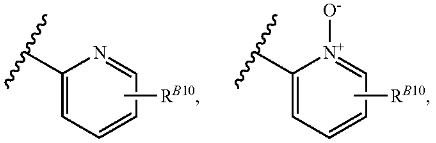

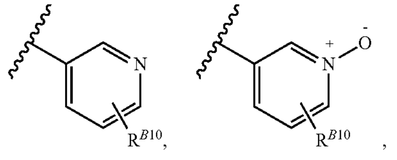

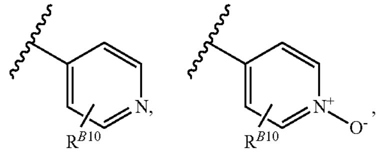

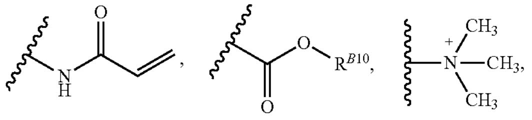

-continued

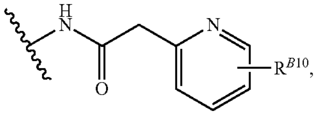

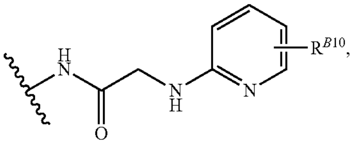

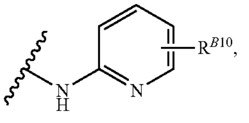 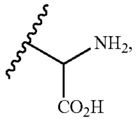

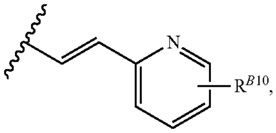 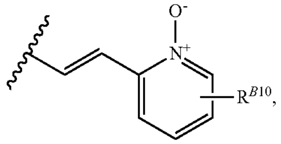

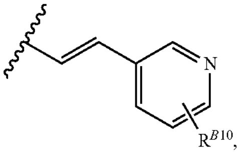 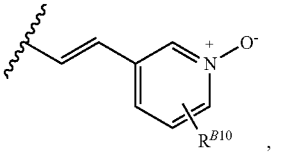

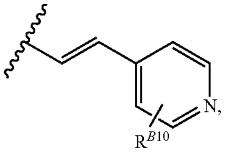 or 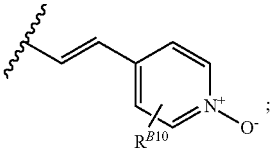

$R^{B10}$ is hydrogen, halogen, —$CX^{B10}_3$, —$CHX^{B10}_2$, —$CH_2X^{B10}$, —$OCX^{B10}_3$, —$OCH_2X^{B10}$, —$OCHX^{B10}_2$, —CN, —$SO_{nB10}R^{B10D}$, —$SO_{vB10}NR^{B10A}R^{B10B}$, —NHC(O)$NR^{B10A}R^{B10B}$, —$N(O)_{mB10}$, —$NR^{B10A}R^{B10B}$, —C(O)$R^{B10C}$, —C(O)$OR^{B10C}$, —C(O)$NR^{B10A}R^{B10B}$, —$OR^{B10D}$, —$NR^{B10A}SO_2R^{B10D}$, —$NR^{B10A}C(O)R^{B10C}$, —$NR^{B10A}C(O)OR^{B10C}$, —$NR^{B10A}OR^{B10C}$, —$NR^{B10A}C(NR^{B10C})R^{B10D}$, —$NR^{B10A}C(NR^{B10C})NR^{B10A}R^{B10B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment 7. The method of one of embodiments 1 to 6, wherein $R^{B1}$ is —Cl, —$NH_2$, —$N_3$, —SH,

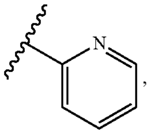 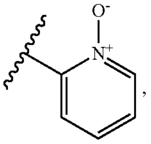

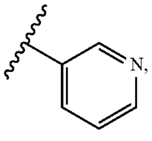 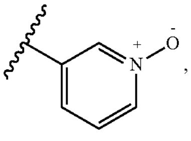

-continued

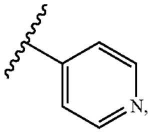 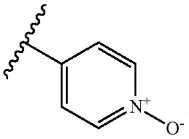

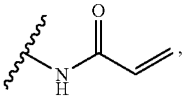 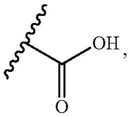 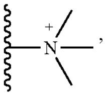

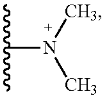 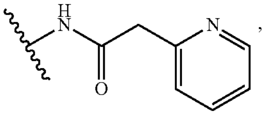

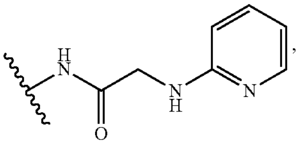

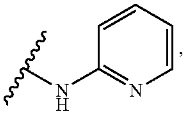 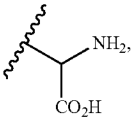

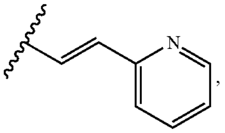 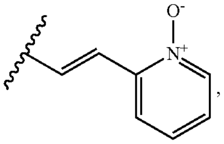

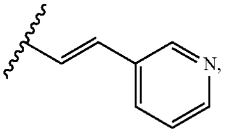 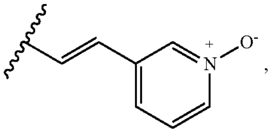

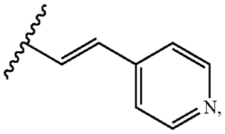 or 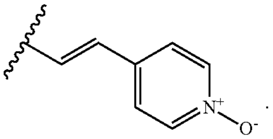

Embodiment 8. The method of one of embodiments 1 to 7, wherein $L^{B1}$-$R^{B1}$ is

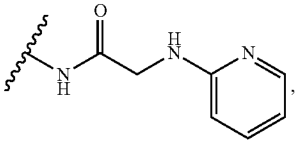 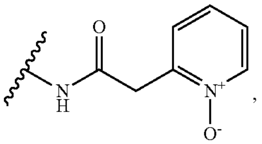

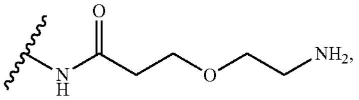

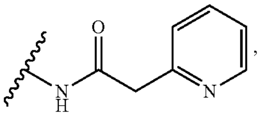

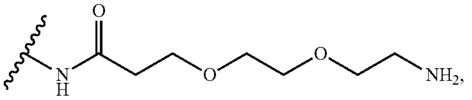

-continued

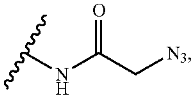, 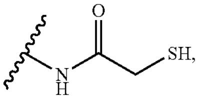,

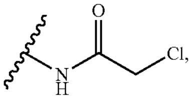, 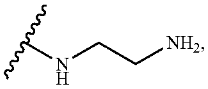,

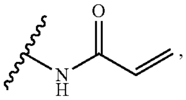, 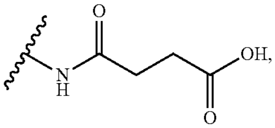,

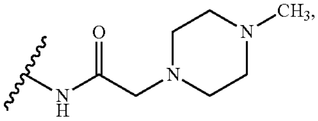, 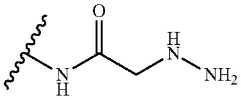,

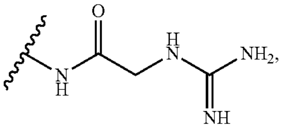, 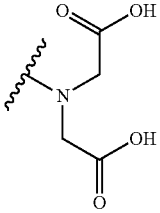,

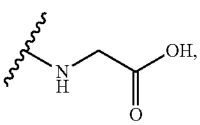, 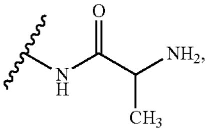,

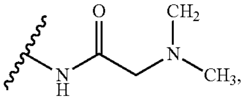, 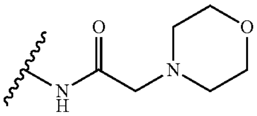,

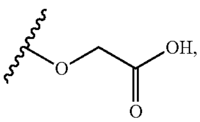, 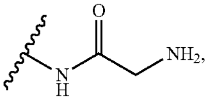,

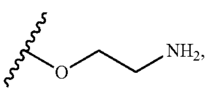, 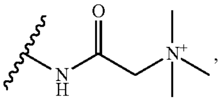,

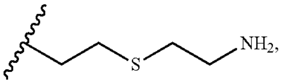, 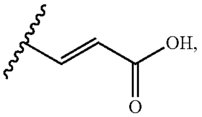,

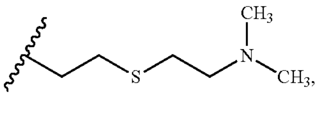, 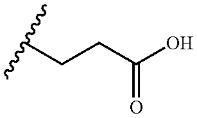,

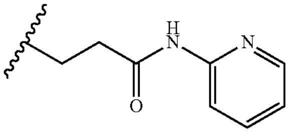,

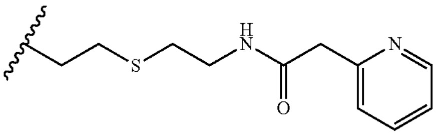,

-continued

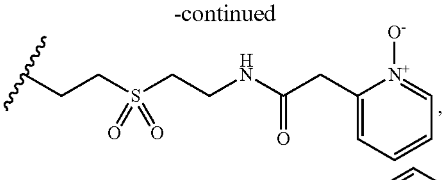,

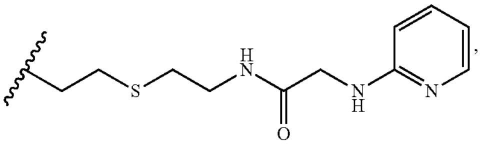,

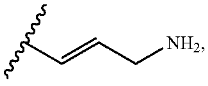, 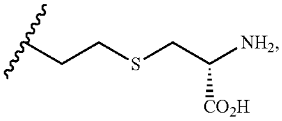,

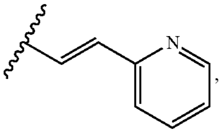, 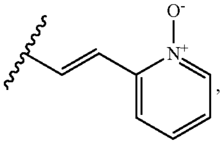,

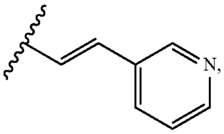, 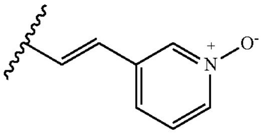,

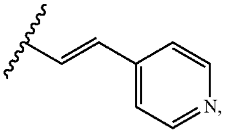, 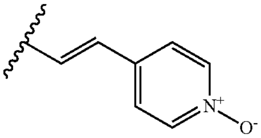,

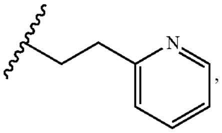, 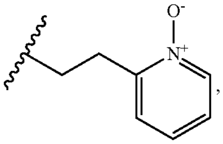,

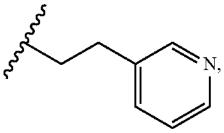, 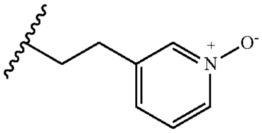,

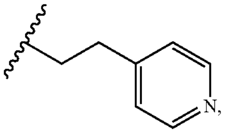 or 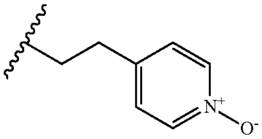.

Embodiment 9. The method of one of embodiments 1 to 8, wherein the concentration of the compound in circulating blood is greater than 3-fold the concentration of the compound in the CNS.

Embodiment 10. The method of one of embodiments 1 to 9, wherein the concentration of the compound in circulating blood is greater than 20-fold the concentration of the compound in the CNS.

Embodiment 11. The method of one of embodiments 1 to 10, wherein the compound is unable to cross the blood-brain barrier.

Embodiment 12. The method of one of embodiments 1 to 11, wherein the compound is unable to enter the central nervous system of a subject following administration to the subject outside of the central nervous system.

Embodiment 13. The method of one of embodiments 1 to 12, wherein the anti-CNS disease drug is capable of entering the central nervous system and the compound is incapable of entering the central nervous system following co-administration outside of the central nervous system of the subject.

Embodiment 14. The method of one of embodiments 1 to 13, wherein the compound does not bind calcineurin.

Embodiment 15. The method of one of embodiments 1 to 14, wherein the compound does not inhibit development and/or proliferation of T cells.

Embodiment 16. The method of one of embodiments 1 to 15, wherein the compound does not reduce the body's immune response.

Embodiment 17. The method of one of embodiments 1 to 16, comprising reduced side effects associated with the anti-CNS disease drug compared to absence of the compound.

Embodiment 18. The method of one of embodiments 1 to 17, comprising enhanced therapeutic effects of the anti-CNS disease drug compared to absence of the compound.

Embodiment 19. The method of one of embodiments 1 to 18, wherein the anti-CNS disease drug has the formula:

$A\text{-}L^1\text{-}R^1$;

wherein

A is an immunophilin-binding moiety;

$L^1$ is a bond or a covalent linker; and $R^1$ is a kinase inhibitor, a pseudokinase inhibitor, a GTPase inhibitor, a histone-modifying enzyme inhibitor, or a monovalent anti-viral agent.

Embodiment 20. The method of embodiment 19, wherein the immunophilin-binding moiety of the anti-CNS disease drug is a cyclophilin-binding moiety or an FKBP-binding moiety.

Embodiment 21. The method of one of embodiments 19 to 20, wherein the immunophilin-binding moiety of the anti-CNS disease drug is

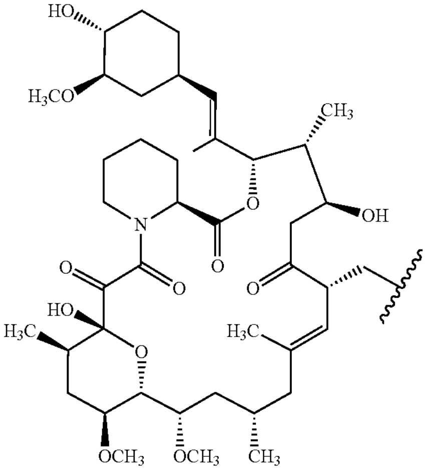

,

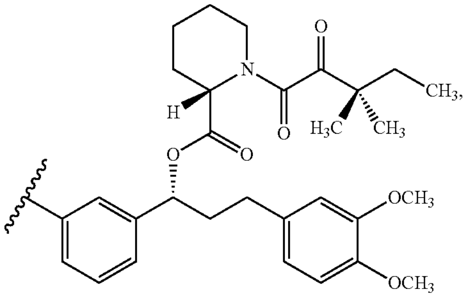

,

-continued

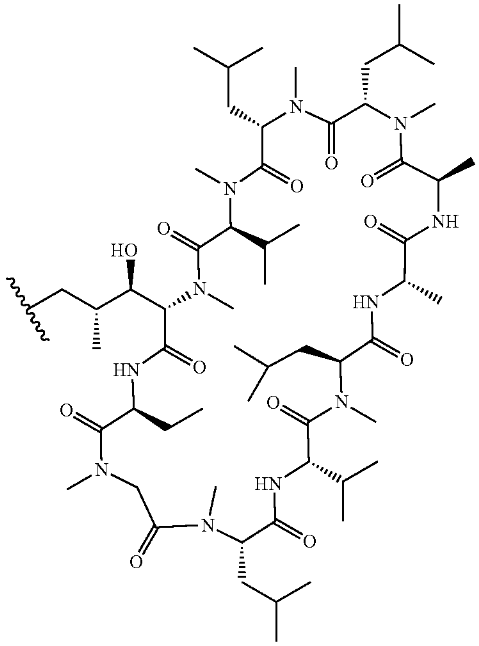

,

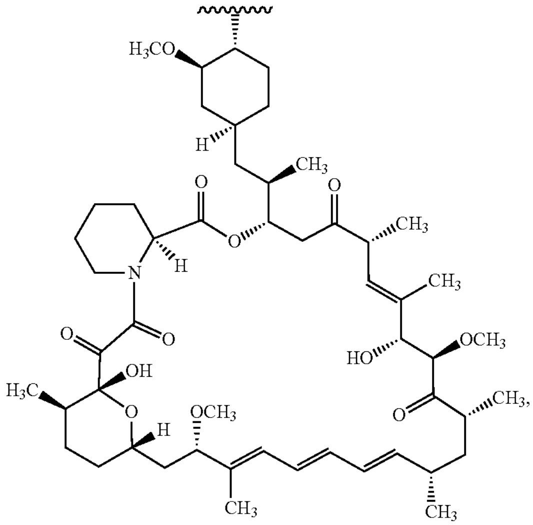

, or

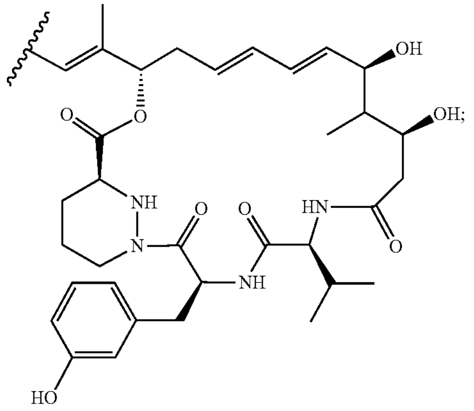

;

or an analog thereof.

Embodiment 22. The method of one of embodiments 19 to 20, wherein the immunophilin-binding moiety of the anti-CNS disease drug is

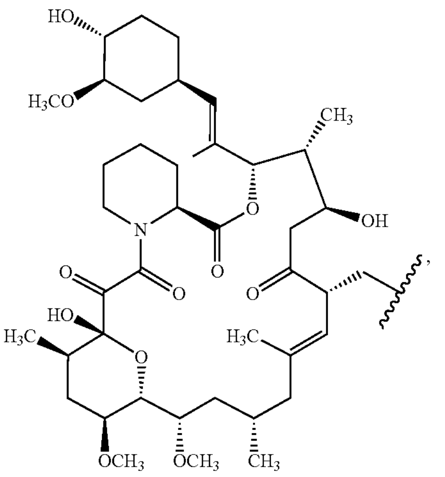

,

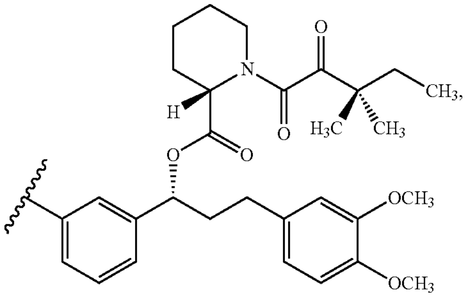

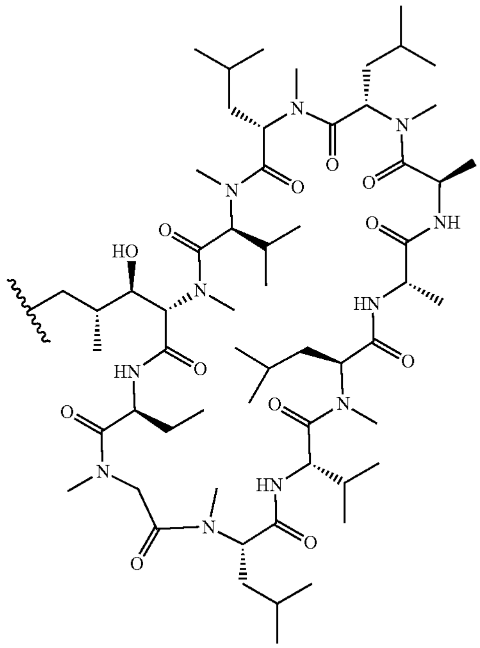

, or

-continued

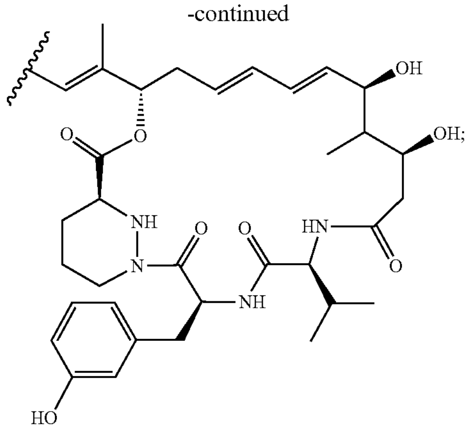

or an analog thereof.

Embodiment 23. The method of one of embodiments 19 to 21, wherein $L^1$ is $L^2$-$L^3$-$L^4$-$L^5$-$L^6$;

$L^2$ is connected directly to the moiety of an immunophilin-binding compound;

$L^2$ is —$S(O)_2$—, —$N(R^2)$—, —O—, —S—, —C(O)—, —C(O)$N(R^2)$—, —$N(R^2)$C(O)—, —$N(R^2)$C(O)NH—, —NHC(O)$N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —$S(O)_2$—, —$N(R^3)$—, —O—, —S—, —C(O)—, —C(O)$N(R^3)$—, —$N(R^3)$C(O)—, —$N(R^3)$C(O)NH—, —NHC(O)$N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^4$ is a bond, —$S(O)_2$—, —$N(R^4)$—, —O—, —S—, —C(O)—, —C(O)$N(R^4)$—, —$N(R^4)$C(O)—, —$N(R^4)$C(O)NH—, —NHC(O)$N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^5$ is a bond, —$S(O)_2$—, —$N(R^5)$—, —O—, —S—, —C(O)—, —C(O)$N(R^5)$—, —$N(R^5)$C(O)—, $R^5$)C(O)NH—, —NHC(O)$N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^6$ is a bond, —$S(O)_2$—, —$N(R^6)$—, —O—, —S—, —C(O)—, —C(O)$N(R^6)$—, —$N(R^6)$C(O)—, $R^6$)C(O)NH—, —NHC(O)$N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^2$, $R^3$, $R^4$, $R^5$, and $R^6$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 24. The method of embodiment 23, wherein $L^3$, $L^4$, $L^5$, and $L^6$ are a bond.

Embodiment 25. The method of embodiment 23, wherein $L^2$ is a substituted or unsubstituted alkylene, substituted or unsubstituted heteroalkylene, substituted or unsubstituted cycloalkylene, or substituted or unsubstituted heterocycloalkylene;

$L^3$ is a bond, substituted or unsubstituted alkylene, substituted or unsubstituted heteroalkylene, substituted or unsubstituted cycloalkylene, or substituted or unsubstituted heterocycloalkylene;

$L^4$ is a bond, substituted or unsubstituted alkylene, or substituted or unsubstituted heteroalkylene;

$L^5$ is a bond; and $L^6$ is a bond.

Embodiment 26. The method of embodiment 23, wherein $L^2$ is an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^3$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or an unsubstituted 5 to 6 membered heterocycloalkylene, and $L^4$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^5$ is a bond; and $L^6$ is a bond.

Embodiment 27. The method of one of embodiments 19 to 21, wherein $L^1$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

Embodiment 28. The method of one of embodiments 19 to 21, wherein $L^1$ is

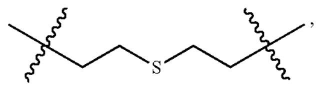

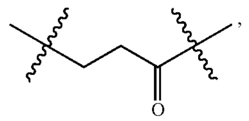

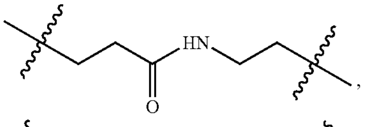

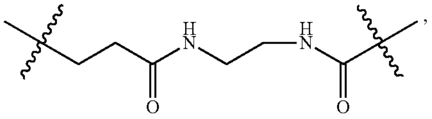

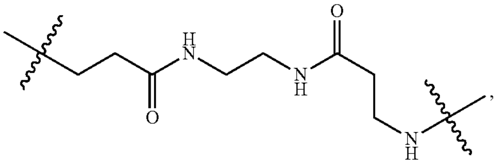

-continued

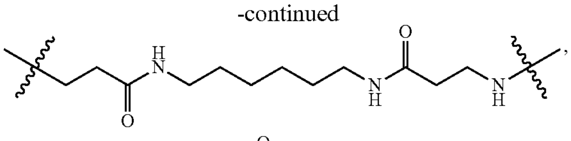

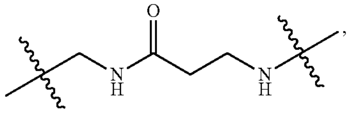

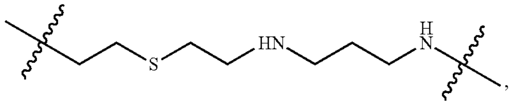

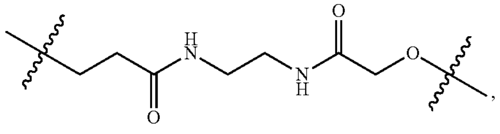

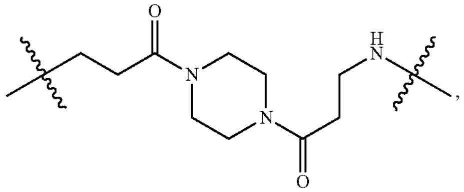

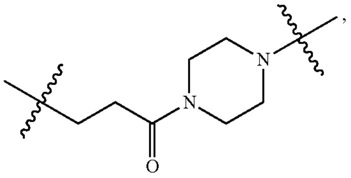

or

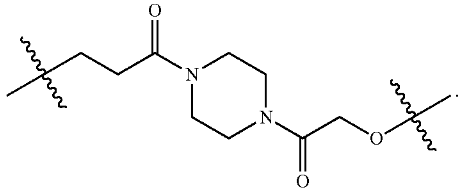

Embodiment 29. The method of one of embodiments 19 to 21, wherein $L^1$ is a bond.

Embodiment 30. The method of one of embodiments 19 to 21, wherein $L^1$ is a substituted or unsubstituted alkylene or substituted or unsubstituted heteroalkylene.

Embodiment 31. The method of one of embodiments 19 to 30, wherein $R^1$ is a monovalent kinase inhibitor.

Embodiment 32. The method of embodiment 31, wherein the kinase is not mTOR.

Embodiment 33. The method of one of embodiments 31 to 32, wherein the monovalent kinase inhibitor is a monovalent Src kinase inhibitor.

Embodiment 34. The method of one of embodiments 31 to 32, wherein the monovalent Src kinase inhibitor is a monovalent dasatinib or monovalent dasatinib derivative.

Embodiment 35. The method of embodiment 34, wherein the monovalent dasatinib derivative has the formula:

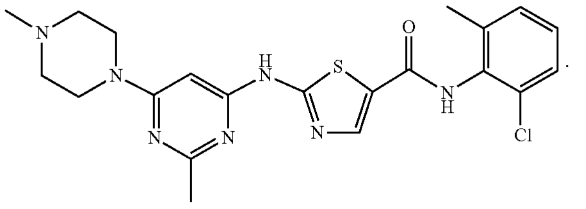 [SMILES: Cc1nc(Nc2ncc(C(=O)Nc3c(C)cccc3Cl)s2)cc(N2CCN(C)CC2)n1]

Embodiment 36. The method of one of embodiments 31 to 32, wherein the monovalent kinase inhibitor is a monovalent Raf inhibitor, VEGFR inhibitor, PDGFR inhibitor, or c-Kit inhibitor.

Embodiment 37. The method of embodiment 36, wherein the monovalent Raf inhibitor, VEGFR inhibitor, PDGFR inhibitor, or c-Kit inhibitor is a monovalent sorafenib or monovalent sorafenib derivative.

Embodiment 38. The method of embodiment 37, wherein the monovalent sorafenib derivative has the formula:

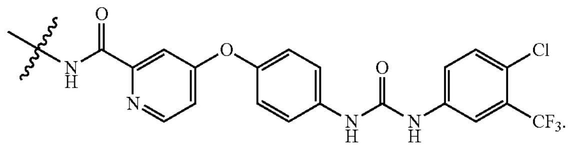 [SMILES: *NC(=O)c1cc(Oc2ccc(NC(=O)Nc3ccc(Cl)c(C(F)(F)F)c3)cc2)ccn1]

Embodiment 39. The method of one of embodiments 31 to 32, wherein the monovalent kinase inhibitor is a monovalent EGFR inhibitor.

Embodiment 40. The method of embodiment 39, wherein the monovalent EGFR inhibitor is a monovalent lapatinib, monovalent lapatinib derivative, monovalent erlotinib, monovalent erlotinib derivative, monovalent gefitinib, or monovalent gefitinib derivative.

Embodiment 41. The method of embodiment 40, wherein the monovalent EGFR inhibitor has the formula:

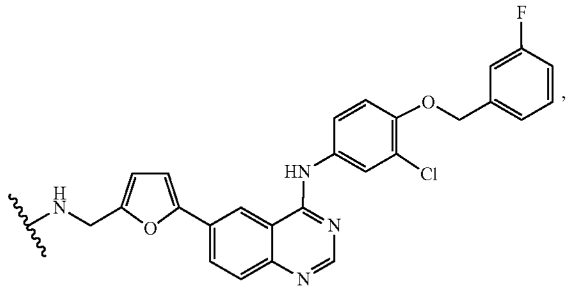

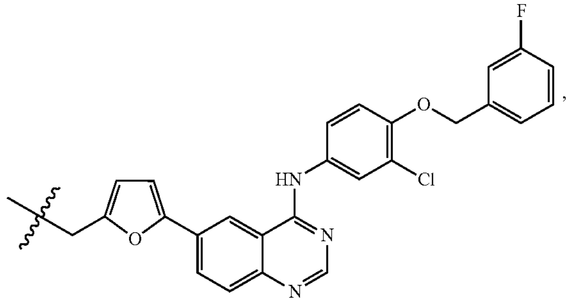

-continued

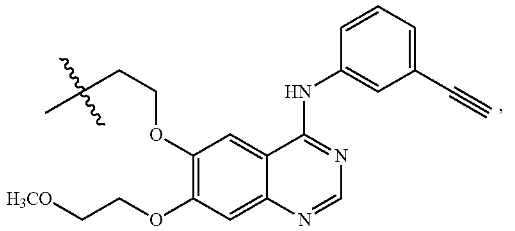

or

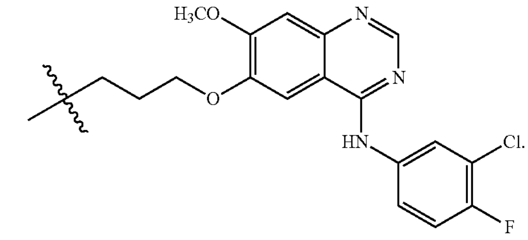

Embodiment 42. The method of one of embodiments 31 to 32, wherein the monovalent kinase inhibitor is a monovalent LRRK2 inhibitor.

Embodiment 43. The method of embodiment 42, wherein the monovalent LRRK2 inhibitor is a monovalent GNE-7915 or monovalent GNE-7915 derivative.

Embodiment 44. The method of embodiment 43, wherein the monovalent GNE-7915 derivative has the formula:

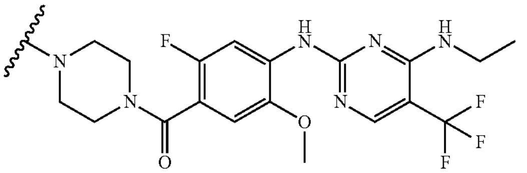

or

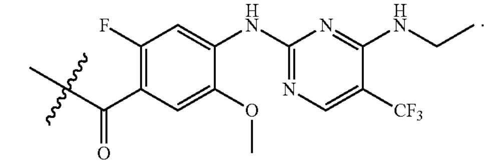

Embodiment 45. The method of one of embodiments 19 to 30, wherein $R^1$ is a monovalent KRAS inhibitor.

Embodiment 46. The method of embodiment 45, wherein the monovalent KRAS inhibitor is a monovalent KRAS G12C inhibitor or a monovalent KRAS M72C inhibitor.

Embodiment 47. The method of embodiment 26, wherein the monovalent KRAS inhibitor has the formula:

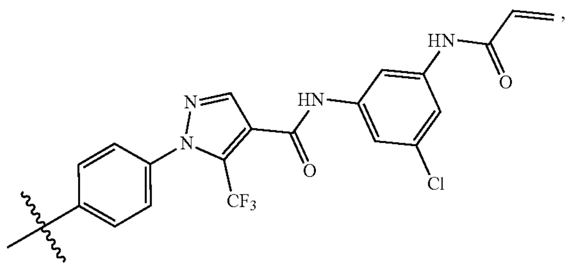

-continued

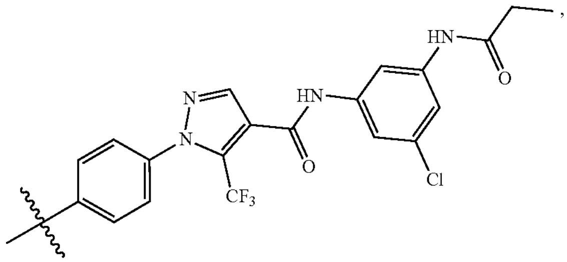

,

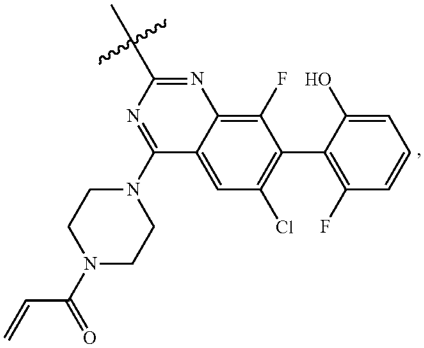

, or

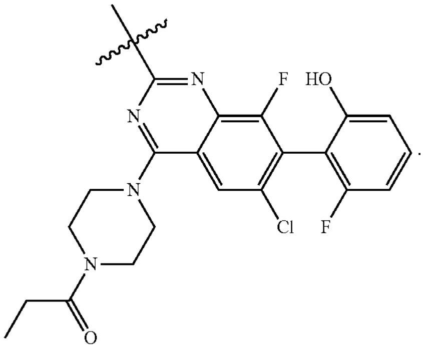

.

Embodiment 48. The method of one of embodiments 19 to 30, wherein $R^1$ is a monovalent MAP4K inhibitor.

Embodiment 49. The method of embodiment 48, wherein the monovalent MAP4K inhibitor is a monovalent HGK inhibitor.

Embodiment 50. The method of embodiment 49, wherein the monovalent HGK inhibitor has the formula:

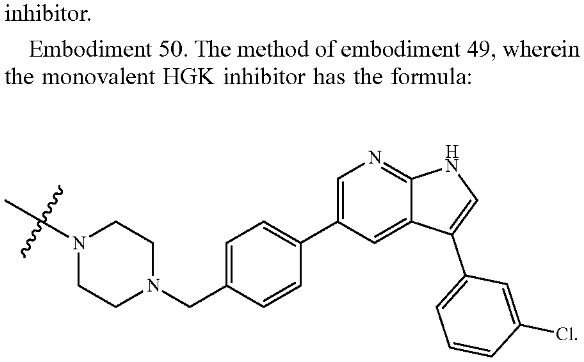

.

Embodiment 5L The method of one of embodiments 19 to 30, wherein $R^1$ is a monovalent MAP3K inhibitor.

Embodiment 52. The method of embodiment 51, wherein the monovalent MAP3K inhibitor is a monovalent DLK inhibitor.

Embodiment 53. The method of embodiment 52, wherein the monovalent HGK inhibitor has the formula:

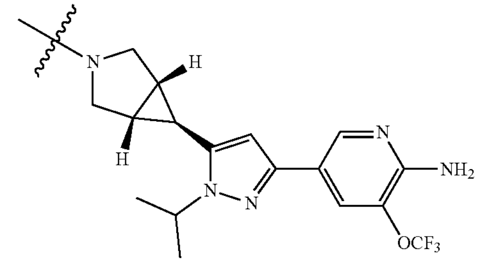

or

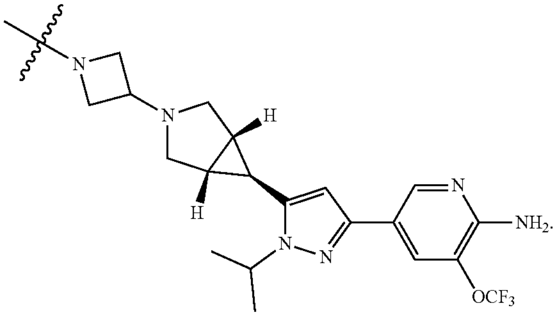

.

Embodiment 54. A compound having the formula:

$A^B$-$L^{B1}$-$R^{B1}$, or a pharmaceutically acceptable salt thereof;

wherein $A^B$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, $-CX^{B1}_3$, $-CHX^{B1}_2$, $-CH_2X^{B1}$, $-OCX^{B1}_3$, $-OCH_2X^{B1}$, $-OCHX^{B1}_2$, —CN, $-SO_{nB1}R^{B1D}$, $-SO_{vB1}NR^{B1A}R^{B1B}$, $-NHC(O)NR^{B1A}R^{B1B}$, $-N(O)_{mB1}$, $-NR^{B1A}R^{B1B}$, $-C(O)R^{B1C}$, $-C(O)OR^{B1C}$, $-C(O)NR^{B1A}R^{B1B}$, $-OR^{B1D}$, $-NR^{B1A}SO_2R^{B1D}$, $-NR^{B1A}C(O)R^{B1C}$, $-NR^{B1A}C(O)OR^{B1C}$, $-NR^{B1A}OR^{B1C}$, $-NR^{B1A}C(NR^{B1C})R^{B1D}$, $-NR^{B1A}C(NR^{B1C})NR^{B1A}R^{B1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHC(NH)H, $-NHC(NH)NH_2$, —NHOH, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2;

$X^{B1}$ is independently —F, —Cl, —Br, or —I;

when $L^{B1}$ is a bond, $R^{B1}$ is not H; and $A^B$ is not

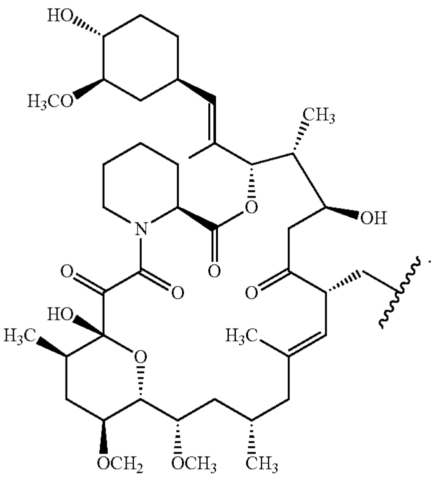

Embodiment 55. The compound of embodiment 54, wherein the immunophilin-binding moiety is

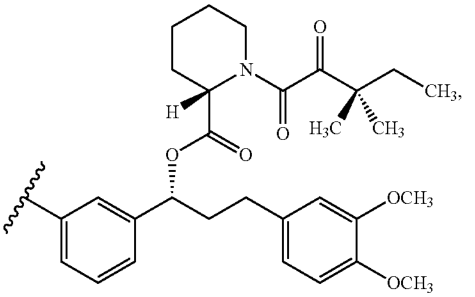

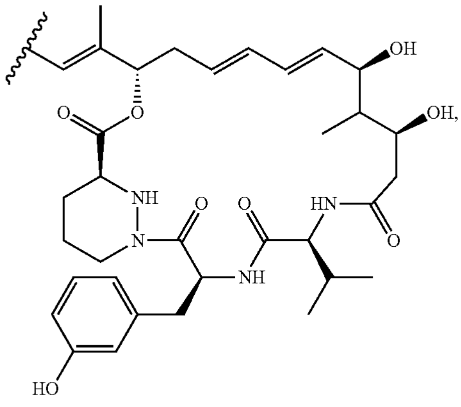

-continued

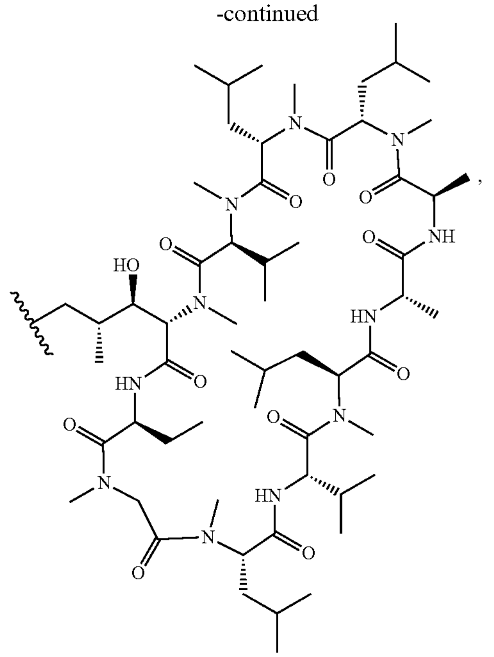

or

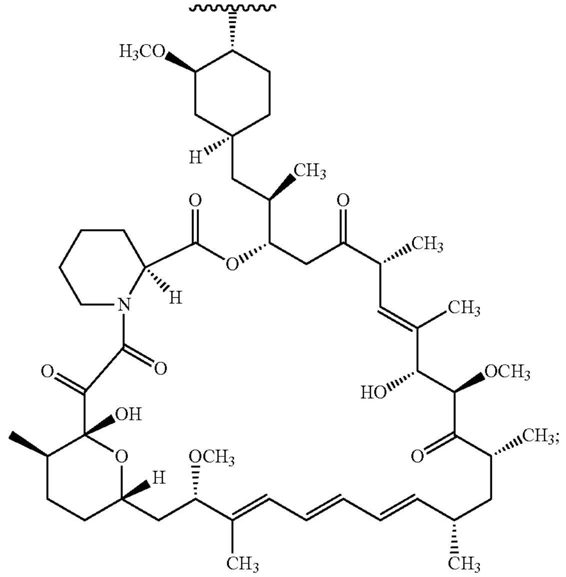 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or an analog thereof.

Embodiment 56. The compound of one of embodiments 54 to 55, wherein $L^{B1}$ is $L^{B2}$-$L^{B3}$-$L^{B4}$;

$L^{B2}$ is a bond, —S(O)$_2$—, —N($R^{B2}$)—, —O—, —S—, —C(O)—, —C(O)N($R^{B2}$)—, —N($R^{B2}$)C(O)—, —N($R^{B2}$)C(O)NH—, —NHC(O)N($R^{B2}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —S(O)$_2$—, —N($R^{B3}$)—, —O—, —S—, —C(O)—, —C(O)N($R^{B3}$)—, —N($R^{B3}$)C(O)—, —N($R^{B3}$)C(O)NH—, —NHC(O)N($R^{B3}$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 57. The compound of one of embodiments 54 to 56, wherein $L^{B1}$ is

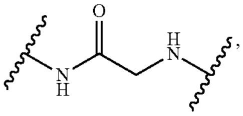,
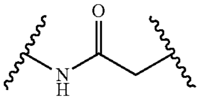,
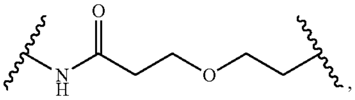,
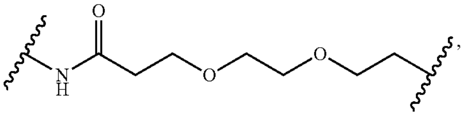,
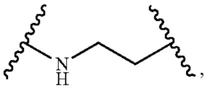,
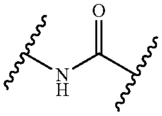,
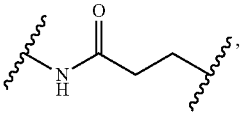,
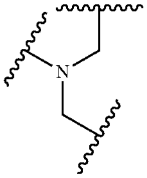,
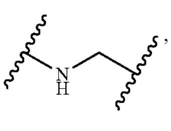,
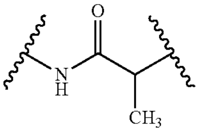,
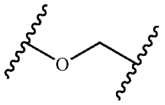,
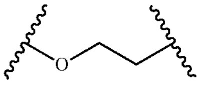,
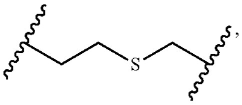,
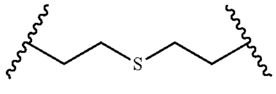, -continued

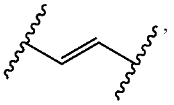,
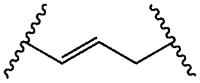,
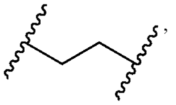,
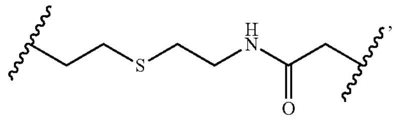,
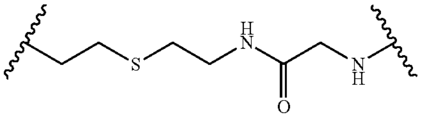,
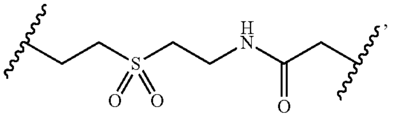, or
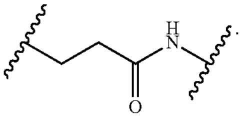.

Embodiment 58. The compound of one of embodiments 54 to 57, wherein $R^{B1}$ is halogen, —$NR^{B1A}R^{B1B}$, —$N_3$, —$SR^{B1D}$,

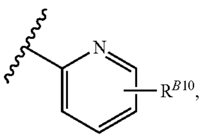,
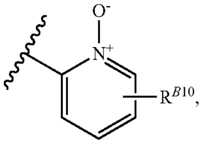,
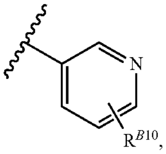,
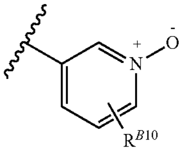,
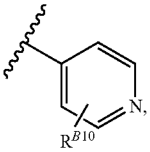,
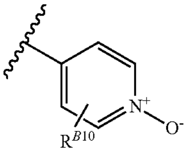,
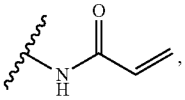,
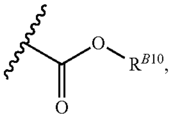,
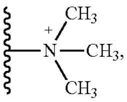,
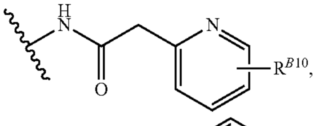,
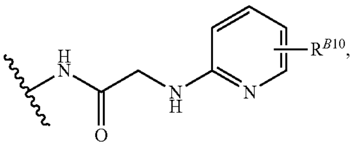,
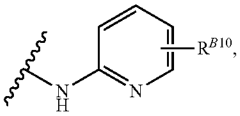,
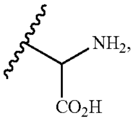

-continued

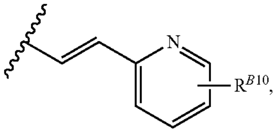
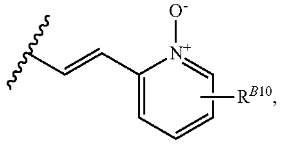
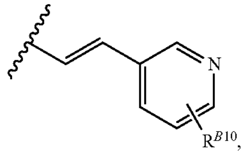
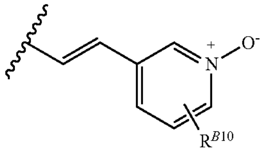
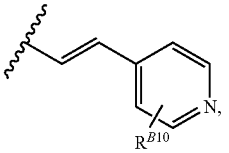
or
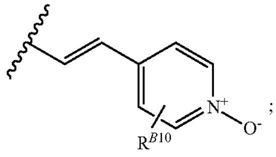
;

$R^{B10}$ is hydrogen, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—N(O)_{mB10}$, $—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—NR^{B10A}C(NR^{B10C})R^{B10D}$, $—NR^{B10A}C(NR^{B10C})NR^{B10A}R^{B10B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment 59. The compound of one of embodiments 54 to 58, wherein $R^{B1}$ is —Cl, $—NH_2$, $—N_3$, —SH,

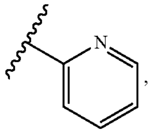
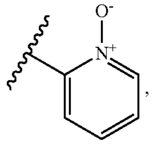
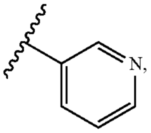
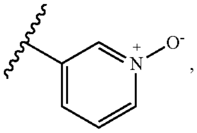
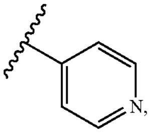
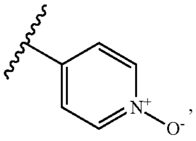
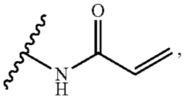
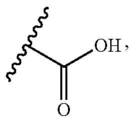
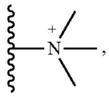
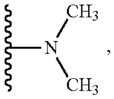
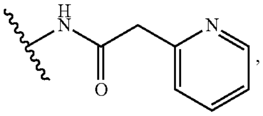

-continued

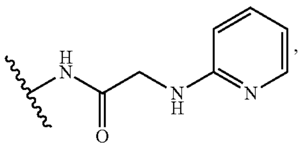
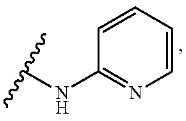
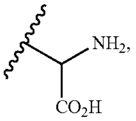
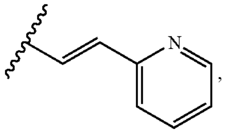
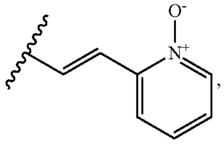
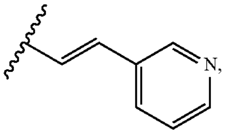
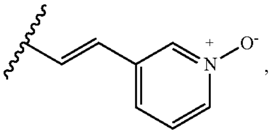
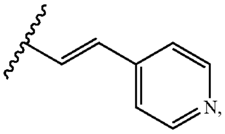
or
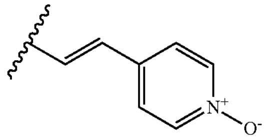

Embodiment 60. The compound of one of embodiments 54 to 59, wherein $L^{B1}$-$R^{B1}$ is

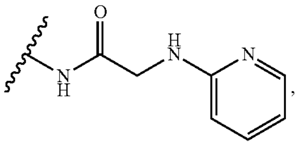
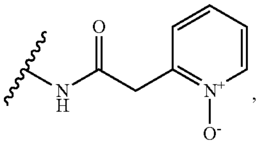
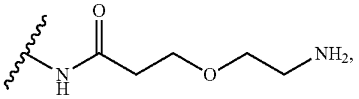
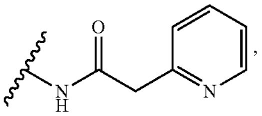
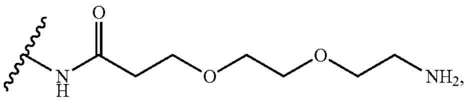
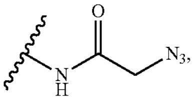
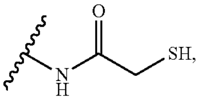
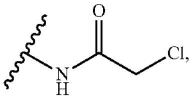
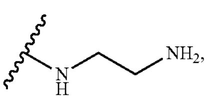
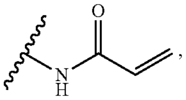
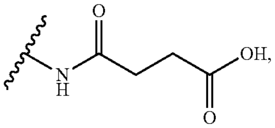

-continued
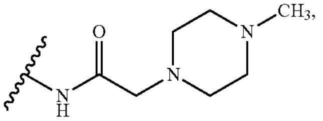
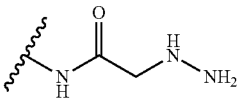
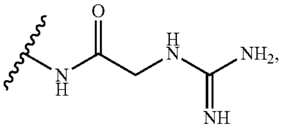
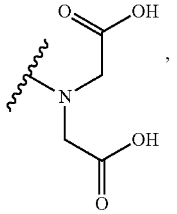
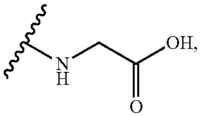
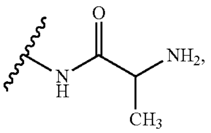
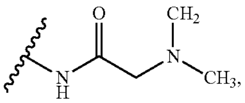
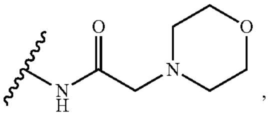
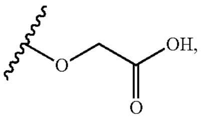
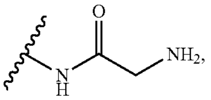
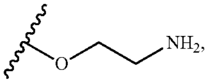
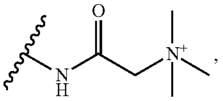
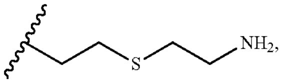
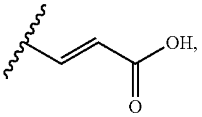
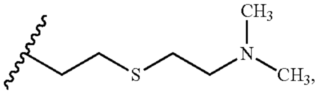
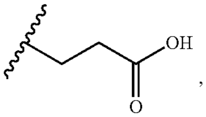
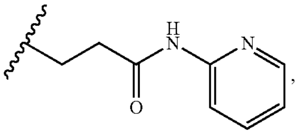
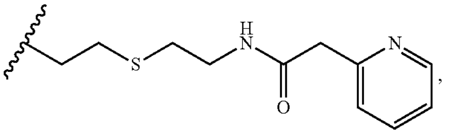
-continued
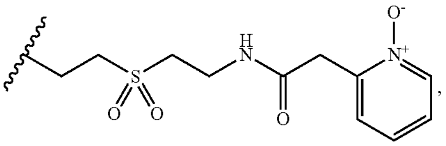
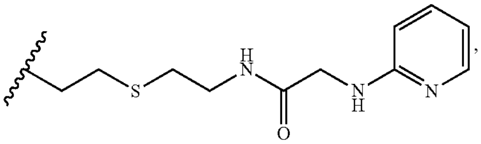
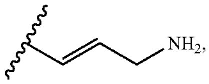
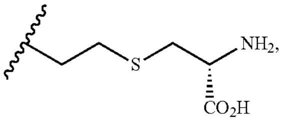
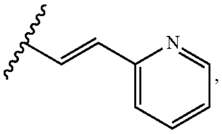
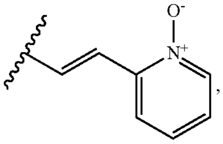
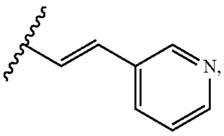
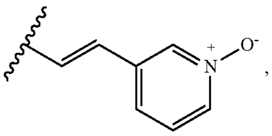
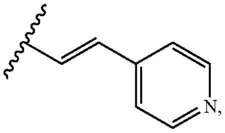
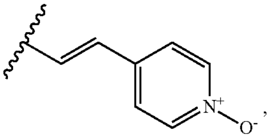
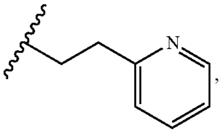
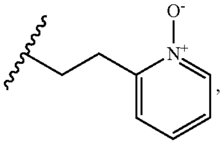
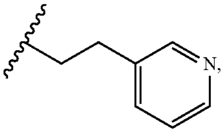
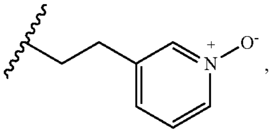
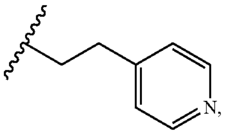
or
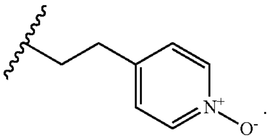
Embodiment 6L The compound of one of embodiments 54 to 60, wherein the compound is not

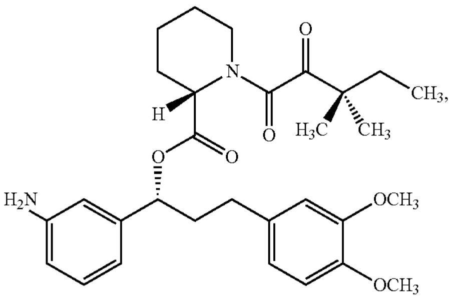
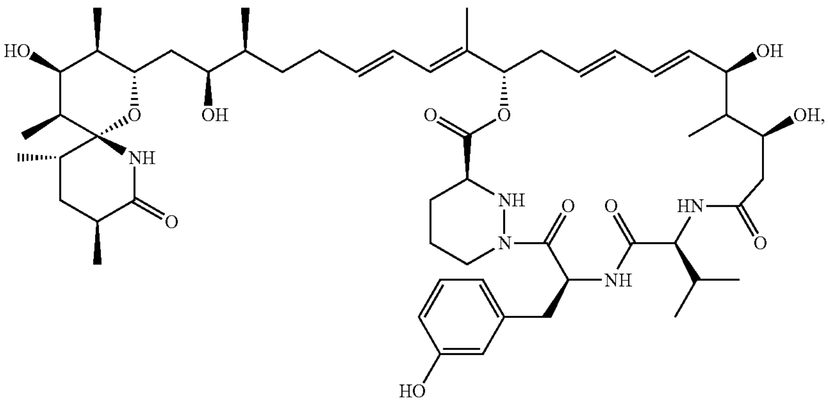
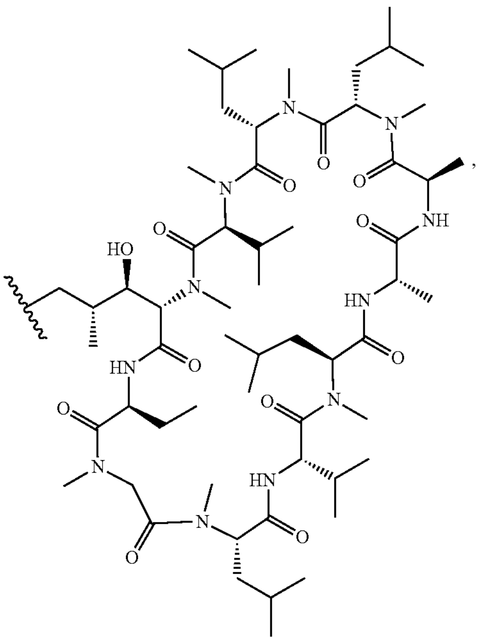
, or
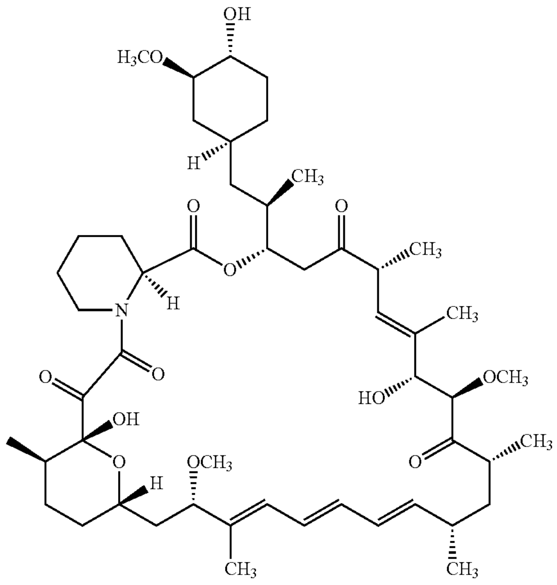
.

Embodiment 62. A compound having the formula:

$A^{B}$-$L^{B1}$-$R^{B1}$, or a pharmaceutically acceptable salt thereof;

wherein $A^{B}$ is an immunophilin-binding moiety having the formula

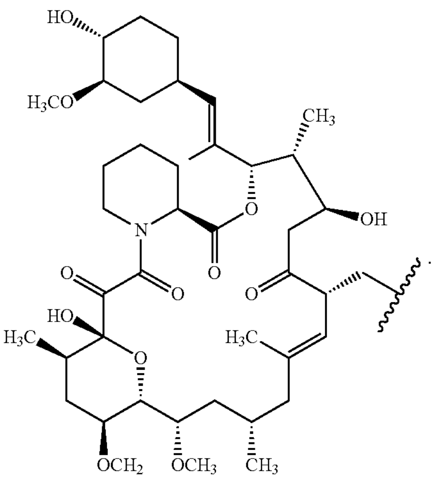

or an analog thereof;

$L^{B1}$-$R^{B1}$ is a polar moiety;

$L^{B1}$ is $L^{B2}$-$L^{B3}$-$L^{B4}$;

$L^{B2}$ is $S(O)_2$—, —$N(R^{B2})$—, —O—, —S—, —C(O)N($R^{B2}$)—, —$N(R^{B2})C(O)$—, —$N(R^{B2})C(O)NH$—, —$NHC(O)N(R^{B2})$—, —C(O)O—, —OC(O)—;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{B2}$, $R^{B3}$, and $R^{B4}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1}$ is hydrogen, halogen, —$CX^{B1}_3$, —$CHX^{B1}_2$, —$CH_2X^{B1}$, —$OCX^{B1}_3$, —$OCH_2X^{B1}$, —$OCHX^{B1}_2$, —CN, —$SO_{nB1}R^{B1D}$, —$SO_{vB1}NR^{B1A}R^{B1B}$, —$NHC(O)NR^{B1A}R^{B1B}$, —$N(O)_{mB1}$, —$NR^{B1A}R^{B1B}$, —$C(O)R^{B1C}$, —$C(O)OR^{B1C}$, —$C(O)NR^{B1A}R^{B1B}$, —$OR^{B1D}$, —$NR^{B1A}SO_2R^{B1D}$, —$NR^{B1A}C(O)R^{B1C}$, —$NR^{B1A}C(O)OR^{B15C}$, —$NR^{B1A}OR^{B1C}$, —$NR^{B1A}C(NR^{B1C})R^{B1D}$, —$NR^{B1A}C(NR^{B1C})NR^{B1A}R^{B1B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{B1A}$ and $R^{B1B}$ substituents bonded to the same nitrogen atom may be joined to form a substituted or unsubstituted heterocycloalkyl or substituted or unsubstituted heteroaryl;

nB1 is independently an integer from 0 to 4;

mB1 and vB1 are independently 1 or 2; and $X^{B1}$ is independently —F, —Cl, —Br, or —I.

Embodiment 63. The compound of embodiment 62, wherein $L^{B1}$ is

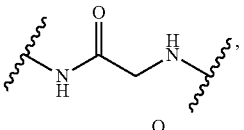,
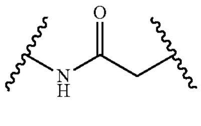,
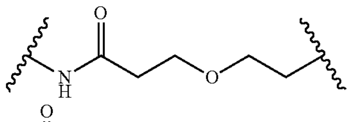,
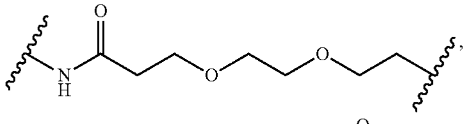,
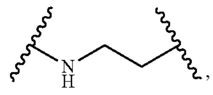,
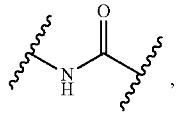,
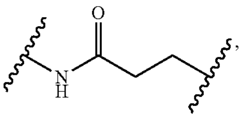,
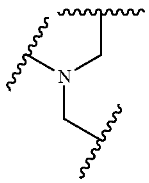, -continued

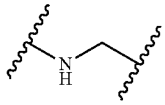, 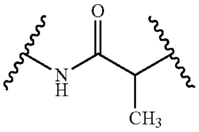,

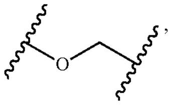, or 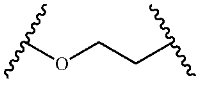.

Embodiment 64. The compound of one of embodiments 62 to 63, wherein R is halogen, $—NR^{B1A}R^{B1B}$, $—N_3$, $—SR^{B1D}$,

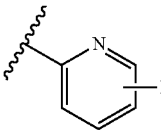, 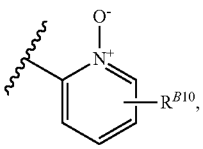,

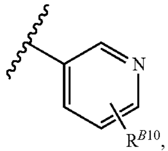, 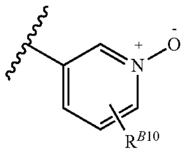,

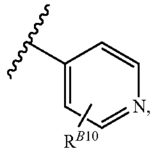, 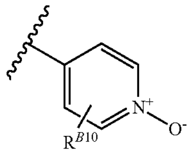,

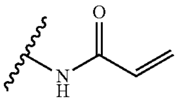, 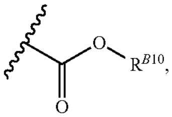, 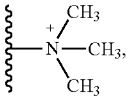

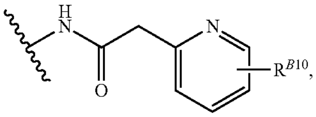

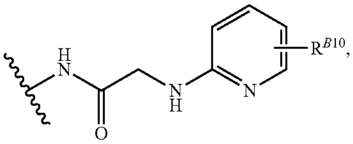

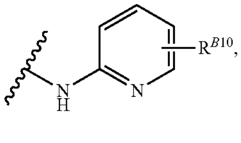, 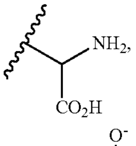

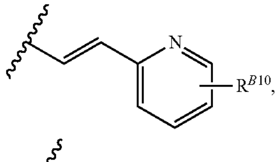, 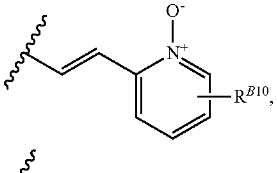,

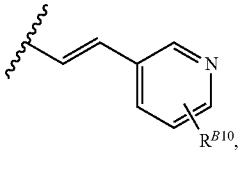, 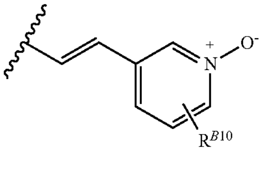,

-continued

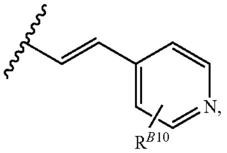 or 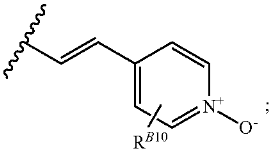;

$R^{B10}$ is hydrogen, halogen, $—CX^{B10}_3$, $—CHX^{B10}_2$, $—CH_2X^{B10}$, $—OCX^{B10}_3$, $—OCH_2X^{B10}$, $—OCHX^{B10}_2$, —CN, $—SO_{nB10}R^{B10D}$, $—SO_{vB10}NR^{B10A}R^{B10B}$, $—NHC(O)NR^{B10A}R^{B10B}$, $—N(O)_{mB10}$, $—NR^{B10A}R^{B10B}$, $—C(O)R^{B10C}$, $—C(O)OR^{B10C}$, $—C(O)NR^{B10A}R^{B10B}$, $—OR^{B10D}$, $—NR^{B10A}SO_2R^{B10D}$, $—NR^{B10A}C(O)R^{B10C}$, $—NR^{B10A}C(O)OR^{B10C}$, $—NR^{B10A}OR^{B10C}$, $—NR^{B10A}C(NR^{B10C})R^{B10D}$, $—NR^{B10A}C(NR^{B10C})NR^{B10A}R^{B10B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is independently an integer from 0 to 4;

mB10 and v10 are independently 1 or 2; and $X^{B10}$ is independently —F, —Cl, —Br, or —I.

Embodiment 65. The compound of one of embodiments 62 to 64, wherein $R^{B1}$ is —Cl, $—NH_2$, $—N_3$, —SH,

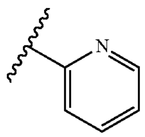, 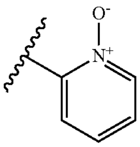,

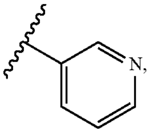 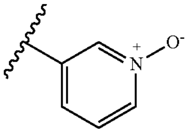,

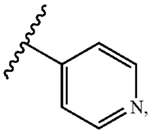 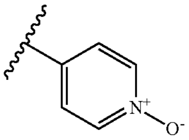,

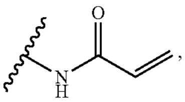, 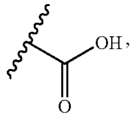

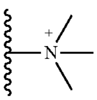, 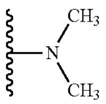, 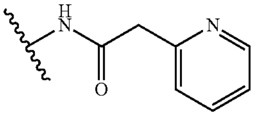,

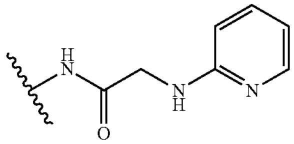, 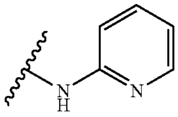,

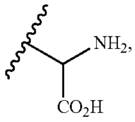

-continued

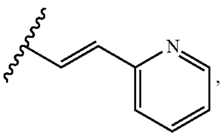, 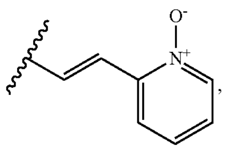,

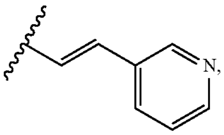 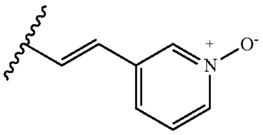,

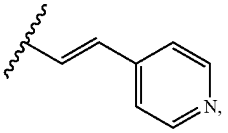 or 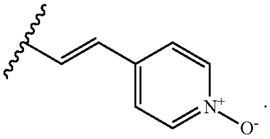.

Embodiment 66. The compound of one of embodiments 62 to 65, wherein $L^{B1}$-$R^{B1}$ is

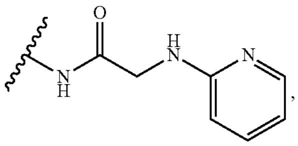, 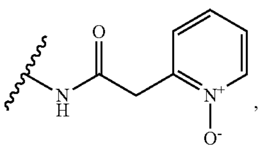,

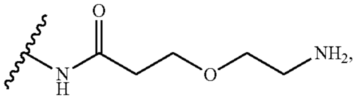

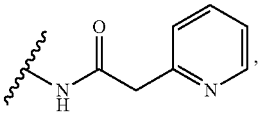

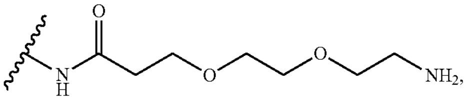

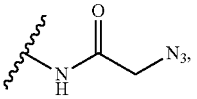 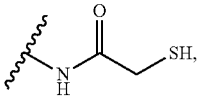

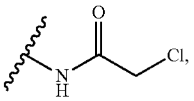 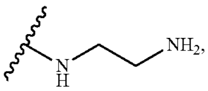

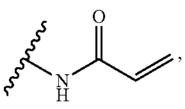, 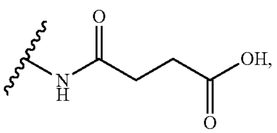

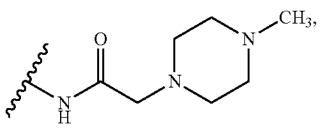

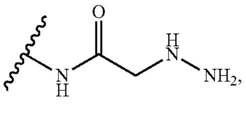 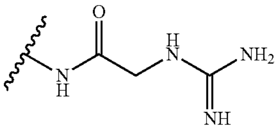,

-continued

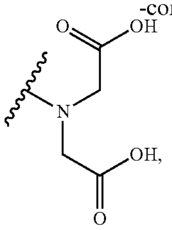 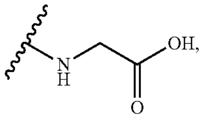

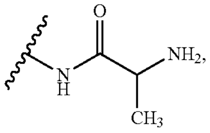 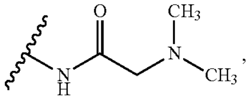,

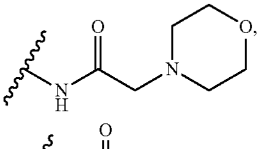 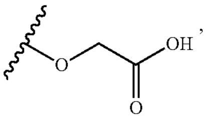,

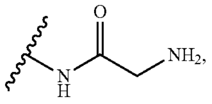 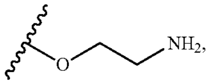 or

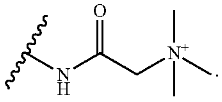

Embodiment 67. A compound having the formula:

$A^B$-$L^{B1}$-$R^{B1}$, or a pharmaceutically acceptable salt thereof;

wherein $A^B$ is an immunophilin-binding moiety having the formula

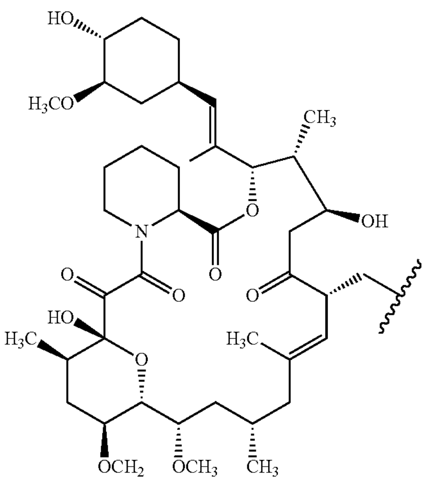, or an analog thereof;

$L^{B1}$-$R^{B1}$ is a polar moiety;

$L^{B1}$ is

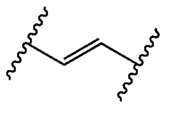 or 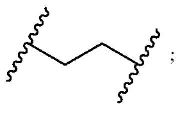;

and $R^{B1}$ is substituted or unsubstituted heteroaryl.

Embodiment 68. The compound of embodiment 67, wherein $R^{B1}$ is substituted or unsubstituted pyridyl.

Embodiment 69. A compound having the formula:

$A^B$-$L^{B1}$-$R^{B1}$, or a pharmaceutically acceptable salt thereof;

wherein $A^B$ is an immunophilin-binding moiety having the formula

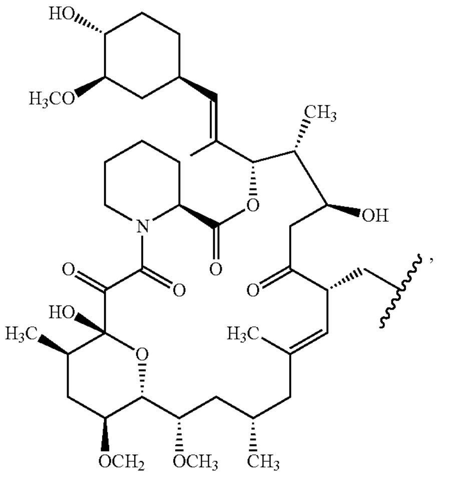

or an analog thereof;

$L^{B1}$-$R^{B1}$ is a polar moiety;

$L^{B1}$ is

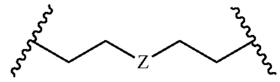

;

Z is —S— or —$SO_2$—;

$R^{B1}$ is —$NR^{B1A}R^{B1B}$ or —$NHC(O)CH_2R^{B1C}$;

$R^{B1A}$ and $R^{B1B}$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —NHC(NH)$NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{B1C}$ is substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 70. The compound of embodiment 69, wherein $R^{B1A}$, $R^{B1B}$, or $R^{B1C}$ are independently substituted or unsubstituted pyridyl.

Embodiment 71. The compound of one of embodiments 54 to 70, wherein the immunophilin-binding moiety is a cyclophilin-binding moiety or an FKBP-binding moiety.

Embodiment 72. A pharmaceutical composition comprising a pharmaceutically acceptable excipient and a compound of one of embodiments 54 to 71.

Embodiment 73. The pharmaceutical composition of embodiment 72, further comprising an anti-CNS disease drug.

EXAMPLES

Example 1: Brain-Specific Inhibition of mTOR to Mitigate Systemic Toxicity

We describe a novel method for inhibition of mTOR activity specific to the brain. mTOR is a protein kinase that plays a central role in regulating cell growth and proliferation, and is estimated to be overactivated in 30% of cancers. Therapeutic agents targeting mTOR have been widely pursued as potential therapies for cancer, as well as neurological disorders such as epilepsy. For example, a third-generation mTOR inhibitor, RapaLink-1, has been shown to be efficacious in driving glioblastoma regression in animal models (7). However, the success of these therapies is often hampered by insufficient amount of drug that can cross the blood-brain barrier. Even when this condition is met, the application of these drugs is confounded by the toxicity caused by system-wide inhibition of mTOR (e.g., immunosuppression, hyperglycemia, mucocytis in particular is a class specific effect of all mTOR inhibitors). Our disclosure provides a distinct solution to this problem through the combination of 1) a brain-permeable mTOR inhibitor and 2) a brain-impermeable ligand of another protein, FKBP (referred to as "blocker" hereafter). This "binary pharmacology" is enabled by the unique mechanism of action of RapaLink-1 and rapamycin that they require an auxiliary protein, FKBP, to exert its function. It represents a novel therapeutic modality to focus the pharmacological effects of RapaLink-1/rapamycin in the brain while minimizing systemic exposure.

Our invention is generally applicable in areas where brain-specific inhibition of mTOR can lead to a therapeutic advantage. A few examples include glioblastoma, epilepsy, tuberous sclerosis (TSC), and alcohol use disorders.

Glioblastoma is a particularly deadly type of cancer with poor prognosis, with more than 10,000 diagnoses each year in the US alone. Glioblastoma tumors are difficult to remove surgically and lack effective treatment options. Our invention may be directly applied to develop a new drug for the treatment of glioblastoma with high efficacy and low toxicity.

Epilepsy is the fourth most common neurological disorder—2015 statistics from the CDC show 1.2% of the US population (3.4 million) have active epilepsy. Despite the abundance of drugs approved for epilepsy, most current drugs are anticonvulsants and work by suppressing seizures as symptomatic therapy but do not address the rooting cause. One-third of patients do not respond to these drugs and are defined as "medically intractable." Treatment of epilepsy by mTOR inhibitors has shown promises as a new angle to tackle this disease.

Tuberous Sclerosis (TSC) affects as many as 25,000 to 40,000 individuals in the United States and about 1 to 2 million individuals worldwide, with an estimated prevalence of one in 6,000 newborns (according to NUT). It is a genetic disease that causes benign tumor to grow in the brain and results in seizures, behavioral problems, developmental delay, etc. mTOR inhibitors directly address the mechanistic cause of the disease (overactive mTOR), and everolimus (a rapamycin analog) has been approved as treatment for this disease. Our invention can be similarly adopted in this disease area to provide a safe and effective TSC drug.

Alcohol Use Disorder (AUD) affects approximately 15% of the world population and imposes significant medical and economical burdens. Recent research has shown the important role of mTOR signaling in the body's regulation of drinking behavior, and suggested pharmacological inhibition as a promising strategy to treat AUD. Our invention can be similarly adopted in this disease area to provide a safe and effective AUD drug.

TABLE 1 mTOR inhibition is an attractive strategy for treating many brain-related diseases (e.g., glioblastoma, epilepsy, tuberous sclerosis, alcohol addiction), yet systemic mTOR inhibition is known to cause multiple toxic side effects (e.g., hyperglycemia, immune suppression mucositis).

| Drug/ Candidate | Diphen-hydramine | GNE-7915 | GSK-2656157 | Rapamycin |
|---|---|---|---|---|
| Target | $H_1$ receptor | LRRK2 | PERK | mTOR |
| Application | Allergy | Parkinson's Disease | Parkinson's Disease | Glioblastoma, epilepsy, tuberous sclerosis, alcohol addiction |
| Adverse effects | CNS effects (drowsiness) | Lung toxicity | Pancreas toxicity | Hyperglycemia, immune suppression, mucositis |

Chronic mTOR inhibition and growth suppression in children. While mTOR inhibitors could be used in childhood diseases, this therapy has to be of limited duration, as chronic inhibition of mTOR is associated with growth failure (2,3). The fact that chronic use of mTOR inhibitors leads to short stature limits application of these agents in children who might need these agents chronically. Examples include children with tuberous sclerosis, neurofibromatosis, or similar disorders, where long-term delivery of mTOR inhibitors will likely increase IQ and behavior, but cannot be delivered chronically due to growth failure. Our ability to deliver mTOR inhibitors to the brain, while sparing exposure to the periphery, should allow use of these inhibitors chronically, in a broad range of developmental disorders in which chronic mTOR activation is associated with disease burden.

Unlike traditional methods that improve brain drug uptake by modifying the drug itself (e.g., increasing hydrophobicity, synthesizing prodrugs), our approach features a new therapeutic modality by the combination of a known brain-permeable mTOR inhibitor (RapaLink-1/rapamycin) with a brain-impermeable compound with no therapeutic effects itself. In doing so, we not only increase the distribution of the drug in the brain, but also eliminate its undesired effects in peripheral tissues. In addition, there is no need to change the nature of the "active component"—rapamycin is an approved drug and all the previously characterized molecular mechanism of actions will continue to apply.

Products developed with this technology will have augmented therapeutic effects in brain where the disease is but minimal systemic toxicity. Existing technologies (drugs) do not address this problem and system-wide mTOR inhibition is often associated with side effects.

Use of a combination of a brain-targeted drug and non-brain permeable auxiliary drug is precedented, but not to inhibit mTOR (Table 2).

TABLE 2

Known combinations of a blood-brain barrier (BBB)-permeable and a BBB-impermeable agent.

| Sinemet [Merck] (Levodopa + Carbidopa) | Duavee [Pfizer] (Estrone sulfate + Bazadoxifene) |
|---|---|
| Levodopa: BBB-permeable, precursor to dopamine (converted by dopamine decarboxylase) | Estrone sulfate: BBB-permeable, estrogen receptor agonist |
| Carbidopa: BBB-impermeable, dopamine decarboxylase inhibitor | Bazadoxifene: BBB-impermeable, estrogen receptor modulator |

We have designed and synthesized several "blocker" molecules and shown that they can potently bind FKBP and thus render RapaLink-1 ineffective in cell culture. Four of these molecules have been tested in mice in combination with RapaLink-1; mice treated with these combination therapies showed augmented inhibition of mTOR in the brain (compared to RapaLink-1 alone) but no detectable change in mTOR signaling in peripheral tissues (skeletal muscle).

Example 2: Building a Focused, Non-BBB Permeable FKBP Ligand Library

A focused, non-BBB permeable FKBP ligand library was generated using the following workflow: (1) compound synthesis; (2) FKBP12 binding assay; (3) compound screen by western blot (S6-phosphorylation); and (4) in vivo brain/periphery distribution in mouse model.

TABLE 3

Compound structures of SLF-focused library.

ZZY01-025

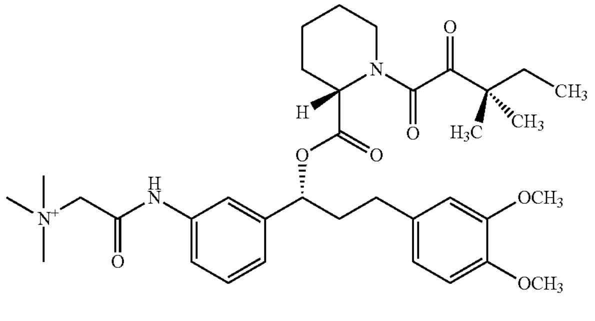

TABLE 3-continued
Compound structures of SLF-focused library.
ZZY01-038
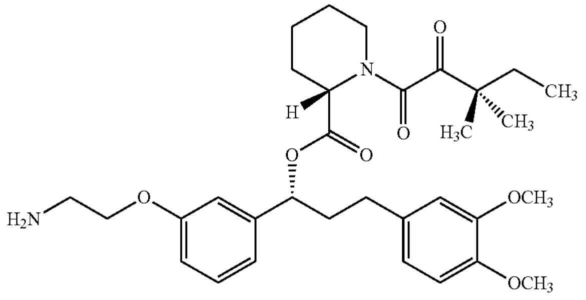
ZZY01-040
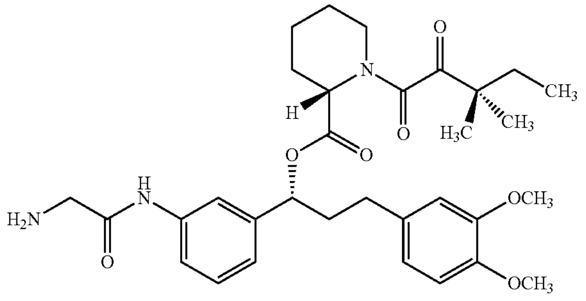
ZZY01-041
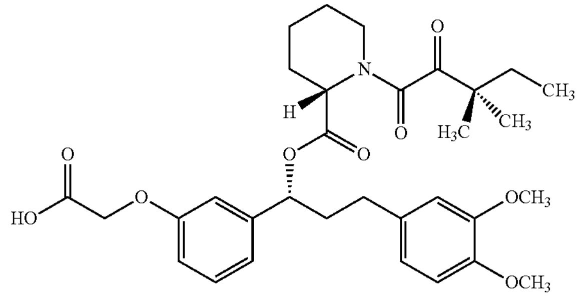
ZZY01-043
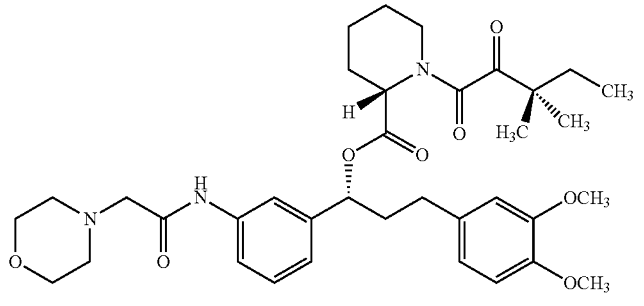
ZZY01-044
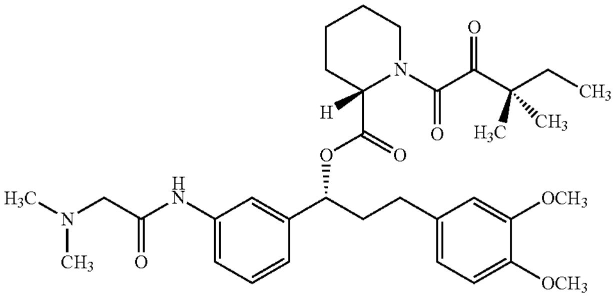

TABLE 3-continued
| Compound structures of SLF-focused library. |
| --- |
| ZZY01-059 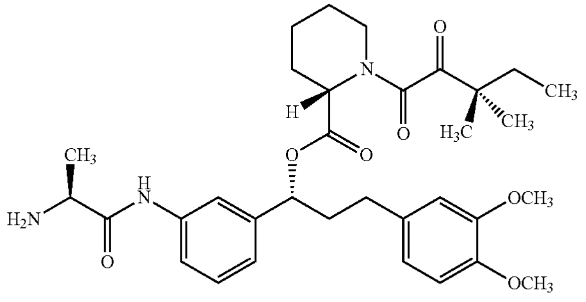 |
| ZZY01-060A 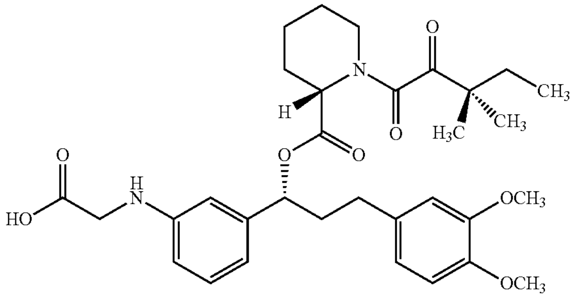 |
| ZZY01-060B 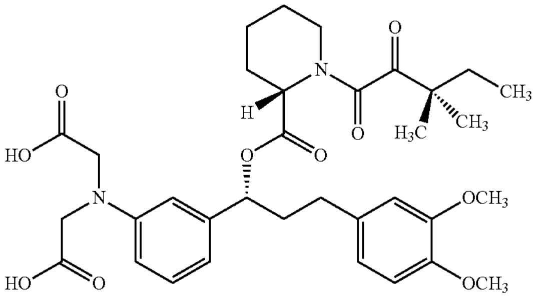 |
| ZZY01-065 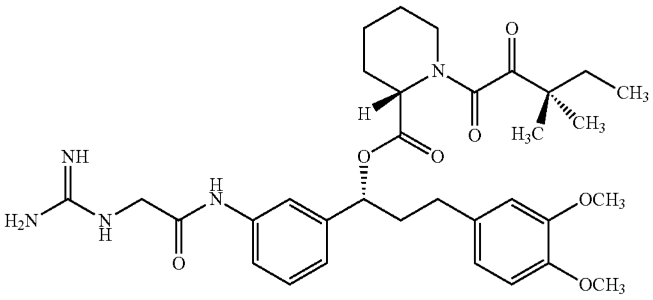 |
| ZZY01-070 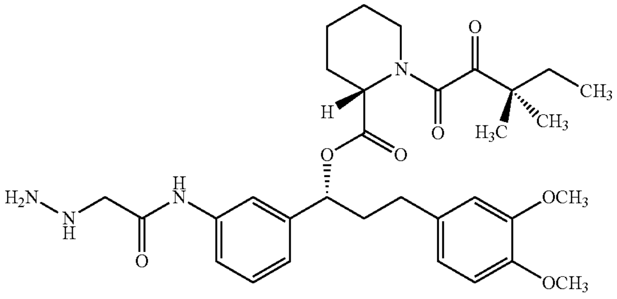 |

TABLE 3-continued
| Compound structures of SLF-focused library. |
| --- |
ZZY01-072
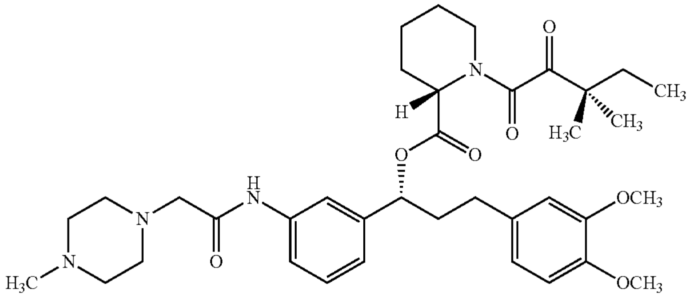
ZZY01-083
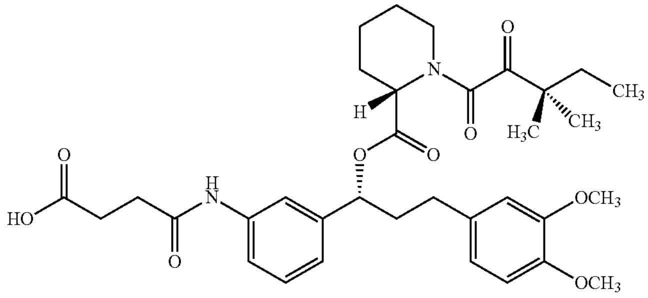
ZZY02-014
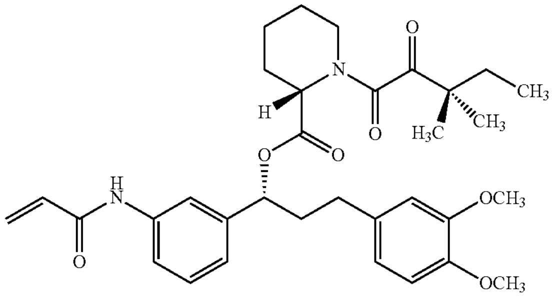
ZZY02-032
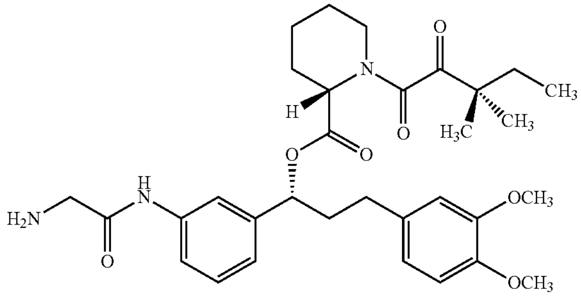
ZZY02-033
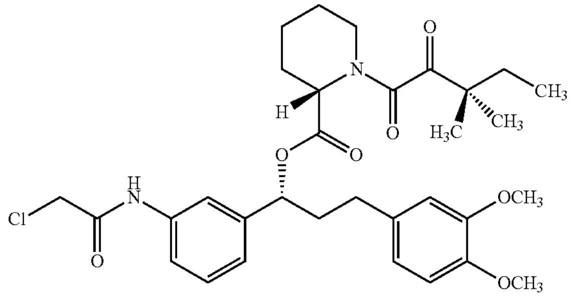

TABLE 3-continued
Compound structures of SLF-focused library.
ZZY02-055
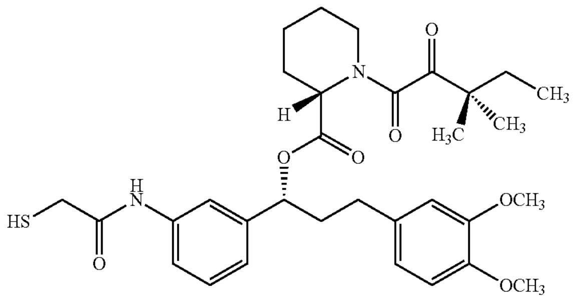
ZZY02-096
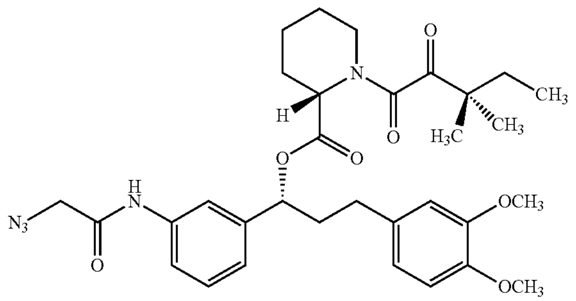
ZZY03-077
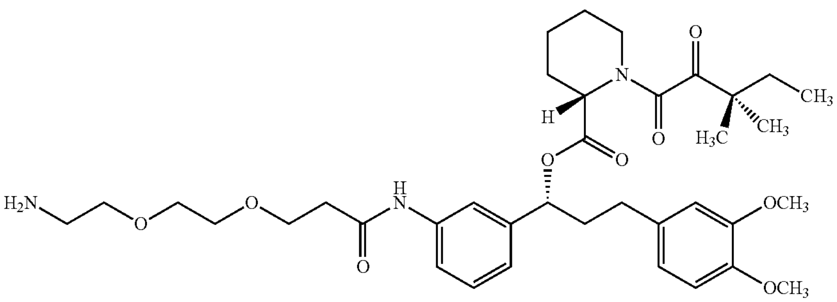
ZZY03-083
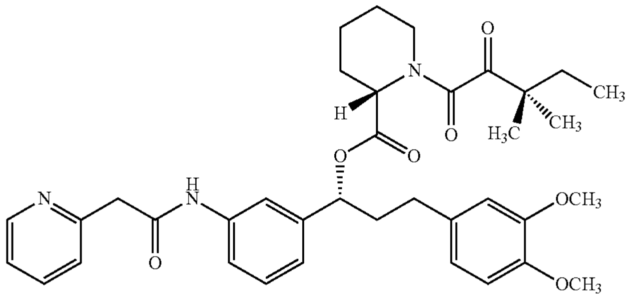
ZZY03-084
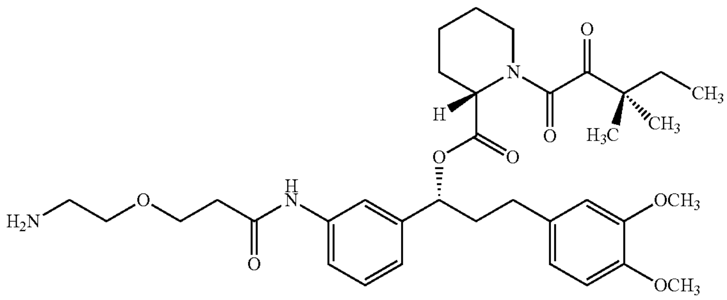

TABLE 3-continued
| Compound structures of SLF-focused library. |
| --- |
| ZZY03-087 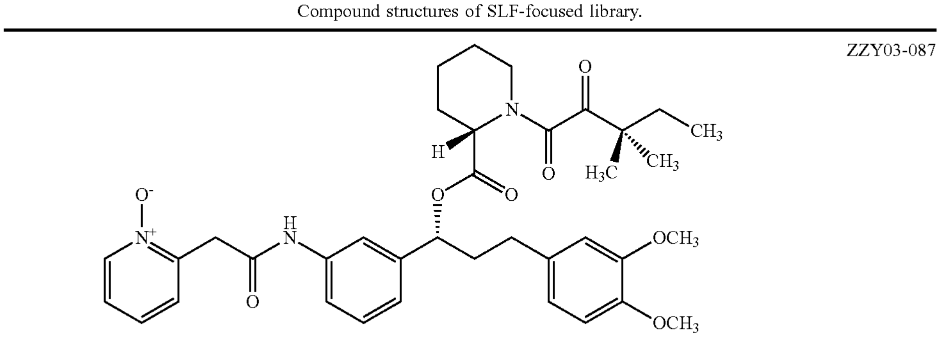 |
| ZZY03-091 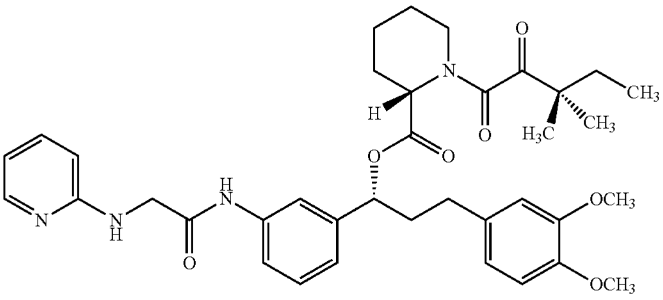 |
TABLE 4
| Compound structures of FK506-focused library. |
| --- |
| ZZY05-011 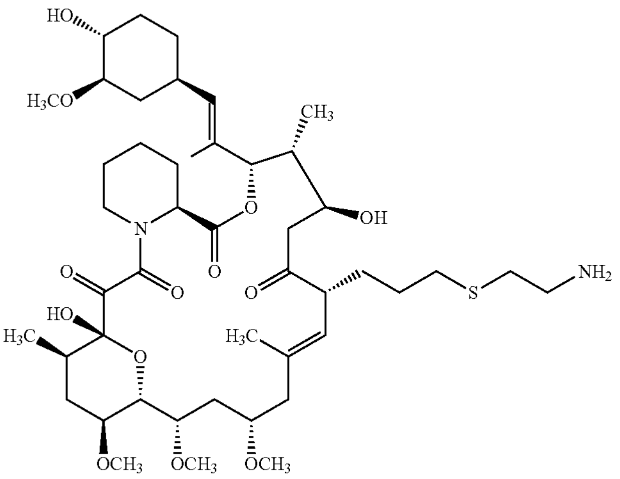 [SMILES: CO[C@H]1C/C(C)=C/[C@@H](CCCSCCN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |

TABLE 4-continued
| Compound structures of FK506-focused library. | |
| --- | --- |
| 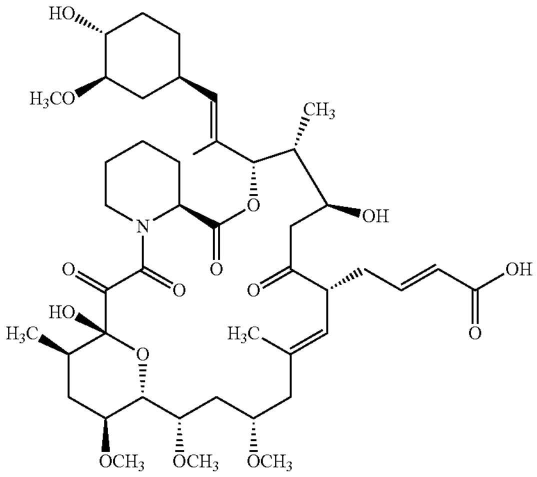 [SMILES: CO[C@H]1C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | ZZY05-012 |
| 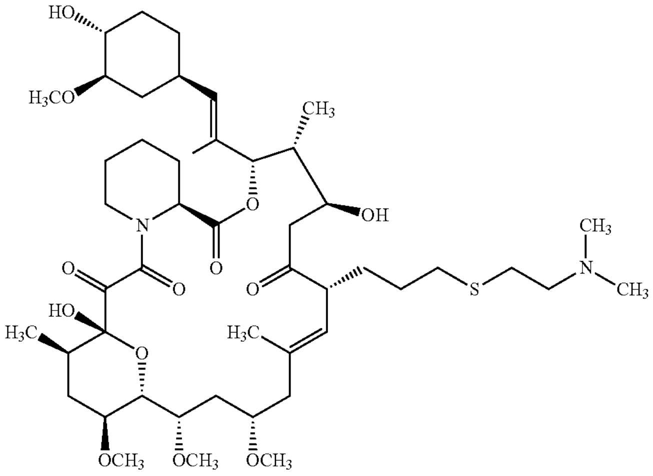 | ZZY05-013 |
| 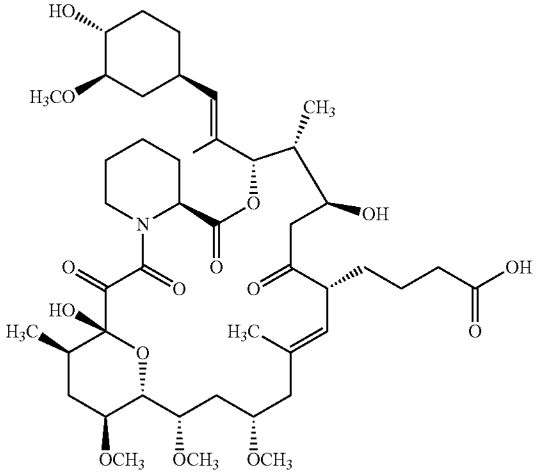 [SMILES: CO[C@H]1C/C(C)=C/[C@@H](CCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | ZZY05-020 |

TABLE 4-continued
| Compound structures of FK506-focused library. |
| --- |
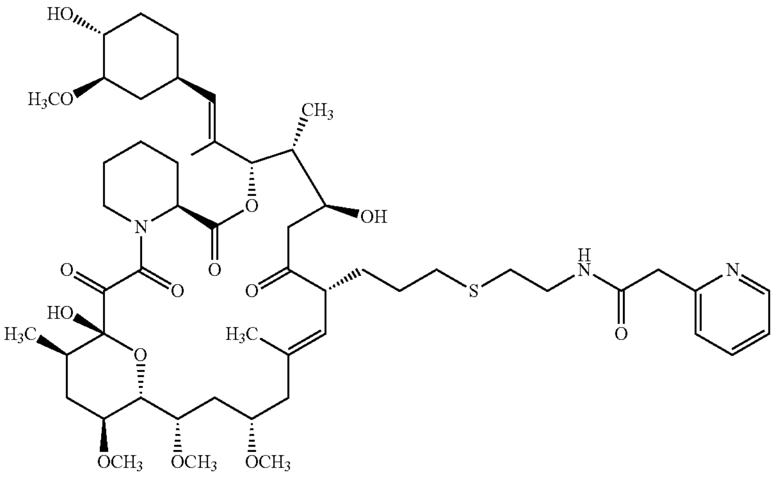 [SMILES: CO[C@H]1C/C(C)=C/[C@@H](CCCSCCNC(=O)Cc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-026
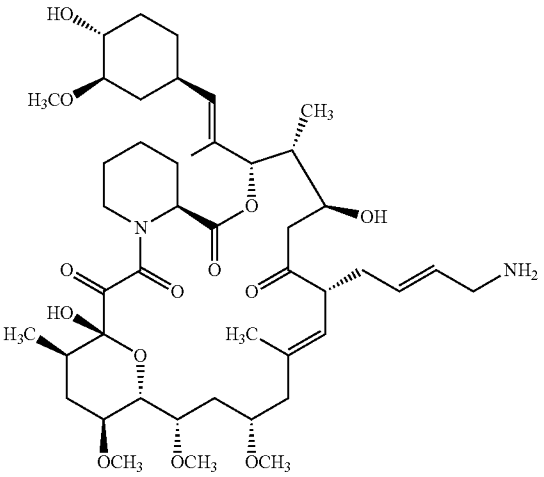 [SMILES: CO[C@H]1C/C(C)=C/[C@@H](C/C=C/CN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-027
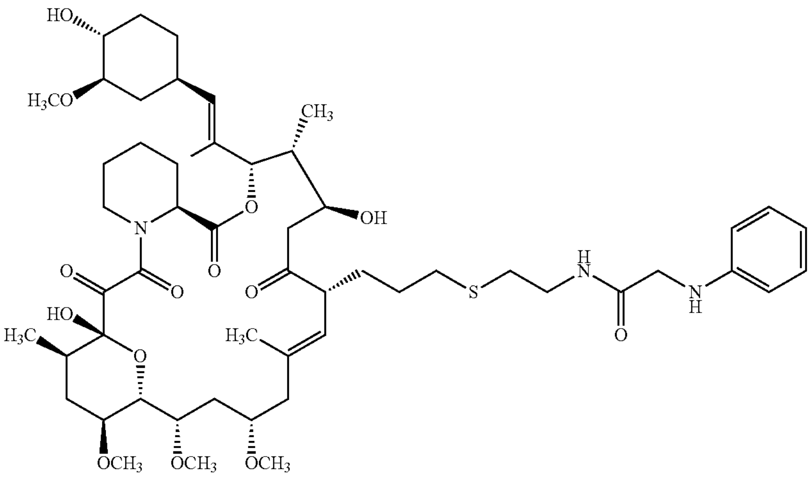 [SMILES: CO[C@H]1C/C(C)=C/[C@@H](CCCSCCNC(=O)CNc2ccccc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-028

TABLE 4-continued
| Compound structures of FK506-focused library. | |
|---|---|
| 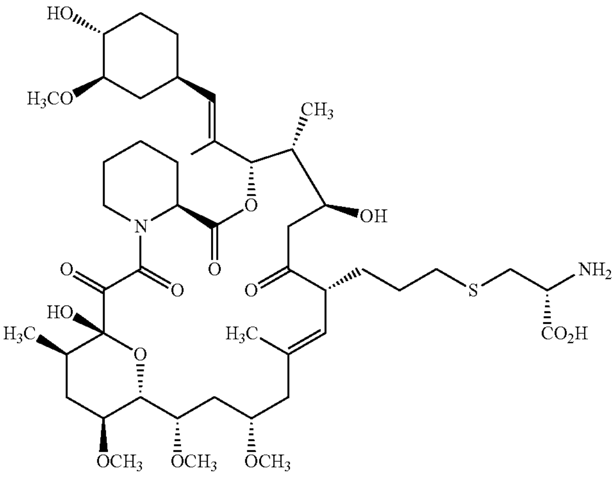 [SMILES: CO[C@H]1C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | ZZY05-037 |
| 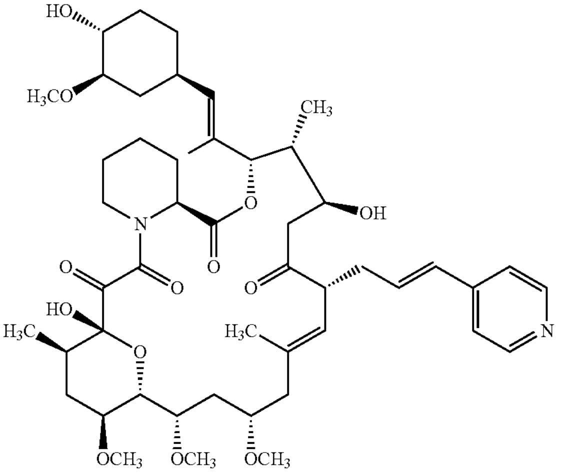 [SMILES: CO[C@H]1C/C(C)=C/[C@@H](C/C=C/c2ccncc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | ZZY05-050 |
| 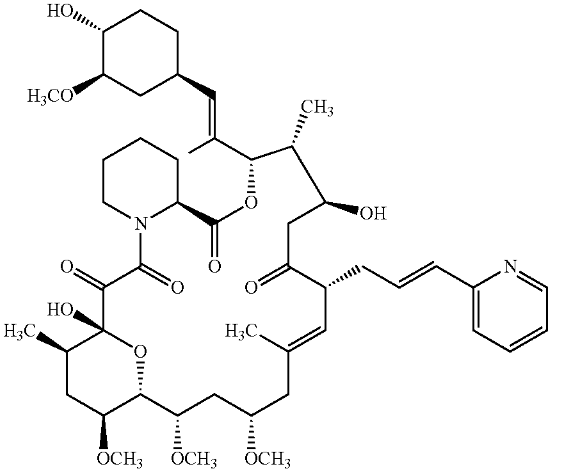 [SMILES: CO[C@H]1C/C(C)=C/[C@@H](C/C=C/c2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | ZZY05-051 |

TABLE 4-continued
| Compound structures of FK506-focused library. |
|---|
| 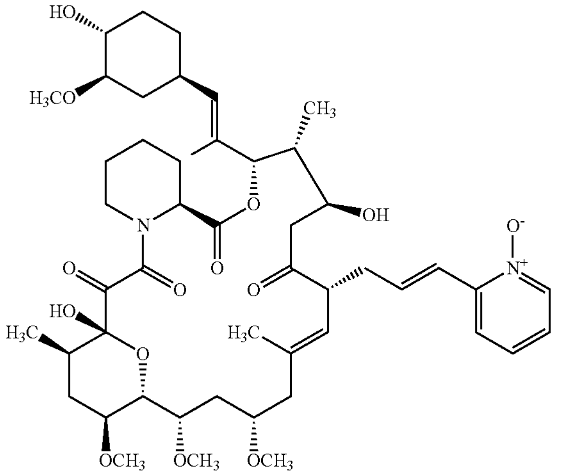 [SMILES: CO[C@H]1C/C(C)=C/[C@@H](C/C=C/c2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] ZZY05-060 |
| 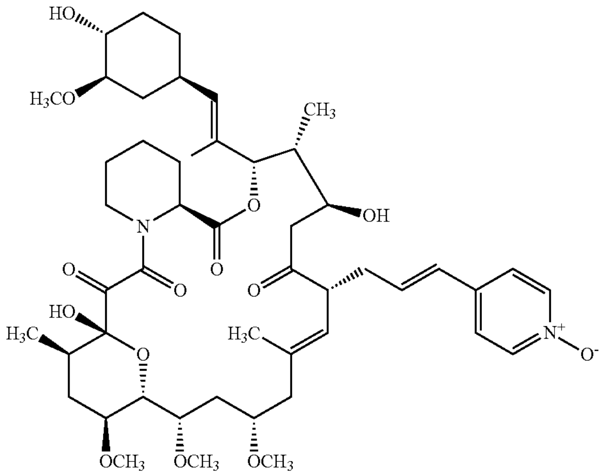 [SMILES: CO[C@H]1C/C(C)=C/[C@@H](C/C=C/c2cc[n+]([O-])cc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] ZZY05-061 |
| 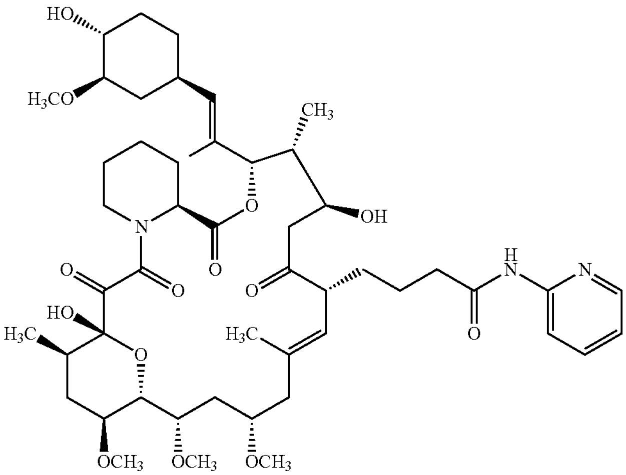 [SMILES: CO[C@H]1C/C(C)=C/[C@@H](CCCC(=O)Nc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] ZZY05-064 |

TABLE 4-continued
| Compound structures of FK506-focused library. |
| --- |
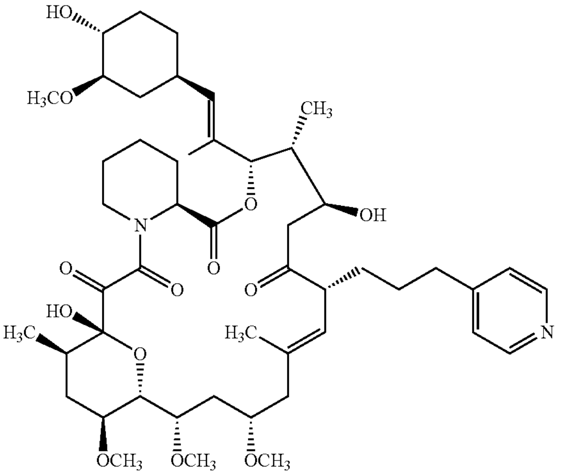 [SMILES: CO[C@H]1C/C(C)=C/[C@@H](CCCc2ccncc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-084/ZZY06-039
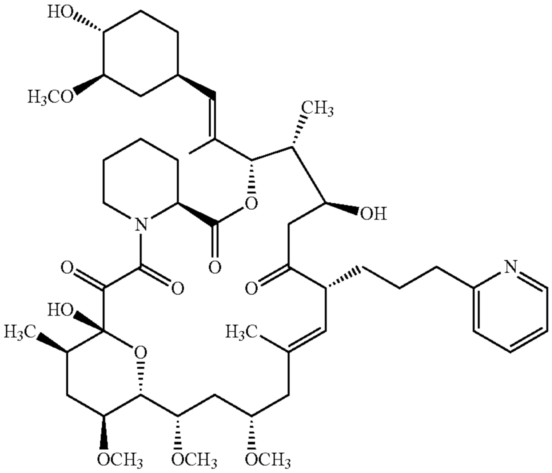 [SMILES: CO[C@H]1C/C(C)=C/[C@@H](CCCc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-085
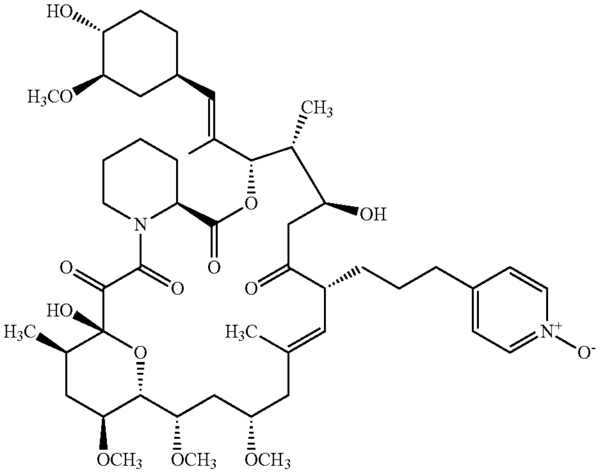 [SMILES: CO[C@H]1C/C(C)=C/[C@@H](CCCc2cc[n+]([O-])cc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C]
ZZY05-086

TABLE 4-continued

| Compound structures of FK506-focused library. | |
|---|---|
| 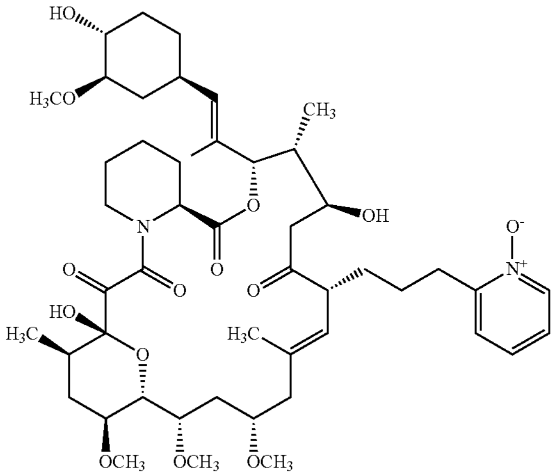 [SMILES: CO[C@H]1C/C(C)=C/[C@@H](CCCc2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | ZZY-05-092/ZZY06-041 |
| 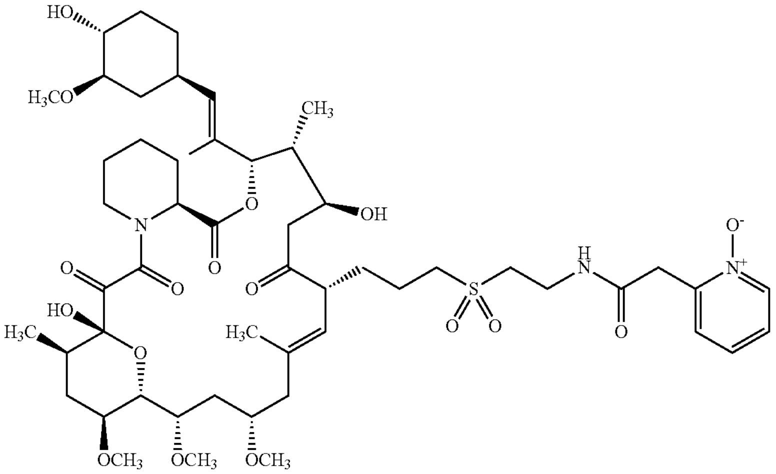 [SMILES: CO[C@H]1C/C(C)=C/[C@@H](CCCS(=O)(=O)CCNC(=O)Cc2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | ZZY05-094 |

Example 3: Biological Data

TABLE 5

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| SLF | 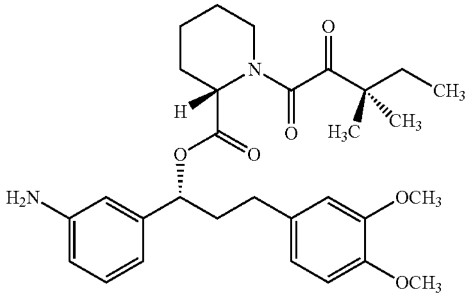 | 23 | 3 | 0 | | 4.71 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY01-025 | 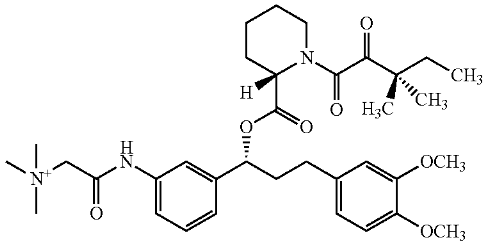 | 95 | 1 | ND | | 0.97 |
| ZZY01-038 | 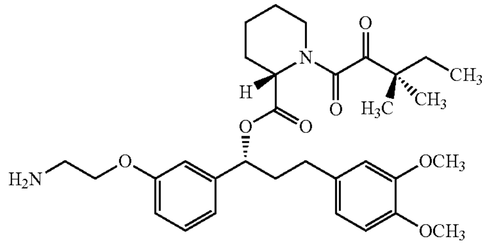 | 9.4 | 1 | ND | | 5.05 |
| ZZY01-040 | 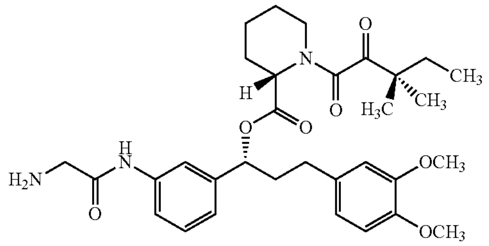 | 21.3 | 3 | ND | | 4.04 |
| ZZY01-041 | 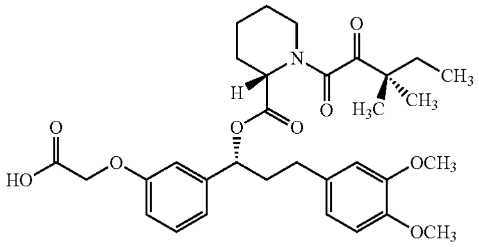 | 38 | 0 | ND | | 5.14 |
| ZZY01-043 | 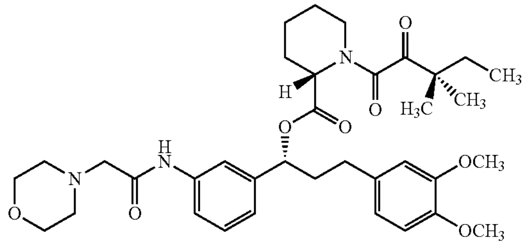 | 15 | 3 | ND | | 5.08 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY01-044 | 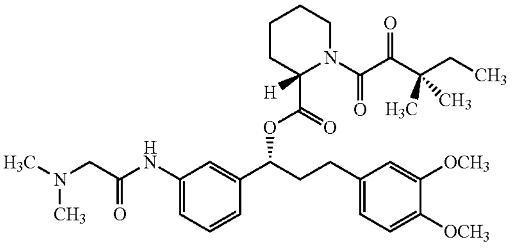 | 12.7 | 3 | ND | | 4.99 |
| ZZY01-059 | 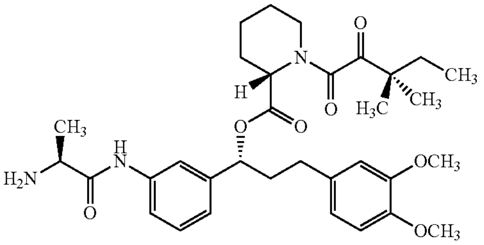 | 13.6 | 3 | ND | | 4.35 |
| ZZY01-060A | 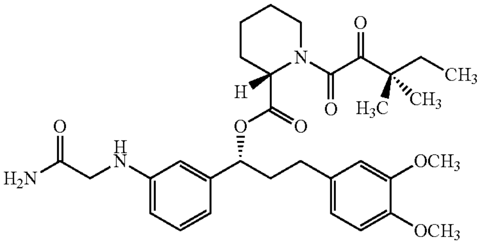 | 46.4 | 0 | ND | | 4.89 |
| ZZY01-060B | 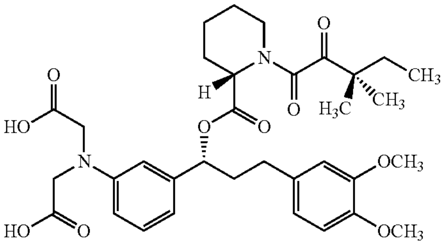 | 75.0 | 1 | ND | | 5.11 |
| ZZY01-065 | 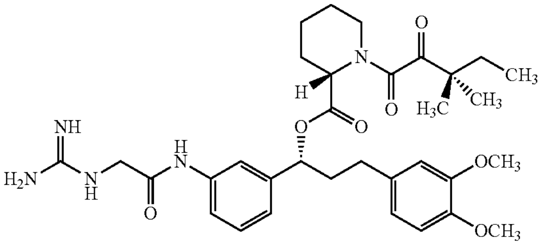 | 37.8 | 2 | ND | | 3.47 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY01-070 | 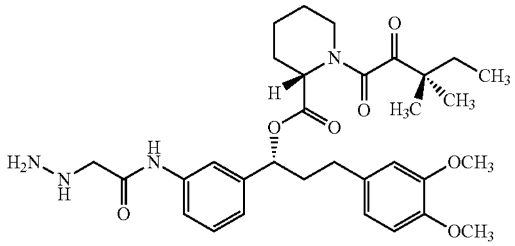 | 21.0 | 1 | ND | | 3.77 |
| ZZY01-072 | 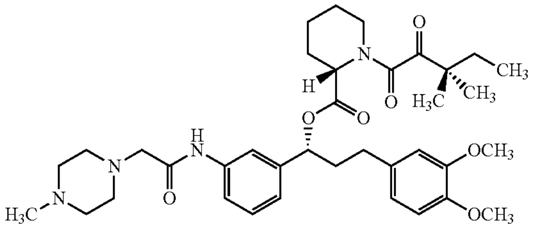 | 12.5 | 3 | ND | | 4.16 |
| ZZY01-083 | 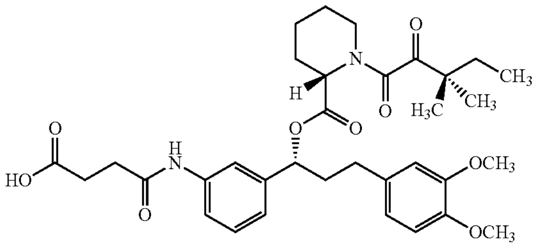 | 13.3 | 1 | ND | | 4.73 |
| ZZY02-014 | 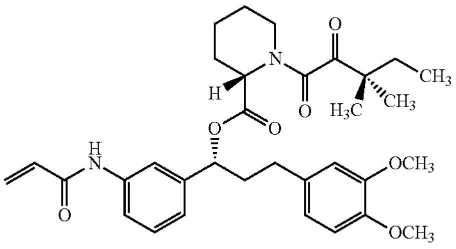 | 64.0 | 3 | ND | | 5.2 |
| ZZY02-032 | 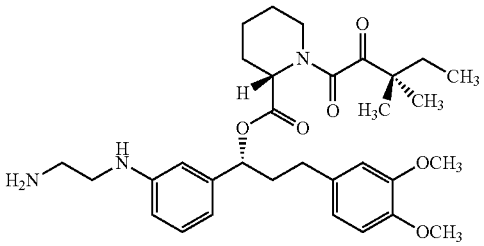 | 36.4 | 0 | ND | | 4.74 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
|---|---|---|---|---|---|---|
| ZZY02-033 | 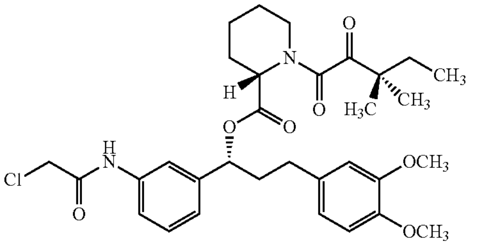 | 10.3 | 0 | ND | | 5.56 |
| ZZY02-055 | 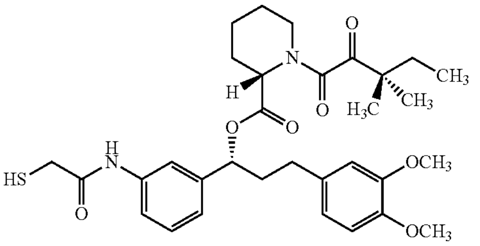 | 63.8 | 0 | ND | | 4.97 |
| ZZY02-096 | 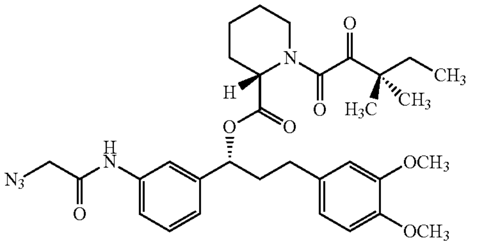 | 6.0 | 2 | ND | | 5.83 |
| ZZY03-077 | 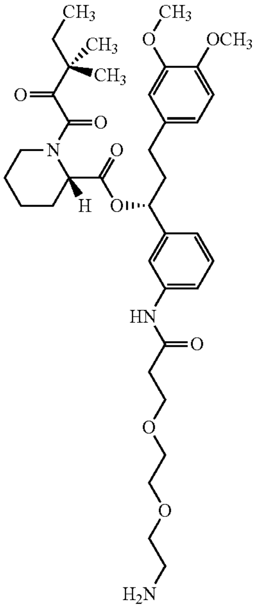 | 43.7 | 3 | ND | | 4.31 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
| --- | --- | --- | --- | --- | --- | --- |
| ZZY03-083 | 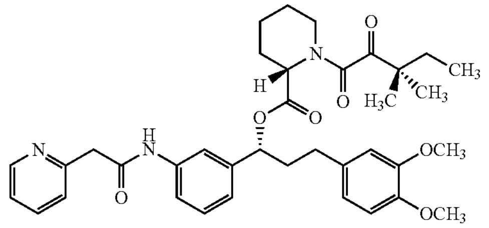 | 31.1 | 3 | 0 | | 4.99 |
| ZZY03-084 | 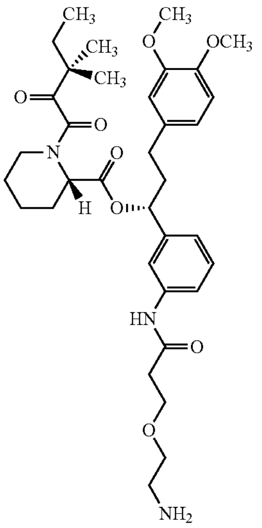 | 18.6 | 2 | ND | | 4.45 |
| ZZY03-087 | 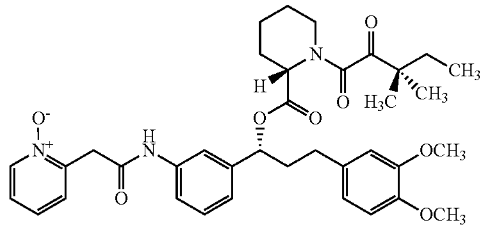 | 28.8 | 3 | 0 | Blocks rapamycin in muscle, potentiates rapamycin in brain | 3.11 |
| ZZY03-091 | 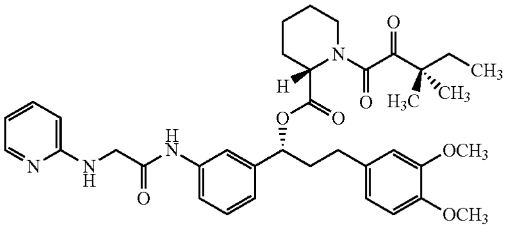 | 37.3 | 2 | ND | | 5.65 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
|---|---|---|---|---|---|---|
| FK506 | 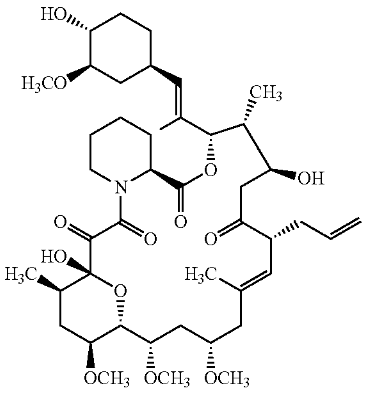 [SMILES: C=CC[C@@H]1/C=C(\C)C[C@H](OC)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC] | 0.8 | 3 | 3 | | 5.77 |
| ZZY05-011 | 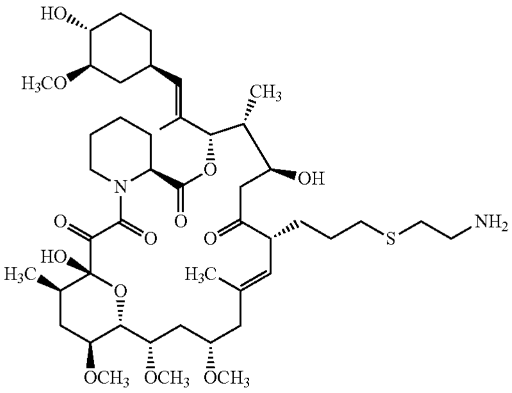 [SMILES: CO[C@H]1C/C(C)=C/[C@@H](CCCSCCN)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.69 | 3 | 3 | | 5.12 |
| ZZY05-012 | 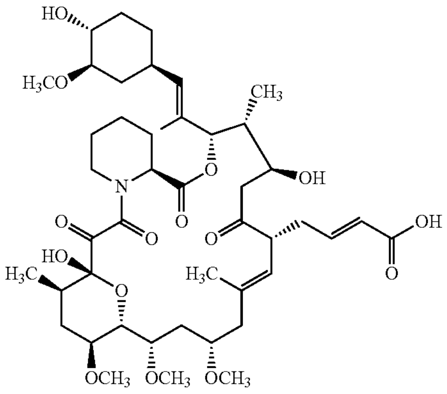 [SMILES: CO[C@H]1C/C(C)=C/[C@@H](C/C=C/C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.39 | 0 | 0 | | 4.86 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY05-013 | 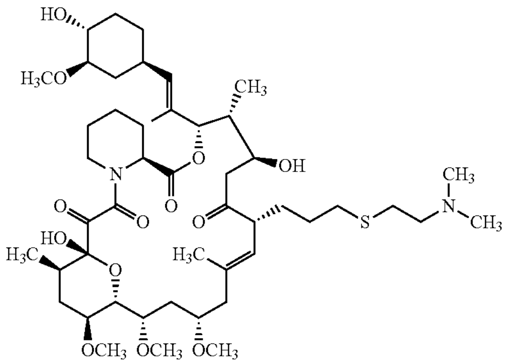 | 1.36 | 3 | 3 | | 6.02 |
| ZZY05-020 | 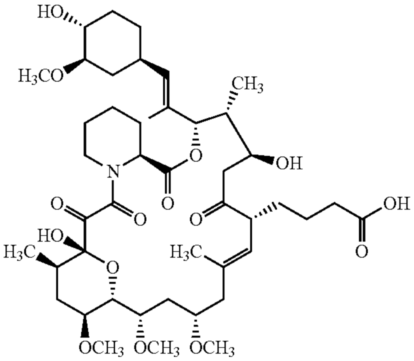 [SMILES: CO[C@H]1C/C(C)=C/[C@@H](CCCC(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 1.49 | 2 | 0 | | 4.84 |
| ZZY05-026 | 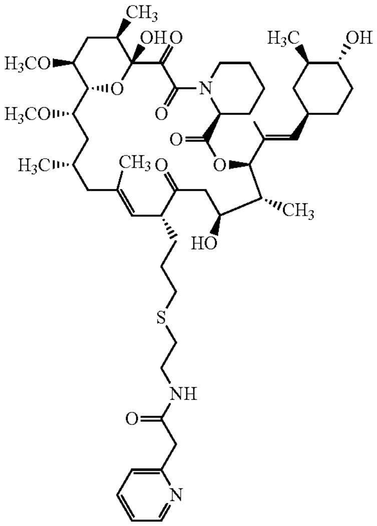 [SMILES: CO[C@H]1C[C@@H](C)C/C(C)=C/[C@@H](CCCSCCNC(=O)Cc2ccccn2)C(=O)C[C@H](O)[C@@H](C)[C@H](/C(C)=C/[C@@H]2CC[C@@H](O)[C@H](C)C2)OC(=O)[C@@H]2CCCCN2C(=O)C(=O)[C@]2(O)O[C@H]1[C@@H](OC)C[C@H]2C] | 3.7 | 3 | 3 | Dose: 1 mg/kg Rapalink-1 + 40 mg/kg ZZY05-026; Blocks Rapalink-1 in muscle, Potentiates RapaLink-1 in brain | 5.23 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
|---|---|---|---|---|---|---|
| ZZY05-028 | 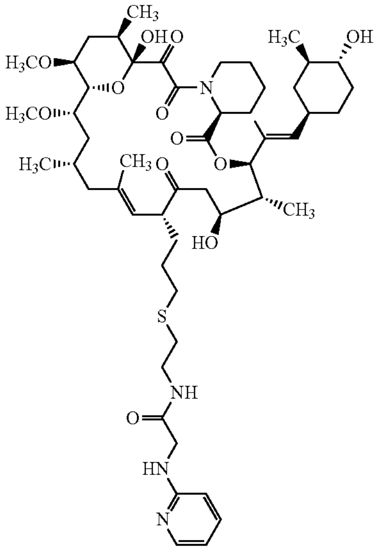 [SMILES: CO[C@H]1C[C@@H](C)C/C(C)=C/[C@@H](CCCSCCNC(=O)CNc2ccccn2)C(=O)C[C@H](O)[C@@H](C)[C@H](/C(C)=C/[C@@H]2CC[C@@H](O)[C@H](C)C2)OC(=O)[C@@H]2CCCCN2C(=O)C(=O)[C@]2(O)O[C@H]1[C@@H](OC)C[C@H]2C] | 2.5 | 3 | 3 | | 6.01 |
| ZZY05-037 | 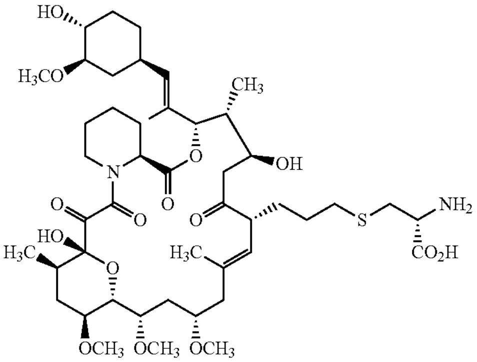 [SMILES: CO[C@H]1C/C(C)=C/[C@@H](CCCSC[C@H](N)C(=O)O)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 8.7 | ND | 1 | | 3.04 |
| ZZY05-050 | 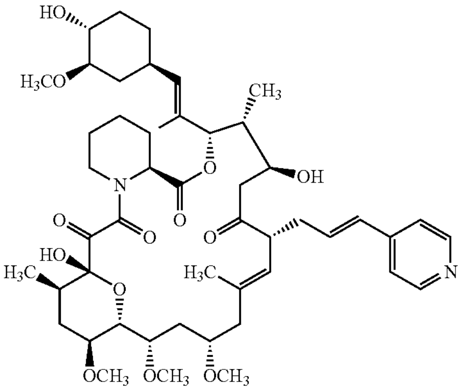 [SMILES: CO[C@H]1C/C(C)=C/[C@@H](C/C=C/c2ccncc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 3.6 | ND | 3 | | 5.87 |

TABLE 5-continued
RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.
| Compound | Structure | Kd FKBP12 (nM) | Rapamycin Blockade | RapaLink-1 Blockade | In Vivo | cLogP |
|---|---|---|---|---|---|---|
| ZZY05-051 | 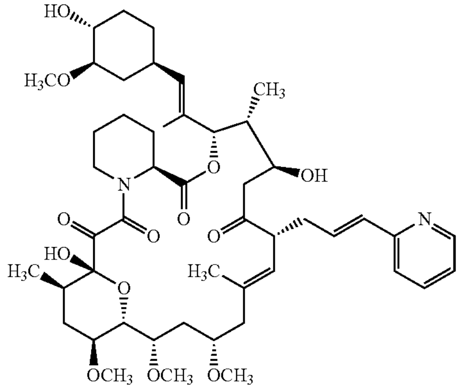 [SMILES: CO[C@H]1C/C(C)=C/[C@@H](C/C=C/c2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 1.2 | ND | 3 | | 5.87 |
| ZZY05-060 | 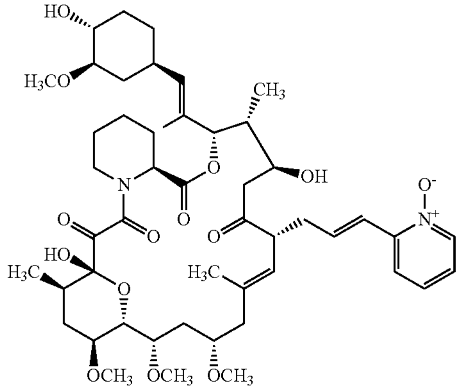 [SMILES: CO[C@H]1C/C(C)=C/[C@@H](C/C=C/c2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.62 | ND | 1 | | 4 |
| ZZY05-061 | 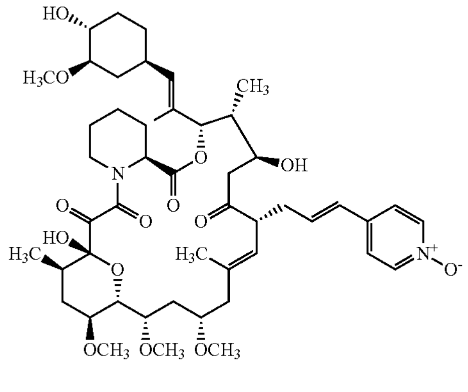 [SMILES: CO[C@H]1C/C(C)=C/[C@@H](C/C=C/c2cc[n+]([O-])cc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.21 | ND | 0 | | 4 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY05-064 | 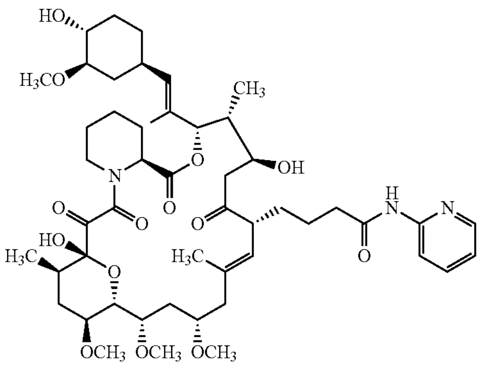 [SMILES: CO[C@H]1C/C(C)=C/[C@@H](CCCC(=O)Nc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 0.2 | ND | 3 | | 5.53 |
| ZZY05-085 | 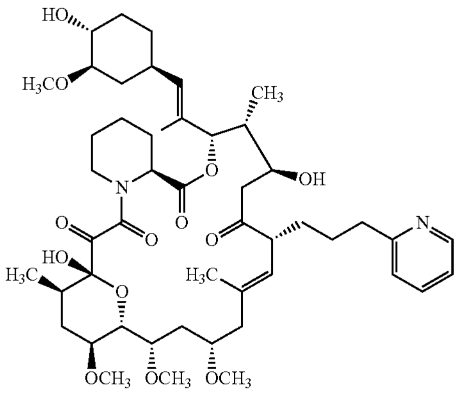 [SMILES: CO[C@H]1C/C(C)=C/[C@@H](CCCc2ccccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 1.5 | ND | 3 | Appears to have blocked Rapalink-1 in brain | 4.3 |
| ZZY05-086 | 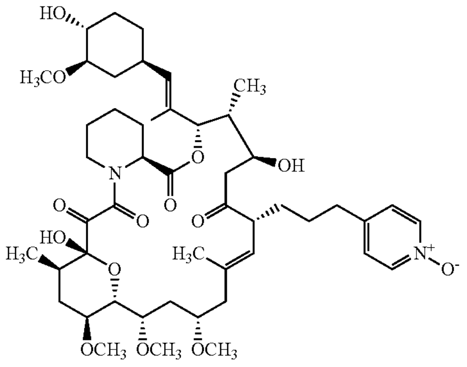 [SMILES: CO[C@H]1C/C(C)=C/[C@@H](CCCc2cc[n+]([O-])cc2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 1.6 | ND | 3 | | 4.3 |

TABLE 5-continued

RapaBlock analogs. Blockade score is assessed by Western Blot analysis of p-S6 level after combination treatment of MCF7 cells with [10 nM Rapa/Rapalink + 10 μM candidate compound] for 24 h. P-S6 level is quantified as fraction of DMSO control: 0: <20%; 1: 20-40%; 2: 40%-70%; 3: >70%.

| Compound | Structure | Kd FKBP12 (nM) | Rapamycin Blockade | RapaLink-1 Blockade | In Vivo | cLogP |
|---|---|---|---|---|---|---|
| ZZY05-092 / ZZY06-041 | 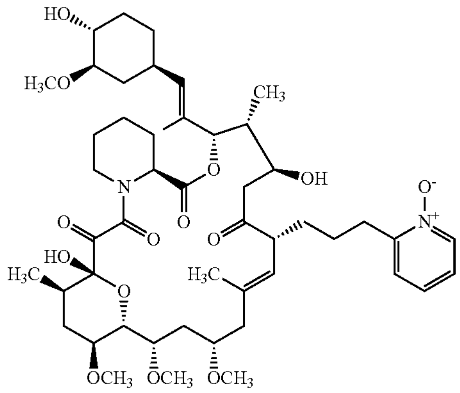 [SMILES: CO[C@H]1C/C(C)=C/[C@@H](CCCc2cccc[n+]2[O-])C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] | 2.5 | ND | 3 | Dose: 1 mg/kg Rapalink-1 + 40mg/kg ZZY05-092 Blocks Rapalink-1 in muscle; Potentiates Rapalink-1 in brain | 4.3 |

Example 4: Bispecific Chemical Ligands Allow Programmable Kinase Inhibition

Dysregulation of kinase activity underlies a variety of human diseases. While many small molecule kinase inhibitors have demonstrated remarkable success in precision medicine, the temporal (timing) and spatial (tissue distribution) control of their activity remains an intractable challenge. Here we present a strategy to build a new class of kinase inhibitors that overcome these limitations. Created by chemically linking kinase inhibitors and the immunosuppressant FK506, the resultant bispecific ligands show kinase inhibitory activity that depends on the endogenous protein FKBP12 and hence can be modulated by co-administration with an exogenous FKBP12 ligand. Using this approach, we successfully constructed highly potent, cell-permeable, programmable inhibitors of Src-family kinases, HER2 and LRRK2 based on dasatinib, lapatinib and GNE-7915, respectively. The method described here may be adapted for other kinases and even other classes of therapeutic targets.

Protein kinases orchestrate an intricate network of cellular signaling events, and their dysregulation are implicated in many human diseases including cancer, autoimmunity and neurodegenerative disorders. Inhibition of aberrant kinases by small molecule ligands proves to be a fruitful therapeutic strategy that remains widely pursued in various disease areas (48 FDA-approved kinase inhibitors as of December 2018). Nonetheless, methods are lacking to allow reversal of the effects of kinase inhibitors of or tissue-directed kinase inhibition. These features are highly desirable, as systemic kinase inhibition often is unnecessary and contributes to toxicity. Here we describe a method to construct bispecific chemical ligands that induce the association of protein kinases and a ubiquitously expressed protein, FKBP12, by chemically linking a kinase inhibitor to a high affinity ligand of FKBP, FK506. We show that these bispecific ligands are cell-permeable and effect potent, specific and long-lasting inhibition of their respective targets, and that their cellular activity is amenable to modulation with a separate ligand of FKBP12. We exemplify our approach with three case studies: an inhibitor of Src-family kinases based on dasatinib, an inhibitor of EGFR/HER2 based on lapatinib, and an inhibitor of LRRK2 based GNE7915.

It is important to point out that several other FKBP12-binding hybrids have been reported with diverse pharmacological properties. For example, Briesewtiz et al. discovered that linking an pYEEI peptide to FK506 or SLF led to an increase or decrease of its affinity for the SH2 domain of Fyn in the presence of FKBP12, respectively. Gestwicki et al. demonstrated that SLF-Congo Red is a bifunctional molecule that recruits FKBP12 to β-amyloids and uses the steric bulk of FKBP12 to inhibit β-amyloid aggregation. Marinec et al. reported that an amprenavir-SLF hybrid preferentially partitions into red blood cells which express high levels of FKBP12 protein, creating an intracellular reservoir of the HIV protease inhibitor and significantly increasing its serum half-life. Many properties observed with our bispecific kinase inhibitors are congruent with these precedents. However, a distinct advantage unique to our compounds is that their activity is highly dependent on the availability of FKBP12 protein; they are poor kinase inhibitors in the absence of FKBP12 and therefore their cellular activity can be conveniently modulated with another FKBP12 ligand (vide infra).

We chose dasatinib, an FDA-approved pan-Src family kinase inhibitor, for our model study as abundant literature on its pharmacological properties and structural information is available to aid our initial design and analysis. Inspection of the crystal structures of FKBP12—FK506 complex (PDB: 1FKJ) and dasatinib-Src complex (PDB: 3G5D) revealed that the allyl group at the C21 position of FK506 and the hydroxylethyl group in dasatinib on the piperazine ring are exposed to solvent and serve as suitable sites for chemical fusing. Previous structure-activity relationship studies on FK506 and dasatinib also indicate that chemical alterations at these two sites have minimal impact on their affinities for their respective targets. We envisioned that modifying the C21 allyl group confers an additional advantage: substituents larger than allyl at this position will ablate FK506's ability to inhibit its natural target calcineurin, an undesirable activity in our present application. To synthesize the bispecific ligand FK506-Dasatinib, we employed HATU-mediated amide coupling reaction to join a carboxylic acid derived from FK506 and a secondary amine derived from Dasatinib. The synthetic route used is amenable to incorporating linkers with various length and geometry for further optimization.

Figure 14B:
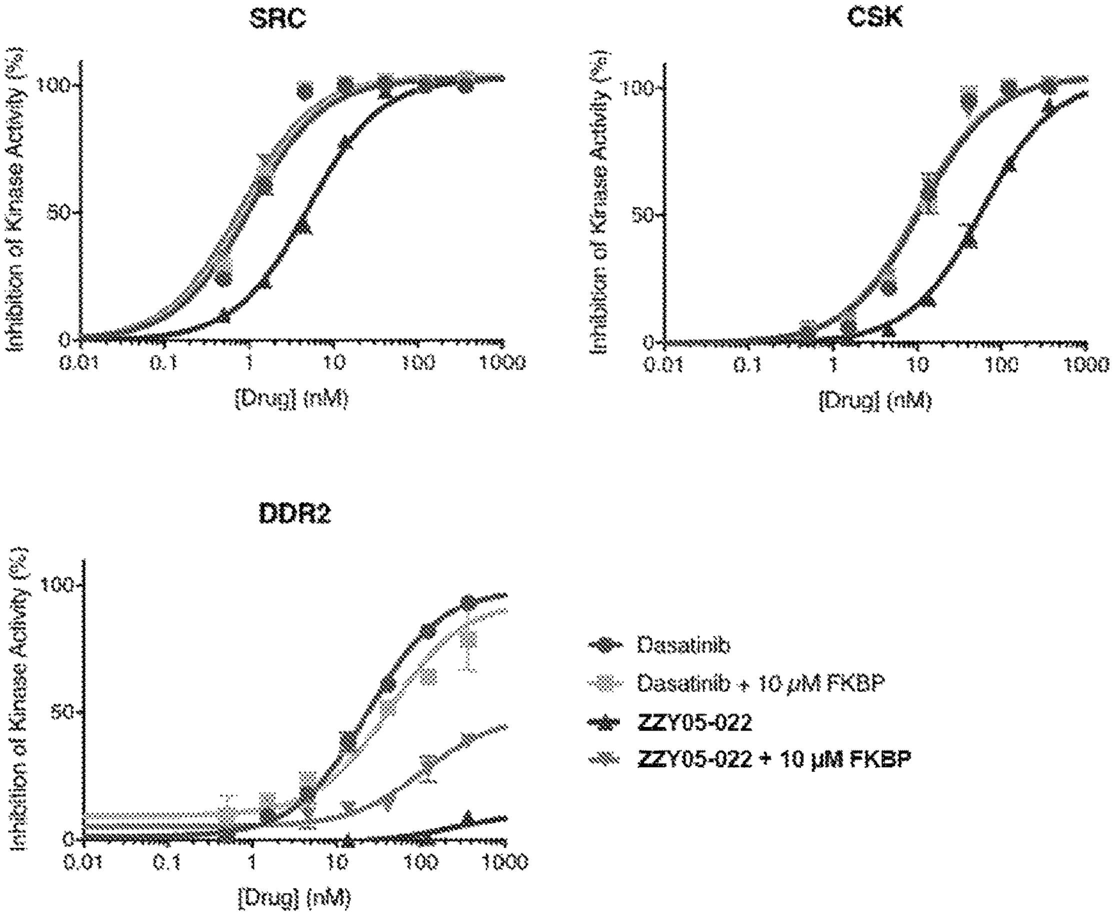
Figure 14C:
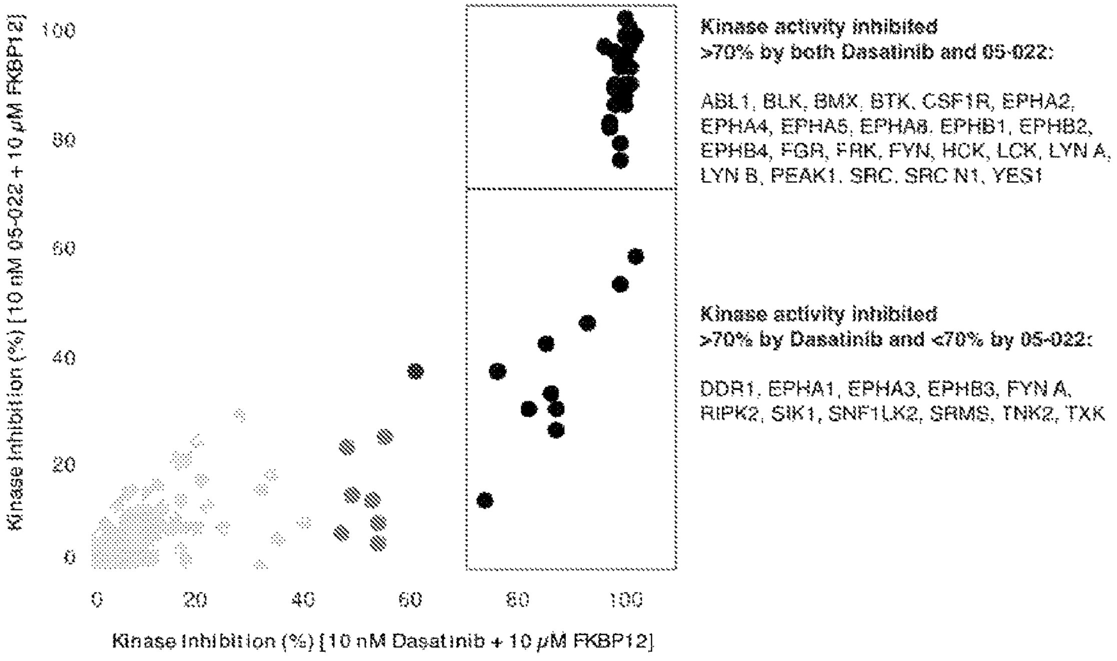
Figure 14D:

Using a fluorescence polarization assay, we found that FK506-Dasatinib maintained potent binding to FKBP12 ($K_d$=23 nM), consistent with our previous anticipation. To assess the kinase inhibition activity of FK506-Dasatinib, we performed in vitro kinase assays with ATP concentrations at the apparent Km values of each kinase. Three kinases were chosen in this preliminary investigation: Src, Csk and DDR2. Src and Csk are both Src-family tyrosine kinases but with opposite functions in cellular signal transduction, while DDR2 is a receptor tyrosine kinase also potently inhibited by dasatinib. Under standard assay conditions, FK506-Dasatinib showed weaker inhibitory activity toward all three kinases compared to dasatinib, with $IC_{50}$ values more than ten-fold greater those of the latter (FIG. 14B). To further mimic the cellular environment, we supplemented the assay buffer with 10 μM recombinant FKBP12, a concentration chosen to match the estimated intracellular concentration of FKBP proteins. At this FKBP concentration, we also ensured that >99.7% of the FK506-Dasatinib population would be in complex with FKBP12. Under the new assay conditions, we observed a significant left-shift of the inhibition curves for FK506-Dasatinib, whereas the potency of dasatinib remained unchanged. For Src and Csk, the two inhibitors achieved equipotent inhibition upon FKBP12 supplementation. Meanwhile, for DDR2, though enhancement of activity of FK506-Dasatinib was also observed, it was still inferior to dasatinib, failing to fully inhibit this kinase even at 1 μM concentration. This difference prompted us to investigate if linking FK506 to dasatinib had reshaped its selectivity for kinase targets. We profiled these two inhibitors against a panel of 485 protein kinases at 10 nM inhibitor concentration and with 10 μM supplemented FKBP12 protein (FIG. 14C). Of these 485 kinases, 23 were inhibited >70% by both inhibitors, and another 11 were inhibited >70% by dasatinib but not FK506-Dasatinib. Overall, FK506-Dasatinib did not achieve greater inhibition of any kinase tested than dasatinib at 10 nM, but certain kinases (for example, DDR1) appeared to be more disfavored by FK506-Dasatinib than others. This differential attenuation of inhibitory activity may be attributed to the favorable or unfavorable interactions with FKBP12 that the kinase must experience in order to bind the FK506-Dasatinib/FKBP12 complex. In this model, we envision that when FKBP12 binds FK506-dasatinib, a composite surface is formed that presents the dasatinib moiety and surveys various proteins for energetically favorable binding events (FIG. 14D).

Figure 15A:
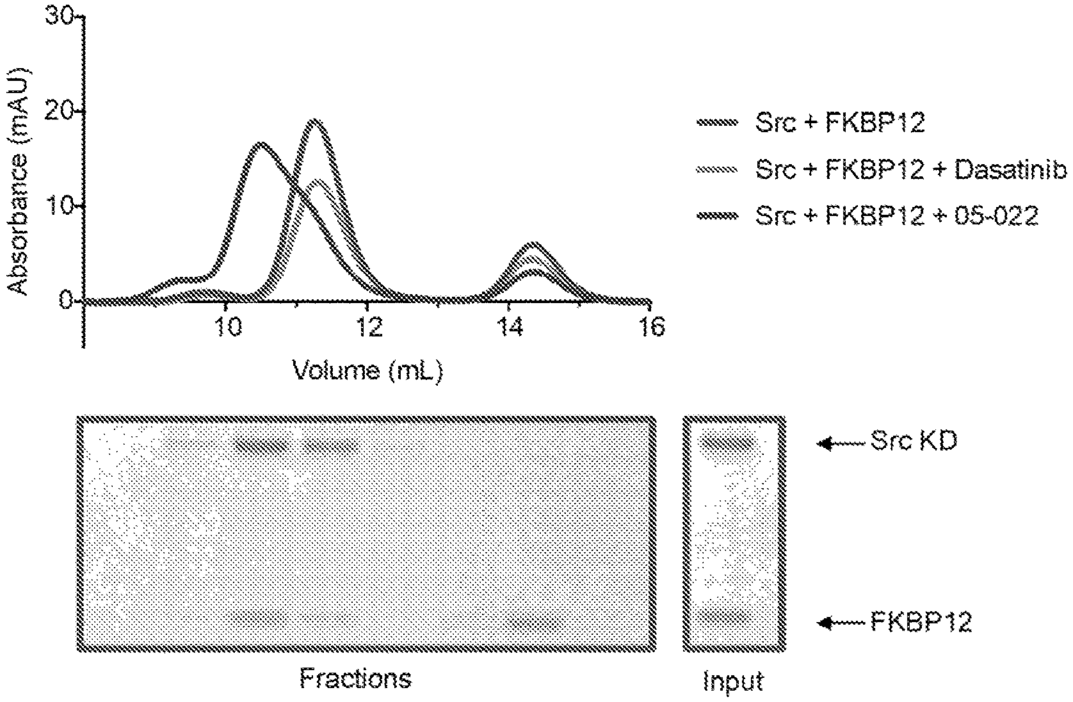
FIGS. 15A-15C. FK506-Dasatinib forms a stable ternary complex with Src and Dasatinib.
Figure 15B:
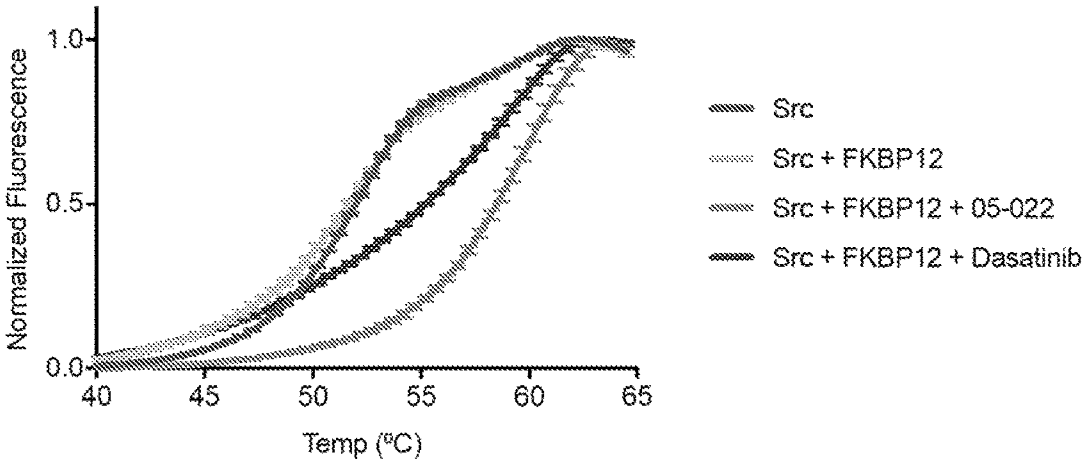
Figure 15C:
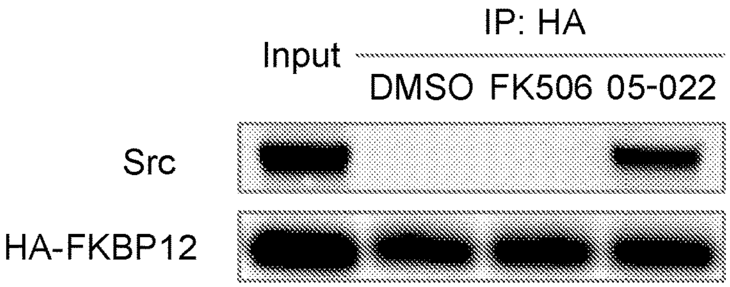

The participation of FKBP12 in the inhibition of kinases by FK506-dasatinib is further revealed by its ligand-dependent association with kinases. Addition of FK506-Dasatinib to a mixture of recombinant Src kinase domain (33 kDa) and FKBP12 (12 kDa) induced the formation of a stable complex (~50 kDa) that can be purified by size exclusion chromatography (FIG. 15A). The molecular weight of the complex suggests a 1:1:1 stoichiometry consistent with the anticipated binding mechanism of FK506-dasatinib. Differential scanning fluorimetry suggested that formation of this complex led to stabilization of both protein components toward thermal denaturation to a greater extent than dasatinib alone (FIG. 15B). Such tripartite interactions are preserved in more complex native environments—Src co-immunoprecipitated with HA-FKBP12 in Jurkat cell lysates treated with FK506-Dasatinib, but not FK506 (FIG. 15C).

Figure 16A:
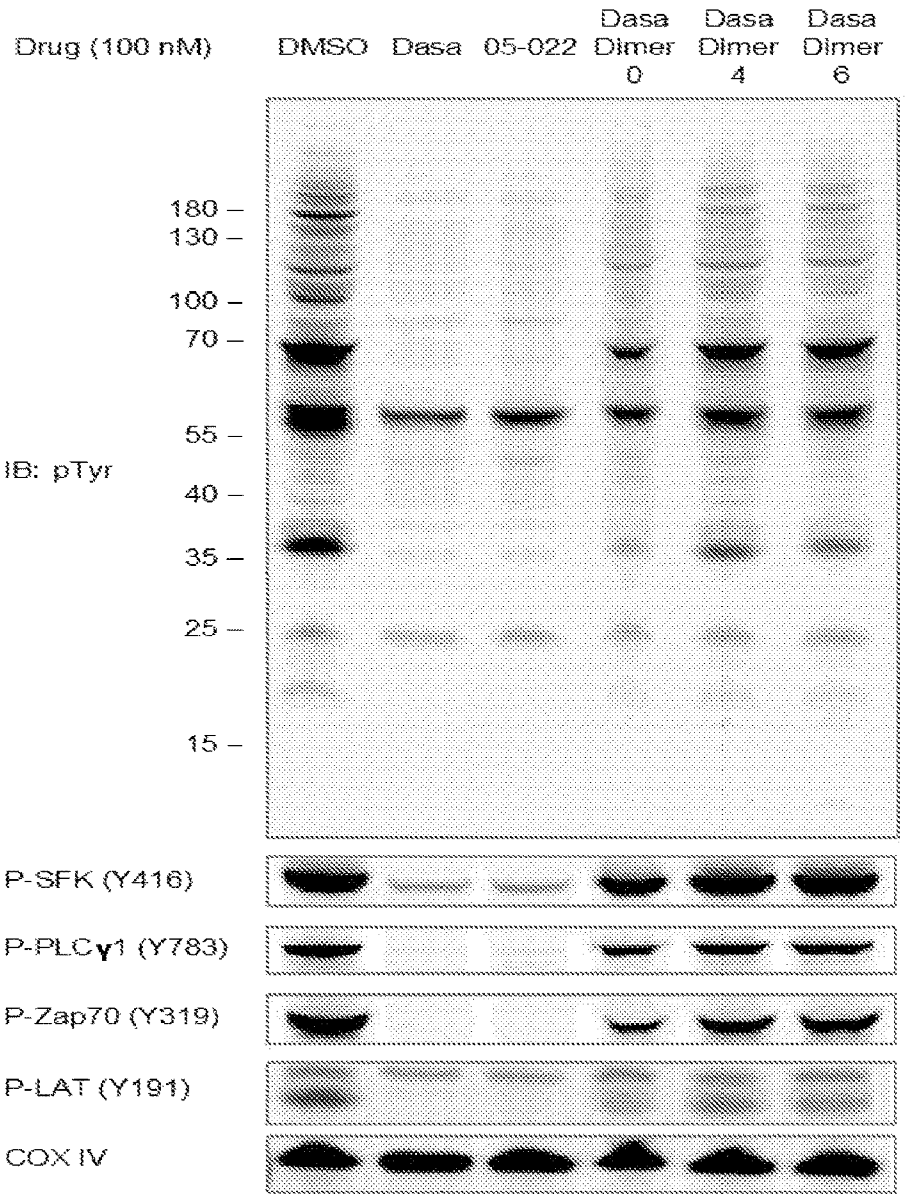
FIGS. 16A-16D. FK506-Dasatinib is a potent cell-permeable Src-family kinase inhibitor with long cellular retention time.
Figure 16B:
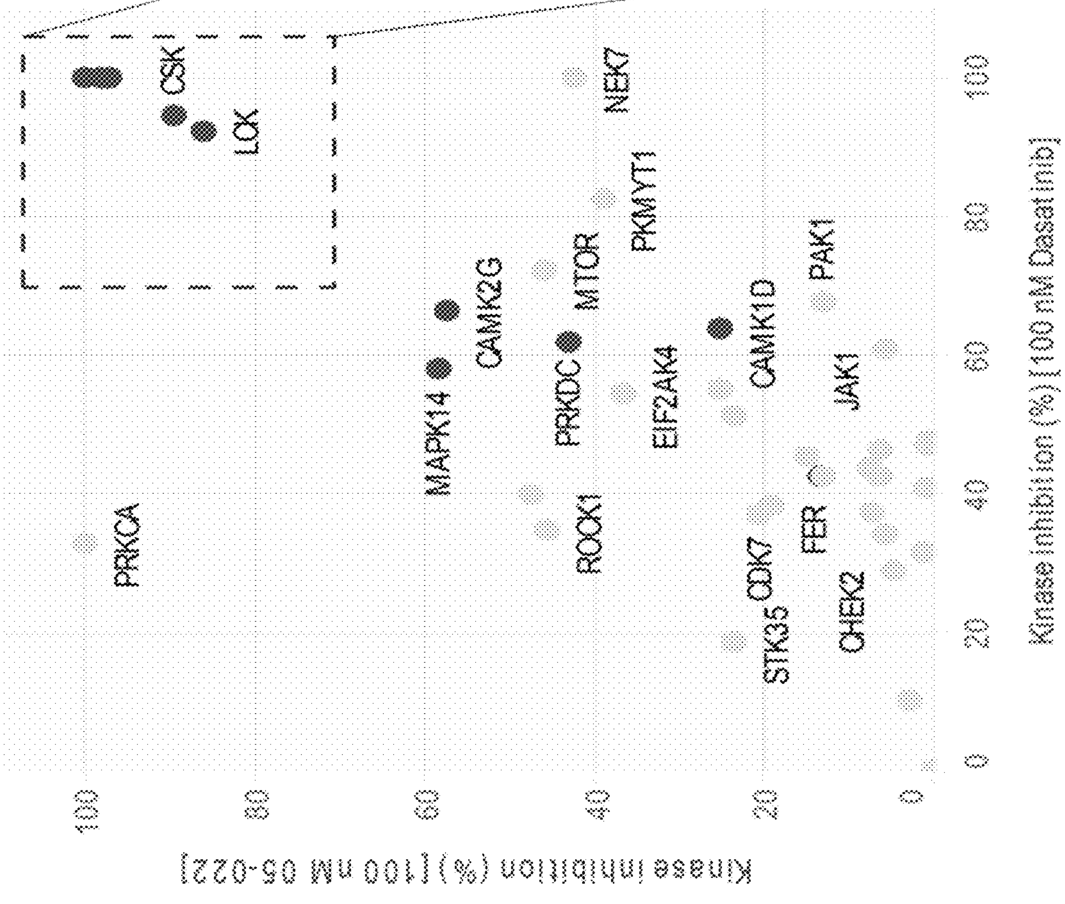
Figure 16C:
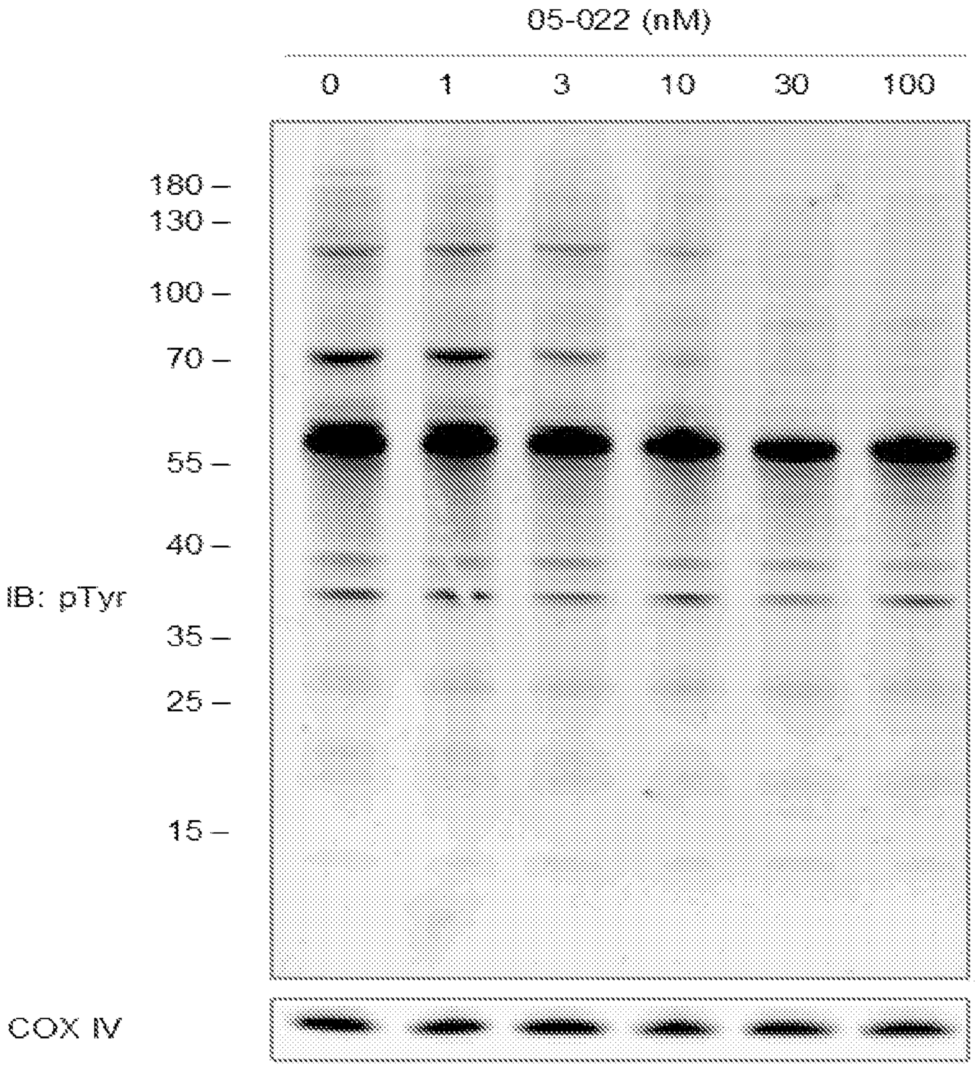
Figure 16D:
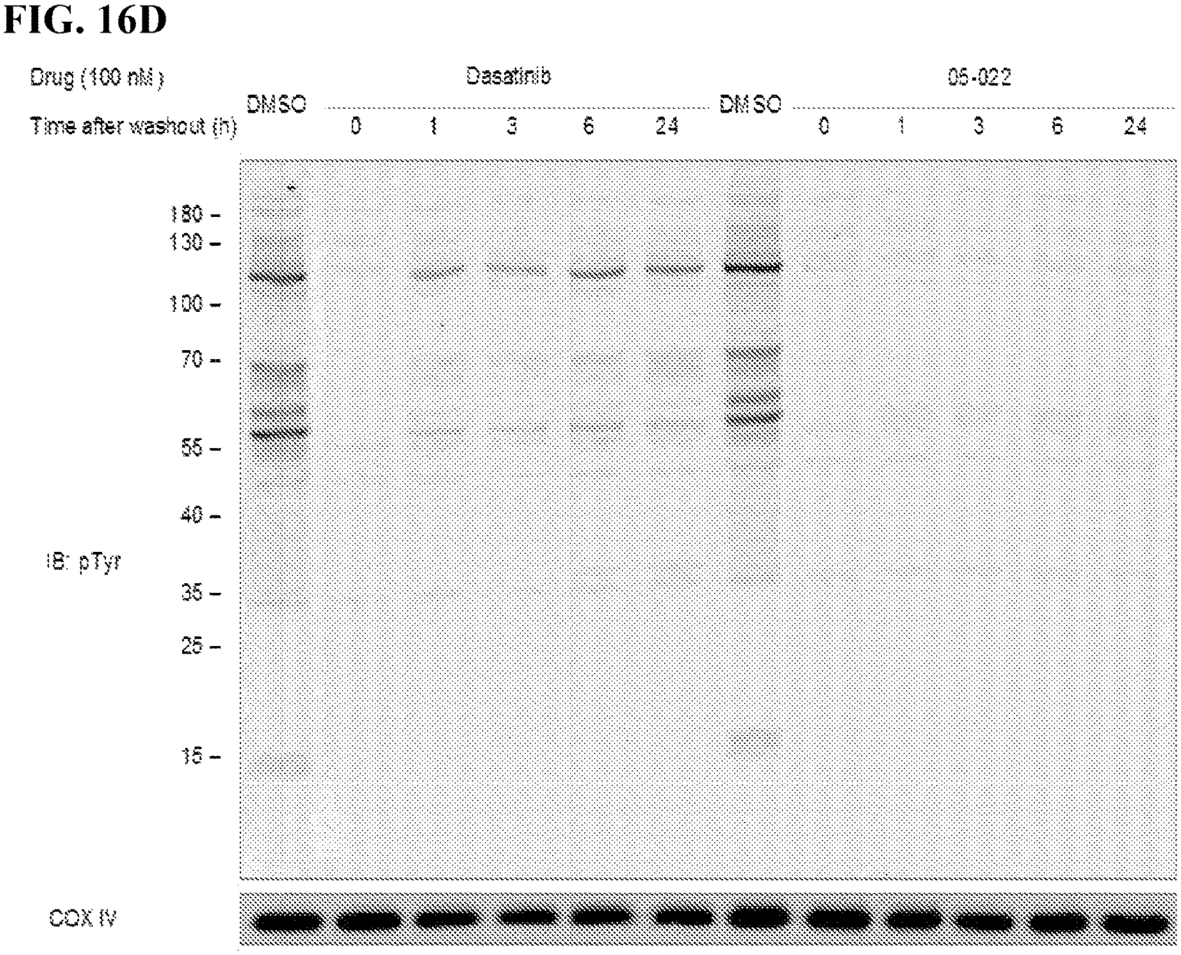
Figure 19B:
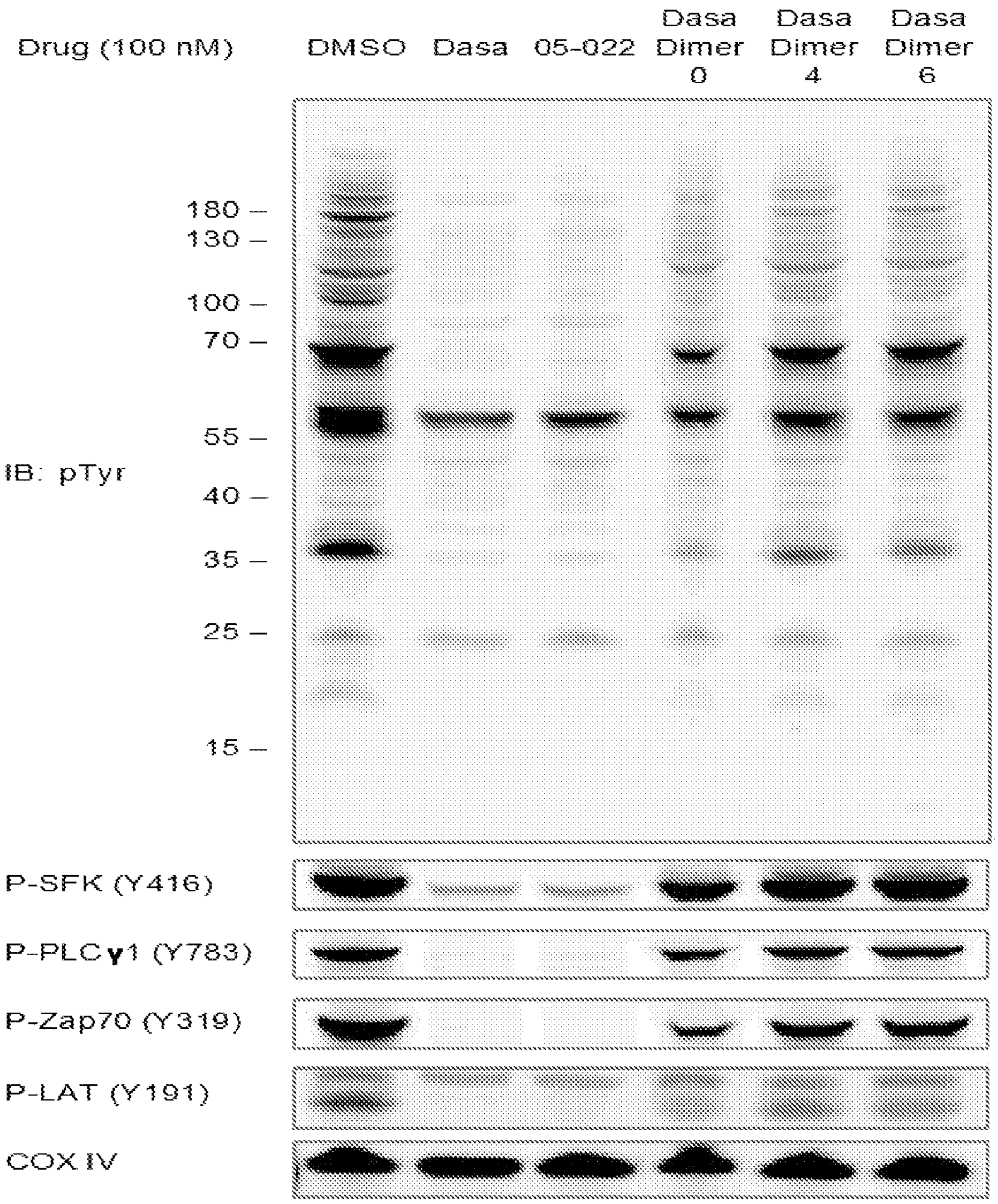
Figure 20:
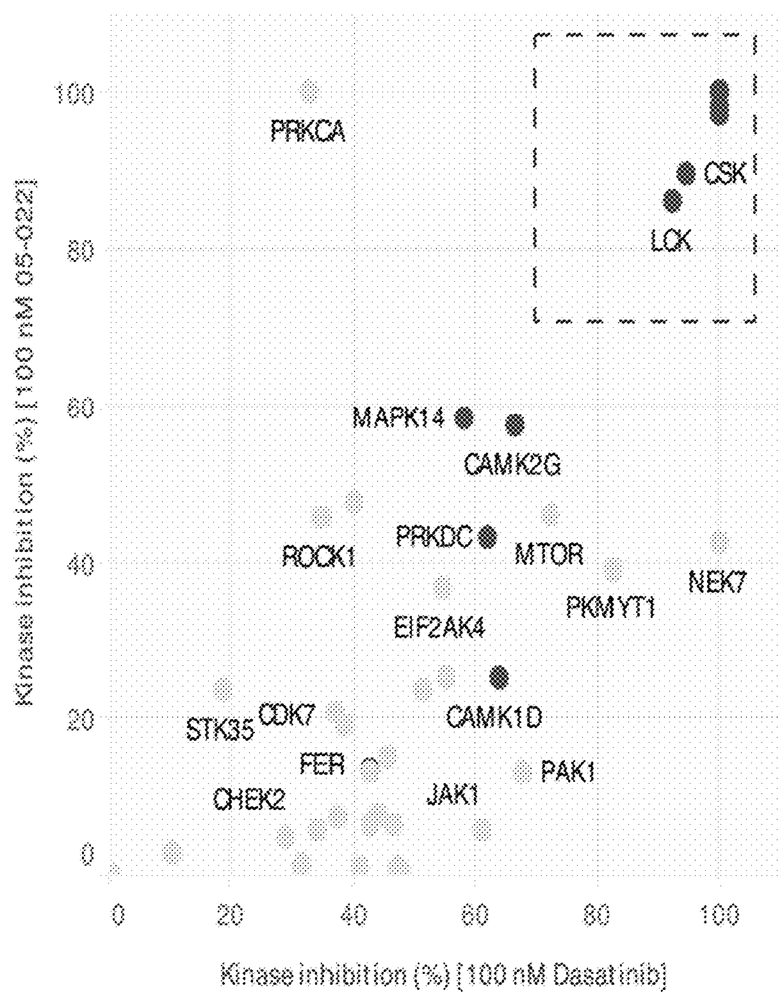
FIG. 20. In cell profiling of kinase inhibition by dasatinib and FK506-dasatinib using chemoproteomic probe XO44.
Figure 21A:
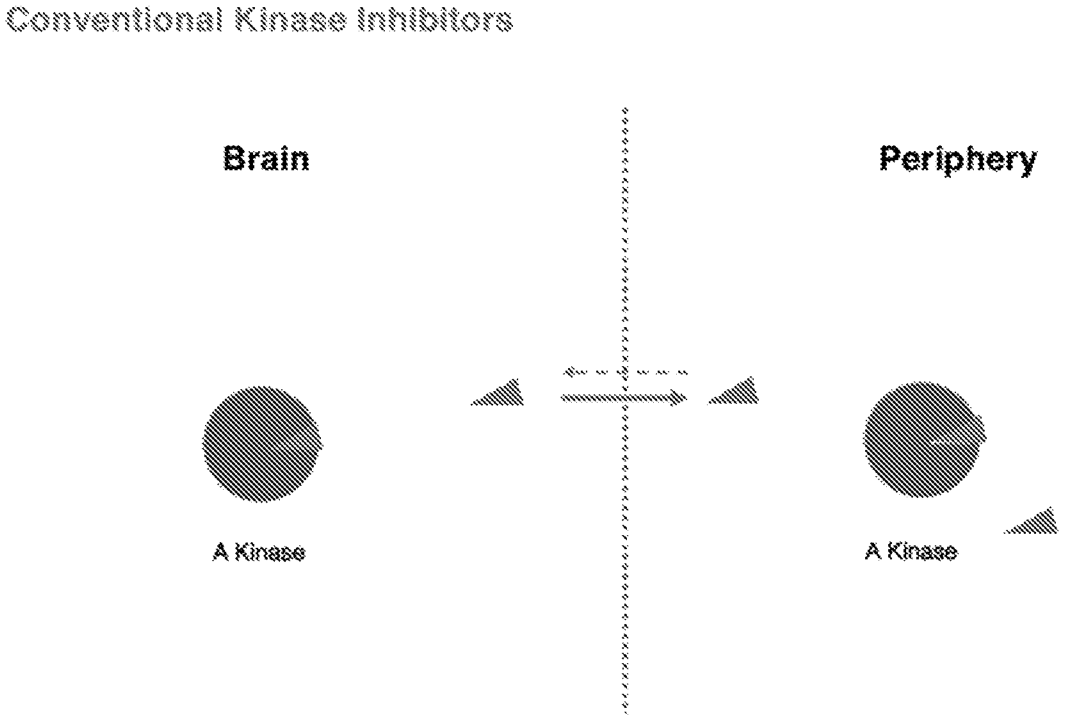
Figure 21B:
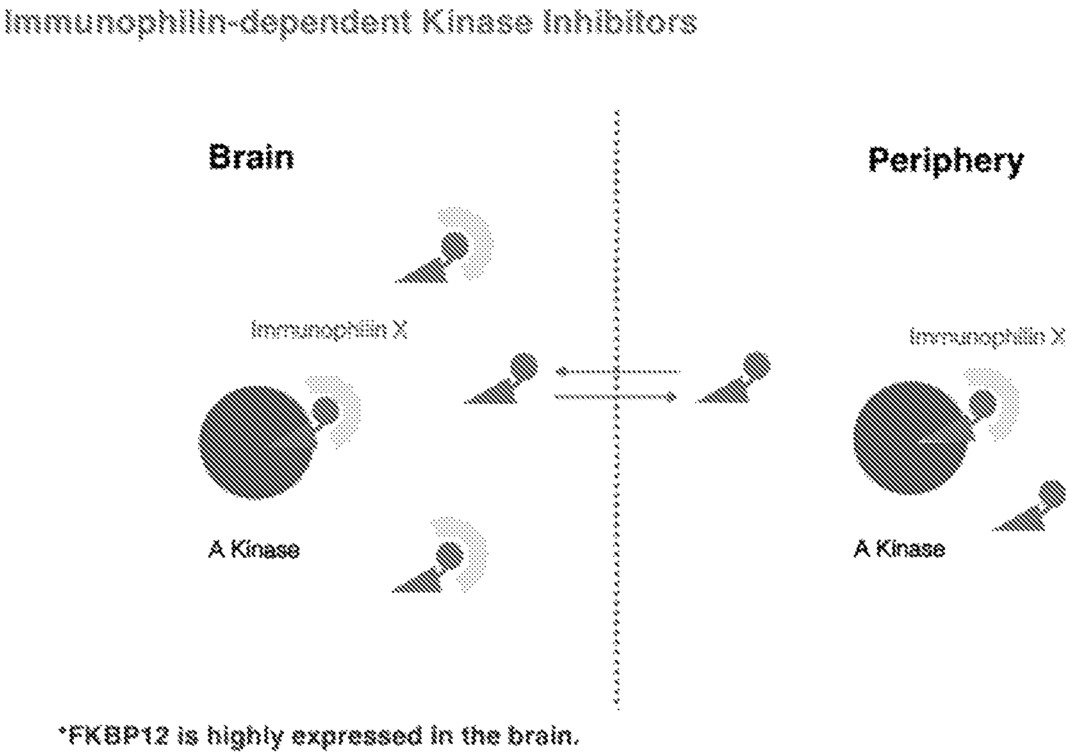
Figure 23A:
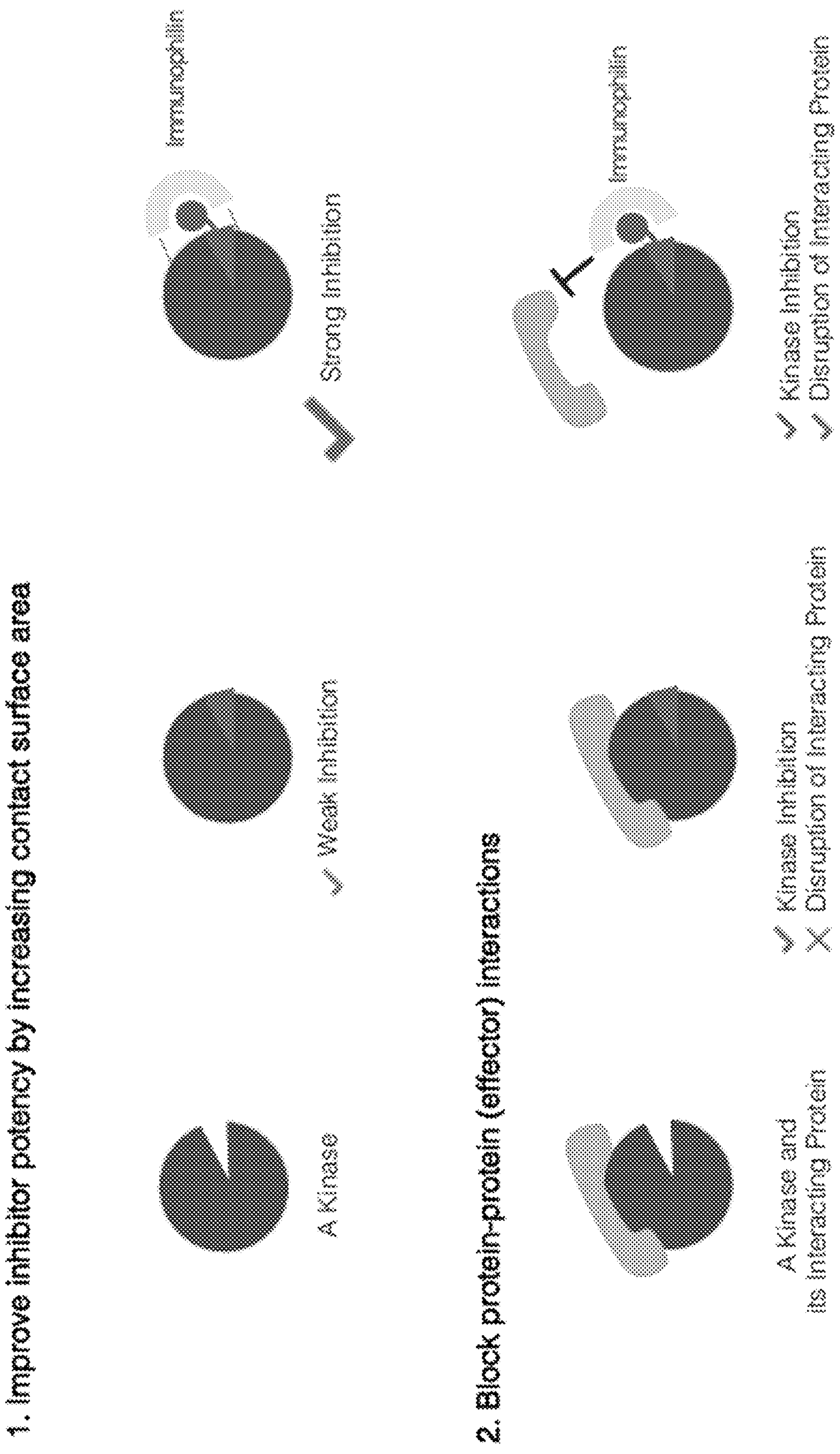
FIGS. 23A-23C. Potential advantages.
Figure 23B:
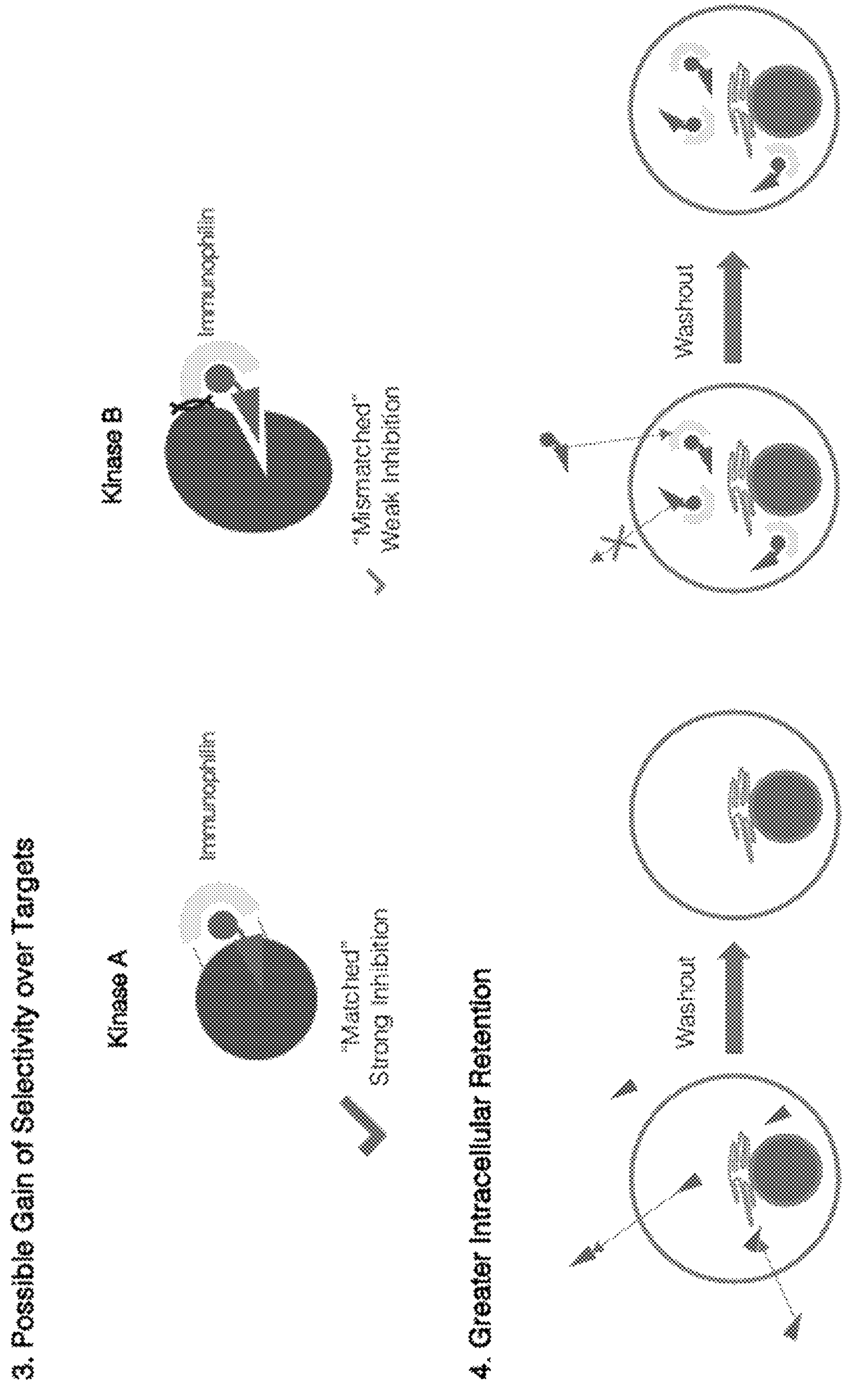
Figure 23C:
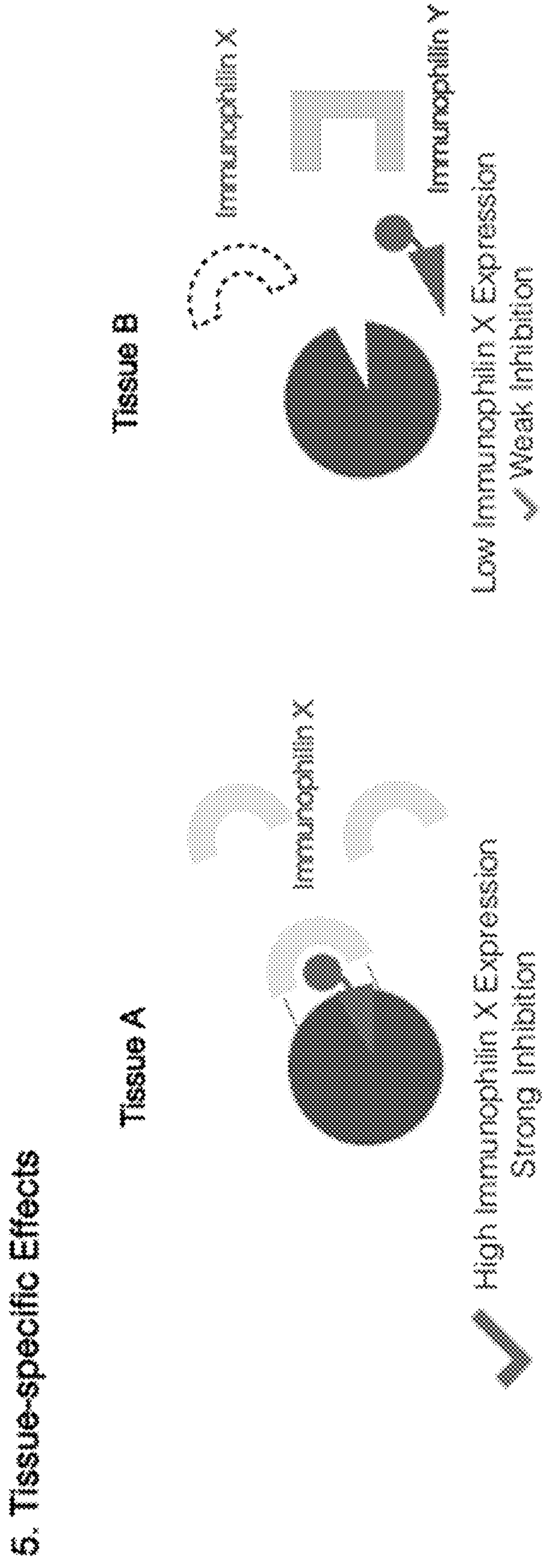
Figure 26:
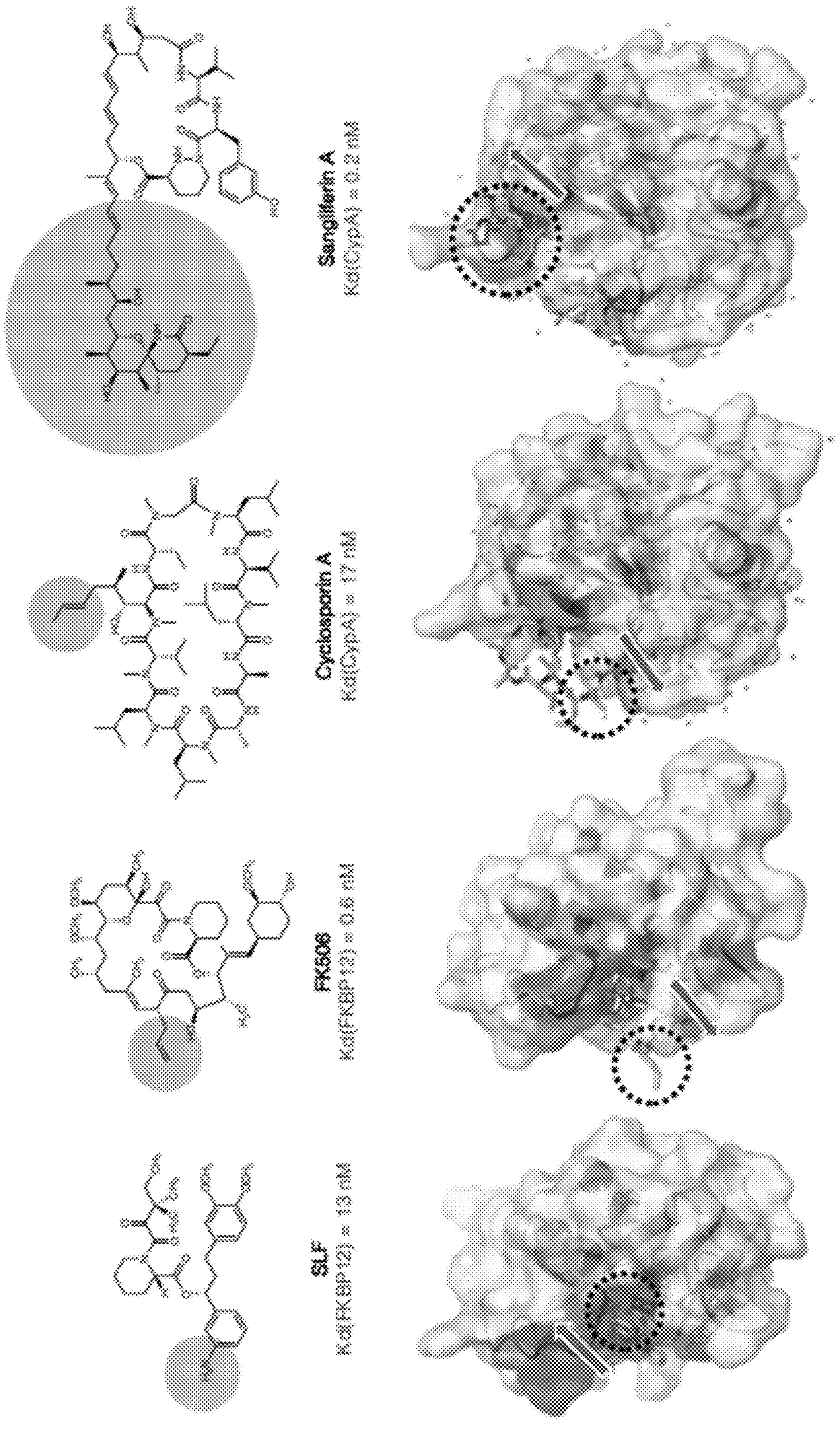
FIG. 26. Src kinase inhibitors. Proof of concept study and brain tumor applications. Immunophilin ligands.
Figure 27:
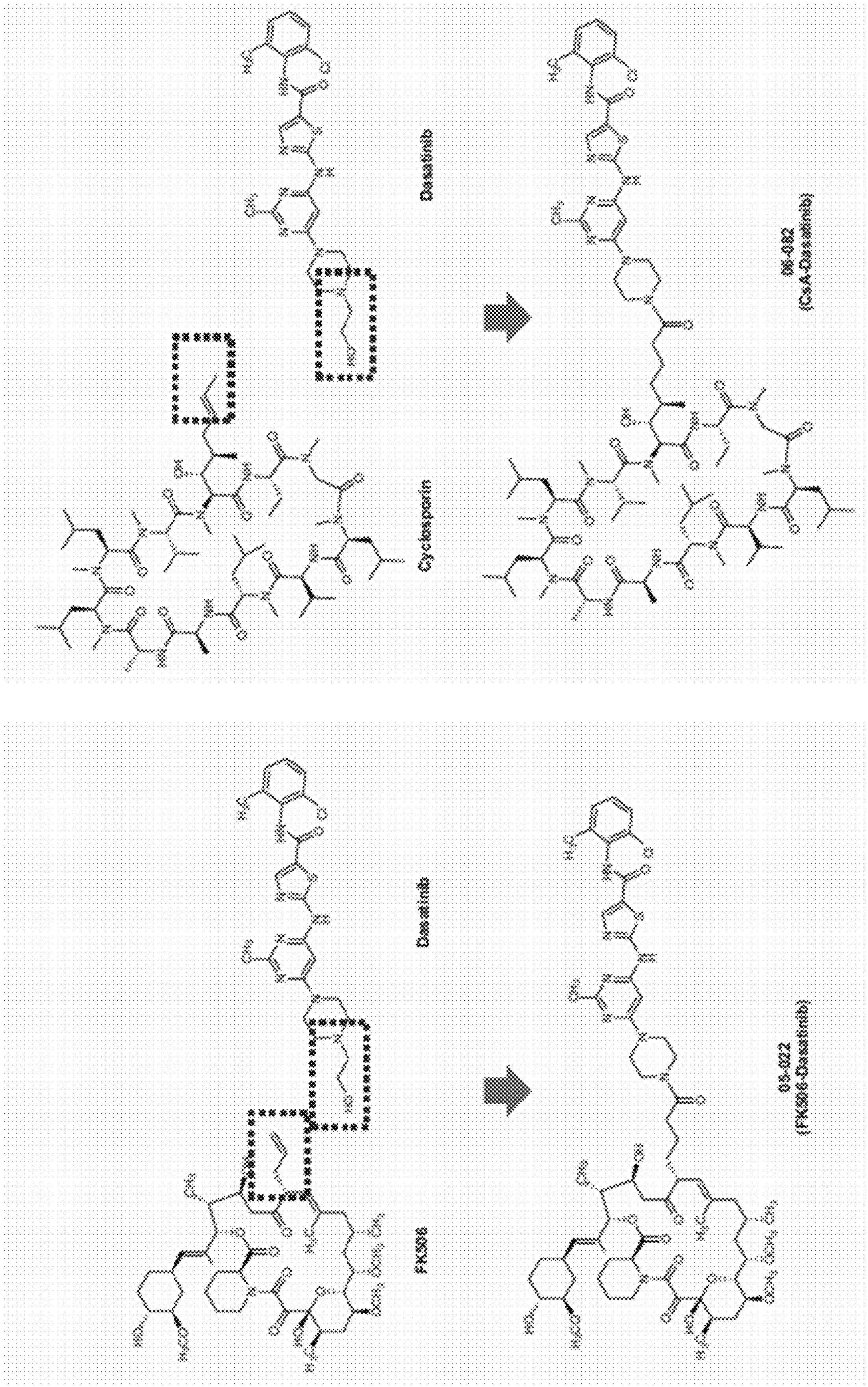
FIG. 27. Design of chimeric kinase inhibitors.
Figure 29:
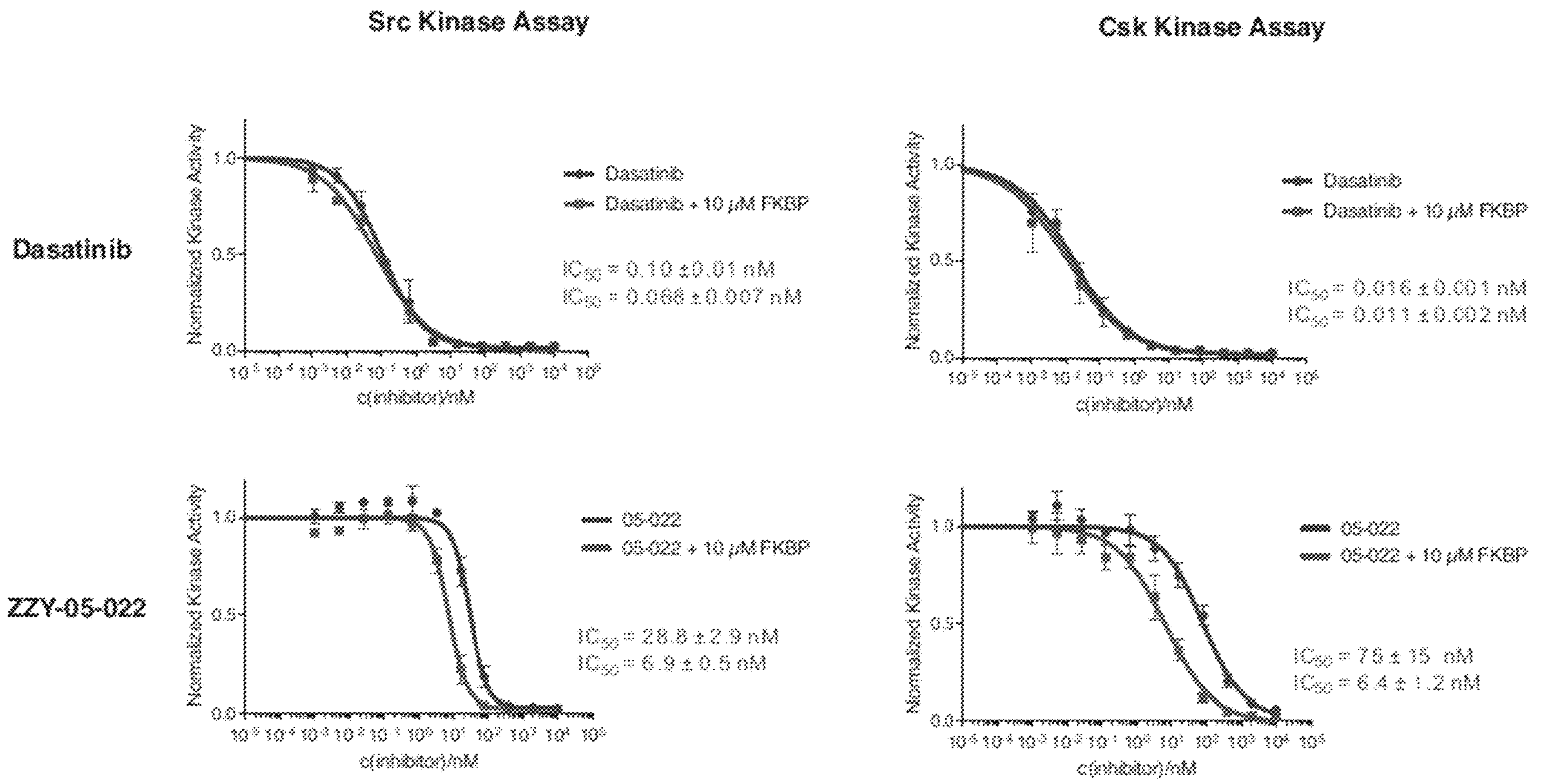
FIG. 29. Activity of ZZY05-022 is dependent on FKBP12.
Figure 30A:
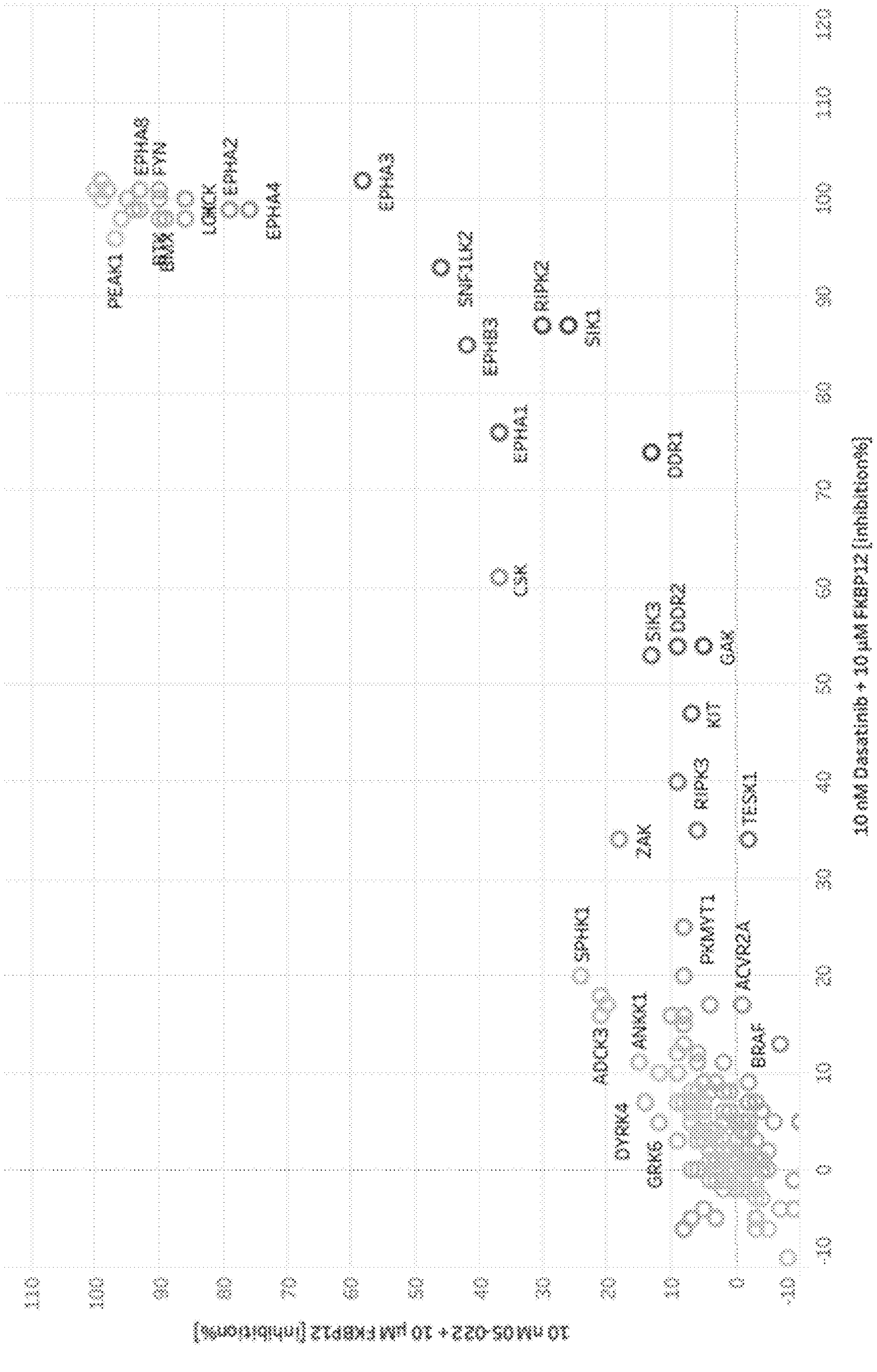
FIGS. 30A-30B. ZZY05-022 has similar target scope to dasatinib.
Figure 30B:
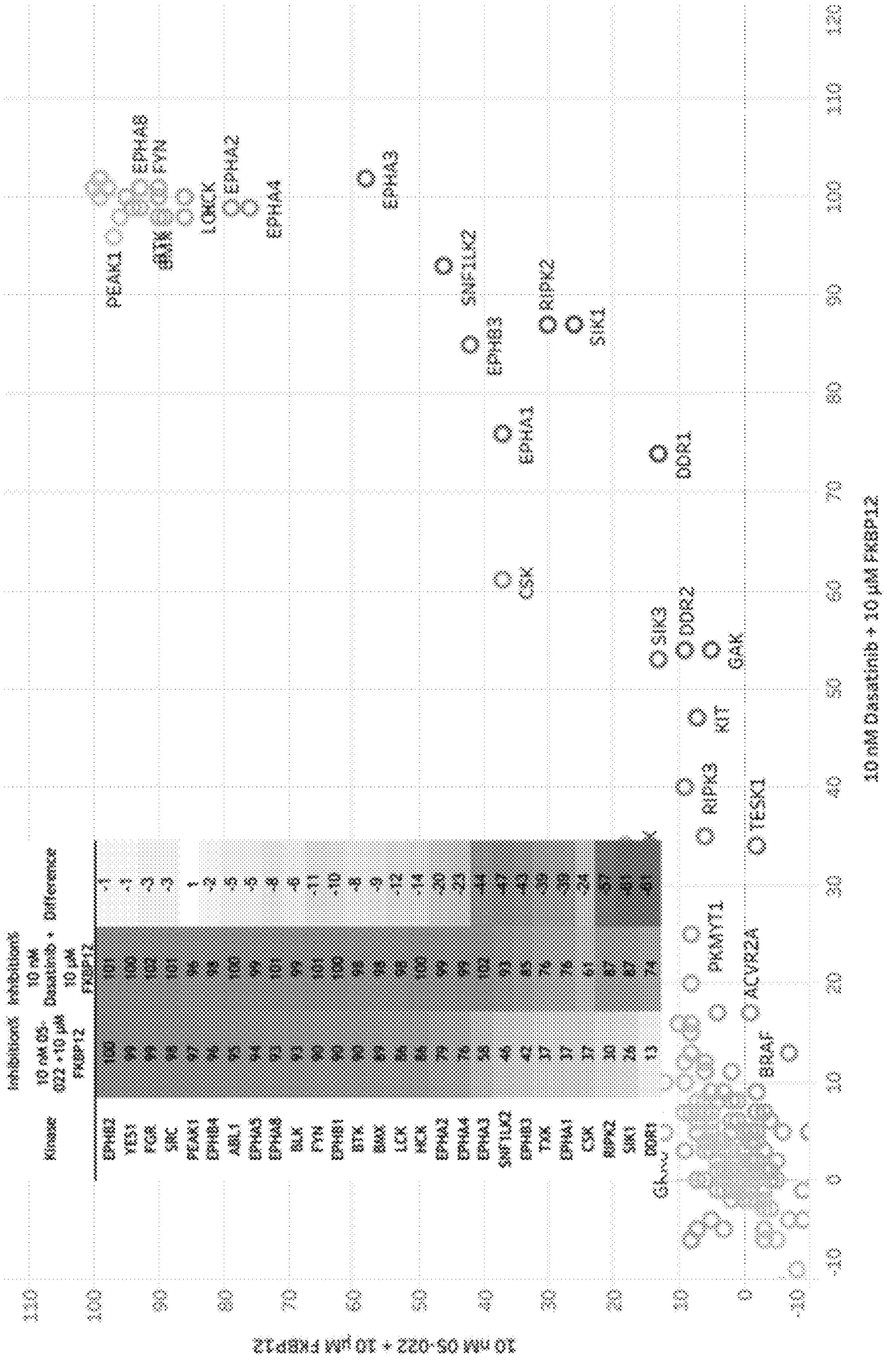
Figure 31:
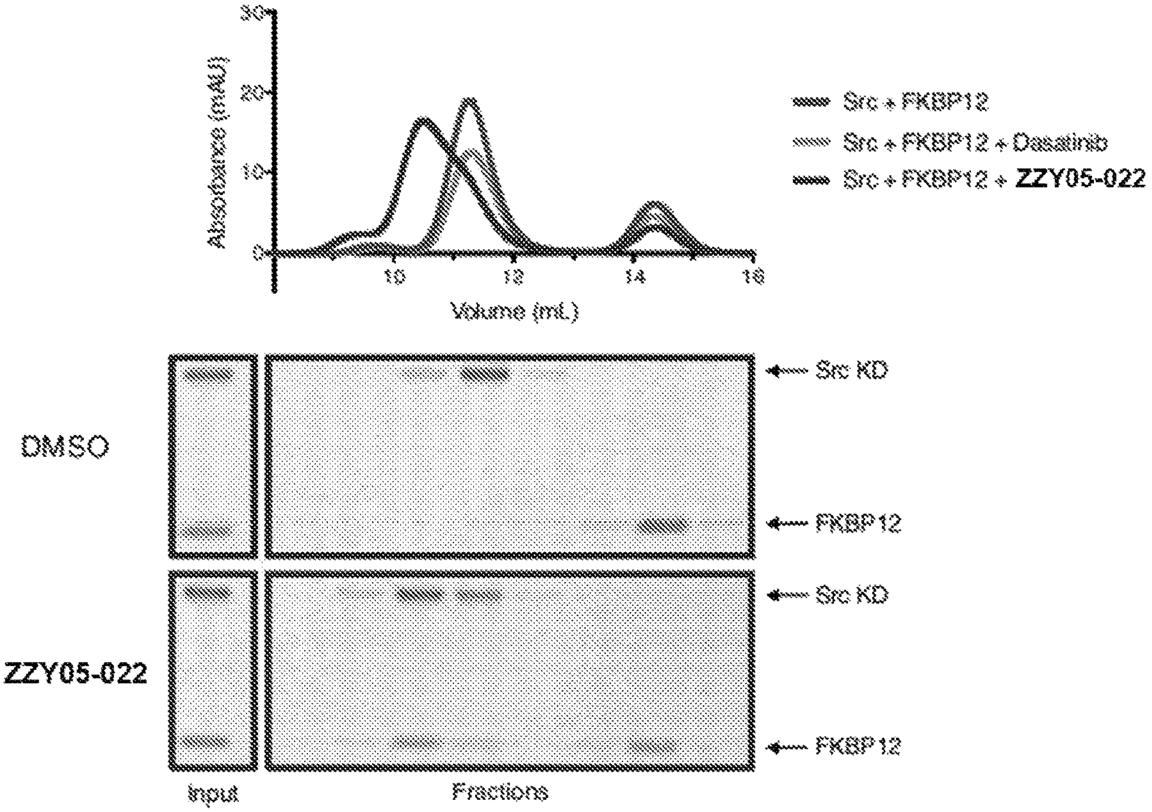
FIG. 31. Src, FKBP12, and ZZY05-022 form a stable ternary complex. Concentrations at injection: Src kinase domain (50 μM), FKBP12 (50 μM), dasatinib or ZZY05-022 (100 μM).
Figure 32:
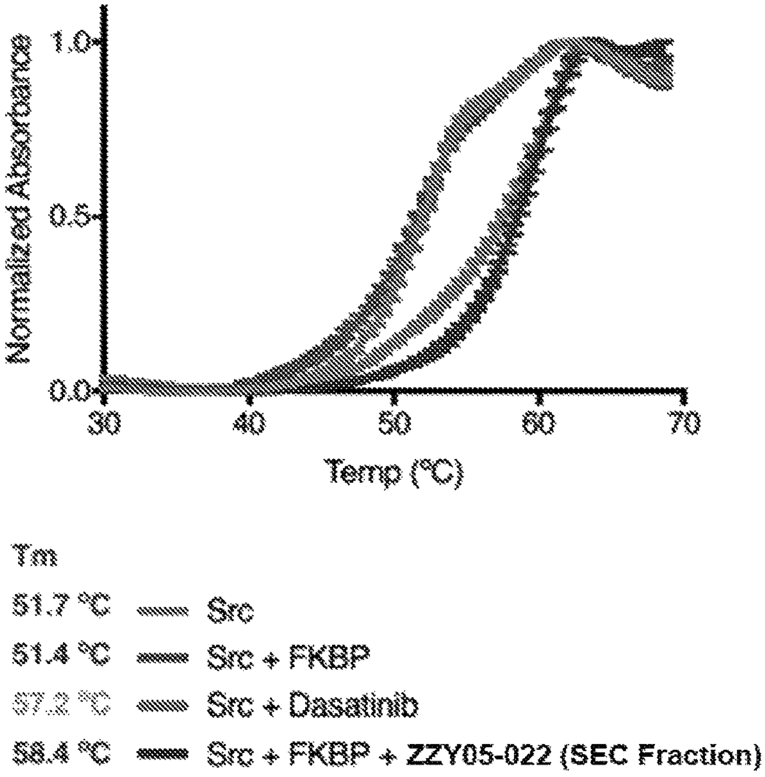
FIG. 32. Src, FKBP12, and ZZY05-022 form a stable ternary complex. Assay concentrations: Src kinase domain (1 μM), FKBP12 (0 or 1 μM), dasatinib (1 μM), ZZY05-022 (1 μM), SYPRO Orange (5×).
Figure 33:
FIG. 33. Src, FKBP12, and ZZY05-022 form a stable ternary complex. Pulldown was performed with Jurkat cell lysate (1 mg/mL, 200 μL), supplemented with 2 μg HA-FKBP12. Pulldown/wash buffer: 50 mM Tris 7.4, 120 mM NaCl, 1% NP-40, 1 mM EDTA, phosphatase/protease inhibitors.
Figure 34A:
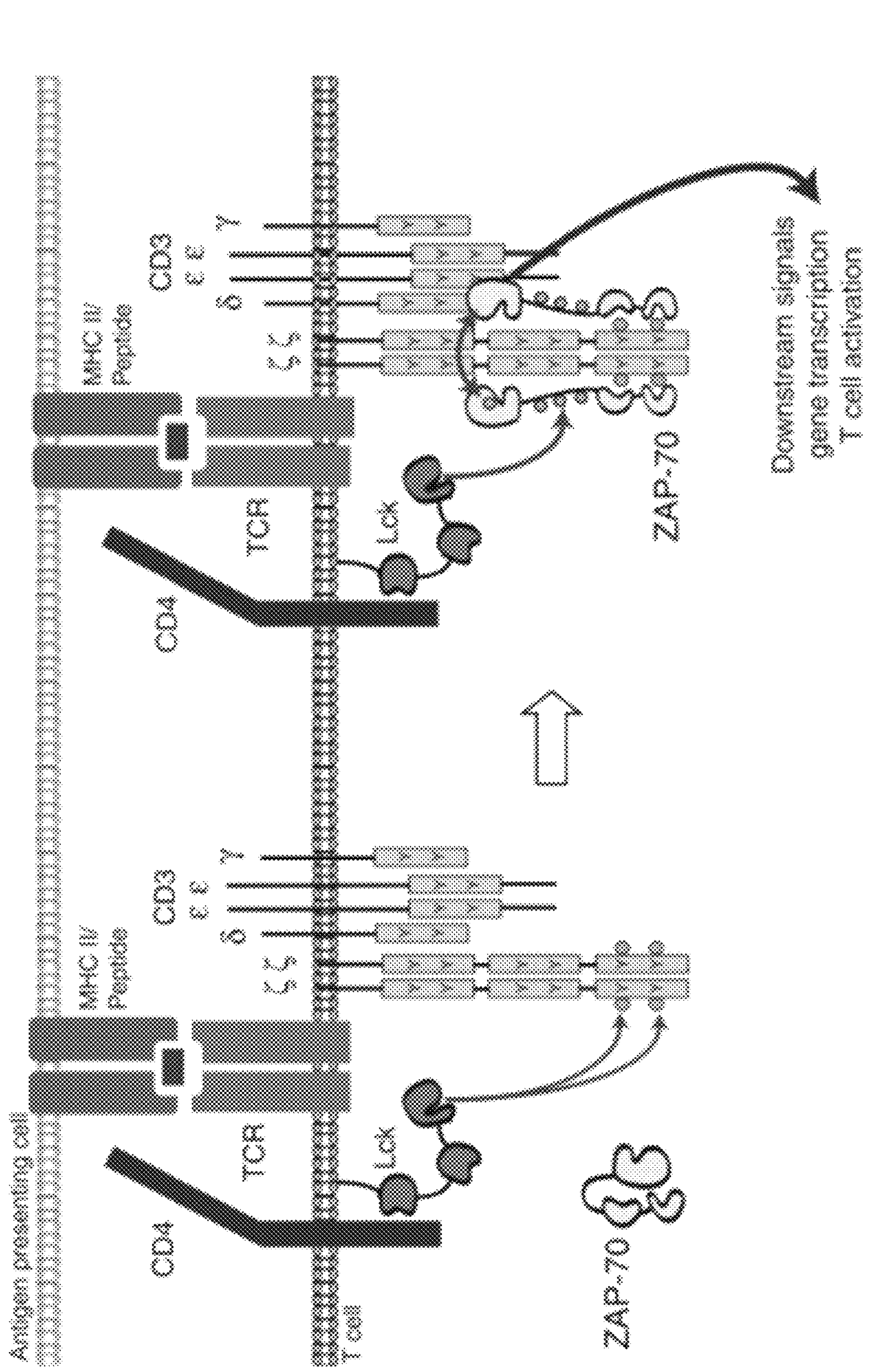
FIGS. 34A-34B. ZZY05-022 potently inhibits p-Tyr signaling in Jurkat cells.
Figure 34B:
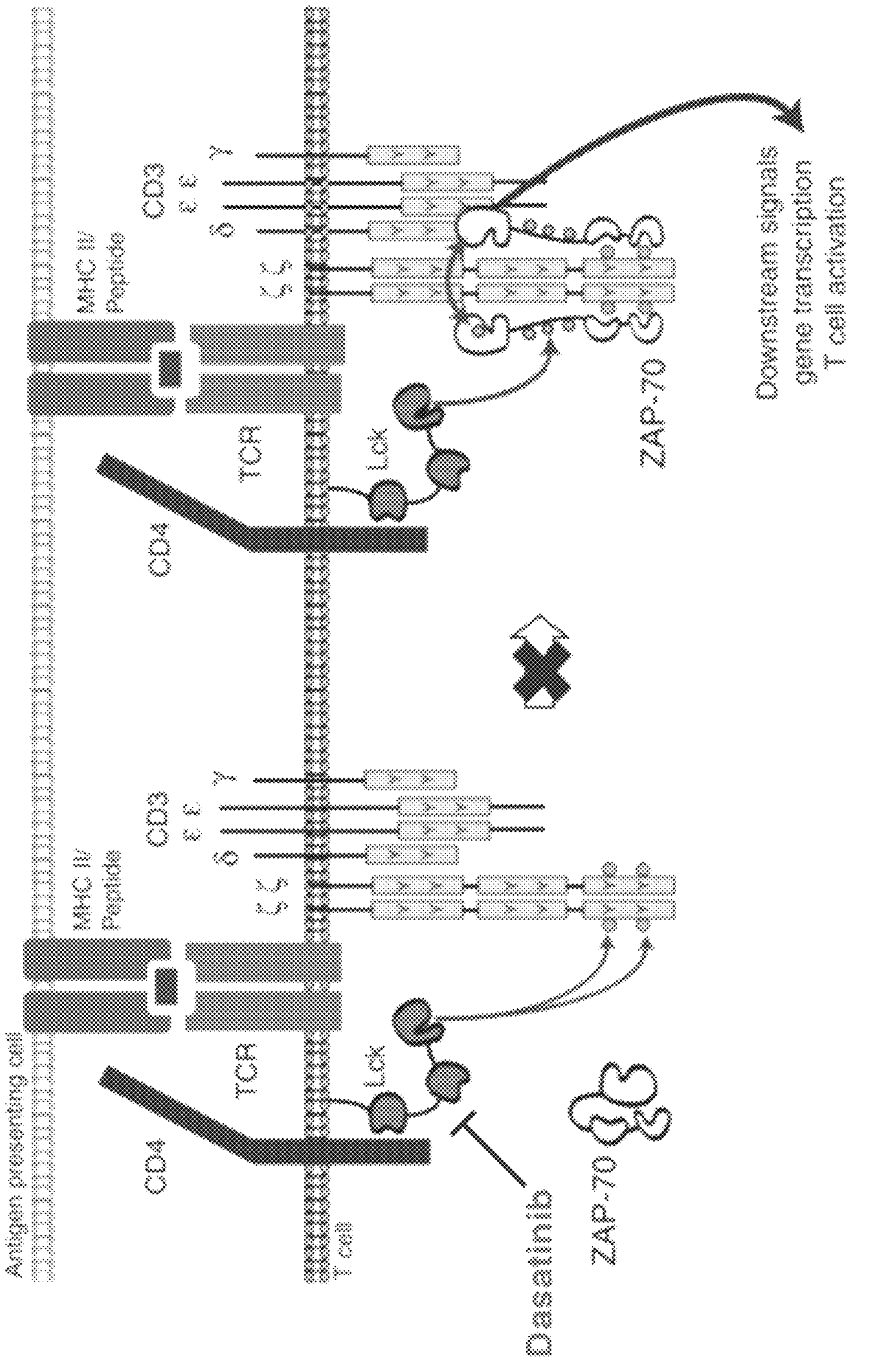
Figure 35:
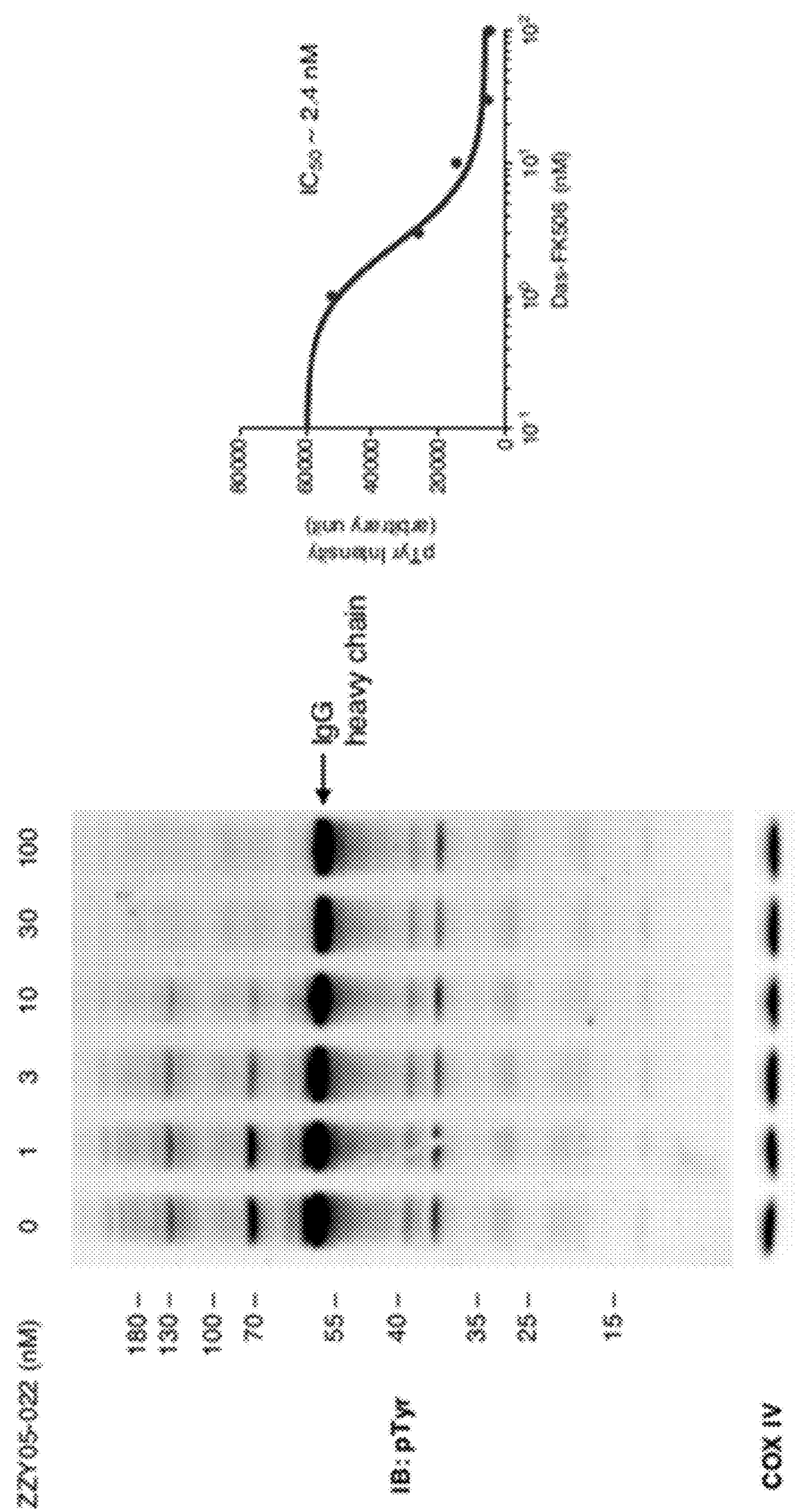
FIG. 35. ZZY05-022 potently inhibits p-Tyr signaling from CD3 crosslinking in Jurkat cells. Jurkat cells ($1\times10^6$/mL) were treated with the indicated drugs for 1 h, then stimulated with anti-CD3 mAb OKT3 (5 μg/mL) for 5 min. before lysis and analysis.
Figure 36:
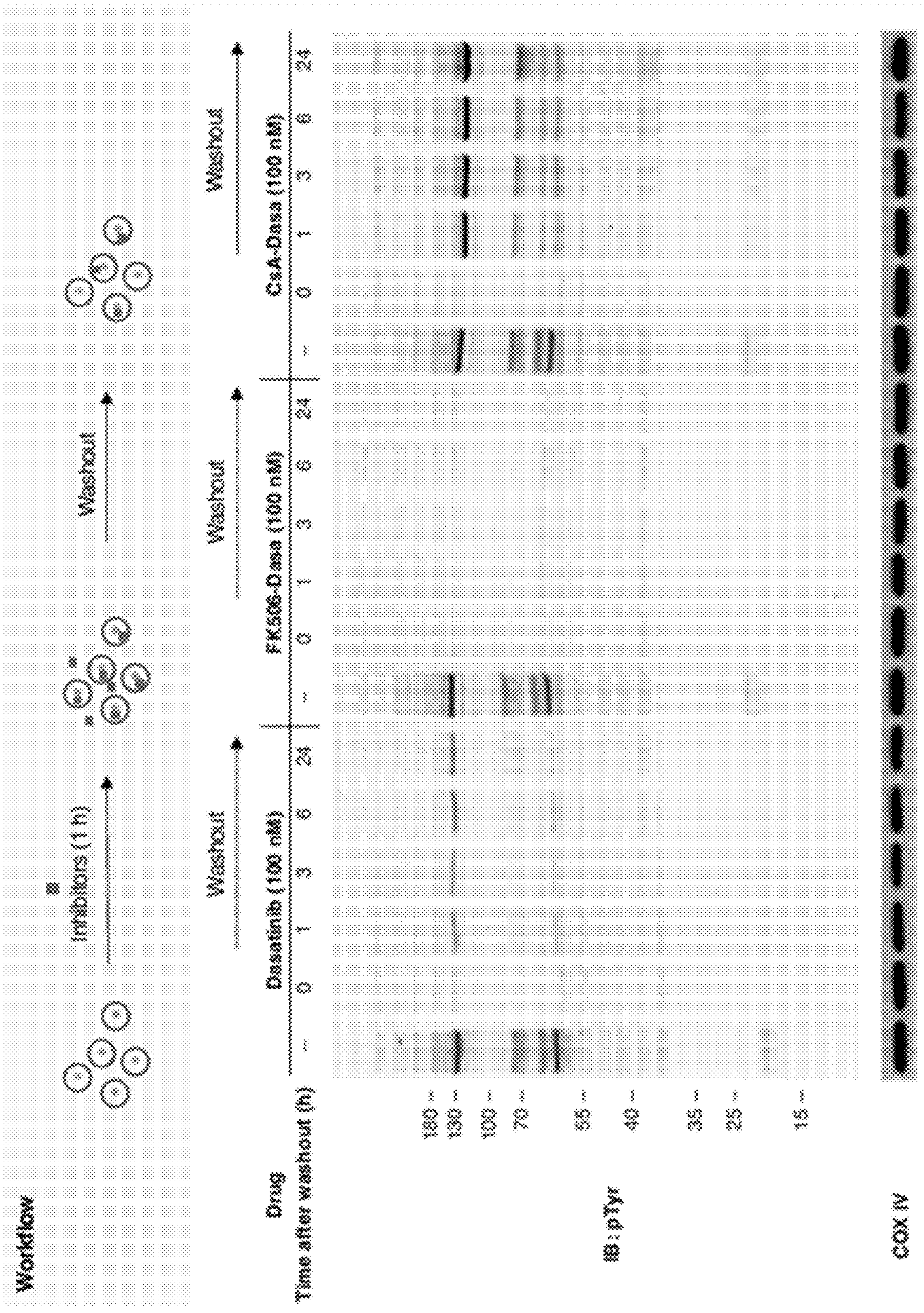
FIG. 36. Effect of ZZY05-022 is durable after washout. Jurkat cells ($1\times10^6$/mL) were treated with 100 nM of the indicated compounds for 1 h, then were washed 3 times with PBS and resuspended in culture media. Samples were taken at the indicated time points and lysed immediately.
Figure 37:
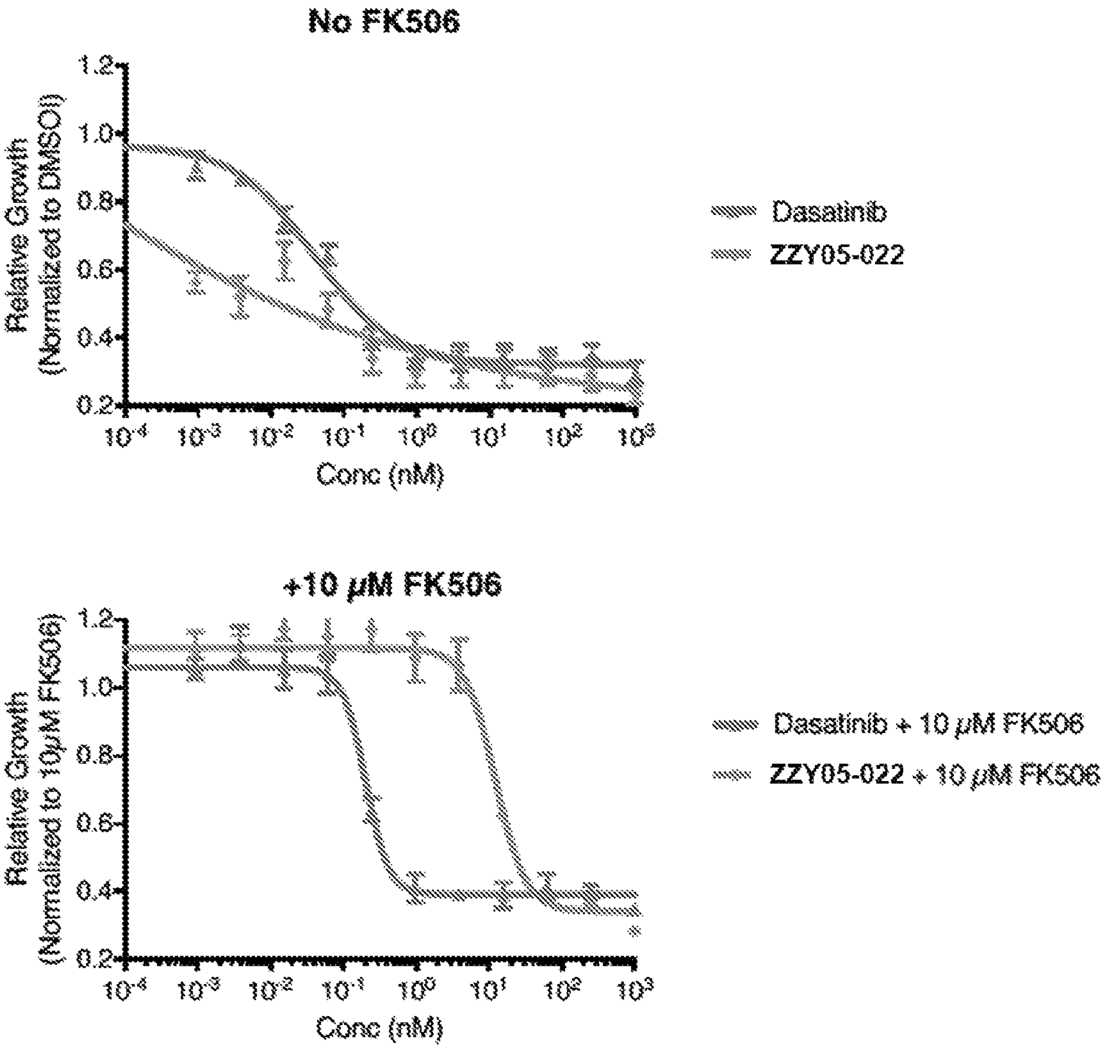
FIG. 37. ZZY05-022 shows FKBP-dependent growth inhibition of Bcr-Abl Cell Line. K562 (seeding density $5\times10^4$/mL) cells, 72 h treatment.
Figure 39:
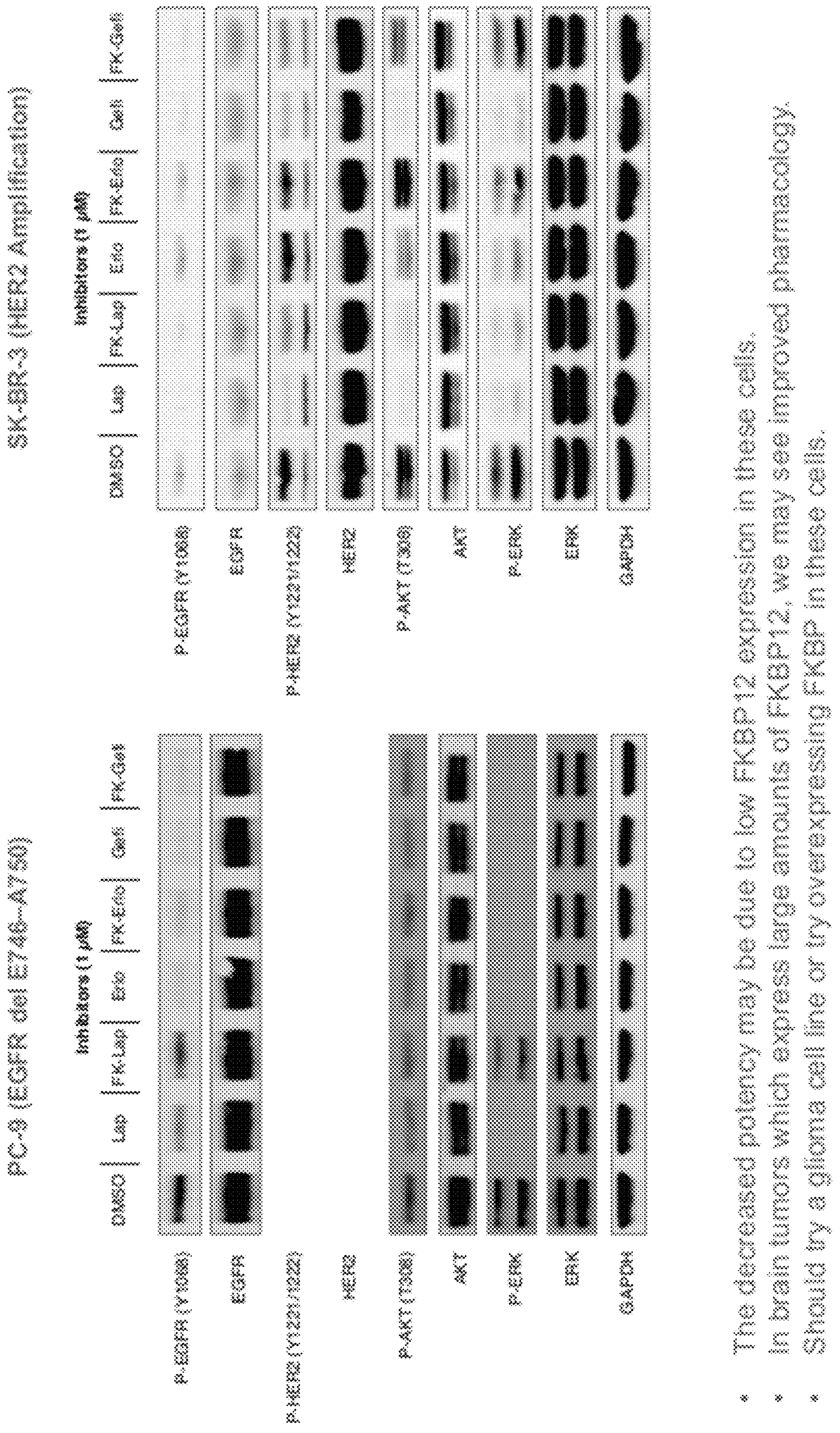
FIG. 39. FK506-EGFRi displays similar pharmacology to parent inhibitor, albeit slightly less polar. PC-9 or SK-BR-3 cells, 4 h treatment.
Figure 40:
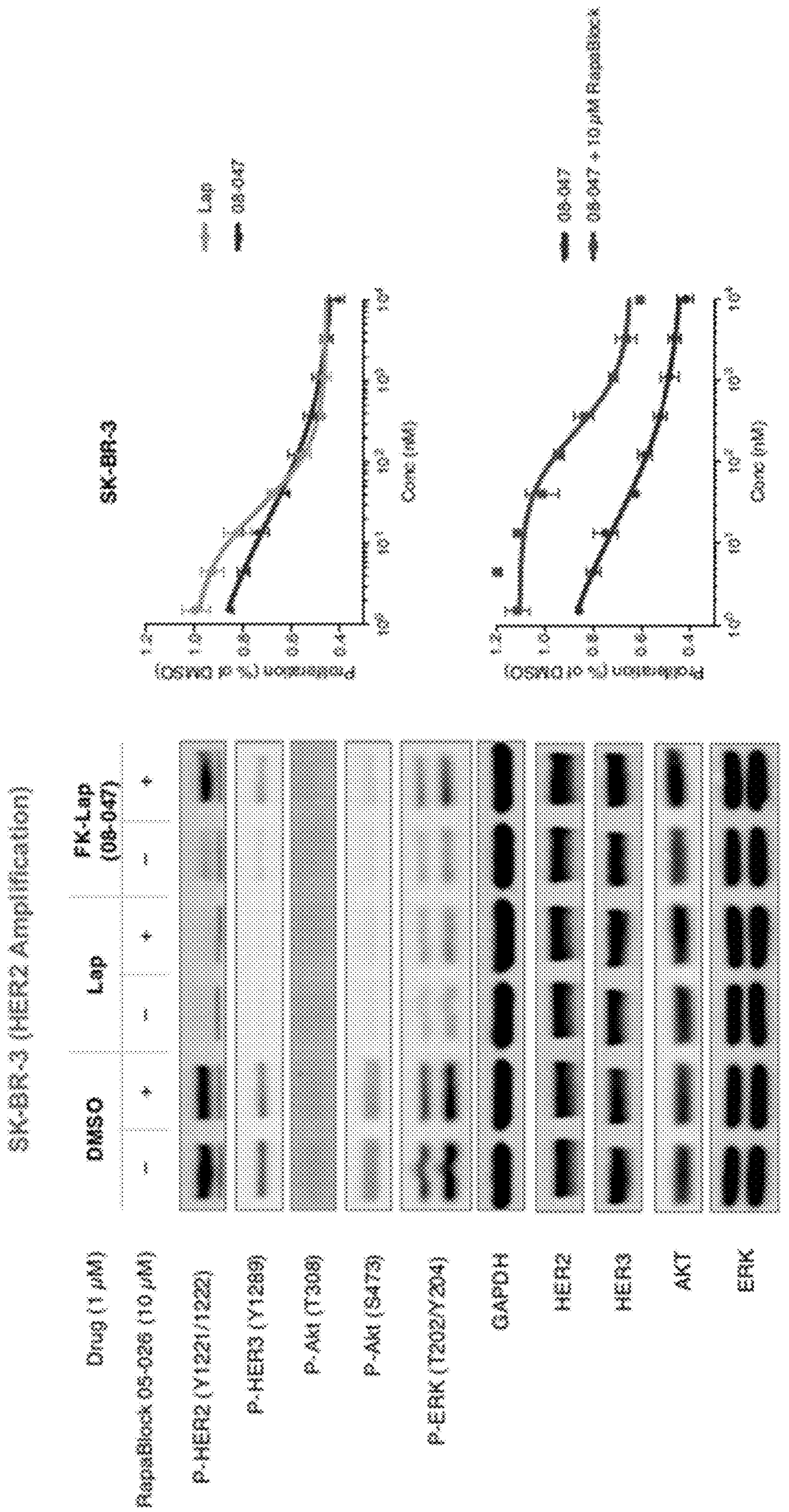
FIG. 40. The inhibitory effects of FK506-EGFRi is dependent on FKBP12, and is reversed by RapaBlock.
Figure 42:
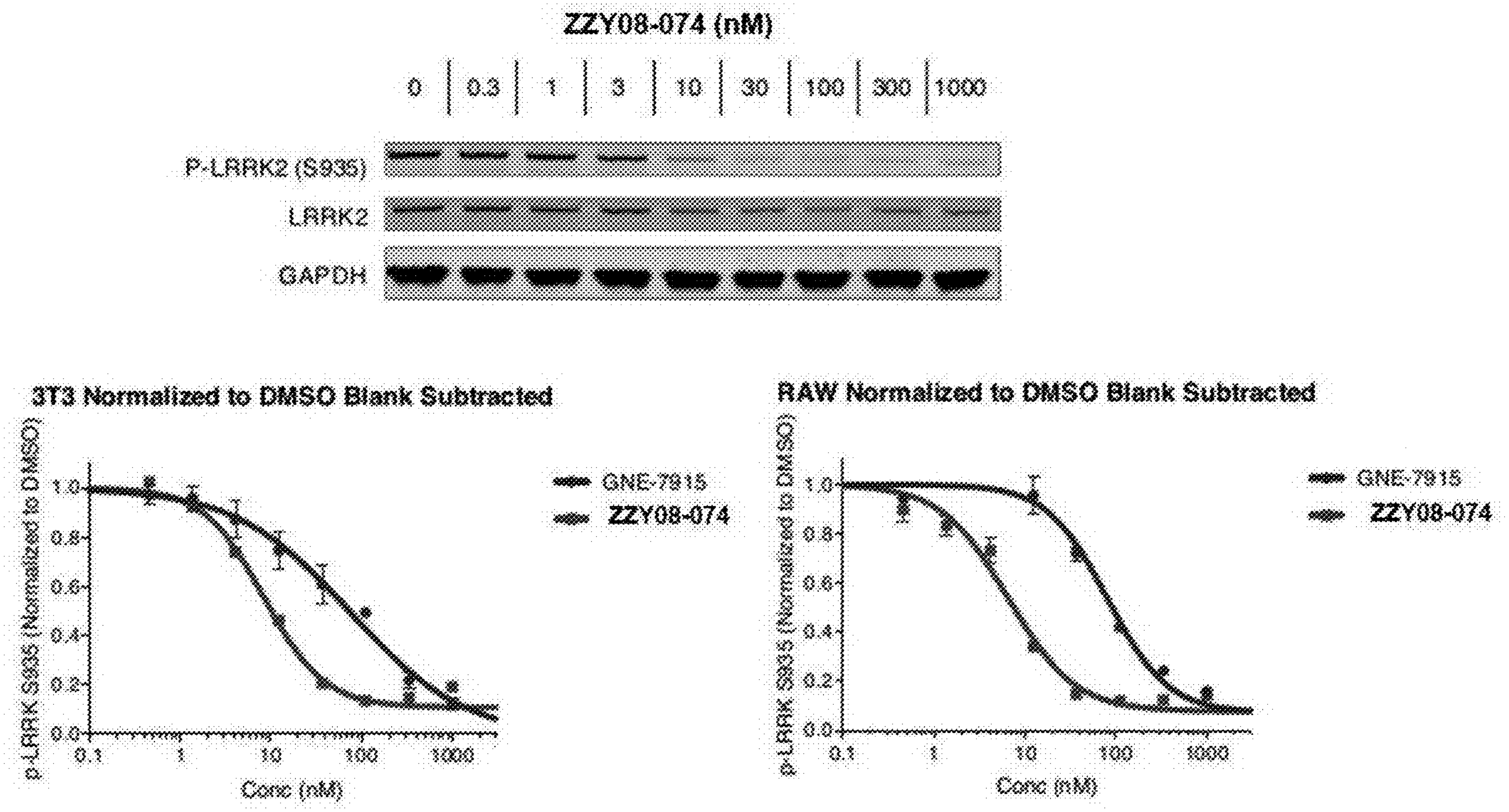
FIG. 42. Compound ZZY08-074 demonstrates more potent cellular activity than its parent compound GNE-7915. 3T3 or RAW264.7 cells (MJFF cell line), 2 h treatment.
Figure 43:
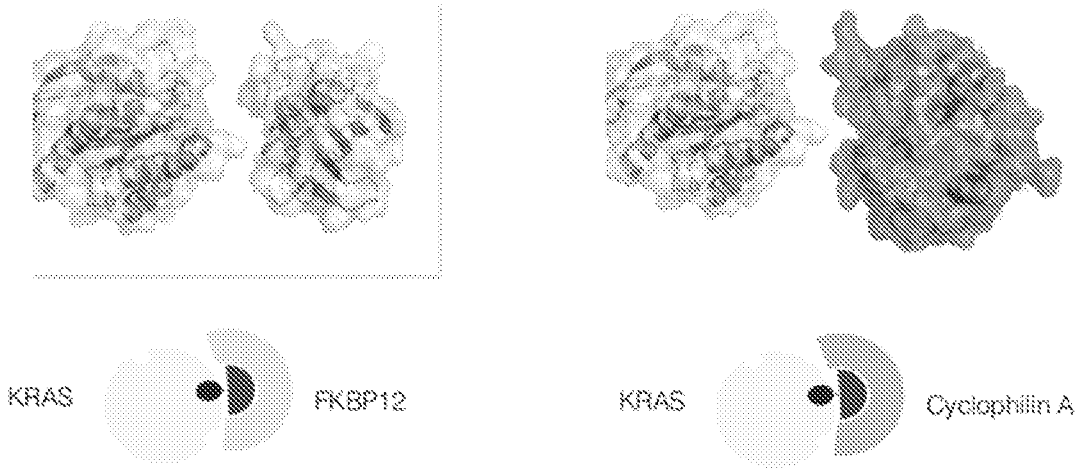
FIG. 43. Dimerizing KRAS and immunophilins.
Figure 44:
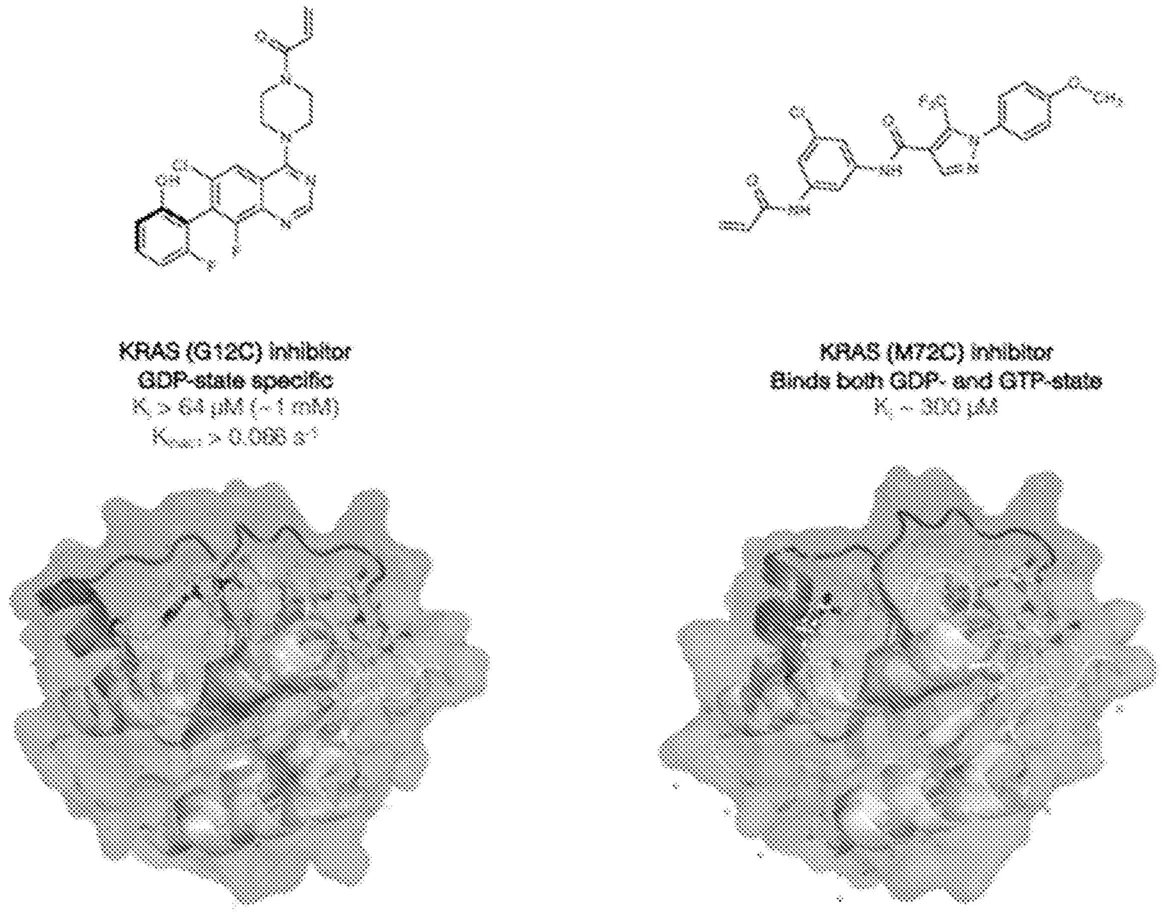
FIG. 44. KRAS Inhibitors.
Figure 45:
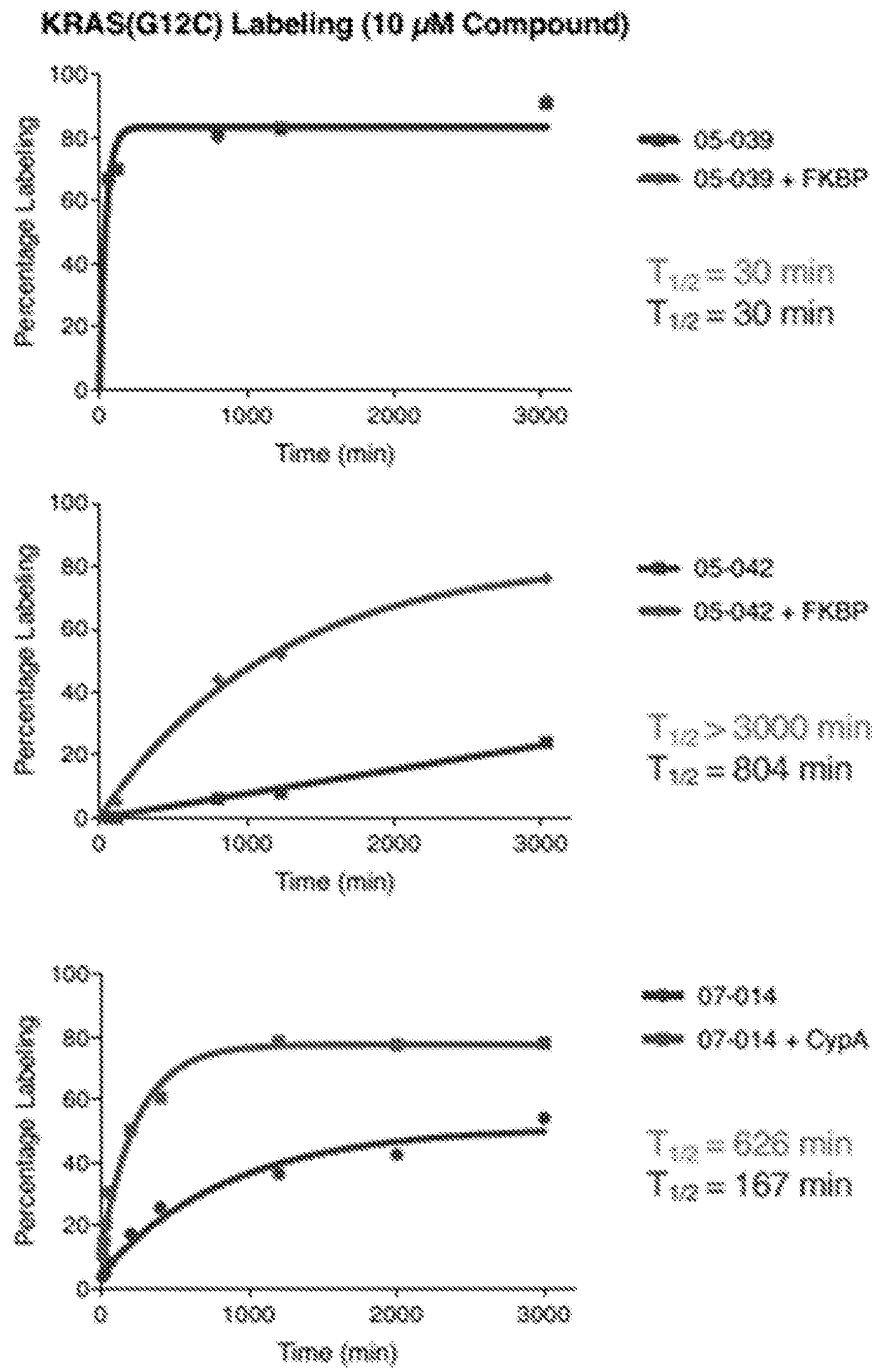
FIG. 45. Immunophilins accelerate the reaction between $KRAS^{G12C}$ and hybrid ligands. Assay conditions: 4 μM K-Ras+10 μM immunophilin (if indicated)+10 μM Compound; 20 nM HEPES 7.5, 150 mM NaCl, 1 mM $MgCl_2$, 23° C., 1% DMSO. Percentage labeled was measured by LC-MS analysis of the reaction mixture.
Figure 47:
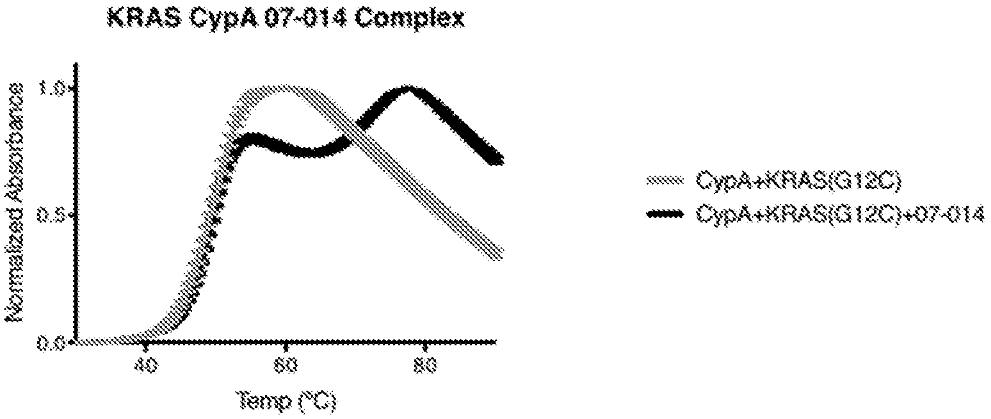
FIG. 47. The KRAS•CypA•ZZY07-014 complex displays 2-stage melting curve.
Figure 48:
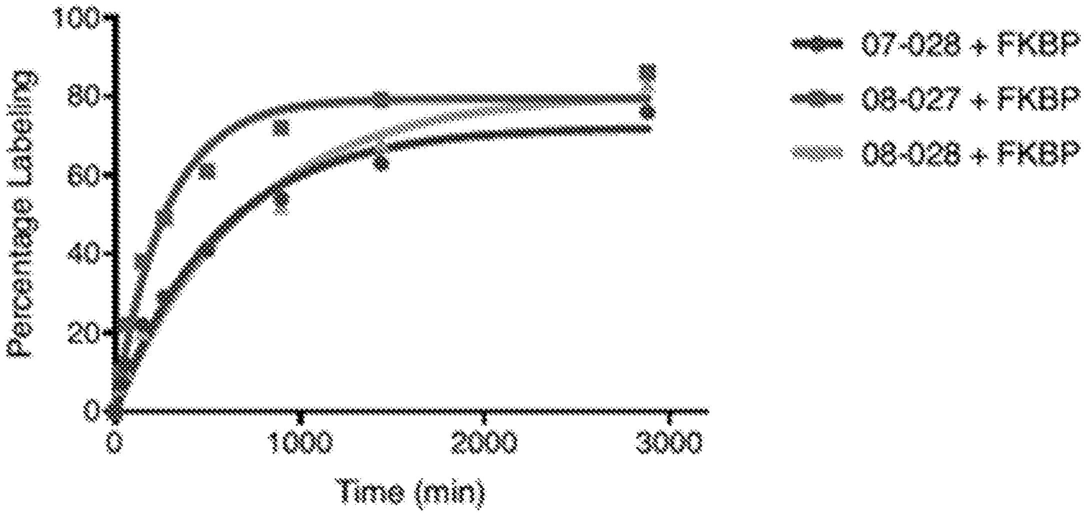
FIG. 48. Limited linker chemistry improves reaction kinetics. Assay conditions: 4 μM K-Ras+10 μM immunophilin (if indicated)+10 μM Compound; 20 nM HEPES 7.5, 150 mM NaCl, 1 mM $MgCl_2$, 23° C., 1% DMSO.
Figure 49:
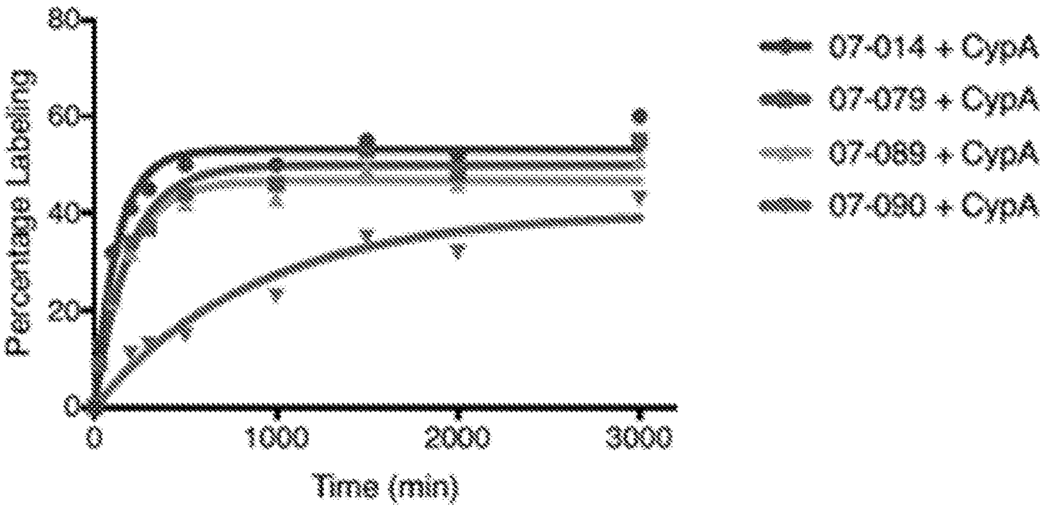
FIG. 49. Changing the linker. Assay conditions: 4 μM K-Ras+10 μM immunophilin (if indicated)+10 μM Compound; 20 nM HEPES 7.5, 150 mM NaCl, 1 mM $MgCl_2$, 23° C., 1% DMSO.
Figure 50:
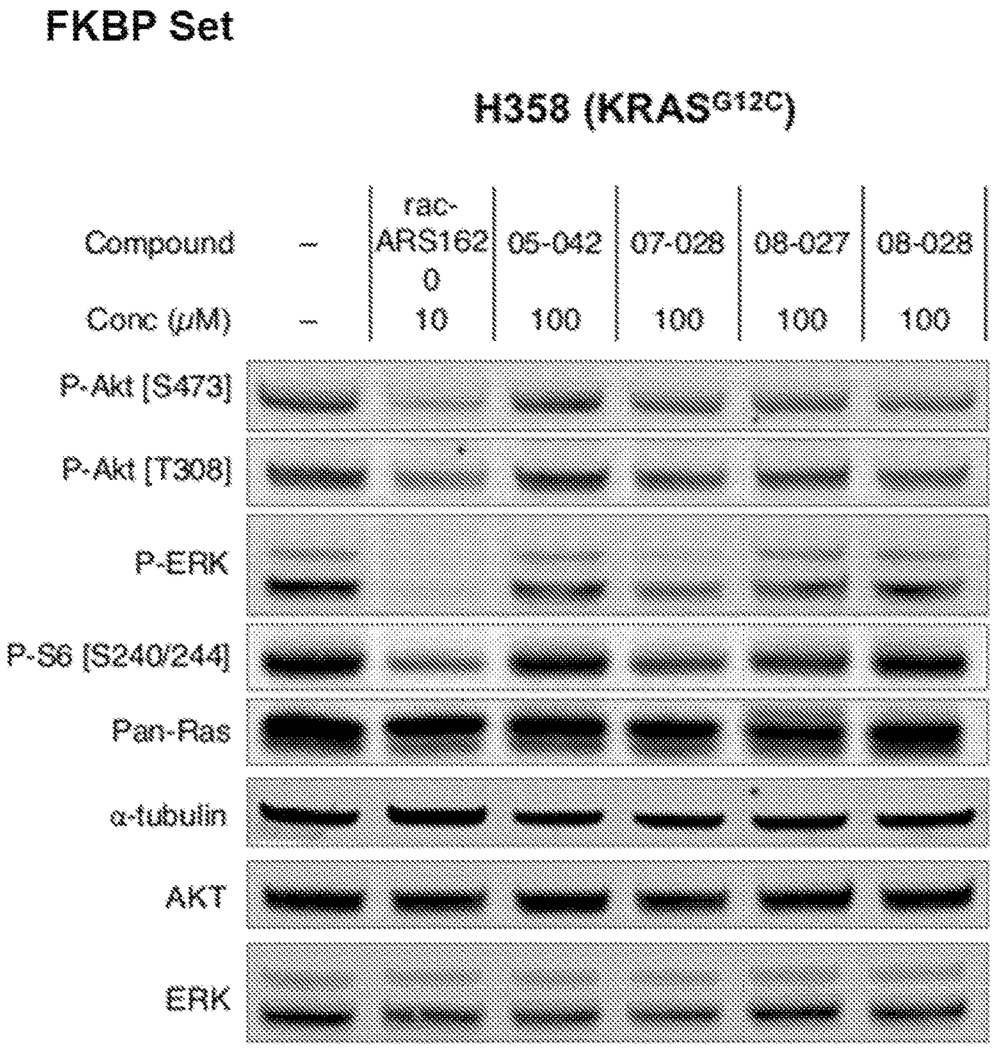
FIG. 50. Cellular efficacy, 24 h.
Figure 51:
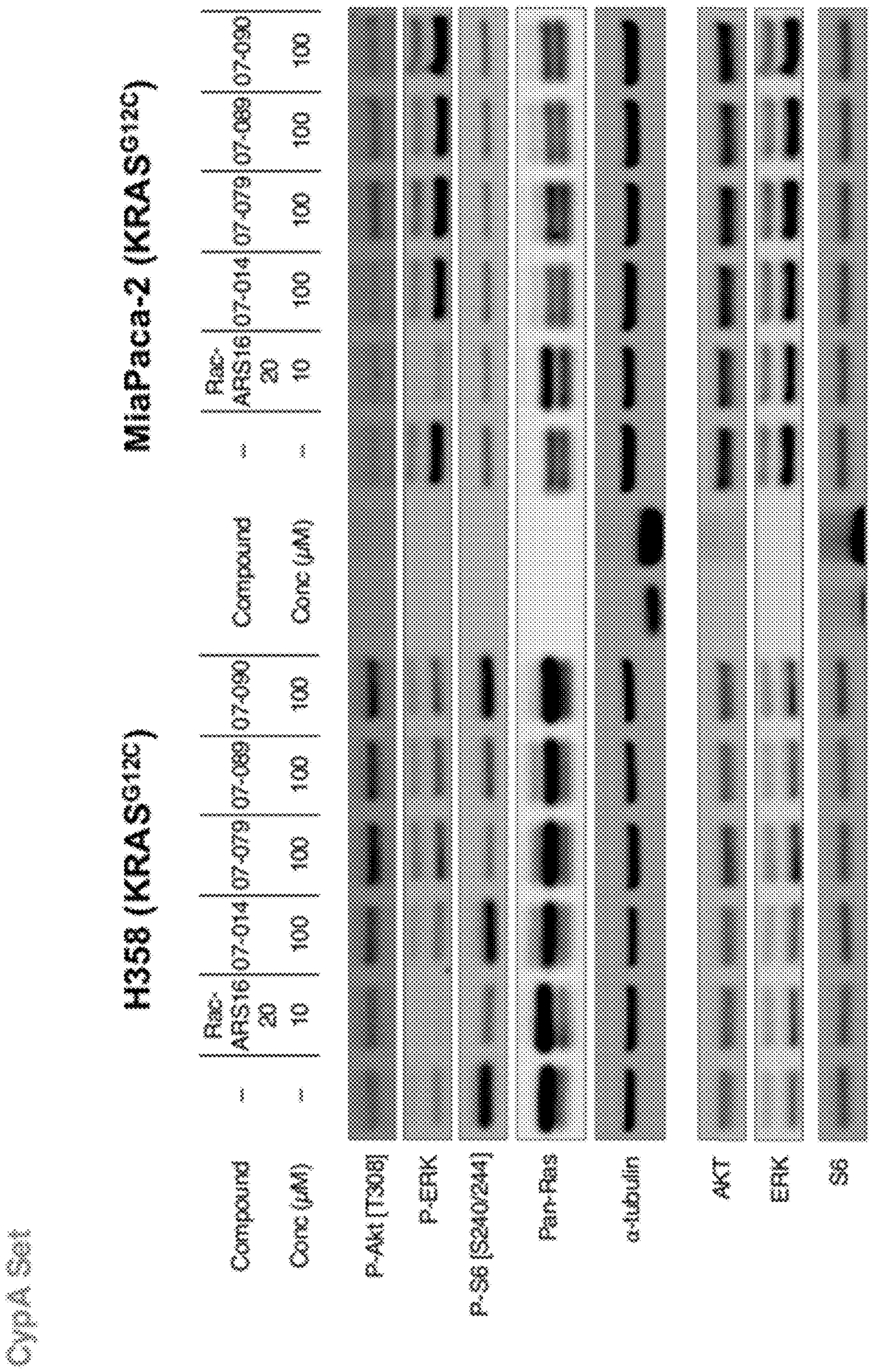
FIG. 51. Cellular efficacy, 24 h.
Figure 52:
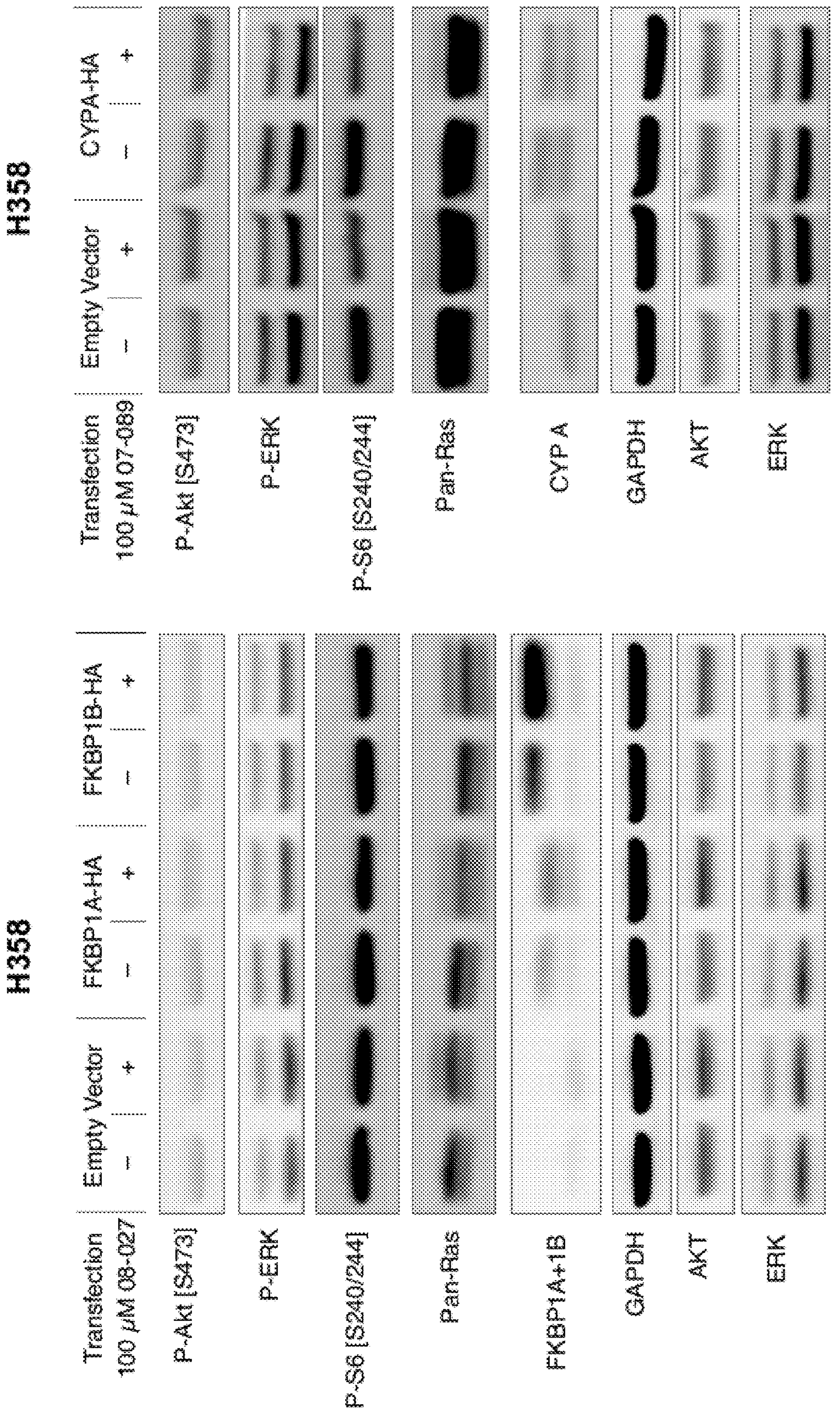
FIG. 52. Overexpression of either FKBP or CypA did not improve cellular efficacy. H358 cells, treated with inhibitors for another 24 h, 24 h post-transfection.
Figure 54:
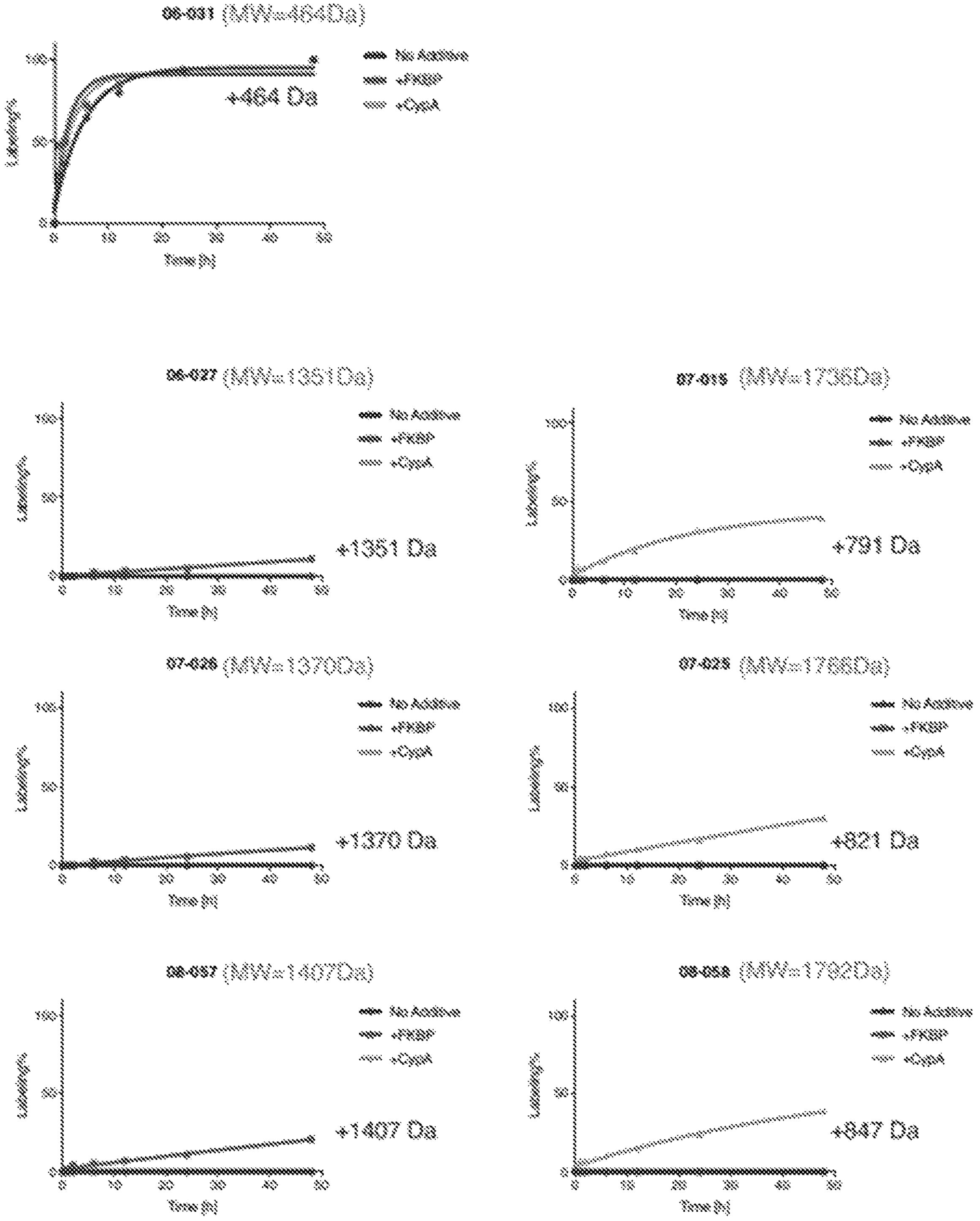
FIG. 54. Molecules built on the M72C inhibitor scaffold display similar dependence on immunophilins. Assay conditions: 4 μM H-Ras M72C (GDP)+10 μM immunophilin (if indicated)+10 μM Compound; 20 nM HEPES 7.5, 150 mM NaCl, 1 mM $MgCl_2$, 23° C., 1% DMSO.
Figure 56:
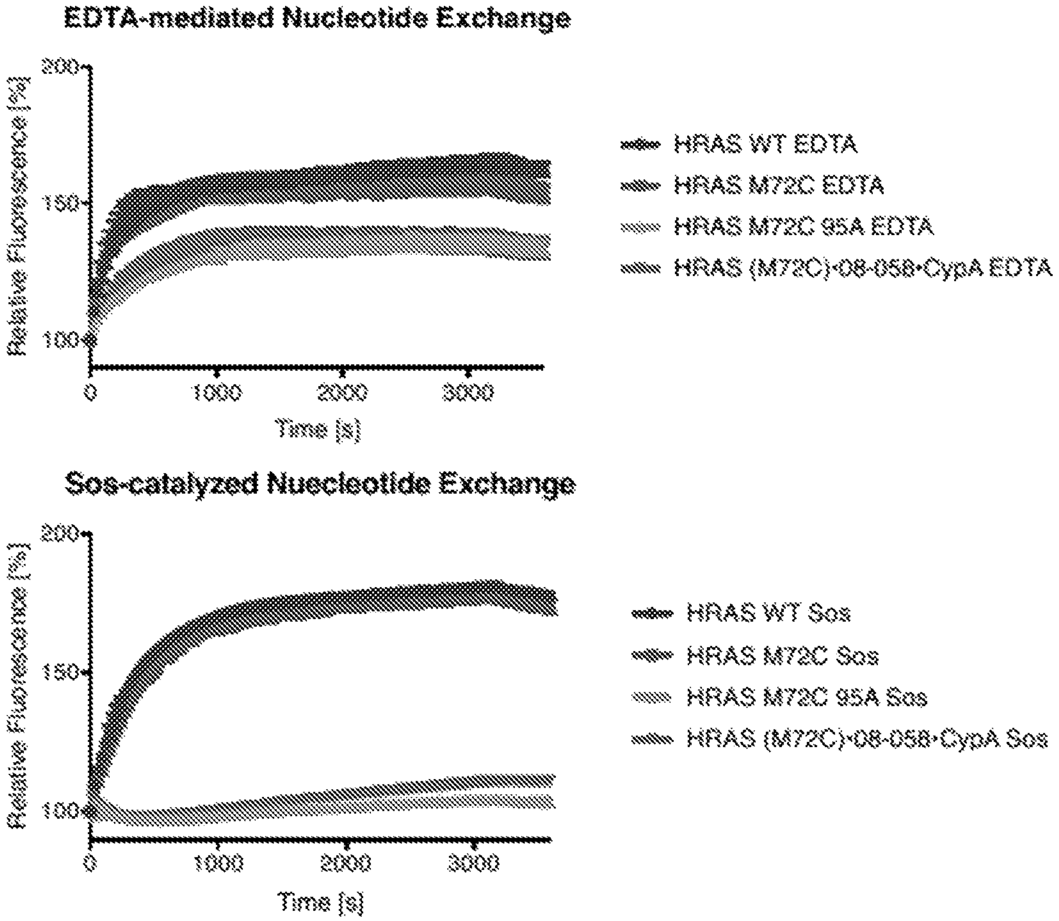
FIG. 56. HRAS•CypA•ZZY08-058 forms a ternary complex, and inhibits Sos-mediated nucleotide exchange. Assay conditions: 1 μM Ras•GDP, 1 μM Mant-GDP, 20 mM EPES 7.5, 150 mM NaCl, 10 mM EDTA or 1 μM Sos. 95 A is synonymous to ZZY06-031.
Figure 57:
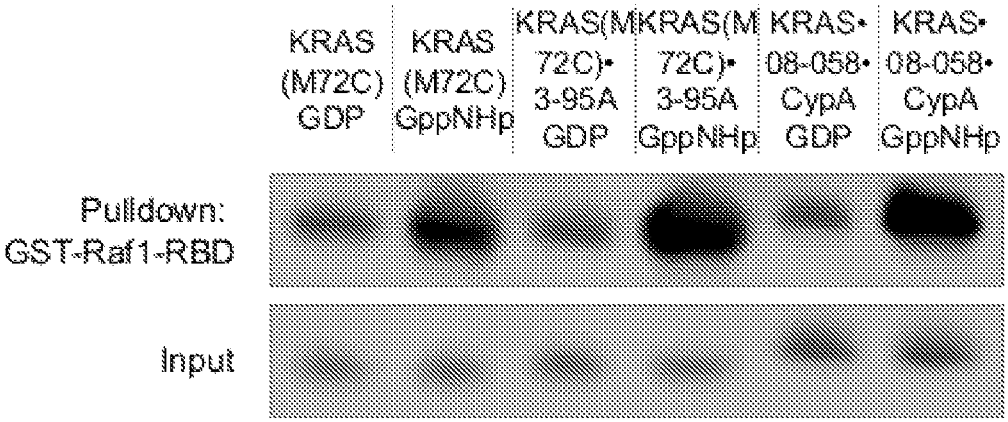
FIG. 57. HRAS•CypA•08-058 ternary complex does not seem to impair Ras*Raf binding. Pulldown conditions: 100 nM KRAS, 50 μg/mLBSA, 20 mM HEPES 7.5, 150 mM NaCl, 5 mM $MgCl_2$, 1 mM DDT, 1% NP-40. GppNHp loaded proteins were prepared by EDTA-mediated nucleotide exchange.
Figure 59:
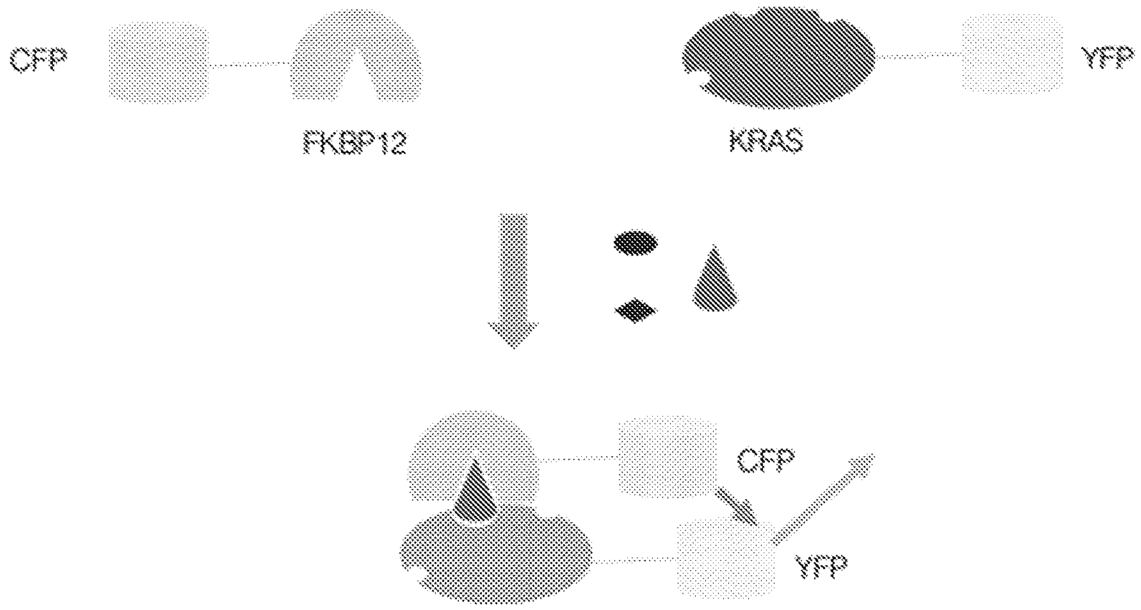
FIG. 59. Screening novel "dimerizers".

To evaluate the efficacy of FK506-Dasatinib in cells, we studied its effect on CD3 crosslinking-triggered T cell activation. Src family kinases, notably Lek and Fyn, are key regulators of T cell receptor (TCR) signal transduction, and dasatinib is known to block T cell activation by inhibiting these kinases. We stimulated Jurkat cells with an anti-CD3 monoclonal antibody (OKT3) in the presence of dasatinib or FK506-dasatinib and monitored their activation by Western blot. At 100 nM, both dasatinib and FK506-dasatinib dampened the of total phospho-tyrosine level and suppressed the phosphorylation of several proteins involved in TCR signaling including Src-family kinases, PLCgamma1, ZAP70 and LAT (FIG. 16A). Interestingly, three homodimers of dasatinib containing linkers of various length (FIG. 19A) had no measurable inhibition of phosphotyrosine signal. FK506-dasatinib was effective at concentrations as low as 10 nM ($EC_{50}$=3.4 nM, FIG. 16C). To profile the target scope of FK506-dasatinib in live cells, we employed a lysine-targeted chemoproteomic probe XO44, which irreversibly reacts with a conserved lysine in the ATP pocket of kinases and allows the quantification of the occupancy of the intracellular kinome by inhibitors by label-free mass spectrometry. We found that with both dasatinib and FK506-dasatinib at 100 nM, an identical set of 9 kinases were inhibited >70% (FIG. 16B and FIG. 20) among the 139 kinases captured by the probe. This is consistent with previous knowledge of dasatinib as well as our findings in the biochemical profiling with purified kinases. That the selectivity of FK506-dasatinib was indistinguishable from dasatinib was not surprising—none of kinases displaying differential response to the two inhibitors in the biochemical assay (FIG. 14C) were highly expressed in Jurkat cells or detected by the XO44 probe. Notwithstanding, one remarkable distinction of FK506-dasatinib from dasatinib we observed was its prolonged residence time in cells. We measured the change of phosphotyrosine levels at various timepoints after treating Jurkat cells with 100 nM dasatinib or FK506-dasatinib for 1 h and removing the drug (FIG. 16D). Restored phosphotyrosine bands were seen at as early as 1 h in dasatinib-treated cells. By contrast, no increase in phosphotyrosine signals could be detected even at 24 h after the drug washout in FK506-dasatinib-treated cells, suggesting a mechanism that supports durable cellular retention of the drug. Unusually long cellular retention times have also been previously observed with other drugs that engage FKBP proteins. We believe that in these cases, the abundant intracellular FKBP proteins serve as a sink for these drugs, capturing them as in a FKBP-drug complex that cannot cross the plasma membrane to exit the cell and hence significantly lengthening their residence inside the cell.

Figure 13A:
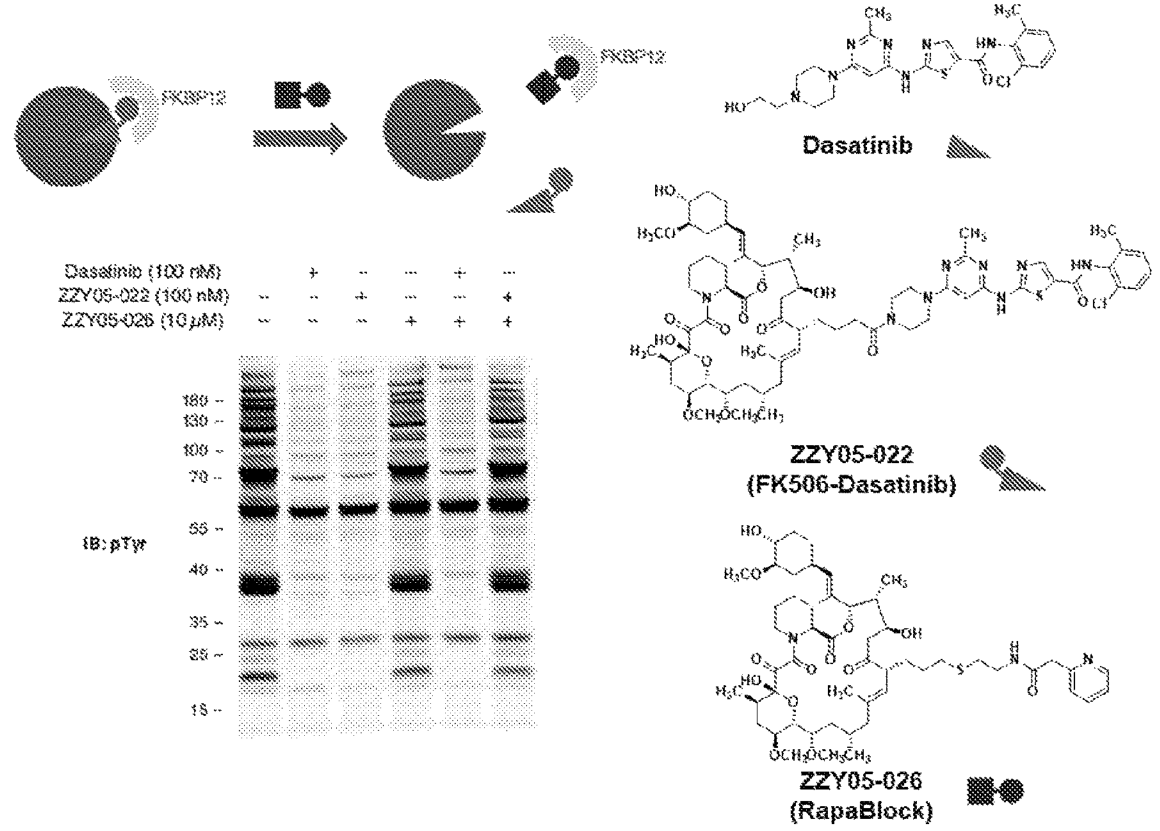
FIGS. 13A-13B. FK506-Dasatinib is a programmable kinase inhibitor whose activity can be attenuated by a competing FKBP ligand (RapaBlock).
Figure 13B:
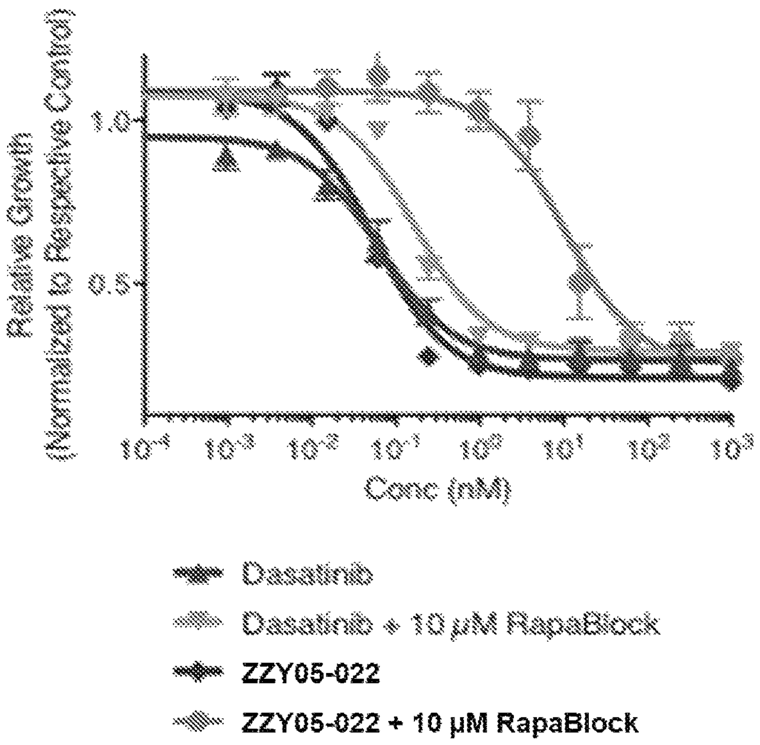

The unique dependency of FK506-dasatinib on FKBP proteins implied that it may be exploited to modulate the function of these molecules. We reasoned that if FK506-dasatinib is co-administered with another ligand of FKBP ("blocker"), the latter would attenuate the activity FK506-dasatinib by competing for the intracellular pool of FKBP. We chose RapaBlock, a non-immunosuppressive FK506 analog developed in our lab that maintains potent binding to FKBP12 ($K_d$=3.7 nM), as the blocker molecule. When a combination of 100 nM FK506-dasatinib and 10 μM RapaBlock were used in the Jurkat cell activation assay, the inhibition of phosphotyrosine signaling by FK506-dasatinib was completely neutralized (FIG. 13A, lanes 3 and 6). Meanwhile, the blocker compound had no in dasatinib-treated samples (FIG. 13A, lanes 2 and 5). In a separate application, we measured growth inhibition of K562 cells, a Bcr-Abl-driven cell lines sensitive to dasatinib treatment (FIG. 13B). Absent ZZY05-026, dasatinib and FK506-dasatinib inhibited the growth of K562 cells with comparable potency ($IC_{50}$ of 0.063 nM and 0.053 nM, respectively). Addition of 10 μM RapaBlock caused a >200-fold increase of the $IC_{50}$ value for FK506-Dasatinib (10.2 nM), in contrast to the minute shift of $IC_{50}$ for dasatinib (0.16 nM).

Figure 17B:
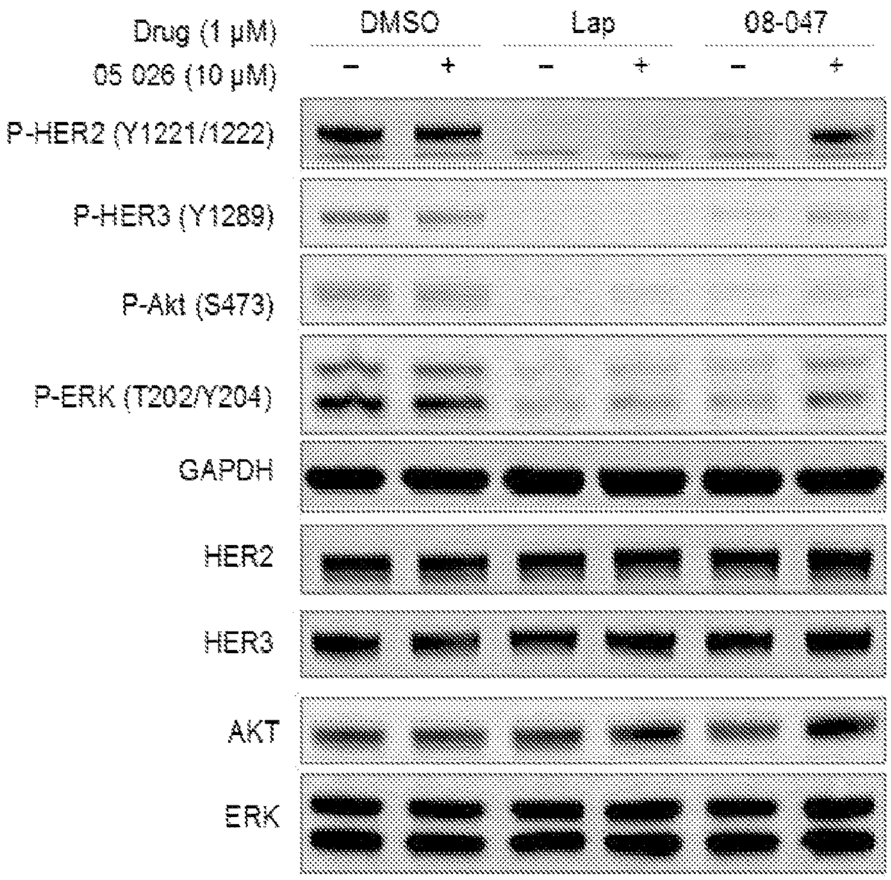
Figure 17C:
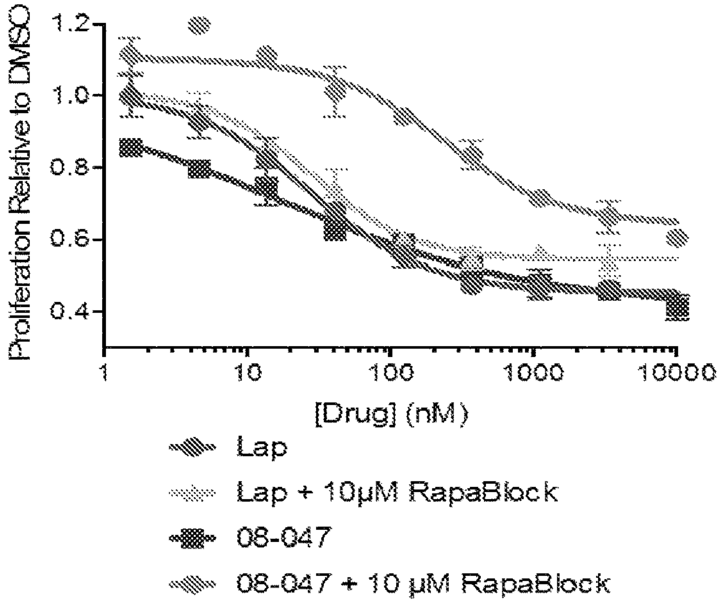
Figure 17F:
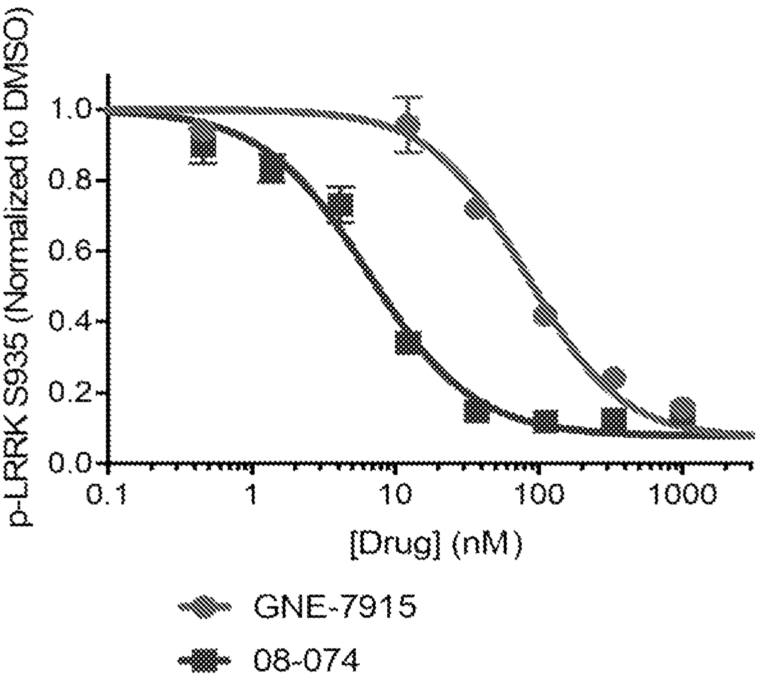
Figure 18:
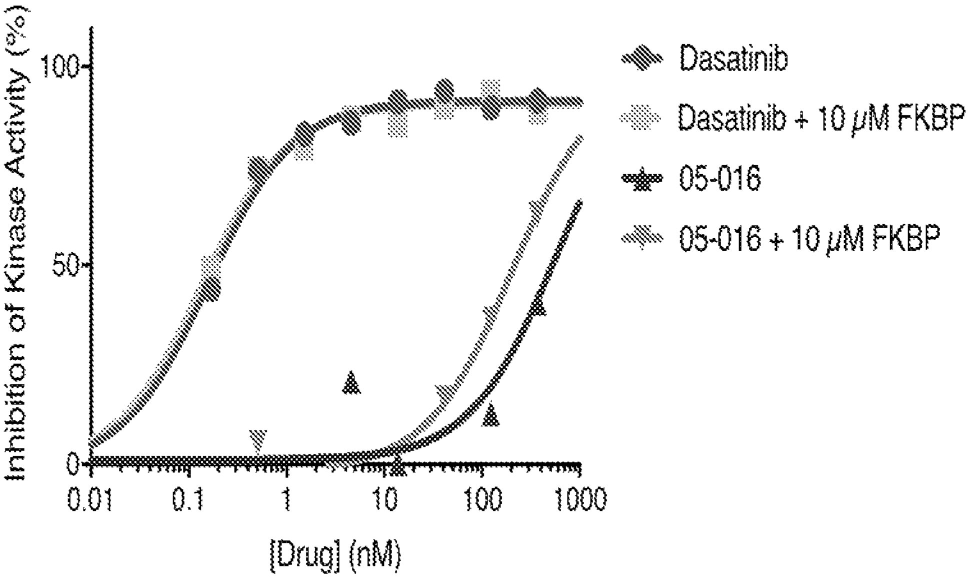
FIG. 18. A bispecific molecule built from Dasatinib and a different FKBP ligand (SLF) shows greatly diminished activity.

We extended our design strategy and prepared two other bispecific ligands based on the structures of an FDA-approved HER2/EGFR inhibitor (lapatinib) and an LRRK2 inhibitor in clinical development (GNE7915). FK506-lapatinib suppressed HER2 signaling in SK-BR-3 cells (a cell line with HER2-amplification) at 1 μM and inhibited the growth of this cell line with an $IC_{50}$ comparable to that of lapatinib (FIGS. 17A-17C). Both effects were attenuated by the addition of 10 μM RapaBlock. Interestingly, FK506-GNE7915 appeared to be more efficacious than its parent molecule GNE7915 at inhibiting the autophosphorylation of LRRK2, a kinase currently pursued as a promising therapeutic target for Parkinson's disease. Similar to the cases of FK506-dasatinib and FK506-lapatinib, RapaBlock rescued the inhibition of LRRK2 phosphorylation by FK506-GNE7915 to a near-baseline level. With the three case studies presented above, we anticipate that the same workflow could be applied to convert other kinase inhibitors into FKBP-dependent formats with similar if not better cellular activities, with the important recognition that exceptions may occur as in the case with FK506-Dasatinib/DDR2.

By chemically linking FK506 and ATP-site kinase inhibitors at their respective solvent-exposed sites, we have developed a method to build a new class of kinase inhibitors whose activity depends on an endogenous protein, FKBP12. These inhibitors are characterized by their ability to mediate the formation of a ternary complex of the drug, the target kinase and FKBP12, as well as their aptitude for activity modulation by another ligand of FKBP12. De novo complex formation has been exploited by nature as a strategy to create highly specific bioactive compounds, with notable examples including rapamycin (mTOR inhibitor), FK506 (calcineurin inhibitor), cyclosporin A (calcineurin inhibitor) and sanglifehrin (IMPDH2 inhibitor). Medicinal chemistry innovations have led to compounds with improved pharmaceutical property or efficacy (e.g., the third-generation mTOR inhibitor RapaLink-1), yet with the same target as the parent natural inhibitor. Our method expands the targetable space by this mode of action far beyond those addressed by known natural products. The amenability of these bispecific kinase inhibitors towards activity modulation by a second molecule is unique and offers an additional dimension of pharmacological control. In theory, timed administration of the blocker molecule or using blocker molecules that have defined tissue distribution will allow us to choreograph the temporal and spatial effects of the inhibitor and achieve programmable kinase inhibition. While we have focused on protein kinases in this study, it seems reasonable to expect that the approach is also applicable to other classes of therapeutic targets, such as GTPases and histone modification enzymes.

Example 5: Immunophilin-Dependent Inhibitor Compounds

TABLE 6

Compound structures of EGFR analogs.

| Compound | Structure |
|---|---|
| ZZY07-057 | 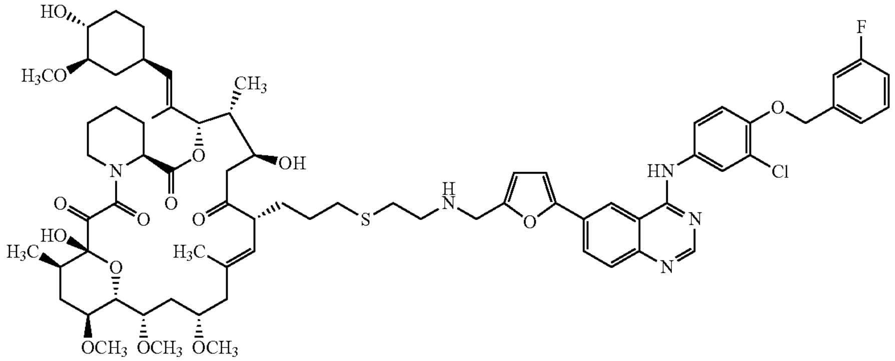 [SMILES: CO[C@H]1C/C(C)=C/[C@@H](CCCSCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |
| ZZY07-058 | 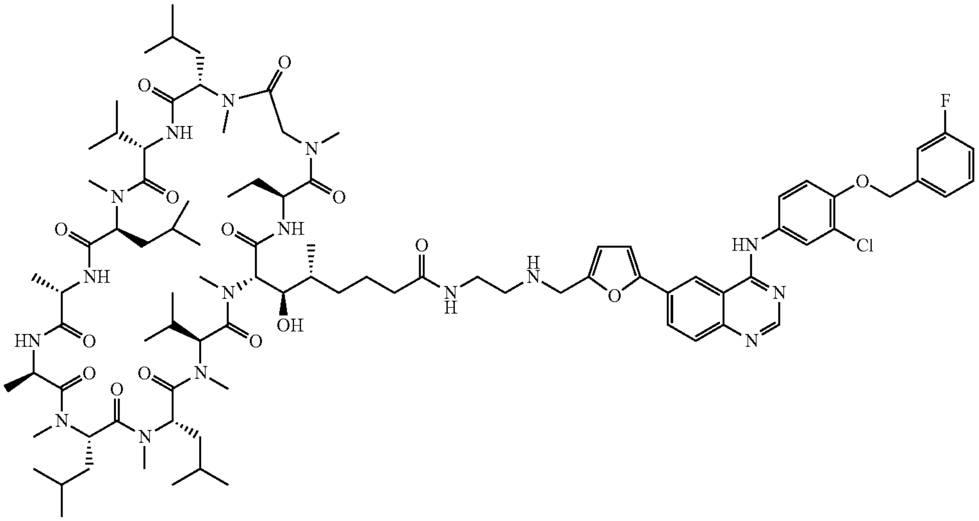 [SMILES: CC[C@@H]1NC(=O)[C@H]([C@H](O)[C@H](C)CCCC(=O)NCCNCc2ccc(-c3ccc4ncnc(Nc5ccc(OCc6cccc(F)c6)c(Cl)c5)c4c3)o2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O] |

TABLE 6-continued
| Compound structures of EGFR analogs. | |
|---|---|
| Compound | Structure |
| ZZY08-025 | 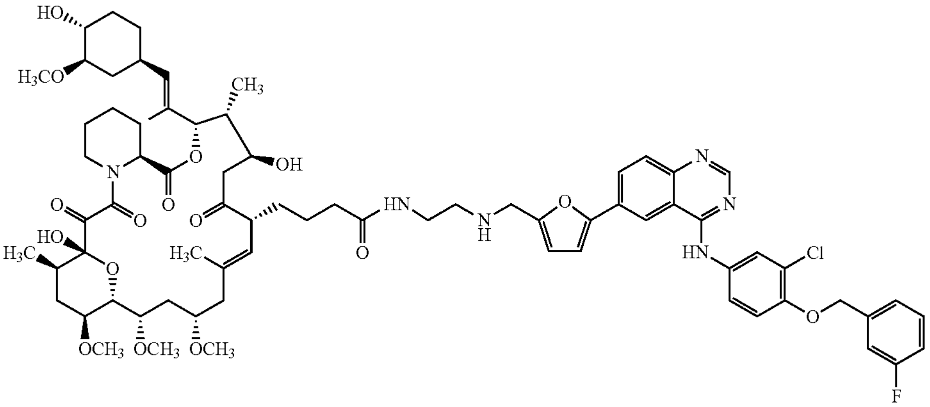 [SMILES: CO[C@H]1C/C(C)=C/[C@@H](CCCC(=O)NCCNCc2ccc(-c3ccc4ncnc(Nc5ccc(OCc6cccc(F)c6)c(Cl)c5)c4c3)o2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |
| ZZY08-047 | 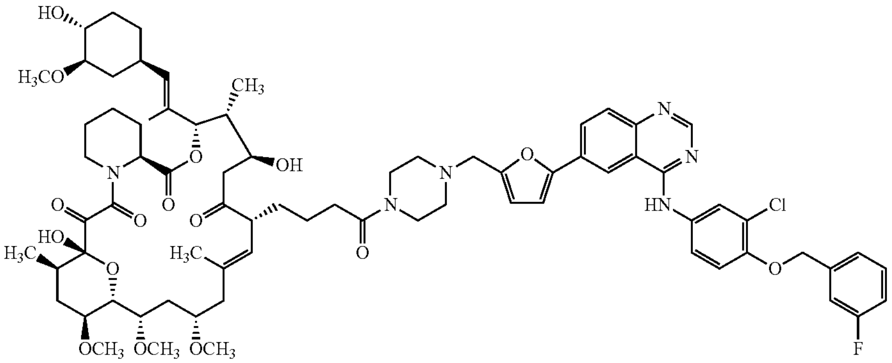 [SMILES: CO[C@H]1C/C(C)=C/[C@@H](CCCC(=O)N2CCN(Cc3ccc(-c4ccc5ncnc(Nc6ccc(OCc7cccc(F)c7)c(Cl)c6)c5c4)o3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |
| ZZY08-068 | 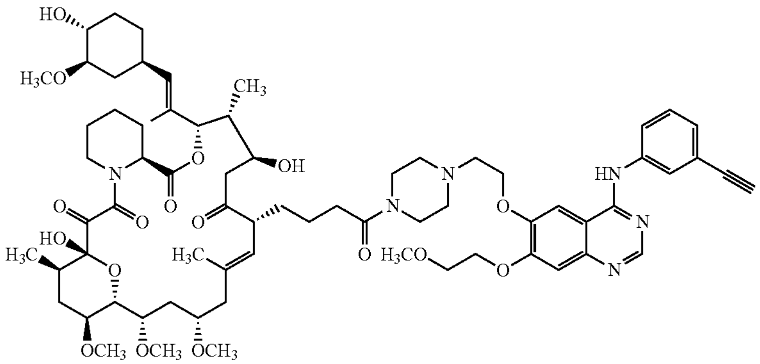 [SMILES: C#Cc1cccc(Nc2ncnc3cc(OCCOC)c(OCCN4CCN(C(=O)CCC[C@@H]5/C=C(\C)C[C@H](OC)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc23)c1] |
| ZZY08-069 | 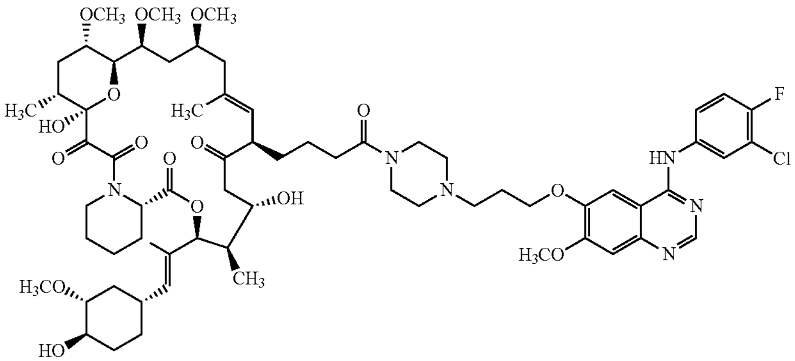 [SMILES: COc1cc2ncnc(Nc3ccc(F)c(Cl)c3)c2cc1OCCCN1CCN(C(=O)CCC[C@@H]2/C=C(\C)C[C@H](OC)C[C@H](OC)[C@H]3O[C@@](O)(C(=O)C(=O)N4CCCC[C@H]4C(=O)O[C@H](/C(C)=C/[C@@H]4CC[C@@H](O)[C@H](OC)C4)[C@H](C)[C@@H](O)CC2=O)[C@H](C)C[C@@H]3OC)CC1] |

TABLE 7
| Compound structures of LRRK analogs. | |
|---|---|
| Compound | Structure |
| ZZY08-074 | 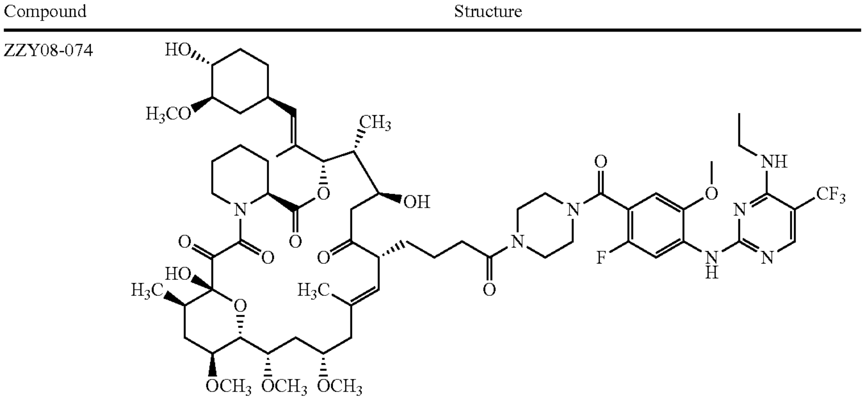 |
TABLE 8
| Compound structures of KRAS analogs. | |
|---|---|
| Compound | Structure |
| ZZY06-027 | 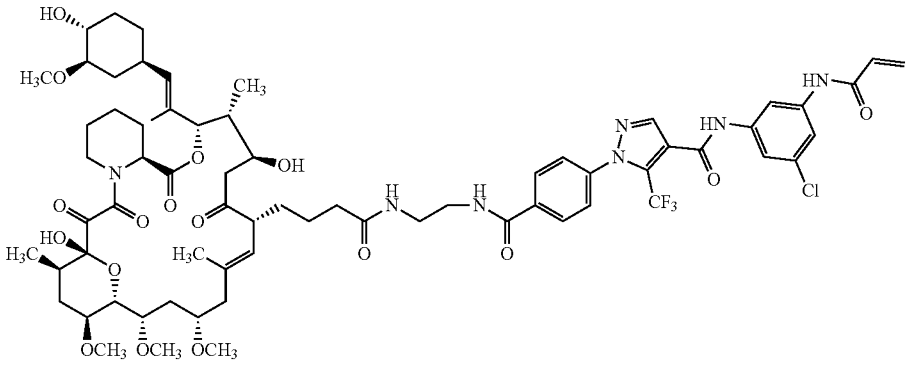 [SMILES: C=CC(=O)Nc1cc(Cl)cc(NC(=O)c2cnn(-c3ccc(C(=O)NCCNC(=O)CCC[C@@H]4/C=C(\C)C[C@H](OC)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1] |
| ZZY07-015 | 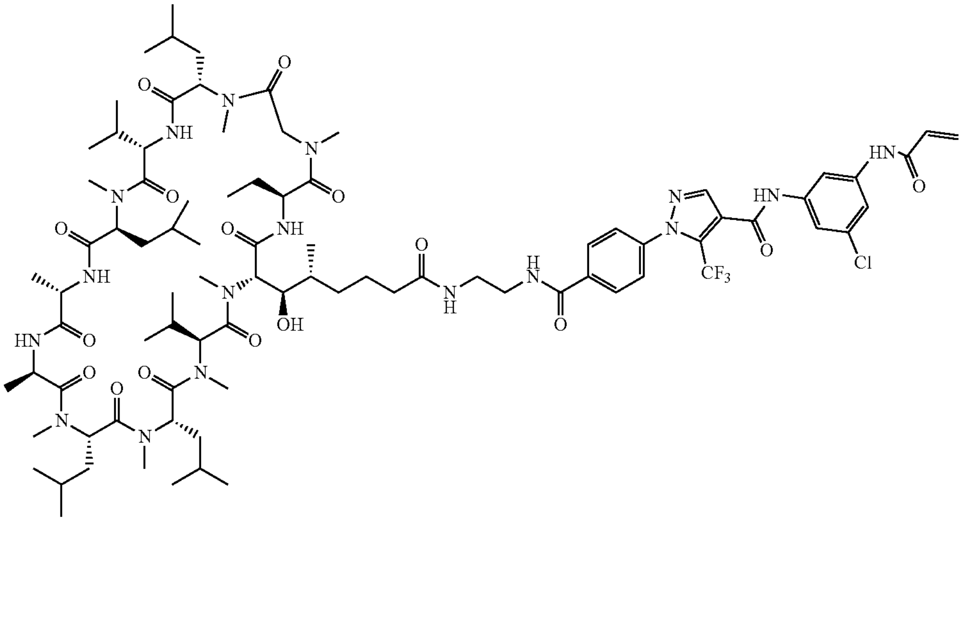 [SMILES: C=CC(=O)Nc1cc(Cl)cc(NC(=O)c2cnn(-c3ccc(C(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1] |

TABLE 8-continued
| Compound structures of KRAS analogs. | |
|---|---|
| Compound | Structure |
| ZZY07-025 | 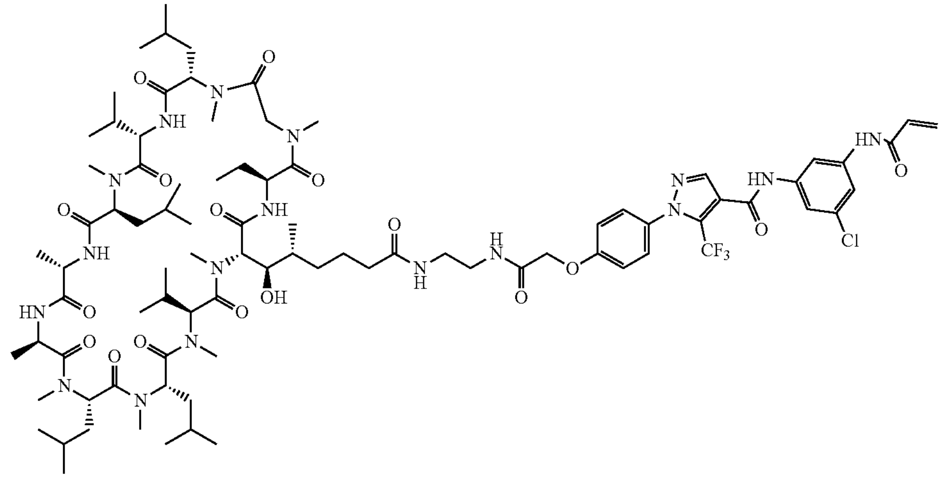 [SMILES: C=CC(=O)Nc1cc(Cl)cc(NC(=O)c2cnn(-c3ccc(OCC(=O)NCCNC(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)cc3)c2C(F)(F)F)c1] |
| ZZY08-027 | 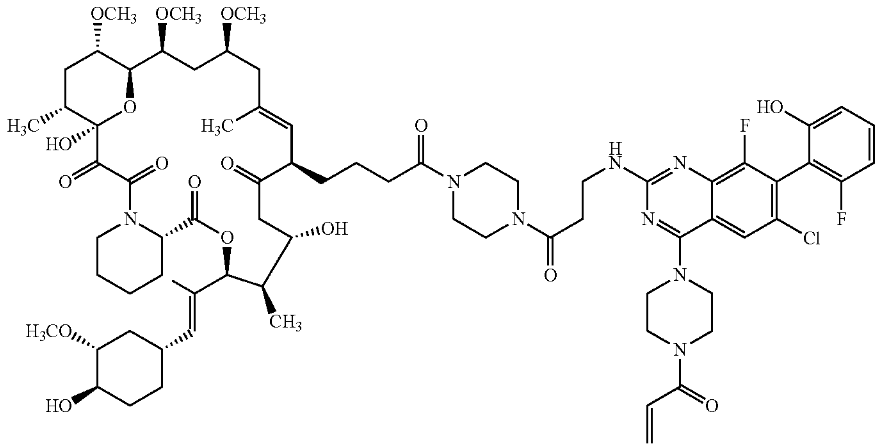 [SMILES: C=CC(=O)N1CCN(c2nc(NCCC(=O)N3CCN(C(=O)CCC[C@@H]4/C=C(\C)C[C@H](OC)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)CC3)nc3c(F)c(-c4c(O)cccc4F)c(Cl)cc23)CC1] |
| ZZY08-028 | 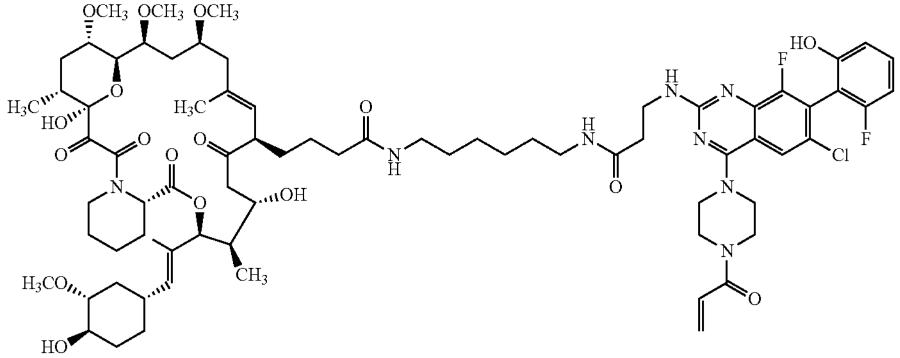 [SMILES: C=CC(=O)N1CCN(c2nc(NCCC(=O)NCCCCCCNC(=O)CCC[C@@H]3/C=C(\C)C[C@H](OC)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1] |

TABLE 8-continued
| Compound structures of KRAS analogs. | |
|---|---|
| Compound | Structure |
| ZZY08-057 | 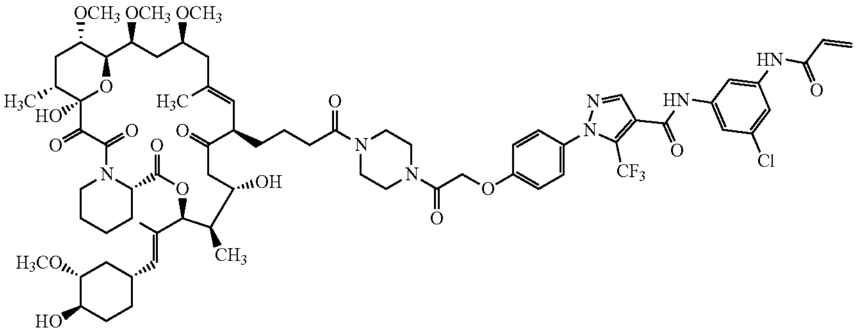 [SMILES: C=CC(=O)Nc1cc(Cl)cc(NC(=O)c2cnn(-c3ccc(OCC(=O)N4CCN(C(=O)CCC[C@@H]5/C=C(\C)C[C@H](OC)C[C@H](OC)[C@H]6O[C@@](O)(C(=O)C(=O)N7CCCC[C@H]7C(=O)O[C@H](/C(C)=C/[C@@H]7CC[C@@H](O)[C@H](OC)C7)[C@H](C)[C@@H](O)CC5=O)[C@H](C)C[C@@H]6OC)CC4)cc3)c2C(F)(F)F)c1] |
| ZZY08-058 | 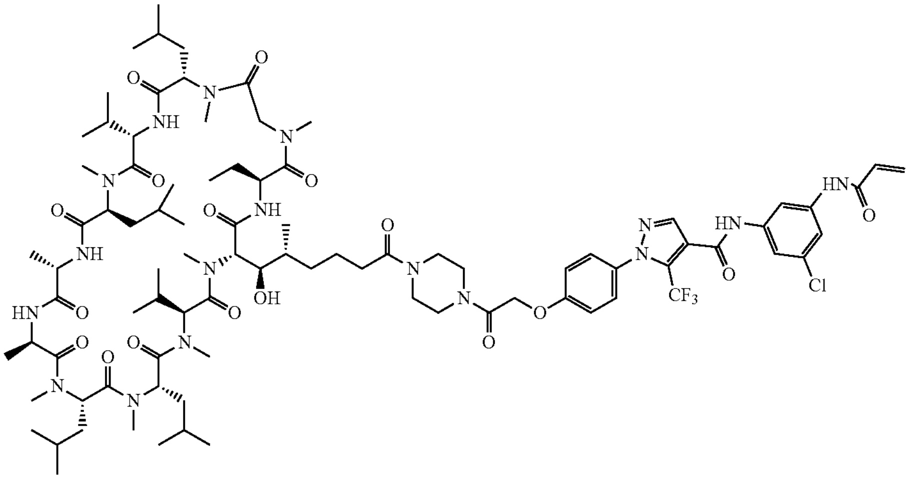 [SMILES: C=CC(=O)Nc1cc(Cl)cc(NC(=O)c2cnn(-c3ccc(OCC(=O)N4CCN(C(=O)CCC[C@@H](C)[C@@H](O)[C@H]5C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N5C)CC4)cc3)c2C(F)(F)F)c1] |
| ZZY05-042/ ZZY07-028 | 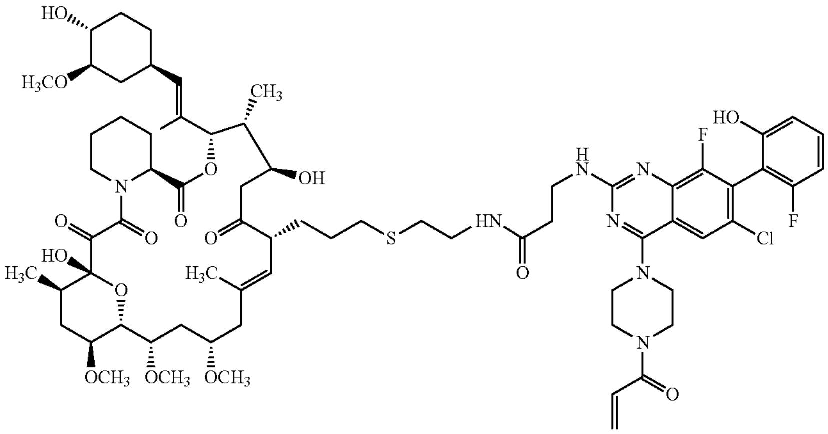 [SMILES: C=CC(=O)N1CCN(c2nc(NCCC(=O)NCCSCCC[C@@H]3/C=C(\C)C[C@H](OC)C[C@H](OC)[C@H]4O[C@@](O)(C(=O)C(=O)N5CCCC[C@H]5C(=O)O[C@H](/C(C)=C/[C@@H]5CC[C@@H](O)[C@H](OC)C5)[C@H](C)[C@@H](O)CC3=O)[C@H](C)C[C@@H]4OC)nc3c(F)c(-c4c(O)cccc4F)c(Cl)cc23)CC1] |

TABLE 8-continued
| Compound structures of KRAS analogs. | |
|---|---|
| Compound | Structure |
| ZZY07-014 | 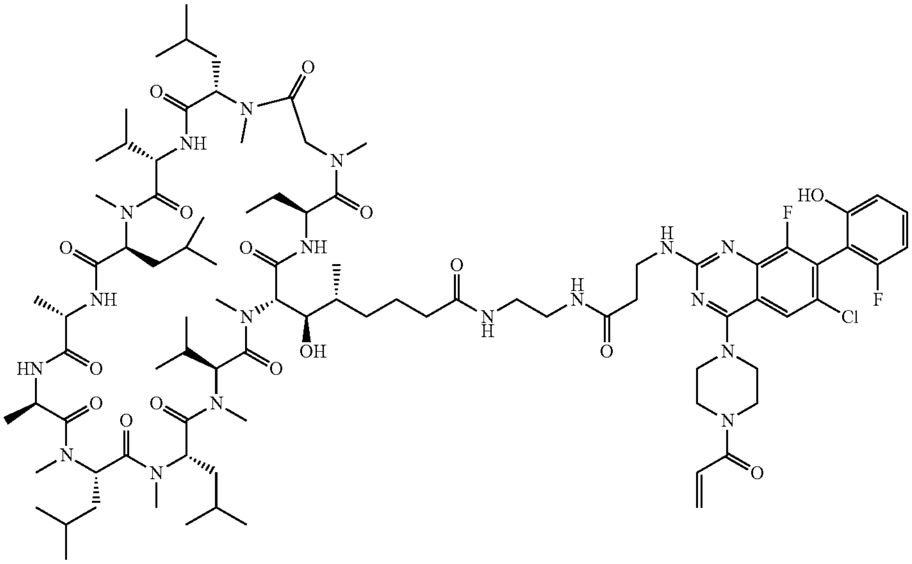 [SMILES: C=CC(=O)N1CCN(c2nc(NCCC(=O)NCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1] |
| ZZY07-079 | 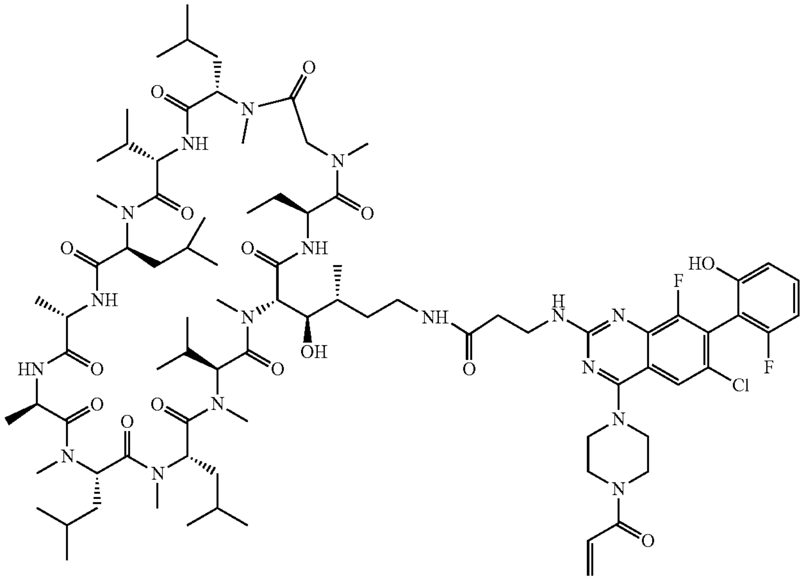 [SMILES: C=CC(=O)N1CCN(c2nc(NCCC(=O)NCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1] |

TABLE 8-continued
| Compound structures of KRAS analogs. | |
|---|---|
| Compound | Structure |
| ZZY07-089 | 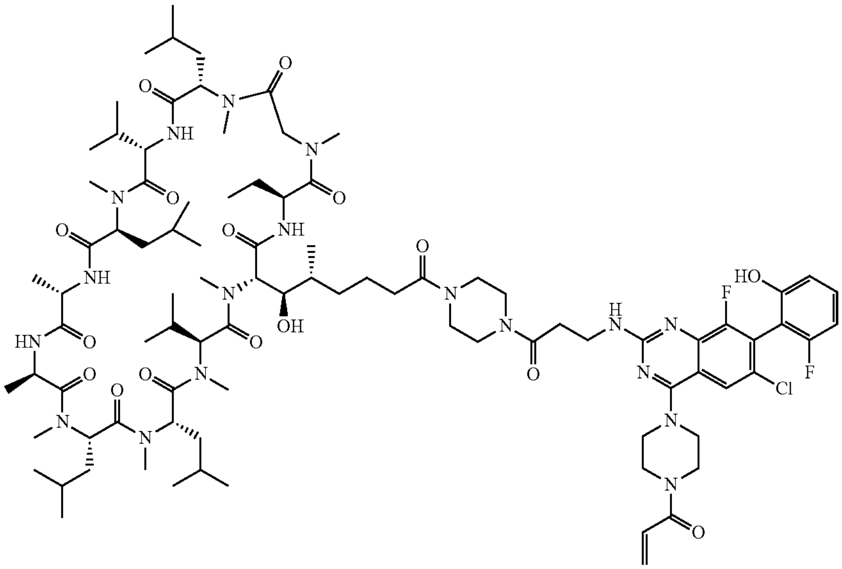 [SMILES: C=CC(=O)N1CCN(c2nc(NCCC(=O)N3CCN(C(=O)CCC[C@@H](C)[C@@H](O)[C@H]4C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N4C)CC3)nc3c(F)c(-c4c(O)cccc4F)c(Cl)cc23)CC1] |
| ZZY07-090 | 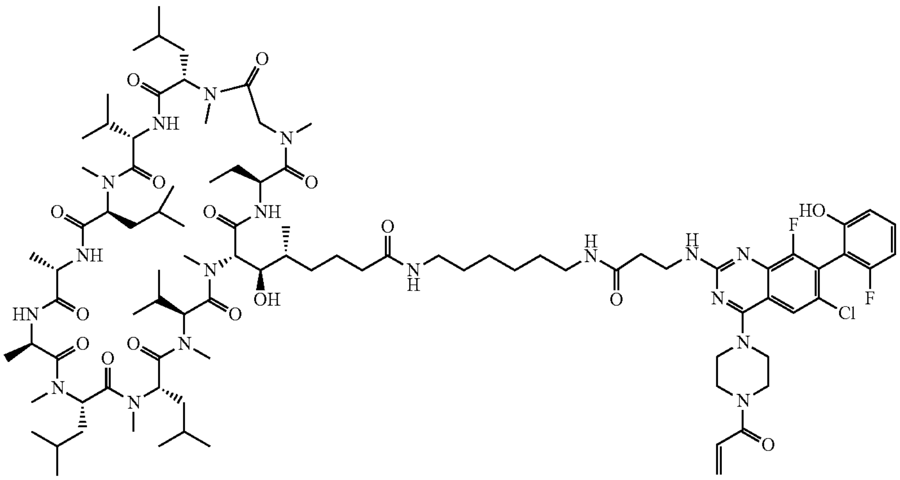 [SMILES: C=CC(=O)N1CCN(c2nc(NCCC(=O)NCCCCCCNC(=O)CCC[C@@H](C)[C@@H](O)[C@H]3C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N3C)nc3c(F)c(-c4c(O)cccc4F)c(Cl)cc23)CC1] |

TABLE 9
| Compound structures of Cyclosporin analogs. | |
|---|---|
| Compound | Structure |
| ZZY06-082 | 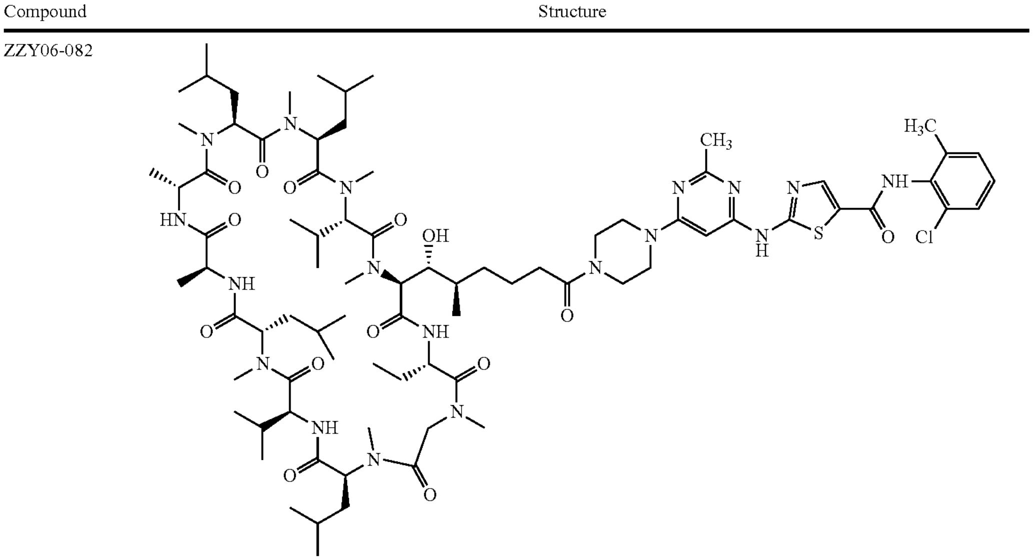 |
| ZZY06-083 | 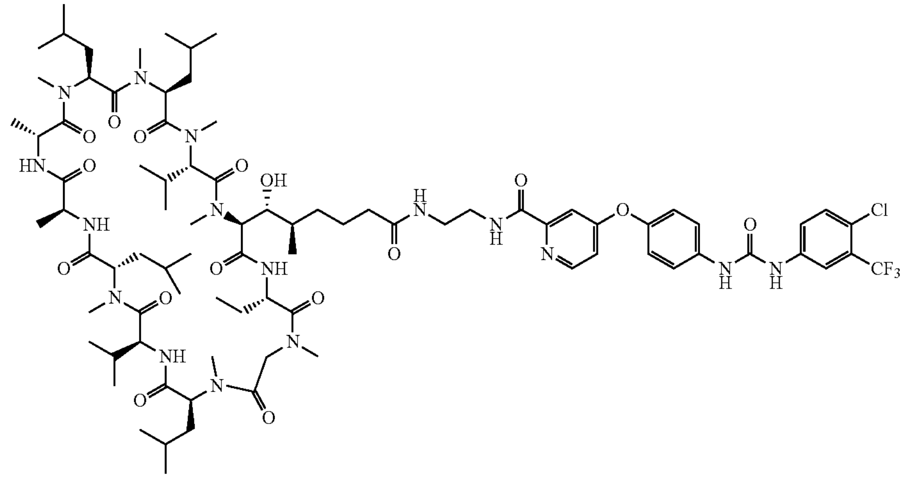 [SMILES: CC[C@@H]1NC(=O)[C@H]([C@H](O)[C@H](C)CCCC(=O)NCCNC(=O)c2cc(Oc3ccc(NC(=O)Nc4ccc(Cl)c(C(F)(F)F)c4)cc3)ccn2)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O] |
TABLE 10
| Additional analogs. | |
|---|---|
| Compound | Structure |
| ZZY05-016 | 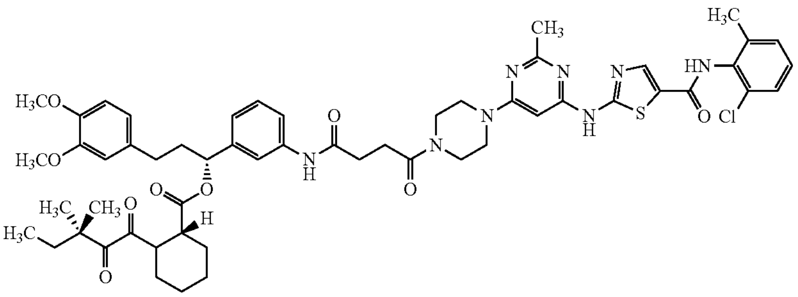 |

TABLE 10-continued

| Additional analogs. | |
|---|---|
| Compound | Structure |
| ZZY05-049 | 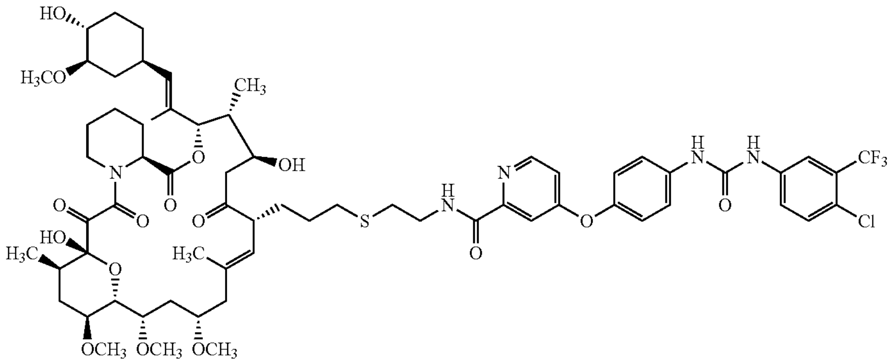 [SMILES: CO[C@H]1C/C(C)=C/[C@@H](CCCSCCNC(=O)c2cc(Oc3ccc(NC(=O)Nc4ccc(Cl)c(C(F)(F)F)c4)cc3)ccn2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |
| ZZY07-026 | 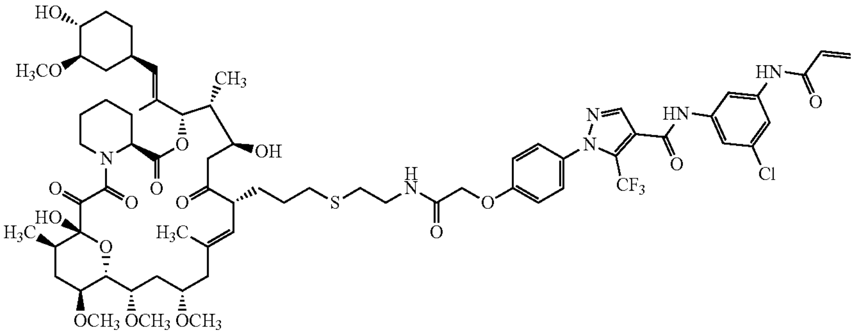 [SMILES: C=CC(=O)Nc1cc(Cl)cc(NC(=O)c2cnn(-c3ccc(OCC(=O)NCCSCCC[C@@H]4/C=C(\C)C[C@H](OC)C[C@H](OC)[C@H]5O[C@@](O)(C(=O)C(=O)N6CCCC[C@H]6C(=O)O[C@H](/C(C)=C/[C@@H]6CC[C@@H](O)[C@H](OC)C6)[C@H](C)[C@@H](O)CC4=O)[C@H](C)C[C@@H]5OC)cc3)c2C(F)(F)F)c1] |
| ZZY05-022 | 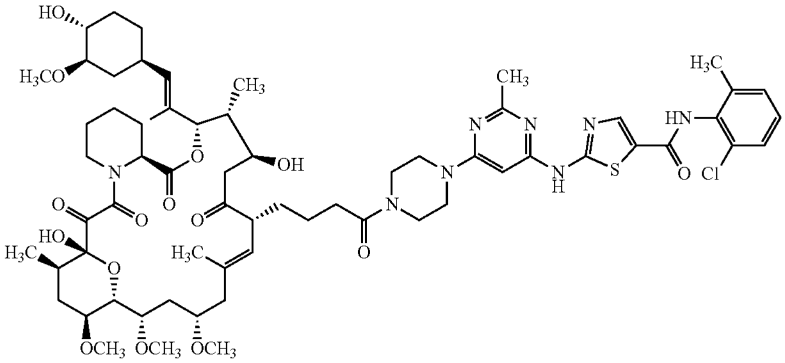 [SMILES: CO[C@H]1C/C(C)=C/[C@@H](CCCC(=O)N2CCN(c3cc(Nc4ncc(C(=O)Nc5c(C)cccc5Cl)s4)nc(C)n3)CC2)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C1)[C@@H](OC)C[C@H]2C] |

Example 6: Materials and Methods

Note on rotamers in $^1$H NMR data. All of the SLF analogs and FK506 analogs synthesized here exist as a mixture of two amide rotamers in $CDCl_3$ or $CD_3OD$. Due to extensive spectral overlap of the two, the coupling pattern of certain protons can be complicated even if they should display clear splitting patterns in theory. Sometimes, overlapping peaks prevent the identification of all peaks of the minor rotamer, and on occasion, of the major rotamer. In this document, only $^1$H NMR peaks of the major rotamer are reported in the best effort of resolving the peaks.

Cyclosporin analogs demonstrate more complicated conformational flexibility. In $CD_3OD$, most compounds exist as >6 conformational isomers (Ko, S. Y.; Dalvit, C. *Int. J. Pept. Protein Res.* 1992, 40, 380-382.). In $CDCl_3$ the spectra are generally less complicated, and for certain compounds, only two conformational isomers are observed. For these compounds the $^1$H NMR spectra in $CDCl_3$ are resolvable, and peaks belonging to the major conformation are reported.

Mini-workup. When a mini-workup (A/B) is indicated in the procedure, it was performed as follows: an aliquot (5 μL) of the reaction mixture was retrieved with a glass pipet and added to a plastic vial containing 0.2 mL organic solvent A and 0.2 mL aqueous solution B. The vial was shaken vigorously and allowed to stand until the two layers partitioned. The organic layer was then used for TLC or LC-MS analysis as specified in the procedure.

Monitoring reaction progress by LC-MS. When analysis of the reaction mixture is indicated in the procedure, it was performed as follows. An aliquot (1 μL) of the reaction mixture (or the organic phase of a mini-workup mixture) was diluted with 100 μL 1:1 acetonitrile:water. 1 μL of the diluted solution was injected onto a Waters Acquity UPLC BEH C18 1.7 μm column and eluted with a linear gradient of 5-95% acetonitrile/water (+0.1% formic acid) over 3.0 min. Chromatograms were recorded with a UV detector set at 254 nm and a time-of-flight mass spectrometer (Waters Xevo G2-XS).

General experimental procedures. All reactions were performed in oven-dried glassware fitted with rubber septa under a positive pressure of argon, unless otherwise noted. Air- and moisture-sensitive liquids were transferred via syringe or stainless steel cannula. Solutions were concentrated by rotary evaporation at or below 40° C. Analytical thin-layer chromatography (TLC) was performed using glass plates pre-coated with silica gel (0.25-mm, 60-A pore size, 230-400 mesh, Merck KGA) impregnated with a fluorescent indicator (254 nm). TLC plates were visualized by exposure to ultraviolet light (UV), then were stained by submersion in a 10% solution of phosphomolybdic acid (PMA) in ethanol or an acidic ethanolic solution of p-anisaldehyde (this solution was prepared by sequential additions of concentrated sulfuric acid (5.0 mL), glacial acetic acid (1.5 mL) and p-anisaldehyde (3.7 mL) to absolute ethanol (135 mL) at 23° C. with efficient stirring), followed by brief heating on a hot plate. Flash column chromatography was performed with Teledyne ISCO CombiFlash EZ Prep chromatography system, employing pre-packed silica gel cartridges (Teledyne ISCO RediSep).

Solvents and reagents. Anhydrous solvents were purchased from Acros Organics. Except for those specified in the Starting Materials section, all chemical reagents were purchased from Sigma-Aldrich and AK Scientific. Commercial solvents and reagents were used as received.

Starting materials. SLF was purchased from Cayman Chemical and/or synthesized following the synthetic route reported by Holt el al. 3'-desamino-3'-hydroxy SLF was synthesized following the synthetic route reported by Holt et al. (Holt, D. A. et al. *J. Am. Chem. Soc.* 1993, 115, 9925-9938). Cyclosporin A and FK506 were purchased from LC Laboratories. Sorafenib acid [4-(4-(3-(4-chloro-3-(trifluoromethyl)phenyl)ureido)phenoxy)picolinic acid] was purchased from BOC Sciences. Des(hydroxyethyl)dasatinib [N-(2-chloro-6-methylphenyl)-2-((2-methyl-6-(piperazin-1-yl)pyrimidin-4-yl)amino)thiazole-5-carboxamide] was purchased from 5A Chemicals. Lapatinib aldehyde [5-(4-((3-chloro-4-((3-fluorobenzyl)oxy)phenyl)amino)quinazolin-6-yl)furan-2-carbaldehyde] was purchased from AK Scientific. Desmethoxychloro erlotinib [6-(2-chloroethoxy)-N-(3-ethynylphenyl)-7-(2-methoxyethoxy)quinazolin-4-amine] was purchased from AstaTech. Desmethoxy chloro gefitinib [N-(3-chloro-4-fluorophenyl)-6-(3-chloropropoxy)-7-methoxyquinazolin-4-amine] was purchased from AstaTech. tert-Butyl 4-(7-bromo-6-chloro-2-((3-ethoxy-3-oxopropyl)amino)-8-fluoroquinazolin-4-yl)piperazine-1-carboxylate was purchased from Pharmaron Inc.

Instrumentation. Proton nuclear magnetic resonance ($^1H$ NMR) spectra and carbon nuclear magnetic resonance ($^{13}C$ NMR) spectra were recorded on Bruker Avancelll HD 2-channel instrument (400 MHz/100 MHz) at 23° C. Proton chemical shifts are expressed in parts per million (ppm, 6 scale) and are referenced to residual protium in the NMR solvent ($CHCl_3$: δ 7.26, $D_2HCOD$: δ 3.31). Carbon chemical shifts are expressed in parts per million (ppm, δ scale) and are referenced to the carbon resonance of the NMR solvent ($CDCl_3$: δ 77.0, $CD_3OD$: δ 49.0). Data are represented as follows: chemical shift, multiplicity (s=singlet, d=doublet, t=triplet, q=quartet, dd=doublet of doublets, dt=doublet of triplets, m=multiplet, br=broad, app=apparent), integration, and coupling constant (J) in Hertz (Hz). High-resolution mass spectra were obtained using a Waters Xevo G2-XS time-of-flight mass spectrometer. Unless otherwise specified, diastereomeric ratios of products are reported as (major diastereomer):(sum of minor diastereomers).

Synthetic Procedures.

SLF Analogs.

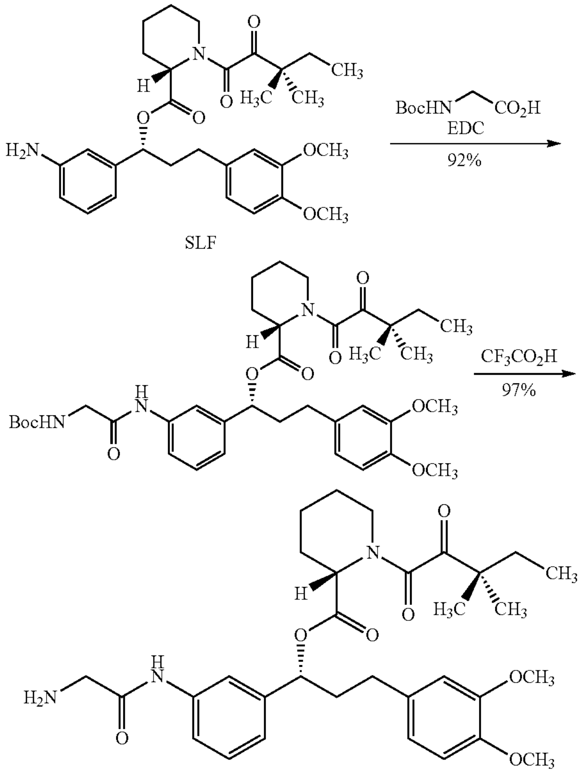

SLF

ZZY01-040

EDC (548.08 mg, 2.86 mmol) was added in one portion to a stirred solution of SLF (1.00 g, 1.91 mmol) and Boc-Gly-OH (500 mg, 2.86 mmol) in dichloromethane (9.5 mL) at 0° C. The resulting mixture was allowed to warm to 23° C. over 30 min, then was kept stirred at 23° C. After a total of 5 h, TLC analysis (50% ethyl acetate-hexanes) showed that the reaction was complete. The reaction mixture was directly concentrated under reduced pressure, and the residue was purified by column chromatography (20-50% ethyl acetate-hexanes, 40-g CombiFlash column) to afford the product as a white foam (1.20 g, 92%). The product exists as a 6:1 mixture of amide rotamers. $^1H$ NMR (400 MHz, Chloroform-d) δ 8.33 (s, 1H), 7.62 (d, J=8.1 Hz, 1H), 7.51-7.45 (m, 1H), 7.30 (t, J=7.9 Hz, 1H), 7.03 (d, J=7.8 Hz, 1H), 6.77 (d, J=8.7 Hz, 1H), 6.73-6.63 (m, 2H), 5.80 (dd, J=IN, 5.6 Hz, 1H), 5.34 (d, J=5.5 Hz, 1H), 5.27 (s, 1H), 3.98-3.89 (m, 2H), 3.86 (s, 3H), 3.84 (s, 3H), 3.34 (d, J=13.7 Hz, 1H), 3.07 (td, J=12.9, 3.0 Hz, 1H), 2.64-2.49 (m, 2H), 2.35 (d, J=13.6 Hz, 1H), 2.28-2.15 (m, 1H), 2.12-2.02 (m, 1H), 1.78-1.58 (m, 5H), 1.47 (s, 9H), 1.46-1.34 (m, 2H), 1.24 (s, 3H), 1.24 (s, 3H), 0.91 (t, J=7.5 Hz, 3H). HRMS (ESI): Calcd for $(C_{37}H_{51}N_3O_9+H)^+$: 682.3704, Found: 682.3699.

A solution of [(1R)-1-[3-[[2-(tert-butoxycarbonylamino)acetyl]amino]phenyl]-3-(3,4-dimethoxyphenyl)propyl] (2S)-1-(3,3-dimethyl-2-oxo-pentanoyl)piperidine-2-carboxylate (1.20 g, 1.76 mmol) in dichloromethane (8.4 mL) was cooled to 0° C., then trifluoroacetic acid (8.4 mL) was added dropwise. The resulting yellow solution was stirred at 0° C. until TLC analysis (50% ethyl acetate-hexanes, mini-workup with ether/aqueous sodium bicarbonate solution) showed full consumption of the starting material. The reaction solution was concentrated in vacuo, and the residue was partitioned between dichloromethane (10 mL) and saturated sodium bicarbonate solution (10 mL). The layers were separated, and the aqueous layer was extracted with dichlomethane (2×10 mL). The combined organic layers were dried over sodium sulfate, and the dried solution was concentrated in vacuo to afford the product as a white foam (997 mg, 97%). 6:1 mixture of rotamers. $^1$H NMR (400 MHz, Chloroform-d) δ 7.30-7.22 (m, 1H), 7.00-6.88 (m, 2H), 6.88-6.80 (m, 2H), 6.80-6.74 (m, 1H), 6.70-6.65 (m, 2H), 5.77 (dd, J=7.8, 5.9 Hz, 1H), 5.31 (d, J=5.5 Hz, 1H), 4.53 (s, 2H), 3.86 (s, 3H), 3.85 (s, 3H), 3.36 (d, J=13.0 Hz, 1H), 3.14 (td, J=13.1, 3.2 Hz, 1H), 2.66-2.45 (m, 2H), 2.36 (d, J=13.7 Hz, 1H), 2.31-2.15 (m, 1H), 2.04 (s, 1H), 1.82-1.58 (m, 5H), 1.42-1.29 (m, 2H), 1.23 (s, 3H), 1.21 (s, 3H), 0.89 (t, J=7.5 Hz, 3H). HRMS 1.59 (ESI): Calcd for $(C_{32}H_{43}N_3O_7+H)^+$: 582.3179, Found: 582.3176.

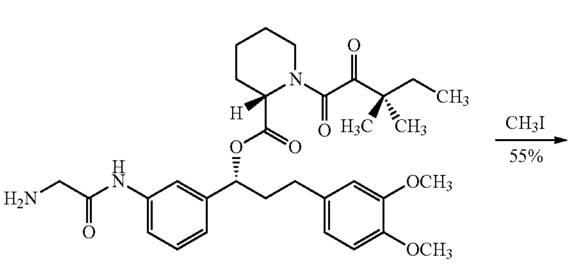

ZZY01-040

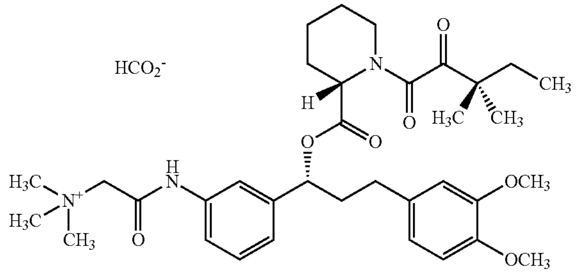

ZZY01-025

Sodium bicarbonate (36.5 mg, 0.430 mmol) and iodomethane (107 μL, 1.72 mmol) were added to a solution of ZZY01-040 (50 mg, 0.090 mmol) in THF (0.50 mL) at 23° C. The resulting suspension was stirred at 23° C., and the reaction progress was monitored by LC-MS. After 24 h, the bulk of the solvent was removed by rotary evaporation. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (29.5 mg, 55%). 6:1 mixture of rotamers. $^1$H NMR (400 MHz, Methanol-$d_4$) δ 8.35 (s, 1H), 7.81-7.64 (m, 1H), 7.51-7.43 (m, 1H), 7.43-7.33 (m, 1H), 7.18 (app t, J=8.1 Hz, 1H), 6.92-6.85 (m, 1H), 6.85-6.79 (m, 1H), 6.79-6.70 (m, 1H), 5.83-5.70 (m, 1H), 5.29-5.22 (m, 1H), 4.31 (s, 2H), 3.83 (s, 3H), 3.82 (s, 3H), 3.41 (s, 10H), 3.30-3.19 (m, 1H), 2.75-2.55 (m, 2H), 2.37 (d, J=13.6 Hz, 1H), 2.34-2.19 (m, 1H), 2.17-2.02 (m, 1H), 1.86-1.58 (m, 5H), 1.58-1.29 (m, 2H), 1.25 (s, 3H), 1.23 (s, 3H), 0.90 (t, J=7.4 Hz, 3H). HRMS (ESI): Calcd for $(C_{35}H_{50}N_3O_7)^+$: 624.3642, Found: 624.3636.

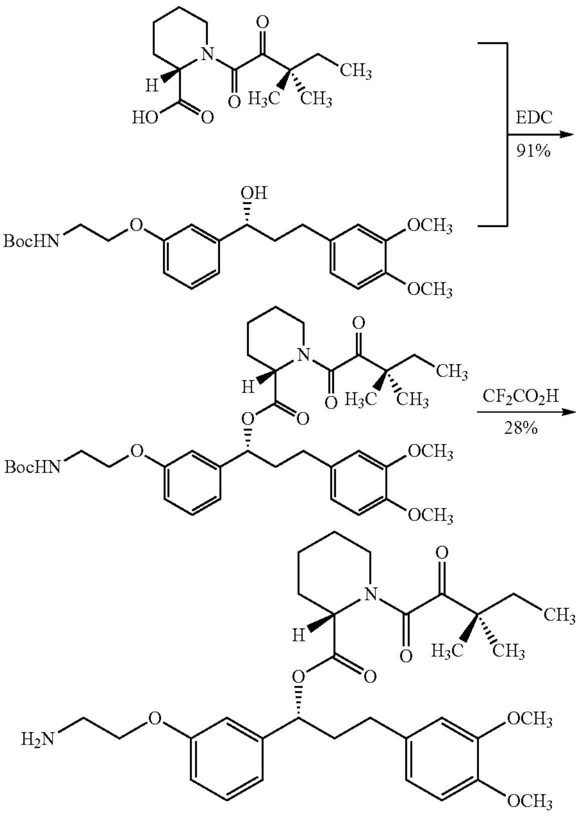

ZZY01-038 tert-Butyl N-[2-[3-[(1R)-3-(3,4-dimethoxyphenyl)-1-hydroxy-propyl]phenoxy]ethyl]carbamate (65 mg, 0.15 mmol) and (2S)-1-(3,3-dimethyl-2-oxo-pentanoyl)piperidine-2-carboxylic acid (42.3 mg, 0.17 mmol) were dissolved in dry di chloromethane (3.0 mL). The resulting solution was cooled to 0° C., then EDC (43.5 mg, 0.23 mmol) was added in one portion as a solid. The ice bath was removed and the reaction mixture was allowed to warm to 23° C. In 4 h, TLC analysis (50% ethyl acetate-hexanes) showed that the reaction was complete. The reaction mixture was directly concentrated, and the residue was purified by column chromatography (4-g CombiFlash column, 10-50% ethyl acetate-hexanes) to afford the product as a colorless film (92 mg, 91%).

50% Trifluoroacetic acid-dichloromethane (1 mL) was added to [(1R)-1-[3-[2-(tert-butoxycarbonylamino)ethoxy]phenyl]-3-(3,4-dimethoxyphenyl)propyl] (2S)-1-(3,3-dimethyl-2-oxo-pentanoyl)piperidine-2-carboxylate (95 mg, 0.14 mmol) in a 20-mL scintillation vial at 0° C. The resulting solution was warmed to 23° C. over 5 min. TLC analysis (mini-workup with ether/sodium bicarbonate, 50% ethyl acetate-hexanes) showed complete consumption of the starting material. The product has an Rf of 0 in this solvent system. The reaction mixture was concentrated under reduced pressure. The residue was partitioned between dichloromethane (5 mL) and saturated sodium bicarbonate solution (5 mL). The layers were separated, and the aqueous layer was extracted with dichloromethane (2×5 mL). The combined organic layers were dried over sodium sulfate, and the dried solution was concentrated. The residue was purified by column chromatography (3-5% methanol-dichloromethane+0.3-0.5% saturated aqueous ammonium hydroxide solution, 4-g CombiFlash column) to afford the product as a colorless film (23 mg, 28%). 6:1 mixture of rotamers. $^1$H NMR (400 MHz, Chloroform-d) δ 7.29-7.22 (m, 1H), 6.95-6.88 (m, 2H), 6.85 (dd, J=8.2, 2.2 Hz, 1H), 6.78 (d, J=8.6 Hz, 1H), 6.72-6.65 (m, 2H), 5.77 (dd, J=ID, 5.8 Hz, 1H), 5.35-5.28 (m, 1H), 4.05-3.94 (m, 2H), 3.86 (s, 3H), 3.85 (s, 3H), 3.35 (d, J=13.6 Hz, 1H), 3.20-3.06 (m, 3H), 2.67-2.43 (m, 2H), 2.42-2.32 (m, 1H), 2.31-2.17 (m, 1H), 2.13-1.97 (m, 1H), 1.76-1.57 (m, 5H), 1.57-1.27 (m, 2H), 1.22 (s, 3H), 1.20 (s, 3H), 0.88 (t, J=7.5 Hz, 3H). HRMS (ESI): Calcd for $(C_{32}H_{44}N_2O_7+H)^+$: 569.3227, Found: 569.3239.

-continued

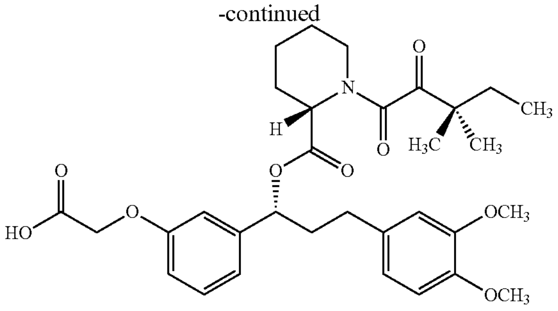

ZZY01-041

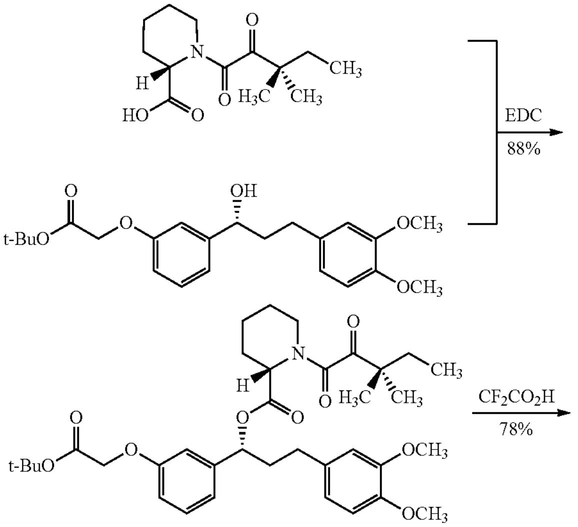

A solution of [(1R)-1-[3-(2-tert-butoxy-2-oxo-ethoxy) phenyl]-3-(3,4-dimethoxyphenyl)propyl] (2S)-1-(3,3-dimethyl-2-oxo-pentanoyl)piperidine-2-carboxylate (453 mg, 0.71 mmol) in dichloromethane (1.42 mL) was cooled to 0° C., then trifluoroacetic acid (1.42 mL) was added dropwise. The resulting yellow solution was stirred at 0° C. until TLC analysis (50% ethyl acetate-hexanes) showed full consumption of the starting material (~2 h). The reaction solution was concentrated in vacuo to afford the product as a brown liquid. The liquid solidified slowly upon standing under vacuum, giving rise to an off-white powder. 6:1 mixture of rotamers. $^1$H NMR (400 MHz, Chloroform-d) δ 7.32-7.23 (m, 1H), 6.93 (d, J=7.7 Hz, 1H), 6.90-6.84 (m, 2H), 6.78 (d, J=7.9 Hz, 1H), 6.68 (d, J=7.7 Hz, 2H), 5.74 (dd, J=8.3, 5.3 Hz, 1H), 5.30 (d, J=7.8 Hz, 1H), 4.75-4.61 (m, 2H), 3.86 (s, 3H), 3.85 (s, 3H), 3.41-3.32 (m, 1H), 3.21 (td, J=13.0, 3.1 Hz, 1H), 2.70-2.48 (m, 2H), 2.39 (d, J=13.8 Hz, 1H), 2.31-2.17 (m, 1H), 2.13-2.03 (m, 1H), 1.86-1.58 (m, 5H), 1.58-1.31 (m, 2H), 1.20 (s, 3H), 1.18 (s, 3H), 0.87 (t, J=7.4 Hz, 3H). HRMS (ESI): Calcd for $(C_{32}H_{41}NO_9+H)^+$: 584.2859, Found: 584.2852.

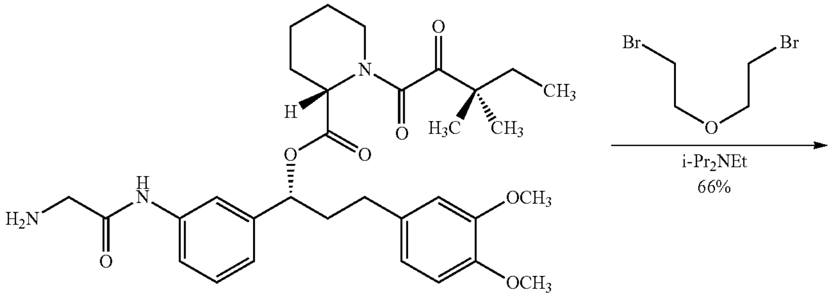

ZZY01-040

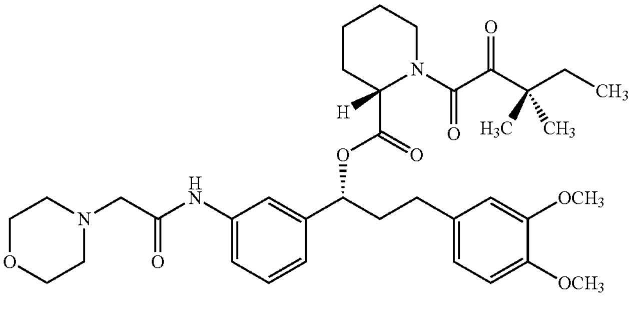

ZZY01-043

A 1-dram vial was charged with ZZY01-040 (50 mg, 0.090 mmol) and a stir bar. DMSO (0.2 mL) and N,N-Diisopropylethylamine (45 μL, 0.26 mmol) were added sequentially. 1-bromo-2-(2-bromoethoxy)ethane (30 mg, 0.13 mmol) was added via syringe. The resulting mixture was stirred at 23° C. and the reaction progress was monitored by TLC analysis (10% methanol-dichloromethane). After 5 h, the reaction mixture was warmed to 55° C. In a total of 22 h, TLC analysis showed full conversion. The reaction mixture was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid. 6:1 mixture of rotamers. $^1$H NMR (400 MHz, Methanol-$d_4$) δ 8.16 (s, 1H), 7.75 (t, J=1.8 Hz, 1H), 7.53-7.46 (m, 1H), 7.35 (t, J=7.9 Hz, 1H), 7.14 (d, J=7.6 Hz, 1H), 6.87 (d, J=8.2 Hz, 1H), 6.84-6.78 (m, 1H), 6.74 (dd, J=8.1, 1.8 Hz, 1H), 5.75 (dd, J=8.6, 4.9 Hz, 1H), 5.24 (d, J=5.4 Hz, 1H), 3.83 (d, J=1.1 Hz, 3H), 3.81 (s, 3H), 3.46-3.38 (m, 1H), 3.27 (td, J=13.2, 3.1 Hz, 1H), 2.73 (s, 6H), 2.69-2.53 (m, 3H), 2.42-2.20 (m, 3H), 2.15-2.02 (m, 2H), 1.80-1.55 (m, 5H), 1.55-1.29 (m, 2H), 1.25 (s, 3H), 1.23 (s, 3H), 0.90 (t, J=7.4 Hz, 3H). HRMS (ESI): Calcd for $(C_{36}H_{49}N_3O_8+H)^+$: 652.3598, Found: 652.3613.

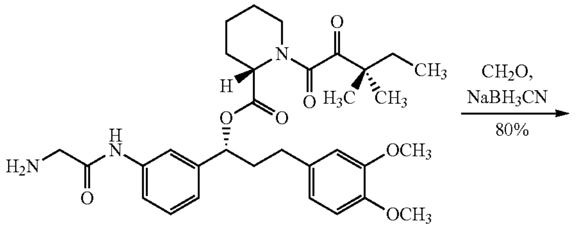

ZZY01-040

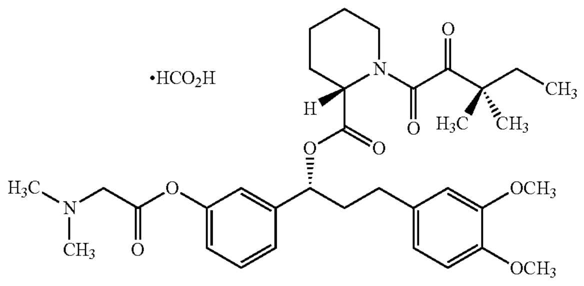

ZZY01-044

A 1-dram vial was charged with ZZY01-040 (50 mg, 0.0900 mmol), a stir bar, and 9:1 methanol:acetic acid (0.5 mL). Formaldehyde (37% aqueous solution, 24 μL, 0.86 mmol) was added via pipette. Sodium cyanoborohydride (11 mg, 0.17 mmol) was added in one portion, and the resulting solution was stirred at 23° C. In 3 h, TLC analysis (10% methanol-dichloromethane+1% 30% aqueous ammonium hydroxide solution) showed full consumption of starting material and formation of a less polar product. The reaction mixture was diluted with 50% acetonitrile-water to a final volume of 5 mL, and the resulting solution was purified by reverse-phase HPLC (5-95% acetonitrile-water with 0.1% formic acid, 50 min, 20 mL/min) to afford the product as a white foam. 6:1 mixture of rotamers. $^1$H NMR (400 MHz, Methanol-$d_4$) δ 8.32 (s, 1H), 7.75 (t, J=1.8 Hz, 1H), 7.51-7.42 (m, 1H), 7.37 (t, J=7.9 Hz, 1H), 7.17 (d, J=7.6 Hz, 1H), 6.88 (d, J=7.4 Hz, 1H), 6.81 (d, J=1.9 Hz, 1H), 6.74 (dd, J=8.2, 1.9 Hz, 1H), 5.74 (dd, J=8.8, 5.0 Hz, 1H), 5.24 (d, J=5.5 Hz, 1H), 3.95 (br s, 2H), 3.83 (s, 3H), 3.82 (s, 3H), 3.47-3.38 (m, 1H), 3.31-3.20 (m, 1H), 2.89 (s, 6H), 2.75-2.53 (m, 2H), 2.41-2.19 (m, 2H), 2.09 (dddd, J=12.4, 9.1, 5.7, 3.7 Hz, 1H), 1.89-1.57 (m, 5H), 1.57-1.29 (m, 2H), 1.25 (s, 3H), 1.23 (s, 3H), 0.90 (t, J=7.4 Hz, 3H). HRMS (ESI): Calcd for $(C_{34}H_{47}N_3O_7+H)^+$: 610.3492, Found: 610.3473.

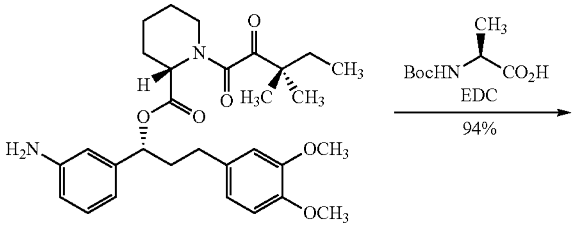

SLF

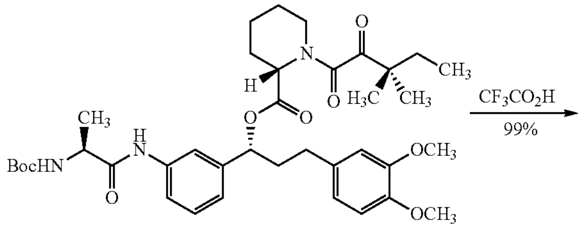

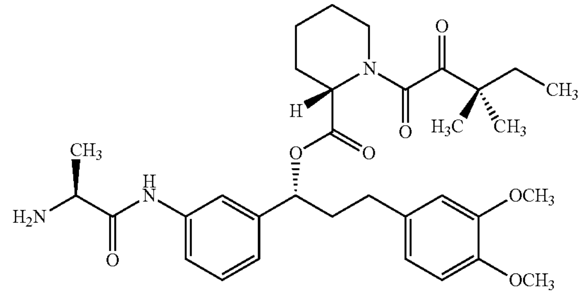

ZZY01-059

EDC (55 mg, 0.29 mmol) was added in one portion to a stirred solution of SLF (100 mg, 0.190 mmol) and D-Boc-Alanine (54 mg, 0.29 mmol) in dichloromethane (9.5 mL) at 0° C. The resulting mixture was allowed to warm to 23° C. over 30 min, then was kept stirred at 23° C. In 2 h, TLC analysis (50% ethyl acetate-hexanes) did not reveal any new spot but LC-MS analysis indicated that a new product with higher mass was being formed. In a total of 20 h, LC-MS analysis showed no detectable starting material. The reaction mixture was directly loaded onto a silica gel column and purified by column chromatography (20-50% ethyl acetate-hexanes) to afford the product as a colorless wax (125 mg, 94%).

Trifluoroacetic acid (0.5 mL) was added dropwise to a solution of [(1R)-1-[3-[[(2S)-2-(tert-butoxycarbonylamino) propanoyl]amino]phenyl]-3-(3,4-dimethoxyphenyl)propyl] (2S)-1-(3,3-dimethyl-2-oxo-pentanoyl)piperidine-2-carboxylate (125 mg, 0.18 mmol) in di chloromethane (0.5 mL) at 23° C. The resulting clear solution was allowed to stand at 23° C. for 1 h. The solution was concentrated in vacuo, and the residue was partitioned between 10 mL di chloromethane and 10 mL saturated sodium bicarbonate solution. The layers were separated, and the aqueous layer was extracted with di chloromethane (2×10 mL). The combined organic layers were dried over sodium sulfate, and the dried solution was concentrated to afford the product as a white foam (108 mg, 99%). 6:1 mixture of rotamers. $^1$H NMR (400 MHz, Chloroform-d) δ 9.52 (s, 1H), 7.71-7.44 (m, 2H), 7.30 (t, J=7.9 Hz, 1H), 7.11-6.99 (m, 1H), 6.84-6.72 (m, 1H), 6.72-6.64 (m, 2H), 5.79 (dd, J=8.0, 5.5 Hz, 1H), 5.38-5.30 (m, 1H), 3.86 (s, 3H), 3.85 (s, 3H), 3.70-3.56 (m, 1H), 3.36 (d, J=13.1 Hz, 1H), 3.16 (t, J=12.9 Hz, 1H), 2.69-2.48 (m, 2H), 2.37 (d, J=13.6 Hz, 1H), 2.24 (ddd, J=13.9, 10.4, 7.0 Hz, 1H), 2.14-2.02 (m, 1H), 1.81-1.51 (m, 5H), 1.52-1.35 (m, 5H), 1.23 (s, 3H), 1.22 (s, 3H), 0.89 (t, J=7.5 Hz, 3H). HRMS (ESI): Calcd for $(C_{33}H_{45}N_3O_7+H)^+$: 596.3336, Found: 596.3351.

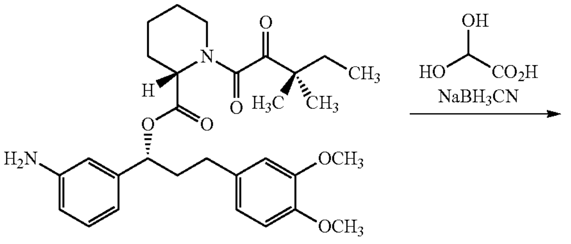

SLF

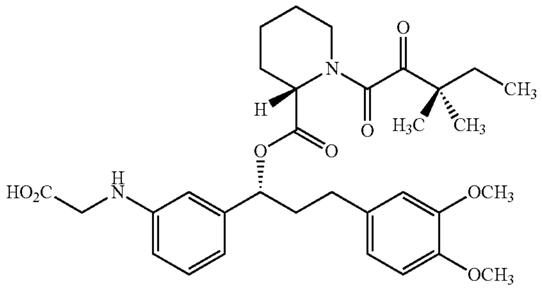

ZZY01-060A
38%

+

-continued

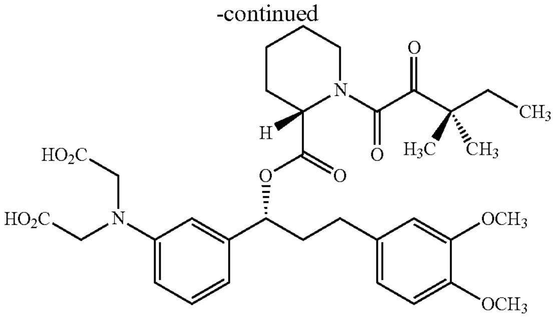

ZZY01-060B
43%

An oven-dried 1-dram vial was charged with SLF (50 mg, 0.10 mmol), glyoxylic acid (18 mg, 0.19 mmol) and a magnetic stir bar. 9:1 Methanol:acetic acid (0.5 mL) was added and the resulting solution was cooled to 0° C. Sodium cyanoborohydride (12 mg, 0.19 mmol) was added in one portion. The mixture was allowed to stir at 4° C. and the progress was monitored by LC-MS. In 1 h, LC-MS indicated that the starting material had been fully consumed and two products had formed in roughly 1:1 ratio. To avoid further bis-alkylation, the reaction mixture was immediately diluted with 50% acetonitrile-water to a volume of 5 mL. The resulting solution was purified by reverse-phase HPLC (5-95% acetonitrile-water+0.1% formic acid, 50 min) to afford the two products as two discrete peaks, both as white powders. 01-060B (26 mg, 43%) eluted faster; 01-060A (21 mg, 38%) eluted slower.

ZZY01-060A. 6:1 mixture of rotamers. $^1$H NMR (400 MHz, Methanol-$d_4$) δ 7.18-7.09 (m, 1H), 6.87 (d, J=8.2 Hz, 1H), 6.85-6.76 (m, 1H), 6.76-6.70 (m, 1H), 6.68 (d, J=ID Hz, 1H), 6.65-6.56 (m, 2H), 5.72-5.65 (m, 1H), 5.24 (d, J=5.4 Hz, 1H), 3.93-3.87 (m, 2H), 3.83 (s, 3H), 3.81 (s, 3H), 3.45-3.38 (m, 1H), 3.19 (td, J=13.1, 3.1 Hz, 1H), 2.69-2.52 (m, 2H), 2.35 (d, J=13.6 Hz, 1H), 2.31-2.15 (m, 1H), 2.13-1.97 (m, 1H), 1.87-8.59 (m, 5H), 1.59-1.28 (m, 2H), 1.26 (s, 3H), 1.24 (s, 3H), 0.91 (t, J=7.5 Hz, 3H). HRMS 9 (ESI): Calcd for $(C_{32}H_{42}N_2O_8+H)^+$: 583.3019, Found: 583.3010.

ZZY01-060B. 6:1 mixture of rotamers. $^1$H NMR (400 MHz, Methanol-$d_4$) δ 7.23 (t, J=7.9 Hz, 1H), 6.87 (d, J=8.2 Hz, 1H), 6.85-6.69 (m, 3H), 6.65-6.56 (m, 2H), 5.71 (dd, J=8.4, 5.3 Hz, 1H), 5.23 (d, J=5.2 Hz, 1H), 4.26-4.19 (m, 4H), 3.83 (s, 3H), 3.82 (s, 3H), 3.42 (d, J=13.5 Hz, 1H), 3.19 (td, J=13.2, 3.0 Hz, 1H), 2.60 (h, J=6.7, 6.2 Hz, 2H), 2.35 (d, J=13.6 Hz, 1H), 2.30-2.17 (m, 1H), 2.14-2.01 (m, 1H), 1.72 (dtdd, J=16.2, 12.6, 8.4, 4.7 Hz, 5H), 1.57-1.29 (m, 2H), 1.26 (s, 3H), 1.24 (s, 3H), 0.91 (t, J=7.4 Hz, 3H). HRMS (ESI): Calcd for $(C_{33}H_{44}N_2O_{10}+H)^+$: 641.3074, Found: 641.3093.

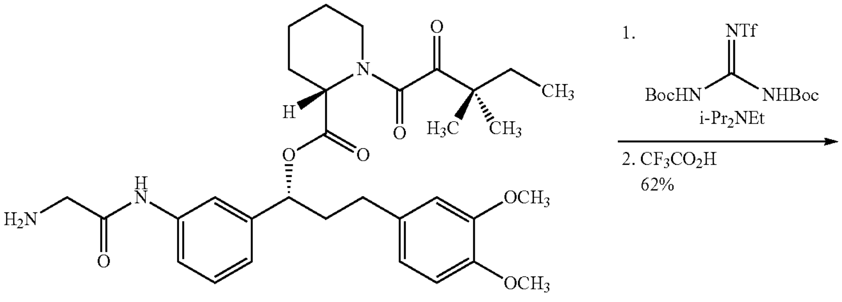

ZZY01-040

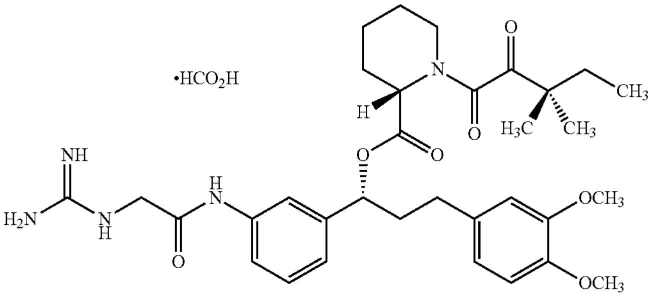

ZZY01-065

An oven-dried 2-mL vial was charged with ZZY01-040 (50 mg, 0.090 mmol), tert-butyl N—[N-tert-butoxycarbonyl-N'-(trifluoromethylsulfonyl)carbamimidoyl]carbamate (50 mg, 0.13 mmol), and a magnetic stir bar. Dichloromethane (0.50 mL) and NA-diisoproylethylamine (30 μL, 0.17 mmol) were added sequentially via syringe. The resulting mixture was allowed to stir at 23° C. In 4 h, LC-MS showed full consumption of the starting material and formation of the desired product mass (Boc protected). Tri fluoroacetic acid (0.5 mL) was added to the reaction mixture via syringe. After stirring for another 1 h, LC-MS analysis showed full deprotection of the Boc groups. The reaction mixture was concentrated under reduced pressure. The residue was diluted with 50% acetonitrile-water to a volume of 4.7 mL, and the solution was purified by reverse-phase HPLC (Waters XBridge C18 column μm particle size 30×250 mm, 5-95% acetonitrile-water+0.1% formic acid, 40 min, 20 mL/min) to afford the product as a white solid (33 mg, 62%). 6:1 mixture of rotamers. $^1H$ NMR (400 MHz, Methanol-$d_4$) δ 8.35 (s, 1H), 7.78 (t, J=1.9 Hz, 1H), 7.44 (ddd, J=8.1, 2.2, 1.1 Hz, 1H), 7.35 (t, J=7.8 Hz, 1H), 7.18-7.11 (m, 1H), 6.87 (d, J=8.2 Hz, 1H), 6.81 (d, J=2.0 Hz, 1H), 6.74 (dd, J=8.2, 2.0 Hz, 1H), 5.74 (dd, J=8.8, 5.0 Hz, 1H), 5.26-5.21 (m, 1H), 4.11 (s, 2H), 3.83 (s, 3H), 3.82 (s, 3H), 3.42 (d, J=13.4 Hz, 1H), 3.27 (dd, J=13.2, 3.0 Hz, 1H), 2.74-2.54 (m, 2H), 2.36 (d, J=14.1 Hz, 1H), 2.32-2.18 (m, 1H), 2.15-2.01 (m, 1H), 1.83-1.55 (m, 5H), 1.55-1.28 (m, 2H), 1.25 (s, 3H), 1.23 (s, 3H), 0.90 (t, J=7.5 Hz, 3H). HRMS (ESI): Calcd for $(C_{33}H_{45}N_5O_7+H)^+$: 624.3397, Found: 624.3381.

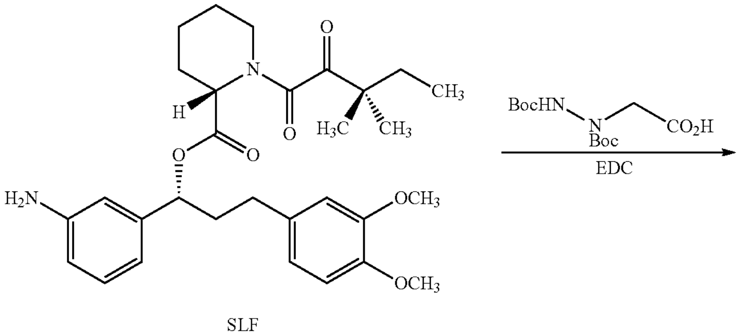

SLF

-continued

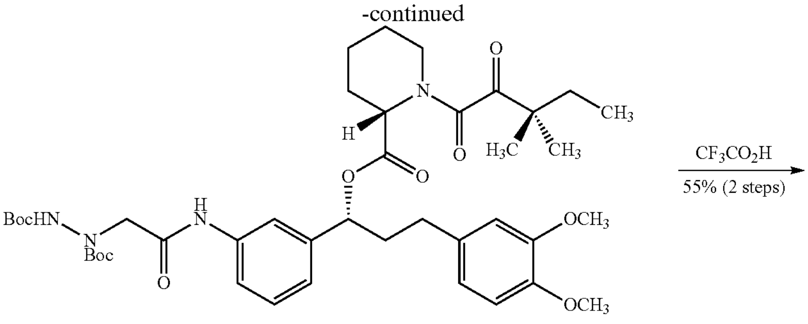

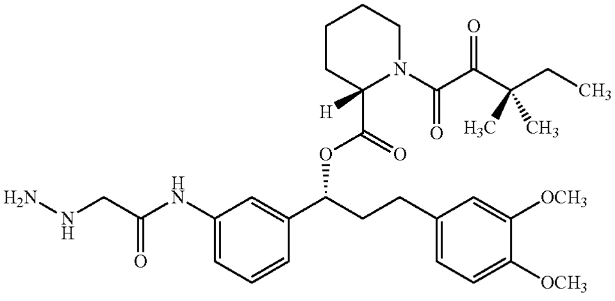

ZZY01-070

EDC (27.4 mg, 0.1400 mmol) was added in one portion to a stirred solution of SLF (50 mg, 0.10 mmol) and 2-[tert-butoxycarbonyl-(tert-butoxycarbonylamino)amino] acetic acid (42 mg, 0.14 mmol) in dichloromethane (0.19 mL) at 0° C. The resulting mixture was allowed to warm to 23° C. over 30 min, then was kept stirred at 23° C. In 3 h, TLC analysis (50% ethyl acetate-hexanes) showed that the reaction was complete. The reaction mixture was directly concentrated under reduced pressure, and the residue was purified by column chromatography (20-50% ethyl acetate-hexanes, 40-g CombiFlash column) to afford the intermediate as a white foam.

The intermediate product was dissolved in dichloromethane (0.5 mL) was cooled to 0° C., then trifluoroacetic acid (0.5 mL) was added dropwise. The resulting yellow solution was stirred at 0° C. until TLC analysis (50% ethyl acetate-hexanes, mini-workup with ether/sodium bicarbonate) showed full consumption of the starting material (~2 h). The reaction solution was concentrated in vacuo, and the residue was partitioned between dichloromethane (10 mL) and saturated sodium bicarbonate solution (10 mL). The layers were separated, and the aqueous layer was extracted with di chloromethane (2×10 mL). The combined organic layers were dried over sodium sulfate, and the dried solution was concentrated in vacuo to afford the product as a white foam (29 mg, 55%). 6:1 mixture of rotamers. $^1H$ NMR (400 MHz, Chloroform-d) δ 7.65-7.46 (m, 2H), 7.33 (t, J=7.9 Hz, 1H), 7.08 (d, J=7.7 Hz, 1H), 6.80 (d, J=8.7 Hz, 1H), 6.75-6.68 (m, 2H), 5.84-5.74 (m, 1H), 5.35 (d, J=5.6 Hz, 1H), 3.93 (s, 2H), 3.88 (s, 3H), 3.87 (s, 3H), 3.38 (d, J=13.2 Hz, 1H), 3.17 (t, J=12.8 Hz, 1H), 2.72-2.47 (m, 2H), 2.38 (d, J=13.3 Hz, 1H), 2.26 (dt, J=16.2, 7.5 Hz, 1H), 2.16-2.03 (m, 1H), 1.83-1.49 (m, 5H), 1.49-1.33 (m, 2H), 1.26 (s, 3H), 1.24 (s, 3H), 0.92 (t, J=7.4 Hz, 3H). HRMS (ESI): Calcd for $(C_{32}H_{44}N_4O_7+H)^+$: 597.3288, Found: 597.3302.

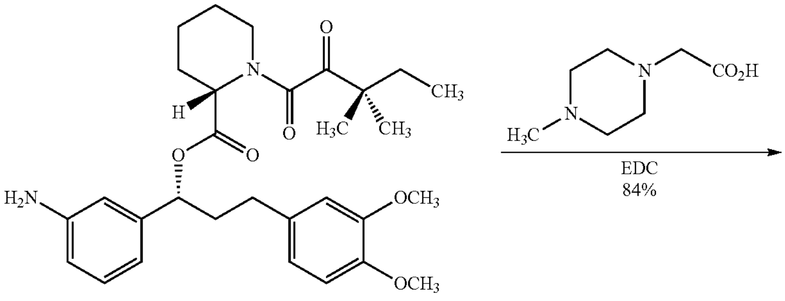

SLF

-continued

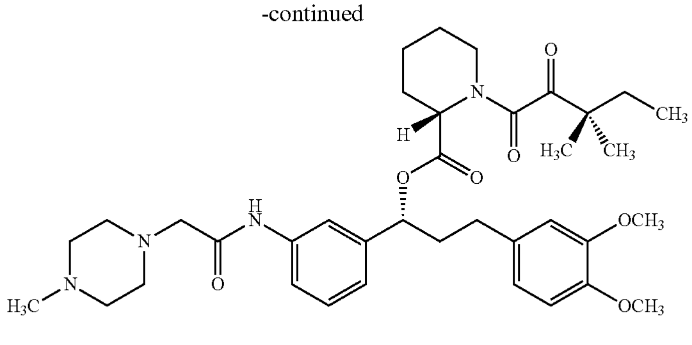

ZZY01-072

An oven-dried 1-dram vial was charged with 2-(4-methylpiperazin-1-yl)acetic acid (30 mg, 0.19 mmol), SLF (50 mg, 0.10 mmol), and a magnetic stir bar. Dichloromethane (0.48 mL) was added via syringe, and the resulting solution was cooled to 0° C. 3-(ethyliminomethyleneamino)-N,N-dimethyl-propan-1-amine hydrochloride (37 mg, 0.19 mmol) was added in one portion to the cooled solution, and the resulting mixture was allowed to warm to 23° C. over 30 min. In 2 h, LC-MS analysis showed full consumption of the starting material. The reaction mixture was directly loaded onto a silica gel column (4-g RediSep) and purified by column chromatography (2-10% methanol in di chloromethane with 0.2-1% saturated aqueous ammonium hydroxide solution) to afford the product as a white solid (53 mg, 84%). 6:1 mixture of rotamers. $^1$H NMR (400 MHz, Chloroform-d) δ 9.13 (s, 1H), 7.58 (d, J=1.8 Hz, 1H), 7.54-7.49 (m, 1H), 7.32 (t, J=7.9 Hz, 1H), 7.09 (d, J=7.9 Hz, 1H), 6.84-6.75 (m, 1H), 6.75-6.65 (m, 2H), 5.78 (dd, J=8.2, 5.4 Hz, 1H), 5.32 (d, J=5.4 Hz, 1H), 3.86 (s, 3H), 3.85 (s, 3H), 3.37 (d, J=13.3 Hz, 1H), 3.20 (td, J=13.1, 3.1 Hz, 1H), 2.71-2.44 (m, 10H), 2.41-2.36 (m, 1H), 2.34 (s, 3H), 2.27 (ddt, J=12.6, 8.6, 4.5 Hz, 1H), 2.16-2.00 (m, 1H), 1.80-1.55 (m, 5H), 1.54-1.29 (m, 2H), 1.23 (s, 3H), 1.21 (s, 3H), 0.89 (t, J=7.4 Hz, 3H). HRMS (ESI): Calcd for $(C_{37}H_{52}N_4O_7+H)^+$: 665.3914, Found: 665.3913.

-continued

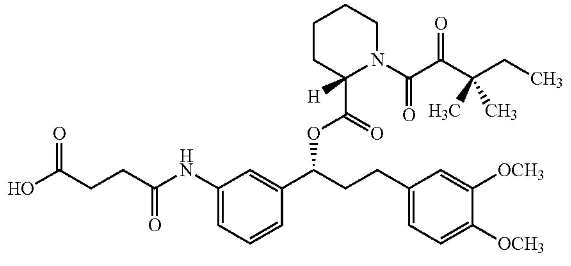

ZZY01-083

Succinic anhydride (14 mg, 0.14 mmol) was added to a solution of SLF (50 mg, 0.10 mmol) in DMF (0.48 mL) at 23° C. The resulting solution was stirred at 23° C. for 16 h. The reaction mixture was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (25 mg, 42%). 6:1 mixture of rotamers. Spectroscopic data was in agreement with that reported by Winter et al. (Winter, G. E. et al. Science 2015, 348, 1376-81.). HRMS (ESI): Calcd for $(C_{33}H_{44}N_2O_9+H)^+$: 625.3125, Found: 625.3102.

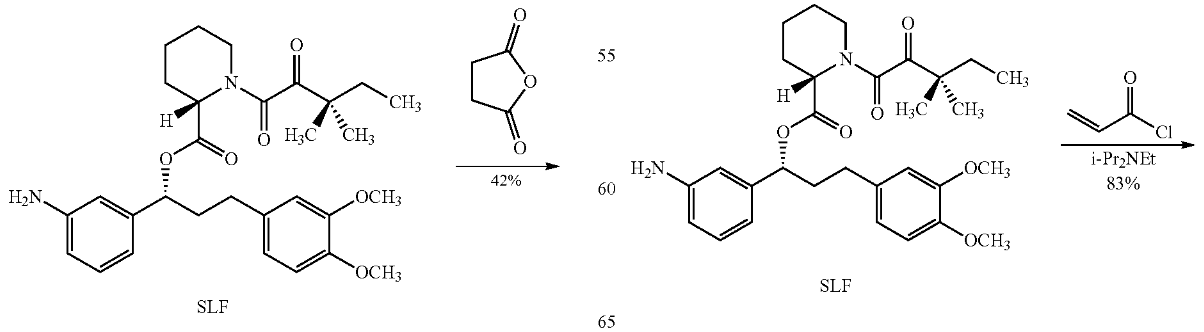

-continued

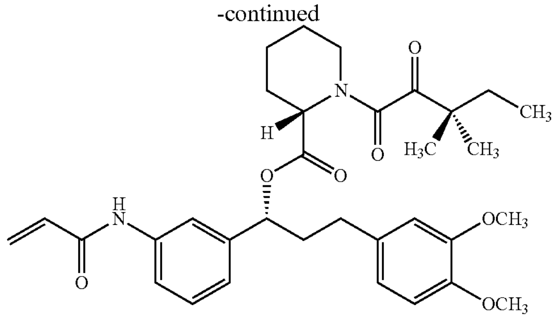

ZZY02-014

Acryloyl chloride (12 μL, 0.010 mmol) was added via pipet to a solution of SLF (5 mg, 0.010 mmol) and N,N-Diisopropylethylamine (17 μL, 0.010 mmol) in dichloromethane (0.10 mL) at 0° C. The resulting solution was stirred at 0° C. for 30 min. At this point, LC-MS analysis showed full consumption of starting material and formation of a single peak corresponding to the desired mass. The reaction mixture was concentrated with a stream of dry air. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to 21 afford the product as a white solid (4.6 mg, 83%). 6:1 mixture of rotamers. $^1H$ NMR (400 MHz, Chloroform-d) δ 8.14 (s, 1H), 7.97 (d, J=8.2 Hz, 1H), 7.47 (s, 1H), 7.35 (t, J=7.9 Hz, 1H), 7.01 (d, J=7.6 Hz, 1H), 6.79 (d, J=7.9 Hz, 1H), 6.75-6.64 (m, 2H), 6.49 (dd, J=16.9, 1.4 Hz, 1H), 6.35 (dd, J=16.9, 10.1 Hz, 1H), 5.86 (dd, J=7.3, 5.6 Hz, 1H), 5.80 (dd, J=10.1, 1.4 Hz, 1H), 5.39 (d, J=5.5 Hz, 1H), 3.88 (s, 3H), 3.87 (s, 3H), 3.32 (d, J=13.6 Hz, 1H), 3.10-2.97 (m, 1H), 2.64-2.52 (m, 2H), 2.38 (d, J=13.5 Hz, 1H), 2.34-2.17 (m, 1H), 2.17-2.00 (m, 1H), 1.87-1.61 (m, 5H), 1.55-1.38 (m, 2H), 1.29 (s, 3H), 1.27 (s, 3H), 0.94 (t, J=7.5 Hz, 3H). HRMS (ESI): Calcd for $(C_{33}H_{42}N_2O_7+H)^+$: 579.3070, Found: 579.3085.

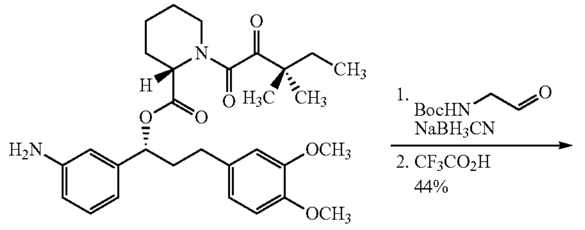

SLF

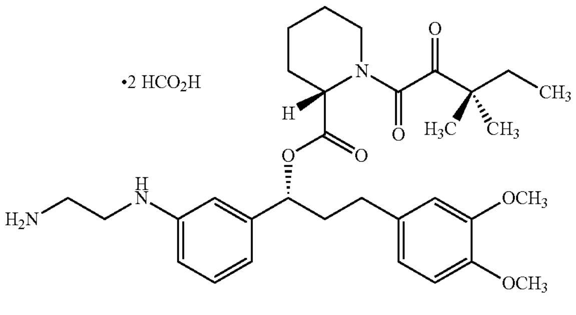

ZZY02-032 tert-Butyl N-(2-oxoethyl)carbamate (17 mg, 0.10 mmol) was added to a solution of SLF (50 mg, 0.10 mmol) in 9:1 methanol:acetic acid (0.5 mL). The resulting solution was stirred at 23° C. for 30 min, then sodium cyanoborohydride (9.0 mg, 0.14 mmol) was added in one portion. The resulting mixture was stirred at 23° C. for another 30 min, at which point LC-MS analysis showed full conversion to the mono-alkylation product. The reaction mixture was concentrated, and the residue was dissolved in trifluoroacetic acid (0.5 mL). After 30 min, LC-MS analysis showed full deprotection of the Boc group. The reaction mixture was concentrated in vacuo. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (24 mg, 44%). 6:1 mixture of rotamers. $^1H$ NMR (400 MHz, Methanol-$d_4$) δ 8.43 (s, 2H), 1.18 (t, J=7.8 Hz, 1H), 6.88 (d, J=8.2 Hz, 1H), 6.79 (d, J=2.0 Hz, 1H), 6.78-6.70 (m, 2H), 6.69-6.60 (m, 2H), 5.69 (dd, J=8.7, 5.0 Hz, 1H), 5.23 (d, J=5.6 Hz, 1H), 3.83 (s, 3H), 3.82 (s, 3H), 3.48-3.37 (m, 4H), 3.24 (td, J=13.1, 3.2 Hz, 1H), 3.15 (td, J=6.0, 2.5 Hz, 2H), 2.72-2.47 (m, 2H), 2.37 (d, J=13.6 Hz, 1H), 2.33-2.18 (m, 1H), 2.18-1.96 (m, 1H), 1.85-1.63 (m, 5H), 1.60-1.29 (m, 2H), 1.24 (s, 3H), 1.23 (s, 3H), 0.91 (t, J=7.5 Hz, 3H). HRMS (ESI): Calcd for $(C_{32}H_{45}N_3O_6+H)^+$: 568.3386, Found: 568.3440.

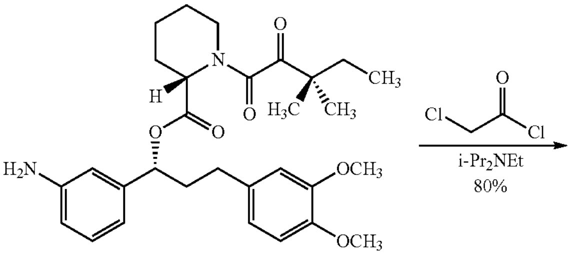

SLF

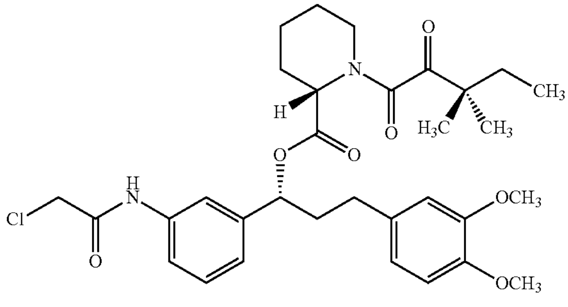

ZZY02-033

2-Chloroacetyl chloride (7.6 μL, 0.10 mmol) was added to a solution of SLF (50 mg, 0.10 mmol) and N,N-Diisopropylethylamine (50 μL, 0.29 mmol) in dichloromethane (0.20 mL) at 0° C. In 40 min, TLC (50% ethyl acetate-hexanes) showed full consumption of the starting material and formation of a just slightly less polar spot. LC-MS analysis confirmed the identity of the product. The reaction mixture was partitioned between dichloromethane (1 mL) and saturated sodium bicarbonate solution (1 mL). The aqueous layer was extracted with dichloromethane (2×1 mL). The combined organic layers were dried over sodium sulfate, and the dried solution was concentrated. The residue was purified by column chromatography (20-50% ethyl acetate-hexanes, 15 min, 4-g CombiFlash column) to afford the product as a white solid (46 mg, 80%). 6:1 mixture of rotamers. $^1$H NMR (400 MHz, Methanol-$d_4$) δ 7.76 (t, J=1.9 Hz, 1H), 7.46 (ddd, J=8.2, 2.2, 1.1 Hz, 1H), 7.34 (t, J=7.9 Hz, 1H), 7.14 (dt, J=7.7, 1.3 Hz, 1H), 6.86 (d, J=8.2 Hz, 1H), 6.80 (d, J=2.0 Hz, 1H), 6.73 (dd, J=8.2, 2.0 Hz, 1H), 5.75 (dd, J=8.8, 5.1 Hz, 1H), 5.24 (d, J=5.2 Hz, 1H), 4.19 (s, 2H), 3.82 (s, 3H), 3.81 (s, 3H), 3.46-3.39 (m, 1H), 3.26 (td, J=13.1, 3.0 Hz, 1H), 2.63 (tdd, J=15.4, 8.6, 5.2 Hz, 2H), 2.46-2.19 (m, 2H), 2.16-2.04 (m, 1H), 1.81-1.57 (m, 5H), 1.55-1.28 (m, 2H), 1.25 (s, 3H), 1.23 (s, 3H), 0.90 (t, J=7.5 Hz, 3H). HRMS (ESI): Calcd for $(C_{32}H_{41}ClN_2O_7+H)^+$: 601.2680, Found: 601.2688.

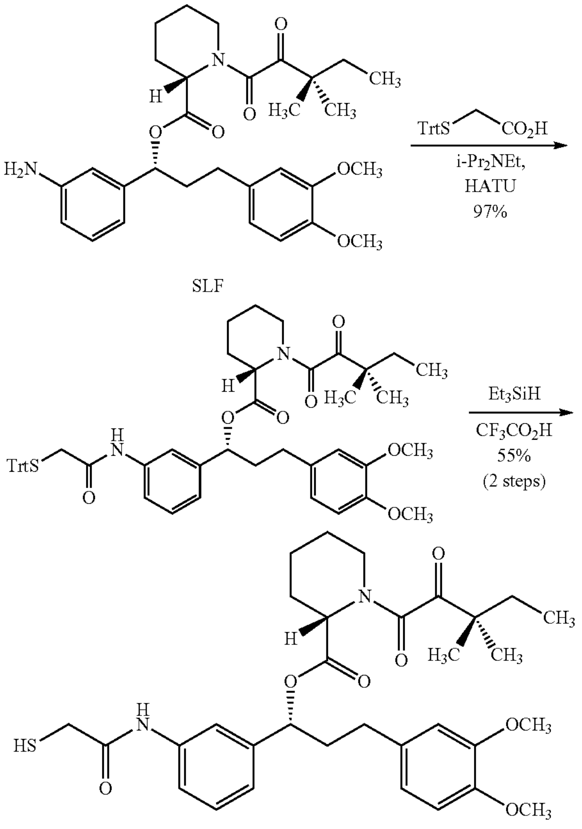

SLF

ZZY02-055

N,N-Diisopropylamine (50 μL, 0.29 mmol) and HATU (54 mg, 0.14 mmol) were added sequentially to a stirred solution of SLF (50 mg, 0.10 mmol) and S-trityl thioglycolic acid (38 mg, 0.11 mmol) in di chloromethane (0.19 mL). The resulting mixture was stirred at 23° C. No reaction was observed at 2 h, likely due to the insolubility of HATU in dichloromethane. DMF (0.2 mL) was added, and the resulting solution was stirred at 23° C. In 2 h, LC-MS analysis showed full conversion to the desired product. The reaction mixture was partitioned between ether (10 mL) and water (10 mL). The aqueous layer was extracted with ether (2×10 mL). The combined organic layers were washed with water (2×10 mL), then with brine (10 mL). The washed solution was dried over magnesium sulfate, and the dried solution was concentrated. The residue was purified by column chromatography (20-100% ethyl acetate-hexanes) to afford the product as a white solid (78 mg, 97%).

Tri ethylsilane (0.15 mL, 0.93 mmol) and trifluoroacetic acid (40 μL, 0.46 mmol) were sequentially added to a stirred solution of the intermediate (78 mg, 0.090 mmol) in dichloromethane (0.19 mL) at 23° C. The resulting yellow solution was stirred at 23° C. for 1 h, at which point the yellow color had completely faded. The reaction mixture was concentrated, and the residue was purified by column chromatography (50-100% ethyl acetate-hexanes) to afford the product as a white solid (49 mg, 86%). 6:1 mixture of rotamers. $^1$H NMR (400 MHz, Chloroform-d) δ 8.72 (s, 1H), 7.67 (ddd, J=8.1, 2.2, 1.0 Hz, 1H), 7.49 (d, J=2.0 Hz, 1H), 7.31 (t, J=7.9 Hz, 1H), 7.04 (dt, J=7.7, 1.2 Hz, 1H), 6.76 (d, J=8.7 Hz, 1H), 6.71-6.63 (m, 2H), 5.80 (dd, J=IN, 5.6 Hz, 1H), 5.37-5.31 (m, 1H), 3.85 (s, 3H), 3.83 (s, 3H), 3.39 (d, J=9.0 Hz, 2H), 3.36-3.29 (m, 1H), 3.15-3.01 (m, 1H), 2.64-2.48 (m, 2H), 2.48-2.31 (m, 2H), 2.30-2.17 (m, 1H), 2.09 (t, J=9.0 Hz, 1H), 1.78-1.57 (m, 5H), 1.51-1.33 (m, 2H), 1.23 (s, 6H), 0.89 (t, J=7.5 Hz, 3H). HRMS (ESI): Calcd for $(C_{32}H_{42}N_2O_7S+H)^+$: 599.2791, Found: 599.2778.

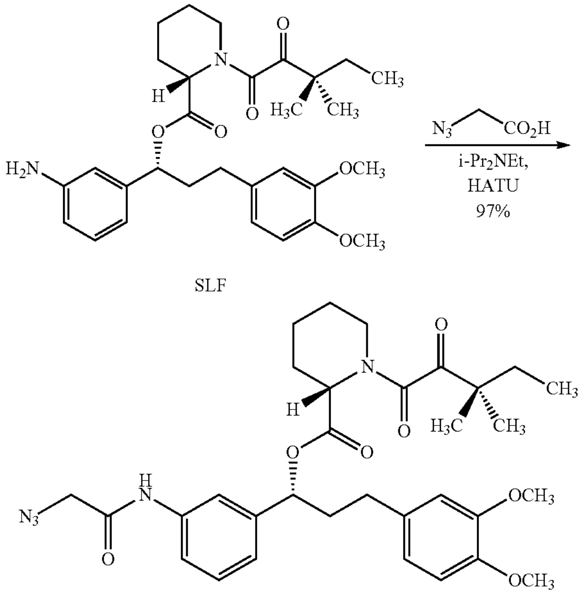

SLF

ZZY02-096

N,N-Diisopropylamine (50 μL, 0.29 mmol) and HATU (54 mg, 0.14 mmol) were added sequentially to a stirred solution of SLF (50 mg, 0.10 mmol), 2-azidoacetic acid (8.6 μL, 0.11 mmol) in 9:1 dichloromethane:DMF (0.19 mL). In 2 h, LC-MS analysis showed full conversion to the desired product. The reaction mixture was partitioned between ether (10 mL) and water (10 mL). The aqueous layer was extracted with ether (2×10 mL). The combined organic layers were washed with water (2×10 mL), then with brine (10 mL). The washed solution was dried over magnesium sulfate, and the dried solution was concentrated. The residue was purified by column chromatography (20-100% ethyl acetate-hexanes) to afford the product as a white solid (56 mg, 97%). 6:1 mixture of rotamers. $^1$H NMR (400 MHz, Chloroform-d) δ 8.29 (s, 1H), 7.71 (ddd, J=8.1, 2.3, 1.0 Hz, 1H), 7.50 (t, J=1.9 Hz, 1H), 7.34 (t, J=7.9 Hz, 1H), 7.07 (d, J=7.5 Hz, 1H), 6.82-6.74 (m, 1H), 6.74-6.57 (m, 2H), 5.81 (dd, J=7.7, 5.6 Hz, 1H), 5.34 (d, J=5.5 Hz, 1H), 4.17-4.10 (m, 2H), 3.86 (s, 3H), 3.85 (s, 3H), 3.33 (d, J=13.7 Hz, 1H), 3.15-3.01 (m, 1H), 2.66-2.41 (m, 2H), 2.36 (d, J=13.6 Hz, 1H), 2.31-2.16 (m, 1H), 2.11-1.99 (m, 1H), 1.78-1.59 (m, 5H), 1.51-1.33 (m, 2H), 1.24 (s, 6H), 0.91 (t, J=7.5 Hz, 3H). HRMS (ESI): Calcd for $(C_{32}H_{41}N_5O_7+H)^+$: 608.3084, Found: 608.3110.

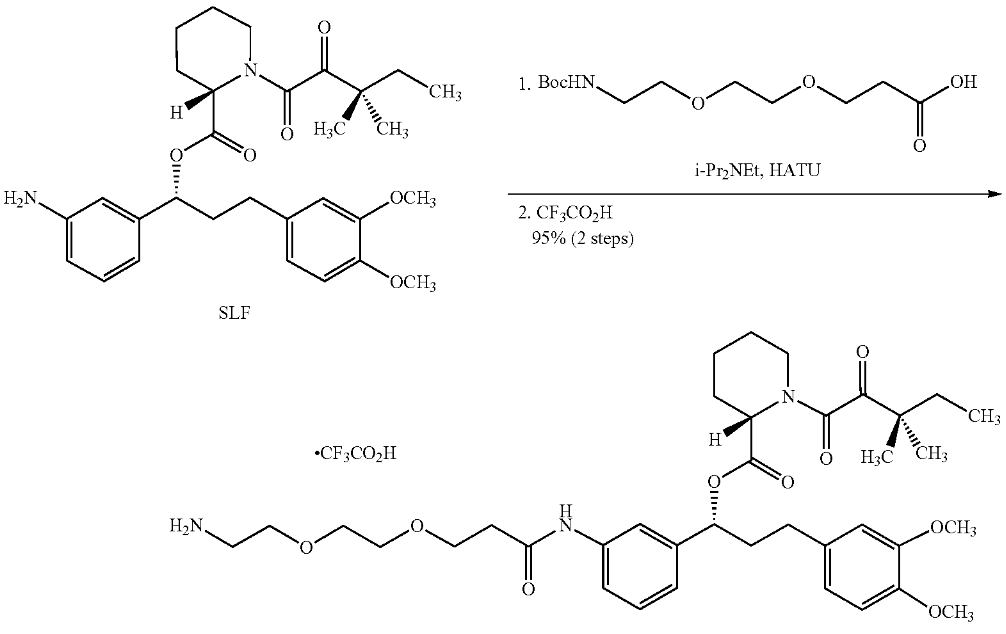

SLF

ZZY03-077

N,N-Diisopropylethylamine (16.6 μL, 0.10 mmol) and HATU (72 mg, 0.19 mmol) were added sequentially to a solution of SLF (50 mg, 0.10 mmol) and 3-[2-[2-(tert-butoxycarbonylamino)ethoxy]ethoxy]propanoic acid (40 mg, 0.14 mmol) in 9:1 dichloromethane:DMF (0.2 mL). The resulting mixture was stirred at 23° C. for 12 h, at which point LC-MS analysis showed full conversion to the desired product. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a yellow oil.

The intermediate product (70 mg, 0.090 mmol) was dissolved in 1:1 dichloromethane:trifluoroacetic acid (1.0 mL). The resulting solution was allowed to stand at 23° C. for 1 h, then was concentrated under reduced pressure to afford the product as a yellow foam (71 mg, 95%). 6:1 mixture of rotamers. $^1$H NMR (400 MHz, Methanol-$d_4$) δ 7.70 (t, J=1.9 Hz, 1H), 7.52-7.44 (m, 1H), 7.34 (t, J=7.9 Hz, 1H), 7.14 (d, J=8.0 Hz, 1H), 6.88 (d, J=8.1 Hz, 1H), 6.81 (d, J=2.1 Hz, 1H), 6.75 (dd, J=8.2, 2.0 Hz, 1H), 5.73 (dd, J=8.8, 5.0 Hz, 1H), 5.24 (d, J=5.6 Hz, 1H), 3.86 (t, J=6.5 Hz, 2H), 3.84 (s, 3H), 3.82 (s, 4H), 3.71-3.64 (m, 8H), 3.42 (d, J=13.9 Hz, 1H), 3.26 (dd, J=13.4, 3.3 Hz, 1H), 3.09-2.99 (m, 2H), 2.70-2.54 (m, 4H), 2.37 (d, J=14.3 Hz, 1H), 2.34-2.22 (m, 1H), 2.15-2.03 (m, 1H), 1.84-1.59 (m, 5H), 1.59-1.29 (m, 2H), 1.25 (s, 3H), 1.24 (s, 3H), 0.90 (t, J=7.5 Hz, 3H). HRMS (ESI): Calcd for $(C_{37}H_{53}N_3O_9+H)^+$: 684.3860, Found: 684.3851.

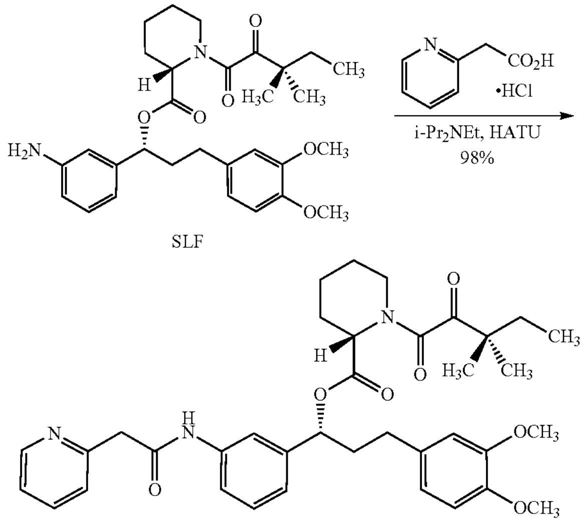

SLF

ZZY03-083

N,N-Diisopropylethylamine (16.6 μL, 0.10 mmol) and HATU (72 mg, 0.1900 mmol) were added sequentially to a solution of SLF (50 mg, 0.10 mmol) and 2-(2-pyridyl)acetic acid hydrochloride (25 mg, 0.14 mmol) in 9:1 dichloromethane:DMF (0.2 mL). The resulting mixture was stirred at 23° C. for 12 h, at which point LC-MS analysis showed full conversion to the desired product. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a white solid (60 mg, 98%). 6:1 mixture of rotamers. $^1$H NMR (400 MHz, Chloroform-d) δ 9.91 (s, 1H), 8.62 (dd, J=5.3, 1.7 Hz, 1H), 7.93 (t, J=7.6 Hz, 1H), 7.61 (s, 1H), 7.54 (t, J=7.5 Hz, 2H), 7.44 (t, J=6.5 Hz, 1H), 7.34-7.23 (m, 1H), 7.05 (d, J=7.7 Hz, 1H), 6.82-6.73 (m, 1H), 6.74-6.63 (m, 2H), 5.76 (dd, J=8.1, 5.4 Hz, 1H), 5.32 (d, J=5.4 Hz, 1H), 4.05 (s, 2H), 3.85 (s, 3H), 3.85 (s, 3H), 3.37 (d, J=13.3 Hz, 1H), 3.18 (td, J=13.0, 3.1 Hz, 1H), 2.69-2.46 (m, 2H), 2.36 (d, J=13.5 Hz, 1H), 2.33-2.19 (m, 1H), 2.19-1.99 (m, 1H), 1.79-1.57 (m, 5H), 1.57-1.29 (m, 2H), 1.23 (s, 3H), 1.21 (s, 3H), 0.88 (t, J=7.4 Hz, 3H). HRMS (ESI): Calcd for $(C_{37}H_{45}N_3O_7+H)^+$: 644.3336, Found: 644.3350.

1H), 6.80 (d, J=2.0 Hz, 1H), 6.74 (dd, J=8.1, 2.0 Hz, 1H), 5.70 (dd, J=8.7, 4.8 Hz, 1H), 5.24 (d, J=5.6 Hz, 1H), 3.80 (s, 3H), 3.79 (s, 3H), 3.72 (dd, J=62, 4.1 Hz, 2H), 3.38 (d, J=14.0 Hz, 1H), 3.25 (dd, J=12.9, 3.1 Hz, 1H), 3.17 (s, 4H), 2.72-2.51 (m, 4H), 2.37 (d, J=13.9 Hz, 1H), 2.32-2.17 (m, 1H), 2.17-2.04 (m, 1H), 1.84-1.56 (m, 5H), 1.55-1.33 (m, 2H), 1.21 (s, 3H), 1.20 (s, 3H), 0.87 (t, J=7.5 Hz, 3H). HRMS (ESI): Calcd for $(C_{35}H_{49}N_3O_8+H)^+$: 640.3598, Found: 640.3611.

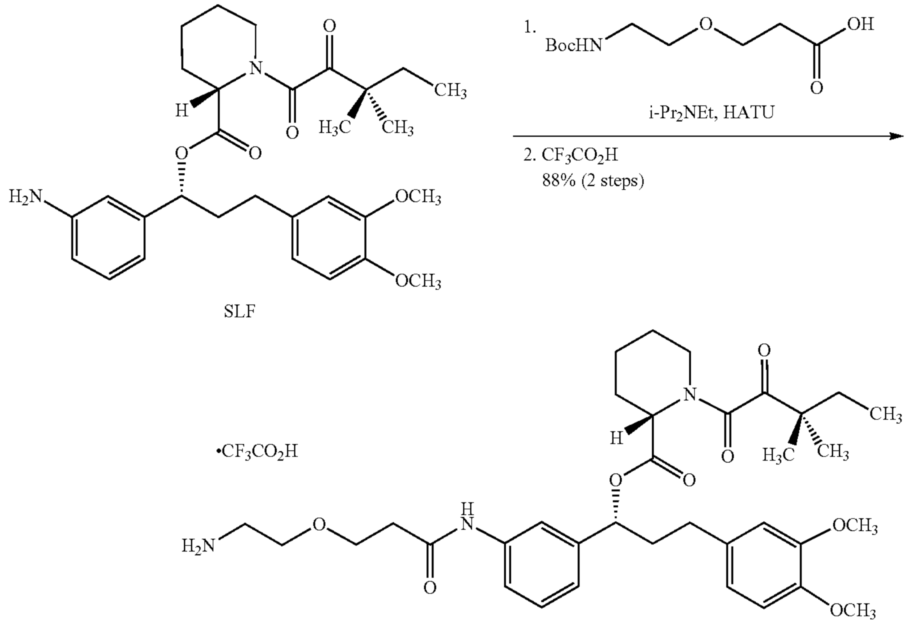

SLF

ZZY03-084

N,N-Diisopropylethylamine (16.6 μL, 0.10 mmol) and HATU (72 mg, 0.19 mmol) were added sequentially to a solution of SLF (50 mg, 0.10 mmol) and 3-[2-(tert-butoxycarbonylamino)ethoxy]propanoic acid (33 mg, 0.14 mmol) in 9:1 dichloromethane:DMF (0.2 mL). The resulting mixture was stirred at 23° C. for 12 h, at which point LC-MS analysis showed full conversion to the desired product. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a yellow oil. The oil was dissolved in 1:1 dichloromethane:trifluoroacetic acid (1.0 mL). The resulting colorless solution was allowed to stand at 23° C. for 1 h, then was concentrated in vacuo to afford the product as a white foam (62 mg, 88%). 6:1 mixture of rotamers. $^1$H NMR (400 MHz, Acetonitrile-$d_3$) δ 8.85 (s, 1H), 7.68 (s, 1H), 7.51 (d, J=8.1 Hz, 1H), 7.35 (t, J=7.9 Hz, 1H), 7.11 (d, J=7.6 Hz, 1H), 6.86 (d, J=8.2 Hz,

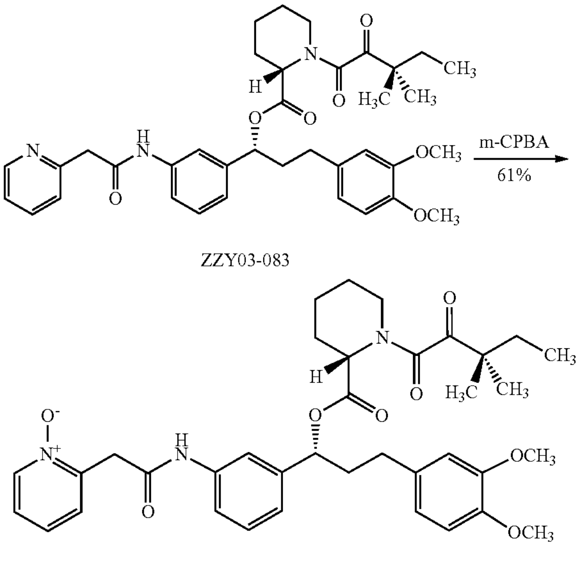

ZZY03-083

ZZY03-087

3-Chlorobenzenecarboperoxoic acid (5.4 mg, 0.020 mmol) was added to an ice-cold solution of ZZY03-083 (10 mg, 0.020 mmol) in dichloromethane (0.16 mL). The resulting pale yellow solution was stirred at 0° C. for 1 h. LC-MS analysis showed complete conversion to the desired m/z. Tri ethylamine (10 μL) was added to consume the excess mCPBA. After warming to 23° C., the solution was concentrated under reduced pressure. The residue was diluted with 50% acetonitrile-water to a volume of 4.7 mL, and the solution was purified by reverse-phase HPLC (Waters XBridge C18 column 5 μm particle size 30×250 mm, 5-95% acetonitrile-water+0.1% formic acid, 40 min, 20 mL/min) to afford the product as a white solid (6.3 mg, 61%). 6:1 mixture of rotamers. $^1$H NMR (400 MHz, Chloroform-d) δ 10.91 (s, 1H), 8.46-8.37 (m, 1H), 7.60-7.49 (m, 3H), 7.45 (t, J=7.7 Hz, 1H), 7.36 (t, J=7.0 Hz, 1H), 7.33-7.24 (m, 1H), 7.09-7.00 (m, 1H), 6.80 (d, J=8.8 Hz, 1H), 6.74-6.67 (m, 2H), 5.77 (dd, J=8.1, 5.6 Hz, 1H), 5.33 (d, J=5.4 Hz, 1H), 4.12 (s, 2H), 3.88 (s, 3H), 3.87 (s, 3H), 3.40 (d, J=13.4 Hz, 1H), 3.22 (td, J=13.0, 3.1 Hz, 1H), 2.68-2.48 (m, 2H), 2.38 (d, J=13.7 Hz, 1H), 2.33-2.17 (m, 1H), 2.14-2.02 (m, 1H), 1.84-1.58 (m, 5H), 1.58-1.30 (m, 2H), 1.26 (s, 3H), 1.23 (s, 3H), 0.90 (t, J=7.4 Hz, 3H). HRMS (ESI): Calcd for $(C_{37}H_{45}N_3O_8+H)^+$: 660.3285, Found: 660.3268.

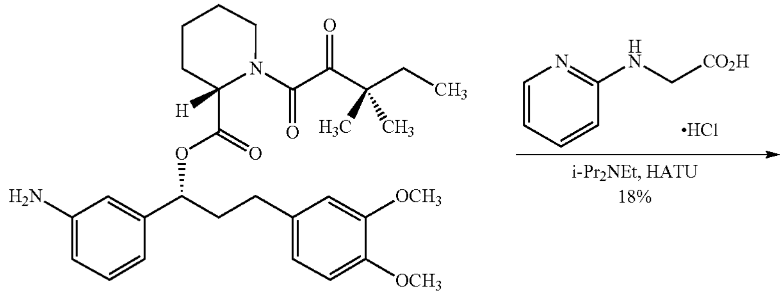

SLF

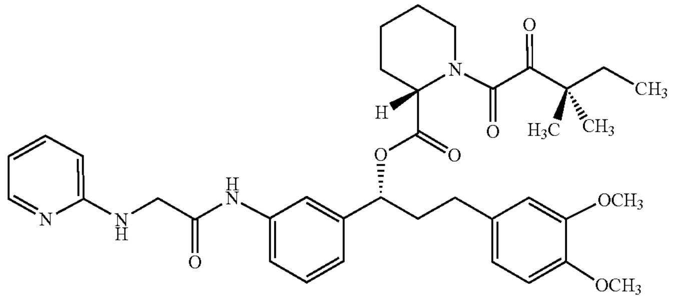

ZZY03-091

HATU (72 mg, 0.19 mmol) was added to a mixture of SLF (50 mg, 0.10 mmol), 2-(2-pyridylamino)acetic acid hydrochloride (27 mg, 0.14 mmol), N,N-Diisopropylethylamine (34 μL, 0.20 mmol) in 9:1 dichloromethane:DMF (0.2 mL). The resulting mixture was stirred at 23° C. for 12 h, at which point LC-MS analysis showed ~50% conversion to the desired product. Additional 2-(2-pyridylamino)acetic acid hydrochloride (27 mg, 0.14 mmol) and HATU (72 mg, 0.19 mmol) were added, and the mixture was stirred for another 1 h. LC-MS analysis showed no further progress. The reaction mixture was partitioned between ethyl acetate (1 mL) and water (1 mL). The aqueous layer was extracted with ethyl acetate (3×1 mL). The combined organic layers were dried over sodium sulfate, then was concentrated under reduced pressure. The residue was purified by column chromatography (50-100% ethyl acetate-hexanes, 4-g CombiFlash column) to afford the product as a yellow solid (11.2 mg, 18%). 6:1 mixture of rotamers. $^1$H NMR (400 MHz, Chloroform-d) δ 7.92 (s, 1H), 7.83 (s, 1H), 7.65 (d, J=8.3 Hz, 1H), 7.59 (s, 1H), 7.36-7.28 (m, 1H), 7.20-6.99 (m, 3H), 6.87 (t, J=6.4 Hz, 1H), 6.85-6.75 (m, 1H), 6.75-6.64 (m, 2H), 5.81-5.74 (m, 1H), 5.33 (d, J=5.2 Hz, 1H), 4.54-4.35 (m, 2H), 3.86 (s, 3H), 3.85 (s, 3H), 3.37 (d, J=13.7 Hz, 1H), 3.26-2.99 (m, 2H), 2.66-2.46 (m, 2H), 2.37 (d, J=13.4 Hz, 1H), 2.33-2.18 (m, 1H), 2.14-2.02 (m, 1H), 1.80-1.64 (m, 5H), 1.51-1.32 (m, 2H), 1.23 (s, 3H), 1.21 (s, 3H), 0.88 (t, J=7.4 Hz, 3H). HRMS (ESI): Calcd for $(C_{37}H_{46}N_4O_7+H)^+$: 659.3444, Found: 659.3436.

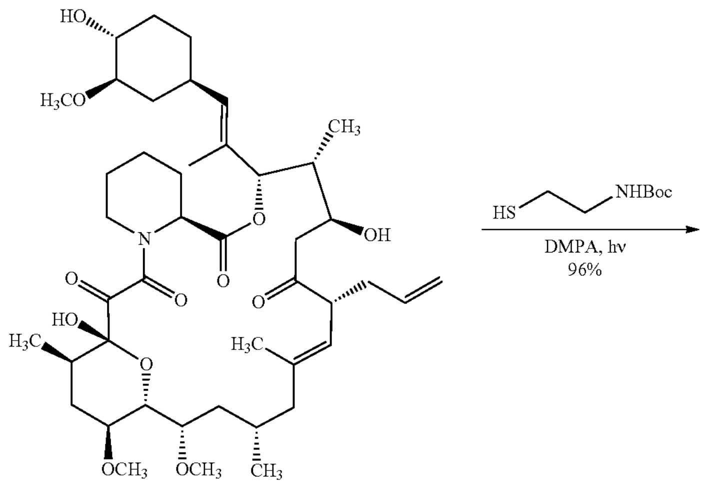
FK506
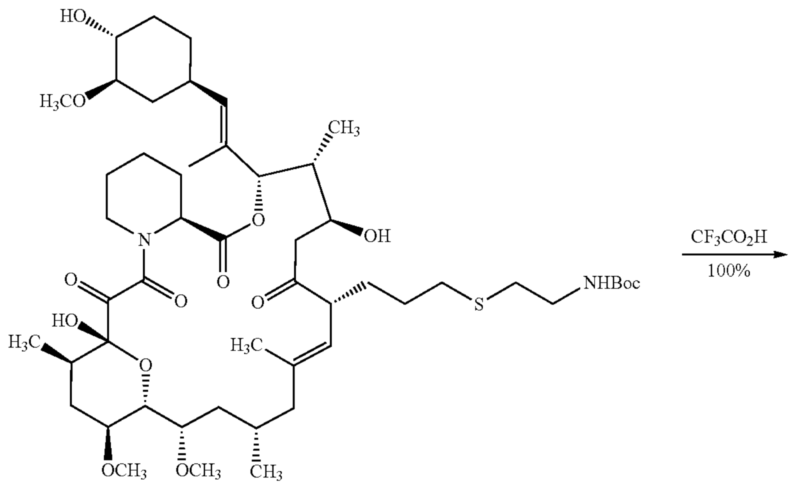
ZZY05-009
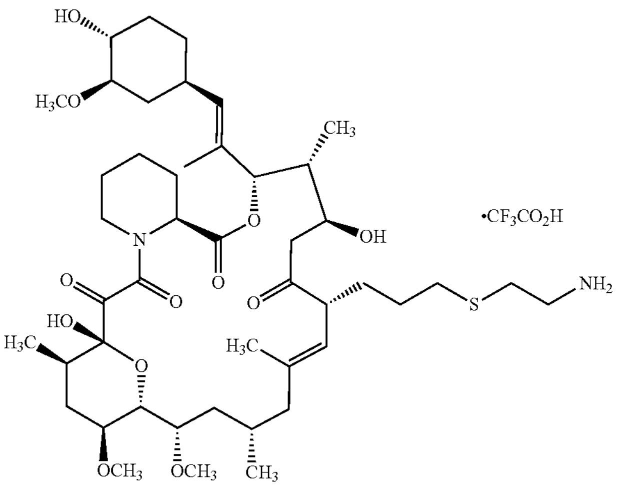
ZZY05-011 tert-Butyl N-(2-sulfanylethyl)carbamate (23 mg, 0.13 mmol) and dimethoxyphenylacetophenone (DMPA, 3.2 mg, 0.010 mmol) were added sequentially to a solution of FK506 (100 mg, 0.120 mmol) in dichloromethane (1.2 mL) at 23° C. After all reactants had dissolved, the vial was placed above a hand-held UV-light operating at 365 nm wavelength (the light was placed upside-down so that the contents of vial were directly irradiated). The irradiation was maintained for 15 min, at which point TLC analysis (100% ethyl acetate) showed full consumption of FK506 and formation of a slightly more polar product. The reaction solution was directly loaded onto a 12-g silica gel column. Purification by column chromatography (50-100% ethyl acetate-hexanes, 12-g RediSep® Rf column, Teledyne ISCO, Lincoln, Nebr.) afforded the product as a white foam (117 mg, 96%).

Trifluoroacetic acid (0.5 mL) was added dropwise to a solution of ZZY05-009 (117 mg, 0.120 mmol) in dichloromethane (0.5 mL) at 0° C. The resulting mixture was stirred at 0° C. for 1 h, at which point LC-MS analysis showed full deprotection of the Boc group. The reaction solution was concentrated under reduced pressure and the product was dried azeotropically by rotary evaporation of its suspension in toluene to afford the product as an off-white powder (119 mg, 100%). NMR: 3:2 mixture of rotamers. $^1$H NMR (400 MHz, Methanol-$d_4$) δ 5.29-5.07 (m, 2H), 4.95 (d, J=11.7 Hz, 1H), 4.64 (s, 1H), 4.37 (d, J=13.4 Hz, 1H), 4.13-3.93 (m, 2H), 3.78-3.70 (m, 2H), 3.69-3.54 (m, 2H), 3.44 (s, 3H), 3.42 (s, 3H), 3.41-3.39 (m, 3H), 3.36 (s, 3H), 3.19-3.09 (m, 2H), 3.09-2.96 (m, 2H), 2.84-2.75 (m, 2H), 2.60 (t, J=6.9 Hz, 2H), 2.43-2.26 (m, 4H), 2.27-2.10 (m, 4H), 2.10-1.89 (m, 4H), 1.84-1.73 (m, 6H), 1.73-1.60 (m, 6H), 1.61-1.29 (m, 8H), 1.04-0.98 (m, 2H), 0.98-0.87 (m, 9H). HRMS (ESI): Calcd for $(C_{46}H_{76}N_2O_{12}S+H)^+$: 881.5197, Found: 881.5207.

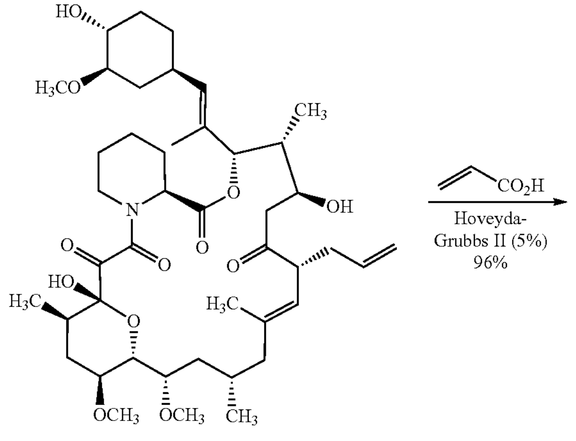

FK506

-continued

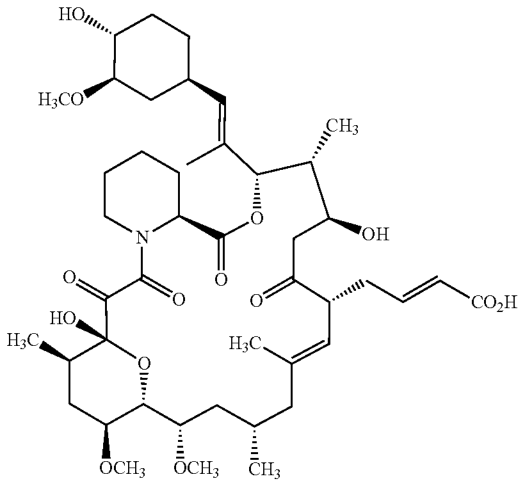

ZZY05-012

A flame-dried 10-mL microwave vial was flushed with dry argon, and then was charged with FK506 (100 mg, 0.120 mmol), DCE (1.20 mL), and a magnetic stir bar. Acrylic acid (170 mg, 2.49 mmol) and Grubbs Catalyst 2nd Gen (5.3 mg, 0.010 mmol) were added sequentially. The vial was flushed with argon again and sealed with a rubber cap. The reaction mixture was heated at 85° C. for 1 h in a CEM Discover SP microwave reactor. After cooling to 23° C., TLC analysis (100% ethyl acetate) of the reaction mixture showed full disappearance of the starting material and formation of a highly polar new spot. The reaction solution was concentrated in vacuo. The residue was purified by column chromatography (20-100% ethyl acetate-hexanes, 12-g RediSep® Rf column, Teledyne ISCO, Lincoln, Nebr.) to afford the product as a yellow powder (101 mg, 96%). NMR: 3:2 mixture of rotamers. $^1$H NMR (400 MHz, Chloroform-d) δ 7.01-6.88 (m, 1H), 5.86 (d, J=15.5 Hz, 1H), 5.34 (s, 1H), 5.11 (app t, J=8.8 Hz, 1H), 5.03 (app d, J=8.4 Hz, 1H), 4.68 (d, J=5.2 Hz, 1H), 4.46 (d, J=13.9 Hz, 1H), 3.96-3.84 (m, 1H), 3.72 (d, J=9.3 Hz, 1H), 3.68-3.54 (m, 1H), 3.55-3.41 (m, 3H), 3.43 (s, 3H), 3.41 (s, 3H), 3.32 (s, 3H), 3.08-2.96 (m, 3H), 2.86-2.78 (m, 1H), 2.74-2.62 (m, 1H), 2.49-2.26 (m, 3H), 2.24-2.08 (m, 3H), 2.06-1.98 (m, 2H), 1.98-1.86 (m, 2H), 1.86-1.71 (m, 4H), 1.71-1.60 (m, 6H), 1.59-1.32 (m, 8H), 1.14-1.05 (m, 2H), 1.03 (d, J=6.3 Hz, 3H), 0.96 (d, J=6.4 Hz, 3H), 0.90 (d, J=7.1 Hz, 3H). HRMS (ESI): Calcd for $(C_{45}H_{69}NO_{14}-H)^-$: 846.4640, Found: 846.4601.

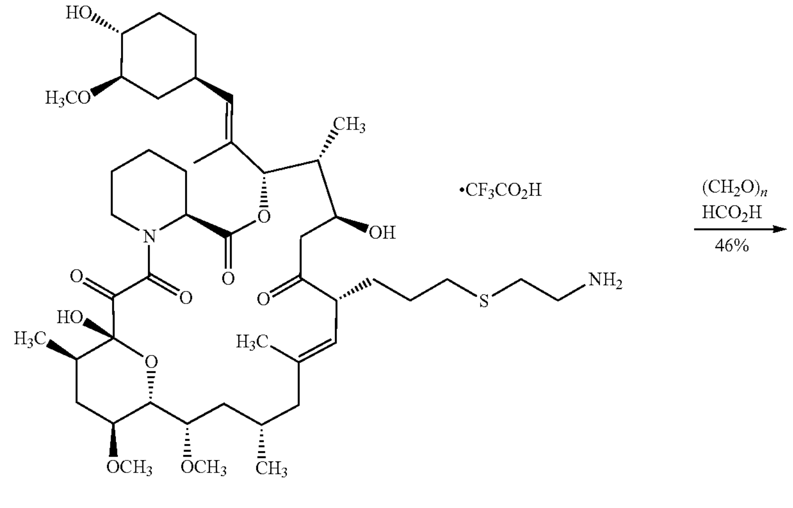

ZZY05-011

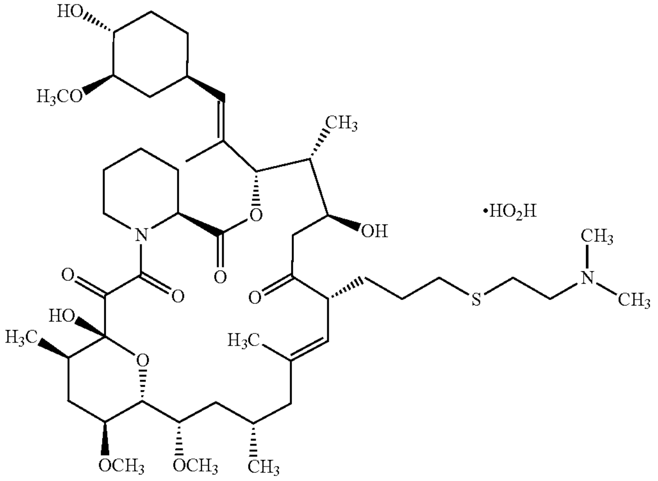

ZZY05-013

Paraformaldehyde (3.0 mg, 0.10 mmol) and formic acid (4.6 mg, 0.10 mmol) were added sequentially to a solution of ZZY05-011 (10 mg, 0.010 mmol) in chloroform (0.2 mL). The suspension was heated to 70° C. for 1 h. In 1 h, LC-MS analysis showed formation of two peaks, both of which had the desired mass. The reaction mixture was cooled to 23° C. The reaction mixture was partitioned between saturated aqueous sodium bicarbonate solution (1 mL) and di chloromethane (1 mL). The layers were separated, and the aqueous layer was extracted with dichloromethane (2×1 mL). The combined organic layers were dried over sodium sulfate. The dried solution was filtered, and the filtrate was concentrated. The residue was diluted with 50% acetonitrile-water to a volume of 4.7 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (4.2 mg, 46%). 3:2 mixture of rotamers. $^1$H NMR (400 MHz, Methanol-$d_4$) δ 5.31-5.09 (m, 2H), 4.97 (d, J=9.9 Hz, 1H), 4.65 (s, 1H), 4.37 (d, J=13.5 Hz, 1H), 4.12-3.89 (m, 2H), 3.80-3.70 (m, 1H), 3.70-3.59 (m, 2H), 3.59-3.47 (m, 2H), 3.44 (s, 3H), 3.42 (s, 3H), 3.40-3.37 (m, 3H), 3.36 (s, 3H), 3.09-2.98 (m, 2H), 2.90 (s, 6H), 2.89-2.84 (m, 2H), 2.68-2.60 (m, 2H), 2.42-2.27 (m, 4H), 2.27-2.13 (m, 4H), 2.13-1.76 (m, 6H), 1.76-1.67 (m, 6H), 1.68-1.29 (m, 8H), 1.16-1.03 (m, 2H), 1.01-0.87 (m, 9H). HRMS (ESI): Calcd for $(C_{48}H_{80}N_2O_{12}S+H)^+$: 909.5510, Found: 909.5502.

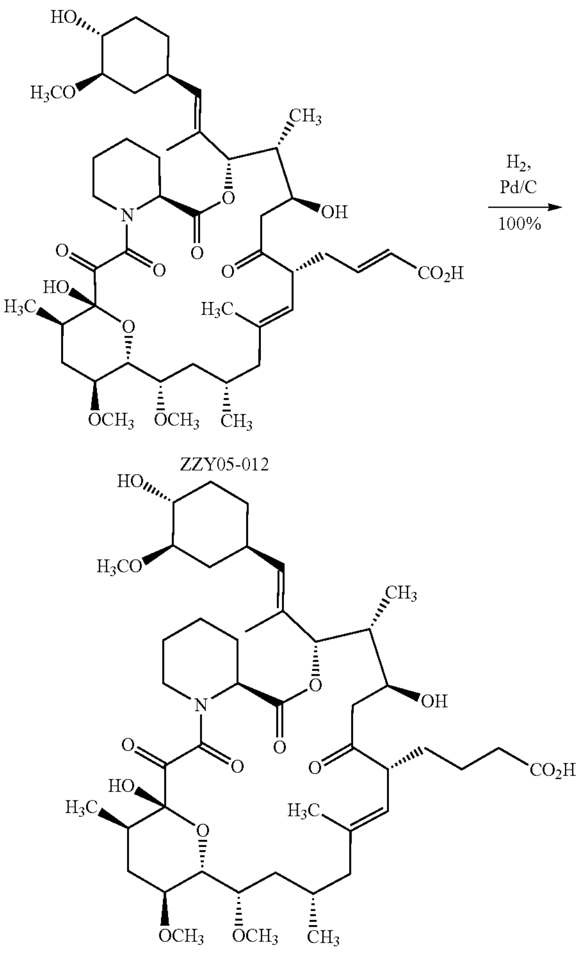

ZZY05-012

ZZY05-020

10 wt % Palladium on carbon (13 mg, 0.010 mmol) was added to a solution of ZZY05-012 (50 mg, 0.060 mmol) in methanol (5 mL) at 23° C. under an atmosphere of argon. The reaction flask was evacuated until effervescence occurred, then flushed with hydrogen gas. The process was repeated three times. The resulting suspension was stirred at 23° C. for 16 h under an atmosphere of hydrogen. The reaction flask was purged with argon, and the reaction suspension was filtered through a pad of Celite. The filter cake was rinsed with ethyl acetate (20 mL). The combined filtrate was concentrated in vacuo, and the residue was purified by column chromatography (0-10% methanol-dichloromethane+0.1% acetic acid) to afford the product as a white solid (50 mg, 100%). 3:2 mixture of rotamers. $^1H$ NMR. (400 MHz, Chloroform-d) δ 5.35-5.31 (m, 1H), 5.13-5.07 (m, 1H), 5.03 (d, J=10.3 Hz, 1H), 4.61 (d, J=5.4 Hz, 1H), 4.43 (d, J=13.8 Hz, 1H), 4.01-3.89 (m, 1H), 3.70 (d, J=9.6 Hz, 1H), 3.64-3.52 (m, 1H), 3.42 (s, 3H), 3.40 (s, 3H), 3.43-3.36 (m, 3H), 3.31 (s, 3H), 3.10-2.93 (m, 3H), 2.79 (dd, J=15.9, 3.0 Hz, 1H), 2.45-2.25 (m, 5H), 2.26-2.10 (m, 3H), 2.09-1.88 (m, 6H), 1.89-1.71 (m, 6H), 1.60 (s, 6H), 1.60-1.35 (m, 8H), 1.13-1.03 (m, 2H), 1.00 (d, J=6.3 Hz, 3H), 0.94 (d, J=6.4 Hz, 3H), 0.88 (d, J=7.1 Hz, 3H). HRMS (ESI): 2 Calcd for $(C_{45}H_{71}NO_{14}-H)^-$: 848.4796, Found: 848.4809.

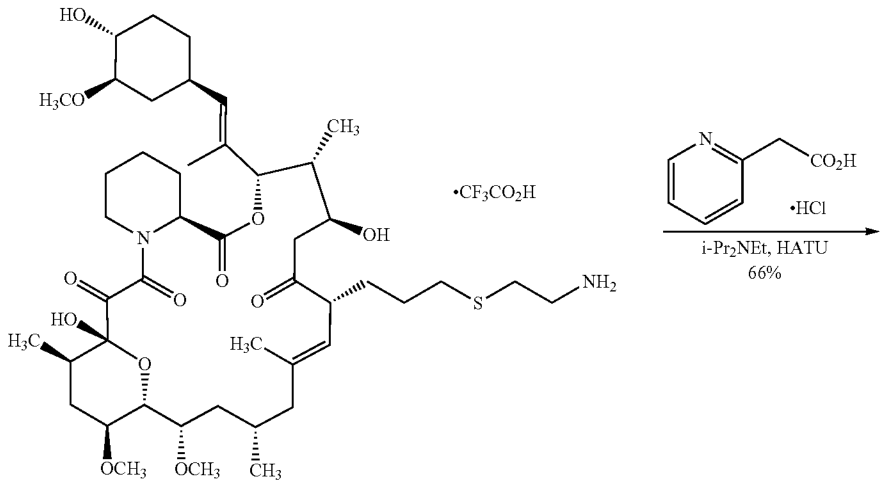

ZZY05-011

-continued

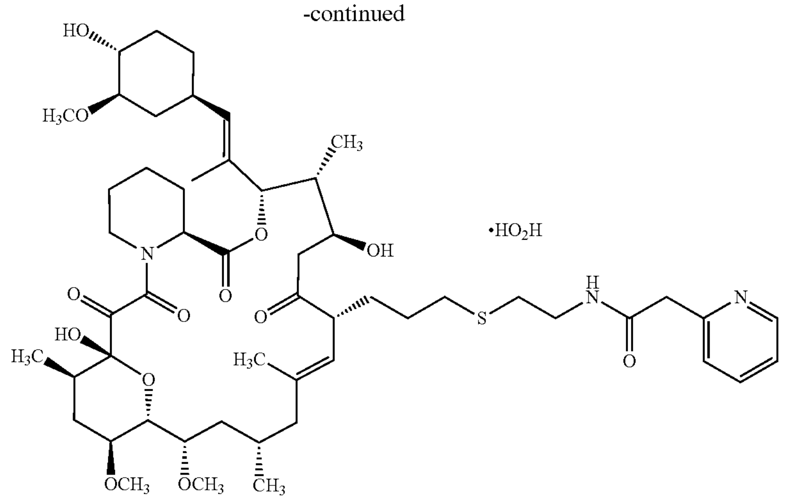

ZZY05-026

An oven-dried one-dram vial was charged with ZZY05-011 (15 mg, 0.020 mmol), 2-(2-pyridyl)acetic acid hydrochloride (4.4 mg, 0.030 mmol), DMF (0.17 mL), N,N-Diisopropylethylamine (15 μL, 0.090 mmol), and a magnetic stir bar. HATU (7.7 mg, 0.020 mmol) was added as a solid at 23° C., and the resulting mixture was stirred at 23° C. for 30 min. At this point, LC-MS analysis showed full consumption of the starting amine and formation of a single peak corresponding to the desired mass. The residue was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (11.2 mg, 66%). 3:2 mixture of rotamers. $^1H$ NMR (400 MHz, Methanol-$d_4$) δ 8.54-8.45 (m, 1H), 8.13 (br s, 1H), 7.88-7.74 (m, 2H), 7.44 (d, J=7.9 Hz, 1H), 7.37-7.31 (m, 1H), 5.29-5.08 (m, 2H), 4.93 (s, 1H), 4.63 (s, 1H), 4.36 (d, J=13.4 Hz, 1H), 4.12-3.92 (m, 2H), 3.79-3.71 (m, 2H), 3.70-3.45 (m, 4H), 3.43 (s, 3H), 3.42 (s, 3H), 3.41-3.38 (m, 3H), 3.36 (s, 3H), 3.09-2.98 (m, 1H), 2.85 (dd, J=14.4, 6.2 Hz, 1H), 2.64 (t, J=7.0 Hz, 2H), 2.54 (t, J=6.4 Hz, 2H), 2.44-2.27 (m, 4H), 2.27-2.08 (m, 4H), 2.08-1.74 (m, 6H), 1.74-1.64 (m, 6H), 1.64-1.33 (m, 8H), 1.18-1.01 (m, 2H), 0.99-0.86 (m, 9H). HRMS (ESI): Calcd for $(C_{53}H_{81}N_3O_{13}S+H)^+$: 1000.5568, Found: 1000.5567.

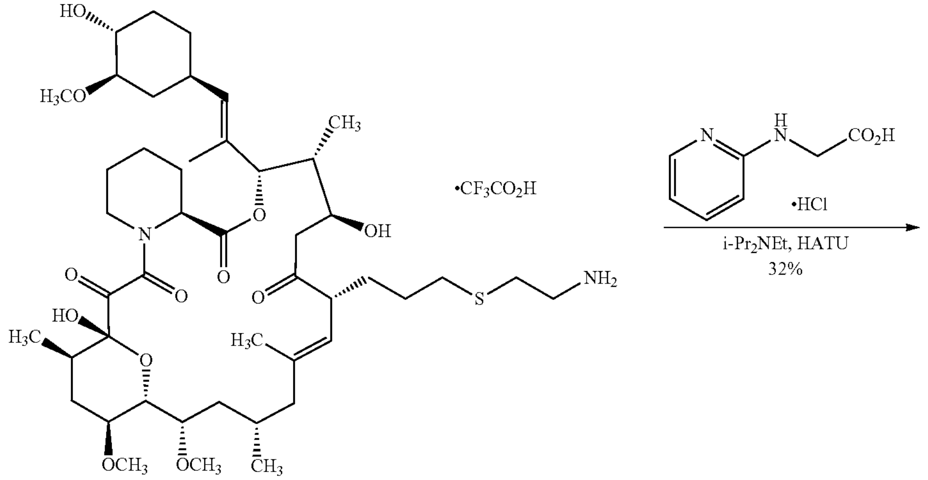

ZZY05-011

-continued

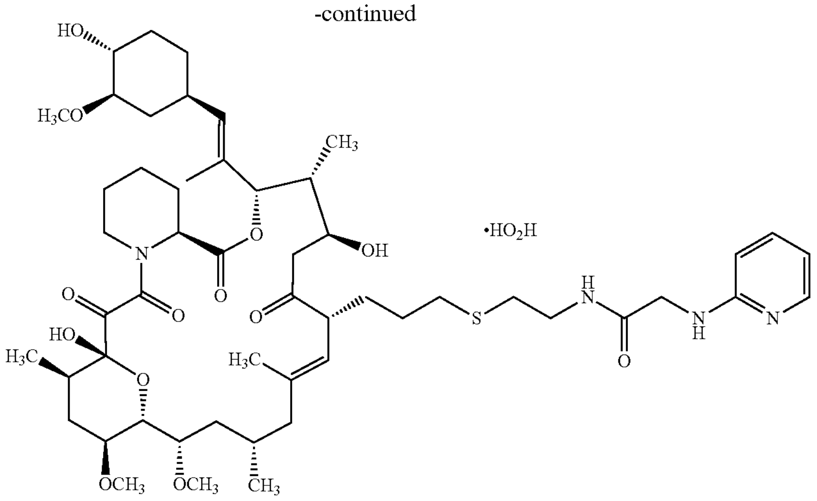

ZZY05-028

An oven-dried one-dram vial was charged with ZZY05-011 (15 mg, 0.020 mmol), 2-(2-pyridylamino)acetic acid hydrochloride (4.8 mg, 0.030 mmol), DMF (0.17 mL), N,N-Diisopropylethylamine (15 μL, 0.090 mmol), and a magnetic stir bar. HATU (7.8 mg, 0.020 mmol) was added as a solid at 23° C., and the resulting mixture was stirred at 23° C. for 30 min. At this point, LC-MS analysis showed full consumption of the starting amine and formation of a single peak corresponding to the desired mass. The residue was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.5 mg, 32%). 3:2 mixture of rotamers. HRMS (ESI): Calcd for $(C_{53}H_{82}N_4O_{13}S+H)^+$: 1015.5677, Found: 1015.5701.

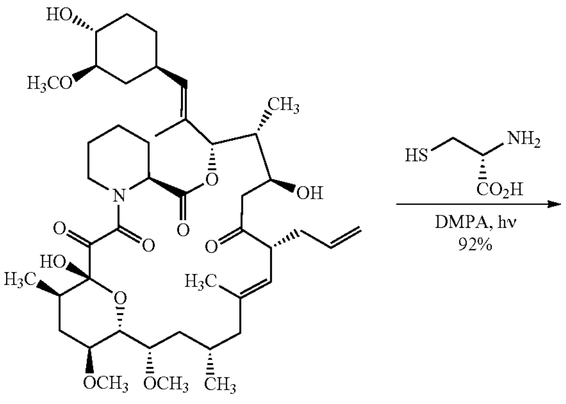

FK506

-continued

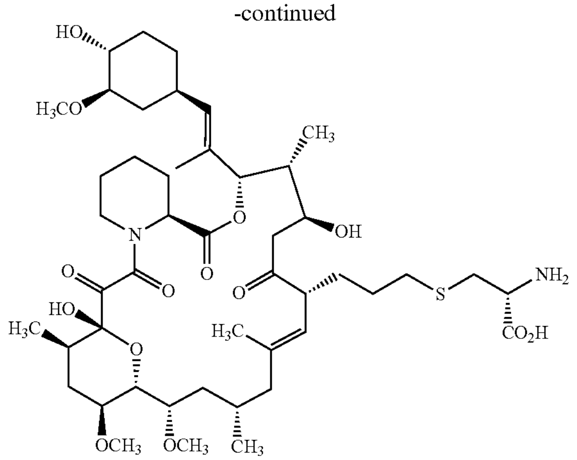

ZZY05-037

L-Cysteine (16 mg, 0.13 mmol) and DMPA (3.2 mg, 0.012 mmol) were added sequentially to a solution of FK506 (100 mg, 0.12 mmol) in 1:1 Methanol (0.25 mL):Water (0.25 mL) at 23° C. After all reactants had dissolved, the vial was placed above a hand-held UV-light operating at 365 nm wavelength (the light was placed upside-down so that the contents of vial were directly irradiated). The irradiation was maintained for 15 min, at which point TLC analysis showed full disappearance of the starting material. The reaction solution was directly diluted with 50% acetonitrile-water to a volume of 4.7 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (105 mg, 92%). 3:2 mixture of rotamers. $^1H$ NMR (400 MHz, Methanol-$d_4$) δ 5.31-5.10 (m, 2H), 4.94 (s, 1H), 4.63 (d, J=7.9 Hz, 1H), 4.37 (d, J=13.2 Hz, 1H), 4.10-3.94 (m, 1H), 3.78-3.69 (m, 1H), 3.67-3.45 (m, 3H), 3.43 (s, 3H), 3.42 (s, 3H), 3.41-3.39 (m, 3H), 3.36 (s, 3H), 3.15 (ddd, J=14.7, 3.8, 1.2 Hz, 1H), 3.11-2.97 (m, 1H), 2.97-2.71 (m, 4H), 2.62 (t, J=7.1 Hz, 1H), 2.43-2.28 (m, 4H), 2.28-2.11 (m, 4H), 2.09-1.75 (m, 6H), 1.75-1.68 (m, 6H), 1.68-1.28 (m, 8H), 1.21-1.00 (m, 2H), 1.00-0.86 (m, 9H). HRMS (ESI): Calcd for $(C_{47}H_{76}N_2O_{14}S+H)^+$: 925.5095, Found: 925.5092.

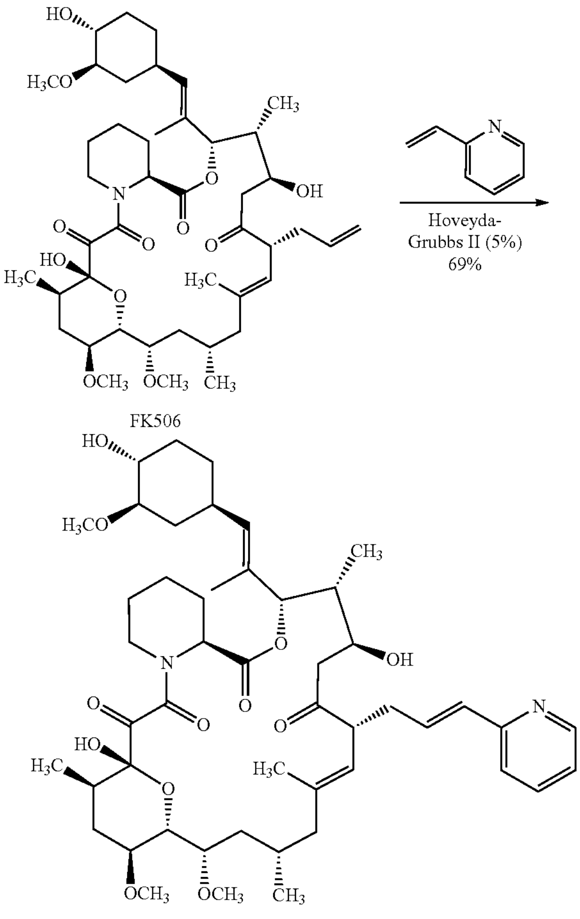

FK506

ZZY05-050

A 15-ml microwave vial was dried with gentle flame under vacuum. The vial was cooled to 23° C., flushed with argon, then charged with FK506 (50 mg, 0.062 mmol), DCE (0.62 mL) and a magnetic stir bar. Argon was bubbled through the resulting solution via a 19-gauge needle for 1 min. 2-Vinylpyridine (6.7 μL, 0.062 mmol) was added via pipette, and Grubbs-Hovey da $2^{nd}$ Gen Catalyst (4.0 mg, 0.0062 mmol) was added in one portion as a solid. The mixture was stirred briefly (giving a bright green solution) before being loaded on a CEM DiscoverSP microwave reactor. Microwave reaction was performed at 100° C. for 30 min with 1 min pre-equilibration. After cooling to 23° C., the reaction mixture was analyzed by TLC (100% ethyl acetate), which showed formation of an UV-active, more polar spot. The reaction mixture was directly loaded onto a 4-g RediSep (Teledyne ISCO) column. Elution with 100% ethyl acetate gave the product as a yellow solid (38 mg, 69%). 3:2 mixture of rotamers. $^1H$ NMR (400 MHz, Chloroform-d) δ 8.55-8.47 (m, 1H), 7.66-7.56 (m, 1H), 7.24 (tt, J=8.1, 1.1 Hz, 1H), 7.16-7.06 (m, 1H), 6.69-6.56 (m, 1H), 6.57-6.46 (m, 1H), 5.38-5.30 (m, 1H), 5.16-5.00 (m, 2H), 4.63 (d, J=5.3 Hz, 1H), 4.44 (d, J=14.1 Hz, 1H), 4.02-3.84 (m, 2H), 3.77-3.67 (m, 1H), 3.66-3.50 (m, 2H), 3.42 (s, 3H), 3.40 (s, 3H), 3.38-3.35 (m, 1H), 3.31 (s, 3H), 3.07-2.96 (m, 3H), 2.86-2.64 (m, 3H), 2.51-2.23 (m, 4H), 2.24-1.85 (m, 8H), 1.71-1.60 (m, 6H), 1.60-1.31 (m, 8H), 1.14-1.03 (m, 2H), 1.01 (d, J=6.3 Hz, 3H), 0.94 (d, J=6.7 Hz, 3H), 0.89 (d, J=7.2 Hz, 3H). HRMS (ESI): Calcd for $(C_{49}H_{72}N_2O_{12}+H)^+$: 881.5163, Found: 881.5207.

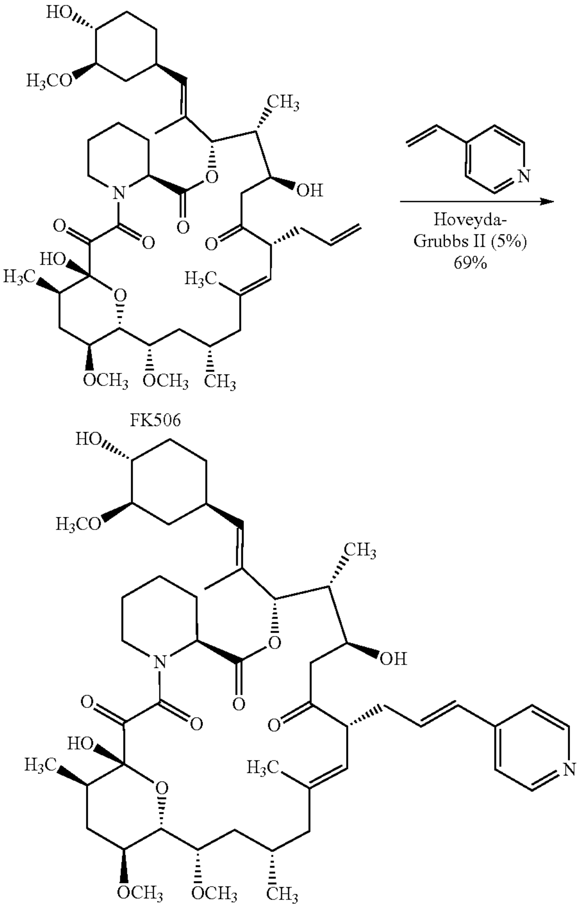

FK506

ZZY05-051

A 15-ml microwave vial was dried with gentle flame under vacuum. The vial was cooled to 23° C., flushed with argon, then charged with FK506 (50 mg, 0.060 mmol), DCE (0.62 mL) and a magnetic stir bar. Argon was bubbled through the resulting solution via a 19-gauge needle for 1 min. 4-Vinylpyridine (6.7 μL, 0.060 mmol) was added via pipette, and Grubbs-Hovey da $2^{nd}$ Gen Catalyst (4.0 mg, 0.0062 mmol) was added in one portion as a solid. The mixture was stirred briefly (giving a bright green solution) before being loaded on a CEM DiscoverSP microwave reactor. Microwave reaction was performed at 100° C. for 30 min with 1 min pre-equilibration. After cooling to 23° C., the reaction mixture was analyzed by TLC (100% ethyl acetate), which showed formation of an UV-active, more polar spot. The reaction mixture was directly loaded onto a 4-g RediSep (Teledyne ISCO) column. Elution with 100% ethyl acetate gave the product as a yellow solid (38 mg, 69%). 3:2 mixture of rotamers. $^1H$ NMR (400 MHz, Chloroform-d) δ 8.56-8.49 (m, 2H), 8.21 (br s, 1H), 7.27-7.18 (m, 2H), 6.49-6.32 (m, 2H), 5.35 (s, 1H), 5.17-5.05 (m, 2H), 4.67 (d, J=5.5 Hz, 1H), 4.46 (d, J=13.7 Hz, 1H), 4.04-3.86 (m, 1H), 3.72 (d, J=9.6 Hz, 1H), 3.61 (d, J=10.6 Hz, 1H), 3.56-3.45 (m, 1H), 3.43 (s, 3H), 3.41 (s, 3H), 3.39-3.36 (m, 2H), 3.32 (s, 3H), 3.08-2.98 (m, 3H), 2.84 (dd, J=16.3, 2.6 Hz, 1H), 2.80-2.60

(m, 2H), 2.55-2.25 (m, 4H), 2.26-1.88 (m, 6H), 1.88-1.71 (m, 4H), 1.71-1.61 (m, 6H), 1.61-1.26 (m, 8H), 1.14-1.04 (m, 2H), 1.01 (d, J=6.3 Hz, 3H), 0.96 (d, J=6.4 Hz, 3H), 0.90 (d, J=7.2 Hz, 3H). HRMS (ESI): Calcd for $(C_{49}H_{72}N_2O_{12}+H)^+$: 881.5163, Found: 881.5207.

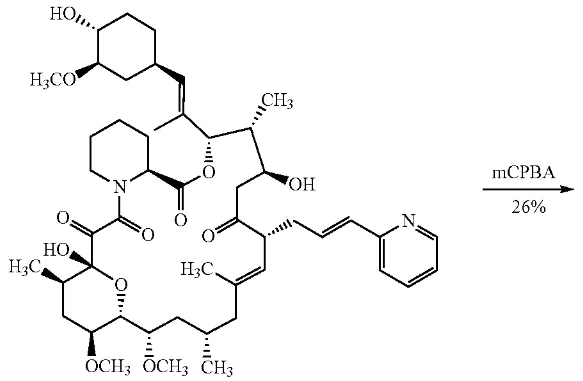

ZZY05-050

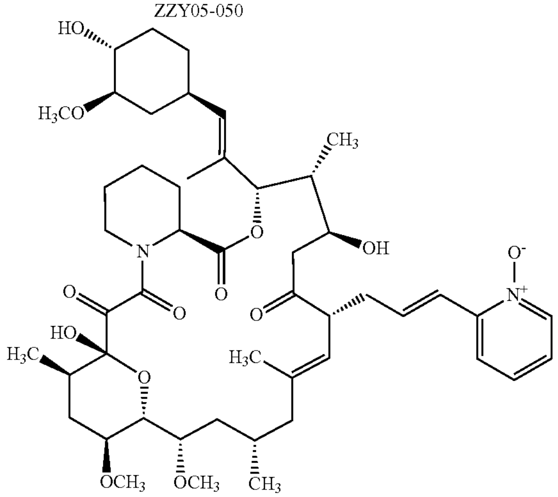

ZZY05-060 mCPBA (3.4 mg, 0.010 mmol) was added as a 10 wt % solution in dichloromethane (34 uL) to a solution of ZZY05-050 (10 mg, 0.010 mmol) in dichloromethane (0.11 mL) at 0° C. In 4 h, most of the starting material had been consumed judged by TLC analysis (100% ethyl acetate)—the product did not move in this solvent system. 10% Methanol-dichloromethane resolved the product spot (with streak). Attempted purification by column chromatography (0-10% methanol-dichloromethane) afforded a white solid. The material was further again by reverse-phase HPLC (5-95% acetonitrile-water+0.1% formic acid over 40 min). The product-containing fraction were pooled and concentrated in vacuo to afford the product as a while solid (2.6 mg, 26%). 3:2 mixture of rotamers. $^1$H NMR (400 MHz, Chloroform-d) δ 8.14-8.08 (m, 2H), 7.22-7.10 (m, 2H), 6.38-6.17 (m, 2H), 5.34 (s, 1H), 5.14-5.03 (m, 2H), 4.65 (d, J=6.0 Hz, 1H), 4.44 (d, J=13.4 Hz, 1H), 4.04-3.84 (m, 2H), 3.69 (d, J=9.6 Hz, 1H), 3.68-3.52 (m, 2H), 3.41 (s, 3H), 3.39 (s, 3H), 3.38-3.34 (m, 3H), 3.30 (s, 3H), 3.08-2.95 (m, 3H), 2.81 (d, J=16.1 Hz, 1H), 2.75-2.58 (m, 2H), 2.52-2.21 (m, 4H), 2.21-1.72 (m, 6H), 1.72-1.52 (m, 6H), 1.53-1.13 (m, 8H), 1.12-1.02 (m, 2H), 0.99 (d, J=6.3 Hz, 3H), 0.94 (d, J=6.4 Hz, 3H), 0.87 (d, J=7.2 Hz, 3H). HRMS (ESI): Calcd for $(C_{49}H_{72}N_2O_{13}+H)^+$: 897.5112, Found: 897.5134.

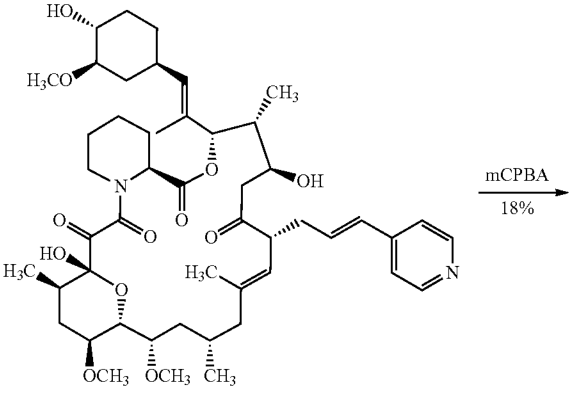

ZZY05-051

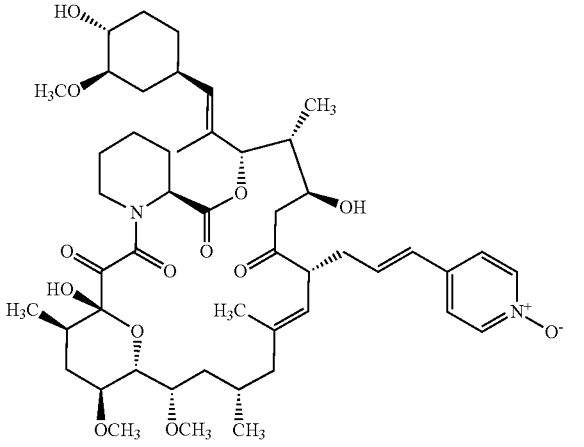

ZZY05-061 mCPBA (3.4 mg, 0.010 mmol) was added as a 10 wt % solution in dichloromethane (34 uL) to a solution of ZZY05-051 (10 mg, 0.010 mmol) in dichloromethane (0.11 mL) at 0° C. In 4 h, most of the starting material had been consumed judged by TLC analysis (100% ethyl acetate)—the product did not move in this solvent system. 10% Methanol-dichloromethane resolved the product spot (with streak). Attempted purification by column chromatography (0-10% methanol-dichloromethane) afforded a white solid. The material was further purified by reverse-phase HPLC (5-95% acetonitrile-water+0.1% formic acid over 40 min). The product-containing fraction were pooled and concentrated in vacuo to afford the product as a while solid (1.8 mg, 18%). 3:2 mixture of rotamers. $^1$H NMR (400 MHz, Chloroform-d) δ 8.19 (d, J=5.8 Hz, 1H), 7.47-7.37 (m, 1H), 7.26-7.08 (m, 2H), 7.08-6.93 (m, 1H), 6.54 (dd, J=15.7, 7.8 Hz, 1H), 5.29 (s, 1H), 5.17-5.07 (m, 2H), 4.55-4.27 (m, 2H), 4.27-4.13 (m, 1H), 3.80-3.49 (m, 3H), 3.41 (s, 3H), 3.38 (s, 3H), 3.37-3.32 (m, 3H), 3.29 (s, 3H), 3.10-2.93 (m, 3H), 2.84 (d, J=16.9 Hz, 1H), 2.75-2.55 (m, 2H), 2.50-2.23 (m, 4H), 2.25-1.79 (m, 6H), 1.75-1.64 (m, 6H), 1.54-1.27 (m, 8H), 1.07-0.98 (m, 2H), 0.96 (d, J=7.1 Hz, 3H), 0.92 (d, J=6.9 Hz, 3H), 0.89 (d, J=4.6 Hz, 3H). HRMS (ESI): Calcd for $(C_{49}H_{72}N_2O_{13}+H)^+$: 897.5112, Found: 897.5134.

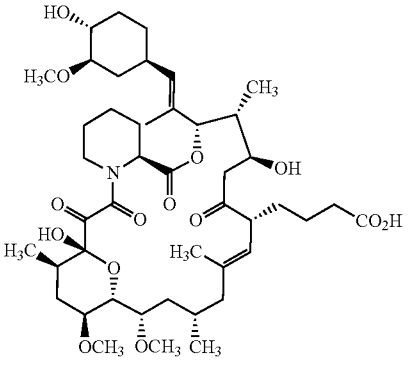

ZZY05-020

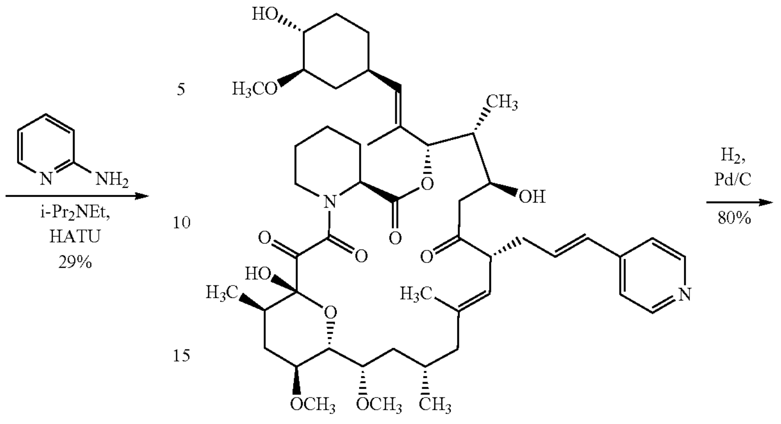

ZZY05-051

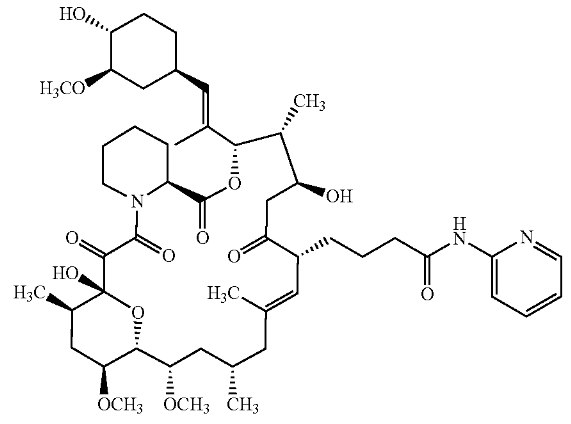

ZZY05-064

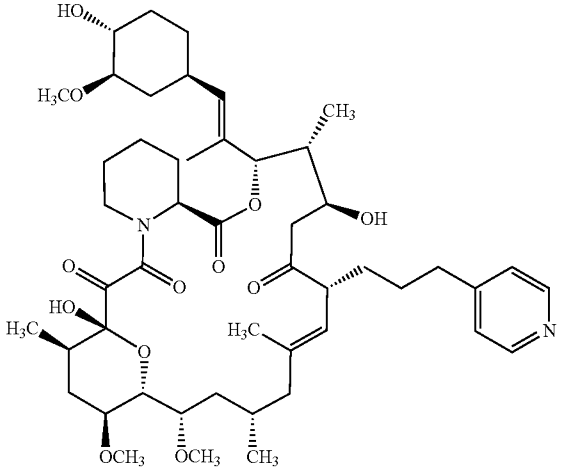

ZZY05-084

N,N-Diisopropylethylamine (12.3 μL, 0.071 mmol) and HATU (11 mg, 0.028 mmol) were added sequentially to a stirred solution of ZZY05-020 (20 mg, 0.024 mmol) and 2-aminopyridine (2.7 mg, 0.028 mmol) in DMF (0.24 mL) at 23° C. In 24 h, LC-MS analysis showed full consumption of the staring acid. The reaction mixture was diluted with 50% acetonitrile-water to a volume of 4.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (6.4 mg, 29%). 3:2 mixture of rotamers. $^1$H NMR (400 MHz, Chloroform-d) δ 9.18 (br s, 1H), 8.29 (d, J=8.6 Hz, 1H), 8.24-8.16 (m, 1H), 7.79-7.72 (m, 1H), 7.09-7.04 (m, 1H), 5.35 (d, J=2.5 Hz, 1H), 5.14-4.98 (m, 2H), 4.65 (d, J=5.4 Hz, 1H), 4.45 (d, J=13.8 Hz, 1H), 4.03-3.84 (m, 2H), 3.81-3.68 (m, 1H), 3.68-3.55 (m, 2H), 3.43 (s, 3H), 3.41 (s, 3H), 3.41-3.36 (m, 3H), 3.32 (s, 3H), 3.13-2.93 (m, 2H), 2.81 (dd, J=16.2, 2.2 Hz, 1H), 2.51-2.25 (m, 6H), 2.25-1.72 (m, 8H), 1.71-1.58 (m, 6H), 1.57-1.19 (m, 8H), 1.18-1.05 (m, 2H), 1.02 (d, J=6.2 Hz, 3H), 0.96 (d, J=6.4 Hz, 3H), 0.89 (d, J=7.2 Hz, 3H). HRMS (ESI): Calcd for $(C_{50}H_{75}N_3O_{13}+H)^+$: 926.5378, Found: 926.5380.

A 20-mL vial was charged with ZZY05-051 (20 mg, 0.020 mmol), Ethyl acetate (1.0 mL) and Palladium on carbon (10 wt %, 2.4 mg). The vial was briefly purged with argon, and then fitted with a rubber septum. Hydrogen was bubbled through the solution via a 19-gauge needle for 5 min, then the mixture was stirred under hydrogen atmosphere at 23° C. In a total of 3 h, LC-MS showed full conversion to the desired m/z. The reaction mixture was filtered through a pad of Celite, and the filter cake was rinsed with ethyl acetate (5 mL). The combined filtrate was concentrated to afford the product as a pale-yellow foam (16 mg, 80%). 3:2 mixture of rotamers. $^1$H NMR (400 MHz, Chloroform-d) δ 8.53-8.47 (m, 2H), 7.13-7.07 (m, 2H), 5.34 (d, J=2.7 Hz, 1H), 5.13-4.97 (m, 2H), 4.63 (d, J=5.4 Hz, 1H), 4.45 (d, J=13.7 Hz, 2H), 4.00-3.86 (m, 2H), 3.78-3.66 (m, 1H), 3.66-3.55 (m, 1H), 3.55-3.45 (m, 1H), 3.43 (s, 3H), 3.41 (s, 3H), 3.40-3.38 (m, 2H), 3.32 (s, 3H), 3.10-2.98 (m, 2H), 2.78 (dd, J=15.9, 2.9 Hz, 1H), 2.62 (app t, J=7.7 Hz, 2H), 2.40-2.24 (m, 3H), 2.24-2.13 (m, 3H), 2.06 (s, 6H), 1.86-1.71 (m, 4H), 1.71-1.57 (m, 6H), 1.57-1.33 (m, 8H), 1.15-1.05 (m, 2H), 1.02 (d, J=6.3 Hz, 3H), 0.95 (d, J=6.4 Hz, 3H), 0.87 (d, J=7.1 Hz, 3H). HRMS (ESI): Calcd for $(C_{49}H_{74}N_2O_{12}+H)^+$: 883.5320, Found: 883.5332.

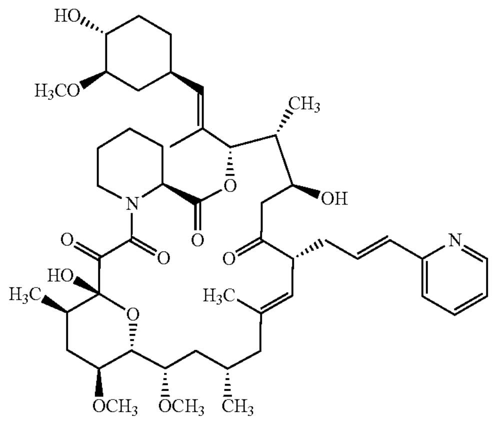

ZZY05-050

$H_2$,
Pd/C
80%

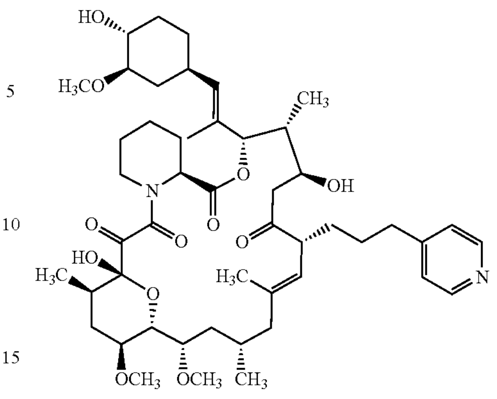

ZZY05-084 mCPBA
38%

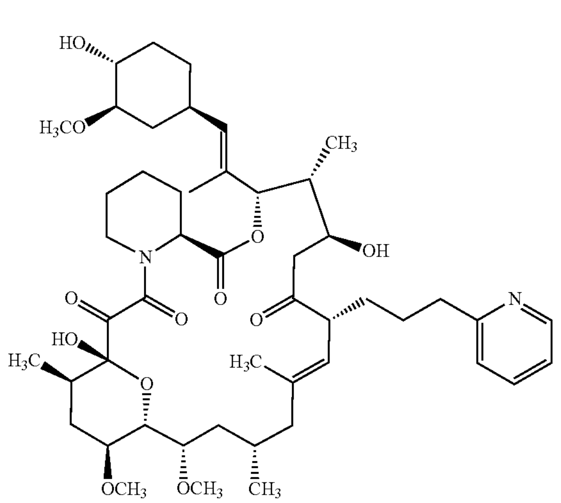

ZZY05-085

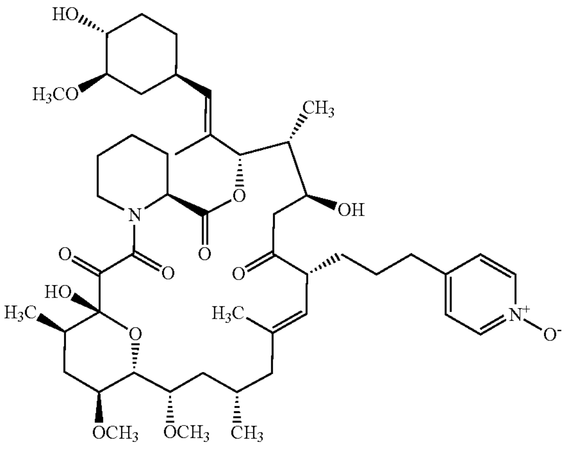

ZZY05-086

A 20-mL vial was charged with ZZY05-050 (20 mg, 0.020 mmol), Ethyl acetate (1.0 mL) and Palladium on carbon (10 wt %, 2.4 mg). The vial was briefly purged with argon, and then fitted with a rubber septum. Hydrogen was bubbled through the solution via a 19-gauge needle for 5 min, then the mixture was stirred under hydrogen atmosphere at 23° C. In a total of 3 h, LC-MS showed full conversion to the desired m/z. The reaction mixture was filtered through a pad of Celite, and the filter cake was rinsed with ethyl acetate (5 mL). The combined filtrate was concentrated to afford the product as a pale-yellow foam (20 mg, 99%). 3:2 mixture of rotamers. $^1H$ NMR (400 MHz, Chloroform-d) δ 8.56-8.43 (m, 2H), 7.61 (tt, J=IN 2.3 Hz, 2H), 7.21-7.07 (m, 4H), 5.37 (s, 1H), 5.28-5.15 (m, 1H), 5.15-4.96 (m, 2H), 4.62 (d, J=5.0 Hz, 1H), 4.45 (d, J=13.5 Hz, 1H), 4.00-3.86 (m, 1H), 3.74 (d, J=9.8 Hz, 1H), 3.67-3.55 (m, 1H), 3.52-3.25 (m, 3H), 3.43 (s, 3H), 3.41 (s, 3H), 3.32 (s, 3H), 3.09-2.95 (m, 1H), 2.92-2.75 (m, 2H), 2.73-2.64 (m, 1H), 2.43-2.11 (m, 3H), 2.11-1.84 (m, 4H), 1.84-1.70 (m, 4H), 1.70-1.57 (m, 6H), 1.57-1.33 (m, 8H), 1.15-1.05 (m, 2H), 1.03 (d, J=6.5 Hz, 3H), 0.96 (d, J=6.1 Hz, 3H), 0.87 (d, J=7.2 Hz, 3H). HRMS (ESI): Calcd for $(C_{49}H_{74}N_2O_{12}+H)^+$: 883.5320, Found: 883.5332.

m-CPBA (4.8 mg, 0.018 mmol) was added as a 10 wt % solution in di chloromethane (48 μL) to a solution of ZZY05-084 (16 mg, 0.018 mmol) in dichloromethane at 0° C. The reaction progress was monitored by LC-MS. In a total of 6 h, LC-MS showed full conversion to the desired m/z. The reaction mixture was directly concentrated under reduced pressure. The residue was diluted with 50% acetonitrile-water to a volume of 3.0 mL, and the solution was filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) to afford the product as a white solid (6.2 mg, 38%). 3:2 mixture of rotamers. $^1H$ NMR (400 MHz, Chloroform-d) δ 8.24-8.14 (m, 2H), 7.13 (t, J=6.8 Hz, 2H), 5.35 (s, 1H), 5.13-4.96 (m, 3H), 4.65 (d, J=5.4 Hz, 1H), 4.45 (d, J=13.6 Hz, 1H), 3.95-3.84 (m, 1H), 3.74-3.67 (m, 1H), 3.66-3.54 (m, 1H), 3.43 (s, 3H), 3.41 (s, 3H), 3.32 (s, 3H), 3.45-3.27 (m, 3H), 3.11-2.97 (m, 3H), 2.79 (dd, J=16.2, 2.7 Hz, 1H), 2.67-2.59 (m, 2H), 2.31 (d, J=9.4 Hz, 2H), 2.25-2.10 (m, 3H), 2.10-1.96 (m, 2H), 1.96-1.73 (m, 6H), 1.72-1.57 (m, 6H), 1.57-1.19 (m, 8H), 1.15-1.05 (m, 2H), 1.03 (d, J=6.3 Hz, 3H), 0.96 (d, J=6.3 Hz, 4H), 0.88 (d, J=7.2 Hz, 3H). HRMS (ESI): Calcd for $(C_{49}H_{74}N_2O_{13}+H-H_2O)^+$: 881.5164, Found: 881.5146.

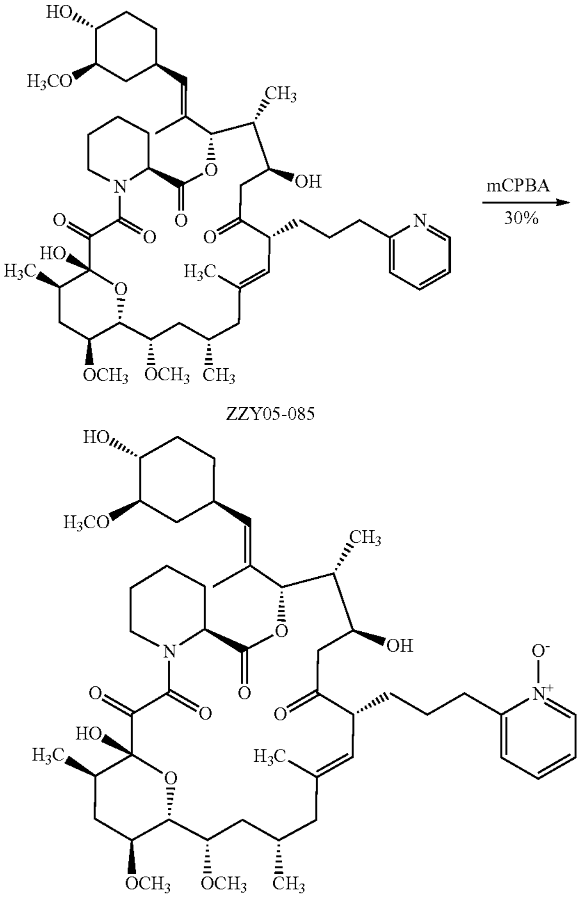

ZZY05-085

ZZY05-092 m-CPBA (6.6 mg, 0.025 mmol) was added as a 10 wt % solution in dichloromethane (66 μL) to a solution of ZZY05-085 (22 mg, 0.025 mmol) in dichloromethane at 0° C. The reaction progress was monitored by LC-MS. In a total of 6 h, LC-MS showed full conversion to the desired m/z. The reaction mixture was directly concentrated under reduced pressure. The residue was diluted with 50% acetonitrile-water to a volume of 3.0 mL, and the solution was filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) to afford the product as a white solid (6.6 mg, 30%). 3:2 mixture of rotamers. $^1$H NMR (400 MHz, Chloroform-d) δ 8.32-8.22 (m, 2H), 8.03 (s, 1H), 7.24-7.11 (m, 3H), 5.34 (s, 1H), 5.13 (d, J=9.6 Hz, 1H), 5.10-5.04 (m, 1H), 4.78-4.67 (m, 1H), 4.58 (d, J=3.3 Hz, 1H), 4.43 (d, J=13.8 Hz, 1H), 3.93 (t, J=10.2 Hz, 1H), 3.77-3.68 (m, 1H), 3.64-3.52 (m, 1H), 3.41 (s, 3H), 3.39 (s, 3H), 3.48-3.23 (m, 3H), 3.30 (s, 3H), 3.06-2.91 (m, 3H), 2.83-2.73 (m, 1H), 2.73-2.65 (m, 1H), 2.41-2.23 (m, 3H), 2.22-2.08 (m, 3H), 2.06-1.94 (m, 2H), 1.94-1.71 (m, 6H), 1.71-1.50 (m, 6H), 1.50-1.30 (m, 8H), 1.06 (d, J=13.4 Hz, 2H), 1.00 (d, J=6.5 Hz, 3H), 0.93 (d, J=5.8 Hz, 3H), 0.86 (d, J=7.2 Hz, 3H). HRMS (ESI): Calcd for $(C_{49}H_{74}N_2O_{13}+H-H_2O)^+$: 881.5164, Found: 881.5150.

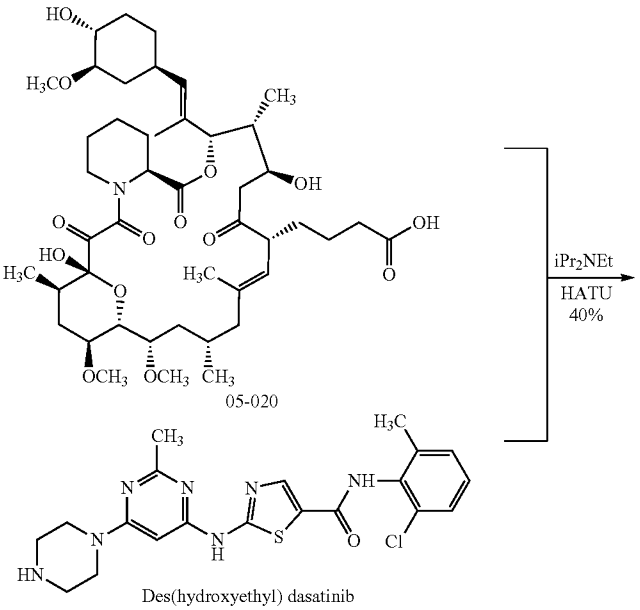

05-020

Des(hydroxyethyl) dasatinib

-continued

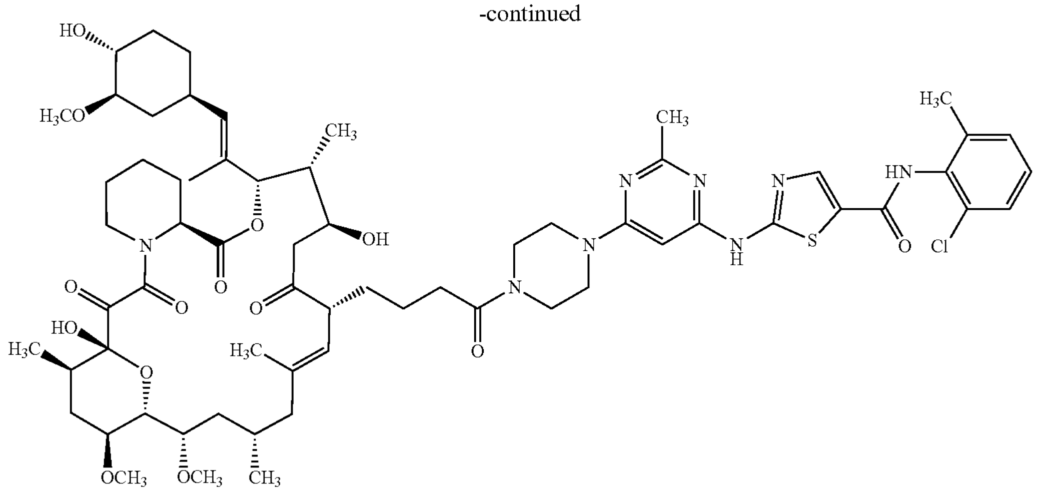

05-022

An oven-dried 1-dram vial was charged with 05-020 (10 mg, 0.012 mmol), des(hydroxyethyl)dasatinib (5.8 mg, 0.012 mmol), DMF (0.20 mL) and a magnetic stir bar. The solution was cooled to 0° C., then N,N-diisopropylethylamine (6.2 μL, 0.035 mmol) and HATU (5.4 mg, 0.010 mmol) were added sequentially. The resulting mixture was stirred at 0° C. and the reaction progress was monitored by LC-MS. In 30 min, LC-MS analysis indicated that the starting material had been fully consumed. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.9 mg, 40%). 3:2 mixture of rotamers. $^1$H NMR (400 MHz, Chloroform-d) δ 8.19 (s, 1H), 7.99 (br s, 1H), 7.42-7.31 (m, 2H), 7.26-7.10 (m, 2H), 5.89 (s, 1H), 5.39 (s, 1H), 5.16-5.06 (m, 1H), 4.66 (d, J=5.4 Hz, 1H), 4.48 (d, J=13.8 Hz, 1H), 3.99-3.94 (m, 1H), 3.81-3.68 (m, 5H), 3.68-3.53 (m, 5H), 3.44 (s, 3H), 3.41 (s, 3H), 3.46-3.33 (m, 3H), 3.32 (s, 3H), 3.10-2.98 (m, 3H), 2.79 (d, J=14.7 Hz, 1H), 2.55 (s, 3H), 2.43-2.38 (m, 1H), 2.37 (s, 3H), 2.35-2.25 (m, 2H), 2.24-1.98 (m, 5H), 1.97-1.72 (m, 6H), 1.71-1.62 (m, 6H), 1.62-1.32 (m, 8H), 1.12-1.04 (m, 2H), 1.02 (d, J=6.2 Hz, 3H), 0.95 (d, J=5.6 Hz, 3H), 0.89 (d, J=7.2 Hz, 3H). HRMS (ESI): Calcd for $(C_{65}H_{91}ClN_8O_{14}S+H)^+$: 1275.6142, Found: 1275.6085.

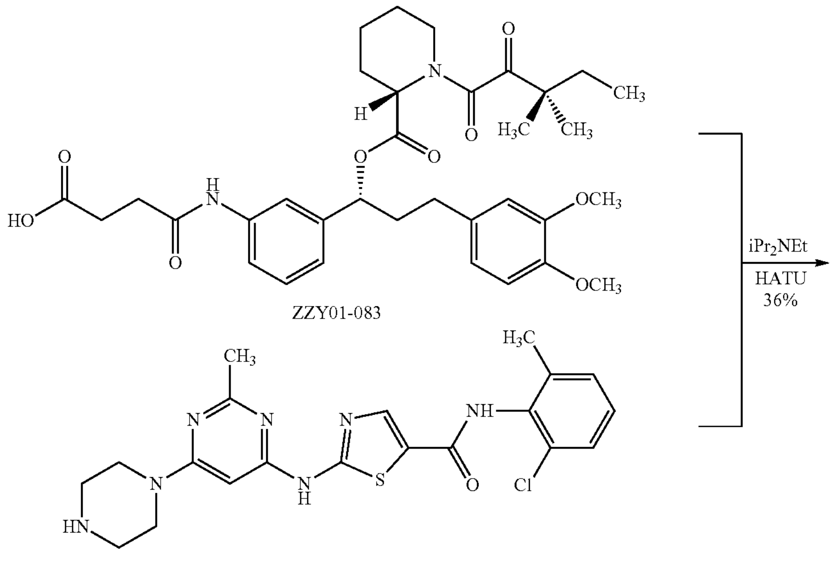

ZZY01-083

Des(hydroxyethyl) dasatinib

-continued

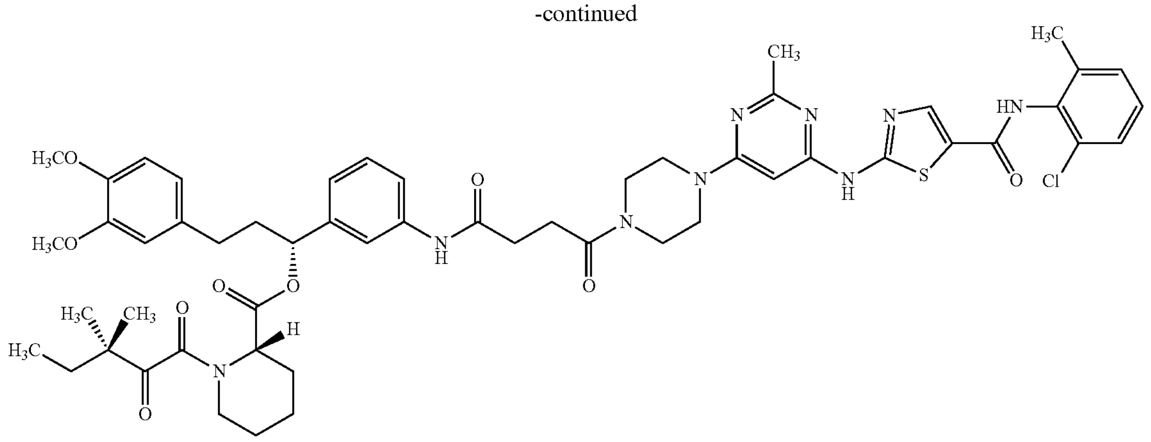

ZZY05-016

An oven-dried 1-dram vial was charged with des(hydroxyethyl)dasatinib (10 mg, 0.023 mmol), ZZY01-083 (14 mg, 0.023 mmol), DMF (0.11 mL), N,N-diisopropylethylamine (12 μL, 0.068 mmol) and a magnetic stir bar. The solution was cooled to 0° C., then HATU (12.8 mg, 0.034 mmol) was added as a solid. The resulting mixture was stirred at 0° C. and the reaction progress was monitored by LC-MS. In 30 min, LC-MS analysis indicated that the starting material had been fully consumed. The residue was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (8.5 mg, 36%). 6:1 mixture of rotamers. $^1$H NMR (400 MHz, Chloroform-d) δ 9.80 (br s, 1H), 8.10 (br s, 1H), 7.86 (br s, 1H), 7.66 (d, J=8.1 Hz, 1H), 7.40-7.27 (m, 2H), 7.24-7.13 (m, 3H), 6.96 (d, J=7.8 Hz, 1H), 6.79-6.71 (m, 1H), 6.70-6.58 (m, 2H), 5.98 (s, 1H), 5.69 (t, J=6.8 Hz, 1H), 5.22 (d, J=5.6 Hz, 1H), 3.95-3.84 (m, 1H), 3.83 (s, 3H), 3.82 (s, 3H), 3.81-3.71 (m, 1H), 3.66 (d, 4H), 3.45-3.39 (m, 4H), 3.27 (d, J=13.6 Hz, 1H), 3.05 (t, J=13.1 Hz, 1H), 2.95-2.76 (m, 3H), 2.52 (q, 5H), 2.34 (s, 3H), 2.27-2.11 (m, 2H), 2.08-1.93 (m, 1H), 1.72-1.46 (m, 5H), 1.46-1.30 (m, 2H), 1.17 (s, 3H), 1.16 (s, 3H), 0.85 (t, J=7.4 Hz, 3H). HRMS (ESI): Calcd for $(C_{54}H_{64}ClN_9O_9S+H)^+$: 1050.4314, Found: 1050.4298.

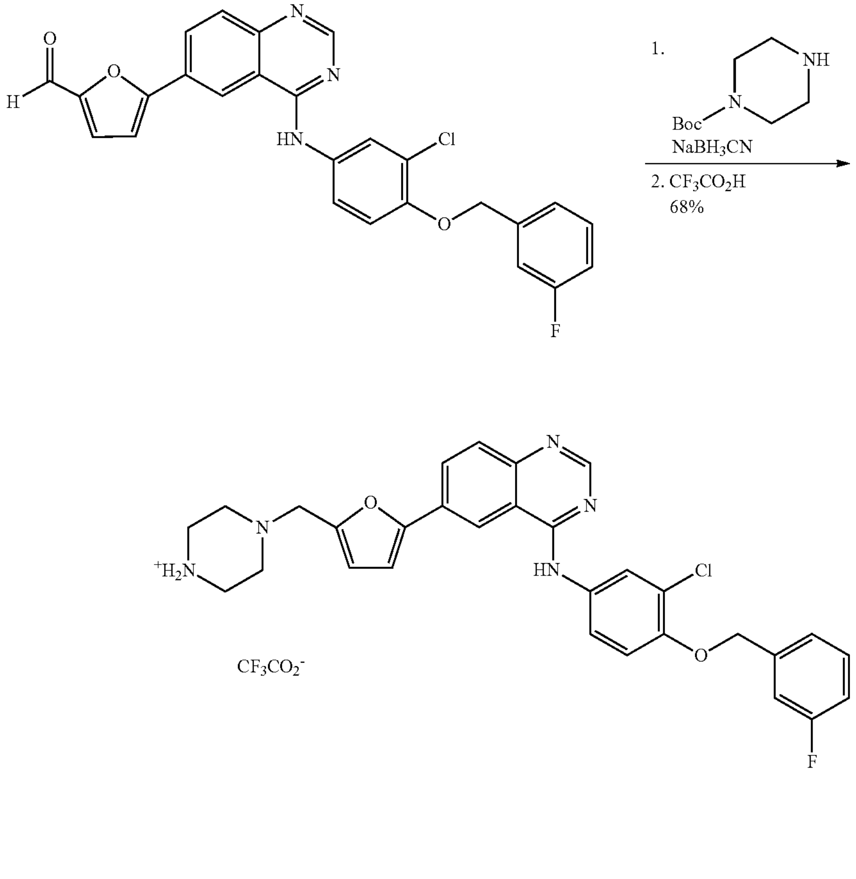

A suspension of 5-[4-[3-chloro-4-[(3-fluorophenyl)methoxy]anilino]quinazolin-6-yl]furan-2-carbaldehyde (100 mg, 0.211 mmol) in 9:1 methanol (1.8 mL):acetic acid (0.2 mL) was sonicated until a fine suspension was formed. 1-Boc-Piperazine (79 mg, 0.42 mmol) was added and the resulting mixture was stirred at 23° C. for 30 min. Sodium cyanoborohydride (20 mg, 0.32 mmol) was added in a single portion at 23° C. The precipitates dissolved over time to a point with a few speckles left in 1 h. At this point TLC analysis (100% ethyl acetate) showed full consumption of the aldehyde starting material. The reaction mixture was concentrated under reduced pressure. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-100% ethyl acetate-hexanes) to afford the product as a yellow powder. The yellow powder was resuspended in dichloromethane (2.0 mL), and trifluoroacetic acid (2.0 mL) was added dropwise, giving rise to a bright yellow solution. After standing at 23° C. for 1 h, the solution was concentrated under reduced pressure to afford the product as a yellow powder (93 mg, 68%). HRMS (ESI): Calcd for $(C_{30}H_{27}ClFN_5O_2+H)^+$: 544.1910, Found: 544.1882.

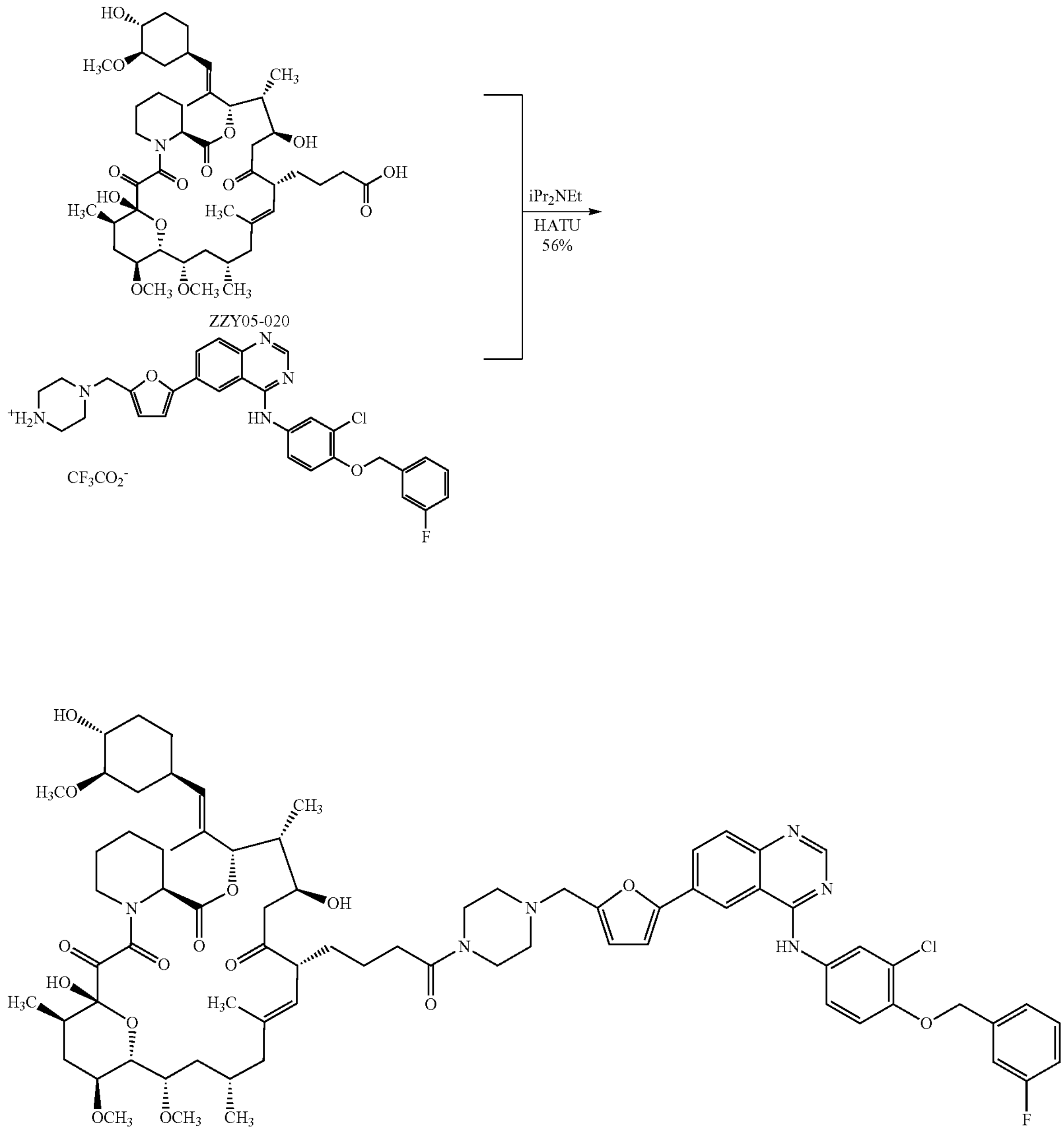

ZZY05-020

ZZY08-047
(FK506-Lapatinib)

N,N-Diisopropylethylamine (12.3 μL, 0.071 mmol) and HATU (9.8 mg, 0.026 mmol) were added sequentially to a stirred solution of ZZY05-020 (20 mg, 0.024 mmol) and Lapatinib-piperidine (17 mg, 0.026 mmol) in 9:1 dichloromethane (0.9 mL):DMF (0.1 mL). The resulting yellow solution was stirred at 23° C. for 1 h. At this point, LC-MS analysis showed full consumption of the acid starting material and formation of a new specie with the desired m/z. The reaction mixture was concentrated under reduced pressure to remove dichloromethane. The residue was diluted with 50% acetonitrile-water to a volume of 4.1 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (18.7 mg, 56%). 3:2 mixture of rotamers. $^1$H NMR (400 MHz, Chloroform-d) δ 8.71 (s, 1H), 8.07-7.94 (m, 2H), 7.90 (d, J=8.7 Hz, 2H), 7.72 (d, J=9.2 Hz, 1H), 7.43-7.34 (m, 1H), 7.27-7.19 (m, 3H), 7.09-6.97 (m, 2H), 6.76 (d, J=3.2 Hz, 1H), 6.55 (s, 1H), 5.42 (s, 1H), 5.18 (d, 3H), 5.12-5.04 (m, 2H), 4.70 (d, J=4.7 Hz, 1H), 4.43 (d, J=13.4 Hz, 1H), 4.07-3.92 (m, 2H), 3.92-3.80 (m, 1H), 3.80-3.66 (m, 2H), 3.61 (d, J=10.1 Hz, 1H), 3.52 (s, 2H), 3.43 (s, 3H), 3.41 (s, 3H), 3.45-3.36 (m, 3H), 3.32 (s, 3H), 3.09-2.95 (m, 2H), 2.95-2.69 (m, 2H), 2.44-2.22 (m, 3H), 2.22-2.09 (m, 3H), 2.05-1.70 (m, 8H), 1.69-1.60 (m, 6H), 1.62-1.32 (m, 8H), 1.11-1.04 (m, 2H), 1.02 (d, J=6.3 Hz, 3H), 0.96 (d, J=6.3 Hz, 3H), 0.86 (d, J=7.3 Hz, 3H). HRMS (ESI): Calcd for $(C_{75}H_{96}ClFN_6O_{15}+2H)^{2+}$: 688.3381, Found: 688.3373.

Ref: *J. Med Chem.* 2012, 55, 9416.

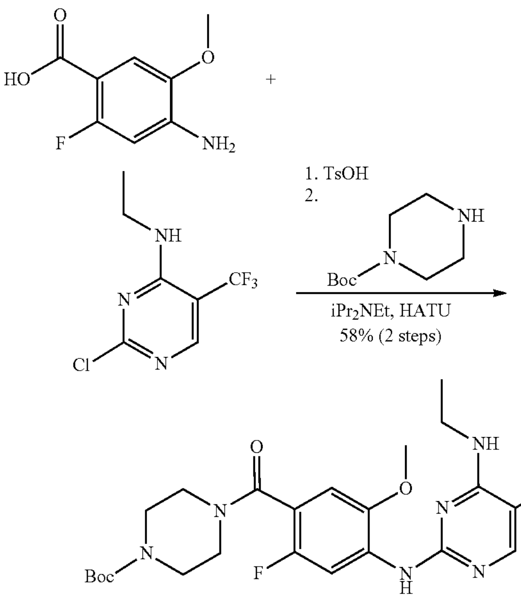

A 20-mL vial was charged with 4-amino-2-fluoro-5-methoxy-benzoic acid (100 mg, 0.54 mmol), 2-chloro-N-ethyl-5-(trifluoromethyl)pyrimidin-4-amine (146 mg, 0.650 mmol), p-toluenesulfonic acid monohydrate (51 mg, 0.27 mmol) and 1,4-dioxane (8.1 mL). The mixture was heated to 100° C. with constant stirring. Despite heating not all the solids dissolved. After 2 h, LC-MS analysis showed full conversion to the desired product. The reaction mixture was then cooled to room temperature. The insoluble solids were collected by filtration, washed with 1,4-dioxane (100 mL) and ethyl (50 mL), and air-dried for 12 h to afford the product as a white solid. The crude material was used in the next step without further purification. Dichloromethane (2.67 mL) and N,N-diisopropylamine (93 μL, 0.53 mmol) were added to the crude product from the last reaction. The resulting suspension was cooled to 0° C., and HATU (308 mg, 0.802 mmol) was added in one portion. The mixture was stirred at 0° C. for 15 min before warming to 23° C. and stirring for another 45 min. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-50% ethyl acetate-hexanes, 4-g RediSep® Rf column, Teledyne ISCO, Lincoln, Nebr.) to afford the product as a white powder (151 mg, 58% over 2 steps). $^1$H NMR (400 MHz, Chloroform-d) δ 8.41 (br s, 1H), 8.18 (s, 1H), 6.91 (d, J=6.0 Hz, 1H), 3.92 (s, 3H), 3.76 (s, 2H), 3.68-3.58 (m, 2H), 3.58-3.47 (m, 2H), 3.49-3.35 (m, 4H), 1.48 (s, 9H), 1.34 (t, J=7.2 Hz, 3H). HRMS (ESI): Calcd for $(C_{24}H_{30}F_4N_6O_4+H)^+$: 543.2343, Found: 543.2389.

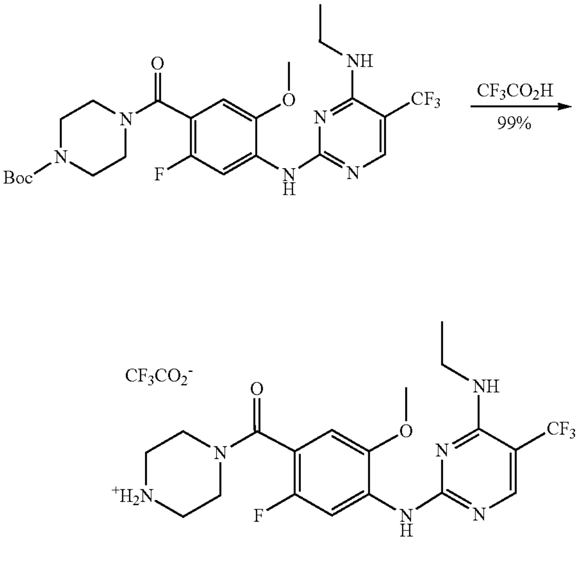

Trifluoroacetic acid (0.50 mL) was added dropwise to a solution of tert-butyl 4-[4-10 [[4-(ethylamino)-5-(trifluoromethyl)pyrimidin-2-yl]amino]-2-fluoro-5-methoxy-benzoyl]piperazine-1-carboxylate (151 mg, 0.28 mmol) in dichloromethane (0.50 mL) at 23° C. and the resulting solution was allowed to stand at 23° C. for 1 h. The reaction mixture was concentrated in vacuo to afford the product as a white solid. To assist removal of residual trifluoroacetic acid, the solids were triturated with ether (10 mL), and the supernatant was removed. The resulting solids were dried under vacuum over night to afford the product as a white powder (153 mg, 99%). $^1$H NMR (400 MHz, Methanol-$d_4$) δ 8.38 (d, J=11.9 Hz, 1H), 8.29 (d, J=1.1 Hz, 1H), 7.14 (d, J=6.1 Hz, 1H), 4.08-4.01 (m, 2H), 4.00 (s, 3H), 3.78-3.69 (m, 2H), 3.66 (q, J=7.2 Hz, 2H), 3.41-3.25 (m, 4H), 1.32 (t, J=7.1 Hz, 3H). HRMS (ESI): Calcd for $(C_{19}H_{21}F_4N_6O_2+H)^+$: 443.1813, Found: 443.1786.

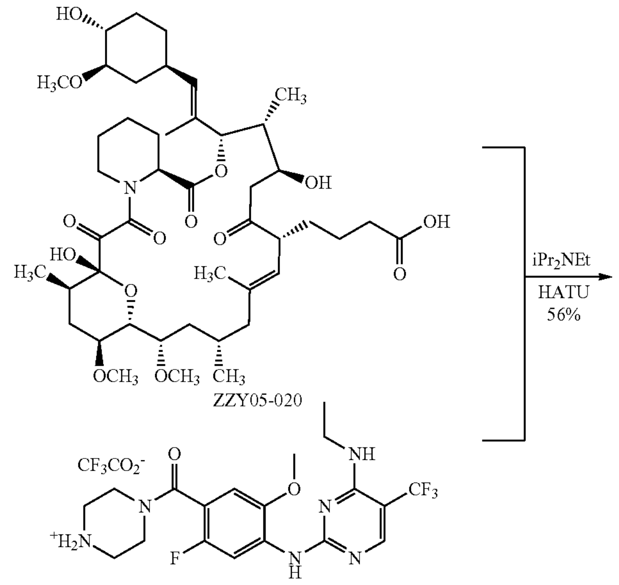

ZZY05-020

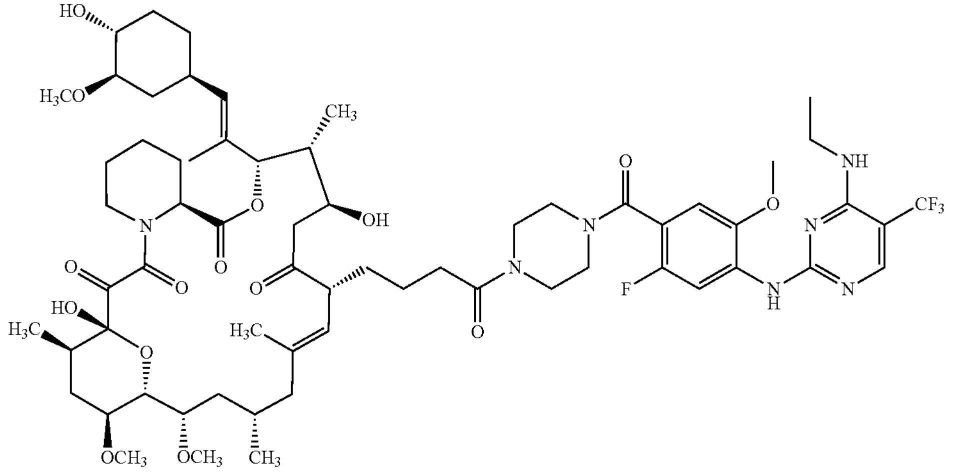

ZZY08-074

An oven-dried 1-dram vial was charged with ZZY05-020 (20 mg, 0.024 mmol), Pip-GNE7915 (13 mg, 0.023 mmol), DMF (0.12 mL) and a magnetic stir bar. N,N-Diisopropylethylamine (12 μL, 0.071 mmol) was added and the mixture was stirred until all reactants had dissolved. HATU (11 mg, 0.030 mmol) was added as a 10% (w/v) solution in DMF (110 μL), and the reaction progress was monitored by LC-MS. In 30 min, LC-MS analysis showed that the FK506-acid starting material had been fully consumed and a new product with desired m/z had formed. The reaction mixture was partitioned between saturated aqueous sodium bicarbonate solution (5 mL) and dichloromethane (5 mL). The layers were separated, and the aqueous layer was extracted with di chloromethane (2×5 mL). The combined organic layers were dried over sodium sulfate. The dried solution was filtered, and the filtrate was concentrated. The residue was purified by column chromatography (0-10% methanol-dichloromethane, 4-g RediSep® Rf column, Teledyne ISCO, Lincoln, Nebr.) to afford the product as a white powder (16.7 mg, 56%). 3:2 mixture of rotamers. $^1$H NMR (400 MHz, Chloroform-d) δ 8.45 (d, J=12.4 Hz, 1H), 8.20 (s, 1H), 7.87 (s, 1H), 6.91 (s, 1H), 5.34 (s, 1H), 5.26-5.16 (m, 1H), 5.16-4.92 (m, 2H), 4.61 (d, J=5.4 Hz, 1H), 4.42 (d, J=13.4 Hz, 1H), 3.92 (s, 3H), 3.85-3.65 (m, 5H), 3.65-3.51 (m, 5H), 3.51-3.43 (m, 3H), 3.40 (s, 3H), 3.38 (s, 3H), 3.43-3.31 (m, 3H), 3.29 (s, 3H), 3.24-3.19 (m, 1H), 3.19-3.12 (m, 1H), 3.05-2.96 (m, 2H), 2.79 (dd, J=15.9, 2.4 Hz, 1H), 2.67 (br s, 1H), 2.43-2.22 (m, 5H), 2.22-1.94 (m, 5H), 1.94-1.69 (m, 6H), 1.69-1.60 (m, 6H), 1.60-1.40 (m, 8H), 1.33 (t, J=7.2 Hz, 3H), 1.10-1.02 (m, 2H), 0.99 (d, J=6.3 Hz, 3H), 0.93 (d, J=5.9 Hz, 3H), 0.85 (d, J=7.6 Hz, 3H). HRMS (ESI): Calcd for $(C_{64}H_{91}F_4N_7O_{15}+H)^+$: 1274.6587, Found: 1274.6560.

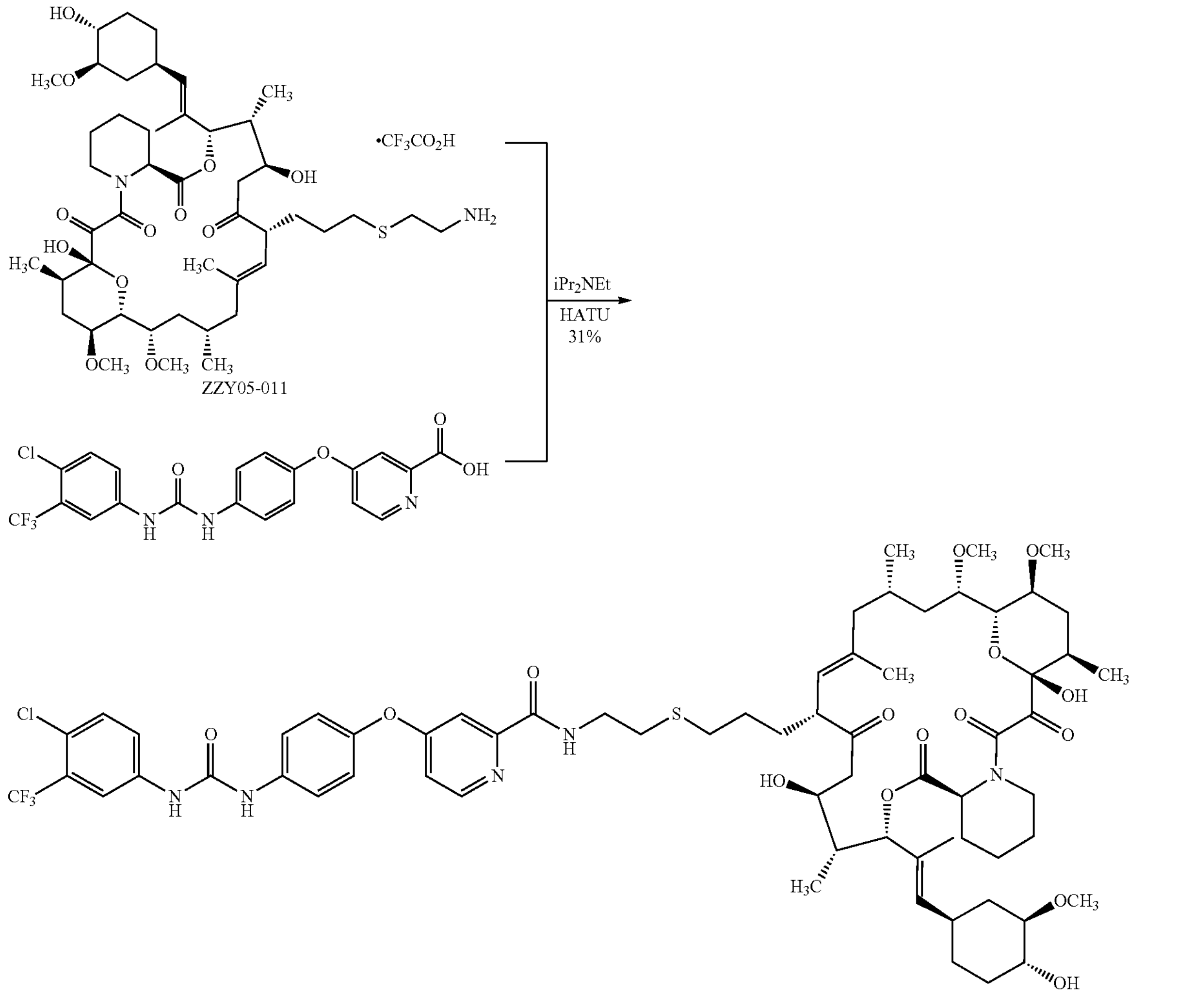

ZZY05-049
(FK506-Sorafenib)

A 1-dram vial was charged with ZZY05-011 (22 mg, 0.022 mmol), 4-[4-[[4-chloro-3-(trifluoromethyl)phenyl]carbamoylamino]phenoxy]pyridine-2-carboxylic acid (10 mg, 0.022 mmol), DMF (0.11 mL), and a magnetic stir bar. The resulting mixture was stirred until all reactants had dissolved. N,N-diisopropylamine (12 µL, 0.066 mmol) and HATU (10 mg, 0.026 mmol) were added sequentially at 23° C., and the resulting solution was stirred at 23° C. for 15 min. LC-MS analysis at this point showed full consumption of the starting material and formation of the desired product. The reaction mixture was diluted with 50% acetonitrile-water to a volume of 4.0 mL, and the solution was filtered through a 0.45 µM PTFE syringe filter. The filtrate was purified by reverse-phase HPLC (Waters XBridge C18 column 5 µm particle size 30×250 mm, 5-95% acetonitrile-water+0.1% formic acid, 40 min, 20 mL/min) to afford the product as a white solid (9.1 mg, 31%). 3:2 mixture of rotamers. $^1H$ NMR (400 MHz, Chloroform-d) δ 8.51-8.37 (m, 2H), 7.93 (s, 1H), 7.82-7.68 (m, 2H), 7.60-7.49 (m, 2H), 7.49-7.35 (m, 1H), 7.18-7.12 (m, 1H), 7.12-7.00 (m, 2H), 5.36 (s, 1H), 5.12-4.99 (m, 2H), 4.62 (s, 1H), 4.43 (d, J=13.4 Hz, 1H), 4.34 (s, 1H), 4.04-3.97 (m, 1H), 3.73-3.63 (m, 2H), 3.63-3.48 (m, 2H), 3.42 (s, 3H), 3.41 (s, 3H), 3.40-3.36 (m, 3H), 3.33 (s, 3H), 3.09-2.99 (m, 1H), 2.94 (t, J=12.1 Hz, 1H), 2.85-2.66 (m, 4H), 2.54 (t, J=7.5 Hz, 2H), 2.40-2.24 (m, 2H), 2.23-1.94 (m, 5H), 1.94-1.60 (m, 6H), 1.57 (d, J=8.4 Hz, 6H), 1.55-1.26 (m, 8H), 1.12-0.99 (m, 2H), 0.96 (d, J=6.3 Hz, 3H), 0.88 (d, J=7.2 Hz, 3H). HRMS (ESI): Calcd for $(C_{66}H_{87}ClF_3N_5O_{15}S+H)^+$: 1314.5638, Found: 1314.5674.

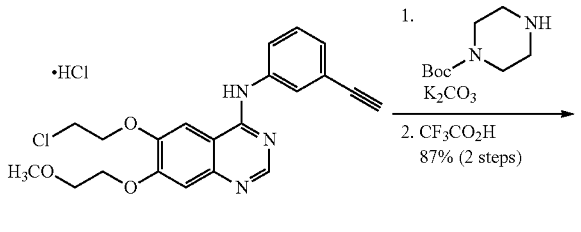

-continued

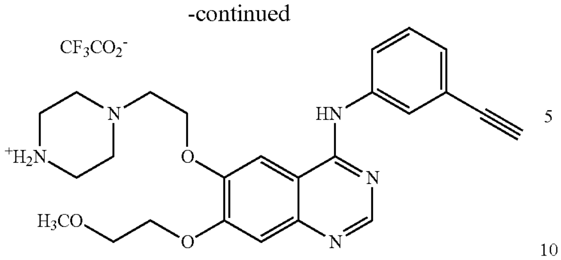

ZZY08-066

An oven-dried 1-dram vial was charged with 6-(2-chloroethoxy)-N-(3-ethynylphenyl)-7-(2-methoxyethoxy)quinazolin-4-amine hydrochloride (100 mg, 0.23 mmol), 1-Boc-piperazine (86 mg, 0.46 mmol), Potassium carbonate (95 mg, 0.69 mmol). DMF (1.15 mL) was added via syringe. The vial was flushed with argon and closed with a rubber septum fitted with a needle connected to an argon source. The mixture was warmed to 80° C. In 1 h, LC-MS analysis showed consumption of the starting material and formation of one single product with the desired m/z. The reaction mixture was partitioned between ethyl acetate (5 mL) and water (5 mL), and the layers were separated. The aqueous layer was extracted with ethyl acetate (3×5 mL). The combined organic layers were dried over sodium sulfate, and the dried solution was concentrated. The residue was purified by column chromatography (0-10% methanol-dichloromethane) to afford the product as a brown solid (112 mg, 88%). tert-butyl 4-[2-[4-(3-ethynylanilino)-7-(2-methoxyethoxy)quinazolin-6-yl]oxyethyl]piperazine-1-carboxylate (112 mg, 0.20 mmol) was dissolved in 1:1 dichloromethane (0.50 mL):Trifluroacetic Acid (0.50 mL) at 23° C. and the resulting solution was allowed to stand at 23° C. for 1 h. At this point, LC-MS analysis showed full consumption of the starting material and formation of one single product with desired m/z. The reaction mixture was concentrated in vacuo to give a syrup, which was triturated with ether (10 mL) to afford the product as a white powder (113 mg, 98%). $^1$H NMR (400 MHz, Methanol-$d_4$) δ 8.69 (s, 1H), 8.01 (s, 1H), 7.84 (t, J=1.7 Hz, 1H), 7.70 (dt, J=IN, 1.9 Hz, 1H), 7.49-7.36 (m, 2H), 7.26 (s, 1H), 4.45 (t, J=4.9 Hz, 2H), 4.41-4.33 (m, 2H), 3.88-3.79 (m, 2H), 3.57 (s, 1H), 3.43 (s, 3H), 3.37-3.29 (m, 4H), 3.22 (t, J=4.9 Hz, 2H), 3.17 (d, J=6.8, 3.8 Hz, 4H). HRMS (ESI): Calcd for $(C_{25}H_{29}N_5O_3+H)^+$: 448.2343, Found: 448.2350.

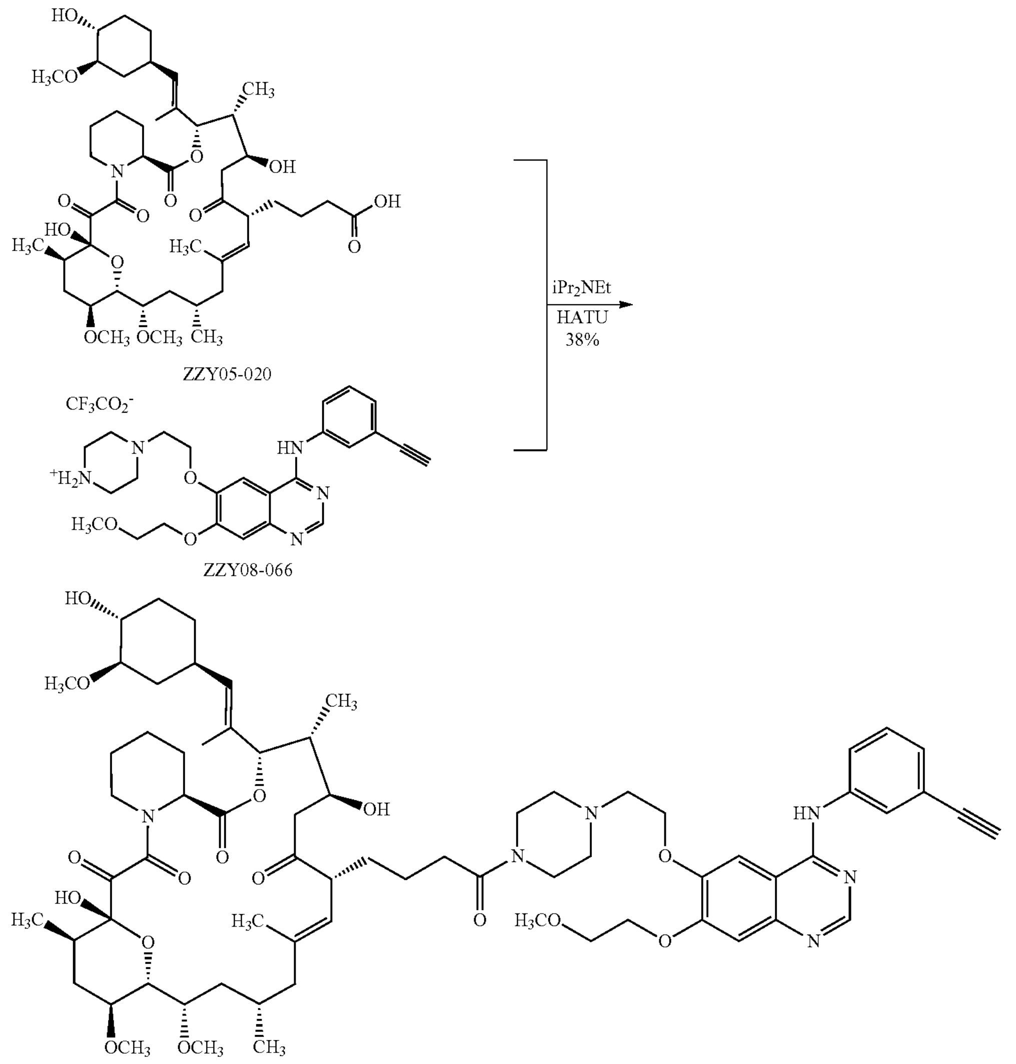

ZZY05-020

ZZY08-066

ZZY08-068

A 1-dram vial was charged with 05-020 (20 mg, 0.024 mmol), Pip-Erlotinib (13 mg, 0.024 mmol), DMF (0.12 mL) and a magnetic stir bar. N,N-Diisopropylethylamine (12 μL, 0.071 mmol) was added and the mixture was stirred until all reactants had gone into solution. HATU (10.7 mg, 0.0282 mmol) was added as a freshly made 10% w/v solution in DMF. The mixture was stirred at 23° C. while the reaction progress was monitored by LC-MS. In a total of 1 h, LC-MS analysis showed full consumption of the starting material. The reaction mixture was partitioned between ethyl acetate (5 mL) and water (5 mL), and the layers were separated. The aqueous layer was extracted with ethyl acetate (2×5 mL). The combined organic layers were dried over sodium sulfate, and the dried solution was concentrated. The residue was purified by column chromatography (0-10% methanol-dichloromethane) to afford the product as a pale-yellow solid (11.5 mg, 38%). 3:2 mixture of rotamers. $^1$H NMR. (400 MHz, Chloroform-d) δ 8.64 (s, 1H), 7.87 (dt, J=8.4, 1.4 Hz, 1H), 7.81-7.74 (m, 1H), 7.40-7.30 (m, 2H), 7.25-7.23 (m, 2H), 5.37 (s, 1H), 5.09-4.98 (m, 2H), 4.68 (d, J=4.8 Hz, 1H), 4.38 (d, J=12.9 Hz, 1H), 4.31-4.24 (m, 4H), 4.05-3.90 (m, 1H), 3.90-3.80 (m, 4H), 3.66-3.50 (m, 2H), 3.46 (s, 3H), 3.39 (s, 3H), 3.38 (s, 3H), 3.38-3.33 (m, 3H), 3.29 (s, 3H), 3.09 (s, 1H), 3.05-2.93 (m, 2H), 2.80-2.53 (m, 4H), 2.37-2.20 (m, 4H), 2.19-2.06 (m, 4H), 2.06-1.83 (m, 4H), 1.83-1.51 (m, 8H), 1.49-1.28 (m, 14H), 1.10-1.02 (m, 2H), 0.98 (d, J=6.2 Hz, 3H), 0.92 (d, J=5.6 Hz, 3H), 0.85 (d, J=7.2 Hz, 3H). HRMS (ESI): Calcd for $(C_{70}H_{98}N_6O_{16}+H)^+$: 1279.7117, Found: 1279.7131.

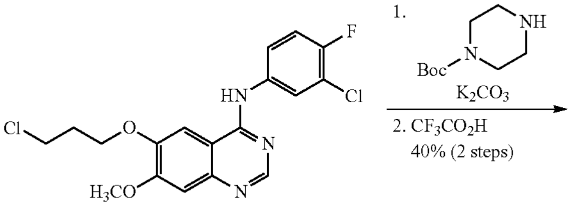

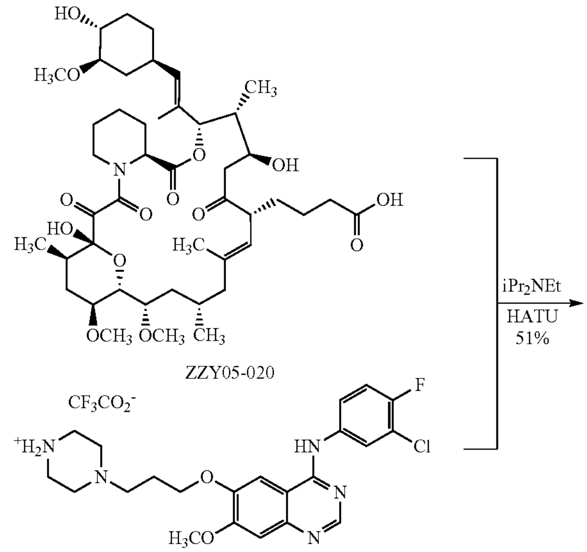

ZZY05-020

ZZY08-067

-continued

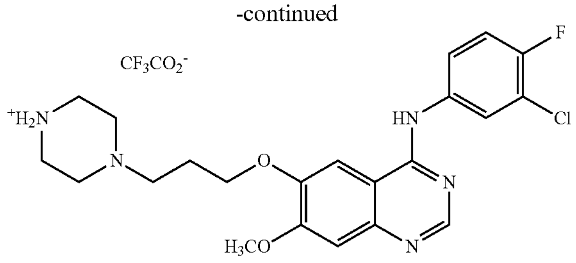

ZZY08-067

An oven-dried 1-dram vial was charged with N-(3-chloro-4-fluoro-phenyl)-6-(3-chloropropoxy)-7-methoxy-quinazolin-4-amine (100 mg, 0.25 mmol), 1-Boc-piperazine (94 mg, 0.50 mmol), Potassium carbonate (105 mg, 0.76 mmol) and a magnetic stir bar. DMF (2.00 mL) was added via syringe. The vial was flushed with argon and closed with a rubber septum fitted with a needle connected to an argon source. The mixture was warmed to 80° C. In 1 h, LC-MS analysis showed consumption of the starting material and formation of one single product with the desired m/z. The reaction mixture was partitioned between ethyl acetate (5 mL) and water (5 mL), and the layers were separated. The aqueous layer was extracted with ethyl acetate (3×5 mL). The combined organic layers were dried over sodium sulfate, and the dried solution was concentrated. The residue was purified by column chromatography (0-10% methanol-dichloromethane) to afford the product as a white solid (57 mg, 41%). tert-Butyl 4-[3-[4-(3-chloro-4-fluoro-anilino)-7-methoxy-quinazolin-6-yl]oxypropyl]piperazine-1-carboxylate (57 mg, 0.104 mmol) was dissolved in 1:1 dichloromethane (0.50 mL):trifluroacetic acid (0.50 mL), and the resulting solution was allowed to stand at 23° C. for 1 h. The solution was concentrated in vacuo to afford the product as a brown solid (58 mg, 99%). $^1$H NMR (400 MHz, Methanol-d$_4$) δ 8.76 (s, 1H), 8.00 (s, 1H), 7.95 (dd, J=6.6, 2.6 Hz, 1H), 7.68 (ddd, J=8.9, 4.2, 2.6 Hz, 1H), 7.40 (t, J=0.9 Hz, 1H), 7.28 (s, 1H), 4.38 (t, J=5.7 Hz, 2H), 4.11 (s, 3H), 3.50 (t, J=5.3 Hz, 4H), 3.32-3.28 (m, 4H, this peak is covered by the $CD_2HOD$ solvent peak), 3.20 (t, J=7.1 Hz, 2H), 2.34 (p, J=6.4 Hz, 2H). HRMS (ESI): Calcd for $(C22H_{25}ClN_5O2+H)^+$: 446.1754, Found: 446.1748.

-continued

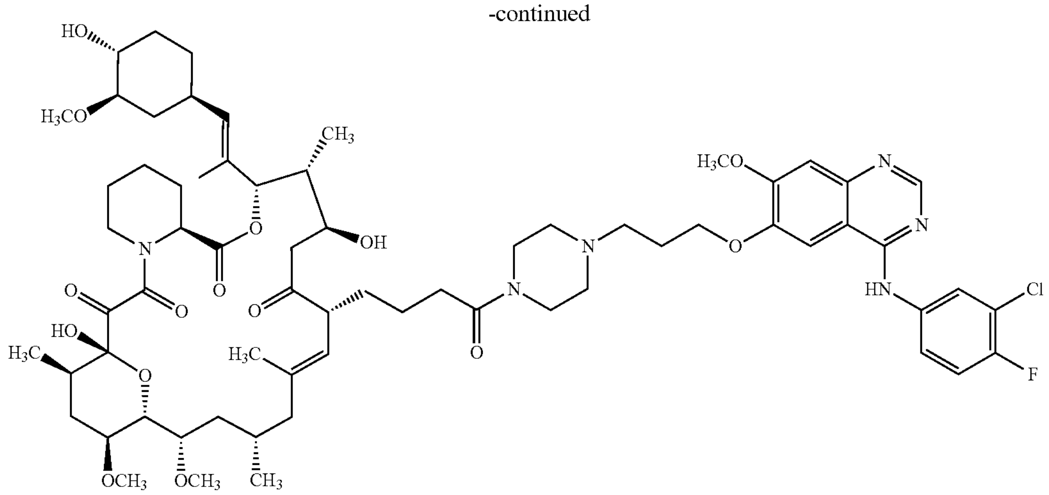

ZZY08-069

A 1-dram vial was charged with ZZY05-020 (20 mg, 0.024 mmol), Pip-gefetinib (13 mg, 0.024 mmol), DMF (0.12 mL) and a magnetic stir bar. N,N-Diisopropylethylamine (12 μL, 0.071 mmol) was added and the mixture was stirred until all reactants had gone into solution. HATU (10.7 mg, 0.0282 mmol) was added as a 10% w/v solution in DMF. The resulting solution was stirred at 23° C. and the reaction progress was monitored by LC-MS. In 15 min, LC-MS showed ~80% consumption of the amine starting material. Additional HATU (1.07 mg, as 10% solution in DMF) was added. In a total of 1 h, LC-MS analysis showed full consumption of the starting material. The reaction mixture was partitioned between ethyl acetate (5 mL) and water (5 mL), and the layers were separated. The aqueous layer was extracted with ethyl acetate (2×5 mL). The combined organic layers were dried over sodium sulfate, and the dried solution was concentrated. The residue was purified by column chromatography (0-10% methanol-dichloromethane) to afford the product as a pale-yellow solid (15.5 mg, 51%). 3:2 mixture of rotamers. $^1$H NMR (400 MHz, Chloroform-d) δ 8.63 (s, 1H), 8.03-7.87 (m, 1H), 7.70 (d, J=5.7 Hz, 1H), 7.50-7.38 (m, 1H), 7.24 (s, 1H), 7.20-7.12 (m, 2H), 5.40 (s, 1H), 5.21-5.02 (m, 3H), 4.73 (s, 1H), 4.39 (d, J=13.3 Hz, 1H), 4.29-4.14 (m, 4H), 4.14-4.03 (m, 2H), 3.99 (s, 3H), 3.83 (d, J=9.7 Hz, 1H), 3.80-3.56 (m, 4H), 3.51-3.47 (m, 3H), 3.42 (s, 3H), 3.39 (s, 3H), 3.35 (br s, 3H), 3.22 (s, 2H), 8-2.71 (m, 6H), 2.40-2.11 (m, 5H), 2.11-1.90 (m, 5H), 1.87-1.65 (m, 6H), 1.62-1.53 (m, 6H), 1.53-1.32 (m, 8H), 1.06-1.01 (m, 2H), 0.96 (d, J=6.0 Hz, 3H), 0.91 (d, J=6.6 Hz, 3H), 0.87 (d, J=6.5 Hz, 3H). HRMS (ESI): Calcd for $(C_{67}H_{94}ClFN_6O_{15}+H)^+$: 1277.6528, Found: 1277.6564.

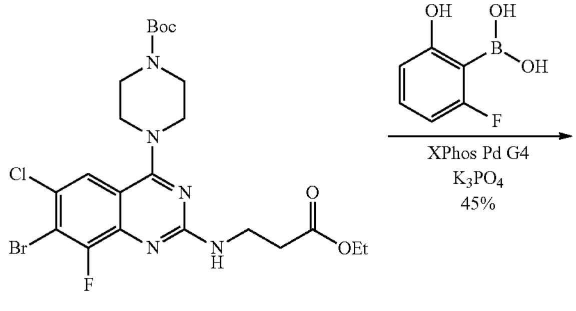

-continued

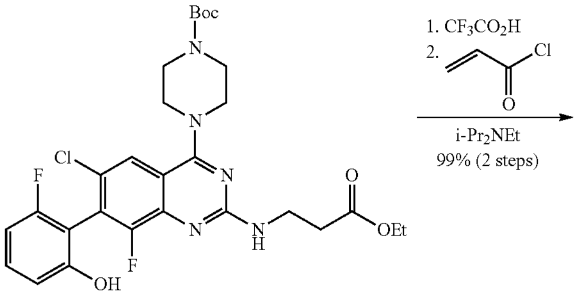

(±)-ZZY04-100

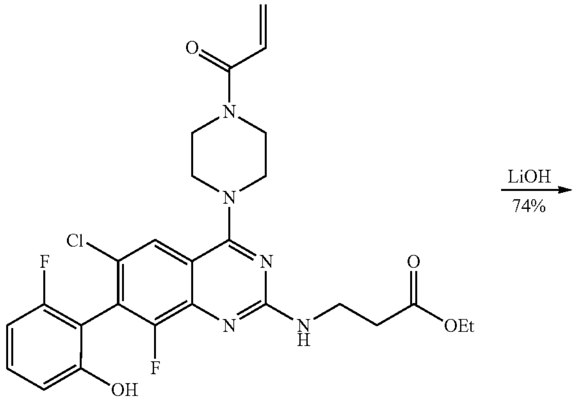

(±)-ZZY05-023

-continued

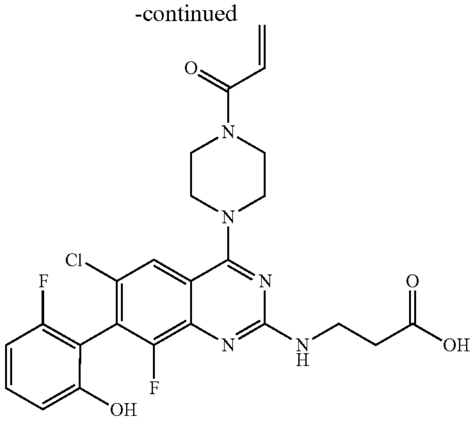

(±)-ZZY05-039

A 20-mL vial was charged with (2-fluoro-6-hydroxy-phenyl)boronic acid (278 mg, 1.78 mmol), tert-butyl 4-[7-bromo-6-chloro-2-[(3-ethoxy-3-oxo-propyl)amino]-8-fluoro-quinazolin-4-yl]piperazine-1-carboxylate (200 mg, 0.36 mmol), XPhos Pd G4 precatalyst (14.2 mg, 0.018 mmol), and 1:1 THF:water (4.0 mL). Argon was bubbled through the mixture for 5 min, then the vial was closed with a rubber septum fitted with a needle connected to an argon source. A 0.5 M aqueous solution of potassium phosphate (0.91 mL, 2.14 mmol) was added dropwise via syringe. After 16 h, both LC-MS and TLC analysis showed only ~50% conversion. Additional catalyst (14.2 mg) was added and the mixture was stirred at 50° C. for another 2 h. However, no further progress was detected after this second portion of catalyst. The reaction mixture was partitioned between ethyl acetate (10 mL) and 10% citric acid (10 mL). The layers were separated, and the aqueous layer was extracted with ethyl acetate (2×10 ml). The combined organic layers were dried over sodium sulfate, and the dried solution was concentrated. The residue was purified by column chromatography (20-50% ethyl acetate-hexanes, 4-g RediSep® Rf column, Teledyne ISCO, Lincoln, Nebr.) to afford the product as a yellow powder (97 mg, 46%) and recovered bromide starting material (72 mg, 36%). $^{1}$H NMR (400 MHz, Chloroform-d) δ 7.39 (s, 1H), 7.34-7.24 (m, 1H), 6.85 (d, J=8.3 Hz, 1H), 6.70 (t, J=8.5 Hz, 1H), 5.66 (s, 1H), 4.16 (q, J=7.1 Hz, 2H), 3.74 (app q, J=6.6 Hz, 2H), 3.71-3.51 (m, 8H), 2.65 (td, J=6.5, 1.4 Hz, 2H), 1.50 (s, 9H), 1.26 (t, J=7.1 Hz, 3H). HRMS (ESI): Calcd for $(C_{28}H_{32}ClF_2N_5O_5+H)^+$: 592.2138, Found: 592.2148.

tert-Butyl 4-[6-chloro-2-[(3-ethoxy-3-oxo-propyl)amino]-8-fluoro-7-(2-fluoro-6-hydroxy-phenyl)quinazolin-4-yl]piperazine-1-carboxylate (97 mg, 0.16 mmol) was dissolved in 1:1 trifluoroacetic acid (0.50 mL):dichloromethane (0.50 mL) and the resulting mixture was allowed to stand at 23° C. for 1 h. The solution was then concentrated under reduced pressure to afford the product as a yellow foam. Dichloromethane (1.45 mL) and N,N-diisopropylethylamine (43 μL, 0.25 mmol) were added sequentially to the foam. After stirring for 10 min, the material had fully dissolved. The solution was cooled to −78° C., and acryloyl chloride (14 μL, 0.170 mmol) was added dropwise via syringe. The resulting solution was warmed to 0° C., and the reaction progress was monitored by LC-MS. In 30 min, LC-MS analysis showed conversion to a single product with the desired m/z. The reaction mixture was partitioned between water (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-80% ethyl acetate-hexanes, 4-g RediSep® Rf column, Teledyne ISCO, Lincoln, Nebr.) to afford the product as a yellow powder (100 mg, 99%). $^{1}$H NMR (400 MHz, Methanol-$d_4$) δ 8.05 (s, 1H), 7.70 (dd, J=13.0, 5.9 Hz, 1H), 7.45-7.29 (m, 3H), 6.82 (dt, J=8.4, 0.8 Hz, 1H), 6.80-6.73 (m, 1H), 4.41 (s, 4H), 3.93-3.84 (m, 2H), 3.56-3.49 (m, 6H), 2.74 (t, J=6.3 Hz, 2H), 1.20 (t, J=7.0 Hz, 3H). HRMS (ESI): Calcd for $(C_{26}H_{26}ClF_2N_5O_4+H)^+$: 546.1719, Found: 546.1733.

Lithium hydroxide hydrate (1:1:1) (23 mg, 0.55 mmol) was added to a solution of ethyl 3-[[6-chloro-8-fluoro-7-(2-fluoro-6-hydroxy-phenyl)-4-(4-prop-2-enoylpiperazin-1-yl)quinazolin-2-yl]amino]propanoate (100 mg, 0.18 mmol) in 1:1 water (1.10 mL):THF (1.10 mL). The resulting mixture was stirred at 23° C., and the reaction progress was monitored by LC-MS. In 2 h, the ethyl ester had fully hydrolyzed. The volatile solvents were removed by rotary evaporation. The remaining aqueous suspension was acidified with 10% citric acid (2 mL), and then extracted with ethyl acetate (3×10 mL). The combined organic layers were dried over sodium sulfate, and the dried solution was concentrated to afford the product (71 mg, 74%). $^{1}$H NMR (400 MHz, Methanol-$d_4$) δ 7.83 (s, 1H), 7.32 (td, J=8.3, 6.7 Hz, 1H), 6.91-6.77 (m, 2H), 6.73 (ddd, J=92, 8.3, 1.0 Hz, 1H), 6.29 (dd, J=16.8, 1.9 Hz, 1H), 5.82 (dd, J=10.6, 1.9 Hz, 1H), 4.11-3.84 (m, 8H), 3.78 (t, J=6.5 Hz, 2H), 2.68 (t, J=6.5 Hz, 2H). HRMS (ESI): Calcd for $(C24H_{22}ClF_2N_5O_4+H)^+$: 518.1396, Found: 518.1397.

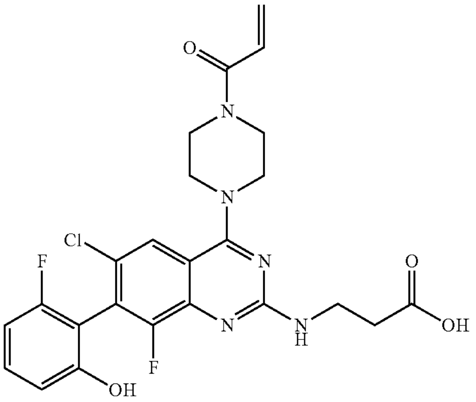

(±)-ZZY05-039

-continued

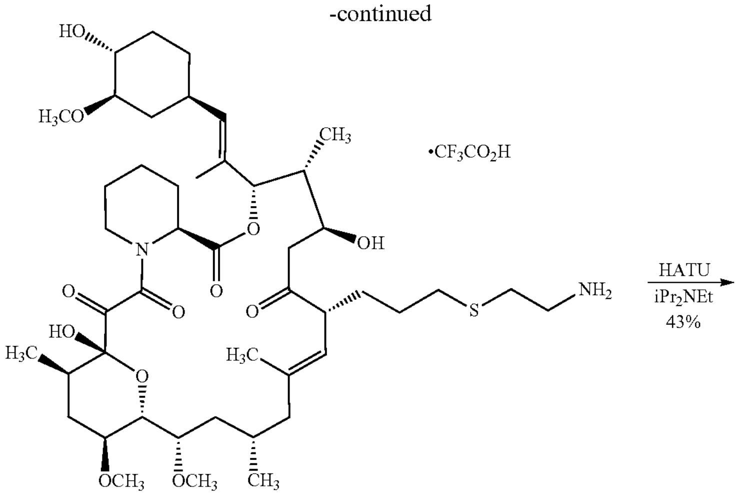

ZZY05-011

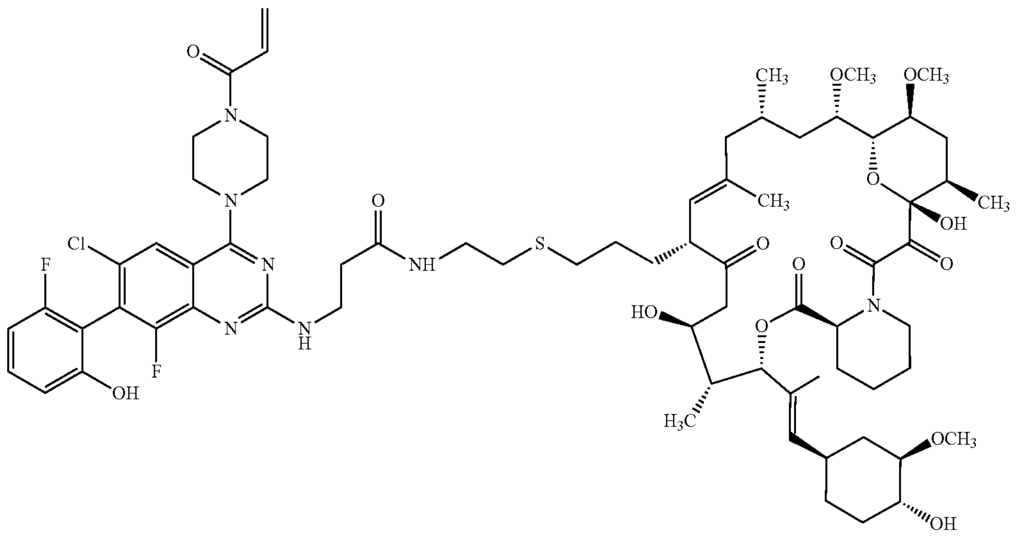

ZZY05-042

A 1-dram vial was charged with (±)-ZZY05-039 (5.0 mg, 0.010 mmol), ZZY05-011 (9.6 mg, 0.010 mmol), and DMF (0.30 mL). N,N-Diisopropylethylamine (5.0 μL, 0.030 mmol) and HATU (4.4 mg, 0.012 mmol) were added sequentially to the solution at 23° C., and the resulting mixture was stirred at 23° C. while the reaction progress was monitored by LC-MS. In 15 min, LC-MS showed full consumption of the amine starting material and formation of a new product with the expected m/z. The reaction mixture was diluted with 50% acetonitrile-water to a volume of 4.7 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.7 mg, 43%). 3:2 mixture of rotamers. $^1$H NMR (400 MHz, Chloroform-d) δ 8.28 (s, 1H), 7.77-7.62 (m, 1H), 6.90-6.72 (m, 2H), 6.64 (dd, J=16.9, 10.7 Hz, 1H), 6.39 (d, J=16.8 Hz, 1H), 5.80 (d, J=10.3 Hz, 1H), 5.35 (d, J=3.5 Hz, 1H), 5.11-4.96 (m, 2H), 4.61-4.32 (m, 2H), 4.07-3.73 (m, 6H), 3.72-3.53 (m, 2H), 3.42 (s, 3H), 3.42 (s, 3H), 3.41 (s, 3H), 3.40-3.37 (m, 3H), 3.17-2.86 (m, 6H), 2.68-2.52 (m, 4H), 2.49-2.24 (m, 6H), 2.24-1.86 (m, 8H), 1.86-1.70 (m, 6H), 1.70-1.61 (m, 6H), 1.61-1.24 (m, 8H), 1.14-1.05 (m, 2H), 1.05-0.81 (m, 9H). HRMS (ESI): Calcd for $(C_{70}H_{96}ClF_2N_7O_{15}S+H)^+$: 1380.6420, Found: 1380.6404.

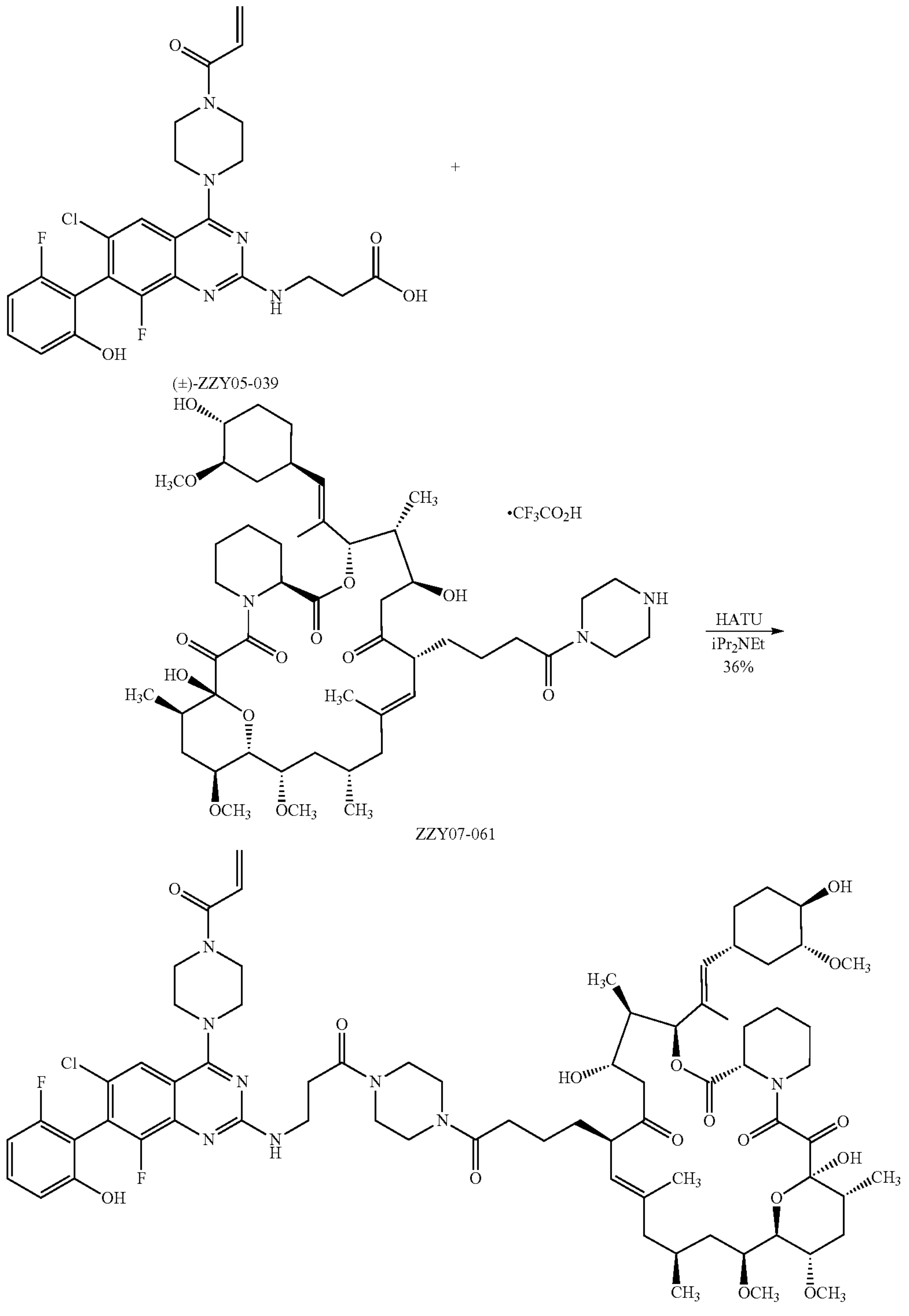

(±)-ZZY05-039

ZZY07-061

ZZY08-027

A 1-dram vial was charged with (±)-ZZY05-039 (5.5 mg, 0.011 mmol), ZZY08-019 (10.0 mg, 0.010 mmol), and DMF (0.30 mL). N,N-Diisopropylethylamine (5.0 μL, 0.030 mmol) and HATU (7.6 mg, 0.019 mmol) were added sequentially to the solution at 23° C., and the resulting mixture was stirred at 23° C. while the reaction progress was monitored by LC-MS. In 15 min, LC-MS showed full consumption of the amine starting material and formation of a new product with the expected m/z. The reaction mixture was diluted with 50% acetonitrile-water to a volume of 4.2 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (4.9 mg, 36%). 3:2 mixture of rotamers. $^1$H NMR (400 MHz, Methanol-$d_4$) δ 8.09 (s, 1H), 7.46-7.29 (m, 1H), 6.89-6.71 (m, 3H), 6.33 (d, J=16.6 Hz, 1H), 5.85 (d, J=10.6 Hz, 1H), 5.33-5.09 (m, 3H), 4.34 (br s, 4H), 4.06-3.83 (m, 4H), 3.77-3.52 (m, 10H), 3.43 (s, 3H), 3.42 (s, 3H), 3.41-3.38 (m, 2H), 3.35 (s, 3H), 3.09-2.94 (m, 2H), 2.94-2.75 (m, 4H), 2.50-2.27 (m, 6H), 2.27-1.87 (m, 6H), 1.88-1.72 (m, 4H), 1.72-1.52 (m, 6H), 1.52-1.28 (m, 8H), 1.15-1.02 (m, 2H), 1.02-0.86 (m, 9H). HRMS (ESI): Calcd for $(C_{73}H_{99}ClF_2N_8O_{16}+H)^+$: 1417.6914, Found: 1417.6904.
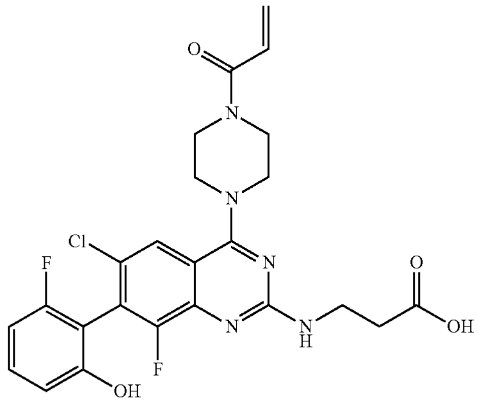
(±)-ZZY05-039
+
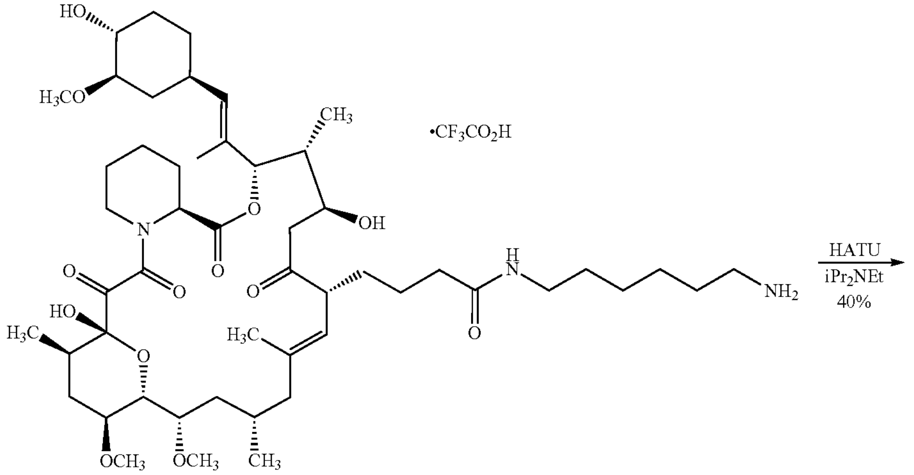
ZZY07-062
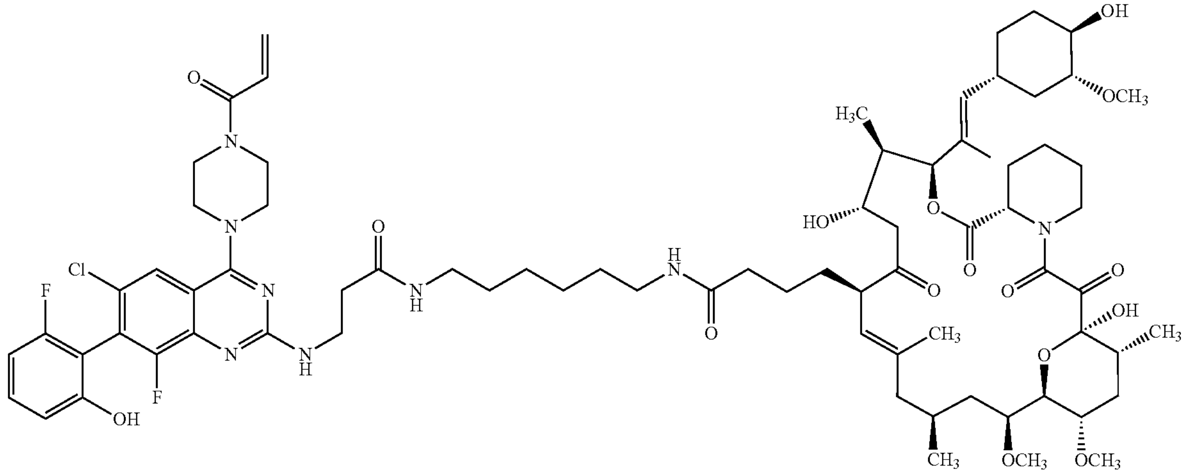
ZZY08-028

A 1-dram vial was charged with (±)-ZZY05-039 (5.5 mg, 0.011 mmol), ZZY08-062 (10.0 mg, 0.010 mmol), and DMF (0.30 mL). N,N-Diisopropylethylamine (5.0 μL, 0.030 mmol) and HATU (7.6 mg, 0.019 mmol) were added sequentially to the solution at 23° C., and the resulting mixture was stirred at 23° C. while the reaction progress was monitored by LC-MS. In 15 min, LC-MS showed full consumption of the amine starting material and formation of a new product with the expected m/z. The reaction mixture was diluted with 50% acetonitrile-water to a volume of 4.2 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.5 mg, 40%). 3:2 mixture of rotamers. $^1$H NMR (400 MHz, Methanol-$d_4$) δ 7.77 (s, 1H), 7.35-7.26 (m, 1H), 6.89-6.68 (m, 3H), 6.28 (d, J=16.1 Hz, 1H), 5.82 (d, J=12.3 Hz, 1H), 5.28-5.19 (m, 1H), 5.18-4.99 (m, 2H), 4.60 (s, 2H), 4.40-4.26 (m, 1H), 4.17-4.06 (m, 1H), 3.95-3.83 (m, 8H), 3.84-3.74 (m, 2H), 3.56-3.47 (m, 2H), 3.44 (s, 3H), 3.43 (s, 3H), 3.40 (s, 3H), 3.39-3.36 (m, 2H), 3.20-3.02 (m, 4H), 2.61-2.50 (m, 2H), 2.44-2.29 (m, 4H), 2.25-2.09 (m, 4H), 2.09-1.89 (m, 4H), 1.89-1.65 (m, 6H), 1.65-1.33 (m, 10H), 1.31-1.23 (m, 8H), 1.12-1.02 (m, 2H), 1.03-0.78 (m, 9H). HRMS (ESI): Calcd for $(C_{75}H_{105}ClF_2N_8O_{16}+H)^+$: 1447.7383, Found: 1447.7435.

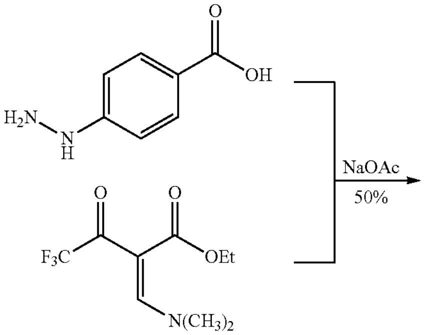

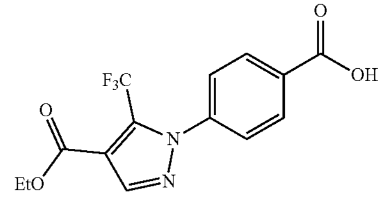

ZZY06-005

A 20-mL vial was charged with ethyl (2Z)-2-(dimethylaminomethylene)-4,4,4-trifluoro-3-oxo-butanoate (526 mg, 2.20 mmol), 4-hydrazinobenzoic acid (304 mg, 2.00 mmol), sodium acetate (180 mg, 2.2 mmol) and ethanol (5.0 mL). The mixture was warmed to 70° C. and kept stirred at that temperature. In 4 h, a large amount of precipitation had formed. TLC analysis (50% ethyl acetate-hexanes) showed full conversion of the starting material to a less polar compound. The reaction mixture was filtered through a sintered glass funnel. The collected solids were rinsed with cold ethanol (10 mL) and then ether (10 mL). The combined filtrate was concentrated under reduced pressure. The residue was purified by column chromatography (0-60% ethyl acetate-hexanes+0.1% acetic acid, 4-g RediSep® Rf column, Teledyne ISCO, Lincoln, Nebr.) to afford the product as a yellow powder (332 mg, 50%). $^1$H NMR (400 MHz, Chloroform-d) δ 8.31-8.22 (m, 2H), 8.16 (d, J=0.7 Hz, 1H), 7.57 (d, J=8.5 Hz, 2H), 4.39 (q, J=7.1 Hz, 2H), 1.40 (t, J=7.2 Hz, 3H). HRMS (ESI): Calcd for $(C_{14}H_{11}F_3N_2O_4-H)^-$: 327.0593, Found: 327.0589.

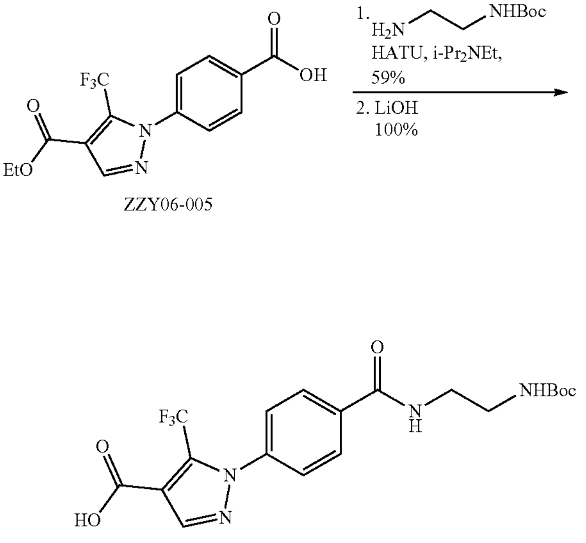

ZZY06-005

ZZY06-015

N,N-diisopropylethylamine (0.32 mL, 1.83 mmol) and HATU (278.01 mg, 0.730 mmol) were added sequentially to a mixed solution of N-tert-Boc-ethylenediamine (117.14 mg, 0.7300 mmol) and 4-[4-ethoxycarbonyl-3-(trifluoromethyl)pyrazol-1-yl]benzoic acid (200.mg, 0.6100 mmol) in 9:1 dichloromethane:DMF (1.2 mL). The resulting mixture was stirred at 23° C. for 30 min, at which point LC-MS analysis showed full consumption of the acid starting material and formation of a slightly less polar compound. The reaction mixture was concentrated under reduced pressure. The residue was purified by column chromatography (20-50% ethyl acetate-hexanes, 4-g RediSep® Rf column, Teledyne ISCO, Lincoln, Nebr.) to afford the product as a yellow powder (170 mg, 59%). Lithium hydroxide hydrate (27 mg, 0.64 mmol) was added to a suspension of ethyl 1-[4-[2-(tert-butoxycarbonylamino)ethylcarbamoyl]phenyl]-3-(trifluoromethyl)pyrazole-4-carboxylate (100 mg, 0.21 mmol) in 1:1:1 methanol (0.50 mL):THF (0.50 mL):Water (0.50 mL) at 23° C. The resulting mixture turned into a clear solution immediately. In 30 min, LC-MS analysis showed full conversion to the carboxylic acid. 10% Aqueous citric acid (3 mL) was added, and the resulting mixture was extracted with ethyl acetate (3×10 mL). The combined organic layers were dried over sodium sulfate, and the dried solution was concentrated to afford the product as a white powder (99 mg, 100%). $^1$H NMR (400 MHz, Chloroform-d) δ 8.21 (s, 1H), 8.01 (d, J=8.3 Hz, 2H), 7.53 (d, J=8.9 Hz, 2H), 3.66-3.58 (m, 2H), 3.54-3.41 (m, 2H), 1.45 (s, 9H). HRMS (ESI): Calcd for $(C_{19}H_{21}F_3N_4O_5-H)^-$: 441.1386, Found: 441.1370.

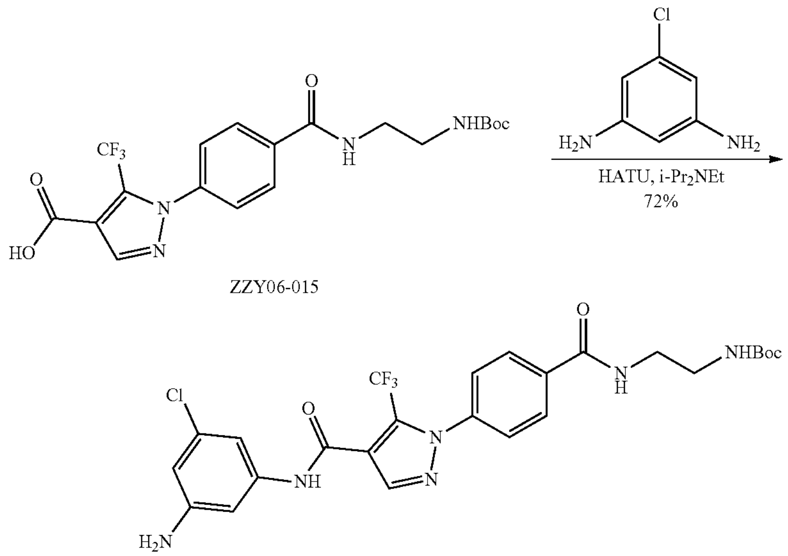

ZZY06-015

ZZY06-018

N,N-Diisopropylamine (87 μL, 0.50 mmol) and HATU (45 mg, 0.12 mmol) were added sequentially to a solution of 1-[4-[2-(tert-butoxycarbonylamino)ethylcarbamoyl]phenyl]-3-(trifluoromethyl)pyrazole-4-carboxylic acid (44 mg, 0.100 mmol) and 5-Chloro-1,3-benzenediamine (57 mg, 0.40 mmol) in 9:1 dichloromethane:DMF (0.5 mL) at 23° C. and the reaction progress was monitored by LC-MS. In 1 h, LC-MS analysis showed full consumption of the acid starting material and formation of a single, desired product. TLC analysis (100% ethyl acetate) showed that the excess diamine was easily separated from the product in this case. The reaction mixture was directly loaded onto a silica gel cartridge (~2 g). Purification by column chromatography (20-100% ethyl acetate-hexanes, 4-g RediSep Rf Column, Teledyne ISCO, Lincoln, Nebr.) afforded the product as a white solid (51 mg, 72%). $^1$H NMR (400 MHz, Methanol-$d_4$) δ 8.11 (s, 1H), 8.03 (d, J=8.5 Hz, 2H), 7.61 (d, J=8.6 Hz, 2H), 7.02 (s, 1H), 6.98 (s, 1H), 6.52 (t, J=1.9 Hz, 1H), 3.59-3.45 (m, 2H), 3.43-3.28 (m, 2H), 1.43 (s, 9H). HRMS (ESI): Calcd for $(C_{25}H_{27}ClF_3N_6O_4+H)^+$: 567.1734, Found: 567.1751.

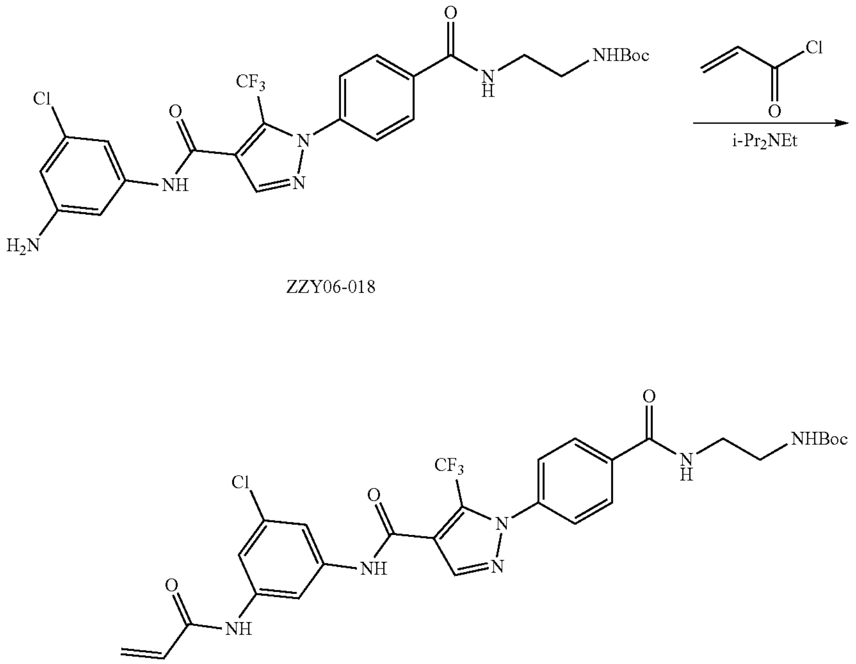

ZZY06-018

ZZY06-022

Acryloyl chloride (10.7 μL, 0.13 mmol) was added dropwise to an ice-cold solution of tert-butyl N-[2-[[4-[4-[(3-amino-5-chloro-phenyl)carbamoyl]-5-(trifluoromethyl)pyrazol-1-yl]benzoyl]amino]ethyl]carbamate (51 mg, 0.090 mmol) and triethylamine (37 μL, 0.27 mmol) in dichloromethane (1.0 mL) at 0° C. Upon addition the reaction mixture turned into a polymer-like gel. Nevertheless, TLC analysis (100% ethyl acetate) showed a new UV-active spot being formed. LC-MS analysis of an aliquot of filtered material showed full consumption of the starting material. The reaction mixture was partitioned between saturated aqueous sodium bicarbonate solution (5 mL) and dichloromethane (5 mL). The mixture was filtered to remove the polymeric material. The layers were separated, and the aqueous layer was extracted with dichloromethane (2×25 mL). The combined organic layers were dried over sodium sulfate. The dried solution was filtered, and the filtrate was concentrated. The residue was purified by column chromatography (20-100% ethyl acetate-hexanes, 4-g RediSep® Rf column, Teledyne ISCO, Lincoln, Nebr.) to afford the product as a yellow solid (22 mg, 39%). $^1$H NMR (400 MHz, Methanol-$d_4$) δ 8.18 (s, 1H), 8.05 (d, J=8.3 Hz, 2H), 8.02-7.96 (m, 1H), 7.68-7.61 (m, 3H), 7.56 (s, 1H), 6.47-6.40 (m, 2H), 5.82 (dd, J=8.9, 2.9 Hz, 1H), 3.54-3.45 (m, 4H), 1.44 (s, 9H). HRMS (ESI): Calcd for $(C_{28}H_{28}ClF_3N_6O_5+H)^+$: 621.1840, Found: 621.1855.

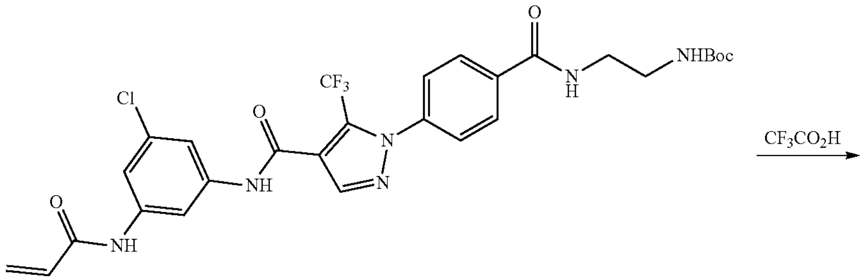

ZZY06-022

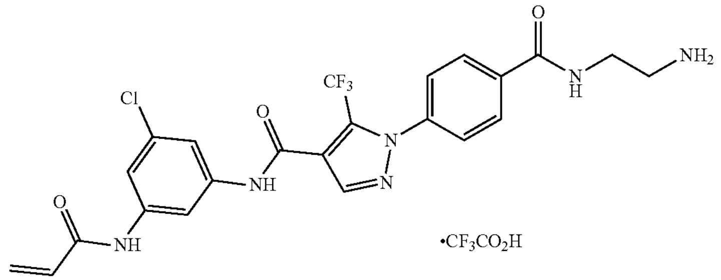

ZZY06-025 tert-Butyl N-[2-[[4-[4-[[3-chloro-5-(prop-2-enoylamino)phenyl]carbamoyl]-5-(trifluoromethyl)pyrazol-1-yl]benzoyl]amino]ethyl] carbamate (23.mg, 0.040 mmol) was dissolved in 50% trifluoroacetic acid-dichloromethane (1.0 mL). The resulting solution was allowed to stand at 23° C. for 1 h. LC-MS analysis at this point showed full convertion of the starting material to a single product. The reaction mixture was directly concentrated to afford the product as a white solid (23 mg, 98%). $^1$H NMR (400 MHz, Methanol-$d_4$) δ 8.22-8.19 (m, 1H), 8.10 (d, J=8.8 Hz, 2H), 8.00 (t, J=1.9 Hz, 1H), 7.68 (d, J=8.5 Hz, 2H), 7.61 (t, J=1.9 Hz, 1H), 7.56 (t, J=1.9 Hz, 1H), 6.46-6.36 (m, 2H), 5.82 (dd, J=9.0, 2.9 Hz, 1H), 3.77-3.69 (m, 2H), 3.22 (t, J=5.9 Hz, 2H). HRMS (ESI): Calcd for $(C_{23}H_{20}ClF_3N_6O_3+H)^+$: 521.1316, Found: 521.1319.

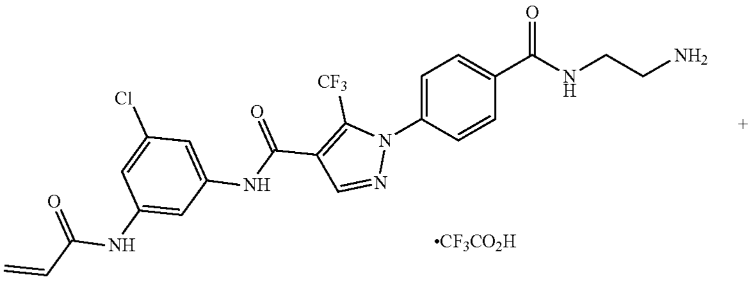

ZZY06-025

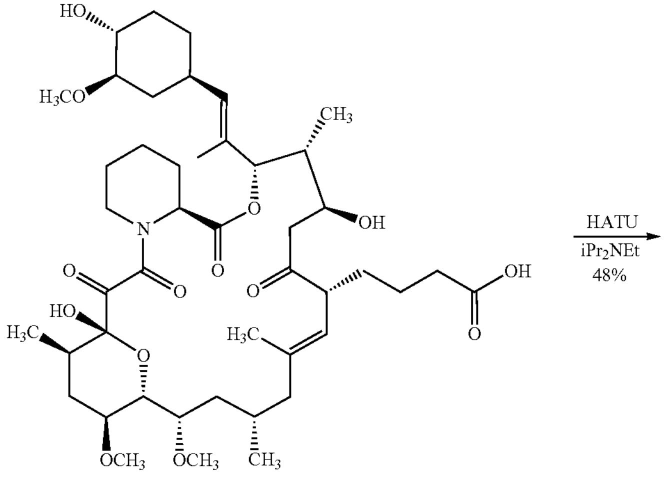

ZZY05-020

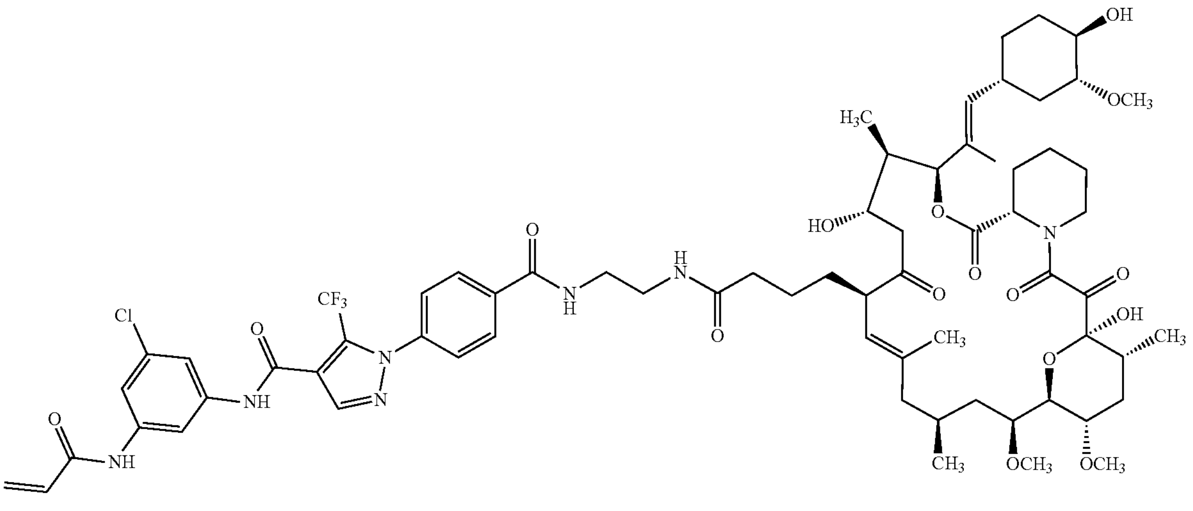

ZZY06-027

N,N-Diisopropylethylamine (8.2 μL, 0.047 mmol) and HATU (9.0 mg, 0.024 mmol) were added sequentially to a mixed solution of ZZY05-020 (14.7 mg, 0.017 mmol) and ZZY06-025 (10 mg, 0.016 mmol) in DMF (0.20 mL) at 23° C. The resulting mixture was stirred at 23° C., and the reaction progress was monitored by LC-MS. In 1 h, LC-MS analysis showed full consumption of the acid starting material. The residue was diluted with 50% acetonitrile-water to a volume of 3.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (10.2 mg, 48%). 3:2 mixture of rotamers. $^1H$ NMR (400 MHz, Chloroform-d) δ 9.01 (s, 1H), 8.21 (s, 1H), 8.00 (s, 1H), 7.92 (d, J=8.5 Hz, 3H), 7.78 (s, 1H), 7.64 (d, J=13.4 Hz, 2H), 7.59-7.46 (m, 3H), 6.52-6.46 (m, 1H), 6.43 (d, J=17.1 Hz, 1H), 6.28 (dd, J=16.8, 10.2 Hz, 1H), 5.76 (d, J=11.1 Hz, 1H), 5.30 (s, 1H), 5.07-4.94 (m, 2H), 4.63 (d, J=4.3 Hz, 1H), 4.39 (d, J=13.5 Hz, 1H), 3.96-3.88 (m, 2H), 3.68-3.44 (m, 5H), 3.39 (s, 3H), 3.38 (s, 3H), 3.36-3.33 (m, 3H), 3.28 (s, 3H), 3.25-3.16 (m, 2H), 3.06-2.95 (m, 2H), 2.90 (t, J=12.7 Hz, 1H), 2.62 (d, J=15.6 Hz, 1H), 2.39-1.91 (m, 10H), 1.91-1.61 (m, 6H), 1.61-1.55 (m, 6H), 1.56-1.29

(m, 8H), 1.06-1.00 (m, 2H), 0.96 (d, J=6.3 Hz, 3H), 0.91 (d, J=5.7 Hz, 3H), 0.83 (d, J=7.2 Hz, 3H). HRMS (ESI): Calcd for $(C_{68}H_{89}ClF_3N_7O_{16}-H)^-$: 1350.5928, Found: 1350.5908.

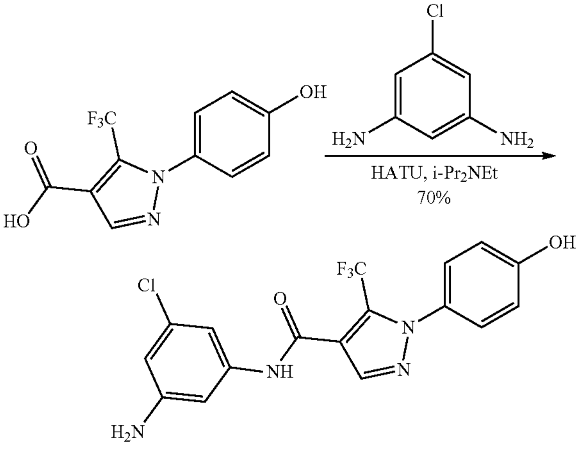

ZZY07-004

An oven-dried 20-mL vial was charged with 1-(4-hydroxyphenyl)-5-(trifluoromethyl)pyrazole-4-carboxylic acid (50 mg, 0.18 mmol), 5-Chloro-1,3-benzenediamine (131 mg, 0.92 mmol) and a magnetic stir bar. DMF (0.37 mL) was added and the mixture was stirred until all reactants had dissolved. N,N-Diisopropylethylamine (96 μL, 0.55 mmol) and HATU (91 mg, 0.24 mmol) were added sequentially. Stirring was continued and the reaction progress was monitored by LC-MS. In 8 h, LC-MS analysis showed full consumption of the starting material and formation of one major product and one minor product. The minor product had an m/z that matched a dimer (bis-acylation). The reaction mixture was diluted with 50% acetonitrile-water to a volume of 10.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (51 mg, 70%). $^1$H NMR (400 MHz, Methanol-$d_4$) δ 8.05 (s, 1H), 7.30 (d, J=8.8 Hz, 2H), 7.03-6.98 (m, 2H), 6.98-6.89 (m, 2H), 6.52 (t, J=1.9 Hz, 1H). HRMS (ESI): Calcd for $(C_{17}H_{12}ClF_3N_4O_2+H)^+$: 397.0679, Found: 397.0689.

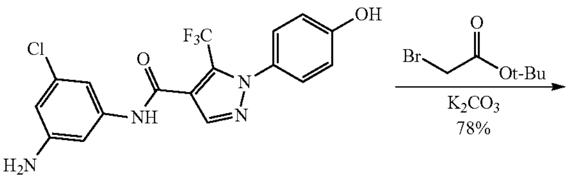

ZZY07-004

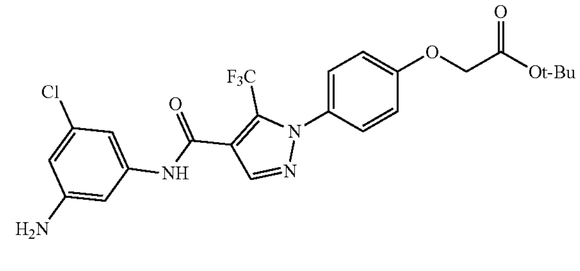

ZZY07-019

An oven-dried 1-dram vial was charged with N-(3-amino-5-chloro-phenyl)-1-(4-hydroxyphenyl)-5-(trifluoromethyl)pyrazole-4-carboxamide (30 mg, 0.076 mmol), Potassium carbonate (21 mg, 0.15 mmol), DMF (0.13 mL), and a magnetic stir bar. tert-Butyl bromoacetate (11 μL, 0.076 mmol) was added via pipette, and the resulting mixture was stirred at 23° C. In 16 h, LC-MS indicated that the starting material had been fully consumed and two products had formed. One had the desired m/z and the other seemed to be a bis-alkylation product. The reaction mixture was partitioned between saturated aqueous sodium bicarbonate solution (5 mL) and ethyl acetate (5 mL). The layers were separated, and the aqueous layer was extracted with ethyl acetate (2×5 mL). The combined organic layers were dried over sodium sulfate. The dried solution was filtered, and the filtrate was concentrated. The residue was purified by column chromatography (20-80% ethyl acetate-hexanes, 4-g RediSep® Rf column, Teledyne ISCO, Lincoln, Nebr.) to afford the product as a yellow powder (30 mg, 78%). $^1$H NMR (400 MHz, Chloroform-d) δ 7.96 (s, 1H), 7.51 (s, 1H), 7.40-7.32 (m, 2H), 7.10 (d, J=2.3 Hz, 1H), 7.04-6.94 (m, 2H), 6.79 (t, J=1.8 Hz, 1H), 6.47 (t, J=1.9 Hz, 1H), 4.58 (s, 2H), 3.83 (s, 2H), 1.49 (s, 9H). HRMS (ESI): Calcd for $(C_{23}H_{22}ClF_3N_4O_4+H)^+$: 511.1360, Found: 511.1376.

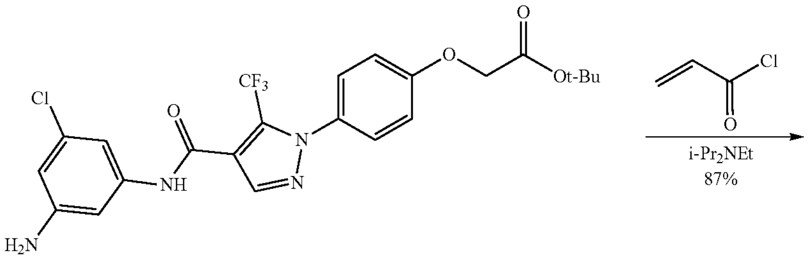

ZZY07-019

-continued

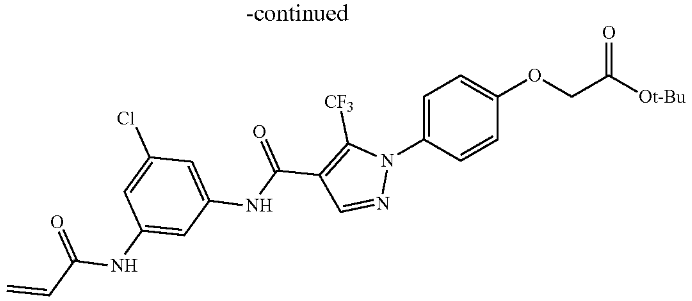

ZZY07-022

A solution of tert-butyl 2-[4-[4-[(3-amino-5-chloro-phenyl)carbamoyl]-5-(trifluoromethyl)pyrazol-1-yl]phenoxy] acetate (30 mg, 0.060 mmol) in dichloromethane (0.39 mL) was cooled to 0° C. Triethylamine (16.37 μL, 0.12 mmol) and Acryloyl chloride (5.7 μL, 0.071 mmol) were added sequentially via syringe. The resulting solution was stirred at 0° C. for 30 min, at which point TLC analysis (50% ethyl acetate-hexanes) indicated full conversion of the starting material to a slightly less polar spot. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-80% ethyl acetate-hexanes, 4-g RediSep® Rf column, Teledyne ISCO, Lincoln, Nebr.) to afford the product as a yellow powder (29 mg, 87%). $^1$H NMR (400 MHz, Chloroform-d) δ 8.81 (s, 1H), 8.33 (s, 1H), 7.94 (s, 1H), 7.82-7.75 (m, 1H), 7.38 (dt, J=11.3, 1.8 Hz, 2H), 7.27 (d, J=7.1 Hz, 1H), 7.00-6.88 (m, 2H), 6.32 (dd, J=16.9, 1.4 Hz, 1H), 6.18 (dd, J=16.9, 10.2 Hz, 1H), 5.68 (dd, J=10.1, 1.4 Hz, 1H), 4.55 (s, 2H), 1.48 (s, 9H). HRMS (ESI): Calcd for $(C_{26}H_{24}ClF_3N_4O_5+H)^+$: 565.1466, Found: 565.1466.

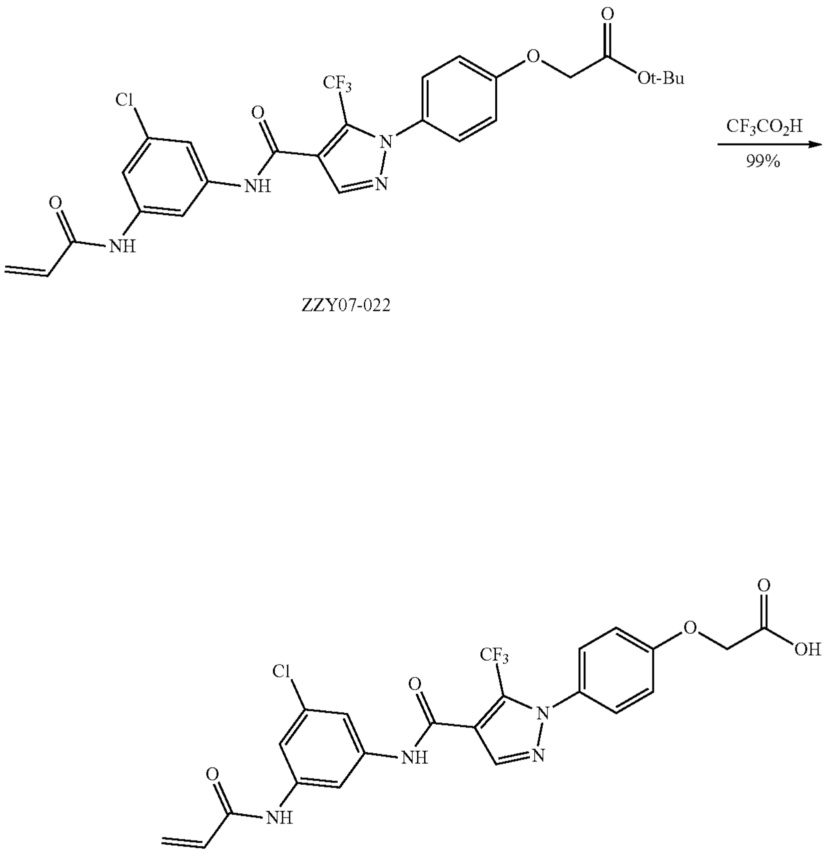

ZZY07-022

ZZY07-023 tert-Butyl 2-[4-[4-[[3-chloro-5-(prop-2-enoylamino)phenyl]carbamoyl]-5-(trifluoromethyl)pyrazol-1-yl]phenoxy] acetate (29 mg, 0.050 mmol) was dissolved in 1:1 dichloromethane (0.200 mL):trifluroacetic Acid (0.2000 mL) and the resulting solution was allowed to stand at 23° C. for 1 h. The solution was then concentrated to afford the product as a white solid (26 mg, 99%). HRMS (ESI): Calcd for $(C_{22}H_{16}ClF_3N_4O_5+H)^+$: 509.0840, Found: 509.0847.

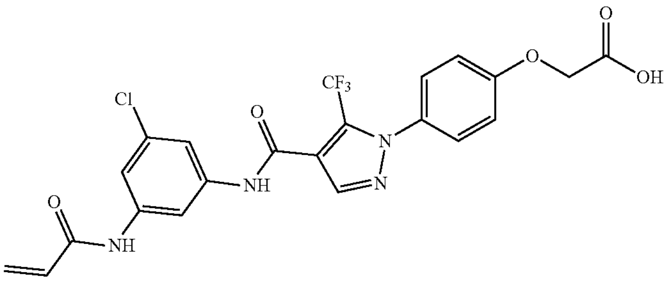

+

ZZY06-023

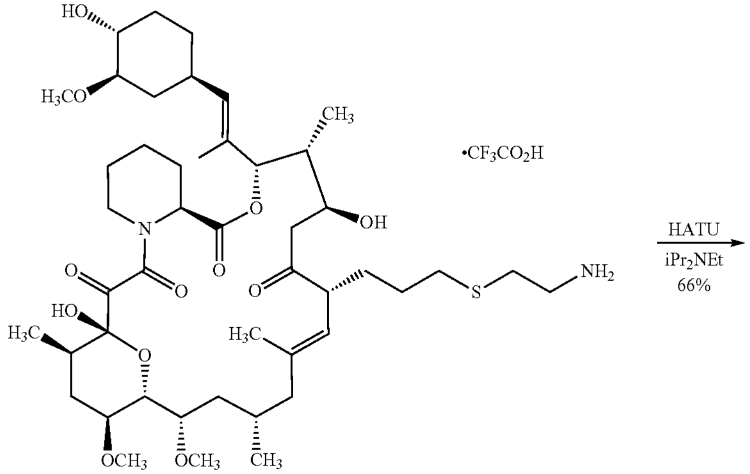

ZZY05-011

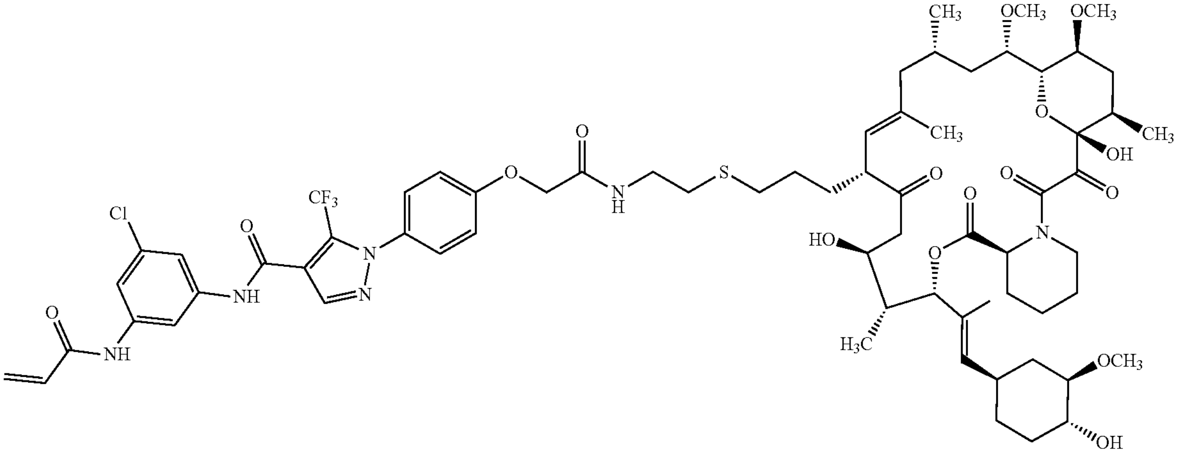

ZZY07-026

An oven-dried 1-dram vial was charged with ZZY06-023 (7.7 mg, 0.015 mmol), ZZY05-011 (15 mg, 0.015 mmol), DMF (0.11 mL), and a magnetic stir bar. N,N-Diisopropylethylamine (7.9 μL, 0.045 mmol) and HATU (6.9 mg, 0.018 mmol) were added sequentially, and the resulting solution was stirred at 23° C. Within 30 min, LC-MS analysis showed that the starting material (FK506-amine) was fully consumed. The residue was diluted with 1:1:1 methanol-acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (13.7 mg, 66%). $^1$H NMR (400 MHz, Chloroform-d) δ 8.37 (s, 1H), 8.07-7.99 (m, 1H), 7.65 (s, 1H), 7.59 (s, 1H), 7.45 (d, J=8.8 Hz, 2H), 7.09 (d, J=8.9 Hz, 2H), 6.47 (dd, J=16.8, 1.3 Hz, 1H), 6.28 (dd, J=16.8, 10.3 Hz, 1H), 5.81 (d, J=9.9 Hz, 1H), 5.32 (s, 1H), 5.11-4.97

(m, 2H), 4.66-4.62 (m, 3H), 4.43 (d, J=13.3 Hz, 1H), 4.22 (s, 1H), 3.95-3.85 (m, 2H), 3.68 (d, J=9.4 Hz, 1H), 3.64-3.51 (m, 4H), 3.42 (s, 3H), 3.41 (s, 3H), 3.41-3.37 (m, 3H), 3.32 (s, 3H), 3.08-2.98 (m, 2H), 2.70 (app t, J=6.4 Hz, 4H), 2.43 (d, J=7.0 Hz, 1H), 2.38-2.24 (m, 2H), 2.24-2.13 (m, 3H), 2.12-1.86 (m, 5H), 1.85-1.68 (m, 6H), 1.66-1.54 (m, 6H), 1.53-1.25 (m, 8H), 1.10-1.03 (m, 2H), 1.00 (d, J=6.3 Hz, 3H), 0.96 (d, J=6.2 Hz, 3H), 0.88 (d, J=7.1 Hz, 3H). HRMS (ESI): Calcd for $(C_{68}H_{90}ClF_3N_6O_{16}S-H)^-$: 1369.5697, Found: 1369.5664.
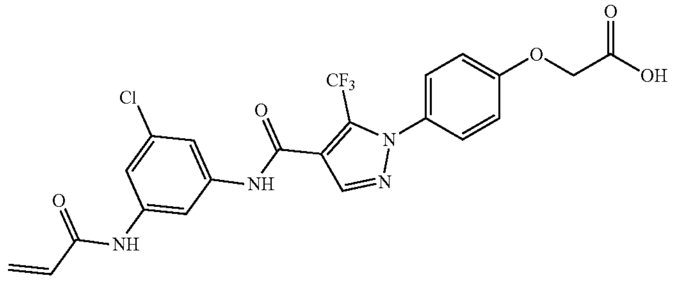
ZZY06-023
+
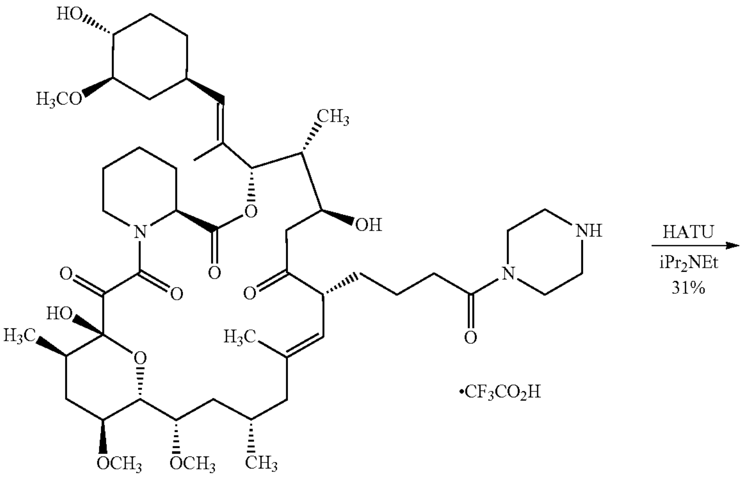
ZZY07-061
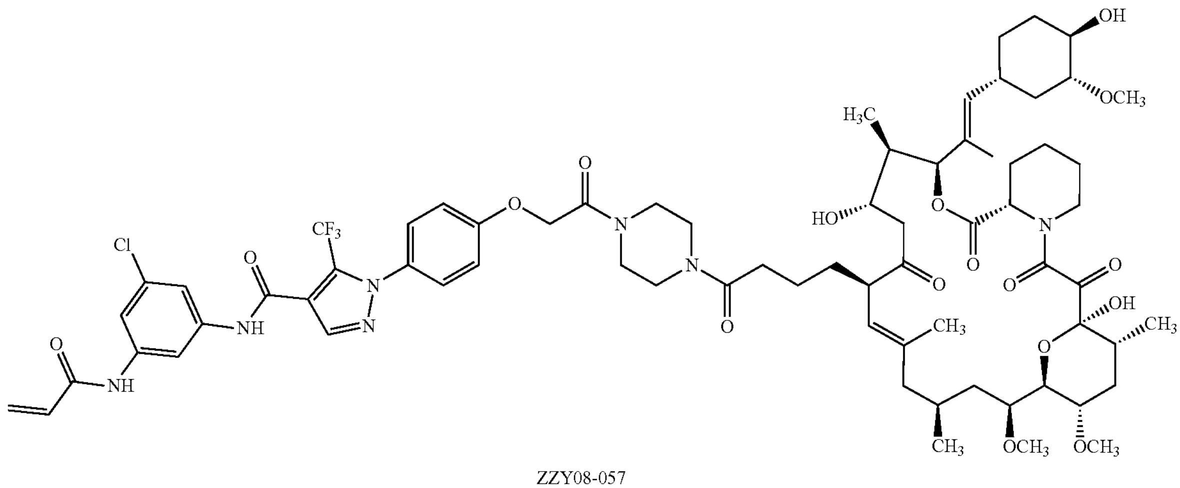
ZZY08-057

An oven-dried 1-dram vial was charged with ZZY06-023 (5.4 mg, 0.011 mmol) and ZZY07-061 (10 mg, 0.010 mmol), DMF (0.20 mL) and magnetic stir bar. N,N-Diisopropylethylamine (8.4 μL, 0.048 mmol) and HATU (4.4 mg, 0.012 mmol) were added sequentially to the solution, and the mixture was stirred at 23° C. while the reaction progress was monitored by LC-MS. In 1 h, LC-MS analysis showed full consumption of the FK506 starting material. The residue was diluted with 50% acetonitrile-water to a volume of 4.4 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (4.3 mg, 31%). $^1H$ NMR (400 MHz, Chloroform-d) δ 7.99 (s, 1H), 7.94-7.80 (m, 1H), 7.61-7.47 (m, 2H), 7.43-7.34 (m, 2H), 7.12-7.04 (m, 2H), 6.45 (d, J=16.9 Hz, 1H), 6.29-6.18 (m, 1H), 5.81 (d, J=10.4 Hz, 1H), 5.35 (s, 1H), 5.15-4.94 (m, 2H), 4.84-4.77 (m, 3H), 4.45-4.31 (m, 1H), 3.99-3.77 (m, 2H), 3.72-3.53 (m, 10H), 3.41 (s, 3H), 3.37 (s, 3H), 3.35-3.31 (m, 3H), 3.30 (s, 3H), 3.05-2.97 (m, 2H), 2.84-2.63 (m, 1H), 2.42-2.20 (m, 5H), 2.01 (d, 5H), 1.67 (s, 6H), 1.61-1.52 (m, 6H), 1.51-1.26 (m, 8H), 1.10-1.01 (m, 2H), 1.00 (d, J=6.3 Hz, 3H), 0.93 (d, J=6.8 Hz, 3H), 0.85 (d, J=7.1 Hz, 3H). HRMS (ESI): Calcd for $(C_{71}H_{93}ClF_3N_7O_{17}+H)^+$: 1408.6347, Found: 1408.6415.

Cyclosporin Derivatives.

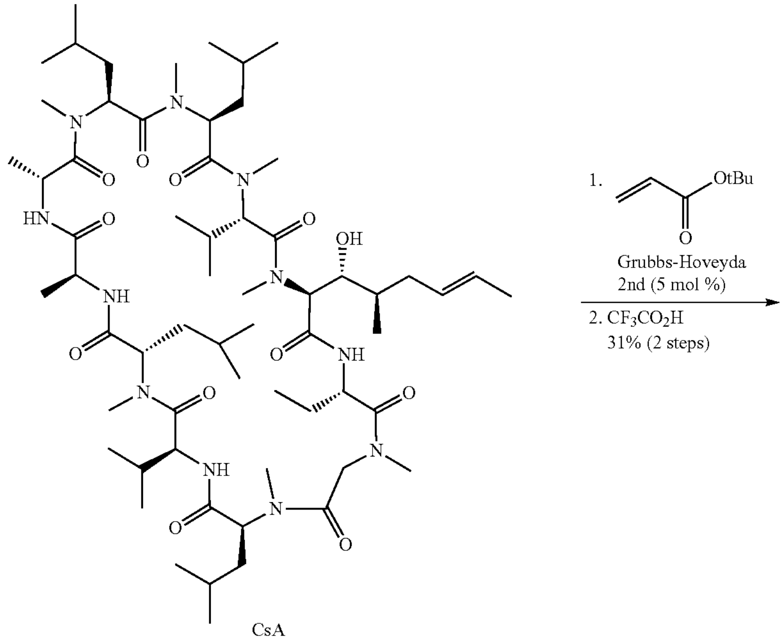

CsA

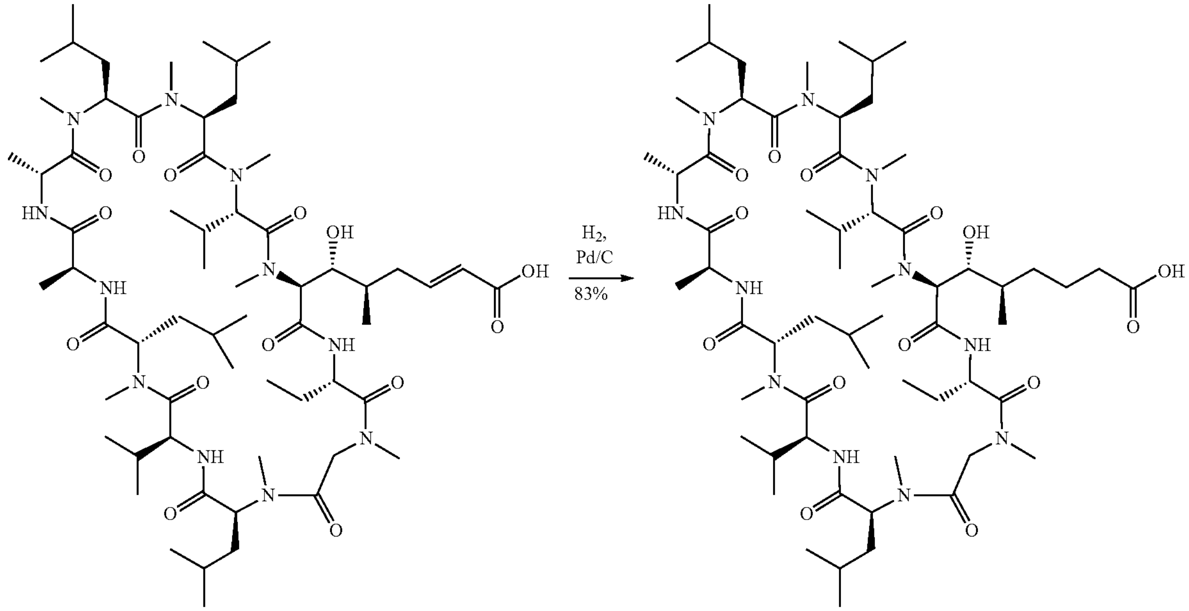

ZZY06-058

ZZY06-067

A flame-dried 10-mL microwave vial was flushed with dry argon, and then was charged with cyclosporin A (100 mg, 0.083 mmol), 1,2-dichloroethane (1.24 mL), and a magnetic stir bar. tert-Butyl acrylate (0.24 mL, 1.66 mmol) and Grubbs-Hoveyda Catalyst 2nd Gen (3.5 mg, 0.042 mmol) were added sequentially. The vial was flushed with argon again and sealed with a rubber cap. The reaction mixture was heated at 70° C. for 1 h in a CEM Discover SP microwave reactor with constant stirring. After cooling to 23° C., LC-MS analysis showed ~50% conversion to the desired product mass. The vial was returned to the micro wave reactor and heated for an additional 3 h at 70° C. The reaction mixture was cooled to 23° C. and directly loaded onto a silica gel cartridge (~4 g). Purification by column chromatography (0-20% methanol-dichloromethane, 4-g RediSep Rf Column, Teledyne ISCO, Lincoln, Nebr.) afforded the product as a brown solid. The purity of this material was ~80% by $^1$H NMR analysis.

Trifluoroacetic acid (0.5 mL) was added to a solution of the product from the cross-metathesis reaction in dichloromethane (0.5 mL). In 1 h, LC-MS analysis showed full consumption of the tert-butyl ester starting material (m/z=1288). The reaction mixture was concentrated under vacuum. The residue was diluted with 50% acetonitrile-water to a volume of 4.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (31 mg, 31% over 2 steps).

A 100-mL round bottom flask was charged with ZZY06-058 (412 mg, 0.33 mmol), 1:1 Ethyl acetate (6.6 mL): methanol (6.6 mL) and a magnetic stir bar. Argon was bubbled through the solution for 5 min, then Palladium on carbon (10 wt %, 71 mg, 0.033 mmol) was added. The vessel was fitted with a rubber septum and a hydrogen balloon was attached via a 19-gauge needle. An additional needle was attached to allow a gentle flow of hydrogen to bubble through the solution at a continuous rate. At 3 h, LC-MS could no longer detect any starting material. The hydrogen balloon was switched to one filled with argon, and bubbling was continued for 5 min. The reaction mixture was then filtered through a tightly packed plug of Celite (~2 g). Concentration of the filtrate afforded a colorless glass. The material was purified by reverse-phase HPLC in multiple batches with the following procedure. The residue was divided into batches and dissolved in 50% methanol-water (100 mg in 5 mL, 150 mg in 8 mL, then 150 mg in 8 mL), and the solutions were filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) in batches, and the product-containing fractions were pooled to afford the product as a white solid (343 mg, 83%). $^1$H NMR (400 MHz, Chloroform-d) δ 7.99 (d, J=9.2 Hz, 1H), 7.63 (d, J=7.5 Hz, 1H), 5.68 (dd, J=11.0, 4.1 Hz, 1H), 5.39 (d, J=7.3 Hz, 1H), 5.31-5.23 (m, 1H), 5.17-5.05 (m, 3H), 5.00 (q, J=7.5 Hz, 1H), 4.88-4.81 (m, 1H), (d, J=14.3 Hz, 1H), 4.63 (t, J=8.8 Hz, 1H), 4.51 (dt, J=14.6, 7.5 Hz, 1H), 3.87 (t, J=6.3 Hz, 1H), 3.42 (s, 3H), 3.40-3.35 (m, 4H), 3.30 (d, J=11.8 Hz, 1H), 3.23 (s, 3H), 3.19 (s, 3H), 3.18 (d, J=17.2 Hz, 1H), 3.09 (s, 3H), 2.87 (d, J=17.6 Hz, 1H), 2.78-2.68 (m, 1H), 2.69 (s, 3H), 2.67 (s, 3H), 2.48-2.30 (m, 2H), 2.23 (t, J=6.9 Hz, 2H), 2.22-1.87 (m, 5H), 1.80-1.37 (m, 13H), 1.34 (d, J=7.3 Hz, 3H), 1.26 (d, J=6.9 Hz, 3H), 1.24-1.12 (m, 3H), 1.07-0.79 (m, 39H, 13 methyl doublets). HRMS (ESI): Calcd for $(C_{62}H_{111}N_{11}O_{14}—H)^+$: 1232.8234, Found: 1232.8215

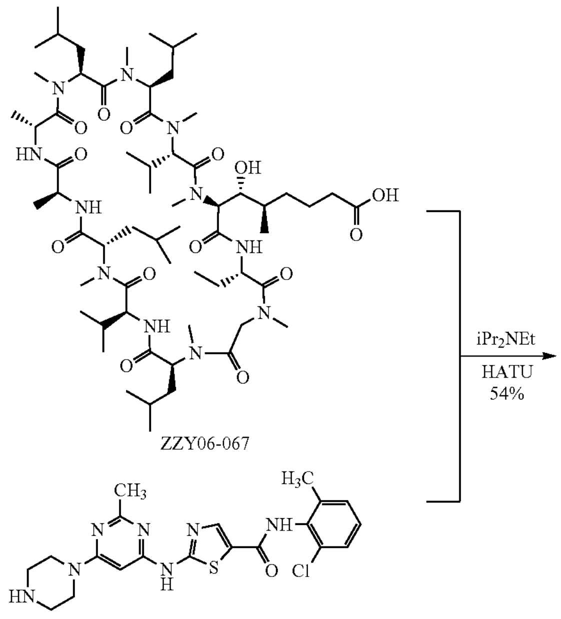

ZZY06-067

Des(hydroxyethyl) dasatinib

-continued

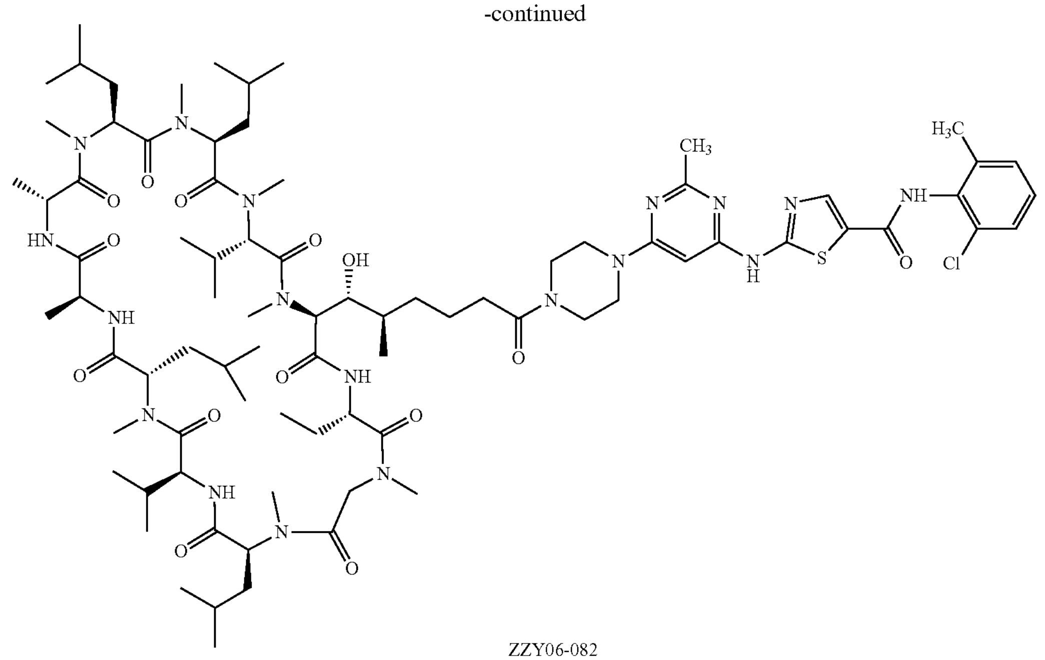

ZZY06-082

A 1-dram vial was charged with Cyclosporin C4 Acid (20 mg, 0.016 mmol), des(hydroxyethyl)dasatinib (7.9 mg, 0.018 mmol), DMF (0.20 mL), N,N-Diisopropylethylamine (8.5 μL, 0.049 mmol) and a magnetic stir bar. The solution was cooled to 0° C., then HATU (7.4 mg, 0.019 mmol) was added as a solid. The resulting mixture was stirred at 0° C. In 30 min, LC-MS analysis indicated that the starting material had been fully consumed. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (14.5 mg, 54%). $^1$H NMR spectrum of this compound contains at least three conformational isomers and cannot be resolved. HRMS (ESI): Calcd for $(C_{82}H_{131}ClN_{18}O_{14}S+2H)^{2+}$: 830.4789, Found: 830.4791.

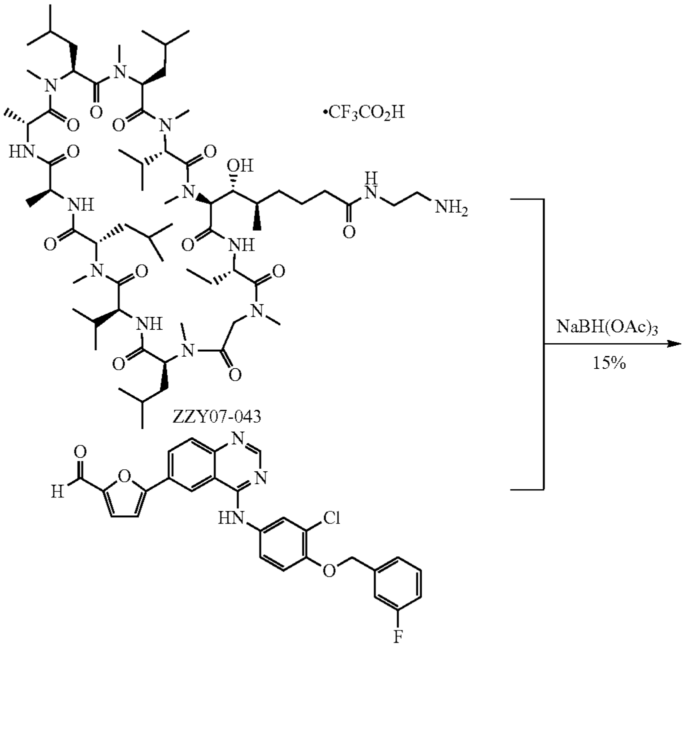

-continued

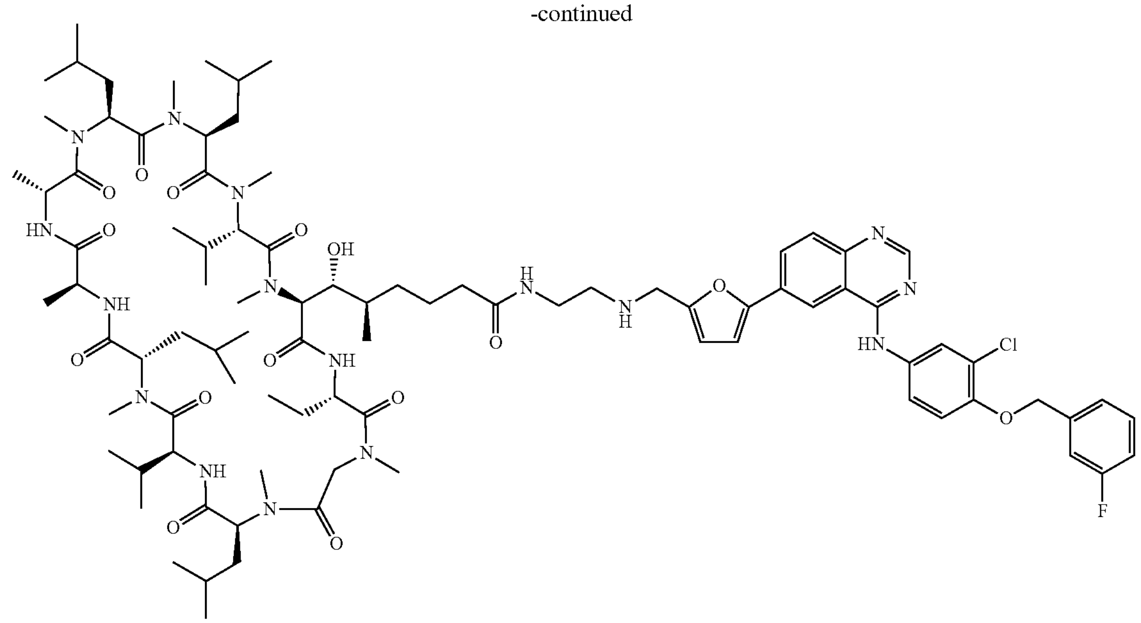

ZZY07-058

An oven-dried 1-dram vial was charged with ZZY07-043 (15 mg, 0.011 mmol), Lapatinib aldehyde (5.0 mg, 0.011 mmol), dichloromethane (0.11 mL) and a magnetic stir bar. Sodium triacetoxyborohydride (4.5 mg, 0.021 mmol) was added as a solid. In about 5 min, all the solids had gone into solution. The reaction mixture was kept stirred for a total of 2 h, at which point LC-MS still showed presence of both starting materials. Additional sodium triacetoxyborohydride (4.5 mg, 0.021 mmol) was added. In a total of 6 h, LC-MS showed full consumption of the amine starting material. The reaction solution was concentrated to dryness until vacuum. The residue was diluted with 50% acetonitrile-water to a volume of 3.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (2.7 mg, 15%). $^1$H NMR spectrum of this compound contains at least three conformational isomers and cannot be resolved. HRMS (ESI): Calcd for $(C_{90}H_{134}ClFN_{16}O_{15}+2H)^{2+}$: 867.5021, Found: 867.5022.

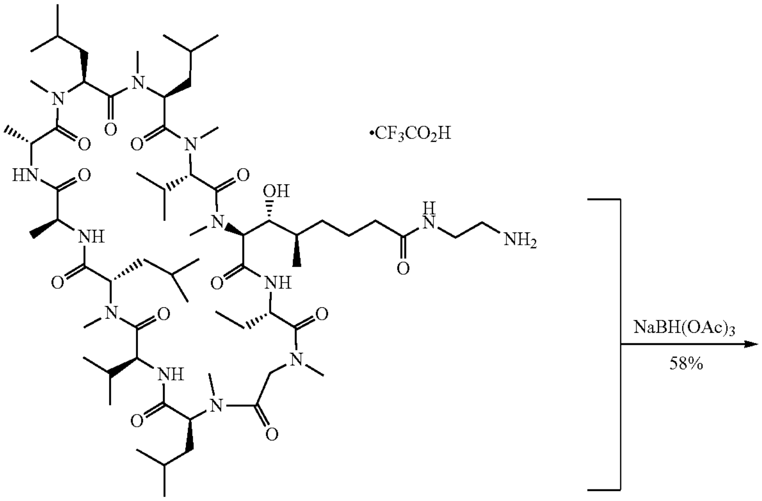

ZZY07-043

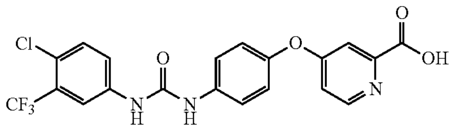

-continued

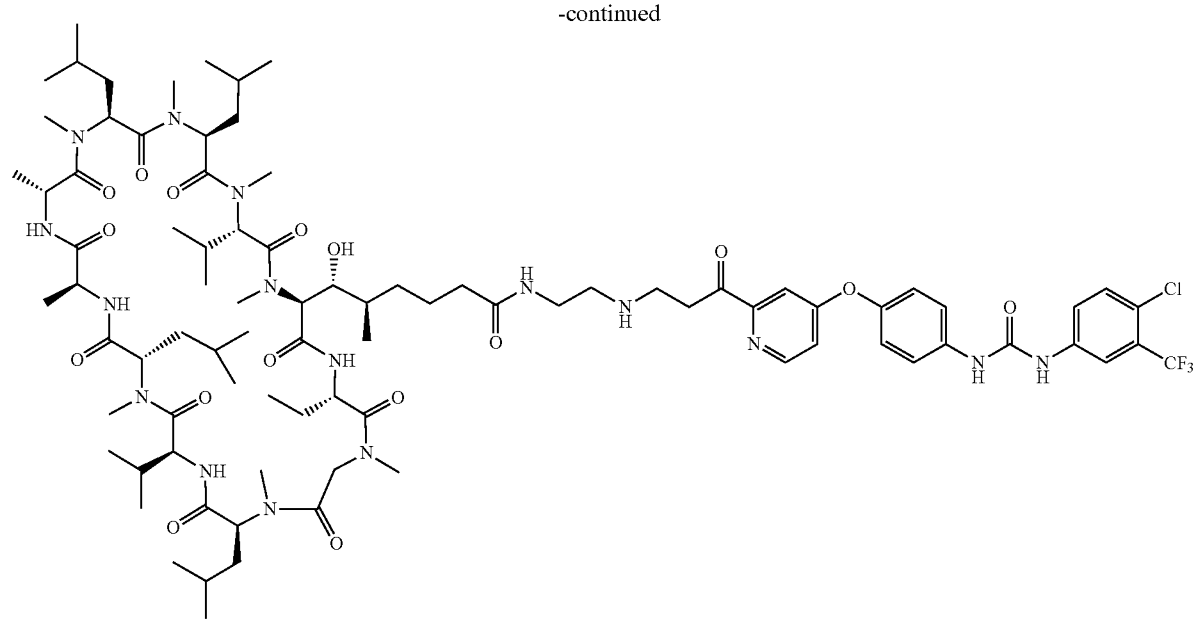

ZZY06-083

A 1-dram vial was charged with ZZY07-043 (20 mg, 0.016 mmol), sorafenib acid (11 mg, 0.018 mmol), DMF (0.20 mL), N,N-Diisopropylethylamine (8.5 μL, 0.048 mmol) and a magnetic stir bar. The solution was cooled to 0° C., then HATU (7.4 mg, 0.019 mmol) was added as a solid. The resulting mixture was stirred at 0° C. and the reaction progress was monitored by LC-MS. In 30 min, LC-MS analysis indicated that the starting material had been fully consumed. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (16.2 mg, 58%). $^1$H NMR spectrum of this compound contains at least three conformational isomers and cannot be resolved. HRMS (ESI): Calcd for $(C_{84}H_{128}ClF_3N_{16}O_{16}+2H)^+$: 855.4746, Found: 855.4745.

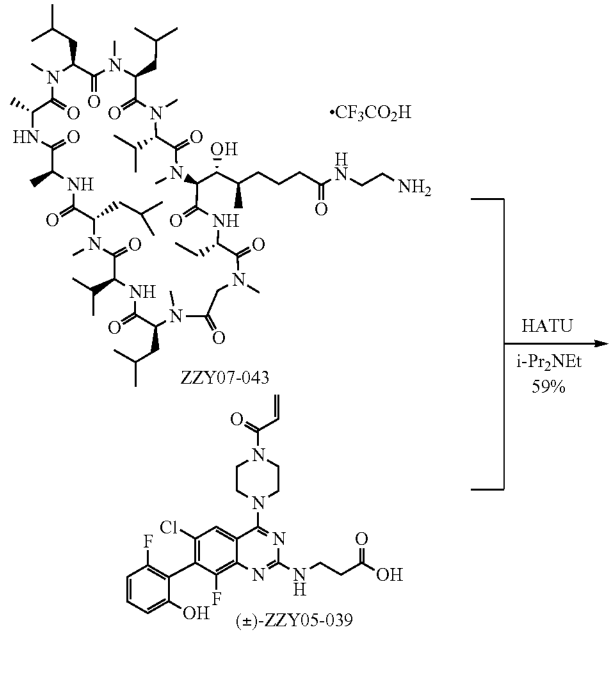

-continued

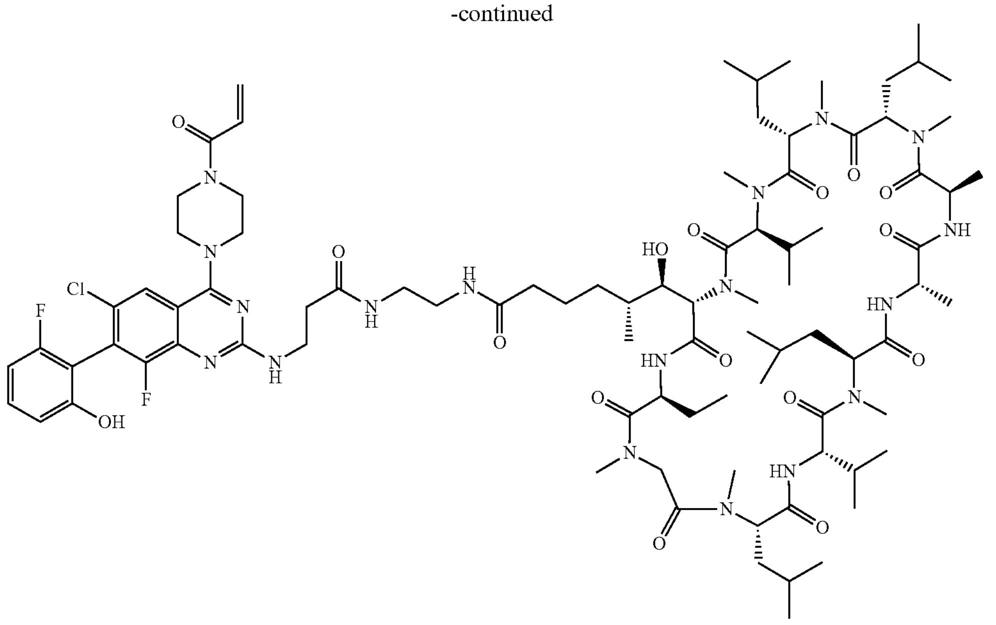

ZZY07-014

An oven dried one-dram vial was charged with ZZY07-043 (10 mg, 0.076 mmol), ZZY05-039 (4.3 mg, 0.083 mmol), DMF (0.10 mL), and a magnetic stir bar. N,N-Diisopropylethylamine (4.0 μL, 0.023 mmol) and HATU (4.3 mg, 0.011 mmol) were added sequentially to the reaction mixture at 23° C. In 40 min, LC-MS analysis showed 100% conversion. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white powder (7.9 mg, 58%). HRMS (ESI): Calcd for $(C_{88}H_{137}ClF_2N_{18}O_{16}+2H)^+$: 888.5136, Found: 888.5137.

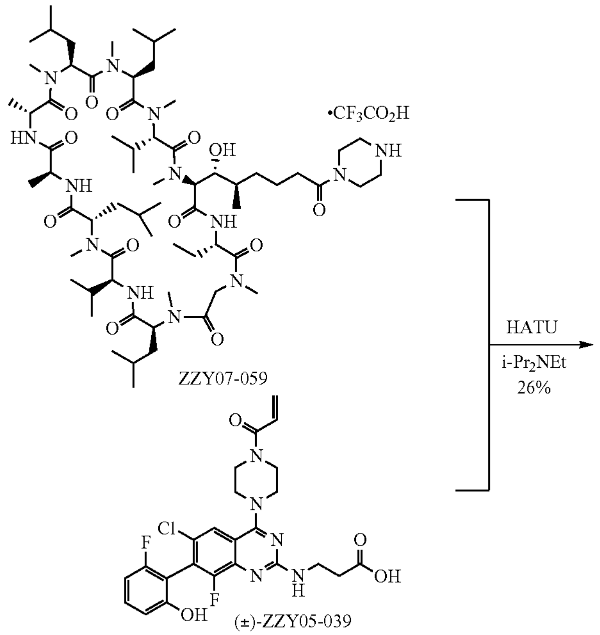

ZZY07-059

(±)-ZZY05-039

-continued

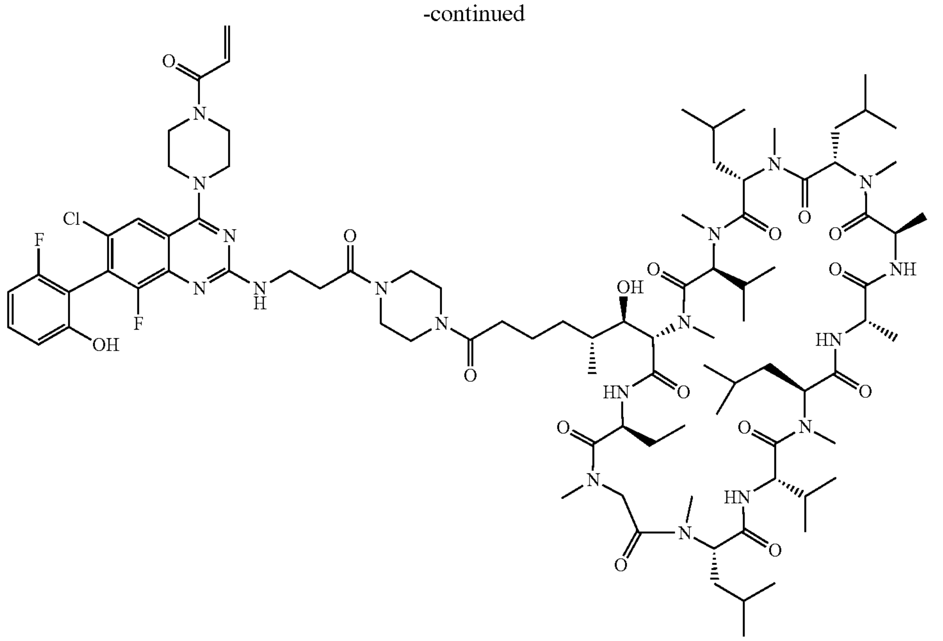

ZZY07-089

An oven dried one-dram vial was charged with ZZY07-059 (10 mg, 0.071 mmol), ZZY05-039 (4.0 mg, 0.078 mmol), DMF (0.10 mL), and a magnetic stir bar. N,N-Diisopropylethylamine (3.7 μL, 0.023 mmol) and HATU (3.0 mg, 0.011 mmol) were added sequentially to the reaction mixture at 23° C. In 1 h, LC-MS analysis showed full consumption of the starting material. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white powder (3.3 mg, 26%). HRMS (ESI): Calcd for $(C_{90}H_{139}ClF_2N_{18}O_{16}+2H)^+$: 901.5214, Found: 901.5244.

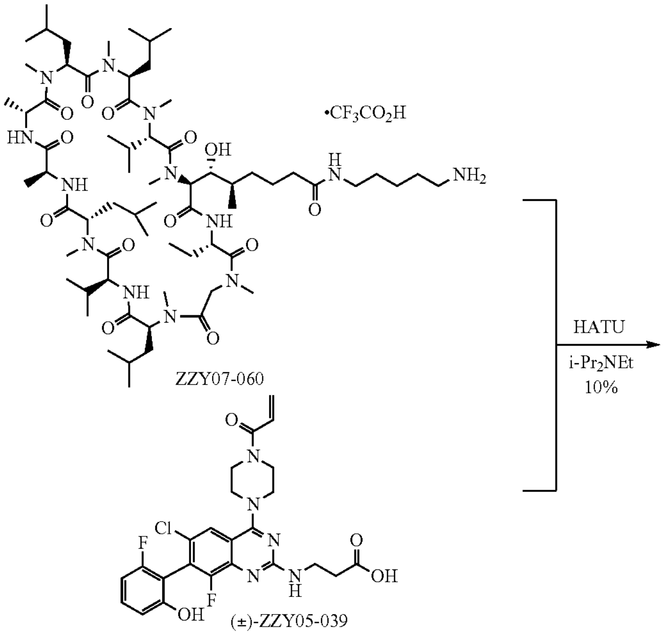

ZZY07-060

(±)-ZZY05-039

-continued

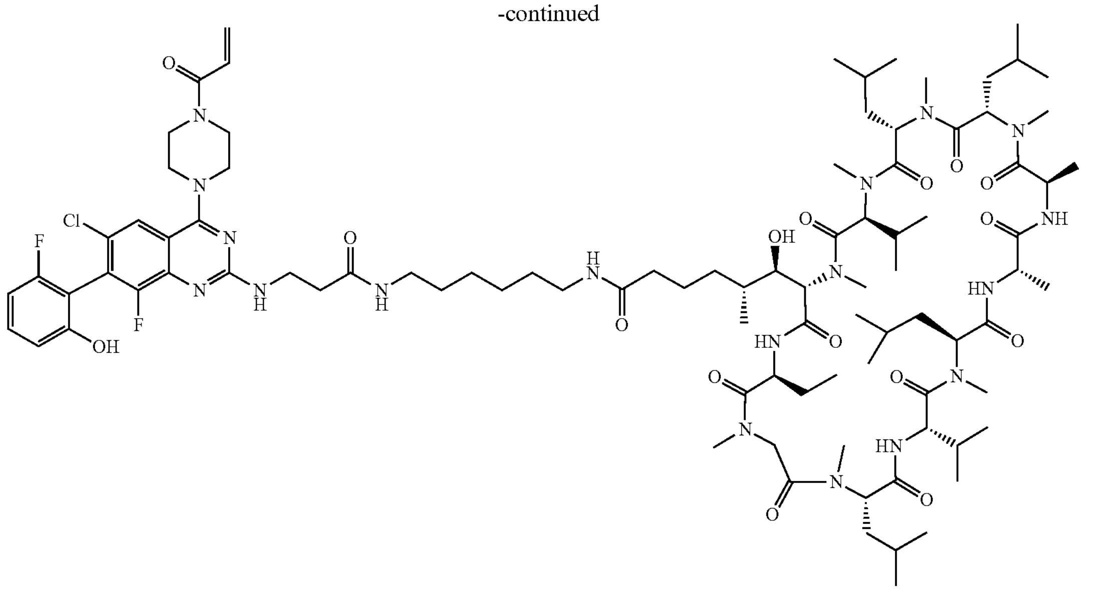

ZZY07-090

An oven dried one-dram vial was charged with ZZY07-060 (10 mg, 0.071 mmol), ZZY05-039 (4.0 mg, 0.078 mmol), DMF (0.10 mL), and a magnetic stir bar. N,N-Diisopropylethylamine (3.7 μL, 0.023 mmol) and HATU (3.0 mg, 0.011 mmol) were added sequentially to the reaction mixture at 23° C. In 1 h, LC-MS analysis showed full consumption of the starting material. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white powder (1.3 mg, 10%). HRMS (ESI): Calcd for $(C_{92}H_{145}ClF_2N_{18}O_{16}+2H)^+$: 916.5450, Found: 916.5455.

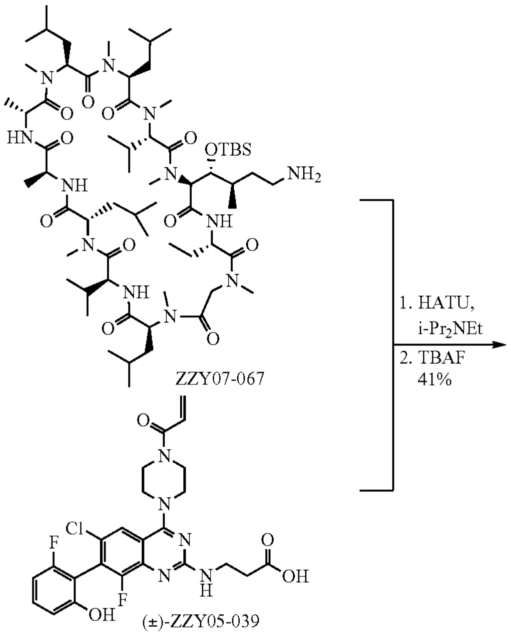

ZZY07-067

(±)-ZZY05-039

-continued

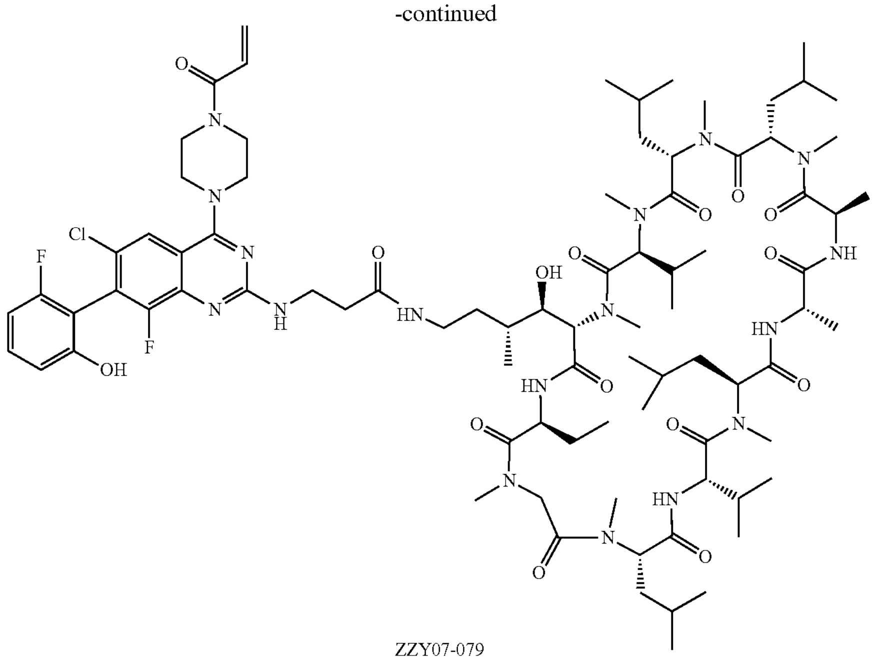

ZZY07-079

A 1-dram vial was charged with ZZY07-067 (7.0 mg, 0.0054 mmol), ZZY05-039 (3.3 mg, 0.0064 mmol) and a magnetic stir bar. DMF (0.10 mL) and N,N-Diisopropylethylamine (4.7 μL, 0.027 mmol) were added sequentially via pipette. HATU (2.5 mg, 0.0064 mmol) was added as a freshly prepared 10% w/v DMF solution via pipette. The resulting solution was stirred at 23° C. and the reaction progress was monitored by LC-MS. In 12 h, LC-MS analysis showed full consumption of the amine starting material and formation of a new species. The reaction mixture was diluted with 0.1 mL THF, and a 1.0 M 6 solution of tetra-n-butylammonium fluoride in THF (27 μL, 0.027 mmol) was added 7 dropwise via syringe. In 2 h, LC-MS showed full deprotection of the TBS group. The 8 residue was diluted with 50% acetonitrile-water to a volume of 3.9 mL, and the solution was 9 filtered through a 0.45 μM PTFE syringe filter. The filtrate was purified by reverse-phase HPLC (Waters XBridge C18 column 5 μm particle size 30×250 mm, 50-95% acetonitrile-water+0.1% formic acid, 40 min, 20 mL/min) to afford the product as a white solid (3.7 mg, 41%). HRMS (ESI): Calcd for $(C_{84}H_{130}ClF_2N_{17}O_{15}-H)^-$: 1688.9511, Found: 1688.9529.

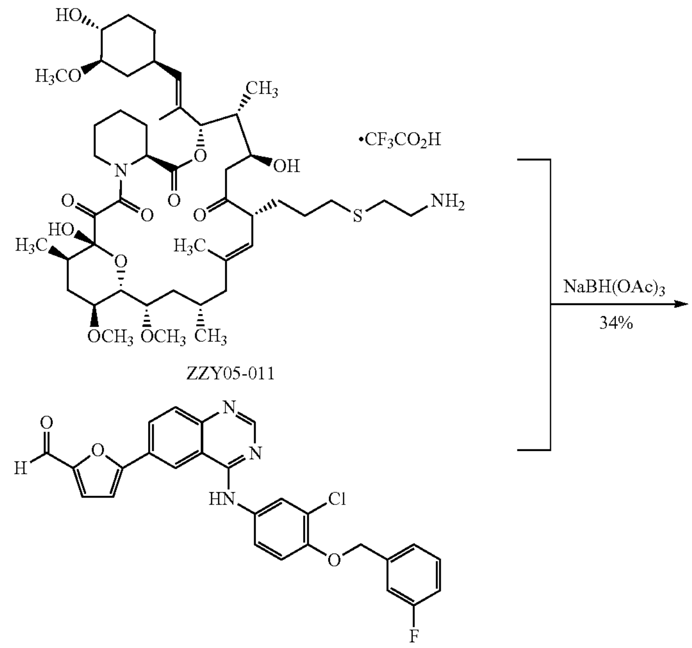

-continued

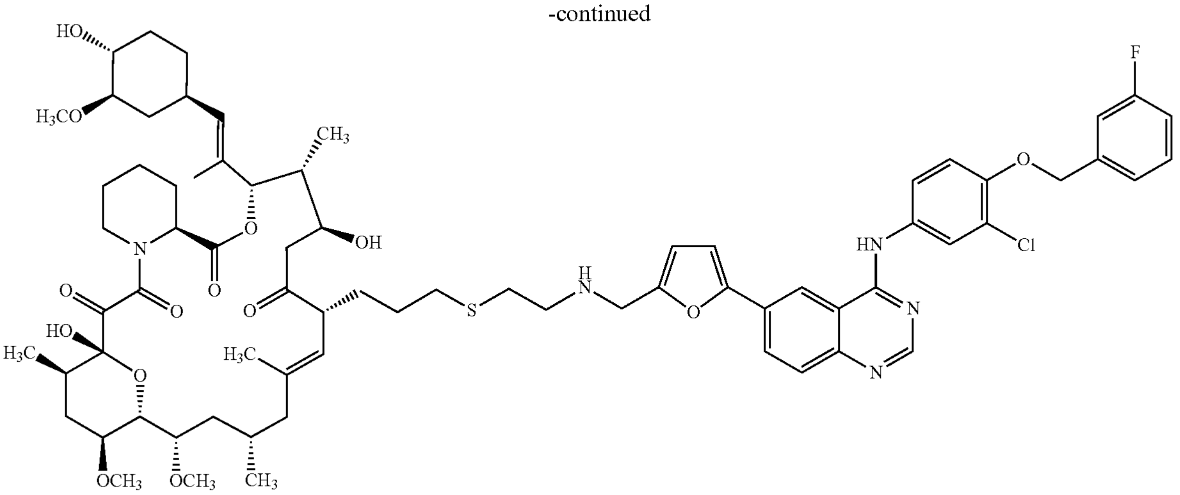

ZZY07-057

An oven-dried one-dram vial was charged with ZZY05-011 (10.5 mg, 0.0106 mmol), Lapatinib aldehyde (5.0 mg, 0.0106 mmol) and a magnetic stir bar. DCM (0.11 mL) was added via syringe. The resulting mixture was stirred at 23° C. for 10 min. The aldehyde reactant did not fully dissolve. Sodium triacetoxyborohydride (4.5 mg, 0.0211 mmol) was added as a solid. In about 5 min, all the solids had gone into solution. The reaction mixture was kept stirred for a total of 2 h, at which point no starting material amine could be detected. The reaction solution was concentrated to dryness under vacuum. The residue was diluted with 50% acetonitrile-water to a volume of 3.5 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (4.8 mg, 34%). HRMS (ESI): Calcd for $(C_{72}H_{93}ClFN_5O_{14}S+2H)^{2+}$: 669.8134, Found: 669.7951.

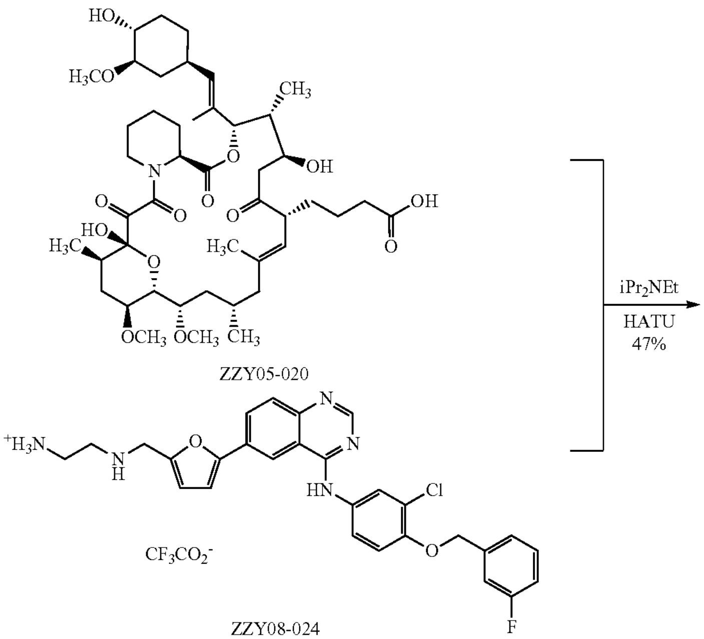

ZZY05-020

ZZY08-024

-continued

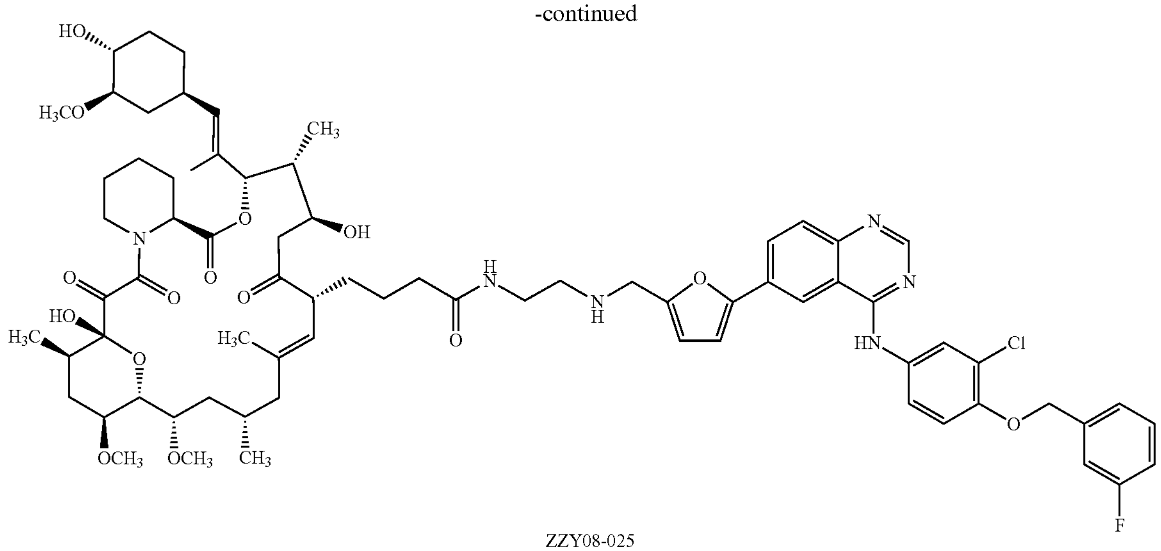

ZZY08-025

An oven-dried 1-dram vial was charged ZZY05-020 (20 mg, 0.024 mmol), ZZY08-024 (15 mg, 0.024 mmol), DMF (0.12 mL) and a magnetic stir bar. N,N-Diisopropylethylamine (12.3 μL, 0.071 mmol) was added and the mixture was stirred until all reactants had gone into solution. HATU (10.7 mg, 0.0282 mmol) was added as a 10% solution in DMF. The resulting solution was stirred at 23° C. and the reaction progress was monitored by LC-MS. In 15 min, LC-MS showed full consumption of the amine starting material. The reaction mixture was diluted with 50% acetonitrile-water to a volume of 4.2 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a yellow solid (15 mg, 47%). HRMS (ESI): Calcd for $(C_{73}H_{94}ClFN_6O_{15}+2H)^{2+}$: 675.3303, Found: 675.3334.

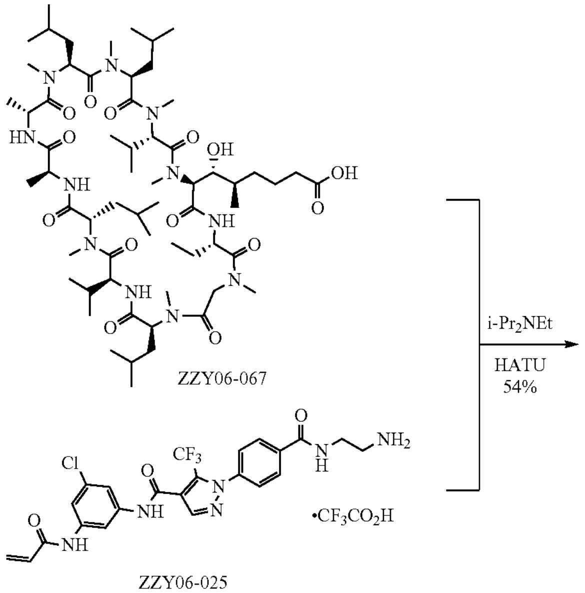

ZZY06-067

ZZY06-025

-continued

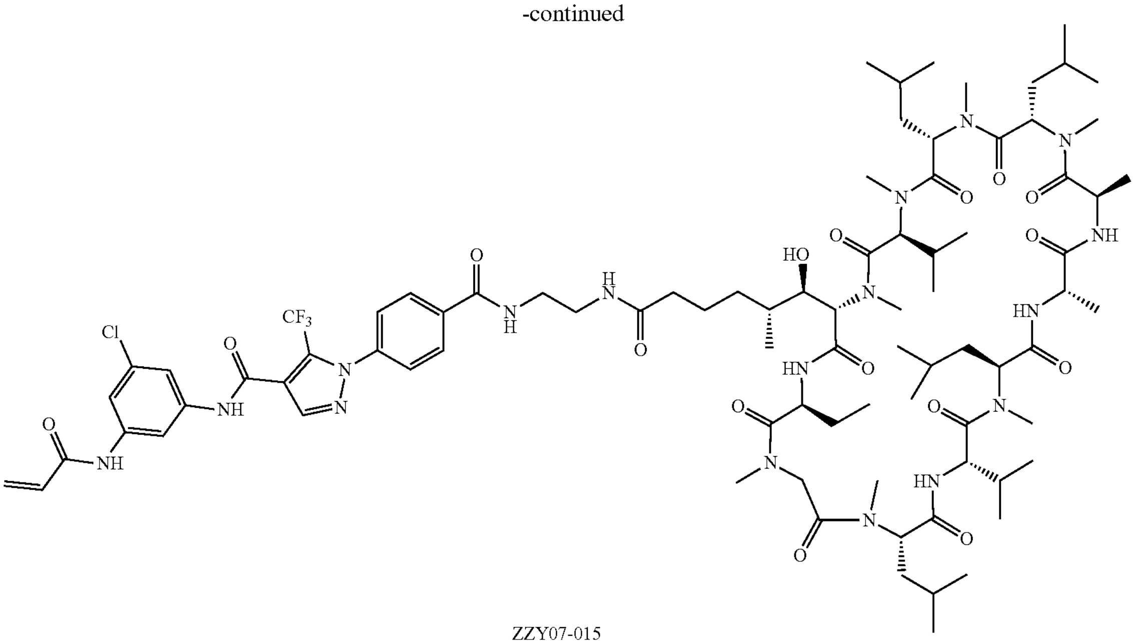

ZZY07-015

An oven-dried 1-dram vial was charged ZZY06-067 (19.5 mg, 0.016 mmol), ZZY06-025 (10 mg, 0.016 mmol), DMF (0.10 mL) and a magnetic stir bar. N,N-Diisopropylethylamine (8.2 μL, 0.047 mmol) and HATU (7.8 mg, 0.020 mmol) were added sequentially to the reaction mixture at 23° C. In 2 h, LC-MS showed full conversion of the starting material. The reaction mixture was diluted with 50% acetonitrile-water to a volume of 5.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (13.6 mg, 54%). HRMS (ESI): Calcd for $(C_{85}H_{129}ClF_3N_{17}O_{16}-H)^-$: 1734.9366, Found: 1734.9539.

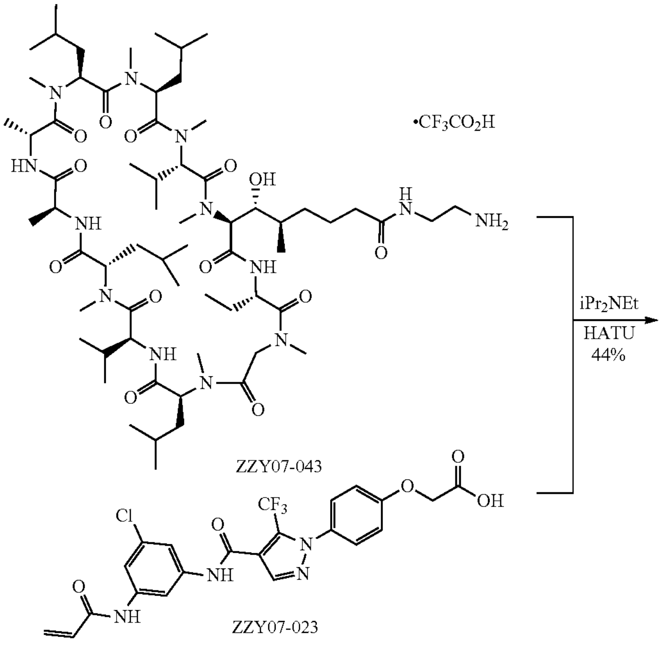

ZZY07-043

ZZY07-023

-continued

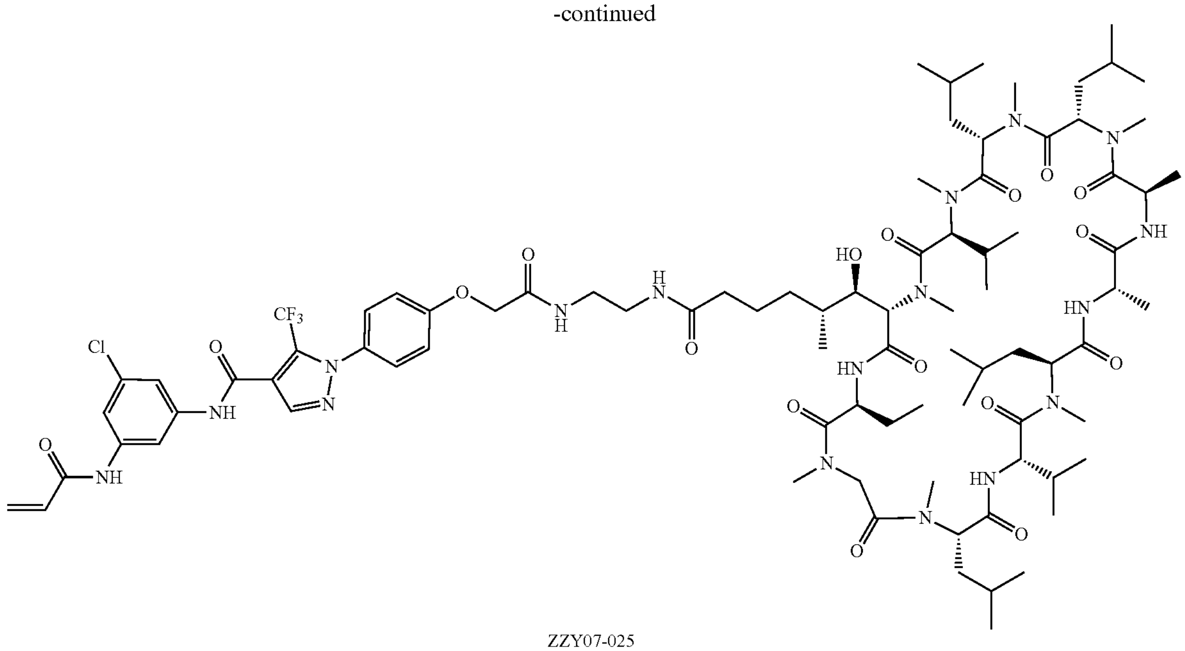

ZZY07-025

An oven-dried 1-dram vial was charged ZZY07-043 (15 mg, 0.011 mmol), ZZY07-023 (5.7 mg, 0.011 mmol), DMF (0.11 mL) and a magnetic stir bar. N,N-Diisopropylethylamine (5.9 µL, 0.034 mmol) and HATU (5.2 mg, 0.014 mmol) were added sequentially to the reaction mixture at 23° C. In 2 h, LC-MS showed full conversion of the starting material. The reaction mixture was diluted with 50% acetonitrile-water to a volume of 5.0 mL, and the solution was filtered through a 0.45 µM PTFE syringe filter. The filtrate was purified by reverse-phase HPLC (Waters XBridge C18 column 5 µm particle size 30×250 mm, 5-95% acetonitrile-water+0.1% formic acid, 40 min, 20 mL/min) to afford the product as a white solid (8.9 mg, 44%). HRMS (ESI): Calcd for $(C_{86}H_{131}ClF_3N_{17}O_{17}-H)^-$: 1764.9471, Found: 1764.9409.

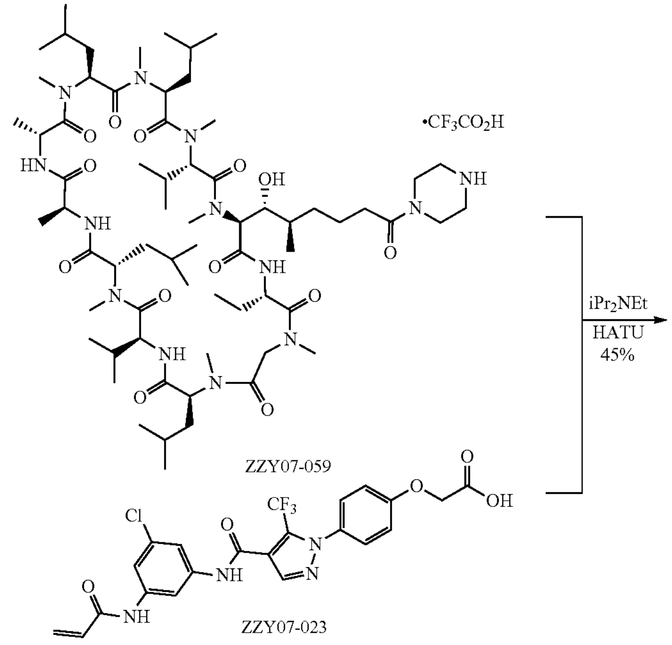

ZZY07-059

ZZY07-023

-continued

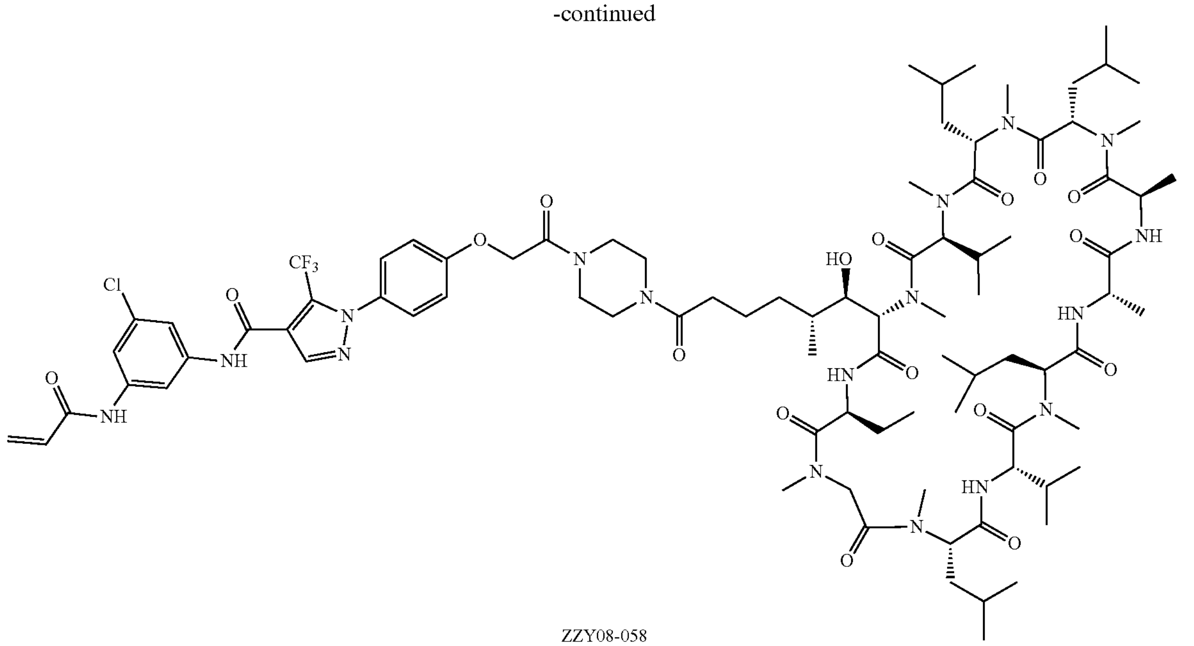

ZZY08-058

A mixture of ZZY07-059 (12 mg, 0.0085 mmol) and ZZY07-023 (4.7 mg, 0.0093 mmol) was dried by azeotropic evaporation of their suspension in benzene (1 mL). The residue was dissolved in DMF (0.20 mL). N,N-Diisopropylethylamine (8.4 μL, 0.048 mmol) and HATU (3.5 mg, 0.0093 mmol) were added sequentially to the solution, and the mixture was stirred at 23° C. while the reaction progress was monitored by LC-MS. In 1 h, LC-MS showed full consumption of the 07-059 starting material. The residue was diluted with 50% acetonitrile-water to a volume of 4.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (6.9 mg, 45%). HRMS (ESI): Calcd for $(C_{88}H_{133}ClF_3N_{17}O_{17}+2H)^{2+}$: 896.9931, Found: 896.9883.

Example 7: Blocker Compounds in Combination with mTOR Inhibitors

Figure 61A:
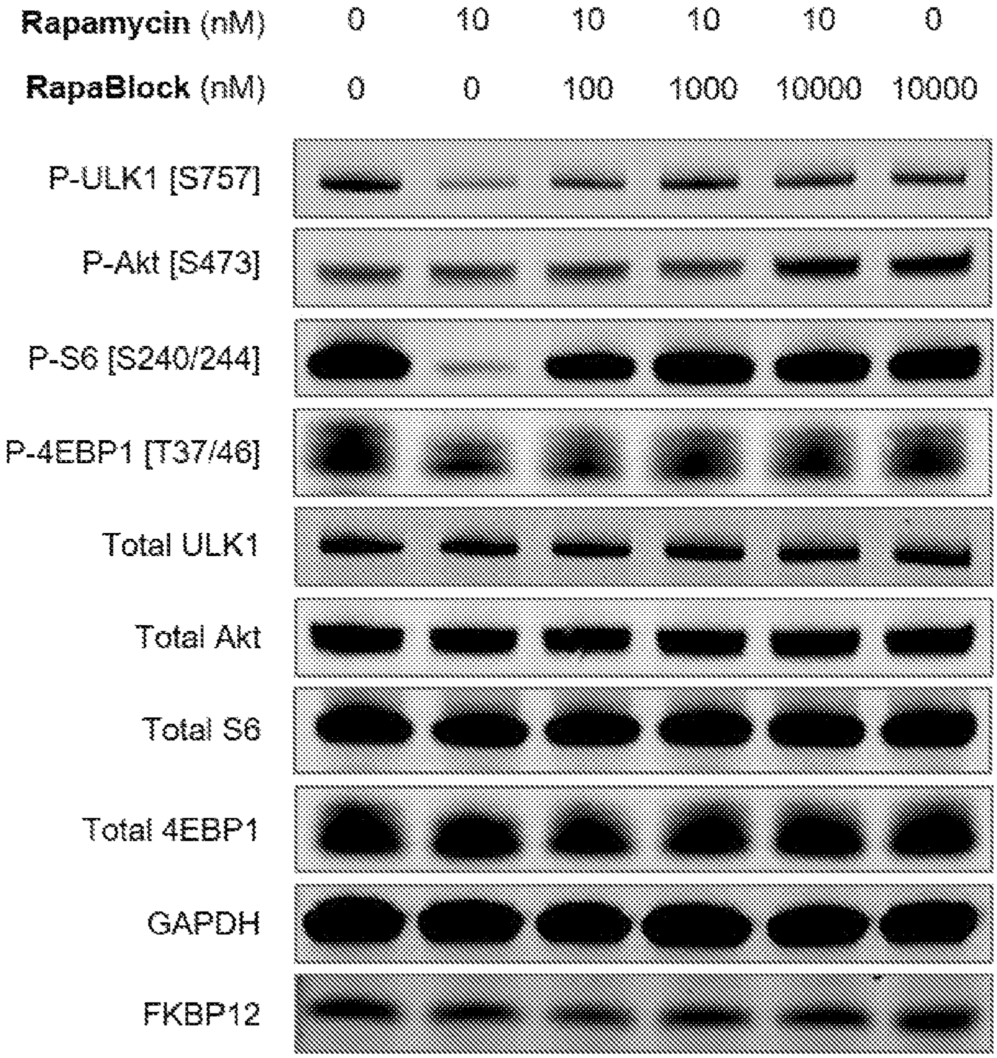
FIGS. 61A-61B. RapaBlock rescues mTOR inhibition by Rapamycin (FIG. 61A) or RapaLink-1 (FIG. 61B) in cells.
Figure 61B:
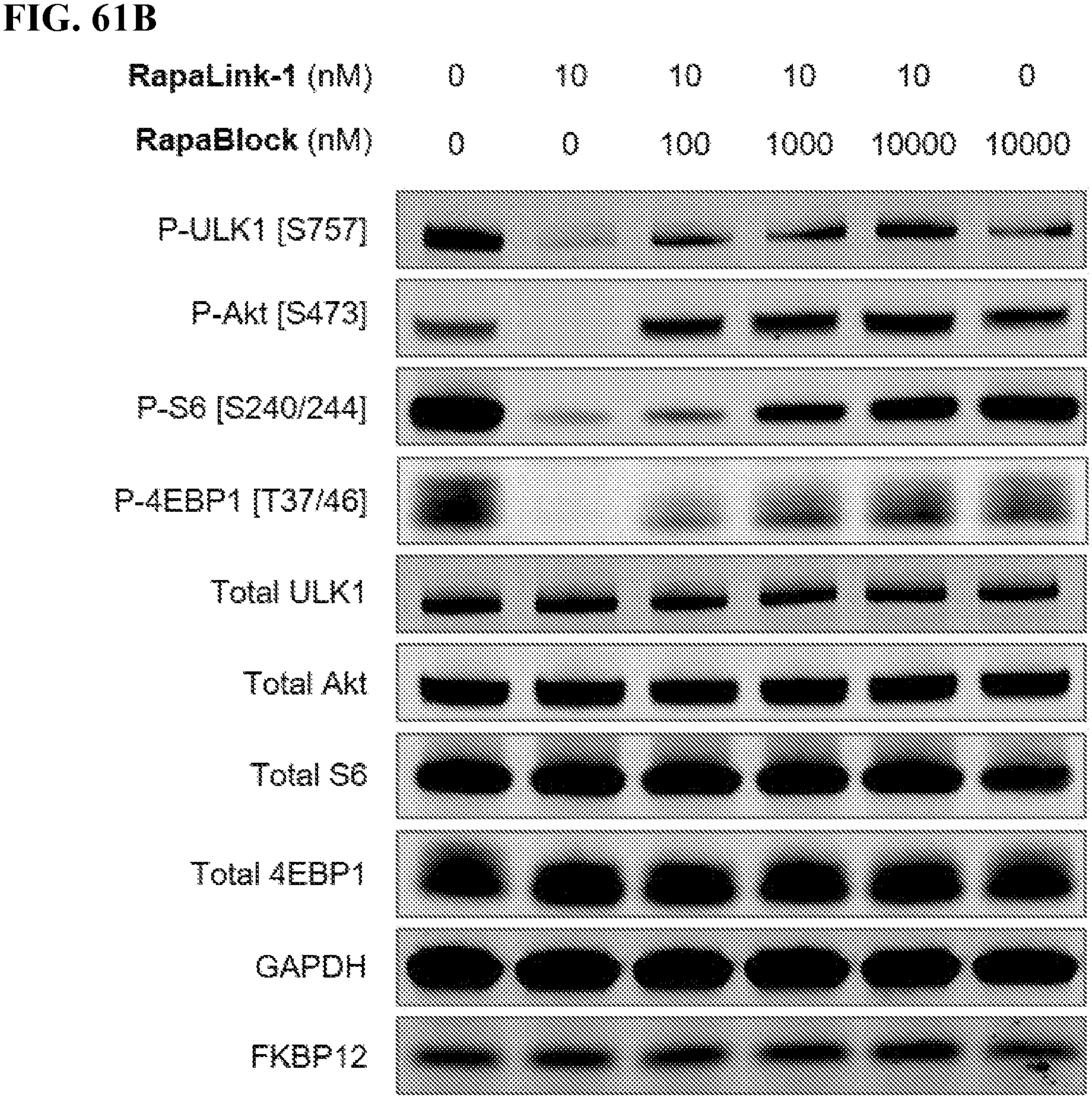

RapaBlock rescues mTOR inhibition by Rapamycin or RapaLink-1 in cells (FIGS. 61A-61B).

Experimental procedure. MCF7 cells were grown in 6-well tissue culture plates (2 plates total) to ~80% confluence (10% FBS in DMEM, 5% CO2, 37° C.). Cells were treated with the following drug combinations with a fixed final DMSO concentration of 1%. The cells were incubated at 37° C. for 4 h. The media was removed by aspiration and the cells were washed twice with ice-cold PBS (1 mL/well). Cells were scraped in the presence of 0.5 mL PBS/well, collected in microfuge vials and pelleted by centrifugation at 7,000 g for 1 min. The supernatant was removed by aspiration and the cell pellet was resuspended in 30 μL ice-cold RIPA Buffer supplemented with cOmplete protease inhibitors and PhosStop phosphotase inhibitors (Roche). Lysis was performed by incubating the suspension on ice for 10 min, and the resulting lysates were clarified by centrifugation at 14,000 g for 10 min. The clarified lysates were transferred into new microfuge tubes. Protein concentrations were determined with BCA assay and normalized to 2.0 mg/mL by dilution with RIPA buffer. Concentration-normalized lysates (30 μL/sample) were mixed with 7.5 μL 5×SDS Sample Buffer and boiled at 95° C. for 5 min. Proteins were resolved by electrophoresis on a 4-12% Novex Bis-Tris gel (200 V, 35 min, MES Running Buffer) and the bands were transferred onto a 0.45 μM nitrocellulose membrane (75 V, 30 min). Western blot analysis was performed following the standard protocol with the antibodies in Table 11.

TABLE 11

Antibodies used in Western blot analysis.

| MW | Antibody 1 | Source | Species | Dilution | Antibody 2 | Source | Species | Dilution |
|---|---|---|---|---|---|---|---|---|
| 100-55 | P-AKT[S473] | CST-4060 | Rabbit | 1:1000 | AKT | CST-2020 | Mouse | 1:1000 |
| 55-25 | P-S6[S240/244] | CST-5364 | Rabbit | 1:2000 | S6 | CST-2317 | Mouse | 1:1000 |
| 100+ | P-ULK1[S757] | | Rabbit | 1:1000 | | | | |
| 25- | P-4EBP1[T37/46] | CST-2855 | Rabbit | 1:1000 | FKBP12 | Ab58072 | Mouse | 1:500 |
| 55-25 | GAPDH | 60004-1-Ig | Mouse | 1:50000 | S6 | CST-2217 | Rabbit | 1:1000 |
| 100+ | ULK1 | | Rabbit | 1:1000 | | | | |
| 25- | 4EBP1 | CST-9644 | Rabbit | 1:1000 | | | | |

Primary antibodies were added as solutions in 5% BSA-TBST, and the membranes were incubated at 4° C. overnight (16 h). The membranes were washed with TBST for three times (5 mL and 5 min for each wash). Secondary antibody binding was performed with LICOR IRDye 680RD Goat Anti-Mouse IgG or IRDye 800RD Goat Anti-Rabbit IgG in 5% non-fat milk-TBST (1:5000) at 23° C. for 1 h. Membranes were washed three times with TBST (5 mL and 5 min for each wash) before being imaged on a LICOR CLx Imaging System.

Figure 62A:
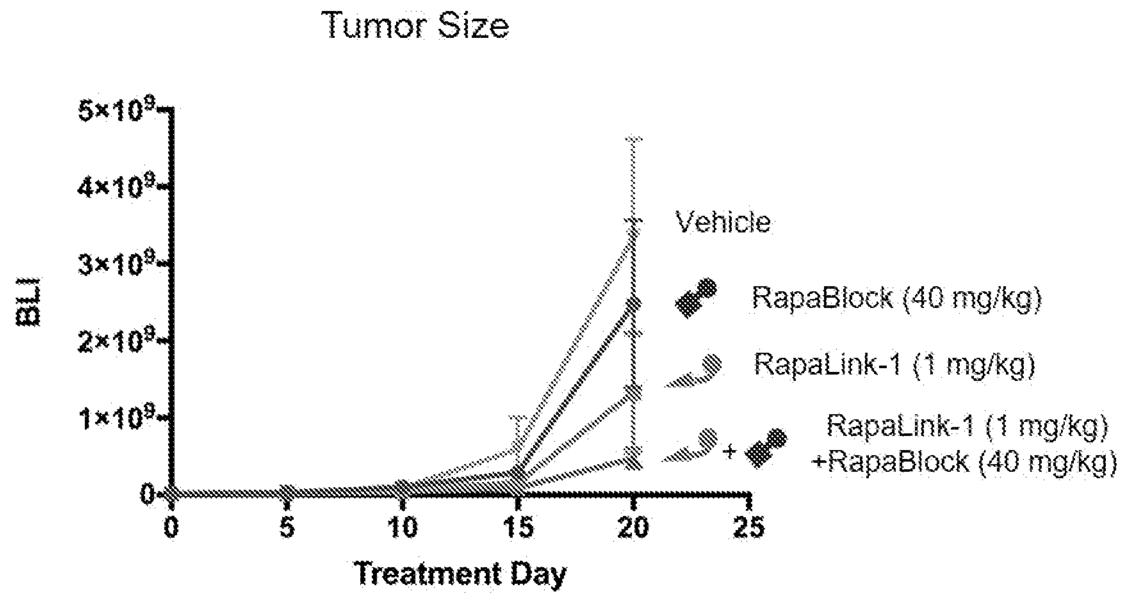
FIGS. 62A-62B. Combination of RapaBlock and RapaLink-1 is efficacious against glioblastoma xenograft in vivo. U87MG cells expressing luciferase were implanted intracranially. Treatment was started on day 0. Drugs were administered every 5 days intraperitoneally: RapaLink-1 (1 mg/kg); RapaBlock (40 mg/kg). BLI—Bioluminescence Imaging.
Figure 62B:
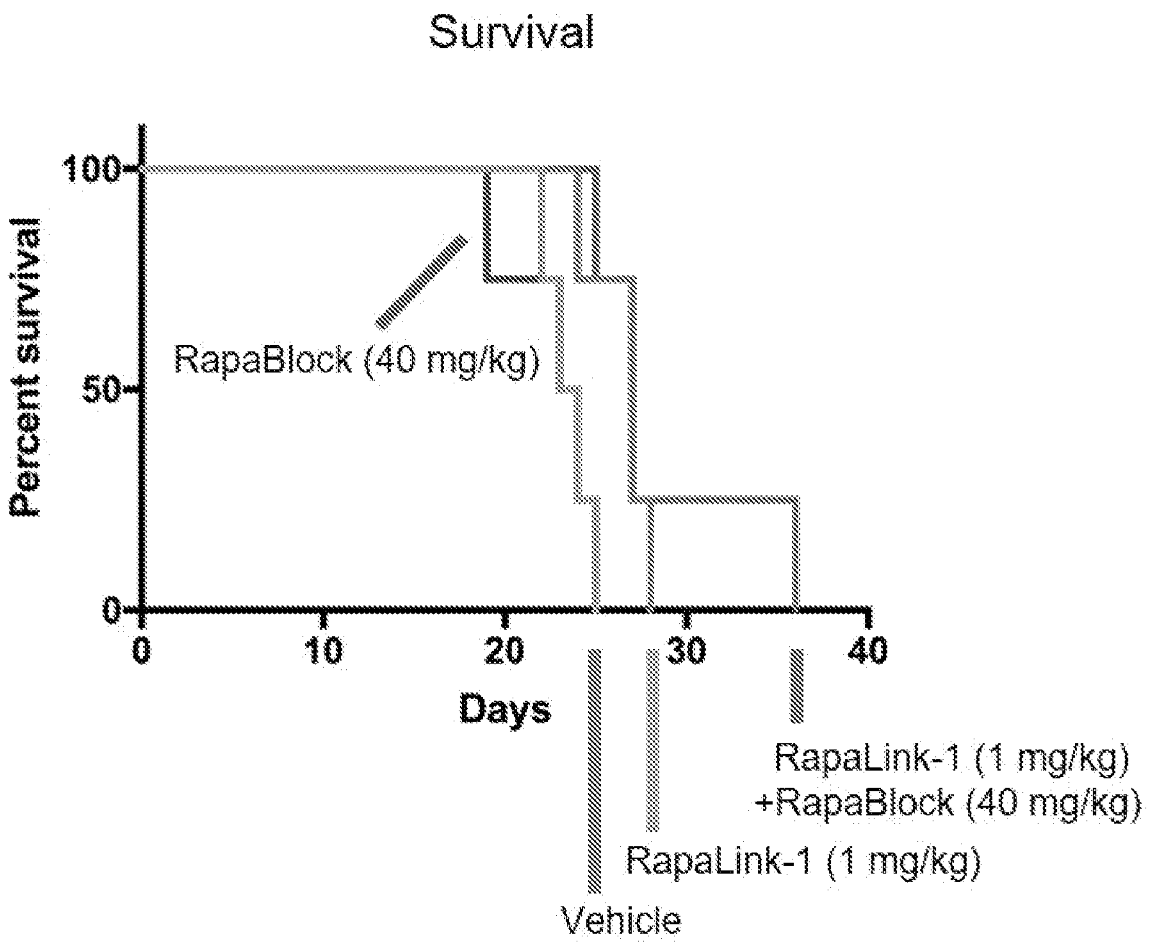

Combination of RapaBlock and RapaLink-1 is efficacious against glioblastoma xenograft in vivo (FIGS. 62A-62B).

Experimental procedure. Orthotopic injections and treatment studies: female BALB/Cnu/nu, mice (4 to 6 weeks old) were anesthetized using ketamine and xylazine. U87MG ($3\times10^5$) cells expressing firefly luciferase were injected intracranially (Hamilton syringe) at coordinates 2 mm anterior and 1.5 mm lateral of the right hemisphere relative to bregma, at a depth of 3 mm. Whole-brain bioluminescence was measured for each mouse every 3 to 5 days. When bioluminescence reached $10^7$ photons/s (U87MG), mice were sorted into four groups of equal mean bioluminescent signal, and therapy initiated. Mice were treated with i.p. injection of vehicle (20% DMSO, 40% PEG-300, and 40% PBS [v/v], daily), RapaLink-1 (1 mg/kg, every 5 days), RapaBlock (40 mg/kg, every 5 days) or a combination of RapaLink-1 (1 mg/kg) and RapaBlock (40 mg/kg, every 5 days). Mice were monitored daily and euthanized when they exhibited neurological deficits or 15% reduction from initial body weight.

Example 8: HGK Inhibitors

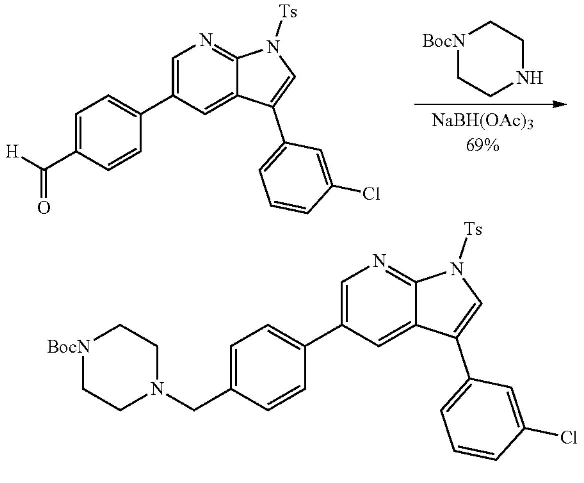

N-Boc-Piperazine (229 mg, 1.23 mmol) and sodium triacetoxyborohydride (196 mg, 0.924 mmol) were added sequentially to a stirred solution of 4-[3-(3-chlorophenyl)-1-(p-tolylsulfonyl)pyrrolo[2,3-b]pyridin-5-yl]benzaldehyde (44) (300 mg, 0.6161 mmol) in DCM (3.0803 mL) at 23° C. The resulting mixture was stirred at 23° C. and the reaction progress was monitored by LC-MS. In 18 h, LC-MS analysis showed full consumption of the aldehyde starting material. The reaction mixture was partitioned between saturated aqueous sodium bicarbonate solution (5 mL) and dichloromethane (5 mL). The layers were separated, and the aqueous layer was extracted with dichloromethane (2×5 mL). The combined organic layers were dried over sodium sulfate. The dried solution was filtered, and the filtrate was concentrated. The residue was purified by column chromatography (20-50% ethyl acetate-hexanes, 4-g RediSep® Rf column, Teledyne ISCO, Lincoln, Nebr.) to afford the product as a yellow powder (279 mg, 69%). $^1H$ NMR (400 MHz, $CDCl_3$) δ 8.72 (d, J=2.1 Hz, 1H), 8.23-8.13 (m, 3H), 7.94 (s, 1H), 7.62 (t, J=1.8 Hz, 1H), 7.59-7.49 (m, 3H), 7.47-7.42 (m, 2H), 7.43-7.30 (m, 4H), 3.58 (s, 2H), 3.55-3.43 (m, 4H), 2.50-2.34 (m, 7H), 1.48 (s, 9H). HRMS (ESI): Calcd for $(C_{36}H_{37}ClN_4O_4S+H)^+$: 657.2302, Found: 657.2278.

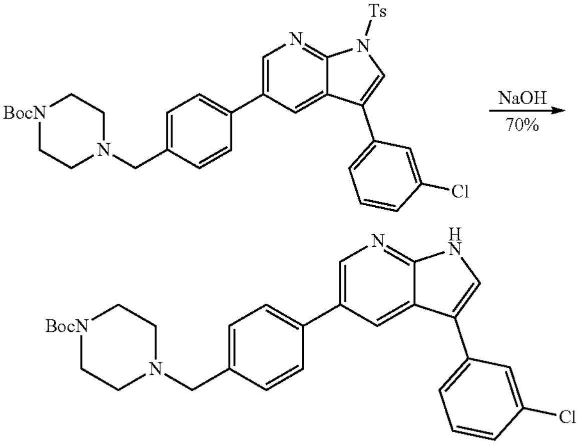

tert-butyl 4-[[4-[3-(3-chlorophenyl)-1-(p-tolylsulfonyl)pyrrolo[2,3-b]pyridin-5-yl]phenyl]methyl]piperazine-1-carboxylate (279 mg, 0.43 mmol) was dissolved in a 1:1:1 mixture of acetone (2 mL):methanol (2 mL): 2 M aqueous NaOH (2 mL). The mixture was heated to 65° C. In 1 h, LC-MS analysis showed full deprotection of the tosyl group. The reaction mixture was partitioned between ethyl acetate (10 mL) and 1 N NaOH (10 mL). The aqueous layer was extracted with ethyl acetate (2×10 mL). The combined organic layers were dried over sodium sulfate, and the dried solution was concentrated. The residue was purified by column chromatography (20-50% ethyl acetate-hexanes, 4-g RediSep® Rf column, Teledyne ISCO, Lincoln, Nebr.) to afford the product as a yellow powder (150 mg, 70%). $^1H$ NMR (400 MHz, $CDCl_3$) δ 9.43 (s, 1H), 8.64 (d, J=2.1 Hz, 1H), 8.38 (d, J=2.0 Hz, 1H), 7.70-7.55 (m, 5H), 7.50-7.37 (m, 3H), 7.32 (ddd, J=8.0, 2.1, 1.1 Hz, 1H), 3.61 (s, 2H), 3.48 (t, J=5.1 Hz, 4H), 2.46 (t, J=5.1 Hz, 4H), 1.49 (s, 9H). HRMS (ESI): Calcd for $(C_{29}H_{31}ClN_4O_2+H)^+$: 503.2214, Found: 503.2233.

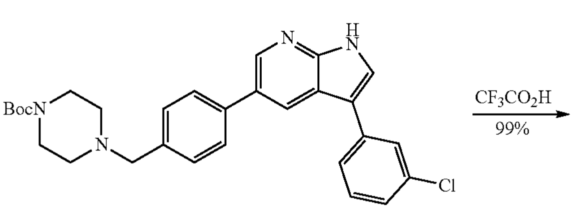

-continued

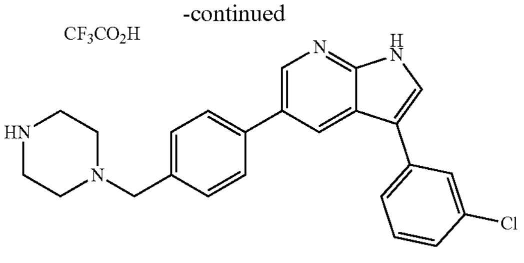

tert-butyl 4-[[4-[3-(3-chlorophenyl)-1H-pyrrolo[2,3-b]pyridin-5-yl]phenyl]methyl]piperazine-1-carboxylate (150 mg, 0.299 mmol) was dissolved in 50% trifluoroacetic acid-dichloromethane (2.0 mL) and the resulting solution was allowed to stand at 23° C. for 1 h. At this point, LC-MS analysis showed full consumption of the starting material and formation of the desired product. The reaction mixture was concentrated under reduced pressure and the residue was triturated with ether and dried under vacuum to afford the product as a yellow solid (151 mg, 99%). $^1$H NMR (400 MHz, $CDCl_3$) δ 9.43 (s, 1H), 8.64 (d, J=2.1 Hz, 1H), 8.38 (d, J=2.0 Hz, 1H), 7.70-7.55 (m, 5H), 7.50-7.37 (m, 3H), 7.32 (ddd, J=8.0, 2.1, 1.1 Hz, 1H), 3.61 (s, 2H), 3.48 (t, J=5.1 Hz, 4H), 2.46 (t, J=5.1 Hz, 4H), 1.49 (s, 9H). HRMS (ESI): Calcd for $(C_{24}H_{23}ClN_4+H)^+$: 403.1689, Found: 403.1698.

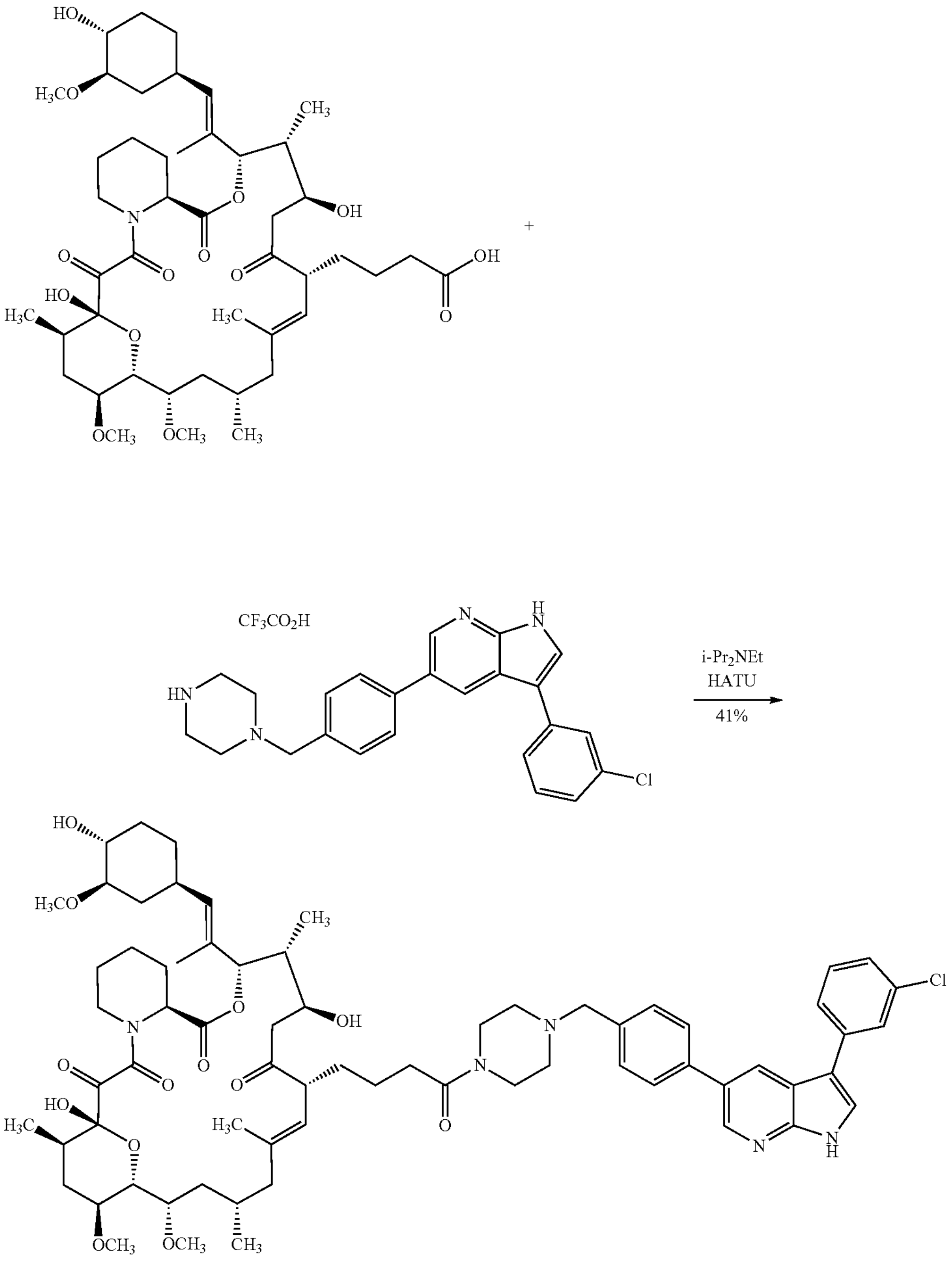

N,N-Diisopropylethylamine (6.2 μL, 0.035 mmol) and HATU (4.5 mg, 0.012 mmol) were added sequentially to a stirred solution of 3-(3-chlorophenyl)-5-[4-(piperazin-1-ylmethyl)phenyl]-1H-pyrrolo[2,3-b]pyridine trifluoroacetic acid salt (6.1 mg, 0.012 mmol) and FK506-C4-Acid (10 mg, 0.012 mmol) in DMF (0.2 mL) at 23° C. The resulting mixture quickly turned yellow, and LC-MS analysis at 15 min showed full consumption of the FK506 acid starting material. The reaction mixture was diluted with 50% acetonitrile-water to a volume of 3.0 mL, and the solution was filtered through a 0.45 μM PTFE syringe filter. The filtrate was purified by reverse-phase HPLC (Waters XBridge C18 column 5 μm particle size 30×250 mm, 5-95% acetonitrile-water+0.1% formic acid, 40 min, 20 mL/min) to afford the product as a white solid (5.9 mg, 41%). HRMS (ESI): Calcd for $(C_{69}H92ClN_5O_{13}+2H)^{2+}$: 617.8268, Found: 617.8257.

REFERENCES

1. Fan, Q. W. et al. A Kinase Inhibitor Targeted to mTORC1 Drives Regression in Glioblastoma. Cancer Cell 31, 424-435 (2017). 2. González, D. et al. Growth of kidney-transplanted pediatric patients treated with sirolimus. Pediatr Nephrol 26, 961-966 (2011). 3. Álvarez-Garcia, Ó. et al. Rapamycin induces growth retardation by disrupting angiogenesis in the growth plate. Kidney Int. 78, 561-568 (2010). 4. Briesewitz, R., Ray, G. T., Wandless, T. J. & Crabtree, G. R. Affinity modulation of small-molecule ligands by borrowing endogenous protein surfaces. Proc. Natl. Acad. Sci. U.S.A 96, 1953-8 (1999). 5. Modulating a pharmacokinetic property of a drug by administering a bifunctional molecule containing the drug. US 20050209265, U.S. Pat. No. 6,887,842. 6. Administering bifunctional molecules containing a drug moiety and presenter protein ligand for therapy. US20050209146. 7. Bifunctional molecules and therapies based thereon. US20020147133. 8. Targeted bifunctional molecules and therapies based thereon U.S. Pat. No. 7,498,025. 9. Small Molecule Composite Surfaces As Inhibitors Of Protein-Protein Interactions. US 20160333054. 10. Gestwicki, J. E. Harnessing Chaperones to Generate Small-Molecule Inhibitors of Amyloid. Aggregation. 865, 865-870 (2011). 11. Neurodegenerative protein aggregation inhibition methods and compounds. US20050209173. 12. Marinec, P. S. et al. FK506-binding protein (FKBP) partitions a modified HIV protease inhibitor into blood cells and prolongs its lifetime in vivo. Proc. Natl. Acad. Sci. U.S.A 106, 1336-1341 (2009). 13. Marinec, P. S., Lancia, J. K. & Gestwicki, J. E. Bifunctional molecules evade cytochrome P450 metabolism by forming protective complexes with FK506-binding protein. *Mol. Biosyst.* 4, 571-578 (2008). 14. Dunyak, B. M., Nakamura, R. L., Frankel, A. D. & Gestwicki, J. E. Selective Targeting of Cells via Bispecific Molecules That Exploit Coexpression of Two Intracellular Proteins. *ACS Chem. Biol* 10, 2441-2447 (2015). 15. Methods of screening bifunctional molecules for modulated pharmacokinetic properties US 20070054348. 16. Pharmacokinetics of protease inhibitors and other drugs. US 20080306098. 17. Braun, P. D. et al. A bifunctional molecule that displays context-dependent cellular activity. J. Am. Chem. Soc. 125, 7575-7580 (2003). 18. Sellmyer, M. A., Stankunas, K., Briesewitz, R., Crabtree, G. R. & Wandless, T. J. Engineering small molecule specificity in nearly identical cellular environments. Bioorganic Med. Chem. Lett. 17, 2703-2705 (2007). 19. Wu, X. et al. Creating diverse target-binding surfaces on FKBP12: Synthesis and evaluation of a rapamycin analogue library. ACS Comb. Sci. 13, 486-495 (2011). 20. Small Molecule Composite Surfaces As Inhibitors Of Protein-Protein Interactions. U.S. Pat. No. 9,260,484. US20160333054. US 20140200186. 21. Guo, Z. et al. Rapamycin-inspired macrocycles with new target specificity. Nat. Chem. (2018). doi:10.1038/s41557-018-0187-4. 22. Synthesis and composition of rapafucin libraries. WO2017136708A1. 23. Guo, Z.-F., Zhang, R. & Liang, F.-S. Facile functionalization of FK506 for biological studies by the thiol-ene 'click' reaction. RSC Adv. 4, 11400 (2014). 24. Marinec, P. S. et al. Synthesis of orthogonally reactive FK506 derivatives via olefin cross metathesis. *Bioorganic Med Chem.* 17, 5763-5768 (2009). 25. Nambu, M. et al. A calcineurin antifungal strategy with analogs of FK506. Bioorganic Med. Chem. Lett. 27, 2465-2471 (2017). 26. Preparation of cyclosporin A analogs as Cyclophilin A inhibitors for treating dry eye and other conditions. PCT Int. Appl., 2013181339. 27. Synthesis of cyclosporin derivatives for use in diagnosis or treatment of disease, plant protection, or pest control. PCT Int. Appl., 2013030208. 28. Preparation of non-immunosuppressive cyclosporin A analogs modified on the (4R)-4-[(E)-2-butenyl]-4-methyl-L-threonine side chain by heterocyclic rings as potent cyclophilin A inhibitors for treating dry eye and other conditions. PCT Int. Appl., 2016160362. 29. Preparation of non-immunosuppressive analogs of cyclosporin A derivatives possessing a (4R)-4-[(E)-2-butenyl]-4-methyl-L-threonine cyclized side-chain as potent inhibitors of cyclophilin D. PCT Int. Appl., 2016112321. 30. Preparation of cyclosporins for the treatment of immune disorders. U.S. Pat. Appl. Publ., 20040110666. 31. Preparation of cyclosporins for the treatment of immune disorders. U.S. Pat. Appl. Publ., 20040157768. 32. Preparation of cyclosporin alkyne analogs for preventing or treating viral-induced disorders. U.S., 7696165. 33. Preparation of cyclosporin alkene analogues for preventing or treating viral-induced disorders. PCT Int. Appl., 2007112345. 34. Preparation of cyclosporin alkyne/alkene analogues for preventing or treating viral-induced disorders. PCT Int. Appl., 2007112352. 35. Preparation of cyclosporin alkynes as pharmaceutical agents. U.S. Pat. Appl. Publ., 20060074015. 36. Preparation of cyclosporin alkyne analogues for preventing or treating viral-induced disorders. PCT Int. Appl., 2007112357. 37. Preparation of cyclosporin analogues for pharmaceutical use. U.S. Pat. Appl. Publ., 20060069015. 38. Preparation of novel cyclosporins. PCT Int. Appl., 200408262. 39. Preparation of cyclosporin A analogs modified at amino acid 1 and 3 as cyclophilin ligands with reduced immunosuppressivity for treating cyclophilin mediated diseases. PCT Int. Appl., 2012079172. 40. A semisynthetic approach to olefinic analogs of amino acid one (MeBMT) in cyclosporin A. Tetrahedron Letters, 30(32), 4215-18; 1989. 41. Semisynthetic di- and tri-functionalized non-immunosuppressive cyclosporin A derivatives as potential anti-HIV 1 drugs. Synlett, (2), 316-320; 2004. 42. Preparation of novel cyclosporin A derivatives. Bioconjugate Chemistry, 3(1), 32-6; 1992. 43. Rutaganira, F. U. et al. Design and Structural Characterization of Potent and Selective Inhibitors of Phosphatidylinositol 4 Kinase III β. (2016). doi: 10.1021/acs.jmedchem.5b01311. 44. Bos, P. H. et al. Development of MAP4 Kinase Inhibitors as Motor Neuron-Protecting Agents. *Cell Chem. Biol.* 26, 1703-1715.e37 (2019).

What is claimed is:

1. A method of treating a CNS disease in a subject in need of such treatment, comprising co-administering outside the CNS of said subject an anti-CNS disease drug and a compound having the formula:

$A^B$-$L^{B1}$-$R^{B1}$, or a pharmaceutically acceptable salt thereof, wherein $A^B$ is an immunophilin-binding moiety;

$L^{B1}$-$R^{B1}$ is a polar moiety;

$L^{B1}$ is a bond, a covalent linker, or a bioconjugate linker;

$R^{B1}$ is hydrogen, halogen, $—CXB_3^1$, $—CHXB_2^1$, $—CH_2X^{B1}$, $—OCXB_3^1$, $—OCH_2X^{B1}$, $—OCHXB_2^1$, —CN, $—SO_{nB1}R^{B1D}$, $—SO_{vB1}NR^{B1A}R^{B1B}$, $—NHC(O)NR^{B1A}R^{B1B}$, $—N(O)_m{}^{B1}$, $—NR^{B1A}R^{B1B}$, $—C(O)R^{B1C}$, $—C(O)OR^{B1C}$, $—C(O)NR^{B1A}R^{B1B}$, $—OR^{B1D}$, $—NR^{B1A}SO_2R^{B1D}$, $—NR^{B1A}C(O)R^{B1C}$, $—NR^{B1A}C(O)OR^{B1C}$, $—NR^{B1A}OR^{B1C}$, $—NR^{B1A}C(NR^{B1C})R^{B1D}$, $—NR^{B1A}C(NR^{B1C})NR^{B1A}R^{B1B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{B1A}$, $R^{B1B}$, $R^{B1C}$, and $R^{B1D}$ are independently hydrogen, halogen, $—CCl_3$, $—CBr_3$, $—CF_3$, $—Cl_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHC(NH)H, $—NHC(NH)NH_2$, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{B1A}$ and $R^{B1B}$ substituents bonded to the same nitrogen atom may be joined to form a substituted or unsubstituted heterocycloalkyl or substituted or unsubstituted heteroaryl;

nB1 is an integer from 0 to 4;

mB1 and vB1 are independently 1 or 2;

$X^{B1}$ is independently —F, —Cl, —Br, or —I;

when $L^{B1}$ is a bond, $R^{B1}$ is not H;

wherein the anti-CNS disease drug has the formula:

A-$L^1$-$R^1$;

wherein

A is an immunophilin-binding moiety;

$L^1$ is a bond or a covalent linker; and $R^1$ is a monovalent kinase inhibitor, a monovalent pseudokinase inhibitor, a monovalent GTPase inhibitor, a monovalent histone-modifying enzyme inhibitor, a monovalent anti-cancer agent, a monovalent anti-neurodegenerative disease agent, or a monovalent anti-viral agent;

wherein the anti-CNS disease drug is capable of entering the central nervous system and the compound is incapable of entering the central nervous system following co-administration outside of the central nervous system of the subject.

2. The method of claim 1, wherein the immunophilin-binding moiety of the compound is a cyclophilin-binding moiety or an FKBP-binding moiety.

3. The method of claim 1, wherein $L^{B1}$ is $L^{B2}$-$L^{B3}$-$L^{B4}$, $L^{B2}$ is a bond, —$S(O)_2$—, —$N(R^{B2})$—, —O—, —S—, —C(O)—, —$C(O)N(R^{B2})$—, —$N(R^{B2})C(O)$—, —$N(R^{B2})C(O)NH$—, —$NHC(O)N(R^{B2})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B3}$ is a bond, —$S(O)_2$—, —$N(R^{B3})$—, —O—, —S—, —C(O)—, —$C(O)N(R^{B3})$—, —$N(R^{B3})C(O)$—, —$N(R^{B3})C(O)NH$—, —$NHC(O)N(R^{B3})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{B4}$ is a bond, —$S(O)_2$—, —$N(R^{B4})$—, —O—, —S—, —C(O)—, —$C(O)N(R^{B4})$—, —$N(R^{B4})C(O)$—, —$N(R^{B4})C(O)NH$—, —$NHC(O)N(R^{B4})$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{B2}$, $R^{B3}$, and $R^{B4}$ are independently hydrogen, halogen, —$CCl_3$, —$CBr_3$, —$CF_3$, -$Cl_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHC(NH)H, —$NHC(NH)NH_2$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

4. The method of claim 1, wherein $R^{B1}$ is halogen, —$NR^{B1A}R^{B1B}$, —$N_3$, —$SR^{B1D}$,

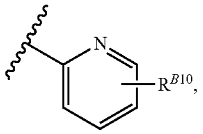, 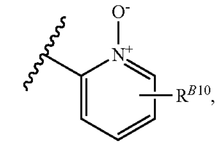,

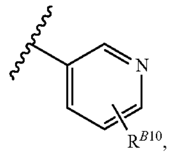, 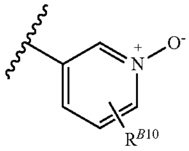,

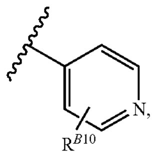, 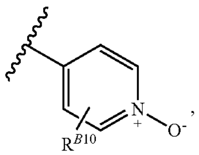,

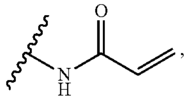, 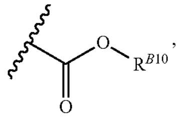,

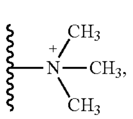, 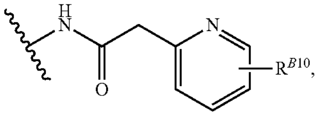,

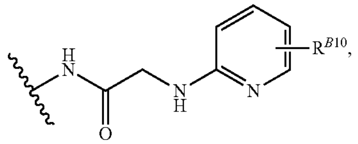,

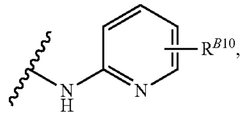, 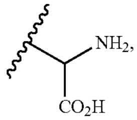,

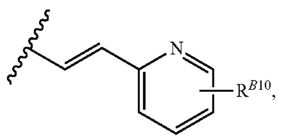, 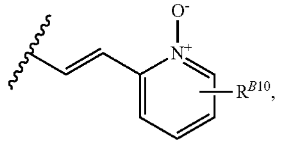,

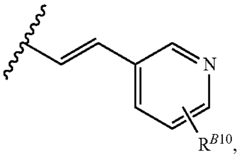, 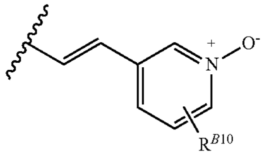,

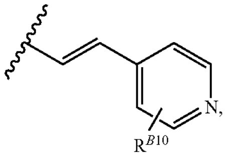 or 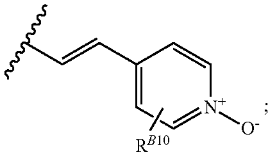;

$R^{B10}$ is hydrogen, halogen, —$CX_3^{B10}$, —$CHX_2^{10}$, —$CH_2X^{B10}$, —$OCX_3^{B10}$, —$OCH_2X^{B10}$, —$OCHX_2^{10}$, —CN, —$SO_{nB10}R^{B10D}$, —$SO_{vB10}NR^{B10A}R^{B10B}$, —$NHC(O)NR^{B10A}R^{B10B}$, —$N(O)_m^{B10}$, —$NR^{B10A}R^{B10B}$, —$C(O)R^{B10C}$, —$C(O)OR^{B10C}$, —$C(O)NR^{B10A}R^{B10B}$, —$OR^{B10D}$, —$NR^{B10A}SO_2R^{B10D}$, —$NR^{B10A}C(O)R^{B10C}$, —$NR^{B10A}C(O)OR^{B10C}$, —$NR^{B10A}OR^{B10C}$, —$NR^{B10A}C(NR^{B10C})R^{B10D}$, —$NR^{B10A}C(NR^{B10C})NR^{B10A}R^{B10B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

nB10 is an integer from 0 to 4;

mB10 and v10 are independently 1 or 2; and $X^{B10}$ is independently —F, —Cl, —Br, or —I.

5. The method of claim 1, wherein the immunophilin-binding moiety of the compound is

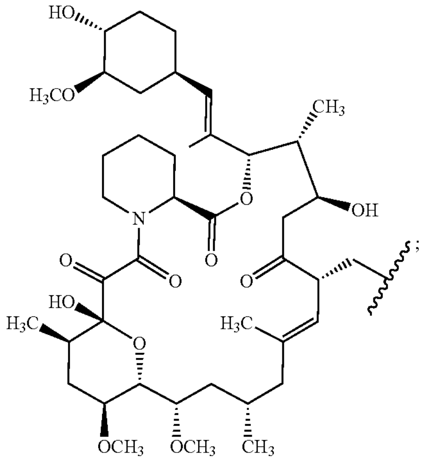 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or a stereoisomeric form thereof.

6. The method of claim 1, wherein the immunophilin-binding moiety of the compound is

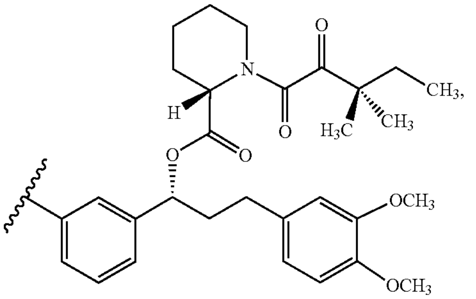

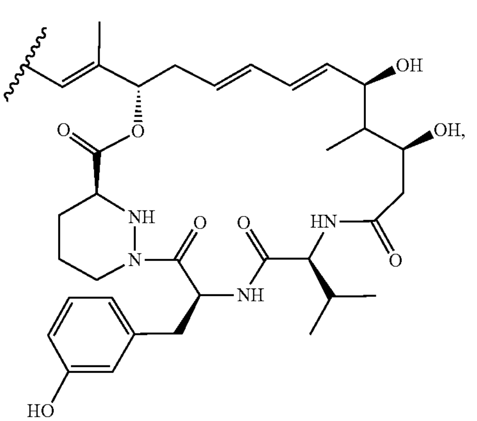

-continued

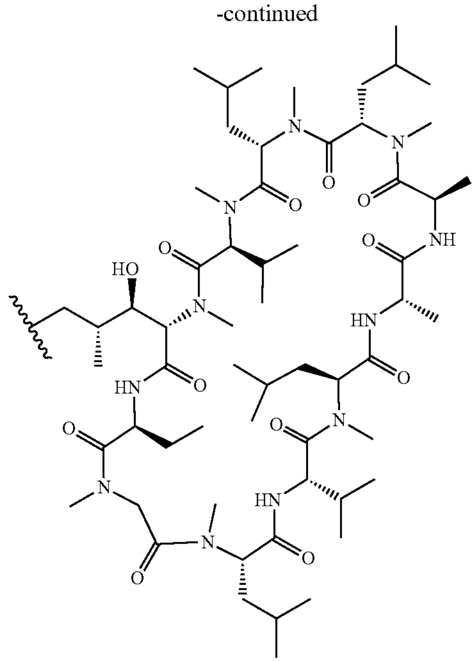

, or

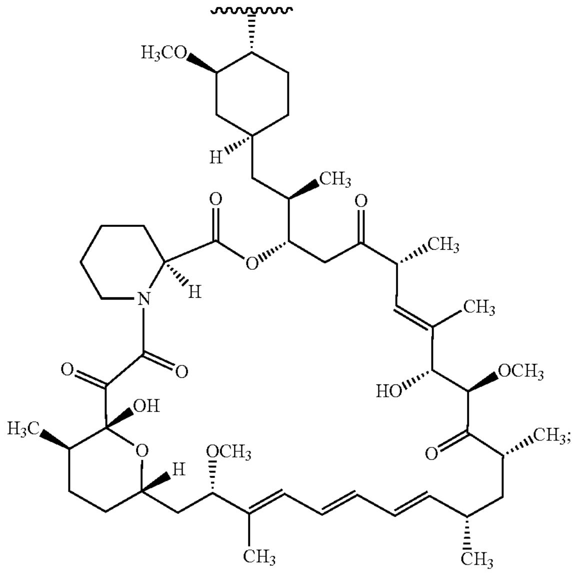 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or a stereoisomeric form thereof.

7. The method of claim 1, wherein $R^{B1}$ is $—SO_{nB1}R^{B1D}$, $—SO_{vB1}NR^{B1A}R^{B1B}$, or $—NR^{B1A}SO_2R^{B1D}$.

8. The method of claim 1, wherein $R^{B1}$ is substituted or unsubstituted heterocycloalkyl.

9. The method of claim 1, wherein $R^1$ is

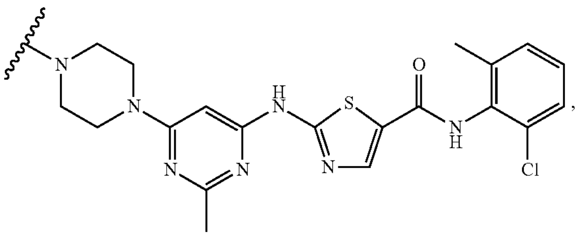

-continued
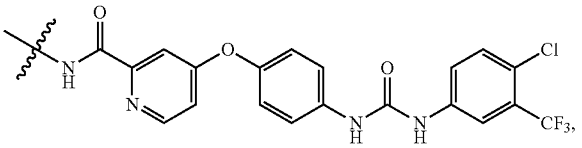
,
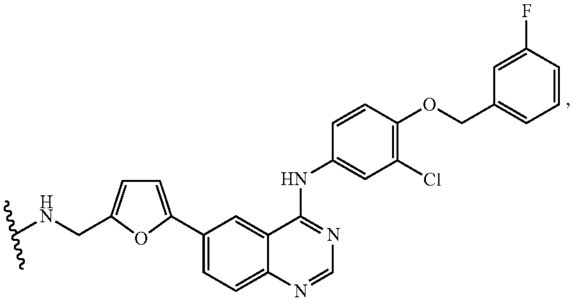
,
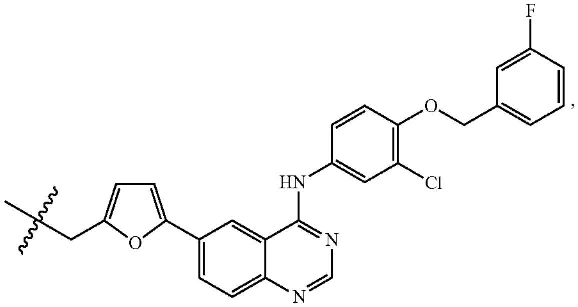
,
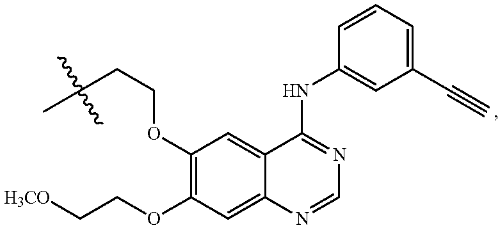
,
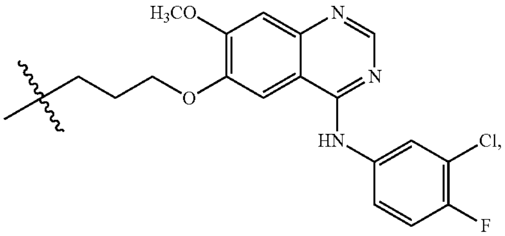
,
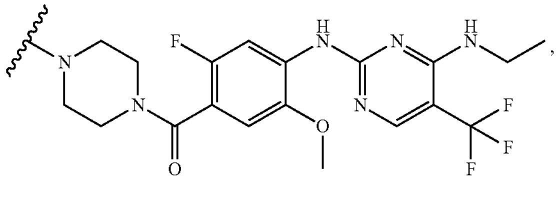
,
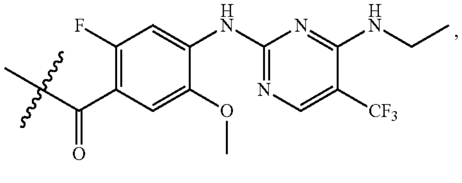
,
-continued
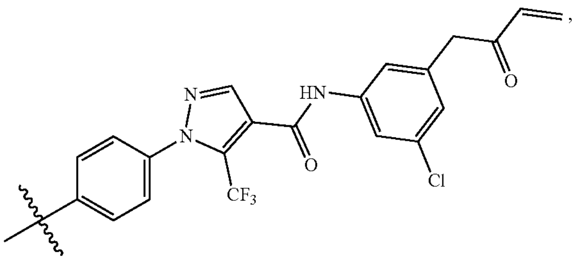
,
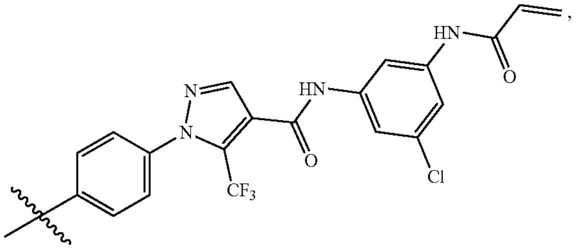
,
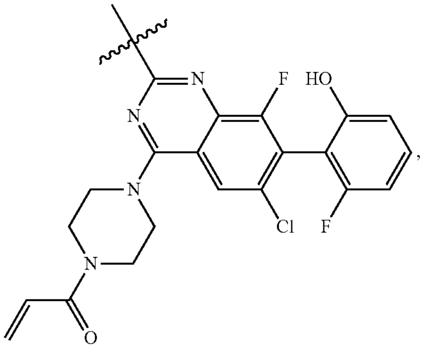
,
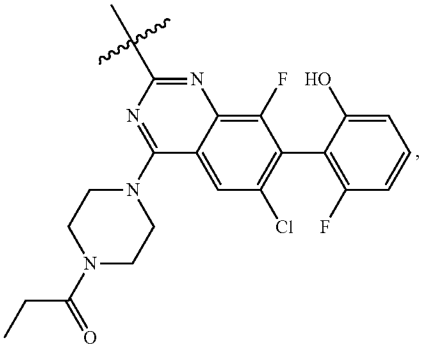
,
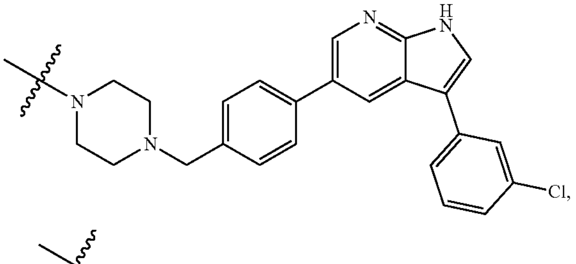
,
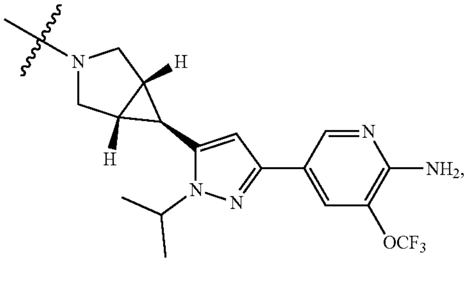
, or -continued

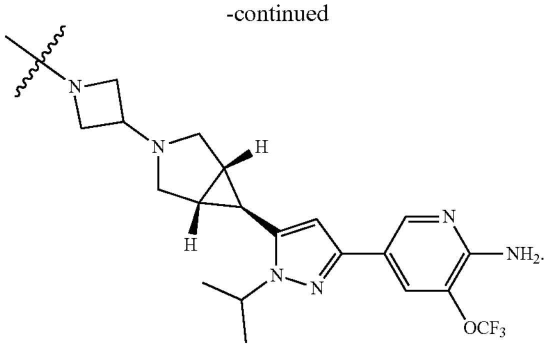

10. The method of claim 1, wherein the immunophilin-binding moiety of the anti-CNS disease drug is a cyclophilin-binding moiety or an FKBP-binding moiety.

11. The method of claim 1, wherein $L^1$ is $L^2$-$L^3$-$L^4$-$L^5$-$L^6$; $L^2$ is connected directly to A;

$L^2$ is-$S(O)_2$—, —$N(R^2)$—, —O—, —S—, —C(O)—, —$C(O)N(R^2)$—, —$N(R^2)C(O)$—, —$N(R^2)C(O)NH$—, —$NHC(O)N(R^2)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^5$ is a bond, —$S(O)_2$—, —$N(R^5)$—, —O—, —S—, —C(O)—, —$C(O)N(R^5)$—, —$N(R^5)C(O)$—, —$N(R^5)C(O)NH$—, —$NHC(O)N(R^5)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^6$ is a bond, —$S(O)_2$—, —$N(R^6)$—, —O—, —S—, —C(O)—, —$C(O)N(R^6)$—, —$N(R^6)C(O)$—, —$N(R^6)C(O)NH$—, —$NHC(O)N(R^6)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^2$, $R^3$, $R^4$, $R^5$, and $R^6$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

12. The method of claim 11, wherein $L^2$ is a substituted or unsubstituted alkylene, substituted or unsubstituted heteroalkylene, substituted or unsubstituted cycloalkylene, or substituted or unsubstituted heterocycloalkylene;

$L^3$ is a bond, substituted or unsubstituted alkylene, substituted or unsubstituted heteroalkylene, substituted or unsubstituted cycloalkylene, or substituted or unsubstituted heterocycloalkylene;

$L^4$ is a bond, substituted or unsubstituted alkylene, or substituted or unsubstituted heteroalkylene;

$L^5$ is a bond; and $L^6$ is a bond.

13. The method of claim 11, wherein $L^2$ is an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^3$ is a bond, an unsubstituted $C_3$-$C_7$ alkylene, an oxo-substituted $C_3$-$C_7$ alkylene, an unsubstituted 3 to 17 membered heteroalkylene, an oxo-substituted 3 to 17 membered heteroalkylene, or an unsubstituted 5 to 6 membered heterocycloalkylene, and $L^4$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene;

$L^5$ is a bond; and $L^6$ is a bond.

14. The method of claim 1, wherein $L^1$ is a bond, an unsubstituted $C_3$-$C_7$ alkylene, an oxo-substituted $C_3$-$C_7$ alkylene, an unsubstituted 3 to 17 membered heteroalkylene, or an oxo-substituted 3 to 17 membered heteroalkylene.

15. The method of claim 1, wherein $R^1$ is a monovalent kinase inhibitor, a monovalent KRAS inhibitor, a monovalent MAP4K inhibitor, or a monovalent MAP3K inhibitor;

wherein the monovalent kinase inhibitor is a monovalent Src kinase inhibitor, a monovalent Raf inhibitor, a monovalent VEGFR inhibitor, a monovalent PDGFR inhibitor, a monovalent c-Kit inhibitor, a monovalent EGFR inhibitor, or a monovalent LRRK2 inhibitor.

16. The method of claim 1, wherein the immunophilin-binding moiety of the anti-CNS disease drug is

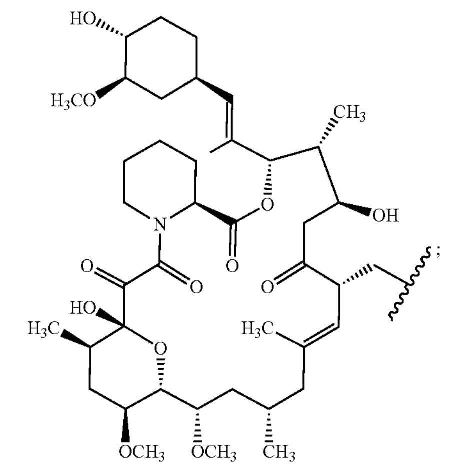 [SMILES: *C[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

or a stereoisomeric form thereof.

17. The method of claim 1, wherein the immunophilin-binding moiety of the anti-CNS disease drug is

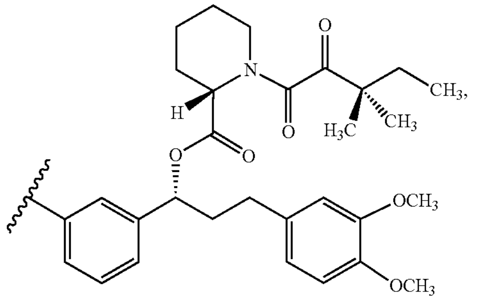

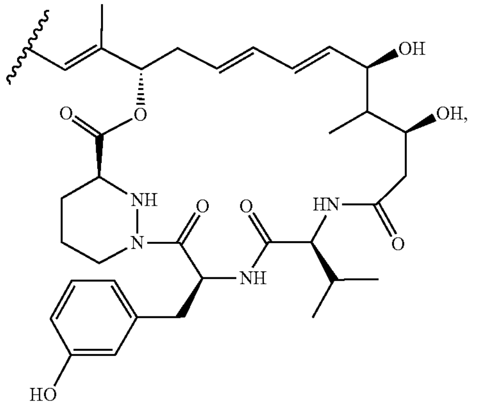

-continued

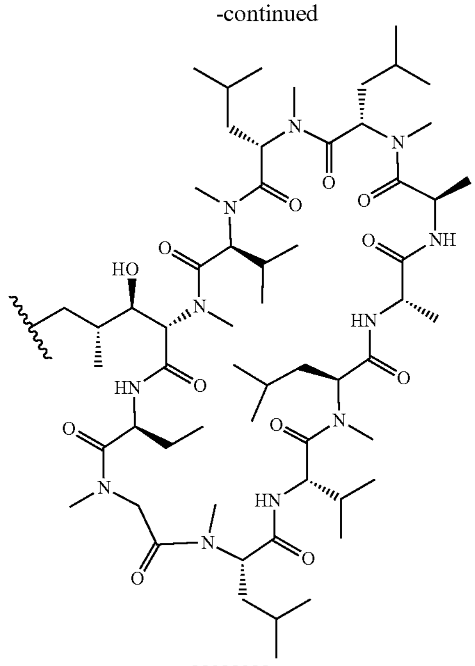

, or

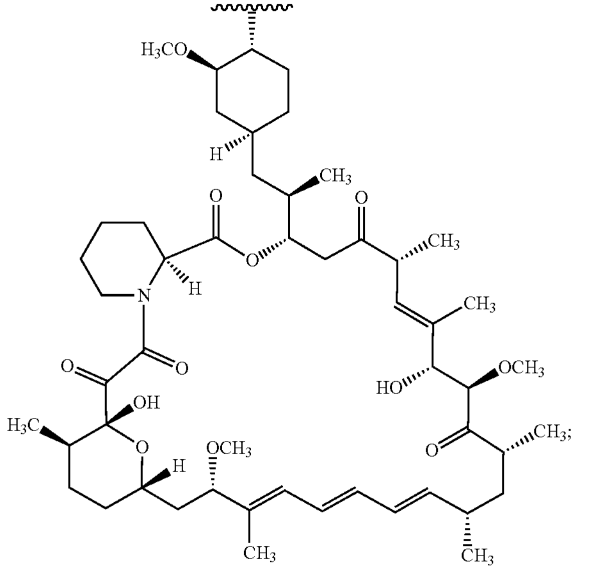 [SMILES: *[C@@H]1CC[C@@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC]

or a stereoisomeric form thereof.

18. The method of claim 1, wherein the CNS disease is cancer, a neurodegenerative disease, epilepsy, Tuberous Sclerosis (TSC), or a disease associated with aberrant enzyme activity.

19. The method of claim 18, wherein the CNS disease is epilepsy or TSC.

20. The method of claim 18, wherein the CNS disease is a neurodegenerative disease.

* * * * *

SEQUENCE LISTING

<160> NUMBER OF SEQ ID NOS: 12

<210> SEQ ID NO 1
<211> LENGTH: 2549
<212> TYPE: PRT
<213> ORGANISM: Artificial Sequence
<220> FEATURE:
<223> OTHER INFORMATION: Synthetic polypeptide

<400> SEQUENCE: 1

```
Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
```

```
        355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780
```

```
Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys Asp  Gly Ala Ile
        995                 1000                1005

Arg Glu  Phe Leu Phe Gln Gln  Leu Gly Met Leu Val  Ser Phe Val
    1010                 1015                 1020

Lys Ser  His Ile Arg Pro Tyr  Met Asp Glu Ile Val  Thr Leu Met
    1025                 1030                 1035

Arg Glu  Phe Trp Val Met Asn  Thr Ser Ile Gln Ser  Thr Ile Ile
    1040                 1045                 1050

Leu Leu  Ile Glu Gln Ile Val  Val Ala Leu Gly Gly  Glu Phe Lys
    1055                 1060                 1065

Leu Tyr  Leu Pro Gln Leu Ile  Pro His Met Leu Arg  Val Phe Met
    1070                 1075                 1080

His Asp  Asn Ser Pro Gly Arg  Ile Val Ser Ile Lys  Leu Leu Ala
    1085                 1090                 1095

Ala Ile  Gln Leu Phe Gly Ala  Asn Leu Asp Asp Tyr  Leu His Leu
    1100                 1105                 1110

Leu Leu  Pro Pro Ile Val Lys  Leu Phe Asp Ala Pro  Glu Ala Pro
    1115                 1120                 1125

Leu Pro  Ser Arg Lys Ala Ala  Leu Glu Thr Val Asp  Arg Leu Thr
    1130                 1135                 1140

Glu Ser  Leu Asp Phe Thr Asp  Tyr Ala Ser Arg Ile  Ile His Pro
    1145                 1150                 1155

Ile Val  Arg Thr Leu Asp Gln  Ser Pro Glu Leu Arg  Ser Thr Ala
    1160                 1165                 1170

Met Asp  Thr Leu Ser Ser Leu  Val Phe Gln Leu Gly  Lys Lys Tyr
    1175                 1180                 1185
```

-continued

```
Gln Ile  Phe Ile Pro Met Val  Asn Lys Val Leu Val  Arg His Arg
    1190                 1195                 1200

Ile Asn  His Gln Arg Tyr Asp  Val Leu Ile Cys Arg  Ile Val Lys
    1205                 1210                 1215

Gly Tyr  Thr Leu Ala Asp Glu  Glu Glu Asp Pro Leu  Ile Tyr Gln
    1220                 1225                 1230

His Arg  Met Leu Arg Ser Gly  Gln Gly Asp Ala Leu  Ala Ser Gly
    1235                 1240                 1245

Pro Val  Glu Thr Gly Pro Met  Lys Lys Leu His Val  Ser Thr Ile
    1250                 1255                 1260

Asn Leu  Gln Lys Ala Trp Gly  Ala Ala Arg Arg Val  Ser Lys Asp
    1265                 1270                 1275

Asp Trp  Leu Glu Trp Leu Arg  Arg Leu Ser Leu Glu  Leu Leu Lys
    1280                 1285                 1290

Asp Ser  Ser Ser Pro Ser Leu  Arg Ser Cys Trp Ala  Leu Ala Gln
    1295                 1300                 1305

Ala Tyr  Asn Pro Met Ala Arg  Asp Leu Phe Asn Ala  Ala Phe Val
    1310                 1315                 1320

Ser Cys  Trp Ser Glu Leu Asn  Glu Asp Gln Gln Asp  Glu Leu Ile
    1325                 1330                 1335

Arg Ser  Ile Glu Leu Ala Leu  Thr Ser Gln Asp Ile  Ala Glu Val
    1340                 1345                 1350

Thr Gln  Thr Leu Leu Asn Leu  Ala Glu Phe Met Glu  His Ser Asp
    1355                 1360                 1365

Lys Gly  Pro Leu Pro Leu Arg  Asp Asp Asn Gly Ile  Val Leu Leu
    1370                 1375                 1380

Gly Glu  Arg Ala Ala Lys Cys  Arg Ala Tyr Ala Lys  Ala Leu His
    1385                 1390                 1395

Tyr Lys  Glu Leu Glu Phe Gln  Lys Gly Pro Thr Pro  Ala Ile Leu
    1400                 1405                 1410

Glu Ser  Leu Ile Ser Ile Asn  Asn Lys Leu Gln Gln  Pro Glu Ala
    1415                 1420                 1425

Ala Ala  Gly Val Leu Glu Tyr  Ala Met Lys His Phe  Gly Glu Leu
    1430                 1435                 1440

Glu Ile  Gln Ala Thr Trp Tyr  Glu Lys Leu His Glu  Trp Glu Asp
    1445                 1450                 1455

Ala Leu  Val Ala Tyr Asp Lys  Lys Met Asp Thr Asn  Lys Asp Asp
    1460                 1465                 1470

Pro Glu  Leu Met Leu Gly Arg  Met Arg Cys Leu Glu  Ala Leu Gly
    1475                 1480                 1485

Glu Trp  Gly Gln Leu His Gln  Gln Cys Cys Glu Lys  Trp Thr Leu
    1490                 1495                 1500

Val Asn  Asp Glu Thr Gln Ala  Lys Met Ala Arg Met  Ala Ala Ala
    1505                 1510                 1515

Ala Ala  Trp Gly Leu Gly Gln  Trp Asp Ser Met Glu  Glu Tyr Thr
    1520                 1525                 1530

Cys Met  Ile Pro Arg Asp Thr  His Asp Gly Ala Phe  Tyr Arg Ala
    1535                 1540                 1545

Val Leu  Ala Leu His Gln Asp  Leu Phe Ser Leu Ala  Gln Gln Cys
    1550                 1555                 1560

Ile Asp  Lys Ala Arg Asp Leu  Leu Asp Ala Glu Leu  Thr Ala Met
    1565                 1570                 1575

Ala Gly  Glu Ser Tyr Ser Arg  Ala Tyr Gly Ala Met  Val Ser Cys
```

```
    1580                1585                1590

His Met  Leu Ser Glu Leu Glu  Glu Val Ile Gln Tyr  Lys Leu Val
    1595                1600                1605

Pro Glu  Arg Arg Glu Ile Ile  Arg Gln Ile Trp Trp  Glu Arg Leu
    1610                1615                1620

Gln Gly  Cys Gln Arg Ile Val  Glu Asp Trp Gln Lys  Ile Leu Met
    1625                1630                1635

Val Arg  Ser Leu Val Val Ser  Pro His Glu Asp Met  Arg Thr Trp
    1640                1645                1650

Leu Lys  Tyr Ala Ser Leu Cys  Gly Lys Ser Gly Arg  Leu Ala Leu
    1655                1660                1665

Ala His  Lys Thr Leu Val Leu  Leu Leu Gly Val Asp  Pro Ser Arg
    1670                1675                1680

Gln Leu  Asp His Pro Leu Pro  Thr Val His Pro Gln  Val Thr Tyr
    1685                1690                1695

Ala Tyr  Met Lys Asn Met Trp  Lys Ser Ala Arg Lys  Ile Asp Ala
    1700                1705                1710

Phe Gln  His Met Gln His Phe  Val Gln Thr Met Gln  Gln Gln Ala
    1715                1720                1725

Gln His  Ala Ile Ala Thr Glu  Asp Gln Gln His Lys  Gln Glu Leu
    1730                1735                1740

His Lys  Leu Met Ala Arg Cys  Phe Leu Lys Leu Gly  Glu Trp Gln
    1745                1750                1755

Leu Asn  Leu Gln Gly Ile Asn  Glu Ser Thr Ile Pro  Lys Val Leu
    1760                1765                1770

Gln Tyr  Tyr Ser Ala Ala Thr  Glu His Asp Arg Ser  Trp Tyr Lys
    1775                1780                1785

Ala Trp  His Ala Trp Ala Val  Met Asn Phe Glu Ala  Val Leu His
    1790                1795                1800

Tyr Lys  His Gln Asn Gln Ala  Arg Asp Glu Lys Lys  Lys Leu Arg
    1805                1810                1815

His Ala  Ser Gly Ala Asn Ile  Thr Asn Ala Thr Thr  Ala Ala Thr
    1820                1825                1830

Thr Ala  Ala Thr Ala Thr Thr  Thr Ala Ser Thr Glu  Gly Ser Asn
    1835                1840                1845

Ser Glu  Ser Glu Ala Glu Ser  Thr Glu Asn Ser Pro  Thr Pro Ser
    1850                1855                1860

Pro Leu  Gln Lys Lys Val Thr  Glu Asp Leu Ser Lys  Thr Leu Leu
    1865                1870                1875

Met Tyr  Thr Val Pro Ala Val  Gln Gly Phe Phe Arg  Ser Ile Ser
    1880                1885                1890

Leu Ser  Arg Gly Asn Asn Leu  Gln Asp Thr Leu Arg  Val Leu Thr
    1895                1900                1905

Leu Trp  Phe Asp Tyr Gly His  Trp Pro Asp Val Asn  Glu Ala Leu
    1910                1915                1920

Val Glu  Gly Val Lys Ala Ile  Gln Ile Asp Thr Trp  Leu Gln Val
    1925                1930                1935

Ile Pro  Gln Leu Ile Ala Arg  Ile Asp Thr Pro Arg  Pro Leu Val
    1940                1945                1950

Gly Arg  Leu Ile His Gln Leu  Leu Thr Asp Ile Gly  Arg Tyr His
    1955                1960                1965

Pro Gln  Ala Leu Ile Tyr Pro  Leu Thr Val Ala Ser  Lys Ser Thr
    1970                1975                1980
```

Thr Thr Ala Arg His Asn Ala Ala Asn Lys Ile Leu Lys Asn Met
1985 1990 1995

Cys Glu His Ser Asn Thr Leu Val Gln Gln Ala Met Met Val Ser
2000 2005 2010

Glu Glu Leu Ile Arg Val Ala Ile Leu Trp His Glu Met Trp His
2015 2020 2025

Glu Gly Leu Glu Glu Ala Ser Arg Leu Tyr Phe Gly Glu Arg Asn
2030 2035 2040

Val Lys Gly Met Phe Glu Val Leu Glu Pro Leu His Ala Met Met
2045 2050 2055

Glu Arg Gly Pro Gln Thr Leu Lys Glu Thr Ser Phe Asn Gln Ala
2060 2065 2070

Tyr Gly Arg Asp Leu Met Glu Ala Gln Glu Trp Cys Arg Lys Tyr
2075 2080 2085

Met Lys Ser Gly Asn Val Lys Asp Leu Thr Gln Ala Trp Asp Leu
2090 2095 2100

Tyr Tyr His Val Phe Arg Arg Ile Ser Lys Gln Leu Pro Gln Leu
2105 2110 2115

Thr Ser Leu Glu Leu Gln Tyr Val Ser Pro Lys Leu Leu Met Cys
2120 2125 2130

Arg Asp Leu Glu Leu Ala Val Pro Gly Thr Tyr Asp Pro Asn Gln
2135 2140 2145

Pro Ile Ile Arg Ile Gln Ser Ile Ala Pro Ser Leu Gln Val Ile
2150 2155 2160

Thr Ser Lys Gln Arg Pro Arg Lys Leu Thr Leu Met Gly Ser Asn
2165 2170 2175

Gly His Glu Phe Val Phe Leu Leu Lys Gly His Glu Asp Leu Arg
2180 2185 2190

Gln Asp Glu Arg Val Met Gln Leu Phe Gly Leu Val Asn Thr Leu
2195 2200 2205

Leu Ala Asn Asp Pro Thr Ser Leu Arg Lys Asn Leu Ser Ile Gln
2210 2215 2220

Arg Tyr Ala Val Ile Pro Leu Ser Thr Asn Ser Gly Leu Ile Gly
2225 2230 2235

Trp Val Pro His Cys Asp Thr Leu His Ala Leu Ile Arg Asp Tyr
2240 2245 2250

Arg Glu Lys Lys Lys Ile Leu Leu Asn Ile Glu His Arg Ile Met
2255 2260 2265

Leu Arg Met Ala Pro Asp Tyr Asp His Leu Thr Leu Met Gln Lys
2270 2275 2280

Val Glu Val Phe Glu His Ala Val Asn Asn Thr Ala Gly Asp Asp
2285 2290 2295

Leu Ala Lys Leu Leu Trp Leu Lys Ser Pro Ser Ser Glu Val Trp
2300 2305 2310

Phe Asp Arg Arg Thr Asn Tyr Thr Arg Ser Leu Ala Val Met Ser
2315 2320 2325

Met Val Gly Tyr Ile Leu Gly Leu Gly Asp Arg His Pro Ser Asn
2330 2335 2340

Leu Met Leu Asp Arg Leu Ser Gly Lys Ile Leu His Ile Asp Phe
2345 2350 2355

Gly Asp Cys Phe Glu Val Ala Met Thr Arg Glu Lys Phe Pro Glu
2360 2365 2370

Lys Ile Pro Phe Arg Leu Thr Arg Met Leu Thr Asn Ala Met Glu
2375 2380 2385

Val Thr Gly Leu Asp Gly Asn Tyr Arg Ile Thr Cys His Thr Val
2390 2395 2400

Met Glu Val Leu Arg Glu His Lys Asp Ser Val Met Ala Val Leu
2405 2410 2415

Glu Ala Phe Val Tyr Asp Pro Leu Leu Asn Trp Arg Leu Met Asp
2420 2425 2430

Thr Asn Thr Lys Gly Asn Lys Arg Ser Arg Thr Arg Thr Asp Ser
2435 2440 2445

Tyr Ser Ala Gly Gln Ser Val Glu Ile Leu Asp Gly Val Glu Leu
2450 2455 2460

Gly Glu Pro Ala His Lys Lys Thr Gly Thr Thr Val Pro Glu Ser
2465 2470 2475

Ile His Ser Phe Ile Gly Asp Gly Leu Val Lys Pro Glu Ala Leu
2480 2485 2490

Asn Lys Lys Ala Ile Gln Ile Ile Asn Arg Val Arg Asp Lys Leu
2495 2500 2505

Thr Gly Arg Asp Phe Ser His Asp Asp Thr Leu Asp Val Pro Thr
2510 2515 2520

Gln Val Glu Leu Leu Ile Lys Gln Ala Thr Ser His Glu Asn Leu
2525 2530 2535

Cys Gln Cys Tyr Ile Gly Trp Cys Pro Phe Trp
2540 2545

<210> SEQ ID NO 2
<211> LENGTH: 1210
<212> TYPE: PRT
<213> ORGANISM: Artificial Sequence
<220> FEATURE:
<223> OTHER INFORMATION: Synthetic polypeptide

<400> SEQUENCE: 2

Met Arg Pro Ser Gly Thr Ala Gly Ala Ala Leu Leu Ala Leu Leu Ala
1 5 10 15

Ala Leu Cys Pro Ala Ser Arg Ala Leu Glu Glu Lys Lys Val Cys Gln
20 25 30

Gly Thr Ser Asn Lys Leu Thr Gln Leu Gly Thr Phe Glu Asp His Phe
35 40 45

Leu Ser Leu Gln Arg Met Phe Asn Asn Cys Glu Val Val Leu Gly Asn
50 55 60

Leu Glu Ile Thr Tyr Val Gln Arg Asn Tyr Asp Leu Ser Phe Leu Lys
65 70 75 80

Thr Ile Gln Glu Val Ala Gly Tyr Val Leu Ile Ala Leu Asn Thr Val
85 90 95

Glu Arg Ile Pro Leu Glu Asn Leu Gln Ile Ile Arg Gly Asn Met Tyr
100 105 110

Tyr Glu Asn Ser Tyr Ala Leu Ala Val Leu Ser Asn Tyr Asp Ala Asn
115 120 125

Lys Thr Gly Leu Lys Glu Leu Pro Met Arg Asn Leu Gln Glu Ile Leu
130 135 140

His Gly Ala Val Arg Phe Ser Asn Asn Pro Ala Leu Cys Asn Val Glu
145 150 155 160

Ser Ile Gln Trp Arg Asp Ile Val Ser Ser Asp Phe Leu Ser Asn Met
165 170 175

-continued

```
Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
```

-continued

```
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020
```

-continued

```
Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200

Ser Ser  Glu Phe Ile Gly Ala
    1205                 1210
```

<210> SEQ ID NO 3
<211> LENGTH: 1255
<212> TYPE: PRT
<213> ORGANISM: Artificial Sequence
<220> FEATURE:
<223> OTHER INFORMATION: Synthetic polypeptide

<400> SEQUENCE: 3

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160
```

Leu Cys Tyr Gln Asp Thr Ile Leu Trp Lys Asp Ile Phe His Lys Asn
165 170 175

Asn Gln Leu Ala Leu Thr Leu Ile Asp Thr Asn Arg Ser Arg Ala Cys
180 185 190

His Pro Cys Ser Pro Met Cys Lys Gly Ser Arg Cys Trp Gly Glu Ser
195 200 205

Ser Glu Asp Cys Gln Ser Leu Thr Arg Thr Val Cys Ala Gly Gly Cys
210 215 220

Ala Arg Cys Lys Gly Pro Leu Pro Thr Asp Cys Cys His Glu Gln Cys
225 230 235 240

Ala Ala Gly Cys Thr Gly Pro Lys His Ser Asp Cys Leu Ala Cys Leu
245 250 255

His Phe Asn His Ser Gly Ile Cys Glu Leu His Cys Pro Ala Leu Val
260 265 270

Thr Tyr Asn Thr Asp Thr Phe Glu Ser Met Pro Asn Pro Glu Gly Arg
275 280 285

Tyr Thr Phe Gly Ala Ser Cys Val Thr Ala Cys Pro Tyr Asn Tyr Leu
290 295 300

Ser Thr Asp Val Gly Ser Cys Thr Leu Val Cys Pro Leu His Asn Gln
305 310 315 320

Glu Val Thr Ala Glu Asp Gly Thr Gln Arg Cys Glu Lys Cys Ser Lys
325 330 335

Pro Cys Ala Arg Val Cys Tyr Gly Leu Gly Met Glu His Leu Arg Glu
340 345 350

Val Arg Ala Val Thr Ser Ala Asn Ile Gln Glu Phe Ala Gly Cys Lys
355 360 365

Lys Ile Phe Gly Ser Leu Ala Phe Leu Pro Glu Ser Phe Asp Gly Asp
370 375 380

Pro Ala Ser Asn Thr Ala Pro Leu Gln Pro Glu Gln Leu Gln Val Phe
385 390 395 400

Glu Thr Leu Glu Glu Ile Thr Gly Tyr Leu Tyr Ile Ser Ala Trp Pro
405 410 415

Asp Ser Leu Pro Asp Leu Ser Val Phe Gln Asn Leu Gln Val Ile Arg
420 425 430

Gly Arg Ile Leu His Asn Gly Ala Tyr Ser Leu Thr Leu Gln Gly Leu
435 440 445

Gly Ile Ser Trp Leu Gly Leu Arg Ser Leu Arg Glu Leu Gly Ser Gly
450 455 460

Leu Ala Leu Ile His His Asn Thr His Leu Cys Phe Val His Thr Val
465 470 475 480

Pro Trp Asp Gln Leu Phe Arg Asn Pro His Gln Ala Leu Leu His Thr
485 490 495

Ala Asn Arg Pro Glu Asp Glu Cys Val Gly Glu Gly Leu Ala Cys His
500 505 510

Gln Leu Cys Ala Arg Gly His Cys Trp Gly Pro Gly Pro Thr Gln Cys
515 520 525

Val Asn Cys Ser Gln Phe Leu Arg Gly Gln Glu Cys Val Glu Glu Cys
530 535 540

Arg Val Leu Gln Gly Leu Pro Arg Glu Tyr Val Asn Ala Arg His Cys
545 550 555 560

Leu Pro Cys His Pro Glu Cys Gln Pro Gln Asn Gly Ser Val Thr Cys
565 570 575

```
Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
```

-continued

```
        995                 1000                1005

Leu Glu  Asp Asp Asp Met Gly  Asp Leu Val Asp Ala  Glu Glu Tyr
    1010                 1015                 1020

Leu Val  Pro Gln Gln Gly Phe  Phe Cys Pro Asp Pro  Ala Pro Gly
    1025                 1030                 1035

Ala Gly  Gly Met Val His His  Arg His Arg Ser Ser  Ser Thr Arg
    1040                 1045                 1050

Ser Gly  Gly Gly Asp Leu Thr  Leu Gly Leu Glu Pro  Ser Glu Glu
    1055                 1060                 1065

Glu Ala  Pro Arg Ser Pro Leu  Ala Pro Ser Glu Gly  Ala Gly Ser
    1070                 1075                 1080

Asp Val  Phe Asp Gly Asp Leu  Gly Met Gly Ala Ala  Lys Gly Leu
    1085                 1090                 1095

Gln Ser  Leu Pro Thr His Asp  Pro Ser Pro Leu Gln  Arg Tyr Ser
    1100                 1105                 1110

Glu Asp  Pro Thr Val Pro Leu  Pro Ser Glu Thr Asp  Gly Tyr Val
    1115                 1120                 1125

Ala Pro  Leu Thr Cys Ser Pro  Gln Pro Glu Tyr Val  Asn Gln Pro
    1130                 1135                 1140

Asp Val  Arg Pro Gln Pro Pro  Ser Pro Arg Glu Gly  Pro Leu Pro
    1145                 1150                 1155

Ala Ala  Arg Pro Ala Gly Ala  Thr Leu Glu Arg Pro  Lys Thr Leu
    1160                 1165                 1170

Ser Pro  Gly Lys Asn Gly Val  Val Lys Asp Val Phe  Ala Phe Gly
    1175                 1180                 1185

Gly Ala  Val Glu Asn Pro Glu  Tyr Leu Thr Pro Gln  Gly Gly Ala
    1190                 1195                 1200

Ala Pro  Gln Pro His Pro Pro  Pro Ala Phe Ser Pro  Ala Phe Asp
    1205                 1210                 1215

Asn Leu  Tyr Tyr Trp Asp Gln  Asp Pro Pro Glu Arg  Gly Ala Pro
    1220                 1225                 1230

Pro Ser  Thr Phe Lys Gly Thr  Pro Thr Ala Glu Asn  Pro Glu Tyr
    1235                 1240                 1245

Leu Gly  Leu Asp Val Pro Val
    1250                 1255


<210> SEQ ID NO 4
<211> LENGTH: 2527
<212> TYPE: PRT
<213> ORGANISM: Artificial Sequence
<220> FEATURE:
<223> OTHER INFORMATION: Synthetic polypeptide

<400> SEQUENCE: 4

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu Arg Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
```

-continued 85 90 95

Gln Ser Leu Met Gly Pro Gln Asp Val Gly Asn Asp Trp Glu Val Leu
100 105 110

Gly Val His Gln Leu Ile Leu Lys Met Leu Thr Val His Asn Ala Ser
115 120 125

Val Asn Leu Ser Val Ile Gly Leu Lys Thr Leu Asp Leu Leu Leu Thr
130 135 140

Ser Gly Lys Ile Thr Leu Leu Ile Leu Asp Glu Glu Ser Asp Ile Phe
145 150 155 160

Met Leu Ile Phe Asp Ala Met His Ser Phe Pro Ala Asn Asp Glu Val
165 170 175

Gln Lys Leu Gly Cys Lys Ala Leu His Val Leu Phe Glu Arg Val Ser
180 185 190

Glu Glu Gln Leu Thr Glu Phe Val Glu Asn Lys Asp Tyr Met Ile Leu
195 200 205

Leu Ser Ala Leu Thr Asn Phe Lys Asp Glu Glu Glu Ile Val Leu His
210 215 220

Val Leu His Cys Leu His Ser Leu Ala Ile Pro Cys Asn Asn Val Glu
225 230 235 240

Val Leu Met Ser Gly Asn Val Arg Cys Tyr Asn Ile Val Val Glu Ala
245 250 255

Met Lys Ala Phe Pro Met Ser Glu Arg Ile Gln Glu Val Ser Cys Cys
260 265 270

Leu Leu His Arg Leu Thr Leu Gly Asn Phe Phe Asn Ile Leu Val Leu
275 280 285

Asn Glu Val His Glu Phe Val Val Lys Ala Val Gln Gln Tyr Pro Glu
290 295 300

Asn Ala Ala Leu Gln Ile Ser Ala Leu Ser Cys Leu Ala Leu Leu Thr
305 310 315 320

Glu Thr Ile Phe Leu Asn Gln Asp Leu Glu Glu Lys Asn Glu Asn Gln
325 330 335

Glu Asn Asp Asp Glu Gly Glu Glu Asp Lys Leu Phe Trp Leu Glu Ala
340 345 350

Cys Tyr Lys Ala Leu Thr Trp His Arg Lys Asn Lys His Val Gln Glu
355 360 365

Ala Ala Cys Trp Ala Leu Asn Asn Leu Leu Met Tyr Gln Asn Ser Leu
370 375 380

His Glu Lys Ile Gly Asp Glu Asp Gly His Phe Pro Ala His Arg Glu
385 390 395 400

Val Met Leu Ser Met Leu Met His Ser Ser Ser Lys Glu Val Phe Gln
405 410 415

Ala Ser Ala Asn Ala Leu Ser Thr Leu Leu Glu Gln Asn Val Asn Phe
420 425 430

Arg Lys Ile Leu Leu Ser Lys Gly Ile His Leu Asn Val Leu Glu Leu
435 440 445

Met Gln Lys His Ile His Ser Pro Glu Val Ala Glu Ser Gly Cys Lys
450 455 460

Met Leu Asn His Leu Phe Glu Gly Ser Asn Thr Ser Leu Asp Ile Met
465 470 475 480

Ala Ala Val Val Pro Lys Ile Leu Thr Val Met Lys Arg His Glu Thr
485 490 495

Ser Leu Pro Val Gln Leu Glu Ala Leu Arg Ala Ile Leu His Phe Ile
500 505 510

-continued

Val Pro Gly Met Pro Glu Glu Ser Arg Glu Asp Thr Glu Phe His His
515 520 525

Lys Leu Asn Met Val Lys Lys Gln Cys Phe Lys Asn Asp Ile His Lys
530 535 540

Leu Val Leu Ala Ala Leu Asn Arg Phe Ile Gly Asn Pro Gly Ile Gln
545 550 555 560

Lys Cys Gly Leu Lys Val Ile Ser Ser Ile Val His Phe Pro Asp Ala
565 570 575

Leu Glu Met Leu Ser Leu Glu Gly Ala Met Asp Ser Val Leu His Thr
580 585 590

Leu Gln Met Tyr Pro Asp Asp Gln Glu Ile Gln Cys Leu Gly Leu Ser
595 600 605

Leu Ile Gly Tyr Leu Ile Thr Lys Lys Asn Val Phe Ile Gly Thr Gly
610 615 620

His Leu Leu Ala Lys Ile Leu Val Ser Ser Leu Tyr Arg Phe Lys Asp
625 630 635 640

Val Ala Glu Ile Gln Thr Lys Gly Phe Gln Thr Ile Leu Ala Ile Leu
645 650 655

Lys Leu Ser Ala Ser Phe Ser Lys Leu Leu Val His His Ser Phe Asp
660 665 670

Leu Val Ile Phe His Gln Met Ser Ser Asn Ile Met Glu Gln Lys Asp
675 680 685

Gln Gln Phe Leu Asn Leu Cys Cys Lys Cys Phe Ala Lys Val Ala Met
690 695 700

Asp Asp Tyr Leu Lys Asn Val Met Leu Glu Arg Ala Cys Asp Gln Asn
705 710 715 720

Asn Ser Ile Met Val Glu Cys Leu Leu Leu Leu Gly Ala Asp Ala Asn
725 730 735

Gln Ala Lys Glu Gly Ser Ser Leu Ile Cys Gln Val Cys Glu Lys Glu
740 745 750

Ser Ser Pro Lys Leu Val Glu Leu Leu Leu Asn Ser Gly Ser Arg Glu
755 760 765

Gln Asp Val Arg Lys Ala Leu Thr Ile Ser Ile Gly Lys Gly Asp Ser
770 775 780

Gln Ile Ile Ser Leu Leu Leu Arg Arg Leu Ala Leu Asp Val Ala Asn
785 790 795 800

Asn Ser Ile Cys Leu Gly Gly Phe Cys Ile Gly Lys Val Glu Pro Ser
805 810 815

Trp Leu Gly Pro Leu Phe Pro Asp Lys Thr Ser Asn Leu Arg Lys Gln
820 825 830

Thr Asn Ile Ala Ser Thr Leu Ala Arg Met Val Ile Arg Tyr Gln Met
835 840 845

Lys Ser Ala Val Glu Glu Gly Thr Ala Ser Gly Ser Asp Gly Asn Phe
850 855 860

Ser Glu Asp Val Leu Ser Lys Phe Asp Glu Trp Thr Phe Ile Pro Asp
865 870 875 880

Ser Ser Met Asp Ser Val Phe Ala Gln Ser Asp Asp Leu Asp Ser Glu
885 890 895

Gly Ser Glu Gly Ser Phe Leu Val Lys Lys Lys Ser Asn Ser Ile Ser
900 905 910

Val Gly Glu Phe Tyr Arg Asp Ala Val Leu Gln Arg Cys Ser Pro Asn
915 920 925

-continued

```
Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
        995                 1000                1005

His Leu  Glu His Leu Glu Lys  Leu Glu Leu His Gln  Asn Ala Leu
    1010                1015                1020

Thr Ser  Phe Pro Gln Gln Leu  Cys Glu Thr Leu Lys  Ser Leu Thr
    1025                1030                1035

His Leu  Asp Leu His Ser Asn  Lys Phe Thr Ser Phe  Pro Ser Tyr
    1040                1045                1050

Leu Leu  Lys Met Ser Cys Ile  Ala Asn Leu Asp Val  Ser Arg Asn
    1055                1060                1065

Asp Ile  Gly Pro Ser Val Val  Leu Asp Pro Thr Val  Lys Cys Pro
    1070                1075                1080

Thr Leu  Lys Gln Phe Asn Leu  Ser Tyr Asn Gln Leu  Ser Phe Val
    1085                1090                1095

Pro Glu  Asn Leu Thr Asp Val  Val Glu Lys Leu Glu  Gln Leu Ile
    1100                1105                1110

Leu Glu  Gly Asn Lys Ile Ser  Gly Ile Cys Ser Pro  Leu Arg Leu
    1115                1120                1125

Lys Glu  Leu Lys Ile Leu Asn  Leu Ser Lys Asn His  Ile Ser Ser
    1130                1135                1140

Leu Ser  Glu Asn Phe Leu Glu  Ala Cys Pro Lys Val  Glu Ser Phe
    1145                1150                1155

Ser Ala  Arg Met Asn Phe Leu  Ala Ala Met Pro Phe  Leu Pro Pro
    1160                1165                1170

Ser Met  Thr Ile Leu Lys Leu  Ser Gln Asn Lys Phe  Ser Cys Ile
    1175                1180                1185

Pro Glu  Ala Ile Leu Asn Leu  Pro His Leu Arg Ser  Leu Asp Met
    1190                1195                1200

Ser Ser  Asn Asp Ile Gln Tyr  Leu Pro Gly Pro Ala  His Trp Lys
    1205                1210                1215

Ser Leu  Asn Leu Arg Glu Leu  Leu Phe Ser His Asn  Gln Ile Ser
    1220                1225                1230

Ile Leu  Asp Leu Ser Glu Lys  Ala Tyr Leu Trp Ser  Arg Val Glu
    1235                1240                1245

Lys Leu  His Leu Ser His Asn  Lys Leu Lys Glu Ile  Pro Pro Glu
    1250                1255                1260

Ile Gly  Cys Leu Glu Asn Leu  Thr Ser Leu Asp Val  Ser Tyr Asn
    1265                1270                1275

Leu Glu  Leu Arg Ser Phe Pro  Asn Glu Met Gly Lys  Leu Ser Lys
    1280                1285                1290

Ile Trp  Asp Leu Pro Leu Asp  Glu Leu His Leu Asn  Phe Asp Phe
    1295                1300                1305

Lys His  Ile Gly Cys Lys Ala  Lys Asp Ile Ile Arg  Phe Leu Gln
    1310                1315                1320

Gln Arg  Leu Lys Lys Ala Val  Pro Tyr Asn Arg Met  Lys Leu Met
```

-continued

```
    1325                1330                1335

Ile Val  Gly Asn Thr Gly Ser  Gly Lys Thr Thr Leu  Leu Gln Gln
    1340                1345                1350

Leu Met  Lys Thr Lys Lys Ser  Asp Leu Gly Met Gln  Ser Ala Thr
    1355                1360                1365

Val Gly  Ile Asp Val Lys Asp  Trp Pro Ile Gln Ile  Arg Asp Lys
    1370                1375                1380

Arg Lys  Arg Asp Leu Val Leu  Asn Val Trp Asp Phe  Ala Gly Arg
    1385                1390                1395

Glu Glu  Phe Tyr Ser Thr His  Pro His Phe Met Thr  Gln Arg Ala
    1400                1405                1410

Leu Tyr  Leu Ala Val Tyr Asp  Leu Ser Lys Gly Gln  Ala Glu Val
    1415                1420                1425

Asp Ala  Met Lys Pro Trp Leu  Phe Asn Ile Lys Ala  Arg Ala Ser
    1430                1435                1440

Ser Ser  Pro Val Ile Leu Val  Gly Thr His Leu Asp  Val Ser Asp
    1445                1450                1455

Glu Lys  Gln Arg Lys Ala Cys  Met Ser Lys Ile Thr  Lys Glu Leu
    1460                1465                1470

Leu Asn  Lys Arg Gly Phe Pro  Ala Ile Arg Asp Tyr  His Phe Val
    1475                1480                1485

Asn Ala  Thr Glu Glu Ser Asp  Ala Leu Ala Lys Leu  Arg Lys Thr
    1490                1495                1500

Ile Ile  Asn Glu Ser Leu Asn  Phe Lys Ile Arg Asp  Gln Leu Val
    1505                1510                1515

Val Gly  Gln Leu Ile Pro Asp  Cys Tyr Val Glu Leu  Glu Lys Ile
    1520                1525                1530

Ile Leu  Ser Glu Arg Lys Asn  Val Pro Ile Glu Phe  Pro Val Ile
    1535                1540                1545

Asp Arg  Lys Arg Leu Leu Gln  Leu Val Arg Glu Asn  Gln Leu Gln
    1550                1555                1560

Leu Asp  Glu Asn Glu Leu Pro  His Ala Val His Phe  Leu Asn Glu
    1565                1570                1575

Ser Gly  Val Leu Leu His Phe  Gln Asp Pro Ala Leu  Gln Leu Ser
    1580                1585                1590

Asp Leu  Tyr Phe Val Glu Pro  Lys Trp Leu Cys Lys  Ile Met Ala
    1595                1600                1605

Gln Ile  Leu Thr Val Lys Val  Glu Gly Cys Pro Lys  His Pro Lys
    1610                1615                1620

Gly Ile  Ile Ser Arg Arg Asp  Val Glu Lys Phe Leu  Ser Lys Lys
    1625                1630                1635

Arg Lys  Phe Pro Lys Asn Tyr  Met Ser Gln Tyr Phe  Lys Leu Leu
    1640                1645                1650

Glu Lys  Phe Gln Ile Ala Leu  Pro Ile Gly Glu Glu  Tyr Leu Leu
    1655                1660                1665

Val Pro  Ser Ser Leu Ser Asp  His Arg Pro Val Ile  Glu Leu Pro
    1670                1675                1680

His Cys  Glu Asn Ser Glu Ile  Ile Ile Arg Leu Tyr  Glu Met Pro
    1685                1690                1695

Tyr Phe  Pro Met Gly Phe Trp  Ser Arg Leu Ile Asn  Arg Leu Leu
    1700                1705                1710

Glu Ile  Ser Pro Tyr Met Leu  Ser Gly Arg Glu Arg  Ala Leu Arg
    1715                1720                1725
```

-continued

```
Pro Asn  Arg Met Tyr Trp Arg  Gln Gly Ile Tyr Leu  Asn Trp Ser
    1730                 1735                 1740

Pro Glu  Ala Tyr Cys Leu Val  Gly Ser Glu Val Leu  Asp Asn His
    1745                 1750                 1755

Pro Glu  Ser Phe Leu Lys Ile  Thr Val Pro Ser Cys  Arg Lys Gly
    1760                 1765                 1770

Cys Ile  Leu Leu Gly Gln Val  Val Asp His Ile Asp  Ser Leu Met
    1775                 1780                 1785

Glu Glu  Trp Phe Pro Gly Leu  Leu Glu Ile Asp Ile  Cys Gly Glu
    1790                 1795                 1800

Gly Glu  Thr Leu Leu Lys Lys  Trp Ala Leu Tyr Ser  Phe Asn Asp
    1805                 1810                 1815

Gly Glu  Glu His Gln Lys Ile  Leu Leu Asp Asp Leu  Met Lys Lys
    1820                 1825                 1830

Ala Glu  Glu Gly Asp Leu Leu  Val Asn Pro Asp Gln  Pro Arg Leu
    1835                 1840                 1845

Thr Ile  Pro Ile Ser Gln Ile  Ala Pro Asp Leu Ile  Leu Ala Asp
    1850                 1855                 1860

Leu Pro  Arg Asn Ile Met Leu  Asn Asn Asp Glu Leu  Glu Phe Glu
    1865                 1870                 1875

Gln Ala  Pro Glu Phe Leu Leu  Gly Asp Gly Ser Phe  Gly Ser Val
    1880                 1885                 1890

Tyr Arg  Ala Ala Tyr Glu Gly  Glu Glu Val Ala Val  Lys Ile Phe
    1895                 1900                 1905

Asn Lys  His Thr Ser Leu Arg  Leu Leu Arg Gln Glu  Leu Val Val
    1910                 1915                 1920

Leu Cys  His Leu His His Pro  Ser Leu Ile Ser Leu  Leu Ala Ala
    1925                 1930                 1935

Gly Ile  Arg Pro Arg Met Leu  Val Met Glu Leu Ala  Ser Lys Gly
    1940                 1945                 1950

Ser Leu  Asp Arg Leu Leu Gln  Gln Asp Lys Ala Ser  Leu Thr Arg
    1955                 1960                 1965

Thr Leu  Gln His Arg Ile Ala  Leu His Val Ala Asp  Gly Leu Arg
    1970                 1975                 1980

Tyr Leu  His Ser Ala Met Ile  Ile Tyr Arg Asp Leu  Lys Pro His
    1985                 1990                 1995

Asn Val  Leu Leu Phe Thr Leu  Tyr Pro Asn Ala Ala  Ile Ile Ala
    2000                 2005                 2010

Lys Ile  Ala Asp Tyr Gly Ile  Ala Gln Tyr Cys Cys  Arg Met Gly
    2015                 2020                 2025

Ile Lys  Thr Ser Glu Gly Thr  Pro Gly Phe Arg Ala  Pro Glu Val
    2030                 2035                 2040

Ala Arg  Gly Asn Val Ile Tyr  Asn Gln Gln Ala Asp  Val Tyr Ser
    2045                 2050                 2055

Phe Gly  Leu Leu Leu Tyr Asp  Ile Leu Thr Thr Gly  Gly Arg Ile
    2060                 2065                 2070

Val Glu  Gly Leu Lys Phe Pro  Asn Glu Phe Asp Glu  Leu Glu Ile
    2075                 2080                 2085

Gln Gly  Lys Leu Pro Asp Pro  Val Lys Glu Tyr Gly  Cys Ala Pro
    2090                 2095                 2100

Trp Pro  Met Val Glu Lys Leu  Ile Lys Gln Cys Leu  Lys Glu Asn
    2105                 2110                 2115
```

-continued

```
Pro Gln  Glu Arg Pro Thr Ser  Ala Gln Val Phe Asp  Ile Leu Asn
    2120                 2125                 2130

Ser Ala  Glu Leu Val Cys Leu  Thr Arg Arg Ile Leu  Leu Pro Lys
    2135                 2140                 2145

Asn Val  Ile Val Glu Cys Met  Val Ala Thr His His  Asn Ser Arg
    2150                 2155                 2160

Asn Ala  Ser Ile Trp Leu Gly  Cys Gly His Thr Asp  Arg Gly Gln
    2165                 2170                 2175

Leu Ser  Phe Leu Asp Leu Asn  Thr Glu Gly Tyr Thr  Ser Glu Glu
    2180                 2185                 2190

Val Ala  Asp Ser Arg Ile Leu  Cys Leu Ala Leu Val  His Leu Pro
    2195                 2200                 2205

Val Glu  Lys Glu Ser Trp Ile  Val Ser Gly Thr Gln  Ser Gly Thr
    2210                 2215                 2220

Leu Leu  Val Ile Asn Thr Glu  Asp Gly Lys Lys Arg  His Thr Leu
    2225                 2230                 2235

Glu Lys  Met Thr Asp Ser Val  Thr Cys Leu Tyr Cys  Asn Ser Phe
    2240                 2245                 2250

Ser Lys  Gln Ser Lys Gln Lys  Asn Phe Leu Leu Val  Gly Thr Ala
    2255                 2260                 2265

Asp Gly  Lys Leu Ala Ile Phe  Glu Asp Lys Thr Val  Lys Leu Lys
    2270                 2275                 2280

Gly Ala  Ala Pro Leu Lys Ile  Leu Asn Ile Gly Asn  Val Ser Thr
    2285                 2290                 2295

Pro Leu  Met Cys Leu Ser Glu  Ser Thr Asn Ser Thr  Glu Arg Asn
    2300                 2305                 2310

Val Met  Trp Gly Gly Cys Gly  Thr Lys Ile Phe Ser  Phe Ser Asn
    2315                 2320                 2325

Asp Phe  Thr Ile Gln Lys Leu  Ile Glu Thr Arg Thr  Ser Gln Leu
    2330                 2335                 2340

Phe Ser  Tyr Ala Ala Phe Ser  Asp Ser Asn Ile Ile  Thr Val Val
    2345                 2350                 2355

Val Asp  Thr Ala Leu Tyr Ile  Ala Lys Gln Asn Ser  Pro Val Val
    2360                 2365                 2370

Glu Val  Trp Asp Lys Lys Thr  Glu Lys Leu Cys Gly  Leu Ile Asp
    2375                 2380                 2385

Cys Val  His Phe Leu Arg Glu  Val Met Val Lys Glu  Asn Lys Glu
    2390                 2395                 2400

Ser Lys  His Lys Met Ser Tyr  Ser Gly Arg Val Lys  Thr Leu Cys
    2405                 2410                 2415

Leu Gln  Lys Asn Thr Ala Leu  Trp Ile Gly Thr Gly  Gly Gly His
    2420                 2425                 2430

Ile Leu  Leu Leu Asp Leu Ser  Thr Arg Arg Leu Ile  Arg Val Ile
    2435                 2440                 2445

Tyr Asn  Phe Cys Asn Ser Val  Arg Val Met Met Thr  Ala Gln Leu
    2450                 2455                 2460

Gly Ser  Leu Lys Asn Val Met  Leu Val Leu Gly Tyr  Asn Arg Lys
    2465                 2470                 2475

Asn Thr  Glu Gly Thr Gln Lys  Gln Lys Glu Ile Gln  Ser Cys Leu
    2480                 2485                 2490

Thr Val  Trp Asp Ile Asn Leu  Pro His Glu Val Gln  Asn Leu Glu
    2495                 2500                 2505

Lys His  Ile Glu Val Arg Lys  Glu Leu Ala Glu Lys  Met Arg Arg
```

```
    2510                2515                2520

Thr Ser  Val Glu
    2525


<210> SEQ ID NO 5
<211> LENGTH: 189
<212> TYPE: PRT
<213> ORGANISM: Artificial Sequence
<220> FEATURE:
<223> OTHER INFORMATION: Synthetic polypeptide

<400> SEQUENCE: 5

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 6
<211> LENGTH: 188
<212> TYPE: PRT
<213> ORGANISM: Artificial Sequence
<220> FEATURE:
<223> OTHER INFORMATION: Synthetic polypeptide

<400> SEQUENCE: 6

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95
```

```
Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 7
<211> LENGTH: 2102
<212> TYPE: PRT
<213> ORGANISM: Artificial Sequence
<220> FEATURE:
<223> OTHER INFORMATION: Synthetic polypeptide

<400> SEQUENCE: 7

```
Met Ala Ala Ala Pro Ala Arg Gly Gly Gly Gly Gly Gly Gly Gly Gly
1               5                   10                  15

Gly Gly Cys Ser Gly Ser Gly Ser Ser Ala Ser Arg Gly Phe Tyr Phe
            20                  25                  30

Asn Thr Val Leu Ser Leu Ala Arg Ser Leu Ala Val Gln Arg Pro Ala
        35                  40                  45

Ser Leu Glu Lys Val Gln Lys Leu Leu Cys Met Cys Pro Val Asp Phe
    50                  55                  60

His Gly Ile Phe Gln Leu Asp Glu Arg Arg Arg Asp Ala Val Ile Ala
65                  70                  75                  80

Leu Gly Ile Phe Leu Ile Glu Ser Asp Leu Gln His Lys Asp Cys Val
                85                  90                  95

Val Pro Tyr Leu Leu Arg Leu Leu Lys Gly Leu Pro Lys Val Tyr Trp
            100                 105                 110

Val Glu Glu Ser Thr Ala Arg Lys Gly Arg Gly Ala Leu Pro Val Ala
        115                 120                 125

Glu Ser Phe Ser Phe Cys Leu Val Thr Leu Leu Ser Asp Val Ala Tyr
    130                 135                 140

Arg Asp Pro Ser Leu Arg Asp Glu Ile Leu Glu Val Leu Leu Gln Val
145                 150                 155                 160

Leu His Val Leu Leu Gly Met Cys Gln Ala Leu Glu Ile Gln Asp Lys
                165                 170                 175

Glu Tyr Leu Cys Lys Tyr Ala Ile Pro Cys Leu Ile Gly Ile Ser Arg
            180                 185                 190

Ala Phe Gly Arg Tyr Ser Asn Met Glu Glu Ser Leu Leu Ser Lys Leu
        195                 200                 205

Phe Pro Lys Ile Pro Pro His Ser Leu Arg Val Leu Glu Glu Leu Glu
    210                 215                 220

Gly Val Arg Arg Arg Ser Phe Asn Asp Phe Arg Ser Ile Leu Pro Ser
225                 230                 235                 240

Asn Leu Leu Thr Val Cys Gln Glu Gly Thr Leu Lys Arg Lys Thr Ser
                245                 250                 255

Ser Val Ser Ser Ile Ser Gln Val Ser Pro Glu Arg Gly Met Pro Pro
            260                 265                 270
```

-continued

```
Pro Ser Ser Pro Gly Gly Ser Ala Phe His Tyr Phe Glu Ala Ser Cys
        275                 280                 285

Leu Pro Asp Gly Thr Ala Leu Glu Pro Glu Tyr Tyr Phe Ser Thr Ile
    290                 295                 300

Ser Ser Ser Phe Ser Val Ser Pro Leu Phe Asn Gly Val Thr Tyr Lys
305                 310                 315                 320

Glu Phe Asn Ile Pro Leu Glu Met Leu Arg Glu Leu Leu Asn Leu Val
                325                 330                 335

Lys Lys Ile Val Glu Glu Ala Val Leu Lys Ser Leu Asp Ala Ile Val
            340                 345                 350

Ala Ser Val Met Glu Ala Asn Pro Ser Ala Asp Leu Tyr Tyr Thr Ser
        355                 360                 365

Phe Ser Asp Pro Leu Tyr Leu Thr Met Phe Lys Met Leu Arg Asp Thr
    370                 375                 380

Leu Tyr Tyr Met Lys Asp Leu Pro Thr Ser Phe Val Lys Glu Ile His
385                 390                 395                 400

Asp Phe Val Leu Glu Gln Phe Asn Thr Ser Gln Gly Glu Leu Gln Lys
                405                 410                 415

Ile Leu His Asp Ala Asp Arg Ile His Asn Glu Leu Ser Pro Leu Lys
            420                 425                 430

Leu Arg Cys Gln Ala Asn Ala Ala Cys Val Asp Leu Met Val Trp Ala
        435                 440                 445

Val Lys Asp Glu Gln Gly Ala Glu Asn Leu Cys Ile Lys Leu Ser Glu
    450                 455                 460

Lys Leu Gln Ser Lys Thr Ser Ser Lys Val Ile Ile Ala His Leu Pro
465                 470                 475                 480

Leu Leu Ile Cys Cys Leu Gln Gly Leu Gly Arg Leu Cys Glu Arg Phe
                485                 490                 495

Pro Val Val Val His Ser Val Thr Pro Ser Leu Arg Asp Phe Leu Val
            500                 505                 510

Ile Pro Ser Pro Val Leu Val Lys Leu Tyr Lys Tyr His Ser Gln Tyr
        515                 520                 525

His Thr Val Ala Gly Asn Asp Ile Lys Ile Ser Val Thr Asn Glu His
    530                 535                 540

Ser Glu Ser Thr Leu Asn Val Met Ser Gly Lys Lys Ser Gln Pro Ser
545                 550                 555                 560

Met Tyr Glu Gln Leu Arg Asp Ile Ala Ile Asp Asn Ile Cys Arg Cys
                565                 570                 575

Leu Lys Ala Gly Leu Thr Val Asp Pro Val Ile Val Glu Ala Phe Leu
            580                 585                 590

Ala Ser Leu Ser Asn Arg Leu Tyr Ile Ser Gln Glu Ser Asp Lys Asp
        595                 600                 605

Ala His Leu Ile Pro Asp His Thr Ile Arg Ala Leu Gly His Ile Ala
    610                 615                 620

Val Ala Leu Arg Asp Thr Pro Lys Val Met Glu Pro Ile Leu Gln Ile
625                 630                 635                 640

Leu Gln Gln Lys Phe Cys Gln Pro Pro Ser Pro Leu Asp Val Leu Ile
                645                 650                 655

Ile Asp Gln Leu Gly Cys Leu Val Ile Thr Gly Asn Gln Tyr Ile Tyr
            660                 665                 670

Gln Glu Val Trp Asn Leu Phe Gln Gln Ile Ser Val Lys Ala Ser Ser
        675                 680                 685

Val Val Tyr Ser Ala Thr Lys Asp Tyr Lys Asp His Gly Tyr Arg His
```

```
    690                 695                 700

Cys Ser Leu Ala Val Ile Asn Ala Leu Ala Asn Ile Ala Ala Asn Ile
705                 710                 715                 720

Gln Asp Glu His Leu Val Asp Glu Leu Leu Met Asn Leu Leu Glu Leu
                725                 730                 735

Phe Val Gln Leu Gly Leu Glu Gly Lys Arg Ala Ser Glu Arg Ala Ser
            740                 745                 750

Glu Lys Gly Pro Ala Leu Lys Ala Ser Ser Ser Ala Gly Asn Leu Gly
        755                 760                 765

Val Leu Ile Pro Val Ile Ala Val Leu Thr Arg Arg Leu Pro Pro Ile
    770                 775                 780

Lys Glu Ala Lys Pro Arg Leu Gln Lys Leu Phe Arg Asp Phe Trp Leu
785                 790                 795                 800

Tyr Ser Val Leu Met Gly Phe Ala Val Glu Gly Ser Gly Leu Trp Pro
                805                 810                 815

Glu Glu Trp Tyr Glu Gly Val Cys Glu Ile Ala Thr Lys Ser Pro Leu
            820                 825                 830

Leu Thr Phe Pro Ser Lys Glu Pro Leu Arg Ser Val Leu Gln Tyr Asn
        835                 840                 845

Ser Ala Met Lys Asn Asp Thr Val Thr Pro Ala Glu Leu Ser Glu Leu
    850                 855                 860

Arg Ser Thr Ile Ile Asn Leu Leu Asp Pro Pro Pro Glu Val Ser Ala
865                 870                 875                 880

Leu Ile Asn Lys Leu Asp Phe Ala Met Ser Thr Tyr Leu Leu Ser Val
                885                 890                 895

Tyr Arg Leu Glu Tyr Met Arg Val Leu Arg Ser Thr Asp Pro Asp Arg
            900                 905                 910

Phe Gln Val Met Phe Cys Tyr Phe Glu Asp Lys Ala Ile Gln Lys Asp
        915                 920                 925

Lys Ser Gly Met Met Gln Cys Val Ile Ala Val Ala Asp Lys Val Phe
    930                 935                 940

Asp Ala Phe Leu Asn Met Met Ala Asp Lys Ala Lys Thr Lys Glu Asn
945                 950                 955                 960

Glu Glu Glu Leu Glu Arg His Ala Gln Phe Leu Leu Val Asn Phe Asn
                965                 970                 975

His Ile His Lys Arg Ile Arg Arg Val Ala Asp Lys Tyr Leu Ser Gly
            980                 985                 990

Leu Val Asp Lys Phe Pro His Leu  Leu Trp Ser Gly Thr  Val Leu Lys
        995                 1000                1005

Thr Met  Leu Asp Ile Leu Gln  Thr Leu Ser Leu Ser  Leu Ser Ala
    1010                1015                1020

Asp Ile  His Lys Asp Gln Pro  Tyr Tyr Asp Ile Pro  Asp Ala Pro
    1025                1030                1035

Tyr Arg  Ile Thr Val Pro Asp  Thr Tyr Glu Ala Arg  Glu Ser Ile
    1040                1045                1050

Val Lys  Asp Phe Ala Ala Arg  Cys Gly Met Ile Leu  Gln Glu Ala
    1055                1060                1065

Met Lys  Trp Ala Pro Thr Val  Thr Lys Ser His Leu  Gln Glu Tyr
    1070                1075                1080

Leu Asn  Lys His Gln Asn Trp  Val Ser Gly Leu Ser  Gln His Thr
    1085                1090                1095

Gly Leu  Ala Met Ala Thr Glu  Ser Ile Leu His Phe  Ala Gly Tyr
    1100                1105                1110
```

-continued

```
Asn Lys Gln Asn Thr Thr Leu Gly Ala Thr Gln Leu Ser Glu Arg
    1115                1120                1125

Pro Ala Cys Val Lys Lys Asp Tyr Ser Asn Phe Met Ala Ser Leu
    1130                1135                1140

Asn Leu Arg Asn Arg Tyr Ala Gly Glu Val Tyr Gly Met Ile Arg
    1145                1150                1155

Phe Ser Gly Thr Thr Gly Gln Met Ser Asp Leu Asn Lys Met Met
    1160                1165                1170

Val Gln Asp Leu His Ser Ala Leu Asp Arg Ser His Pro Gln His
    1175                1180                1185

Tyr Thr Gln Ala Met Phe Lys Leu Thr Ala Met Leu Ile Ser Ser
    1190                1195                1200

Lys Asp Cys Asp Pro Gln Leu Leu His His Leu Cys Trp Gly Pro
    1205                1210                1215

Leu Arg Met Phe Asn Glu His Gly Met Glu Thr Ala Leu Ala Cys
    1220                1225                1230

Trp Glu Trp Leu Leu Ala Gly Lys Asp Gly Val Glu Val Pro Phe
    1235                1240                1245

Met Arg Glu Met Ala Gly Ala Trp His Met Thr Val Glu Gln Lys
    1250                1255                1260

Phe Gly Leu Phe Ser Ala Glu Ile Lys Glu Ala Asp Pro Leu Ala
    1265                1270                1275

Ala Ser Glu Ala Ser Gln Pro Lys Pro Cys Pro Pro Glu Val Thr
    1280                1285                1290

Pro His Tyr Ile Trp Ile Asp Phe Leu Val Gln Arg Phe Glu Ile
    1295                1300                1305

Ala Lys Tyr Cys Ser Ser Asp Gln Val Glu Ile Phe Ser Ser Leu
    1310                1315                1320

Leu Gln Arg Ser Met Ser Leu Asn Ile Gly Gly Ala Lys Gly Ser
    1325                1330                1335

Met Asn Arg His Val Ala Ala Ile Gly Pro Arg Phe Lys Leu Leu
    1340                1345                1350

Thr Leu Gly Leu Ser Leu Leu His Ala Asp Val Val Pro Asn Ala
    1355                1360                1365

Thr Ile Arg Asn Val Leu Arg Glu Lys Ile Tyr Ser Thr Ala Phe
    1370                1375                1380

Asp Tyr Phe Ser Cys Pro Pro Lys Phe Pro Thr Gln Gly Glu Lys
    1385                1390                1395

Arg Leu Arg Glu Asp Ile Ser Ile Met Ile Lys Phe Trp Thr Ala
    1400                1405                1410

Met Phe Ser Asp Lys Lys Tyr Leu Thr Ala Ser Gln Leu Val Pro
    1415                1420                1425

Pro Asp Asn Gln Asp Thr Arg Ser Asn Leu Asp Ile Thr Val Gly
    1430                1435                1440

Ser Arg Gln Gln Ala Thr Gln Gly Trp Ile Asn Thr Tyr Pro Leu
    1445                1450                1455

Ser Ser Gly Met Ser Thr Ile Ser Lys Lys Ser Gly Met Ser Lys
    1460                1465                1470

Lys Thr Asn Arg Gly Ser Gln Leu His Lys Tyr Tyr Met Lys Arg
    1475                1480                1485

Arg Thr Leu Leu Leu Ser Leu Leu Ala Thr Glu Ile Glu Arg Leu
    1490                1495                1500
```

-continued

Ile Thr Trp Tyr Asn Pro Leu Ser Ala Pro Glu Leu Glu Leu Asp
1505 1510 1515

Gln Ala Gly Glu Asn Ser Val Ala Asn Trp Arg Ser Lys Tyr Ile
1520 1525 1530

Ser Leu Ser Glu Lys Gln Trp Lys Asp Asn Val Asn Leu Ala Trp
1535 1540 1545

Ser Ile Ser Pro Tyr Leu Ala Val Gln Leu Pro Ala Arg Phe Lys
1550 1555 1560

Asn Thr Glu Ala Ile Gly Asn Glu Val Thr Arg Leu Val Arg Leu
1565 1570 1575

Asp Pro Gly Ala Val Ser Asp Val Pro Glu Ala Ile Lys Phe Leu
1580 1585 1590

Val Thr Trp His Thr Ile Asp Ala Asp Ala Pro Glu Leu Ser His
1595 1600 1605

Val Leu Cys Trp Ala Pro Thr Asp Pro Pro Thr Gly Leu Ser Tyr
1610 1615 1620

Phe Ser Ser Met Tyr Pro Pro His Pro Leu Thr Ala Gln Tyr Gly
1625 1630 1635

Val Lys Val Leu Arg Ser Phe Pro Pro Asp Ala Ile Leu Phe Tyr
1640 1645 1650

Ile Pro Gln Ile Val Gln Ala Leu Arg Tyr Asp Lys Met Gly Tyr
1655 1660 1665

Val Arg Glu Tyr Ile Leu Trp Ala Ala Ser Lys Ser Gln Leu Leu
1670 1675 1680

Ala His Gln Phe Ile Trp Asn Met Lys Thr Asn Ile Tyr Leu Asp
1685 1690 1695

Glu Glu Gly His Gln Lys Asp Pro Asp Ile Gly Asp Leu Leu Asp
1700 1705 1710

Gln Leu Val Glu Glu Ile Thr Gly Ser Leu Ser Gly Pro Ala Lys
1715 1720 1725

Asp Phe Tyr Gln Arg Glu Phe Asp Phe Phe Asn Lys Ile Thr Asn
1730 1735 1740

Val Ser Ala Ile Ile Lys Pro Tyr Pro Lys Gly Asp Glu Arg Lys
1745 1750 1755

Lys Ala Cys Leu Ser Ala Leu Ser Glu Val Lys Val Gln Pro Gly
1760 1765 1770

Cys Tyr Leu Pro Ser Asn Pro Glu Ala Ile Val Leu Asp Ile Asp
1775 1780 1785

Tyr Lys Ser Gly Thr Pro Met Gln Ser Ala Ala Lys Ala Pro Tyr
1790 1795 1800

Leu Ala Lys Phe Lys Val Lys Arg Cys Gly Val Ser Glu Leu Glu
1805 1810 1815

Lys Glu Gly Leu Arg Cys Arg Ser Asp Ser Glu Asp Glu Cys Ser
1820 1825 1830

Thr Gln Glu Ala Asp Gly Gln Lys Ile Ser Trp Gln Ala Ala Ile
1835 1840 1845

Phe Lys Val Gly Asp Asp Cys Arg Gln Asp Met Leu Ala Leu Gln
1850 1855 1860

Ile Ile Asp Leu Phe Lys Asn Ile Phe Gln Leu Val Gly Leu Asp
1865 1870 1875

Leu Phe Val Phe Pro Tyr Arg Val Val Ala Thr Ala Pro Gly Cys
1880 1885 1890

Gly Val Ile Glu Cys Ile Pro Asp Cys Thr Ser Arg Asp Gln Leu

```
    1895                1900                1905

Gly Arg  Gln Thr Asp Phe Gly  Met Tyr Asp Tyr Phe  Thr Arg Gln
    1910                1915                1920

Tyr Gly  Asp Glu Ser Thr Leu  Ala Phe Gln Gln Ala  Arg Tyr Asn
    1925                1930                1935

Phe Ile  Arg Ser Met Ala Ala  Tyr Ser Leu Leu Leu  Phe Leu Leu
    1940                1945                1950

Gln Ile  Lys Asp Arg His Asn  Gly Asn Ile Met Leu  Asp Lys Lys
    1955                1960                1965

Gly His  Ile Ile His Ile Asp  Phe Gly Phe Met Phe  Glu Ser Ser
    1970                1975                1980

Pro Gly  Gly Asn Leu Gly Trp  Glu Pro Asp Ile Lys  Leu Thr Asp
    1985                1990                1995

Glu Met  Val Met Ile Met Gly  Gly Lys Met Glu Ala  Thr Pro Phe
    2000                2005                2010

Lys Trp  Phe Met Glu Met Cys  Val Arg Gly Tyr Leu  Ala Val Arg
    2015                2020                2025

Pro Tyr  Met Asp Ala Val Val  Ser Leu Val Thr Leu  Met Leu Asp
    2030                2035                2040

Thr Gly  Leu Pro Cys Phe Arg  Gly Gln Thr Ile Lys  Leu Leu Lys
    2045                2050                2055

His Arg  Phe Ser Pro Asn Met  Thr Glu Arg Glu Ala  Ala Asn Phe
    2060                2065                2070

Ile Met  Lys Val Ile Gln Ser  Cys Phe Leu Ser Asn  Arg Ser Arg
    2075                2080                2085

Thr Tyr  Asp Met Ile Gln Tyr  Tyr Gln Asn Asp Ile  Pro Tyr
    2090                2095                2100


<210> SEQ ID NO 8
<211> LENGTH: 562
<212> TYPE: PRT
<213> ORGANISM: Artificial Sequence
<220> FEATURE:
<223> OTHER INFORMATION: Synthetic polypeptide

<400> SEQUENCE: 8

Met Ala Ser Ala Ser Ser Gly Pro Ser Ser Ser Val Gly Phe Ser Ser
1               5                   10                  15

Phe Asp Pro Ala Val Pro Ser Cys Thr Leu Ser Ser Ala Ala Ser Gly
            20                  25                  30

Ile Lys Arg Pro Met Ala Ser Glu Val Leu Glu Ala Arg Gln Asp Ser
        35                  40                  45

Tyr Ile Ser Leu Val Pro Tyr Ala Ser Gly Met Pro Ile Lys Lys Ile
    50                  55                  60

Gly His Arg Ser Val Asp Ser Ser Gly Glu Thr Thr Tyr Lys Lys Thr
65                  70                  75                  80

Thr Ser Ser Ala Leu Lys Gly Ala Ile Gln Leu Gly Ile Thr His Thr
                85                  90                  95

Val Gly Ser Leu Ser Thr Lys Pro Glu Arg Asp Val Leu Met Gln Asp
            100                 105                 110

Phe Tyr Val Val Glu Ser Ile Phe Phe Pro Ser Glu Gly Ser Asn Leu
        115                 120                 125

Thr Pro Ala His His Tyr Asn Asp Phe Arg Phe Lys Thr Tyr Ala Pro
    130                 135                 140

Val Ala Phe Arg Tyr Phe Arg Glu Leu Phe Gly Ile Arg Pro Asp Asp
```

-continued

```
145                 150                 155                 160

Tyr Leu Tyr Ser Leu Cys Ser Glu Pro Leu Ile Glu Leu Cys Ser Ser
                165                 170                 175

Gly Ala Ser Gly Ser Leu Phe Tyr Val Ser Ser Asp Asp Glu Phe Ile
            180                 185                 190

Ile Lys Thr Val Gln His Lys Glu Ala Glu Phe Leu Gln Lys Leu Leu
        195                 200                 205

Pro Gly Tyr Tyr Met Asn Leu Asn Gln Asn Pro Arg Thr Leu Leu Pro
    210                 215                 220

Lys Phe Tyr Gly Leu Tyr Cys Val Gln Ala Gly Gly Lys Asn Ile Arg
225                 230                 235                 240

Ile Val Val Met Asn Asn Leu Leu Pro Arg Ser Val Lys Met His Ile
                245                 250                 255

Lys Tyr Asp Leu Lys Gly Ser Thr Tyr Lys Arg Arg Ala Ser Gln Lys
            260                 265                 270

Glu Arg Glu Lys Pro Leu Pro Thr Phe Lys Asp Leu Asp Phe Leu Gln
        275                 280                 285

Asp Ile Pro Asp Gly Leu Phe Leu Asp Ala Asp Met Tyr Asn Ala Leu
    290                 295                 300

Cys Lys Thr Leu Gln Arg Asp Cys Leu Val Leu Gln Ser Phe Lys Ile
305                 310                 315                 320

Met Asp Tyr Ser Leu Leu Met Ser Ile His Asn Ile Asp His Ala Gln
                325                 330                 335

Arg Glu Pro Leu Ser Ser Glu Thr Gln Tyr Ser Val Asp Thr Arg Arg
            340                 345                 350

Pro Ala Pro Gln Lys Ala Leu Tyr Ser Thr Ala Met Glu Ser Ile Gln
        355                 360                 365

Gly Glu Ala Arg Arg Gly Gly Thr Met Glu Thr Asp Asp His Met Gly
    370                 375                 380

Gly Ile Pro Ala Arg Asn Ser Lys Gly Glu Arg Leu Leu Leu Tyr Ile
385                 390                 395                 400

Gly Ile Ile Asp Ile Leu Gln Ser Tyr Arg Phe Val Lys Lys Leu Glu
                405                 410                 415

His Ser Trp Lys Ala Leu Val His Asp Gly Asp Thr Val Ser Val His
            420                 425                 430

Arg Pro Gly Phe Tyr Ala Glu Arg Phe Gln Arg Phe Met Cys Asn Thr
        435                 440                 445

Val Phe Lys Lys Ile Pro Leu Lys Pro Ser Pro Ser Lys Lys Phe Arg
    450                 455                 460

Ser Gly Ser Ser Phe Ser Arg Arg Ala Gly Ser Ser Gly Asn Ser Cys
465                 470                 475                 480

Ile Thr Tyr Gln Pro Ser Val Ser Gly Glu His Lys Ala Gln Val Thr
                485                 490                 495

Thr Lys Ala Glu Val Glu Pro Gly Val His Leu Gly Arg Pro Asp Val
            500                 505                 510

Leu Pro Gln Thr Pro Pro Leu Glu Glu Ile Ser Glu Gly Ser Pro Ile
        515                 520                 525

Pro Asp Pro Ser Phe Ser Pro Leu Val Gly Glu Thr Leu Gln Met Leu
    530                 535                 540

Thr Thr Ser Thr Thr Leu Glu Lys Leu Glu Val Ala Glu Ser Glu Phe
545                 550                 555                 560

Thr His
```

<210> SEQ ID NO 9
<211> LENGTH: 594
<212> TYPE: PRT
<213> ORGANISM: Artificial Sequence
<220> FEATURE:
<223> OTHER INFORMATION: Synthetic polypeptide

<400> SEQUENCE: 9

```
Met Gly Lys Lys Ser Arg Val Lys Thr Gln Lys Ser Gly Thr Gly Ala
1               5                   10                  15

Thr Ala Thr Val Ser Pro Lys Glu Ile Leu Asn Leu Thr Ser Glu Leu
            20                  25                  30

Leu Gln Lys Cys Ser Ser Pro Ala Pro Gly Pro Gly Lys Glu Trp Glu
        35                  40                  45

Glu Tyr Val Gln Ile Arg Thr Leu Val Glu Lys Ile Arg Lys Lys Gln
    50                  55                  60

Lys Gly Leu Ser Val Thr Phe Asp Gly Lys Arg Glu Asp Tyr Phe Pro
65                  70                  75                  80

Asp Leu Met Lys Trp Ala Ser Glu Asn Gly Ala Ser Val Glu Gly Phe
                85                  90                  95

Glu Met Val Asn Phe Lys Glu Glu Gly Phe Gly Leu Arg Ala Thr Arg
            100                 105                 110

Asp Ile Lys Ala Glu Glu Leu Phe Leu Trp Val Pro Arg Lys Leu Leu
        115                 120                 125

Met Thr Val Glu Ser Ala Lys Asn Ser Val Leu Gly Pro Leu Tyr Ser
    130                 135                 140

Gln Asp Arg Ile Leu Gln Ala Met Gly Asn Ile Ala Leu Ala Phe His
145                 150                 155                 160

Leu Leu Cys Glu Arg Ala Ser Pro Asn Ser Phe Trp Gln Pro Tyr Ile
                165                 170                 175

Gln Thr Leu Pro Ser Glu Tyr Asp Thr Pro Leu Tyr Phe Glu Glu Asp
            180                 185                 190

Glu Val Arg Tyr Leu Gln Ser Thr Gln Ala Ile His Asp Val Phe Ser
        195                 200                 205

Gln Tyr Lys Asn Thr Ala Arg Gln Tyr Ala Tyr Phe Tyr Lys Val Ile
    210                 215                 220

Gln Thr His Pro His Ala Asn Lys Leu Pro Leu Lys Asp Ser Phe Thr
225                 230                 235                 240

Tyr Glu Asp Tyr Arg Trp Ala Val Ser Ser Val Met Thr Arg Gln Asn
                245                 250                 255

Gln Ile Pro Thr Glu Asp Gly Ser Arg Val Thr Leu Ala Leu Ile Pro
            260                 265                 270

Leu Trp Asp Met Cys Asn His Thr Asn Gly Leu Ile Thr Thr Gly Tyr
        275                 280                 285

Asn Leu Glu Asp Asp Arg Cys Glu Cys Val Ala Leu Gln Asp Phe Arg
    290                 295                 300

Ala Gly Glu Gln Ile Tyr Ile Phe Tyr Gly Thr Arg Ser Asn Ala Glu
305                 310                 315                 320

Phe Val Ile His Ser Gly Phe Phe Phe Asp Asn Asn Ser His Asp Arg
                325                 330                 335

Val Lys Ile Lys Leu Gly Val Ser Lys Ser Asp Arg Leu Tyr Ala Met
            340                 345                 350

Lys Ala Glu Val Leu Ala Arg Ala Gly Ile Pro Thr Ser Ser Val Phe
        355                 360                 365
```

Ala Leu His Phe Thr Glu Pro Pro Ile Ser Ala Gln Leu Leu Ala Phe
370 375 380

Leu Arg Val Phe Cys Met Thr Glu Glu Glu Leu Lys Glu His Leu Leu
385 390 395 400

Gly Asp Ser Ala Ile Asp Arg Ile Phe Thr Leu Gly Asn Ser Glu Phe
405 410 415

Pro Val Ser Trp Asp Asn Glu Val Lys Leu Trp Thr Phe Leu Glu Asp
420 425 430

Arg Ala Ser Leu Leu Leu Lys Thr Tyr Lys Thr Thr Ile Glu Glu Asp
435 440 445

Lys Ser Val Leu Lys Asn His Asp Leu Ser Val Arg Ala Lys Met Ala
450 455 460

Ile Lys Leu Arg Leu Gly Glu Lys Glu Ile Leu Glu Lys Ala Val Lys
465 470 475 480

Ser Ala Ala Val Asn Arg Glu Tyr Tyr Arg Gln Gln Met Glu Glu Lys
485 490 495

Ala Pro Leu Pro Lys Tyr Glu Glu Ser Asn Leu Gly Leu Leu Glu Ser
500 505 510

Ser Val Gly Asp Ser Arg Leu Pro Leu Val Leu Arg Asn Leu Glu Glu
515 520 525

Glu Ala Gly Val Gln Asp Ala Leu Asn Ile Arg Glu Ala Ile Ser Lys
530 535 540

Ala Lys Ala Thr Glu Asn Gly Leu Val Asn Gly Glu Asn Ser Ile Pro
545 550 555 560

Asn Gly Thr Arg Ser Glu Asn Glu Ser Leu Asn Gln Glu Ser Lys Arg
565 570 575

Ala Val Glu Asp Ala Lys Gly Ser Ser Ser Asp Ser Thr Ala Gly Val
580 585 590

Lys Glu

<210> SEQ ID NO 10
<211> LENGTH: 3859
<212> TYPE: PRT
<213> ORGANISM: Artificial Sequence
<220> FEATURE:
<223> OTHER INFORMATION: Synthetic polypeptide

<400> SEQUENCE: 10

Met Ala Phe Val Ala Thr Gln Gly Ala Thr Val Val Asp Gln Thr Thr
1 5 10 15

Leu Met Lys Lys Tyr Leu Gln Phe Val Ala Ala Leu Thr Asp Val Asn
20 25 30

Thr Pro Asp Glu Thr Lys Leu Lys Met Met Gln Glu Val Ser Glu Asn
35 40 45

Phe Glu Asn Val Thr Ser Ser Pro Gln Tyr Ser Thr Phe Leu Glu His
50 55 60

Ile Ile Pro Arg Phe Leu Thr Phe Leu Gln Asp Gly Glu Val Gln Phe
65 70 75 80

Leu Gln Glu Lys Pro Ala Gln Gln Leu Arg Lys Leu Val Leu Glu Ile
85 90 95

Ile His Arg Ile Pro Thr Asn Glu His Leu Arg Pro His Thr Lys Asn
100 105 110

Val Leu Ser Val Met Phe Arg Phe Leu Glu Thr Glu Asn Glu Glu Asn
115 120 125

Val Leu Ile Cys Leu Arg Ile Ile Ile Glu Leu His Lys Gln Phe Arg

-continued

```
    130                 135                 140

Pro Pro Ile Thr Gln Glu Ile His His Phe Leu Asp Phe Val Lys Gln
145                 150                 155                 160

Ile Tyr Lys Glu Leu Pro Lys Val Val Asn Arg Tyr Phe Glu Asn Pro
                165                 170                 175

Gln Val Ile Pro Glu Asn Thr Val Pro Pro Pro Glu Met Val Gly Met
            180                 185                 190

Ile Thr Thr Ile Ala Val Lys Val Asn Pro Glu Arg Glu Asp Ser Glu
        195                 200                 205

Thr Arg Thr His Ser Ile Ile Pro Arg Gly Ser Leu Ser Leu Lys Val
    210                 215                 220

Leu Ala Glu Leu Pro Ile Ile Val Val Leu Met Tyr Gln Leu Tyr Lys
225                 230                 235                 240

Leu Asn Ile His Asn Val Val Ala Glu Phe Val Pro Leu Ile Met Asn
                245                 250                 255

Thr Ile Ala Ile Gln Val Ser Ala Gln Ala Arg Gln His Lys Leu Tyr
            260                 265                 270

Asn Lys Glu Leu Tyr Ala Asp Phe Ile Ala Ala Gln Ile Lys Thr Leu
        275                 280                 285

Ser Phe Leu Ala Tyr Ile Ile Arg Ile Tyr Gln Glu Leu Val Thr Lys
    290                 295                 300

Tyr Ser Gln Gln Met Val Lys Gly Met Leu Gln Leu Leu Ser Asn Cys
305                 310                 315                 320

Pro Ala Glu Thr Ala His Leu Arg Lys Glu Leu Leu Ile Ala Ala Lys
                325                 330                 335

His Ile Leu Thr Thr Glu Leu Arg Asn Gln Phe Ile Pro Cys Met Asp
            340                 345                 350

Lys Leu Phe Asp Glu Ser Ile Leu Ile Gly Ser Gly Tyr Thr Ala Arg
        355                 360                 365

Glu Thr Leu Arg Pro Leu Ala Tyr Ser Thr Leu Ala Asp Leu Val His
    370                 375                 380

His Val Arg Gln His Leu Pro Leu Ser Asp Leu Ser Leu Ala Val Gln
385                 390                 395                 400

Leu Phe Ala Lys Asn Ile Asp Asp Glu Ser Leu Pro Ser Ser Ile Gln
                405                 410                 415

Thr Met Ser Cys Lys Leu Leu Leu Asn Leu Val Asp Cys Ile Arg Ser
            420                 425                 430

Lys Ser Glu Gln Glu Ser Gly Asn Gly Arg Asp Val Leu Met Arg Met
        435                 440                 445

Leu Glu Val Phe Val Leu Lys Phe His Thr Ile Ala Arg Tyr Gln Leu
    450                 455                 460

Ser Ala Ile Phe Lys Lys Cys Lys Pro Gln Ser Glu Leu Gly Ala Val
465                 470                 475                 480

Glu Ala Ala Leu Pro Gly Val Pro Thr Ala Pro Ala Ala Pro Gly Pro
                485                 490                 495

Ala Pro Ser Pro Ala Pro Val Pro Ala Pro Pro Pro Pro Pro Pro Pro
            500                 505                 510

Pro Pro Pro Ala Thr Pro Val Thr Pro Ala Pro Val Pro Pro Phe Glu
        515                 520                 525

Lys Gln Gly Glu Lys Asp Lys Glu Asp Lys Gln Thr Phe Gln Val Thr
    530                 535                 540

Asp Cys Arg Ser Leu Val Lys Thr Leu Val Cys Gly Val Lys Thr Ile
545                 550                 555                 560
```

-continued

Thr Trp Gly Ile Thr Ser Cys Lys Ala Pro Gly Glu Ala Gln Phe Ile
565 570 575

Pro Asn Lys Gln Leu Gln Pro Lys Glu Thr Gln Ile Tyr Ile Lys Leu
580 585 590

Val Lys Tyr Ala Met Gln Ala Leu Asp Ile Tyr Gln Val Gln Ile Ala
595 600 605

Gly Asn Gly Gln Thr Tyr Ile Arg Val Ala Asn Cys Gln Thr Val Arg
610 615 620

Met Lys Glu Glu Lys Glu Val Leu Glu His Phe Ala Gly Val Phe Thr
625 630 635 640

Met Met Asn Pro Leu Thr Phe Lys Glu Ile Phe Gln Thr Thr Val Pro
645 650 655

Tyr Met Val Glu Arg Ile Ser Lys Asn Tyr Ala Leu Gln Ile Val Ala
660 665 670

Asn Ser Phe Leu Ala Asn Pro Thr Thr Ser Ala Leu Phe Ala Thr Ile
675 680 685

Leu Val Glu Tyr Leu Leu Asp Arg Leu Pro Glu Met Gly Ser Asn Val
690 695 700

Glu Leu Ser Asn Leu Tyr Leu Lys Leu Phe Lys Leu Val Phe Gly Ser
705 710 715 720

Val Ser Leu Phe Ala Ala Glu Asn Glu Gln Met Leu Lys Pro His Leu
725 730 735

His Lys Ile Val Asn Ser Ser Met Glu Leu Ala Gln Thr Ala Lys Glu
740 745 750

Pro Tyr Asn Tyr Phe Leu Leu Leu Arg Ala Leu Phe Arg Ser Ile Gly
755 760 765

Gly Gly Ser His Asp Leu Leu Tyr Gln Glu Phe Leu Pro Leu Leu Pro
770 775 780

Asn Leu Leu Gln Gly Leu Asn Met Leu Gln Ser Gly Leu His Lys Gln
785 790 795 800

His Met Lys Asp Leu Phe Val Glu Leu Cys Leu Thr Val Pro Val Arg
805 810 815

Leu Ser Ser Leu Leu Pro Tyr Leu Pro Met Leu Met Asp Pro Leu Val
820 825 830

Ser Ala Leu Asn Gly Ser Gln Thr Leu Val Ser Gln Gly Leu Arg Thr
835 840 845

Leu Glu Leu Cys Val Asp Asn Leu Gln Pro Asp Phe Leu Tyr Asp His
850 855 860

Ile Gln Pro Val Arg Ala Glu Leu Met Gln Ala Leu Trp Arg Thr Leu
865 870 875 880

Arg Asn Pro Ala Asp Ser Ile Ser His Val Ala Tyr Arg Val Leu Gly
885 890 895

Lys Phe Gly Gly Ser Asn Arg Lys Met Leu Lys Glu Ser Gln Lys Leu
900 905 910

His Tyr Val Val Thr Glu Val Gln Gly Pro Ser Ile Thr Val Glu Phe
915 920 925

Ser Asp Cys Lys Ala Ser Leu Gln Leu Pro Met Glu Lys Ala Ile Glu
930 935 940

Thr Ala Leu Asp Cys Leu Lys Ser Ala Asn Thr Glu Pro Tyr Tyr Arg
945 950 955 960

Arg Gln Ala Trp Glu Val Ile Lys Cys Phe Leu Val Ala Met Met Ser
965 970 975

-continued

```
Leu Glu Asp Asn Lys His Ala Leu Tyr Gln Leu Leu Ala His Pro Asn
            980                 985                 990

Phe Thr Glu Lys Thr Ile Pro Asn  Val Ile Ile Ser His  Arg Tyr Lys
        995                 1000                 1005

Ala Gln  Asp Thr Pro Ala Arg  Lys Thr Phe Glu Gln  Ala Leu Thr
    1010                 1015                 1020

Gly Ala  Phe Met Ser Ala Val  Ile Lys Asp Leu Arg  Pro Ser Ala
    1025                 1030                 1035

Leu Pro  Phe Val Ala Ser Leu  Ile Arg His Tyr Thr  Met Val Ala
    1040                 1045                 1050

Val Ala  Gln Gln Cys Gly Pro  Phe Leu Leu Pro Cys  Tyr Gln Val
    1055                 1060                 1065

Gly Ser  Gln Pro Ser Thr Ala  Met Phe His Ser Glu  Glu Asn Gly
    1070                 1075                 1080

Ser Lys  Gly Met Asp Pro Leu  Val Leu Ile Asp Ala  Ile Ala Ile
    1085                 1090                 1095

Cys Met  Ala Tyr Glu Glu Lys  Glu Leu Cys Lys Ile  Gly Glu Val
    1100                 1105                 1110

Ala Leu  Ala Val Ile Phe Asp  Val Ala Ser Ile Ile  Leu Gly Ser
    1115                 1120                 1125

Lys Glu  Arg Ala Cys Gln Leu  Pro Leu Phe Ser Tyr  Ile Val Glu
    1130                 1135                 1140

Arg Leu  Cys Ala Cys Cys Tyr  Glu Gln Ala Trp Tyr  Ala Lys Leu
    1145                 1150                 1155

Gly Gly  Val Val Ser Ile Lys  Phe Leu Met Glu Arg  Leu Pro Leu
    1160                 1165                 1170

Thr Trp  Val Leu Gln Asn Gln  Gln Thr Phe Leu Lys  Ala Leu Leu
    1175                 1180                 1185

Phe Val  Met Met Asp Leu Thr  Gly Glu Val Ser Asn  Gly Ala Val
    1190                 1195                 1200

Ala Met  Ala Lys Thr Thr Leu  Glu Gln Leu Leu Met  Arg Cys Ala
    1205                 1210                 1215

Thr Pro  Leu Lys Asp Glu Glu  Arg Ala Glu Glu Ile  Val Ala Ala
    1220                 1225                 1230

Gln Glu  Lys Ser Phe His His  Val Thr His Asp Leu  Val Arg Glu
    1235                 1240                 1245

Val Thr  Ser Pro Asn Ser Thr  Val Arg Lys Gln Ala  Met His Ser
    1250                 1255                 1260

Leu Gln  Val Leu Ala Gln Val  Thr Gly Lys Ser Val  Thr Val Ile
    1265                 1270                 1275

Met Glu  Pro His Lys Glu Val  Leu Gln Asp Met Val  Pro Pro Lys
    1280                 1285                 1290

Lys His  Leu Leu Arg His Gln  Pro Ala Asn Ala Gln  Ile Gly Leu
    1295                 1300                 1305

Met Glu  Gly Asn Thr Phe Cys  Thr Thr Leu Gln Pro  Arg Leu Phe
    1310                 1315                 1320

Thr Met  Asp Leu Asn Val Val  Glu His Lys Val Phe  Tyr Thr Glu
    1325                 1330                 1335

Leu Leu  Asn Leu Cys Glu Ala  Glu Asp Ser Ala Leu  Thr Lys Leu
    1340                 1345                 1350

Pro Cys  Tyr Lys Ser Leu Pro  Ser Leu Val Pro Leu  Arg Ile Ala
    1355                 1360                 1365

Ala Leu  Asn Ala Leu Ala Ala  Cys Asn Tyr Leu Pro  Gln Ser Arg
```

-continued

```
    1370                1375                1380

Glu Lys  Ile Ile Ala Ala Leu  Phe Lys Ala Leu Asn  Ser Thr Asn
    1385                1390                1395

Ser Glu  Leu Gln Glu Ala Gly  Glu Ala Cys Met Arg  Lys Phe Leu
    1400                1405                1410

Glu Gly  Ala Thr Ile Glu Val  Asp Gln Ile His Thr  His Met Arg
    1415                1420                1425

Pro Leu  Leu Met Met Leu Gly  Asp Tyr Arg Ser Leu  Thr Leu Asn
    1430                1435                1440

Val Val  Asn Arg Leu Thr Ser  Val Thr Arg Leu Phe  Pro Asn Ser
    1445                1450                1455

Phe Asn  Asp Lys Phe Cys Asp  Gln Met Met Gln His  Leu Arg Lys
    1460                1465                1470

Trp Met  Glu Val Val Val Ile  Thr His Lys Gly Gly  Gln Arg Ser
    1475                1480                1485

Asp Gly  Asn Glu Ser Ile Ser  Glu Cys Gly Arg Cys  Pro Leu Ser
    1490                1495                1500

Pro Phe  Cys Gln Phe Glu Glu  Met Lys Ile Cys Ser  Ala Ile Ile
    1505                1510                1515

Asn Leu  Phe His Leu Ile Pro  Ala Ala Pro Gln Thr  Leu Val Lys
    1520                1525                1530

Pro Leu  Leu Glu Val Val Met  Lys Thr Glu Arg Ala  Met Leu Ile
    1535                1540                1545

Glu Ala  Gly Ser Pro Phe Arg  Glu Pro Leu Ile Lys  Phe Leu Thr
    1550                1555                1560

Arg His  Pro Ser Gln Thr Val  Glu Leu Phe Met Met  Glu Ala Thr
    1565                1570                1575

Leu Asn  Asp Pro Gln Trp Ser  Arg Met Phe Met Ser  Phe Leu Lys
    1580                1585                1590

His Lys  Asp Ala Arg Pro Leu  Arg Asp Val Leu Ala  Ala Asn Pro
    1595                1600                1605

Asn Arg  Phe Ile Thr Leu Leu  Leu Pro Gly Gly Ala  Gln Thr Ala
    1610                1615                1620

Val Arg  Pro Gly Ser Pro Ser  Thr Ser Thr Met Arg  Leu Asp Leu
    1625                1630                1635

Gln Phe  Gln Ala Ile Lys Ile  Ile Ser Ile Ile Val  Lys Asn Asp
    1640                1645                1650

Asp Ser  Trp Leu Ala Ser Gln  His Ser Leu Val Ser  Gln Leu Arg
    1655                1660                1665

Arg Val  Trp Val Ser Glu Asn  Phe Gln Glu Arg His  Arg Lys Glu
    1670                1675                1680

Asn Met  Ala Ala Thr Asn Trp  Lys Glu Pro Lys Leu  Leu Ala Tyr
    1685                1690                1695

Cys Leu  Leu Asn Tyr Cys Lys  Arg Asn Tyr Gly Asp  Ile Glu Leu
    1700                1705                1710

Leu Phe  Gln Leu Leu Arg Ala  Phe Thr Gly Arg Phe  Leu Cys Asn
    1715                1720                1725

Met Thr  Phe Leu Lys Glu Tyr  Met Glu Glu Glu Ile  Pro Lys Asn
    1730                1735                1740

Tyr Ser  Ile Ala Gln Lys Arg  Ala Leu Phe Phe Arg  Phe Val Asp
    1745                1750                1755

Phe Asn  Asp Pro Asn Phe Gly  Asp Glu Leu Lys Ala  Lys Val Leu
    1760                1765                1770
```

-continued

```
Gln His  Ile Leu Asn Pro Ala  Phe Leu Tyr Ser Phe  Glu Lys Gly
    1775                 1780                 1785

Glu Gly  Glu Gln Leu Leu Gly  Pro Pro Asn Pro Glu  Gly Asp Asn
    1790                 1795                 1800

Pro Glu  Ser Ile Thr Ser Val  Phe Ile Thr Lys Val  Leu Asp Pro
    1805                 1810                 1815

Glu Lys  Gln Ala Asp Met Leu  Asp Ser Leu Arg Ile  Tyr Leu Leu
    1820                 1825                 1830

Gln Tyr  Ala Thr Leu Leu Val  Glu His Ala Pro His  His Ile His
    1835                 1840                 1845

Asp Asn  Asn Lys Asn Arg Asn  Ser Lys Leu Arg Arg  Leu Met Thr
    1850                 1855                 1860

Phe Ala  Trp Pro Cys Leu Leu  Ser Lys Ala Cys Val  Asp Pro Ala
    1865                 1870                 1875

Cys Lys  Tyr Ser Gly His Leu  Leu Leu Ala His Ile  Ile Ala Lys
    1880                 1885                 1890

Phe Ala  Ile His Lys Lys Ile  Val Leu Gln Val Phe  His Ser Leu
    1895                 1900                 1905

Leu Lys  Ala His Ala Met Glu  Ala Arg Ala Ile Val  Arg Gln Ala
    1910                 1915                 1920

Met Ala  Ile Leu Thr Pro Ala  Val Pro Ala Arg Met  Glu Asp Gly
    1925                 1930                 1935

His Gln  Met Leu Thr His Trp  Thr Arg Lys Ile Ile  Val Glu Glu
    1940                 1945                 1950

Gly His  Thr Val Pro Gln Leu  Val His Ile Leu His  Leu Ile Val
    1955                 1960                 1965

Gln His  Phe Lys Val Tyr Tyr  Pro Val Arg His His  Leu Val Gln
    1970                 1975                 1980

His Met  Val Ser Ala Met Gln  Arg Leu Gly Phe Thr  Pro Ser Val
    1985                 1990                 1995

Thr Ile  Glu Gln Arg Arg Leu  Ala Val Asp Leu Ser  Glu Val Val
    2000                 2005                 2010

Ile Lys  Trp Glu Leu Gln Arg  Ile Lys Asp Gln Gln  Pro Asp Ser
    2015                 2020                 2025

Asp Met  Asp Pro Asn Ser Ser  Gly Glu Gly Val Asn  Ser Val Ser
    2030                 2035                 2040

Ser Ser  Ile Lys Arg Gly Leu  Ser Val Asp Ser Ala  Gln Glu Val
    2045                 2050                 2055

Lys Arg  Phe Arg Thr Ala Thr  Gly Ala Ile Ser Ala  Val Phe Gly
    2060                 2065                 2070

Arg Ser  Gln Ser Leu Pro Gly  Ala Asp Ser Leu Leu  Ala Lys Pro
    2075                 2080                 2085

Ile Asp  Lys Gln His Thr Asp  Thr Val Val Asn Phe  Leu Ile Arg
    2090                 2095                 2100

Val Ala  Cys Gln Val Asn Asp  Asn Thr Asn Thr Ala  Gly Ser Pro
    2105                 2110                 2115

Gly Glu  Val Leu Ser Arg Arg  Cys Val Asn Leu Leu  Lys Thr Ala
    2120                 2125                 2130

Leu Arg  Pro Asp Met Trp Pro  Lys Ser Glu Leu Lys  Leu Gln Trp
    2135                 2140                 2145

Phe Asp  Lys Leu Leu Met Thr  Val Glu Gln Pro Asn  Gln Val Asn
    2150                 2155                 2160
```

-continued

```
Tyr Gly  Asn Ile Cys Thr Gly  Leu Glu Val Leu Ser  Phe Leu Leu
    2165                 2170                 2175

Thr Val  Leu Gln Ser Pro Ala  Ile Leu Ser Ser Phe  Lys Pro Leu
    2180                 2185                 2190

Gln Arg  Gly Ile Ala Ala Cys  Met Thr Cys Gly Asn  Thr Lys Val
    2195                 2200                 2205

Leu Arg  Ala Val His Ser Leu  Leu Ser Arg Leu Met  Ser Ile Phe
    2210                 2215                 2220

Pro Thr  Glu Pro Ser Thr Ser  Ser Val Ala Ser Lys  Tyr Glu Glu
    2225                 2230                 2235

Leu Glu  Cys Leu Tyr Ala Ala  Val Gly Lys Val Ile  Tyr Glu Gly
    2240                 2245                 2250

Leu Thr  Asn Tyr Glu Lys Ala  Thr Asn Ala Asn Pro  Ser Gln Leu
    2255                 2260                 2265

Phe Gly  Thr Leu Met Ile Leu  Lys Ser Ala Cys Ser  Asn Asn Pro
    2270                 2275                 2280

Ser Tyr  Ile Asp Arg Leu Ile  Ser Val Phe Met Arg  Ser Leu Gln
    2285                 2290                 2295

Lys Met  Val Arg Glu His Leu  Asn Pro Gln Ala Ala  Ser Gly Ser
    2300                 2305                 2310

Thr Glu  Ala Thr Ser Gly Thr  Ser Glu Leu Val Met  Leu Ser Leu
    2315                 2320                 2325

Glu Leu  Val Lys Thr Arg Leu  Ala Val Met Ser Met  Glu Met Arg
    2330                 2335                 2340

Lys Asn  Phe Ile Gln Ala Ile  Leu Thr Ser Leu Ile  Glu Lys Ser
    2345                 2350                 2355

Pro Asp  Ala Lys Ile Leu Arg  Ala Val Val Lys Ile  Val Glu Glu
    2360                 2365                 2370

Trp Val  Lys Asn Asn Ser Pro  Met Ala Ala Asn Gln  Thr Pro Thr
    2375                 2380                 2385

Leu Arg  Glu Lys Ser Ile Leu  Leu Val Lys Met Met  Thr Tyr Ile
    2390                 2395                 2400

Glu Lys  Arg Phe Pro Glu Asp  Leu Glu Leu Asn Ala  Gln Phe Leu
    2405                 2410                 2415

Asp Leu  Val Asn Tyr Val Tyr  Arg Asp Glu Thr Leu  Ser Gly Ser
    2420                 2425                 2430

Glu Leu  Thr Ala Lys Leu Glu  Pro Ala Phe Leu Ser  Gly Leu Arg
    2435                 2440                 2445

Cys Ala  Gln Pro Leu Ile Arg  Ala Lys Phe Phe Glu  Val Phe Asp
    2450                 2455                 2460

Asn Ser  Met Lys Arg Arg Val  Tyr Glu Arg Leu Leu  Tyr Val Thr
    2465                 2470                 2475

Cys Ser  Gln Asn Trp Glu Ala  Met Gly Asn His Phe  Trp Ile Lys
    2480                 2485                 2490

Gln Cys  Ile Glu Leu Leu Leu  Ala Val Cys Glu Lys  Ser Thr Pro
    2495                 2500                 2505

Ile Gly  Thr Ser Cys Gln Gly  Ala Met Leu Pro Ser  Ile Thr Asn
    2510                 2515                 2520

Val Ile  Asn Leu Ala Asp Ser  His Asp Arg Ala Ala  Phe Ala Met
    2525                 2530                 2535

Val Thr  His Val Lys Gln Glu  Pro Arg Glu Arg Glu  Asn Ser Glu
    2540                 2545                 2550

Ser Lys  Glu Glu Asp Val Glu  Ile Asp Ile Glu Leu  Ala Pro Gly
```

```
    2555                2560                2565

Asp Gln  Thr Ser Thr Pro Lys  Thr Lys Glu Leu Ser  Glu Lys Asp
    2570                2575                2580

Ile Gly  Asn Gln Leu His Met  Leu Thr Asn Arg His  Asp Lys Phe
    2585                2590                2595

Leu Asp  Thr Leu Arg Glu Val  Lys Thr Gly Ala Leu  Leu Ser Ala
    2600                2605                2610

Phe Val  Gln Leu Cys His Ile  Ser Thr Thr Leu Ala  Glu Lys Thr
    2615                2620                2625

Trp Val  Gln Leu Phe Pro Arg  Leu Trp Lys Ile Leu  Ser Asp Arg
    2630                2635                2640

Gln Gln  His Ala Leu Ala Gly  Glu Ile Ser Pro Phe  Leu Cys Ser
    2645                2650                2655

Gly Ser  His Gln Val Gln Arg  Asp Cys Gln Pro Ser  Ala Leu Asn
    2660                2665                2670

Cys Phe  Val Glu Ala Met Ser  Gln Cys Val Pro Pro  Ile Pro Ile
    2675                2680                2685

Arg Pro  Cys Val Leu Lys Tyr  Leu Gly Lys Thr His  Asn Leu Trp
    2690                2695                2700

Phe Arg  Ser Thr Leu Met Leu  Glu His Gln Ala Phe  Glu Lys Gly
    2705                2710                2715

Leu Ser  Leu Gln Ile Lys Pro  Lys Gln Thr Thr Glu  Phe Tyr Glu
    2720                2725                2730

Gln Glu  Ser Ile Thr Pro Pro  Gln Gln Glu Ile Leu  Asp Ser Leu
    2735                2740                2745

Ala Glu  Leu Tyr Ser Leu Leu  Gln Glu Glu Asp Met  Trp Ala Gly
    2750                2755                2760

Leu Trp  Gln Lys Arg Cys Lys  Tyr Ser Glu Thr Ala  Thr Ala Ile
    2765                2770                2775

Ala Tyr  Glu Gln His Gly Phe  Phe Glu Gln Ala Gln  Glu Ser Tyr
    2780                2785                2790

Glu Lys  Ala Met Asp Lys Ala  Lys Lys Glu His Glu  Arg Ser Asn
    2795                2800                2805

Ala Ser  Pro Ala Ile Phe Pro  Glu Tyr Gln Leu Trp  Glu Asp His
    2810                2815                2820

Trp Ile  Arg Cys Ser Lys Glu  Leu Asn Gln Trp Glu  Ala Leu Thr
    2825                2830                2835

Glu Tyr  Gly Gln Ser Lys Gly  His Ile Asn Pro Tyr  Leu Val Leu
    2840                2845                2850

Glu Cys  Ala Trp Arg Val Ser  Asn Trp Thr Ala Met  Lys Glu Ala
    2855                2860                2865

Leu Val  Gln Val Glu Val Ser  Cys Pro Lys Glu Met  Ala Trp Lys
    2870                2875                2880

Val Asn  Met Tyr Arg Gly Tyr  Leu Ala Ile Cys His  Pro Glu Glu
    2885                2890                2895

Gln Gln  Leu Ser Phe Ile Glu  Arg Leu Val Glu Met  Ala Ser Ser
    2900                2905                2910

Leu Ala  Ile Arg Glu Trp Arg  Arg Leu Pro His Val  Val Ser His
    2915                2920                2925

Val His  Thr Pro Leu Leu Gln  Ala Ala Gln Gln Ile  Ile Glu Leu
    2930                2935                2940

Gln Glu  Ala Ala Gln Ile Asn  Ala Gly Leu Gln Pro  Thr Asn Leu
    2945                2950                2955
```

```
Gly Arg  Asn Asn Ser Leu His  Asp Met Lys Thr Val  Val Lys Thr
    2960                 2965                 2970

Trp Arg  Asn Arg Leu Pro Ile  Val Ser Asp Asp Leu  Ser His Trp
    2975                 2980                 2985

Ser Ser  Ile Phe Met Trp Arg  Gln His His Tyr Gln  Gly Lys Pro
    2990                 2995                 3000

Thr Trp  Ser Gly Met His Ser  Ser Ser Ile Val Thr  Ala Tyr Glu
    3005                 3010                 3015

Asn Ser  Ser Gln His Asp Pro  Ser Ser Asn Asn Ala  Met Leu Gly
    3020                 3025                 3030

Val His  Ala Ser Ala Ser Ala  Ile Ile Gln Tyr Gly  Lys Ile Ala
    3035                 3040                 3045

Arg Lys  Gln Gly Leu Val Asn  Val Ala Leu Asp Ile  Leu Ser Arg
    3050                 3055                 3060

Ile His  Thr Ile Pro Thr Val  Pro Ile Val Asp Cys  Phe Gln Lys
    3065                 3070                 3075

Ile Arg  Gln Gln Val Lys Cys  Tyr Leu Gln Leu Ala  Gly Val Met
    3080                 3085                 3090

Gly Lys  Asn Glu Cys Met Gln  Gly Leu Glu Val Ile  Glu Ser Thr
    3095                 3100                 3105

Asn Leu  Lys Tyr Phe Thr Lys  Glu Met Thr Ala Glu  Phe Tyr Ala
    3110                 3115                 3120

Leu Lys  Gly Met Phe Leu Ala  Gln Ile Asn Lys Ser  Glu Glu Ala
    3125                 3130                 3135

Asn Lys  Ala Phe Ser Ala Ala  Val Gln Met His Asp  Val Leu Val
    3140                 3145                 3150

Lys Ala  Trp Ala Met Trp Gly  Asp Tyr Leu Glu Asn  Ile Phe Val
    3155                 3160                 3165

Lys Glu  Arg Gln Leu His Leu  Gly Val Ser Ala Ile  Thr Cys Tyr
    3170                 3175                 3180

Leu His  Ala Cys Arg His Gln  Asn Glu Ser Lys Ser  Arg Lys Tyr
    3185                 3190                 3195

Leu Ala  Lys Val Leu Trp Leu  Leu Ser Phe Asp Asp  Asp Lys Asn
    3200                 3205                 3210

Thr Leu  Ala Asp Ala Val Asp  Lys Tyr Cys Ile Gly  Val Pro Pro
    3215                 3220                 3225

Ile Gln  Trp Leu Ala Trp Ile  Pro Gln Leu Leu Thr  Cys Leu Val
    3230                 3235                 3240

Gly Ser  Glu Gly Lys Leu Leu  Leu Asn Leu Ile Ser  Gln Val Gly
    3245                 3250                 3255

Arg Val  Tyr Pro Gln Ala Val  Tyr Phe Pro Ile Arg  Thr Leu Tyr
    3260                 3265                 3270

Leu Thr  Leu Lys Ile Glu Gln  Arg Glu Arg Tyr Lys  Ser Asp Pro
    3275                 3280                 3285

Gly Pro  Ile Arg Ala Thr Ala  Pro Met Trp Arg Cys  Ser Arg Ile
    3290                 3295                 3300

Met His  Met Gln Arg Glu Leu  His Pro Thr Leu Leu  Ser Ser Leu
    3305                 3310                 3315

Glu Gly  Ile Val Asp Gln Met  Val Trp Phe Arg Glu  Asn Trp His
    3320                 3325                 3330

Glu Glu  Val Leu Arg Gln Leu  Gln Gln Gly Leu Ala  Lys Cys Tyr
    3335                 3340                 3345
```

Ser Val Ala Phe Glu Lys Ser Gly Ala Val Ser Asp Ala Lys Ile
3350 3355 3360

Thr Pro His Thr Leu Asn Phe Val Lys Lys Leu Val Ser Thr Phe
3365 3370 3375

Gly Val Gly Leu Glu Asn Val Ser Asn Val Ser Thr Met Phe Ser
3380 3385 3390

Ser Ala Ala Ser Glu Ser Leu Ala Arg Arg Ala Gln Ala Thr Ala
3395 3400 3405

Gln Asp Pro Val Phe Gln Lys Leu Lys Gly Gln Phe Thr Thr Asp
3410 3415 3420

Phe Asp Phe Ser Val Pro Gly Ser Met Lys Leu His Asn Leu Ile
3425 3430 3435

Ser Lys Leu Lys Lys Trp Ile Lys Ile Leu Glu Ala Lys Thr Lys
3440 3445 3450

Gln Leu Pro Lys Phe Phe Leu Ile Glu Glu Lys Cys Arg Phe Leu
3455 3460 3465

Ser Asn Phe Ser Ala Gln Thr Ala Glu Val Glu Ile Pro Gly Glu
3470 3475 3480

Phe Leu Met Pro Lys Pro Thr His Tyr Tyr Ile Lys Ile Ala Arg
3485 3490 3495

Phe Met Pro Arg Val Glu Ile Val Gln Lys His Asn Thr Ala Ala
3500 3505 3510

Arg Arg Leu Tyr Ile Arg Gly His Asn Gly Lys Ile Tyr Pro Tyr
3515 3520 3525

Leu Val Met Asn Asp Ala Cys Leu Thr Glu Ser Arg Arg Glu Glu
3530 3535 3540

Arg Val Leu Gln Leu Leu Arg Leu Leu Asn Pro Cys Leu Glu Lys
3545 3550 3555

Arg Lys Glu Thr Thr Lys Arg His Leu Phe Phe Thr Val Pro Arg
3560 3565 3570

Val Val Ala Val Ser Pro Gln Met Arg Leu Val Glu Asp Asn Pro
3575 3580 3585

Ser Ser Leu Ser Leu Val Glu Ile Tyr Lys Gln Arg Cys Ala Lys
3590 3595 3600

Lys Gly Ile Glu His Asp Asn Pro Ile Ser Arg Tyr Tyr Asp Arg
3605 3610 3615

Leu Ala Thr Val Gln Ala Arg Gly Thr Gln Ala Ser His Gln Val
3620 3625 3630

Leu Arg Asp Ile Leu Lys Glu Val Gln Ser Asn Met Val Pro Arg
3635 3640 3645

Ser Met Leu Lys Glu Trp Ala Leu His Thr Phe Pro Asn Ala Thr
3650 3655 3660

Asp Tyr Trp Thr Phe Arg Lys Met Phe Thr Ile Gln Leu Ala Leu
3665 3670 3675

Ile Gly Phe Ala Glu Phe Val Leu His Leu Asn Arg Leu Asn Pro
3680 3685 3690

Glu Met Leu Gln Ile Ala Gln Asp Thr Gly Lys Leu Asn Val Ala
3695 3700 3705

Tyr Phe Arg Phe Asp Ile Asn Asp Ala Thr Gly Asp Leu Asp Ala
3710 3715 3720

Asn Arg Pro Val Pro Phe Arg Leu Thr Pro Asn Ile Ser Glu Phe
3725 3730 3735

Leu Thr Thr Ile Gly Val Ser Gly Pro Leu Thr Ala Ser Met Ile 3740 3745 3750

Ala Val Ala Arg Cys Phe Ala Gln Pro Asn Phe Lys Val Asp Gly
3755 3760 3765

Ile Leu Lys Thr Val Leu Arg Asp Glu Ile Ile Ala Trp His Lys
3770 3775 3780

Lys Thr Gln Glu Asp Thr Ser Ser Pro Leu Ser Ala Ala Gly Gln
3785 3790 3795

Pro Glu Asn Met Asp Ser Gln Gln Leu Val Ser Leu Val Gln Lys
3800 3805 3810

Ala Val Thr Ala Ile Met Thr Arg Leu His Asn Leu Ala Gln Phe
3815 3820 3825

Glu Gly Gly Glu Ser Lys Val Asn Thr Leu Val Ala Ala Ala Asn
3830 3835 3840

Ser Leu Asp Asn Leu Cys Arg Met Asp Pro Ala Trp His Pro Trp
3845 3850 3855

Leu

<210> SEQ ID NO 11
<211> LENGTH: 1239
<212> TYPE: PRT
<213> ORGANISM: Artificial Sequence
<220> FEATURE:
<223> OTHER INFORMATION: Synthetic polypeptide

<400> SEQUENCE: 11

Met Ala Asn Asp Ser Pro Ala Lys Ser Leu Val Asp Ile Asp Leu Ser
1 5 10 15

Ser Leu Arg Asp Pro Ala Gly Ile Phe Glu Leu Val Glu Val Val Gly
20 25 30

Asn Gly Thr Tyr Gly Gln Val Tyr Lys Gly Arg His Val Lys Thr Gly
35 40 45

Gln Leu Ala Ala Ile Lys Val Met Asp Val Thr Glu Asp Glu Glu Glu
50 55 60

Glu Ile Lys Leu Glu Ile Asn Met Leu Lys Lys Tyr Ser His His Arg
65 70 75 80

Asn Ile Ala Thr Tyr Tyr Gly Ala Phe Ile Lys Lys Ser Pro Pro Gly
85 90 95

His Asp Asp Gln Leu Trp Leu Val Met Glu Phe Cys Gly Ala Gly Ser
100 105 110

Ile Thr Asp Leu Val Lys Asn Thr Lys Gly Asn Thr Leu Lys Glu Asp
115 120 125

Trp Ile Ala Tyr Ile Ser Arg Glu Ile Leu Arg Gly Leu Ala His Leu
130 135 140

His Ile His His Val Ile His Arg Asp Ile Lys Gly Gln Asn Val Leu
145 150 155 160

Leu Thr Glu Asn Ala Glu Val Lys Leu Val Asp Phe Gly Val Ser Ala
165 170 175

Gln Leu Asp Arg Thr Val Gly Arg Arg Asn Thr Phe Ile Gly Thr Pro
180 185 190

Tyr Trp Met Ala Pro Glu Val Ile Ala Cys Asp Glu Asn Pro Asp Ala
195 200 205

Thr Tyr Asp Tyr Arg Ser Asp Leu Trp Ser Cys Gly Ile Thr Ala Ile
210 215 220

Glu Met Ala Glu Gly Ala Pro Pro Leu Cys Asp Met His Pro Met Arg
225 230 235 240

-continued

```
Ala Leu Phe Leu Ile Pro Arg Asn Pro Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Glu Val Pro Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Gln Leu Arg Glu Gln
    370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Arg Leu Glu Glu Gln Gln Arg Arg Glu
                405                 410                 415

Arg Glu Ala Arg Arg Gln Gln Glu Arg Glu Gln Arg Arg Arg Glu Gln
            420                 425                 430

Glu Glu Lys Arg Arg Leu Glu Glu Leu Glu Arg Arg Arg Lys Glu Glu
        435                 440                 445

Glu Glu Arg Arg Arg Ala Glu Glu Glu Lys Arg Arg Val Glu Arg Glu
    450                 455                 460

Gln Glu Tyr Ile Arg Arg Gln Leu Glu Glu Glu Gln Arg His Leu Glu
465                 470                 475                 480

Val Leu Gln Gln Gln Leu Leu Gln Glu Gln Ala Met Leu Leu Glu Cys
                485                 490                 495

Arg Trp Arg Glu Met Glu Glu His Arg Gln Ala Glu Arg Leu Gln Arg
            500                 505                 510

Gln Leu Gln Gln Glu Gln Ala Tyr Leu Leu Ser Leu Gln His Asp His
        515                 520                 525

Arg Arg Pro His Pro Gln His Ser Gln Gln Pro Pro Pro Pro Gln Gln
    530                 535                 540

Glu Arg Ser Lys Pro Ser Phe His Ala Pro Glu Pro Lys Ala His Tyr
545                 550                 555                 560

Glu Pro Ala Asp Arg Ala Arg Glu Val Glu Asp Arg Phe Arg Lys Thr
                565                 570                 575

Asn His Ser Ser Pro Glu Ala Gln Ser Lys Gln Thr Gly Arg Val Leu
            580                 585                 590

Glu Pro Pro Val Pro Ser Arg Ser Glu Ser Phe Ser Asn Gly Asn Ser
        595                 600                 605

Glu Ser Val His Pro Ala Leu Gln Arg Pro Ala Glu Pro Gln Val Pro
    610                 615                 620

Val Arg Thr Thr Ser Arg Ser Pro Val Leu Ser Arg Arg Asp Ser Pro
625                 630                 635                 640

Leu Gln Gly Ser Gly Gln Gln Asn Ser Gln Ala Gly Gln Arg Asn Ser
                645                 650                 655
```

```
Thr Ser Ile Glu Pro Arg Leu Leu Trp Glu Arg Val Glu Lys Leu Val
            660                 665                 670

Pro Arg Pro Gly Ser Gly Ser Ser Ser Gly Ser Ser Asn Ser Gly Ser
        675                 680                 685

Gln Pro Gly Ser His Pro Gly Ser Gln Ser Gly Ser Gly Glu Arg Phe
    690                 695                 700

Arg Val Arg Ser Ser Ser Lys Ser Glu Gly Ser Pro Ser Gln Arg Leu
705                 710                 715                 720

Glu Asn Ala Val Lys Lys Pro Glu Asp Lys Lys Glu Val Phe Arg Pro
                725                 730                 735

Leu Lys Pro Ala Asp Leu Thr Ala Leu Ala Lys Glu Leu Arg Ala Val
            740                 745                 750

Glu Asp Val Arg Pro Pro His Lys Val Thr Asp Tyr Ser Ser Ser Ser
        755                 760                 765

Glu Glu Ser Gly Thr Thr Asp Glu Glu Asp Asp Asp Val Glu Gln Glu
    770                 775                 780

Gly Ala Asp Glu Ser Thr Ser Gly Pro Glu Asp Thr Arg Ala Ala Ser
785                 790                 795                 800

Ser Leu Asn Leu Ser Asn Gly Glu Thr Glu Ser Val Lys Thr Met Ile
                805                 810                 815

Val His Asp Asp Val Glu Ser Glu Pro Ala Met Thr Pro Ser Lys Glu
            820                 825                 830

Gly Thr Leu Ile Val Arg Gln Thr Gln Ser Ala Ser Ser Thr Leu Gln
        835                 840                 845

Lys His Lys Ser Ser Ser Ser Phe Thr Pro Phe Ile Asp Pro Arg Leu
    850                 855                 860

Leu Gln Ile Ser Pro Ser Ser Gly Thr Thr Val Thr Ser Val Val Gly
865                 870                 875                 880

Phe Ser Cys Asp Gly Met Arg Pro Glu Ala Ile Arg Gln Asp Pro Thr
                885                 890                 895

Arg Lys Gly Ser Val Val Asn Val Asn Pro Thr Asn Thr Arg Pro Gln
            900                 905                 910

Ser Asp Thr Pro Glu Ile Arg Lys Tyr Lys Lys Arg Phe Asn Ser Glu
        915                 920                 925

Ile Leu Cys Ala Ala Leu Trp Gly Val Asn Leu Leu Val Gly Thr Glu
    930                 935                 940

Ser Gly Leu Met Leu Leu Asp Arg Ser Gly Gln Gly Lys Val Tyr Pro
945                 950                 955                 960

Leu Ile Asn Arg Arg Arg Phe Gln Gln Met Asp Val Leu Glu Gly Leu
                965                 970                 975

Asn Val Leu Val Thr Ile Ser Gly Lys Lys Asp Lys Leu Arg Val Tyr
            980                 985                 990

Tyr Leu Ser Trp Leu Arg Asn Lys  Ile Leu His Asn Asp  Pro Glu Val
        995                 1000                 1005

Glu Lys  Lys Gln Gly Trp Thr  Thr Val Gly Asp Leu  Glu Gly Cys
    1010                 1015                 1020

Val His  Tyr Lys Val Val Lys  Tyr Glu Arg Ile Lys  Phe Leu Val
    1025                 1030                 1035

Ile Ala  Leu Lys Ser Ser Val  Glu Val Tyr Ala Trp  Ala Pro Lys
    1040                 1045                 1050

Pro Tyr  His Lys Phe Met Ala  Phe Lys Ser Phe Gly  Glu Leu Val
    1055                 1060                 1065

His Lys  Pro Leu Leu Val Asp  Leu Thr Val Glu Glu  Gly Gln Arg
```

1070 1075 1080

Leu Lys Val Ile Tyr Gly Ser Cys Ala Gly Phe His Ala Val Asp
1085 1090 1095

Val Asp Ser Gly Ser Val Tyr Asp Ile Tyr Leu Pro Thr His Ile
1100 1105 1110

Gln Cys Ser Ile Lys Pro His Ala Ile Ile Ile Leu Pro Asn Thr
1115 1120 1125

Asp Gly Met Glu Leu Leu Val Cys Tyr Glu Asp Glu Gly Val Tyr
1130 1135 1140

Val Asn Thr Tyr Gly Arg Ile Thr Lys Asp Val Val Leu Gln Trp
1145 1150 1155

Gly Glu Met Pro Thr Ser Val Ala Tyr Ile Arg Ser Asn Gln Thr
1160 1165 1170

Met Gly Trp Gly Glu Lys Ala Ile Glu Ile Arg Ser Val Glu Thr
1175 1180 1185

Gly His Leu Asp Gly Val Phe Met His Lys Arg Ala Gln Arg Leu
1190 1195 1200

Lys Phe Leu Cys Glu Arg Asn Asp Lys Val Phe Phe Ala Ser Val
1205 1210 1215

Arg Ser Gly Gly Ser Ser Gln Val Tyr Phe Met Thr Leu Gly Arg
1220 1225 1230

Thr Ser Leu Leu Ser Trp
1235

<210> SEQ ID NO 12
<211> LENGTH: 859
<212> TYPE: PRT
<213> ORGANISM: Artificial Sequence
<220> FEATURE:
<223> OTHER INFORMATION: Synthetic polypeptide

<400> SEQUENCE: 12

Met Ala Cys Leu His Glu Thr Arg Thr Pro Ser Pro Ser Phe Gly Gly
1 5 10 15

Phe Val Ser Thr Leu Ser Glu Ala Ser Met Arg Lys Leu Asp Pro Asp
20 25 30

Thr Ser Asp Cys Thr Pro Glu Lys Asp Leu Thr Pro Thr His Val Leu
35 40 45

Gln Leu His Glu Gln Asp Ala Gly Gly Pro Gly Gly Ala Ala Gly Ser
50 55 60

Pro Glu Ser Arg Ala Ser Arg Val Arg Ala Asp Glu Val Arg Leu Gln
65 70 75 80

Cys Gln Ser Gly Ser Gly Phe Leu Glu Gly Leu Phe Gly Cys Leu Arg
85 90 95

Pro Val Trp Thr Met Ile Gly Lys Ala Tyr Ser Thr Glu His Lys Gln
100 105 110

Gln Gln Glu Asp Leu Trp Glu Val Pro Phe Glu Glu Ile Leu Asp Leu
115 120 125

Gln Trp Val Gly Ser Gly Ala Gln Gly Ala Val Phe Leu Gly Arg Phe
130 135 140

His Gly Glu Glu Val Ala Val Lys Lys Val Arg Asp Leu Lys Glu Thr
145 150 155 160

Asp Ile Lys His Leu Arg Lys Leu Lys His Pro Asn Ile Ile Thr Phe
165 170 175

Lys Gly Val Cys Thr Gln Ala Pro Cys Tyr Cys Ile Leu Met Glu Phe

-continued

```
            180                 185                 190

Cys Ala Gln Gly Gln Leu Tyr Glu Val Leu Arg Ala Gly Arg Pro Val
        195                 200                 205

Thr Pro Ser Leu Leu Val Asp Trp Ser Met Gly Ile Ala Gly Gly Met
    210                 215                 220

Asn Tyr Leu His Leu His Lys Ile Ile His Arg Asp Leu Lys Ser Pro
225                 230                 235                 240

Asn Met Leu Ile Thr Tyr Asp Asp Val Val Lys Ile Ser Asp Phe Gly
                245                 250                 255

Thr Ser Lys Glu Leu Ser Asp Lys Ser Thr Lys Met Ser Phe Ala Gly
            260                 265                 270

Thr Val Ala Trp Met Ala Pro Glu Val Ile Arg Asn Glu Pro Val Ser
        275                 280                 285

Glu Lys Val Asp Ile Trp Ser Phe Gly Val Val Leu Trp Glu Leu Leu
    290                 295                 300

Thr Gly Glu Ile Pro Tyr Lys Asp Val Asp Ser Ser Ala Ile Ile Trp
305                 310                 315                 320

Gly Val Gly Ser Asn Ser Leu His Leu Pro Val Pro Ser Ser Cys Pro
                325                 330                 335

Asp Gly Phe Lys Ile Leu Leu Arg Gln Cys Trp Asn Ser Lys Pro Arg
            340                 345                 350

Asn Arg Pro Ser Phe Arg Gln Ile Leu Leu His Leu Asp Ile Ala Ser
        355                 360                 365

Ala Asp Val Leu Ser Thr Pro Gln Glu Thr Tyr Phe Lys Ser Gln Ala
    370                 375                 380

Glu Trp Arg Glu Glu Val Lys Leu His Phe Glu Lys Ile Lys Ser Glu
385                 390                 395                 400

Gly Thr Cys Leu His Arg Leu Glu Glu Glu Leu Val Met Arg Arg Arg
                405                 410                 415

Glu Glu Leu Arg His Ala Leu Asp Ile Arg Glu His Tyr Glu Arg Lys
            420                 425                 430

Leu Glu Arg Ala Asn Asn Leu Tyr Met Glu Leu Asn Ala Leu Met Leu
        435                 440                 445

Gln Leu Glu Leu Lys Glu Arg Glu Leu Leu Arg Arg Glu Gln Ala Leu
    450                 455                 460

Glu Arg Arg Cys Pro Gly Leu Leu Lys Pro His Pro Ser Arg Gly Leu
465                 470                 475                 480

Leu His Gly Asn Thr Met Glu Lys Leu Ile Lys Lys Arg Asn Val Pro
                485                 490                 495

Gln Lys Leu Ser Pro His Ser Lys Arg Pro Asp Ile Leu Lys Thr Glu
            500                 505                 510

Ser Leu Leu Pro Lys Leu Asp Ala Ala Leu Ser Gly Val Gly Leu Pro
        515                 520                 525

Gly Cys Pro Lys Gly Pro Pro Ser Pro Gly Arg Ser Arg Arg Gly Lys
    530                 535                 540

Thr Arg His Arg Lys Ala Ser Ala Lys Gly Ser Cys Gly Asp Leu Pro
545                 550                 555                 560

Gly Leu Arg Thr Ala Val Pro Pro His Glu Pro Gly Gly Pro Gly Ser
                565                 570                 575

Pro Gly Gly Leu Gly Gly Gly Pro Ser Ala Trp Glu Ala Cys Pro Pro
            580                 585                 590

Ala Leu Arg Gly Leu His His Asp Leu Leu Leu Arg Lys Met Ser Ser
        595                 600                 605
```

-continued

```
Ser Ser Pro Asp Leu Leu Ser Ala Ala Leu Gly Ser Arg Gly Arg Gly
    610                 615                 620

Ala Thr Gly Gly Ala Gly Asp Pro Gly Ser Pro Pro Pro Ala Arg Gly
625                 630                 635                 640

Asp Thr Pro Pro Ser Glu Gly Ser Ala Pro Gly Ser Thr Ser Pro Asp
                645                 650                 655

Ser Pro Gly Gly Ala Lys Gly Glu Pro Pro Pro Pro Val Gly Pro Gly
            660                 665                 670

Glu Gly Val Gly Leu Leu Gly Thr Gly Arg Glu Gly Thr Ser Gly Arg
        675                 680                 685

Gly Gly Ser Arg Ala Gly Ser Gln His Leu Thr Pro Ala Ala Leu Leu
    690                 695                 700

Tyr Arg Ala Ala Val Thr Arg Ser Gln Lys Arg Gly Ile Ser Ser Glu
705                 710                 715                 720

Glu Glu Glu Gly Glu Val Asp Ser Glu Val Glu Leu Thr Ser Ser Gln
                725                 730                 735

Arg Trp Pro Gln Ser Leu Asn Met Arg Gln Ser Leu Ser Thr Phe Ser
            740                 745                 750

Ser Glu Asn Pro Ser Asp Gly Glu Glu Gly Thr Ala Ser Glu Pro Ser
        755                 760                 765

Pro Ser Gly Thr Pro Glu Val Gly Ser Thr Asn Thr Asp Glu Arg Pro
    770                 775                 780

Asp Glu Arg Ser Asp Asp Met Cys Ser Gln Gly Ser Glu Ile Pro Leu
785                 790                 795                 800

Asp Pro Pro Pro Ser Glu Val Ile Pro Gly Pro Glu Pro Ser Ser Leu
                805                 810                 815

Pro Ile Pro His Gln Glu Leu Leu Arg Glu Arg Gly Pro Pro Asn Ser
            820                 825                 830

Glu Asp Ser Asp Cys Asp Ser Thr Glu Leu Asp Asn Ser Asn Ser Val
        835                 840                 845

Asp Ala Leu Arg Pro Pro Ala Ser Leu Pro Pro
    850                 855
```